US012655150B2

(12) United States Patent
Rennie et al.

(10) Patent No.: US 12,655,150 B2
(45) Date of Patent: Jun. 16, 2026

(54) TEAD INHIBITORS AND USES THEREOF

(71) Applicant: Cedilla Therapeutics, Inc., Cambridge, MA (US)

(72) Inventors: Glen Robert Rennie, Somerville, MA (US); C. Eric Schwartz, Marblehead, MA (US); Louise Kirman, Swampscott, MA (US); Dale Porter, Cambridge, MA (US); Ling Song, Cambridge, MA (US)

(73) Assignee: Cedilla Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/704,126

(22) Filed: Mar. 25, 2022

(65) Prior Publication Data

US 2023/0098872 A1 Mar. 30, 2023

Related U.S. Application Data

(60) Provisional application No. 63/292,367, filed on Dec. 21, 2021, provisional application No. 63/226,972, filed on Jul. 29, 2021, provisional application No. 63/166,769, filed on Mar. 26, 2021.

(51) Int. Cl.

| | |
|---|---|
| ***C07D 487/04*** | (2006.01) |
| ***C07D 215/14*** | (2006.01) |
| ***C07D 215/233*** | (2006.01) |
| ***C07D 239/74*** | (2006.01) |
| ***C07D 401/04*** | (2006.01) |
| ***C07D 401/12*** | (2006.01) |
| ***C07D 405/04*** | (2006.01) |
| ***C07D 471/04*** | (2006.01) |
| ***C07D 471/14*** | (2006.01) |
| ***C07D 519/00*** | (2006.01) |

(52) U.S. Cl.

CPC ......... *C07D 487/04* (2013.01); *C07D 215/14* (2013.01); *C07D 215/233* (2013.01); *C07D 239/74* (2013.01); *C07D 401/04* (2013.01); *C07D 401/12* (2013.01); *C07D 405/04* (2013.01); *C07D 471/04* (2013.01); *C07D 471/14* (2013.01); *C07D 519/00* (2013.01)

(58) Field of Classification Search

CPC ............. C07D 487/04; C07D 215/233; C07D 401/04; C07D 471/04; C07D 519/00

See application file for complete search history.

(56) References Cited

U.S. PATENT DOCUMENTS

| | | | | |
|---|---|---|---|---|
| 6,440,995 | B1 * | 8/2002 | Alanine | A61P 25/14 546/159 |
| 10,787,428 | B2 | 9/2020 | Danjo et al. | |
| 2009/0081165 | A1 * | 3/2009 | Schmitz | A61P 31/12 514/314 |
| 2013/0324523 | A1 | 12/2013 | Kudo et al. | |
| 2014/0128392 | A1 * | 5/2014 | McCall | C07D 409/04 514/249 |
| 2017/0233345 | A1 | 8/2017 | Vakalopoulos et al. | |
| 2018/0009784 | A1 * | 1/2018 | Freeze | A61P 35/00 |
| 2019/0106423 | A1 | 4/2019 | Hudson et al. | |
| 2020/0097389 | A1 | 3/2020 | Smith et al. | |
| 2020/0347009 | A1 | 11/2020 | Konradi et al. | |
| 2022/0017491 | A1 | 1/2022 | Lim et al. | |
| 2023/0053649 | A1 | 2/2023 | Rennie et al. | |
| 2023/0115350 | A1 | 4/2023 | Rennie et al. | |

FOREIGN PATENT DOCUMENTS

| | | | | |
|---|---|---|---|---|
| CN | 112010789 | A | 12/2020 | |
| CN | 113527151 | A | 10/2021 | |
| EP | 2952514 | A1 | 12/2015 | |
| EP | 3124482 | A1 | 2/2017 | |
| RU | 2572076 | C2 | 12/2015 | |
| RU | 2734240 | C2 | 10/2020 | |
| WO | WO 1986/06721 | A1 * | 11/1986 | C07D 401/04 |
| WO | WO-2005/063712 | A1 | 7/2005 | |
| WO | WO-2005/118580 | A2 | 12/2005 | |
| WO | WO-2006/053785 | A1 | 5/2006 | |
| WO | WO-2008/061108 | A2 | 5/2008 | |
| WO | WO-2009/029375 | A1 | 3/2009 | |
| WO | WO-2011/031896 | A2 | 3/2011 | |
| WO | WO-2013/058644 | A1 | 4/2013 | |
| WO | WO-2013/086229 | A1 | 6/2013 | |
| WO | WO-2014/015523 | A1 | 1/2014 | |
| WO | WO-2014/076237 | A1 | 5/2014 | |
| WO | WO-2015/060365 | A1 | 4/2015 | |
| WO | WO-2015/073528 | A1 | 5/2015 | |
| WO | WO-2016/023885 | A1 | 2/2016 | |
| WO | WO-2016118565 | A1 * | 7/2016 | A61K 31/47 |
| WO | WO-2017/064277 | A1 | 4/2017 | |
| WO | WO-2017061957 | A1 * | 4/2017 | A61K 31/496 |
| WO | WO-2017/184547 | A1 | 10/2017 | |
| WO | WO-2017/189958 | A1 | 11/2017 | |

(Continued)

OTHER PUBLICATIONS

M. Stone (Matthew T. Stone, Organic Letters 2011 13 (9), 2326-2329, DOI: 10.1021/ol200579a. (Year: 2011).*

A. Patra, et al. (Organic Letters 2018 20 (4), 1086-1089, DOI: 10.1021/acs.orglett.7b04055. (Year: 2018).*

L. Montse, et al. Journal of Medicinal Chemistry, 2004, vol. 47, No. 26, p. 5684-6594. (Year: 2004).*

Wang, Q., et al. (2015), Adv. Synth. Catal., 357: 2479-2484. (Year: 2015).*

Ajaybabu V. et al., Identification of Quinolinols as Activators of TEAD-Dependent Transcription, ACS Chemical Biology, 14(12): 2909-2921 (2019).

(Continued)

*Primary Examiner* — James H Alstrum-Acevedo
*Assistant Examiner* — Manahil Mirghani Ali Abdalhameed
(74) *Attorney, Agent, or Firm* — Choate, Hall & Stewart LLP; Kristen C. Buteau; Lauren E. Markham

(57) ABSTRACT

The present disclosure provides compounds, pharmaceutically acceptable compositions thereof, and methods of using the same.

8 Claims, 1 Drawing Sheet

Specification includes a Sequence Listing.

(56) References Cited

FOREIGN PATENT DOCUMENTS

| | | | |
|---|---|---|---|
| WO | WO-2018/235926 | A1 | 12/2018 |
| WO | WO-2019/232216 | A1 | 12/2019 |
| WO | WO-2020/051099 | A1 | 3/2020 |
| WO | WO-2020/081572 | A1 | 4/2020 |
| WO | WO-2020/087063 | A1 | 4/2020 |
| WO | WO-2020/096416 | A1 | 5/2020 |
| WO | WO-2020/097389 | A1 | 5/2020 |
| WO | WO-2020/138271 | A1 | 7/2020 |
| WO | WO-2020/140052 | A1 | 7/2020 |
| WO | WO-2020/154350 | A1 | 7/2020 |
| WO | WO-2020/190774 | A1 | 9/2020 |
| WO | WO-2020/214734 | A1 | 10/2020 |
| WO | WO-2020/243423 | A1 | 12/2020 |
| WO | WO-2021/081211 | A1 | 4/2021 |
| WO | WO-2021/097110 | A1 | 5/2021 |
| WO | WO-2021/108483 | A1 | 6/2021 |
| WO | WO-2021/133896 | A1 | 7/2021 |
| WO | WO-2021/204823 | A1 | 10/2021 |
| WO | WO-2022/006548 | A1 | 1/2022 |
| WO | WO-2022/018072 | A1 | 1/2022 |
| WO | WO-2022/020716 | A1 | 1/2022 |
| WO | WO-2022/023460 | A1 | 2/2022 |
| WO | WO-2022/037568 | A1 | 2/2022 |
| WO | WO-2022/072741 | A1 | 4/2022 |
| WO | WO-2022/120354 | A1 | 6/2022 |
| WO | WO-2022/159986 | A1 | 7/2022 |
| WO | WO-2022/164835 | A1 | 8/2022 |
| WO | WO-2022/204452 | A1 | 9/2022 |
| WO | WO-2022/272036 | A1 | 12/2022 |
| WO | WO-2023/009785 | A1 | 2/2023 |
| WO | WO-2022/272036 | A9 | 3/2023 |

OTHER PUBLICATIONS

Black D S. et al., Product Class 13: 1h-Pyrroles, Science Of Synthesis, Thieme Verlag, Stuttgart, DE, 9: 441-552 (2002).

Boopathy, G. and Hong, W., Role of Hippo Pathway-YAP/TAZ Signaling in Angiogenesis, Frontiers in Cell and Development Biology, 7(49):1-12 (2019).

Chan, P. et al., Autopalmitoylation of TEAD Proteins Regulates Transcriptional Output of Hippo Pathway, Nat. Chem. Biol., 12(4):282-289 (2016).

Gibault, F. et al., Toward the Discovery of a Novel Class of YAP?TEAD Interaction Inhibitors by Virtual Screening Approach Targeting YAP?TEAD Protein?Protein Interface, Cancers, vol. 10, No. 5:140 (2018).

Holden, J. and Cunningham, C. N., Targeting the Hippo Pathway and Cancer through the TEAD Family of Transcription Factors, Cancers, 10:1-15 (2018).

Huh, H. D. et al., Regulation of TEAD Transcription Factors in Cancer Biology, Cells, 8:1-22 (2019).

Kunig, V. et al., TEAD-YAP Interaction Inhibitors and MDM2 Binders from DNA-Encoded Indole-Focused Ugi Peptidomimetics, Angewandte Chemie, Wiley—V Ch Verlag Gmbh & Co. Kgaa, De, 132(46): 20518-20522 (2020).

Mokrov, GV. et al., Design, synthesis and anxiolytic-like activity of 1-arylpyrrolo[1,2-a]pyrazine-3-carboxamides, Bioorganic, Elsevier, Amsterdam, NL, 23(13):3368-3378 (2015).

Noland, C. L. et al., Palmitoylation of TEAD Transcription Factors Is Required for Their Stability and Function in Hippo Pathway Signaling, Structure, 24(1):179-186 (2016).

Smith, S. et al., Antiproliferative and Antimigratory Effects of a Novel TEAD-YAP Interaction Inhibitor Identified Using in Silico Molecular Docking, Journal of Medicinal Chemistry, 62(3):1291-1305 (2019).

Yu, F. et al., Regulation of the Hippo-YAP Pathway by G-Protein-Coupled Receptor Signaling, Cell, 150:780-791 (2012).

International Search Report for PCT/US22/21842, 12 pages (mailed Jul. 25, 2022).

PUBCHEM-SID:401548881 Deposit Date: Dec. 7, 2019 (Dec. 7, 2019) pp. 1-5; p. 2.

Deposit Date: Apr. 8, 2019 (Apr. 8, 2019) pp. 1-7; p. 2.

International Search Report for PCT/US22/34860, 4 pages (mailed Oct. 19, 2022).

Deposit Date: Jan. 20, 2016 (Jan. 20, 2016) pp. 1-5.

International Search Report for PCT/US22/38805, 5 pages (mailed Dec. 6, 2022).

Written Opinion for PCT/US22/21842, 22 pages (mailed Jul. 25, 2022).

Written Opinion for PCT/US22/21842, 6 pages (mailed Oct. 19, 2022).

Written Opinion for PCT/US22/38805, 5 pages (mailed Dec. 6, 2022).

Civicos, J. F. et al., Copper- versus palladium-catalyzed aromatization of 2-(methoxycarbonyl) tetralones: synthesis of methyl 1-hydroxy-2-naphthoates, Tetrahedron, 72(16): 1897-1902 (2016).

Lutz, R. et al., Antimalarials. 5.alpha.-Dibutylaminomethyl- and. alpha.-(2-piperidyl)-3-quinolinemethanols, Journal Of Medicinal Chemistry, 14(1): 17-24 (1971).

Suschitzky, H. et al., Synthesis of heterocyclic compounds. Part XXX. Reactions of o-alkylamino- and o-dialkylamino-anilines with some [alpha][beta]-unsaturated carbonyl compounds, J. Chem. Soc., Perkin Trans. 1, 23:249-2413 (1975).

* cited by examiner

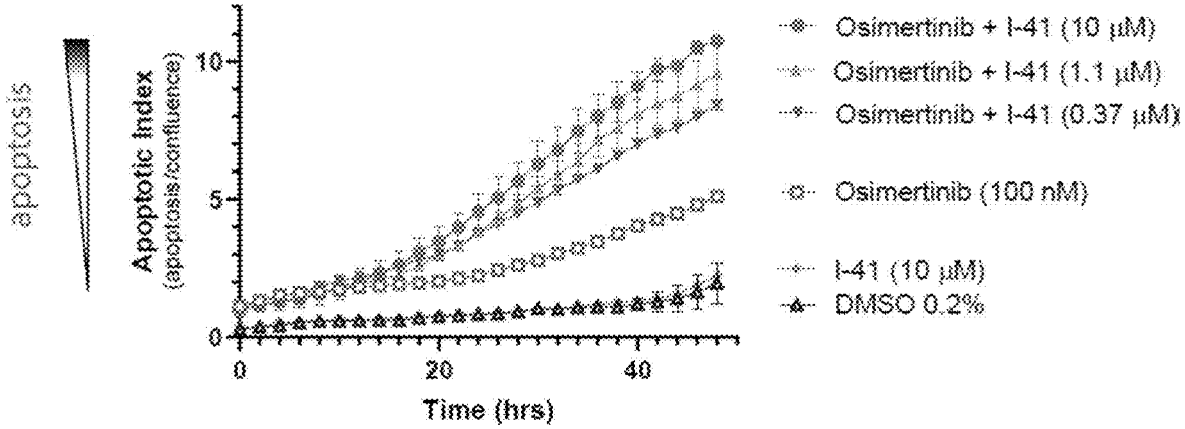
apoptosis
Apoptotic Index
(apoptosis/confluence)
10
5
0
0
20
40
Time (hrs)
Osimertinib + I-41 (10 μM)
Osimertinib + I-41 (1.1 μM)
Osimertinib + I-41 (0.37 μM)
Osimertinib (100 nM)
I-41 (10 μM)
DMSO 0.2%

TEAD INHIBITORS AND USES THEREOF

CROSS REFERENCE TO RELATED APPLICATIONS

This application claims the benefit of U.S. Provisional Application No. 63/166,769, filed Mar. 26, 2021, U.S. Provisional Application No. 63/226,972, filed Jul. 29, 2021, and U.S. Provisional Application No. 63/292,367, filed Dec. 21, 2021, each of which is herein incorporated by reference in its entirety.

TECHNICAL FIELD OF INVENTION

The present disclosure relates to compounds and methods useful for inhibition of Transcriptional Enhancer Associate Domain (TEAD) transcription factors. The disclosure also provides pharmaceutically acceptable compositions comprising compounds of the present disclosure and methods of using said compositions in the treatment of various diseases, disorders, and conditions as described herein.

SEQUENCE LISTING

The instant application contains a Sequence Listing which has been submitted electronically in ASCII format and is hereby incorporated by reference in its entirety. Said ASCII copy, created on Apr. 19, 2022, is named 2013757-0010_SL.txt and is 15,748 bytes in size.

BACKGROUND OF THE INVENTION

Yes-associated protein (YAP) and transcriptional co-activator with PDZ-binding motif (TAZ) are transcriptional co-activators of the Hippo signaling pathway and regulate cell proliferation, migration, and apoptosis. Inhibition of the Hippo signaling pathway promotes YAP/TAZ translocation to the nucleus, where YAP/TAZ interact with TEAD transcription factors to co-activate the expression of target genes and promote cell proliferation. Hyperactivation of YAP and TAZ and/or mutations in one or more members of the Hippo signaling pathway have been implicated in various diseases, disorders, and conditions.

SUMMARY OF THE INVENTION

In some embodiments, the present disclosure provides the recognition that there remains a need to find inhibitors of the Hippo signaling pathway useful as therapeutic agents. It has now been found that compounds of the present disclosure, and pharmaceutically acceptable salts and compositions thereof, are effective as inhibitors of TEAD transcription factors (e.g., TEAD1, TEAD2, TEAD3, and/or TEAD4). Such compounds have general Formula I:

I

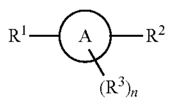

or a pharmaceutically acceptable salt thereof, wherein:

Ring A is a 9- to 13-membered bicyclic or tricyclic heteroaryl ring having 1-4 heteroatoms independently selected from nitrogen, oxygen, and sulfur;

$R^1$ is halogen, OR, $N(R)_2$, CN, C(O)R, C(O)OR, $C(O)N(R)_2$, $SO_2N(R)_2$, $C(O)N(R)SO_2R$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^2$ is OR, $N(R)_2$, or an optionally substituted group selected from $C_{1-6}$ aliphatic, a 3- to 6-membered saturated or partially unsaturated carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^3$ is halogen, OR, $N(R)_2$, CN, C(O)R, C(O)OR, $C(O)N(R)_2$, $SO_2N(R)_2$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur; and n is 0, 1, or 2.

Compounds described herein, and pharmaceutically acceptable compositions thereof, are useful for treating a variety of diseases, disorders, or conditions associated with the Hippo signaling pathway. Such diseases, disorders, or conditions include those described herein.

Compounds provided herein are also useful for the study of the Hippo signaling pathway in, e.g., biological and pathological phenomena, and the comparative evaluation of new TEAD transcription factor inhibitors.

BRIEF DESCRIPTION OF THE DRAWING

FIG. 1 depicts administration of compound I-41 in combination with Osimertinib to PC-9 cells.

DETAILED DESCRIPTION OF CERTAIN EMBODIMENTS

1. General Description of Certain Embodiments of the Invention

In certain embodiments, the present disclosure provides inhibitors of TEAD transcription factors. In some embodiments, such compounds include those of the formulae described herein, or a pharmaceutically acceptable salt thereof, wherein each variable is as defined and described herein.

In one aspect, the present disclosure provides compounds of Formula I:

I

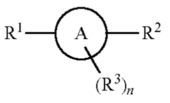

or a pharmaceutically acceptable salt thereof, wherein:

Ring A is a 9- to 13-membered bicyclic or tricyclic heteroaryl ring having 1-4 heteroatoms independently selected from nitrogen, oxygen, and sulfur;

$R^1$ is halogen, OR, $N(R)_2$, CN, C(O)R, C(O)OR, $C(O)N(R)_2$, $SO_2N(R)_2$, $C(O)N(R)SO_2R$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^2$ is OR, $N(R)_2$, or an optionally substituted group selected from $C_{1-6}$ aliphatic, a 3- to 6-membered saturated or partially unsaturated carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^3$ is halogen, OR, $N(R)_2$, CN, C(O)R, C(O)OR, $C(O)N(R)_2$, $SO_2N(R)_2$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur; and n is 0, 1, or 2.

In one aspect, the present disclosure provides compounds of Formula I':

I'

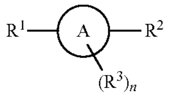

or a pharmaceutically acceptable salt thereof, wherein:

Ring A is a 9- to 13-membered bicyclic or tricyclic heteroaryl ring having 1-4 heteroatoms independently selected from nitrogen, oxygen, and sulfur;

$R^1$ is halogen, OR, $N(R)_2$, CN, C(O)R, C(O)OR, $C(O)N(R)_2$, C(O)N(R)LR, $SO_2R$, $SO_2N(R)_2$, SON(R)R, $C(O)N(R)SO_2R$, OC(O)R, N(R)C(O)R, $N(R)SO_2R$, $N(R)C(O)N(R)_2$, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

L is an optionally substituted bivalent straight $C_{2-12}$ hydrocarbon chain wherein 1-4 carbon atoms of L are optionally and independently replaced by a group selected from —O— or —N(R)—;

$R^2$ is OR, $N(R)_2$, or an optionally substituted group selected from $C_{1-6}$ aliphatic, a 3- to 6-membered saturated or partially unsaturated carbocyclic ring, a 4- to 12-membered saturated or partially unsaturated bridged bicyclic carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, a 5- to 6-membered heteroaryl ring having 1-4 heteroatoms independently selected from nitrogen, oxygen, and sulfur, and a 7- to 12-membered bridged bicyclic heterocyclic ring having 1-3 heteroatoms independently selected from nitrogen, oxygen, and sulfur;

$R^3$ is oxo, halogen, OR, $N(R)_2$, SR, CN, C(O)R, C(O)OR, $C(O)N(R)_2$, $SO_2N(R)_2$, OC(O)R, N(R)C(O)R, $N(R)SO_2R$, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur; or:

two R groups on the same nitrogen atom may, together with the atoms to which they are attached, form an optionally substituted saturated or partially unsaturated 3- to 6-membered heterocyclic ring having 0-1 additional heteroatoms selected from nitrogen, oxygen, and sulfur; and n is 0, 1, or 2.

2. Compounds and Definitions

Compounds of the present disclosure include those described generally above, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle", "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

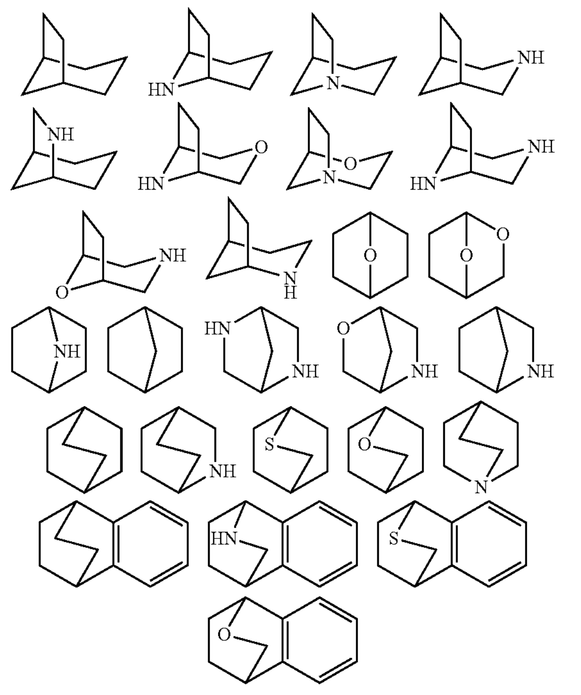

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "partially unsaturated", as used herein, refers to a ring moiety that includes at least one double or triple bond. The term "partially unsaturated", as used herein, is intended to encompass rings having multiple sites of unsaturation, but is not intended to include aryl or heteroaryl moieties, as herein defined.

The term "lower alkyl", as used herein, refers to a $C_{1-4}$ straight or branched alkyl group. Exemplary lower alkyl groups are methyl, ethyl, propyl, isopropyl, butyl, isobutyl, and tert-butyl.

The term "halogen" means F, Cl, Br, or I.

The term "aryl", as used herein, refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments, "aryl" refers to an aromatic ring system which includes, but not limited to, phenyl, biphenyl, naphthyl, anthracyl and the like, which may bear one or more substituents. Also included within the scope of the term "aryl" is a group in which an aromatic ring is fused to one or more non-aromatic rings, such as indanyl, phthalimidyl, naphthimidyl, phenanthridinyl, or tetrahydronaphthyl, and the like.

The term "heteroaryl", as used herein, does not differ significantly from the common meaning of the term in the art, and refers to a cyclic aromatic radical having from five to twelve ring atoms of which one ring atom is selected from S, O and N; zero, one, two, three, four, or five ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

The term "heteroaryl" as used herein, refers to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" as used herein, refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, tetrahydroquinolinyl, and tetrahydroisoquinolinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples of heteroaryl rings on compounds of Formula I and subgenera thereof include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Additionally, it will be appreciated that, when two groups cyclize to form an optionally substituted heteroaryl ring having at least one nitrogen atom, the nitrogen atom in the ring can be, as valency permits, N or N-Rt, as defined infra.

As used herein, the terms "heterocycle", "heterocyclyl", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, tetrahydroquinolinyl, or tetrahydroisoquinolinyl where the radical or point of attachment is on the heterocyclyl ring. A heterocyclyl group may be mono- or bicyclic.

Additionally, it will be appreciated that, when two groups cyclize to form an optionally substituted heterocyclic ring having at least one nitrogen atom, the nitrogen atom in the ring can be, as valency permits, N or $N—R^{\dagger}$, as defined infra.

As described herein, compounds may contain "optionally substituted" moieties. In general, the term "substituted", whether preceded by the term "optionally" or not, means that one or more hydrogens of the designated moiety of compounds are replaced with a suitable substituent. "Substituted" applies to one or more hydrogens that are either explicit or implicit from the structure (e.g., 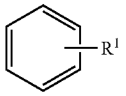 refers to at least 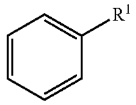 ; and

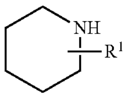 refers to at least 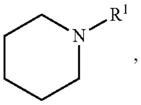 ,

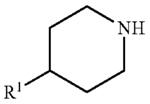 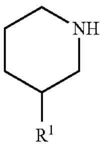 , or 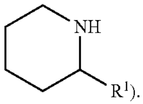 ).

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^{\circ}$; $—(CH_2)_{0-4}OR^{\circ}$; $—O(CH_2)_{0-4}R^{\circ}$, $—O—(CH_2)_{0-4}C(O)OR^{\circ}$; $—(CH_2)_{0-4}CH(OR^{\circ})_2$; $—(CH_2)_{0-4}SR^{\circ}$; $—(CH_2)_{0-4}Ph$, which may be substituted with $R^{\circ}$; $—(CH_2)_{0-4}O(CH_2)_{0-1}Ph$ which may be substituted with $R^{\circ}$; $—CH{=}CHPh$, which may be substituted with $R^{\circ}$; $—(CH_2)_{0-4}O(CH_2)_{0-1}$-pyridyl which may be substituted with $R^{\circ}$; $—NO_2$; $—CN$; $—N_3$; $—(CH_2)_{0-4}N(R^{\circ})_2$; $—(CH_2)_{0-4}N(R^{\circ})C(O)R^{\circ}$; $—N(R^{\circ})C(S)R^{\circ}$; $—(CH_2)_{0-4}N(R^{\circ})C(O)NR^{\circ}_2$; $—N(R^{\circ})C(S)NR^{\circ}_2$; $—(CH_2)_{0-4}N(R^{\circ})C(O)OR^{\circ}$; $—N(R^{\circ})N(R^{\circ})C(O)R^{\circ}$; $—N(R^{\circ})N(R^{\circ})C(O)NR^{\circ}_2$; $—N(R^{\circ})N(R^{\circ})C(O)OR^{\circ}$; $—(CH_2)_{0-4}C(O)R^{\circ}$; $—C(S)R^{\circ}$; $—(CH_2)_{0-4}C(O)OR^{\circ}$; $—(CH_2)_{0-4}C(O)SR^{\circ}$; $—(CH_2)_{0-4}C(O)OSiR^{\circ}_3$; $—(CH_2)_{0-4}OC(O)R^{\circ}$; $—OC(O)(CH_2)_{0-4}SR^{\circ}$, $SC(S)SR^{\circ}$; $—(CH_2)_{0-4}SC(O)R^{\circ}$; $—(CH_2)_{0-4}C(O)NR^{\circ}_2$; $—C(S)NR^{\circ}_2$; $—C(S)SR^{\circ}$; $—SC(S)SR^{\circ}$, $—(CH_2)_{0-4}OC(O)NR^{\circ}_2$; $—C(O)N(OR^{\circ})R^{\circ}$; $—C(O)C(O)R^{\circ}$;

—$C(O)CH_2C(O)R^\circ$; —$C(NOR^\circ)R^\circ$; —$(CH_2)_{0\text{-}4}SSR^\circ$; —$(CH_2)_{0\text{-}4}S(O)_2R^\circ$; —$(CH_2)_{0\text{-}4}S(O)_2OR^\circ$; —$(CH_2)_{0\text{-}4}OS(O)_2R^\circ$; —$S(O)_2NR^\circ_2$; —$(CH_2)_{0\text{-}4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(CH_2)_{0\text{-}4}N(R^\circ)CN$; —($C_{1\text{-}4}$ straight or branched alkylene)O—$N(R^\circ)_2$; or —($C_{1\text{-}4}$ straight or branched alkylene)C(O)O—$N(R^\circ)_2$, wherein each $R^\circ$ may be substituted as defined below and is independently hydrogen, $C_{1\text{-}6}$ aliphatic, —$CH_2Ph$, —$O(CH_2)_{0\text{-}1}Ph$, —$CH_2$-(5- to 6 membered heteroaryl ring), or a 5- to 6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0\text{-}2}R^\bullet$, -(halo$R^\bullet$), —$(CH_2)_{0\text{-}2}OH$, —$(CH_2)_{0\text{-}2}OR^\bullet$, —$(CH_2)_{0\text{-}2}CH(OR^\bullet)_2$; —O(halo$R^\bullet$), —CN, —$N_3$, —$(CH_2)_{0\text{-}2}C(O)R^\bullet$, —$(CH_2)_{0\text{-}2}C(O)OH$, —$(CH_2)_{0\text{-}2}C(O)OR^\bullet$, —$(CH_2)_{0\text{-}2}SR^\bullet$, —$(CH_2)_{0\text{-}2}SH$, —$(CH_2)_{0\text{-}2}NH_2$, —$(CH_2)_{0\text{-}2}NHR^\bullet$, —$(CH_2)_{0\text{-}2}NR^\bullet_2$, —$NO_2$, —$SiR^\bullet_3$, —$OSiR^\bullet_3$, —$C(O)SR^\bullet$, —($C_{1\text{-}4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1\text{-}4}$ aliphatic, —$CH_2Ph$, —$O(CH_2)_{0\text{-}1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2\text{-}3}$—O—, or —$S(C(R^*_2))_{2\text{-}3}S$—, wherein each independent occurrence of $R^*$ is selected from hydrogen, $C_{1\text{-}6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group of a compound of Formula I, and subgenera thereof, include: —$O(CR^\bullet_2)_{2\text{-}3}$—O—, wherein each independent occurrence of $R^\bullet$ is selected from hydrogen, $C_{1\text{-}6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1\text{-}4}$ aliphatic, —$CH_2Ph$, —$O(CH_2)_{0\text{-}1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR_2$, —$C(S)NR^{\backslash}_2$, —$C(NH)NR^\dagger_2$, or —$N(R^{\backslash})S(O)_2R^{\backslash}$; wherein each $R^{\backslash}$ is independently hydrogen, $C_{1\text{-}6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\backslash}$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1\text{-}4}$ aliphatic, —$CH_2Ph$, —$O(CH_2)_{0\text{-}1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1\text{-}4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present disclosure. Unless otherwise stated, all tautomeric forms are within the scope of the disclosure. Additionally, unless otherwise stated, the present disclosure also includes compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the present disclosure. In some embodiments, compounds of this disclosure comprise one or more deuterium atoms.

Combinations of substituents and variables envisioned by this disclosure are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof, or purified versions thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

As used herein, a "disease or disorder associated with TEAD" or, alternatively, "an TEAD-mediated disease or disorder" means any disease or other deleterious condition in which TEAD, or a mutant thereof, is known or suspected to play a role.

The term "subject", as used herein, means a mammal and includes human and animal subjects, such as domestic animals (e.g., horses, dogs, cats, etc.). The terms "subject" and "patient" are used interchangeably. In some embodiments, the "patient" or "subject" means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The amount of compounds described herein that may be combined with the carrier materials to produce a composition in a single dosage form will vary depending upon the host treated, the particular mode of administration, etc.

The expression "unit dosage form" as used herein refers to a physically discrete unit of a provided compound and/or compositions thereof appropriate for the subject to be treated. It will be understood, however, that the total daily usage of the active agent (i.e., compounds and compositions described herein) will be decided by the attending physician within the scope of sound medical judgment. The specific effective dose level for any particular subject (i.e., patient) or organism will depend upon a variety of factors including the disorder being treated and the severity of the disorder; activity of specific active agent employed; specific composition employed; age, body weight, general health, sex and diet of the subject; time of administration, route of administration, and rate of excretion of the specific active agent employed; duration of the treatment, and like factors well known in the medical arts.

The term "parenteral" as used herein includes subcutaneous, intravenous, intramuscular, intra-articular, intra-synovial, intrasternal, intrathecal, intrahepatic, intralesional and intracranial injection or infusion techniques.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a provided compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a "therapeutically effective amount" is at least a minimal amount of a provided compound, or composition containing a provided compound, which is sufficient for treating one or more symptoms of an TEAD-mediated disease or disorder.

As used herein, the terms "treatment," "treat," and "treating" refer to partially or completely alleviating, inhibiting, delaying onset of, preventing, ameliorating and/or relieving a disorder or condition, or one or more symptoms of the disorder or condition, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

3. Description of Exemplary Embodiments

In some embodiments, the present disclosure provides a compound of formula I.

I

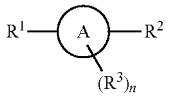

or a pharmaceutically acceptable salt thereof, wherein:

Ring A is a 9- to 13-membered bicyclic or tricyclic heteroaryl ring having 1-4 heteroatoms independently selected from nitrogen, oxygen, and sulfur;

$R^1$ is halogen, OR, $N(R)_2$, CN, C(O)R, C(O)OR, C(O)N$(R)_2$, $SO_2N(R)_2$, C(O)N(R)$SO_2$R, OC(O)R, N(R)C(O)R, N(R)$SO_2$R, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^2$ is OR, $N(R)_2$, or an optionally substituted group selected from $C_{1-6}$ aliphatic, a 3- to 6-membered saturated or partially unsaturated carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^3$ is halogen, OR, $N(R)_2$, CN, C(O)R, C(O)OR, C(O)N$(R)_2$, $SO_2N(R)_2$, OC(O)R, N(R)C(O)R, N(R)$SO_2$R, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur; and n is 0, 1, or 2.

In one aspect, the present disclosure provides compounds of Formula I':

I'

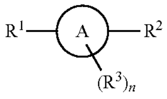

or a pharmaceutically acceptable salt thereof, wherein:

Ring A is a 9- to 13-membered bicyclic or tricyclic heteroaryl ring having 1-4 heteroatoms independently selected from nitrogen, oxygen, and sulfur;

$R^1$ is halogen, OR, $N(R)_2$, CN, C(O)R, C(O)OR, C(O)N$(R)_2$, C(O)N(R)L, $SO_2$R, $SO_2N(R)_2$, SON(R)R, C(O)N(R)$SO_2$R, OC(O)R, N(R)C(O)R, N(R)$SO_2$R, N(R)C(O)N$(R)_2$, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

L is an optionally substituted bivalent straight $C_{2-12}$ hydrocarbon chain wherein 1-4 carbon atoms of L are optionally and independently replaced by a group selected from —O— or —N(R)—;

$R^2$ is OR, $N(R)_2$, or an optionally substituted group selected from $C_{1-6}$ aliphatic, a 3- to 6-membered saturated or partially unsaturated carbocyclic ring, a 4- to 12-membered saturated or partially unsaturated bridged bicyclic carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, a 5- to 6-membered heteroaryl ring having 1-4 heteroatoms independently selected from nitrogen, oxygen, and sulfur, and a 7- to 12-membered bridged bicyclic heterocyclic ring having 1-3 heteroatoms independently selected from nitrogen, oxygen, and sulfur;

$R^3$ is oxo, halogen, OR, $N(R)_2$, SR, CN, C(O)R, C(O)OR, $C(O)N(R)_2$, $SO_2N(R)_2$, OC(O)R, N(R)C(O)R, N(R)$SO_2$R, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur;

two R groups on the same nitrogen atom may, together with the atoms to which they are attached, form an optionally substituted saturated or partially unsaturated 3- to 6-membered heterocyclic ring having 0-1 additional heteroatoms selected from nitrogen, oxygen, and sulfur; and n is 0, 1, or 2.

As defined generally above, Ring A is a 9- to 13-membered bicyclic or tricyclic heteroaryl ring having 1-4 heteroatoms independently selected from nitrogen, oxygen, and sulfur.

In some embodiments, Ring A is a 9-membered bicyclic heteroaryl ring having 1-4 heteroatoms independently selected from nitrogen, oxygen, and sulfur. In some embodiments, Ring A is a 9-membered bicyclic heteroaryl ring having 1-4 nitrogen atoms. In some embodiments, Ring A is a 9-membered bicyclic heteroaryl ring having 1-3 nitrogen atoms. In some embodiments, Ring A is a 9-membered bicyclic heteroaryl ring having 2-4 nitrogen atoms. In some embodiments, Ring A is a 9-membered bicyclic heteroaryl ring having 2-3 nitrogen atoms.

In some embodiments, Ring A is a 10-membered bicyclic heteroaryl ring having 1-4 heteroatoms independently selected from nitrogen, oxygen, and sulfur. In some embodiments, Ring A is a 10-membered bicyclic heteroaryl ring having 1-4 nitrogen atoms. In some embodiments, Ring A is a 10-membered bicyclic heteroaryl ring having 1-2 nitrogen atoms. In some embodiments, Ring A is a 10-membered bicyclic heteroaryl ring having 1-3 nitrogen atoms.

In some embodiments, Ring A is a 13-membered tricyclic heteroaryl ring having 1-4 heteroatoms independently selected from nitrogen, oxygen, and sulfur. In some embodiments, Ring A is a 13-membered tricyclic heteroaryl ring having 1-4 nitrogen atoms. In some embodiments, Ring A is a 13-membered tricyclic heteroaryl ring having 1-3 nitrogen atoms. In some embodiments, Ring A is a 13-membered tricyclic heteroaryl ring having 2-3 nitrogen atoms.

In some embodiments, Ring A is selected from

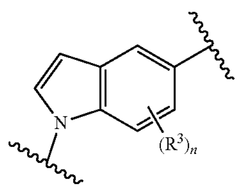
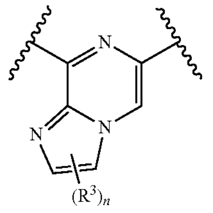
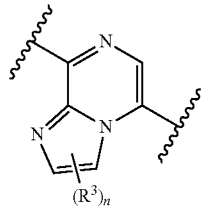
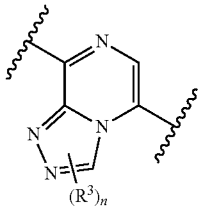
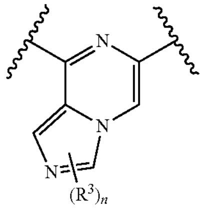
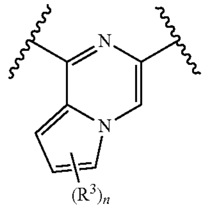
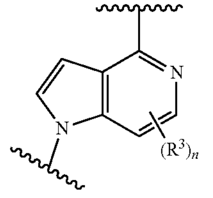
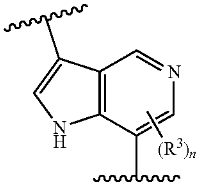
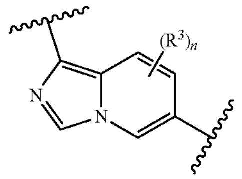
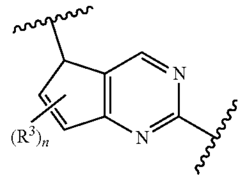
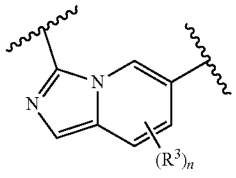
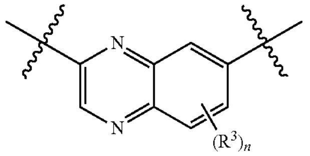
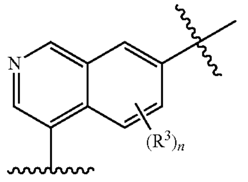
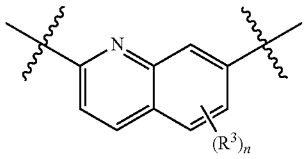

-continued
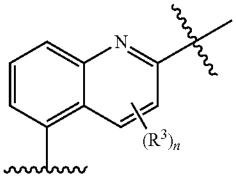
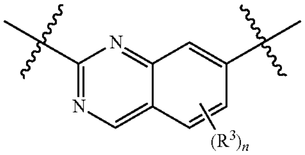
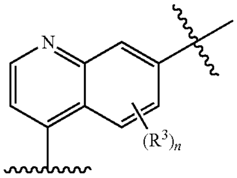
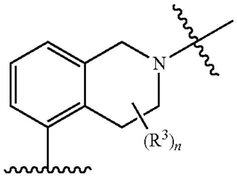
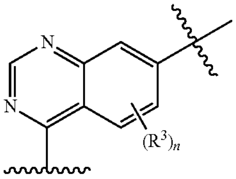
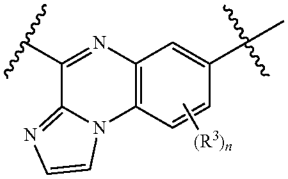
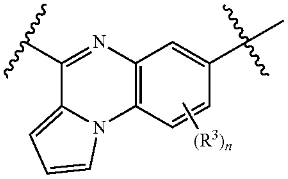
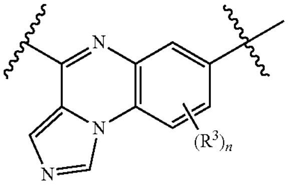
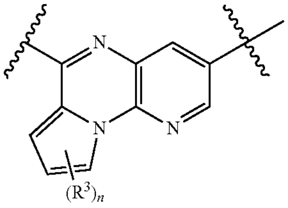
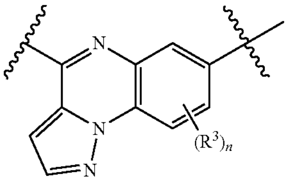
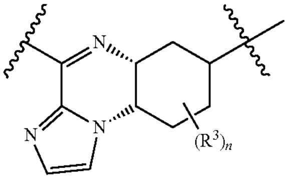
In some embodiments, Ring A is selected from
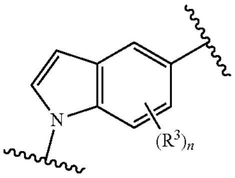
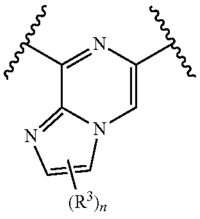
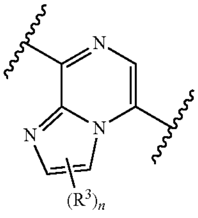
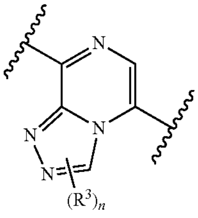
-continued
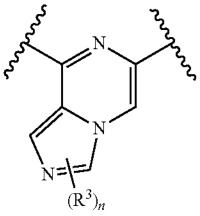
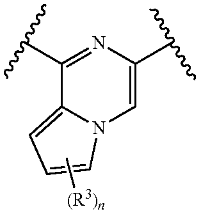
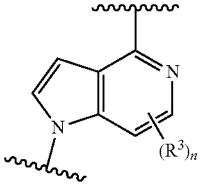
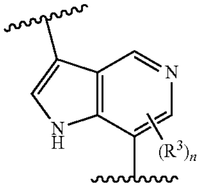
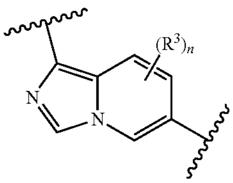
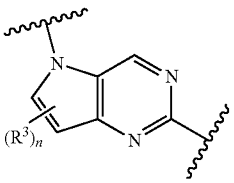
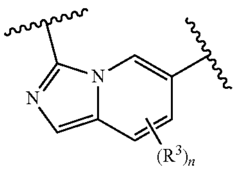
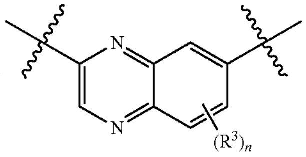
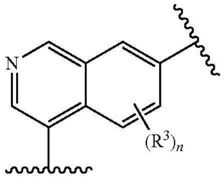
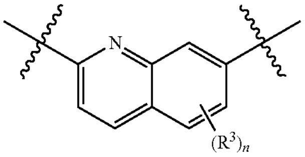
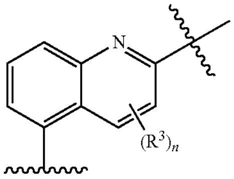
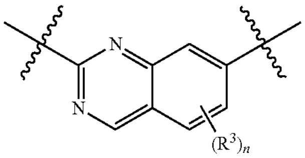
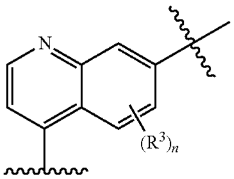
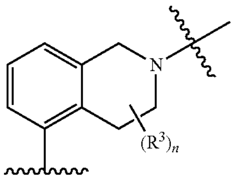
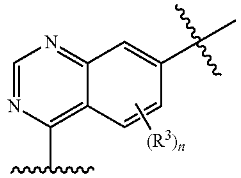
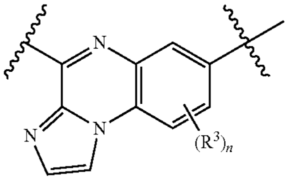

-continued
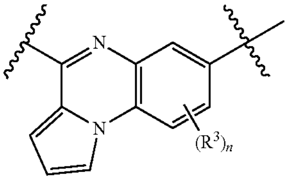
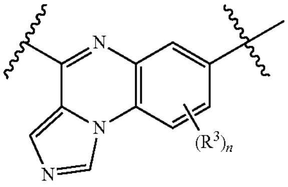
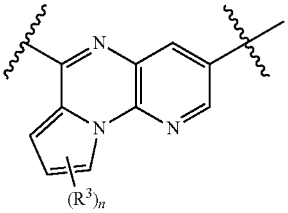
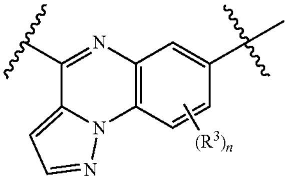
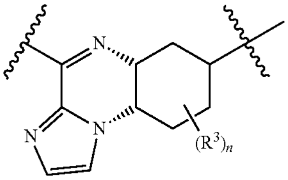
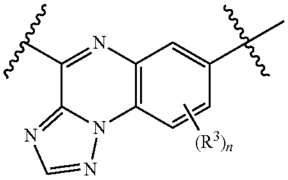
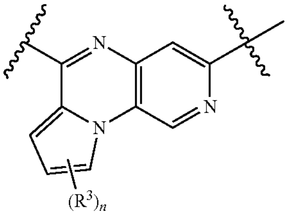
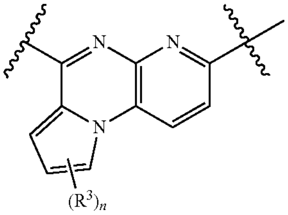
-continued
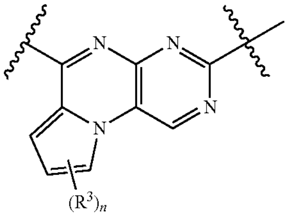
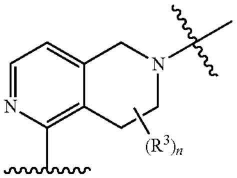
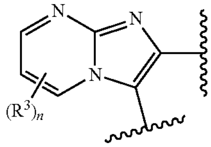
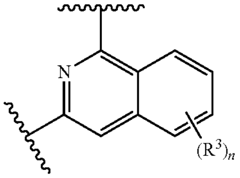
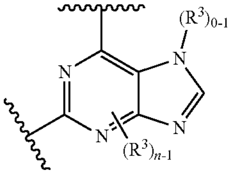
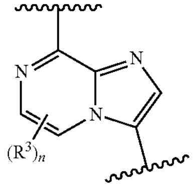
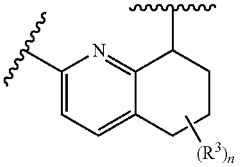
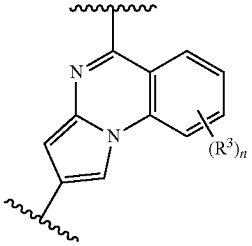
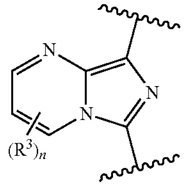
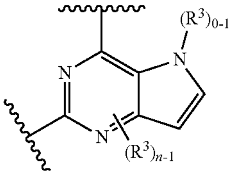
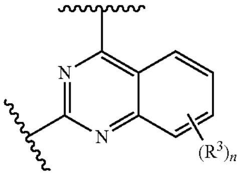
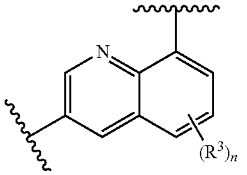
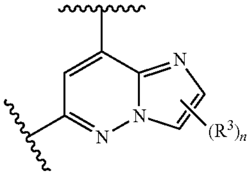
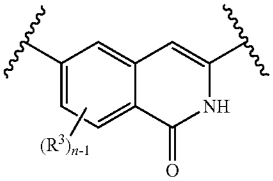
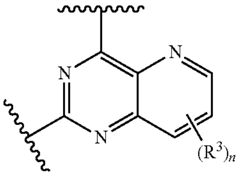
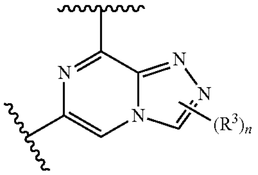
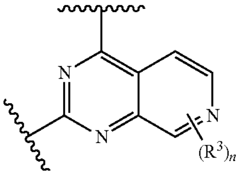

-continued

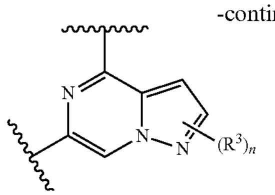

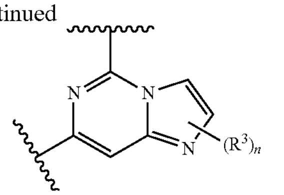

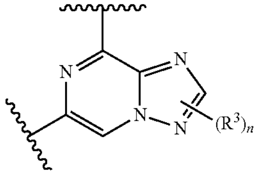

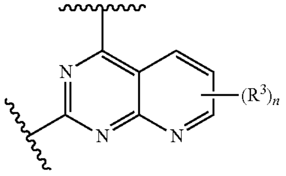

As defined generally above, $R^1$ is halogen, OR, $N(R)_2$, CN, C(O)R, C(O)OR, $C(O)N(R)_2$, $SO_2N(R)_2$, $C(O)N(R)SO_2R$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur. In some embodiments, $R^1$ is selected from halogen, OR, $N(R)_2$, CN, C(O)R, C(O)OR, $C(O)N(R)_2$, $SO_2N(R)_2$, $C(O)N(R)SO_2R$, OC(O)R, N(R)C(O)R, and $N(R)SO_2R$. In some embodiments, $R^1$ is selected from halogen, OR, and $N(R)_2$. In some embodiments, $R^1$ is selected from C(O)R, C(O)OR, $C(O)N(R)_2$, $SO_2N(R)_2$, and $C(O)N(R)SO_2R$. In some embodiments, $R^1$ is selected from OC(O)R, N(R)C(O)R, and $N(R)SO_2R$.

In some embodiments, $R^1$ is halogen, OR, $N(R)_2$, CN, C(O)R, C(O)OR, $C(O)N(R)_2$, C(O)N(R)L, $SO_2R$, $SO_2N(R)_2$, SON(R)R, $C(O)N(R)SO_2R$, OC(O)R, N(R)C(O)R, $N(R)SO_2R$, $N(R)C(O)N(R)_2$, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur. In some embodiments, $R^1$ is selected from OR, CN, C(O)R, C(O)OR, $C(O)N(R)_2$, C(O)N(R)L, $SO_2R$, N(R)C(O)R, $C(O)N(R)SO_2R$, $N(R)SO_2R$, $N(R)C(O)N(R)_2$, or an optionally substituted group selected from $C_{1-6}$ aliphatic a 3- to 6-membered saturated or partially unsaturated carbocyclic ring, and a 5- to 6-membered heteroaryl ring having 1-4 heteroatoms independently selected from nitrogen, oxygen, and sulfur.

In some embodiments, $R^1$ is halogen, OR, $N(R)_2$, CN, C(O)R, C(O)OR, $C(O)N(R)_2$, $SO_2R$, $SO_2N(R)_2$, SON(R)R, $C(O)N(R)SO_2R$, OC(O)R, N(R)C(O)R, $N(R)SO_2R$, $N(R)C(O)N(R)_2$, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur.

In some embodiments, $R^1$ is halogen. In some embodiments, $R^1$ is OR. In some embodiments, $R^1$ is $N(R)_2$. In some embodiments, $R^1$ is CN. In some embodiments, $R^1$ is C(O)R. In some embodiments, $R^1$ is C(O)OR. In some embodiments, $R^1$ is $C(O)N(R)_2$. In some embodiments, $R^1$ is $SO_2N(R)_2$. In some embodiments, $R^1$ is $C(O)N(R)SO_2R$. In some embodiments, $R^1$ is OC(O)R. In some embodiments, $R^1$ is N(R)C(O)R. In some embodiments, $R^1$ is $N(R)SO_2R$. In some embodiments, $R^1$ is $SO_2R$. In some embodiments, $R^1$ is SON(R)R. In some embodiments, $R^1$ is $N(R)C(O)N(R)_2$. In some embodiments, $R^1$ is C(O)N(R)L, where L is an optionally substituted bivalent straight $C_{2-12}$ hydrocarbon chain wherein 1-4 carbon atoms of L are optionally and independently replaced by a group selected from —O— or —N(R)—. In some such embodiments, L is a bivalent straight $C_{6-12}$ hydrocarbon chain wherein 1-4 carbon atoms of L are optionally and independently replaced by a group selected from —O— or —N(R)—. In some such embodiments, L is

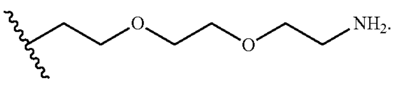 [SMILES: *CCOCCOCCN]

In some embodiments, $R^1$ is an optionally substituted 3- to 6-membered saturated or partially unsaturated carbocyclic ring. In some embodiments, $R^1$ is optionally substituted cyclopropyl. In some embodiments, $R^1$ is selected from an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur. In some embodiments, $R^1$ is optionally substituted $C_{1-6}$ aliphatic. In some embodiments, $R^1$ is optionally substituted $C_{1-4}$ aliphatic. In some embodiments, $R^1$ is optionally substituted $C_{1-2}$ aliphatic. In some embodiments, $R^1$ is $C_{1-12}$ aliphatic optionally substituted with —CN, —$R^°$, —$OR^°$, —$C(O)OR^°$, —$N(R^°)C(O)R^°$, —$N(R^°)S(O)_2R^°$, wherein $R^°$ is selected from hydrogen, $C_{1-6}$ aliphatic, and a 5-6-membered heteroaryl ring having 1-4 heteroatoms independently selected from nitrogen, oxygen, or sulfur. In some such embodiments, $R^°$ is selected from hydrogen, —$CH_3$, —$CH{=}CH_2$, and a 5-membered heteroaryl ring having 1-4 heteroatoms independently selected from nitrogen, oxygen, or sulfur.

In some embodiments, $R^1$ is $C_{1-12}$ aliphatic optionally substituted with —CN, —$R^°$, —$OR^°$, —$C(O)OR^°$, —$N(R^°)C(O)R^°$, —$N(R^°)S(O)_2R^°$, wherein $R^°$ is selected from hydrogen, $C_{1-6}$ aliphatic, and a 5-6-membered saturated, partially unsaturated, or aryl ring having 0-4 heteroatoms independently selected from nitrogen, oxygen, or sulfur. In some such embodiments, $R^°$ is selected from hydrogen, —$CH_3$, —$CH_2$—$CH_3$, —$CH{=}CH_2$, —$CH{=}CH_2$—$CH_2$, and a 5-6-membered saturated, partially unsaturated, or aryl ring having 0-4 heteroatoms independently selected from nitrogen, oxygen, or sulfur.

In some embodiments, $R^1$ is an optionally substituted a 3- to 7-membered saturated or partially unsaturated heterocyclic ring having 1-2 heteroatoms independently selected from nitrogen, oxygen, and sulfur. In some embodiments, $R^1$ is an optionally substituted a 3-membered saturated or partially unsaturated heterocyclic ring having 1 heteroatom selected from nitrogen, oxygen, and sulfur. In some embodiments, $R^1$ is an optionally substituted a 4-membered saturated or partially unsaturated heterocyclic ring having 1 heteroatom selected from nitrogen, oxygen, and sulfur. In some embodiments, $R^1$ is an optionally substituted a 5-membered saturated or partially unsaturated heterocyclic ring having 1 heteroatom selected from nitrogen, oxygen, and sulfur. In some embodiments, $R^1$ is an optionally substituted 5-membered saturated or partially unsaturated heterocyclic ring having 2 heteroatoms independently selected from nitrogen, oxygen, and sulfur. In some embodiments, $R^1$ is an optionally substituted 5-membered partially unsaturated heterocyclic ring having 2 heteroatoms independently selected from nitrogen, oxygen, and sulfur. In some embodiments, $R^1$ is an optionally substituted a 6-membered saturated or partially unsaturated heterocyclic ring having 2 heteroatoms independently selected from nitrogen, oxygen, and sulfur. In some embodiments, $R^1$ is optionally substituted oxetanyl. In some embodiments, $R^1$ is optionally substituted azetidinyl. In some embodiments, $R^1$ is optionally substituted pyrrolidinyl. In some embodiments, $R^1$ is optionally substituted piperadinyl. In some embodiments, $R^1$ is optionally substituted piperazinyl.

In some embodiments, $R^1$ is optionally substituted phenyl.

In some embodiments, $R^1$ is an optionally substituted 5- to 6-membered heteroaryl ring having 1-4 heteroatoms independently selected from nitrogen, oxygen, and sulfur. In some embodiments, $R^1$ is an optionally substituted 5-membered heteroaryl ring having 1-4 heteroatoms independently selected from nitrogen, oxygen, and sulfur. In some embodiments, $R^1$ is an optionally substituted 5-membered heteroaryl ring having 2-4 heteroatoms independently selected from nitrogen, oxygen, and sulfur. In some embodiments, $R^1$ is optionally substituted tetrazolyl. In some embodiments, $R^1$ is optionally substituted oxadiazolyl. In some embodiments, $R^1$ is optionally substituted imidazolyl. In some embodiments, $R^1$ is optionally substituted triazolyl.

In some embodiments, $R^1$ is an optionally substituted 6-membered heteroaryl ring having 1-2 nitrogen atoms. In some embodiments, $R^1$ is selected from pyridyl, pyrimidinyl, or pyrazinyl.

In some embodiments, $R^1$ is selected from the group consisting of OR, CN, C(O)R, C(O)OR, $C(O)N(R)_2$, N(R)C(O)R, $C(O)N(R)SO_2R$, $N(R)SO_2R$, or an optionally substituted group selected from $C_{1-6}$ aliphatic and a 5- to 6-membered heteroaryl ring having 1-4 heteroatoms independently selected from nitrogen, oxygen, and sulfur. In some such embodiments, $R^1$ is selected from the group consisting of OR, CN, C(O)R, C(O)OR, $C(O)N(R)_2$, N(R)C(O)R, $C(O)N(R)SO_2R$, $N(R)SO_2R$, an optionally substituted 5-membered saturated or partially unsaturated heterocyclic ring having 2 heteroatoms independently selected from nitrogen, oxygen, and sulfur, an optionally substituted 5- to 6-membered heteroaryl ring having 1-4 heteroatoms independently selected from nitrogen, oxygen, and sulfur, or a group selected from

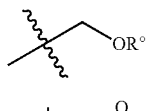 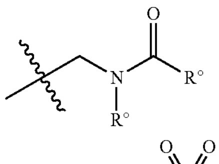

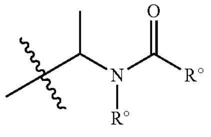 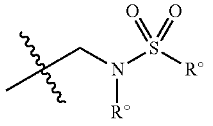

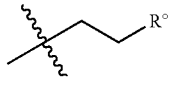 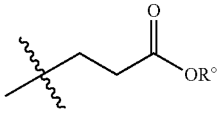

-continued

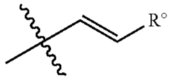 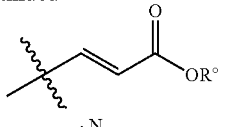

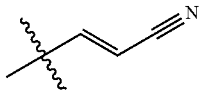

In some embodiments, $R^1$ is selected from the group consisting of OR, CN, C(O)R, C(O)OR, $C(O)N(R)_2$, N(R)C(O)R, $C(O)N(R)SO_2R$, $N(R)SO_2R$, $SO_2R$, $SO_2N(R)_2$, $N(R)C(O)N(R)_2$, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, and a 5- to 6-membered heteroaryl ring having 1-4 heteroatoms independently selected from nitrogen, oxygen, and sulfur. In some such embodiments, $R^1$ is selected from the group consisting of OR, CN, C(O)R, C(O)OR, $C(O)N(R)_2$, N(R)C(O)R, $C(O)N(R)SO_2R$, $N(R)SO_2R$, $SO_2R$, $SO_2N(R)_2$, $N(R)C(O)N(R)_2$, an optionally substituted cyclopropyl ring, an optionally substituted 4- to 6-membered saturated or partially unsaturated heterocyclic ring having 1-2 heteroatoms independently selected from nitrogen, oxygen, and sulfur, an optionally substituted 5- to 6-membered heteroaryl ring having 1-4 heteroatoms independently selected from nitrogen, oxygen, and sulfur, or a group selected from

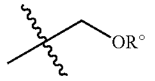 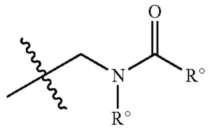

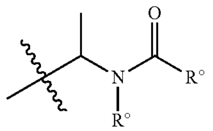 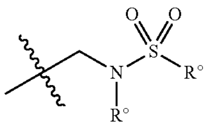

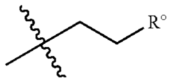 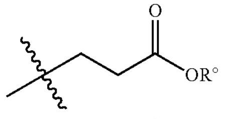

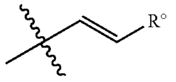 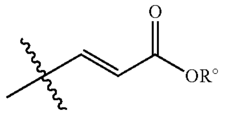

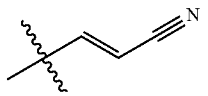 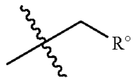

In some embodiments, $R^1$ is an optionally substituted $C_{1-12}$ aliphatic group selected from

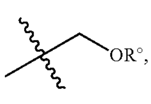, 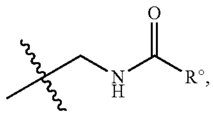,

-continued
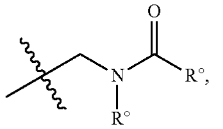 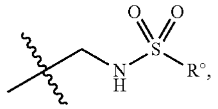
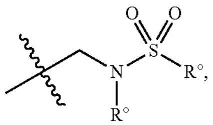 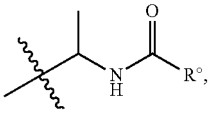
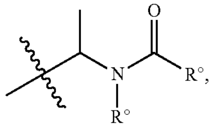 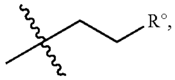
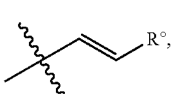 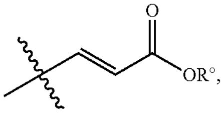
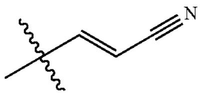
, and
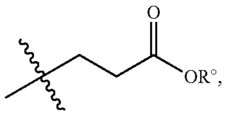
In some embodiments, $R^1$ is an optionally substituted $C_{1-3}$ aliphatic group selected from
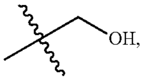 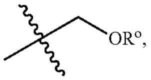
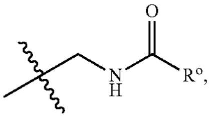 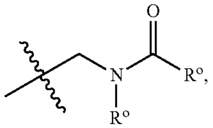
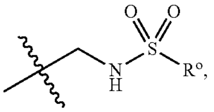 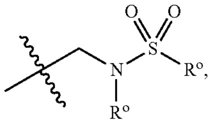
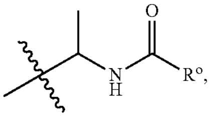 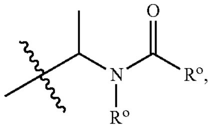
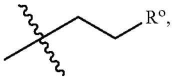 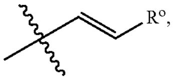
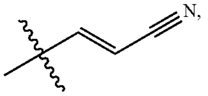 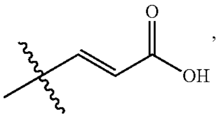
,
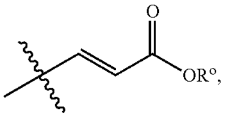 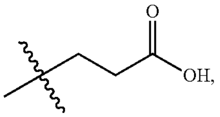
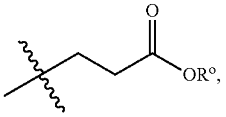 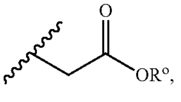
-continued
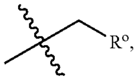 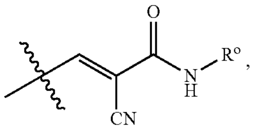
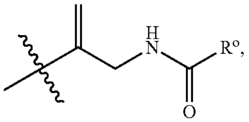 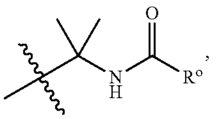
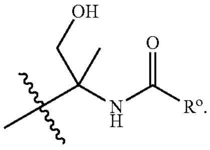
In some embodiments, $R^1$ is an optionally substituted $C_{1-12}$ aliphatic group selected from
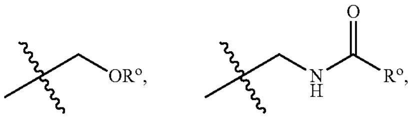
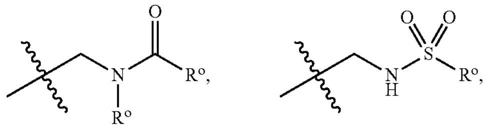
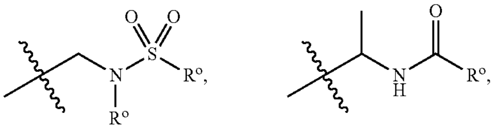
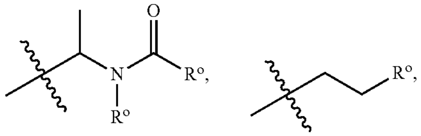
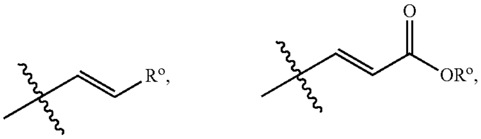
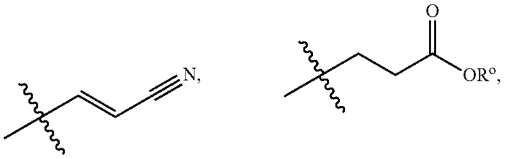
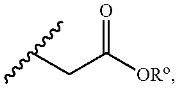 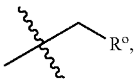
and
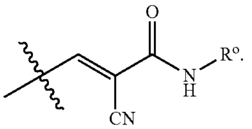
In some embodiments, $R^1$ is an optionally substituted $C_{1-12}$ aliphatic group selected from

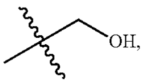
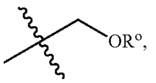
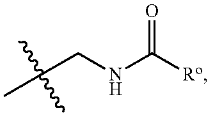
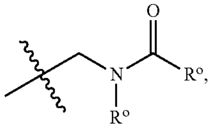
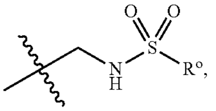
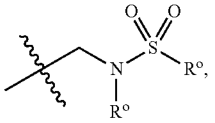
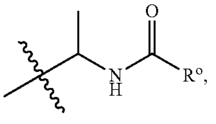
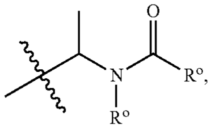
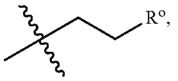
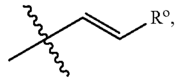
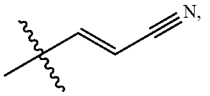
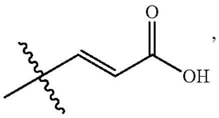
,
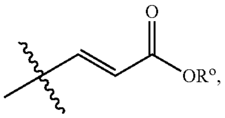
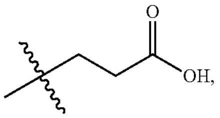
and
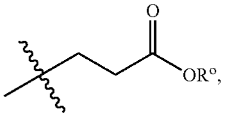

wherein $R^{\circ}$ is $C_{1-6}$ aliphatic or a 5-6-membered saturated, partially unsaturated, or aryl ring having 0-4 heteroatoms independently selected from nitrogen, oxygen, or sulfur, wherein $R^{\circ}$ is optionally substituted with halogen, —$(CH_2)_{0-2}R^{\bullet}$, -(halo$R^{\bullet}$), —$(CH_2)_{0-2}$ H, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —OSi$R^{\bullet}$3, —C(O)S$R^{\bullet}$, —($C_{1-4}$ straight or branched alkylene)C(O)O$R^{\bullet}$, or —SS$R^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. In some such embodiments, $R^{\circ}$ is $C_{1-6}$ aliphatic optionally substituted with halogen, —$R^{\bullet}$, -(halo$R^{\bullet}$), —OH, —O$R^{\bullet}$, —O(halo$R^{\bullet}$), —CN, —C(O)$R^{\bullet}$, —C(O)OH, —C(O)O$R^{\bullet}$, —$NH_2$, —NH$R^{\bullet}$, and —$NR^{\bullet}_2$.

In some embodiments, $R^1$ is an optionally substituted $C_{1-3}$ aliphatic group selected from

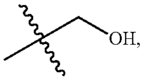
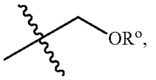

-continued

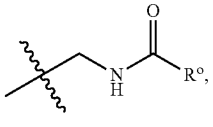
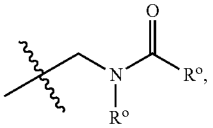
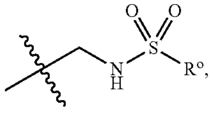
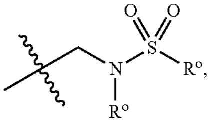
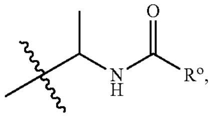
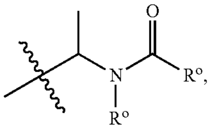
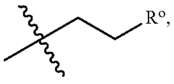
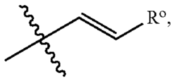
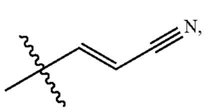
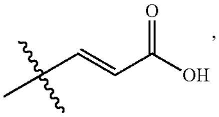
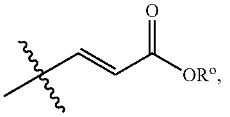
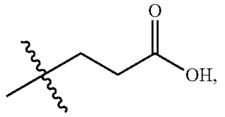
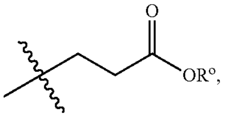
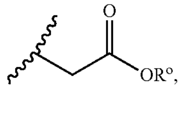
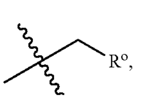
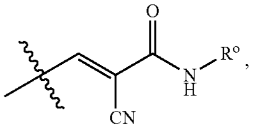
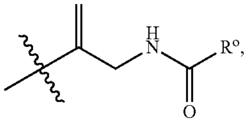
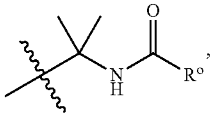

wherein $R^{\circ}$ is $C_{1-6}$ aliphatic or a 5-6-membered saturated, partially unsaturated, or aryl ring having 0-4 heteroatoms independently selected from nitrogen, oxygen, or sulfur, wherein $R^{\circ}$ is optionally substituted with halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_0$—2C(O)O$R^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —C(O)S$R^{\bullet}$, —($C_{1-4}$ straight or branched alkylene)C(O)O$R^{\bullet}$, or —SS$R^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. In some such embodiments, $R^{\circ}$ is $C_{1-6}$ aliphatic optionally substituted with halogen, —$R^{\bullet}$, -(halo$R^{\bullet}$), —OH, —O$R^{\bullet}$, —O(halo$R^{\bullet}$), —CN, —C(O)$R^{\bullet}$, —C(O)OH, —C(O)O$R^{\bullet}$, —$NH_2$, —NH$R^{\bullet}$, and —$NR^{\bullet}_2$.

In some embodiments, $R^1$ is an optionally substituted $C_{1-12}$ aliphatic group selected from

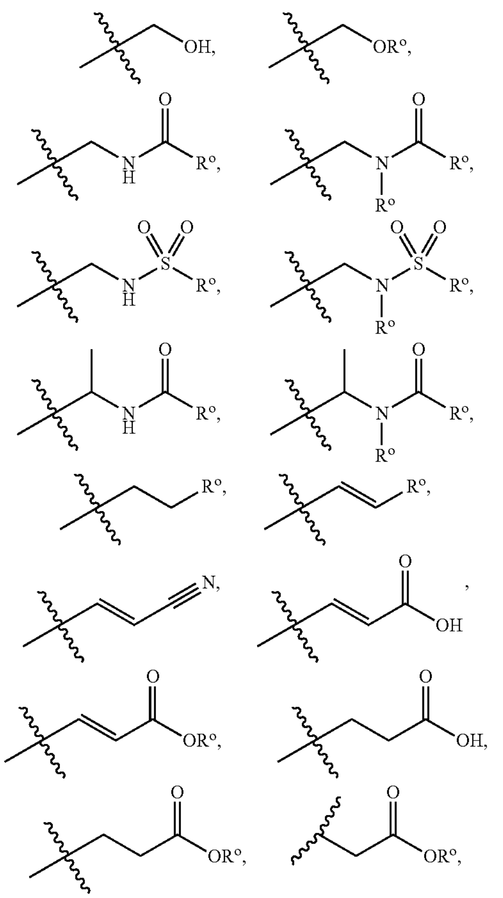

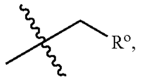

and

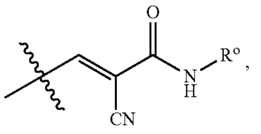

wherein $R^{\circ}$ is $C_{1-6}$ aliphatic or a 5-6-membered saturated, partially unsaturated, or aryl ring having 0-4 heteroatoms independently selected from nitrogen, oxygen, or sulfur, wherein $R^{\circ}$ is optionally substituted with halogen, $-(CH_2)_{0-2}R^{\bullet}$, -(halo$R^{\bullet}$), $-(CH_2)_{0-2}OH$, $-(CH_2)_{0-2}OR^{\bullet}$, $-(CH_2)_{0-2}CH(OR^{\bullet})_2$; —O(halo$R^{\bullet}$), —CN, $-N_3$, $-(CH_2)_{0-2}C(O)R^{\bullet}$, $-(CH_2)_{0-2}C(O)OH$, $-(CH_2)_{0-2}C(O)OR^{\bullet}$, $-(CH_2)_{0-2}SR^{\bullet}$, $-(CH_2)_{0-2}SH$, $-(CH_2)_{0-2}NH_2$, $-(CH_2)_{0-2}NHR^{\bullet}$, $-(CH_2)_{0-2}NR^{\bullet}_2$, $-NO_2$, $-SiR^{\bullet}_3$, $-OSiR^{\bullet}3$, $-C(O)SR^{\bullet}$, —($C_{1-4}$ straight or branched alkylene)$C(O)OR^{\bullet}$, or $-SSR^{\bullet}$ wherein each $R^{\bullet}$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. In some such embodiments, $R^{\circ}$ is $C_{1-6}$ aliphatic optionally substituted with halogen, $-R^{\bullet}$, -(halo$R^{\bullet}$), —OH, $-OR^{\bullet}$, —O(halo$R^{\bullet}$), —CN, $-C(O)R^{\bullet}$, —C(O)OH, $-C(O)OR^{\bullet}$, $-NH_2$, $-NHR^{\bullet}$, and $-NR^{\bullet}_2$.

In some embodiments, $R^1$ is selected from —CN, —OH, $-OCH_3$,

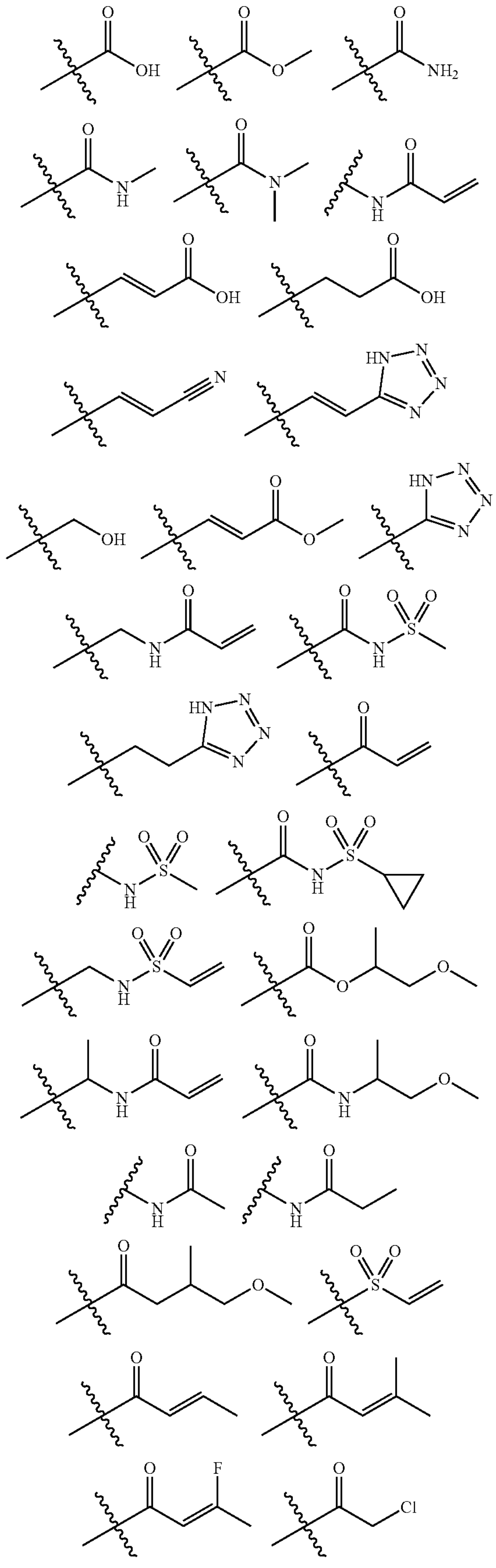

-continued
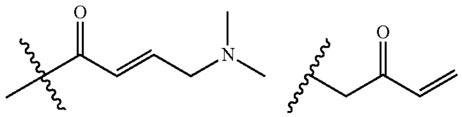
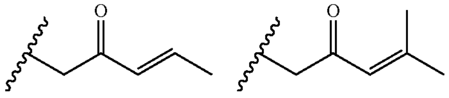
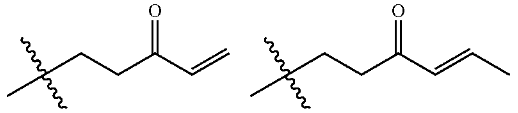
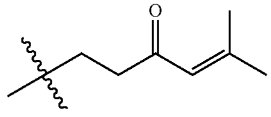
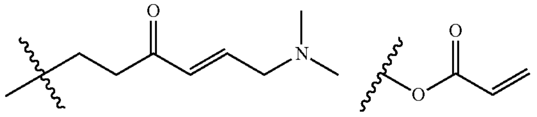
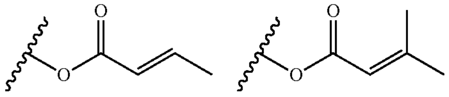
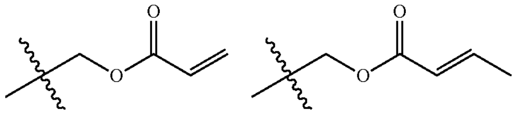
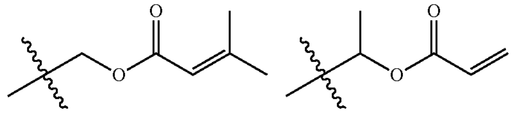
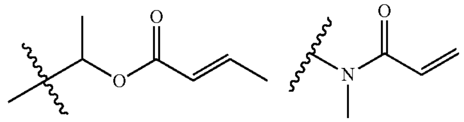
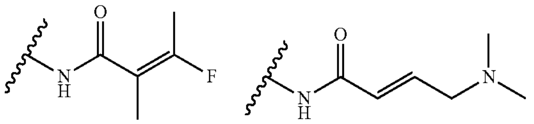
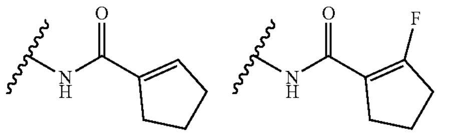
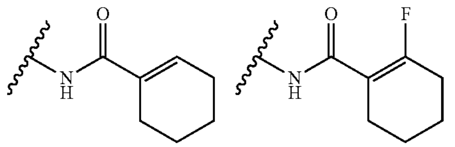
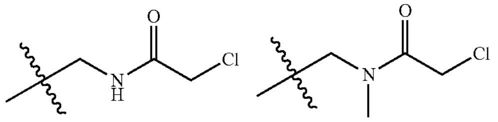
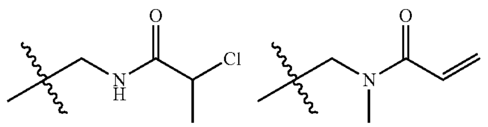
-continued
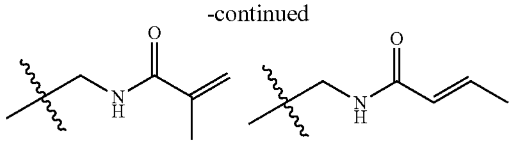
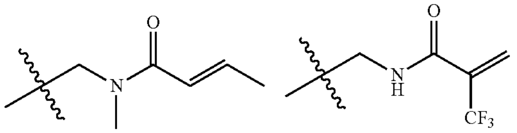
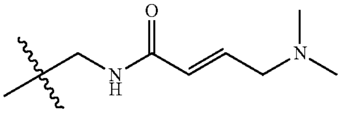
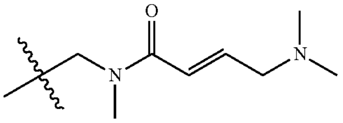
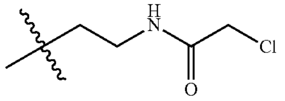
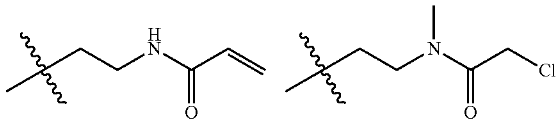
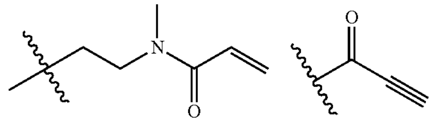
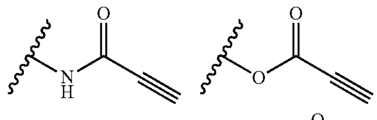
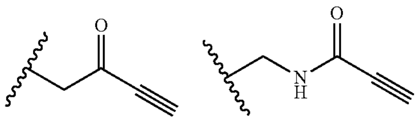
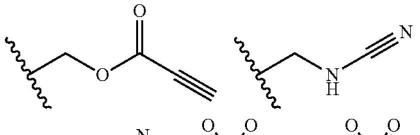
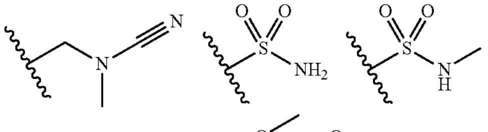
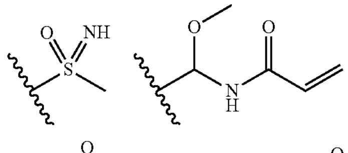
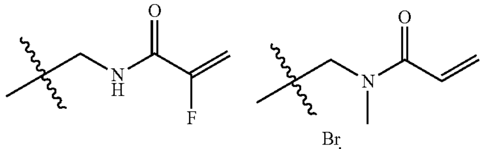
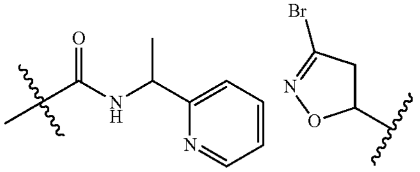

In some embodiments, $R^1$ is selected from —CN, —OH, —$OCH_3$,
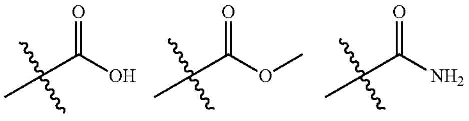
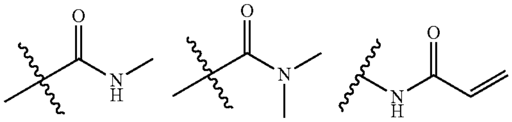
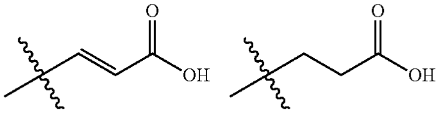
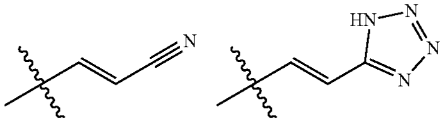
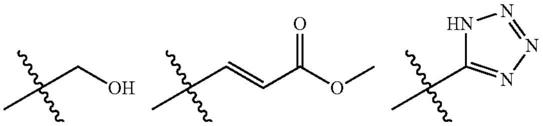
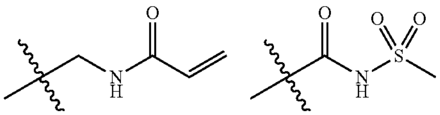
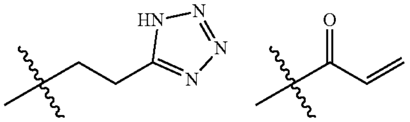
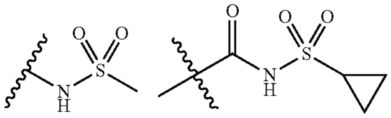
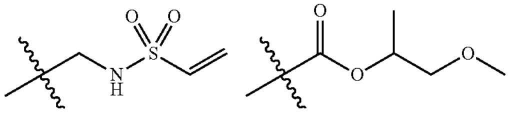
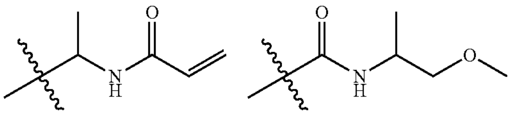
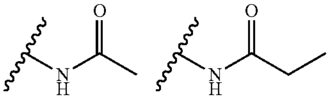
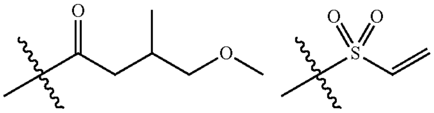
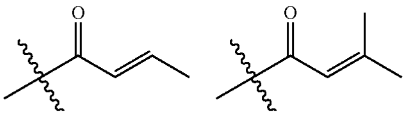
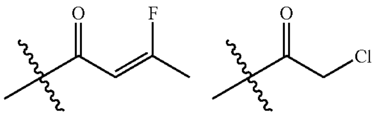
-continued
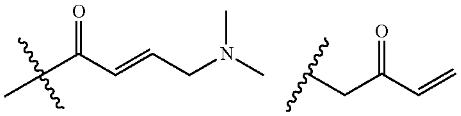
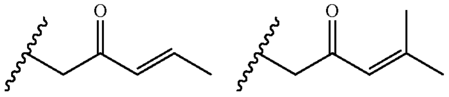
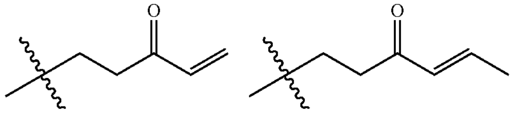
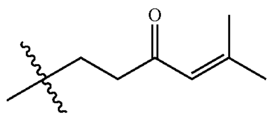
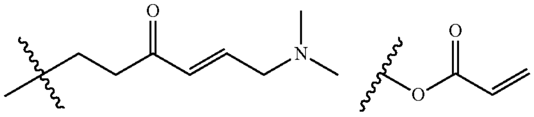
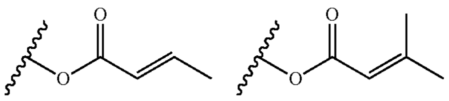
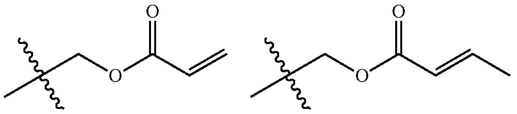
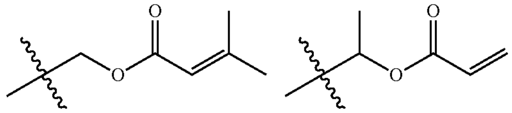
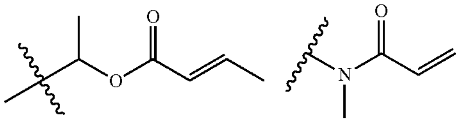
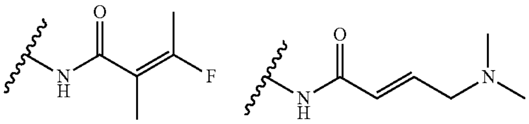
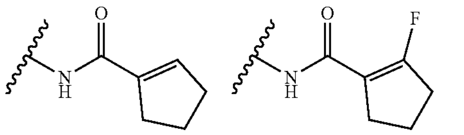
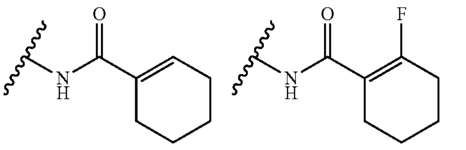
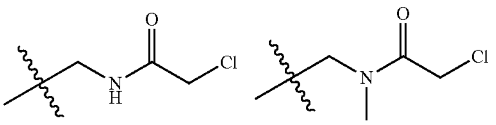
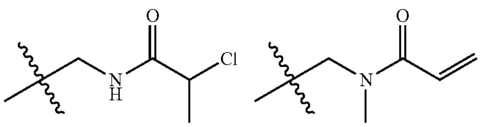

-continued
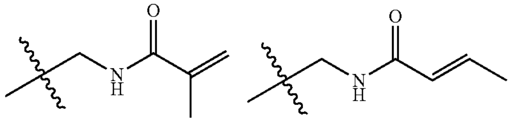
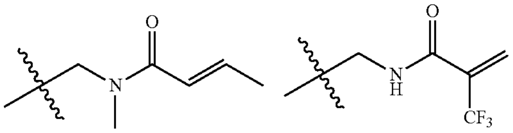
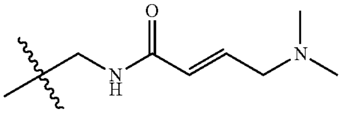
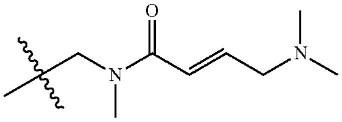
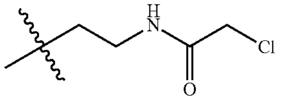
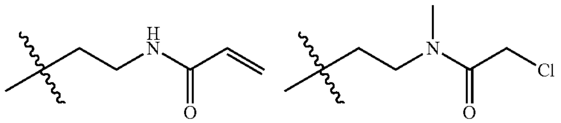
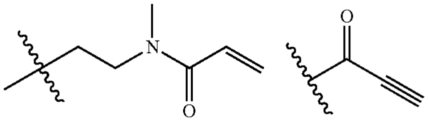
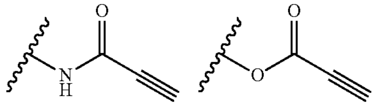
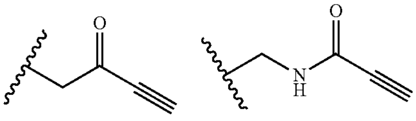
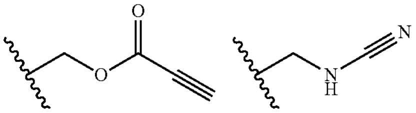
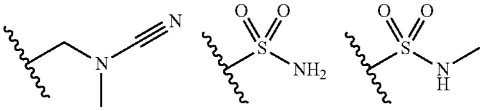
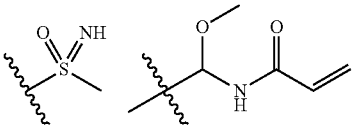
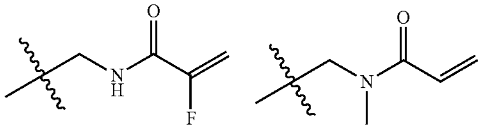
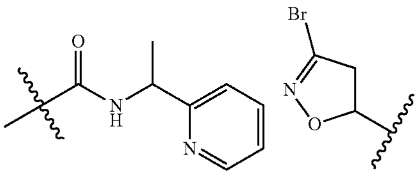
-continued
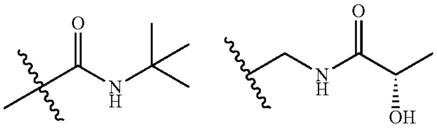
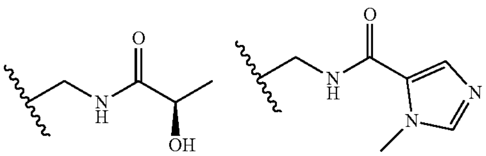
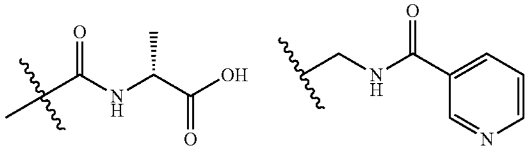
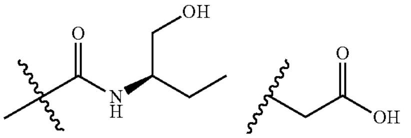
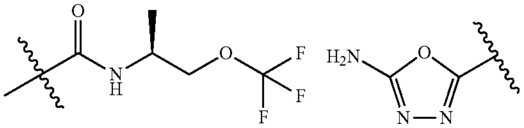
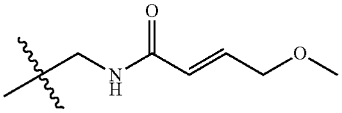
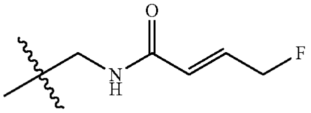
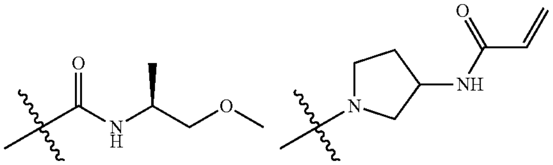
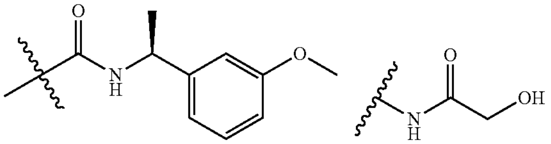
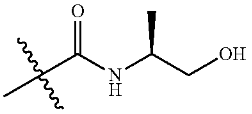
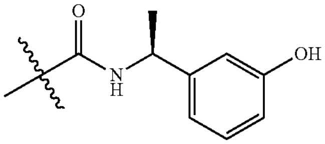
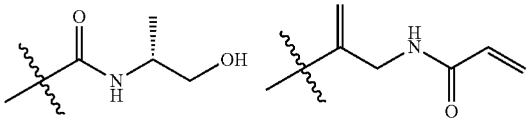

-continued
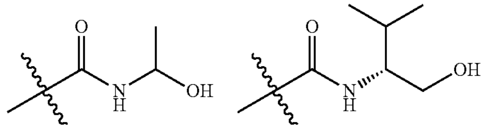
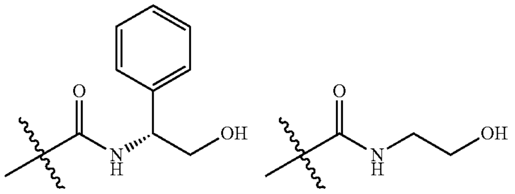
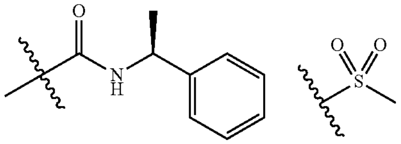
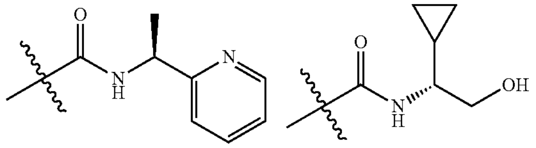
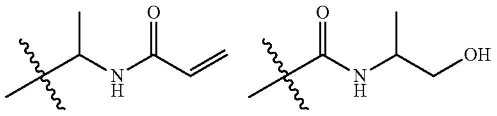
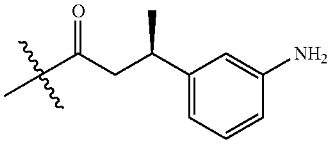
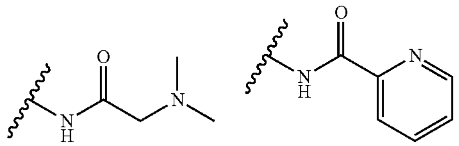
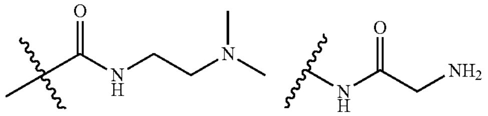
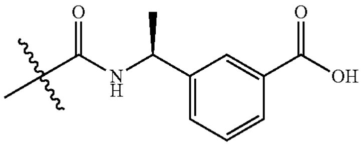
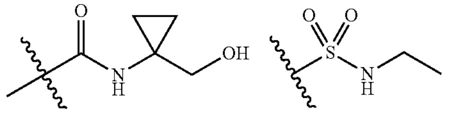
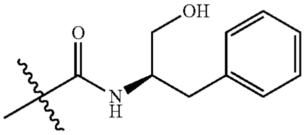
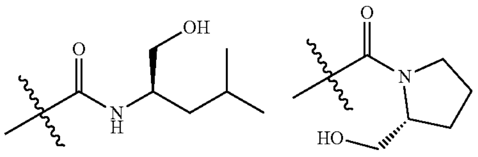
-continued
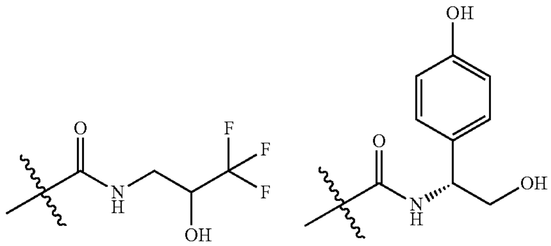
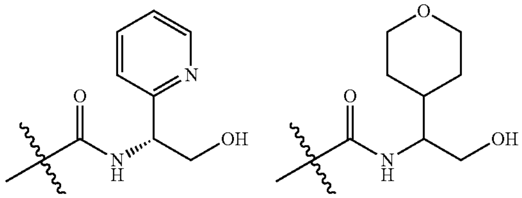
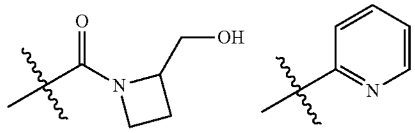
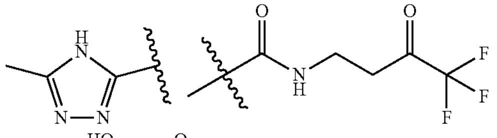
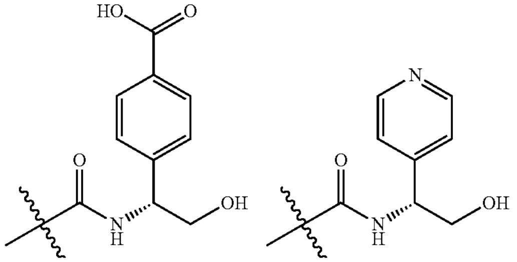
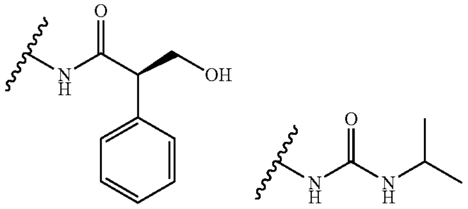
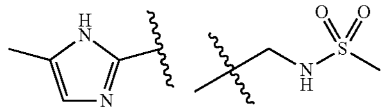
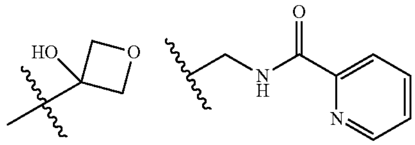
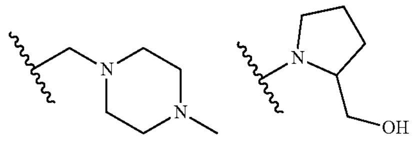
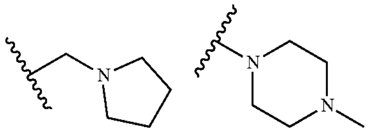

-continued

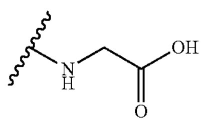
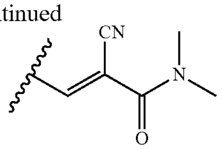
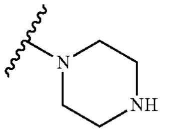
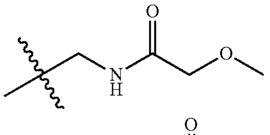
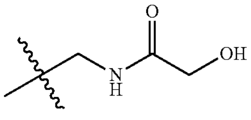
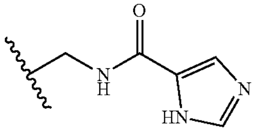
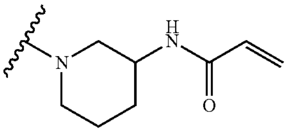

—C(O)$CH_3$

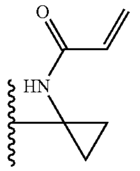
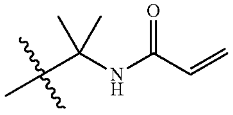
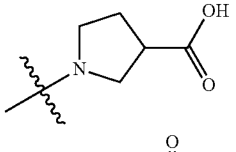
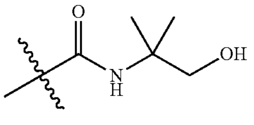
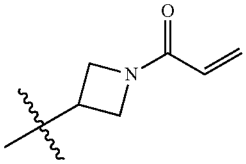
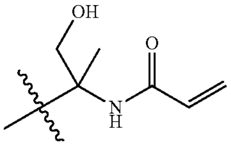
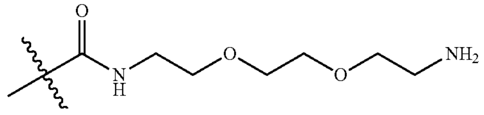

As defined generally above, $R^2$ is OR, $N(R)_2$, or an optionally substituted group selected from $C_{1-6}$ aliphatic, a 3- to 6-membered saturated or partially unsaturated carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur. In some embodiments, $R^2$ is OR or $N(R)_2$. In some embodiments, $R^2$ is $N(R)_2$. In some embodiments, $R^2$ is OR.

In some embodiments, $R^2$ is OR, $N(R)_2$, or an optionally substituted group selected from $C_{1-6}$ aliphatic, a 3- to 6-membered saturated or partially unsaturated carbocyclic ring, a 4- to 12-membered saturated or partially unsaturated bridged bicyclic carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, a 5- to 6-membered heteroaryl ring having 1-4 heteroatoms independently selected from nitrogen, oxygen, and sulfur, and a 7- to 12-membered bridged bicyclic heterocyclic ring having 1-3 heteroatoms independently selected from nitrogen, oxygen, and sulfur.

In some embodiments, $R^2$ is an optionally substituted group selected from $C_{1-6}$ aliphatic, a 3- to 6-membered saturated or partially unsaturated carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur.

In some embodiments, $R^2$ is optionally substituted phenyl. In some embodiments, $R^2$ is phenyl optionally substituted with halogen, CN, $R^°$, or $OR^°$. In some embodiments, $R^2$ is phenyl optionally substituted with halogen, CN, $R^°$, $OR^°$, wherein $R^°$ is $C_{1-6}$ aliphatic or a 5-6-membered saturated, partially unsaturated, or aryl ring having 0-4 heteroatoms independently selected from nitrogen, oxygen, or sulfur. In some embodiments, $R^°$ is optionally substituted with halogen or -(haloR$^•$), wherein $R^•$ is $C_{1-4}$ aliphatic. In some embodiments, $R^°$ is optionally substituted with —$CF_3$.

In some embodiments, $R^2$ is optionally substituted $C_{1-6}$ aliphatic. In some embodiments, $R^2$ is $C_{1-6}$ aliphatic. In some embodiments, $R^2$ is $C_{1-3}$ aliphatic. In some embodiments, $R^2$ is $C_{4-6}$ aliphatic. In some embodiments, $R^2$ is $C_{5-6}$ aliphatic. In some such embodiments, $R^2$ is 3,3-dimethylbut-1-ynyl.

In some embodiments, $R^2$ is $C_{1-6}$ aliphatic optionally substituted with $R^°$. In some such embodiments, $R^°$ is a 5- to 6-membered saturated, partially unsaturated, or aryl ring having 0-4 heteroatoms independently selected from nitrogen, oxygen, or sulfur. In some such embodiments, $R^°$ is phenyl. In some embodiments, $R^2$ is $C_{1-4}$ aliphatic optionally substituted with $R^°$. In some embodiments, $R^2$ is $C_{1-12}$ aliphatic optionally substituted with $R^°$. In some embodiments, $R^2$ is $C_{1-2}$ aliphatic optionally substituted with $R^°$, wherein $R^°$ is phenyl optionally substituted with R*. In some such embodiments, $R^•$ is $C_{1-4}$ aliphatic.

In some embodiments, $R^2$ is an optionally substituted 3- to 6-membered saturated or partially unsaturated carbocyclic ring. In some embodiments, $R^2$ is an optionally substituted 3-membered saturated or partially unsaturated carbocyclic ring. In some embodiments, $R^2$ is an optionally substituted 4-membered saturated or partially unsaturated carbocyclic ring. In some embodiments, $R^2$ is an optionally substituted 5-membered saturated or partially unsaturated carbocyclic ring. In some embodiments, $R^2$ is an optionally substituted 6-membered saturated or partially unsaturated carbocyclic ring. In some embodiments, $R^2$ is an optionally substituted cyclopropyl, cyclobutyl, cyclopentyl, or cyclohexyl. In some embodiments, $R^2$ is a 3- to 6-membered saturated or partially unsaturated carbocyclic ring, wherein the carbocyclic ring is optionally substituted with $R^°$. In some such embodiments, $R^{\circ}$ is $C_{1-6}$ aliphatic or a 5-6-membered saturated, partially unsaturated, or aryl ring having 0-4 heteroatoms independently selected from nitrogen, oxygen, or sulfur. In some embodiments, $R^2$ is a 3- to 6-membered saturated or partially unsaturated carbocyclic ring, wherein the carbocyclic ring is optionally substituted with $R^{\circ}$, wherein $R^{\circ}$ is $C_{1-6}$ aliphatic or phenyl.

In some embodiments, $R^2$ is an optionally substituted bicyclopentyl.

In some embodiments, $R^2$ is an optionally substituted saturated or partially unsaturated 3- to 7-membered monocyclic heterocyclic ring having 1-2 heteroatoms independently selected from nitrogen, oxygen, and sulfur. In some embodiments, $R^2$ is an optionally substituted saturated or partially unsaturated 3-membered monocyclic heterocyclic ring having 1 heteroatom selected from nitrogen, oxygen, and sulfur. In some embodiments, $R^2$ is an optionally substituted saturated or partially unsaturated 4-membered monocyclic heterocyclic ring having 1 heteroatom selected from nitrogen, oxygen, and sulfur. In some embodiments, $R^2$ is an optionally substituted saturated or partially unsaturated 5-membered monocyclic heterocyclic ring having 1 heteroatom selected from nitrogen, oxygen, and sulfur. In some embodiments, $R^2$ is an optionally substituted saturated or partially unsaturated 6-membered monocyclic heterocyclic ring having 1-2 heteroatoms independently selected from nitrogen, oxygen, and sulfur. In some embodiments, $R^2$ is an optionally substituted saturated or partially unsaturated 7-membered monocyclic heterocyclic ring having 1-2 heteroatoms independently selected from nitrogen, oxygen, and sulfur. In some embodiments, $R^2$ is an optionally substituted saturated or partially unsaturated 5- to 6-membered monocyclic heterocyclic ring having 1-2 heteroatoms independently selected from nitrogen, oxygen, and sulfur. In some embodiments, $R^2$ is an optionally substituted saturated or partially unsaturated 6-membered monocyclic heterocyclic ring having 1 heteroatom selected from nitrogen, oxygen, and sulfur. In some embodiments, $R^2$ is an optionally substituted saturated or partially unsaturated 6-membered monocyclic heterocyclic ring having 2 heteroatoms independently selected from nitrogen, oxygen, and sulfur. In some embodiments, $R^2$ is an optionally substituted pyrrolidinyl, piperidinyl, tetrahydropyranyl, piperazinyl, or morpholinyl. In some embodiments, $R^2$ is a saturated or partially unsaturated 3- to 7-membered monocyclic heterocyclic ring having 1-2 heteroatoms independently selected from nitrogen, oxygen, and sulfur, wherein the heterocyclic ring is optionally substituted with a group selected from halogen and $R^{\circ}$. In some such embodiments, $R^{\circ}$ is $C_{1-6}$ aliphatic optionally substituted with halogen.

In some embodiments, $R^2$ is an optionally substituted saturated or partially unsaturated 6- to 10-membered bicyclic heterocyclic ring having 1-2 heteroatoms independently selected from nitrogen, oxygen, and sulfur. In some embodiments, $R^2$ is an optionally substituted saturated or partially unsaturated 6- to 10-membered bicyclic heterocyclic ring having 1 heteroatom selected from nitrogen, oxygen, and sulfur. In some embodiments, $R^2$ is an optionally substituted saturated or partially unsaturated 6-membered bicyclic heterocyclic ring having 1-2 heteroatoms independently selected from nitrogen, oxygen, and sulfur. In some embodiments, $R^2$ is an optionally substituted saturated or partially unsaturated 7-membered bicyclic heterocyclic ring having 1-2 heteroatoms independently selected from nitrogen, oxygen, and sulfur. In some embodiments, $R^2$ is an optionally substituted saturated or partially unsaturated 8-membered bicyclic heterocyclic ring having 1-2 heteroatoms independently selected from nitrogen, oxygen, and sulfur. In some embodiments, $R^2$ is an optionally substituted saturated or partially unsaturated 9-membered bicyclic heterocyclic ring having 1-2 heteroatoms independently selected from nitrogen, oxygen, and sulfur. In some embodiments, $R^2$ is an optionally substituted saturated or partially unsaturated 10-membered bicyclic heterocyclic ring having 1-2 heteroatoms independently selected from nitrogen, oxygen, and sulfur. In some embodiments, $R^2$ is a saturated or partially unsaturated 6- to 10-membered bicyclic heterocyclic ring having 1-2 heteroatoms independently selected from nitrogen, oxygen, and sulfur, wherein the heterocyclic ring is optionally substituted with halogen or $R^{\circ}$. In some such embodiments, $R^{\circ}$ is $C_{1-6}$ aliphatic optionally substituted with halogen.

In some embodiments, $R^2$ is an optionally substituted 8- to 11-membered spirocyclic heterocyclic ring having 1-3 heteroatoms independently selected from nitrogen, oxygen, and sulfur. In some embodiments, $R^2$ is an optionally substituted 8- to 11-membered spirocyclic heterocyclic ring having 1-2 heteroatoms independently selected from nitrogen, oxygen, and sulfur. In some embodiments, $R^2$ is an optionally substituted 8-membered spirocyclic heterocyclic ring having 1-3 heteroatoms independently selected from nitrogen, oxygen, and sulfur. In some embodiments, $R^2$ is an optionally substituted 9-membered spirocyclic heterocyclic ring having 1-3 heteroatoms independently selected from nitrogen, oxygen, and sulfur. In some embodiments, $R^2$ is an optionally substituted 10-membered spirocyclic heterocyclic ring having 1-3 heteroatoms independently selected from nitrogen, oxygen, and sulfur. In some embodiments, $R^2$ is an optionally substituted 11-membered spirocyclic heterocyclic ring having 1-3 heteroatoms independently selected from nitrogen, oxygen, and sulfur. In some embodiments, $R^2$ is an 8- to 11-membered spirocyclic heterocyclic ring having 1-2 heteroatoms independently selected from nitrogen, oxygen, and sulfur, wherein the spirocyclic ring is optionally substituted with a group selected from halogen and $R^{\circ}$. In some such embodiments, $R^{\circ}$ is $C_{1-6}$ aliphatic optionally substituted with halogen.

In some embodiments, $R^2$ is an optionally substituted 5- to 6-membered heteroaryl ring having 1-4 heteroatoms independently selected from nitrogen, oxygen, and sulfur. In some embodiments, $R^2$ is an optionally substituted 5-membered heteroaryl ring having 1-4 heteroatoms independently selected from nitrogen, oxygen, and sulfur. In some embodiments, $R^2$ is an optionally substituted 6-membered heteroaryl ring having 1-2 nitrogen atoms. In some such embodiments, $R^2$ is an optionally substituted pyridyl or pyrimidinyl. In some embodiments, $R^2$ is a 5- to 6-membered heteroaryl ring having 1-4 heteroatoms independently selected from nitrogen, oxygen, and sulfur, wherein the heteroaryl ring is optionally substituted with $R^{\circ}$. In some such embodiments, $R^{\circ}$ is $C_{1-6}$ aliphatic.

In some embodiments, $R^2$ is an optionally substituted 7- to 12-membered bridged bicyclic heterocyclic ring having 1-3 heteroatoms independently selected from nitrogen, oxygen, and sulfur. In some embodiments, $R^2$ is an optionally substituted 9-membered bridged bicyclic heterocyclic ring having 1-3 heteroatoms independently selected from nitrogen, oxygen, and sulfur. In some embodiments, $R^2$ is an optionally substituted 9-membered bridged bicyclic heterocyclic ring having 1 nitrogen heteroatom.

In some embodiments, $R^2$ is OR or $N(R)_2$. In some such embodiments, R is optionally substituted $C_{1-6}$ aliphatic or phenyl.

In some embodiments, $R^2$ is selected from the group consisting of cyclopropyl, cyclobutyl, cyclohexyl, trifluoromethyl, phenyl,
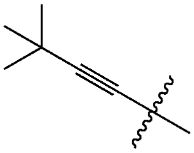
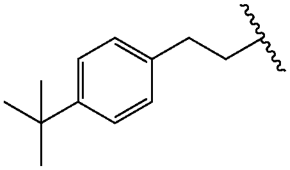
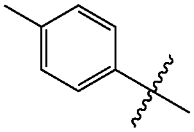
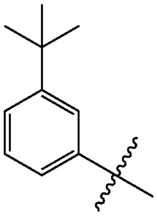
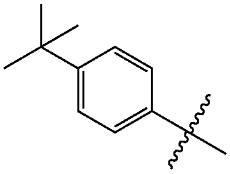
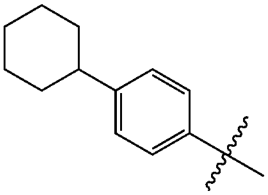
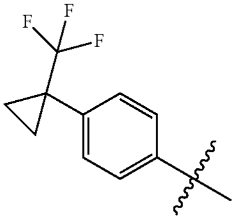
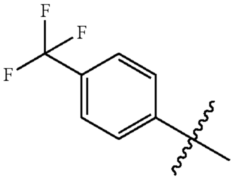
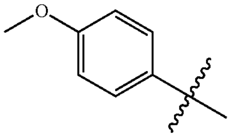
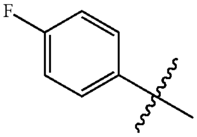
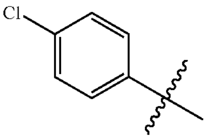
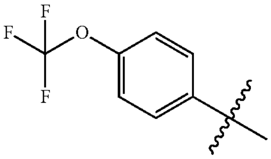
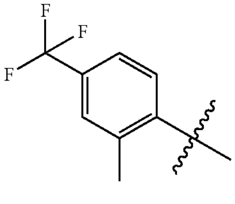
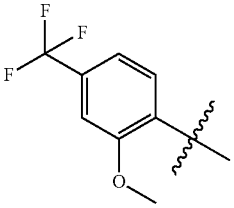
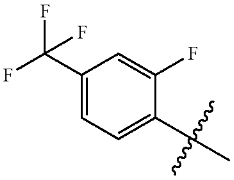
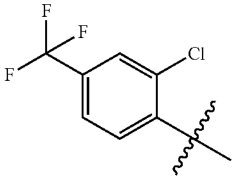
-continued
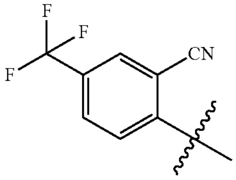
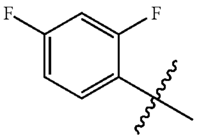
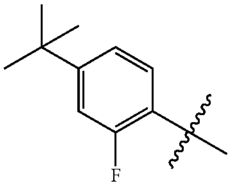
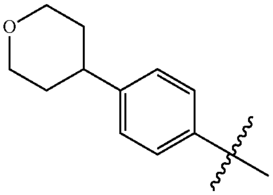
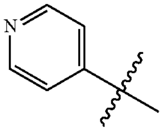
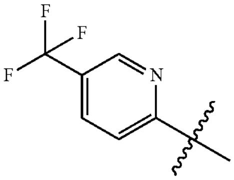
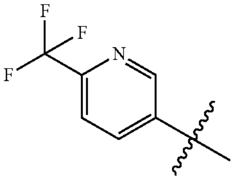
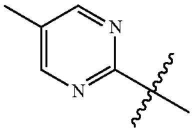
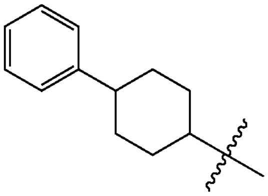
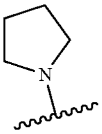
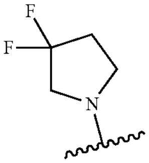
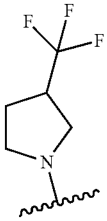
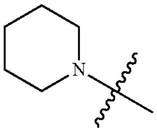
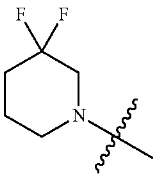
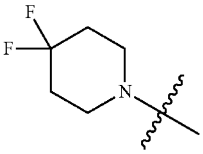
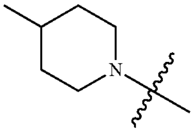
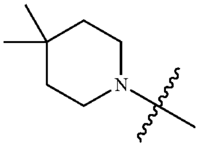
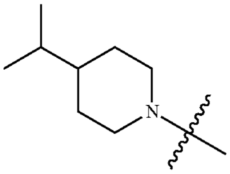
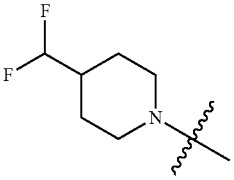

-continued
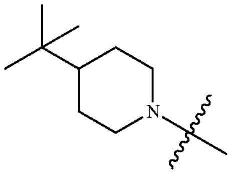
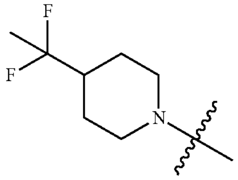
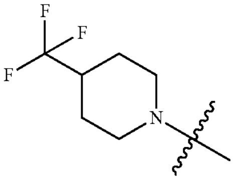
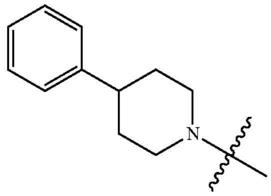
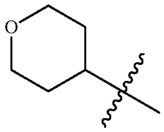
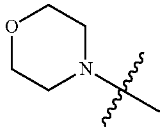
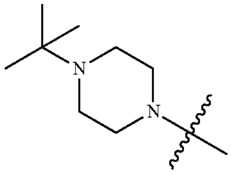
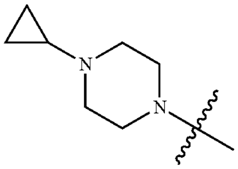
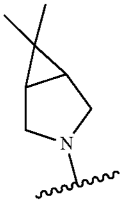
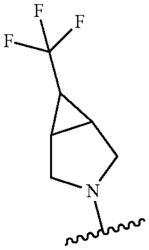
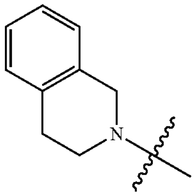
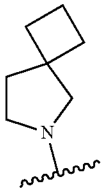
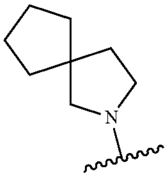
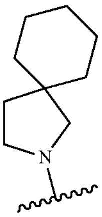
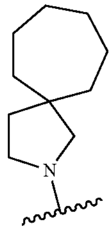
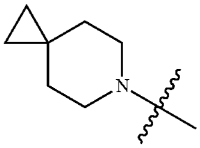
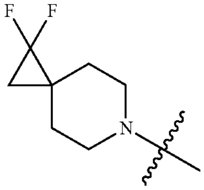
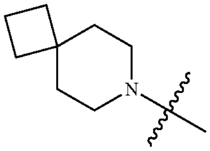
-continued
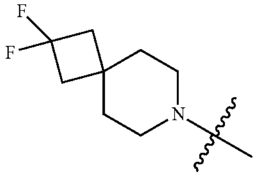
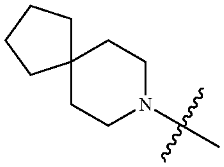
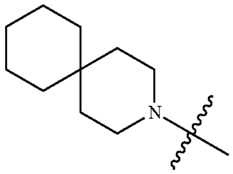
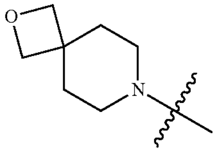
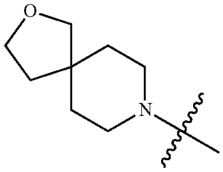
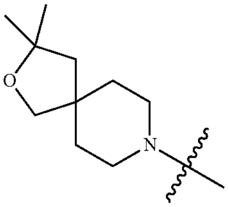
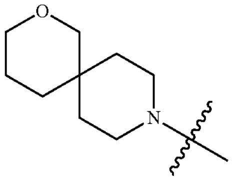
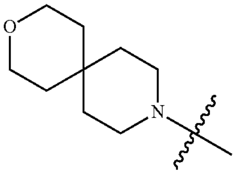
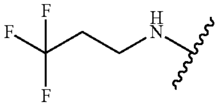
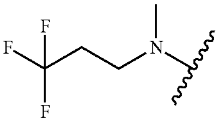
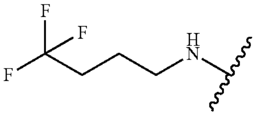
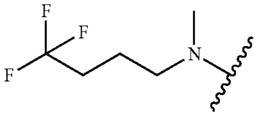
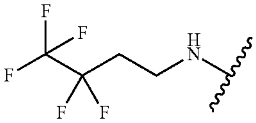
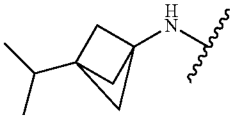
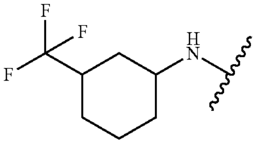
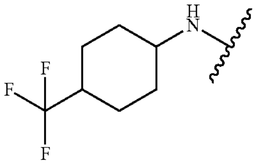
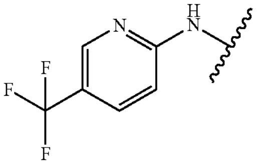
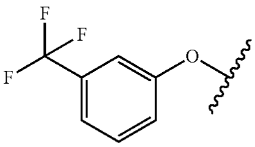
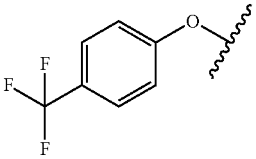
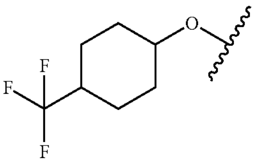

-continued
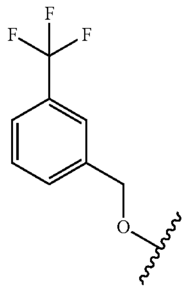
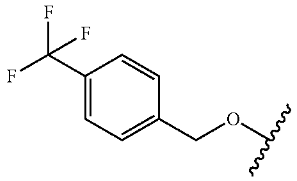
In some embodiments, $R^2$ is selected from the group consisting of cyclopropyl, cyclobutyl, cyclohexyl, trifluoromethyl, phenyl,
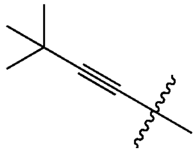
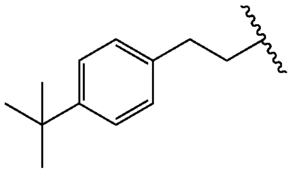
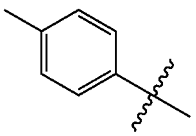
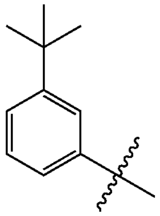
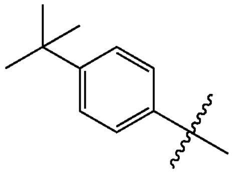
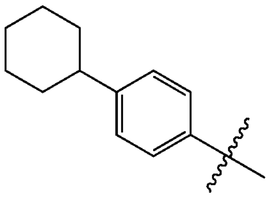
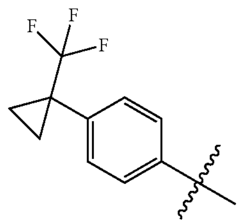
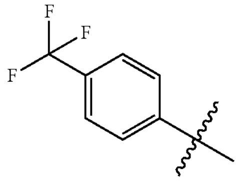
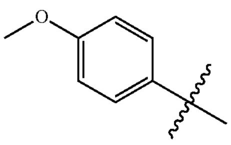
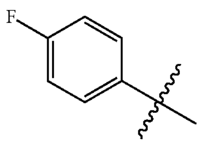
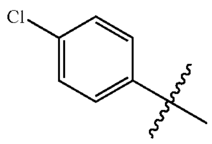
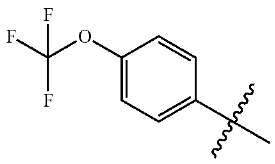
-continued
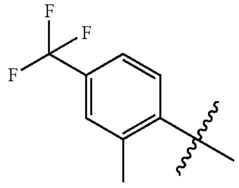
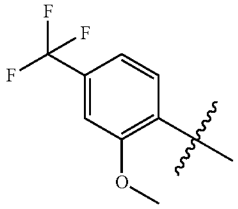
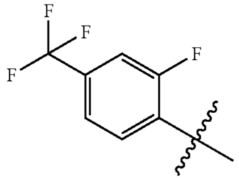
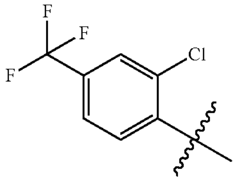
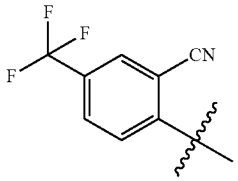
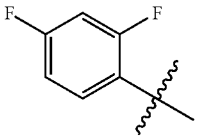
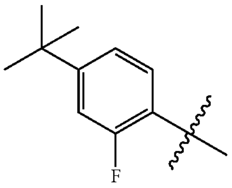
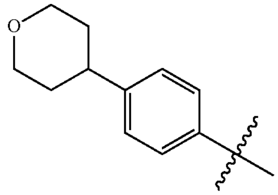
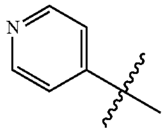
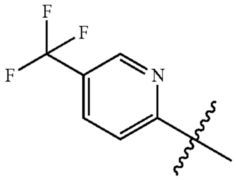
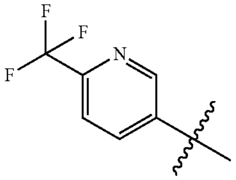
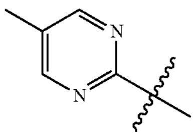
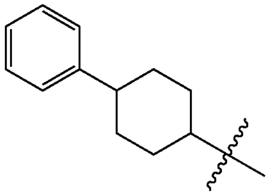
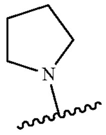
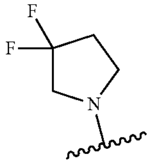
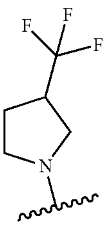
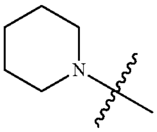
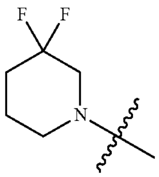
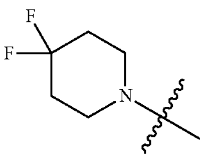

-continued
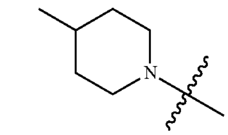
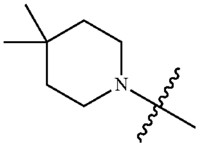
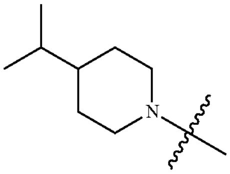
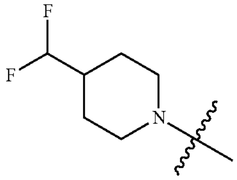
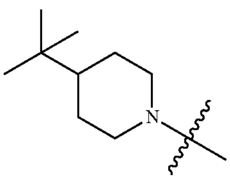
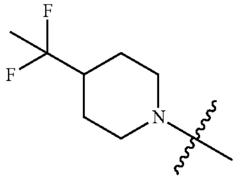
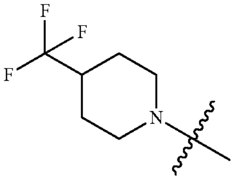
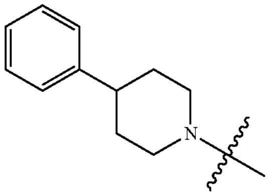
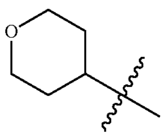
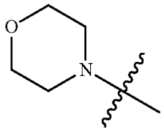
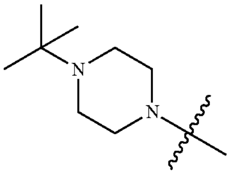
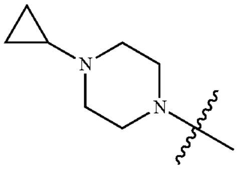
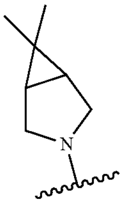
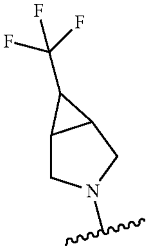
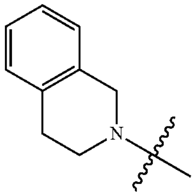
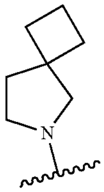
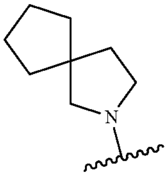
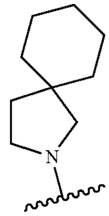
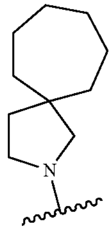
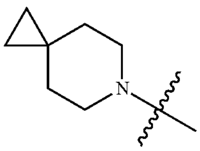
-continued
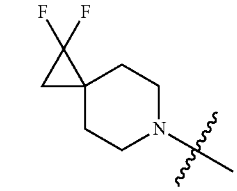
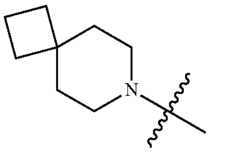
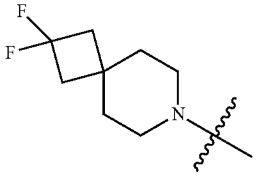
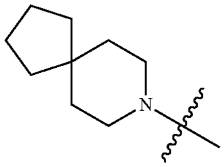
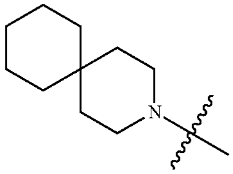
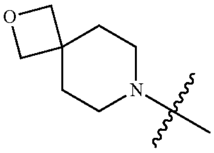
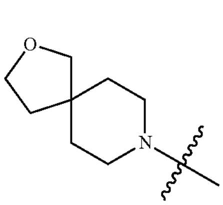
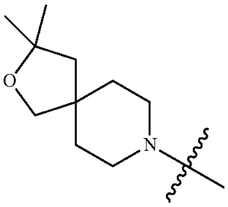
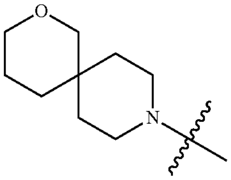
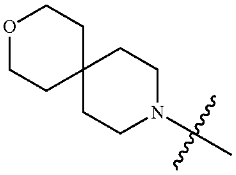
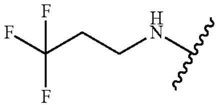
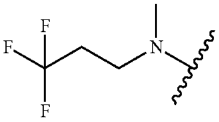
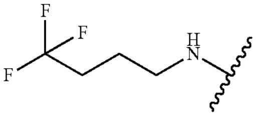
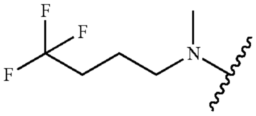
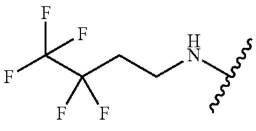
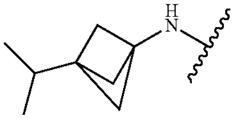
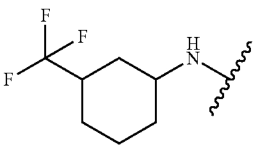
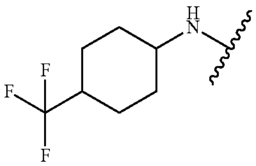
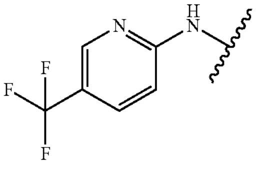
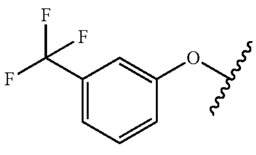

-continued

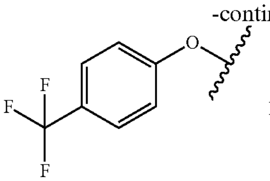
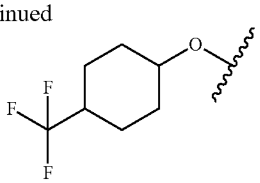
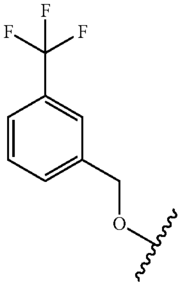
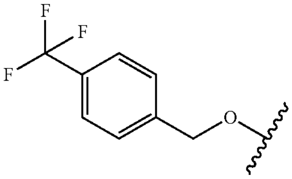
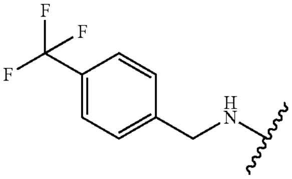
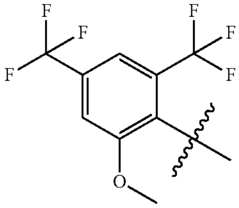
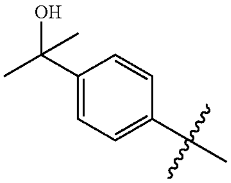
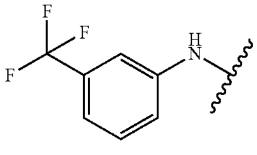
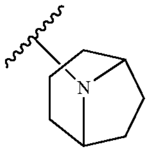
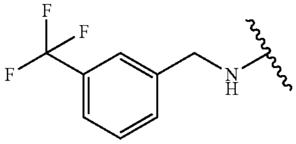
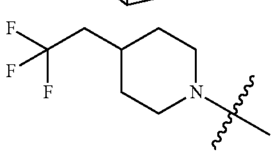
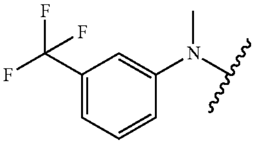
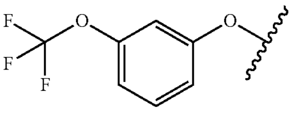
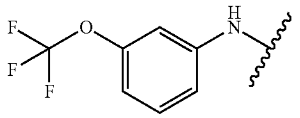
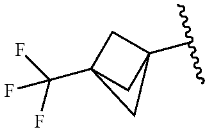
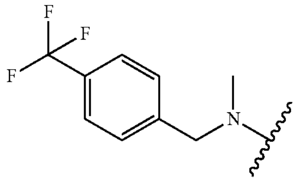
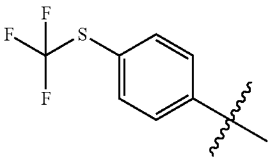
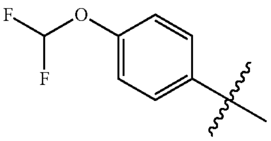

-continued

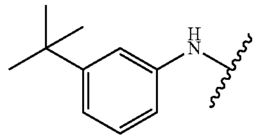
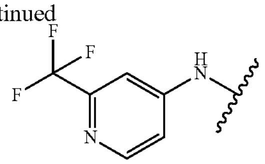
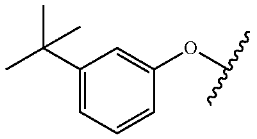
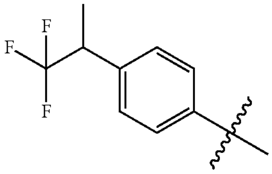
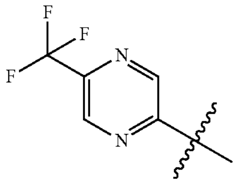
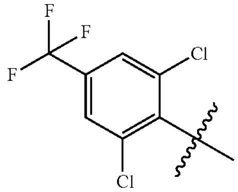
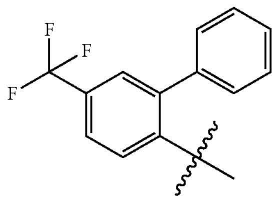
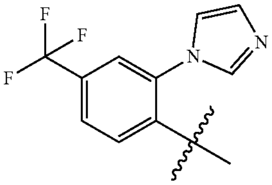
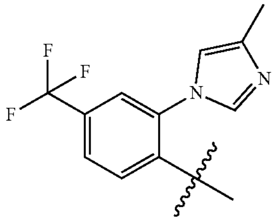
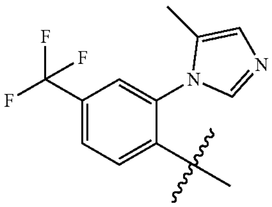
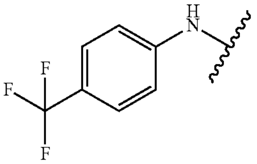
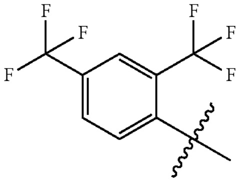

As defined generally above, $R^3$ is halogen, OR, $N(R)_2$, CN, C(O)R, C(O)OR, $C(O)N(R)_2$, S02$N(R)_2$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur. In some embodiments, $R^3$ is selected from halogen, OR, $N(R)_2$, CN, C(O)R, C(O)OR, $C(O)N(R)_2$, $SO_2N(R)_2$, OC(O)R, N(R)C(O)R, and $N(R)SO_2R$. In some embodiments, $R^3$ is halogen. In some embodiments, $R^3$ is selected from OR and $N(R)_2$. In some embodiments, $R^3$ is OR. In some embodiments, $R^3$ is OH. In some embodiments, $R^3$ is $OCH_3$. In some embodiments, $R^3$ is $OCF_2H$. In some embodiments, $R^3$ is O-cyclopropyl. In some embodiments, $R^3$ is $OC(CH_3)_2$. In some embodiments, $R^3$ is $OCH_2CH_3$. In some embodiments, $R^3$ is $OCH_2$-cyclopropyl. In some embodiments, $R^3$ is selected from CN, C(O)R, C(O)OR, $C(O)N(R)_2$, and $SO_2N(R)_2$. In some embodiments, $R^3$ is selected from CN, C(O)R, C(O)OR, $C(O)N(R)_2$, SR, and $SO_2N(R)_2$. In some embodiments, $R^3$ is selected from OC(O)R, N(R)C(O)R, and $N(R)SO_2R$. In some embodiments, $R^3$ is N(R)C(O)R. In some embodiments, $R^3$ is NHC(O)R. In some embodiments, $R^3$ is NHC(O)CH═$CH_2$. In some embodiments, $R^3$ is $C(O)CH_3$. In some embodiments, $R^3$ is $N(R)_2$. In some embodiments, $R^3$ is $NH_2$ or $N(CH_3)_2$.

In some embodiments, $R^3$ is an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur. In some embodiments, $R^3$ is optionally substituted $C_{1-6}$ aliphatic. In some embodiments, $R^3$ is optionally substituted $C_{1-4}$ aliphatic. In some embodiments, $R^3$ is optionally substituted $C_{1-2}$ aliphatic. In some embodiments, $R^3$ is $C_{1-6}$ aliphatic optionally substituted with halogen. In some embodiments, $R^3$ is selected from $CH_3$ and $CF_3$. In some embodiments, $R^3$ is CCH or $C(CH_3)_2$. In some embodiments, $R^3$ is $C_{1-6}$ aliphatic optionally substituted with $OR^{\circ}$. In some embodiments, $R^3$ is $CH_2OH$ or $CH_2OCH_3$.

In some embodiments, $R^3$ is an optionally substituted 3- to 7-membered saturated or partially unsaturated heterocyclic ring having 1-2 heteroatoms independently selected from nitrogen, oxygen, and sulfur. In some embodiments, $R^3$ is an optionally substituted 3- to 6-membered saturated or partially unsaturated heterocyclic ring having 1-2 heteroatoms independently selected from nitrogen, oxygen, and sulfur. In some embodiments, $R^3$ is an optionally substituted 3- to 5-membered saturated or partially unsaturated heterocyclic ring having 1 heteroatom selected from nitrogen, oxygen, and sulfur. In some embodiments, $R^3$ is an optionally substituted 6-membered saturated or partially unsaturated heterocyclic ring having 1-2 heteroatoms independently selected from nitrogen, oxygen, and sulfur.

In some embodiments, $R^3$ is an optionally substituted 5- to 6-membered heteroaryl ring having 1-4 heteroatoms independently selected from nitrogen, oxygen, and sulfur. In some embodiments, $R^3$ is an optionally substituted 5-membered heteroaryl ring having 1-4 heteroatoms independently selected from nitrogen, oxygen, and sulfur. In some embodiments, $R^3$ is an optionally substituted 6-membered heteroaryl ring having 1-4 heteroatoms independently selected from nitrogen, oxygen, and sulfur.

In some embodiments, $R^3$ is oxo, halogen, OR, $N(R)_2$, SR, CN, C(O)R, C(O)OR, $C(O)N(R)_2$, $SO_2N(R)_2$, OC(O)R, N(R)C(O)R, $N(R)SO_2R$, or an optionally substituted group selected from $C_{1-6}$ aliphatic, a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur.

In some embodiments, $R^3$ is CN.

In some embodiments, $R^3$ is SR.

In some embodiments, $R^3$ is an optionally substituted 3- to 6-membered saturated or partially unsaturated carbocyclic ring. In some embodiments, $R^3$ is an optionally substituted cyclopropyl.

As defined generally above, each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur. In some embodiments, R is hydrogen. In some embodiments, R is an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3-to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur.

In some embodiments, two R groups on the same nitrogen atom may, together with the atoms to which they are attached, form an optionally substituted saturated or partially unsaturated 3- to 6-membered heterocyclic ring having 0-1 additional heteroatoms selected from nitrogen, oxygen, and sulfur. In some embodiments, two R groups on the same nitrogen atom may, together with the atoms to which they are attached, form an optionally substituted saturated 3- to 6-membered heterocyclic ring having 0-1 additional heteroatoms selected from nitrogen, oxygen, and sulfur. In some embodiments, two R groups on the same nitrogen atom may, together with the atoms to which they are attached, form an optionally substituted saturated 3-membered heterocyclic ring having 0-1 additional heteroatoms selected from nitrogen, oxygen, and sulfur. In some embodiments, two R groups on the same nitrogen atom may, together with the atoms to which they are attached, form an optionally substituted saturated 4-membered heterocyclic ring having 0-1 additional heteroatoms selected from nitrogen, oxygen, and sulfur. In some embodiments, two R groups on the same nitrogen atom may, together with the atoms to which they are attached, form an optionally substituted saturated 5-membered heterocyclic ring having 0-1 additional heteroatoms selected from nitrogen, oxygen, and sulfur. In some embodiments, two R groups on the same nitrogen atom may, together with the atoms to which they are attached, form an optionally substituted saturated 6-membered heterocyclic ring having 0-1 additional heteroatoms selected from nitrogen, oxygen, and sulfur.

In some embodiments, R is optionally substituted $C_{1-6}$ aliphatic. In some embodiments, R is $C_{1-6}$ aliphatic. In some embodiments, R is $C_{1-4}$ aliphatic. In some embodiments, R is $C_{1-2}$ aliphatic. In some embodiments, R is selected from $CH_3$, $CH_2CH_3$, cyclopropyl, and CH═$CH_2$. In some embodiments, R is selected from $CH_3$, $CH_2CH_3$, cyclopropyl, CH═$CH_2$, isopropyl, and t-butyl, In some embodiments, R is $C_{1-6}$ aliphatic optionally substituted with halogen, $R^{\circ}$, or $OR^{\circ}$. In some embodiments, R is $C_{1-4}$ aliphatic optionally substituted with halogen, $R^{\circ}$, or $OR^{\circ}$. In some such embodiments, $R^{\circ}$ is $C_{1-6}$ aliphatic or phenyl optionally substituted with -(halo$R^{\bullet}$), wherein $R^{\bullet}$ is $C_{1-4}$ aliphatic.

In some embodiments, R is $C_{1-6}$ aliphatic optionally substituted with halogen, $R^{\circ}$, $OR^{\circ}$, $N(R^{\circ})_2$, or $C(O)OR^{\circ}$. In some such embodiments, each $R^{\circ}$ is independently hydrogen, $C_{1-6}$ aliphatic, phenyl, or a 5- to 6-membered saturated, partially unsaturated, or aryl ring having 0-4 heteroatoms independently selected from nitrogen, oxygen, or sulfur, optionally substituted with -(halo$R^•$), OH, $OR^•$, $NH_2$, C(O)OH, wherein $R^•$ is $C_{1-4}$ aliphatic.

In some embodiments, R is selected from:

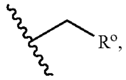, 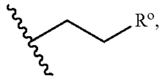, 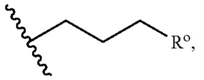,

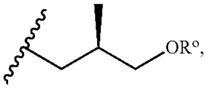, 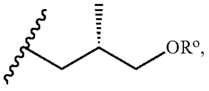,

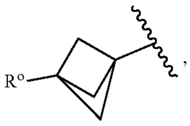, 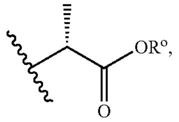,

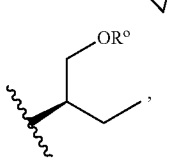, 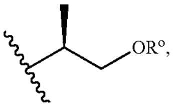, 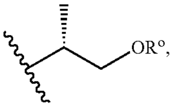,

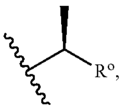, 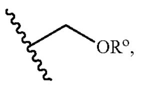, 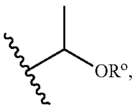,

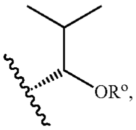, 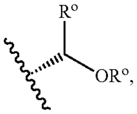, 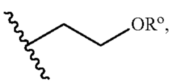,

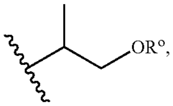, 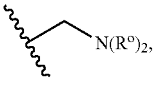, 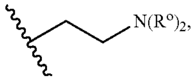,

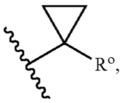, 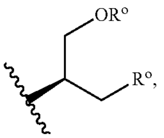, 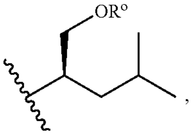,

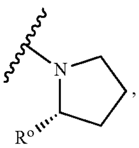, 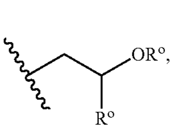, 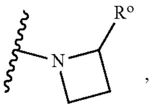,

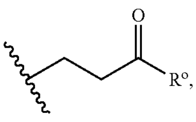, 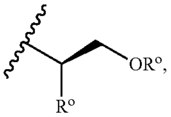,

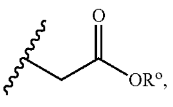, 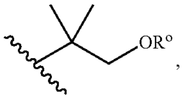,

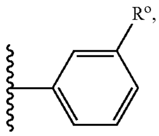, 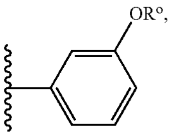, 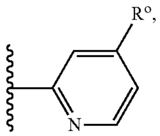,

-continued

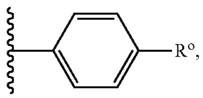, 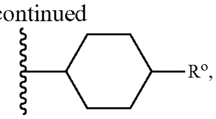, and

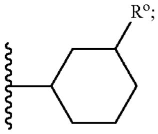;

wherein R° is hydrogen, $C_{1-6}$ aliphatic, or a 5-6-membered saturated, partially unsaturated, or aryl ring having 0-4 heteroatoms independently selected from nitrogen, oxygen, or sulfur, wherein R° is optionally substituted with halogen, $—(CH_2)_{0-2}R^•$, -(halo$R^•$), $—(CH_2)_{0-2}OH$, $—(CH_2)_{0-2}OR^•$, $—(CH_2)_{0-2}CH(OR^•)_2$; —O(halo$R^•$), —CN, $—N_3$, $—(CH_2)_{0-2}C(O)R^•$, $—(CH_2)_{0-2}C(O)OH$, $—(CH_2)_0—2C(O)OR^•$, $—(CH_2)_{0-2}SR^•$, $—(CH_2)_{0-2}SH$, $—(CH_2)_{0-2}NH_2$, $—(CH_2)_{0-2}NHR^•$, $—(CH_2)_{0-2}NR^•_2$, $—NO_2$, $—SiR^•_3$, $—OSiR^•3$, $—C(O)SR^•$, —($C_{1-4}$ straight or branched alkylene)C(O)$OR^•$, or $—SSR^•$ wherein each $R^•$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. In some such embodiments, R° is $C_{1-6}$ aliphatic optionally substituted with halogen, $—R^•$, -(halo$R^•$), —OH, $—OR^•$, —O(halo$R^•$), —CN, $—C(O)R^•$, —C(O)OH, —C(O)$OR^•$, $—NH_2$, $—NHR^•$, and $—NR^•_2$.

In some embodiments, R is an optionally substituted 3- to 6-membered saturated or partially unsaturated carbocyclic ring. In some embodiments, R is an optionally substituted 3- to 6-membered saturated or partially unsaturated carbocyclic ring. In some embodiments, R is an optionally substituted 4- to 6-membered saturated or partially unsaturated carbocyclic ring. In some embodiments, R is an optionally substituted 6-membered saturated or partially unsaturated carbocyclic ring. In some embodiments, R is a 6-membered saturated or partially unsaturated carbocyclic ring optionally substituted with R°. In some such embodiments, R° is $C_{1-6}$ aliphatic optionally substituted with halogen. In some embodiments, R is a 6-membered saturated or partially unsaturated carbocyclic ring optionally substituted with R°, wherein R° is $C_{1-6}$ aliphatic optionally substituted with halogen.

In some embodiments, R is a 3-membered saturated or partially unsaturated carbocyclic ring optionally substituted with R° or $—(CH_2)_{0-4}OR°$, wherein R° is hydrogen or $C_{1-6}$ aliphatic.

In some embodiments, R is an optionally substituted 4- to 6-membered saturated or partially unsaturated bridged bicyclic or spirocyclic carbocyclic ring. In some embodiments, R is an optionally substituted 4- to 6-membered saturated bridged bicyclic carbocyclic ring.

In some embodiments, R is an optionally substituted saturated or partially unsaturated 3- to 6-membered heterocyclic ring having 1-3 heteroatoms independently selected from nitrogen, oxygen, and sulfur. In some embodiments, R is optionally substituted phenyl. In some embodiments, R is phenyl optionally substituted with R°. In some such embodiments, R° is $C_{1-6}$ aliphatic optionally substituted with halogen.

In some embodiments, R is an optionally substituted saturated or partially unsaturated 4- to 5-membered heterocyclic ring having 1-3 heteroatoms independently selected from nitrogen, oxygen, and sulfur. In some embodiments, R is a saturated or partially unsaturated 4- to 5-membered heterocyclic ring having 1-3 heteroatoms independently selected from nitrogen, oxygen, and sulfur, optionally substituted with R° or —$(CH_2)_{0-4}$OR°, wherein R° is hydrogen or $C_{1-6}$ aliphatic.

In some embodiments, R is phenyl optionally substituted with R° or OR°. In some such embodiments, R° is $C_{1-6}$ aliphatic optionally substituted with halogen.

In some embodiments, R is an optionally substituted 5- to 6-membered heteroaryl ring having 1-4 heteroatoms independently selected from nitrogen, oxygen, and sulfur. In some embodiments, R is an optionally substituted 6-membered heteroaryl ring having 1-4 heteroatoms independently selected from nitrogen, oxygen, and sulfur. In some embodiments, R is optionally substituted pyridyl. In some embodiments, R is pyridyl optionally substituted with R°. In some such embodiments, R° is $C_{1-6}$ aliphatic optionally substituted with halogen.

In some embodiments, R is selected from hydrogen and optionally substituted $C_{1-6}$ aliphatic. In some embodiments, R is selected from hydrogen and optionally substituted $C_{1-4}$ aliphatic. In some embodiments, R is selected from hydrogen and optionally substituted $C_{1-2}$ aliphatic.

In some embodiments, R is selected from H, $CH_3$, $CH_2CH_3$, cyclopropyl,

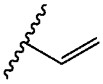
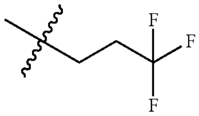
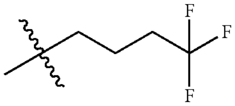
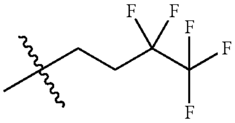
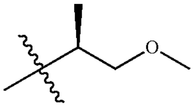
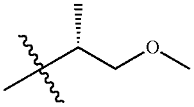
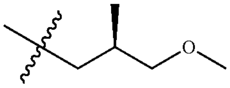
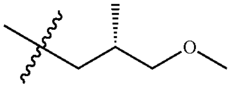
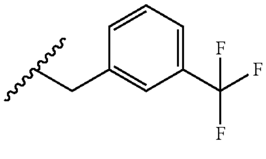
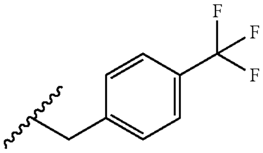
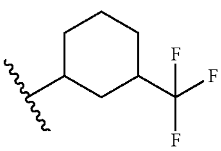
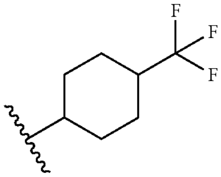
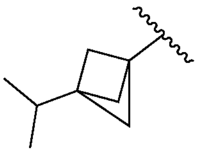
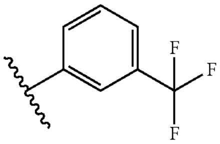

-continued

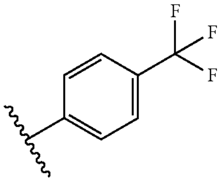

In some embodiments, R is selected from H, $CH_3$, $CH_2CH_3$, cyclopropyl,

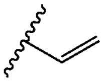
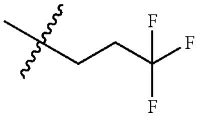
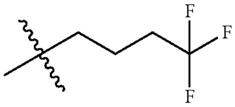
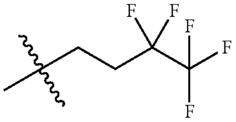
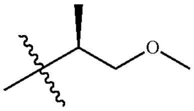
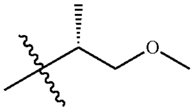
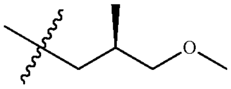
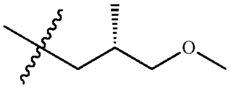
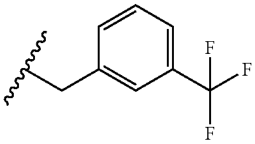
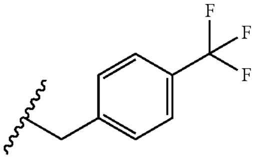
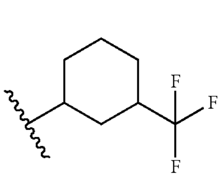
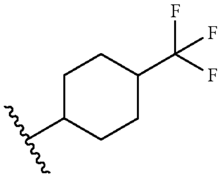
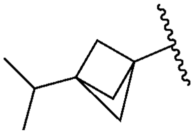
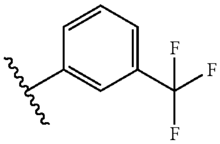
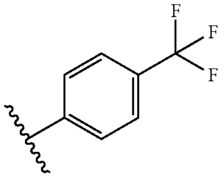
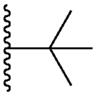
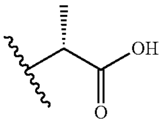
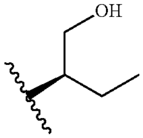
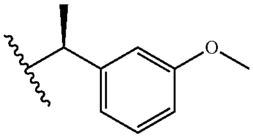
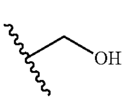
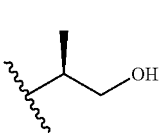
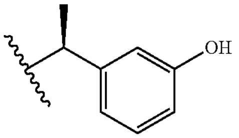

-continued
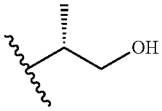
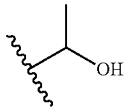
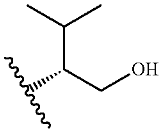
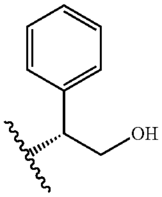
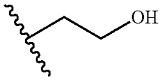
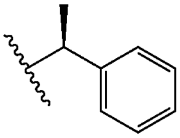
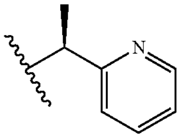
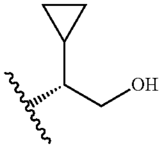
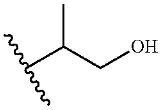
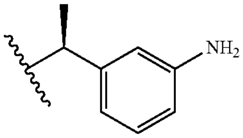
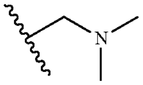
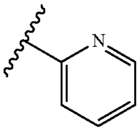
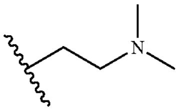
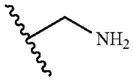
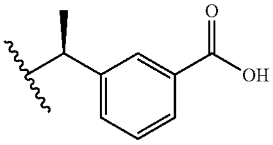
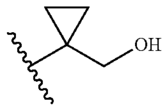
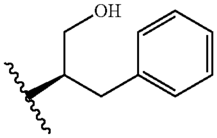
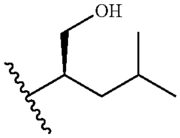
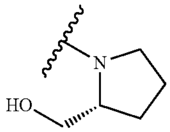
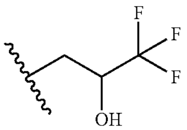
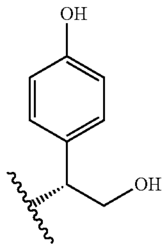
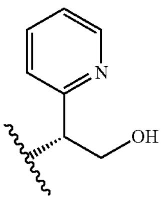
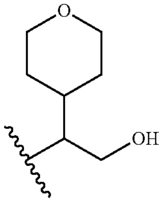
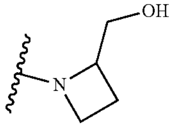
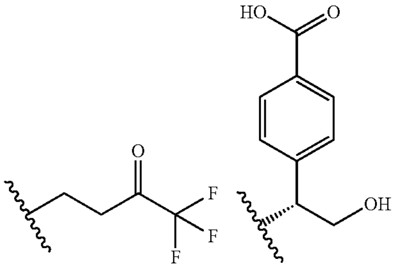
-continued
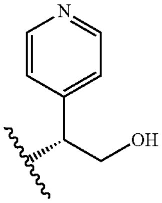
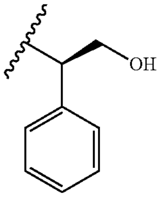
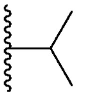
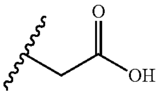
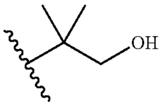
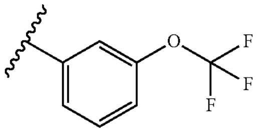
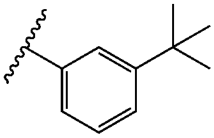
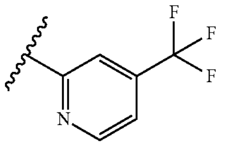
As defined generally above, n is 0, 1, or 2. In some embodiments, n is 0. In some embodiments, n is 1 or 2. In some embodiments, n is 0 or 1. In some embodiments, n is 1. In some embodiments, n is 2.
In some embodiments, the present disclosure provides a compound of formulae I-a, I-b, I-c, I-d, I-e, I-f, I-g, I-h, I-i, I-j, I-k, I-l, I-m, I-n, I-o, I-p, I-q, I-r, I-s, I-t, I-u, I-v, I-w, I-x, I-y, and I-z:
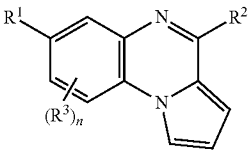
I-a
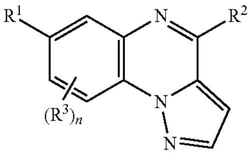
I-b
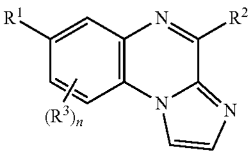
I-c
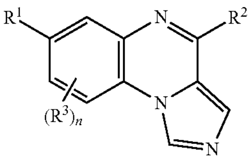
I-d -continued
I-e
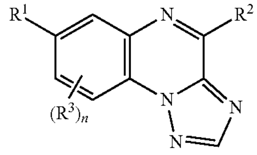
I-f
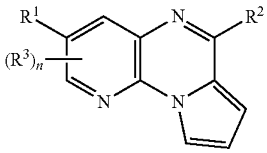
I-g
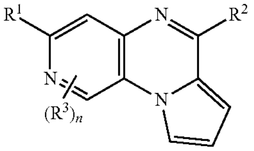
I-h
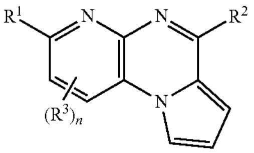
I-i
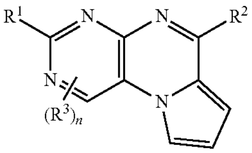
I-j
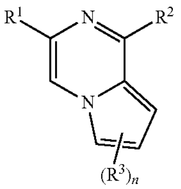
I-k
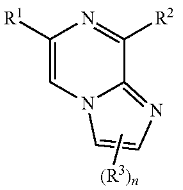
I-l
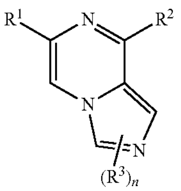
I-m
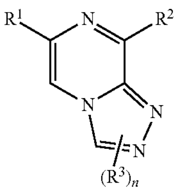
-continued
I-n
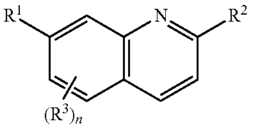
I-o
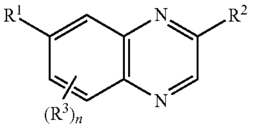
I-p
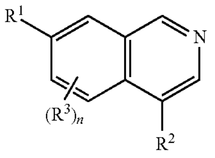
I-q
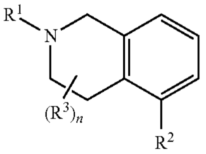
I-r
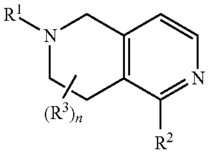
I-s
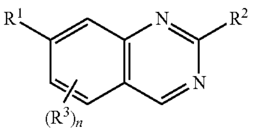
I-t
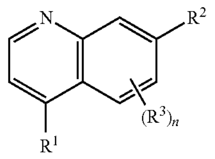
I-u
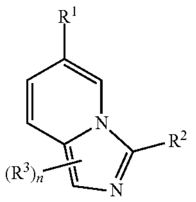
I-v
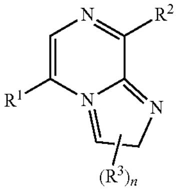

-continued

I-w

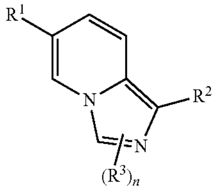

I-x

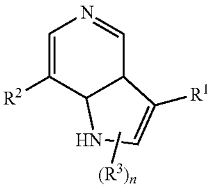

I-y

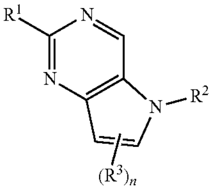

I-z

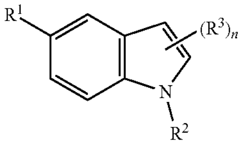

or a pharmaceutically acceptable salt thereof, wherein each of $R^1$, $R^2$, $R^3$, and n is as defined above and described herein.

In some embodiments, the present disclosure provides a compound of formulae I-a, I-b, I-c, I-d, I-e, I-f, I-g, I-h, I-i, I-j, I-k, I-1, I-m, I-n, I-o, I-p, I-q, I-r, I-s, I-t, I-u, I-v, I-w, I-x, I-y, I-z, I-aa, I-bb, I-cc, I-dd, I-ee, I-ff, I-gg, I-hh, I-ii, I-jj, I-kk, I-11, I-mm, I-nn, I-oo, I-pp, I-qq, I-rr, I-ss, and I-tt:

I-a

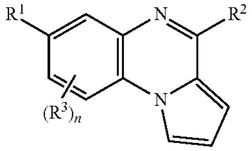

I-b

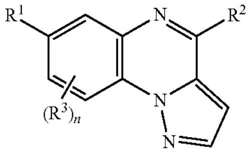

I-c

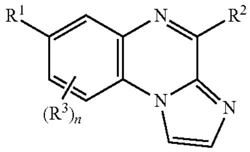

-continued

I-d

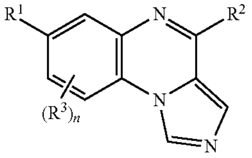

I-e

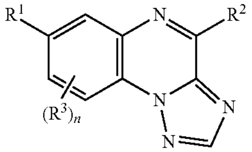

I-f

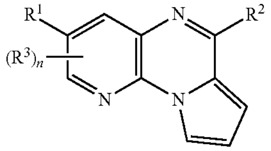

I-g

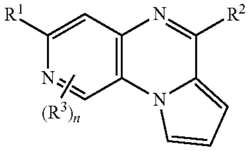

I-h

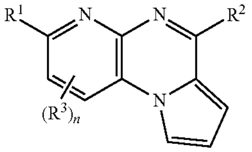

I-i

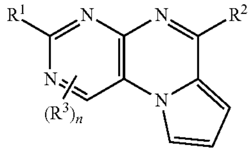

I-j

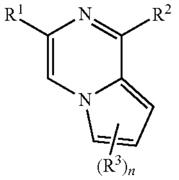

I-k

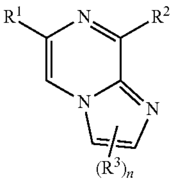

I-l

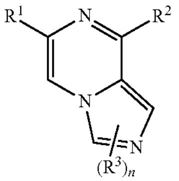

-continued
I-m
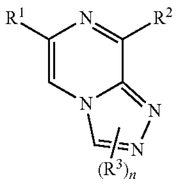
I-n
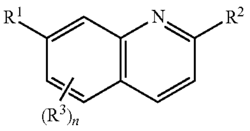
I-o
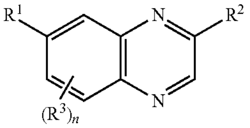
I-p
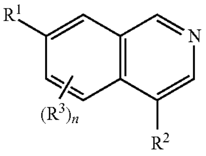
I-q
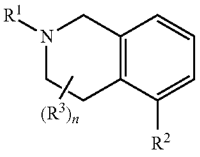
I-r
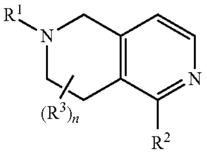
I-s
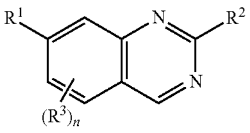
I-t
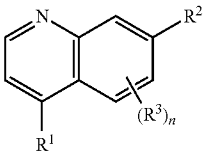
I-u
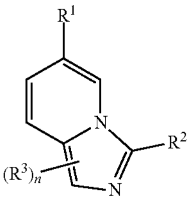
-continued
I-v
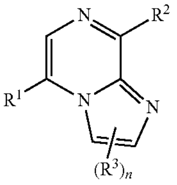
I-w
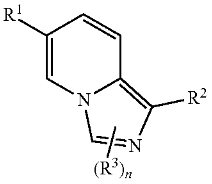
I-x
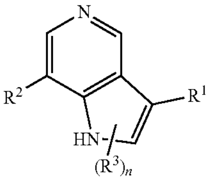
I-y
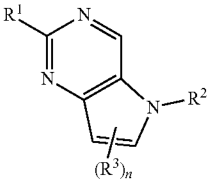
I-z
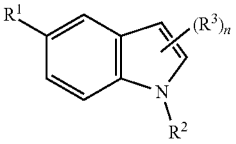
I-aa
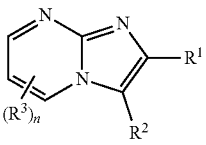
I-bb
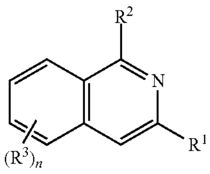
I-cc
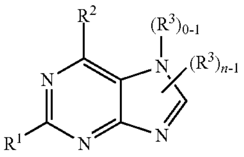
I-dd
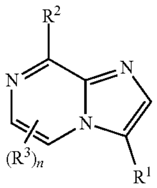

-continued
I-ee
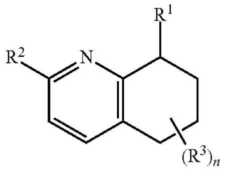
I-ff
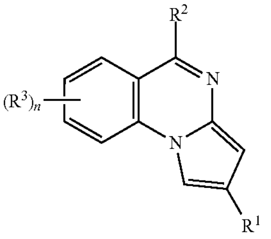
I-gg
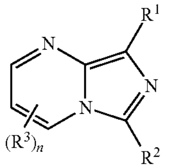
I-hh
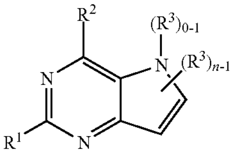
I-ii
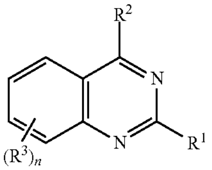
I-jj
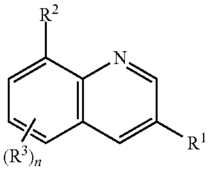
I-kk
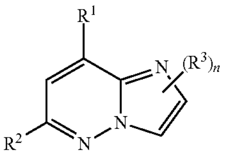
I-ll
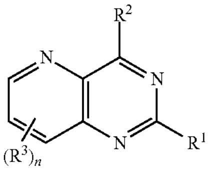
-continued
I-mm
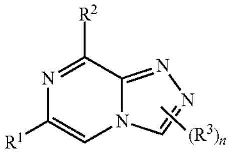
I-nn
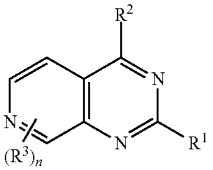
I-oo
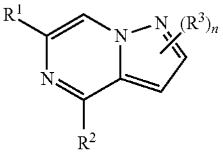
I-pp
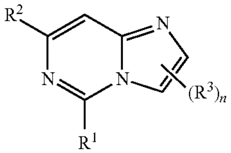
I-qq
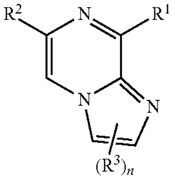
I-rr
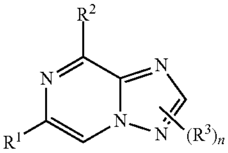
I-ss
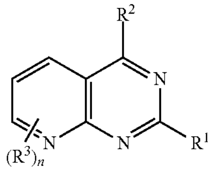
I-tt
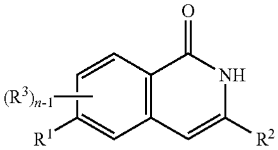
or a pharmaceutically acceptable salt thereof, wherein each of $R^1$, $R^2$, $R^3$, and n is as defined above and described herein.
In some embodiments, the present disclosure provides a compound of formulae I-a-i, I-a-i, I-c-i, I-c-ii, I-j-i, I-j-ii, I-k-i, I-k-ii, I-k-iii, and I-n-i:

I-a-i

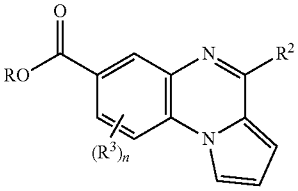

I-a-ii

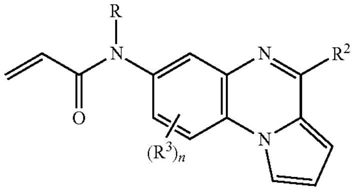

I-c-i

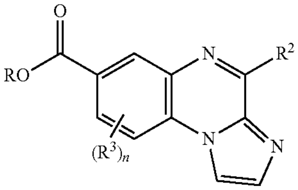

I-c-ii

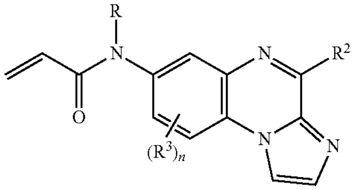

I-j-i

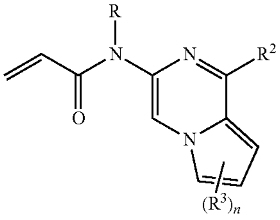

I-j-ii

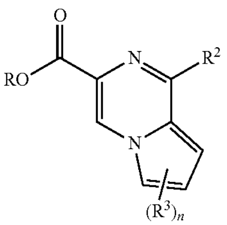

I-k-i

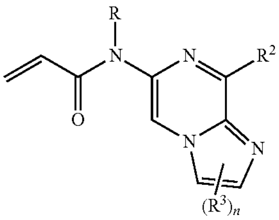

-continued

I-k-ii

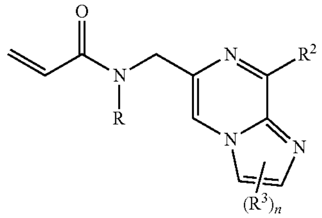

I-k-iii

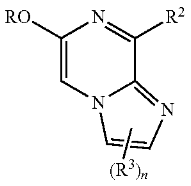

I-n-i

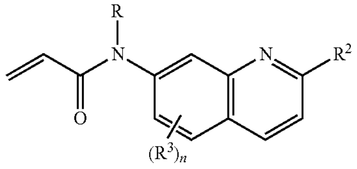

or a pharmaceutically acceptable salt thereof, wherein each of $R^1$, $R^2$, $R^3$, R, and n is as defined above and described herein.

In some embodiments, the present disclosure provides a compound of formulae I-a-i, I-a-ii, I-c-i, I-c-ii, I-ji, I-j-ii, I-k-i, I-k-ii, I-k-iii, I-k-iv, I-n-i, I-n-ii, I-n-iii, I-n-iv, I-n-v, I-bb-i, I-bb-ii, I-ii-i, and I-ii-ii:

I-a-i

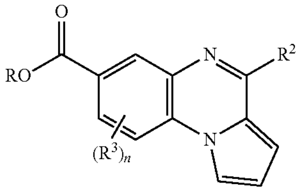

I-a-ii

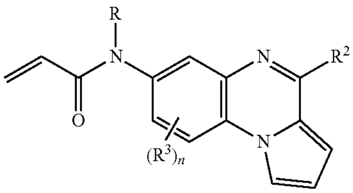

I-c-i

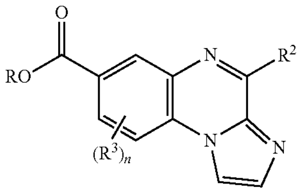

-continued
I-c-ii
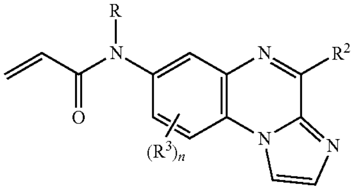
I-j-i
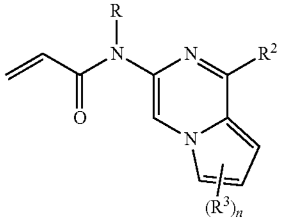
I-j-ii
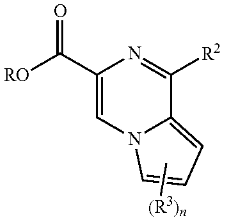
I-k-i
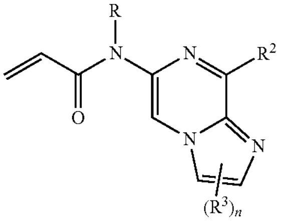
I-k-ii
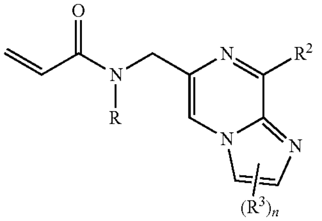
I-k-iii
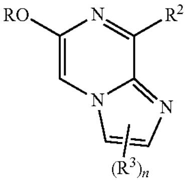
I-k-iv
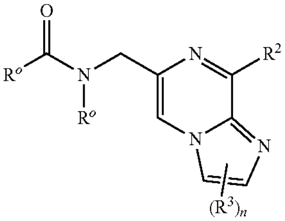
-continued
I-n-i
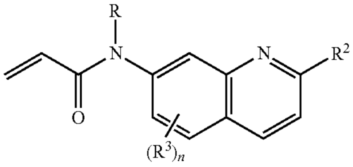
I-n-ii
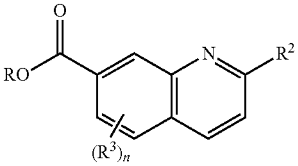
I-n-iii
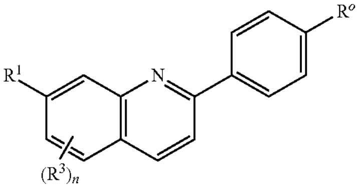
I-n-iv
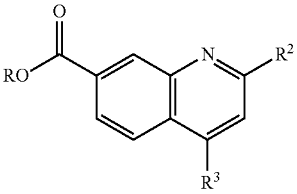
I-n-v
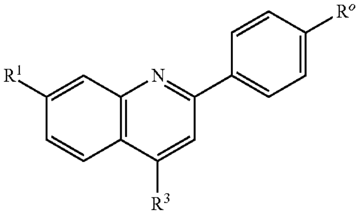
I-bb-i
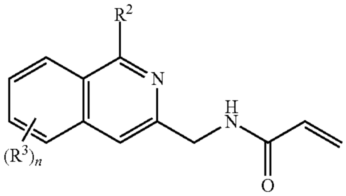
I-bb-ii
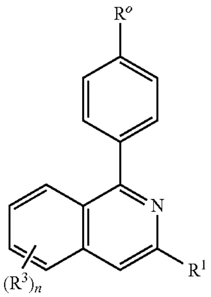

-continued
I-ii-i
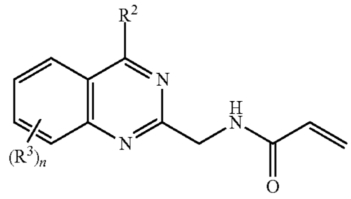
I-ii-ii
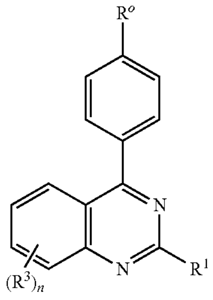
or a pharmaceutically acceptable salt thereof, wherein each of $R^1$, $R^2$, $R^3$, R, $R^{\circ}$, and n is as defined above and described herein.
In some embodiments, a provided compound is selected from the group consisting of
I-1
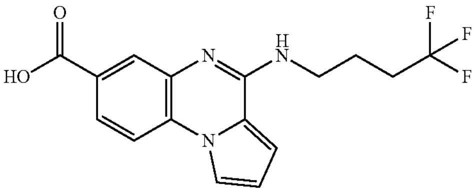
I-2
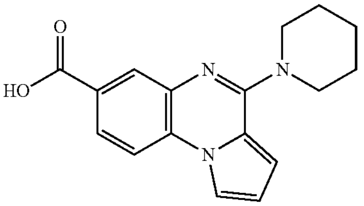
I-3
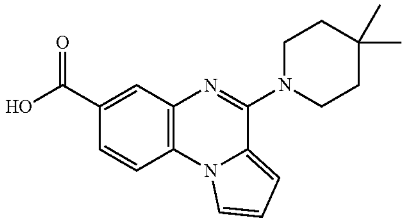
I-4
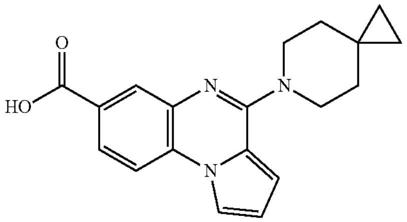
-continued
I-5
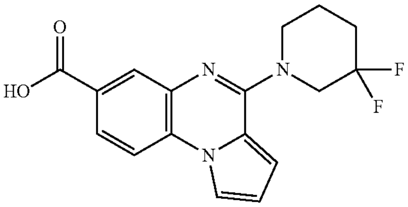
I-6
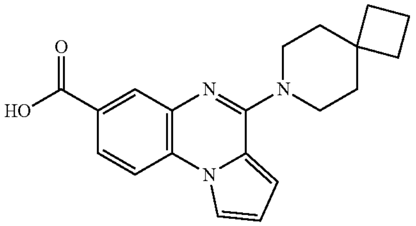
I-7
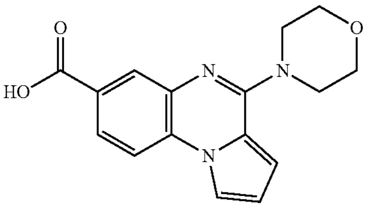
I-8
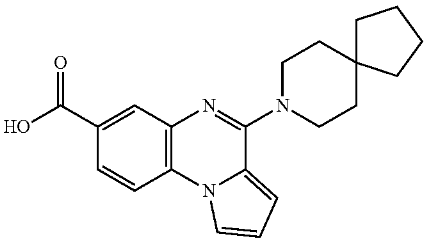
I-9
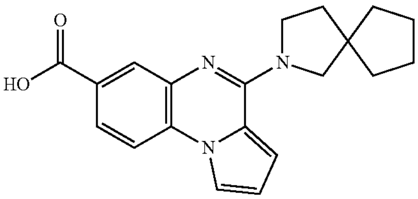
I-10
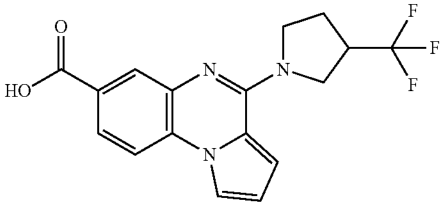
I-11
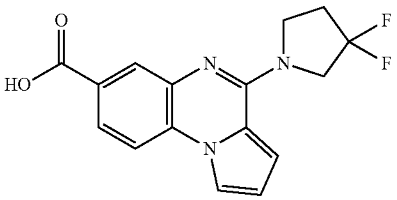

-continued
I-12
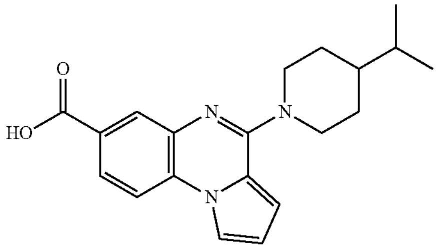
I-13
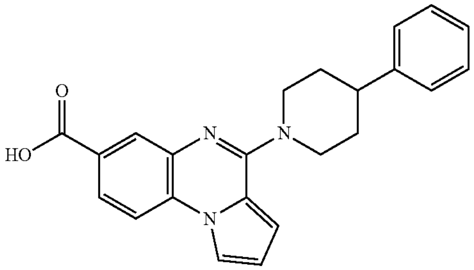
I-14
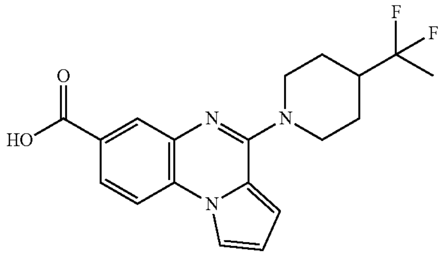
I-15
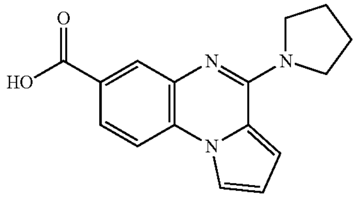
I-16
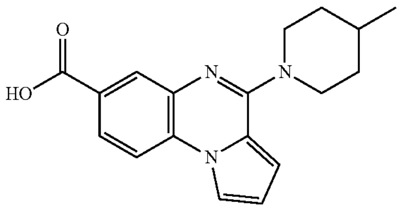
I-17
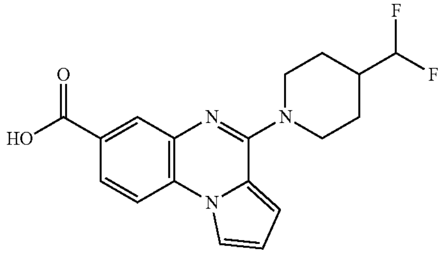
-continued
I-18
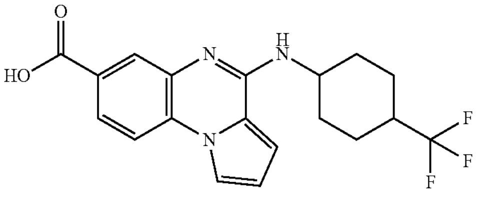
I-19
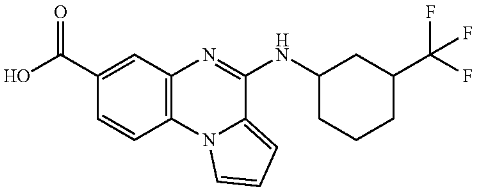
I-20
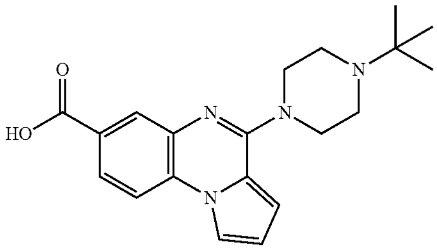
I-21
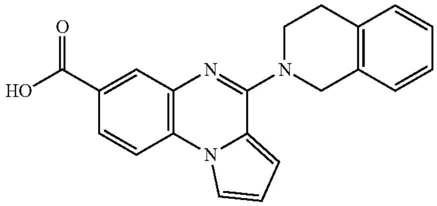
I-22
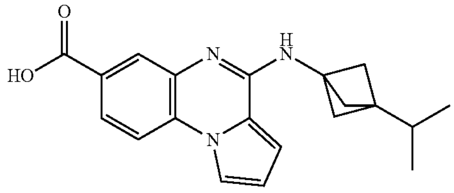
I-23
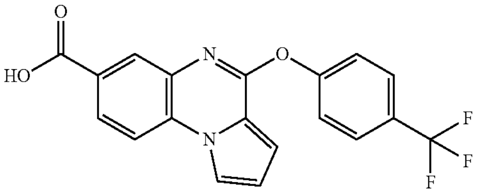
I-24
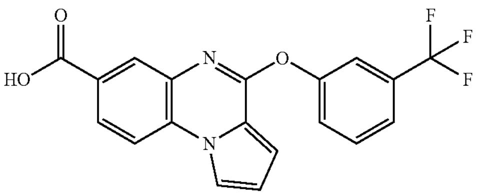

-continued
I-25
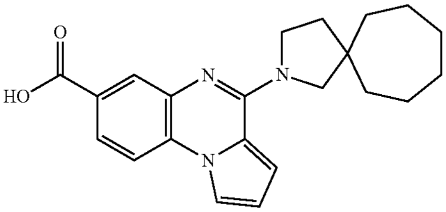
I-26
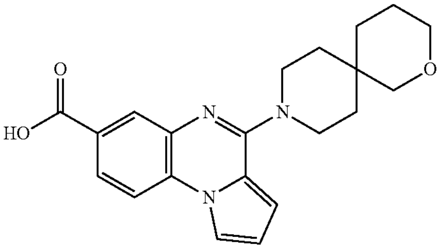
I-27
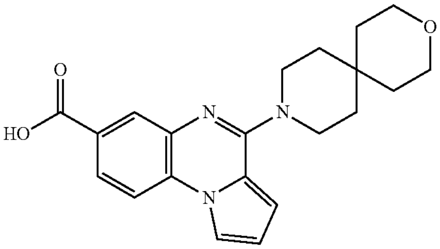
I-28
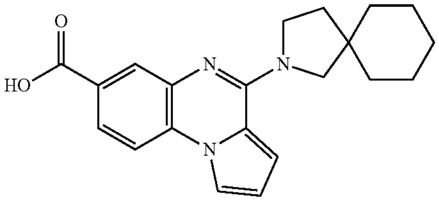
I-29
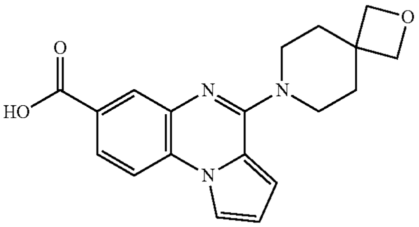
I-30
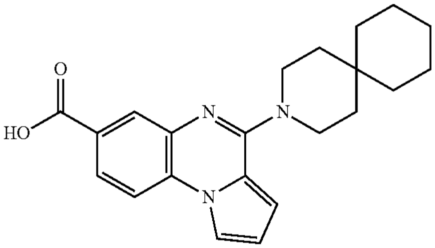
-continued
I-31
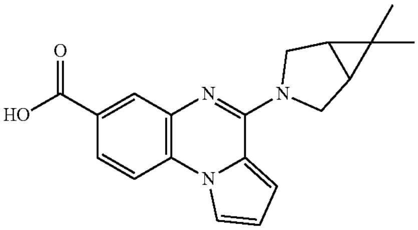
I-32
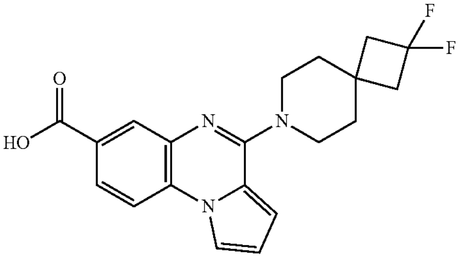
I-33
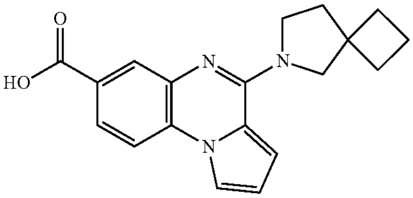
I-34
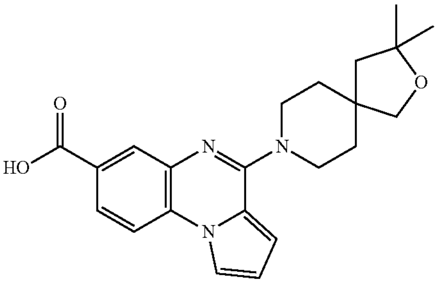
I-35
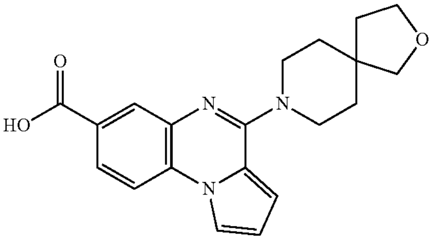
I-36
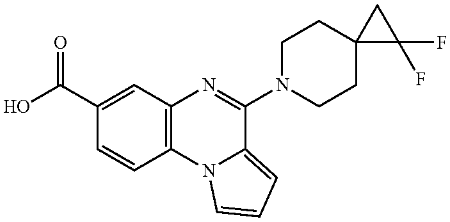

-continued
I-37
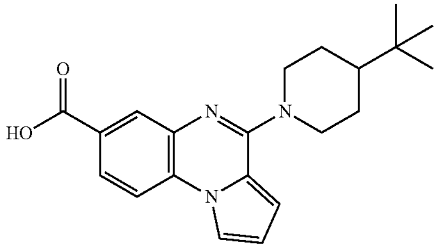
I-38
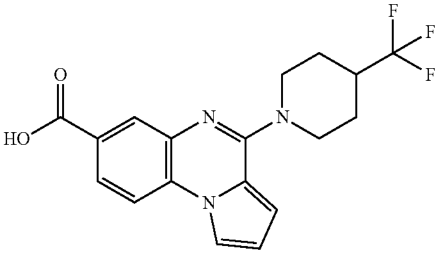
I-39
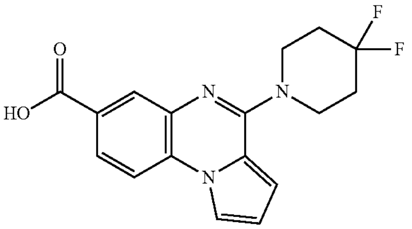
I-40
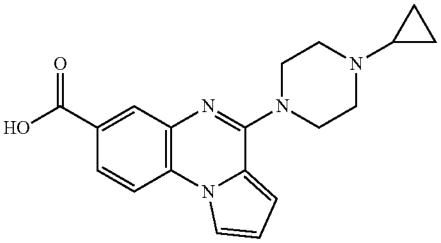
I-41
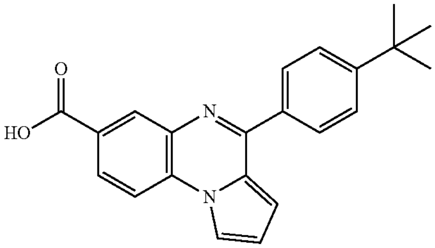
I-42
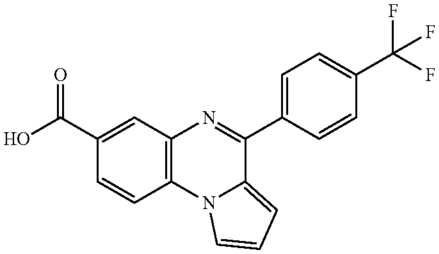
-continued
I-43
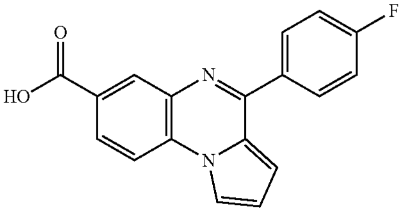
I-44
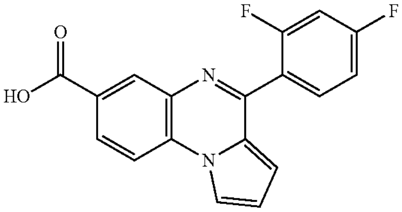
I-45
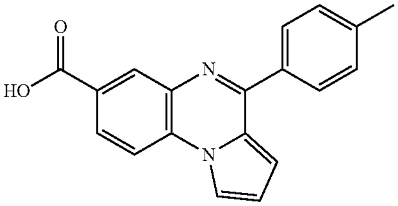
I-46
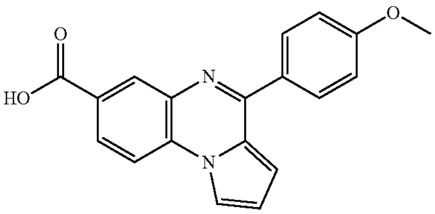
I-47
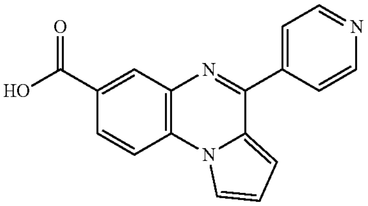
I-48
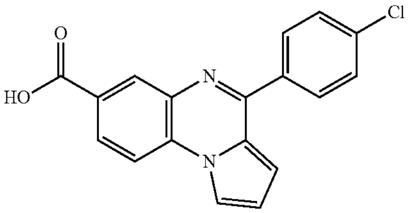
I-49
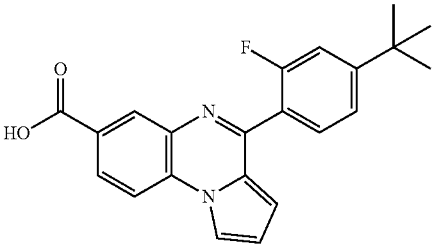

-continued
I-50
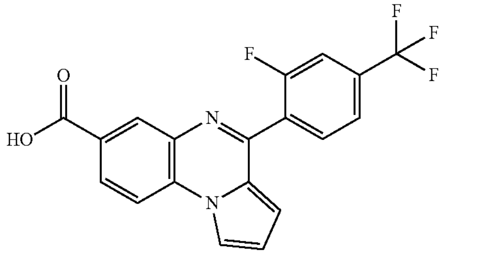
I-51
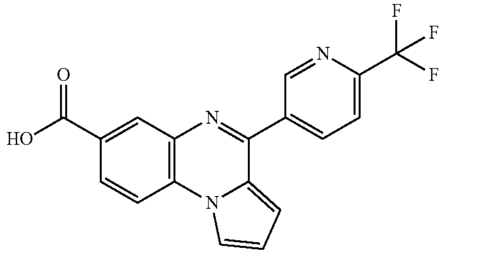
I-52
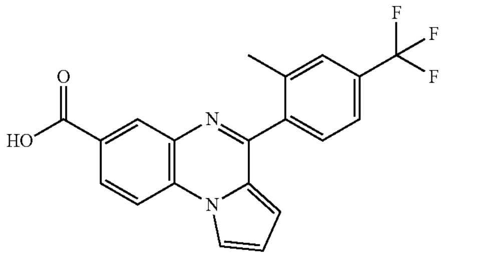
I-53
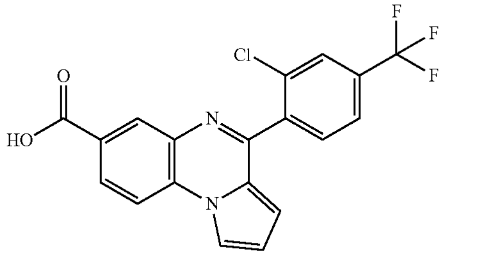
I-54
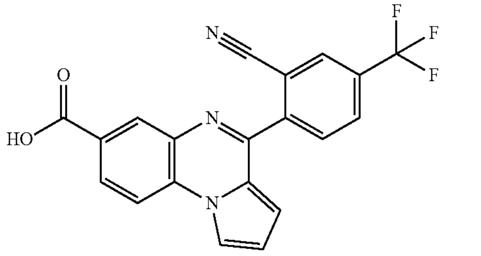
I-55
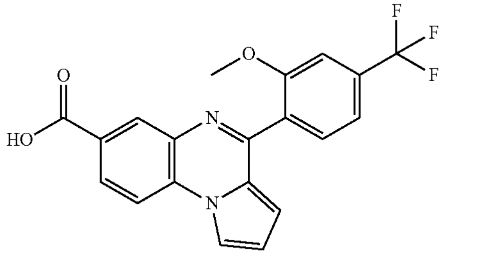
-continued
I-56
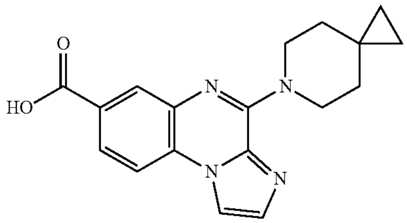
I-57
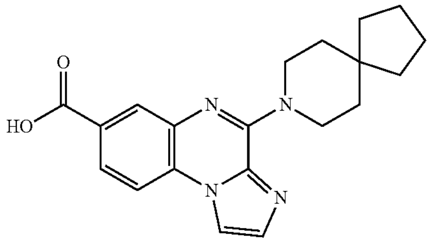
I-58
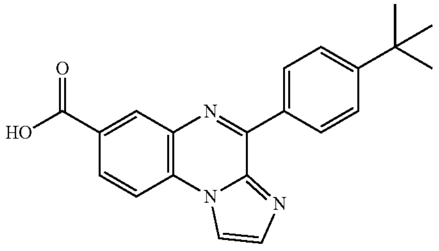
I-59
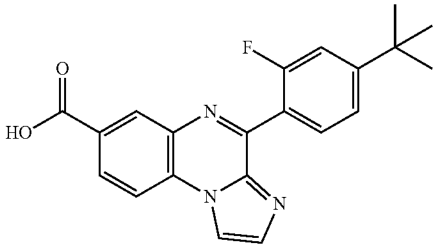
I-60
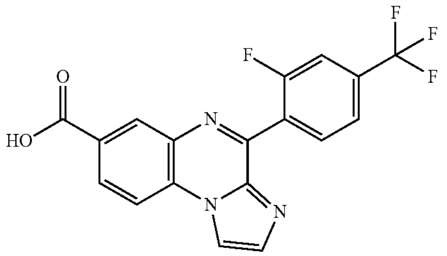
I-61
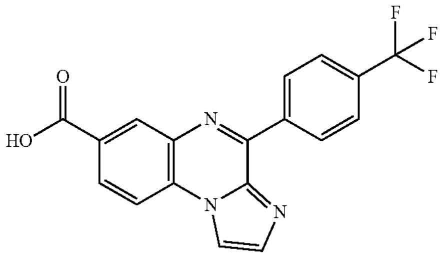

I-62
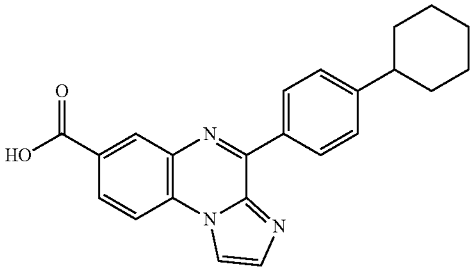
I-63
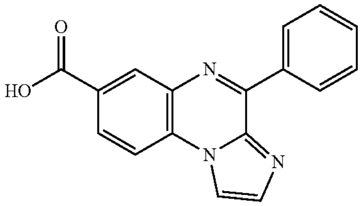
I-64
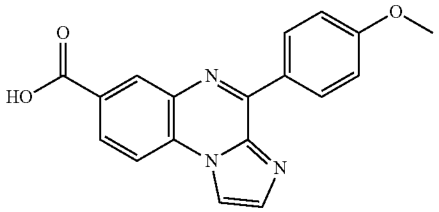
I-65
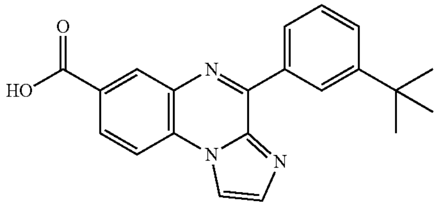
I-66
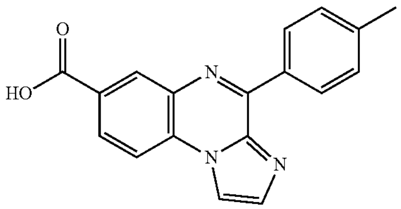
I-67
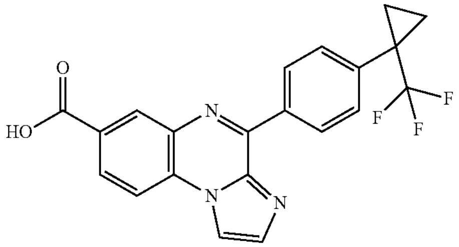
I-68
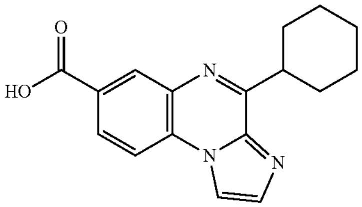
I-69
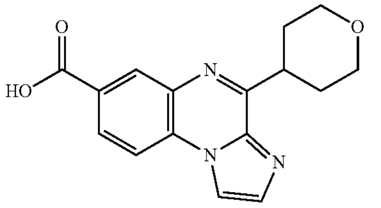
I-70
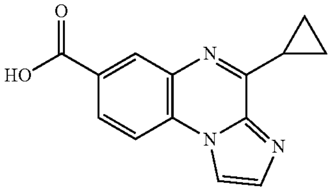
I-71
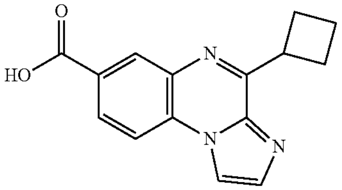
I-72
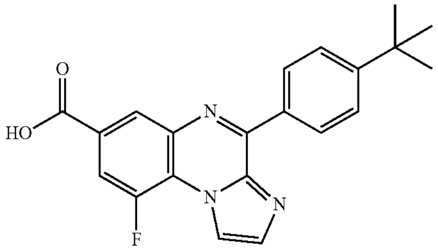
I-73
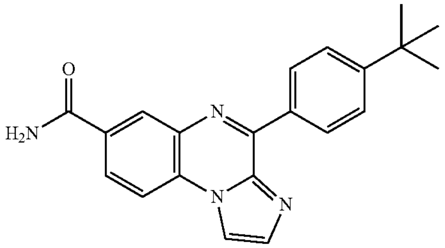
I-74
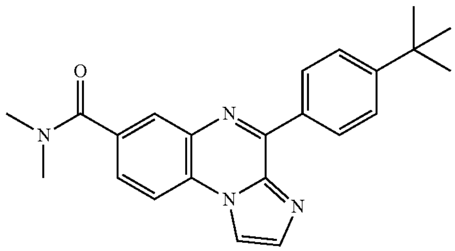
I-75
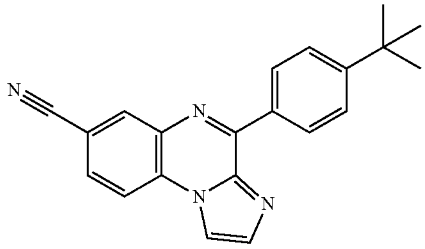

-continued
I-76
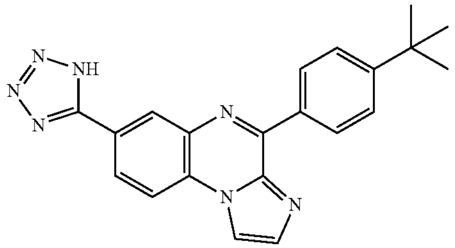
I-77
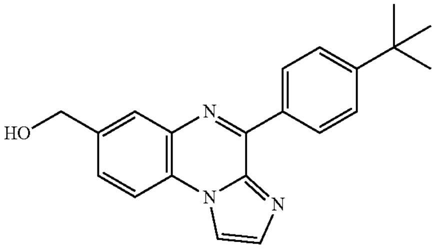
I-78
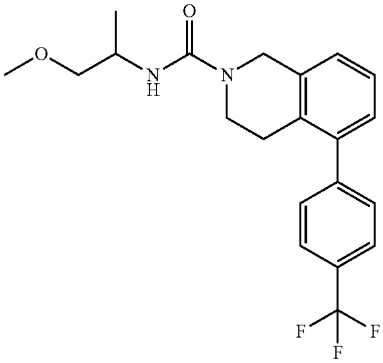
I-79
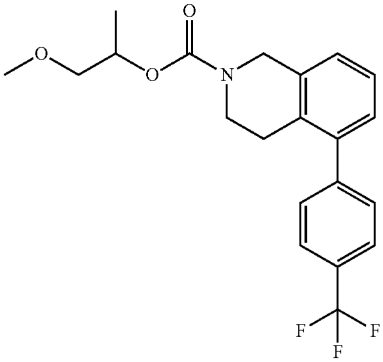
I-80
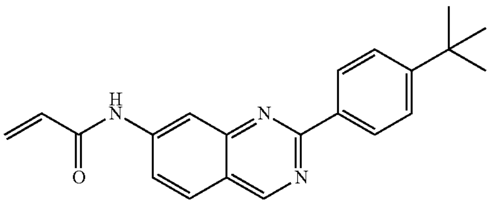
I-81
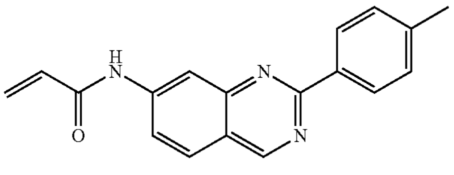
-continued
I-82
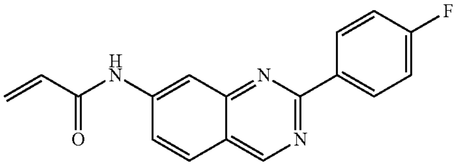
I-83
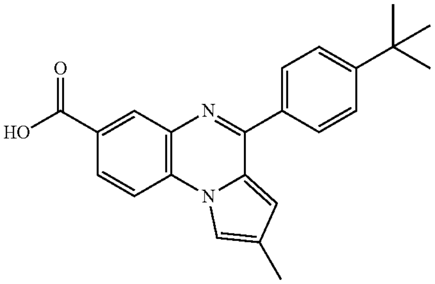
I-84
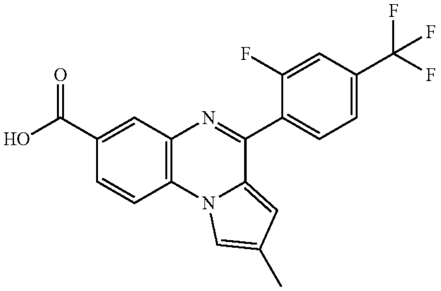
I-85
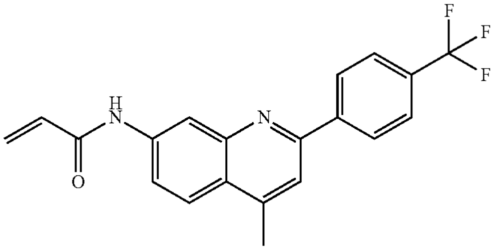
I-86
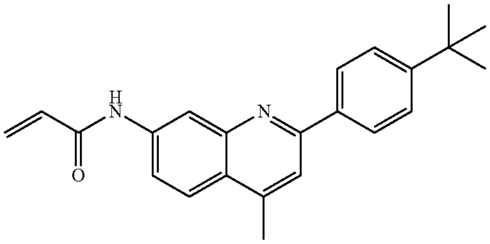
I-87
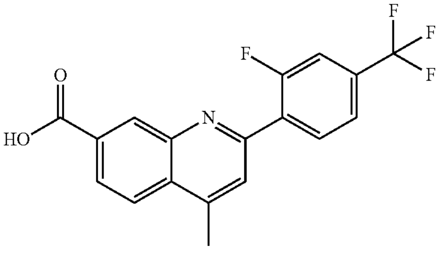

-continued
I-88
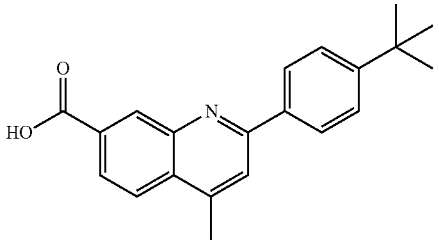
I-89
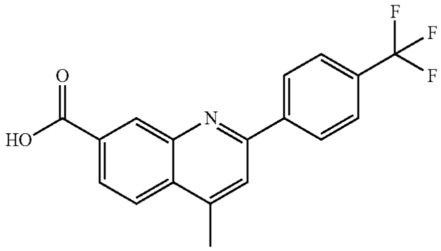
I-90
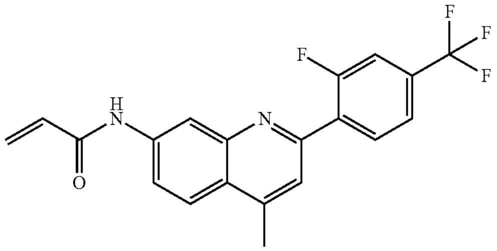
I-91
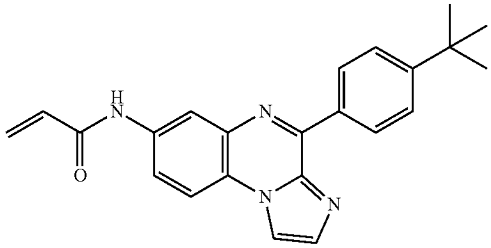
I-92
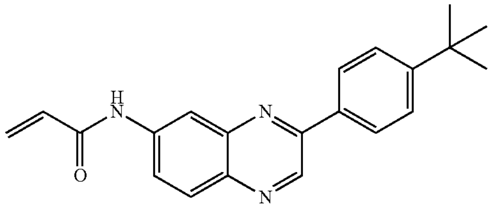
I-93
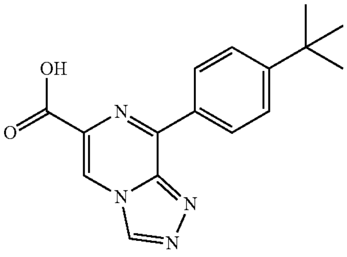
-continued
I-94
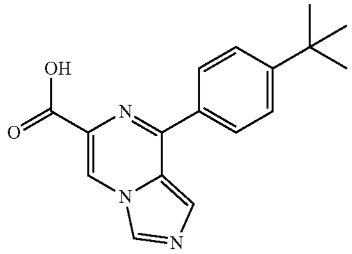
I-95
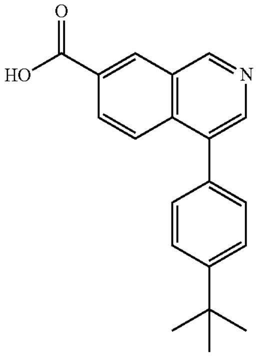
I-96
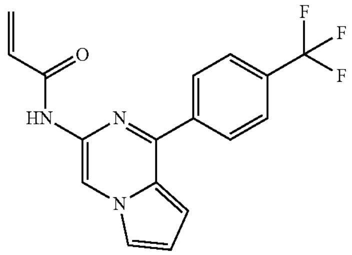
I-97
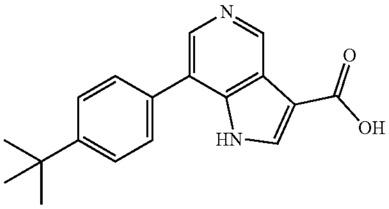
I-98
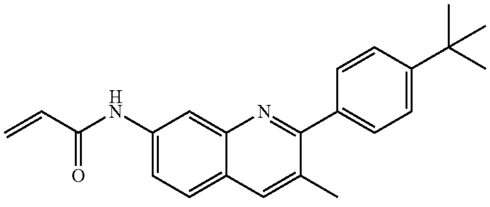
I-99
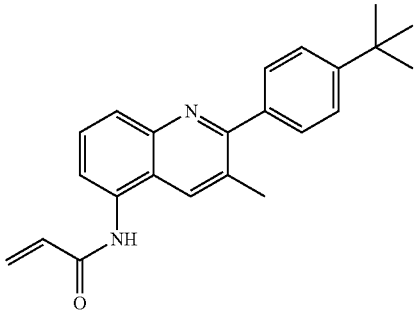

-continued
I-100
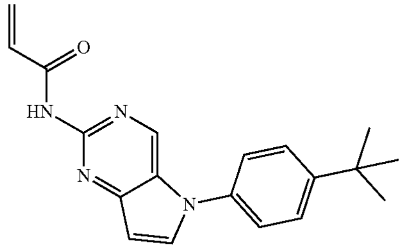
I-101
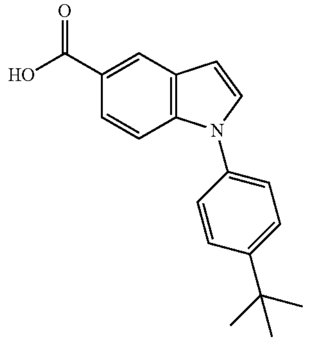
I-102
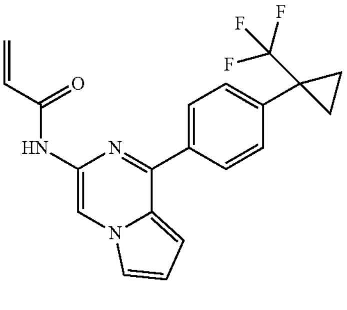
I-103
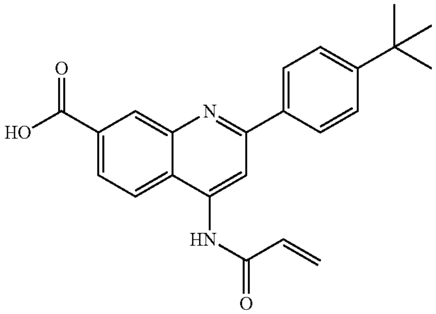
I-104
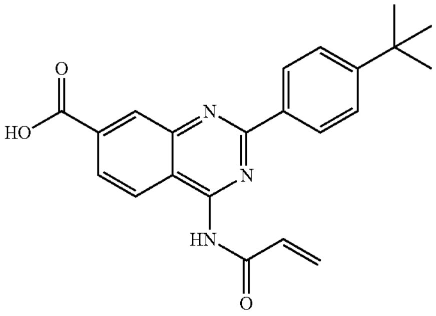
-continued
I-105
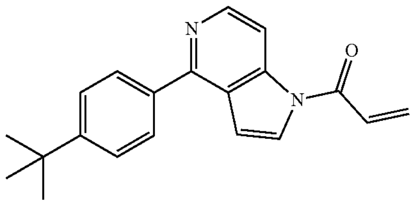
I-106
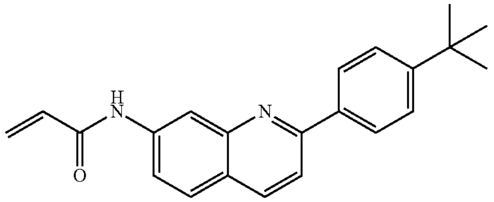
I-107
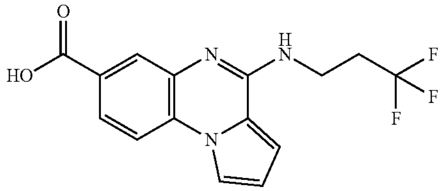
I-108
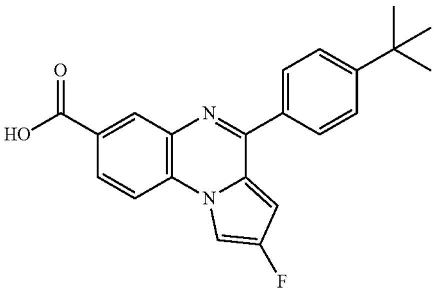
I-109
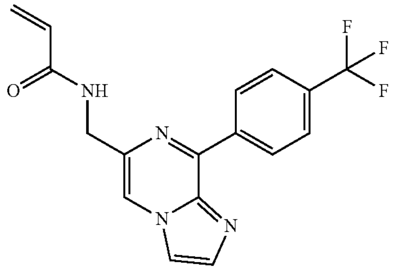
I-110
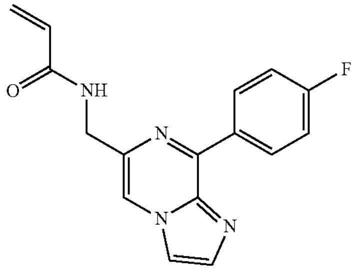

-continued
I-111
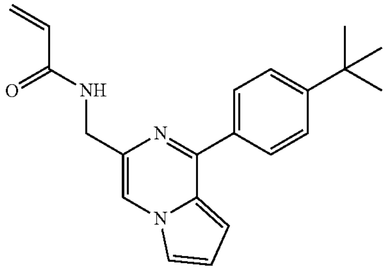
I-112
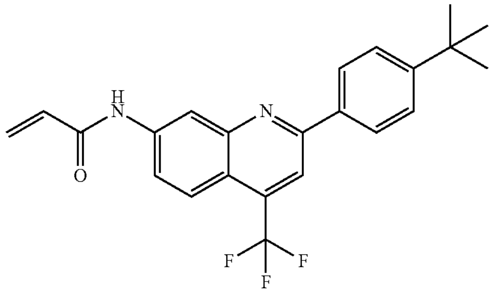
I-113
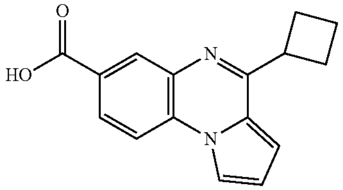
I-114
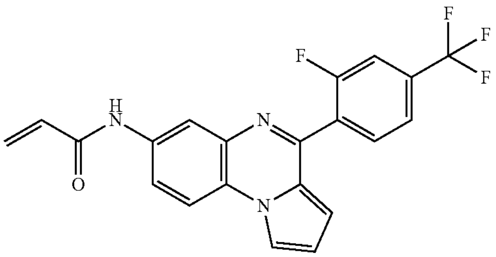
I-115
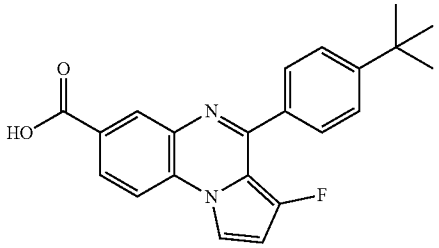
I-116
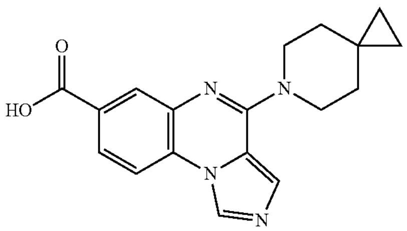
-continued
I-117
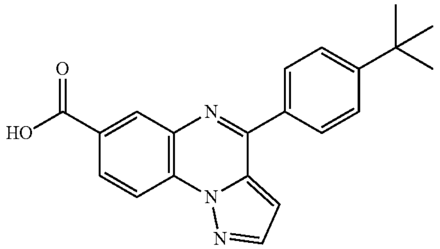
I-118
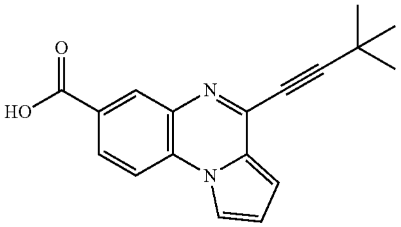
I-119
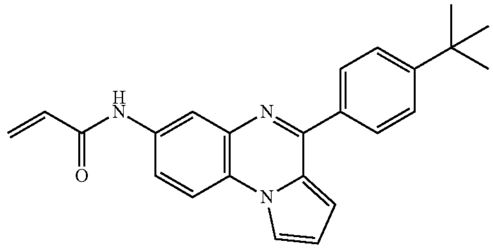
I-120
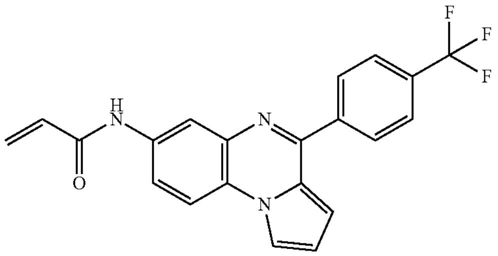
I-121
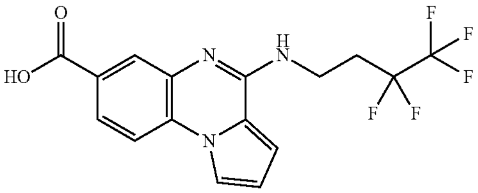
I-122
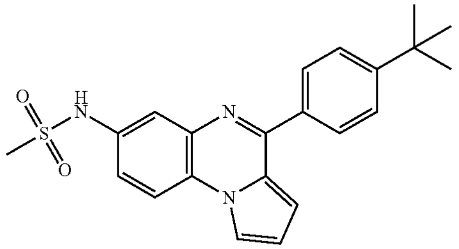

-continued
I-123
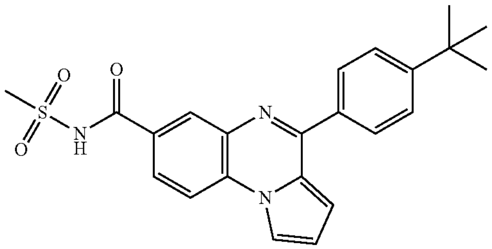
I-124
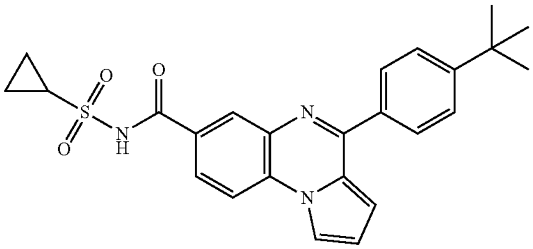
I-125
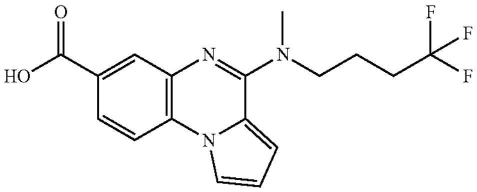
I-126
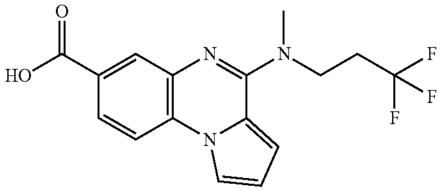
I-127
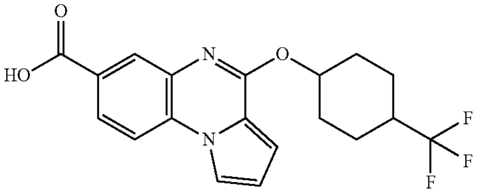
I-128
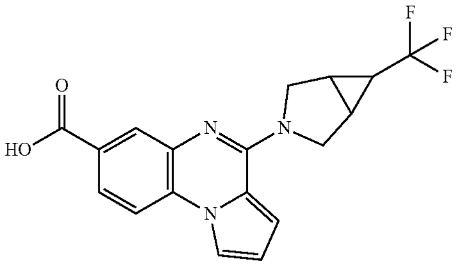
I-129
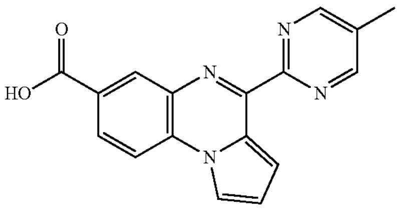
-continued
I-130
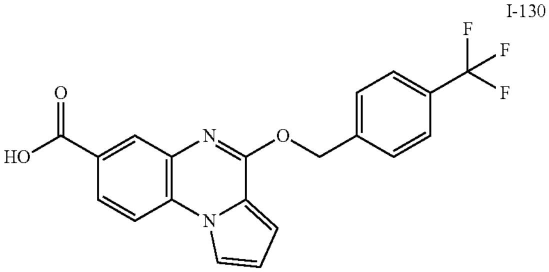
I-131
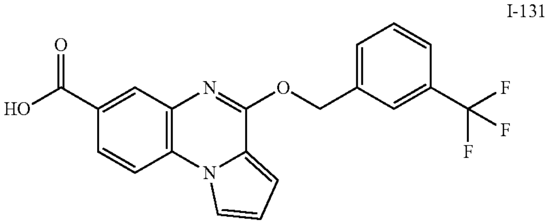
I-132
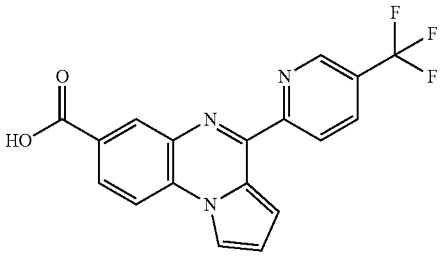
I-133
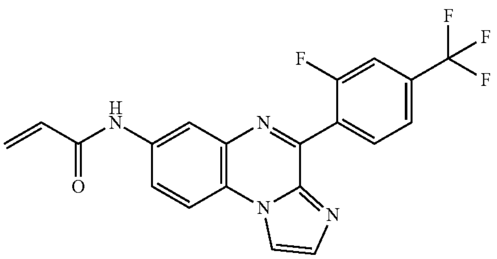
I-134
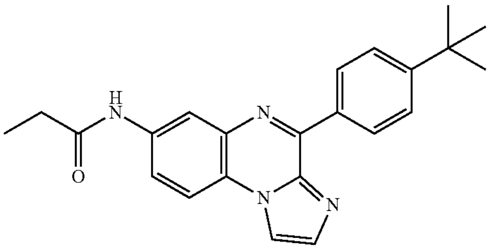
I-135
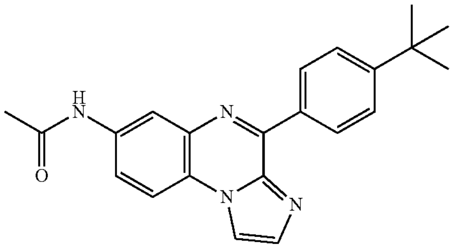

-continued
I-136
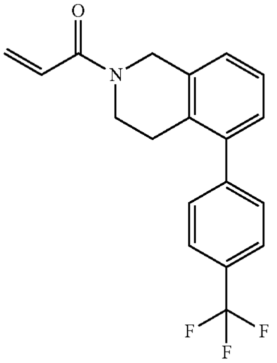
I-137
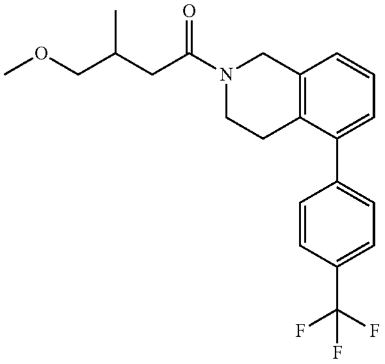
I-138
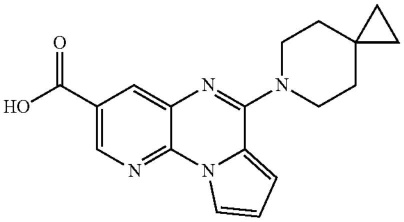
I-139
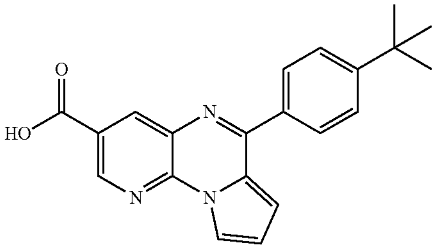
I-140
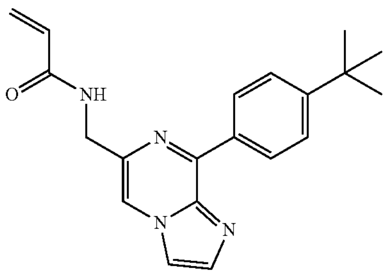
-continued
I-141
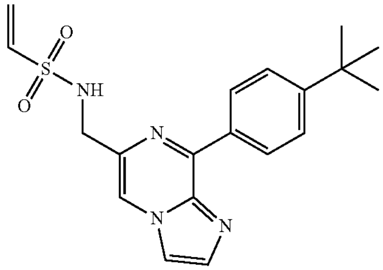
I-142
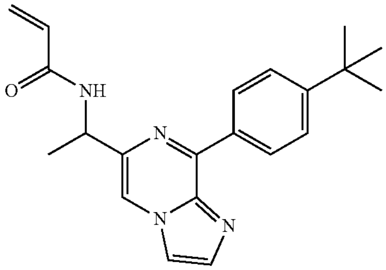
I-143
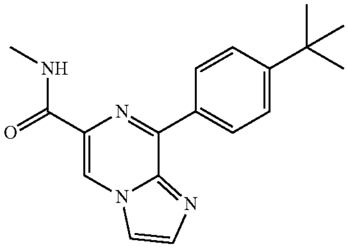
I-144
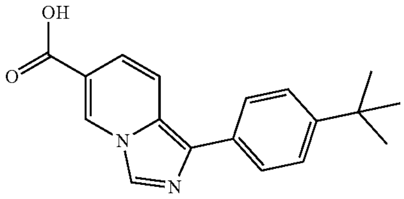
I-145
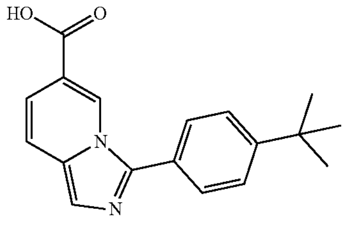
I-146
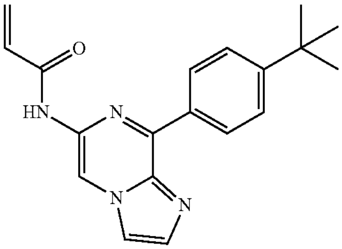

I-147
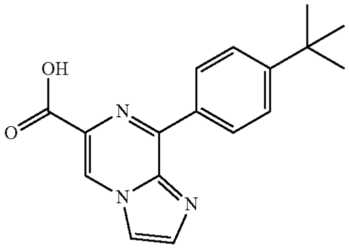
I-148
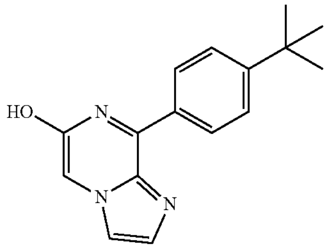
I-149
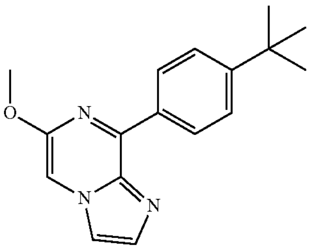
I-150
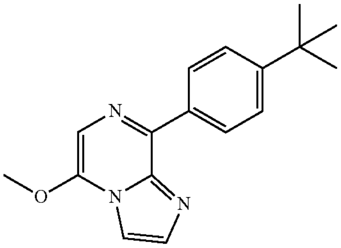
I-151
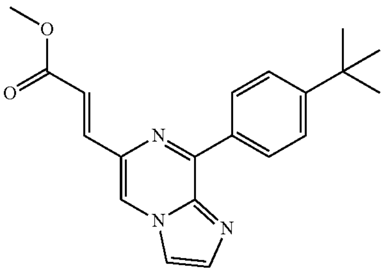
I-152
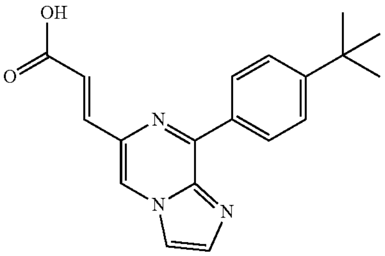
I-153
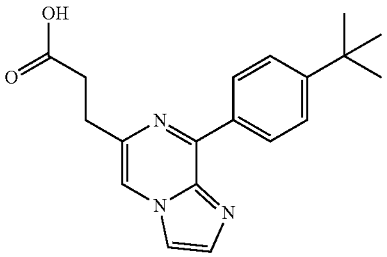
I-154
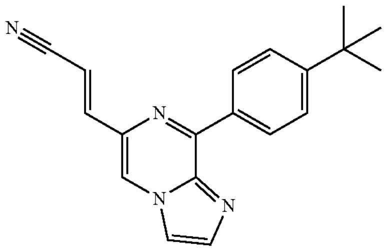
I-155
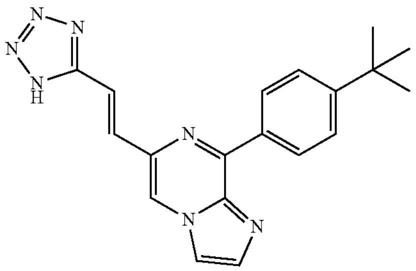
I-156
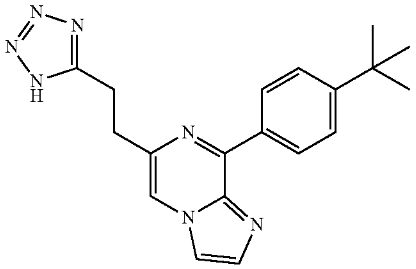
I-157
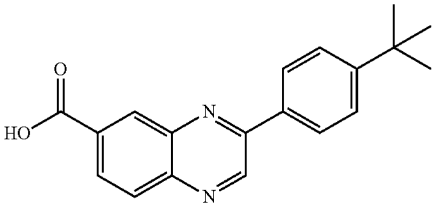
I-158
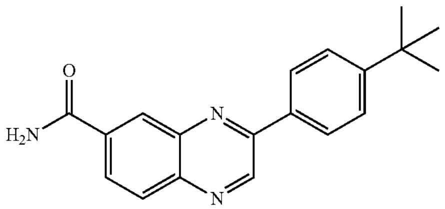

-continued
I-159
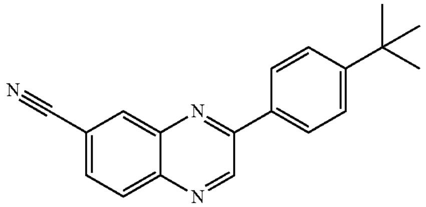
I-160
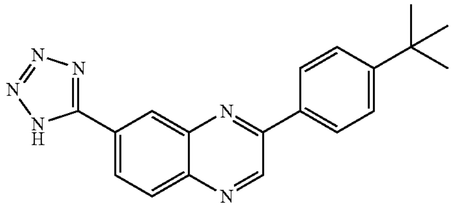
I-161
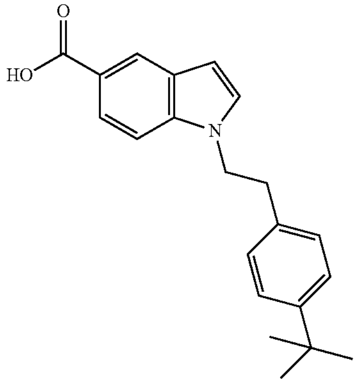
I-162
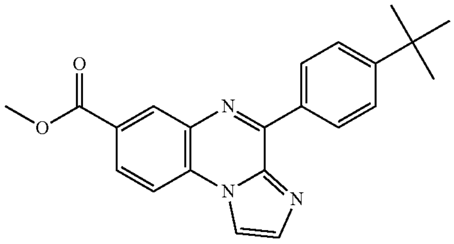
I-163
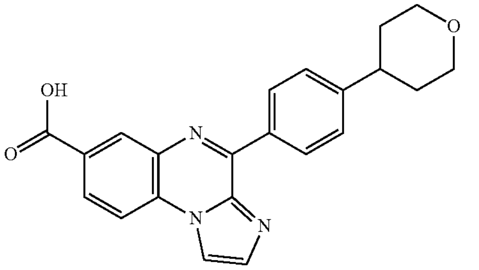
I-164
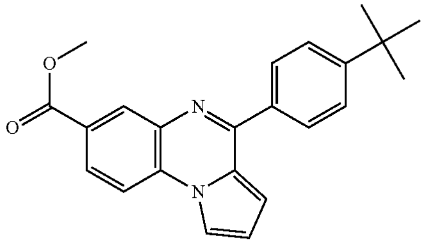
-continued
I-165
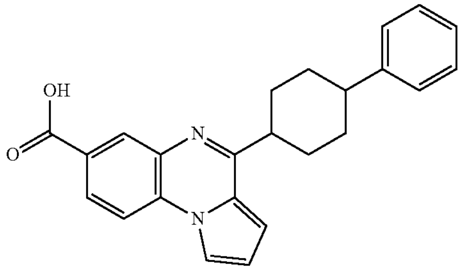
I-166
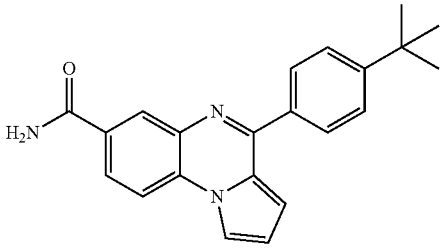
I-167
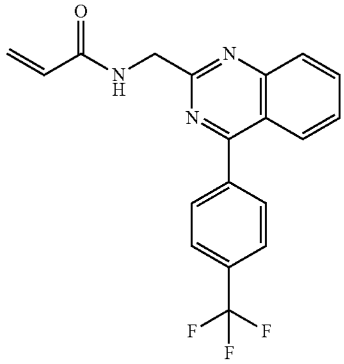
I-168
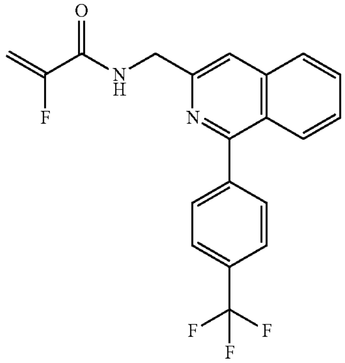
I-169
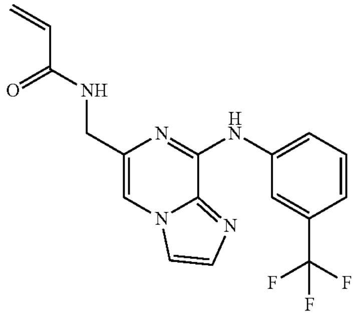

-continued
I-170
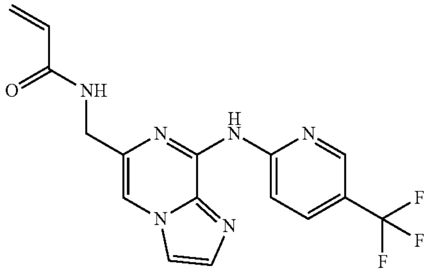
I-171
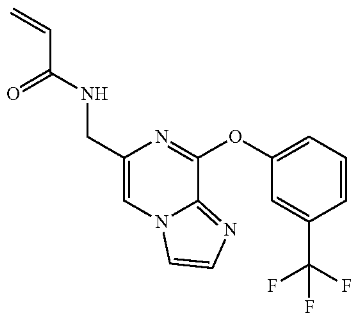
I-172
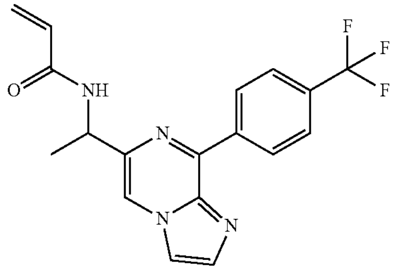
I-173
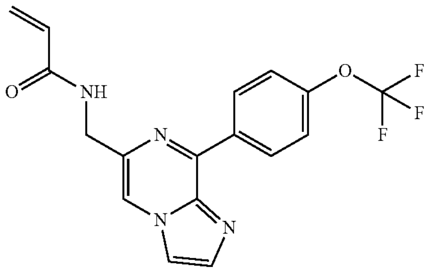
I-174
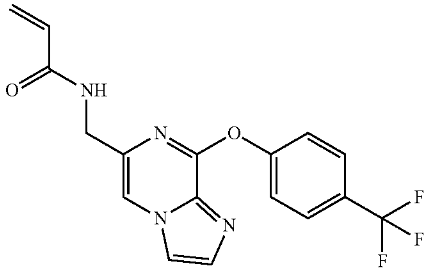
-continued
I-175
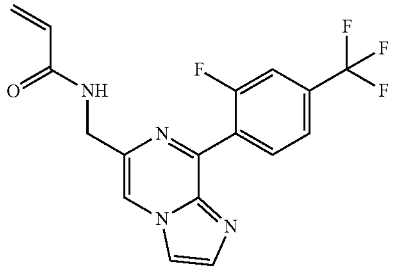
I-176
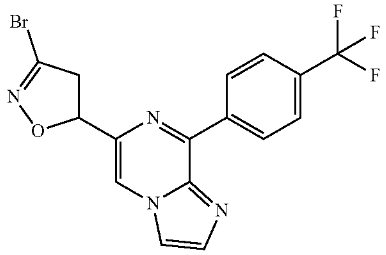
I-177
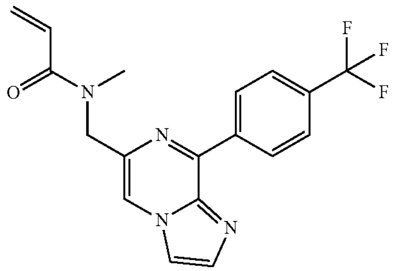
I-178
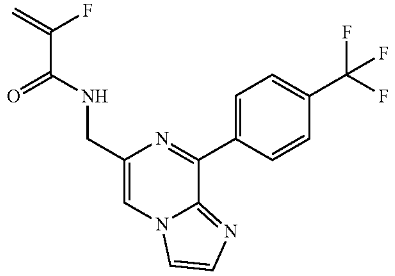
I-179
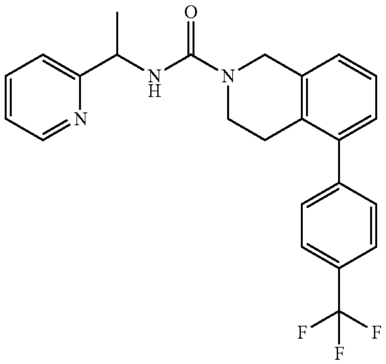

-continued
I-180
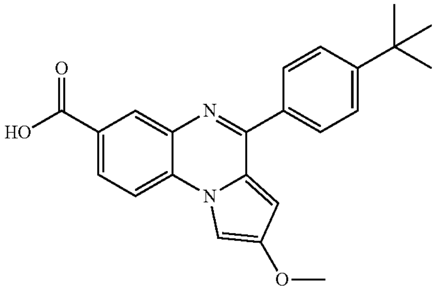
I-181
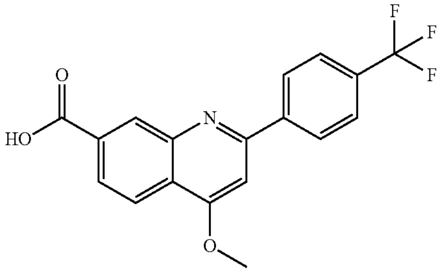
or a pharmaceutically acceptable salt thereof.
In some embodiments, a provided compound is selected from the group consisting of
I-182
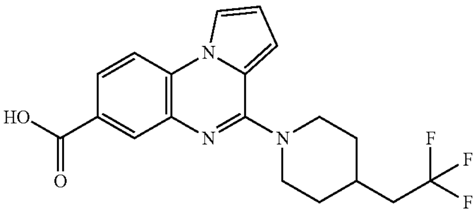
I-183
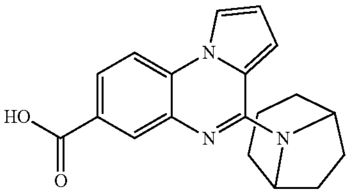
I-184
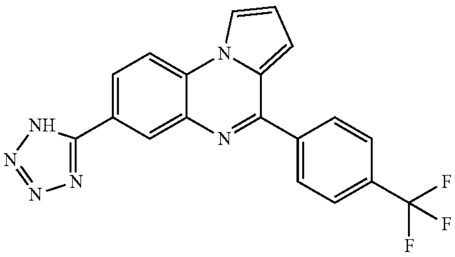
-continued
I-185
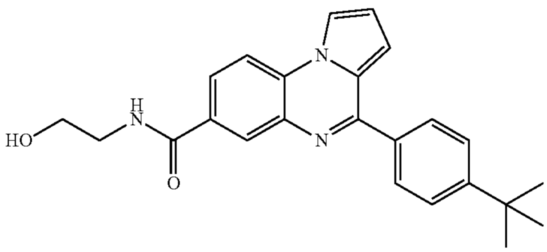
I-186
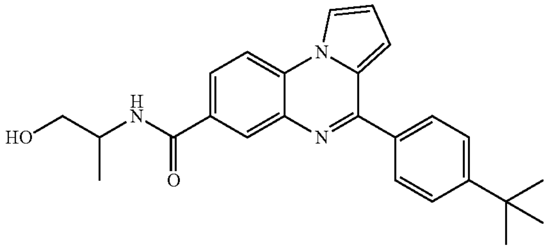
I-187
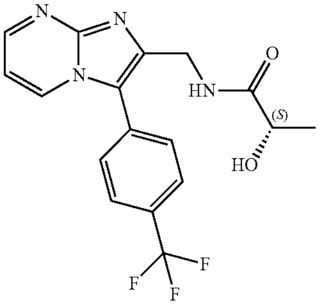
I-188
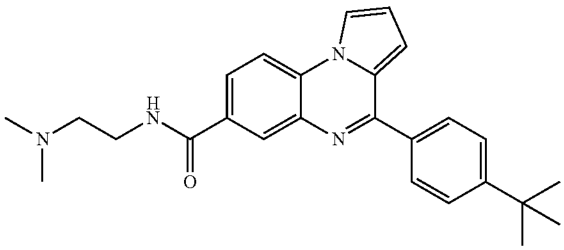
I-189
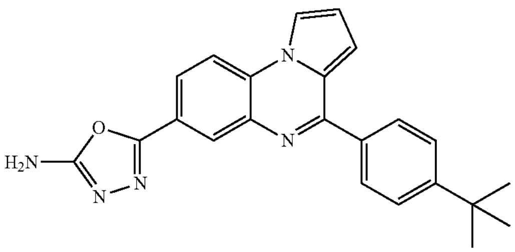

-continued
I-190
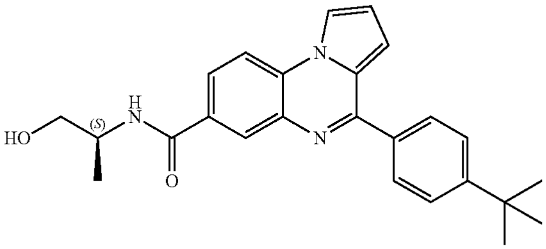
I-191
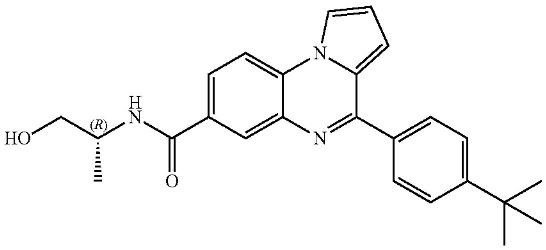
I-192
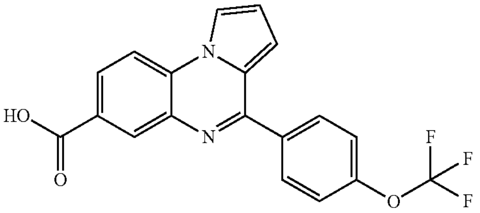
I-193
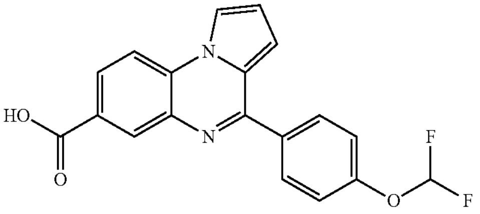
I-194
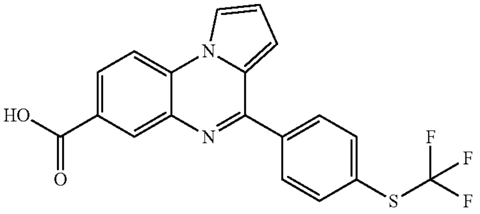
I-195
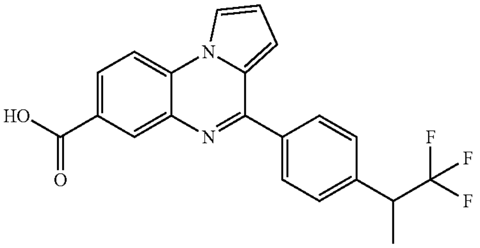
-continued
I-196
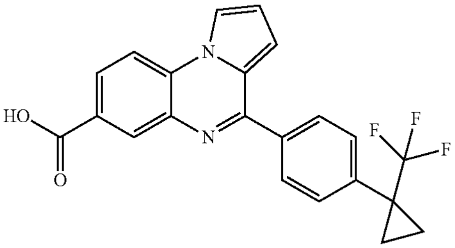
I-197
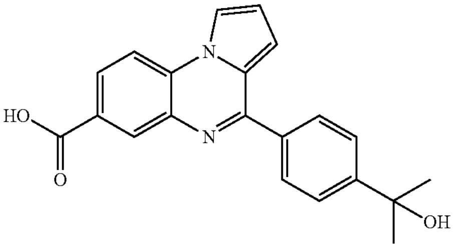
I-198
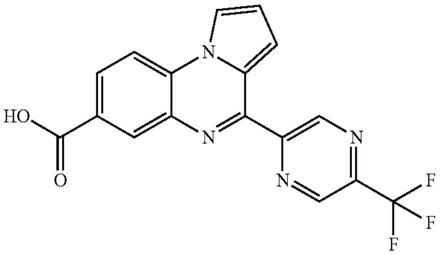
I-199
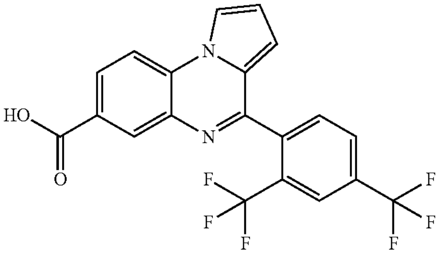
I-200
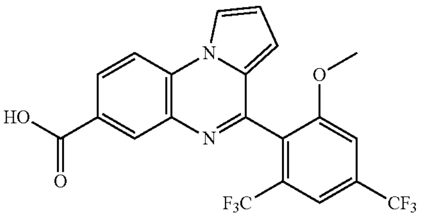
I-201
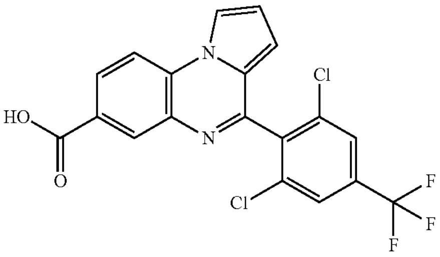

-continued
I-202
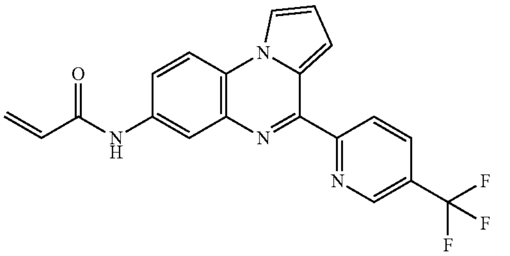
I-203
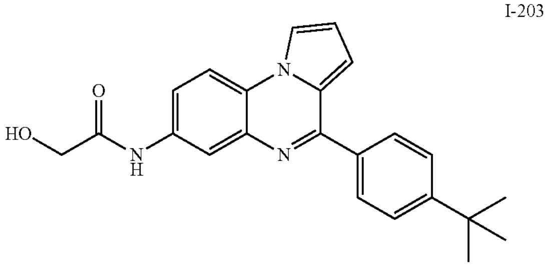
I-204
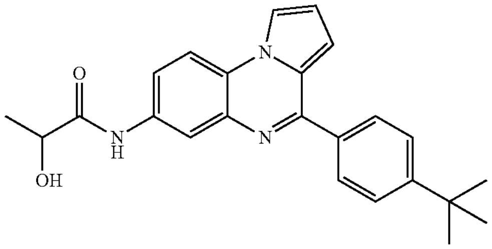
I-205
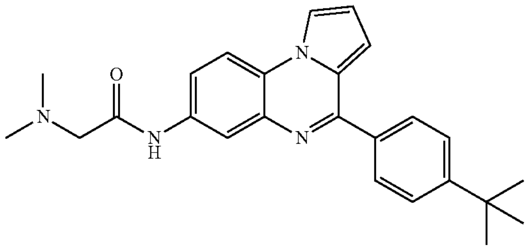
I-206
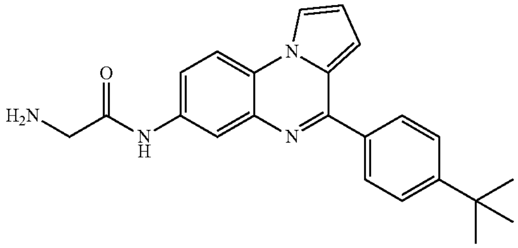
I-207
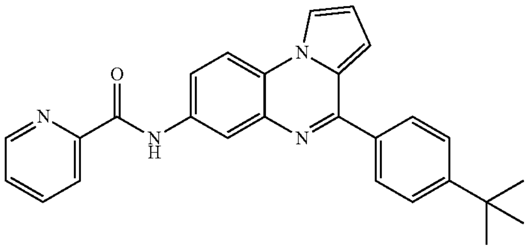
-continued
I-208
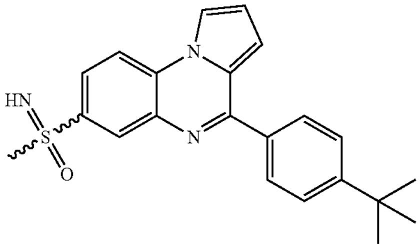
first eluting isomer ,
I-208a
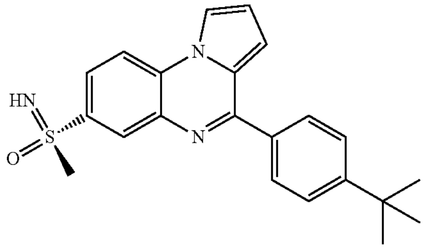
I-209
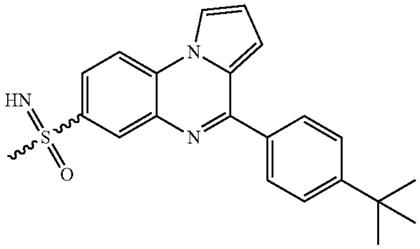
second eluting isomer ,
I-209a
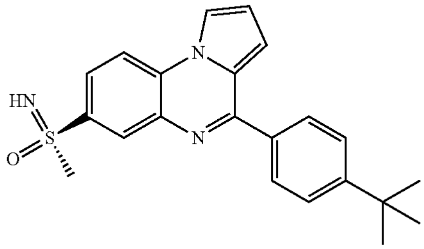
I-210
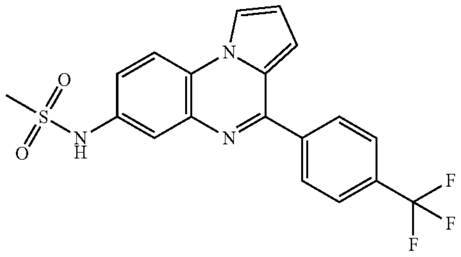
I-211
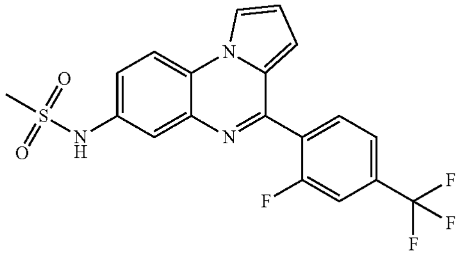

I-212
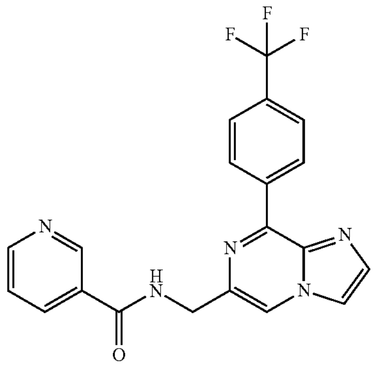
I-213
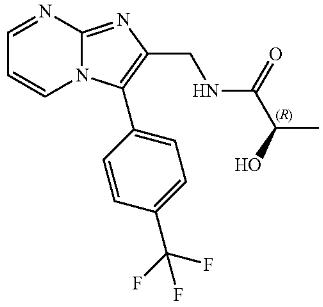
I-214
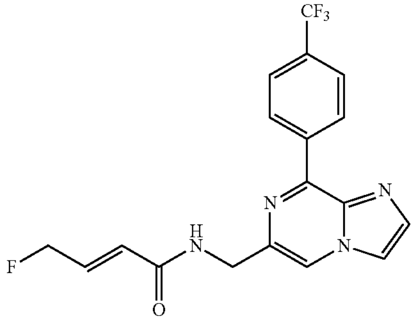
I-215
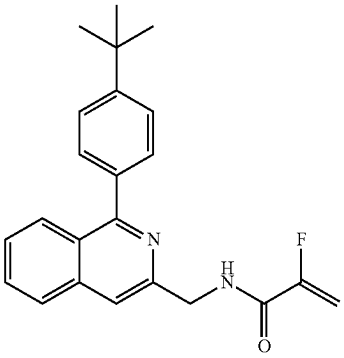
I-216
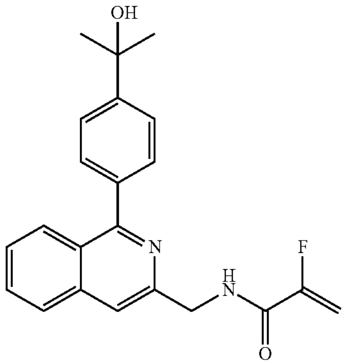
I-217
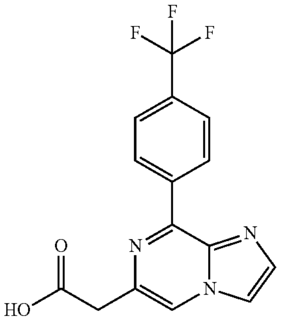
I-218
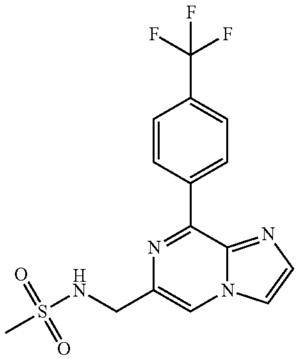
I-219
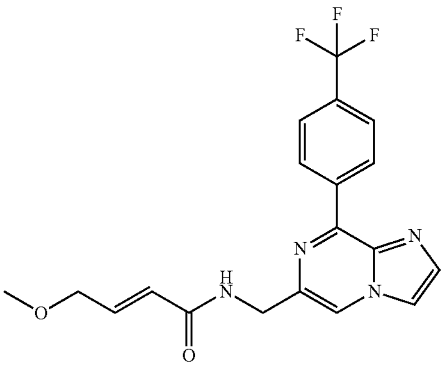

-continued
I-220
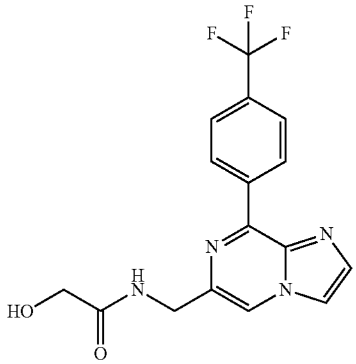
I-221
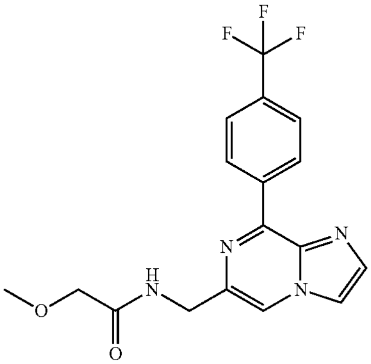
I-222
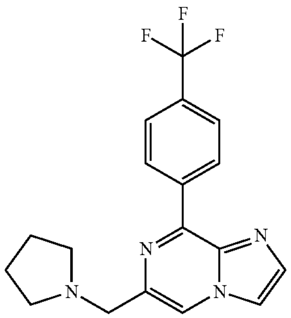
I-223
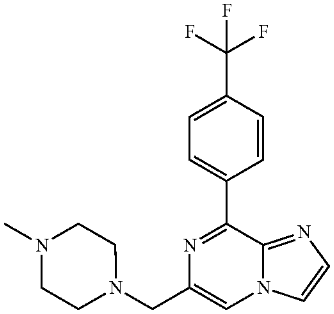
-continued
I-224
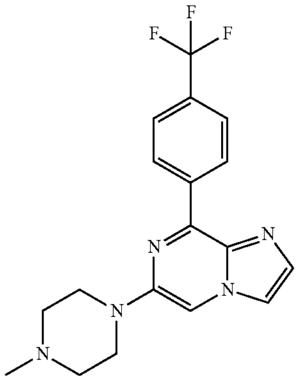
I-225
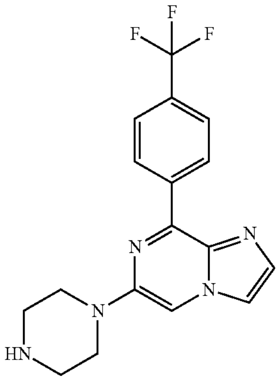
I-226
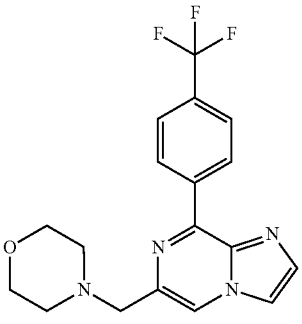
I-227
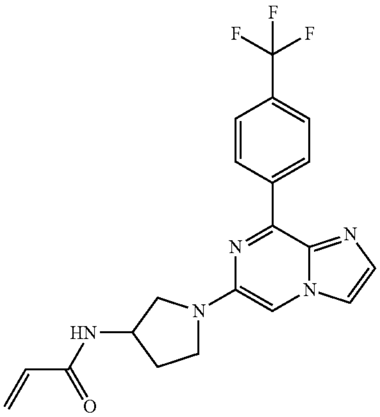

-continued
I-228
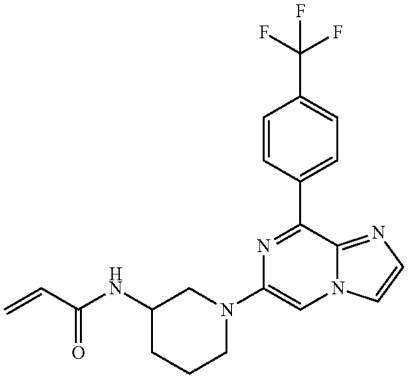
I-229
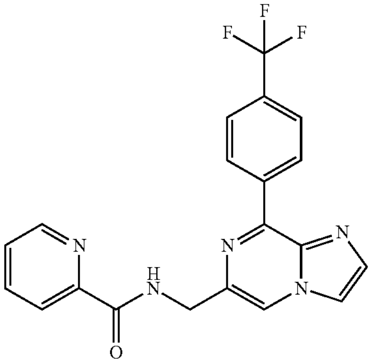
I-230
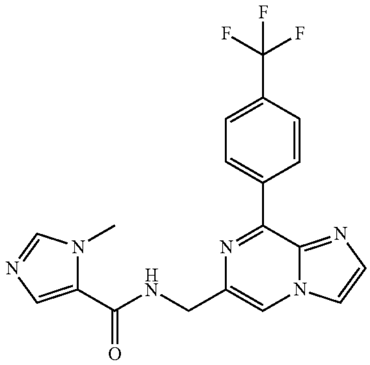
I-231
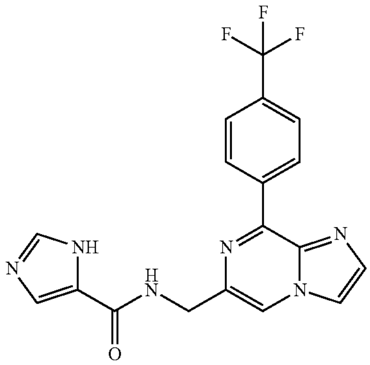
-continued
I-232
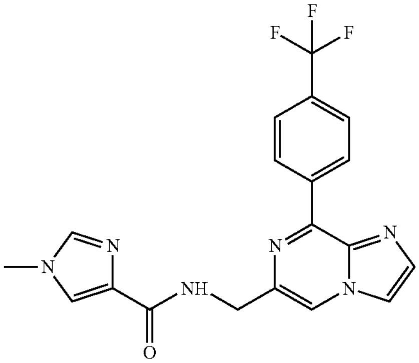
I-233
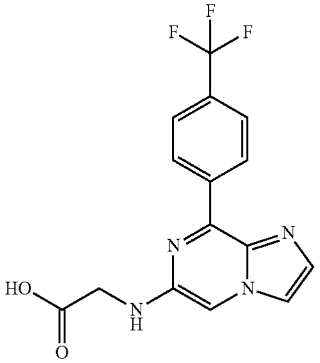
I-234
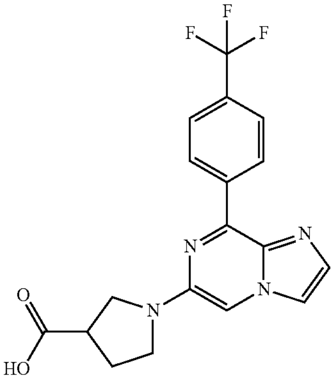
I-235
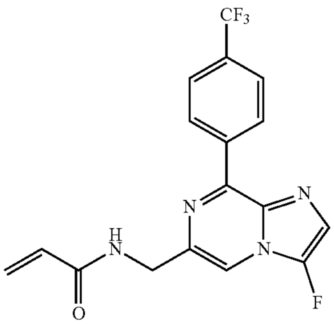

-continued
I-236
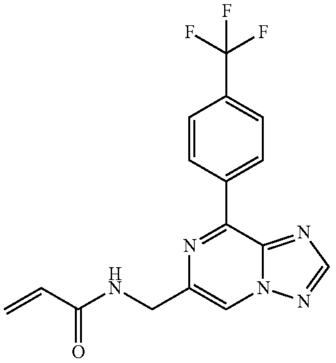
I-237
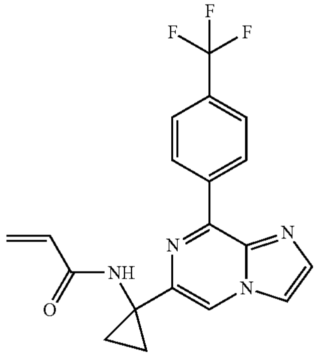
I-238
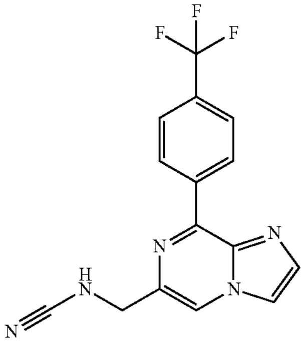
I-239
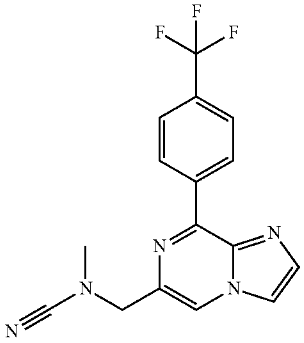
-continued
I-240
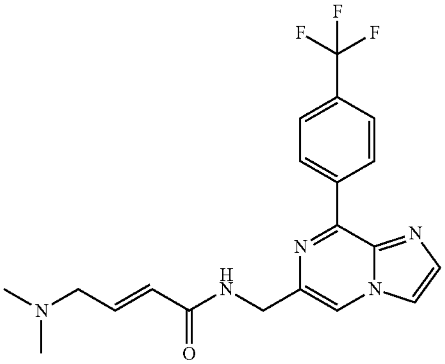
I-241
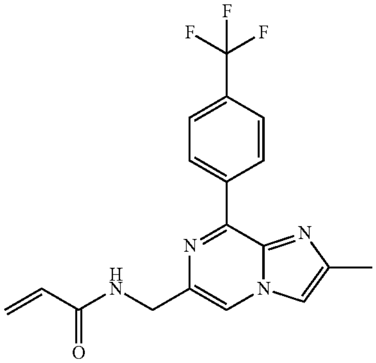
I-242
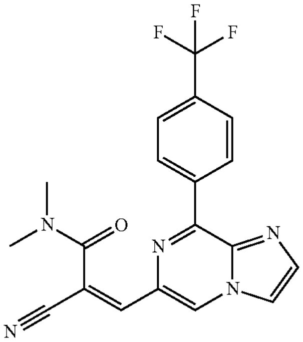
I-243
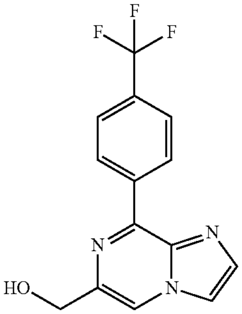

-continued
I-244
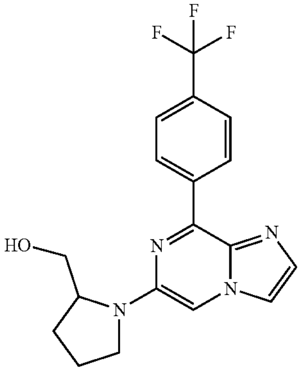
I-245
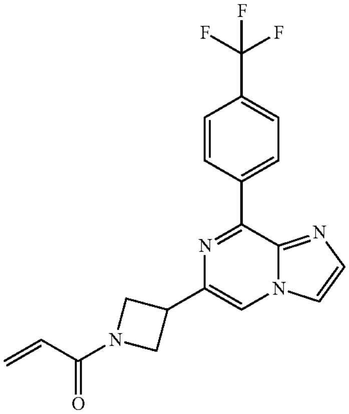
I-246
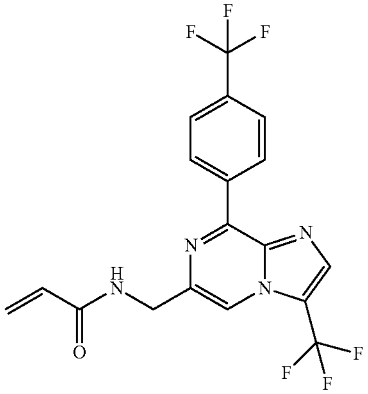
I-247
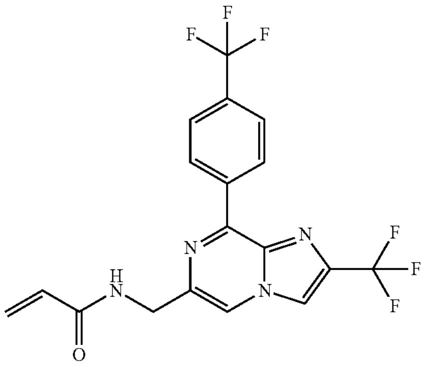
-continued
I-248
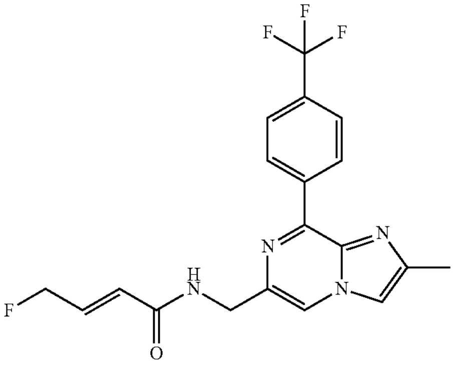
I-249
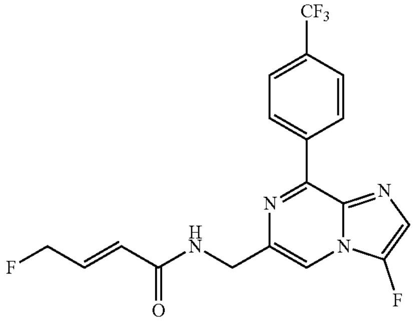
I-250
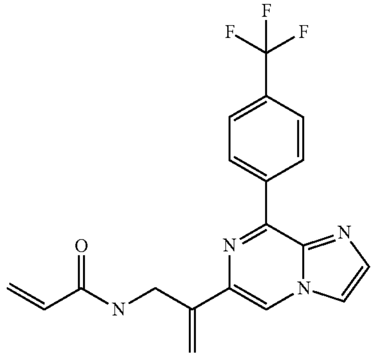
I-251
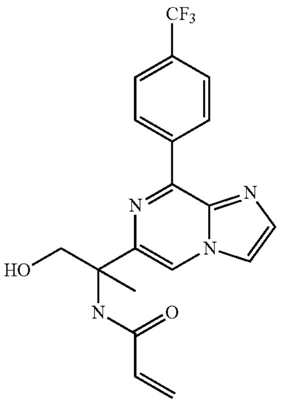

-continued
I-252
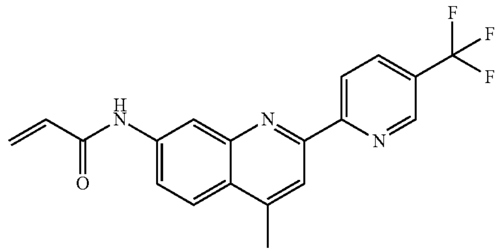
I-253
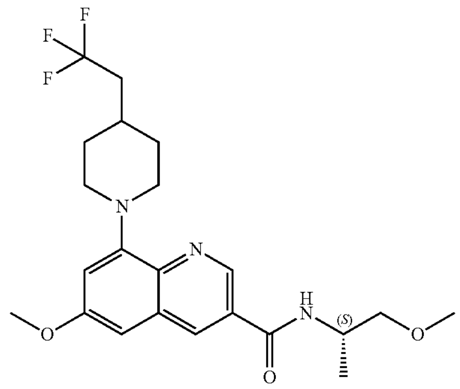
I-254
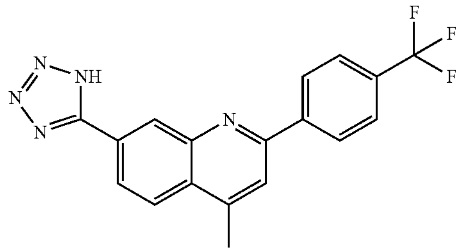
I-255
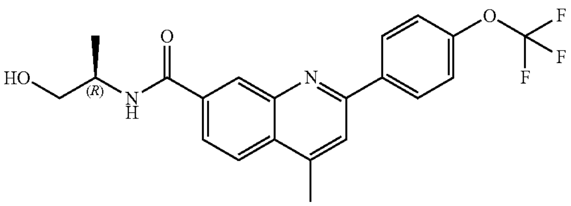
I-256
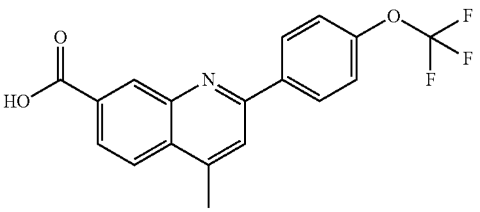
-continued
I-257
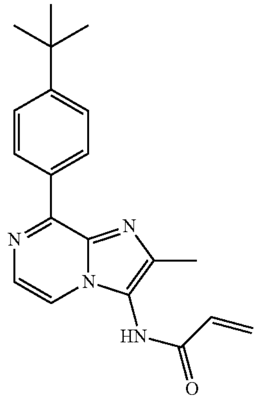
I-258
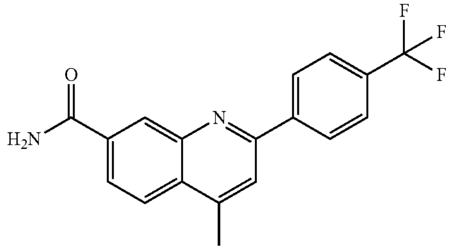
I-259
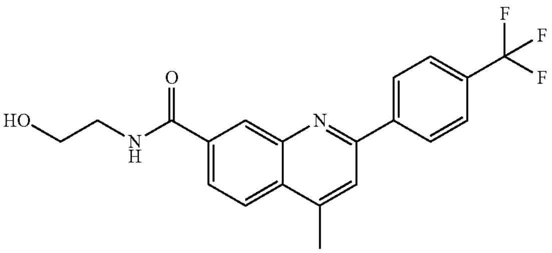
I-260
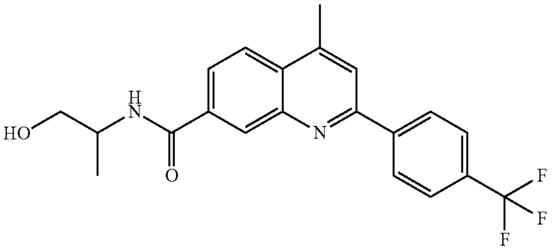
I-261
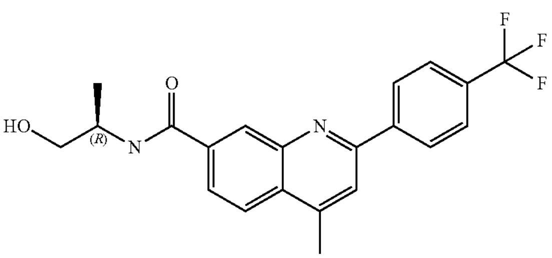

-continued
I-262
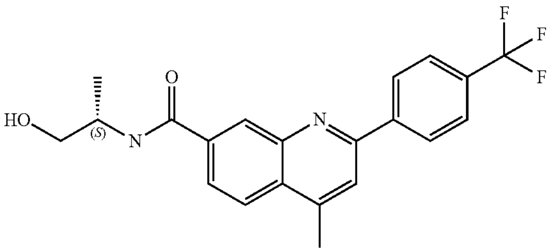
I-263
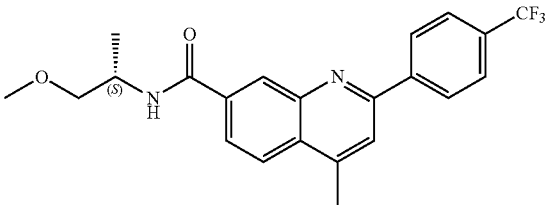
I-264
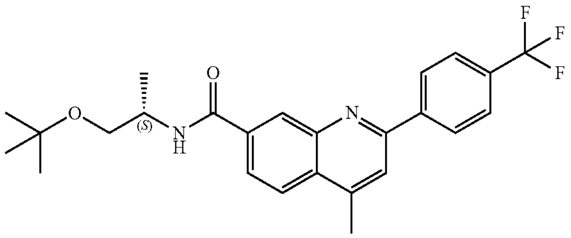
I-265
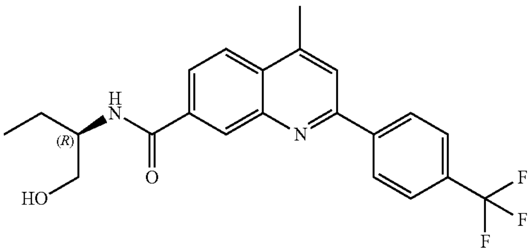
I-266
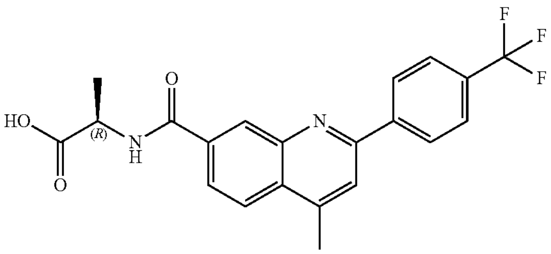
I-267
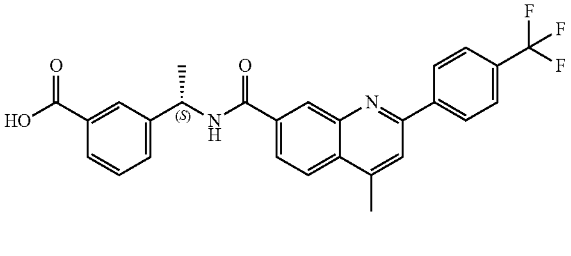
-continued
I-268
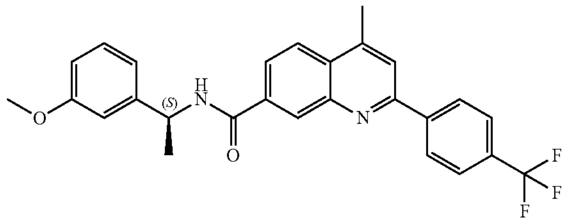
I-269
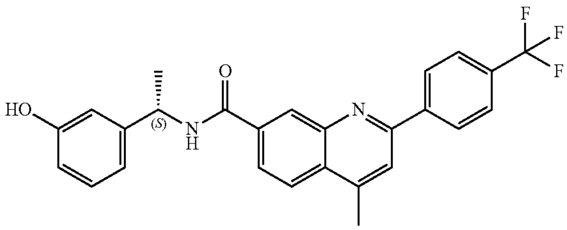
I-270
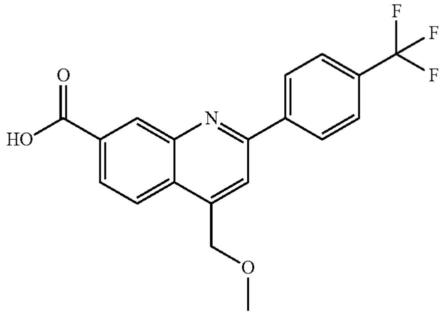
I-271
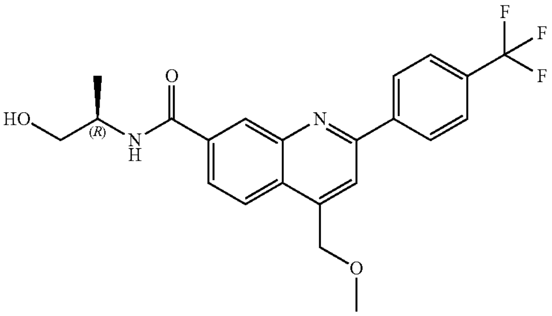
I-272
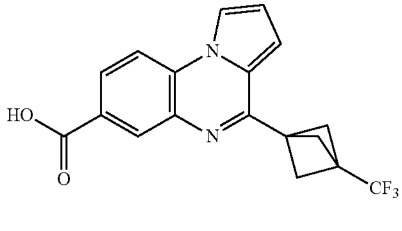

-continued
I-273
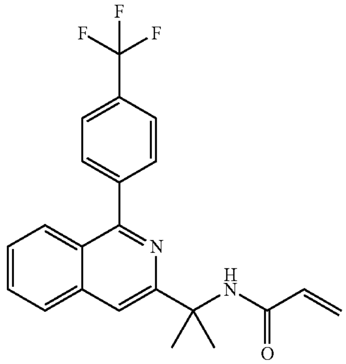
I-274
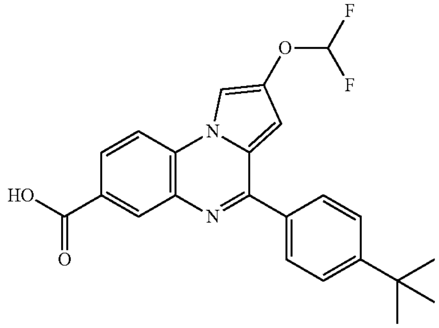
I-275
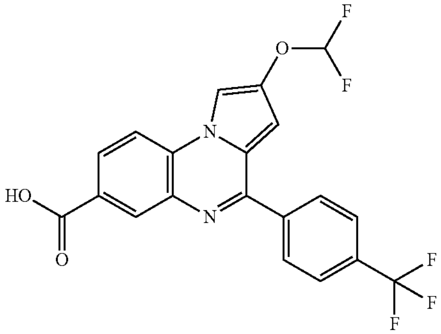
I-276
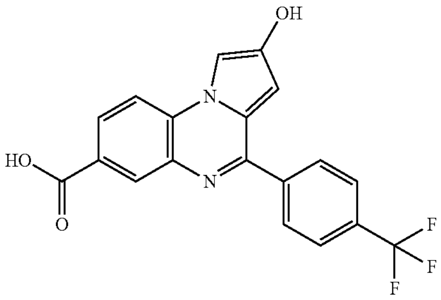
I-277
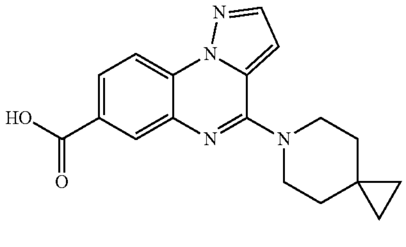
-continued
I-278
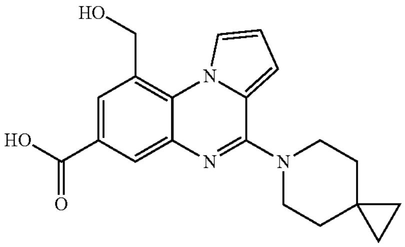
I-279
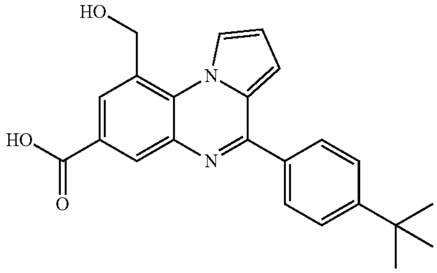
I-280
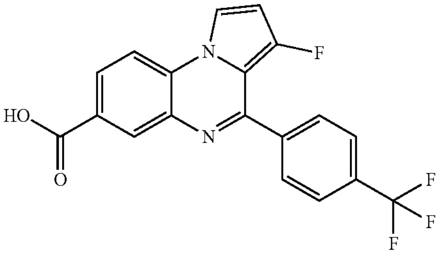
I-281
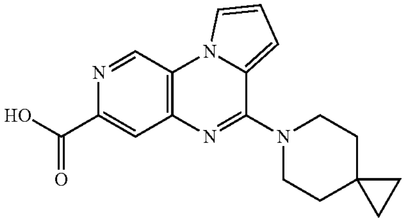
I-282
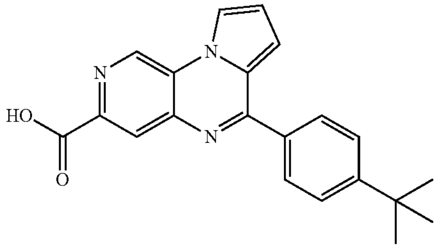
I-283
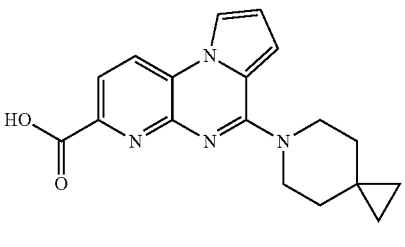

-continued
I-284
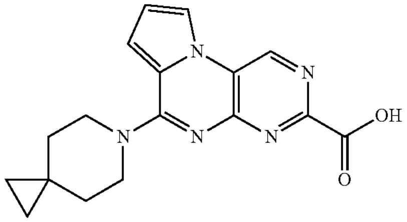
I-285
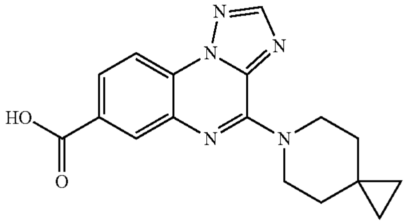
I-286
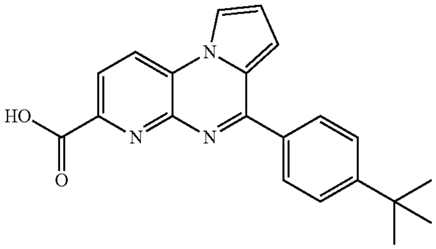
I-287
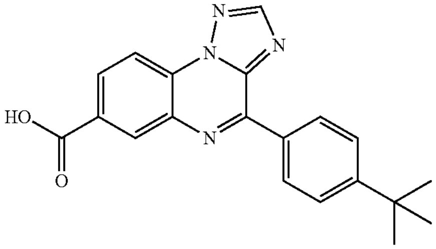
I-288
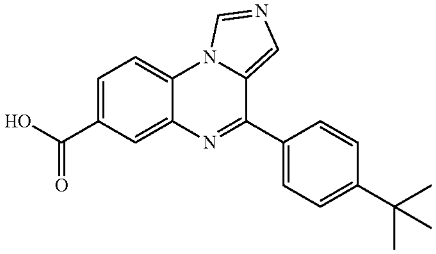
I-289
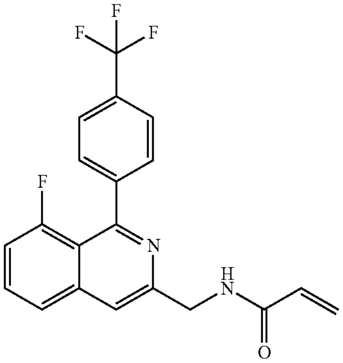
-continued
I-290
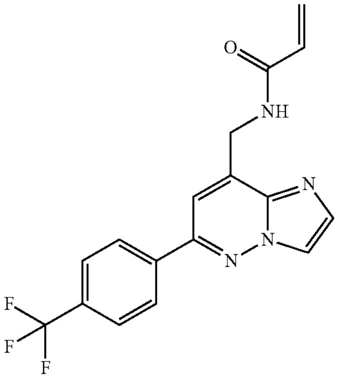
I-291
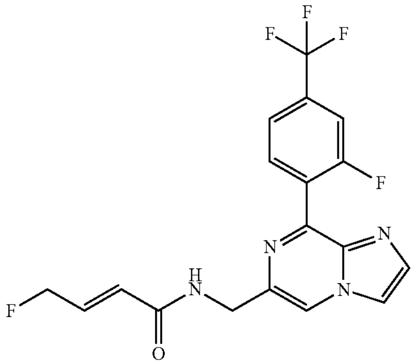
I-292
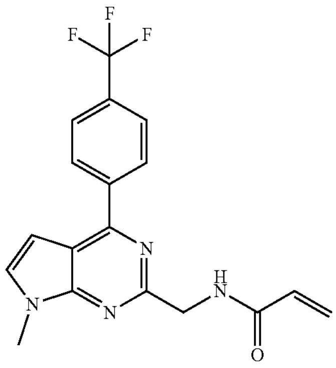
I-293
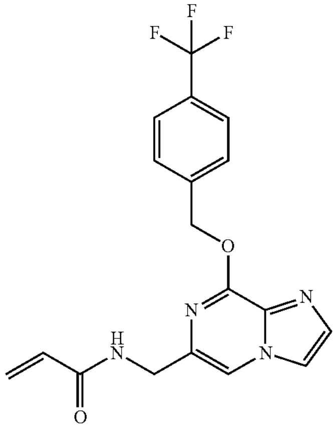

-continued
I-294
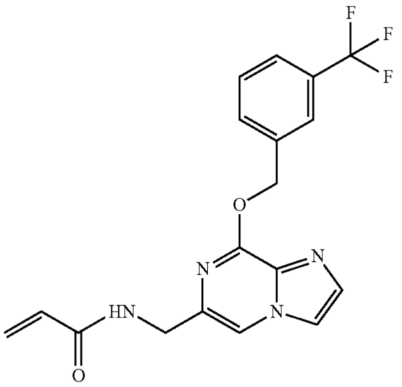
I-295
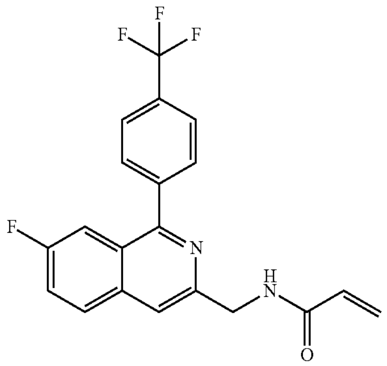
I-296
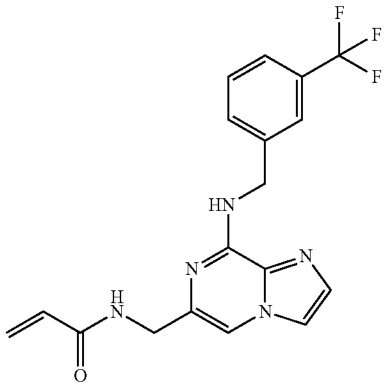
I-297
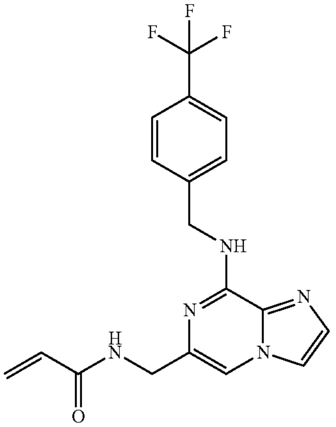
-continued
I-298
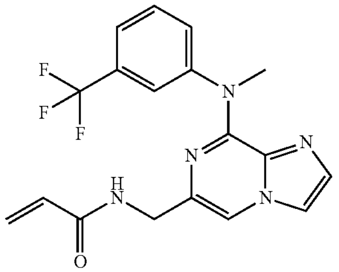
I-299
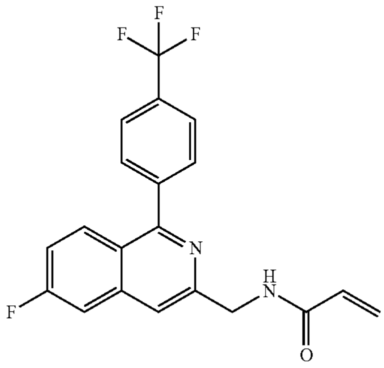
I-300
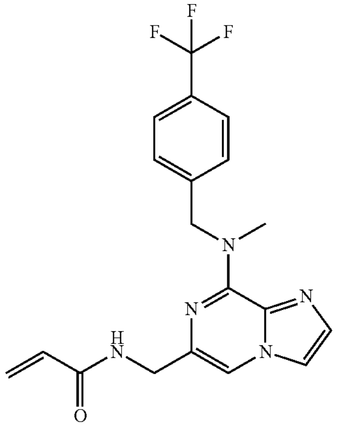
I-301
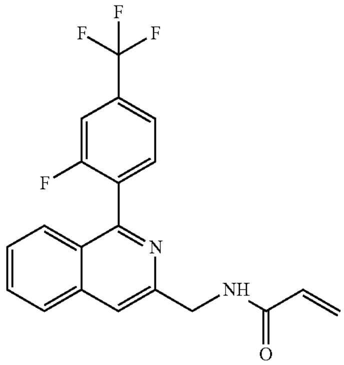

-continued
I-302
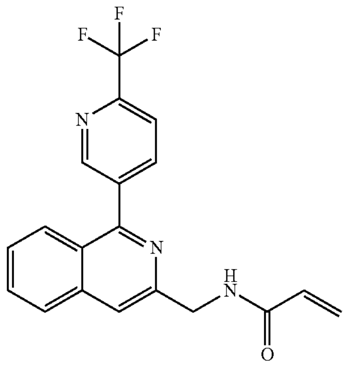
I-303
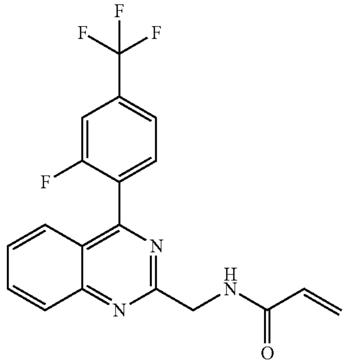
I-304
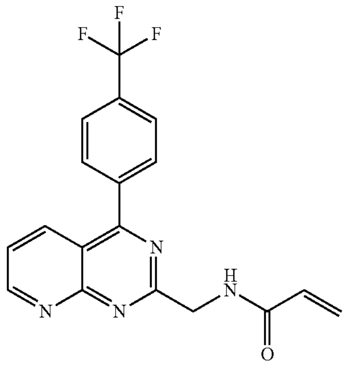
I-305
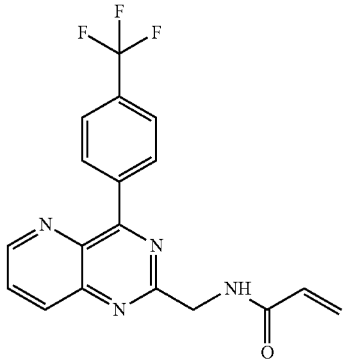
-continued
I-306
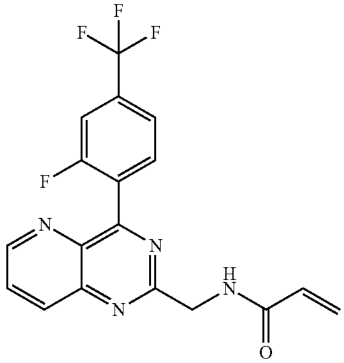
I-307
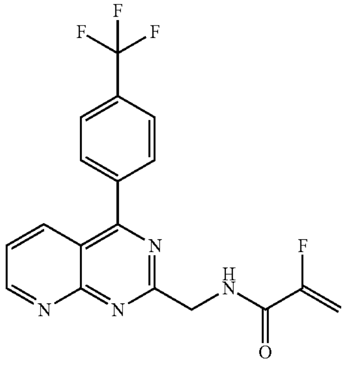
I-308
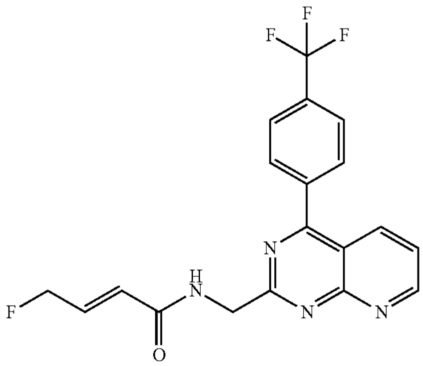
I-309
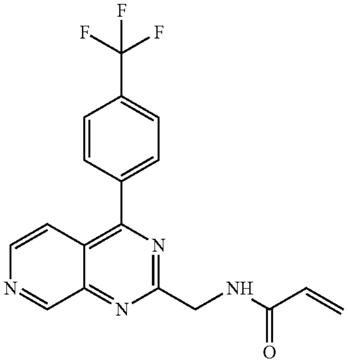

-continued
I-310
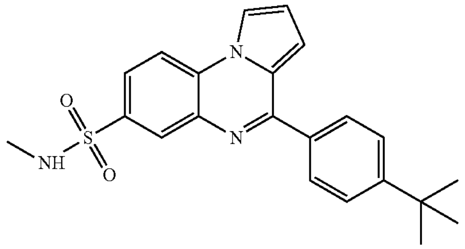
I-311
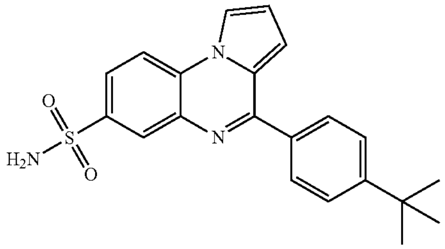
I-312
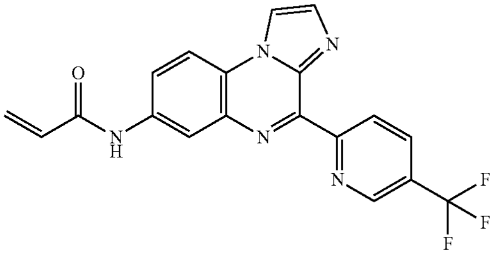
I-313
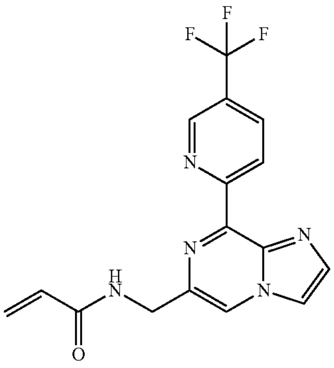
I-314
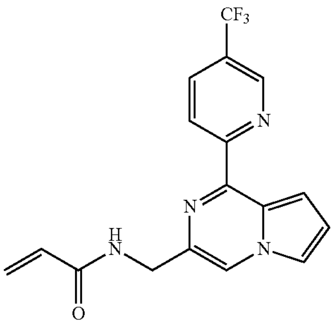
-continued
I-315
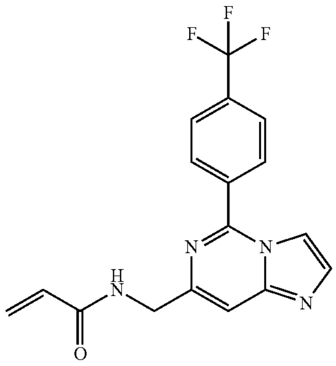
I-316
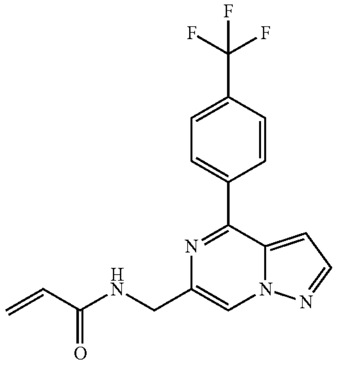
I-317
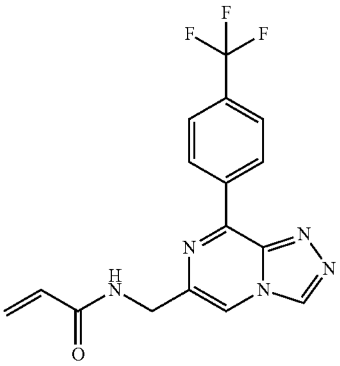
I-318
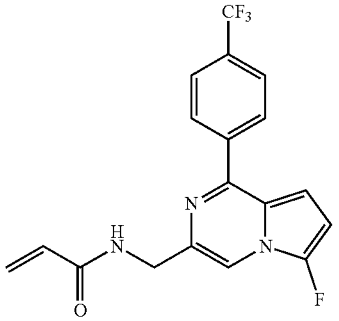

-continued
I-319
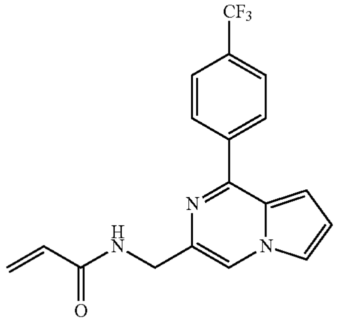
I-320
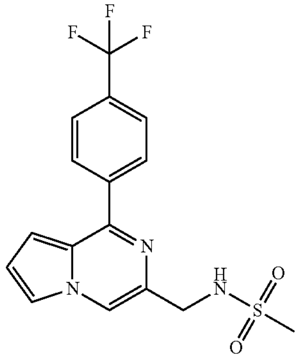
I-321
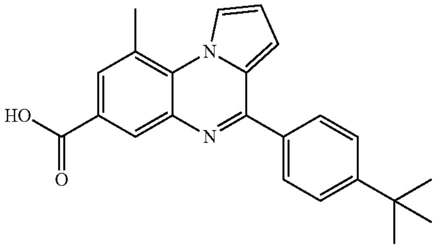
I-322
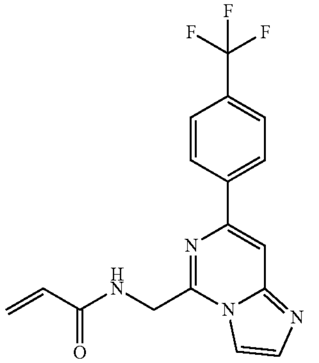
I-323
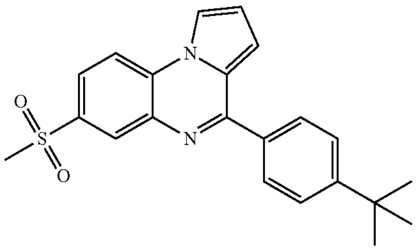
-continued
I-324
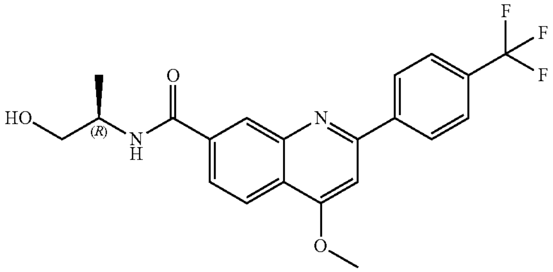
I-325
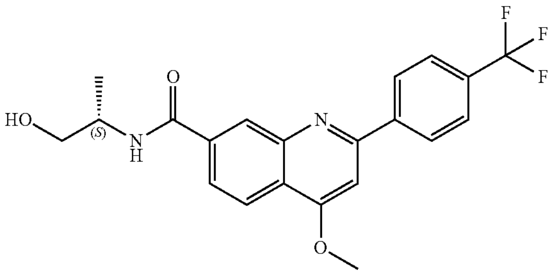
I-326
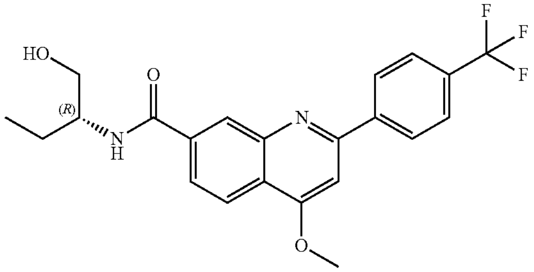
I-327
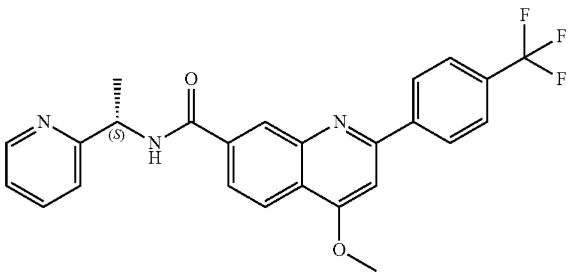
I-328
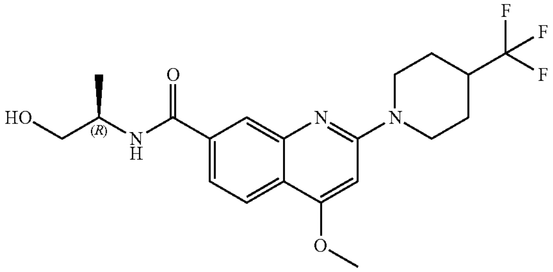

-continued
I-329
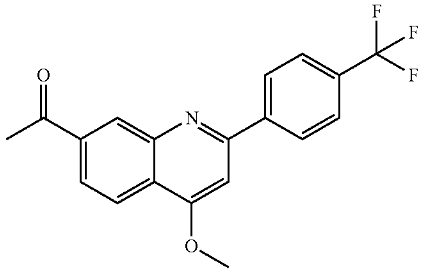
I-330
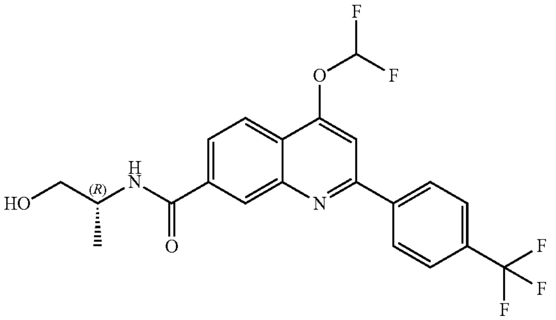
I-331
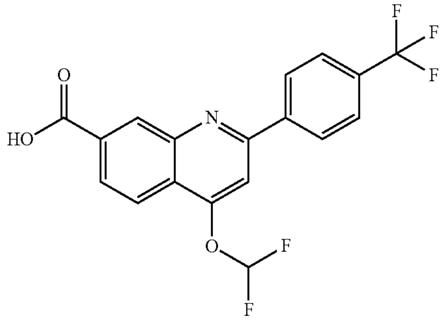
I-332
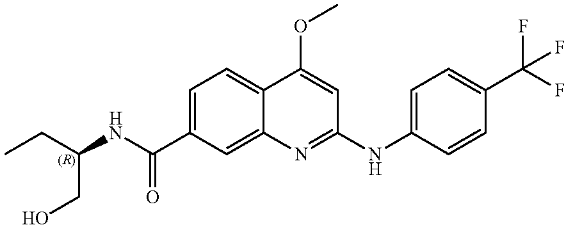
I-333
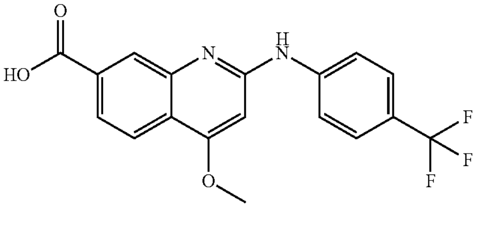
-continued
I-334
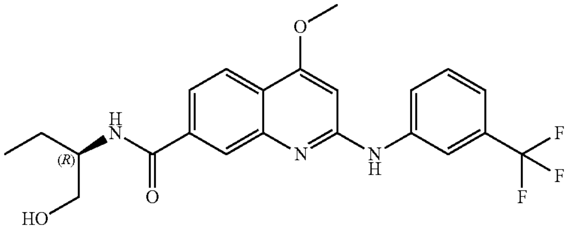
I-335
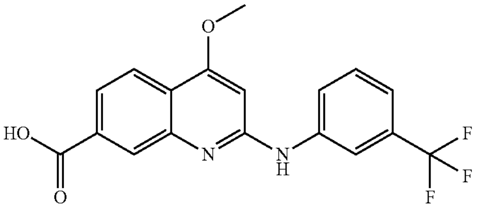
I-336
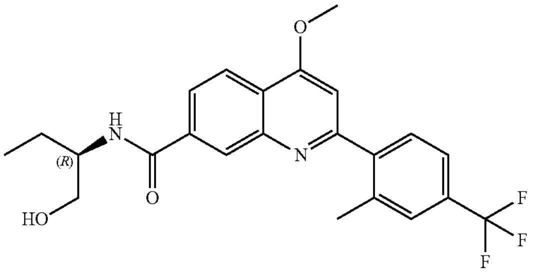
I-337
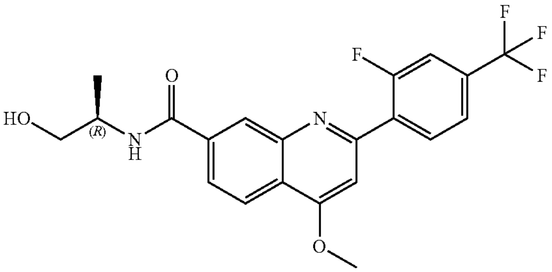
I-338
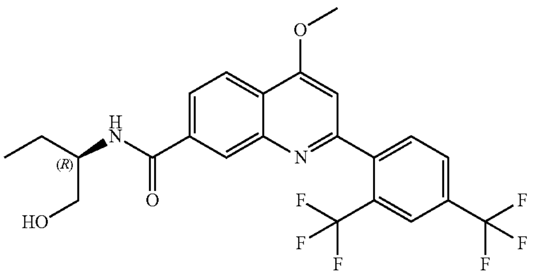

-continued
I-339
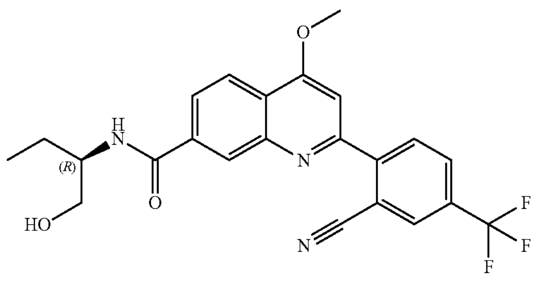
I-340
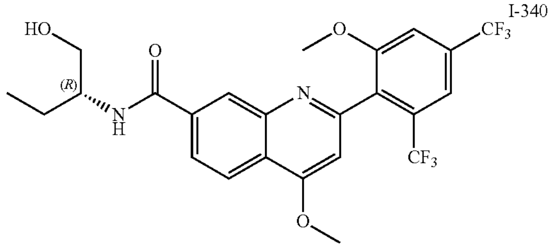
I-341
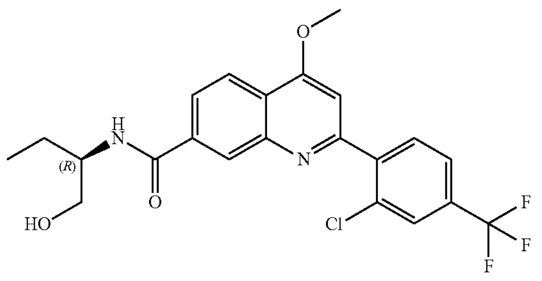
I-342
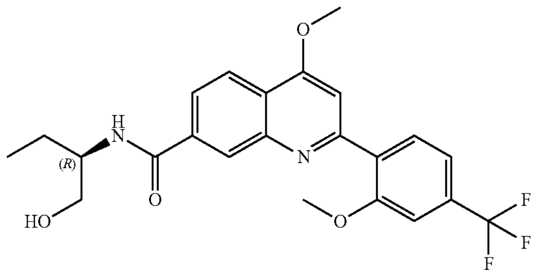
I-343
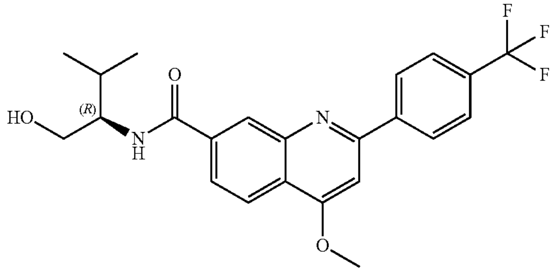
-continued
I-344
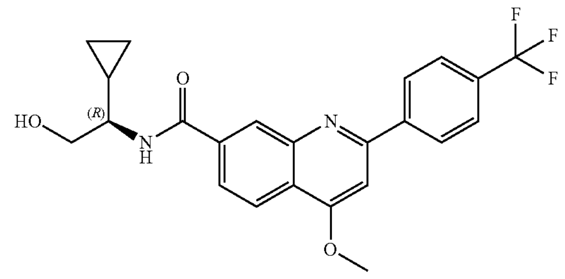
I-345
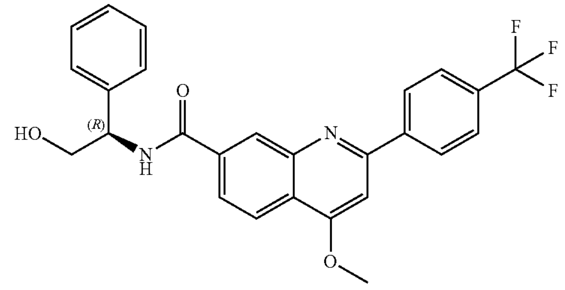
I-346
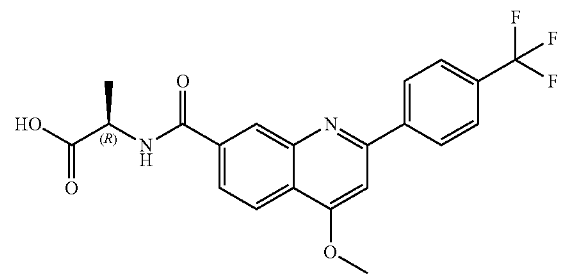
I-347
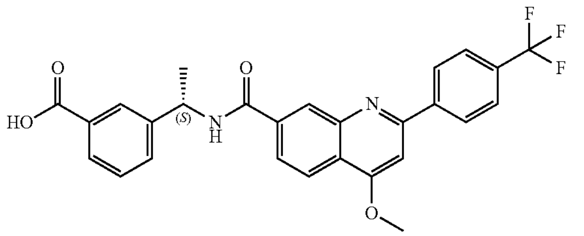
I-348
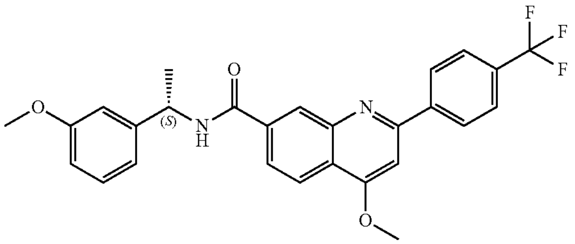

-continued
I-349
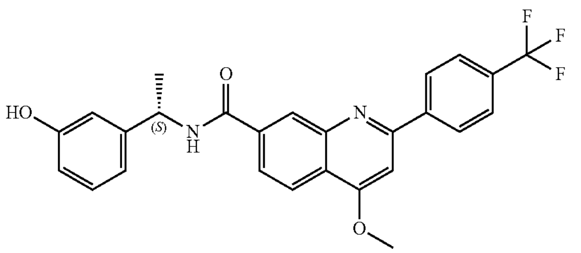
I-350
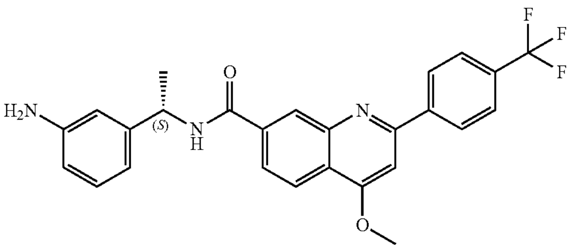
I-351
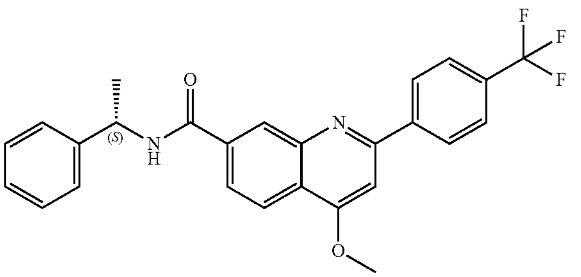
I-352
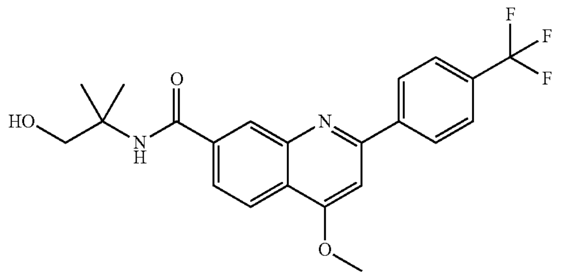
I-353
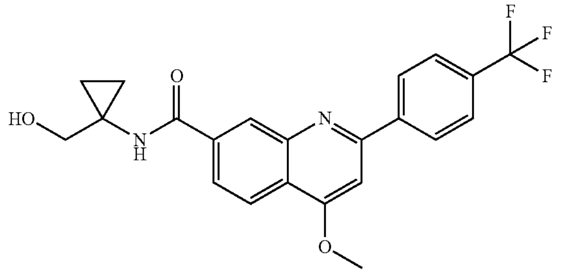
-continued
I-354
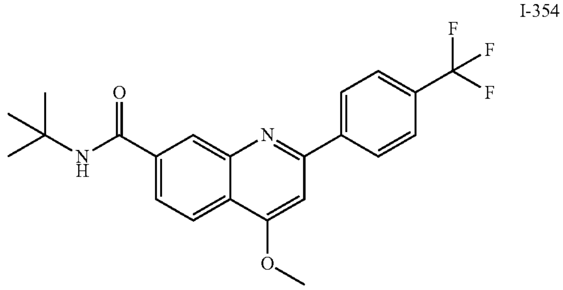
I-355
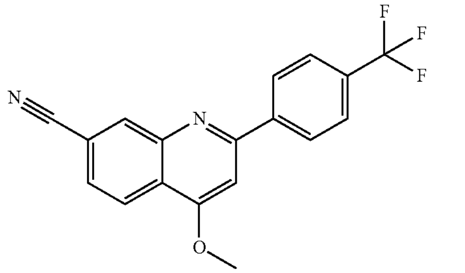
I-356
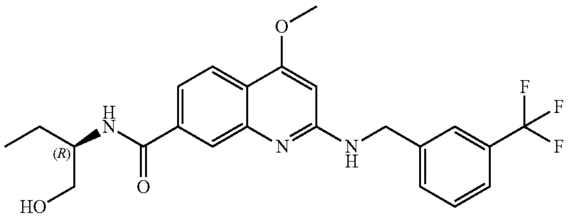
I-357
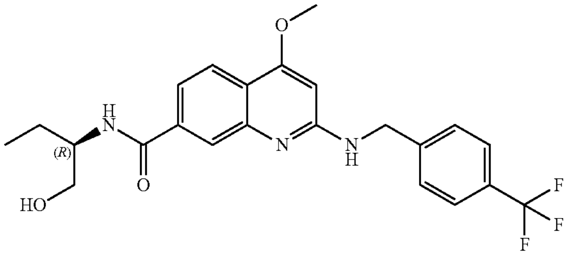
I-358
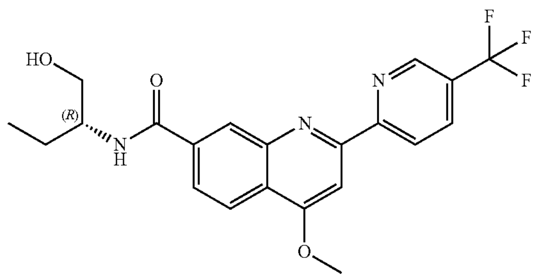
I-359
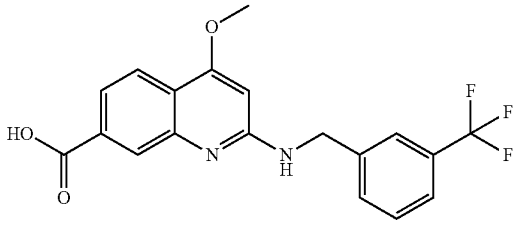

-continued
I-360
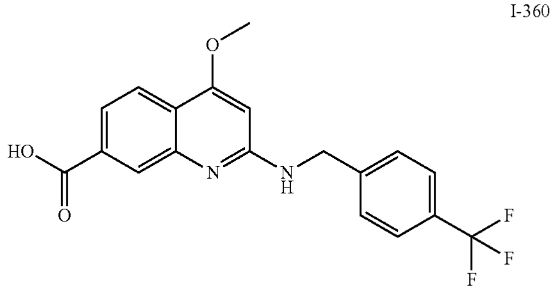
I-361
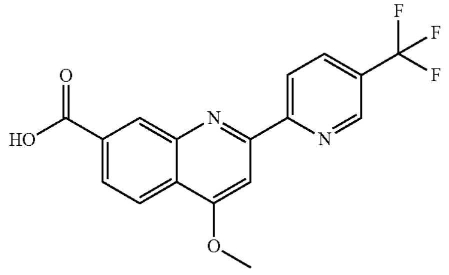
I-362
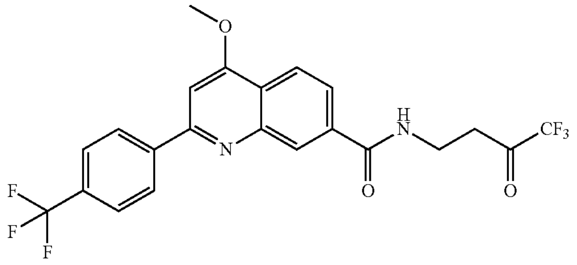
I-363
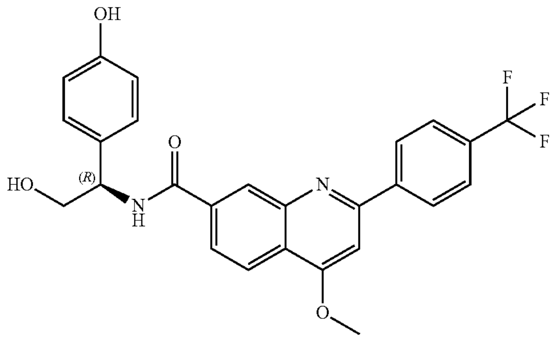
I-364
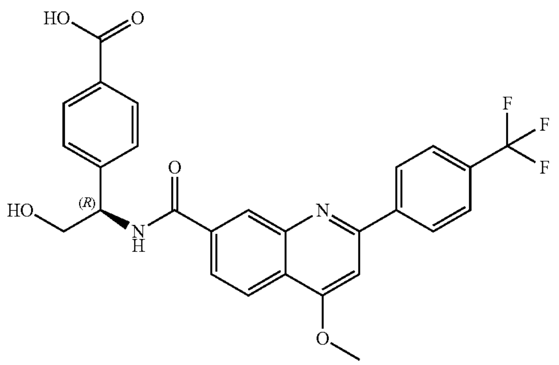
-continued
I-365
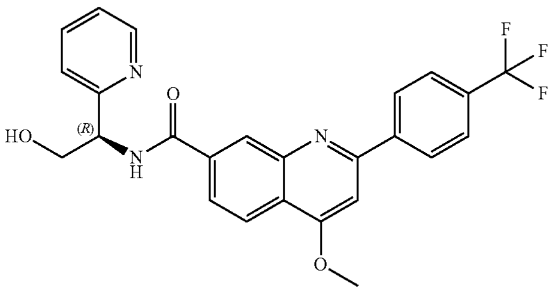
I-366
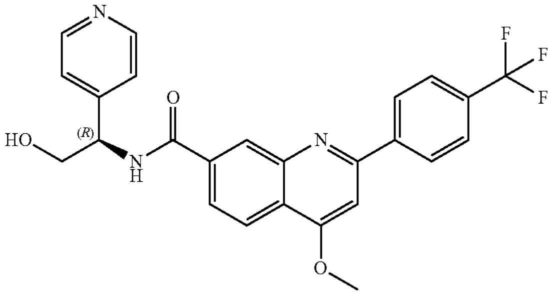
I-367
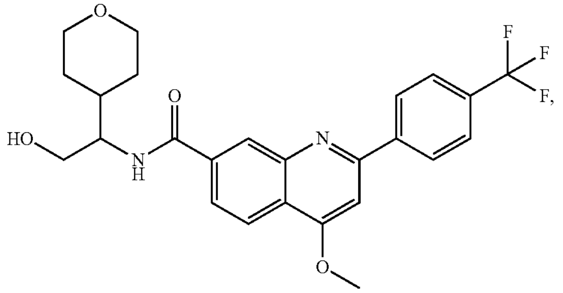
first eluting isomer
I-367a
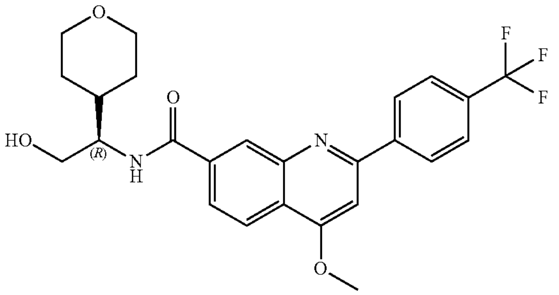
I-368
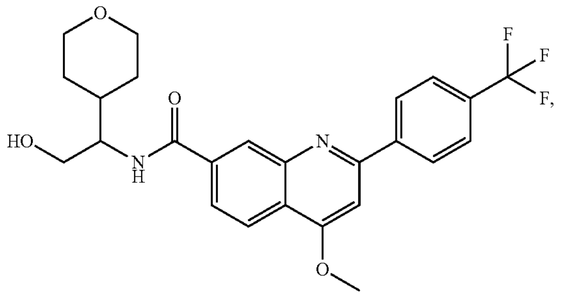
second eluting isomer -continued
I-368a
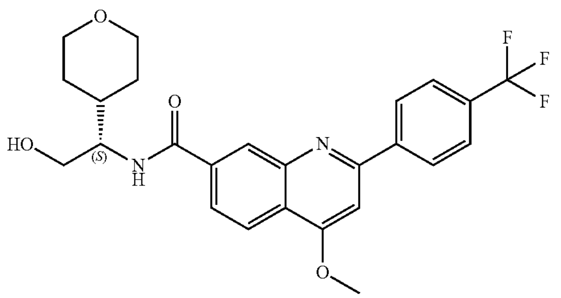
I-369
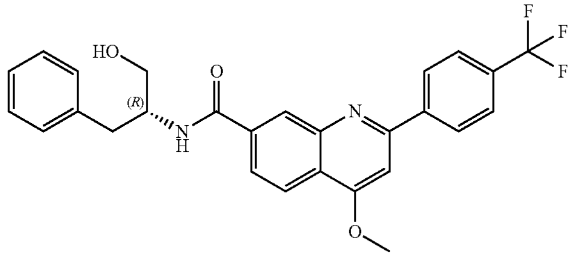
I-370
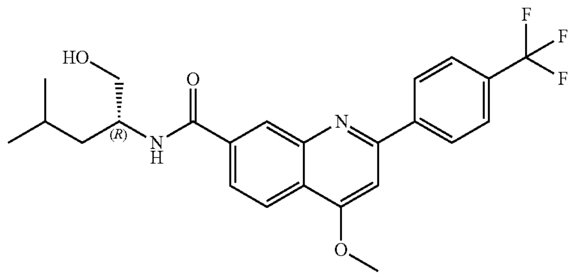
I-371
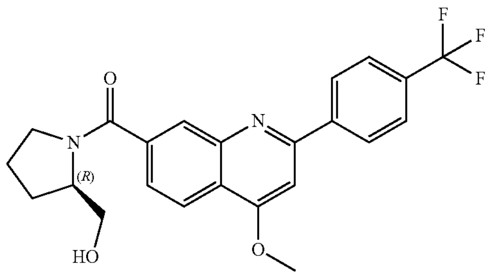
I-372
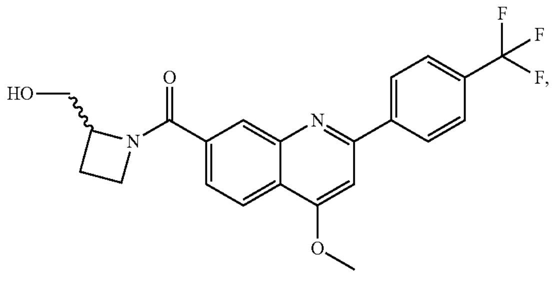
first eluting isomer
-continued
I-372a
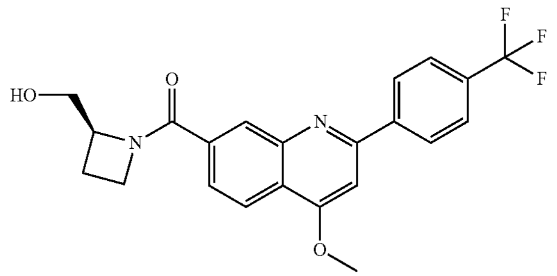
I-373
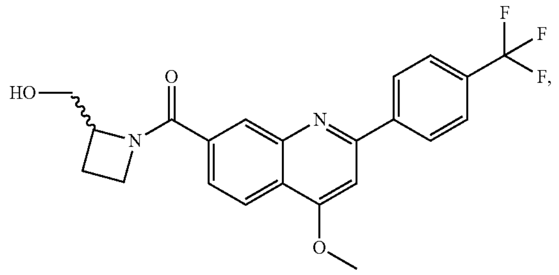
second eluting isomer
I-373a
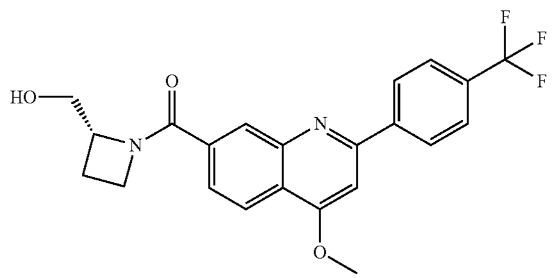
I-374
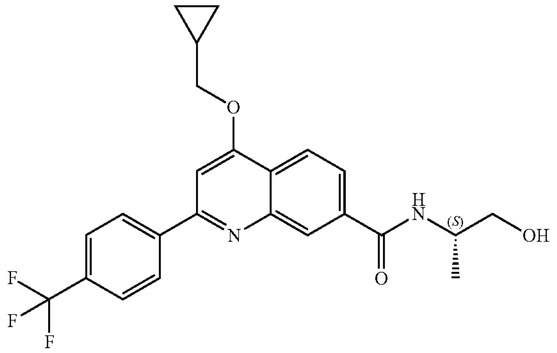

-continued
I-375
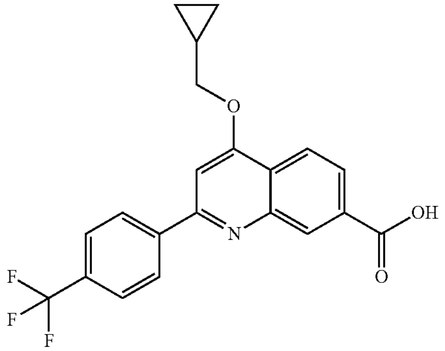
I-376
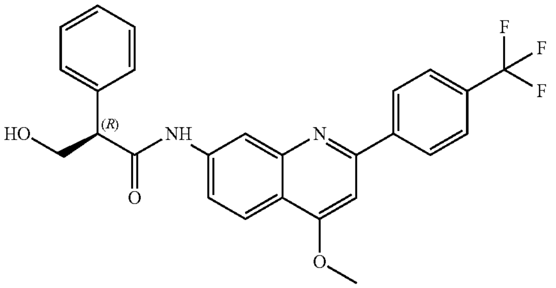
I-377
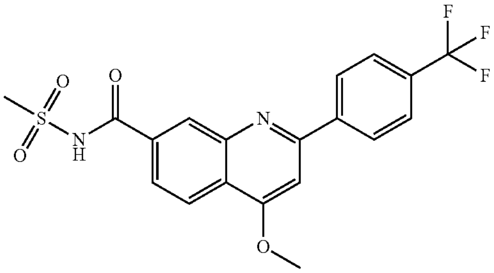
I-378
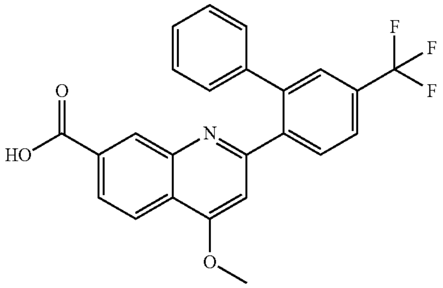
I-379
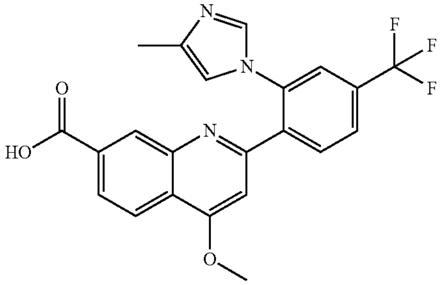
-continued
I-380
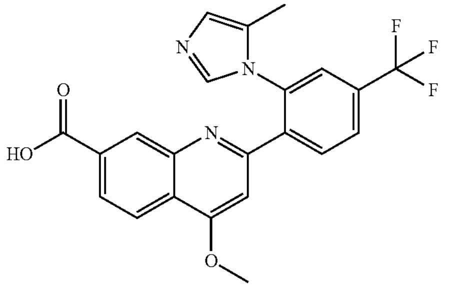
I-381
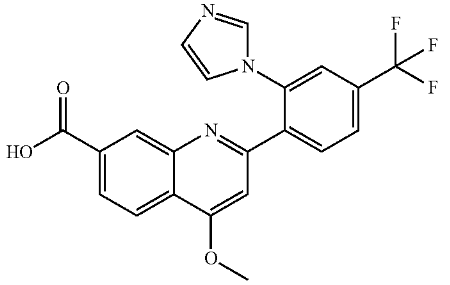
I-382
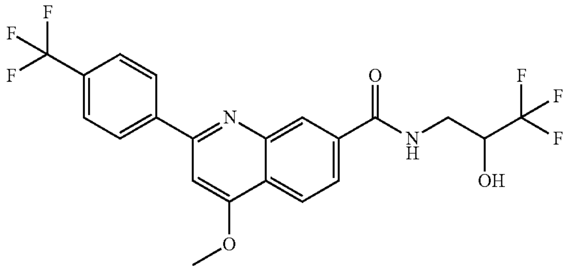
I-383
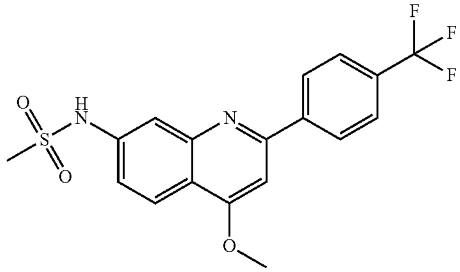
I-384
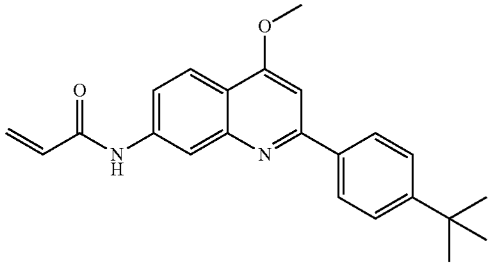
I-385
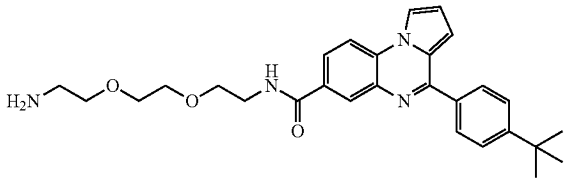

I-386
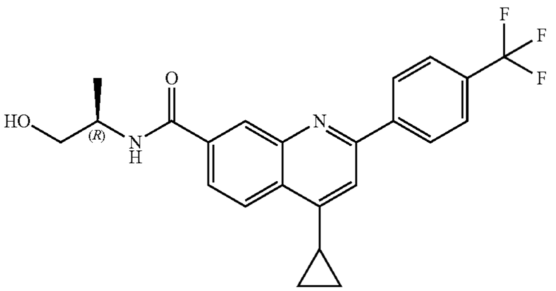
I-387
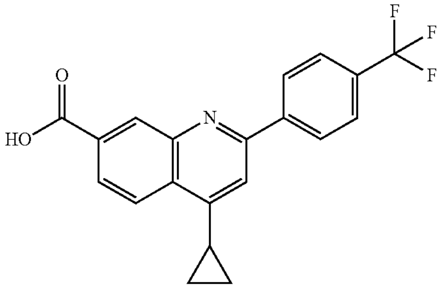
I-388
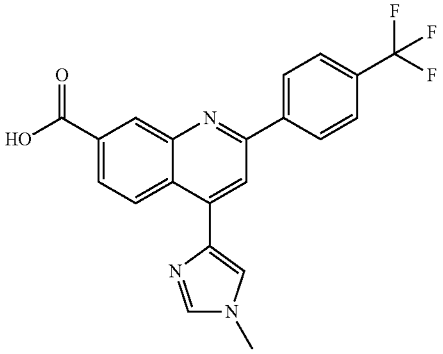
I-389
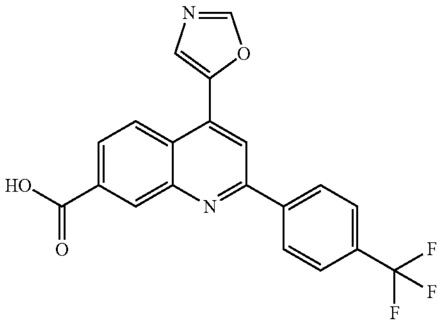
I-390
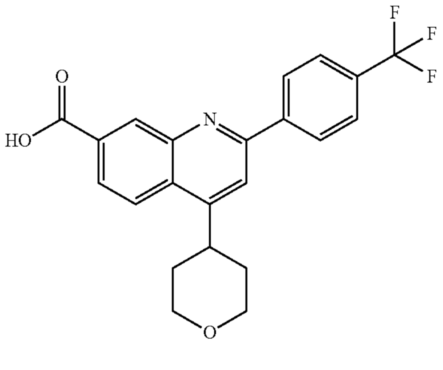
I-391
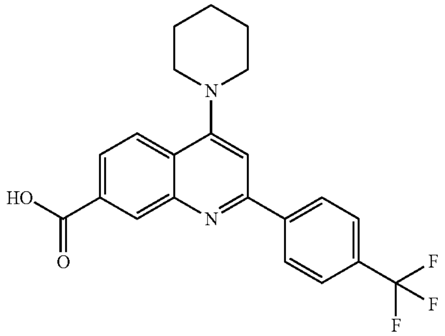
I-392
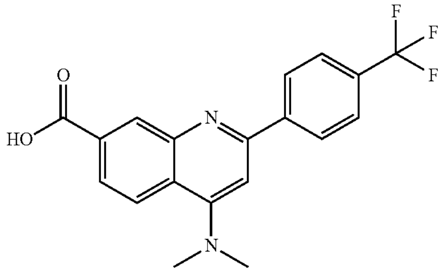
I-393
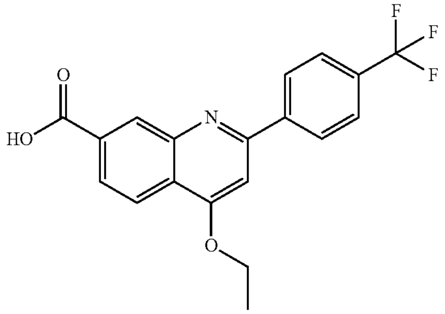
I-394
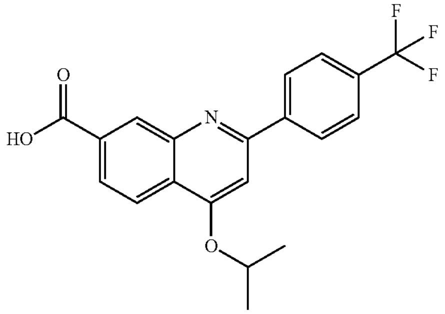
I-395
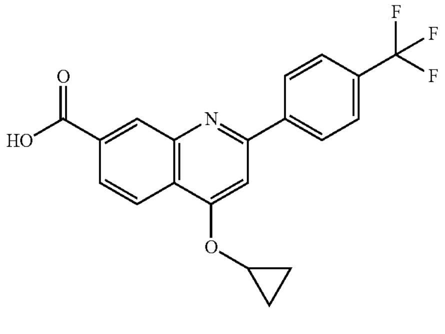

-continued
I-396
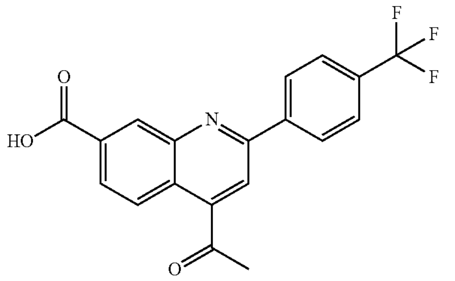
I-397
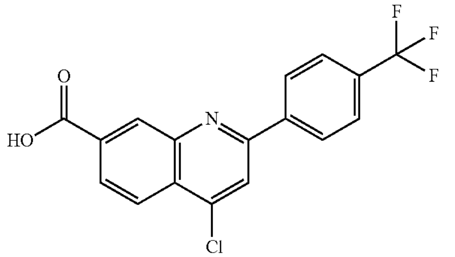
I-398
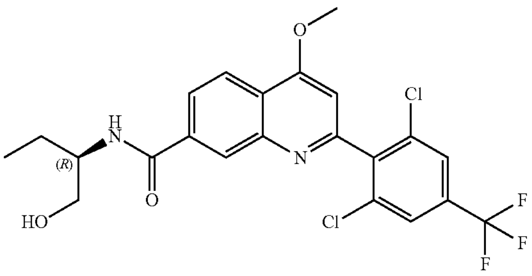
I-399
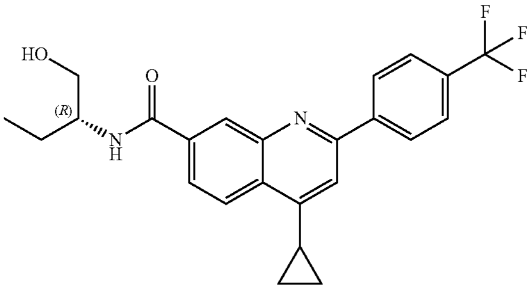
I-400
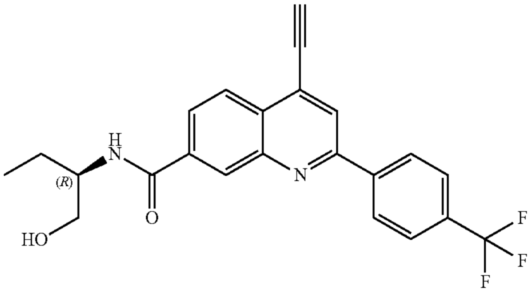
-continued
I-401
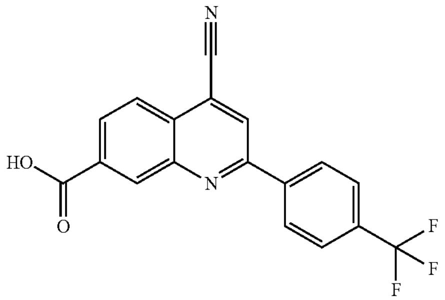
I-402
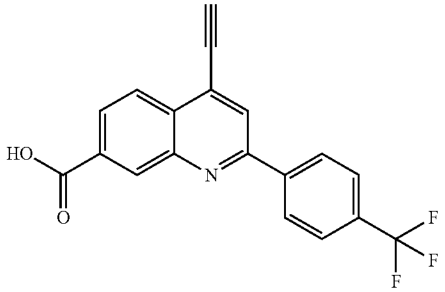
I-403
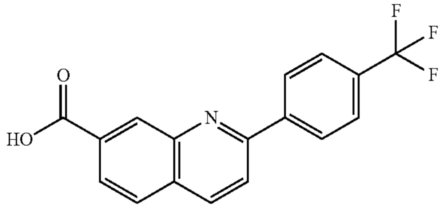
I-404
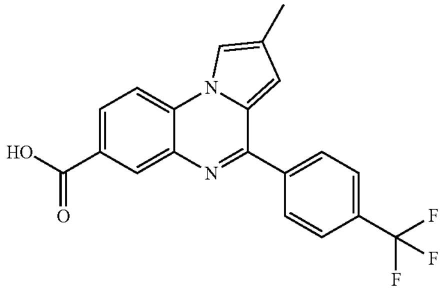
I-405
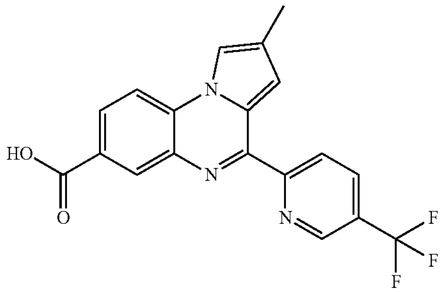

-continued
I-406
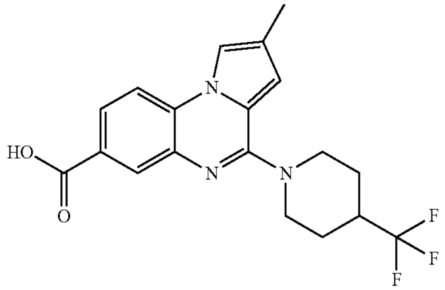
I-407
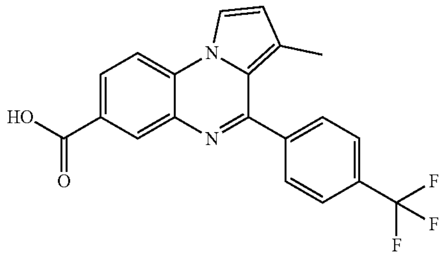
I-408
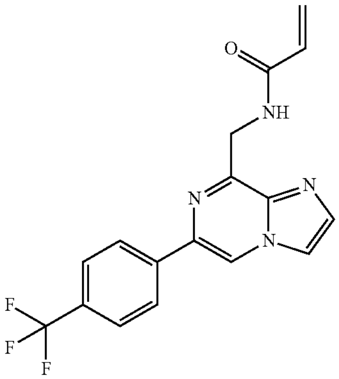
I-409
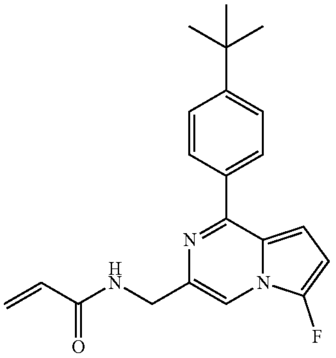
I-410
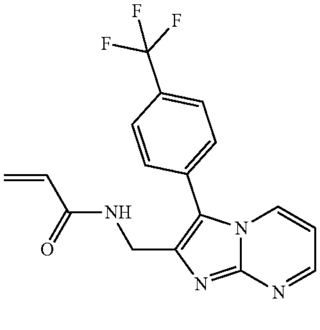
-continued
I-411
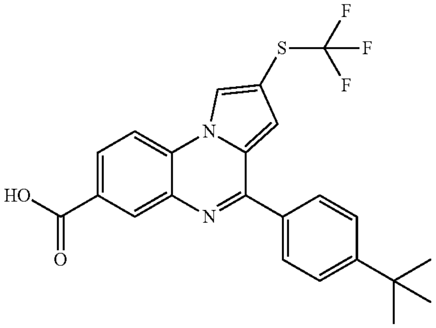
I-412
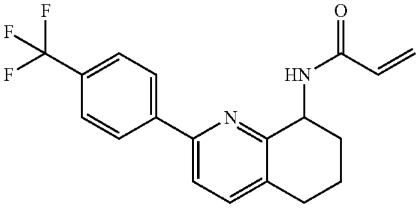
I-413
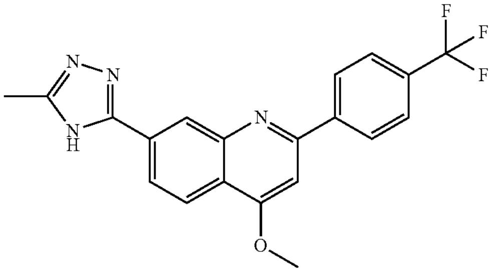
I-414
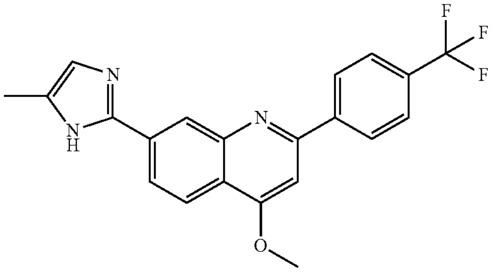
I-415
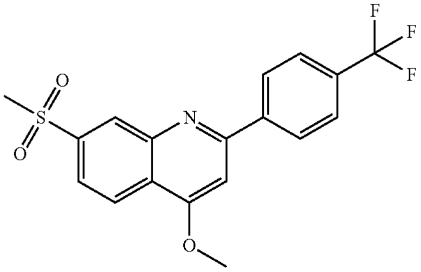

-continued
I-416
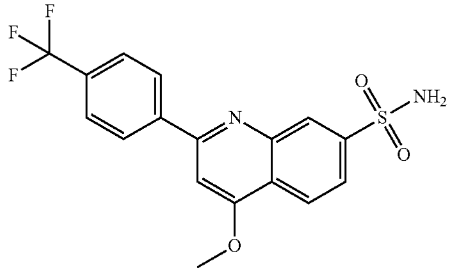
I-417
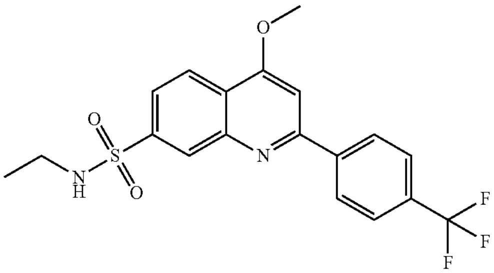
I-418
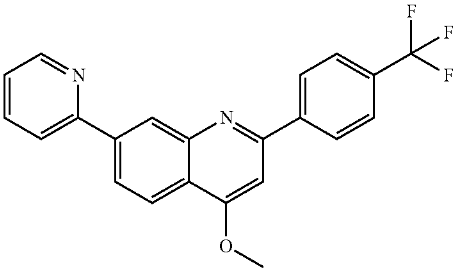
I-419
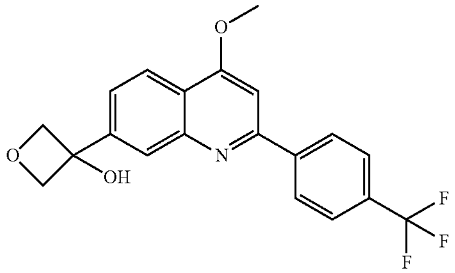
I-420
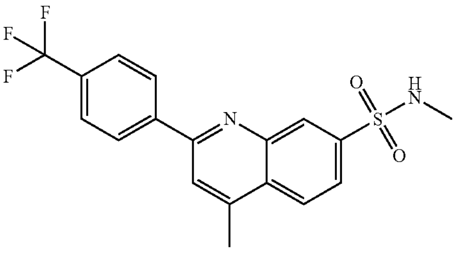
-continued
I-421
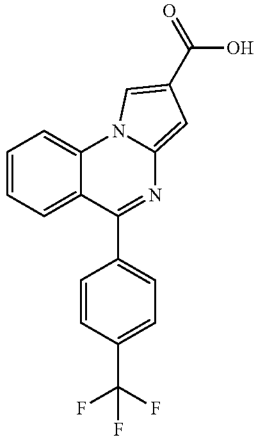
I-422
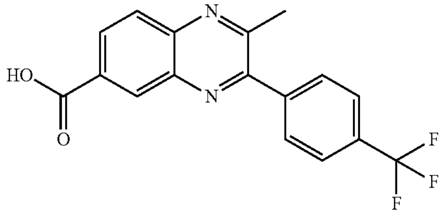
I-423
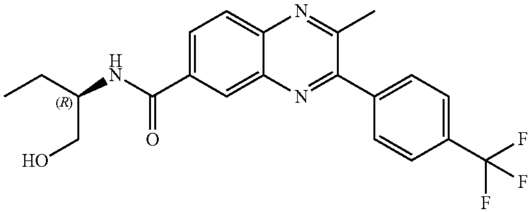
I-424
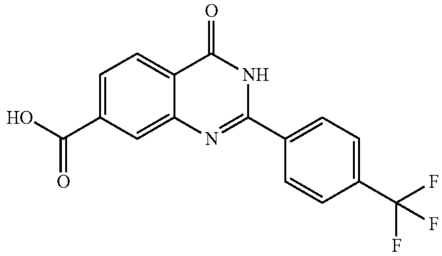
I-425
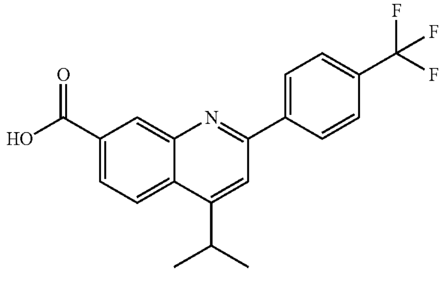

-continued
I-426
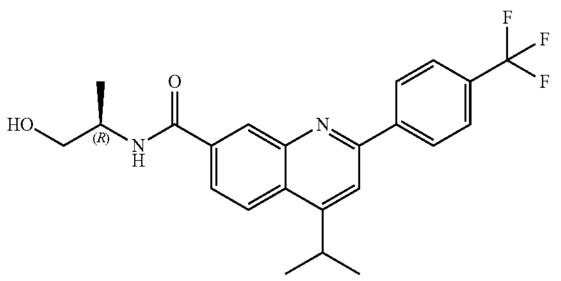
I-427
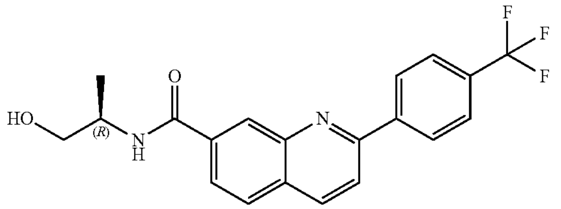
I-428
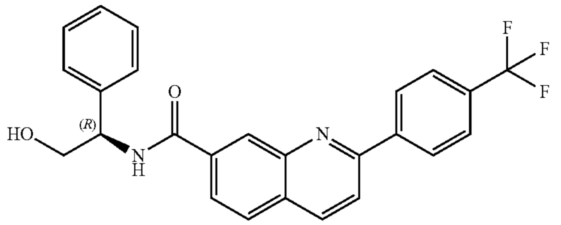
I-429
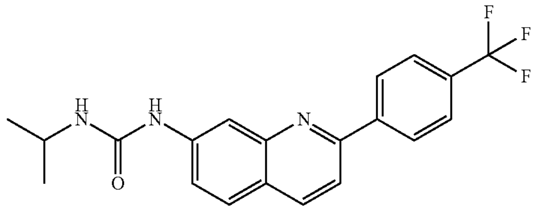
I-430
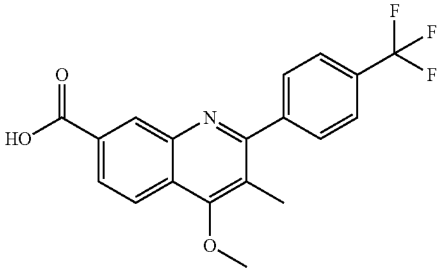
I-431
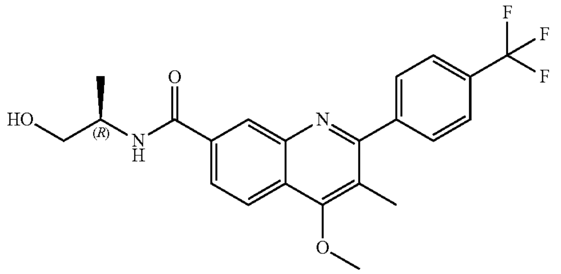
-continued
I-432
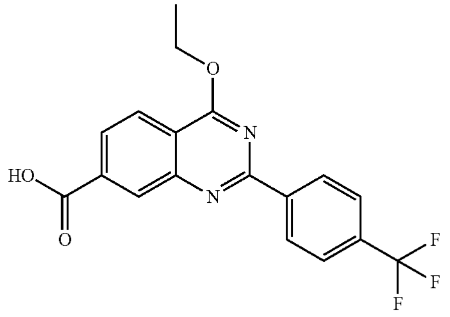
I-433
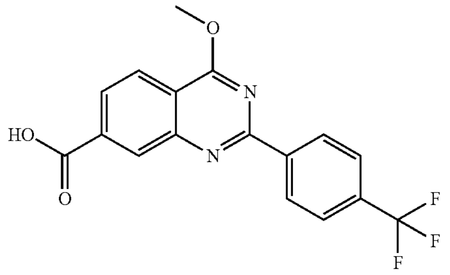
I-434
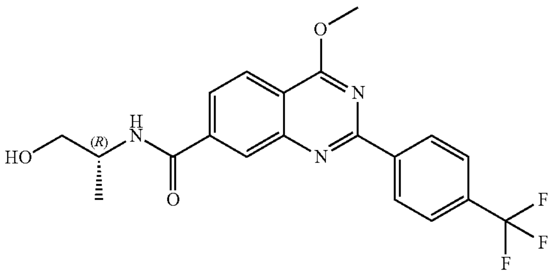
I-435
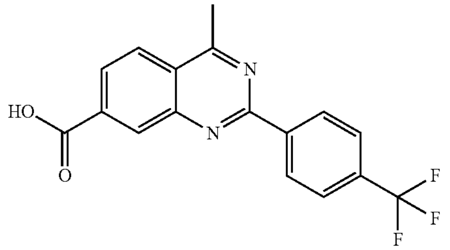
I-436
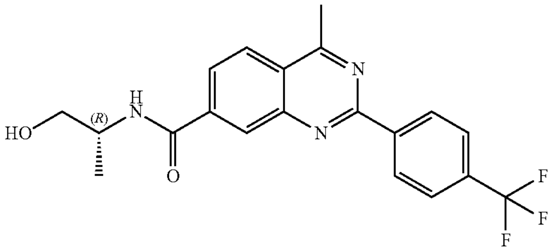

-continued
I-437
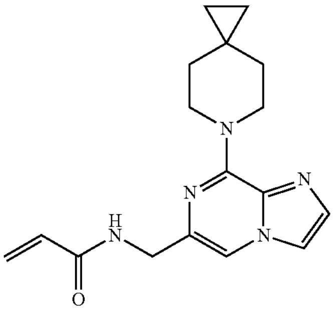
I-438
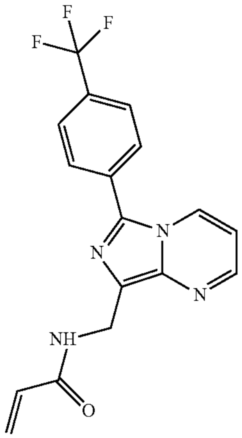
I-439
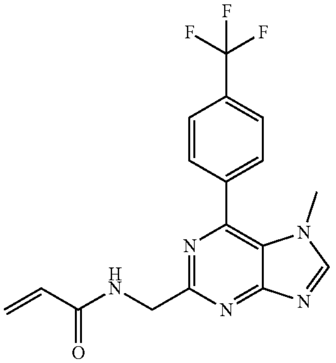
I-440
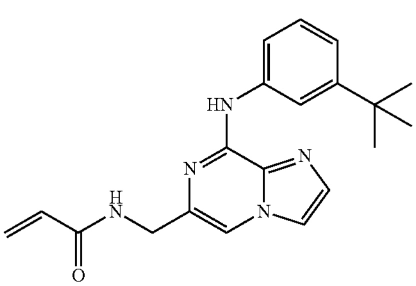
-continued
I-441
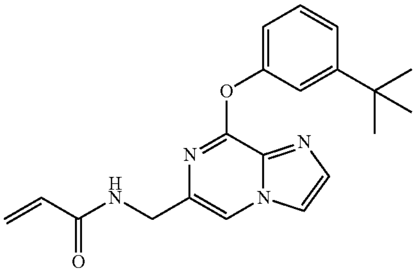
I-442
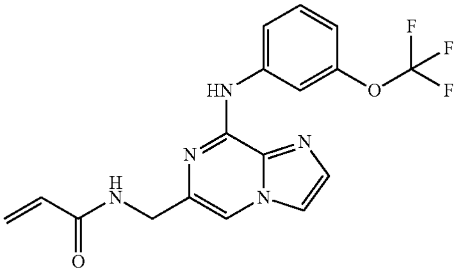
I-443
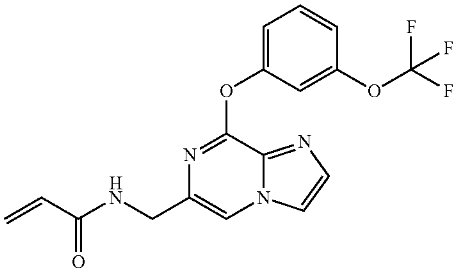
I-444
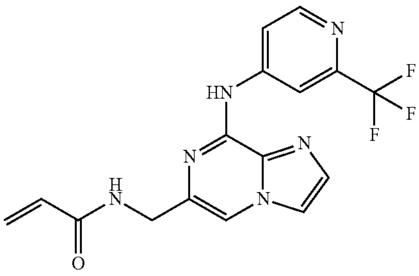
I-445
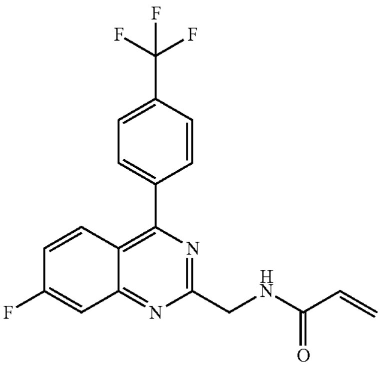

-continued

I-446

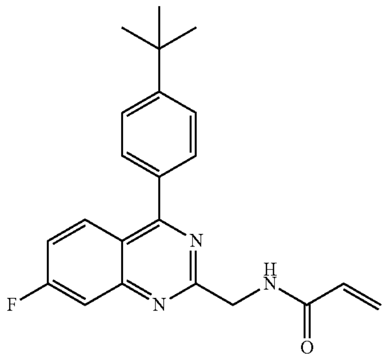

I-447

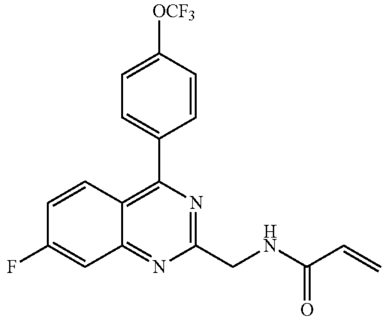

I-448

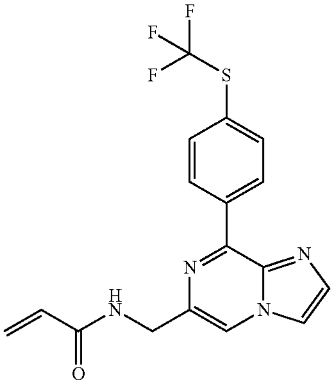

I-449

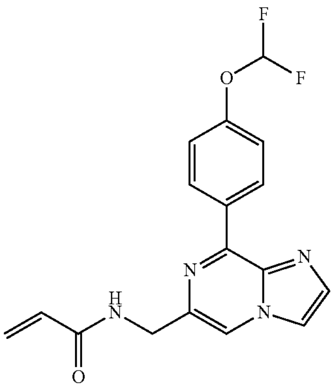

-continued

I-450

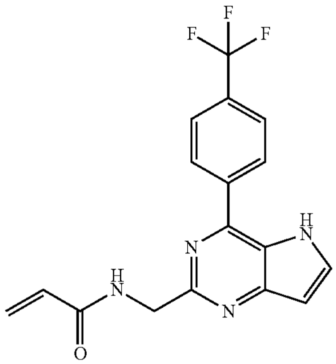

I-451

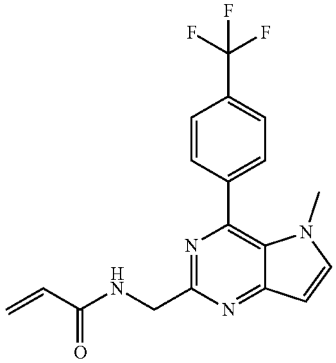

or a pharmaceutically acceptable salt thereof.

4. Uses, Formulation, and Administration

Pharmaceutically Acceptable Compositions

According to another embodiment, the present disclosure provides a composition comprising a compound described herein or a pharmaceutically acceptable salt thereof and a pharmaceutically acceptable carrier, adjuvant, or vehicle. In certain embodiments, the amount of compound in compositions described herein is such that it is effective to measurably inhibit activity of a TEAD transcription factor, or a mutant thereof, in a biological sample or in a patient. In certain embodiments, a composition described herein is formulated for administration to a patient in need of such composition. In some embodiments, a composition described herein is formulated for oral administration to a patient.

Compounds and compositions, according to method of the present disclosure, are administered using any amount and any route of administration effective for treating or lessening the severity of a disorder provided herein (i.e., a TEAD-mediated disease or disorder). The exact amount required will vary from subject to subject, depending on the species, age, and general condition of the subject, the severity of the infection, the particular agent, its mode of administration, and the like. Compounds described herein are preferably formulated in unit dosage form for ease of administration and uniformity of dosage.

Compositions of the present disclosure may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions described herein are administered without food. In other embodiments, pharmaceutically acceptable compositions described herein are administered with food. Pharmaceutically acceptable compositions described herein may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions described herein may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds described herein include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Uses of Compounds and Pharmaceutically Acceptable Compositions

The Hippo Signaling Pathway

The Hippo signaling pathway (also known as the Salvador/Warts/Hippo (SWH) pathway) is a key regulator of cell proliferation, death, and differentiation. In one aspect, a key function of the Hippo signaling pathway is the regulation of transcriptional co-activators Yes-associated protein (YAP; also known as YAP1 or YAP65) and its paralog, PDZ-binding motif (TAZ; also known as WWTR1). For example, the Hippo signaling pathway phosphorylates and inhibits YAP/TAZ activity by promoting their cytoplasmic retention and degradation, thereby inhibiting the growth promoting function regulated by YAP/TAZ. In an un-phosphorylated/de-phosphorylated state, YAP, together with TAZ, are transported into the nucleus where they interact with the TEAD family of transcriptions factors to upregulate genes that promote proliferation and migration, and inhibit apoptosis. Without wishing to be bound by a particular theory, in some instances, unregulated upregulation of these genes involved in proliferation, migration, and anti-apoptosis leads to the development of a disease, disorder, or condition (e.g., cancer). In some embodiments, overexpression of YAP/TAZ is associated with a disease, disorder, or condition (e.g., cancer).

Additional key members of the Hippo signaling pathway include the serine/threonine kinases MST1/2 (homologues of Hippo/Hpo of Drosophilia), Lats1/2 (homologues of Warts/Wts) and their adaptor proteins Sav1 (homologue of Salvador/Sav) and Mob (MOBKL1A and MOBKL1Bl; homologues of Mats), respectively. In general, MST1/2 kinases complex with scaffold protein Sav1, which in turn phosphorylate and activate Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] (SEQ ID NO: 5) consensus motifs, wherein X denotes any amino acid residue. YAP comprises five [HXRXXS] (SEQ ID NO: 5) consensus motifs. In some instances, Lats1/2 phosphorylates YAP at one or more of the consensus motifs. In some instances, Lats1/2 phosphorylates YAP at all five of the consensus motifs. In some instances, Lats1/2 phosphorylates YAP at S127. In one aspect, the phosphorylation of YAP S127 promotes 14-3-3 protein binding and results in cytoplasmic sequestration of YAP.

Mutation of YAP at the S127 position thereby disrupts its interaction with 14-3-3 and subsequently promotes nuclear translocation.

Additional phosphorylation occurs at S381 of YAP. Phosphorylation of YAP at S381 and on the corresponding site in TAZ primes both proteins for further phosphorylation events by CK1δ/ε in the degradation motif, which then signals for interaction with the β-TRCP E3 ubiquitin ligase, leading to polyubiquitination and degradation of YAP.

In some instances, Lats1/2 phosphorylates TAZ at the [HXRXXS] (SEQ ID NO: 5) consensus motifs, wherein X denotes any amino acid residue. TAZ comprises four [HXRXXS] (SEQ ID NO: 5) consensus motifs. In some instances, Lats1/2 phosphorylates TAZ at one or more of the consensus motifs. In some instances, Lats1/2 phosphorylates TAZ at all four of the consensus motifs. In some instances, Lats1/2 phosphorylates TAZ at S89. In one aspect, the phosphorylation of TAZ S89 promotes 14-3-3 protein binding and results in cytoplasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes $SCF^{\beta\text{-}TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g., Cdc4), Skpl, a bridging protein, and RBX1, which contains a small RING Finger domain which interacts with E2-ubiquitin conjugating enzyme. In some cases, the F-box family comprises more than 40 members, in which exemplary members include F-box/WD repeat-containing protein IA (FBXWIA, β-TrCPl, Fbxwl, hsSlimb, plkappaBalpha-E3 receptor subunit) and S-phase kinase-associated proteins 2 (SKP2). In some embodiments, the SCF complex (e.g., $SCF^{\beta\text{-}TRCP}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA6, UBA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE20, UBE2Q1, UBE2Q2, UBE2R1, UBE2R2, UBE2S, UBE2T, UBE2U, UBE2V1, UBE2V2, UBE2Z, ATG2, BIRC5, and UFCI. In some embodiments, ubiquitinated YAP/TAZ further undergoes the degradation process through the 26S proteasome.

In some embodiments, the Hippo signaling pathway is regulated upstream by several different families of regulators. For example, in some instances, the Hippo signaling pathway is regulated by the G-protein and its coupled receptors, the Crumbs complex, regulators upstream of the MST kinases, and the adherens junction.

In some embodiments, the Hippo signaling pathway is regulated by G protein-coupled receptors (GPCR) and G protein (also known as guanine nucleotide-binding proteins) family of proteins. G proteins are molecular switches that transmit extracellular stimuli into the cell through GPCRs. In some instances, there are two classes of G proteins: monomeric small GTPases and heterotrimeric G protein complexes. In one aspect, the heterotrimeric G protein complexes comprise alpha ($G_\alpha$), beta ($G_\beta$), and gamma ($G_\gamma$) subunits. In other aspects, there are several classes of $G_\alpha$ subunits: e.g., $G_{q/11}\alpha$, $G_{12/13}\alpha$, $G_{i/o}\alpha$ (G inhibitory, G other), and $G_s\alpha$ (stimulatory).

In some instances, $G_{q/11}\alpha$, $G_{12/13}\alpha$, $G_i\alpha$, and $G_0\alpha$ coupled GPCRs activate YAP/TAZ and promote nuclear translocation. In other instances, $G_s\alpha$ coupled GPCRs suppress YAP/TAZ activity, leading to YAP/TAZ degradation. In some instances, $G_{q/11}\alpha$, $G_{12/13}\alpha$, $G_i\alpha$, and $G_0\alpha$ coupled GPCRs activate YAP/TAZ through inhibition of Lats1/2 activity. In other instances, $G_s\alpha$ coupled GPCRs promotes or induces Lats1/2 activity, thereby leading to YAP/TAZ degradation. See Yu et al., *Cell*. (2012) 150, 780-791.

In some embodiments, the Hippo signaling pathway is regulated by the Crumbs (Crb) complex. The Crumbs complex is a key regulator of cell polarity and cell shape. In some instances, the Crumbs complex comprises transmembrane CRB proteins that assemble multi-protein complexes that function in cell polarity. In some instances, CRB complexes recruit members of the Angiomotin (AMOT) family of adaptor proteins that interact with the Hippo signaling pathway. In some instances, AMOT directly binds to YAP, promotes YAP phosphorylation, and inhibits its nuclear localization. Zhao et al., *Genes & Dev*. (2011) 25, 51-63.

In some instances, the Hippo signaling pathway is regulated by other components (e.g., TAO kinases and cell polarity kinase PAR-1) that modulate the activity of MST kinases. MST kinases monitor actin cytoskeletal integrity.

In some instances, the Hippo signaling pathway is regulated by molecules of the adherens junction. In some instances, E-Cadherin (E-cad) suppresses YAP nuclear localization and activity through regulating MST activity. In some embodiments, E-cad-associated protein a-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

TEAD

In some embodiments, un-phosphorylated and/or dephosphorylated YAP/TAZ accumulates in the nucleus. In one aspect, once within the nucleus, YAP/TAZ interacts with the TEAD family of transcriptions factors (e.g., human TEAD1 (UniProt KB ID P28347-1 (SEQ IDNO: 1)); human TEAD2 (UniProtKB ID Q15562 (SEQ IDNO: 2)); human TEAD3 (UniProtKB ID Q99594 (SEQ ID NO: 3)); and human TEAD4 (UniProtKB ID Q15561 (SEQ ID NO: 4)) to activate genes that promote proliferation and migration, and inhibit apoptosis, such as, e.g., CTFG, Cyr61, and FGF1. In one aspect, without wishing to be bound by a particular theory, since TEAD is a downstream transcription factor of the Hippo pathway, inhibiting the function of TEAD is an attractive therapeutic strategy to reduce aberrant Hippo signaling and gene transcription.

TEAD1-4 are composed of a highly conserved TEA DNA binding domain and YAP binding domain, which is separated by a proline rich region. Despite the high homology shared between human TEAD1-4, the individual TEAD proteins are differentially expressed in a tissue- and development-dependent manner. For example, in some instances, TEAD1 is required for heart biogenesis, TEAD2 for embryonic development, TEAD4 for activating skeletal muscle genes, and TERAD3 has been shown to be specifically expressed in the placenta and several embryonic tissues during development. Holden et al. Cancers (2018) 10, 81, 1-15.

Proteomic and biochemical studies have shown that the TEAD family of transcription factors are palmitoylated at evolutionarily conserved cysteine residues. Three cysteine residues were found that are evolutionarily conserved and mutated to serine in human TEAD1 (C53S, C327S and C359S) to test whether the mutation affects TEAD1 palmitoylation. The C359S mutant showed the greatest loss of palmitoylation, and C327S and C53S also showed decreased palmitoylation. These results suggest that C359 plays a key role in TEAD1 palmitoylation. Furthermore, combination mutation of all three cysteine residues, C53/327/359S (3CS), completely ablated TEAD1 palmitoylation, indicating that these residues are involved in TEAD1 palmitoylation. In one aspect, it has been found that TEADs undergo PAT-independent autopalmitoylation, under physiological concentrations of palmitoyl-CoA. Furthermore, autopalmitoylation plays key roles in regulating TEAD-YAP association and their physiological functions in vitro and in vivo. Chan, et al. Nature Chem. Biol. (2016) 12, 282-289; Noland, et al. Structure, (2016) 24, 1-8; Gibault et al. J. Med. Chem. (2018) 61, 5057-5072. Therefore, in one aspect, palmitoylation of TEADs play important roles in regulating Hippo signaling pathway transcriptional complexes.

It will be understood that the term "YAP/TAZ" refers to YAP, TAZ, or both YAP and TAZ.

In some embodiments, compounds disclosed herein modulate the interaction between YAP/TAZ and TEAD. In some embodiments, compounds disclosed herein bind to TEAD and/or prevent interaction between YAP/TAZ and TEAD.

In some embodiments, compounds disclosed herein irreversibly bind to a TEAD transcription factor (e.g., TEAD1, TEAD2, TEAD3, or TEAD4). In some embodiments, compounds disclosed herein covalently binds to a TEAD transcription factor (e.g., TEAD1, TEAD2, TEAD3, or TEAD4). In some embodiments, compounds disclosed covalently inhibit the activity of a TEAD transcription factor (e.g., TEAD1, TEAD2, TEAD3, or TEAD4). In some embodiments, compounds disclosed irreversibly inhibit the activity of a TEAD transcription factor (e.g., TEAD1, TEAD2, TEAD3, or TEAD4).

In some embodiments, compounds disclosed herein bind to TEAD1 at C53. In some embodiments, compounds disclosed herein bind to TEAD1 at C327. In some embodiments, compounds disclosed herein bind to TEAD1 at C359. In some embodiments, compounds disclosed herein bind to TEAD1 at C405. In some embodiments, compounds disclosed herein bind to TEAD1 at C53 and C327. In some embodiments, compounds disclosed herein bind to TEAD1 at C53 and C359. In some embodiments, compounds disclosed herein bind to TEAD1 at C53 and C405. In some embodiments, compounds disclosed herein bind to TEAD1 at C327 and C359. In some embodiments, compounds disclosed herein bind to TEAD1 at C327 and C405. In some embodiments, compounds disclosed herein bind to TEAD1 at C359 and C405. In some embodiments, compounds disclosed herein bind to TEAD1 at C53, C327, and C359. In some embodiments, compounds disclosed herein bind to TEAD1 at C53, C327, and C405. In some embodiments, compounds disclosed herein bind to TEAD1 at C53, C359, and C405. In some embodiments, compounds disclosed herein bind to TEAD1 at C327, C359, and C405. In some embodiments, compounds disclosed herein bind to TEAD1 at C53, C327, C359, and C405.

In some embodiments, compounds disclosed herein bind to TEAD2 at C368. In some embodiments, compounds disclosed herein bind to TEAD2 at C380. In some embodiments, compounds disclosed herein bind to TEAD2 at C368 and C380

In some embodiments, compounds disclosed herein bind to TEAD3 at C368. In some embodiments, compounds disclosed herein bind to TEAD3 at C371. In some embodiments, compounds disclosed herein bind to TEAD3 at C368 and C368.

In some embodiments, compounds disclosed herein bind to TEAD4 at C367.

In some embodiments, compounds disclosed herein bind to a TEAD transcription factor (e.g., TEAD1, TEAD2, TEAD3, or TEAD4) and disrupt or inhibit the interaction between YAP/TAZ and the TEAD transcription factor. In some embodiments, compounds disclosed herein bind to TEAD1 and disrupt or inhibit the interaction between YAP/TAZ and TEAD1. In some embodiments, compounds disclosed herein bind to TEAD2 and disrupt or inhibit the interaction between YAP/TAZ and TEAD2. In some embodiments, compounds disclosed herein bind to TEAD3 and disrupt or inhibit the interaction between YAP/TAZ and TEAD3. In some embodiments, compounds disclosed herein bind to TEAD4 and disrupt or inhibit the interaction between YAP/TAZ and TEAD4.

In some embodiments, compounds disclosed herein bind to TEAD1 at C53, and disrupt or inhibit the interaction between YAP/TAZ and TEAD1. In some embodiments, compounds disclosed herein bind to TEAD1 at C327, and disrupt or inhibit the interaction between YAP/TAZ and TEAD1. In some embodiments, compounds disclosed herein bind to TEAD1 at C359, and disrupt or inhibit the interaction between YAP/TAZ and TEAD1. In some embodiments, compounds disclosed herein bind to TEAD1 at C405, and disrupt or inhibit the interaction between YAP/TAZ and TEAD1. In some embodiments, compounds disclosed herein bind to TEAD1 at C53 and C327, and disrupt or inhibit the interaction between YAP/TAZ and TEAD1. In some embodiments, compounds disclosed herein bind to TEAD1 at C53 and C359, and disrupt or inhibit the interaction between YAP/TAZ and TEAD1. In some embodiments, compounds disclosed herein bind to TEAD1 at C53 and C405, and disrupt or inhibit the interaction between YAP/TAZ and TEAD1. In some embodiments, compounds disclosed herein bind to TEAD1 at C327 and C359, and disrupt or inhibit the interaction between YAP/TAZ and TEAD1. In some embodiments, compounds disclosed herein bind to TEAD1 at C327 and C405, and disrupt or inhibit the interaction between YAP/TAZ and TEAD1. In some embodiments, compounds disclosed herein bind to TEAD1 at C359 and C405, and disrupt or inhibit the interaction between YAP/TAZ and TEAD1. In some embodiments, compounds disclosed herein bind to TEAD1 at C53, C327, and C359, and disrupt or inhibit the interaction between YAP/TAZ and TEAD1. In some embodiments, compounds disclosed herein bind to TEAD1 at C53, C327, and C405, and disrupt or inhibit the interaction between YAP/TAZ and TEAD1. In some embodiments, compounds disclosed herein bind to TEAD1 at C53, C359, and C405, and disrupt or inhibit the interaction between YAP/TAZ and TEAD1. In some embodiments, compounds disclosed herein bind to TEAD1 at C327, C359, and C405, and disrupt or inhibit the interaction between YAP/TAZ and TEAD1. In some embodiments, compounds disclosed herein bind to TEAD1 at C53, C327, C359, and C405, and disrupt or inhibit the interaction between YAP/TAZ and TEAD1.

In some embodiments, compounds disclosed herein bind to TEAD2 at C368, and disrupt or inhibit the interaction between YAP/TAZ and TEAD2. In some embodiments, compounds disclosed herein bind to TEAD2 at C380, and disrupt or inhibit the interaction between YAP/TAZ and TEAD2. In some embodiments, compounds disclosed herein bind to TEAD2 at C368 and C380, and disrupt or inhibit the interaction between YAP/TAZ and TEAD2.

In some embodiments, compounds disclosed herein bind to TEAD3 at C368, and disrupt or inhibit the interaction between YAP/TAZ and TEAD3. In some embodiments, compounds disclosed herein bind to TEAD3 at C371, and disrupt or inhibit the interaction between YAP/TAZ and TEAD3. In some embodiments, compounds disclosed herein bind to TEAD3 at C368 and C368, and disrupt or inhibit the interaction between YAP/TAZ and TEAD3.

In some embodiments, compounds disclosed herein bind to TEAD4 at C367, and disrupt or inhibit the interaction between YAP/TAZ and TEAD4.

In some embodiments, compounds disclosed herein bind to a TEAD transcription factor (e.g., TEAD1, TEAD2, TEAD3, or TEAD4) and prevent TEAD transcription palmitoylation. In some embodiments, compounds disclosed herein bind to TEAD1 and prevent TEAD1 palmitoylation. In some embodiments, compounds disclosed herein bind to TEAD1 and prevent TEAD1 palmitoylation at C53. In some embodiments, compounds disclosed herein bind to TEAD1 and prevent TEAD1 palmitoylation at C327. In some embodiments, compounds disclosed herein bind to TEAD1 and prevent TEAD1 palmitoylation at C359. In some embodiments, compounds disclosed herein bind to TEAD1 and prevent TEAD1 palmitoylation at C405. In some embodiments, compounds disclosed herein bind to TEAD1 and prevent TEAD1 palmitoylation at C53 and C327. In some embodiments, compounds disclosed herein bind to TEAD1 and prevent TEAD1 palmitoylation at C53 and C359. In some embodiments, compounds disclosed herein bind to TEAD1 and prevent TEAD1 palmitoylation at C53 and C459. In some embodiments, compounds disclosed herein bind to TEAD1 and prevent TEAD1 palmitoylation at C327 and C359. In some embodiments, compounds disclosed herein bind to TEAD1 and prevent TEAD1 palmitoylation at C327 and C405. In some embodiments, compounds disclosed herein bind to TEAD1 and prevent TEAD1 palmitoylation at C359 and C405. In some embodiments, compounds disclosed herein bind to TEAD1 and prevent TEAD1 palmitoylation at C53, C327, and C359. In some embodiments, compounds disclosed herein bind to TEAD1 and prevent TEAD1 palmitoylation at C53, C327, and C405. In some embodiments, compounds disclosed herein bind to TEAD1 and prevent TEAD1 palmitoylation at C327, C359, and C405. In some embodiments, compounds disclosed herein bind to TEAD1 and prevent TEAD1 palmitoylation at C53, C327, C359, and C405.

In some embodiments, compounds disclosed herein bind to TEAD2 and prevent TEAD2 palmitoylation at C368. In some embodiments, compounds disclosed herein bind to TEAD2 and prevent TEAD2 palmitoylation at C380. In some embodiments, compounds disclosed herein bind to TEAD2 and prevent TEAD2 palmitoylation at C368 and C380.

In some embodiments, compounds disclosed herein bind to TEAD3 and prevent TEAD3 palmitoylation at C368. In some embodiments, compounds disclosed herein bind to TEAD3 and prevent TEAD3 palmitoylation at C371. In some embodiments, compounds disclosed herein bind to TEAD3 and prevent TEAD3 palmitoylation at C368 and C371.

In some embodiments, compounds disclosed herein bind to TEAD4 and prevent TEAD4 palmitoylation at C367.

In some embodiments, compounds disclosed herein bind to a TEAD transcription factor (e.g., TEAD1, TEAD2, TEAD3, or TEAD4), prevent TEAD transcription factor palmitoylation, and disrupt or inhibit the interaction between YAP/TAZ and the TEAD transcription factor. In some embodiments, compounds disclosed herein bind to TEAD1, prevent TEAD1 palmitoylation, and disrupt or inhibit the interaction between YAP/TAZ and TEAD1. In some embodiments, compounds disclosed herein bind to TEAD1, prevent TEAD1 palmitoylation at C53, and disrupt or inhibit the interaction between YAP/TAZ and TEAD1. In some embodiments, compounds disclosed herein bind to TEAD1, prevent TEAD1 palmitoylation at C327, and disrupt or inhibit the interaction between YAP/TAZ and TEAD1. In some embodiments, compounds disclosed herein bind to TEAD1, prevent TEAD1 palmitoylation at C359, and disrupt or inhibit the interaction between YAP/TAZ and TEAD1. In some embodiments, compounds disclosed herein bind to TEAD1, prevent TEAD1 palmitoylation at C405, and disrupt or inhibit the interaction between YAP/TAZ and TEAD1. In some embodiments, compounds disclosed herein bind to TEAD1, prevent TEAD1 palmitoylation at C53 and C327, and disrupt or inhibit the interaction between YAP/TAZ and TEAD1. In some embodiments, compounds disclosed herein bind to TEAD1, prevent TEAD1 palmitoylation at C53 and C359, and disrupt or inhibit the interaction between YAP/TAZ and TEAD1. In some embodiments, compounds disclosed herein bind to TEAD1, prevent TEAD1 palmitoylation at C53 and C459, and disrupt or inhibit the interaction between YAP/TAZ and TEAD1. In some embodiments, compounds disclosed herein bind to TEAD1, prevent TEAD1 palmitoylation at C327 and C359, and disrupt or inhibit the interaction between YAP/TAZ and TEAD1. In some embodiments, compounds disclosed herein bind to TEAD1, prevent TEAD1 palmitoylation at C327 and C405, and disrupt or inhibit the interaction between YAP/TAZ and TEAD1. In some embodiments, compounds disclosed herein bind to TEAD1, prevent TEAD1 palmitoylation at C359 and C405, and disrupt or inhibit the interaction between YAP/TAZ and TEAD1. In some embodiments, compounds disclosed herein bind to TEAD1, prevent TEAD1 palmitoylation at C53, C327, and C359, and disrupt or inhibit the interaction between YAP/TAZ and TEAD1. In some embodiments, compounds disclosed herein bind to TEAD1, prevent TEAD1 palmitoylation at C53, C327, and C405, and disrupt or inhibit the interaction between YAP/TAZ and TEAD1. In some embodiments, compounds disclosed herein bind to TEAD1, prevent TEAD1 palmitoylation at C327, C359, and C405, and disrupt or inhibit the interaction between YAP/TAZ and TEAD1. In some embodiments, compounds disclosed herein bind to TEAD1, prevent TEAD1 palmitoylation at C53, C327, C359, and C405, and disrupt or inhibit the interaction between YAP/TAZ and TEAD1.

In some embodiments, compounds disclosed herein bind to TEAD2, prevent TEAD2 palmitoylation at C368, and disrupt or inhibit the interaction between YAP/TAZ and TEAD1. In some embodiments, compounds disclosed herein bind to TEAD2, prevent TEAD2 palmitoylation at C380, and disrupt or inhibit the interaction between YAP/TAZ and TEAD1. In some embodiments, compounds disclosed herein bind to TEAD2, prevent TEAD2 palmitoylation at C368 and C380, and disrupt or inhibit the interaction between YAP/TAZ and TEAD1.

In some embodiments, compounds disclosed herein bind to TEAD3, prevent TEAD3 palmitoylation at C368, and disrupt or inhibit the interaction between YAP/TAZ and TEAD1. In some embodiments, compounds disclosed herein bind to TEAD3, prevent TEAD3 palmitoylation at C371, and disrupt or inhibit the interaction between YAP/TAZ and TEAD1. In some embodiments, compounds disclosed herein bind to TEAD3, prevent TEAD3 palmitoylation at C368 and C371, and disrupt or inhibit the interaction between YAP/TAZ and TEAD1.

In some embodiments, compounds disclosed herein bind to TEAD4, prevent TEAD4 palmitoylation at C367, and disrupt or inhibit the interaction between YAP/TAZ and TEAD1.

The activity of a compound described herein as an inhibitor of TEAD (e.g., TEAD1, TEAD2, TEAD3, and/or TEAD4), or a variant or mutant thereof, can be assayed in vitro, in vivo, or in a cell line. In vitro assays include assays that determine inhibition of TEAD (e.g., TEAD1, TEAD2, TEAD3, and/or TEAD4), or a variant or mutant thereof. Alternate in vitro assays quantitate the ability of the inhibitor to bind to TEAD (e.g., TEAD1, TEAD2, TEAD3, and/or TEAD4) or a variant or mutant thereof. Detailed conditions for assaying a compound described herein as an inhibitor of TEAD (e.g., TEAD1, TEAD2, TEAD3, and/or TEAD4), or a variant or mutant thereof, are set forth in the Examples below. See, for example, Example 2.

The provided compounds are inhibitors of TEAD (e.g., TEAD1, TEAD2, TEAD3, and/or TEAD4) and are therefore useful for treating one or more disorders associated with activity of TEAD (e.g., TEAD1, TEAD2, TEAD3, and/or TEAD4). Thus, in some aspects and embodiments, the present disclosure provides a method for treating a TEAD-mediated disease, disorder, or condition comprising the step of administering to a patient in need thereof a compound of the present disclosure, or pharmaceutically acceptable composition thereof.

In some embodiments, the present disclosure provides a method of inhibiting TEAD (e.g., TEAD1, TEAD2, TEAD3, and/or TEAD4) comprising contacting a cell with a compound of formula I.

As used herein, the term "TEAD-mediated" disorders or conditions as used herein means any disease or other deleterious condition in which TEAD (e.g., TEAD1, TEAD2, TEAD3, and/or TEAD4), or a mutant thereof, is known to play a role. Accordingly, another embodiment of the present disclosure relates to treating or lessening the severity of one or more diseases in which TEAD (e.g., TEAD1, TEAD2, TEAD3, and/or TEAD4), or a mutant thereof, is known to play a role.

In some embodiments, the present disclosure provides methods of treating, reducing the severity of, delaying the onset of, or inhibiting the progress of a disease or disorder, or one or more symptoms thereof of a disease or disorder characterized by or associated with increased TEAD (e.g., TEAD1, TEAD2, TEAD3, and/or TEAD4) expression and/or increased TEAD (e.g., TEAD1, TEAD2, TEAD3, and/or TEAD4) activity, comprising the step of administering to a patient in need thereof a therapeutically effective a compound of the present disclosure, or pharmaceutically acceptable composition thereof. In some embodiments, the present disclosure provides methods of treating, reducing the severity of, delaying the onset of, or inhibiting the progress of a disease or disorder, or one or more symptoms thereof of a disease or disorder in which inhibition or antagonizing of TEAD (e.g., TEAD1, TEAD2, TEAD3, and/or TEAD4) activity is beneficial comprising the step of administering to a patient in need thereof a compound described herein, or pharmaceutically acceptable composition thereof. In some aspects and embodiments, provided herein are methods of treating, reducing the severity of, delaying the onset of, or inhibiting the progress of a disease or disorder, or one or more symptoms thereof of a disease or disorder in which inhibition or antagonizing of the Hippo signaling pathway is beneficial comprising the step of administering to a patient in need thereof a therapeutically effective compound of the present disclosure, or pharmaceutically acceptable composition thereof.

In some aspects and embodiments, the present disclosure provides a method for treating one or more disorders, diseases, and/or conditions wherein the disorder, disease, or condition includes, but is not limited to, a cellular proliferative disorder, comprising administering to a patient in need thereof, a TEAD inhibitor compound as described herein, or a pharmaceutical salt or composition thereof. In some embodiments, a cellular proliferative disorder is cancer. In some embodiments, the cancer is characterized by increased TEAD (e.g., TEAD1, TEAD2, TEAD3, and/or TEAD4) expression and/or increased TEAD (e.g., TEAD1, TEAD2, TEAD3, and/or TEAD4) activity.

In some embodiments, provided methods include the co-administration of a provided compound and at least one mitogen-activated protein kinase (MAPK) inhibitor. In some embodiments, provided methods include the co-administration of a provided compound and at least one inhibitor of the RAS/MAPK pathway. In some embodiments, provided methods include the co-administration of a provided compound and at least one epidermal growth factor receptor (EGFR) inhibitor. In some embodiments, an inhibitor of the RAS/MAPK pathway is a KRAS inhibitor, RAF inhibitor (e.g., a BRAF monomer or RAF dimer inhibitor), a MEK inhibitor, an ERK inhibitor, an EGFR inhibitor, or a MAPK inhibitor, or a combination thereof. In some embodiments, an inhibitor of the RAS/MAPK pathway is an EGFR inhibitor or a MAPK inhibitor, or a combination thereof. Examples of EGFR inhibitors, MAPK inhibitors, and/or RAS/MAPK pathway inhibitors are disclosed in Moore A. R. Rosenberg, S. C., McCormock, F. et al. *Nat. Rev. Discov.* (2020) and include, e.g., Osimertinib (TAGRISSO®, AstraZeneca), sotorasib (AMG 510 from Amgen), MRTX849 (from Mirati Therapeutics), JNJ-74699157/ARS-3248 (from J&J Wellspring Biosciences), LY3499446 (from Eli Lilly), GDCBI 1701963 (from Boehringer Ingelheim), mRNA-5671 (from Moderna Therapeutics), G12D inhibitor (from Mirati Therapeutics), RAS(ON) inhibitors (from Revolution Medicines), BBP-454 (from BridgeBio Pharma), SP600125, PLX4032, GW5074, AZD6244, PD98059, simvastatin, alisertib, teriflunomide, NSC95397, PD325901, PD98059, lovastatin, sorafenib (NEXAVAR®, Bayer Labs), vermurafenib (ZELBORAF®, Hoffman La Roche Inc.), dabrafenib (TAFLINAR®, Novartis Pharmaceuticals Corporation), selumetinib (KOSELUGO™, AstraZeneca Pharmaceuticals LP), trametinib (MEKINIST®, Novartis Pharmaceuticals Corporation), uxliertinib, silimarin, sirolimus (RAPAMUNE®, PV Prism CV), lapatinib (TYKERB®/TYVERB®, GlaxoSmithKline), crizotinib (XALKORI®, PF Prism CV), taselisib (Roche), PF-0491502, pF502, enterolactone, PLX4720, PD0325901, PD184352, SC-514, alisterib (MLN8237), SB415286, PLX4720, obtaoclax (GX15-070), pimasterib, venetoclax (ABT-199/VENCLEXTA®/VENCLYXTO®), eprenetapopt (APR-246), gemcitabine (GEMZAR®), birinapant (TL32711), pexmetinib (ARRY-614), afuresertib, ralimetinib (LY2228820, Eli Lilly), cobimetinib (COTELLIC®, Exelixis/Genentech), prexasertib (LY2606368), erlotinib (TARCEVA®, OSI Pharmaceuticals), bevacizumab (AVASTIN®, Genentech), belvarafenib (Hanmi Pharm./Genentech, Inc.) and binimetinib (MEKTOVI®, Array Biopharma Inc.).

As used herein, the terms "increased expression" and/or "increased activity" of a substance, such as TEAD, in a sample or cancer or patient refers to an increase in the amount of the substance, such as TEAD, of about 5%, about 100%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 2-fold, about 3-fold, about 4-fold, about 5-fold, about 6-fold, about 7-fold, about 8-fold, about 9-fold, about 10-fold, about 20-fold, about 25-fold, about 50-fold, about 100-fold, or higher, relative to the amount of the substance, such as TEAD, in a control sample or control samples, such as an individual or group of individuals who are not suffering from the disease or disorder (e.g., cancer) or an internal control, as determined by techniques known in the art. A subject can also be determined to have an "increased expression" or "increased activity" of TEAD if the expression and/or activity of TEAD is increased by one standard deviation, two standard deviations, three standard deviations, four standard deviations, five standard deviations, or more, relative to the mean (average) or median amount of TEAD in a control group of samples or a baseline group of samples or a retrospective analysis of patient samples. As practiced in the art, such control or baseline expression levels can be previously determined, or measured prior to the measurement in the sample or cancer or subject, or can be obtained from a database of such control samples.

In some embodiments, the present disclosure provides a method for treating or lessening the severity of a cancer including, without limitation, a hematological cancer, a lymphoma, a myeloma, a leukemia, a neurological cancer, skin cancer, breast cancer, a prostate cancer, a colorectal cancer, lung cancer, head and neck cancer, a gastrointestinal cancer, a liver cancer, a pancreatic cancer, a genitourinary cancer, a bone cancer, renal cancer, and a vascular cancer. In some embodiments, the cancer is or has metastasized. In some embodiments, the cancer is relapsed or refractory cancer. In some embodiments, the cancer is a relapsed or refractory solid tumor. In some embodiments, the cancer is a relapsed or refractory hematological malignancy. In some embodiments, the cancer is or has been characterized by or has been established to have one or more genetic alterations in the Hippo pathway (e.g., NF2, LATS1/2, AMOTL2, SAV1, TAOK1-3, etc.). In some embodiments, the cancer is or has been characterized by or has been established to have one or more genetic alterations that affect or alter the stability of Hippo pathway components (e.g., BAP1, SOCS6, etc.). In some embodiments, the cancer is or has been characterized by or has been established to have a YAP/TAZ gene translocation (e.g., WWTR1(TAZ)-CAMTA1, YAP1-TFE3, etc.). In some embodiments, the cancer is selected from those disclosed in WO 2019/113236, the entire contents of which are hereby incorporated by reference.

In some embodiments, the cancer is mediated by activation YAP/TAZ. In some embodiments of the methods and uses described herein, the cancer is mediated by modulation of the interaction of YAP/TAZ with TEAD (e.g., TEADI, TEAD2, TEAD3, and/or TEAD4). In some embodiments, the cancer is characterized by or associated with increased TEAD (e.g., TEAD1, TEAD2, TEAD3, and/or TEAD4) expression and/or increased TEAD (e.g., TEAD1, TEAD2, TEAD3, and/or TEAD4) activity. In some embodiments, the cancer being treated is a cancer in which YAP/TAZ is localized in the nucleus of the cancer cells. In some embodiments, the cancer being treated is or has been characterized or established by one or more YAP/TAZ genetic amplifications or mutations.

In some embodiments, the cancer is characterized by a mutant Gα-protein. In some embodiments, a mutant Gα-protein is $G_{12}$, $G_{13}$, $G_q$, $G_{11}$, $G_i$, $G_o$, or $G_s$. In some embodiments, a mutant Gα-protein is $G_{12}$. In some embodiments, a mutant Gα-protein is $G_{13}$. In some embodiments, a mutant Gα-protein is $G_q$. In some embodiments, a mutant Gα-protein is $G_{11}$. In some embodiments, a mutant Gα-protein is $G_i$. In some embodiments, a mutant Gα-protein is Go. In some embodiments, a mutant Gα-protein is $G_s$.

In some embodiments, the cancer is lung cancer, thyroid cancer, ovarian cancer, colorectal cancer, prostate cancer, cancer of the pancreas, cancer of the esophagus, liver cancer, breast cancer, skin cancer, or mesothelioma. In some embodiments, the cancer is mesothelioma, such as malignant mesothelioma. In some embodiments, the cancer is leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell-involved cancers (including cervical squamous cell carcinoma, lung squamous cell carcinoma, esphageal squamous cell carcinoma, head and neck squamous cell carcinoma, bladder urothelial carcinoma), basal cell carcinoma, adenocarcinoma, sweat gland carcinoma, sebaceous gland carcmoma, papillary carcmoma, papillary adenocarcinomas, cystadenocarcinoma, medullary carcinoma, bronchogenic carcinoma, renal cell carcinoma, hepatoma, bile duct carcinoma (i.e. cholangiocarcinoma), choriocarcinoma, seminoma, embryonal carcinoma, Wilm's tumor, cervical cancer, endometrial/uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, epithelioid hemangioendothelioma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g., Grade I-Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

In some embodiments, the cancer is mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcmoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcmoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcmoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is being treated adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, the cancer is a viral-associated cancer, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells; as well as virus-associated tumors in gastric cancer, nasopharyngeal carcinoma, cervical cancer, vaginal cancer, vulvar cancer, squamous cell carcinoma of the head and neck, and Merkel cell carcinoma.

In some embodiments, the cancer is melanoma cancer. In some embodiments, the cancer is breast cancer. In some embodiments, the cancer is lung cancer. In some embodiments, the cancer is small cell lung cancer (SCLC). In some embodiments, the cancer is non-small cell lung cancer (NSCLC).

Exemplification

As depicted in the Examples below, in certain exemplary embodiments, compounds are prepared according to the following general procedures. It will be appreciated that, although the general methods depict the synthesis of certain compounds of the present disclosure, the following general methods, and other methods known to one of ordinary skill in the art, can be applied to all compounds and subclasses and species of each of these compounds, as described herein.

Example 1. Synthesis of Exemplary Compounds

Example 1.1. Synthesis of 4-((4,4,4-Trifluorobutyl) amino) pyrrolo[1,2-a]quinoxaline-7-carboxylic acid (I-1)

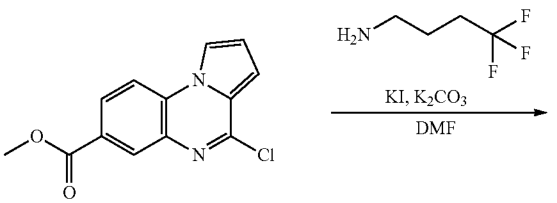

X-1109A3

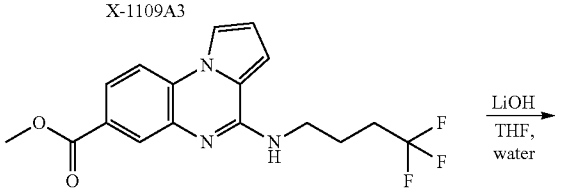

X-1156A1

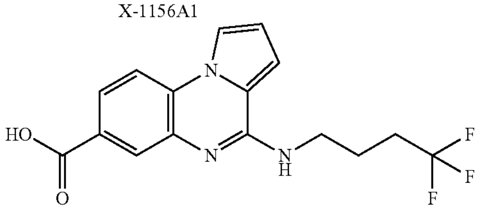

I-1

Methyl 4-((4,4,4-trifluorobutyl)amino)pyrrolo[1,2-a]quinoxaline-7-carboxylate (X-1156A1). To a stirred solution of methyl 4-chloropyrrolo[1,2-a]quinoxaline-7-carboxylate (X-1109A3) (0.500 g, 1.92 mmol) and 4,4,4-trifluorobutan-1-amine hydrochloride (0.376 g, 2.30 mmol) in DMF (5 mL) were added potassium carbonate (0.664 g, 4.80 mmol) and potassium iodide (0.032 g, 0.19 mmol) at room temperature under nitrogen and the resulting mixture was stirred at 90° C. for 16 h. After cooling to room temperature, reaction mixture poured in ice-water (50 mL) and was extracted with ethyl acetate (50 mL×3). Combined organic extracts were washed with brine (50 mL), dried over anhydrous $Na_2SO_4$ and concentrated in vacuo. The resulting crude was purified by reverse phase (C-18) silica gel column chromatography using acetonitrile-water=0:1→1:0 as gradient, to afford methyl 4-((4,4,4-trifluorobutyl)amino)pyrrolo[1,2-a]quinoxaline-7-carboxylate (X-1156A1) (0.090 g, 60%) as an off white solid. MS: $[MH]^+$ 352.0.

4-((4,4,4-Trifluorobutyl) amino) pyrrolo[1,2-a] quinoxaline-7-carboxylic acid (I-1). To a stirred solution of methyl 4-((4,4,4-trifluorobutyl) amino) pyrrolo[1,2-a] quinoxaline-7-carboxylate (X-1156A1) (0.200 g, 0.56 mmol) in a mixture of THF-water (3:1; 5.0 mL) was added lithium hydroxide monohydrate (0.071 g, 1.70 mmol) at room temperature under nitrogen and the resulting mixture was heated at 70° C. for 2 h. After cooling to room temperature, the reaction mixture was concentrated under reduced pressure, obtained crude was diluted with water (40 mL) and was extracted with ethyl acetate (40 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 4-((4,4,4-trifluorobutyl)amino)pyrrolo[1,2-a]quinoxaline-7-carboxylic acid (I-1) (0.060 g, 37%) as a white solid. $^1H$ NMR (400 MHz, DMSO-$d_6$) δ 12.86 (br. s, 1H), 8.26-8.26 (d, J=1.6 Hz, 1H), 8.12-8.10 (d, J=8.4 Hz, 1H), 8.00-7.99 (d, J=1.6 Hz, 1H), 7.73-7.71 (dd, J=8.4, 1.6 Hz, 1H), 7.65-7.63 (m, 1H), 7.09-7.08 (d, J=3.2 Hz, 1H), 6.79. 6.77 (m, 1H), 3.63-3.60 (m, 2H), 2.42-2.35 (m, 2H), 1.92-1.87 (m, 2H). MS: $[MH]^+$ 338.1.

The following compounds were prepared in a manner analogous to the procedures described above for 4-((4,4,4-Trifluorobutyl) amino) pyrrolo[1,2-a] quinoxaline-7-carboxylic acid (I-1):

4-(Piperidin-1-yl)pyrrolo[1,2-a]quinoxaline-7-carboxylic acid as a hydrochloride salt (I-2) (0.090 g, 52%) as a pink solid. $^1H$ NMR (400 MHz, DMSO-$d_6$) δ 13.31 (br, 1H), 12.50 (br, 1H) 8.65 (s, 1H), 8.55 (br. s, 1H), 8.34-8.32 (d, J=8.8 Hz, 1H), 7.94-7.92 (d, J=8.4 Hz, 1H), 7.56 (br. s, 1H), 7.06 (s, 1H), 4.00 (s, 4H), 1.79 (s, 6H). MS: $[MH]^+$ 296.1.

4-(4,4-Dimethylpiperidin-1-yl)pyrrolo[1,2-a]quinoxaline-7-carboxylic acid as a hydrochloride salt (I-3) (0.190 g, 63%) as an off-white solid. $^1H$ NMR (400 MHz, DMSO-$d_6$) δ 13.32 (br. s, 1H), 12.60 (br. s, 1H), 8.66 (br. s, 2H), 8.33-8.31 (d, J=8.8 Hz, 1H), 7.93-7.91 (d, J=8.4 Hz, 1H), 7.61 (br. s, 1H), 7.05 (s, 1H), 4.02 (br. s, 4H), 1.62 (br. s, 4H), 1.05 (s, 6H). MS: [MH]+ 324.1.

4-(6-Azaspiro[2.5]octan-6-yl)pyrrolo[1,2-a]quinoxaline-7-carboxylic acid as a hydrochloride salt (I-4) (0.100 g, 86%) as a white solid. $^1H$ NMR (400 MHz, DMSO-$d_6$) δ 13.34 (br, 1H), 12.71 (br, 1H), 8.66 (s, 1H), 8.58 (br. s, 1H), 8.35-8.32 (d, J=8.8, 1H), 7.94-7.92 (d, J=8.4 Hz, 1H), 7.56 (br. s, 1H), 7.06 (s, 1H), 4.06 (s, 4H), 1.64 (s, 4H), 0.46 (s, 4H). MS: $[MH]^+$ 322.1.

4-(3,3-Difluoropiperidin-1-yl)pyrrolo[1,2-a]quinoxaline-7-carboxylic acid (I-5) (0.088 g, 51%) as an off-white solid. $^1$H NMR (400 MHz, DMSO-$d_6$) δ 13.01 (br, 1H), 8.41-8.40 (d, J=2.0 Hz, 1H), 8.22-8.80 (d, J=8.8 Hz, 1H), 8.09-8.08 (d, J=1.6 Hz, 1H), 7.86-7.84 (dd, J=8.4, 1.6 Hz, 1H), 7.02-7.01 (d, J=3.2 Hz, 1H), 6.90-6.88 (t, J=3.2 Hz, 1H), 4.08-4.02 (t, J=12.4 Hz, 2H), 3.77 (s, 2H), 2.19-2.12 (m, 2H), 1.93 (br. s, 2H). MS: [MH]+ 332.1.

4-(7-Azaspiro[3.5]nonan-7-yl)pyrrolo[1,2-a]quinoxaline-7-carboxylic acid (I-6) (0.030 g, 28%) as an off white solid. $^1$H NMR (400 MHz, DMSO-$d_6$) δ 12.90 (br, 1H), 8.34-8.33 (d, J=1.6 Hz, 1H), 8.17-8.15 (d, J=8.4 Hz, 1H), 8.03 (s, 1H), 7.79-7.77 (d, J=7.6 Hz, 1H), 6.95-6.95 (d, J=3.6 Hz, 1H), 6.85-6.83 (t, J=3.6, Hz, 1H), 3.68-3.64 (t, J=5.2 Hz, 1H), 1.90-1.88 (m, 2H), 1.83-1.80 (m, 4H), 1.71-1.60 (m, 4H). MS: [MH]+ 336.1

4-Morpholinopyrrolo[1,2-a]quinoxaline-7-carboxylic acid (I-7) (0.060 g, 58%) as an off white solid. $^1$H NMR (400 MHz, DMSO-$d_6$) δ 13.22 (br, 1H), 8.61 (s, 1H), 8.52 (br. s, 1H), 8.33-8.31 (d, J=8.8 Hz, 1H), 7.93-7.91 (d, J=8.4 Hz, 1H), 7.49 (br. s, 1H), 7.03 (s, 1H), 4.00 (br. s, 4H), 3.84 (br. s, 4H). MS: [MH]+ 298.0.

4-(8-Azaspiro[4.5]decan-8-yl)pyrrolo[1,2-a]quinoxaline-7-carboxylic acid (I-8) (0.055 g, 38%) as a white solid. $^1$H NMR (400 MHz, DMSO-$d_6$) δ 12.92 (br. s, 1H), 8.34 (s, 1H), 8.17-8.15 (d, J=8.4 Hz, 1H), 8.02 (s, 1H), 7.79-7.77 (d, J=8.0 Hz, 1H), 6.96-6.95 (d, J=3.6 Hz, 1H), 6.84 (s, 1H), 3.74 (s, 4H), 1.62-1.57 (m, 8H), 1.50-1.49 (d, J=5.6 Hz, 4H). MS: [MH]+ 350.1.

4-(2-Azaspiro[4.4]nonan-2-yl)pyrrolo[1,2-a]quinoxaline-7-carboxylic acid (I-9) (0.015 g, 6%) as an off-white solid. $^1$H NMR (400 MHz, DMSO-$d_6$) δ 12.80 (br, 1H), 8.34 (s, 1H), 8.10-8.07 (d, J=8.4 Hz, 1H), 7.92 (s, 1H), 7.67-7.65 (d, J=7.2 Hz, 1H), 7.11-7.10 (d, J=3.6 Hz, 1H), 6.81 (s, 1H), 3.92 (s, 2H), 3.72 (s, 2H), 1.92-1.91 (m, 2H), 1.71-1.60 (m, 8H). MS: [MH]+336.1.

4-(3-(Trifluoromethyl)pyrrolidin-1-yl)pyrrolo[1,2-a]quinoxaline-7-carboxylic acid (I-10) (0.035 g, 18%) as a yellow solid. $^1$H NMR (400 MHz, DMSO-$d_6$) δ 12.88 (br. s, 1H), 8.39-8.38 (d, J=1.6 Hz, 1H), 8.14-8.12 (d, J=8.0 Hz, 1H), 7.98-7.97 (d, J=1.6 Hz, 1H), 7.72-7.69 (dd, J=8.4, 1.6 Hz, 1H), 7.14-7.13 (d, J=4.0 Hz, 1H), 6.85-6.84 (t, J=4.0 Hz, 1H), 4.15-3.90 (m, 4H), 3.43-3.39 (m, 1H), 2.36-2.30 (m, 1H), 2.21-2.14 (m, 1H). MS: [MH]+ 350.1.

4-(3, 3-Difluoropyrrolidin-1-yl)pyrrolo[1,2-a]quinoxaline-7-carboxylic acid (I-11) (0.012 g, 7%) as a yellow solid. $^1$H NMR (400 MHz, DMSO-$d_6$) δ 12.90 (br. s, 1H), 8.41 (s, 1H), 8.17-8.14 (d, J=8.8 Hz, 1H), 8.00 (s, 1H), 7.75-7.73 (d, J=8.4 Hz, 1H), 7.16-7.15 (d, J=3.2 Hz, 1H), 6.86 (s, 1H), 4.30-4.24 (t, J=12.8 Hz, 2H), 4.13-4.10 (t, J=7.2 Hz, 2H), 2.62-2.49 (m, 2H). MS: [MH]+ 318.1.

4-(4-Isopropylpiperidin-1-yl)pyrrolo[1,2-a]quinoxaline-7-carboxylic acid (I-12) (0.060 g, 35%) as a yellow solid. $^1$H NMR (400 MHz, DMSO-$d_6$) δ 12.92 (br, 1H), 8.34 (s, 1H), 8.17-8.15 (d, J=8.8 Hz, 1H), 8.03-8.03 (d, J=1.2 Hz, 1H), 7.79-7.77 (d, J=8.4 Hz, 1H), 6.97-6.96 (d, J=3.6 Hz, 1H), 6.86-6.84 (m, 1H), 4.55-4.52 (d, J=12.8 Hz, 2H), 2.99-2.94 (t, J=10.4 Hz, 2H), 1.79-1.77 (d, J=8.8 Hz, 2H), 1.45 (br. s, 1H), 1.33 (br. s, 3H), 0.90-0.88 (d, J=6.8 Hz, 6H). MS: [MH]+ 338.1.

4-(4-Phenylpiperidin-1-yl)pyrrolo[1,2-a]quinoxaline-7-carboxylic acid (I-13) (0.038 g, 26%) as a yellow solid. $^1$H NMR (400 MHz, DMSO-$d_6$) δ 12.93 (br. s, 1H), 8.37 (s, 1H), 8.20-8.18 (d, J=8.8 Hz, 1H), 8.06 (s, 1H), 7.81-7.79 (d, J=8.4 Hz, 1H), 7-31-7.29 (m, 4H), 7.21-7.20 (m, 1H), 7.03-7.02 (d, J=4.0 Hz, 1H), 6.88-6.86 (m, 1H), 4.65-4.62 (d, J=12.8 Hz, 2H), 3.18-3.12 (t, J=12.4 Hz, 2H), 2.91-2.85 (t, J=12.0 Hz, 1H), 2.46 (1H, merged with DMSO-d6 moisture peak), 1.94-1.91 (m, 2H), 1.86-1.86 (m, 2H) MS: [MH]+ 372.1.

4-(4-(1,1-Difluoroethyl)piperidin-1-yl)pyrrolo[1,2-a]quinoxaline-7-carboxylic acid as a hydrochloride salt (I-14) (0.120 g, 75%) as a white solid. $^1$H NMR (400 MHz, DMSO-$d_6$) δ 13.28 (br, 1H), 12.69 (br, 1H), 8.65 (s, 1H), 8.56 (br. s, 1H), 8.34-8.32 (d, J=8.4 Hz, 1H), 7.94-7.92 (d, J=8.4 Hz, 1H), 7.56 (br. s, 1H), 7.06 (s, 1H), 4.61-4.58 (d, J=13.2 Hz, 2H), 3.51 (br. s, 2H), 2.36-2.32 (m, 1H), 2.00-1.98 (d, J=7.6 Hz, 2H), 1.73-1.67 (m, 2H), 1.67-1.58 (t, J=19.6 Hz, 2H). MS: [MH]+ 360.1.

4-(Pyrrolidin-1-yl)pyrrolo[1,2-a]quinoxaline-7-carboxylic acid as a hydrochloride salt (I-15) (0.100 g, 58%) as a pink solid. $^1$H NMR (400 MHz, DMSO-$d_6$) δ 13.33 (br. s, 1H), 11.75 (br. s, 1H), 8.69 (s, 1H), 8.63 (br. s, 1H), 8.33-8.31 (d, J=8.4 Hz, 1H), 7.91-7.89 (d, J=8.0 Hz, 1H), 7.69 (br. s, 1H), 7.06 (s, 1H), 4.11 (br. s, 2H), 3.91 (br. s, 2H), 2.10 (s, 4H). MS: [MH]+282.1.

4-(4-Methylpiperidin-1-yl)pyrrolo[1,2-a]quinoxaline-7-carboxylic acid (I-16) (0.050 g, 35%) as an off white solid. $^1$H NMR (400 MHz, DMSO-$d_6$) δ 12.94 (br, 1H), 8.33 (s, 1H), 8.16-8.14 (d, J=8.8 Hz, 1H), 8.03-8.02 (d, J=1.6 Hz, 1H), 7.79-7.77 (dd, J=8.8, 1.6 Hz, 1H), 6.95-6.95 (d, J=3.6 Hz, 1H), 6.85-6.84 (t, J=3.6 Hz, 1H), 4.47-4.44 (d, J=13.6 Hz, 2H), 3.06-3.00 (m, 2H), 1.77-1.68 (m, 3H), 1.30-1.26 (m, 2H), 0.97-0.95 (d, J=6.0 Hz, 3H). MS: [MH]+ 310.1.

4-(4-(Difluoromethyl)piperidin-1-yl)pyrrolo[1,2-a]quinoxaline-7-carboxylic acid (I-17) (0.012 g, 14%) as a light yellow solid. $^1$H NMR (400 MHz, DMSO-$d_6$) δ 13.33 (br, 1H), 12.63 (br, 1H), 8.65 (s, 1H), 8.53 (br. s, 1H), 8.34-8.32 (d, J=8.4 Hz, 1H), 7.94-7.92 (d, J=8.0 Hz, 1H), 7.56 (br. s, 1H), 7.06 (s, 1H), 6.18-5.89 (dt, J=56.4, 4.0 Hz, 1H), 4.58-4.55 (d, J=13.2 Hz, 2H), 3.75 (br. s, 2H), 2.35-2.32 (m, 1H), 1.95-1.93 (d, J=11.6 Hz, 2H), 1.71-1.66 (m, 2H). MS: [MH]+ 346.0.

4-((4-(Trifluoromethyl)cyclohexyl)amino)pyrrolo[1,2-a]quinoxaline-7-carboxylic acid as a hydrochloride salt (I-18) (0.150 g, 91%) as a yellow solid. $^1$H NMR (400 MHz, DMSO-$d_6$) δ 13.34 (br, 1H), 12.65 (br, 1H), 9.85-9.50 (m, 1H), 8.75 (br. s, 1H), 8.59 (s, 1H), 8.33-8.31 (d, J=8.4 Hz, 1H), 7.96-7.94 (d, J=6.8 Hz, 2H), 6.98 (s, 1H), 4.54-4.39 (m, 1H), 2.13-2.11 (m, 1H), 2.01-1.84 (m, 6H), 1.66-1.52 (m, 1H). MS: [MH]+ 378.1

4-((3-(Trifluoromethyl)cyclohexyl)amino)pyrrolo[1,2-a]quinoxaline-7-carboxylic acid (I-19) (0.070 g, 38%) as an off-white solid. $^1$H NMR (400 MHz, DMSO-$d_6$) δ 12.86 (br. s, 1H), 8.26 (s, 1H), 8.12-8.10 (d, J=8.4 Hz, 1H), 7.99 (s, 1H), 7.72-7.70 (d, J=7.6 Hz, 1H), 7.36-7.34 (d, J=8.0 Hz, 1H), 7.14-7.14 (d, J=2.8 Hz, 1H), 6.78-6.77 (d, J=2.8 Hz, 1H), 4.30-4.28 (m, 1H), 2.22-2.19 (d, J=11.6 Hz, 1H), 2.08-2.05 (m, 1H), 1.89-1.86 (d, J=11.2 Hz, 2H), 1.75-1.63 (m, 1H), 1.52-146 (m, 1H), 1.41-1.30 (m, 2H), 1.26-1.16 (m, 1H). MS: [MH]+ 378.1.

4-(4-(tert-Butyl)piperazin-1-yl)pyrrolo[1,2-a]quinoxaline-7-carboxylic acid (I-20) (0.030 g, 17%) as a yellow solid. $^1$H NMR (400 MHz, DMSO-$d_6$) δ 12.87 (br, 1H), 8.36 (s, 1H), 8.19-8.17 (d, J=8.4 Hz, 1H), 8.04 (s, 1H), 7.80-7.78 (d, J=8.0 Hz, 1H), 7.02-7.01 (d, J=3.2 Hz, 1H), 6.86 (s, 1H), 3.75 (s, 4H), 2.69 (s, 4H), 1.06 (s, 9H). MS: [MH]+353.2.

4-(3,4-Dihydroisoquinolin-2(1H)-yl)pyrrolo[1,2-a]quinoxaline-7-carboxylic acid as a hydrochloride salt (I-21) (0.075 g, 65%) as an off white solid. $^1$H NMR (400 MHz, DMSO-$d_6$) δ 12.92 (br, 1H), 8.40-8.39 (d, J=2.0 Hz, 1H), 8.19-8.07 (d, J=8.4 Hz, 1H), 8.08-8.07 (d, J=1.6 Hz, 1H), 7.79-7.77 (dd, J=8.0, 1.6 Hz, 1H), 7.32-7.15 (m, 5H), 6.90

(s, 1H), 4.97 (s, 2H), 4.08-4.05 (t, J=6.0 Hz, 2H), 3.07-3.04 (t, J=6.0 Hz, 2H). MS: [MH]+ 344.1.

4-((3-Isopropylbicyclo[1.1.1]pentan-1-yl)amino)pyrrolo[1,2-a]quinoxaline-7-carboxylic acid as a hydrochloride salt. (I-22) (0.011 g, 23%) as a white solid. $^1$H NMR (400 MHz, DMSO-$d_6$) δ 12.96 (br, 1H), 8.24 (s, 1H), 8.09-8.07 (d, J=8.4 Hz, 1H), 8.00-7.97 (d, J=10.8 Hz, 2H), 7.73-7.71 (d, J=8.4 Hz, 1H), 7.46-7.35 (m, 1H), 7.11-7.10 (d, J=2.8 Hz, 1H), 6.75 (s, 1H), 2.01 (s, 6H), 1.85-1.79 (m, 1H), 0.90-0.88 (d, J=6.8 Hz, 6H). MS: [MH]+ 336.1.

4-(4-(Trifluoromethyl) phenoxy) pyrrolo[1,2-a] quinoxaline-7-carboxylic acid (I-23) (0.050 g, 74%) as a white solid. $^1$H NMR (400 MHz, DMSO-$d_6$) δ 13.08 (s, 1H), 8.61-8.60 (d, J=1.2 Hz, 1H), 8.39-8.37 (d, J=8.4 Hz, 1H), 8.03-8.00 (m, 3H), 7.89-7.87 (d, J=8.8 Hz, 2H), 7.65-7.63 (d, J=8.4 Hz, 2H), 7.22-7.20 (d, J=3.2 Hz, 1H), 7.03-7.02 (t, J=3.2 Hz, 1H). MS: [MH]+373.0.

4-(3-(Trifluoromethyl) phenoxy) pyrrolo[1,2-a] quinoxaline-7-carboxylic acid (I-24) (0.170 g, 88%) as a white solid. $^1$H NMR (400 MHz, DMSO-$d_6$) δ 13.09 (br. s, 1H), 8.61-8.60 (d, J=1.2 Hz, 1H), 8.38-8.36 (d, J=8.4 Hz, 1H), 8.02-7.99 (dd, J=8.4, 1.6 Hz, 1H), 7.96-7.95 (d, J=1.6 Hz, 1H), 7.82 (s, 1H), 7.75-7.70 (m, 3H), 7.21-7.20 (d, J=2.8 Hz, 1H), 7.03-7.01 (t, J=3.6 Hz, 1H). MS: [MH]+ 373.1

4-(2-Azaspiro[4.6]undecan-2-yl)pyrrolo[1,2-a]quinoxaline-7-carboxylic acid as a hydrochloride salt (I-25) (0.080 g, 56%) as an off-white solid. $^1$H NMR (400 MHz, DMSO-$d_6$) δ 13.13 (br. s, 1H), 11.61 (br. s, 1H), 8.54 (br. s, 1H), 8.29-8.22 (m, 2H), 7.81 (br. s, 1H), 7.45 (br, 1H), 6.96 (br. s, 1H), 4.00 (br. s, 2H), 3.70 (br. s, 2H), 1.96-1.91 (br. s, 2H), 1.67-1.55 (m, 12H). MS: [MH]+ 364.3.

4-(2-Oxa-9-azaspiro[5.5]undecan-9-yl)pyrrolo[1,2-a]quinoxaline-7-carboxylic acid (I-26) (0.040 g, 21%) as a white solid. $^1$H NMR (400 MHz, DMSO-$d_6$) δ 13.00 (br, 1H), 8.34 (s, 1H), 8.16-8.14 (d, J=8.8 Hz, 1H), 8.02 (s, 1H), 7.78-7.76 (d, J=8.4 Hz, 1H), 6.98-6.97 (d, J=3.6 Hz, 1H), 6.85-6.83 (t, J=3.2 Hz, 1H), 3.75 (br. s, 4H), 3.55 (s, 2H), 3.42 (br. s, 2H), 1.60-1.56 (m, 8H). MS: [MH]+ 366.2.

4-(3-Oxa-9-azaspiro [5.5] undecan-9-yl) pyrrolo[1,2-a] quinoxaline-7-carboxylic acid as a hydrochloride salt (I-27) (0.250 g, 80%) as a white solid. $^1$H NMR (400 MHz, DMSO-$d_6$) δ 13.32 (br, 1H), 12.54 (br, 1H), 8.66 (s, 2H), 8.33-8.31 (d, J=8.4 Hz, 1H), 7.93-7.91 (d, J=8.4, 1H), 7.60 (s, 1H), 7.06 (s, 1H), 4.01 (s, 4H), 3.60 (br. s, 4H), 1.78 (s, 4H), 1.54 (s, 4H). MS: [MH]+366.1.

4-(2-Azaspiro [4.5] decan-2-yl) pyrrolo[1,2-a] quinoxaline-7-carboxylic acid (I-28) (0.090 g, 47%) as a white solid. $^1$H NMR (400 MHz, DMSO-$d_6$) δ 13.24 (br. s, 1H), 11.74 (br. s, 1H), 8.70-8.53 (m, 2H), 8.28-8.26 (d, J=7.2 Hz, 1H), 7.87 (s, 1H), 7.63-7.62 (d, J=5.2 Hz, 1H), 7.02 (s, 1H), 4.09 (br. s, 2H), 3.80 (br. s, 2H), 1.96 (s, 2H), 1.50 (br s, 10H). MS: [MH]+ 350.1.

4-(2-Oxa-7-azaspiro[3.5]nonan-7-yl)pyrrolo[1,2-a]quinoxaline-7-carboxylic acid (I-29) (0.070 g, 19%) as a white solid. $^1$H NMR (400 MHz, DMSO-$d_6$) δ 13.29 (br, 1H), 8.64 (s, 1H), 8.48 (br. s, 1H), 8.33-8.31 (d, J=8.8 Hz, 1H), 7.94-7.92 (d, J=8.8 Hz, 1H), 7.52 (br. s, 1H), 7.05 (s, 1H), 4.42 (s, 4H), 3.91 (s, 4H), 2.07 (s, 4H). MS: [MH]+ 338.1.

4-(3-Azaspiro[5.5]undecan-3-yl)pyrrolo[1,2-a]quinoxaline-7-carboxylic acid as a hydrochloride salt (I-30) (0.040 g, 21%) as an off-white solid. $^1$H NMR (400 MHz, DMSO-$d_6$) δ 13.34 (br, 1H), 12.51 (br, 1H), 8.65 (br. s, 2H), 8.33-8.31 (d, J=8.8 Hz, 1H), 7.92-7.90 (d, J=8.4 Hz, 1H), 7.62 (br. s, 1H), 7.05 (s, 1H), 3.99 (s, 4H), 1.68 (s, 4H), 1.44 (s, 9H). MS: [MH]+ 364.2.

4-(6,6-Dimethyl-3-azabicyclo[3.1.0]hexan-3-yl)pyrrolo[1,2-a]quinoxaline-7-carboxylic acid as a hydrochloride salt (I-31) (0.155 g, 87%) as an off-white solid. $^1$H NMR (400 MHz, DMSO-$d_6$) δ 13.30 (br. s, 1H), 11.67 (br. s, 1H), 8.69 (br. s, 1H), 8.65 (br. s, 1H), 8.32-8.30 (d, J=8.4 Hz, 1H), 7.92-7.90 (d, J=8.0 Hz, 1H), 7.71 (br. s, 1H), 7.06 (s, 1H), 4.36 (br. s, 1H) 4.14 (br. s, 1H), 4.04 (br. s, 1H), 3.93 (br. s, 1H), 1.82 (s, 2H), 1.11 (s, 3H), 0.91 (s, 3H). MS: [MH]+ 322.1.

4-(2,2-Difluoro-7-azaspiro [3.5] nonan-7-yl) pyrrolo[1,2-a] quinoxaline-7-carboxylic acid (I-32) (0.092 g, 53%) as a white solid. $^1$H NMR (400 MHz, DMSO-$d_6$) δ 12.94 (br. s, 1H), 8.36 (s, 1H), 8.19-8.17 (d, J=8.4 Hz, 1H), 8.05 (s, 1H), 7.81-7.79 (d, J=8.4 Hz, 1H), 6.98 (s, 1H), 6.87-6.86 (m, 1H), 3.70 (s, 4H), 2.46-2.43 (m, 4H), 1.77 (m, 4H). MS: [MH]+ 372.2.

4-(6-Azaspiro[3.4]octan-6-yl)pyrrolo[1,2-a]quinoxaline-7-carboxylic acid as a hydrochloride salt (I-33) (0.045 g, 26%) as an off-white solid. $^1$H NMR (400 MHz, DMSO-$d_6$) δ 12.77 (br, 1H), 8.33 (s, 1H), 8.10-8.07 (d, J=8.4 Hz, 1H), 7.93 (s, 1H), 7.70-7.65 (d, J=8.0 Hz, 1H), 7.12-7.10 (d, J=3.2 Hz, 1H), 6.81 (s, 1H), 3.88-3.82 (m, 4H), 2.09-1.99 (m, 4H), 1.98-1.89 (m, 4H). MS: [MH]+ 322.1.

4-(3,3-Dimethyl-2-oxa-8-azaspiro [4.5] decan-8-yl) pyrrolo[1,2-a] quinoxaline-7-carboxylic acid (I-34) (0.025 g, 19%) as a white solid. $^1$H NMR (400 MHz, DMSO-$d_6$) δ 12.92 (br. s, 1H), 8.35 (s, 1H), 8.18-8.16 (d, J=8.4 Hz, 1H), 8.03 (s, 1H), 7.80-7.77 (dd, J=8.4, 1.6 Hz, 1H), 6.96 (s, 1H), 6.86-6.84 (t, J=3.2 Hz, 1H), 3.75-3.69 (m, 4H), 3.62 (s, 2H), 1.68 (br. s, 6H), 1.21 (s, 6H). MS: [MH]+ 380.1.

4-(2-Oxa-8-azaspiro[4.5]decan-8-yl)pyrrolo[1,2-a]quinoxaline-7-carboxylic acid as a hydrochloride salt (I-35) (0.080 g, 47%) as a white solid. $^1$H NMR (400 MHz, DMSO-$d_6$) δ 13.30 (br. s, 1H), 12.40 (br. s, 1H), 8.63 (s, 1H), 8.46 (br. s, 1H), 8.33-8.31 (d, J=8.4 Hz, 1H), 7.94-7.92 (d, J=7.6 Hz, 1H), 7.52 (br, 1H), 7.05 (s, 1H), 4.02 (br. s, 2H), 3.96 (br. s, 2H), 3.82-3.79 (t, J=3.2 Hz, 14 Hz, 2H), 3.55 (s, 2H), 1.86-1.83 (t, J=7.2 Hz, 2H), 1.79 (br. s, 4H). MS: [MH]+ 352.2.

4-(1,1-Difluoro-6-azaspiro[2.5]octan-6-yl)pyrrolo[1,2-a]quinoxaline-7-carboxylic acid (I-36) (0.080 g, 42%) as an off-white solid. $^1$H NMR (400 MHz, DMSO-$d_6$) δ 13.24 (br, 1H), 8.60 (br. s, 1H), 8.42 (br, 1H), 8.32-8.30 (d, J=8.0 Hz, 1H), 7.92-7.90 (d, J=8.0 Hz, 1H), 7.47-7.45 (br, 1H), 7.02 (s, 1H), 4.06 (br. s, 2H), 3.93 (br. s, 2H), 1.93 (br. s, 2H) 1.79 (br. s, 2H), 1.46-1.44 (br. s, 2H). MS: [MH]+ 358.1.

4-(4-(tert-Butyl)piperidin-1-yl)pyrrolo[1,2-a]quinoxaline-7-carboxylic acid (I-37) (0.220 g, 69%) as an off-white solid. $^1$H NMR (400 MHz, DMSO-$d_6$) δ 12.93 (br. s, 1H), 8.35 (s, 1H), 8.18-8.16 (d, J=8.4 Hz, 1H), 8.04 (s, 1H), 7.80-7.78 (d, J=8.4, 1H), 6.97 (s, 1H), 6.85 (s, 1H), 4.60-4.57 (d, J=12.4 Hz, 2H), 2.97-2.91 (t, J=12.0 Hz, 2H) 1.80-1.78 (br. s, 2H), 1.33 (br. s, 3H), 0.87 (s, 9H). MS: [MH]+ 352.2.

4-(4-(Trifluoromethyl)piperidin-1-yl)pyrrolo[1,2-a]quinoxaline-7-carboxylic acid (I-38) (0.200 g, 74%) as a white solid. $^1$H NMR (400 MHz, DMSO-$d_6$) δ 13.39 (br. s, 1H), 8.66 (s, 1H), 8.55 (s, 1H), 8.35-8.33 (d, J=8.4 Hz, 1H), 7.96-7.93 (d, J=8.4 Hz, 1H), 7.54 (br. s, 1H), 7.06 (s, 1H), 4.62-4.59 (d, J=13.2 Hz, 2H), 3.83-3.73 (m, 2H), 2.93-2.84 (m, 1H), 2.07-2.02 (d, J=11.6 Hz, 2H), 1.84-1.78 (m, 2H). MS: [MH]+ 364.1.

4-(4,4-Difluoropiperidin-1-yl) pyrrolo[1,2-a]quinoxaline-7-carboxylic acid (I-39) (0.100 g, 52%) as an off-white solid. $^1$H NMR (400 MHz, DMSO-$d_6$) δ 13.19 br. (s, 1H), 8.60 (br. s, 1H), 8.48-8.35 (m, 1H), 8.33-8.31 (d, J=8.4 Hz, 1H), 7.94-7.92 (d, J=8.4 Hz, 1H), 7.42 (br. s, 1H), 7.03 (s, 1H), 4.04 (br. s, 4H), 2.28 (br. s, 4H). MS: [MH]+ 332.58.

4-(4-Cyclopropylpiperazin-1-yl) pyrrolo[1,2-a]quinoxaline-7-carboxylic acid (I-40) (0.050 g, 34%) as an off-white solid. $^1$H NMR (400 MHz, DMSO-$d_6$) δ 12.82 (br. S, 1H), 8.37-8.36 (d, J=2.4 Hz, 1H), 8.19-8.17 (d, J=8.4 Hz, 1H), 8.06-8.05 (d, J=1.6 Hz, 1H), 7.81-7.79 (dd, J=2.0, 1.6 Hz, 1H), 7.02-7.01 (d, J=3.6 Hz, 1H), 6.88-6.86 (t, J=3.6 Hz, 1H), 3.72-3.70 (t, J=4.4 Hz, 4H), 2.72-2.70 (t, J=4.8 Hz, 4H), 1.70-1.67 (m, 1H), 0.47-0.37 (m, 4H). MS: [MH]+ 337.0.

Example 1.2. Synthesis of 4-(4-(tert-Butyl)phenyl) pyrrolo[1,2-a]quinoxaline-7-carboxylic acid (I-41)

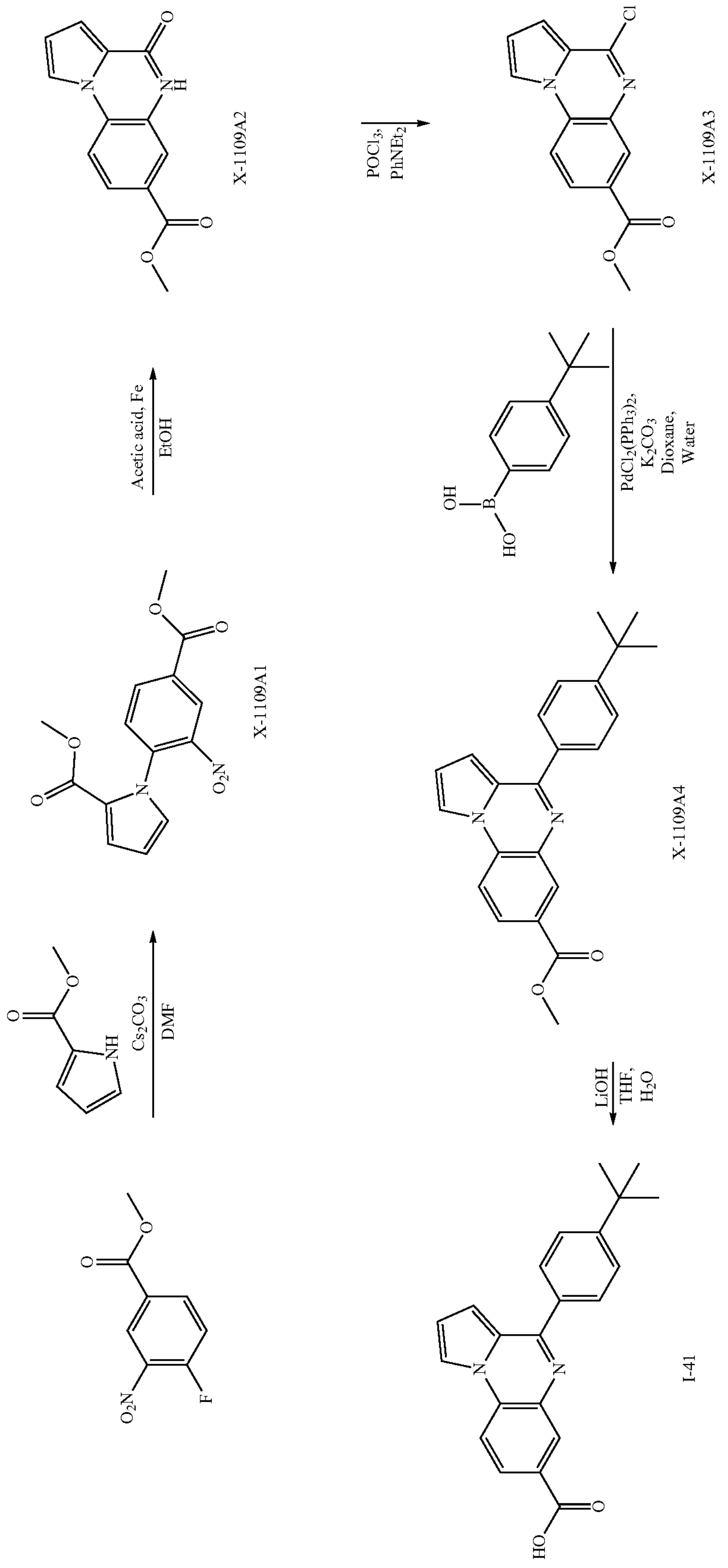
Cs2CO3
DMF
X-1109A1
Acetic acid, Fe
EtOH
X-1109A2
POCl3,
PhNEt2
X-1109A3
PdCl2(PPh3)2,
K2CO3
Dioxane,
Water
X-1109A4
LiOH
THF,
H2O
I-41

Methyl 1-(4-(methoxycarbonyl)-2-nitrophenyl)-1H-pyrrole-2-carboxylate (X-1109A1). Cesium Carbonate (40.0 g, 201.0 mmol) was added to a stirred suspension of methyl 4-fluoro-3-nitrobenzoate (20.0 g, 100.0 mmol) and ethyl 1H-pyrrole-2-carboxylate (12.5 g, 100.0 mmol) in DMF (90 mL) at room temperature and stirred at 50° C. for 5 h. The reaction mixture was slowly poured into ice water (1000 mL) and the resulting precipitate was collected by filtration, washed with cold water (500 mL) and dried in vacuo, to afford ethyl 1-(4-(methoxycarbonyl)-2-nitrophenyl)-1H-pyrrole-2-carboxylate (X-1109A1) (25.0 g, 81%) as an off-white solid, which was used in next step without further purification. MS: $[MH]^+$ 305.1.

Methyl 4-oxo-4,5-dihydropyrrolo[1,2-a]quinoxaline-7-carboxylate (X-1109A2). To a stirred solution of ethyl 1-(4-(methoxycarbonyl)-2-nitrophenyl)-1H-pyrrole-2-carboxylate (X-1109A1) (25.0 g, 75.6 mmol) in acetic acid (400 mL) was added Fe powder (33.26 g, 604.0 mmol) at room temperature and reaction stirred at 60° C. for 2 h. After cooling to room temperature, reaction mixture was filtered and the precipitate was washed with water. The precipitate was taken in 10% methanol in dichloromethane, stirred for 30 min and filtered through a celite bed and filtrate was concentrated under reduced pressure, to afford methyl 4-oxo-4,5-dihydropyrrolo[1,2-a]quinoxaline-7-carboxylate (X-1109A2) (17.0 g, 89%) as an off white solid, which was used in next step without further purification. MS: $[MH]^+$ 243.1.

Methyl 4-chloropyrrolo[1,2-a]quinoxaline-7-carboxylate (X-1109A3). $POCl_3$ (170 mL) was added drop wise, via addition funnel, to a solution of methyl 4-oxo-4,5-dihydropyrrolo[1,2-a]quinoxaline-7-carboxylate (X-1109A2) (17 g, 70.2 mmol) in N, N-diethyl aniline (5 mL) at 0° C. under nitrogen and heated 100° C. to reflux for 2 h. Reaction mixture was allowed to cool to room temperature and was slowly poured into ice-water. The resulting precipitate was filtered and the residue was washed with cold water until the pH of the filtrate became neutral (pH~6-7) and dried in vacuo, to afford methyl 4-chloropyrrolo[1,2-a]quinoxaline-7-carboxylate (X-1109A3) (13.0 g, 71%) as an off-white solid, which was used in next step without further purification. MS: $[MH]^+$ 261.0.

Methyl 4-(4-(tert-butyl)phenyl)pyrrolo[1,2-a]quinoxaline-7-carboxylate (X-1109A4). To a stirred solution of methyl 4-chloropyrrolo[1,2-a]quinoxaline-7-carboxylate (X-1109A3) (4.0 g, 15.3 mmol) in a mixture of dioxane-water (3:1, 50 mL) were added (4-(tert-butyl)phenyl)boronic acid (3.56 g, 20.0 mmol) and $K_2CO_3$ (6.36 g, 46.0 mmol) at room temperature. The reaction mixture was degassed (purging with nitrogen) for 20 min followed by addition of $PdCl_2(PPh_3)_2$ (0.32 g, 0.46 mmol) and the reaction mixture was heated at 100° C. for 45 min. The reaction mixture was cooled to room temperature, diluted with water (250 mL) and was extracted with ethyl acetate (200 mL×3). The combined organic extracts were dried over anhydrous $Na_2SO_4$ and concentrated under reduce pressure. The crude product was purified by silica gel column chromatography, using ethyl acetate-Hexane=1:9→1:4 as gradient, to afford methyl 4-(4-(tert-butyl)phenyl)pyrrolo[1,2-a]quinoxaline-7-carboxylate (X-1109A4) (5.0 g, 90%) as an off-white solid. $^1$H NMR (400 MHz, DMSO-$d_6$) δ 8.63 (dd, J=2.8, 1.2 Hz, 1H), 8.44 (dd, J=5.2, 3.2 Hz, 2H), 8.12 (dd, J=8.6, 1.8 Hz, 1H), 8.02-7.94 (m, 2H), 7.66-7.58 (m, 2H), 7.15-7.14 (m, 1H), 7.05 (dd, J=4.0, 2.8 Hz, 1H), 3.93 (s, 3H), 1.37 (s, 9H). MS: $[MH]^+$ 359.1.

4-(4-(tert-Butyl)phenyl)pyrrolo[1,2-a]quinoxaline-7-carboxylic acid (I-41). To a stirred solution of methyl 4-(4-(tert-butyl)phenyl)pyrrolo[1,2-a]quinoxaline-7-carboxylate (X-1109A4) (5.0 g, 13.90 mmol) in a mixture of THF-water (3:1; 20 mL) was added lithium hydroxide monohydrate (1.44 g, 34.90 mmol) at room temperature under nitrogen and the resulting reaction mixture was heated at 60° C. for 2 h. After cooling to room temperature, the reaction mixture was concentrated under reduced pressure, crude mass was diluted with water (200 mL) and was extracted with ethyl acetate (100×2 mL) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was dried in vacuo to afford 4-(4-(tert-butyl)phenyl)pyrrolo[1,2-a]quinoxaline-7-carboxylic acid (I-41) (4.2 g, 87%) as a white solid. $^1$H NMR (400 MHz, DMSO-$d_6$) δ 13.17 (br. s, 1H), 8.63-8.62 (d, J=1.6 Hz, 1H), 8.43-8.41 (m, 2H), 8.11-8.09 (dd, J=8.4, 1.6 Hz, 1H), 7.98-7.96 (d, J=8.4 Hz, 2H), 7.62-7.60 (d, J=8.4 Hz, 2H), 7.13-7.12 (dd, J=4.0, 1.2 Hz, 1H), 7.05-7.04 (m, 1H), 1.36 (s, 9H). MS: $[MH]^+$ 345.1.

The following compounds were prepared in a manner analogous to the procedures described above for 4-(4-(tert-Butyl)phenyl)pyrrolo[1,2-a]quinoxaline-7-carboxylic acid (I-41):

4-(4-(Trifluoromethyl)phenyl)pyrrolo[1,2-a]quinoxaline-7-carboxylic acid (I-42) (1.400 g, 45%) as an off-white solid. $^1$H NMR (400 MHz, DMSO-$d_6$) δ 13.22 (br, 1H), 8.70-8.69 (d, J=1.6 Hz, 1H), 8.47-8.45 (m, 2H), 8.25-8.23 (d, J=8.0 Hz, 2H), 8.16-8.14 (dd, J=8.4, 1.2 Hz, 1H), 7.98-7.96 (d, J=8.0 Hz, 2H), 7.15-7.14 (d, J=3.6 Hz, 1H), 7.10-7.08 (m, 1H). MS: [MH]+357.57.

4-(4-Fluorophenyl)pyrrolo[1,2-a]quinoxaline-7-carboxylic acid (I-43) (0.060 g, 21%) as a white solid. $^1$H NMR (400 MHz, DMSO-$d_6$) δ 13.21 (br. s, 1H), 8.66 (s, 1H), 8.45-8.43 (m, 2H), 8.14-8.07 (m, 3H), 7.46-7.41 (t, J=8.4 Hz, 2H), 7.12-7.06 (m, 2H). MS: $[MH]^+$ 307.1.

4-(2,4-Difluorophenyl)pyrrolo[1,2-a]quinoxaline-7-carboxylic acid (I-44) (0.018 g, 24%) as a yellow solid. $^1$H NMR (400 MHz, DMSO-$d_6$) 13.23 (br. s, 1H), 8.66 (s, 1H), 8.48-8.46 (d, J=8.8 Hz, 1H), 8.43 (s, 1H), 8.17-8.15 (d, J=8.0 Hz, 1H), 7.85-7.83 (m, 1H), 7.54-7.49 (t, J=9.6 Hz, 1H), 7.34-7.30 (t, J=8.0 Hz, 1H), 7.04 (s, 1H), 6.80 (s, 1H). MS: $[MH]^+$ 325.0.

4-(p-Tolyl)pyrrolo[1,2-a]quinoxaline-7-carboxylic acid (I-45) (0.080 g, 39%) as an off-white solid. $^1$H NMR (400 MHz, DMSO-$d_6$) δ 8.54 (s, 1H), 8.42 (s, 1H), 8.28-8.25 (d, J=8.4 Hz, 1H), 8.11-8.09 (d, J=8.0 Hz, 1H), 7.93-7.91 (d, J=8.0 Hz, 2H), 7.41-7.39 (d, J=8.0 Hz, 2H), 7.04-7.03 (d, J=3.6 Hz, 1H), 7.00-6.98 (m, 1H), 2.43 (s, 3H). MS: $[MH]^+$ 303.5.

4-(4-Methoxyphenyl)pyrrolo[1,2-a]quinoxaline-7-carboxylic acid (I-46) (0.100 g, 17%) as an off-white solid. $^1$H NMR (400 MHz, DMSO-$d_6$) δ 13.17 (br. s, 1H), 8.62 (s, 1H), 8.43 (s, 1H), 8.42-8.40 (d, J=8.4 Hz, 1H), 8.10-8.08 (d, J=8.4 Hz, 1H), 8.03-8.01 (d, J=8.4 Hz, 2H), 7.16-7.12 (m, 3H), 7.05 (br. s, 1H), 3.87 (s, 3H). MS: $[MH]^+$ 319.5.

4-(Pyridin-4-yl)pyrrolo[1,2-a]quinoxaline-7-carboxylic acid (I-47) (0.250 g, 23%) as a yellow solid. $^1$H NMR (400 MHz, DMSO-$d_6$) δ 13.25 (br. s, 1H), 8.83-8.82 (d, J=4.8 Hz, 2H), 8.70 (s, 1H), 8.48-8.47 (br. s, 2H), 8.17-8.15 (d, J=8.4 Hz, 1H), 7.99-7.98 (d, J=4.8 Hz, 2H), 7.20-7.19 (d, J=3.2 Hz, 1H), 7.10 (s, 1H). MS: $[MH]^+$ 290.4.

4-(4-Chlorophenyl)pyrrolo[1,2-a]quinoxaline-7-carboxylic acid (I-48) (0.200 g, 70%) as an off-white solid. $^1$H NMR (400 MHz, DMSO-$d_6$) δ 13.21 (br. s, 1H), 8.66-8.65 (d, J=1.6 Hz, 1H), 8.44-8.42 (m, 2H), 8.14-8.11 (dd, J=8.4, 1.2 Hz, 1H), 8.06-8.04 (d, J=8.4 Hz, 2H), 7.67-7.65 (d, J=8.4 Hz, 2H), 7.12-7.11 (d, J=3.6 Hz, 2H), 7.08-7.06 (t, J=3.6 Hz, 2H). MS: $[MH]^+$323.4/$[MH+2]^+$ 323.4.

4-(4-(tert-Butyl)-2-fluorophenyl)pyrrolo[1,2-a]quinoxaline-7-carboxylic acid (I-49) (0.070 g, 48%) as an off-white solid. $^1$H NMR (400 MHz, DMSO-$d_6$) δ 13.22 (br. s, 1H), 8.63-8.62 (d, J=1.6 Hz, 1H), 8.45-8.43 (d, J=8.8 Hz, 1H), 8.41-8.40 (d, J=2.0 Hz, 1H), 8.16-8.13 (dd, J=8.8, 2.0 Hz, 1H), 7.71-7.67 (t, J=8.0 Hz, 1H), 7.44-7.41 (m, 2H), 7.02-7.01 (m, 1H), 6.78 (br. S, 1H), 1.36 (s, 9H). MS: $[MH]^+$ 363.1.

4-(2-Fluoro-4-(trifluoromethyl)phenyl)pyrrolo[1,2-a]quinoxaline-7-carboxylic acid (I-50) (11.5 g, 79%) as an off-white solid. $^1$H NMR (400 MHz, DMSO-$d_6$) δ 13.25 (br. s, 1H), 8.68-8.68 (d, J=1.6 Hz, 1H), 8.49-8.47 (d, J=8.4 Hz, 1H), 8.44-8.43 (d, J=1.6 Hz, 1H), 8.19-8.16 (dd, J=8.8, 1.6 Hz, 1H), 8.02-7.95 (m, 2H), 7.82-7.80 (d, J=8.0 Hz, 1H), 7.06-7.04 (m, 1H), 6.84 (s, 1H). MS: $[MH]^+$ 375.5.

4-(6-(Trifluoromethyl)pyridin-3-yl)pyrrolo[1,2-a]quinoxaline-7-carboxylic acid (I-51) as an off-white solid (0.180 g, 69%). $^1$H NMR (400 MHz, DMSO-$d_6$) δ 13.25 (br. s, 1H), 9.36 (s, 1H), 8.70-8.68 (d, J=8.8 Hz, 2H), 8.47-8.45 (m, 2H), 8.16-8.12 (t, J=8.4 Hz, 2H), 7.22-7.21 (d, J=4.0 Hz, 1H), 7.11-7.09 (m, 1H). MS: $[MH]^+$ 358.0.

4-(2-Methyl-4-(trifluoromethyl)phenyl)pyrrolo[1,2-a]quinoxaline-7-carboxylic acid (I-52) (0.210 g, 90%) as a yellow solid. $^1$H NMR (400 MHz, DMSO-$d_6$): 13.24 (br, 1H), 8.73 (s, 1H), 8.52-8.50 (d, J=8.8 Hz, 1H), 8.47-8.46 (d, J=1.2 Hz, 1H), 8.19-8.17 (dd, J=8.4, 1.6 Hz, 7.83 (s, 1H), 7.75 (s, 2H), 7.06-7.04 (t, J=3.2 Hz, 1H), 6.71-6.70 (d, J=3.6 Hz, 1H), 2.35 (s, 3H). MS: $[MH]^+$ 371.1.

4-(2-Chloro-4-(trifluoromethyl)phenyl)pyrrolo[1,2-a]quinoxaline-7-carboxylic acid (I-53) (0.060 g, 56%) as an off-white solid. $^1$H NMR (400 MHz, DMSO-$d_6$) 13.24 (br. s, 1H), 8.68 (s, 1H), 8.50-8.48 (d, J=8.4 Hz, 1H), 8.43-8.42 (d, J=1.2 Hz, 1H), 8.19-8.17 (d, J=8.4 Hz, 1H), 8.13 (s, 1H), 7.94-7.89 (m, 2H), 7.03-7.01 (t, J=3.2 Hz, 1H), 6.65-6.64 (d, J=3.6 Hz, 1H). MS: $[MH]^+$ 391/$[MH+2]^+$ 392.9.

4-(2-Cyano-4-(trifluoromethyl)phenyl)pyrrolo[1,2-a]quinoxaline-7-carboxylic acid (I-54) (0.040 g, 27%) as a yellow solid. $^1$H NMR (400 MHz, DMSO-$d_6$) δ 13.32 (br, 1H), 8.75 (s, 1H), 8.62 (s, 1H), 8.52-8.50 (d, J=8.8 Hz, 1H), 8.45-8.45 (d, J=1.2 Hz, 1H), 8.30-8.25 (m, 2H), 8.22-8.19 (dd, J=8.4, 2.0 Hz, 1H), 7.11-7.09 (t, J=4.0 Hz, 1H), 6.97-6.96 (d, J=3.6 Hz, 1H). MS: $[MH]^+$ 382.1.

4-(2-Methoxy-4-(trifluoromethyl)phenyl)pyrrolo[1,2-a]quinoxaline-7-carboxylic acid (I-55) (0.050 g, 51%) as a white solid. $^1$H NMR (400 MHz, DMSO-$d_6$) δ 13.20 (br. s, 1H), 8.59 (s, 1H), 8.45-8.40 (m, 2H), 8.16-8.14 (d, J=8.4 Hz, 1H), 7.70-7.68 (d, J=7.6 Hz, 1H), 7.52-5.47 (m, 3H), 6.97 (s, 1H), 6.62-6.61 (d, J=3.2 Hz, 1H), 3.82 (s, 3H). MS: $[MH]^+$ 387.6.

Example 1.3. Synthesis of 4-(6-Azaspiro[2.5]octan-6-yl)imidazo[1,2-a]quinoxaline-7-carboxylic acid (I-56)

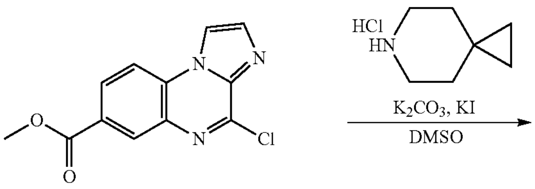

X-1107A3

-continued

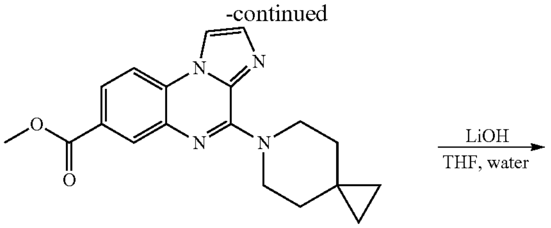

X-1329A1

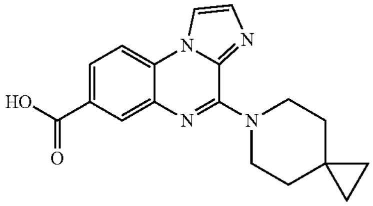

I-56

Methyl 4-(6-azaspiro[2.5]octan-6-yl)imidazo[1,2-a]quinoxaline-7-carboxylate (X-1329A1). To a stirred solution of methyl 4-chloroimidazo[1,2-a]quinoxaline-7-carboxylate (X-1107A3) (0.200 g, 0.77 mmol) in DMSO (3 mL) were added 6-azaspiro[2.5]octane hydrochloride (0.110 g, 0.77 mmol), $K_2CO_3$ (0.310 g, 2.30 mmol) and KI (0.02 g, 0.15 mmol) sequentially at room temperature under nitrogen and the resulting reaction mixture was heated at 100° C. for 1 h. Reaction mixture was cooled to room temperature, quenched with water (20 mL) and was extracted with ethyl acetate (30 mL×3). Collected organic extracts were dried over anhydrous $Na_2SO_4$ and concentrated under reduced pressure. Obtained crude mass was triturated by n-hexane to afford methyl 4-(6-azaspiro[2.5]octan-6-yl)imidazo[1,2-a]quinoxaline-7-carboxylate (X-1329A1) [0.170 g, 66% (crude)] as an off-white solid. MS: $[MH]^+$ 337.1.

4-(6-Azaspiro[2.5]octan-6-yl)imidazo[1,2-a]quinoxaline-7-carboxylic acid (I-56). To a stirred solution of methyl 4-(6-azaspiro[2.5]octan-6-yl)imidazo[1,2-a]quinoxaline-7-carboxylate (X-1329A1) (0.170 g, 0.51 mmol) in a mixture of THF-water (2:1; 10 mL) was added lithium hydroxide monohydrate (0.063 g, 1.52 mmol) at room temperature under nitrogen and the resulting reaction mixture was heated at 60° C. for 1 h. After cooling to room temperature, the reaction mixture was diluted with water (80 mL) and was extracted with ethyl acetate (50×2 mL) to get rid of unwanted organic impurities Aqueous layer was acidified (pH~2-3) with an aqueous 1N HCl solution, the resulting precipitate was collected by filtration and washed with cold water until the pH of the filtrate became neutral (pH~6-7). Obtained solid was dried in vacuo to afford 4-(6-azaspiro[2.5]octan-6-yl)imidazo[1,2-a]quinoxaline-7-carboxylic acid (I-56) (0.110 g, 61%) as an off-white solid. $^1$H NMR (400 MHz, DMSO-$d_6$) δ 13.06 (br. s, 1H), 8.71 (s, 1H), 8.22-8.20 (d, J=8.4 Hz, 1H), 8.09-8.08 (d, J=1.2 Hz, 1H), 7.82-7.80 (dd, J=8.4, 1.2 Hz, 1H), 7.70 (s, 1H), 4.39 (br. s, 4H), 1.49-1.47 (t, J=5.2 Hz, 4H), 0.39 (s, 4H). MS: $[MH]^+$ 323.2.

The following compound was prepared in a manner analogous to the procedures described above for 4-(6-Azaspiro[2.5]octan-6-yl)imidazo[1,2-a]quinoxaline-7-carboxylic acid (I-56):

4-(8-Azaspiro[4.5]decan-8-yl)imidazo[1,2-a]quinoxaline-7-carboxylic acid (I-57) (0.130 g, 80%) as an off-white solid. $^1H$ NMR (400 MHz, DMSO-$d_6$) δ 13.29 (br. s, 1H), 8.81 (s, 1H), 8.40 (s, 1H), 8.30-8.27 (d, J=8.4 Hz, 1H), 7.90-7.88 (d, J=8.0 Hz, 1H), 7.81 (s, 1H), 4.42 (br. s, 4H), 1.63 (s, 8H), 1.50 (s, 4H). MS: $[MH]^+$ 351.3.

Example 1.4. Synthesis of 4-(4-(tert-Butyl)phenyl)imidazo[1,2-a]quinoxaline-7-carboxylic acid (I-58)

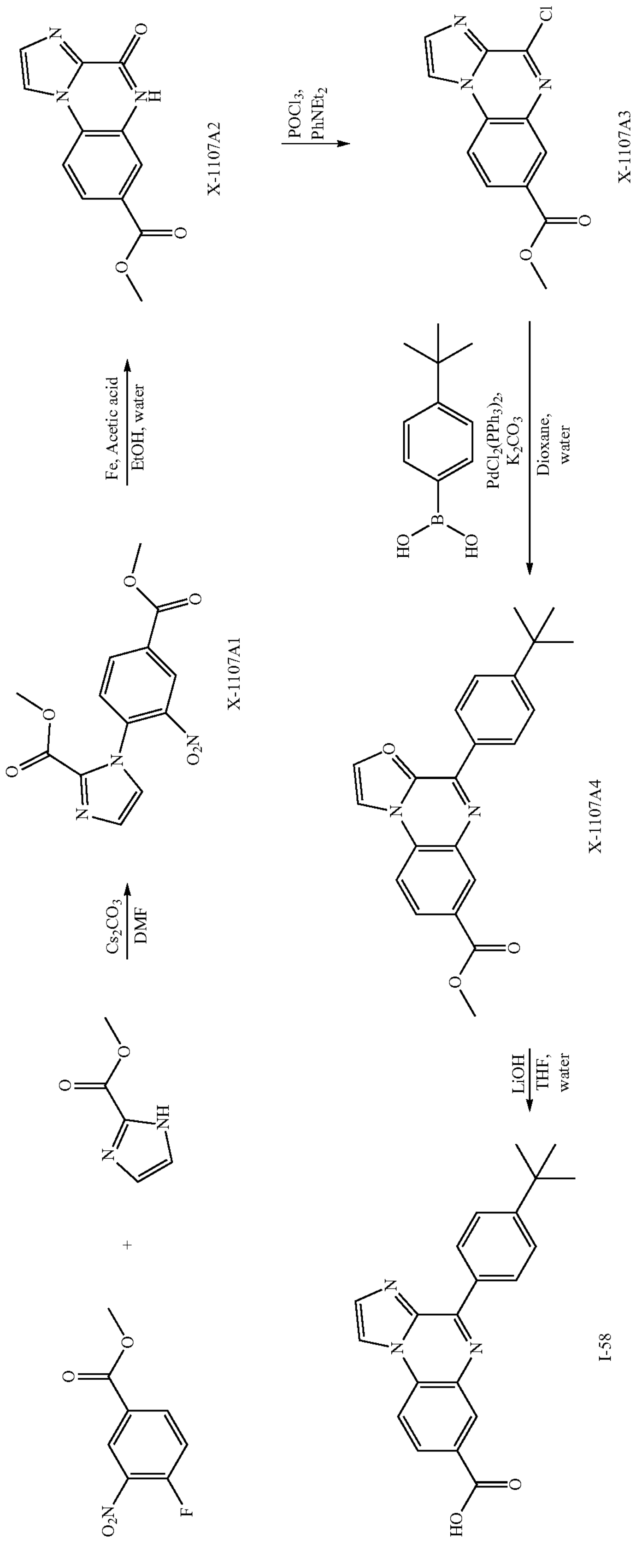
Cs$_2$CO$_3$
DMF
X-1107A1
Fe, Acetic acid
EtOH, water
X-1107A2
POCl$_3$,
PhNEt$_2$
X-1107A3
PdCl$_2$(PPh$_3$)$_2$,
K$_2$CO$_3$
Dioxane,
water
X-1107A4
LiOH
THF,
water
I-58

Methyl 1-(4-(methoxycarbonyl)-2-nitrophenyl)-1H-imidazole-2-carboxylate (X-1107A1). Cesium carbonate (41.03 g, 124.99 mmol) and methyl 1H-imidazole-2-carboxylate (5.0 g, 35.7 mmol) were added to a stirred solution of methyl 4-fluoro-3-nitrobenzoate (7.10 g, 35.7 mmol) in DMF (15 mL) at room temperature and the reaction mixture was stirred at room temperature for 4 h. After cooling to room temperature, reaction mixture was slowly poured in ice water (300 mL) and resulting precipitates were collected by filtration and dried in vacuo to afford methyl 1-(4-(methoxycarbonyl)-2-nitrophenyl)-1H-imidazole-2-carboxylate (X-1107A1) (7.00 g, 62%) as a yellow solid. MS: $[MH]^+$ 305.2.

Methyl 4-oxo-4,5-dihydroimidazo[1,2-a]quinoxaline-7-carboxylate (X-1107A2). To a stirred solution of methyl 1-(4-(methoxycarbonyl)-2-nitrophenyl)-1H-imidazole-2-carboxylate (X-1107A1) (7.00 g, 21.94 mmol) in ethanol-acetic acid-water (5:5:2.5, 15 mL) and Fe powder (9.6 g, 175.4 mmol) was added at −78° C. and resulting reaction mixture was stirred at room temperature for 5 h. The reaction mixture was dilute with DCM-MeOH (1:1, 3 L) and filtered through celite. Filtrate was concentrated under reduced pressure. The crude product was purified by silica gel (C-18) column chromatography, using acetonitrile-water=3:7→4:6 as gradient, to afford methyl 4-oxo-4,5-dihydroimidazo[1,2-a]quinoxaline-7-carboxylate (X-1107A2) (0.80 g, 15%) as a brown solid. MS: $[MH]^+$ 244.0.

Methyl 4-chloroimidazo[1,2-a]quinoxaline-7-carboxylate (X-1107A3). $POCl_3$ (8 mL, 10.0 Vol) was slowly added to a stirred suspension of methyl 4-oxo-4,5-dihydroimidazo[1,2-a]quinoxaline-7-carboxylate (X-1107A2) (0.8 g, 3.29 mmol) in diethylaniline (1.4 mL) at 0° C. under nitrogen and the reaction mixture was heated at 90° C. for 3 h. After cooling to room temperature, reaction mixture was slowly poured in ice water (1000 mL) resulting precipitates were collected by filtration and dried in vacuo, to afford methyl 4-chloroimidazo[1,2-a]quinoxaline-7-carboxylate (X-1107A3) (0.6 g, 70%) as an off-white solid. MS: $[MH]^+$ 261.9.

Methyl 4-(4-(tert-butyl)phenyl)imidazo[1,2-a]quinoxaline-7-carboxylate (X-1107A4). To a stirred solution of methyl 4-chloropyrrolo[1,2-a]quinoxaline-7-carboxylate (X-1107A3) (0.6 g, 2.29 mmol) in a mixture of dioxane-water (3:1, 8 mL) were added (4-(tert-butyl)phenyl)boronic acid (0.53 g, 2.98 mmol) and $K_2CO_3$ (0.95 g, 6.89 mmol) at room temperature. The reaction mixture was degassed (purging with nitrogen) for 20 min followed by addition of $PdCl_2$ $(PPh_3)_2$ (0.048 g, 0.006 mmol) and the reaction mixture was heated at 110° C. for 2 h. The reaction mixture was cooled to room temperature, diluted with water (100 mL) and was extracted with ethyl acetate (80 mL×3). The combined organic extracts were washed with brine (50 mL), dried over anhydrous $Na_2SO_4$ and concentrated under reduce pressure. The crude product was purified by silica gel column chromatography, using ethyl acetate-Hexane=2:8→3:7 as gradient, to afford methyl 4-(4-(tert-butyl)phenyl)imidazo[1,2-a]quinoxaline-7-carboxylate (X-1107A4) (0.6 g, 73%) as an yellow solid. MS: $[MH]^+$ 360.6.

4-(4-(tert-Butyl)phenyl)imidazo[1,2-a]quinoxaline-7-carboxylic acid (I-58). To a stirred solution of methyl 4-(4-(tert-butyl)phenyl)imidazo[1,2-a]quinoxaline-7-carboxylate (X-1107A4) (0.5 g, 1.39 mmol) in a mixture of THF-water (8:3; 11 mL) was added lithium hydroxide (0.11 g, 2.78 mmol) at room temperature and the reaction mixture was heated at 60° C. for 2 h. After cooling to room temperature, the reaction mixture was concentrated under reduced pressure, diluted with water (100 mL), and extracted with ethyl acetate (50×2 mL) to remove unwanted organic impurities. The aqueous layer was acidified (pH~2-3) with aqueous 1N HCl, and the resulting precipitate was collected by filtration, and washed with cold water until the pH of the filtrate became neutral (pH~6-7). The obtained solid was dried in vacuo, to afford 4-(4-(tert-butyl)phenyl)imidazo[1,2-a]quinoxaline-7-carboxylic acid (I-58) (0.3 g, 62%) as a white solid. MS: $[MH]^+$ 346.6.

The following compounds were prepared in a manner analogous to the procedures described above for 4-(4-(tert-Butyl)phenyl)imidazo[1,2-a]quinoxaline-7-carboxylic acid (I-58):

4-(4-(tert-Butyl)-2-fluorophenyl)imidazo[1,2-a]quinoxaline-7-carboxylic acid (I-59) (0.102 g, 38%) as an off-white solid. $^1H$ NMR (400 MHz, DMSO-$d_6$) δ 13.49 (br, 1H), 8.98 (s, 1H), 8.58 (s, 1H), 8.56-8.54 (d, J=8.0 Hz, 1H), 8.30-8.28 (d, J=8.4 Hz, 1H), 7.90 (s, 1H), 7.86-7.82 (t, J=8.4 Hz, 1H), 7.45-7.40 (m, 2H), 1.37 (s, 9H). MS: $[MH]^+$ 364.1.

4-(2-Fluoro-4-(trifluoromethyl)phenyl)imidazo[1,2-a]quinoxaline-7-carboxylic acid (I-60) (0.130 g, 46%) as an off-white solid. $^1H$ NMR (400 MHz, DMSO-$d_6$) δ 13.45 (br. s, 1H), 9.03 (s, 1H), 8.61-8.58 (m, 2H), 8.33 (dd, J=8.4, 1.2 Hz, 1H), 8.16-8.12 (t, J=7.2 Hz, 1H), 7.97-7.93 (m, 2H), 7.84-7.82 (d, J=8.0 Hz, 1H). MS: $[MH]^+$ 376.0.

4-(4-(Trifluoromethyl)phenyl)imidazo[1,2-a]quinoxaline-7-carboxylic acid (I-61) (1.10 g, 91%) as an off-white solid. $^1H$ NMR (400 MHz, DMSO-$d_6$) δ 13.42 (br, 1H), 9.02-9.01 (d, J=6.0 Hz, 3H), 8.64-8.63 (d, J=1.6 Hz, 1H), 8.55-8.53 (d, J=8.8 Hz, 1H), 8.28-8.25 (dd, J=8.8, 1.6 Hz, 1H), 7.99-7.97 (m, 3H). MS: $[MH]^+$ 358.1.

4-(4-Cyclohexylphenyl)imidazo[1,2-a]quinoxaline-7-carboxylic acid (I-62) (15 mg, 31%) as a yellow solid. LCMS m/z=372.2 $[M+H]^+$; $^1H$ NMR (400 MHz, DMSO-$d_6$) δ 13.31 (s, 1H), 8.94 (d, J=1.2 Hz, 1H), 8.76-8.69 (m, 2H), 8.59 (d, J=1.8 Hz, 1H), 8.48 (d, J=8.6 Hz, 1H), 8.21 (dd, J=8.6, 1.9 Hz, 1H), 7.94 (d, J=1.2 Hz, 1H), 7.46-7.40 (m, 2H), 2.68-2.56 (m, 1H), 1.91-1.77 (m, 4H), 1.77-1.67 (m, 1H), 1.55-1.35 (m, 4H), 1.32-1.22 (m, 1H).

4-Phenylimidazo[1,2-a]quinoxaline-7-carboxylic acid (I-63) $^1H$ NMR (400 MHz, DMSO-$d_6$) δ 11.65 (s, 1H), 8.18 (s, 1H), 7.97 (s, 3H), 6.99 (s, 2H), 4.87 (d, J=6.8 Hz, 1H), 4.76 (s, 1H), 4.60-4.48 (m, 2H), 4.22 (q, J=8.6 Hz, 3H), 4.11 (dd, J=8.7, 5.4 Hz, 2H), 3.98 (dd, J=10.1, 5.8 Hz, 2H), 3.91 (d, J=11.0 Hz, 3H), 3.73-3.64 (m, 2H), 3.57 (t, J=11.4 Hz, 3H), 3.46-3.34 (m, 1H), 2.74 (dt, J=14.0, 7.2 Hz, 1H), 2.09-1.96 (m, 2H), 1.88 (d, J=13.0 Hz, 2H), 1.73-1.51 (m, 6H). m/z=290.1 $[M+H]^+$.

4-(4-Methoxyphenyl)imidazo[1,2-a]quinoxaline-7-carboxylic acid (I-64) $^1H$ NMR (400 MHz, DMSO-$d_6$) δ 8.96 (d, J=1.2 Hz, 1H), 8.93-8.88 (m, 2H), 8.60 (d, J=1.8 Hz, 1H), 8.50 (d, J=8.8 Hz, 1H), 8.21 (dd, J=8.6, 1.8 Hz, 1H), 7.96 (d, J=1.2 Hz, 1H), 7.19-7.14 (m, 2H), 3.89 (s, 3H). m/z=320.2 $[M+H]^+$.

4-(3-(tert-Butyl)phenyl)imidazo[1,2-a]quinoxaline-7-carboxylic acid (I-65) $^1H$ NMR (400 MHz, DMSO-$d_6$) δ 8.98 (d, J=1.4 Hz, 1H), 8.89 (t, J=1.8 Hz, 1H), 8.63 (dd, J=7.8, 1.6 Hz, 2H), 8.53 (d, J=8.6 Hz, 1H), 8.24 (dd, J=8.6, 2.0 Hz, 1H), 7.99 (d, J=1.2 Hz, 1H), 7.65 (m, 1H), 7.54 (t, J=7.8 Hz, 1H), 1.40 (s, 9H). m/z=346.2 $[M+H]^+$.

4-(p-Tolyl)imidazo[1,2-a]quinoxaline-7-carboxylic acid (I-66) $^1H$ NMR (400 MHz, DMSO-$d_6$) δ 8.95 (s, 1H), 8.78 (d, J=8.0 Hz, 2H), 8.62 (d, J=1.8 Hz, 1H), 8.50 (d, J=8.6 Hz, 1H), 8.23 (dd, J=8.6, 1.8 Hz, 1H), 7.96 (s, 1H), 7.42 (d, J=8.0 Hz, 2H), 2.44 (s, 3H). m/z=304.1 $[M+H]^+$.

4-(4-(1-(Trifluoromethyl)cyclopropyl)phenyl)imidazo[1,2-a]quinoxaline-7-carboxylic acid (I-67) $^1H$ NMR (400 MHz, DMSO-$d_6$) δ 13.36 (s, 1H), 8.99 (d, J=1.4 Hz, 1H), 8.82-8.77 (m, 2H), 8.62 (d, J=1.8 Hz, 1H), 8.53 (d, J=8.6 Hz, 1H), 8.25 (dd, J=8.6, 1.8 Hz, 1H), 7.98 (d, J=1.2 Hz, 1H), 7.70 (d, J=8.2 Hz, 2H), 1.45-1.40 (m, 2H), 1.23 (d, J=7.2 Hz, 2H). m/z=398.1 $[M+H]^+$.

4-Cyclohexylimidazo[1,2-a]quinoxaline-7-carboxylic acid (I-68) $^1H$ NMR (400 MHz, DMSO-$d_6$) δ 8.84 (d, J=1.4 Hz, 1H), 8.48 (d, J=1.8 Hz, 1H), 8.44 (d, J=8.6 Hz, 1H), 8.18 (dd, J=8.6, 1.8 Hz, 1H), 7.84 (s, 1H), 3.63-3.54 (m, 1H), 2.02 (d, J=12.8 Hz, 2H), 1.87 (d, J=13.2 Hz, 2H), 1.81-1.71 (m, 3H), 1.52-1.41 (m, 2H), 1.38-1.29 (m, 1H). LCMS m/z=296.2 $[M+H]^+$.

4-(Tetrahydro-2H-pyran-4-yl)imidazo[1,2-a]quinoxaline-7-carboxylic acid (I-69) $^1H$ NMR (400 MHz, DMSO-$d_6$) δ 8.87 (s, 1H), 8.56-8.43 (m, 2H), 8.19 (dd, J=8.7, 1.8 Hz, 1H), 7.85 (d, J=1.2 Hz, 1H), 4.05-3.99 (m, 2H), 3.85-3.80 (m, 1H), 3.60-3.55 (m, 2H), 2.10-1.92 (m, 4H). LCMS m/z=298.2 $[M+H]^+$.

4-Cyclopropylimidazo[1,2-a]quinoxaline-7-carboxylic acid (I-70) $^1H$ NMR (400 MHz, DMSO-$d_6$) δ 8.85 (d, J=1.4 Hz, 1H), 8.42-8.36 (m, 2H), 8.13 (dd, J=8.6, 1.8 Hz, 1H), 7.86 (d, J=1.2 Hz, 1H), 3.03-2.97 (m, 1H), 1.37-1.33 (m, 2H), 1.22 (dt, J=8.2, 3.4 Hz, 2H). LCMS m/z=254.2 $[M+H]^+$.

4-Cyclobutylimidazo[1,2-a]quinoxaline-7-carboxylic acid (I-71) $^1H$ NMR (400 MHz, DMSO-$d_6$) δ 8.87 (d, J=1.3 Hz, 1H), 8.54 (d, J=1.9 Hz, 1H), 8.47 (d, J=8.6 Hz, 1H), 8.20 (dd, J=8.6, 1.9 Hz, 1H), 7.85 (d, J=1.2 Hz, 1H), 4.42-4.32 (m, 1H), 2.62-2.55 (m, 2H), 2.45-2.38 (m, 2H), 2.19-2.11 (m, 1H), 1.98-1.92 (m, 1H). LCMS m/z=268.2 $[M+H]^+$.

Example 1.5. Synthesis of 4-(4-(tert-Butyl)phenyl)-9-fluoroimidazo[1,2-a]quinoxaline-7-carboxylic acid (I-72)

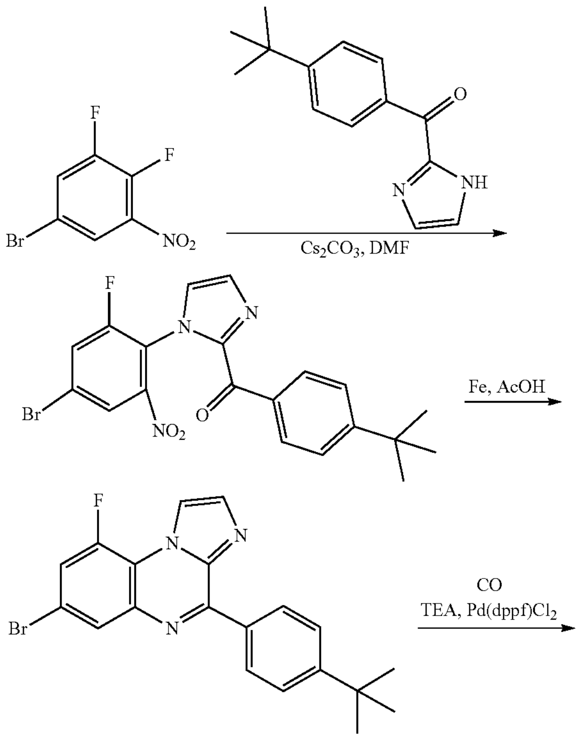

-continued

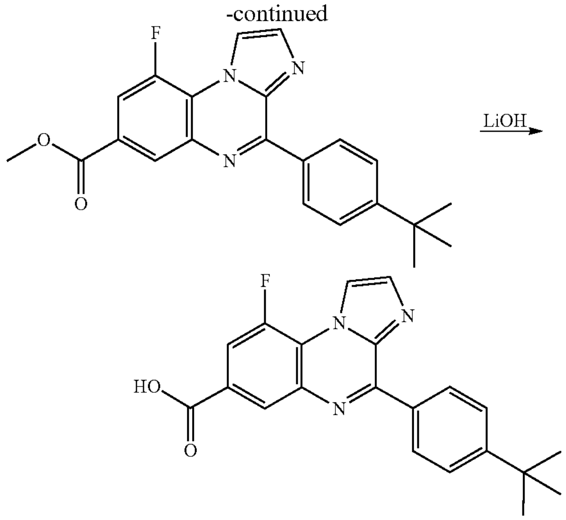

(1-(4-Bromo-2-fluoro-6-nitrophenyl)-1H-imidazol-2-yl)(4-(tert-butyl)phenyl)methanone (CGC-0934-040). To a solution of 5-bromo-1,2-difluoro-3-nitrobenzene (100 mg, 0.42 mmol) in DMF (10 mL) was added (4-(tert-butyl)phenyl)(1H-imidazol-2-yl)methanone (96 mg, 0.42 mmol) and $Cs_2CO_3$ (74 mg, 0.55 mmol). The mixture was heated at 55° C. overnight then cooled to room temperature, diluted with water (60 mL) and extracted with DCM (100 mL×2). The combined organic layers were washed with brine, dried over $Na_2SO_4$, filtered and concentrated to afford (1-(4-bromo-2-fluoro-6-nitrophenyl)-1H-imidazol-2-yl)(4-(tert-butyl)phenyl)methanone (180 mg, 95%) as a white solid. LCMS m/z=446.0 $[M+H]^+$.

7-Bromo-4-(4-(tert-butyl)phenyl)-9-fluoroimidazo[1,2-a]quinoxaline (CGC-0934-041). To a solution of (1-(4-bromo-2-fluoro-6-nitrophenyl)-1H-imidazol-2-yl)(4-(tert-butyl)phenyl)methanone (180 mg, 0.4 mmol) in HOAc (10 mL) was added iron powder (67 mg, 1.2 mmol). The mixture was heated at reflux for 1 h, then cooled to room temperature, diluted with water (30 mL) and extracted with DCM (80 mL×3). The combined organic layers were washed with brine, dried over $Na_2SO_4$, filtered and concentrated. The crude product was purified by prep-TLC (eluent: Pet. Ether: EtOAc=3:1) to afford 7-bromo-4-(4-(tert-butyl)phenyl)-9-fluoroimidazo[1,2-a]quinoxaline (80 mg, 50%) as a white solid. LCMS m/z=398.0 $[M+H]^+$.

Methyl 4-(4-(tert-butyl)phenyl)-9-fluoroimidazo[1,2-a]quinoxaline-7-carboxylate (CGC-0934-045). To a solution of 7-bromo-4-(4-(tert-butyl)phenyl)-9-fluoroimidazo[1,2-a]quinoxaline (50 mg, 0.13 mmol) and TEA (50 mg, 0.5 mmol) in MeOH (5 mL) was added Pd(dppf)C12 (5 mg, 0.01 mmol). The reaction mixture was heated at 60° C. under a CO atmosphere overnight. The mixture was diluted with water (60 mL), extracted with EtOAc (100 mL×2). The combined organic layers were washed with brine, dried over $Na_2SO_4$, filtered and concentrated. The residue was purified by prep-TLC (eluent: Pet. Ether:EtOAc=20:1) to afford 4-(4-(tert-butyl)phenyl)-9-fluoroimidazo[1,2-a]quinoxaline-7-carboxylate (40 mg, 85%) as a yellow solid. LCMS m/z=378.2 $[M+H]^+$.

4-(4-(tert-Butyl)phenyl)-9-fluoroimidazo[1,2-a]quinoxaline-7-carboxylic acid (I-72). To a solution of 4-(4-(tert-butyl)phenyl)-9-fluoroimidazo[1,2-a]quinoxaline-7-carboxylate (40 mg, 0.1 mmol) in a mixture of THE (2 mL), MeOH (2 mL) and water (2 mL) was added LiOH (10 mg, 0.4 mmol). The mixture was stirred at room temperature for 2 h, diluted with water (20 mL) and extracted with EtOAc (30 mL). The aqueous layer was collected and acidified with 1M HCl to pH~2 and extracted with EtOAc (60 mL×3). The combined organic layers were washed with brine, dried over $Na_2SO_4$, filtered and concentrated to afford 4-(4-(tert-butyl) phenyl)-9-fluoroimidazo[1,2-a]quinoxaline-7-carboxylic acid (18 mg, 47%) as a white solid. 1H NMR (400 MHz, DMSO-$d_6$) δ 13.62 (s, 1H), 8.75-8.68 (m, 2H), 8.70-8.64 (m, 1H), 8.42 (d, J=1.5 Hz, 1H), 8.04 (dd, J=12.0, 1.7 Hz, 1H), 7.99 (d, J=1.3 Hz, 1H), 7.68-7.60 (m, 2H), 1.37 (s, 9H). LCMS m/z=364.3 $[M+H]^+$.

Example 1.6. Synthesis of 4-(4-(tert-Butyl)phenyl) imidazo[1,2-a]quinoxaline-7-carboxamide (I-73)

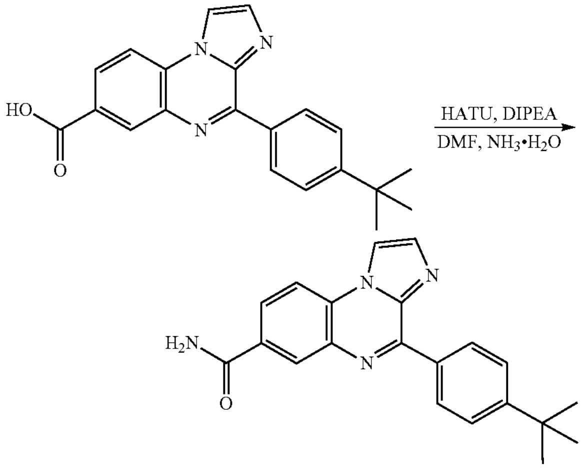

To a solution of 4-(4-(tert-butyl)phenyl)imidazo[1,2-a] quinoxaline-7-carboxylic acid (I-58) (50 mg, 0.14 mmol) in DMF (2 mL) was added HATU (53 mg, 0.14 mmol). The mixture was stirred at room temperature for 30 min. Ammonium hydroxide (28%, 2 mL) and DIPEA (72 mg, 0.56 mmol) were added and the reaction mixture was stirred overnight. The mixture was diluted with water (60 mL) and extracted with EtOAc (100 mL×2). The combined organic layers were washed with brine, dried over $Na_2SO_4$, filtered and concentrated. The crude product was purified by column chromatography on silica gel (DCM:MeOH=20:1) to afford 4-(4-(tert-butyl)phenyl)imidazo[1,2-a]quinoxaline-7-carboxamide (17.5 mg, 36%) as a white solid. $^1H$ NMR (400 MHz, DMSO-$d_6$) δ 8.94 (d, J=1.4 Hz, 1H), 8.78-8.73 (m, 2H), 8.67 (d, J=1.8 Hz, 1H), 8.49 (d, J=8.8 Hz, 1H), 8.30 (s, 1H), 8.22 (dd, J=8.6, 1.8 Hz, 1H), 7.95 (d, J=1.2 Hz, 1H), 7.68-7.60 (m, 2H), 7.58 (s, 1H), 1.37 (s, 9H). LCMS m/z=345.2 $[M+H]^+$.

The following compounds were prepared in a manner analogous to the procedures described above for 4-(4-(tert-butyl)phenyl)imidazo[1,2-a]quinoxaline-7-carboxamide (I-73):

4-(4-(tert-Butyl)phenyl)-N,N-dimethylimidazo[1,2-a] quinoxaline-7-carboxamide (I-74)$^1H$ NMR (400 MHz, DMSO-$d_6$) δ 8.94 (s, 1H), 8.73 (d, J=8.3 Hz, 2H), 8.47 (d, J=8.5 Hz, 1H), 8.11 (d, J=1.8 Hz, 1H), 7.94 (s, 1H), 7.77 (dd, J=8.5, 1.8 Hz, 1H), 7.62 (d, J=8.3 Hz, 2H), 3.08-3.00 (m, 6H), 1.36 (s, 9H). m/z=373.3 $[M+H]^+$.

Example 1.7. Synthesis of 4-(4-(tert-Butyl)phenyl) imidazo[1,2-a]quinoxaline-7-carbonitrile (I-75)

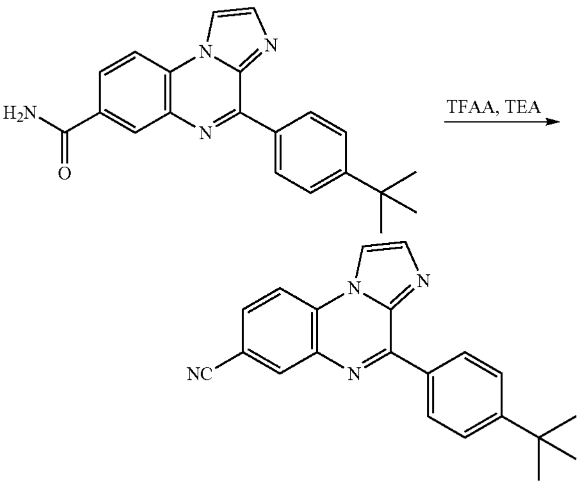

To a solution of 4-(4-(tert-butyl)phenyl)imidazo[1,2-a] quinoxaline-7-carboxamide (I-73) (140 mg, 0.41 mmol) in DCM (2 mL) at 0° C. was added TEA (185 mg, 1.83 mmol) and TFAA (256 mg, 1.22 mmol). The mixture was stirred at room temperature overnight. The mixture was diluted with water (60 mL) and extracted with EtOAc (100 mL×2). The combined organic layers were washed with brine, dried over $Na_2SO_4$, filtered and concentrated. The residue obtained was purified by prep-TLC (eluent: DCM:MeOH=20:1) to afford 4-(4-(tert-butyl)phenyl)imidazo[1,2-a]quinoxaline-7-carbonitrile (100 mg, 76%) as a white solid. $^1H$ NMR (400 MHz, DMSO-$d_6$) δ 8.99 (d, J=1.2 Hz, 1H), 8.75-8.69 (m, 2H), 8.66-8.53 (m, 2H), 8.15 (dd, J=8.6, 1.8 Hz, 1H), 7.98 (d, J=1.2 Hz, 1H), 7.65-7.61 (m, 2H), 1.36 (s, 9H). LCMS m/z=327.2 $[M+H]^+$.

Example 1.8. Synthesis of 4-(4-(tert-Butyl)phenyl)-7-(1H-tetrazol-5-yl)imidazo[1,2-a]quinoxaline (I-76)

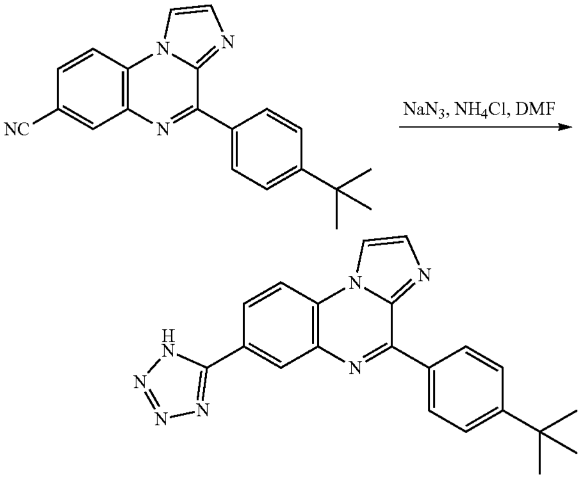

To a solution of 4-(4-(tert-butyl)phenyl)imidazo[1,2-a] quinoxaline-7-carbonitrile (70 mg, 0.21 mmol) in DMF (1 mL) was added $NaN_3$ (42 mg, 0.64 mmol) and $NH_4Cl$ (35 mg, 0.64 mmol). The mixture was heated at 125° C. overnight then cooled to room temperature. The mixture was diluted with water (60 mL) and extracted with EtOAc (100 mL×2). The combined organic layers were washed with brine, dried over $Na_2SO_4$, filtered and concentrated. The residue obtained was triturated with $Et_2O$ to afford 4-(4-(tert-butyl)phenyl)-7-(1H-tetrazol-5-yl)imidazo[1,2-a]quinoxaline (60 mg, 89%) as a yellow solid. $^1$H NMR (400 MHz, DMSO-$d_6$) δ 8.89 (d, J=1.2 Hz, 1H), 8.81-8.72 (m, 2H), 8.64 (d, J=1.6 Hz, 1H), 8.43 (d, J=8.6 Hz, 1H), 8.33 (dd, J=8.6, 1.8 Hz, 1H), 7.91 (d, J=1.2 Hz, 1H), 7.68-7.59 (m, 2H), 1.38 (s, 9H). LCMS m/z=370.2 $[M+H]^+$.

Example 1.9. Synthesis of (4-(4-(tert-Butyl)phenyl) imidazo[1,2-a]quinoxalin-7-yl)methanol (I-77)

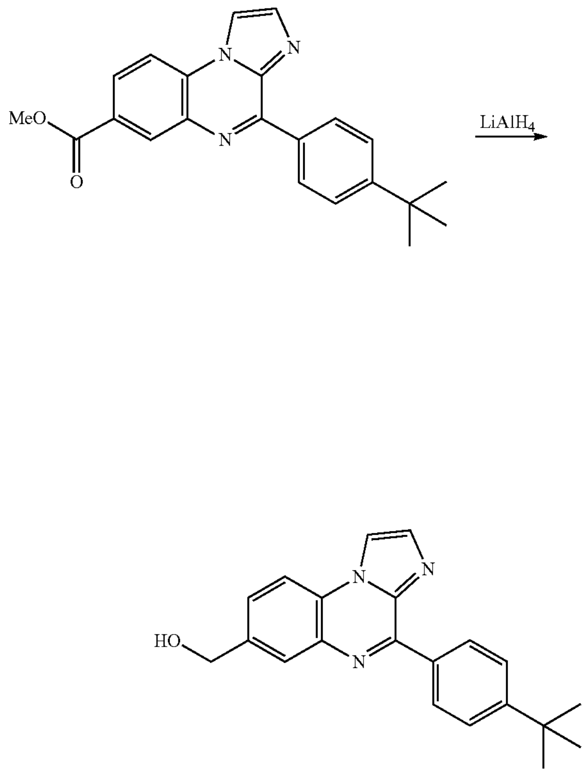

To a solution of methyl 4-(4-(tert-butyl)phenyl)imidazo [1,2-a]quinoxaline-7-carboxylate (CEN2-X-1107A4) (60 mg, 0.166 mmol) in dry THE (1 mL) at 0° C. was added LAH (25 mg, 0.667 mmol). The mixture was then stirred at room temperature for 2 h. The mixture was quenched with water (10 mL) and extracted with EtOAc (30 mL×2). The combined organic layers were washed with brine, dried over $Na_2SO_4$, filtered and concentrated. The crude product was purified by prep-TLC (DCM:MeOH=20:1) to afford (4-(4-(tert-butyl)phenyl)imidazo[1,2-a]quinoxalin-7-yl)methanol (53 mg, 98%) as a white solid. $^1$H NMR (400 MHz, DMSO-$d_6$) δ8.87 (d, J=1.2 Hz, 1H), 8.76-8.71 (m, 2H), 8.37 (d, J=8.6 Hz, 1H), 8.05 (d, J=1.8 Hz, 1H), 7.90 (d, J=1.2 Hz, 1H), 7.68 (dd, J=8.6, 1.9 Hz, 1H), 7.64-7.59 (m, 2H), 5.45 (t, J=5.8 Hz, 1H), 4.72 (d, J=5.8 Hz, 2H), 1.36 (s, 10H). LCMS m/z=332.1 $[M+H]^+$.

Example 1.10. Synthesis of N-(1-methoxypropan-2-yl)-5-(4-(trifluoromethyl)phenyl)-3,4-dihydroisoquinoline-2(1H)-carboxamide (I-78)

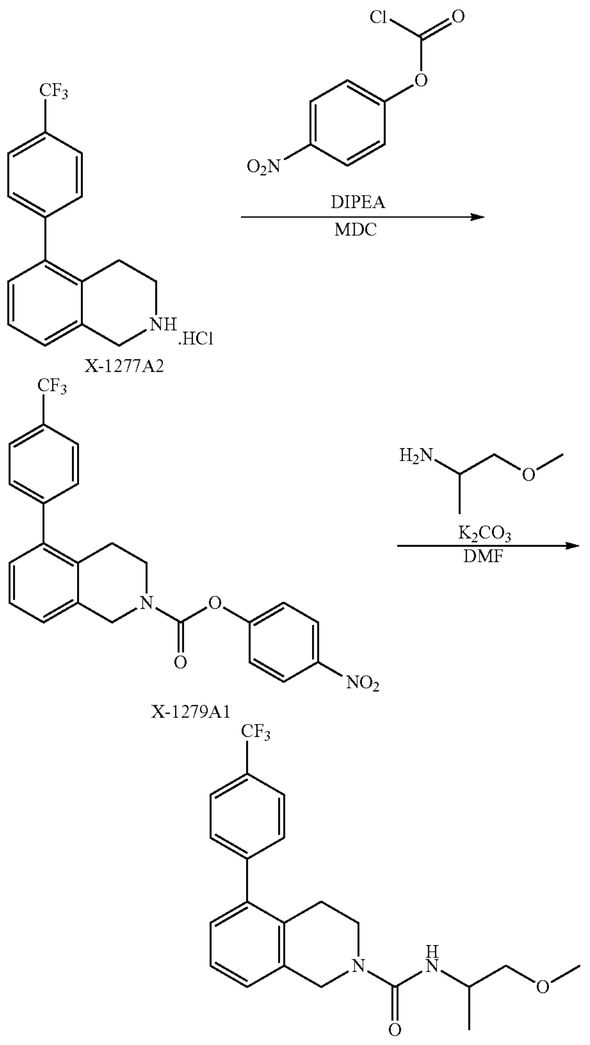

X-1277A2

X-1279A1

I-78

4-Nitrophenyl 5-(4-(trifluoromethyl)phenyl)-3,4-dihydroisoquinoline-2(1H)-carboxylate (X-1279A1). 4-Nitrophenyl carbonochloridate (0.280 g, 1.40 mmol) and DIPEA (0.820 g, 6.36 mmol) were added to a stirred suspension of 5-(4-(trifluoromethyl)phenyl)-1,2,3,4-tetrahydroisoquinoline hydrochloride (X-1277A2) (0.400 g, 1.27 mmol) in DCM (15 mL) at room temperature under nitrogen and reaction mixture was stirred at the same temperature for 30 min. Reaction mixture was poured into water (50 mL) and was extracted with DCM (50 ml×3). Combined organic extracts were dried over $Na_2SO_4$ and concentrated under reduced pressure to afford 4-nitrophenyl 5-(4-(trifluoromethyl)phenyl)-3,4-dihydroisoquinoline-2(1H)-carboxylate (X-1279A1) (0.650 g, 99%) as a yellow semi solid.

N-(1-methoxypropan-2-yl)-5-(4-(trifluoromethyl)phenyl)-3,4-dihydroisoquinoline-2(1H)-carboxamide (I-78). 1-Methoxypropan-2-amine (0.180 g, 1.99 mmol) and potassium carbonate (0.318 g, 2.48 mmol) were added sequentially to a stirred solution of 4-nitrophenyl 5-(4-(trifluoromethyl)phenyl)-3,4-dihydroisoquinoline-2(1H)-carboxylate (X-1279A1) (0.220 g, 0.49 mmol) in DMF (5 mL) at room temperature under nitrogen and the resulting mixture was heated at 80° C. for 16 h. After cooling to room temperature, rection mixture was diluted with water (30 mL) and was extracted with ethyl acetate (50 mL×3). Combined organic extracts were dried over $Na_2SO_4$ and concentrated under reduced pressure. The crude product was purified by reverse phase (C-18) silica gel column chromatography, using acetonitrile-water=0:1→1:0 as gradient, to afford N-(1-methoxypropan-2-yl)-5-(4-(trifluoromethyl)phenyl)-3,4-dihydroisoquinoline-2(1H)-carboxamide (I-78) (0.040 g, 20%) as an off-white solid. $^1$H NMR (400 MHz, DMSO-$d_6$) δ 7.81-7.79 (d, J=8.0 Hz, 2H), 7.58-7.56 (d, J=8.0 Hz, 2H), 7.32-7.28 (t, J=7.6 Hz, 1H), 7.22-7.21 (d, J=7.2 Hz, 1H), 7.15-7.13 (d, J=7.2 Hz, 1H), 6.22-6.20 (d, J=8.0 Hz, 1H), 4.55 (s, 2H), 3.91-3.86 (m, 1H), (t, J=5.6 Hz, 2H), 3.31-3.29 (m, 1H), 3.23 (s, 3H), 3.17-3.13 (m, 1H), 2.65-2.61 (m, 2H), 1.05-1.04 (d, J=5.6 Hz, 3H). MS: $[MH]^+$ 393.1.

The following compound was prepared in a manner analogous but not identical to the procedures described above for N-(1-methoxypropan-2-yl)-5-(4-(trifluoromethyl)phenyl)-3,4-dihydroisoquinoline-2(1H)-carboxamide (I-78):

1-Methoxypropan-2-yl 5-(4-(trifluoromethyl)phenyl)-3,4-dihydroisoquinoline-2(1H)-carboxylate (I-79) (0.080 g, 56%) as a white solid. $^1$H NMR (400 MHz, DMSO-$d_6$) δ 7.80-7.78 (d, J=8.0 Hz, 2H), 7.59-7.57 (d, J=8.0 Hz, 2H), 7.33-7.27 (m, 2H), 7.17-7.15 (d, J=6.8 Hz, 1H), 4.88 (br. s, 1H), 4.61 (s, 2 h), 3.48 (s, 2H), 3.26 (s, 3H), 2.67-2.65 (m, 2H), 1.16 (s, 3H). (Two protons were merged with DMSO $d_6$ Moisture peak). MS: $[MH]^+$ 394.1.

Example 1.11. Synthesis of N-(2-(4-(tert-butyl)phenyl)quinazolin-7-yl)acrylamide (I-80)

dichloromethane (250 mL), filtered through a celite bed and filtrate was concentrated under reduced pressure to afford 2-amino-4-nitrobenzaldehyde (X-1143A2) as an orange solid [12.5 g, 97% (crude)], which was used in next step without further purification. MS: $[MH]^+$ 166.8.

7-Nitroquinazolin-2-ol (X-1143A3). A mixture of 2-amino-4-nitrobenzaldehyde (10.0 g, 60.2 mmol) and urea (36.14 g, 60.2 mmol) were heated at 180° C. for 15 min. After cooling to room temperature, reaction mixture was slowly poured into ice water (1000 mL), the resulting precipitates were collected by filtration and dried in vacuo. The crude product was purified by reverse phase (C-18) silica gel column chromatography, using acetonitrile-water=1:9→1:4 as gradient, to afford 7-nitroquinazolin-2-ol (X-1143A4) as a brown solid (7.8 g, 54%). MS: [MH]- 190.0.

2-Chloro-7-nitroquinazoline (X-1143A4). A solution of 7-nitroquinazolin-2-ol (X-1143A3) (7.8 g, 40.8 mmol) in $POCl_3$ (80 mL, 60.2 mmol) was heated at 80° C. for 3 h. After cooling to room temperature, reaction mixture was slowly quenched with an aqueous solution of saturated $NaHCO_3$ and was extracted with ethyl acetate (200 mL×3). Combined organic extracts were dried over anhydrous $Na_2SO_4$ and concentrated under reduce pressure. The crude product was purified by silica gel column chromatography, using ethyl acetate-hexane=1.5:8.5→1:4 as gradient, to afford 2-chloro-7-nitroquinazoline (X-1143A4) as a yellow solid (1.5 g, 14%). MS: $[MH]^+$ 210.0.

2-(4-(tert-Butyl)phenyl)-7-nitroquinazoline (X-1143A5). To a stirred solution of 2-chloro-7-nitroquinazoline (X-1143A4) (0.200 g, 0.95 mmol) in 1,4-dioxane-water (4:1, 4 mL) were added 4-(tert-butyl)phenyl)boronic acid (0.22 g, 1.24 mmol) and $K_2CO_3$ (0.39 g, 2.87 mmol) sequentially at room temperature under nitrogen. The resulting mixture was degassed (purged with nitrogen) for 20 min followed by the

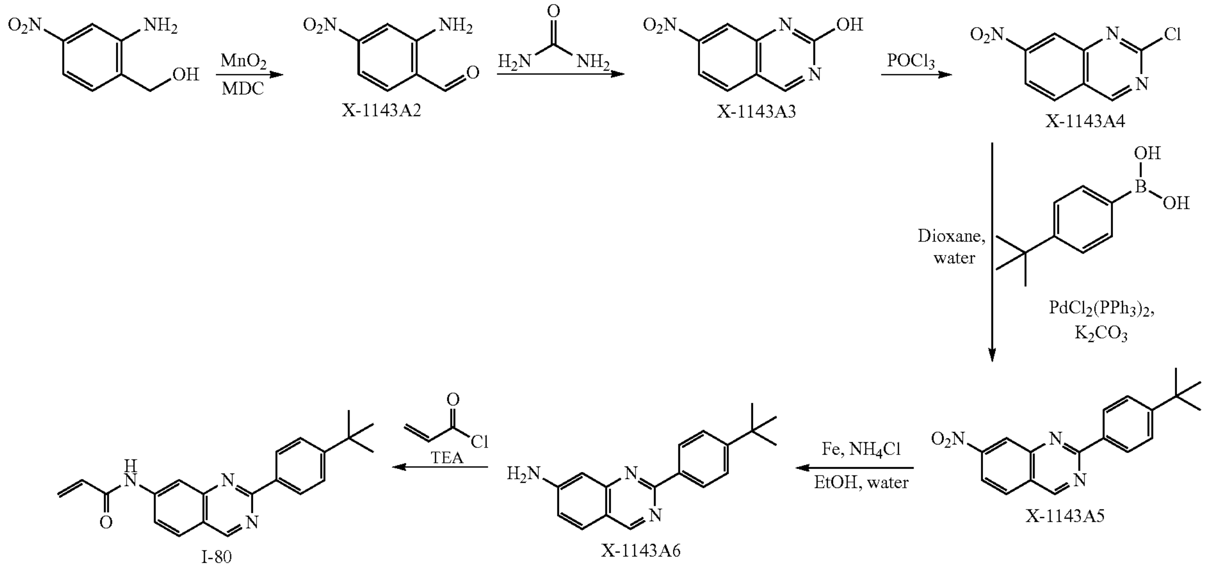

X-1143A2 X-1143A3 X-1143A4 X-1143A5 X-1143A6 I-80

2-Amino-4-nitrobenzaldehyde (X-1143A2). To a stirred solution of (2-amino-4-nitrophenyl) methanol (X-1143A1) (13.0 g, 40.1 mmol) in dichloromethane (600 mL) was added $MnO_2$ (48.9 g, 281.2 mmol) at room temperature and the resulting reaction mixture was allowed to stir at room temperature for 16 h. Reaction mixture was diluted with addition of $PdCl_2(PPh_3)_2$ (0.058 g, 0.080 mmol) and was heated at 110° C. for 2 h. After cooling to room temperature, reaction mixture was diluted with water (20 mL) and was extracted with ethyl acetate (20 mL×3). Combined organic extracts were dried over anhydrous $Na_2SO_4$ and concentrated under reduce pressure. The crude product was purified by silica gel column chromatography, using ethyl acetate-hexane=0.1:9.9→0.5:9.5 as gradient, to afford 2-(4-(tert-butyl)phenyl)-7-nitroquinazoline (X-1143A5) as an white solid (0.13 g, 44%). MS: $[MH]^+$ 307.9.

2-(4-(tert-Butyl)phenyl)quinazolin-7-amine (X-1143A6). To a stirred solution of 2-(4-(tert-butyl)phenyl)-7-nitroquinazoline (X-1143A5) (0.100 g, 0.32 mmol) in ethanol-water (8:2; 10 mL) were added Zn dust (0.170 g, 2.60 mmol) and ammonium chloride (0.16 g, 2.600 mmol) at room temperature and stirred for 2 h at the same temperature. The reaction mixture was filtered through celite and residue was washed with ethyl acetate (50 mL). Combined filtrates were washed with water (20 mL), dried over anhydrous $Na_2SO_4$ and concentrated under reduce pressure to afford 2-(4-(tert-butyl)phenyl)quinazolin-7-amine (X-1143A6) [0.100 g, 85% (crude)] as a brown solid, which was used in next step without further purification. MS: $[MH]^+$ 278.1.

N-(2-(4-(tert-butyl)phenyl)quinazolin-7-yl)acrylamide (I-80). To a stirred solution of 2-(4-(tert-butyl)phenyl)quinazolin-7-amine (X-1143A6) (0.100 g, 0.36 mmol) in dichloromethane (10 mL) were added triethylamine (0.10 g, 1.08 mmol) and acryloyl chloride (0.03 g, 0.39 mmol) respectively at 0° C. under nitrogen and the resulting mixture was stirred at room temperature for 1 h. Reaction mixture was diluted with water (10 mL) and was extracted with ethyl acetate (20 mL×2). Combined organic extracts were dried over anhydrous $Na_2SO_4$ and concentrated under reduce pressure to give a crude mass, which was purified by reverse phase (C-18) silica gel column chromatography, using acetonitrile-water=9:1→1:0 as gradient, to afford N-(2-(4-(tert-butyl)phenyl)quinazolin-7-yl)acrylamide acrylamide (I-80) (0.055 g, 46%) as a white solid. $^1H$ NMR (400 MHz, DMSO-$d_6$) δ 10.72 (s, 1H), 9.51 (s, 1H), 8.58 (s, 1H), 8.49-8.47 (d, J=8.4 Hz, 2H), 8.10-8.08 (d, J=8.4 Hz, 1H), 7.77-8.74 (dd, J=8.8, 1.6 Hz, 1H), 7.59-8.57 (d, J=8.4 Hz, 2H), 6.57-6.50 (d, J=16.8, 10.0 Hz, 1H), 6.40-6.36 (d, J=16.4 Hz, 1H), 5.90-5.87 (d, J=11.6 Hz, 1H), 1.34 (s, 9H). MS: $[MH]^+$ 332.1.

The following compounds were prepared in a manner analogous to the procedures described above for N-(2-(4-(tert-butyl)phenyl)quinazolin-7-yl)acrylamide (I-80):

N-(2-(p-Tolyl)quinazolin-7-yl)acrylamide (I-81) (0.009 g, 13%) as a white sticky solid. $^1H$ NMR (400 MHz, DMSO-$d_6$) δ 10.76 (s, 1H), 9.50 (s, 1H), 8.57 (s, 1H), 8.46-8.44 (d, J=8.0 Hz, 2H), 8.10-8.08 (d, J=8.0 Hz, 1H), 7.78-7.76 (d, J=8.0 Hz, 1H), 7.37-7.35 (d, J=8.0 Hz, 2H), 6.57-6.51 (dd, J=16.8, 10.0 Hz, 1H), 6.40-6.36 (d, J=16.8 Hz, 1H), 5.89-5.87 (d, J=10.0 Hz, 1H), 2.40 (S, 3H). MS: $[MH]^+$ 290.1.

N-(2-(4-Fluorophenyl)quinazolin-7-yl)acrylamide (I-82) (0.025 g, 11%) as a white solid. $^1H$ NMR (400 MHz, DMSO-$d_6$) δ 10.79 (s, 1H), 9.53 (s, 1H), 8.62-8.59 (m, 3H), 8.12-8.10 (d, J=8.8 Hz, 1H), 7.80-7.77 (dd, J=8.8, 2.0 Hz, 1H), 7.41-7.36 (t, J=8.8 Hz, 2H), 6.57-6.51 (d, J=16.8, 10.0 Hz, 1H), 6.40-6.36 (d, J=16.8 Hz, 1H), 5.90-5.87 (d, J=10.0 Hz, 1H). MS: [MH]294.0.

Example 1.12. Synthesis of 4-(4-(tert-Butyl)phenyl)-2-methylpyrrolo[1,2-a]quinoxaline-7-carboxylic acid (I-83)

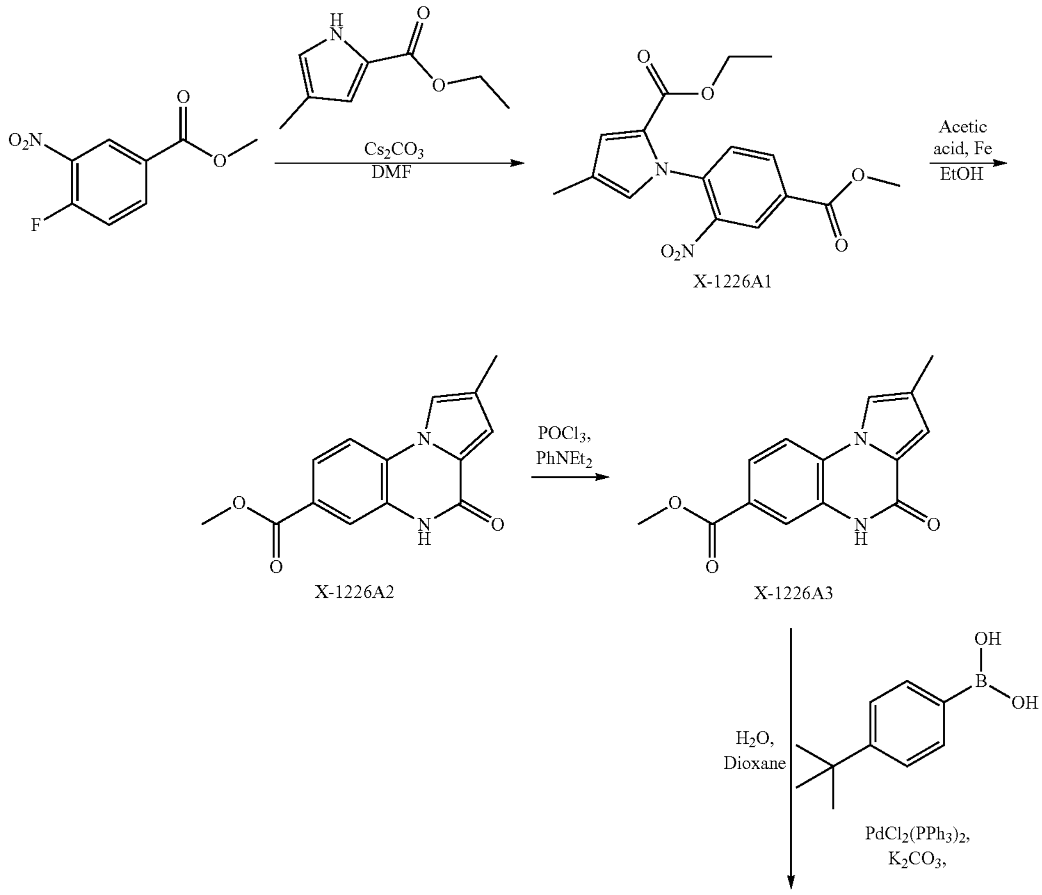

-continued

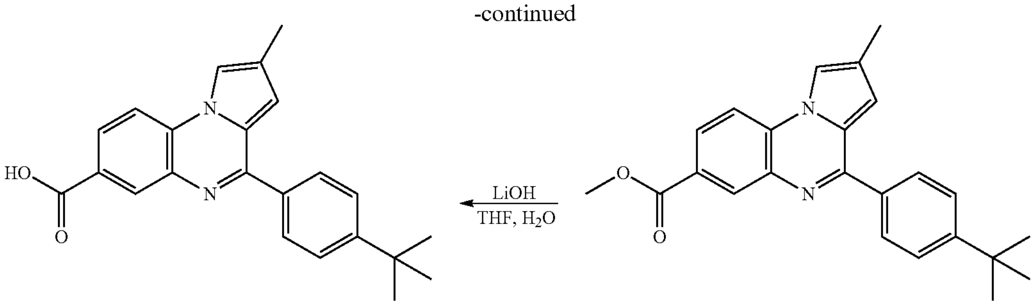

I-83 X-1226A4

Ethyl 1-(4-(methoxycarbonyl)-2-nitrophenyl)-4-methyl-1H-pyrrole-2-carboxylate (X-1226A1). Cesium Carbonate (3.20 g, 10.05 mmol) was added to a stirred suspension of methyl 4-fluoro-3-nitrobenzoate (1.00 g, 5.02 mmol) and ethyl 4-methyl-1H-pyrrole-2-carboxylate (0.768 g, 5.02 mmol) in DMF (5 mL) at room temperature and stirred at 50° C. for 2 h. The reaction mixture was slowly poured into ice water (100 mL) and was extracted with ethyl acetate (150 mL×3). Combined organic extracts were washed with brine (50 mL), dried over anhydrous $Na_2SO_4$ and concentrated in vacuo. The crude product was combined with identically prepared three batches and the combined crude product was purified by silica gel column chromatography, using ethyl acetate-hexane=1:19→1:9 as gradient, to afford ethyl 1-(4-(methoxycarbonyl)-2-nitrophenyl)-4-methyl-1H-pyrrole-2-carboxylate (X-1226A1) (2.4 g, 48%) as an off-white solid. MS: $[MH]^+$ 333.1.

Methyl 2-methyl-4-oxo-4,5-dihydropyrrolo[1,2-a]quinoxaline-7-carboxylate (X-1226A2). To a stirred solution of ethyl 1-(4-(methoxycarbonyl)-2-nitrophenyl)-4-methyl-1H-pyrrole-2-carboxylate (X-1226A1) (2.4 g, 7.22 mmol) in acetic acid (10 mL) was added Fe powder (3.23 g, 57.83 mmol) at room temperature and the resulting suspension was stirred at 80° C. for 2 h. After cooling to room temperature, reaction mixture was filtered and the precipitate was washed with water. The precipitate was taken in 10% methanol in dichloromethane, stirred for 30 min at room temperature, filtered through celite bed and filtrate was concentrated under reduced pressure to give crude product. The crude product purified by trituration using n pentane, to afford methyl 2-methyl-4-oxo-4,5-dihydropyrrolo[1,2-a]quinoxaline-7-carboxylate (X-1226A2) (1.6 g, 86%) as an off-white solid. MS: $[MH]^+$ 257.0.

Methyl 4-chloro-2-methylpyrrolo[1,2-a]quinoxaline-7-carboxylate (X-1226A3). $POCl_3$ (5 mL) was added drop wise, via dropping funnel, to a stirred solution of methyl 2-methyl-4-oxo-4,5-dihydropyrrolo[1,2-a]quinoxaline-7-carboxylate (X-1226A2) (0.5 g, 1.95 mmol) in N, N-diethyl aniline (0.5 mL) at 0° C. under nitrogen. After completion of addition of $POCl_3$, the reaction mixture was slowly brought to reflux and continued heating for 16 h. Reaction mixture was allowed to cool to room temperature and was slowly poured into ice-water. The resulting precipitate was filtered and the residue was washed with cold water. The product was combined with crude from two more identically prepared batches and the combined solid was dried under high vacuum to give methyl 4-chloro-2-methylpyrrolo[1,2-a]quinoxaline-7-carboxylate (X-1226A3) (0.253 g, 15%) as an off-white solid. MS: $[MH]^+$ 275.0.

Methyl 4-(4-(tert-butyl)phenyl)-2-methylpyrrolo[1,2-a]quinoxaline-7-carboxylate (X-1226A4). To a stirred solution of methyl methyl 4-chloro-2-methylpyrrolo[1,2-a]quinoxaline-7-carboxylate (X-1226A3) (0.250 g, 0.91 mmol) in a mixture of 1,4-dioxane-water (3:1, 10 mL) was added (4-(tert-butyl)phenyl)boronic acid (0.244 g, 1.36 mmol) and $K_2CO_3$ (0.378 g, 2.73 mmol) at room temperature under nitrogen. The reaction mixture was degassed (purging with nitrogen) for 20 min followed by the addition of $PdCl_2(PPh_3)_2$ (0.064 g, 0.09 mmol) and the reaction mixture was heated at 90° C. for 2 h. The reaction mixture was cooled to room temperature, diluted with water (50 mL) and was extracted with ethyl acetate (50 mL×3). The combined organic extracts were washed with brine (50 mL), dried over anhydrous $Na_2SO_4$ and concentrated in vacuo. The crude product was purified by silica gel column chromatography, using Ethyl acetate-hexane=1:19→1:9 as gradient, to afford methyl 4-(4-(tert-butyl)phenyl)-2-methylpyrrolo[1,2-a]quinoxaline-7-carboxylate (X-1226A4) (0.300 g, 80%) as an off-white solid. MS: $[MH]^+$ 373.0.

4-(4-(tert-Butyl)phenyl)-2-methylpyrrolo[1,2-a]quinoxaline-7-carboxylic acid (I-83). To a stirred solution of methyl 4-(4-(tert-butyl)phenyl)-2-methylpyrrolo[1,2-a]quinoxaline-7-carboxylate (X-1226A4) (0.200 g, 0.53 mmol) in a mixture of THF-water (1:1; 6 mL) was added lithium hydroxide monohydrate (0.070 g, 1.61 mmol) at room temperature under nitrogen and the resulting reaction mixture was heated at 60° C. for 2 h. After cooling to room temperature, the reaction mixture was concentrated under reduced pressure, diluted with water (20 mL) and was extracted with ethyl acetate (20×2 mL) to remove unwanted organic impurities. The aqueous layer was acidified (pH~2-3) with an aqueous 1N HCl solution and the resulting precipitate was collected by filtration. Obtained residue was washed with cold water until the pH of the filtrate became neutral (pH~6-7) and dried under high vacuum to afford 4-(4-(tert-butyl)phenyl)-2-methylpyrrolo[1,2-a]quinoxaline-7-carboxylic acid (I-83) (0.070 g, 83%) as a yellow solid. 1H NMR (400 MHz, DMSO-$d_6$) δ 13.34 (br, 1H), 8.80 (s, 1H), 8.63 (s, 1H), 8.46-8.44 (d, J=8.8 Hz, 1H), 8.19-8.16 (dd, J=1.6, 1.2 Hz, 1H), 7.99-7.97 (d, J=8.4 Hz, 2H), 7.72-7.70 (d, J=8.4 Hz, 2H), 7.33 (s, 1H), 2.38 (s, 3H), 1.37 (s, 9H). MS: $[MH]^+$ 359.0.

The following compound was prepared in a manner analogous to the procedures described above for 4-(4-(tert-Butyl)phenyl)-2-methylpyrrolo[1,2-a]quinoxaline-7-carboxylic acid (I-83):

4-(2-Fluoro-4-(trifluoromethyl)phenyl)-2-methylpyrrolo[1,2-a]quinoxaline-7-carboxylic acid (I-84) (0.050 g, 41%) as an off-white solid. $^1H$ NMR (400 MHz, DMSO-$d_6$) δ 13.21 (br, 1H), 8.48 (s, 1H), 8.41-8.40 (d, J=1.6 Hz, 1H), 8.37-8.35 (d, J=8.8 Hz, 1H), 8.16-8.13 (dd, J=8.4, 1.6 Hz, 1H), 8.00-7.94 (m, 2H), 7.81-7.79 (d, J=8.0 Hz, 1H), 6.66 (s, 1H), 2.32 (s, 3H). MS: $[MH]^+$ 389.02.

Example 1.13. Synthesis of N-(4-Methyl-2-(4-(trifluoromethyl)phenyl)quinolin-7-yl)acrylamide (I-85)

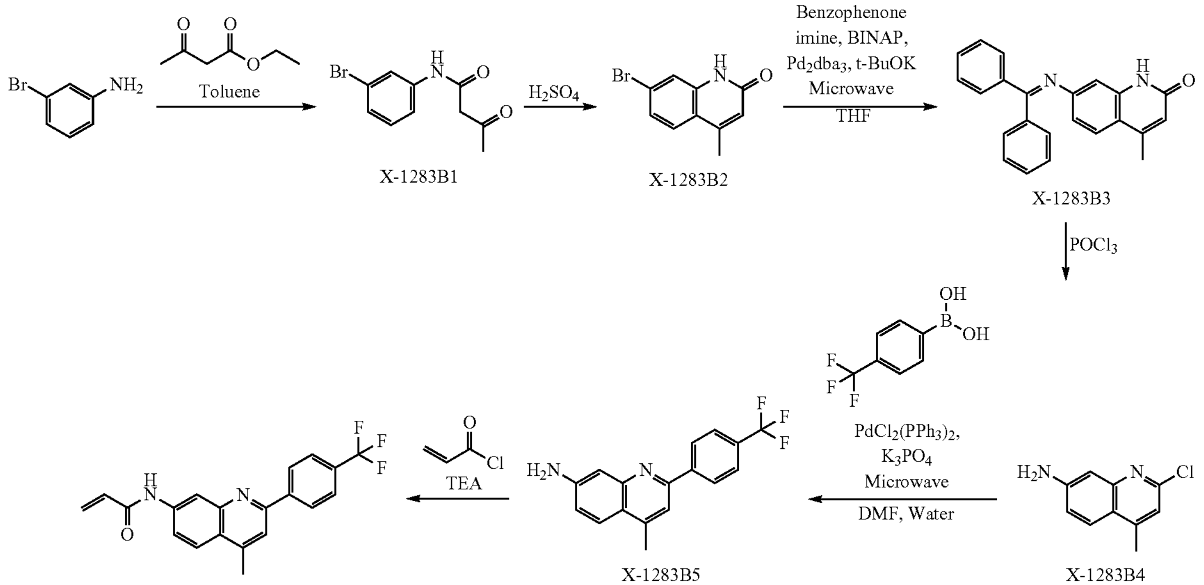

X-1283B1

X-1283B2

X-1283B3

X-1283B4

X-1283B5

I-85

N-(3-bromophenyl)-3-oxobutanamide (X-1283B1) Ethyl 3-oxobutanoate (15.1 g, 116.0 mmol) was added to a stirred solution of 3-bromoaniline (10.0 g, 58.0 mmol) in toluene (130 mL) at room temperature under nitrogen and the resulting solution was stirred at 90° C. for 16 h. After cooling to room temperature, reaction mixture was slowly poured into ice-water (500 mL) and was extracted with ethyl acetate (500 mLx2). Combined organic extracts were dried over $Na_2SO_4$ and concentrated under reduced pressure. The crude product was purified by silica gel column chromatography, using ethyl acetate-hexane=0:1→1:1 as gradient, to afford N-(3-bromophenyl)-3-oxobutanamide (X-1283B1) (4.50 g, 30%) as an off-white solid. MS: [MH]+256.0/[MH+2]$^+$ 258.0.

7-Bromo-4-methylquinolin-2(1H)-one (X-1283B2). A solution of N-(3-bromophenyl)-3-oxobutanamide (X-1283B1) (4.50 g, 17.6 mmol) in $H_2SO_4$ (50 mL) was heated at 120° C. for 1 h. After cooling to room temperature reaction mixture was slowly poured in ice water (500 mL), the resulting precipitate was collected by filtration, washed with cold water (500 mL) and dried under high vacuum to afford 7-bromo-4-methylquinolin-2(1H)-one (X-1283B2) (3.6 g, 86%) as an off-white solid. MS: [MH]$^+$ 237.9.

7-((Diphenylmethylene)amino)-4-methylquinolin-2(1H)-one (X-1283B3). To a stirred solution of 7-bromo-4-methylquinolin-2(1H)-one (X-1283B2) (0.750 g, 3.15 mmol) and benzophenone imine (0.680 g, 3.78 mmol) in THE (15 mL) was added potassium tert-butoxide (1.0 g, 9.45 mmol) at room temperature under nitrogen. The reaction mixture was degassed (purging with nitrogen) for 30 min followed by the addition of $Pd_2(dba)_3$ (0.196 g, 0.31 mmol) and BINAP (0.288 g, 0.031 mmol) at room temperature under nitrogen. The reaction mixture was heated at 120° C. under microwave irradiation for 30 min. Reaction mixture was cooled to room temperature, diluted with water (100 mL) and was extracted with ethyl acetate (100 mLx3). Combined organic extracts were dried over $Na_2SO_4$ and concentrated under reduced pressure. The crude product was combined with an identically-prepared four batches and combined crude batches were purified by reverse phase (C-18) silica gel column chromatography, using acetonitrile-water=0:1→1:0 as gradient, to afford 7-((diphenylmethylene)amino)-4-methylquinolin-2(1H)-one (X-1283B3) (1.40 g, 27%) as a yellow solid. MS: [MH]$^+$ 339.1.

2-Chloro-4-methylquinolin-7-amine (X-1283B4). A solution of 7-((diphenylmethylene)amino)-4-methylquinolin-2(1H)-one (X-1283B3) (1.40 g) in $POCl_3$ (30 mL) was heated at 90° C. for 1 h. After cooling to room temperature, reaction mixture was poured into ice-water (200 mL), basify (pH~7-8) with an aqueous solution of saturated $NaHCO_3$ and was extracted with ethyl acetate (50 mlx3). Combined organic extracts were dried over $Na_2SO_4$ and concentrated under reduced pressure. The crude product was purified by silica gel column chromatography, using ethyl acetate-hexane=0:1→1:4 as gradient, to afford 2-chloro-4-methylquinolin-7-amine (X-1283B4) (0.250 g, 31%) as an off-white solid. MS: [MH]$^+$ 193.0/[MH+2]$^+$195.0.

4-Methyl-2-(4-(trifluoromethyl)phenyl)quinolin-7-amine (X-1283B5). To a stirred solution of 2-chloro-4-methylquinolin-7-amine (X-1283B4) (0.200 g, 1.04 mmol) and (4-(trifluoromethyl)phenyl)boronic acid (0.395 g, 2.08 mmol) in a mixture of DMF-water (4:1, 5 ml) was added tribasic potassium phosphate (0.552 g, 2.60 mmol) at room temperature under nitrogen. The reaction mixture was degassed (purging with nitrogen) for 20 min followed by the addition of $PdCl_2(PPh_3)_2$ (0.0725 g, 0.10 mmol) and the resulting mixture was heated at 110° C. under microwave irradiation for 40 min. Reaction was brought to room temperature, was quenched with water (50 mL) and was extracted with ethyl acetate (50 mLx3). Combined organic extracts were dried over $Na_2SO_4$ and concentrated under reduced pressure. The crude product was purified by reverse phase (C-18) silica gel column chromatography, using acetonitrile-water=0:1→1:0 as gradient, to afford 4-methyl-2-(4-(trifluoromethyl)phenyl)quinolin-7-amine (X-1283B5) (0.230 g, 58%) as an off-white solid. MS: [MH]$^+$ 303.6.

N-(4-Methyl-2-(4-(trifluoromethyl)phenyl)quinolin-7-yl) acrylamide (I-85). Acryloyl Chloride (0.066 g, 0.72 mmol) was added to a stirred solution of 4-methyl-2-(4-(trifluoromethyl)phenyl)quinolin-7-amine (X-1283B5) (0.200 g, 0.66 mmol) and triethylamine (0.200 g, 1.98 mmol) in DCM (5 mL) at 0° C. under nitrogen and reaction mixture was stirred at room temperature for 30 min. Reaction was quenched with water (50 mL) and was extracted with DCM (50 ml×3). Combined organic extracts were dried over $Na_2SO_4$ and concentrated under reduced pressure. The crude product was purified by reverse phase (C-18) silica gel column chromatography, using acetonitrile-water=0:1→1:0 as gradient, to afford N-(4-methyl-2-(4-(trifluoromethyl) phenyl)quinolin-7-yl)acrylamide (I-85) (0.150 g, 55%) as a white solid. $^1$H NMR (400 MHz, DMSO-$d_6$) δ 10.54 (s, 1H), 8.63-8.62 (d, J=2.0 Hz, 1H), 8.48-8.46 (d, J=8.0 Hz, 2H), 8.10-8.08 (d, J=9.2 Hz, 1H), 8.00 (s, 1H), 7.91-7.89 (d, J=8.4 Hz, 2H), 7.78-7.75 (dd, J=8.8, 2.0 Hz, 1H), 6.56-6.49 (dd, J=17.2, 10.0 Hz, 1H), 6.37-6.32 (dd, J=17.2, 1.6 Hz, 1H), 5.85-5.82 (dd, J=10.0, 1.6 Hz, 1H), 2.74 (s, 3H). MS: $[MH]^+$ 357.2.

The following compounds were prepared in a manner analogous to the procedures described above for N-(4-methyl-2-(4-(trifluoromethyl)phenyl)quinolin-7-yl)acrylamide (I-85):

N-(2-(4-(tert-Butyl)phenyl)-4-methylquinolin-7-yl)acrylamide (I-86) (1.00 g, 60%) as yellow solid. $^1$H NMR (400 MHz, DMSO-$d_6$) δ 10.49 (s, 1H), 8.559-8.555 (d, J=1.6 Hz, 1H), 8.18-8.16 (d, J=8.4 Hz, 2H), 8.06-8.03 (d, J=9.2 Hz, 1H), 7.87 (s, 1H), 7.74-7.71 (dd, J=9.2, 1.6 Hz, 1H), 7.56-7.54 (d, J=8.4 Hz, 2H), 6.55-6.48 (dd, J=17.2, 10.0 Hz, 1H), 6.36-6.32 (dd, J=17.2, 1.6 Hz, 1H), 5.84-5.81 (dd, J=8.0, 2.0 Hz, 1H), 2.71 (s, 3H), 1.34 (s, 9H). MS: $[MH]^+$ 345.2.

N-(2-(2-fluoro-4-(trifluoromethyl)phenyl)-4-methylquinolin-7-yl)acrylamide (I-90) (0.035 g, 17%) as a white solid. 1H NMR (400 MHz, DMSO-$d_6$) δ 10.57 (s, 1H), 8.62 (s, 1H), 8.25-8.22 (t, J=7.2 Hz, 1H), 8.14-8.12 (d, J=9.2 Hz, 1H), 7.90-7.87 (d, J=10.4 Hz, 1H), 7.83-7.76 (m, 2H), 7.72 (s, 1H), 6.55-6.49 (dd, J=17.2, 10.4 Hz, 1H), 6.36-6.32 (d, J=17.2 Hz, 1H), 5.85-5.83 (d, J=10.4 Hz, 1H), 2.73 (s, 3H). MS: $[MH]^+$ 375.1.

Example 1.14. Synthesis of 2-(4-(tert-Butyl)phenyl)-4-methylquinoline-7-carboxylic acid (I-88)

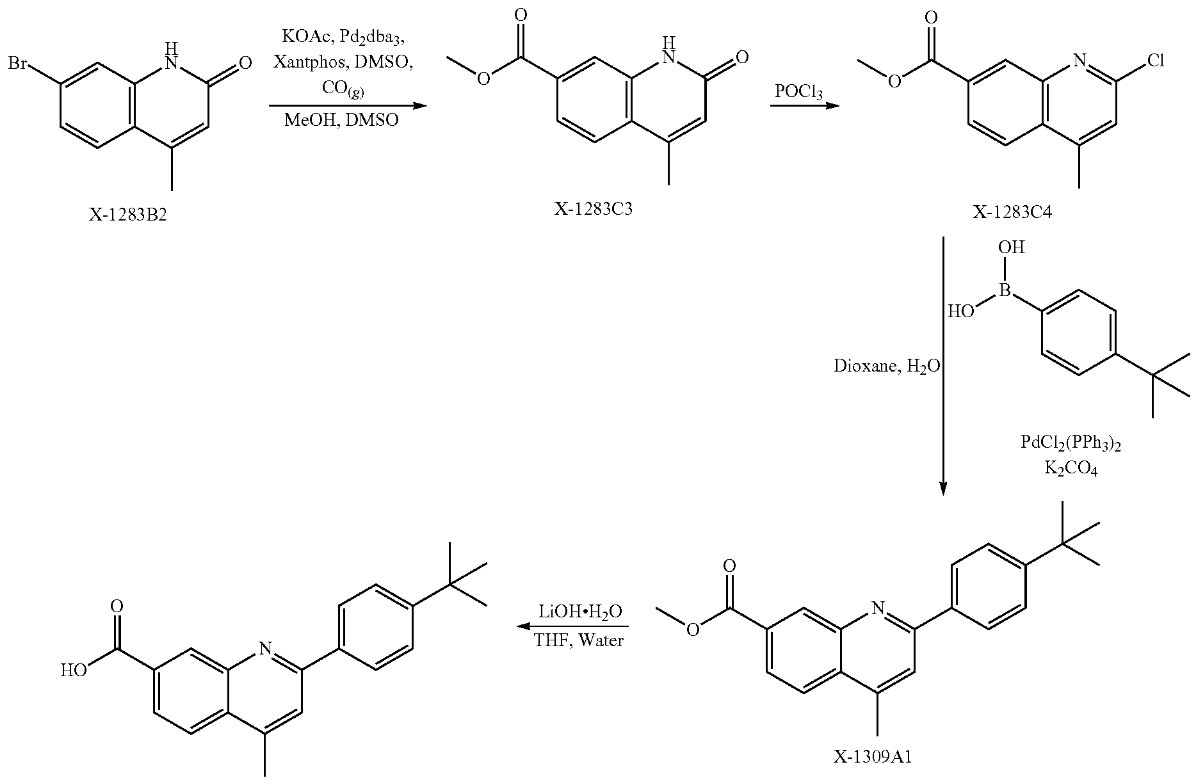

X-1283B2 X-1283C3 X-1283C4 X-1309A1 I-88

Methyl 4-methyl-2-oxo-1,2-dihydroquinoline-7-carboxylate (X-1283C3) Potassium acetate (1.00 g, 10.4 mmol) was added to a stirred solution of 7-bromo-4-methylquinolin-2 (1H)-one (X-1283B2) (0.830 g, 3.48 mmol) in DMSO-methanol (1:5, 18 mL) at room temperature under nitrogen. The reaction mixture was degassed (purging with nitrogen) for 30 min followed by addition of xanthphos (0.201 g, 0.34 mmol) and $Pd_2(dba)_3$ (0.319 g, 0.34 mmol) at room temperature. The resulting mixture was stirred under $CO_{(g)}$ for 1 h at the same temperature followed by heating at 100° C. for 6 h. Reaction mixture was cooled to room temperature, filtered over a celite bed and washed the bed with methanol. Combined filtrates were concentrated under reduced pressure, obtained gummy mass was diluted with water (100 mL) and was extracted with ethyl acetate (100×3). Combined organic extracts were dried over $Na_2SO_4$ and concentrated under reduced pressure. The crude product was combined with an identically prepared two more batches and combined batches were purified by reverse phase (C-18) silica gel column chromatography, using acetonitrile-water=0:1→1:0 as gradient, to afford methyl 4-methyl-2-oxo-1,2-dihydroquinoline-7-carboxylate (X-1283C3) (0.550 g, 20%) as an off-white solid. MS: $[MH]^+$ 218.3.

Methyl 2-chloro-4-methylquinoline-7-carboxylate (X-1283C4). A solution of methyl 4-methyl-2-oxo-1,2-dihydroquinoline-7-carboxylate (X-1283C3) (0.530 g, 2.44 mmol) in $POCl_3$ (10 mL) was heated at 90° C. for 1 h. After cooling to room temperature, reaction mixture was slowly poured into ice-water (250 mL) and the resulting precipitate was collected by filtration. Obtained residue was washed with cold water until the pH of the filtrate became neutral (pH~6-7). Collected solid was dried under high vacuum to afford methyl 2-chloro-4-methylquinoline-7-carboxylate (X-1283C4) (0.450 g, 75%) as a white solid. MS: $[MH]^+$ 236.1/$[MH+2]^+$238.1.

Methyl 2-(4-(tert-butyl)phenyl)-4-methylquinoline-7-carboxylate (X-1309A1). To a stirred solution of methyl 2-chloro-4-methylquinoline-7-carboxylate (X-1283C4) (0.130 g, 0.53 mmol) and (4-(tert-butyl)phenyl)boronic acid (0.176 g, 1.10 mmol) in a mixture of 1,4-dioxane-water (5:1, 6 mL) was added potassium carbonate (0.228 g, 1.65 mmol) at room temperature under nitrogen. The reaction mixture was degassed (purging with nitrogen) for 30 min followed by the addition of $PdCl_2(PPh_3)_2$ (0.038 g, 0.05 mmol) and the resulting mixture was heated at 100° C. for 1 h. After cooling to room temperature, reaction mixture was poured into water (50 mL) and was extracted by ethyl acetate (60 mL×3). Combined organic extracts were dried over $Na_2SO_4$ and concentrated under reduced pressure. The crude product was purified by silica gel column chromatography, using ethyl acetate-hexane=0:1→1:4 as gradient, to afford methyl 2-(4-(tert-butyl)phenyl)-4-methylquinoline-7-carboxylate (X-1309A1) (0.130 g, 65%) as a white solid. MS: $[MH]^+$ 334.2.

2-(4-(tert-Butyl)phenyl)-4-methylquinoline-7-carboxylic acid (I-88). Lithium hydroxide monohydrate (0.049 g, 1.17 mmol) was added to the stirred solution of methyl 2-(4-(tert-butyl)phenyl)-4-methylquinoline-7-carboxylate (X-1309A1) (0.130 g, 0.39 mmol) in a mixture of THF-water-methanol (4:1:0.1, 5.1 mL) at room temperature and the resulting mixture was heated at 60° C. for 2 h. After cooling to room temperature, reaction mixture was concentrated under reduce pressure, crude was diluted with water (30 mL), acidified (pH~3-4) with an aqueous solution of 1N HCl and was extracted with ethyl acetate (30 mL×3). Combined organic extracts were dried over $Na_2SO_4$ and concentrated under reduced pressure. Obtained crude was purified by triturating with n-pentane to afford 2-(4-(tert-butyl)phenyl)-4-methylquinoline-7-carboxylic acid (I-88) (0.050 g, 40%) as a white solid. $^1H$ NMR (400 MHz, DMSO-$d_6$) δ 13.31 (br. s, 1H), 8.58-8.58 (d, J=0.8 Hz, 1H), 8.22-8.20 (d, J=8.4 Hz, 2H), 8.19-8.17 (d, J=8.8 Hz, 1H), 8.11 (s, 1H), 8.06-8.03 (dd, J=8.8, 0.8 Hz, 1H), 7.58-7.56 (d, J=8.4 Hz, 2H) 2.77 (s, 3H), 1.34 (s, 9H). MS: $[MH]^+$ 320.1.

The following compounds were prepared in a manner analogous to the procedures described above for 2-(4-(tert-Butyl)phenyl)-4-methylquinoline-7-carboxylic acid (I-88):

2-(2-Fluoro-4-(trifluoromethyl)phenyl)-4-methylquinoline-7-carboxylic acid (I-87) (0.050 g, 34%) as a white solid. $^1H$ NMR (400 MHz, sDMSO-$d_6$) δ 13.40 (br. S, 1H), 8.62 (s, 1H), 8.27-8.23 (m, 2H), 8.15-8.12 (d, J=8.8 Hz, 1H), 7.94-7.90 (m, 2H), 7.80-7.78 (d, J=8.0 Hz, 1H), 2.80 (s, 3H). MS: $[MH]^+$ 350.1.

4-Methyl-2-(4-(trifluoromethyl)phenyl)quinoline-7-carboxylic acid (I-89) (0.080 g, 55%) as a white solid. $^1H$ NMR (400 MHz, DMSO-$d_6$) δ 13.37 (br. s, 1H), 8.63 (s, 1H), 8.51-8.49 (d, J=8.4 Hz, 2H), 8.24-8.21 (m, 2H), 8.10-8.08 (d, J=8.4 Hz, 1H), 7.93-7.91 (d, J=8.0 Hz, 2H), 2.80 (s, 3H). MS: $[MH]^+$ 332.2.

Example 1.15. Synthesis of N-(4-(4-(tert-butyl)phenyl)imidazo[1,2-a]quinoxalin-7-yl)acrylamide (I-91)

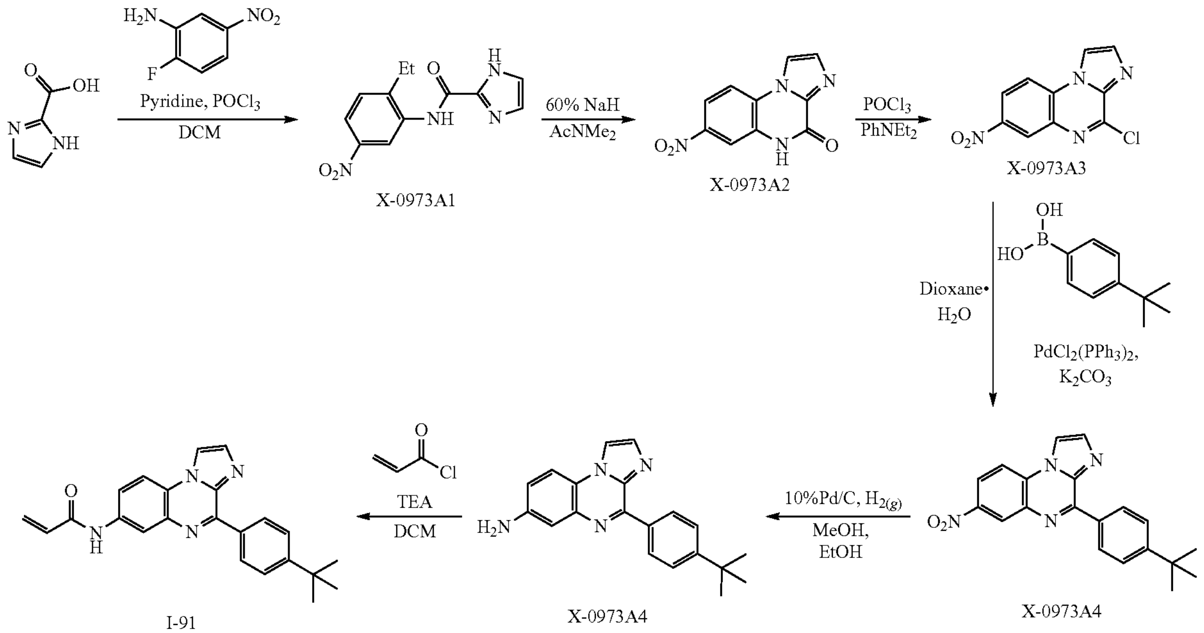

X-0973A1 X-0973A2 X-0973A3 X-0973A4 X-0973A4 I-91

N-(2-Fluoro-5-nitrophenyl)-1H-imidazole-2-carboxamide (X-0973A1). Pyridine (35.2 g, 44.6 mmol) and $POCl_3$ (10.2 g, 66.9 mmol) were added respectively to a stirred solution of 1H-imidazole-2-carboxylic acid (5.0 g, 44.6 mmol) and 2-fluoro-5-nitroaniline (6.9 g, 44.6 mmol) in DCM (50 mL) at 0° C. under nitrogen and stirring was continued for 30 min at same temperature. The reaction mixture was slowly poured in saturated $NaHCO_3$ solution (200 mL) and was extracted with DCM (100 mL×3). Combined organic extracts were dried over anhydrous $Na_2SO_4$ and concentrated under reduced pressure. The crude product was purified by triturating with ethyl acetate to afford N-(2-fluoro-5-nitrophenyl)-1H-imidazole-2-carboxamide (X-0973A1) (3.3 g, 30%) as a brown solid. MS: $[MH]^+$ 251.3.

7-Nitroimidazo[1,2-a]quinoxalin-4(5H)-one (X-0973A2). NaH (60% dispersion in oil; 1.6 g, 39.6 mmol) was added to the stirred solution of N-(2-fluoro-5-nitrophenyl)-1H-imidazole-2-carboxamide (X-0973A1) (3.3 g, 13.2 mmol) in $AcNMe_2$ (27 mL) at room temperature under nitrogen and the resulting mixture was heated at 80° C. for 16 h. Reaction mixture was cooled to room temperature, diluted with MDC-MeOH (9:1, 100 mL) and concentrated under reduced pressure. Obtained crude was purified by reverse phase (C-18) silica gel column chromatography, using acetonitrile-water=0:1→1:0 as gradient, to afford 7-nitroimidazo[1,2-a]quinoxalin-4(5H)-one (X-0973A2) (1.4 g, 46%) as an off-white solid. MS: $[MH]^+$ 231.3.

4-Chloro-7-nitroimidazo[1,2-a]quinoxaline (X-0973A3). N,N-diethylaniline (2.3 mL) was added to a stirred suspension of 7-nitroimidazo[1,2-a]quinoxalin-4(5H)-one (X-0973A2) (1.40 g, 6.08 mmol) in $POCl_3$ (15 mL) at 0° C. and the resulting mixture was heated at 80° C. for 16 h. After cooling to room temperature, the reaction mixture was quenched with slow addition of an aqueous solution of saturated $NaHCO_3$ till the solution became basic (pH~8-9) and was extracted with ethyl acetate (50 mL×3). Combined organic extracts were dried over anhydrous $Na_2SO_4$ and concentrated under reduced pressure. The crude mass was purified by reverse phase (C-18) silica gel column chromatography, using acetonitrile-water=0:1→1:0 as gradient, to furnish 4-chloro-7-nitroimidazo[1,2-a]quinoxaline (X-0973A3) (0.650 g, 43%) as a yellow solid. MS: $[MH]^+$ 249.3/$[MH+2]^+$ 251.3.

4-(4-(tert-Butyl)phenyl)-7-nitroimidazo[1,2-a]quinoxaline (X-0973A4). To a stirred solution of 4-chloro-7-nitroimidazo[1,2-a]quinoxaline (X-0973A3) (0.600 g, 2.41 mmol) in a mixture of 1,4-dioxane-DMF-water (10:1:1, 12 mL) was added (4-(tert-butyl)phenyl)boronic acid (0.550 g, 3.14 mmol) and potassium carbonate (0.860 g, 6.29 mmol) at room temperature under nitrogen. The reaction mixture was degassed (purging with nitrogen) for 30 min followed by the addition of $PdCl_2(PPh_3)_2$ (0.050 g, 0.72 mmol) and the resulting suspension was heated at 80° C. for 3 h. After cooling to room temperature, reaction mixture was diluted with water (80 mL) and was extracted by ethyl acetate (75 mL×3). Combined organic extracts were dried over $Na_2SO_4$ and concentrated under reduced pressure. The crude mass was purified by reverse phase (C-18) silica gel column chromatography using acetonitrile-water=0:1→1:0 as gradient, to afford 4-(4-(tert-butyl)phenyl)-7-nitroimidazo[1,2-a]quinoxaline (X-0973A4) (0.390 g, 43%) as a yellow solid. MS: $[MH]^+$ 347.4.

4-(4-(tert-Butyl)phenyl)imidazo[1,2-a]quinoxalin-7-amine (X-0973A5). 10% Pd in activated carbon (0.350 g) was added carefully to a stirred solution of 4-(4-(tert-butyl)phenyl)-7-nitroimidazo[1,2-a]quinoxaline (X-0973A4) (0.350 g) in a mixture of methanol-ethanol (1:1, 20 mL) at room temperature under nitrogen and the resulting mixture was hydrogenated under balloon pressure at the same temperature. The reaction mixture was filtered through a celite bad, washed the bed with methanol (50 mL) and collected filtrates were concentrated under reduced pressure. The crude mass was purified by reverse phase (C-18) silica gel column chromatography, using acetonitrile-water=0:1→1:0 as gradient, to afford 4-(4-(tert-butyl)phenyl)imidazo[1,2-a]quinoxalin-7-amine (X-0973A5) (0.180 g, 50%) as a yellow solid. MS: $[MH]^+$ 317.4.

N-(4-(4-(tert-butyl)phenyl)imidazo[1,2-a]quinoxalin-7-yl)acrylamide (I-91). Acryloyl chloride (0.045 g, 0.50 mmol) was added to a stirred solution of 4-(4-(tert-butyl)phenyl)imidazo[1,2-a]quinoxalin-7-amine (X-0973A5) (0.160 g, 0.50 mmol) and triethylamine (0.153 g, 1.50 mmol) in DCM (5 mL) at 0° C. temperature under nitrogen. The reaction mixture was stirred for 30 min at same temperature. The reaction mixture was poured in water (50 mL) and was extracted with DCM (50 mL×3). Combined organic extracts were dried over anhydrous $Na_2SO_4$ and concentrated under reduced pressure. The crude product was purified by reverse phase (C-18) silica gel column chromatography, using acetonitrile-water=0:1→41:0 as gradient, to afford N-(4-(4-(tert-butyl)phenyl)imidazo[1,2-a]quinoxalin-7-yl)acrylamide (I-91) (0.070 g, 33%) as a white solid. $^1H$ NMR (400 MHz, DMSO-$d_6$) δ 10.60 (s, 1H), 8.84 (s, 1H), 8.73-8.71 (d, J=8.4 Hz, 2H), 8.57 (s, 1H), 8.39-8.37 (d, J=9.2 Hz, 1H), 7.94-7.91 (dd, J=8.8, 1.6 Hz, 1H), 7.90 (s, 1H), 7.63-7.61 (d, J=8.4 Hz, 2H), 6.56-6.49 (dd, J=17.2, 10 Hz, 1H), 6.37-6.33 (d, J=17.2, 1H), 5.85-5.83 (d, J=10 Hz, 1H), 1.36 (s, 9H). MS: $[MH]^+$ 371.5.

Example 1.16. Synthesis of N-(3-(4-(tert-butyl)phenyl)quinoxalin-6-yl)acrylamide (I-92)

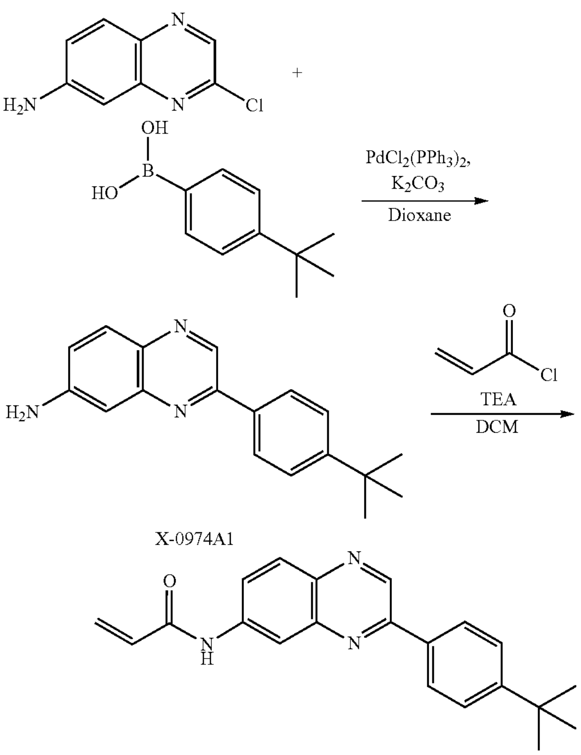

X-0974A1

I-92

3-(4-(tert-Butyl)phenyl)quinoxalin-6-amine (X-0974A1). To a stirred solution of 3-chloroquinoxalin-6-amine (0.500 g, 2.79 mmol) in a mixture of 1,4-dioxane-water (3:1, 9 mL) were added (4-(tert-butyl)phenyl)boronic acid (0.644 g, 3.62 mmol) and potassium carbonate (1.00 g, 7.24 mmol) at room temperature under nitrogen and the reaction mixture was degassed (purging with nitrogen) for 20 min. $PdCl_2(PPh_3)_2$ (0.058 g, 0.08 mmol) added into the reaction mixture at the same temperature and the resulting suspension was heated at 100° C. for 3 h. Reaction mixture was cooled to room temperature, filtered through a celite bed and the filtrate was concentrated under reduced pressure. Obtained crude was diluted with water (50 mL) and was extracted with ethyl acetate (50 mL×3). Combined organic extracts were dried over anhydrous $Na_2SO_4$ and concentrated under reduce pressure to give a crude mass, which was purified by silica gel column chromatography, using ethyl acetate-hexane=0.8:9.2→1:9 as gradient, to afford 3-(4-(tert-butyl)phenyl)quinoxalin-6-amine (X-0974A1) (0.500 g, 65%) as a yellow solid. MS: $[MH]^+$ 278.2.

N-(3-(4-(tert-butyl)phenyl)quinoxalin-6-yl)acrylamide (I-92). To a stirred solution of 3-(4-(tert-butyl)phenyl)quinoxalin-6-amine (X-0974A1) (0.500 g, 1.80 mmol) in DCM (10 mL) were added triethyl amine (0.360 g, 3.56 mmol) and acryloyl chloride (0.162 g, 1.80 mmol) at 0° C. under nitrogen and stirred for 15 min at the same temperature. Reaction mixture was diluted with water (50 mL) and was extracted with ethyl acetate (50×2 mL). The combined organic extracts were washed with brine (50 mL), dried over anhydrous $Na_2SO_4$ and concentrated under reduce pressure. Obtained crude mass was purified by silica gel column chromatography, using ethyl acetate-hexane=1:4→2:3 as gradient, to afford N-(3-(4-(tert-butyl)phenyl)quinoxalin-6-yl)acrylamide (I-92) (0.320 g, 54%) as an off white solid. $^1H$ NMR (400 MHz, DMSO-$d_6$) δ 10.66 (s, 1H), 9.44 (s, 1H), 8.68-8.67 (d, J=2.0 Hz, 1H), 8.28-8.25 (d, J=8.4 Hz, 2H), 8.09-8.06 (d, J=9.2 Hz, 1H), 7.93-7.90 (dd, J=9.2, 2.4 Hz, 1H), 7.64-7.61 (d, J=8.4 Hz, 2H), 6.57-6.51 (dd, J=16.8, 10.0 Hz, 1H), 6.40-6.36 (dd, J=16.8, 1.2 Hz, 1H), 5.89-5.86 (dd, J=10.0, 1.6 Hz, 1H), 1.36 (s, 9H). MS: $[MH]^+$ 332.5.

Example 1.17. Synthesis of 8-(4-(tert-Butyl)phenyl)-[1,2,4]triazolo[4,3-a]pyrazine-6-carboxylic acid (I-93)

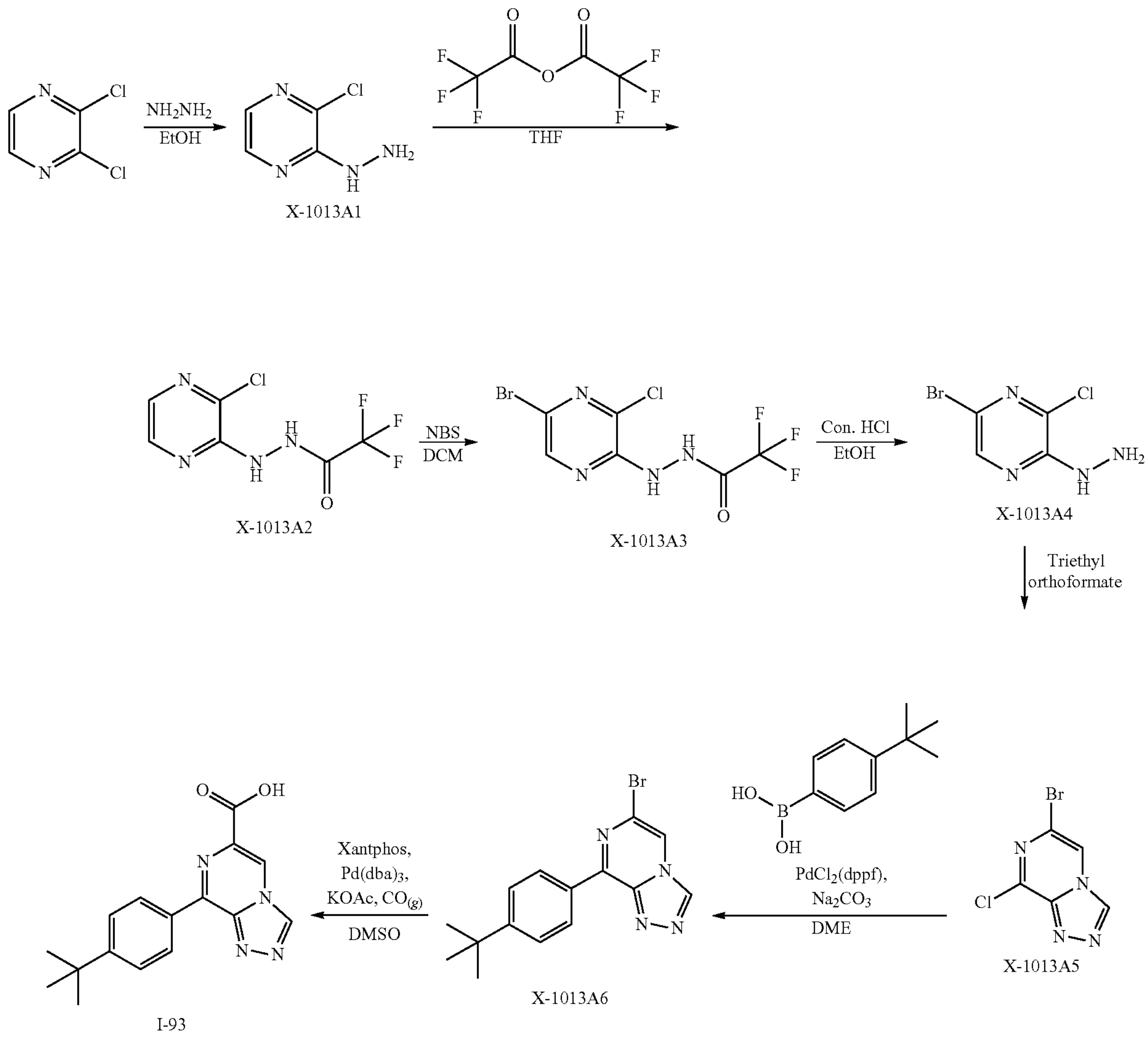

X-1013A1

X-1013A2

X-1013A3

X-1013A4

X-1013A5

X-1013A6

I-93

2-Chloro-3-hydrazinylpyrazine (X-1013A1). To a stirred solution of 2,3-dichloropyrazine (15.00 g, 101.35 mmol) in ethanol (150 mL) was added hydrazine hydrate (10.00 g, 202.70 mmol) at room temperature and the resulting mixture was heated at 80° C. for 1 h. Solvents were distilled off under reduced pressure, resulting crude was diluted with ice-water (100 mL) and the obtained precipitate was collected by filtration. Isolated residue was triturated with n-hexanes (50 mL×2), filtered and solid part was dried under high vacuum to afford 2-chloro-3-hydrazinylpyrazine (X-1013A1) [11.00 g, 75% (crude)] as an off-white solid. Obtained crude was pure enough to proceed to the next step without further purification. MS: $[MH]^+$ 145.2/$[MH+2]^+$147.2.

N'-(3-chloropyrazin-2-yl)-2,2,2-trifluoroacetohydrazide (X-1013A2). To a stirred solution of 2-chloro-3-hydrazinylpyrazine (X-1013A1) (11.00 g, 76.38 mmol) in THE (150 mL) was added 2,2,2-trifluoroacetic anhydride (17.60 g, 83.80 mmol) at −5° C. under nitrogen and stirred for 1 h at the same temperature. Solvents were distilled off under reduced pressure, crude mass was taken in water (100 mL) and was extracted with dichloromethane (200 mL×2). Combined organic extracts were dried over anhydrous $Na_2SO_4$ and concentrated in vacuo. Obtained crude was purified by triturating with n-pentane (100 mL) and dried the residue under high pressure to afford N'-(3-chloropyrazin-2-yl)-2,2,2-trifluoroacetohydrazide (X-1013A2) (8.00 g, 43%) as a brown solid. MS: $[MH]^+$ 241.3/$[MH+2]^+$ 241.3.

N'-(5-bromo-3-chloropyrazin-2-yl)-2,2,2-trifluoroacetohydrazide (X-1013A3). To a stirred solution of N'-(3-chloropyrazin-2-yl)-2,2,2-trifluoroacetohydrazide (X-1013A2) (3.00 g, 12.5 mmol) in chloroform (30 mL) was added n-bromosuccinimide (3.33 g, 18.75 mmol) portion wise at 0° C. under nitrogen and the resulting mixture was stirred at room temperature for 3 h. Reaction mixture was concentrated in vacuo and the resulting crude was purified by silica gel column chromatography, using ethyl acetate-hexane=0:1→3:7 as gradient, to afford N'-(5-bromo-3-chloropyrazin-2-yl)-2,2,2-trifluoroacetohydrazide (X-1013A3) (0.800 g, 20%) as an off-white solid. MS: [MH]—317.4/$[MH^+2]$-319.4/$[MH^+4]$-321.4.

5-Bromo-3-chloro-2-hydrazinylpyrazine (X-1013A4). To a stirred solution of N'-(5-bromo-3-chloropyrazin-2-yl)-2,2,2-trifluoroacetohydrazide (X-1013A3) (0.800 g, 2.52 mmol) in ethanol (10 mL) was added concentrated HCl (0.8 mL) at 0° C. and resulting reaction mixture was heated at 100° C. for 3 h. Reaction mixture was brought to room temperature, slowly poured into ice-water (50 mL) and was extracted with ethyl acetate (50 mL×2). Combined organic extracts were dried over anhydrous $Na_2SO_4$ and concentrated in vacuo. The crude mass was purified by silica gel column chromatography, using ethyl acetate-hexane=0:1→1:1 as gradient, to afford 5-bromo-3-chloro-2-hydrazinylpyrazine (X-1013A4) (0.500 g, 89%) as a yellow solid. MS: $[MH]^+$ 223.3/$[MH+2]^+$ 225.3.

6-Bromo-8-chloro-[1,2,4]triazolo[4,3-a]pyrazine (X-1013A5). A solution of 5-bromo-3-chloro-2-hydrazinylpyrazine (X-1013A4) (0.500 g, 2.26 mmol) in triethyl orthoformate (5 mL) was stirred at 130° C. for 3 h. Reaction mixture was cooled to room temperature, was slowly poured into ice-water (50 mL) and was extracted with ethyl acetate (50 mL×2). Combined organic extracts were dried over anhydrous $Na_2SO_4$ and concentrated under vacuo. The crude was purified by silica gel column chromatography, using ethyl acetate-hexane=0:1→1:1 as gradient, to afford 6-bromo-8-chloro-[1,2,4]triazolo[4,3-a]pyrazine (0.400 g, 76%) as an off white solid. MS: $[MH]^+$233.3/$[MH+2]^+$ 235.3.

6-Bromo-8-(4-(tert-butyl)phenyl)-[1,2,4]triazolo[4,3-a]pyrazine (X-1013A6). To a stirred solution of 6-bromo-8-chloro-[1,2,4]triazolo[4,3-a]pyrazine (0.400 g, 1.72 mmol) (X-1013A5) and (4-(tert-butyl)phenyl)boronic acid (0.308 g, 1.73 mmol) in dimethoxyethane (10 mL) was added sodium carbonate (0.548 g, 5.17 mmol) at room temperature under nitrogen. The reaction solution was degassed (with using nitrogen) for 10 min followed by the addition of $PdCl_2$(dppf) (0.126 g, 0.17 mmol) and the resulting mixture was stirred at 80° C. for 2 h. Reaction mixture was cooled to room temperature, diluted with water (50 mL) and was extracted with ethyl acetate (50 mL×2). Combined organic extracts were dried over anhydrous $Na_2SO_4$ and concentrated under reduced pressure to get a crude mass, which was purified by silica gel column chromatography, using ethyl acetate-hexane=0:1→1:1 as gradient, to afford 6-bromo-8-(4-(tert-butyl)phenyl)-[1,2,4]triazolo[4,3-a]pyrazine (X-1013A6) (0.200 g, 34%) as an off-white solid. MS: $[MH]^+$ 331.5/$[MH+2]^+$333.5.

8-(4-(tert-Butyl)phenyl)-[1,2,4]triazolo[4,3-a]pyrazine-6-carboxylic acid (I-93). To a stirred solution of 6-Bromo-8-(4-(tert-butyl)phenyl)-[1,2,4]triazolo[4,3-a]pyrazine (X-1013A6) (0.200 g, 0.60 mmol) in DMSO (5 mL) was added potassium acetate (0.178 g, 1.81 mmol) at room temperature under nitrogen. The reaction mixture was degassed with purging carbon monoxide for 15 min and were added Xantphos (0.035 g, 0.06 mmol), $Pd_2(dba)_3$ (0.055 g, 0.06 mmol) and the resulting reaction mixture stirred in a Parr autoclave under $CO_{(g)}$ at 100° C. for 3 h. Reaction was cooled to room temperature, basified (pH~8-9) with slow addition of an aqueous solution of saturated $NaHCO_3$ and was extracted with ethyl acetate (50 mL×2) to remove unwanted organic impurities. The aqueous layer was acidified (pH~2-3) with an aqueous solution of 1N HCl and the resulting precipitate was collected by filtration. Solid residue was washed with cold water until the pH of the filtrate became neutral (pH~6-7). Obtained solid was dried under high vacuum to afford a crude mass, which was purified by reverse phase (C-18) silica gel column chromatography, using water-acetonitrile=1:0→1:1 as gradient, to afford 8-(4-(tert-butyl)phenyl)-[1,2,4]triazolo[4,3-a]pyrazine-6-carboxylic acid (I-93) (0.080 g, 33%) as an off-white solid. $^1$H NMR (400 MHz, DMSO-$d_6$) δ 13.60 (br, 1H), 9.56 (s, 1H), 9.27 (s, 1H), 8.78-8.76 (d, J=8.4 Hz, 2H) 7.67-7.65 (d, J=8.4 Hz, 2H), 1.36 (s, 9H). MS: $[MH]^+$ 297.6.

Example 1.18. Synthesis of 8-(4-(tert-Butyl)phenyl) imidazo[1,5-a]pyrazine-6-carboxylic acid (I-94)

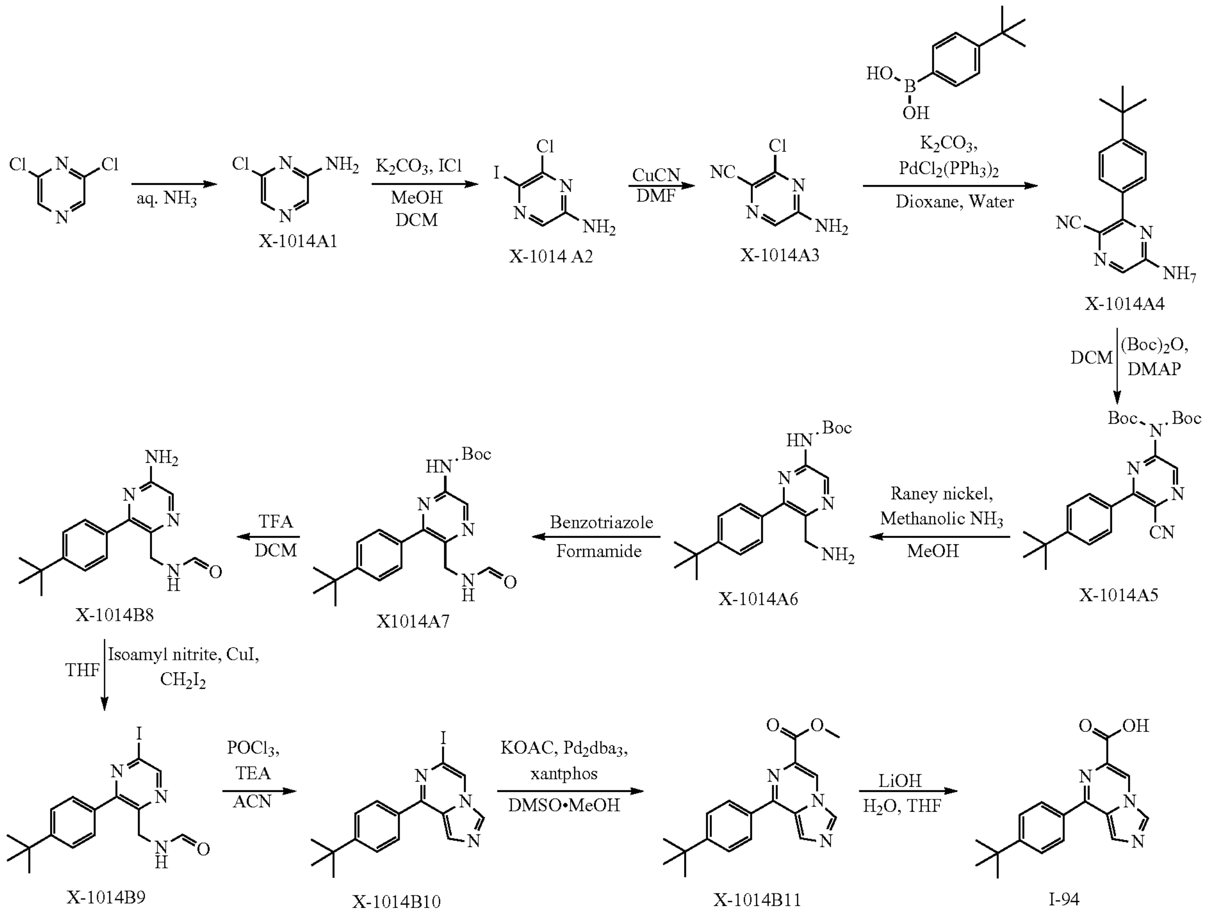

2,6-Dichloropyrazine (X-1014A1). A solution of 2, 6-dichloropyrazine (40.0 g, 268.4 mmol) in 28% aqueous ammonia solution (180 mL) was heated at 100° C. in a Parr Autoclave for 16 h. After cooling to room temperature, reaction mixture was poured into ice-water (500 mL) and the resulting precipitates were collected by filtration. Collected solid was dried in vacuo to afford 2,6-dichloropyrazine (X-1014A1) [28.0 g, 80% (crude)] as a yellow solid, which was used in next step without further purification. MS: $[MH]^+$ 130.1/$[MH+2]^+$ 130.1.

5-Amino-3-6-Chloro-5-iodopyrazin-2-amine (X-1014A2). Iodine monochloride (63.2 g, 390.6 mmol) and potassium carbonate (59.90 g, 434.0 mmol) were added sequentially to a stirred solution of 6-chloropyrazin-2-amine (X-1014A1) (28.0 g, 217.0 mmol) in a mixture of MeOH-DCM (1:4; 280 mL) at room temperature under nitrogen and resulting mixture was stirred at room temperature for 3 h. The reaction mixture was quenched with an aqueous solution of saturated $Na_2S_2O_8$ (500 mL) and was extracted with DCM (500 mL×4). Combined organic extracts were dried over anhydrous $Na_2SO_4$ and concentrated under reduced pressure. The crude was purified by silica gel column chromatography, using ethyl acetate-hexane=0:1→1:9 as gradient, to afford 6-chloro-5-iodopyrazin-2-amine (X-1014A2) (44.0 g, 80%) as a yellow solid. MS: $[MH]^+$ 256.3/$[MH+2]^+$ 258.2.

5-Amino-3-chloropyrazine-2-carbonitrile (X-1014A3). To a stirred solution of 6-chloro-5-iodopyrazin-2-amine (X-1014A2) (44.0 g, 172.6 mmol) in DMF (80 mL) was added CuCN (16.8 g, 188.1 mmol) at room temperature under nitrogen and the resulting mixture was allowed to stir at 150° C. for 1 h. After cooling to room temperature, reaction mixture was poured in aqueous solution of $NH_3$ (200 mL) and was extracted with ethyl acetate (200 mL×3). Combined organic extracts were dried over anhydrous $Na_2SO_4$ and concentrated under reduced pressure to afford 5-amino-3-chloropyrazine-2-carbonitrile (X-1014A3) [32.0 g, quantitative (crude)] as a yellow solid, which was used in the next step without further purification. MS: $[MH]^+$153.2/$[MH+2]^+$155.2.

5-Amino-3-(4-(tert-butyl) phenyl) pyrazine-2-carbonitrile (X-1014A4). To a stirred solution of 5-amino-3-chloropyrazine-2-carbonitrile (X-1014A3) (32.0 g, 207.7 mmol) in a mixture of 1,4-dioxane-$H_2O$ (4:1; 450 mL) was added 4-(tert-butyl)phenyl)boronic acid (48.0 g, 270.1 mmol) and $K_2CO_3$ (74.5 g, 540.0 mmol) at room temperature under nitrogen and reaction mixture was degassed (by purging nitrogen) for 30 min. $PdCl_2(PPh_3)_2$ (4.3 g, 6.20 mmol) was added into the reaction mixture at the same temperature and the resulting suspension was heated at 100° C. for 1 h. After cooling to room temperature, reaction mixture was poured into ice-water (500 mL) and was extracted with ethyl acetate (500 mL×3). Combined organic extracts were dried over anhydrous $Na_2SO_4$ and concentrated under reduced pressure. The crude product was purified by silica gel column chromatography, using ethyl acetate-hexane=1:9→3:7 as gradient, to afford 5-amino-3-(4-(tert-butyl) phenyl) pyrazine-2-carbonitrile (X-1014A4) (38.0 g, 73%) as an orange solid. MS: $[MH]^+$ 253.4.

Di-tert-butyl(6-(4-(tert-butyl)phenyl)-5-cyanopyrazin-2-yl)carbamate (X-1014A5). To a stirred solution of 5-amino-3-(4-(tert-butyl)phenyl)pyrazine-2-carbonitrile (X-1014A4) (33.0 g, 130.9 mmol) in DCM (500 mL) were added 4-Dimethylaminopyridine (7.35 g, 65.4 mmol) and $(Boc)_2O$ (62.8 g, 288.1 mmol) sequentially at 0° C. under nitrogen and the resulting mixture was stirred at room temperature for 2 h. The reaction mixture was poured into ice-water (250 mL) and was extracted with DCM (250 mL×3). Combined organic extracts were dried over anhydrous $Na_2SO_4$ and concentrated under reduced pressure. Isolated crude was purified by triturating with n-pentane to afford di-tert-butyl (6-(4-(tert-butyl)phenyl)-5-cyanopyrazin-2-yl)carbamate (X-1014A5) (47.0 g, 79%) as a yellow solid. MS: $[MH]^+$ 453.8.

tert-Butyl (5-(aminomethyl)-6-(4-(tert-butyl)phenyl) pyrazin-2-yl)carbamate (X-1014A6). To a stirred solution of di-tert-butyl(6-(4-(tert-butyl)phenyl)-5-cyanopyrazin-2-yl) carbamate) (X-1014A5) (47.0 g, 132.0 mmol) in MeOH (1000 mL) were added activated Raney Ni (11.75 g) and methanolic ammonia (100 mL) sequentially in an autoclave at room temperature under nitrogen and the resulting suspension was hydrogenated under 25 psi at 70° C. for 16 h. After cooling to room temperature, reaction mixture was filtered through celite, residue was washed with MeOH (1000 mL) and collected filtrates were concentrated under reduced pressure. Isolated crude was purified by triturating with n-pentane to afford tert-butyl (5-(aminomethyl)-6-(4-(tert-butyl)phenyl) pyrazin-2-yl)carbamate (X-1014A6) [34.0 g, 92% (crude)] as an off-white solid. Obtained crude was pure enough to proceed to the next step without further purification. MS: $[MH]^+$ 357.7.

tert-Butyl (6-(4-(tert-butyl)phenyl)-5-(formamidomethyl) pyrazin-2-yl)carbamate (X-1014A7). To a stirred solution of tert-butyl (5-(amino methyl)-6-(4-(tert-butyl) phenyl) pyrazin-2-yl) carbamate (X-1014A6) (1.0 g, 2.80 mmol) in formamide (4 mL) was added benzotriazole (0.668 g, 5.60 mmol) at room temperature and the resulting solution was heated at 80° C. for 5 h. Reaction mixture was cooled to room temperature, was poured into ice-water (100 mL), resulting precipitates were collected by filtration and dried in vacuo. The crude product was combined with an identically prepared 15 more batches, running in parallel with the mentioned batch and the combined batches were purified by silica gel column chromatography, using ethyl acetate-hexane=1:4→3:7 as gradient, to afford tert-butyl (6-(4-(tert-butyl)phenyl)-5-(formamidomethyl)pyrazin-2-yl)carbamate (X-1014A7) (2.50 g, 15%) as a greenish solid. MS: $[MH]^+$ 385.7.

N-((5-amino-3-(4-(tert-butyl)phenyl)pyrazin-2-yl) methyl)formamide (X-1014B8). To a stirred solution of tert-butyl(6-(4-(tert-butyl)phenyl)-5-(formamidomethyl) pyrazin-2-yl) carbamate (X-1014A7) (2.5 g, 6.5 mmol) in DCM (30 mL) was added TFA (1.5 g, 13.0 mmol) drop-wise at 0° C. under nitrogen and allowed to stir at room temperature for 2 h. Reaction mixture was concentrated in reduced pressure, obtained residue was diluted with ice-water (100 mL), basify (pH~8-9) with an aqueous solution of saturated $NaHCO_3$ and was extracted with DCM (100 mL×3). Combined organic extracts were dried over anhydrous $Na_2SO_4$ and concentrated under reduced pressure to afford N-((5-amino-3-(4-(tert-butyl)phenyl)pyrazin-2-yl) methyl)formamide (X-1014B8) [2.0 g, quantitative (crude)] as a yellow solid, which was used in next step without further purification. MS: $[MH]^+$ 285.6.

N-((3-(4-(tert-butyl)phenyl)-5-iodopyrazin-2-yl)methyl) formamide (X-1014B9). To a stirred solution of N-((5-amino-3-(4-(tert-butyl)phenyl)pyrazin-2-yl)methyl)formamide (X-1014B8) (1.30 g, 4.57 mmol) in THF (20 mL) were added CuI (0.871 g, 4.57 mmol), Isoamyl nitrile (1.6 g, 13.7 mmol) and $CH_2I_2$ (1.2 g, 4.57 mmol) at 0° C. under nitrogen and the resulting mixture was heated at 75° C. for 2 h. After cooling to room temperature, retraction mixture was concentrated under reduced pressure. Obtained crude was purified by silica gel column chromatography, using ethyl acetate-hexane=4:1→1:0 as gradient, to afford N-((3-(4-(tert-butyl)phenyl)-5-iodopyrazin-2-yl)methyl)formamide (X-1014B9) (0.390 g, 22%) as a greenish solid. MS: $[MH]^+$ 396.6.

8-(4-(tert-Butyl)phenyl)-6-iodoimidazo[1,5-a]pyrazine (X-1014B10). To a stirred solution of N-((3-(4-(tert-butyl) phenyl)-5-iodopyrazin-2-yl)methyl)formamide (X-1014B9) (0.390 g, 0.99 mmol) in acetonitrile (5 mL) were added triethylamine (0.299 g, 2.96 mmol) at 0° C. temperature under nitrogen followed by the addition of $POCl_3$ (0.151 g, 0.99 mmol). The reaction mixture was heated at 85° C. for 2 h. after cooling to room temperature, reaction mixture was poured in ice water (100 mL) and was extracted with ethyl acetate (100 mL×3). Combined organic extracts were dried over anhydrous $Na_2SO_4$ and concentrated under reduced pressure. The crude product was purified by silica gel column chromatography, using ethyl acetate-hexane=1:4→2:3 as gradient, to afford 8-(4-(tert-butyl)phenyl)-6-iodoimidazo[1,5-a]pyrazine (X-1014B10) [0.442 g, quantitative (crude)] as a yellow solid. MS: $[MH]^+$ 378.5.

Methyl 8-(4-(tert-butyl)phenyl)imidazo[1,5-a]pyrazine-6-carboxylate (X-1014B11). To a stirred solution of 8-(4-(tert-butyl)phenyl)-6-iodoimidazo[1,5-a]pyrazine (X-1014B10) (0.442 g, 1.17 mmol) in a mixture of DMSO-MeOH (1:1, 10 mL) were added xanthphos (0.067 g, 0.12 mmol) and potassium acetate (0.345 g, 3.52 mmol) at room temperature under nitrogen and the reaction mixture was degassed (purging with nitrogen) for 30 min. $Pd_2(dba)_3$ (0.107 g, 0.12 mmol) was added into the reaction mixture at the same temperature and the resulting suspension was heated at 120° C. under $CO_{(g)}$ atmosphere for 2 h. Reaction mixture was cooled to room temperature, was poured into ice-water (50 mL) and was extracted with ethyl acetate (50 mL×3). Combined organic extracts were dried over anhydrous $Na_2SO_4$ and concentrated under reduced pressure. The crude product was purified by silica gel column chromatography, using ethyl acetate-hexane=1:4→2:3 as gradient, to afford methyl 8-(4-(tert-butyl)phenyl)imidazo[1,5-a]pyrazine-6-carboxylate (X-1014B11) (0.160 g, 44%) as an orange solid. MS: $[MH]^+$ 310.6.

8-(4-(tert-Butyl)phenyl)imidazo[1,5-a]pyrazine-6-carboxylic acid (I-94). Lithium hydroxide monohydrate (0.065 g, 1.55 mmol) was added to a stirred solution of methyl 8-(4-(tert-butyl)phenyl)imidazo[1,5-a]pyrazine-6-carboxylate (X-1014B11) (0.160 g, 0.51 mmol) in a mixture of THE-water (3:2, 10 mL) at room temperature and allowed to stir for 1 h at the same temperature. Solvents were distilled off under reduced pressure, crude mass was acidified (pH 3-4) with an aqueous solution of 1N HCl solution and resulting precipitates were collected by filtration. Isolated solid wad dried under vacuum and was purified by triturating with n-pentane to afford 8-(4-(tert-butyl)phenyl)imidazo[1,5-a]pyrazine-6-carboxylic acid (I-94) (0.080 g, 52%) as a white solid. $^1$H NMR (400 MHz, DMSO-$d_6$) δ 13.25 (br, 1H), 9.10 (s, 1H), 8.79 (s, 1H), 8.07 (s, 3H), 7.63-7.61 (m, 2H), 1.35 (s, 9H). MS: $[MH]^+$ 296.5.

Example 1.19. Synthesis of 4-(4-(tert-Butyl)phenyl)isoquinoline-7-carboxylic acid (I-95)

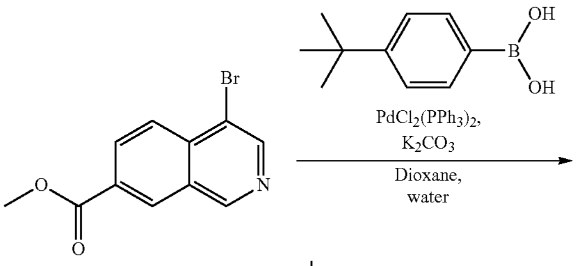

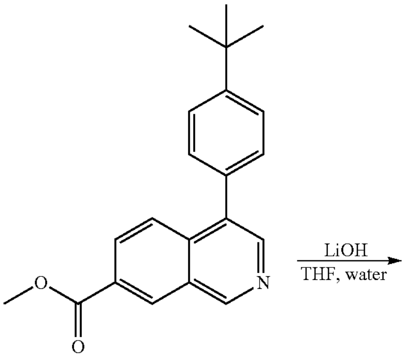

X-1135A1

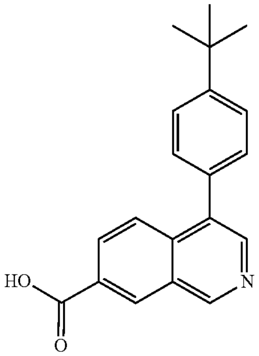

I-95

Methyl 4-(4-(tert-butyl)phenyl)isoquinoline-7-carboxylate (X-1135A1). To a stirred solution of methyl 4-bromoisoquinoline-7-carboxylate (0.200 g, 0.75 mmol) in a mixture of 1,4-dioxane-water (9:1, 20 mL) was added (4-(tert-butyl)phenyl)boronic acid (0.200 g, 1.12 mmol) and $K_2CO_3$ (0.320 g, 2.30 mmol) at room temperature under nitrogen and the resulting mixture was degassed (purging with nitrogen) for 20 min followed by addition of $PdCl_2(PPh_3)_2$ (0.080 g, 0.11 mmol) and the reaction mixture was heated at 90° C. for 3 h. The reaction mixture was cooled to room temperature, diluted with water (60 mL) and extracted with ethyl acetate (50 mL×3). The combined organic extracts were washed with brine (40 mL), dried over anhydrous $Na_2SO_4$ and concentrated in vacuo. The crude product was purified by silica gel column chromatography, using ethyl acetate-hexane=1:19→1:9 as gradient, to afford methyl 4-(4-(tert-butyl)phenyl)isoquinoline-7-carboxylate (X-1135A1) (0.200 g, 83%) as an off-white solid. MS: $[MH]^+$ 319.7.

4-(4-(tert-Butyl)phenyl)isoquinoline-7-carboxylic acid (I-95). To a stirred solution of methyl 4-(4-(tert-butyl)phenyl)isoquinoline-7-carboxylate (X-1135A1) (0.200 g, 0.62 mmol) in a mixture of THF-water-MeOH (2:1:1; 20 mL) was added lithium hydroxide monohydrate (0.132 g, 3.15 mmol) at room temperature and the resulting reaction mixture was stirred at room temperature for 2 h. Reaction mixture was concentrated under reduced pressure, diluted with water (200 mL) and was extracted with ethyl acetate (100 mL×2) to remove unwanted organic impurities. The aqueous layer was acidified (pH~2-3) with aq aqueous 1N HCl solution and the resulting precipitate was collected by filtration. Solid precipitate was washed with cold water until the pH of the filtrate became neutral (pH~6-7) and dried under high vacuum to afford 4-(4-(tert-butyl)phenyl)isoquinoline-7-carboxylic acid (I-95) (0.090 g, 47%) as a white solid. $^1$H NMR (400 MHz, DMSO-$d_6$) δ 13.41 (br. s, 1H), 9.35 (s, 1H), 8.88 (s, 1H), 8.55 (s, 1H), 8.23 (s, 1H), 7.98 (s, 1H), 7.61 (br. s, 2H), 7.51 (br. s, 2H), 1.37 (s, 9H). MS: $[MH]^+$ 306.1.

Example 1.20. Synthesis of N-(1-(4-(trifluoromethyl)phenyl)pyrrolo[1,2-a]pyrazin-3-yl)acrylamide (I-96)

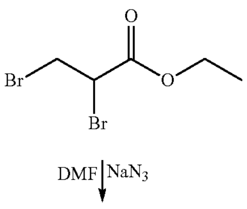

-continued

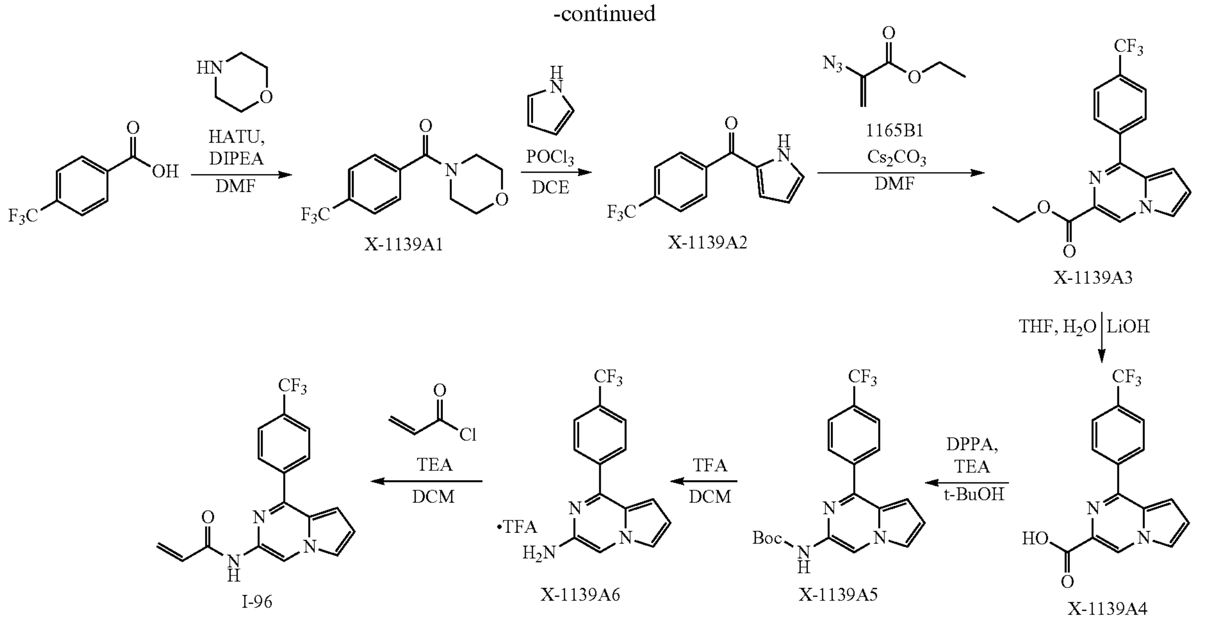

X-1139A1 X-1139A2 X-1139A3 X-1139A4 X-1139A5 X-1139A6 I-96

Morpholino(4-(trifluoromethyl)phenyl)methanone (X-1139A1). Morpholine (2.90 g, 34.20 mmol) was added to a stirred solution of 4-(trifluoromethyl)benzoic acid (5.00 g, 26.20 mmol), HATU (19.90 g, 52.60 mmol) and DIPEA (10.1 g, 78.90 mmol) in DMF (50 ml) at 0° C. under nitrogen and the resulting mixture was stirred at room temperature for 1 h. The reaction mixture was diluted with water (200 mL) and was extracted with diethyl ether (200 ml×2). Combined organic extracts were dried over anhydrous $Na_2SO_4$ and concentrated under reduced pressure. The crude mass was purified by reverse phase (C-18) silica gel column chromatography, using acetonitrile-water=0:1→1:0 as gradient, to afford morpholino(4-(trifluoromethyl)phenyl)methanone (X-1139A1) (6.50 g, 95%) as a yellow solid. MS: [MH]+ 260.1.

(1H-pyrrol-2-yl)(4-(trifluoromethyl)phenyl)methanone (X-1139A2). To a stirred solution of morpholino(4-(trifluoromethyl)phenyl)methanone (X-1139A1) (6.50 g, 25.01 mmol) in dichloroethane (70 mL) was added $POCl_3$ (11.50 g, 75.23 mmol) at room temperature and stirring was continued for 24 h at the same temperature. To the resulting reaction mixture was added a solution of 1H-pyrrole (2.50 g, 37.60 mmol) in dichloroethane (10 mL) at room temperature and stirring was further continued for an additional 24 h. The reaction mixture was diluted with water (100 ml), basified (pH~7-8) with an aqueous solution of saturated $NaHCO_3$ and was extracted with DCM (100 mL×3). Combined organic extracts were dried over anhydrous $Na_2SO_4$ and concentrated under reduced pressure. The crude product was purified by silica gel column chromatography, using ethyl acetate-hexane=0:1→3:7 as gradient, to afford (1H-pyrrol-2-yl)(4-(trifluoromethyl)phenyl)methanone (X-1139A2) (2.80 g, 46%) as an off-white solid. MS: $[MH]^+$ *240.1.

Ethyl 2-azidoacrylate (X-1165B1). Ethyl 2,3-dibromopropanoate (10.0 g, 38.42 mmol) was added to a stirred suspension of sodium azide (8.0 g, 123.03 mmol) in DMF (100 mL) at 60° C. and the reaction mixture was stirred same temperature for 2 h. After cooling to room temperature, reaction mixture was diluted with water (100 mL) and was extracted with ethyl acetate (100 mL×2). Combined organic extract were washed with brine (200 mL), dried over anhydrous $Na_2SO_4$ and concentrated under reduced pressure to afford ethyl 2-azidoacrylate (X-1165bB1) [6.5 g, quantitative (crude)] as a yellow liquid, which was used in next step without further purification.

Ethyl 1-(4-(trifluoromethyl)phenyl)pyrrolo[1,2-a]pyrazine-3-carboxylate (X-1139A3). Cesium carbonate (11.0 g, 33.81) and ethyl 2-azidoacrylate (X-1165B1) (4.8 g, 33.8 mmol) were sequentially added to a stirred solution of (1H-pyrrol-2-yl)(4-(trifluoromethyl)phenyl)methanone (X-1139A2) (2.7 g, 11.30 mmol) at room temperature under nitrogen and stirring was continued at the same temperature for 3 h. The reaction mixture was slowly poured in ice-water (100 mL) and was extracted with ethyl acetate (100 mL×3). Combined organic extracts were washed with brine (100 mL), dried over anhydrous $Na_2SO_4$ and concentrated under reduced pressure. The crude mass was purified by reverse phase (C-18) silica gel column chromatography, using acetonitrile-water=0:1→1:0 as gradient, to afford ethyl 1-(4-(trifluoromethyl)phenyl)pyrrolo[1,2-a]pyrazine-3-carboxylate (X-1139A3) (2.0 g, 51%) as a yellow solid. MS: $[MH]^+$ 335.0.

1-(4-(Trifluoromethyl)phenyl)pyrrolo[1,2-a]pyrazine-3-carboxylic acid (X-1139A4). Lithium hydroxide monohydrate (0.980 g, 23.32 mmol) was added to the stirred solution of ethyl 1-(4-(trifluoromethyl)phenyl)pyrrolo[1,2-a]pyrazine-3-carboxylate (X-1139A3) (1.95 g, 5.83 mmol) in a mixture of THE-water (4:1, 25 mL) at room temperature and stirring was continued at the same temperature for 16 h. The reaction mixture was diluted with water (80 mL), acidified (pH~3-4) with an aqueous solution of 1N HCl and was extracted with ethyl acetate (50 mL×3). Combined organic extracts were dried over anhydrous $Na_2SO_4$ and concentrated under reduced pressure to afford 1-(4-(trifluoromethyl)phenyl)pyrrolo[1,2-a]pyrazine-3-carboxylic acid (X-1139A4) [1.70 g, 92% (crude)] as a green solid, which was carried forward to the next step without further purification. MS: $[MH]^+$ 307.1.

tert-Butyl (1-(4-(trifluoromethyl)phenyl)pyrrolo[1,2-a]pyrazin-3-yl)carbamate (X-1139A5). Diphenyl phosphoryl azide (0.940 g, 3.43 mmol) and triethyamine (0.460 g, 4.57 mmol) were sequentially added to a stirred solution of 1-(4-(trifluoromethyl)phenyl)pyrrolo[1,2-a]pyrazine-3-carboxylic acid (X-1139A4) (0.700 g, 2.28 mmol) in t-BuOH (14 mL) at room temperature under nitrogen and the resulting mixture was heated at 90° C. for 16 h. After cooling to room temperature, reaction mixture was slowly poured into water (100 mL) and was extracted with ethyl acetate (70 mL×3). Combined organic extracts were dried over anhydrous $Na_2SO_4$ and concentrated under reduced pressure. Obtained crude mass was purified by silica gel column chromatography, using ethyl acetate-hexane=0:1→1:4 as gradient, to afford tert-butyl (1-(4-(trifluoromethyl)phenyl) pyrrolo[1,2-a]pyrazin-3-yl)carbamate (X-1139A5) (0.400 g, 46%) as a yellow solid. MS: $[MH]^+$ 378.1.

1-(4-(Trifluoromethyl)phenyl)pyrrolo[1,2-a]pyrazin-3-amine (TFA salt) (X-1139A6). Trifluoroacetic acid (10 mL) was added to a stirred solution of tert-butyl (1-(4-(trifluoromethyl)phenyl)pyrrolo[1,2-a]pyrazin-3-yl)carbamate (X-1139A5) (0.400 g, 1.06 mmol) in DCM (15 mL) at 0° C. under nitrogen and stirred at room temperature for 2 h. Reaction mixture was diluted with DCM (50 mL) and concentrated under reduced pressure to afford 1-(4-(trifluoromethyl)phenyl)pyrrolo[1,2-a]pyrazin-3-amine (TFA salt) (X-1139A6) [0.300 g, quant. (crude)] as a black sticky solid, which was used in next step without further purification. MS: $[MH]^+$ 278.0.

N-(1-(4-(trifluoromethyl)phenyl)pyrrolo[1,2-a]pyrazin-3-yl)acrylamide (I-96) Acryloyl chloride (0.117 g, 1.29 mmol) and triethylamine (0.050 g, 5.40 mmol) were added sequentially to a stirred solution of 1-(4-(trifluoromethyl) phenyl)pyrrolo[1,2-a]pyrazin-3-amine (TFA salt) (X-1139A6) [0.300 g (crude), 1.08 mmol] at 0° C. under nitrogen and the resulting mixture was stirred at room temperature for 30 min. Reaction mixture was diluted with water (50 mL) and was extracted with DCM (50 ml×3). Combined organic extracts were dried over anhydrous $Na_2SO_4$ and concentrated under reduced pressure to give a crude mass, which was purified by reverse phase (C-18) silica gel column chromatography, using acetonitrile-water=0:1→1:0 as gradient, to afford N-(1-(4-(trifluoromethyl) phenyl)pyrrolo[1,2-a]pyrazin-3-yl)acrylamide (I-96) (0.130 g, 36%) as an off-white solid. $^1H$ NMR (400 MHz, DMSO-$d_6$) δ 10.65 (s, 1H), 9.19 (s, 1H), 8.22-8.20 (d, J=8.0 Hz, 2H), 8.02 (s, 1H), 7.95-7.93 (d, J=8.4 Hz, 2H), 6.978-6.974 (d, J=1.6 Hz, 2H), 6.69-6.62 (dd, J=17.2, 10.0 Hz, 1H), 6.31-6.27 (dd, J=17.2, 1.6 Hz, 1H), 5.78-5.75 (dd, J=10.0, 1.6 Hz, 1H). MS: [MH]332.0.

Example 1.21. Synthesis of 7-(4-(tert-Butyl) phenyl)-1H-pyrrolo[3,2-c] pyridine-3-carboxylic acid (1-97)

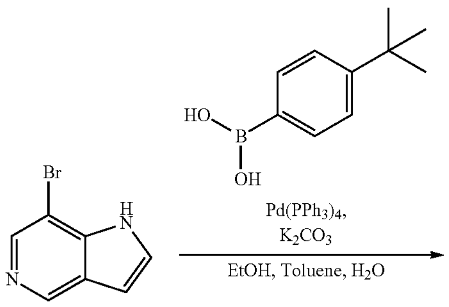

-continued

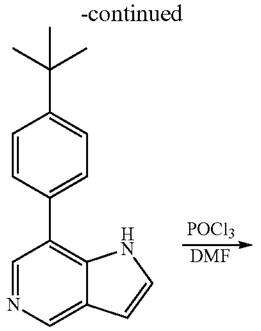

X-1141A1

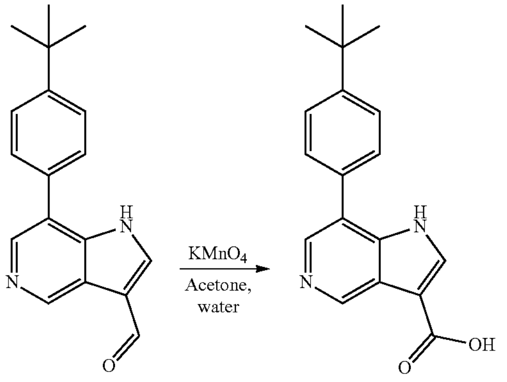

X-1141A2 I-97

7-(4-(tert-Butyl) phenyl)-1H-pyrrolo[3,2-c] pyridine (X-1141A1). To a stirred solution of 7-bromo-1H-pyrrolo [3,2-c] pyridine (0.200 g, 1.01 mmol) in a mixture of toluene-ethanol-water (2:1:1, 12 mL) were added (4-(tert-butyl) phenyl) boronic acid (0.289 g, 1.52 mmol) and potassium carbonate (0.350 g, 2.53 mmol) at room temperature under nitrogen. The resulting solution was degassed (by purging nitrogen) for 30 min followed by the addition of $Pd(PPh_3)_4$ (0.059 g, 0.05 mmol) and was heated at 100° C. for 4 h. Reaction mixture was slowly poured into water (50 mL) and was extracted with ethyl acetate (50 mL×3). Combined organic extracts were dried over anhydrous $Na_2SO_4$ and concentrated in vacuo. The resulting crude was purified by silica gel column chromatography, using methanol-dichoromethane=0:1→1:9 as gradient, to afford 7-(4-(tert-butyl)phenyl)-1H-pyrrolo[3,2-c]pyridine (X-1141A1) (0.204 g, 81%) as an off-white solid. MS: $[MH]^+$ 251.6.

7-(4-(tert-Butyl) phenyl)-1H-pyrrolo[3,2-c] pyridine-3-carbaldehyde (X-1141A2). A mixture of DMF (0.48 mL, 6.18 mmol) and $POCl_3$ (0.394 mL, 4.22 mmol) was stirred at 0° C. for 30 min followed by addition of the 7-(4-(tert-butyl) phenyl)-1H-pyrrolo [3, 2-c] pyridine (X-1141A1) (0.100 g. 0.40 mmol) in dichloroethane (5 mL) under nitrogen and the resulting mixture was heated at 85° C. for 16 h. After cooling to room temperature, the reaction mixture was quenched with an aqueous solution of saturated $NaHCO_3$ and was extracted with ethyl acetate (30 mL×3). Combined organic extracts were washed with brine (50 mL), dried over anhydrous $Na_2SO_4$ and concentrated in vacuo. The resulting crude was purified by reverse phase (C-18) silica gel column chromatography using ACN-water=0: 1→1:0 as gradient, to afford 7-(4-(tert-butyl) phenyl)-1H-pyrrolo[3,2-c] pyridine-3-carbaldehyde (X-1141A2) (0.030 g, 27%) as a brown solid. MS: $[MH]^+$ 279.2.

7-(4-(tert-Butyl) phenyl)-1H-pyrrolo[3,2-c] pyridine-3-carboxylic acid (1-97). To a stirred solution 7-(4-(tert-butyl)

phenyl)-11H-pyrrolo [3,2-c] pyridine-3-carbaldehyde (X-11141A2) (0.030 g, 0.11 mmol) in acetone (5 mL) was added an aqueous (2 mL) solution of $KMnO_4$ (0.029 g, 0.18 mmol) over period of 30 min and stirred for an additional 16 h at the same temperature. Reaction mixture was diluted with water (20 mL) and was extracted by diethyl ether (20 mL×3) to remove unwanted organic impurities. Aqueous layer was acidified (pH~2-3) with an aqueous solution of 1N HCl and was extracted with ethyl acetate (30 mL×3). Combined organic extracts were dried over anhydrous $Na_2SO_4$ and concentrated in vacuo to afford 7-(4-(tert-butyl) phenyl)-11H-pyrrolo[3,2-c] pyridine-3-carboxylic acid (I-97) (0.007 g, 28%) as an off white solid. $^1H$ NMR (400 MHz, DMSO-d($_6$) δ 12.42 (br. s, 1H), 12.20 (br. s, 1H), 9.20 (s, 1H), 8.30 (s, 1H), 8.00-7.99 (d, J=2.8 Hz, 1H), 7.63-7.58 (m, 4H), 1.36 (s, 9H). MS: $[MH]^+$ 295.3.

Example 1.22. Synthesis of N-(2-(4-(tert-butyl)phenyl)-3-methylquinolin-7-yl)acrylamide (I-98) and N-(2-(4-(tert-butyl)phenyl)-3-methylquinolin-5-yl) acrylamide (I-99)

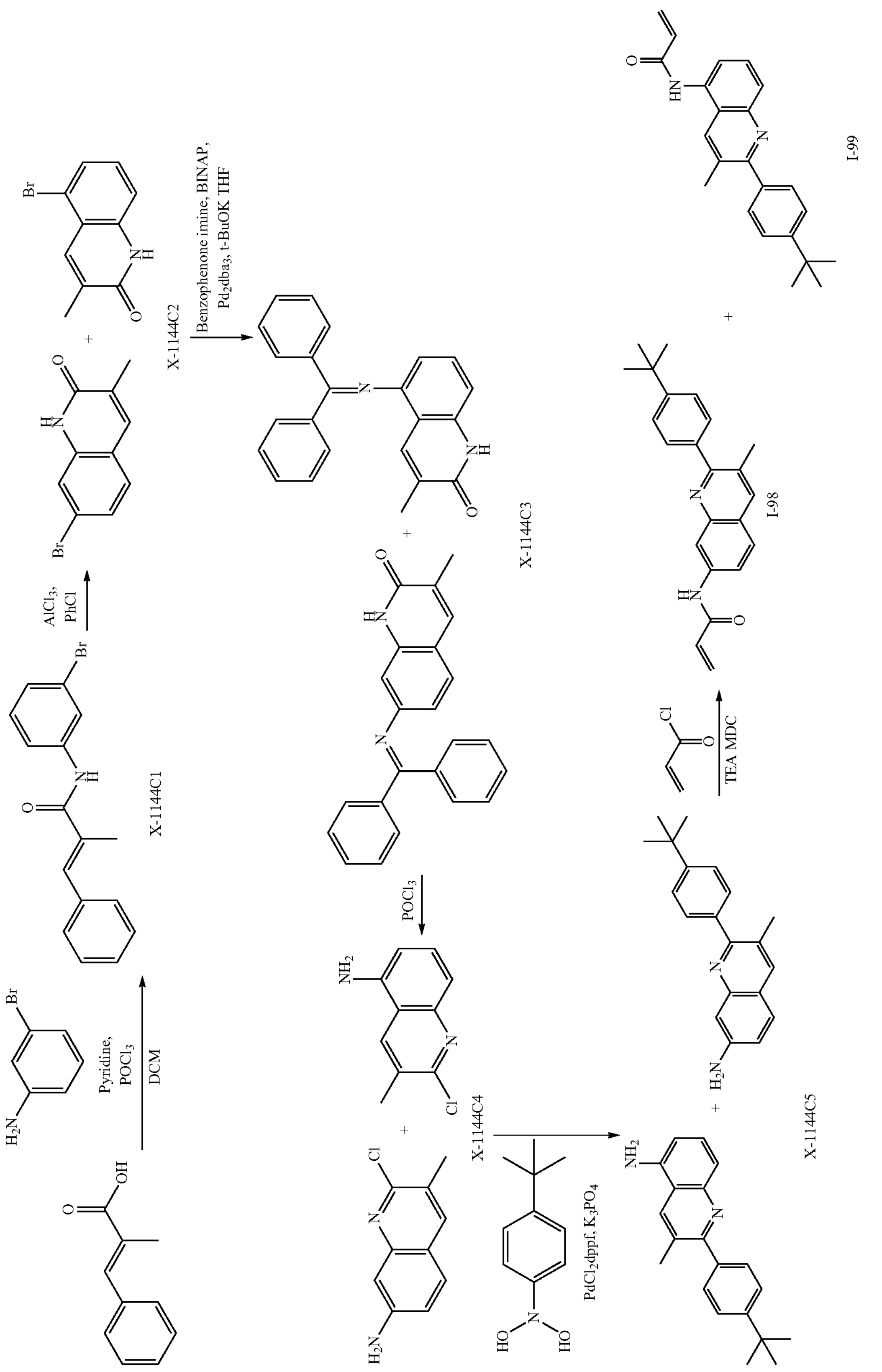
X-1144C1
X-1144C2
X-1144C3
X-1144C4
X-1144C5
I-98
I-99

(E)-N-(3-bromophenyl)-2-methyl-3-phenylacrylamide (X-1144C1). $POCl_3$ (1.72 mL, 18.5 mmol) and pyridine (9.9 mL, 123.0 mmol) were added to a stirred solution of (E)-2-methyl-3-phenylacrylic acid (2.00 g, 12.34 mmol) and 3-bromoaniline (2.0 g, 12.36 mmol) in DCM (20 mL) at 0° C. under nitrogen and the reaction mixture was stirred at 0° C. for 30 min. The reaction mixture was quenched with an aqueous solution of citric acid [10% (v/v); 150 mL) and was extracted with DCM (100 mL×3). Combined organic extracts were dried over anhydrous $Na_2SO_4$ and concentrated under reduced pressure. The crude product was purified by silica gel column chromatography, using ethyl acetate-hexane=0:1→1:4 as gradient, to afford (E)-N-(3-bromophenyl)-2-methyl-3-phenylacrylamide (X-1144C1) (1.90 g, 49%) as yellow solid. MS: $[MH]^+$ 316.5/$[MH+2]^+$ 318.5.

7-Bromo-3-methylquinolin-2(1H)-one and 5-bromo-3-methylquinolin-2(1H)-one (X-1144C2). $AlCl_3$ (4.81 g, 36.15 mmol) was added portion-wise to a stirred solution of (E)-N-(3-bromophenyl)-2-methyl-3-phenylacrylamide (X-1144C1) (1.90 g, 3.03 mmol) in chlorobenzene (20 mL) at 0° C. under nitrogen and the resulting mixture was heated at 125° C. for 30 min. Reaction was cooled to room temperature, dilute with water (50 mL) and was extracted with ethyl acetate (50 mL×3). Combined organic extracts were dried over anhydrous $Na_2SO_4$ and concentrated under reduced pressure. The crude product was purified by silica gel column chromatography, using ethyl acetate-hexane=0:1→1:4 as gradient, to afford a regio-isomeric mixture (3:2) of 7-bromo-3-methylquinolin-2(1H)-one and 5-bromo-3-methylquinolin-2(1H)-one (X-1144C2) (1.00 g, 51%) as an off-white solid. MS: $[MH]^+$ 238.4/$[MH+2]^+$240.4.

7-((Diphenylmethylene)amino)-3-methylquinolin-2(1H)-one and 5-((diphenylmethylene)amino)-3-methylquinolin-2(1H)-one (X-1144C3). Potassium tert-butoxide (1.40 g, 12.62 mmol), benzophenonimine (1.10 g, 6.32 mmol) and BINAP (0.262 g, 0.42 mmol) were added sequentially to a stirred solution of a regio-isomeric mixture (3:2) of 7-bromo-3-methylquinolin-2(1H)-one and 5-bromo-3-methylquinolin-2(1H)-one (X-1144C2) (1.00 g, 4.21 mmol) in THE (15 mL) at room temperature under nitrogen. The reaction mixture was degassed (purged with nitrogen) for 30 min followed by the addition of $Pd_2(dba)_3$ (0.380 g, 0.42 mmol) and subjected to heating at 120° C. under microwave irradiation for 30 min. Reaction mixture was cooled to room temperature, diluted with water (100 mL) and was extracted with ethyl acetate (100 mL×3). Combined organic extracts were dried over anhydrous $Na_2SO_4$ and concentrated under reduced pressure to give a crude mass, which was purified by silica gel column chromatography, using ethyl acetate-hexane=1:9→3:7 as gradient, to afford a regio-isomeric mixture (3:2) of 7-((diphenylmethylene)amino)-3-methylquinolin-2(1H)-one and 5-((diphenylmethylene)amino)-3-methylquinolin-2(1H)-one (X-1144C3) (1.01 g, 70%) as a yellow solid. MS: $[MH]^+$ 339.7.

2-Chloro-3-methylquinolin-7-amine and 2-chloro-3-methylquinolin-5-amine (X-1144C4). A solution of a regio-isomeric mixture (3:2) of 7-((diphenylmethylene)amino)-3-methylquinolin-2(1H)-one and 5-((diphenylmethylene) amino)-3-methylquinolin-2(1H)-one (X-1144C4) (1.00 g, 2.95 mmol) in $POCl_3$ was heated at 100° C. for 30 min. After cooling to room temperature, reaction mixture was slowly poured into water (50 mL) and was extracted with DCM (50 mL×3). Combined organic extracts were dried over anhydrous $Na_2SO_4$ and concentrated under reduced pressure. The crude mass was purified by reverse phase (C-18) silica gel column chromatography, using acetonitrile-water=0:1→1:0 as gradient, to afford a regio-isomeric mixture (3:2) of 2-chloro-3-methylquinolin-7-amine and 2-chloro-3-methylquinolin-5-amine (X-1144C4) (0.420 g, 74%) as a yellow solid. MS: $[MH]^+$ 193.3/$[MH+2]^+$ 195.3.

2-(4-(tert-Butyl)phenyl)-3-methylquinolin-7-amine and 2-(4-(tert-butyl)phenyl)-3-methylquinolin-5-amine (X-1144C5). Potassium phosphate tribasic (0.480 g, 2.29 mmol) was added to a stirred solution of a regio-isomeric mixture (3:2) of 2-chloro-3-methylquinolin-7-amine and 2-chloro-3-methylquinolin-5-amine (X-1144C4) (0.220 g, 1.14 mmol) and (4-(tert-butyl)phenyl)boronic acid (0.244 g, 1.37 mmol) in a mixture of 1,4-dioxane-water (3:1, 12 mL) at room temperature under nitrogen and the resulting mixture was degassed (purged with nitrogen) for 30. $PdCl_2(PPh_3)_2$ (0.080 g, 0.11 mmol) was added into the reaction mixture at the same temperature and reaction the resulting mixture was heated at 90° C. for 3 h. Reaction mixture was filtered through a celite bed and filtrate was concentrated under reduced pressure. Obtained crude was diluted with water (50 mL) and was extracted with ethyl acetate (50 mL×3). Combined organic extracts were dried over anhydrous $Na_2SO_4$ and concentrated under reduced pressure to give a crude mass, which was purified by silica gel column chromatography, using ethyl acetate-hexane=0:1→1:4 as gradient, to afford a regio-isomeric mixture (3:2) of 2-(4-(tert-butyl)phenyl)-3-methylquinolin-7-amine and 2-(4-(tert-butyl)phenyl)-3-methylquinolin-5-amine (X-1144C5) (0.200 g, 60%) as a white solid. MS: $[MH]^+$ 291.1.

N-(2-(4-(tert-butyl)phenyl)-3-methylquinolin-7-yl)acrylamide (I-98) and N-(2-(4-(tert-butyl)phenyl)-3-methylquinolin-5-yl)acrylamide (I-99). Acryloyl chloride (0.074 g, 0.82 mmol) and triethylamine (0.104 g, 1.03 mmol) were added simultaneously to a stirred solution of a regio-isomeric mixture (3:2) of 2-(4-(tert-butyl)phenyl)-3-methylquinolin-7-amine and 2-(4-(tert-butyl)phenyl)-3-methylquinolin-5-amine (X-1144C5) (0.200 g, 0.68 mmol) in dichloromethane (5 mL) at 0° C. under nitrogen and the resulting mixture was stirred for 30 min at the same temperature. Reaction mixture was diluted with water (30 mL) and was extracted with DCM (30 mL×3). Combined organic extracts were dried over anhydrous $Na_2SO_4$ and concentrated under reduced pressure. Obtained crude was purified by preparative HPLC, using acetonitrile-0.05% $NH_3$ in water, to afford N-(2-(4-(tert-butyl)phenyl)-3-methylquinolin-7-yl)acrylamide (I-98) (0.085 g, 36%) as a white solid and N-(2-(4-(tert-butyl)phenyl)-3-methylquinolin-5-yl) acrylamide (I-99) (0.030 g, 15%) as a white solid.

I-98: $^1H$ NMR (400 MHz, DMSO-$d_6$) δ 10.46 (s, 1H), 8.45 (s, 1H), 8.15 (s, 1H), 7.88-7.85 (d, J=8.8 Hz, 1H), 7.74-7.71 (dd, J=8.8, 2.0 Hz, 1H), 7.58-7.56 (d, J=8.4 Hz, 1H), 7.53-7.51 (d, J=8.0 Hz, 1H), 6.54-6.47 (dd, J=16.8, 10.0 Hz, 1H), 6.34-6.30 (dd, J=16.8, 1.6 Hz, 1H), 5.82-5.80 (dd, J=10.0, 1.6 Hz, 1H), 2.43 (s, 3H), 1.35 (s, 9H). MS: $[MH]^+$ 345.1.

I-99: $^1H$ NMR (400 MHz, DMSO-$d_6$) δ 10.23 (s, 1H), 8.36 (s, 1H), 7.88-7.86 (d, J=7.2 Hz, 1H), 7.82-7.80 (d, J=8.4 Hz, 1H) 7.70-7.66 (t, J=8.0, 16.0 Hz, 1H), 7.61-7.59 (d, J=8.4 Hz, 2H), 7.54-7.52 (d, J=8.4 Hz, 2H), 6.74-6.67 (dd, J=16.8, 10.0 Hz, 1H), 6.36-6.31 (dd, J=17.2, 1.6 Hz, 1H), 5.86-5.83 (dd, J=10.0, 1.6 Hz, 1H), 2.50 (s, 3H; merged with DMSO-d6 peaks), 1.35 (s, 9H). MS: $[MH]^+$ 345.1.

Example 1.23. Synthesis of N-(5-(4-(tert-butyl)phenyl)-5H-pyrrolo[3,2-d]pyrimidin-2-yl)acrylamide (I-100)

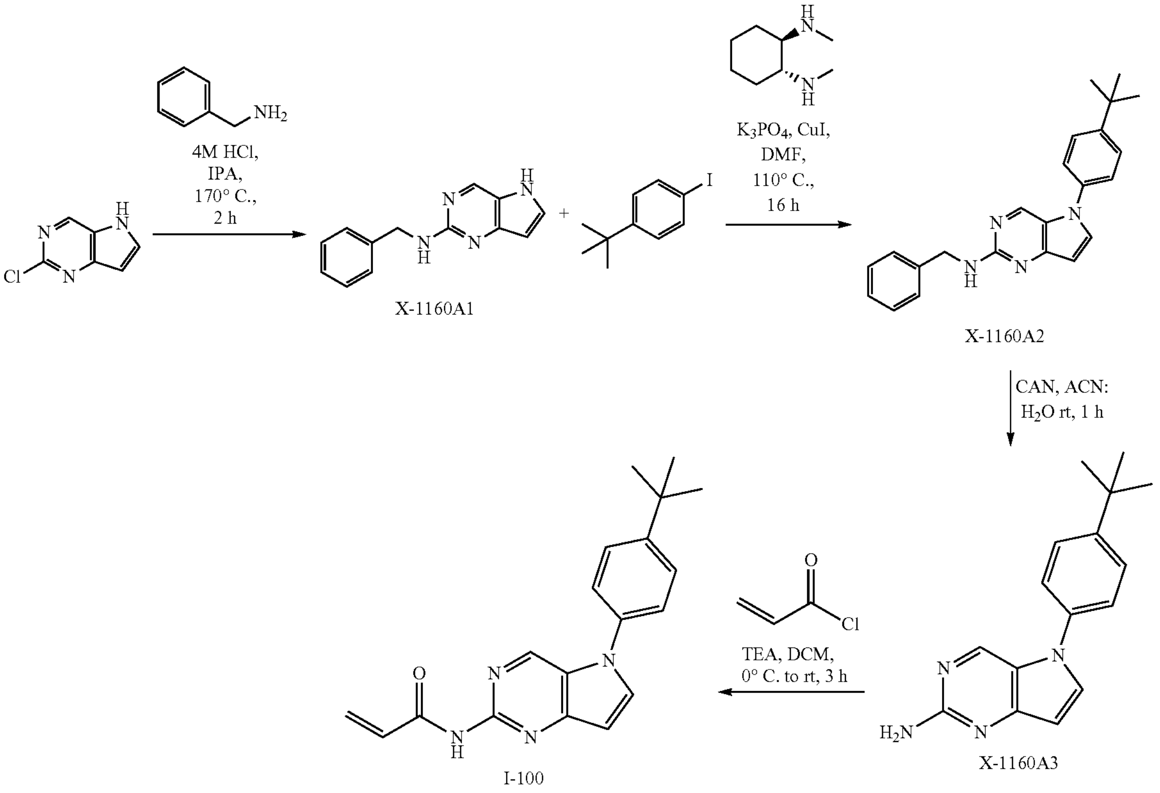

N-benzyl-5H-pyrrolo[3,2-d]pyrimidin-2-amine (X-1160A1). 4 M HCl solution in dioxane (0.81 mL, 3.24 mmol) was added to a stirred solution of 2-chloro-5H-pyrrolo[3,2-d]pyrimidine (0.250 g, 1.60 mmol) and phenylmethanamine (1.00 g, 9.80 mmol) in isopropanol (5 mL) at room temperature under nitrogen and the solution was heated at 170° C. under microwave irradiation for 2 h. After cooling to room temperature, reaction mixture was diluted with water (50 mL) and was extracted with ethyl acetate (50 mL×3). Combined organic extracts were dried over anhydrous $Na_2SO_4$ and concentrated under reduced pressure to afford N-benzyl-5H-pyrrolo[3,2-d]pyrimidin-2-amine (X-1160A1) (0.350 g, 95%) as a brown sticky solid, which was used in next step without further purification. MS: $[MH]^+$ 225.2.

N-benzyl-5-(4-(tert-butyl)phenyl)-5H-pyrrolo[3,2-d]pyrimidin-2-amine (X-1160A2). Potassium phosphate tribasic (0.662 g, 3.10 mmol) was added to a stirred solution of N-benzyl-5H-pyrrolo[3,2-d]pyrimidin-2-amine (X-1160A1) (0.350 g, 1.50 mmol) in DMF (6 mL) at room temperature under nitrogen and the reaction mixture was degassed (purged with nitrogen) for 10 min. 1-(tert-butyl)-4-iodobenzene (0.609 g, 2.30 mmol), CuI (0.029 g, 0.15 mmol) and (1R,2R)—N1,N2-dimethylcyclohexane-1,2-diamine (0.083 g, 0.62 mmol) were added sequentially into the reaction mixture at the same temperature and the resulting mixture was heated at 110° C. for 16 h. After cooling to room temperature, reaction mixture was diluted with cold water (50 mL) and was extracted with ethyl acetate (50 mL×3). Combined organic extracts were washed with brine (50 mL), dried over anhydrous $Na_2SO_4$ and concentrated under reduced pressure. Obtained crude mass was purified by silica gel column chromatography, using ethyl acetate-hexane=1:9→2:3 as gradient, to afford N-benzyl-5-(4-(tert-butyl)phenyl)-5H-pyrrolo[3,2-d]pyrimidin-2-amine (X-1160A2) (0.470 g, 84%) as a brown solid. MS: $[MH]^+$ 357.2.

5-(4-(tert-Butyl)phenyl)-5H-pyrrolo[3,2-d]pyrimidin-2-amine (X-1160A3). Ceric ammonium nitrate (2.100 g, 3.90 mmol) was added to a stirred solution of N-benzyl-5-(4-(tert-butyl)phenyl)-5H-pyrrolo[3,2-d]pyrimidin-2-amine (X-1160A2) (0.470 g, 1.32 mmol) in a mixture of acetonitrile-water (7:3, 10 mL) at 0° C. under nitrogen and the resulting mixture was stirred at room temperature for 1 h. Reaction mixture was quenched with an aqueous solution of saturated $NaHCO_3$ (50 mL) and was extracted with ethyl acetate (50 mL×3). Combined organic extracts were dried over anhydrous $Na_2SO_4$ and concentrated under reduced pressure. The crude product was purified by reverse phase (C-18) silica gel column chromatography, using acetonitrile-water=0:1→1:0 as gradient, to afford 5-(4-(tert-butyl)phenyl)-5H-pyrrolo[3,2-d]pyrimidin-2-amine (X-1160A3) (0.170 g, 48%) as a brown solid. MS: $[MH]^+$ 267.2.

N-(5-(4-(tert-butyl)phenyl)-5H-pyrrolo[3,2-d]pyrimidin-2-yl)acrylamide (I-100). Acryloyl chloride (0.050 g, 0.56 mmol) and triethylamine (0.170 g, 0.17 mmol) were added to a stirred solution of 5-(4-(tert-butyl)phenyl)-5H-pyrrolo[3,2-d]pyrimidin-2-amine (X-1160A3) (0.150 g, 0.56 mmol)

in DCM (5 mL) at 0° C. under nitrogen and the reaction mixture was stirred at room temperature for 3 h. The reaction mixture was diluted with water (50 mL) and was extracted with DCM (30 mL×3). Combined organic extracts were dried over anhydrous $Na_2SO_4$ and concentrated under reduced pressure. Obtained crude was purified by Preparative HPLC, using acetonitrile-0.1% formic acid in water, to afford N-(5-(4-(tert-butyl)phenyl)-5H-pyrrolo[3,2-d]pyrimidin-2-yl)acrylamide (I-100) (0.110 g, 60%) as a white solid. $^1$H NMR (400 MHz, DMSO-$d_6$) δ 10.69 (s, 1H), 8.97 (s, 1H), 8.228-8.220 (d, J=3.2 Hz, 1H), 7.64-7.60 (m, 4H), 6.77-6.76 (d, J=2.8 Hz, 1H), 6.70-6.63 (dd, J=17.2, 10.4 Hz, 1H), 6.31-6.26 (dd, J=16.8, 1.6 Hz, 1H), 5.77-5.74 (dd, J=10.4, 2 Hz, 1H), 1.34 (s, 9H). MS: $[MH]^+$ 321.1.

Example 1.24. Synthesis of 1-(4-(tert-Butyl)phenyl)-1H-indole-5-carboxylic acid (I-101)

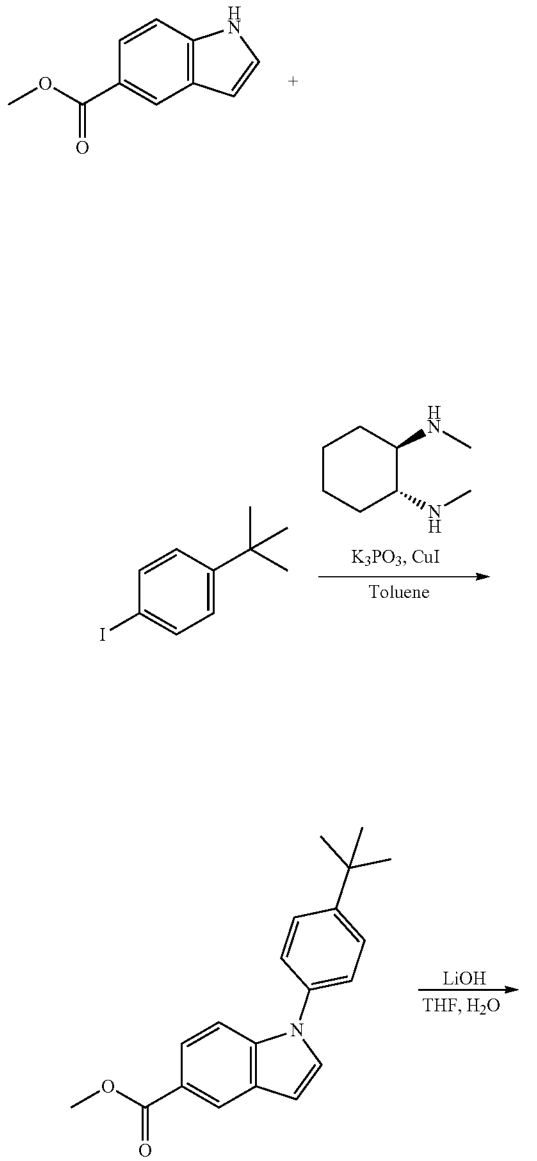

X-1161A1

-continued

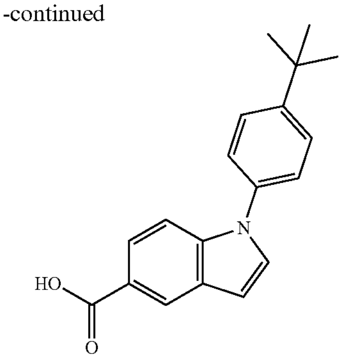

I-101

Methyl 1-(4-(tert-butyl)phenyl)-1H-indole-5-carboxylate (X-1161A1). To a stirred solution of methyl 1H-indole-5-carboxylate (0.300 g, 1.70 mmol) in a toluene (10 mL) were added 1-(tert-butyl)-4-iodobenzene (0.442 g, 1.70 mmol) and (1R,2R)—N1,N2-dimethylcyclohexane-1,2-diamine (0.073 g, 0.51 mmol) followed by the addition of $K_3PO_4$ (1.50 g, 5.10 mmol) and CuI (0.032 g, 0.17 mmol) at room temperature under nitrogen and the resulting mixture was heated at 110° C. for 16 h. After cooling to room temperature, reaction mixture was diluted with dichloromethane (50 mL), filtered through celite and filtrate was concentrated in vacuo. The resulting crude was purified by silica gel column chromatography, using ethyl acetate-hexane=1:19→1:9 as gradient, to afford methyl 1-(4-(tert-butyl)phenyl)-1H-indole-5-carboxylate (X-1161A1) (0.100 g, 19%) as an off-white solid. MS: $[MH]^+$ 308.7.

1-(4-(tert-Butyl)phenyl)-1H-indole-5-carboxylic acid (I-101). To a stirred solution of methyl 1-(4-(tert-butyl)phenyl)-1H-indole-5-carboxylate (X-1161A1) (0.080 g, 0.26 mmol) in a mixture of THF-water (2:1, 2 mL) was added lithium hydroxide monohydrate (0.022 g, 0.52 mmol) at room temperature under nitrogen and the resulting mixture was heated at 100° C. for 16 h. Reaction mixture was concentrated under reduced pressure, obtained crude was diluted with water (20 mL) and was extracted with ethyl acetate (10×2 mL) to remove unwanted organic impurities. Aqueous layer was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 1-(4-(tert-butyl)phenyl)-1H-indole-5-carboxylic acid (I-101) (0.060 g, 79%) as a white solid. $^1$H NMR (400 MHz, DMSO-$d_6$) δ 12.58 (br. s, 1H), 8.32 (s, 1H), 7.81-7.79 (d, J=8.8 Hz, 1H), 7.55-7.74 (d, J=2.8 Hz, 1H), 7.64-7.52 (m, 5H), 6.85-6.84 (d, J=2.8 Hz, 1H), 1.35 (s, 9H). MS: $[MH]^+$ 294.6.

Example 1.25. Synthesis of N-(1-(4-(1-(trifluoromethyl)cyclopropyl)phenyl)pyrrolo[1,2-a]pyrazin-3-yl)acrylamide (I-102)

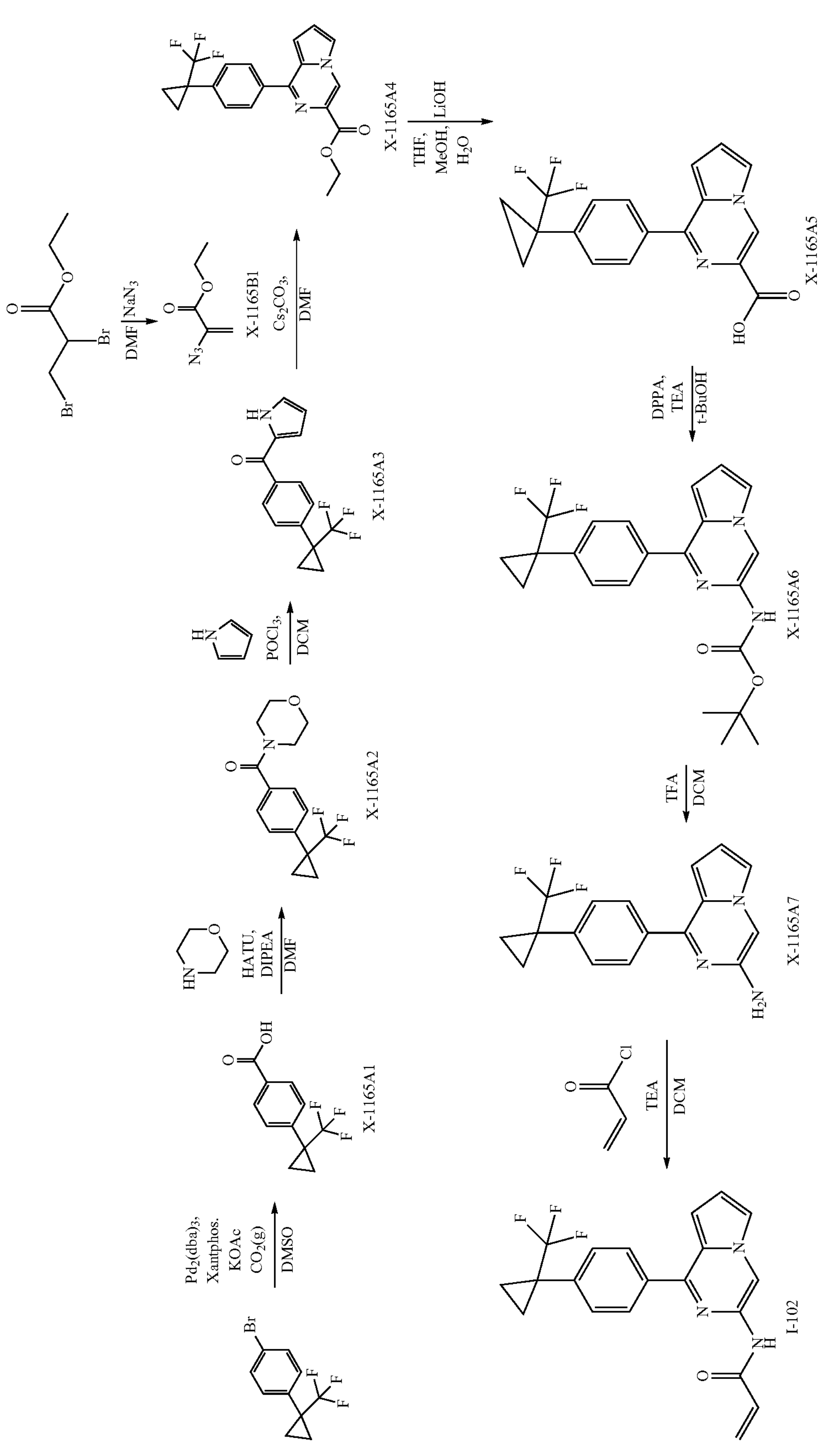
Pd$_2$(dba)$_3$,
Xantphos.
KOAc
CO$_2$(g)
DMSO
X-1165A1
HATU,
DIPEA
DMF
X-1165A2
POCl$_3$,
DCM
X-1165A3
DMF
NaN$_3$
X-1165B1
Cs$_2$CO$_3$,
DMF
X-1165A4
THF,
MeOH,
H$_2$O
LiOH
X-1165A5
DPPA,
TEA
t-BuOH
X-1165A6
TFA
DCM
X-1165A7
TEA
DCM
I-102

4-(1-(Trifluoromethyl)cyclopropyl)benzoic acid (X-1165A1). To a stirred solution of 1-bromo-4-(1-(trifluoromethyl)cyclopropyl)benzene (3.00 g, 11.40 mmol) in DMSO (20 mL) was added potassium acetate (3.3 g, 34.20 mmol) at room temperature under nitrogen. The reaction mixture was degassed [purging with CO (g)] for 20 min followed by addition of $Pd_2$ $(dba)_3$ (0.1 g, 0.11 mmol), Xantphos (0.100 g, 0.11 mmol) and the reaction mixture was heated at 100° C. under CO (g) for 16 h. Reaction mixture was cooled to room temperature, diluted with an aqueous solution of saturated $NaHCO_3$ (100 mL) and was extracted with ethyl acetate (150 mL) to remove unwanted organic impurities. Aqueous layer was acidified (pH~1-2) with an aqueous solution of 1N HCl (50 mL) and was re-extracted with ethyl acetate (150 mL×3). Combined organic extracts were washed with brine (150 mL), dried over anhydrous $Na_2SO_4$ and concentrated under vacuum to afford methyl 4-(1-(trifluoromethyl)cyclopropyl)benzoic acid (X-1165A1) [2.0 g, 76% (crude)] as an off-white solid. $^1H$ NMR (400 MHz, DMSO-$d_6$) δ 13.07 (br. s, 1H), 7.93-8.97 (d, J=8.4 Hz, 2H), 7.60-7.56 (d, J=8.0 Hz, 2H), 1.40-1.36 (m, 2H), 1.95-1.20 (m, 2H).

Morpholino(4-(1-(trifluoromethyl)cyclopropyl)phenyl) methanone (X-1165A2). To a stirred solution of 4-(1-(trifluoromethyl)cyclopropyl)benzoic acid (X-1165A1) (2.00 g, 8.69 mmol) in DMF (20 mL) were added DIPEA (3.36 g, 26.0 mmol), HATU (6.00 g, 17.2 mmol) & morpholine (0.98 g, 11.8 mmol) at 0° C. under nitrogen and the resulting mixture was stirred at room temperature for 1 h. Reaction mixture diluted with water (100 mL) and was extracted with ethyl acetate (150 mL×3). Combined organic extracts were washed with brine (150 mL), dried over anhydrous $Na_2SO_4$ and concentrated in vacuo. The resulting crude was purified by silica gel column chromatography, using ethyl acetate-hexane=1:9→2:8 as gradient, to afford morpholino(4-(1-(trifluoromethyl)cyclopropyl)phenyl)methanone (X-1165A2) (2.50 g, 95%) an off white solid. MS: $[MH]^+$ 300.1.

(1H-Pyrrol-2-yl)(4-(1-(trifluoromethyl)cyclopropyl)phenyl)methanone (CEN2-X-1165A3). A solution of morpholino(4-(1-(trifluoromethyl)cyclopropyl)phenyl)methanone (X-1165A2) (2.50 g; 8.36 mmol) in $POCl_3$ (1.56 mL, 16.6 mmol) was stirred at room temperature for 20 h. A solution of 1H-pyrrole (0.84 g, 16.60 mmol) in DCM (2 mL) was added into the reaction mixture and stirring was continued for an additional 8 h at the same temperature. Reaction mixture was diluted with water (100 mL) and was extracted with ethyl acetate (150 mL×3). Combined organic extracts were washed with brine (150 mL), dried over anhydrous $Na_2SO_4$ and concentrated in vacuo. Isolated crude was purified by silica gel column chromatography, using EtOAc-Hexane=1:9→1:4 as gradient, to afford (1H-pyrrol-2-yl)(4-(1-(trifluoromethyl)cyclopropyl)phenyl) methanone (CEN2-X-1165A3) (1.29 g, 51%) as an off-white solid. MS: $[MH]^+$ 280.1.

Ethyl 2-azidoacrylate (X-1165B1). To a stirred solution of ethyl 2,3-dibromopropanoate (10.0 g, 38.9 mmol) in DMF (20 mL) was added $NaN_3$ (6.32 g, 97.2 mmol) at room temperature under nitrogen and the resulting reaction mixture was heated at 70° C. for 1 h. Reaction mixture diluted with water (300 mL) and was extracted with ethyl acetate (350 mL×3). Combined organic extracts were washed with brine (50 mL), dried over anhydrous $Na_2SO_4$ and concentrated under reduced pressure to afford ethyl 2-azidoacrylate (X-1165B1) [8.0 g, quant. (crude)] as a yellow liquid, which was carried forward to the next step without further purification. $^1H$ NMR (400 MHz, $CDCl_3$) δ 5.87-5.86 (d, J=1.2 Hz, 1H), 5.36-5.35 (d, J=1.2 Hz, 1H), 4.35-4.30 (m, 3H), 1.37-1.34 (t, J=7.2 Hz, 3H).

Ethyl 1-(4-(1-(trifluoromethyl)cyclopropyl)phenyl)pyrrolo[1,2-a]pyrazine-3-carboxylate (X-1165A4). To a stirred solution of (1H-pyrrol-2-yl)(4-(1-(trifluoromethyl)cyclopropyl)phenyl)methanone (CEN2-X-1165A3) (0.250 g, 0.89 mmol) in DMF (5.0 mL) was added ethyl 2-azidoacrylate (X-1165B1) (0.190 g, 1.34 mmol) and $Cs_2CO_3$ (0.873 g, 2.68 mmol) at room temperature under nitrogen and stirred for 1 h at the same temperature. Reaction mixture diluted with water (50 mL) and was extracted with ethyl acetate (50 mL×3). Combined organic extracts were washed with brine (50 mL), dried over anhydrous $Na_2SO_4$, which was combined with another identically prepared batch and the combined batches were concentrated under reduced pressure to afford ethyl 1-(4-(1-(trifluoromethyl)cyclopropyl)phenyl) pyrrolo[1,2-a]pyrazine-3-carboxylate (X-1165A4) [0.60 g, quant. (crude)] as an off-white solid. Obtained crude was taken to the next step without further purification MS: $[MH]^+$ 375.1.

1-(4-(1-(Trifluoromethyl)cyclopropyl)phenyl)pyrrolo[1,2-a]pyrazine-3-carboxylic acid (X-1165A5). To a stirred solution of ethyl 1-(4-(1-(trifluoromethyl)cyclopropyl)phenyl)pyrrolo[1,2-a]pyrazine-3-carboxylate (X-1165A4) (0.500 g, 1.336 mmol) in a mixture of THE-water (2.5:1; 5.0 mL) was added lithium hydroxide monohydrate (0.150 g, 5.34 mmol) at room temperature under nitrogen and the resulting reaction mixture was heated at 70° C. for 3 h. After cooling to room temperature, the reaction mixture was concentrated under reduced pressure, crude mass was diluted with water (200 mL) and was extracted with ethyl acetate (50 mL×2) to remove unwanted organic impurities. Aqueous layer was acidified (pH~2-3) with an aqueous solution of 1N HCl, and was extracted with ethyl acetate (50 mL×3). Combined organic extracts were washed with brine (50 mL), dried over anhydrous $Na_2SO_4$ and concentrated under reduced pressure to afford 1-(4-(1-(trifluoromethyl) cyclopropyl)phenyl)pyrrolo[1,2-a]pyrazine-3-carboxylic acid (X-1165A5) [0.500 g, quant. (crude)] as an off-white solid. Obtained crude was pure enough to proceed to the next step without further purification. MS: $[MH]^+$ 347.0.

tert-Butyl (1-(4-(1-(trifluoromethyl)cyclopropyl)phenyl) pyrrolo[1,2-a]pyrazin-3-yl)carbamate (X-1165A6). To a stirred solution of 1-(4-(1-(trifluoromethyl)cyclopropyl) phenyl)pyrrolo[1,2-a]pyrazine-3-carboxylic acid (X-1165A5) (0.400 g, 1.16 mmol) in t-BuOH (4.0 mL) was added trimethylamine (0.350 g, 3.46 mmol) and DPPA (0.635 g, 2.31 mmol) at room temperature under nitrogen and the resulting mixture was stirred at 100° C. for 16 h. After cooling to room temperature, reaction mixture was poured into water (100 mL) and was extracted with ethyl acetate (100 mL×3). Combined organic extracts were washed with brine (50 mL), dried over anhydrous $Na_2SO_4$ and concentrated under reduced pressure to afford tert-butyl (1-(4-(1-(trifluoromethyl)cyclopropyl)phenyl)pyrrolo[1,2-a]pyrazin-3-yl)carbamate (X-1165A6) [0.60 g, quant. (crude)] as an off-white solid, which was carried forward to the next step without further purification. MS: $[MH]^+$ 418.1.

1-(4-(1-(Trifluoromethyl)cyclopropyl)phenyl)pyrrolo[1,2-a]pyrazin-3-amine (X-1165A7). To a stirred solution of tert-butyl (1-(4-(1-(trifluoromethyl)cyclopropyl)phenyl)pyrrolo[1,2-a]pyrazin-3-yl)carbamate (X-1165A6) (0.250 g, 0.60 mmol) in DCM (1.0 mL) was added TFA (1.48 g, 12.9 mmol) at 0° C. under nitrogen and the resulting reaction mixture was stirred at room temperature for 1 h. Reaction mixture was concentrated under reduced pressure to afford 1-(4-(1-(trifluoromethyl)cyclopropyl)phenyl)pyrrolo[1,2-a]pyrazin-3-amine (X-1165A7) [0.60 g, quant. (crude)] as an off-white solid, which was taken to next step without further purification. MS: $[MH]^+$ 318.0.

N-(1-(4-(1-(trifluoromethyl)cyclopropyl)phenyl)pyrrolo[1,2-a]pyrazin-3-yl)acrylamide (I-102). To a stirred solution of 1-(4-(1-(trifluoromethyl)cyclopropyl)phenyl)pyrrolo[1,2-a]pyrazin-3-amine (X-1165A7) [0.200 g (crude), 0.63 mmol] in DCM (6.0 mL) was added trimethylamine (0.190 g, 1.89 mmol) and acryloyl chloride (0.068 g, 0.75 mmol) at 0° C. under nitrogen and the resulting reaction mixture was stirred at room temperature for 1 h. Reaction mixture diluted with water (50 mL) and was extracted with ethyl acetate (50 mL×3). Obtained crude was purified by reverse phase (C-18) silica gel column chromatography, using acetonitrile-water=0:1→1:0 as gradient, to afford N-(1-(4-(1-(trifluoromethyl)cyclopropyl)phenyl)pyrrolo[1,2-a]pyrazin-3-yl)acrylamide (I-102) (0.040 g, 17%) as an off-white solid. $^1H$ NMR (400 MHz, DMSO-$d_6$) δ 10.56 (s, 1H), 9.13 (s, 1H), 8.04-8.01 (d, J=8.0 Hz, 2H), 7.98 (s, 1H), 7.67-7.64 (d, J=8.0 Hz, 2H), 6.94 (s, 2H), 6.69-6.63 (dd, J=16.0, 10.4 Hz, 1H), 6.31-6.26 (d, J=16.0 Hz, 1H), 5.78-5.74 (d, J=10.4 Hz, 1H), 1.40 (br. s, 2H), 1.22 (br. s, 2H). MS: $[MH]^+$ 372.1.

Example 1.26. Synthesis of 4-Acrylamido-2-(4-(tert-butyl)phenyl)quinoline-7-carboxylic acid (I-103)

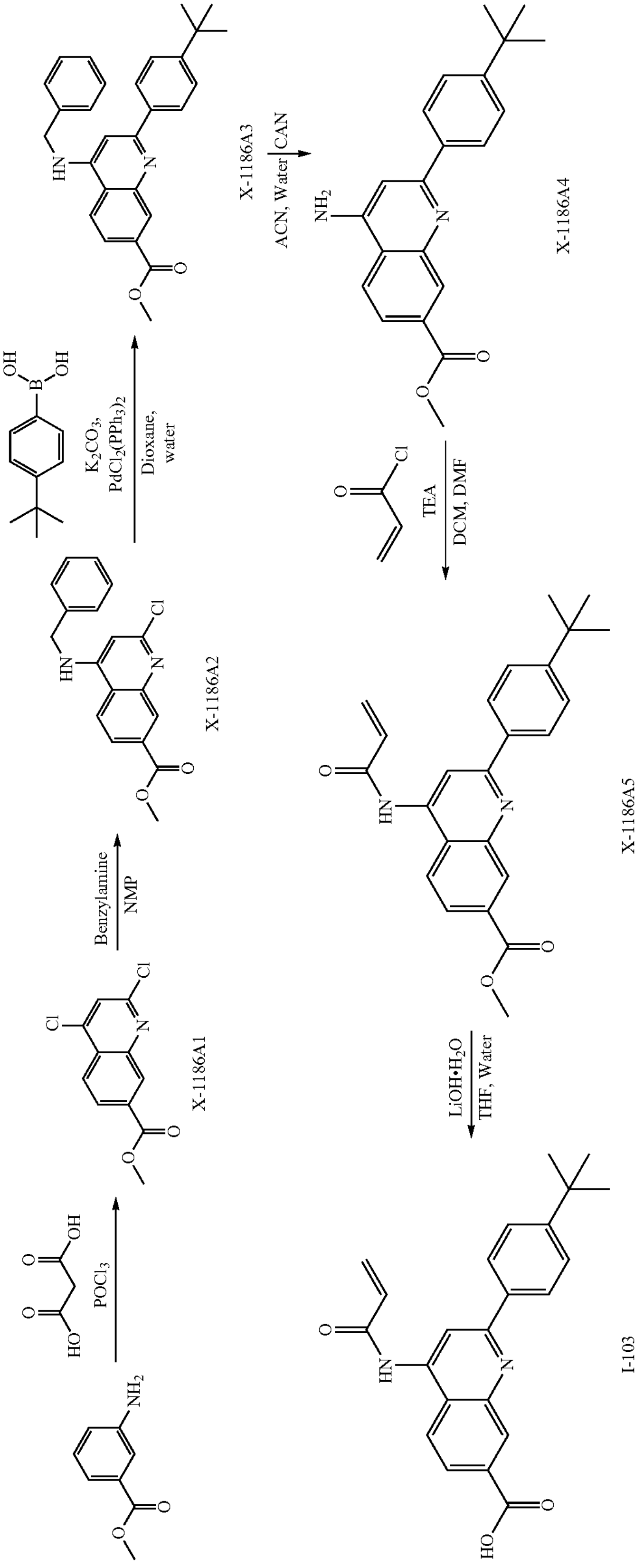
POCl3
X-1186A1
Benzylamine
NMP
X-1186A2
K2CO3,
PdCl2(PPh3)2
Dioxane,
water
X-1186A3
ACN, Water
CAN
X-1186A4
TEA
DCM, DMF
X-1186A5
LiOH•H2O
THF, Water
I-103

Methyl 2,4-dichloroquinoline-7-carboxylate (X-1186A1). Malonic acid (7.4 g, 71.50 mmol) was added to a stirred suspension of methyl 3-aminobenzoate (6.0 g, 39.70 mmol) in $POCl_3$ (30 mL) at 0° C. under nitrogen and the resulting mixture was stirred at 110° C. for 1 h. After cooling to room temperature, reaction mixture was slowly poured into ice water (500 mL), basified (pH~7-8) with slow addition of an aqueous solution of saturated $NaHCO_3$ and was extracted with ethyl acetate (250 mL×3). Combined organic extracts were dried over $Na_2SO_4$ and concentrated under reduced pressure. The crude product was combined with an identically prepared one more batch and the combined batches were purified by silica gel column chromatography, using ethyl acetate-hexane=0:1→1:9 as gradient, to afford methyl 2,4-dichloroquinoline-7-carboxylate (X-1186A1) (0.500 g, 2.5%) as a white solid. MS: $[MH]^+$ 255.9/$[MH+2]^+$ 257.9.

Methyl 4-(benzylamino)-2-chloroquinoline-7-carboxylate (X-1186A2). Benzylamine (0.250 g, 2.35 mmol) was added to a stirred solution of methyl 2,4-dichloroquinoline-7-carboxylate (X-1186A1) (0.500 g, 1.96 mmol) in NMP (10 mL) at room temperature under nitrogen and reaction mixture was stirred at 120° C. under microwave irradiation for 40 min. After cooling to room temperature, reaction mixture was diluted with water (50 mL) and was extracted by ethyl acetate (50 ml×3). Combined organic extracts were dried over $Na_2SO_4$ and concentrated under reduced pressure. The crude product was purified silica gel column chromatography, using ethyl acetate-hexane=0:1→1:4 as gradient, to afford methyl 4-(benzylamino)-2-chloroquinoline-7-carboxylate (X-1186A2) (0.420 g, 65%) as an off-white solid. MS: $[MH]^+$ 327.0/$[MH+2]^+$327.0.

Methyl 4-(benzylamino)-2-(4-(tert-butyl)phenyl)quinoline-7-carboxylate (X-1186A3). To a stirred solution of methyl 4-(benzylamino)-2-chloroquinoline-7-carboxylate (X-1186A2) (0.420 g, 0.99 mmol) and (4-(tert-butyl)phenyl) boronic acid (0.35 g, 1.98 mmol) in a mixture of 1,4-dioxane-water (4:1, 15 mL) was added potassium carbonate (0.34 g, 2.47 mmol) at room temperature. The reaction mixture was degassed (purging with nitrogen) for 30 min followed by the addition of $PdCl_2(PPh_3)_2$ (0.069 g, 0.99 mmol) and the resulting mixture was heated at 90° C. for 16 h. After cooling to room temperature, reaction mixture was slowly poured into water (50 mL) and was extracted by ethyl acetate (50×3). Combined organic solutions were dried over $Na_2SO_4$ and concentrated in vacuo. Obtained crude was purified by silica gel column chromatography using, ethyl acetate-hexane=0:1→1:4 as gradient, to afford methyl 4-(benzylamino)-2-(4-(tert-butyl)phenyl)quinoline-7-carboxylate (X-1186A3) (0.400 g, 73%) as an off-white solid. MS: $[MH]^+$ 425.1.

Methyl 4-amino-2-(4-(tert-butyl)phenyl)quinoline-7-carboxylate (X-1186A4). Ceric ammonium nitrate (2.58 g, 4.71 mmol) was added to a stirred solution of methyl 4-(benzylamino)-2-(4-(tert-butyl)phenyl)quinoline-7-carboxylate (X-1186A3) (0.400 g, 0.94 mmol) in a mixture of acetonitrile-water (7:3, 20 mL) at room temperature and the resulting mixture was heated at 90° C. for 2 h. After cooling to room temperature, reaction mixture was diluted with water (100 mL) and was extracted with ethyl acetate (80 mL×3). Combined organic extracts were dried over $Na_2SO_4$ and concentrated under reduced pressure to afford methyl 4-amino-2-(4-(tert-butyl)phenyl)quinoline-7-carboxylate (X-1186A4) [0.380 g, quant. (crude)] as a yellow sticky oil, which was used in next step without further purification. MS: $[MH]^+$ 335.1.

Methyl 4-acrylamido-2-(4-(tert-butyl)phenyl)quinoline-7-carboxylate (X-1186A5). Acryloyl chloride (0.065 g, 0.71 mmol) was added to a stirred solution of methyl 4-amino-2-(4-(tert-butyl)phenyl)quinoline-7-carboxylate (X-1186A4) (0.200 g, 0.59 mmol) and triethylamine (0.301 g, 2.99 mmol) in a mixture of dichloromethane:DMF (4:1, 10 mL) at 0° C. under nitrogen and reaction mixture was stirred at room temperature for 16 h. The reaction mixture was diluted with water (30 mL) and was extracted with DCM (30 mL×3). Combined organic extracts were dried over $Na_2SO_4$ and concentrated under reduced pressure. The crude product was purified by reverse phase (C-18) silica gel column chromatography, using acetonitrile-water=0:1→1:0 as gradient, to provide ethyl 4-acrylamido-2-(4-(tert-butyl)phenyl)quinoline-7-carboxylate (X-1186A5) (0.050 g, 21%) as an off-white solid. MS: $[MH]^+$ 389.1.

4-Acrylamido-2-(4-(tert-butyl)phenyl)quinoline-7-carboxylic acid (I-103). Lithium hydroxide monohydrate (0.016 g, 0.38 mmol) was added to the stirred solution of methyl 4-acrylamido-2-(4-(tert-butyl)phenyl)quinoline-7-carboxylate (X-1186A5) (0.050 g, 0.12 mmol) in THF-water (9:1, 3.3 mL) at room temperature and reaction mixture was stirred at same temperature for 4 h. The reaction mixture was diluted with water (20 ml) acidified (pH~3-4) with an aqueous solution of 1N HCl and was extracted with ethyl acetate (20 ml×3). Combined organic extracts were dried over $Na_2SO_4$ and concentrated under reduced pressure. The crude product was purified by reverse phase (C-18) silica gel column chromatography, using acetonitrile-water=0:1→1:0 as gradient, to afford 4-acrylamido-2-(4-(tert-butyl)phenyl) quinoline-7-carboxylic acid (I-103) (0.015 g, 31%) as a white solid. $^1H$ NMR (400 MHz, DMSO-$d_6$) δ 13.39 (br, 1H), 10.55 (s, 1H), 8.87 (s, 1H), 8.58 (s, 1H), 8.47-8.45 (d, J=8.8 Hz, 1H), 8.13-8.11 (d, J=8.4 Hz, 2H), 8.08-8.06 (d, J=8.8 Hz, 1H), 7.61-7.59 (d, J=8.4 Hz, 2H), 6.91-6.85 (dd, J=16.8, 10.0 Hz, 1H), 6.45-6.41 (dd, J=16.8, 1.2 Hz, 1H), 5.95-5.93 (d, J=11.6 Hz, 1H), 1.35 (s, 9H). MS: $[MH]^+$ 375.1.

Example 1.27. Synthesis of 4-Acrylamido-2-(4-(tert-butyl)phenyl)quinazoline-7-carboxylic acid (I-104)

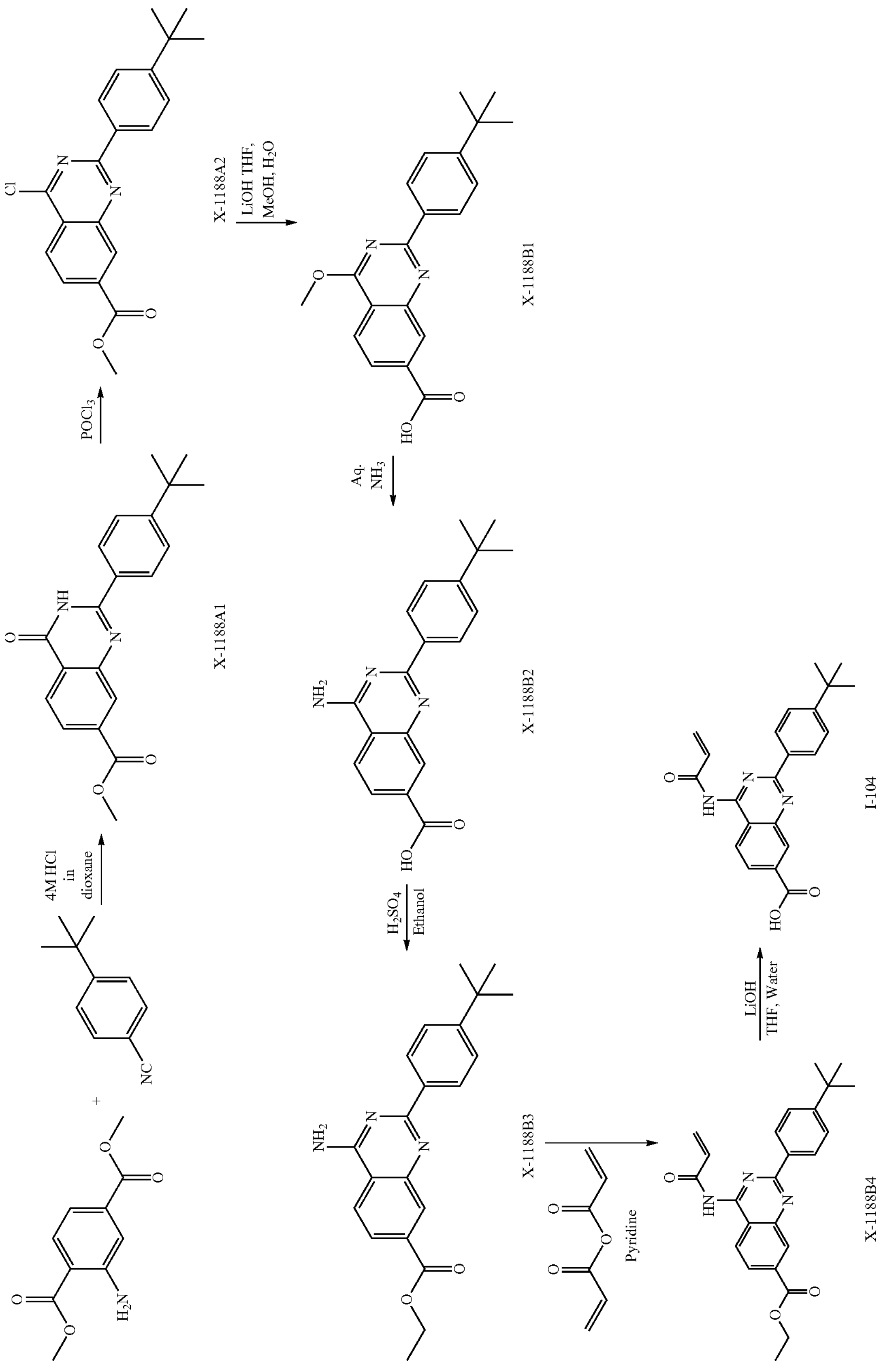
4M HCl
in
dioxane
X-1188A1
POCl3
X-1188A2
LiOH THF,
MeOH, H2O
X-1188B1
Aq.
NH3
X-1188B2
H2SO4
Ethanol
X-1188B3
Pyridine
X-1188B4
LiOH
THF, Water
I-104

Methyl 2-(4-(tert-butyl)phenyl)-4-oxo-3,4-dihydroquinazoline-7-carboxylate (X-1188A1). 4-(tert-Butyl)benzonitrile (5.0 g, 31.5 mmol) was added to a stirred suspension of dimethyl 2-aminoterephthalate (6.00 g, 28.7 mmol) in 4M HCl in dioxane (85 ml) in a pressure vial at room temperature and the resulting mixture was heated at 110° C. for 16 h. After cooling to room temperature, reaction mixture was slowly poured into ice water (200 mL) and was extracted with ethyl acetate (200 mL×3). Combined organic extracts were dried over anhydrous $Na_2SO_4$ and concentrated in vacuo. Obtained crude mass was combined with an identically prepared one more batch and the combined batches were purified by silica gel column chromatography, using ethyl acetate-hexane=0:1→1:4 as gradient, to afford methyl 2-(4-(tert-butyl)phenyl)-4-oxo-3,4-dihydroquinazoline-7-carboxylate (X-1188A1) (1.30 g, 13%) as a white solid. MS: $[MH]^+$ 337.1.

Methyl 2-(4-(tert-butyl)phenyl)-4-chloroquinazoline-7-carboxylate (X-1188A2). A solution of methyl 2-(4-(tert-butyl)phenyl)-4-oxo-3,4-dihydroquinazoline-7-carboxylate (X-1188A1) (1.3 g) in $POCl_3$ (30 mL) was heated at 120° C. for 16 h. After cooling to room temperature, reaction mixture was slowly poured in ice water (200 mL), basified (pH~7-8) with slow addition of an aqueous solution of saturated $NaHCO_3$ and was extracted by ethyl acetate (100 mL×3). Combined organic extracts were dried over anhydrous $Na_2SO_4$ and concentrated under reduced pressure. The crude product was product was purified by silica gel column chromatography, using ethyl acetate-hexane=0:1→1:9 as gradient, to afford methyl 2-(4-(tert-butyl)phenyl)-4-chloroquinazoline-7-carboxylate (X-1188A2) (0.680 g, 49%) as a white solid. MS: $[MH]^+$ 355.1/$[MH+2]^+$ 357.0.

2-(4-(tert-Butyl)phenyl)-4-methoxyquinazoline-7-carboxylic acid (X-1188B1). Lithium hydroxide monohydrate (0.240 g, 5.70 mmol) was added to a stirred solution of methyl 2-(4-(tert-butyl)phenyl)-4-chloroquinazoline-7-carboxylate (X-1188A2) (0.680 g, 1.92 mmol) in a mixture of THF-water-methanol (4:1:1, 12 mL) at room temperature and reaction mixture was stirred at same temperature for 1 h. The reaction mixture was diluted with water (50 mL), acidified (pH~3-4) an aqueous solution of 1N HCl and was extracted with ethyl acetate (50 mL×3). Combined organic extracts were dried over anhydrous $Na_2SO_4$ and concentrated under reduced pressure to afford 2-(4-(tert-butyl)phenyl)-4-methoxyquinazoline-7-carboxylic acid (X-1188B1) [0.600 g, 92% (crude)] as an off-white solid, which was pure enough to proceed to the next step without further purification. MS: $[MH]^+$ 337.1.

4-Amino-2-(4-(tert-butyl)phenyl)quinazoline-7-carboxylic acid (X-1188B2). A suspension of 2-(4-(tert-butyl)phenyl)-4-methoxyquinazoline-7-carboxylic acid (X-1188B1) [0.600 g (crude), 1.78 mmol) in aqueous $NH_3$ (20 mL) was heated at 90° C. for 5 h. After cooling to room temperature, reaction mixture was concentrated under reduced pressure to get a crude mass, which was purified by reverse phase (C-18) silica gel column chromatography, using acetonitrile-water=0:1→1:0 as gradient, to afford 4-amino-2-(4-(tert-butyl)phenyl)quinazoline-7-carboxylic acid (X-1188B2) (0.300 g, 52%) as a white solid. MS: $[MH]^+$ 322.1.

Ethyl 4-amino-2-(4-(tert-butyl)phenyl)quinazoline-7-carboxylate (X-1188B3). Concentrated $H_2SO_4$ (2 mL) was added to a stirred suspension of 4-amino-2-(4-(tert-butyl)phenyl)quinazoline-7-carboxylic acid (X-1188B2) (0.300 g, 0.93 mmol) in ethanol (15 ml) at room temperature and the resulting mixture was heated at 80° C. for 16 h. After cooling to room temperature, reaction mixture was slowly poured into an aqueous solution of saturated $NaHCO_3$ (50 mL) and was extracted with ethyl acetate (50 mL×3). Combined organic extracts were dried over anhydrous $Na_2SO_4$ and concentrated under reduced pressure. The crude product was purified by reverse phase (C-18) silica gel column chromatography, using acetonitrile-water=0:1→1:0 as gradient, to afford ethyl 4-amino-2-(4-(tert-butyl)phenyl)quinazoline-7-carboxylate (X-1188B3) (0.210 g, 64%) as a white solid. MS: $[MH]^+$ 350.1.

Ethyl 4-acrylamido-2-(4-(tert-butyl)phenyl)quinazoline-7-carboxylate (X-1188B4). Acrylic anhydride (0.306 g, 2.43 mmol) was added to a stirred solution of ethyl 4-amino-2-(4-(tert-butyl)phenyl)quinazoline-7-carboxylate (X-1188B3) (0.170 g, 0.48 mmol) in pyridine (7 mL) at 0° C. under nitrogen and the resulting suspension was heated at 80° C. for 1 h. After cooling to room temperature, reaction mixture was diluted with water (50 mL) and was extracted with ethyl acetate (50 mL×3). Combined organic extracts were dried over anhydrous $Na_2SO_4$ and concentrated under reduced pressure. Obtained crude mass was purified by reverse phase (C-18) silica gel column chromatography, using acetonitrile-water=0:1→1:0 as gradient, to afford ethyl 4-acrylamido-2-(4-(tert-butyl)phenyl)quinazoline-7-carboxylate (X-1188B4) (0.060 g, 30%) as an off-white solid. MS: $[MH]^+$ 404.1.

4-Acrylamido-2-(4-(tert-butyl)phenyl)quinazoline-7-carboxylic acid (I-104). Lithium hydroxide monohydrate (0.025 g, 0.59 mmol) was added to a stirred solution of ethyl 4-acrylamido-2-(4-(tert-butyl)phenyl)quinazoline-7-carboxylate (X-1188B4) (0.060 g, 0.14 mmol) in a mixture of THF-water (5:1, 2.4 mL) at room temperature and the reaction mixture was stirred at same temperature for 5 h. The reaction mixture was diluted with water (30 mL), acidified (pH~3-4) with an aqueous solution of 1N HCl and was extracted with ethyl acetate (30 mL×3). Combined organic extracts were dried over anhydrous $Na_2SO_4$ and concentrated under reduced pressure. The crude mass was purified by reverse phase (C-18) silica gel column chromatography, using acetonitrile-water=0:1→1:0 as gradient, to afford 4-acrylamido-2-(4-(tert-butyl)phenyl)quinazoline-7-carboxylic acid (I-104) (0.005 g, 9%) as a white solid. $^1H$ NMR (400 MHz, DMSO-$d_6$) δ 13.67 (br, 1H), 11.23 (br. s, 1H), 8.46-8.34 (m, 3H), 8.08 (s, 1H), 7.60 (s, 2H), 6.92 (br. s, 1H), 6.45-6.41 (d, J=16.4 Hz, 1H), 5.96-5.94 (d, J=8.0 Hz, 1H), 1.34 (s, 9H). MS: $[MH]^+$ 376.1.

Example 1.28. Synthesis of 1-(4-(4-(tert-Butyl)phenyl)-1H-pyrrolo[3,2-c]pyridin-1-yl)prop-2-en-1-one (I-105)

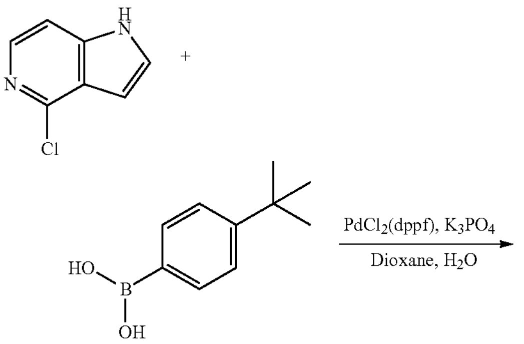

-continued

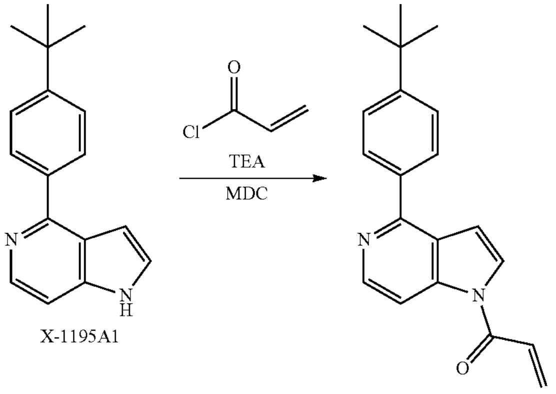

X-1195A1

I-105

4-(4-(tert-Butyl)phenyl)-1H-pyrrolo[3,2-c]pyridine (X-1195A1). Potassium phosphate tribasic (2.70 g, 13.17 mmol) was added to a stirred solution of 4-chloro-1H-pyrrolo[3,2-c]pyridine (0.800 g, 5.26 mmol) and (4-(tert-butyl)phenyl)boronic acid (1.10 g, 6.31 mmol) in a mixture of 1,4-dioxane-water (5:3, 8 mL) at room temperature under nitrogen and the reaction mixture was degassed (purged with nitrogen) for 30 min. $PdCl_2(PPh_3)_2$ (0.307 g, 0.42 mmol) was added into the reaction mixture at the same temperature and reaction the resulting mixture was heated at 90° C. for 1 h. Reaction mixture was filtered through a celite bed and filtrate was concentrated under reduced pressure. Obtained crude was diluted with water (50 mL) and was extracted with ethyl acetate (50 mL×3). Combined organic extracts were dried over anhydrous $Na_2SO_4$ and concentrated under reduced pressure to give a crude mass, which was purified by silica gel column chromatography, using ethyl acetate-hexane=0:1→1:4 as gradient, to afford 4-(4-(tert-butyl)phenyl)-1H-pyrrolo[3,2-c]pyridine (X-1195A1) (1.1 g, 83%) as a white solid. MS: $[MH]^+$ 251.6.

1-(4-(4-(tert-Butyl)phenyl)-1H-pyrrolo[3,2-c]pyridin-1-yl)prop-2-en-1-one (I-105). Acryloyl chloride (0.126 g, 1.40 mmol) and triethylamine (0.21 g, 2.10 mmol) were added to a stirred solution of 4-(4-(tert-butyl)phenyl)-1H-pyrrolo[3,2-c]pyridine (X-1195A1) (0.350 g, 1.40 mmol) in DCM (5 ml) at 0° C. under nitrogen and stirred for 30 min at the same temperature. Reaction mixture was diluted with water (30 mL) and was extracted with DCM (30 mL×3). Combined organic extracts were dried over anhydrous $Na_2SO_4$ and concentrated under reduced pressure, obtained crude was purified by reverse phase (C-18) silica gel column chromatography, using acetonitrile-water=0:1→1:0 as gradient, to afford 1-(4-(4-(tert-butyl)phenyl)-1H-pyrrolo[3,2-c]pyridin-1-yl)prop-2-en-1-one (I-105) (0.060 g, 14%) as an off-white solid. $^1H$ NMR (400 MHz, DMSO-$d_6$) δ 8.58-8.56 (d, J=5.6 Hz, 1H), 8.30-8.27 (m, 2H), 7.90-7.88 (d, J=8.0 Hz, 2H), 7.59-7.57 (d, J=7.6 Hz, 2H), 7.46-7.39 (dd, J=16.8, 10.4 Hz, 1H), 7.09-7.08 (d, J=4.0 Hz, 1H), 6.67-6.63 (d, J=16.4 Hz, 1H), 6.23-6.20 (d, J=10.4 Hz, 1H), 1.35 (s, 9H). MS: $[MH]^+$ 305.6.

Example 1.29. Synthesis of N-(2-(4-(tert-butyl)phenyl)quinolin-7-yl)acrylamide (I-106)

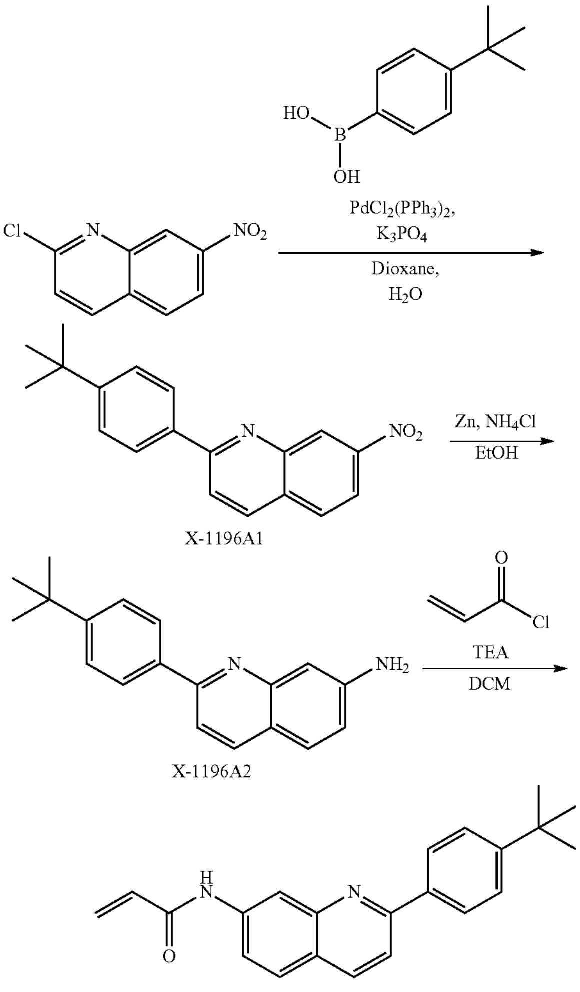

X-1196A1

X-1196A2

I-106

2-(4-(tert-Butyl)phenyl)-7-nitroquinoline (X-1196A1). Potassium phosphate tribasic (0.900 g, 5.77 mmol) was added to a stirred solution of 2-chloro-7-nitroquinoline (0.400 g, 1.92 mmol) and (4-(tert-butyl)phenyl)boronic acid (0.340 g, 1.92 mmol) in a mixture of 1,4-dioxane-water (3:1, 4 mL) at room temperature under nitrogen and the resulting suspension was degassed (purging with nitrogen) for 30 min. $PdCl_2(PPh_3)_2$ (0.067 g, 0.09 mmol) was added into the reaction mixture at the same temperature and reaction the resulting mixture was heated at 100° C. for 3 h. Reaction mixture was filtered through a celite bed and filtrate was concentrated under reduced pressure. Obtained crude was diluted with water (50 mL) and was extracted with ethyl acetate (50 mL×3). Combined organic extracts were dried over anhydrous $Na_2SO_4$ and concentrated under reduced pressure to give a crude mass, which was purified by silica gel column chromatography, using ethyl acetate-hexane=0:1→1:4 as gradient, to afford 2-(4-(tert-butyl)phenyl)-7-nitroquinoline (X-1196A1) (0.400 g, 68%) as a yellow solid. MS: $[MH]^+$ 307.1.

2-(4-(tert-Butyl)phenyl)quinolin-7-amine (X-1196A2). Zn dust (0.700 g, 10.46 mmol) and $NH_4Cl$ (0.550 g, 10.4 mmol) were sequentially added to a stirred solution of 2-(4-(tert-butyl)phenyl)-7-nitroquinoline (X-1196A1) (0.400 g, 1.30 mmol) in EtOH (10 mL) at room temperature under nitrogen and the resulting suspension was heated at 70° C. temperature for 2 h. After cooling to room temperature, reaction mixture was filtered through a celite, filtrate was diluted with water (50 mL) and was extracted with ethyl acetate (50 mL×3). Combined organic extracts were dried over anhydrous $Na_2SO_4$ and concentrated under reduced pressure to afford 2-(4-(tert-butyl)phenyl)quinolin-7-amine (X-1196A2) (0.350 g, 97%) as a yellow solid. The crude was directly used for next step without further purification. MS: $[MH]^+$ 277.2.

N-(2-(4-(tert-butyl)phenyl)quinolin-7-yl)acrylamide (I-106). Acryloyl chloride (0.114 g, 1.26 mmol) and triethylamine (0.400 g, 3.80 mmol) were added simultaneously to a stirred solution of 2-(4-(tert-butyl)phenyl)quinolin-7-amine (X-1196A2) (0.350 g, 1.26 mmol) in DCM (5 mL) at 0° C. under nitrogen and the reaction mixture was stirred at room temperature for 1 h. The reaction mixture was diluted with water (50 mL) and was extracted with DCM (50 mL×3). Combined organic extracts were dried over anhydrous $Na_2SO_4$ and concentrated under reduced pressure. The crude product was purified by reverse phase (C-18) silica gel column chromatography, using acetonitrile-water=0:1→1:0 as gradient, to afford N-(2-(4-(tert-butyl)phenyl)quinolin-7-yl)acrylamide (I-106) (0.200 g, 47%) as an off-white solid. $^1H$ NMR (400 MHz, DMSO-$d_6$) δ 10.51 (s, 1H), 8.58 (s, 1H), 8.35-8.32 (d, J=8.8 Hz, 1H), 8.19-8.17 (d, J=8.0 Hz, 2H), 8.01-7.98 (d, J=8.4 Hz, 1H), 7.94-7.92 (d, J=8.8 Hz, 1H), 7.71-7.69 (d, J=8.8 Hz, 1H), 7.57-7.55 (d, J=8.0 Hz, 2H), 6.56-6.49 (d, J=17.2, 10.0 Hz, 1H), 6.36-6.32 (d, J=16.4 Hz, 1H), 5.84-5.82 (d, J=10.4 Hz, 1H), 1.34 (s, 9H). MS: $[MH]^+$ 331.1.

Example 1.30. Synthesis of 4-((3,3,3-Trifluoropropyl)amino)pyrrolo[1,2-a]quinoxaline-7-carboxylic acid (I-107)

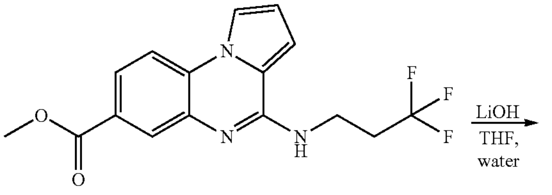

X-1200A1

-continued

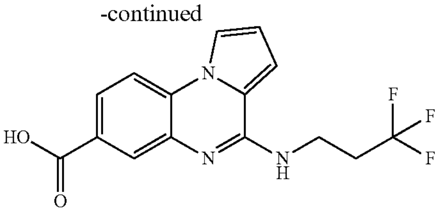

I-107

To a stirred solution of methyl 4-((3,3,3-trifluoropropyl)amino)pyrrolo[1,2-a]quinoxaline-7-carboxylate (X-1201A1) (0.150 g, 0.44 mmol) in a mixture of THF-water (3:1; 10 mL) was added lithium hydroxide monohydrate (0.056 g, 1.33 mmol) at room temperature under nitrogen and the resulting reaction mixture was heated at 70° C. for 2 h. After cooling to room temperature, the reaction mixture was concentrated under reduced pressure, diluted with water (50 mL) and extracted with ethyl acetate (50×2 mL) to remove unwanted organic impurities. The aqueous layer was acidified (pH~2-3) with an aqueous solution of 1N HCl and the resulting precipitate was collected by filtration. Obtained residue was washed with cold water until the pH of the filtrate became neutral (pH~6-7) and, finally, purified by reverse phase (C-18) silica gel column chromatography using acetonitrile-water=0:1→1:0 as gradient, to afford 4-((3,3,3-trifluoropropyl)amino)pyrrolo[1,2-a]quinoxaline-7-carboxylic acid (I-107) (0.030 g, 18%) as an off white solid. $^1H$ NMR (400 MHz, DMSO-$d_6$) δ 8.25 (s, 1H), 8.08-8.06 (d, J=: 8.4 Hz, 1H), 8.02 (s, 1-1) 7.75-7.73 (d, J=6.4 Hz, 2H), 7.04-7.03 (d, J=132 Hz, 1H), 6.77-6.76 (t, J=3.2 Hz, 1H), 3.78-3.76 (m, 2H), 275-2.69 (m, 2H). MS: $[MH]^+$ 324.0.

Example 1.31. Synthesis of 4-(4-(tert-Butyl)phenyl)-2-fluoropyrrolo[1,2-a]quinoxaline-7-carboxylic acid (I-108)

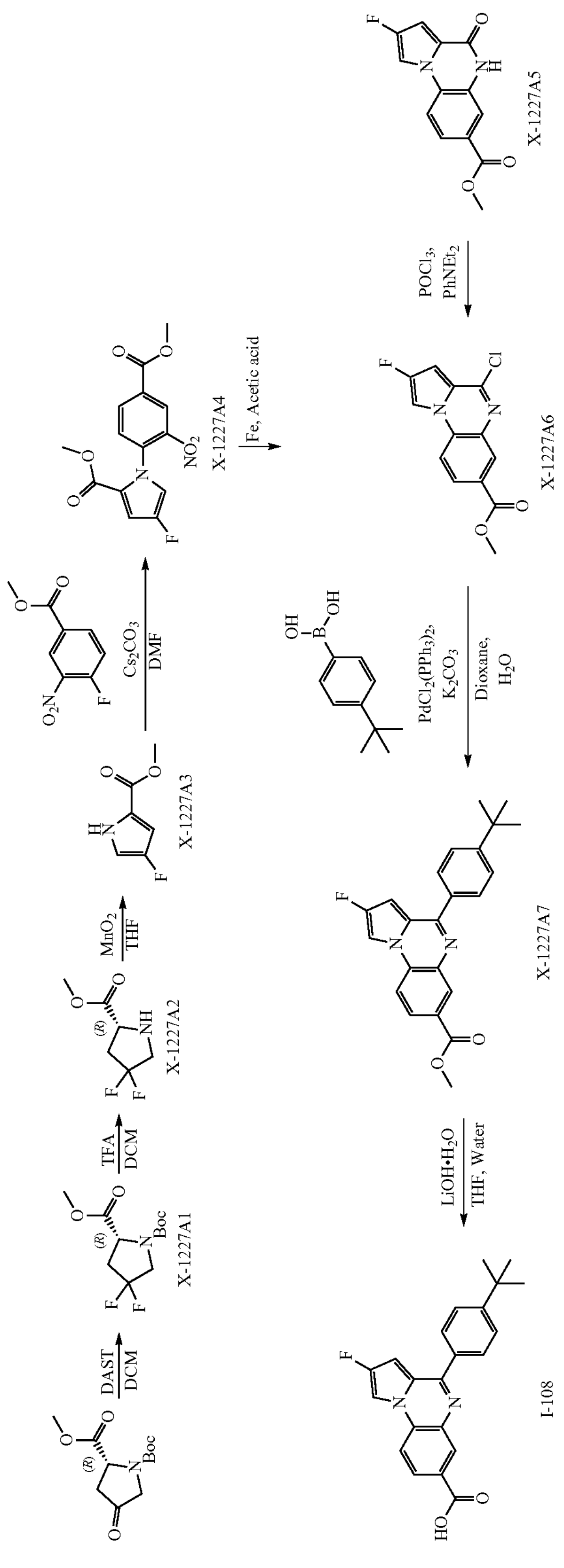
X-1227A1
X-1227A2
X-1227A3
X-1227A4
X-1227A5
X-1227A6
X-1227A7
I-108

1-(tert-Butyl) 2-methyl (R)-4,4-difluoropyrrolidine-1,2-dicarboxylate (X-1227A1). DAST (24.0 g, 148.1 mmol) was added to a stirred suspension of 1-(tert-butyl) 2-methyl (R)-4-oxopyrrolidine-1,2-dicarboxylate (12.0 g, 49.30 mmol) in DCM (50 mL) at 0° C. under nitrogen and stirred at 70° C. for 3 h. The reaction mixture was cooled to room temperature, diluted with water (200 mL) and was extracted with ethyl acetate (200 mL×3). Collected organic extracts were dried over anhydrous $Na_2SO_4$ and concentrated under reduced pressure. The crude product was purified by silica gel column chromatography, using acetate-hexane=0.8:9.2→1:9 as gradient, to afford 1-(tert-butyl) 2-methyl (R)-4,4-difluoropyrrolidine-1,2-dicarboxylate (X-1227A1) (10 g, 77%) as an off-white solid. MS: $[M-56]^+$210.1.

Methyl (R)-4,4-difluoropyrrolidine-2-carboxylate (X-1227A2). TFA (15 mL) was added to a stirred suspension of 1-(tert-butyl) 2-methyl (R)-4,4-difluoropyrrolidine-1,2-dicarboxylate (X-1227A1) (10.0 g, 37.7 mmol) in DCM (80 mL) at 0° C. and stirred at room temperature for 3 h. Reaction mixture was concentrated under reduced pressure to afford methyl (R)-4,4-difluoropyrrolidine-2-carboxylate (X-1227A2) [8.0 g, quantitative (crude)] as an off-white solid, which was used in next step without further purification. MS: $[MH]^+$ 166.0.

Methyl 4-fluoro-1H-pyrrole-2-carboxylate (X-1227A3). $MnO_2$ (5.8 g, 242.4 mmol) was added to a stirred suspension of methyl (R)-4,4-difluoropyrrolidine-2-carboxvlate (X-1227A2) (5.0 g, 30.3 mmol) in THE (50 mL) at room temperature and stirred at 75° C. for 16 h. The reaction mixture was cooled to room temperature, diluted with water (100 mL) and was extracted with ethyl acetate (100 mL×3). Combined organic extracts were dried over anhydrous $Na_2SO_4$ and concentrated under reduced pressure to afford methyl 4-fluoro-1H-pyrrole-2-carboxylate (X-1227A3) (1.4 g, 33%) as an off-white solid, which was used in next step without further purification.

Methyl 4-fluoro-1-(4-(methoxycarbonyl)-2-nitrophenyl)-1H-pyrrole-2-carboxylate (X-1227A4). $Cs_2CO_3$ (4.7 g, 14.5 mmol) and methyl 4-fluoro-3-nitrobenzoate (1.9 g, 9.7 mmol) were sequentially added to a stirred suspension of methyl 4-fluoro-1H-pyrrole-2-carboxylate (X-1227A3) (1.4 g, 9.7 mmol) in DMF (5 mL) at room temperature and the resulting suspension was stirred at 60° C. for 1 h. Reaction mixture was allowed to cool to room temperature and was slowly poured into ice-water. The resulting precipitate was filtered, residue was washed with cold water and dried in vacuo to afford methyl 4-fluoro-1-(4-(methoxycarbonyl)-2-nitrophenyl)-1H-pyrrole-2-carboxylate (X-1227A4) [1.7 g, 54% (crude)] as an off-white solid, which was used to the next step without further purification. MS: $[MH]^+$ 322.9.

Methyl 2-fluoro-4-oxo-4,5-dihydropyrrolo[1,2-a]quinoxaline-7-carboxylate (X-1227A5). To a stirred solution of methyl 4-fluoro-1-(4-(methoxycarbonyl)-2-nitrophenyl)-1H-pyrrole-2-carboxylate (X-1227A4) (1.7 g, 5.27 mmol) in acetic acid (5 mL) was added Fe powder (2.38 g, 43.2 mmol) at room temperature and the resulting reaction was stirred at 60° C. for 1 h. After cooling to room temperature, reaction mixture was filtered and the obtained precipitate was washed with water. The precipitate was taken in 10% methanol in dichloromethane, stirred for 30 min and filtered through a celite bed. Collected filtrate concentrated under reduced pressure to afford methyl 2-fluoro-4-oxo-4,5-dihydropyrrolo[1,2-a]quinoxaline-7-carboxylate (X-1227A5) [0.5 g, 36% (crude)] as a light brown solid, which was taken to the next step without further purification. MS: $[MH]^+$ 261.0.

Methyl 4-chloro-2-fluoropyrrolo[1,2-a]quinoxaline-7-carboxylate (X-1227A6). $POCl_3$ (5 mL) was added drop wise, via syringe, to a solution of methyl 2-fluoro-4-oxo-4,5-dihydropyrrolo[1,2-a]quinoxaline-7-carboxylate (X-1227A5) (0.500 g, 1.92 mmol) in N, N-diethyl aniline (0.2 mL) at 0° C. under nitrogen. After completion of addition of $POCl_3$, the reaction mixture was slowly brought to reflux and continued heating at 100° C. for 2 h. Reaction mixture was allowed to cool to room temperature and was slowly poured into ice-water with stirring. Obtained precipitate was filtered and the residue was washed with ice-water until the pH of the filtrate became neutral (pH~6-7). Solid was dried in vacuo to give methyl 4-chloro-2-fluoropyrrolo[1,2-a]quinoxaline-7-carboxylate (X-1227A6) [0.500 g, 94% (crude)] as an off-white solid, which was used in next step without further purification. MS: $[MH]^+$ 278.9.

Methyl 4-(4-(tert-butyl)phenyl)-2-fluoropyrrolo[1,2-a]quinoxaline-7-carboxylate (X-1227A7). To a stirred solution of methyl 4-chloro-2-fluoropyrrolo[1,2-a]quinoxaline-7-carboxylate (X-1227A6) (0.480 g, 1.73 mmol) in a mixture of 1,4-dioxane-water (3:1, 8 mL) were added (4-(tert-butyl)phenyl)boronic acid (0.400 g, 2.25 mmol) and $K_2CO_3$ (0.7 g, 5.181 mmol) sequentially at room temperature under nitrogen. The reaction mixture was degassed (by purging with nitrogen) for 20 min followed by addition of $PdCl_2(PPh_3)_2$ (0.035 g, 0.05 mmol) and the resulting reaction mixture was heated at 100° C. for 2 h. The reaction mixture was cooled to room temperature, diluted with water (30 mL) and was extracted with ethyl acetate (30 mL×3). Combined organic extracts were washed with brine (30 mL), dried over anhydrous $Na_2SO_4$ and concentrated under reduced pressure. The crude product was purified by silica gel column chromatography, using ethyl acetate-hexane=0.8:9.2→1:9 as gradient, to afford methyl 4-(4-(tert-butyl)phenyl)-2-fluoropyrrolo[1,2-a]quinoxaline-7-carboxylate (X-1227A7) (0.400 g, 62%) as an off-white solid. MS: $[MH]^+$ 377.1.

4-(4-(tert-Butyl)phenyl)-2-fluoropyrrolo[1,2-a]quinoxaline-7-carboxylic acid (I-108). To the stirred solution of Methyl 4-(4-(tert-butyl)phenyl)-2-fluoropyrrolo[1,2-a]quinoxaline-7-carboxylate (X-1227A7) (0.200 g, 0.532 mmol) in a mixture of THF-water (5:2; 7 mL) was added lithium hydroxide monohydrate (0.031 g, 0.001 mmol) at room temperature under nitrogen and the resulting reaction mixture was heated at 70° C. for 2 h. After cooling to room temperature, the reaction mixture was concentrated under reduced pressure, obtained crude mass was diluted with water (20 mL) and was extracted with ethyl acetate (20×2 mL) to remove unwanted organic impurities. The aqueous layer was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 4-(4-(tert-butyl)phenyl)-2-fluoropyrrolo[1,2-a]quinoxaline-7-carboxylic acid (I-108) (0.150 g, 93%) as a yellow solid. 1H NMR (400 MHz, DMSO-$d_6$) δ 8.63 (br. s, 1H), 8.42 (br. s, 1H), 8.19-8.161 (d, J=7.6 Hz, 1H), 8.13-8.11 (d, J=7.2 Hz, 1H), 7.95-7.93 (d, J=8.4 Hz, 2H), 7.62-7.60 (d, J=8.4 Hz, 2H), 6.93 (s, 1H), 1.36 (s, 9H). MS: $[MH]^+$ 363.1.

Example 1.32. Synthesis of N-((8-(4-(trifluoromethyl)phenyl)imidazo[1,2-a]pyrazin-6-yl)methyl) acrylamide (I-109)

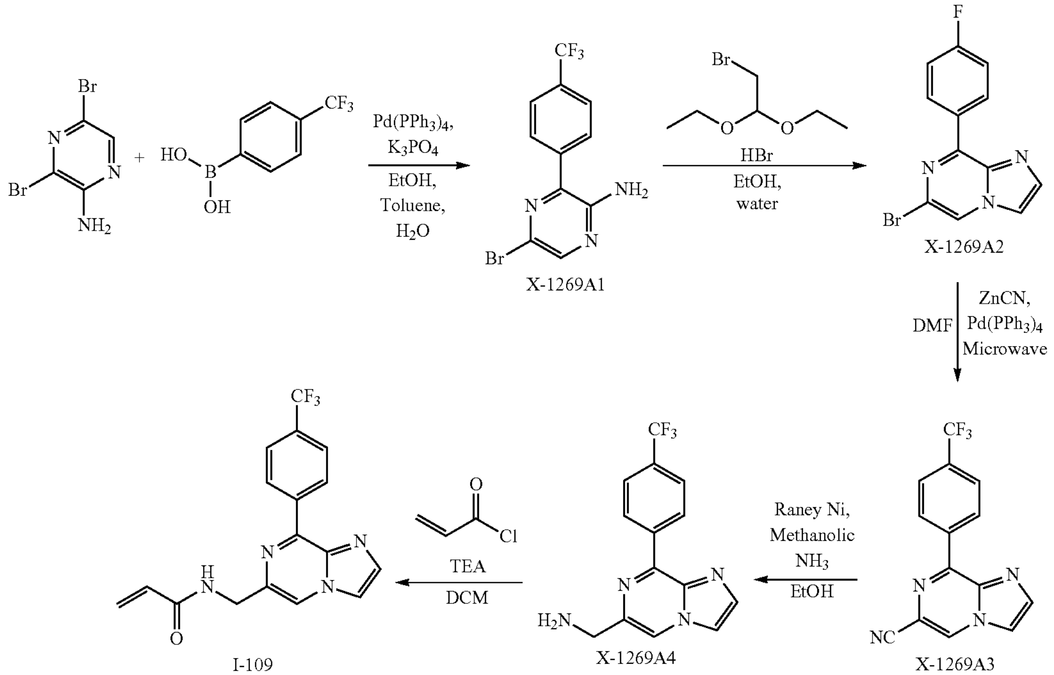

X-1269A1
X-1269A2
X-1269A3
X-1269A4
I-109

5-Bromo-3-(4-(trifluoromethyl)phenyl)pyrazin-2-amine (X-1269A1). To a stirred solution of 3,5-dibromopyrazin-2-amine (1.0 g, 3.95 mmol) in a mixture of toluene-ethanol-water (2:1:1, 20 mL) were added (4-(tert-butyl) phenyl) boronic acid (0.747 g, 3.95 mmol) and an aqueous solution of 2M $K_3PO_4$ (4 mL) at room temperature. The reaction mixture was degassed (by purging with nitrogen) for 30 min followed by the addition of $Pd(PPh_3)_4$ (0.28 g, 0.19 mmol) at the same temperature and the resulting mixture was heated at 100° C. for 2 h. The reaction mixture was cooled to room temperature, diluted with water (100 mL) and was extracted with ethyl acetate (100 mL×3). The combined organic extracts were washed with brine (50 mL), dried over anhydrous $Na_2SO_4$ and concentrated in vacuo. The crude product was combined with an identically prepared two batches and the combined batches were purified by silica gel column chromatography, using ethyl acetate-hexane=0:1→1:0 as gradient, to afford 5-bromo-3-(4-(trifluoromethyl)phenyl)pyrazin-2-amine (X-1269A1) (1.6 g, 64%) as a yellow solid. MS: $[MH]^+$317.9/$[MH+2]^+$319.9.

6-Bromo-8-(4-(trifluoromethyl)phenyl)imidazo[1,2-a]pyrazine (X-1269A2). To a stirred solution of 5-bromo-3-(4-(trifluoromethyl)phenyl)pyrazin-2-amine (X-1269A1) (0.600 g, 1.89 mmol) in ethanol (10 mL) were added 2-bromo-1, 1-diethoxyethane (0.54 mL, 3.79 mmol) and HBr in water (1.4 mL) at room temperature and the resulting mixture was heated at 85° C. for 2 h. After cooling to room temperature, the reaction mixture was quenched with an aqueous solution of saturated $NaHCO_3$ (130 mL) and was extracted with ethyl acetate (50 mL×3). The combined organic extracts were washed with brine (50 mL), dried over anhydrous $Na_2SO_4$ and concentrated in vacuo. The crude product was combined with an identically prepared two batches and the combined batches were purified by silica gel column chromatography, ethyl acetate-hexane=0:1→1:0 as gradient, to afford 6-bromo-8-(4-(trifluoromethyl)phenyl)imidazo[1,2-a]pyrazine (X-1269A2) (1.10 g, 84%) as a brown solid. MS: $[MH]^+$ 341.9/$[MH+2]^+$343.9.

8-(4-(Trifluoromethyl)phenyl)imidazo[1,2-a]pyrazine-6-carbonitrile (X-1269A3). To a stirred solution of 6-bromo-8-(4-(trifluoromethyl)phenyl)imidazo[1,2-a]pyrazine (X-1269A2) (1.00 g, 2.93 mmol) in DMF (10 mL) was added zinc cyanide (0.686 g, 5.86 mmol) at room temperature under nitrogen. The reaction mixture was degassed (by purging nitrogen) for 30 min followed by the addition of $Pd(PPh_3)_4$ (0.710 g, 0.61 mmol) and resulting mixture was heated at 120° C. under microwave irradiation for 30 min. Reaction mixture was cooled to room temperature, slowly poured into water (120 mL) and was extracted with ethyl acetate (100 mL×3). The combined organic extracts were washed with brine (50 mL), dried over anhydrous $Na_2SO_4$ and concentrated in vacuo. The crude product was purified by silica gel column chromatography, using ethyl acetate-hexane=0:1→1:0 as gradient, to afford 8-(4-(trifluoromethyl)phenyl)imidazo[1,2-a]pyrazine-6-carbonitrile (X-1269A3) (0.714 g, 39%) as a yellow solid. MS: $[MH]^+$ 289.1.

(8-(4-(Trifluoromethyl)phenyl)imidazo[1,2-a]pyrazin-6-yl)methanamine (X-1269A4). To a stirred solution of 8-(4-(trifluoromethyl)phenyl)imidazo[1,2-a]pyrazine-6-carbonitrile (X-1269A3) (0.500 g, 1.44 mmol) in MeOH (10 mL) were added Raney Nickel (0.05 g) and ammonia in MeOH (1 mL) at room temperature and the resulting mixture was hydrogenated in Parr Autoclave at 60° C. under 200 psi for 16 h. Reaction mixture was cooled to room temperature, filtered over a celite bed, washed the bed with MeOH (100 mL) and collected filtrates were concentrated under reduced pressure. Obtained crude was acidified (pH~2-3) with an aqueous solution of 1N HCl and was extracted with ethyl acetate (50×2 mL) to remove unwanted organic impurities. The aqueous layer was basified (pH~7-8) with slow addition of an aqueous solution of saturated $NaHCO_3$ (100 mL) and was re-extracted with ethyl acetate (100 mL×2). Collected organic extracts were washed with brine (50 mL), dried over anhydrous Na2SO4 and concentrated in vacuo to give (8-(4-(trifluoromethyl) phenyl) imidazo [1,2-a]pyrazin-6-yl) methanamine (X-1269A4) (0.2 g, 39%) as a white solid. MS: $[MH]^+$ 293.0.

N-((8-(4-(trifluoromethyl)phenyl)imidazo[1,2-a]pyrazin-6-yl)methyl)acrylamide (I-109). To a stirred solution of (8-(4-(trifluoromethyl) phenyl) imidazo [1,2-a]pyrazin-6-yl) methanamine (X-1269A4) (0.200 g, 0.68 mmol) in DCM (5 mL) were added TEA (0.19 mL, 1.36 mmol) followed by acryloyl chloride (0.062 g, 0.68 mmol) at 0° C. under nitrogen and the reaction mixture stirred for 30 min at room temperature. The reaction mixture was slowly poured into water (30 mL) and was extracted with DCM (30 mL×3). The combined organic extracts were washed with brine (30 mL), dried over anhydrous $Na_2SO_4$ and concentrated in vacuo. The resulting crude was purified by reverse phase (C-18) silica gel column chromatography using acetonitrile-0.1% HCOOH in water=0:1→1:0 as gradient, to afford N-((8-(4-(trifluoromethyl)phenyl)imidazo[1,2-a]pyrazin-6-yl)methyl)acrylamide (I-109) (0.030 g, 12%) as a white solid. $^1H$ NMR (400 MHz, DMSO-$d_6$) δ 9.02-9.00 (d, J=8.0 Hz, 2H), 8.83-8.80 (t, J=5.6 Hz, 1H), 8.58 (s, 1H), 8.29 (s, 1H), 7.96-7.94 (d, J=8.4 Hz, 2H), 7.92 (s, 1H), 6.37-6.30 (dd, J=17.2, 10.4 Hz, 1H), 6.18-6.13 (dd, J=17.2, 2.0 Hz, 1H), 5.67-5.64 (dd, J=10.0, 2.0 Hz, 1H), 4.55-4.53 (d, J=6.0 Hz, 2H). MS: $[MH]^+$ 347.0.

Example 1.33. Synthesis of N-((8-(4-fluorophenyl) imidazo[1,2-a]pyrazin-6-yl)methyl)acrylamide (I-110)

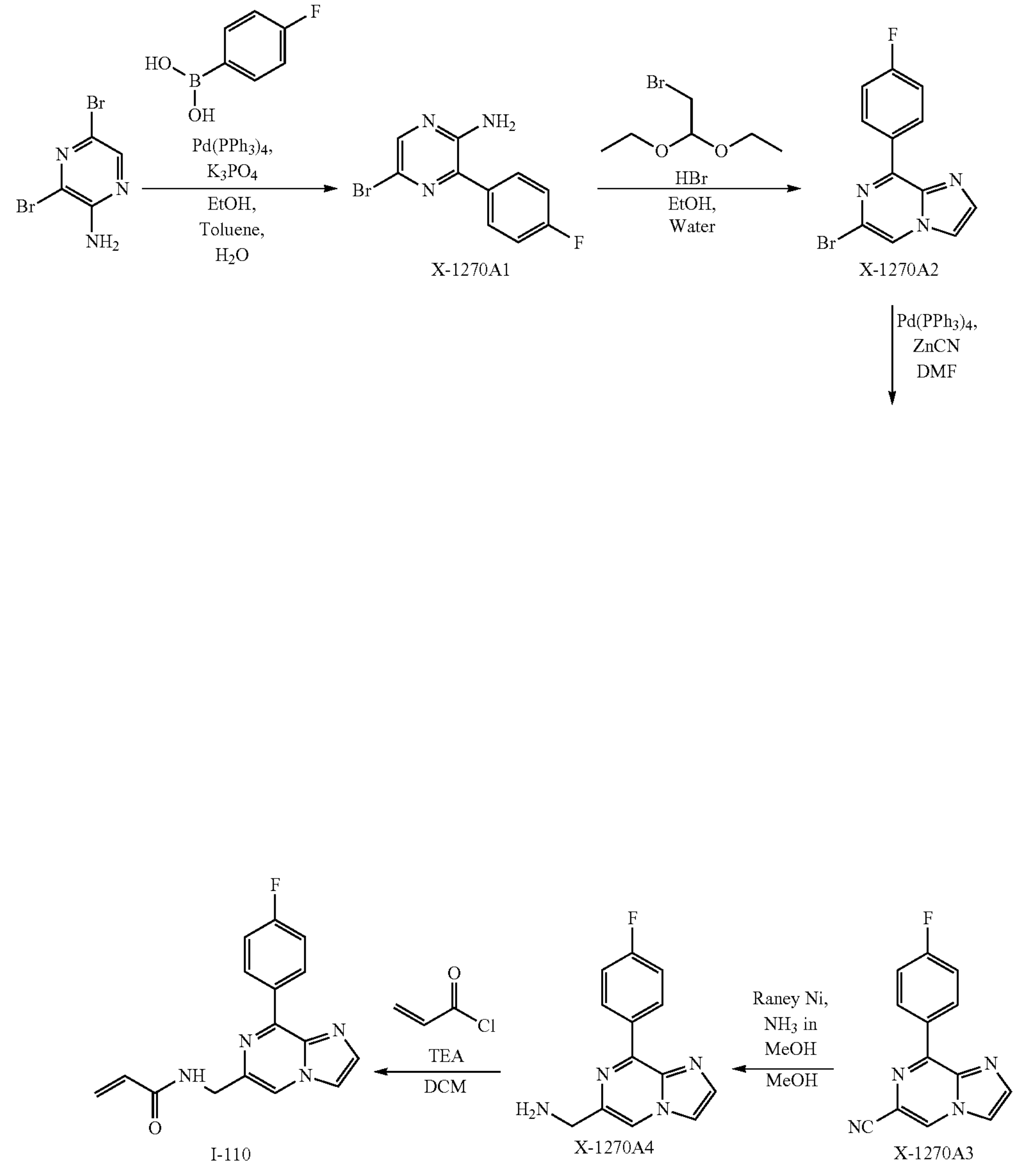

5-Bromo-3-(4-fluorophenyl)pyrazin-2-amine (X-1270A1). To a stirred solution of 3,5-dibromopyrazin-2-amine (1.00 g, 4.0 mmol) in a mixture of toluene-ethanol-water (7:3:1, 10 mL) were added (4-fluorophenyl)boronic acid (0.560 g, 4.00 mmol) and potassium phosphate (2.12 g, 10.0 mmol) sequentially at room temperature under nitrogen. The reaction mixture was degassed (purged with nitrogen) for 20 min followed by the addition of $Pd(PPh_3)_4$ (0.231 g, 0.2 mmol) and the resulting mixture was heated at 100° C. for 16 h. After cooling to room temperature, reaction mixture was diluted with water (100 mL) and was extracted with ethyl acetate (100 mL×3). Combined organic extracts were dried over $Na_2SO_4$ and concentrated under reduce pressure. The crude product was purified by silica gel column chromatography, using ethyl acetate-hexane=0.5:9.5→1:9 as gradient, to afford 5-bromo-3-(4-fluorophenyl)pyrazin-2-amine (X-1270A1) (0.800 g, 75%) as a yellow solid. MS: $[MH]^+$ 268.0/$[MH+2]^+$ 270.0.

6-Bromo-8-(4-fluorophenyl)imidazo[1,2-a]pyrazine (X-1270A2). To a stirred solution of 5-bromo-3-(4-fluorophenyl)pyrazin-2-amine (X-1270A1) (0.800 g, 2.98 mmol) in ethanol (8 mL) were added 2-bromo-1,1-diethoxyethane (1.17 g, 5.90 mmol) and 47% HBr in $H_2O$ (0.549 g, 6.78 mmol) at room temperature and the resulting mixture was heated at 70° C. for 5 h. After cooling to room temperature, the reaction mixture was basified (pH~8-9) with an aqueous solution of saturated $NaHCO_3$ and the resulting precipitate was collected by filtration and washed the residue with cold water. Obtained solid product was dried in vacuo to afford 6-bromo-8-(4-fluorophenyl)imidazo[1,2-a]pyrazine (X-1270A2) [0.800 g, 91% (crude)] as an off-white solid. Obtained crude was taken to the next step without further purification. MS: $[MH]^+$ 291.9.

8-(4-Fluorophenyl)imidazo[1,2-a]pyrazine-6-carbonitrile (X-1270A3). To a stirred solution of 6-Bromo-8-(4-fluorophenyl)imidazo[1,2-a]pyrazine (X-1270A2) [0.800 g (crude), 2.75 mmol] in DMF (8 mL) was added zinc cyanide (0.968 g, 8.27 mmol) at room temperature under nitrogen. The reaction mixture was degassed (purged with nitrogen) for 20 min followed by the addition of $Pd(PPh_3)_4$ (0.637 g, 0.550 mmol) and the resulting suspension was heated at 120° C. for 30 min under microwave irradiation. After cooling to room temperature, reaction mixture was diluted with water (50 mL) and was extracted with ethyl acetate (50 mL×3). Combined organic extracts were dried over $Na_2SO_4$ and concentrated under reduce pressure. Isolated crude was purified by silica gel column chromatography, using ethyl acetate-hexane=0.5:9.5→1:9 as gradient, to afford 8-(4-fluorophenyl)imidazo[1,2-a]pyrazine-6-carbonitrile (X-1270A3) (0.500 g, 76%) as a yellow solid. MS: $[MH]^+$ 239.0.

(8-(4-Fluorophenyl)imidazo[1,2-a]pyrazin-6-yl)methanamine (X-1270A4). To a stirred solution of 8-(4-Fluorophenyl)imidazo[1,2-a]pyrazine-6-carbonitrile (X-1270A3) (0.500 g, 2.10 mmol) in methanol (5 mL) were added raney nickel (0.300 g, 5.11 mmol) and a 7N methanolic ammonia (5 mL) respectively in a Parr Autoclave and the resulting mixture was hydrogenated under 200 psi at 60° C. for 2 h. Reaction mixture was cooled to room temperature, filtered through a celite bed and the collected filtrate was concentrated in vacuo. Obtained product was purified by reverse phase (C-18) silica gel column chromatography, using acetonitrile-water=3:7→4:6 as gradient, to afford (8-(4-fluorophenyl)imidazo[1,2-a]pyrazin-6-yl)methanamine (X-1270A4) (0.200 g, 39%) as an off white solid. MS: $[MH]^+$ 243.1.

N-((8-(4-fluorophenyl)imidazo[1,2-a]pyrazin-6-yl)methyl)acrylamide (I-110). To a stirred solution of (8-(4-fluorophenyl)imidazo[1,2-a]pyrazin-6-yl)methanamine (X-1270A4) (0.200 g, 0.82 mmol) in DCM (3 mL) were added triethylamine (0.417 g, 4.12 mmol) and acryloyl chloride (0.073 g, 0.82 mmol) sequentially at 0° C. under nitrogen and stirred for 10 min. The reaction mixture was diluted with water (50 mL) and was extracted with ethyl acetate (50×2 mL). The combined organic extracts were washed with brine (50 mL), dried over anhydrous $Na_2SO_4$ and concentrated under reduce pressure. The crude product was purified by reverse phase (C-18) silica gel column chromatography, using acetonitrile-0.1% formic acid in water=3:7→5:5 as gradient, to afford N-((8-(4-fluorophenyl)imidazo[1,2-a]pyrazin-6-yl)methyl)acrylamide (I-110) (0.080 g, 33%) as an off white solid. $^1H$ NMR (400 MHz, DMSO-$d_6$) δ (dd, J=8.4, 2.0 Hz, 1H), 8.78 (br. s, 1H), 8.50 (s, 1H), 8.24 (s, 1H), 7.86 (s, 1H), 7.43-7.38 (t, J=8.8 Hz, 2H), 6.37-6.30 (dd, J=16.8, 10.0 Hz, 1H), 6.17-6.13 (dd, J=16.8, 1.2 Hz, 1H), 5.66-5.64 (dd, J=10.0, 1.2 Hz, 1H), 4.52-4.50 (d, J=5.6 Hz, 2H). MS: $[MH]^+$ 297.0

Example 1.34. Synthesis of N-((1-(4-(tert-butyl)phenyl)pyrrolo[1,2-a]pyrazin-3-yl)methyl)acrylamide (I-111)

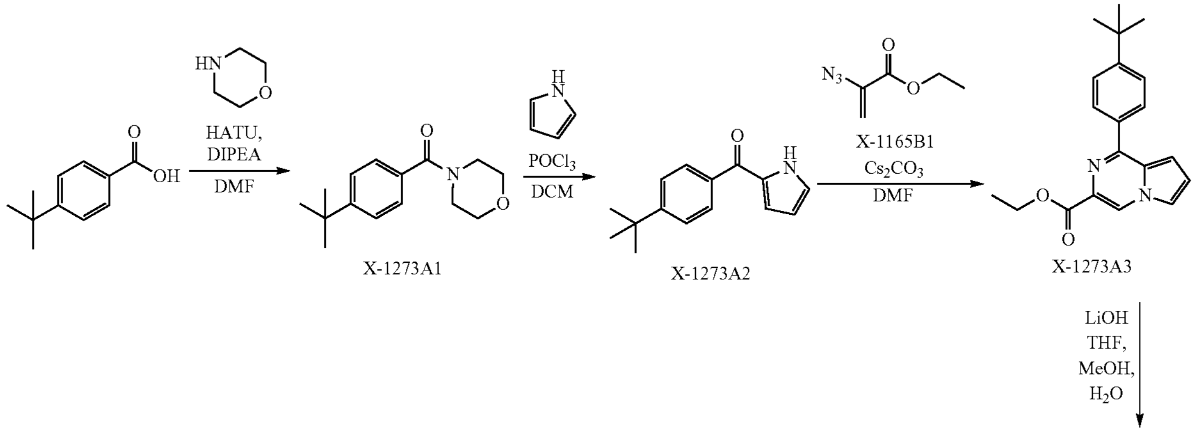

X-1273A1

X-1273A2

X-1273A3

-continued

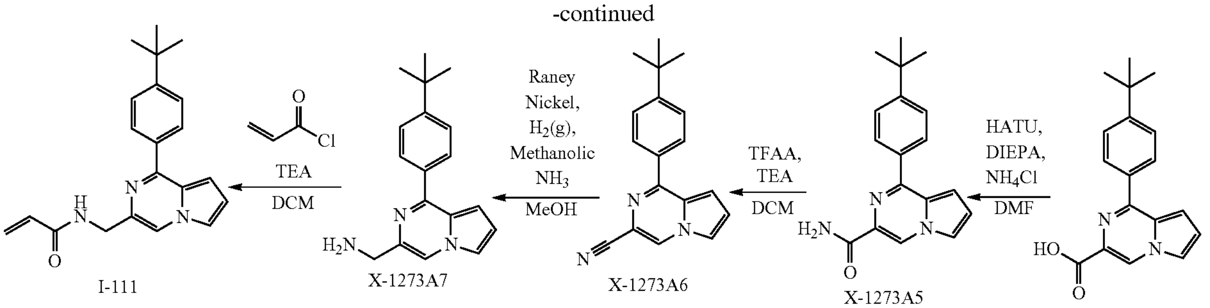

I-111 X-1273A7 X-1273A6 X-1273A5 X-1273A4

(4-(tert-Butyl)phenyl)(morpholino)methanone (X-1273A1). To a stirred solution of 4-(tert-butyl)benzoic acid (5.0 g, 28.07 mmol) in a DMF (50 mL) were added DIPEA (11.0 g, 85.13 mmol) and HATU (21.3 g, 56.02 mmol) sequentially at room temperature under nitrogen. After stirring for 10 min at the same temperature, was added morpholine (3.2 g, 36.74 mmol) and stirring was continued at the same temperature for 16 h. The reaction mixture was slowly poured into ice-water (200 mL) and was extracted with ethyl acetate (100 mL×3). The combined organic extracts were washed with brine (100 mL), dried over anhydrous $Na_2SO_4$ and concentrated in vacuo. The resulting crude was purified by silica gel column chromatography, using ethyl acetate-hexane=0:1→1:0 as gradient, to afford (4-(tert-butyl)phenyl)(morpholino)methanone (X-1273A1) (7.0 g, 99%) as an off white solid. MS: $[MH]^+$ 248.1.

(4-(tert-Butyl)phenyl)(1H-pyrrol-2-yl)methanone (X-1273A2). A mixture of (4-(tert-butyl)phenyl)(morpholino)methanone (X-1273A1) (4.0 g, 16.19 mmol) in $POCl_3$ (7.0 mL) was stirred at room temperature for 16 h. Pyrrole (1.43 g, 21.31 mmol) in DCM (20 mL) was added and stirring was continued for an additional 48 h at the same temperature. The reaction mixture was quenched with slow addition of an aqueous solution of saturated $NaHCO_3$ (130 mL) and was extracted with ethyl acetate (100 mL×3). The combined organic extracts were washed with brine (50 mL), dried over anhydrous $Na_2SO_4$ and concentrated in vacuo. Obtained crude was purified by silica gel column chromatography, using ethyl acetate-hexane=0:1→1:0 as gradient, to afford (4-(tert-butyl)phenyl)(1H-pyrrol-2-yl)methanone (X-1273A2) (2.1 g, 57%) as an off white solid. MS: $[MH]^+$ 228.1.

Ethyl 1-(4-(tert-butyl)phenyl)pyrrolo[1,2-a]pyrazine-3-carboxylate (X-1273A3). To a stirred solution of (4-(tert-butyl)phenyl)(1H-pyrrol-2-yl)methanone (X-1273A2) (2.1 g, 9.25 mmol) in DMF (50 mL) was added cesium carbonate (12.0 g, 36.08 mmol) at room temperature under nitrogen. After 15 min of stirring at the same temperature, was added ethyl 2-azidoacrylate (X-1165B1) (5.0 g, 35.4 mmol) into the reaction mass and stirring was continued for another 3 h. The reaction mixture was slowly poured into ice-water (120 mL) and was extracted with ethyl acetate (100 mL×3). The combined organic extracts were washed with brine (50 mL), dried over anhydrous $Na_2SO_4$ and concentrated in vacuo. Obtained crude mass was purified by silica gel column chromatography, using ethyl acetate-hexane=0:1→1:0 as gradient, to afford ethyl 1-(4-(tert-butyl)phenyl)pyrrolo[1,2-a]pyrazine-3-carboxylate (X-1273A3) (2.4 g, 80%) as an brown oil. MS: $[MH]^+$ 323.6.

1-(4-(tert-Butyl)phenyl)pyrrolo[1,2-a]pyrazine-3-carboxylic acid (X-1273A4). To a stirred solution of ethyl 1-(4-(tert-butyl)phenyl)pyrrolo[1,2-a]pyrazine-3-carboxylate (X-1273A3) (2.4 g, 7.45 mmol) in a mixture of THF-water-MeOH (2:1:1, 20 mL) was added lithium hydroxide monohydrate (1.55 g, 35.75 mmol) at room temperature and resulting reaction mixture was heated at 70° C. for 1 h. Reaction mixture was concentrated under reduced pressure, crude mass was diluted with water (200 mL) and was extracted with ethyl acetate (100×2 mL) to remove unwanted organic impurities. The aqueous layer was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 1-(4-(tert-butyl)phenyl)pyrrolo[1,2-a]pyrazine-3-carboxylic acid (X-1273A4) (2.2 g, 81%) as an off white solid. MS: $[MH]^+$ 295.6.

1-(4-(tert-Butyl)phenyl)pyrrolo[1,2-a]pyrazine-3-carboxamide (X-1273A5). DIPEA (4.8 g, 37.15 mmol) and HATU (21.3 g, 56.02 mmol) were added sequentially to a stirred solution of 1-(4-(tert-butyl)phenyl)pyrrolo[1,2-a]pyrazine-3-carboxylic acid (X-1273A4) (2.2 g, 7.48 mmol) in a DM/IF (50 mL) at room temperature under nitrogen. After 5 min of stirring at the same temperature, was added ammonium chloride (1.1 g, 20.56 mmol) and stirring was continued for 1 h at the same temperature. Reaction mixture was slowly poured in cold water (150 mL) and was extracted with ethyl acetate (100 mL×3). The combined organic extracts were washed with brine (100 mL), dried over anhydrous $Na_2SO_4$ and concentrated in vacuo. The resulting crude was purified by trituration using n-pentane, to afford 1-(4-(tert-butyl)phenyl)pyrrolo[1,2-a]pyrazine-3-carboxamide (X-1273A5) [2.1 g, 95% (crude)] as an off white solid, which was carried forward to next step without further purification. MS: $[MH]^+$ 294.6.

1-(4-(tert-Butyl)phenyl)pyrrolo[1,2-a]pyrazine-3-carbonitrile (X-1273A6). To a stirred solution of 1-(4-(tert-butyl)phenyl)pyrrolo[1,2-a]pyrazine-3-carboxamide (X-1273A5) (1.0 g, 3.40 mmol) in DCM (10 mL) were added trimethylamine (1.4 mL, 10.02 mmol) and TFAA (0.48 mL, 3.40 mmol) at room temperature under nitrogen. After 30 min of stirring at the same temperature, the reaction mixture was slowly poured into water (50 mL) and was extracted with ethyl acetate (50 mL×3). The combined organic extracts were washed with an aqueous solution of saturated $NaHCO_3$ (40 mL×3), brine (50 mL), dried over anhydrous $Na_2SO_4$ and concentrated in vacuo. The crude product was purified by silica gel column chromatography, using ethyl acetate-hexane=1:9→1:0 as gradient, to afford 1-(4-(tert-butyl)phenyl)pyrrolo[1,2-a]pyrazine-3-carbonitrile (X-1273A6) (0.714 g, 78%) as an off white solid. MS: $[MH]^+$ 276.2.

(1-(4-(tert-Butyl)phenyl)pyrrolo[1,2-a]pyrazin-3-yl)methanamine (X-1273A7). To a stirred degassed (purging with nitrogen) solution of 1-(4-(tert-butyl)phenyl)pyrrolo[1, 2-a]pyrazine-3-carbonitrile (X-1273A6) (0.740 g, 1.44 mmol) in MeOH (10 mL) were added Raney Nickel (0.05 g) and ammonia in MeOH (1 mL) at room temperature and the resulting mixture was hydrogenated in Parr Autoclave at 60° C. under 200 psi for 16 h. Reaction mixture was cooled to room temperature, filtered over a celite bed, washed the bed with MeOH (100 mL) and collected filtrates were concentrated under reduced pressure. Obtained crude was acidified (pH~2-3) with an aqueous solution of 1N HCl and was extracted with ethyl acetate (50×2 mL) to remove unwanted organic impurities. The aqueous layer was basified (pH~7-8) with slow addition of an aqueous solution of saturated $NaHCO_3$ (100 mL) and was re-extracted with ethyl acetate (100 mL×2). Collected organic extracts were washed with brine (50 mL), dried over anhydrous $Na_2SO_4$ and concentrated in vacuo to give (1-(4-(tert-butyl)phenyl)pyrrolo[1,2-a]pyrazin-3-yl)methanamine (X-1273A7) (0.300 g, 59%) as an off white solid. MS: $[MH]^+$ 280.6.

N-((1-(4-(tert-butyl)phenyl)pyrrolo[1,2-a]pyrazin-3-yl)methyl)acrylamide (I-111). To a stirred solution of (1-(4-(tert-butyl)phenyl)pyrrolo[1,2-a]pyrazin-3-yl)methanamine (X-1273A7) (0.300 g, 1.07 mmol) in DCM (5 mL) were added TEA (0.45 mL, 3.22 mmol) followed by acryloyl chloride (0.096 g, 1.07 mmol) at 0° C. under nitrogen and the reaction mixture stirred for 30 min at room temperature. The reaction mixture was slowly poured into water (30 mL) and was extracted with DCM (30 mL×3). The combined organic extracts were washed with brine (30 mL), dried over anhydrous $Na_2SO_4$ and concentrated in vacuo. The resulting crude was purified by reverse phase (C-18) silica gel column chromatography using acetonitrile-0.1% HCOOH in water=0:1→1:0 as gradient, to afford N-((1-(4-(tert-butyl)phenyl)pyrrolo[1,2-a]pyrazin-3-yl)methyl)acrylamide (I-111) (0.030 g, 12%) as a white solid. $^1H$ NMR (400 MHz, DMSO-$d_6$) δ 8.66-8.64 (t, J:=: 5.6 Hz, 1H), 8.16 (s, 1H), 7.92-7.88 (m, 3H), 7.58-7.56 (d, J=: 8.0 Hz, 2H), 6.94 (s, 2H), 6.36-6.29 (dd, J=17.2, 10.4 Hz, 1H), 6.16-6.11 (dd, J=17.2, 2.0 Hz, 1H), 5.64-5.61 (dd, J=100, 2.0 Hz, 1H), 4.39-4.38 (d, J=5.6 Hz, 2H), 1.34 (s, 9H) MS: $[MH]^+$ 334.2.

Example 1.35. Synthesis of N-(2-(4-(tert-Butyl)phenyl)-4-(trifluoromethyl)quinolin-7-yl)acrylamide (I-112)

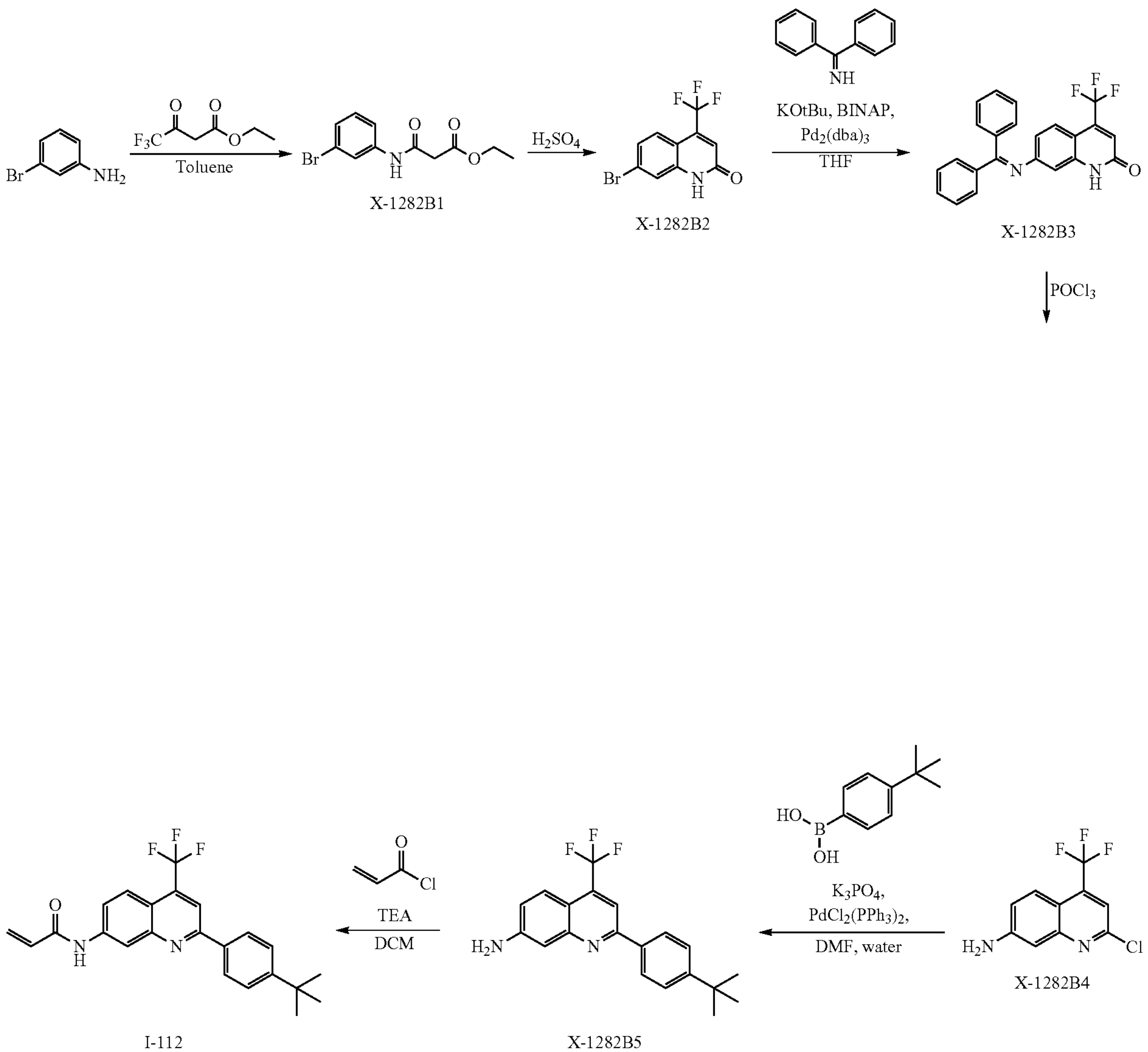

X-1282B1
X-1282B2
X-1282B3
X-1282B4
X-1282B5
I-112

N-(3-bromophenyl)-4,4,4-trifluoro-3-oxobutanamide (X-1282B1). To a stirred solution of 3-bromoaniline (10.00 g, 58.17 mmol) in toluene (100 mL), was added ethyl 4,4,4-trifluoro-3-oxobutanoate (14.98 g, 81.39 mmol) at room temperature and the resulting reaction mixture was stirred at 120° C. for 4 h. The reaction was cooled to room temperature, diluted with water (200 mL) and was extracted with ethyl acetate (200 mL×2). Combined organic extracts were dried over anhydrous $Na_2SO_4$, filtered and concentrated in vacuo. Obtained crude was purified by silica gel column chromatography with using ethyl acetate-hexane=0:1→1:4 to afford a keto-enol mixture of N-(3-bromophenyl)-4,4,4-trifluoro-3-oxobutanamide (5.00 g, 28%) (X-1282B1) as a yellow solid.

7-Bromo-4-(trifluoromethyl)quinolin-2(1H)-one (X-1282B2). A solution of N-(3-bromophenyl)-4,4,4-trifluoro-3-oxobutanamide (5.00 g, 9.70 mmol) (X-1282B1) in conc. $H_2SO_4$ (30 mL) was stirred at 100° C. for 2 h. The reaction mixture was cooled at 0° C. and basified (pH 8-9) with an aqueous solution of saturated $NaHCO_3$ (100 mL) and was extracted with ethyl acetate (100 mL×3). Combined organics was dried over anhydrous $Na_2SO_4$, filtered and concentrated in vacuo. Obtained crude was purified by triturating with using hexane (50 mL), filtered and resulting residue was dried in vacuo to afford 7-bromo-4-(trifluoromethyl)quinolin-2(1H)-one (X-1282B2) (2.40 g, 51%) as a yellow solid. MS: $[MH]^+$ 292.4/$[MH+2]^+$292.4.

7-((Diphenylmethylene)amino)-4-(trifluoromethyl)quinolin-2(1H)-one (X-1282B3). To a stirred solution of 7-bromo-4-(trifluoromethyl)quinolin-2(1H)-one (X-1282B2) (1.250 g, 4.29 mmol) in THE (10 mL) were added diphenylmethanimine (0.777 g, 4.29 mmol), potassium tert-butoxide (1.443 g, 12.88 mmol) at room temperature. The resulting mixture was degassed (with using Nitrogen) for 10 min followed by the addition of $Pd_2(dba)_3$ (0.393 g, 0.42 mmol) and BINAP (0.267 g, 0.42 mmol) and the resulting mixture was stirred at 100° C. for 30 min under microwave irradiation. The reaction was diluted with cold water (50 mL) and was extracted with ethyl acetate (100 mL×2). Combined organics were dried over anhydrous $Na_2SO_4$ and concentrated in vacuo. Obtained crude was mixed with the crude of an identically prepared batch of (1.2 g) and purified together by silica gel column chromatography, using ethyl acetate-hexane=0:1→1:4 as gradient, to afford 7-((diphenylmethylene)amino)-4-(trifluoromethyl)quinolin-2(1H)-one (X-1282B3) (1.50 g, 45%). MS: $[MH]^+$ 393.6.

2-Chloro-4-(trifluoromethyl)quinolin-7-amine (X-1282B4). A solution of 7-((diphenylmethylene)amino)-4-(trifluoromethyl)quinolin-2(1H)-one (X-1282B3) (1.50 g, 3.82 mmol) in $POCl_3$ (10 mL) was stirred at 80° C. for 1 h. Reaction mixture was cooled at 0° C., basified (pH~8-9) with an aqueous solution of saturated $NaHCO_3$ (100 mL) and was extracted with ethyl acetate (200 mL×3). Combined organic extracts were dried over anhydrous $Na_2SO_4$ and concentrated in vacuo. Obtained crude was purified by silica gel column chromatography with using ethyl acetate-hexane=0:1→1:4, to afford 2-chloro-4-(trifluoromethyl)quinolin-7-amine (X-1282B4) (0.500 g, 53%) as a yellow solid. MS: $[MH]^+$ 246.95.

2-(4-(tert-Butyl)phenyl)-4-(trifluoromethyl)quinolin-7-amine (X-1282B5). To a stirred solution of 2-Chloro-4-(trifluoromethyl)quinolin-7-amine (X1282B4) (0.480 g, 1.95 mmol) in a mixture of DMF-water (4:1; 5 mL), were added (4-(tert-butyl)phenyl)boronic acid (0.520 g, 2.92 mmol), tripotassium phosphate (1.035 g, 4.67 mmol) at room temperature under nitrogen. The reaction mixture was degassed (purging with nitrogen) for 20 min followed by addition of $PdCl_2(PPh_3)_2$ (0.137 g, 0.19 mmol) and the resulting mixture was stirred at 110° C. for 1 h. The reaction was diluted with water (50 mL) and was extracted with ethyl acetate (100 mL×2). The combined organic extracts were dried over $Na_2SO_4$, filtered and concentrated in vacuo. The crude was purified by silica gel column chromatography with using ethyl acetate-hexane=0:1→1:4 as gradient, to afford 2-(4-(tert-butyl)phenyl)-4-(trifluoromethyl)quinolin-7-amine (X-1282B5) (0.300 g, 45%) as an off-white solid. MS: $[MH]^+$ 345.61.

N-(2-(4-(tert-butyl)phenyl)-4-(trifluoromethyl)quinolin-7-yl)acrylamide (I-112). To a stirred solution of 2-(4-(tert-butyl)phenyl)-4-(trifluoromethyl)quinolin-7-amine (X1282B5) (0.150 g, 0.43 mmol) in dichloromethane (5 mL) was added triethylamine (0.176 g, 1.74 mmol) at 0° C. After 5 min of stirring at the same temperature, was added acryloyl chloride (0.059 g, 0.65 mmol) and the stirring was continued for 30 min at the same temperature. Reaction was diluted with water (50 mL) and was extracted with dichloromethane (50 mL×3), Combined organic extracts were dried over anhydrous $Na_2SO_4$ and concentrated in vacuo. Obtained crude was purified by neutral alumina column chromatography, using ethyl acetate-hexane=0:1→2:8 as gradient, to afford N-(2-(4-(tert-butyl)phenyl)-4-(trifluoromethyl)quinolin-7-yl)acrylamide (I-112) (0.040 g, 28%) as an off-white solid. $^1H$ NMR (400 MHz, DMSO-$d_6$) δ 10.70 (s, 1H), 8.79-8.78 (d, J=1.6 Hz, 1H), 8.29 (s, 1H), 8.26-8.24 (d, J=8.4 Hz, 2H), 8.08-8.06 (d, J=8.0 Hz, 1H), 7.88-7.85 (dd, J=8.8, 1.6 Hz, 1H), 7.60-7.58 (d, J=8.4 Hz, 2H), 6.56-6.49 (dd, J=17.2, 10.0 Hz, 1H), 6.39-6.35 (d, J=16.8 Hz, 1H), 5.88-5.85 (dd, J=10.0, 1.6 Hz, 1H), 1.34 (s, 9H). MS: $[MH]^+$ 399.7

Example 1.36. Synthesis of 4-Cyclobutylpyrrolo[1,2-a]quinoxaline-7-carboxylic acid (I-113)

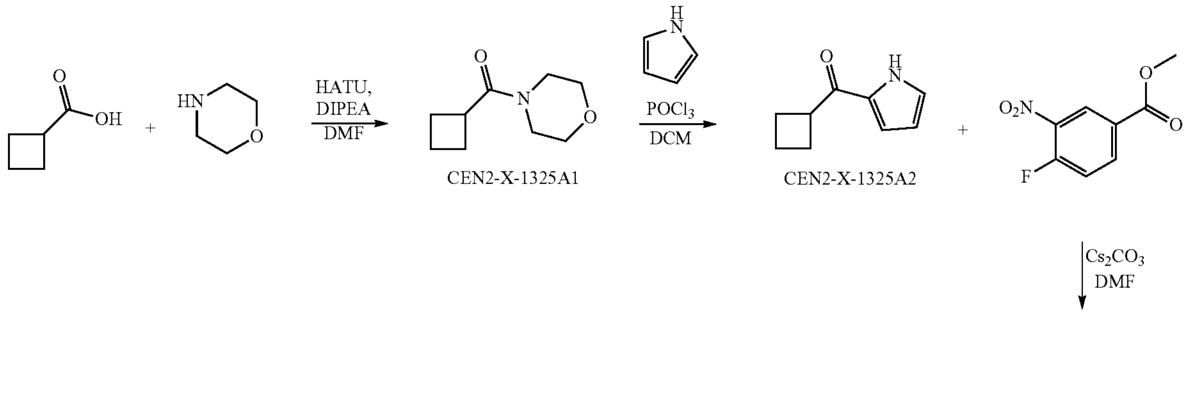

CEN2-X-1325A1
CEN2-X-1325A2

-continued

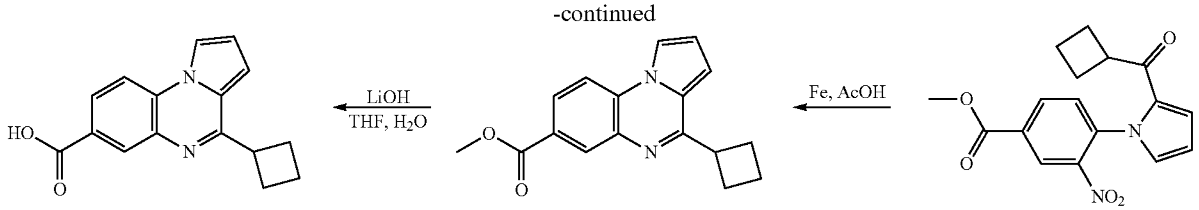

I-113 CEN2-X-1325A4 CEN2-X-1325A3

Cyclobutyl(morpholino)methanone (X-1325A1). Morpholine (2.0 g, 24.0 mmol) was added to a stirred solution of cyclobutanecarboxylic acid (2.0 g, 20.00 mmol), HATU (10.0 g, 40.07 mmol) and DIPEA (7.0 g, 60.07 mmol) in DMF (25 mL) at room temperature under nitrogen and stirred at same temperature for 2 h. The reaction mixture was diluted with water (100 mL) and was extracted with ethyl acetate (100 mL×3). Combined organic extracts were washed with brine (100 mL), dried over anhydrous $Na_2SO_4$ and concentrated under reduced pressure. Obtained crude was purified by silica gel column chromatography, using ethyl acetate-hexane=0:1→1:1 as gradient, to afford cyclobutyl(morpholino)methanone (X-1325A1) (2.0 g, 59%) as an off-white solid. MS: $[MH]^+$ 170.1.

Cyclobutyl(1H-pyrrol-2-yl)methanone (X-1325A2). A solution of cyclobutyl(morpholino)methanone (X-1325A1) (1.00 g, 5.91 mmol) in $POCl_3$ (2.7 g, 17.70 mmol) was stirred at room temperature for 16 h. A solution of 1H-pyrrole (0.600 g, 8.80 mmol) in dichloromethane (4 mL) was added into the reaction solution and stirring was continued at the same temperature for an additional 6 h. Reaction mixture was quenched with water (30 mL), basified (pH~7-8) with an aqueous solution of saturated $NaHCO_3$ and was extracted with ethyl acetate (50 mL×3). Combined organic extracts were dried over anhydrous $Na_2SO_4$ and concentrated under reduced pressure. Obtained crude was purified by silica gel column chromatography, using ethyl acetate-hexane=0:1→1:4 as gradient, to afford cyclobutyl(1H-pyrrol-2-yl)methanone (X-1325A2) [1.2 g, quant (crude)] as an off-white solid, which was carried forward to the next step without further purification. MS: $[MH]^+$ 150.0.

Methyl 4-(2-(cyclobutanecarbonyl)-1H-pyrrol-1-yl)-3-nitrobenzoate (X-1325A3). Methyl 4-fluoro-3-nitrobenzoate (1.7 g, 8.8 mmol) and cesium carbonate (5.0 g, 16.0 mmol) were added to the stirred solution of cyclobutyl(1H-pyrrol-2-yl)methanone (X-1325A2) (1.2 g, 8.0 mmol) in DMF (20 mL) at room temperature under nitrogen and the reaction mixture was heated at 90° C. for 3 h. After cooling to room temperature, reaction mixture was slowly poured in ice water (50 mL) and was extracted with ethyl acetate (50 mL×3). Combined organic extracts were washed with brine (100 mL), dried over anhydrous $Na_2SO_4$ and concentrated under reduced pressure to afford methyl 4-(2-(cyclobutanecarbonyl)-1H-pyrrol-1-yl)-3-nitrobenzoate (X-1325A3) (1.1 g, 41%) as a yellow solid. MS: $[MH]^+$ 329.6.

Methyl 4-cyclobutylpyrrolo[1,2-a]quinoxaline-7-carboxylate (X-1325A4). Iron powder (0.682 g, 12.10 mmol) was added to a stirred solution of methyl 4-(2-(cyclobutanecarbonyl)-1H-pyrrol-1-yl)-3-nitrobenzoate (X-1325A3) (0.800 g, 2.43 mmol) in acetic acid (10 mL) at 0° C. under nitrogen and the resulting mixture was heated at 70° C. for 3 h. After cooling to room temperature, reaction mixture was filtered through celite bed, neutralize (ph~7) by slow addition of an aqueous solution of saturated $NaHCO_3$ and was extracted with ethyl acetate (50 mL×3). Combined organic extracts were dried over anhydrous $Na_2SO_4$ and concentrated under reduced pressure to afford methyl 4-cyclobutylpyrrolo[1,2-a]quinoxaline-7-carboxylate (X-1325A4) [0.500 g, 73% (crude)] as a yellow solid. Isolated product is pure enough to proceed to next step without further purification. MS: $[MH]^+$ 281.6.

4-Cyclobutylpyrrolo[1,2-a]quinoxaline-7-carboxylic acid (I-113). Lithium hydroxide monohydrate (0.090 g, 2.14 mmol) was added to a stirred solution of methyl 4-cyclobutylpyrrolo[1,2-a]quinoxaline-7-carboxylate (X-1325A4) (0.300 g, 1.07 mmol) in a mixture of THE-water (5:2, 7 mL) at room temperature and the resulting mixture was heated at 70° C. for 4 h. After cooling to room temperature, reaction mixture was concentrated under reduce pressure, crude was diluted with water (30 mL), acidified (pH~4-5) with an aqueous solution of 1N HCl solution and was extracted with ethyl acetate (30 mL×3). Combined organic extracts were dried over anhydrous $Na_2SO_4$ and concentrated under reduced pressure. The crude product was purified by triturating with diethyl ether to afford 4-cyclobutylpyrrolo[1,2-a]quinoxaline-7-carboxylic acid (I-113) (0.120 g, 42%) as a white solid. $^1H$ NMR (400 MHz, DMSO-$d_6$) δ 13.12 (br. s, 1H), 8.47-8.46 (d, J=1.6 Hz, 1H), 8.379-8.375 (d, J=1.6 Hz, 1H), 8.34-8.32 (d, J=8.8 Hz, 1H), 8.06-8.03 (dd, J=8.4, 1.6 Hz, 1H), 7.00-6.99 (d, J=3.2 Hz, 1H), 6.94-6.92 (m, 1H), 4.10-4.01 (quin, J=4.4 Hz, 1H), 2.56-2.53 (m, 1H), 2.40-2.34 (m, 2H), 2.17-2.05 (m, 1H), 1.92-1.85 (m, 1H). MS: $[MH]^+$267.5.

Example 1.37. Synthesis of N-(4-(2-Fluoro-4-(trifluoromethyl) phenyl) pyrrolo[1,2-a] quinoxalin-7-yl) acrylamide (I-114)

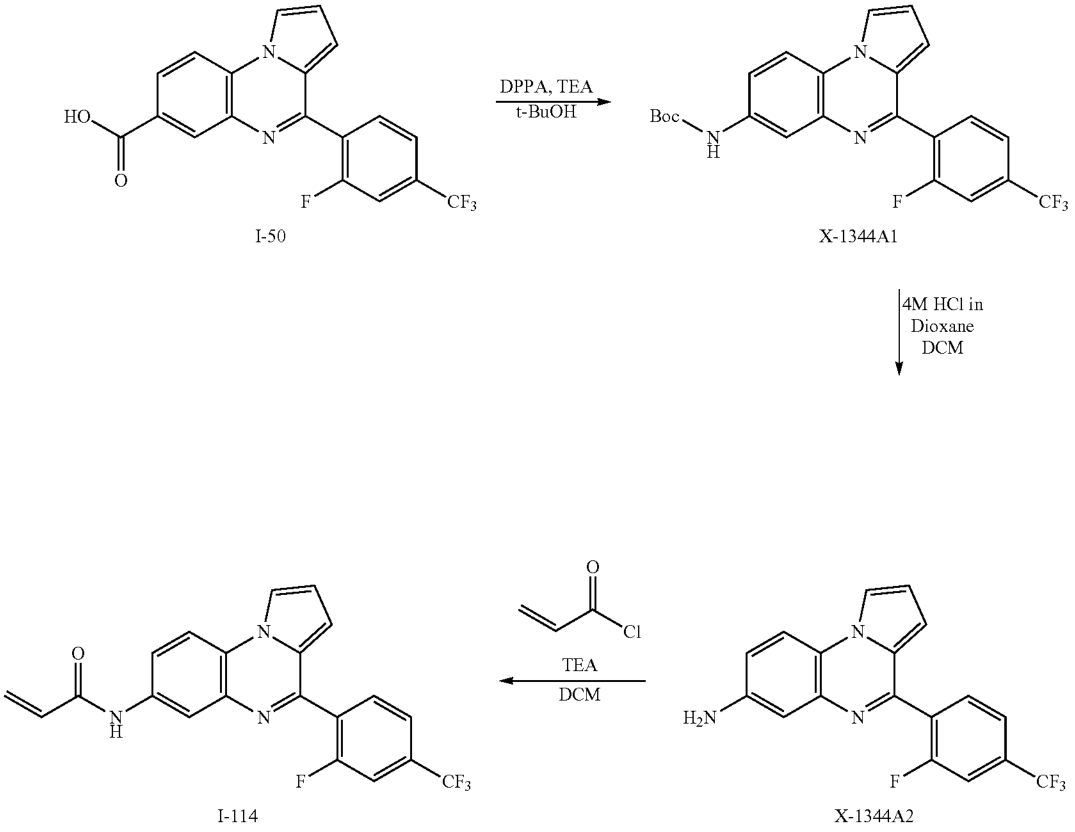

I-50 X-1344A1 X-1344A2 I-114 tert-Butyl (4-(2-fluoro-4-(trifluoromethyl) phenyl) pyrrolo[1,2-a] quinoxalin-7-yl) carbamate (X-1344A1). To a stirred solution of 4-(2-fluoro-4-(trifluoromethyl) phenyl) pyrrolo[1,2-a] quinoxaline-7-carboxylic acid (I-50) (0.400 g, 1.06 mmol) in a tert-butanol (8 mL) were added TEA (0.3 mL, 2.13 mmol) and DPPA (0.441 g, 1.60 mmol) sequentially at room temperature under nitrogen and reaction mixture was heated at 100° C. for 3 h. The reaction mixture was cooled to room temperature, diluted with water (30 mL) and was extracted with ethyl acetate (50 mL×3). Combined organic extracts were washed with brine (30 mL), dried over anhydrous $Na_2SO_4$ and concentrated in vacuo. The crude product was purified by silica gel column chromatography, using ethyl acetate-hexane=0:1→1:0 as gradient, tert-butyl (4-(2-fluoro-4-(trifluoromethyl)phenyl)pyrrolo[1,2-a]quinoxalin-7-yl)carbamate (X-1344A1) (0.419 g, 89%) as a yellow solid. MS: $[MH]^+$ 446.0.

4-(2-Fluoro-4-(trifluoromethyl)phenyl)pyrrolo[1,2-a]quinoxalin-7-amine (X-1344A2). To a stirred solution of tert-butyl (4-(2-fluoro-4-(trifluoromethyl)phenyl)pyrrolo[1,2-a] quinoxalin-7-yl)carbamate (X-1344A1) (0.400 g, 0.89 mmol) in DCM (6 ml) was added 4M HCl in dioxane (6 mL) at 0° C. and stirred at room temperature for 1 h. The reaction mixture was concentrated under reduced pressure and the obtained crude product was purified by trituration using n-pentane, to afford 4-(2-fluoro-4-(trifluoromethyl)phenyl) pyrrolo[1,2-a]quinoxalin-7-amine (X-1344A2) [0.290 g, 93% (crude)] as a yellow solid. MS: $[MH]^+$ 346.0.

N-(4-(2-fluoro-4-(trifluoromethyl) phenyl) pyrrolo[1,2-a] quinoxalin-7-yl) acrylamide (I-114). To a stirred solution of 4-(2-fluoro-4-(trifluoromethyl) phenyl) pyrrolo[1,2-a]quinoxalin-7-amine (X-1344A2) (0.280 g, 0.81 mmol) in)CM (5 mL) were added TEA (0.25 mL, 2.43 mmol) and acryloyl chloride (0.073 g, 0.81 mmole) sequentially at 0° C. under nitrogen and stirred for 30 min at the same temperature. Reaction mixture was slowly poured in water (30 mL) and was extracted with DCM (30 mL×3). Combined organic extracts were washed with brine (30 mL), dried over anhydrous $Na_2SO_4$ and concentrated in vacuo. The crude product was purified by reverse phase (C-18) silica gel column chromatography, using acetonitrile-water=0:1→1:0 as gradient, to afford N-(4-(2-fluoro-4-(trifluoromethyl)phenyl) pyrrolo[1,2-a]quinoxalin-7-yl)acrylamide (I-114) (0.100 g, 30%) as a yellow solid. 1H NMR (400 MHz, DMSO-$d_6$) δ 10.46 (s, 1H), 8.54-8.53 (d, J=1.6 Hz, 1H), 8.36-8.33 (m, 2H), 8.02-7.89 (m, 3H), 7.82-7.70 (d, J=7.6 Hz, 1H), 6.98-6.93 (m 1H), 6.74 (s, 1H), 6.49-6.45 (n, 1H), 6.34-6.29 (dd, J=1.6, 16.8 Hz, 1H), 5.83-5.80 (dd, J=10.0, 2.0 Hz, 1H). MS: $[MH]^+$ 400.0.

Example 1.38. Synthesis of 4-(4-(tert-Butyl)phenyl)-3-fluoropyrrolo[1,2-a]quinoxaline-7-carboxylic acid (I-115)

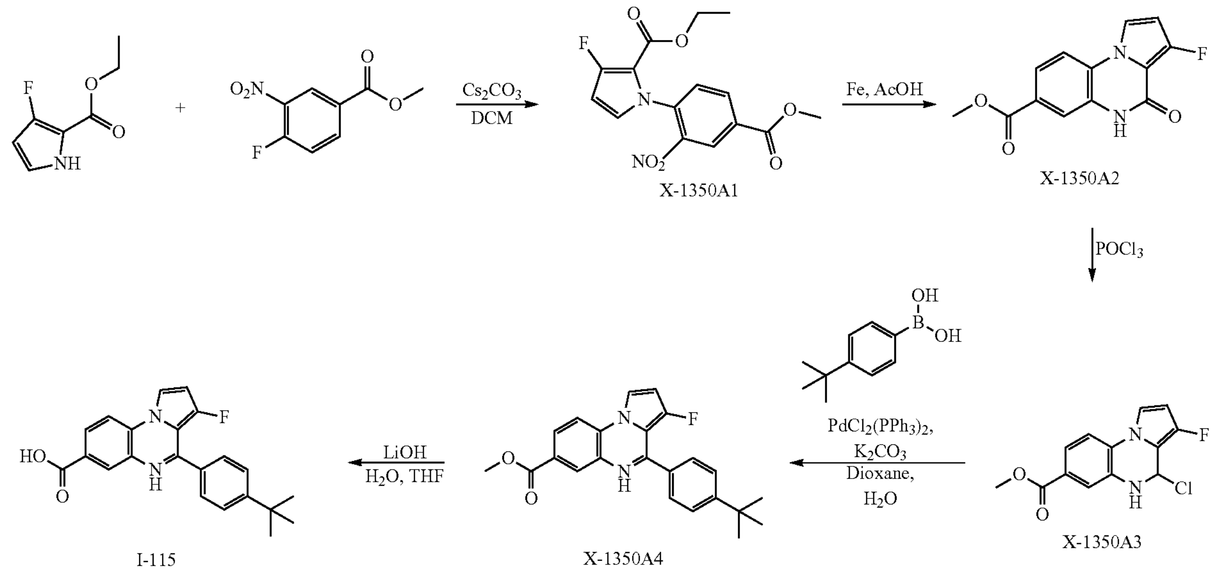

X-1350A1

X-1350A2

X-1350A3

X-1350A4

I-115

Ethyl 3-fluoro-1-(4-(methoxycarbonyl)-2-nitrophenyl)-1H-pyrrole-2-carboxylate (X-1350A1). Cesium carbonate (4.30 g, 14.22 mmol) was added to a stirred solution of methyl 4-fluoro-3-nitrobenzoate (2.40 g, 12.42 mmol) and ethyl 3-fluoro-1H-pyrrole-2-carboxylate (1.50 g, 9.50 mmol) in DMF (5 mL) at room temperature under nitrogen and the resulting mixture was heated at 60° C. for 2 h. After cooling to room temperature, reaction mixture was slowly poured in ice water (100 mL), obtained precipitates were filtered and the residue was washed with water (100 mL). Solid precipitate was, finally, dried in vacuo to afford ethyl 3-fluoro-1-(4-(methoxycarbonyl)-2-nitrophenyl)-1H-pyrrole-2-carboxylate (X-1350A1) [2.50 g, 60% (crude)] as an off-white solid, which was directly used in next step without further purification. MS: $[MH]^+$ 337.6.

Methyl 3-fluoro-4-oxo-4,5-dihydropyrrolo[1,2-a]quinoxaline-7-carboxylate (X-1350A2). Fe powder (3.20 g, 59.5 mmol) was added to a stirred solution of ethyl 3-fluoro-1-(4-(methoxycarbonyl)-2-nitrophenyl)-1H-pyrrole-2-carboxylate (X-1350A1) (2.50 g, 7.40 mmol) in acetic acid (7 mL) at room temperature and the resulting mixture was heated at 60° C. for 1 h. After cooling to room temperature, reaction mixture was filtered through a celite and washed the residue with water (100 mL) to remove acetic acid. Solid residue was dissolved in MeOH-dichloromethane (1:9, 300 mL), stirred for 10 min and was filtered through a celite. Filtrate was concentrated under reduced pressure to afford methyl 3-fluoro-4-oxo-4,5-dihydropyrrolo[1,2-a]quinoxaline-7-carboxylate (X-1350A2) [1.70 g, 88% (crude)] as a grey solid, which was directly used in next step without further purification. MS: $[MH]^+$ 261.5.

Methyl 4-chloro-3-fluoropyrrolo[1,2-a]quinoxaline-7-carboxylate (X-1350A3). A solution of methyl 3-fluoro-4-oxo-4,5-dihydropyrrolo[1,2-a]quinoxaline-7-carboxylate (X-1350A2) (1.70 g, 6.53 mmol) in $POCl_3$ (10 mL) was heated at 100° C. for 2 h. After cooling to room temperature, reaction mixture was slowly poured into ice-water (100 mL) and resulting precipitates were collected by filtration. Solid material was dried in vacuo to give crude mass, which was purified by triturating with ethyl acetate and hexane to afford methyl 4-chloro-3-fluoropyrrolo[1,2-a]quinoxaline-7-carboxylate (X-1350A3) (0.60 g, 33%) as off-white solid. Obtained crude was pure enough to proceed to the next step without further purification. MS: $[MH]^+$ 279.3/$[MH+2]^+$ 281.3.

Methyl 4-(4-(tert-butyl)phenyl)-3-fluoropyrrolo[1,2-a]quinoxaline-7-carboxylate (X-1350A4). Potassium carbonate (0.370 g, 2.67 mmol) was added to a stirred solution of methyl 4-chloro-3-fluoropyrrolo[1,2-a]quinoxaline-7-carboxylate (X-1350A3) (0.250 g, 0.89 mmol) and (4-(tert-butyl)phenyl)boronic acid (0.208 g, 1.16 mmol) in a mixture of 1,4-dioxane-water (5:2, 7 mL) at room temperature and the reaction mixture was degassed (purging with nitrogen) for 30 min. $PdCl_2(PPh_3)_2$ (0.018 g, 0.023 mmol) was added into the reaction mixture at the same temperature and reaction the resulting mixture was heated at 90° C. for 2 h. Reaction mixture was filtered through a celite bed and filtrate was concentrated under reduced pressure. Obtained crude was diluted with water (30 mL) and was extracted with ethyl acetate (30 mL×3). Combined organic extracts were dried over anhydrous $Na_2SO_4$ and concentrated under reduced pressure to give a crude mass, which was purified by silica gel column chromatography, using ethyl acetate-hexane=0:1→1:4 as gradient, to afford methyl 4-(4-(tert-butyl)phenyl)-3-fluoropyrrolo[1,2-a]quinoxaline-7-carboxylate (X-1350A4) (0.300 g, 88%) as an off-white solid. MS: $[MH]^+$ 377.2.

4-(4-(tert-Butyl)phenyl)-3-fluoropyrrolo[1,2-a]quinoxaline-7-carboxylic acid (I-115). Lithium hydroxide monohydrate (0.057 g, 2.39 mmol) was added to a stirred solution of methyl 4-(4-(tert-butyl)phenyl)-3-fluoropyrrolo[1,2-a]quinoxaline-7-carboxylate (X-1350A4) (0.300 g, 0.79 mmol) in a mixture of THF-water (2:1, 6 mL) at room temperature and the reaction mixture was heated at 60° C.

temperature for 2 h. After cooling to room temperature, reaction mixture was diluted with water (30 mL) and was extracted with ethyl acetate (50 mL) to remove unwanted organic impurities. The aqueous part was acidified (pH~3-4) by 1N HCl solution and the resulting precipitates were collected by filtration and dried in vacuo. The crude product was purified by trituration, using n-pentane to afford 4-(4-(tert-butyl)phenyl)-3-fluoropyrrolo[1,2-a]quinoxaline-7-carboxylic acid (I-115) (0.150 g, 52%) as an off-white solid. $^{1}H$ NMR (400 MHz, DMSO-$d_6$) δ 13.20 (s, 1H), 8.53-8.51 (t, J=3.6 Hz, 1H), 8.41-8.39 (d, J=8.8 Hz, 1H), 8.358-8.354 (d, J=1.6 Hz, 1H), 8.10-8.08 (dd, J=8.4, 1.6 Hz, 1H), 7.77-7.75 (m, 2H), 7.58-7.56 (d, J=8.4 Hz, 2H), 6.99-6.98 (d, J=3.2 Hz, 1H), 1.35 (s, 9H). MS: $[MH]^+$ 363.2.

Example 1.39. Synthesis of 4-(6-Azaspiro[2.5]octan-6-yl)imidazo[1,5-a]quinoxaline-7-carboxylic acid (I-116)

(X-1357A1) (1.50 g, 5.70 mmol) in DMSO (15 mL) was added cesium carbonate (5.60 g, 17.11 mmol) at room temperature under nitrogen. The reaction mixture was heated at 110° C. for 2 h. The reaction mixture was cooled to room temperature, diluted with water (100 mL) and was extracted with ethyl acetate (100 mL×3). Combined organic extracts were dried over anhydrous $Na_2SO_4$ and concentrated under reduced pressure to afford methyl 4-oxo-4,5-dihydroimidazo[1,5-a]quinoxaline-7-carboxylate (X-1357A2) [1.40 g, 98% (crude)] as an off-white solid, which was carried forward to the next step without further purification. MS: $[MH]^+$ 244.05.

Methyl 4-chloroimidazo[1,5-a]quinoxaline-7-carboxylate (X-1357A3). To a stirred solution of methyl 4-oxo-4,5-dihydroimidazo[1,5-a]quinoxaline-7-carboxylate (X-1357A2) (1.40 g, 5.76 mmol) in N, N-diethyl aniline (0.8 mL) was added $POCl_3$ (15 mL) at 0° C. and resulting reaction mixture was stirred at 110° C. for 12 h. The reaction mixture was slowly poured into ice-water (100 mL) and was

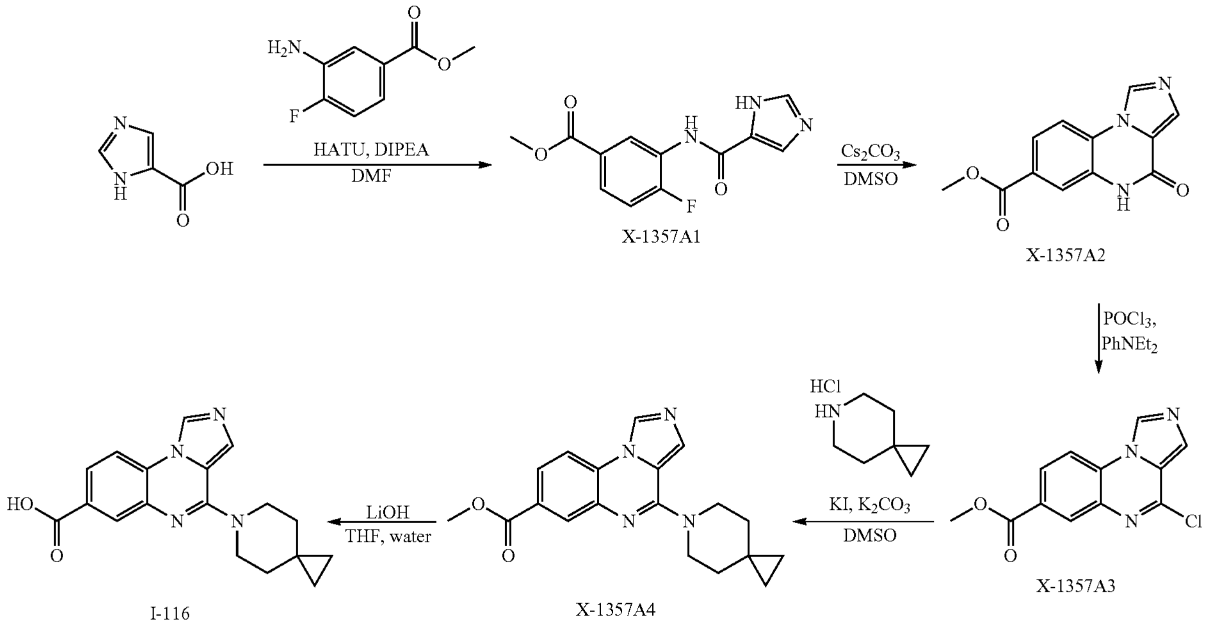

Methyl 4-fluoro-3-(1H-imidazole-5-carboxamido)benzoate (X-1357A1). To a stirred solution of 1H-imidazole-5-carboxylic acid (2.00 g, 17.84 mmol) in DMF (20 mL) were added HATU (10.10 g, 26.77 mmol) and DIPEA (9.1 mL, 53.54 mmol) at room temperature under nitrogen. After 10 min of stirring at the same temperature, was added methyl 3-amino-4-fluorobenzoate (3.01 g, 17.84 mmol) and the resulting mixture was heated at 110° C. for 16 h. The reaction mixture was cooled to room temperature, diluted with water (100 mL) and was extracted with ethyl acetate (100 mL×3). Combined organic extracts were washed with brine (250 mL), dried over anhydrous $Na_2SO_4$ and concentrated under reduced pressure. Obtained crude was purified by silica gel column chromatography, using ethyl acetate-hexane=0:1→1:0 as gradient, to afford methyl 4-fluoro-3-(1H-imidazole-5-carboxamido)benzoate (X-1357A1) (3.00 g, 42%) as an off-white solid. MS: $[MH]^+$ 264.0.

Methyl 4-oxo-4,5-dihydroimidazo[1,5-a]quinoxaline-7-carboxylate (X-1357A2). To a stirred solution of methyl 4-fluoro-3-(1H-imidazole-5-carboxamido)benzoate extracted with ethyl acetate (100 mL×2). Collected organics were dried over anhydrous $Na_2SO_4$ and concentrated under reduced pressure to afford methyl 4-chloroimidazo[1,5-a]quinoxaline-7-carboxylate (X-1357A3)(0.800 g, 36%) as an off white solid. MS: $[MH]^+$ 261.9/$[MH+2]^+$263.9.

Methyl 4-(6-azaspiro[2.5]octan-6-yl)imidazo[1,5-a]quinoxaline-7-carboxylate (X-1357A4). To a stirred solution of methyl 4-chloroimidazo[1,5-a]quinoxaline-7-carboxylate (X-1357A3) (0.200 g, 0.76 mmol) in DMSO (3 mL) were added $K_2CO_3$ (0.264 g, 1.91 mmol), 6-azaspiro[2.5]octane (1.200 g, 0.91 mmol) and KI (0.012 g, 0.07 mmol) at room temperature under nitrogen and the resulting mixture was stirred at 110° C. for 2 h. Reaction was diluted with water (20 mL) and was extracted with ethyl acetate (50 mL×2). Combined organic extracts were dried over anhydrous $Na_2SO_4$ and concentrated under reduced pressure. The crude product was purified by silica gel column chromatography, using ethyl acetate-hexane=0:1→2:3 to afford methyl 4-(6-azaspiro[2.5]octan-6-yl)imidazo[1,5-a]quinoxaline-7-carboxylate (X-1357A4) (0.090 g, 35%) as an off-white solid. MS: $[MH]^+$ 337.1.

4-(6-azaspiro[2.5]octan-6-yl)imidazo[1,5-a]quinoxaline-7-carboxylic acid (I-116). To a stirred solution of methyl 4-(6-azaspiro[2.5]octan-6-yl)imidazo[1,5-a]quinoxaline-7-carboxylate (X-1357A4) (0.090 g, 0.26 mmol) in a mixture of THF-water (4:1; 4.0 mL) was added lithium hydroxide monohydrate (0.033 g, 0.80 mmol) at room temperature and the resulting reaction mixture was heated at 65° C. for 1 h. After cooling to room temperature, the reaction mixture was concentrated under reduced pressure, acidified (pH~2-3) with an aqueous 1N HCl, and the resulting precipitate was collected by filtration. Solid residue was washed with cold water until the pH of the filtrate became neutral (pH~6-7). Obtained solid was triturated with n-pentane and dried under high vacuum to afford 4-(6-azaspiro[2.5]octan-6-yl)imidazo[1,5-a]quinoxaline-7-carboxylic acid (I-116) (0.020 g, 23%) as an off-white solid. $^1$H NMR (400 MHz, DMSO-$d_6$) 9.20 (s, 1H), 8.24-8.22 (d, J=8.4 Hz, 1H), 8.01 (s, 1H), 7.94 (s, 1H), 7.79-7.77 (d, J=8.0 Hz, 1H), 3.90-3.89 (t, J=4.8 Hz, 4H), 1.51-1.48 (t, J=4.8 Hz, 4H), 0.40 (s, 4H). MS: $[MH]^+$ 323.1.

Example 1.40. Synthesis of 4-(4-(tert-Butyl)phenyl)pyrazolo[1,5-a]quinoxaline-7-carboxylic acid (I-117)

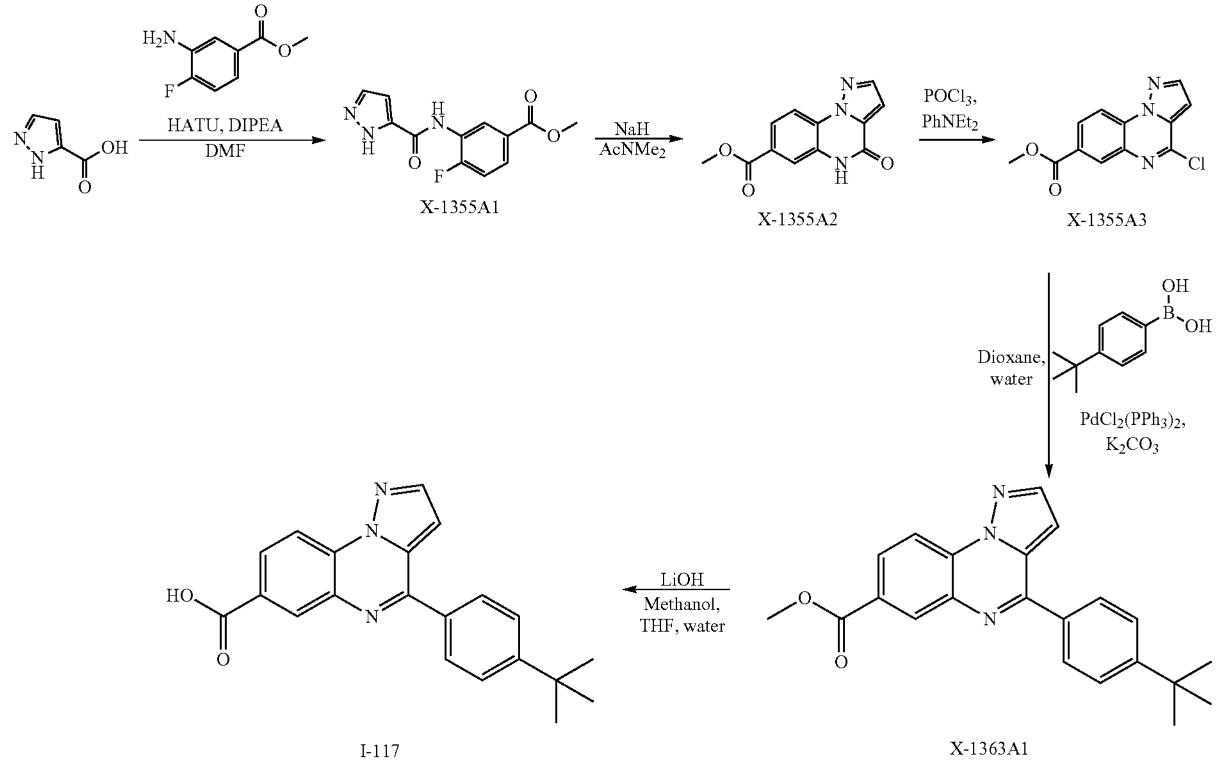

X-1355A1 X-1355A2 X-1355A3

I-117 X-1363A1

Methyl 4-fluoro-3-(1H-pyrazole-5-carboxamido)benzoate (X-1355A1). To a stirred solution of 1H-pyrazole-5-carboxylic acid (1.00 g, 8.92 mmol) in DMF (20 mL) were added HATU (5.00 g, 13.15 mmol), N, N-diisopropylethylamine (2.870 g, 22.24 mmol) at room temperature under nitrogen atmosphere. After 5 min of stirring at the same temperature, was added methyl 3-amino-4-fluorobenzoate (0.600 g, 3.55 mmol) into the reaction solution and reaction was stirred at 100° C. for 16 h. Reaction mixture was cooled to room temperature, crude mass was diluted with ice-water (100 mL) and was extracted with 10% methanol in dichloromethane (200 mL×2). Combined organic extracts were dried over anhydrous $Na_2SO_4$, filtered and concentrated under reduced pressure. This crude was mixed with an identically prepared of (1.0 g) and the combined batches were purified by silica gel column chromatography, using methanol-dichloromethane=0:1→1:9 as gradient, to afford methyl 4-fluoro-3-(1H-pyrazole-5-carboxamido)benzoate (X-1355A1) (1.30 g, 28%) as an off-white solid. MS: $[MH]^+$ 264.0.

Methyl 4-oxo-4,5-dihydropyrazolo[1,5-a]quinoxaline-7-carboxylate (X-1355A2) To a stirred solution of methyl 4-fluoro-3-(1H-pyrazole-5-carboxamido)benzoate (X-1355A1) (1.30 g, 4.94 mmol) in DMF (10 mL) was added cesium carbonate (4.000 g, 12.30 mmol) at room temperature under nitrogen and the resulting mixture was stirred at 110° C. for 6 h. Reaction mixture was cooled to room temperature, crude mass was diluted with ice-water (100 mL) and was extracted with 10% methanol in dichloromethane (200 mL×2). Combined organic extracts were dried over anhydrous $Na_2SO_4$, filtered and concentrated under reduced pressure to get a crude mass, which was purified by silica gel column chromatography, methanol-dichloromethane=0:1→1:9 as a gradient, to afford methyl 4-oxo-4,5-dihydropyrazolo[1,5-a]quinoxaline-7-carboxylate (X-1355A2) (0.500 g, 42%) as a brown solid. MS: $[MH]^+$ 243.9.

Methyl 4-chloropyrazolo[1,5-a]quinoxaline-7-carboxylate (X-1355A3). To a stirred solution of methyl 4-oxo-4,5-dihydropyrazolo[1,5-a]quinoxaline-7-carboxylate (X-1355A2) (0.500 g, 2.05 mmol) in N, N-diethyl aniline (0.50 mL, 3.14 mmol) was added $POCl_3$ (3.5 mL) at 0° C. under nitrogen and the resulting mixture was heated at 110°

C. for 16 h. After cooling to room temperature, reaction mixture was slowly poured into ice-water (50 mL) and the resulting precipitate was collected by filtration. Obtained solid residue was washed with cold water until neutral (pH~6-7) and dried under high vacuum to afford methyl 4-chloropyrazolo[1,5-a]quinoxaline-7-carboxylate (X-1355A3) (0.150 g, 28%) as a yellow solid. MS: $[MH]^+$ 262.0/$[MH+2]^+$264.0.

Methyl 4-(4-(tert-butyl)phenyl)pyrazolo[1,5-a]quinoxaline-7-carboxylate (X-1355A4). To a stirred solution of methyl 4-chloropyrazolo[1,5-a]quinoxaline-7-carboxylate (X-1355A3) (0.140 g, 0.53 mmol) in a mixture of 1,4-dioxane-water (3:1, 3 mL) were added potassium carbonate (0.222 g, 1.60 mmol) and (4-(tert-butyl)phenyl)boronic acid (0.120 g, 0.67 mmol) at room temperature under nitrogen. The reaction mixture was degassed (purging with nitrogen) for 20 min followed by the addition of $PdCl_2$ $(PPh_3)_2$ (0.011 g, 0.01 mmol) and the resulting mixture was heated at 90° C. for 2 h. Reaction mixture was cooled to room temperature, crude mass diluted with water (50 mL) and was extracted with ethyl acetate (50 mL×2). Combined organic extracts were dried over anhydrous $Na_2SO_4$, filtered and concentrated under reduced pressure. Obtained crude was purified by silica gel column chromatography, using ethyl acetate-hexane=0:1→3:7 as gradient, to afford methyl 4-(4-(tert-butyl)phenyl)pyrazolo[1,5-a]quinoxaline-7-carboxylate (X-1355A4) (0.100 g, 52%) as a white solid. MS: $[MH]^+$ 360.2.

4-(4-(tert-Butyl)phenyl)pyrazolo[1,5-a]quinoxaline-7-carboxylic acid (I-117). To a stirred solution of methyl 4-(4-(tert-butyl)phenyl)pyrazolo[1,5-a]quinoxaline-7-carboxylate (X-1355A4) (0.100 g, 0.27 mmol) in a mixture of THE-water (4:1; 3 mL), methanol (0.5 mL) was added lithium hydroxide monohydrate (0.035 g, 0.83 mmol) at room temperature and the resulting reaction mixture was heated at 70° C. for 2 h. After cooling to room temperature, the reaction mixture was acidified (pH~2-3) with an aqueous solution of 1N HCl and the resulting precipitate was collected by filtration. Isolated solid was washed with cold water until the pH became neutral (pH~6-7). Obtained solid was triturated with diethyl ether (20 mL) and the resulting residue was dried under reduced pressure to afford 4-(4-(tert-butyl)phenyl)pyrazolo[1,5-a]quinoxaline-7-carboxylic acid (I-117) (0.050 g, 52%) as an off-white solid. $^1H$ NMR (400 MHz, DMSO-$d_6$) δ 13.35 (br. s, 1H), 8.58 (s, 1H), 8.54-8.52 (d, J=8.8 Hz, 1H), 8.41-8.40 (d, J=2.0 Hz, 1H), 8.28-8.26 (dd, J=8.4, 1.2 Hz, 1H), 8.09-8.07 (d, J=8.4 Hz, 2H), 7.66-7.64 (d, J=8.4 Hz, 2H), 7.36-7.35 (d, J=2.0 Hz, 1H), 1.36 (s, 9H). MS: $[MH]^+$ 346.1.

Example 1.41. Synthesis of 4-(3,3-Dimethylbut-1-yn-1-yl)pyrrolo[1,2-a]quinoxaline-7-carboxylic acid (I-118)

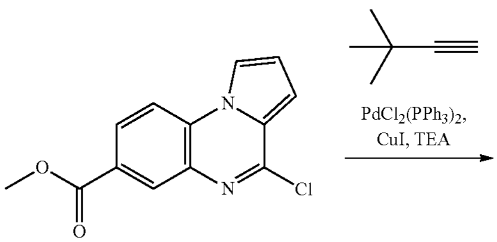

X-1109A3

-continued

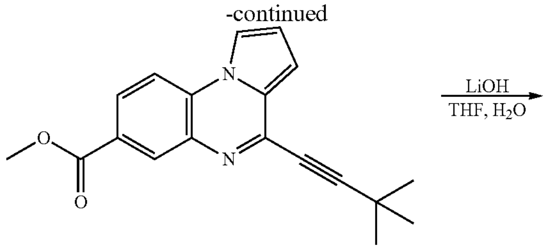

X-1137A1

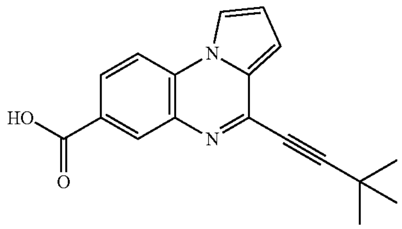

I-118

Methyl 4-(3,3-dimethylbut-1-yn-1-yl)pyrrolo[1,2-a]quinoxaline-7-carboxylate (X-1137A1). To a stirred solution of methyl 4-chloropyrrolo[1,2-a]quinoxaline-7-carboxylate (0.500 g, 8.52 mmol) in TEA (20 mL) were added 3,3-dimethylbut-1-yne (2.09 g, 25.56 mmol) at room temperature under nitrogen. The reaction mixture was degassed (by purging nitrogen) for 30 min followed by the addition of $PdCl_2(PPh_3)_2$ (0.294 g, 0.42 mmol), CuI (0.08 g, 0.42 mmol) sequentially and the resulting mixture was heated at 100° C. for 4 h. The reaction mixture was cooled to room temperature, diluted with water (100 mL) and was extracted with ethyl acetate (100 mL×3). Combined organic extracts were washed with brine (50 mL), dried over anhydrous $Na_2SO_4$ and concentrated in vacuo. The crude product was purified by silica gel column chromatography, using ethyl acetate-hexane=0:1→1:0 as gradient, to afford methyl 4-(3,3-dimethylbut-yn-1-yl)pyrrolo[1,2-a]quinoxaline-7-carboxylate (X-1137A1) (0.350 g, 70%) as an off-white solid. MS: $[MH]^+$ 307.6.

4-(3,3-Dimethylbut-1-yn-1-yl)pyrrolo[1,2-a]quinoxaline-7-carboxylic acid (I-118). To a solution of methyl 4-(3,3-dimethylbut-1-yn-1-yl)pyrrolo[1,2-a]quinoxaline-7-carboxylate (0.350 g, 1.14 mmol) in mixture of THF-water-MeOH (2:1:1, 10 mL) was added lithium hydroxide (0.240 g, 5.72 mmol) at room temperature under nitrogen and the resulting reaction mixture was heated at 70° C. for 2 h. After cooling to room temperature, the reaction mixture was concentrated under reduced pressure, crude mass was diluted with water (20 mL) and was extracted with ethyl acetate (20×2 mL) to remove unwanted organic impurities. The aqueous layer was acidified (pH~2-3) with an aqueous 1N HCl solution and the resulting precipitate was collected by filtration. Obtained residue was washed with cold water until the pH of the filtrate became neutral (pH~6-7) and dried under high vacuum to afford 4-(3,3-dimethylbut-1-yn-1-yl)pyrrolo[1,2-a]quinoxaline-7-carboxylic acid (I-118) (0.200 g, 56%) as a white solid. $^1H$ NMR (400 MHz, DMSO-$d_6$) δ 13.28 (br, 1H), 8.57 (s, 1H), 8.42-8.38 (d, J=8.4 Hz, 1H), 8.35 (s, 1H), 8.13-8.10 (d, J=8.8 Hz, 1H), 7.04 (s, 2H), 1.41 (s, 9H). MS: $[MH]^+$ 293.1.

Example 1.42. Synthesis of N-(4-(4-(tert-butyl)phenyl)pyrrolo[1,2-a]quinoxalin-7-yl)acrylamide (I-119)

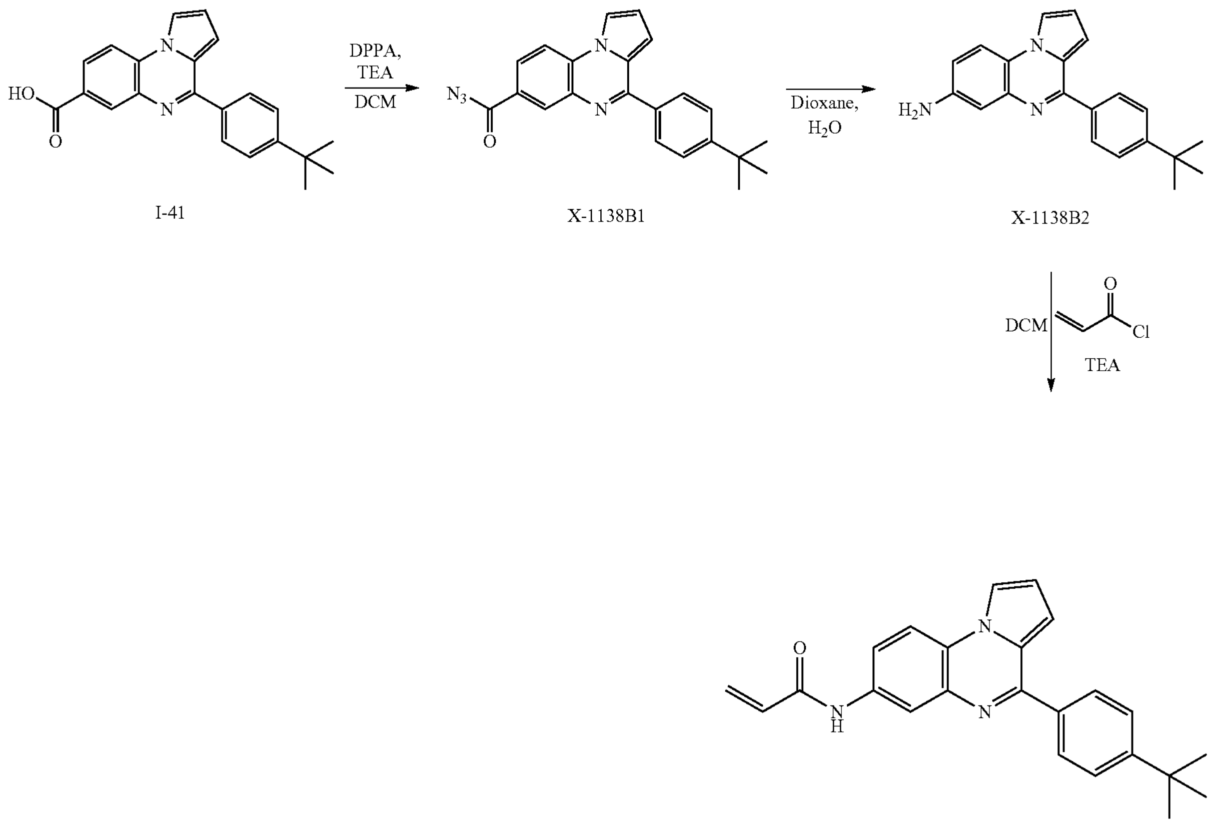

I-41 X-1138B1 X-1138B2 I-119

4-(4-(tert-Butyl)phenyl)pyrrolo[1,2-a]quinoxaline-7-carbonyl azide (X-1138B1). To a stirred solution of 4-(4-(tert-butyl)phenyl)pyrrolo[1,2-a]quinoxaline-7-carboxylic acid (I-41) (1.00 g, 2.90 mmol) in dichloromethane (20 mL) was added triethylamine (0.294 g, 2.90 mmol) at room temperature under nitrogen. After stirring for 5 min at the same temperature, was added was added diphenyl phosphoryl azide (0.799 g, 2.90 mmol) into the resulting solution and stirring was continued for 16 h at room temperature. Reaction mixture was diluted with water (50 mL) and was extracted with dichloromethane (100 mL×2). Combined organic extracts were washed with brine (150 mL), dried over anhydrous $Na_2SO_4$, filtered and concentrated in vacuo to afford 4-(4-(tert-butyl)phenyl)pyrrolo[1,2-a]quinoxaline-7-carbonyl azide (X-1138B1) (0.980 g, 91%) as a yellow solid. MS: $[MH]^+$ 370.2.

4-(4-(tert-Butyl)phenyl)pyrrolo[1,2-a]quinoxalin-7-amine (X-1138B2). A stirred solution of 4-(4-(tert-butyl)phenyl)pyrrolo[1,2-a]quinoxaline-7-carbonyl azide (X-1138B1) (0.980 g, 2.65 mmol) in 1,4-dioxane-water (9:1; 10 mL) was stirred at 100° C. for 2 h. Reaction mixture was concentrated in vacuo to get a crude mass, which was purified by reverse phase (C-18) silica gel column chromatography, using acetonitrile-water=1.5:1→1.8:1 as gradient, to afford 4-(4-(tert-butyl)phenyl)pyrrolo[1,2-a]quinoxalin-7-amine (X-1138B2) (0.100 g, 13%) as a white solid. MS: $[MH]^+$ 316.1.

N-(4-(4-(tert-butyl)phenyl)pyrrolo[1,2-a]quinoxalin-7-yl)acrylamide (I-119). To a stirred solution of 4-(4-(tert-butyl)phenyl)pyrrolo[1,2-a]quinoxalin-7-amine (X-1138B2) (0.090 g, 0.28 mmol) in dichloromethane (5 mL) was added triethylamine (0.043 g, 0.42 mmol) at 0° C. under nitrogen. After 5 min of stirring at the same temperature, was added acryloyl chloride (0.025 g, 0.28 mmol) into the reaction solution and stirred for 15 min at 0° C. Reaction mixture was diluted with water (20 mL) and was extracted with dichloromethane (20 mL×3). Combined organic extracts were washed with brine (30 mL), dried over anhydrous $Na_2SO_4$, filtered and concentrated in vacuo. Obtained crude mass was purified by trituration with n-pentene (50 mL) and diethyl ether (50 mL) to afford N-(4-(4-(tert-butyl)phenyl)pyrrolo[1,2-a]quinoxalin-7-yl)acrylamide (I-119) (0.030 g, 28%) as an off-white solid. $^1H$ NMR (400 MHz, DMSO-$d_6$) δ 10.43 (br. s, 1H), 8.49 (s, 1H), 8.35 (s, 1H), 8.30-8.28 (d, J=8.8 Hz, 1H), 7.97-7.95 (d, J=8.4, 2H), 7.84-7.83 (d, J=7.2 Hz, 1H), 7.62-7.60 (d, J=8.4 Hz, 2H), 7.05-7.04 (d, J=3.2 Hz, 1H), 6.97-6.96 (d, J=2.8 Hz, 1H) 6.53-6.46 (dd, J=16.8, 10.0 Hz, 1H), 6.34-6.30 (d, J=16.0 Hz, 1H), 5.83-5.80 (d, J=10.8 Hz, 1H), 1.37 (s, 9H). MS: $[MH]^+$ 370.1.

Example 1.43. Synthesis of N-(4-(4-(trifluoromethyl)phenyl)pyrrolo[1,2-a]quinoxalin-7-yl)acrylamide (I-120)

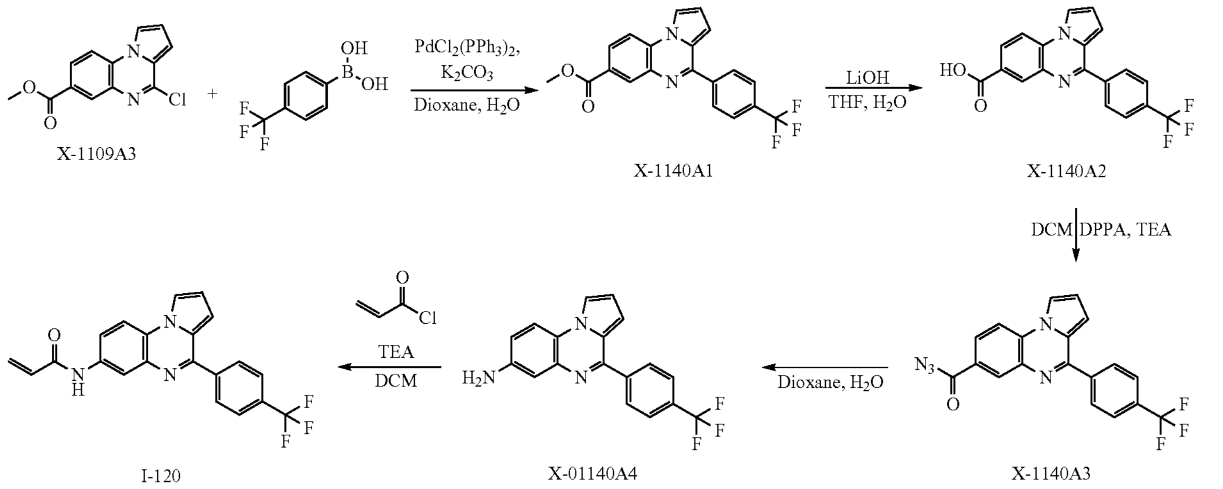

X-1109A3, X-1140A1, X-1140A2, X-1140A3, X-01140A4, I-120

Methyl 4-(4-(trifluoromethyl)phenyl)pyrrolo[1,2-a]quinoxaline-7-carboxylate (X-1140A1). To a stirred solution of methyl 4-chloropyrrolo[1,2-a]quinoxaline-7-carboxylate (X-1109A3) (1.00 g, 3.84 mmol) in a mixture of 1,4-dioxane-water (3:1, 18 mL) was added (4-(trifluoromethyl) phenyl)boronic acid (1.020 g, 5.38 mmol) and potassium carbonate (1.590 g, 11.53 mmol) at room temperature under nitrogen. The reaction mixture was degassed (purging with nitrogen) for 20 min followed by the addition of $PdCl_2(PPh_3)_2$ (0.080 g, 0.11 mmol) and the resulting mixture was heated at 110° C. for 2 h. Reaction mixture was cooled to room temperature, diluted with water (100 mL) and was extracted with ethyl acetate (100 mL×3). Combined organic extracts were washed with brine (100 mL), dried over anhydrous $Na_2SO_4$, filtered and concentrated in vacuo. The crude product was purified by silica gel column chromatography, using ethyl acetate-hexane=0:1→1:9 as gradient, to afford methyl 4-(4-(trifluoromethyl)phenyl)pyrrolo[1,2-a] quinoxaline-7-carboxylate (X-1140A1) (1.20 g, 95%) as yellow solid. MS: $[MH]^+$ 371.6.

4-(4-(Trifluoromethyl)phenyl)pyrrolo[1,2-a]quinoxaline-7-carboxylic acid (X-1140A2). To a stirred solution of methyl 4-(4-(trifluoromethyl)phenyl)pyrrolo[1,2-a]quinoxaline-7-carboxylate (X-1140A1) (1.200 g, 3.24 mmol) in a mixture of THF-water (2:1; 20 mL) was added lithium hydroxide monohydrate (0.272 g, 6.48 mmol) at room temperature and the resulting reaction mixture was heated at 70° C. for 2 h. After cooling to room temperature, the reaction mixture was concentrated under reduced pressure, crude mass was diluted with water (20 mL), acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 4-(4-(trifluoromethyl)phenyl)pyrrolo [1,2-a]quinoxaline-7-carboxylic acid (X-1140A2) (1.10 g, 95%) as an off-white solid. MS: $[MH]^+$ 357.6.

4-(4-(Trifluoromethyl)phenyl)pyrrolo[1,2-a]quinoxaline-7-carbonyl azide (X-1140A3). To a stirred solution of 4-(4-(trifluoromethyl)phenyl)pyrrolo[1,2-a]quinoxaline-7-carboxylic acid (X-1140A2) (0.920 g, 2.58 mmol) in dichloromethane (20 mL) was added triethylamine (0.261 g, 2.58 mmol) at room temperature under nitrogen. After stirring for 5 min at the same temperature, was added was added diphenyl phosphoryl azide (0.710 g, 2.58 mmol) into the resulting solution and stirring was continued for 16 h at room temperature. The reaction mixture was concentrated in vacuo to afford 4-(4-(trifluoromethyl)phenyl)pyrrolo[1,2-a] quinoxaline-7-carbonyl azide (X-1140A3) [0.950 g, 96% (crude)] as an off-white solid, which was carried forward to the next step without further purification. MS: $[MH-N_2]^+$ 354.2.

4-(4-(trifluoromethyl)phenyl)pyrrolo[1,2-a]quinoxalin-7-amine (X-1140A4). A stirred solution of 4-(4-(trifluoromethyl)phenyl)pyrrolo[1,2-a]quinoxaline-7-carbonyl azide (X-1140A3) (0.950 g, 2.66 mmol) in 1,4-dioxane-water (9:1; 10 mL) was stirred at 100° C. for 2 h. Reaction mixture was concentrated in vacuo to get a crude mass, which was purified by reverse phase (C-18) silica gel column chromatography, using acetonitrile-water=0:1→3:2 as gradient, to afford 4-(4-(trifluoromethyl)phenyl)pyrrolo[1,2-a]quinoxalin-7-amine (X-1140A4) (0.210 g, 24%) as an off-white solid. MS: $[MH]^+$ 328.6.

N-(4-(4-(trifluoromethyl)phenyl)pyrrolo[1,2-a]quinoxalin-7-yl)acrylamide (I-120). To a stirred solution of 4-(4-(trifluoromethyl)phenyl)pyrrolo[1,2-a]quinoxalin-7-amine (X-1140A4) (0.200 g, 0.61 mmol) in dichloromethane (5 mL) was added triethylamine (0.092 g, 0.91 mmol) at room temperature under nitrogen. After 5 min of stirring at the same temperature, was added acryloyl chloride (0.055 g, 0.61 mmol) into the reaction solution and stirred for 15 min at 0° C. Reaction mixture was diluted with water (20 mL) and was extracted with dichloromethane (20 mL×3). Combined organic extracts were washed with brine (30 mL), dried over anhydrous $Na_2SO_4$, filtered and concentrated in vacuo. Obtained crude mass was purified by preparative HPLC using 0.1% Formic acid in water-acetonitrile as gradient, to afford N-(4-(4-(trifluoromethyl)phenyl)pyrrolo [1,2-a]quinoxalin-7-yl)acrylamide (I-120) (0.025 g, 6%) as a yellow solid. $^1H$ NMR (400 MHz, DMSO-$d_6$) δ 10.54 (s, 1H) 8.54 (s, 1H), 8.42-8.41 (d, J=1.6 Hz, 1H), 8.34-8-31 (d, J=9.2 Hz, 1H), 8.23-8.21 (d, J=8.0 Hz, 2H), 7.96-7.94 (d, J=8.4 Hz, 2H), 7.88-7.86 (d, J=7.2 Hz, 1H), 7.06-7.05 (d, J=3.6 Hz, 1H), 7.01-6.99 (m, 1H), 6.54-6.48 (dd, J=16.8, 10.0 Hz, 1H) 6.34-6.30 (d, J=16.4 Hz, 1H), 5.82-5.79 (d, J=11.6 Hz, 1H). MS: $[MH]^+$ 382.1.

Example 1.44. Synthesis of 4-((3,3,4,4,4-Pentafluorobutyl)amino)pyrrolo[1,2-a]quinoxaline-7-carboxylic acid (I-121)

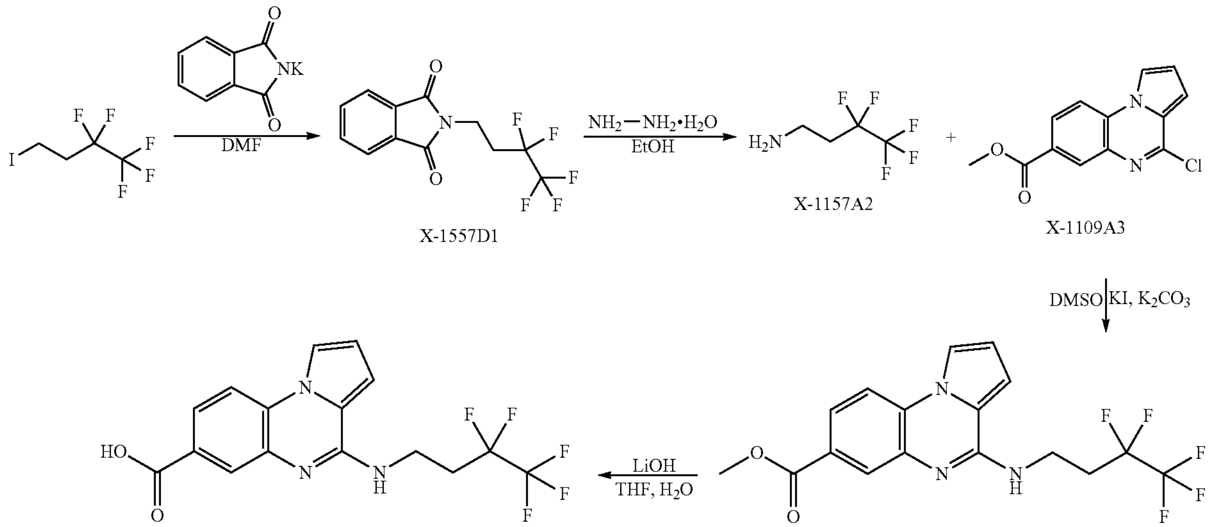

X-1557D1 X-1157A2 X-1109A3 X-1157A3 I-121

2-(3,3,4,4,4-Pentafluorobutyl)isoindoline-1,3-dione (X-1157D1). Potassium 1,3-dioxoisoindolin-2-ide (1.00 g, 5.40 mmol) was added to a stirred solution of 1,1,1,2,2-pentafluoro-4-iodobutane (1.50 g, 5.49 mmol) in DMF (8 mL) at room temperature and the resulting mixture was heated at 80° C. for 1 h. The reaction mixture was cooled to room temperature, crude mass was poured into water (100 mL) and was extracted with ethyl acetate (200 mL×3). Combined organic extracts were dried over anhydrous $Na_2SO_4$ and concentrated under reduced pressure. Obtained crude mass was purified by silica gel column chromatography, using ethyl acetate-hexane=0:1→1:4 as gradient, to afford 2-(3,3,4,4,4-pentafluorobutyl)isoindoline-1,3-dione (X-1157D1) (0.250 g, 70%) as a white solid. MS: [MH] 1294.1.

3,3,4,4,4-Pentafluorobutan-1-amine (X-1157A2). Hydrazine Hydrate (0.047 g, 0.950 mmol) was added to a stirred solution of 2-(3,3,4,4,4-Pentafluorobutyl)isoindoline-1,3-dione (X-1157D1) (0.250 g, 0.87 mmol) in ethanol (2 mL) at room temperature and the resulting mixture was heated at 70° C. for 2 h. Reaction mixture was filter through celite bed, washed with ethyl acetate and the collected filtrates were concentrated under reduced pressure to afford 3,3,4,4,4-pentafluorobutan-1-amine (X-1157D2) [0.230 g, quant. (crude)] as an off-white solid. Obtained crude was pure enough to proceed to the next step without further purification MS: $[MH]^+$ 164.0.

Methyl 4-((3,3,4,4,4-Pentafluorobutyl)amino)pyrrolo[1,2-a]quinoxaline-7-carboxylate (X-1157A3). Potassium carbonate (0.398 g, 2.88 mmol) and potassium iodide (0.032 g, 0.19 mmol) were added sequentially to a stirred solution of methyl 4-chloropyrrolo[1,2-a]quinoxaline-7-carboxylate (X-1109A3) (0.250 g, 0.96 mmol) and 3,3,4,4,4-pentafluorobutan-1-amine (X-1157A2) (0.376 g, 2.3 mmol) in DMSO (3 mL) at room temperature under nitrogen and reaction mixture was heated at 100° C. temperature for 16 h. Reaction mixture was quenched with water (120 mL) and was extracted with ethyl acetate (100 mL×3). Combined organic extracts were dried over anhydrous $Na_2SO_4$ and concentrated under reduced pressure. Obtained crude mass was purified by silica gel column chromatography, using ethyl acetate-hexane=0:1→1:4 as gradient, to afford methyl 4-((4,4,4-trifluorobutyl)amino)pyrrolo[1,2-a]quinoxaline-7-carboxylate (X-1157A3) (0.120 g, 22%) as a yellow solid. MS: $[MH]^+$ 388.0.

4-((3,3,4,4,4-Pentafluorobutyl)amino)pyrrolo[1,2-a]quinoxaline-7-carboxylic acid (I-121). Lithium hydroxide monohydrate (0.038 g, 0.89 mmol) was added to a stirred solution of methyl 4-((3,3,4,4,4-pentafluorobutyl)amino)pyrrolo[1,2-a]quinoxaline-7-carboxylate (X-1157A3) (0.115 g, 0.38 mmol) in a mixture of THF-water (3:1, 4 mL) at room temperature. The reaction mixture was heated at 70° C. for 2 h. The reaction was dilute with water (50 mL), acidified (pH~3-4) with an aqueous solution of 1N HCl and was extracted with ethyl acetate (50 mL×3). Combined organic extracts were dried over anhydrous $Na_2SO_4$ and concentrated under reduced pressure. Obtained crude mass was purified by reverse phase (C-18) silica gel column chromatography, using acetonitrile-water=0:1→1:0 as gradient, to afford 4-((3,3,4,4,4-pentafluorobutyl)amino)pyrrolo[1,2-a]quinoxaline-7-carboxylic acid (I-121) (0.030 g, 26%) as a white solid. $^1H$ NMR (400 MHz, DMSO-$d_6$) δ 12.82 (br, 1H), 8.276-8.272 (d, J=1.6 Hz, 1H), 8.11-8.09 (d, J=8.4 Hz, 1H), 8.023-8.020 (d, J=1.2 Hz, 1H), 7.79-7.74 (m, 2H), 7.049-7.040 (m, 1H), 6.79-6.77 (t, J=3.2 Hz, 1H), 3.84-3.79 (q, J=6.4 Hz, 2H), 2.73-2.63 (m, 2H). MS: $[MH]^+$ 374.0.

Example 1.45. Synthesis of N-(4-(4-(tert-butyl)phenyl)pyrrolo[1,2-a]quinoxalin-7-yl)methanesulfonamide (I-122)

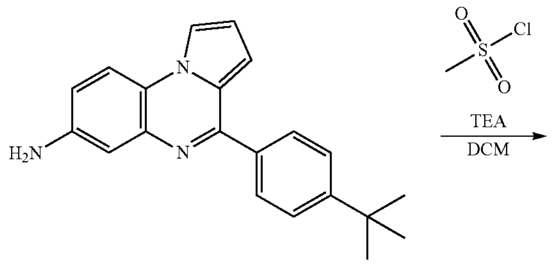

X-1138B2

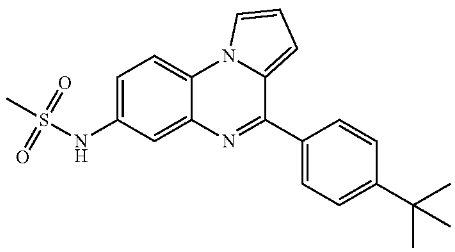

I-122

To a stirred solution of 4-(4-(tert-Butyl)phenyl)pyrrolo[1,2a]quinoxalin-7-amine (X-1138B2) (0.045 g, 0.14 mmol) in dichloromethane (5 mL) were added triethylamine (0.017 g, 0.17 mmol) and methane sulfonyl chloride (0.016 g, 0.14 mmol) at 0° C. under nitrogen and stirred for 15 min at the same temperature. Reaction mixture was diluted with water (20 mL) and was extracted with dichloromethane (20 mL×3). Combined organic extracts were washed with an aqueous solution of 1N HCl (20 mL), dried over anhydrous $Na_2SO_4$ and concentrated in vacuo. The crude product was purified by reverse phase (C-18) silica gel column chromatography, using acetonitrile-water=0:1→2:3 as gradient, to afford N-(4-(4-(tert-butyl)phenyl)pyrrolo[1,2-a]quinoxalin-7-yl)methanesulfonamide (I-122) (0.035 g, 62%) as a yellow solid. $^1H$ NMR (400 MHz, DMSO-$d_6$) δ 9.97 (s, 1H), 8.51 (s, 1H), 8.32-8.30 (d, J=8.8 Hz, 1H), 7.97-7.95 (d, J=8.4 Hz, 2H), 7.76-7.75 (d, J=2.4 Hz, 1H), 7.62-7.60 (d, J=8.0 Hz, 2H), 7.45-7.43 (dd, J=8.0, 2.0 Hz, 1H), 7.06-7.05 (d, J=3.6 Hz, 1H) 6.98-6.97 (m, 1H), 3.05 (s, 3H), 1.37 (s, 9H). MS: $[MH]^+$ 394.2.

Example 1.46. Synthesis of 4-(4-(tert-Butyl)phenyl)-N-(methylsulfonyl)pyrrolo[1,2-a]quinoxaline-7-carboxamide (I-123)

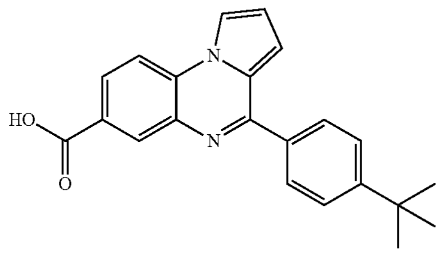

I-41

\+

-continued

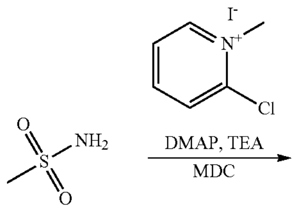

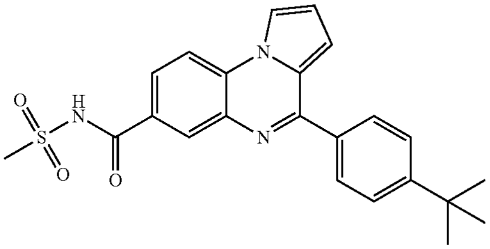

I-123

To a stirred solution of 4-(4-(tert-butyl) phenyl) pyrrolo [1,2-a]quinoxaline-7-carboxylic acid (I-41) (0.100 g, 0.29 mmol) in DCM (3 mL) were added 2-chloro-1-methylpyridin-1-ium iodide (0.089 g, 0.34 mmol), DMAP (0.020 g, 0.014 mmol) and methanesulfonamide (0.055 g, 0.58 mmol) sequentially at room temperature under nitrogen. After 10 min of stirring at the same temperature, was added TEA (0.12 mL, 0.87 mmol) and stirring was continued at room temperature for 2 h. The reaction mixture was slowly poured in water (10 mL) and was extracted with ethyl acetate (10 mL×3). Combined organic extracts were washed with brine (50 mL), dried over anhydrous $Na_2SO_4$ and concentrated in vacuo. The crude product was purified by reverse phase (C-18) silica gel column chromatography using acetonitrile-water=0:1→1:0 as gradient, to afford 4-(4-(tert-butyl)phenyl)-N-(methylsulfonyl)pyrrolo[1,2-a]quinoxaline-7-carboxamide (I-123) (0.060 g, 33%) as a white solid. 1H NMR (400 MHz, DMSO-$d_6$) δ 8.55 (s, 1H), 8.47 (s, 1H), 8.29-8.20 (d, J=8.8 Hz, 1H), 8.16-8.13 (d, J=8.4 Hz, 1H), 8.01-7.97 (d, J=8.0 Hz, 2H), 7.64-7.60 (d, J=8.0 Hz, 2H), 7.08-7.06 (d, J=3.6 Hz, 1H), 6.99 (s, 1H), 2.92 (s, 3H), 1.37 (s, 9H). MS: [MH]+ 422.1.

Example 1.47. Synthesis of 4-(4-(tert-Butyl)phenyl)-N-(cyclopropylsulfonyl)pyrrolo[1,2-a]quinoxaline-7-carboxamide (1-124)

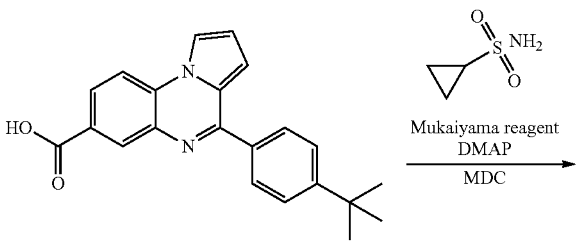

I-41

-continued

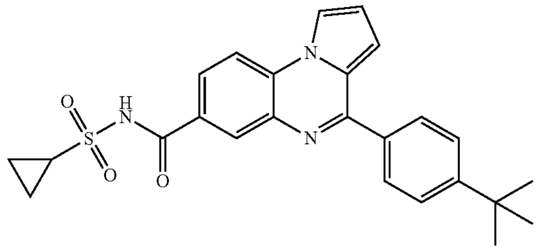

I-124

To a stirred solution of 4-(4-(tert-Butyl)phenyl)pyrrolo[1,2-a]quinoxaline-7-carboxylic acid (I-41) (0.150 g, 0.43 mmol) in dichloromethane (5 mL) were added 4-dimethylaminopyridine (0.003 g, 0.02 mmol), cyclopropane sulfonamide (0.033 g, 0.34 mmol) and Mukaiyama reagent (0.070 g, 0.57 mmol) respectively at room temperature under nitrogen. After stirring for 15 min at the same temperature, was added triethylamine (0.088 g, 0.87 mmol) and the resulting mixture was stirred at room temperature for 1 h. Reaction mixture was diluted with water (20 mL) and was extracted with dichloromethane (25 mL×2). Combined organic extracts were washed with brine (50 mL), dried over anhydrous $Na_2SO_4$, filtered and concentrated in vacuo. The crude product was purified by reverse phase (C-18) silica gel column chromatography, using water-acetonitrile=1:0→7:3 as gradient, to afford 4-(4-(tert-butyl)phenyl)-N-(cyclopropylsulfonyl)pyrrolo[1,2-a]quinoxaline-7-carboxamide (I-124) (0.070 g, 36%) as a yellow solid. $^1$H NMR (400 MHz, DMSO-$d_6$) δ 12.30 (br. s, 1H), 8.65 (s, 1H), 8.53-8.52 (d, J=1.2 Hz, 1H), 8.47-8.44 (d, J=8.8 Hz, 1H), 8.15-8.12 (dd, J=8.8, 1.6 Hz, 1H), 7.99-7.97 (d, J=8.4 Hz, 2H), 7.64-7.61 (d, J=8.4 Hz, 2H), 7.15-7.14 (d, J=3.6 Hz, 1H) 7.07-7.05 (m, 1H), 3.18 (br. s, 1H), 1.37 (s, 9H), 1.18-1.14 (m, 4H). MS: $[MH]^+$ 448.3.

Example 1.48. Synthesis of 4-(Methyl(4,4,4-trifluorobutyl)amino)pyrrolo[1,2-a]quinoxaline-7-carboxylic acid (I-125)

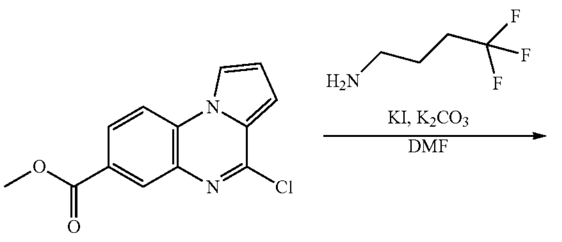

X-1109A3

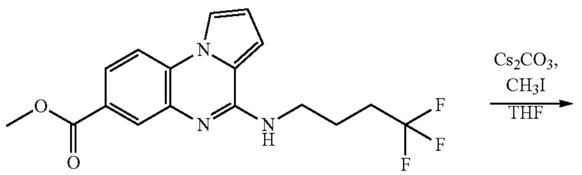

X-1199A1

-continued

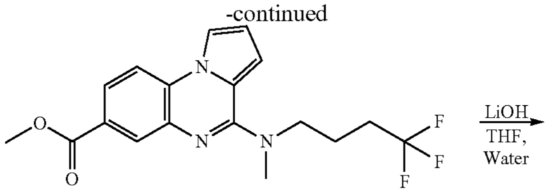

X-1199A2

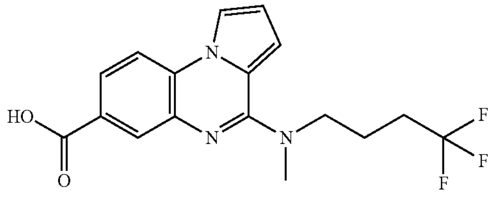

I-125

Methyl 4-((4,4,4-trifluorobutyl) amino) pyrrolo [1,2-a] quinoxaline-7-carboxylate (X-1199A1). To a stirred solution of methyl 4-chloropyrrolo[1,2-a] quinoxaline-7-carboxylate (X-1109A3) (0.500 g, 1.92 mmol) and 4,4,4-trifluorobutan-1-amine hydrochloride (0.376 g, 2.30 mmol) in DMF (5 mL) were added potassium carbonate (0.664 g, 4.80 mmol) and potassium iodide (0.032 g, 0.19 mmol) at room temperature under nitrogen and the resulting mixture was stirred at 90° C. for 16 h. After cooling to room temperature, reaction mixture poured in water (50 mL) and was extracted with ethyl acetate (50 mL×3). Combined organic extracts were washed with brine (50 mL), dried over anhydrous $Na_2SO_4$ and concentrated in vacuo. Obtained crude was purified by silica gel column chromatography, using ethyl acetate-hexane=0:1→1:0 as gradient, to afford methyl 4-((4,4,4-trifluorobutyl) amino)pyrrolo[1,2-a]quinoxaline-7-carboxylate (X-1199A1) (0.930 g, 60%) as an off white solid. MS: $[MH]^+$ 352.1.

Methyl 4-(methyl(4,4,4-trifluorobutyl)amino)pyrrolo[1,2-a]quinoxaline-7-carboxylate (X-1199A2). To a stirred solution of methyl 4-((4,4,4-trifluorobutyl)amino)pyrrolo[1,2-a]quinoxaline-7-carboxylate (X-1199A1) (0.300 g, 0.85 mmol) and $Cs_2CO_3$ (0.833 g, 2.56 mmol) in THF (5 mL) was added $CH_3I$ (0.200 mL, 2.39 mmol) at room temperature under nitrogen and the resulting mixture was stirred at 80° C. for 32 h. After cooling to room temperature, reaction mixture diluted with water (150 mL) and was extracted with ethyl acetate (100 mL×3). Combined organic extracts were washed with brine (50 mL), dried over anhydrous $Na_2SO_4$ and concentrated in vacuo to get a crude mass, which was purified by reverse phase (C-18) silica gel column chromatography, using acetonitrile-water=0:1→1:0 as gradient, to afford a mixture of methyl 4-(methyl(4,4,4-trifluorobutyl) amino)pyrrolo[1,2-a]quinoxaline-7-carboxylate (X-1199A2) and 4-(methyl(4,4,4-trifluorobutyl)amino)pyrrolo[1,2-a]quinoxaline-7-carboxylic acid (I-125) (0.101 g, 32%) as a brown sticky solid. MS: [MH]+ 366.1/1$[MH-14]^+$ 352.1.

4-(Methyl(4,4,4-trifluorobutyl)amino)pyrrolo[1,2-a]quinoxaline-7-carboxylic acid (I-125). Lithium hydroxide monohydrate (0.0.34 g, 0.82 mmol) was added to a stirred solution of a mixture of methyl 4-(methyl(4,4,4-trifluorobutyl)amino)pyrrolo[1,2-a]quinoxaline-7-carboxylate (X-1199A2) (0.100 g, 0.27 mmol) in a mixture of THF-water (2.5:1; 5.0 mL) at room temperature and the resulting reaction mixture was heated at 70° C. for 1 h. After cooling to room temperature, the reaction mixture was concentrated under reduced pressure, diluted with water (30 mL) and extracted with ethyl acetate (30 mL) to remove unwanted organic impurities. The aqueous layer was acidified (pH~2-3) with an aqueous solution of 1N HCl, and the resulting precipitate was collected by filtration. Isolated solid was washed with cold water until the pH of the filtrate became neutral (pH~6-7) and was purified by reverse phase (C-18) silica gel column chromatography, using acetonitrile-water=0:1→1:0 as gradient, to afford 4-(methyl(4,4,4-trifluorobutyl)amino)pyrrolo[1,2-a]quinoxaline-7-carboxylic acid (I-125) (0.070 g, 73%) as an off white solid. $^1$H NMR (400 MHz, DMSO-$d_6$) δ 12.87 (s, 1H), 8.37-8.36 (d, J=1.6 Hz, 1H), 8.12-8.09 (d, J=8.8 Hz, 1H), 7.97-7.96 (d, J=1.6 Hz, 1H), 7.72-7.69 (dd, J=8.4, 1.6 Hz, 1H), 7.10-7.09 (d, J=3.6 Hz, 1H), 6.85-6.83 (t, J=: 3.2 Hz, 1H), 3.84-3.81 (t, J=7.2 Hz, 2H), 3.42 (s, 3H), 2.41-2.34 (m, 2H), 1.94-1.90 (m, 2H), MS: [MH]+352.1.

Example 1.49. Synthesis of 4-(Methyl(3,3,3-trifluoropropyl)amino)pyrrolo[1,2-a]quinoxaline-7-carboxylic acid (I-126)

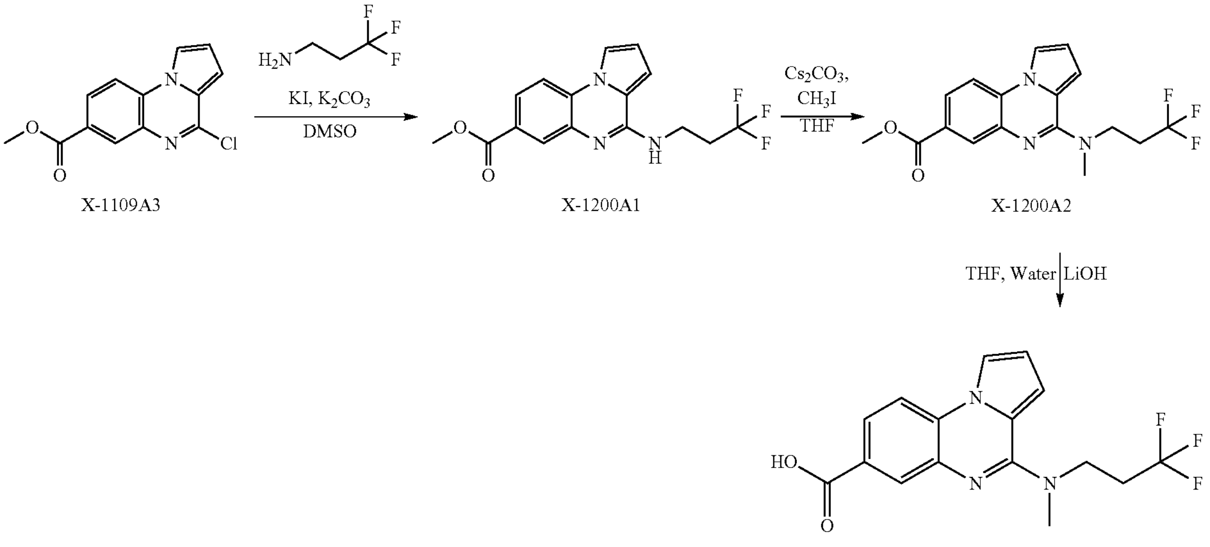

X-1109A3

X-1200A1

X-1200A2

I-126

Methyl 4-((3,3,3-trifluoropropyl)amino)pyrrolo[1,2-a]quinoxaline-7-carboxylate (X-1200A1). To a stirred solution of methyl 4-chloropyrrolo[1,2-a]quinoxaline-7-carboxylate (X-1109A3) (0.650 g, 2.50 mmol) and 3,3,3-trifluoropropan-1-amine hydrochloride (0.370 g, 2.50 mmol) in DMSO (5 mL) were added $K_2CO_3$ (1.03 g, 7.50 mmol) and KI (0.041 g, 0.25 mmol) sequentially at room temperature under nitrogen and the resulting mixture was heated at 100° C. for 16 h. After cooling to room temperature, reaction mixture poured into water (50 mL) and was extracted with ethyl acetate (50 ml×3). Combined organic extracts were washed with brine (50 mL), dried over anhydrous $Na_2SO_4$ and concentrated in vacuo. Obtained crude mass was purified by silica gel column chromatography, using ethyl acetate-hexane=0:1→1:0 as gradient, to afford methyl 4-((3,3,3-trifluoropropyl)amino)pyrrolo[1,2-a]quinoxaline-7-carboxylate (X-1200A1) (0.500 g, 70%) as a yellow solid. MS: $[MH]^+$ 338.06.

Methyl 4-(methyl(3,3,3-trifluoropropyl)amino)pyrrolo[1,2-a]quinoxaline-7-carboxylate (X-1200A2). To a stirred solution of methyl 4-((3,3,3-trifluoropropyl)amino)pyrrolo[1,2-a]quinoxaline-7-carboxylate (X-1200A1) (0.300 g, 0.89 mmol) and $Cs_2CO_3$ (0.867 g, 2.30 mmol) in THF (5 mL) was added $CH_3I$ (1.26 mL, 8.90 mmol) at room temperature under nitrogen and the resulting reaction mixture was heated at 80° C. for 16 h. Reaction mixture was cooled to room temperature, diluted with water (50 mL) and extracted with ethyl acetate (50 mL×3). Combined organic extracts were washed with brine (50 mL), dried over anhydrous $Na_2SO_4$ and concentrated in vacuo. Isolated crude was purified by silica gel column chromatography, using ethyl acetate-hexane=0:1→1:0 as gradient, to afford methyl 4-(methyl(3,3,3-trifluoropropyl)amino)pyrrolo[1,2-a]quinoxaline-7-carboxylate (X-1200A2) (0.120 g, 38%) as yellow solid. MS: $[MH]^+$ 352.0.

4-(Methyl(3,3,3-trifluoropropyl)amino)pyrrolo[1,2-a]quinoxaline-7-carboxylic acid (I-126). To a stirred solution of methyl 4-(methyl(3,3,3-trifluoropropyl)amino)pyrrolo[1,2-a]quinoxaline-7-carboxylate (X-1200A2) (0.120 g, 0.34 mmol) in a mixture of THF-water (3:1; 12 mL) was added lithium hydroxide monohydrate (0.043 g, 1.02 mmol) at room temperature under nitrogen and the resulting reaction mixture was heated at 70° C. for 2 h. After cooling to room temperature, the reaction mixture was concentrated under reduced pressure, diluted with water (30 mL), and was extracted with ethyl acetate (30×2 mL) to remove unwanted organic impurities. The aqueous layer was acidified (pH~2-3) with an aqueous solution of 1N HCl and the resulting precipitate was collected by filtration. Obtained crude was washed with cold water until the pH of the filtrate became neutral (pH~6-7) and dried under high vacuum to afford 4-(methyl(3,3,3-trifluoropropyl)amino)pyrrolo[1,2-a]quinoxaline-7-carboxylic acid (I-126) (0.070 g, 61%) as a yellow solid. $^1$H NMR (400 MHz, DMSO-$d_6$) δ 12.90 (br. s, 1H), 8.39-8.38 (d, J=2.0 Hz, 1H), 8.15-8.13 (d, J=8.8 Hz, 1H), 7.97-7.97 (d, J=1.6 Hz, 1H), 7.74-7.72 (dd, J=8.4, 1.6 Hz, 1H), 7.13-7.12 (d, J=3.6-Hz, 1H), 6.86-6.84 (t, J=4.0 Hz, 1H), 4.00-3.96 (m, 2H), 3.46 (s 3H), 2.72-2.79 (m, 2H). MS: $[MH]^+$ 338.1.

Example 1.50. Synthesis of 4-((4-(Trifluoromethyl) cyclohexyl)oxy)pyrrolo[1,2-a]quinoxaline-7-carboxylic acid (I-127)

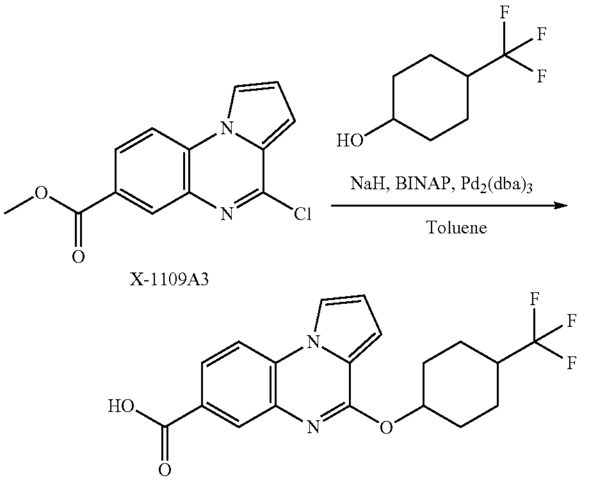

X-1109A3

I-127

To a stirred solution of 4-(trifluoromethyl) cyclohexan-1-ol (0.133 g, 0.79 mmol) in toluene (3 mL) were added NaH (dry powder; 0.038 g, 1.58 mmol) stirred at 0° C. for 20 min under nitrogen. In another vial, BINAP (0.020 g, 0.03 mmol) and $Pd_2(dba)_3$ (0.013 g, 0.07 mmol) were added to a stirred solution of methyl 4-chloropyrrolo[1,2-a] quinoxaline-7-carboxylate (X-1109A3) (0.103 g, 0.39 mmol) in toluene (3 mL) at room temperature and the resulting mixture was degassed (by purging nitrogen) for 20 min. This reaction mixture was added to the previously prepared NaH solution under nitrogen at room temperature and the resulting suspension was heated at 70° C. for 16 h. After cooling to room temperature, reaction mixture poured into water (50 mL) and was extracted with ethyl acetate (75 mL×3). Combined organic extracts were dried over anhydrous $Na_2SO_4$ and concentrated under reduced pressure. The crude product was purified by Prpe. HPLC using acetonitrile-0.05% $NH_3$ in water=0:1→1:0 as gradient, to give a diastereomeric mixture of 4-((4-(trifluoromethyl) cyclohexyl) oxy) pyrrolo [1,2-a]quinoxaline-7-carboxylic acid (I-127) (0.030 g, 7%) as a brown solid. $^1H$ NMR (400 MHz, DMSO-$d_6$) δ 13.09 (br. s, 2H), 8.44 (s, 2H), 8.29-8.27 (d, J=8.4 Hz, 2H), 8.17-8.14 (d, J=10.0 Hz, 2H), 7.95-7.93 (d, J=8.8 Hz, 2H), 6.95-6.87 (m, 4H), 5.60 (br. s, 1H), 5.33-5.29 (m, 1H), 2.32-2.29 (d, J=11.6 Hz, 2H), 2.20-2.17 (d, J=11.6 Hz, 2H), 2.00-1.97 (d, J=11.6 Hz, 2H), 1.81-1.51 (m, 10H). MS: $[MH]^+$ 379.0.

Example 1.51. Synthesis of 4-(6-(Trifluoromethyl)-3-azabicyclo[3.1.0]hexan-3-yl)pyrrolo[1,2-a]quinoxaline-7-carboxylic acid hydrochloride (I-128)

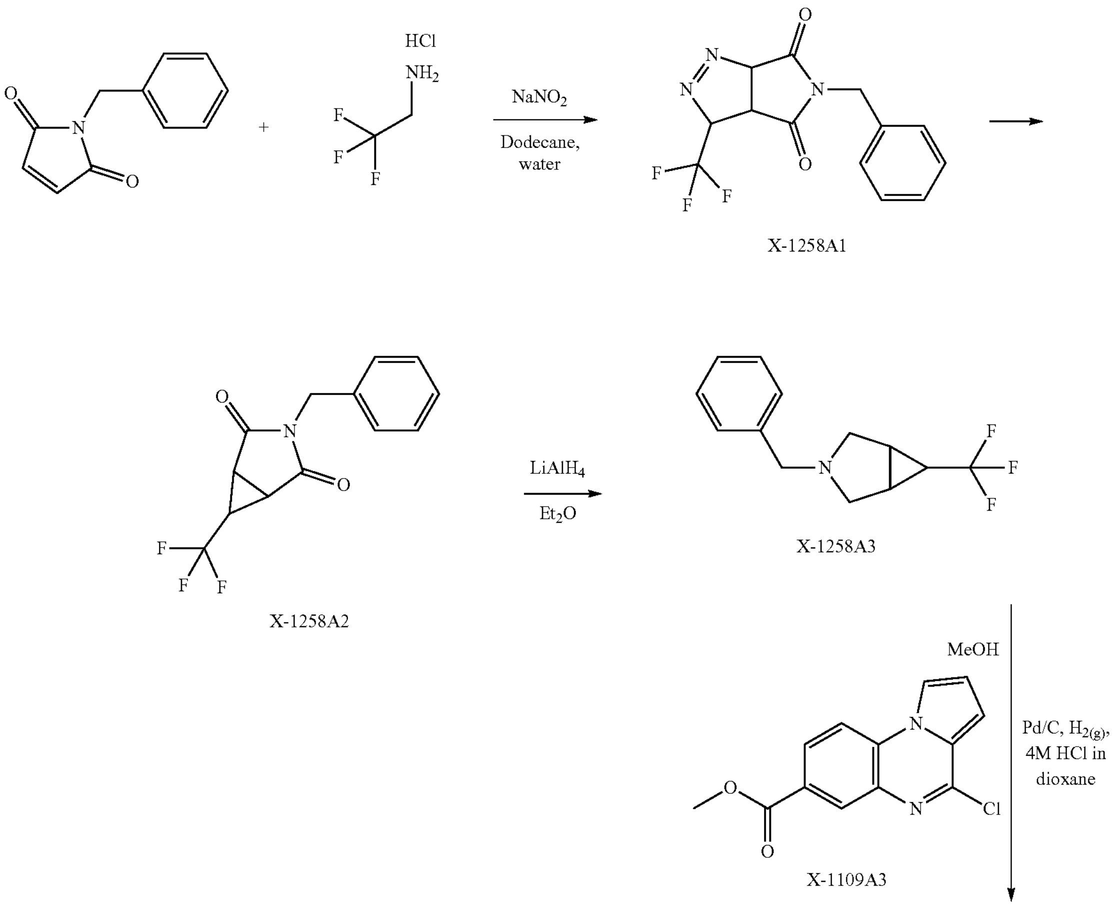

X-1258A1

X-1258A2

X-1258A3

X-1109A3

-continued

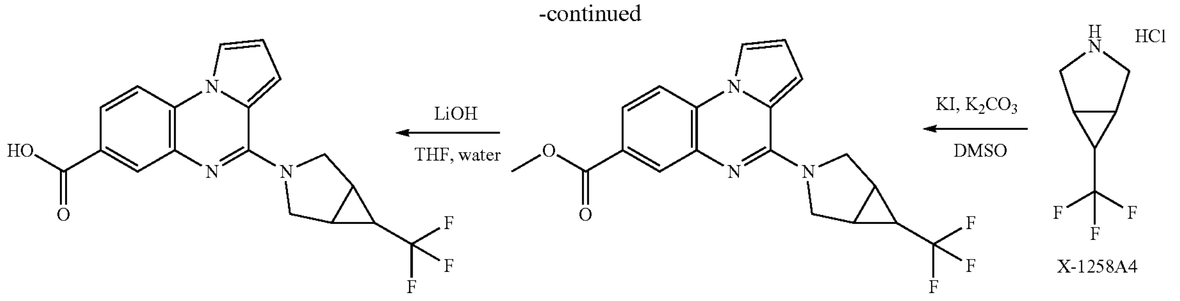

I-128 X-1258A5 X-1258A4

5-Benzyl-3-(trifluoromethyl)-3a, 6a-dihydropyrrolo[3,4-c]pyrazole-4,6(3H,5H)-dione (X-1258A1). A solution of 2,2,2-trifluoroethan-1-amine hydrochloride (7.240 g, 53.38 mmol) in water (15 mL) was slowly added over a period of 30 min, via pressure equalizer dropping funnel, to a stirred mixture of sodium nitrite (3.680 g, 53.34 mmol) in water-dodecane (1:1; 30 mL) at room temperature under nitrogen. Upon addition, the formed $CF_3CHN_2$ was gradually blown off by nitrogen through a drying ($MgSO_4$) trap into a stirred solution of 1-benzyl-1H-pyrrole-2,5-dione (2.000 g, 10.68 mmol) in dichloromethane (30 mL) at room temperature. The reaction mixture was concentrated under reduce pressure to afford 5-benzyl-3-(trifluoromethyl)-3a, 6a-dihydropyrrolo[3,4-c]pyrazole-4,6(3H,5H)-dione (X-1258A1) (3.000 g, 65%) as an off-white solid. $^1H$ NMR (400 MHz, DMSO-$d_6$) δ 7.34-7.23 (m, 5H), 6.42-6.39 (dd, J=2.8, 8.4 Hz, 1H), 6.19-6.17 (m, 1H), 4.54-4.44 (m, 2H), 3.60-3.56 (m, 1H).

3-Benzyl-6-(trifluoromethyl)-3-azabicyclo[3.1.0]hexane-2,4-dione (X-1258A2). 5-Benzyl-3-(trifluoromethyl)-3a, 6a-dihydropyrrolo[3,4-c]pyrazole-4,6(3H,5H)-dione (X1258A1) (3.000 g, 10.10 mmol) was heated in oil bath under vacuum at 150° C. for 7 h. an exothermic evolution of N2 was observed. The formed crude was dissolve in dichloromethane (150 mL), washed with 5% aqueous KMnO4 (100 mL) and washed with water (150 mL). The combined organic extracts were dried over anhydrous $Na_2SO_4$, filtered and concentrated under vacuo. The crude product was purified by silica gel column chromatography, using ethyl acetate:hexane=0:1→5:5 as gradient, to afford 3-benzyl-6-(trifluoromethyl)-3-azabicyclo[3.1.0]hexane-2,4-dione (X-1258A2) (2.800 g, 65%) as a white solid. $^1H$ NMR (400 MHz, $CDCl_3$) δ 7.35-7.30 (m, 5H), 4.54 (s, 2H), 2.81-2.80 (d, J=2.8 Hz, 2H), 2.26-2.23 (m, 1H).

3-Benzyl-6-(trifluoromethyl)-3-azabicyclo[3.1.0]hexane (X-1258A3). To a stirred solution of 3-benzyl-6-(trifluoromethyl)-3-azabicyclo[3.1.0]hexane-2,4-dione (0.800 g, 2.97 mmol) (X-1258A2) in diethyl ether (10 mL) was added lithium aluminum hydride solution (2M in THF; 3.80 mL, 7.43 mmol) at 0° C. under nitrogen and the resulting solution was stirred at 40° C. for 2 h. Reaction was cooled to room temperature and quenched by ice cold water (50 mL) and was extracted with ethyl acetate (50 mL×2). The combined organic extracts were dried over anhydrous $Na_2SO_4$, filtered and concentrated under vacuo, to afford 3-benzyl-6-(trifluoromethyl)-3-azabicyclo[3.1.0]hexane (X-1258A3) (0.600 g, 84%) as a yellow oil. $^1H$ NMR (400 MHz, $CDCl_3$) δ 7.38-7.25 (m, 5H), 3.61 (s, 2H), 3.04-3.02 (d, J=8.8 Hz, 2H), 2.40-2.38 (d, J=8.8 Hz, 2H), 2.04-2.03 (m, 1H), 1.77 (s, 1H).

6-(Trifluoromethyl)-3-azabicyclo[3.1.0]hexane hydrochloride (X-1258A4). To a stirred solution of 3-benzyl-6-(trifluoromethyl)-3-azabicyclo[3.1.0]hexane (X-1258A3) (0.280 g, 1.16 mmol) in methanol (10 mL), was added 10% Pd/C (0.100 g) at room temperature. The resulting reaction mixture was hydrogenated under balloon pressure at room temperature for 3 h. The reaction mixture was filtered through celite bed; filtrate was concentrated under vacuo. To this resulting crude dissolve in dichloromethane (7 mL), was added (4M HCl in 1, 4-Dioxane) (0.5 mL) at 0° C. and stirred at 0° C. to room temperature for 10 min. The reaction mixture was concentrated under vacuo, to afford 6-(trifluoromethyl)-3-azabicyclo[3.1.0]hexane hydrochloride (X-1258 A4) (0.150 g, 86%) as a white solid. MS: $[MH]^+$ 152.06.

Methyl 4-(6-(trifluoromethyl)-3-azabicyclo[3.1.0]hexan-3-yl)pyrrolo[1,2-a]quinoxaline-7-carboxylate (X-1258A5). To a stirred solution of 6-(trifluoromethyl)-3-azabicyclo[3.1.0]hexane hydrochloride (X-1258A4) (0.174 g, 0.66 mmol) in DMSO (8 mL), were added methyl 4-chloropyrrolo[1,2-a]quinoxaline-7-carboxylate (X-1109A3) (0.150 g, 0.80 mmol), potassium carbonate (0.278 g, 2.01 mmol), potassium iodide (0.033 g, 0.20 mmol) under nitrogen atmosphere at room temperature. The reaction was heated at 100° C. for 2 h. The reaction was diluted with water (50 mL) and was extracted with ethyl acetate (50 mL×2), the combined organic extracts were dried over anhydrous $Na_2SO_4$, filtered and concentrated under reduced pressure. The crude was purified by silica gel column chromatography, using ethyl acetate:hexane=0:1→2:8 as gradient to afford methyl 4-(6-(trifluoromethyl)-3-azabicyclo[3.1.0]hexan-3-yl)pyrrolo[1,2-a]quinoxaline-7-carboxylate (X-1258A5) (0.090 g, 25%) as an off-white solid. MS: $[MH]^+$ 376.12.

4-(6-(Trifluoromethyl)-3-azabicyclo[3.1.0]hexan-3-yl)pyrrolo[1,2-a]quinoxaline-7-carboxylic acid hydrochloride (I-128). To a stirred solution of methyl4-(6-(trifluoromethyl)-3-azabicyclo[3.1.0]hexan-3-yl)pyrrolo[1,2-a]quinoxaline-7-carboxylate (X-1258A5) (0.070 g, 0.18 mmol) in a mixture of THE-water (3:1; 5 mL), was added lithium hydroxide monohydrate (0.023 g, 0.55 mmol) at room temperature. The reaction was heated at 80° C. for 2 h. The reaction was allowed to stirred at room temperature and concentrated under vacuo. The reaction mixture was acidified (pH~2-3) with aqueous 1N HCl, and the resulting precipitate was collected by filtration, washed with cold water until the pH of the filtrate became neutral (pH~6-7). The obtained solid was triturated with hexane (15 mL) and dried under vacuo, to afford 4-(6-(trifluoromethyl)-3-azabicyclo[3.1.0]hexan-3-yl)pyrrolo[1,2-a]quinoxaline-7-carboxylic acid hydrochloride (I-128) (0.040 g, 46%) as an off-white solid. $^1H$ NMR (400 MHz, DMSO-$d_6$) δ 13.35 (br. s, 1H), 11.69 (br. s, 1H), 8.68 (s, 1H), 8.53 (br. s, 1H), 8.31 (s, 1H), 7.91 (s, 1H), 7.64 (s, 1H), 7.05 (s, 1H), 4.37-4.35 (d, J=8.0 Hz, 2H), 4.12 (br. s, 2H), 2.49 (s, 2H), 2.06 (s, 1H). MS: $[MH]^+$ 3362.12.

Example 1.52. Synthesis of 4-(5-Methylpyrimidin-2-yl)pyrrolo[1,2-a]quinoxaline-7-carboxylic acid (I-129)

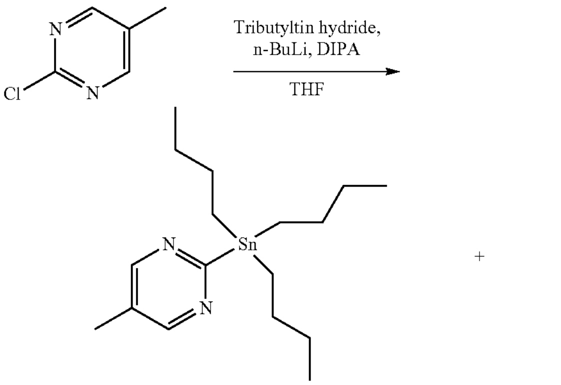

X-1278A1

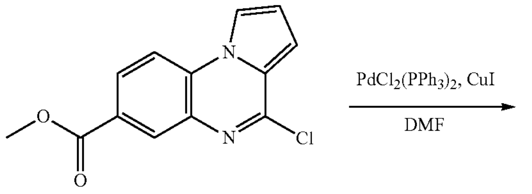

X-1109A3

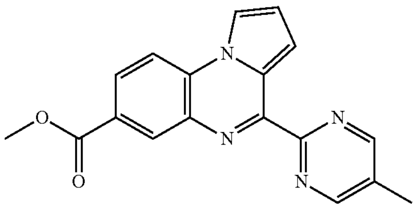

1278A2

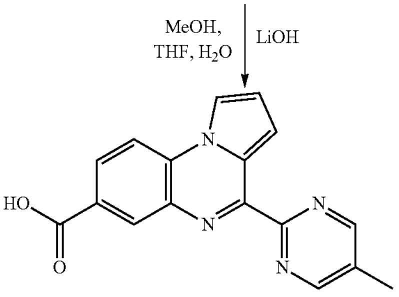

I-129

5-Methyl-2-(tributylstannyl)pyrimidine (X-1278A1). To a stirred solution of DIPA (1.50 g, 12.1 mmol) in THF (25 mL) was added n-BuLi (1.6M in hexane; 19.3 mL, 12.1 mmol) at 0° C. under nitrogen followed by the addition of 2-chloro-5-methylpyrimidine (1.20 g, 9.37 mmol). After stirring for 30 min at the same temperature, was added tributyltin hydride (3.20 g, 11.20 mmol) under nitrogen and the reaction mixture was stirred at room temperature for 2 h. Reaction mixture was quenched with an aqueous solution of saturated $NH_4Cl$ (100 mL) and was extracted with ethyl acetate (50 mL×3). Combined organic extracts were dried over anhydrous $Na_2SO_4$ and concentrated under reduced pressure. The crude product was purified by neutral alumina column chromatography, using ethyl acetate-hexane=0:1→3:7 as gradient, to afford 5-methyl-2-(tributylstannyl)pyrimidine (X-1278A1) (1.10 g, 30%) as a yellow oil. MS: $[MH]^+$ 385.1.

Methyl 4-(5-methylpyrimidin-2-yl)pyrrolo[1,2-a]quinoxaline-7-carboxylate (X-1278A2). 5-methyl-2-(tributylstannyl)pyrimidine (X-1278A1) (0.443 g, 1.73 mmol) was added to a stirred solution of methyl 4-chloropyrrolo[1,2-a]quinoxaline-7-carboxylate (X-1109A3) (0.300 g, 1.15 mmol) in DMF (4 mL) at room temperature under nitrogen. The resulting mixture was degassed (purging with nitrogen) for 30 min followed by the addition of CuI (0.011 g, 0.05 mmol) and $PdCl_2(PPh_3)_2$ (0.080 g, 0.11 mmol) at the same temperature and was heated at 120° C. for 16 h. After cooling to room temperature, reaction mixture was quenched with an aqueous solution of saturated potassium sodium tartrate solution (100 mL) and was extracted with ethyl acetate (50 mL×3). Combined organic extracts were dried over anhydrous $Na_2SO_4$ and concentrated under reduced pressure. Isolated crude was combined with an identically prepared one more batch and the combined crudes were purified by reverse phase (C-18) silica gel column chromatography, using acetonitrile-water=0:1→1:0 as gradient, to afford methyl 4-(5-methylpyrimidin-2-yl)pyrrolo[1,2-a]quinoxaline-7-carboxylate (X-1278A2) (0.190 g, 25%) as an off-white solid. MS: $[MH]^+$ 319.1.

4-(5-Methylpyrimidin-2-yl)pyrrolo[1,2-a]quinoxaline-7-carboxylic acid (I-129). Lithium hydroxide monohydrate (0.031 g, 0.25 mmol) was added to a stirred solution of methyl 4-(5-methylpyrimidin-2-yl)pyrrolo[1,2-a]quinoxaline-7-carboxylate (X-1278A2) (0.080 g, 0.75 mmol) in a mixture of THF-water-methanol (2:1:1, 4 mL) at room temperature and stirred for 2 h at the same temperature. The reaction mixture was diluted with water (20 mL) and was extracted with ethyl acetate (30 mL) to remove unwanted organic impurities. Aqueous part was acidified (pH~4-5) with an aqueous solution of 1N HCl and was extracted with ethyl acetate (30 mL×3). Combined organic extracts were dried over $Na_2SO_4$ and concentrated under reduced pressure to afford 4-(5-methylpyrimidin-2-yl)pyrrolo[1,2-a]quinoxaline-7-carboxylic acid (I-129) (0.045 g, 58%) as a brown solid. $^1H$ NMR (400 MHz, DMSO-$d_6$) δ 12.16 (br, 1H), 8.95 (s, 2H), 8.66 (s, 1H), 8.49-8.47 (m, 2H), 8.18-8.16 (d, J=7.6 Hz, 1H), 7.52-7.51 (d, J=3.2 Hz, 1H), 7.08-7.06 (t, J=3.2 Hz, 1H), 2.42 (s, 3H). MS: $[MH]^+$ 305.0.

Example 1.53. Synthesis of 4-((4-(Trifluoromethyl)benzyl)oxy)pyrrolo[1,2-a]quinoxaline-7-carboxylic acid (I-130)

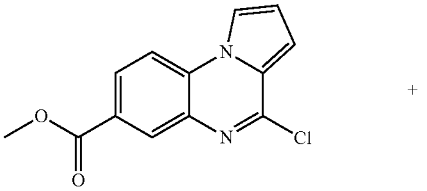

X-1109A3

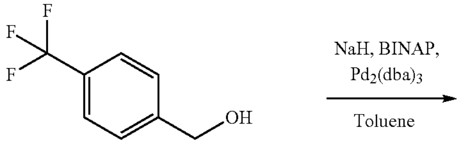

-continued

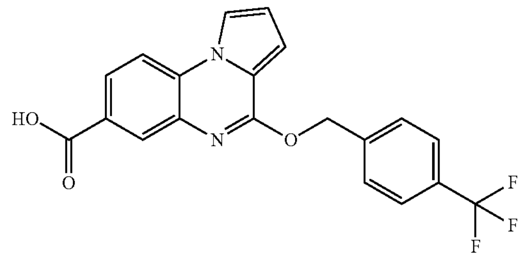

I-130

-continued

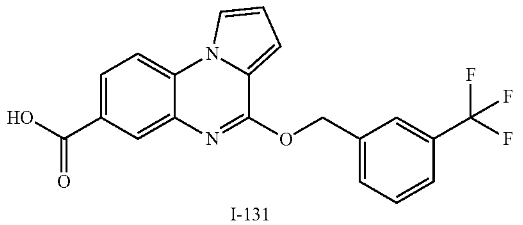

I-131

To a stirred solution of (4-(trifluoromethyl)phenyl)methanol (0.250 g, 1.42 mmol) in toluene (3 mL) was added NaH (60% dispersion in mineral oil; 0.113 g, 2.84 mmol) at 0° C. and the resulting mixture was stirred at 70° C. for 30 min. In a separate RB flask, BINAP (0.035 g, 0.05 mmol) was added to a stirred solution of methyl 4-chloropyrrolo[1,2-a]quinoxaline-7-carboxylate (X-1109A3) (0.184 g, 0.70 mmol) in toluene (18 mL) at room temperature, degassed (by purging with nitrogen) followed by addition of $Pd_2(dba)_3$ (0.013 g, 0.01 mmol) and the resulting suspension was added slowly to the former solution at 70° C. and stirring was continued for 16 h at the same temperature. Reaction mixture was brought to room temperature, diluted with water (30 mL) and was extracted with ethyl acetate (50 mL×2), Combined organic extracts were dried over anhydrous $Na_2SO_4$ and concentrated under reduced pressure to get a crude mass, which was purified by reverse phase (C-18) silica gel column chromatography, using water-acetonitrile=1:0→1:1 as gradient, to afford 4-((4-(trifluoromethyl)benzyl)oxy)pyrrolo[1,2-a]quinoxaline-7-carboxylic acid (I-130) (0.040 g, 11%) as an off-white solid. $^1$H NMR (400 MHz, DMSO-$d_6$) δ 8.37 (s, 1H), 8.14 (s, 1H), 8.08-8.06 (d, J=8.4 Hz, 1H), 7.93-7.91 (d, J=8.0 Hz, 1H), 7.78 (s, 4H), 6.95-6.94 (d, J=3.2 Hz, 1H), 6.84-6.83 (t, J=3.2 Hz, 1H), 5.72 (s, 2H). MS: $[MH]^+$ 387.0.

Example 1.54. Synthesis of 4-((3-(Trifluoromethyl)benzyl)oxy)pyrrolo[1,2-a]quinoxaline-7-carboxylic acid (I-131)

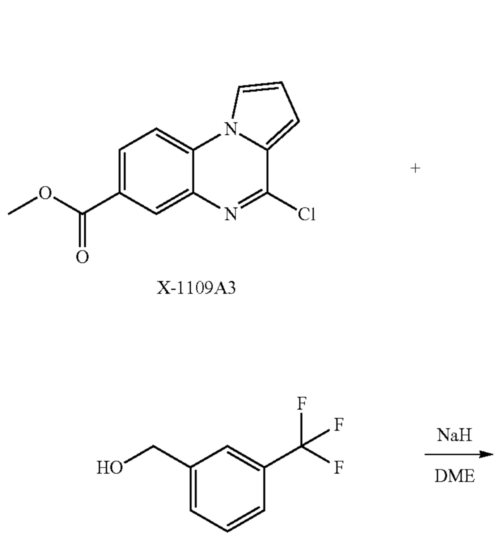

X-1109A3

To a stirred solution of (3-(trifluoromethyl)phenyl)methanol (0.203 g, 1.15 mmol) in dimethoxyethane (3 mL) was added NaH (60% dispersion in mineral oil; 0.090 g, 2.88 mmol) at 0° C. under nitrogen. After stirring for 30 min at the same temperature, was added methyl 4-chloropyrrolo[1,2-a]quinoxaline-7-carboxylate (X-1109A3) (0.300 g, 1.15 mmol) into the reaction solution and the resulting mixture was stirred at 70° C. for 16 h. Reaction was cooled to room temperature, diluted with water (50 mL) and was extracted with ethyl acetate (50 mL×2) to remove unwanted organic impurities. Aqueous layer was acidified (pH~2-3) with an aqueous 1N HCl solution and the resulting precipitate was collected by filtration. Solid residue was washed with cold water until the pH of the filtrate became neutral (pH~6-7) and the obtained crude was purified by preparative HPLC, using 0.05% $NH_3$ in Water-acetonitrile as gradient, to afford 4-((3-(trifluoromethyl)benzyl)oxy)pyrrolo[1,2-a]quinoxaline-7-carboxylic acid (I-131) (0.012 g, 3%) as a white solid. $^1$H NMR (400 MHz, DMSO-$d_6$) δ 13.12 (br, 1H), 8.47 (s, 1H), 8.29-8.27 (d, J=8.8 Hz, 1H), 8.20 (s, 1H), 7.98-7.94 (m, 2H), 7.90-7.89 (d, J=7.6 Hz, 1H), 7.73-7.71 (d, J=7.2 Hz, 1H), 7.68-7.64 (t, J=7.6, 16 Hz, 1H), 7.00-6.99 (d, J=3.2 Hz, 1H), 6.90 (s, 1H), 5.73 (s, 2H). MS: $[MH]^+$ 387.2.

Example 1.55. Synthesis of 4-(5-(Trifluoromethyl)pyridin-2-yl)pyrrolo[1,2-a]quinoxaline-7-carboxylic acid (I-132)

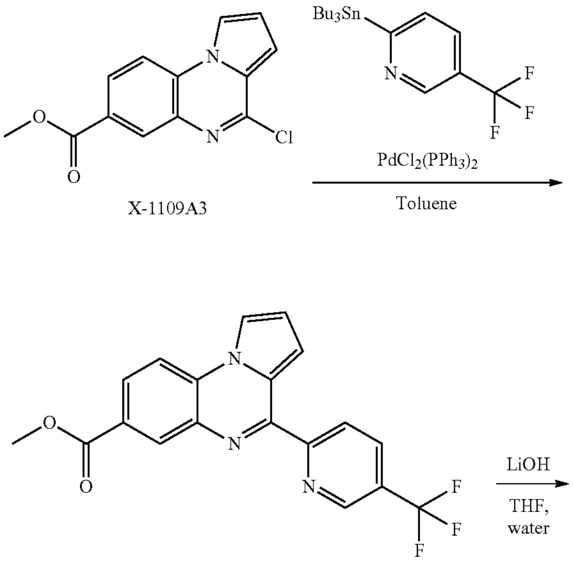

X-1109A3

X-1321A1

-continued

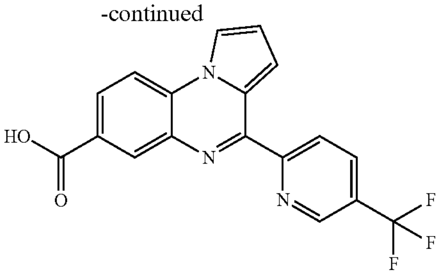

I-132

Methyl 4-(5-(trifluoromethyl)pyridin-2-yl)pyrrolo[1,2-a]quinoxaline-7-carboxylate (X-1321A1). 2-(Tributylstannyl)-5-(trifluoromethyl)pyridine (0.218 g, 0.49 mol) was added to a stirred solution of methyl 4-chloropyrrolo[1,2-a]quinoxaline-7-carboxylate (0.100 g, 0.38 mmol) in toluene (5 mL) at room temperature under nitrogen. Reaction mixture was degassed (purging with nitrogen) for 15 min followed by the addition of $PdCl_2(PPh_3)_2$ (0.013 g, 0.01 mmol) and the resulting mixture was heated at 140° C. for 8 h in seal tube. After cooling to room temperature, reaction mixture was diluted with water (50 mL) and was extracted by ethyl acetate (50 mL×3). Combined organic extracts were dried over anhydrous $Na_2SO_4$ and concentrated under reduced pressure. The crude product was purified by reverse phase (C-18) silica gel column chromatography, using acetonitrile-0.1% FA in water=0:1→1:0 as gradient, to afford methyl 4-(5-(trifluoromethyl)pyridin-2-yl)pyrrolo[1,2-a]quinoxaline-7-carboxylate (X-1321A1) (0.055 g, 38%) as a yellow solid. MS: $[MH]^+$ 372.6.

4-(5-(Trifluoromethyl)pyridin-2-yl)pyrrolo[1,2-a]quinoxaline-7-carboxylic acid (I-132). Lithium hydroxide monohydrate (0.019 g, 0.44 mmol) was added to a stirred solution of methyl 4-(5-(trifluoromethyl)pyridin-2-yl)pyrrolo[1,2-a]quinoxaline-7-carboxylate (X-1321A1) (0.055 g, 0.14 momol) in a mixture of THF-water (3:1, 4 mL) at room temperature and the resulting mixture was heated at 70° C. for 1 h. After cooling to room temperature, reaction mixture was concentrated under reduce pressure, crude was diluted with water (30 mL), acidified (pH~3-4) with 1N HCl solution and was extracted with ethyl acetate (30 mL×3). Combined organic extracts were dried over $Na_2SO_4$ and concentrated under reduced pressure to get a gummy solid, which was purified by triturating with n-pentane to afford 4-(5-(trifluoromethyl)pyridin-2-yl)pyrrolo[1,2-a]quinoxaline-7-carboxylic acid (I-132) (0.030 g, 56%) as a yellow solid. $^1H$ NMR (400 MHz, DMSO-$d_6$) δ 13.27 (br, 1H), 9.22 (s, 1H), 8.73-8.68 (m, 2H), 8.52 (s, 1H), 8.48-8.46 (d, J=8.4 Hz, 2H), 8.18-8.16 (d, J=8.4 Hz, 1H) 7.92-7.91 (d, J=3.6 Hz, 1H), 7.12-7.11 (d, J=3.2 Hz, 1H). MS: $[MH]^+$ 358.1.

Example 1.56. Synthesis of N-(4-(2-Fluoro-4-(trifluoromethyl)phenyl)imidazo[1,2-a]quinoxalin-7-yl) acrylamide (I-133)

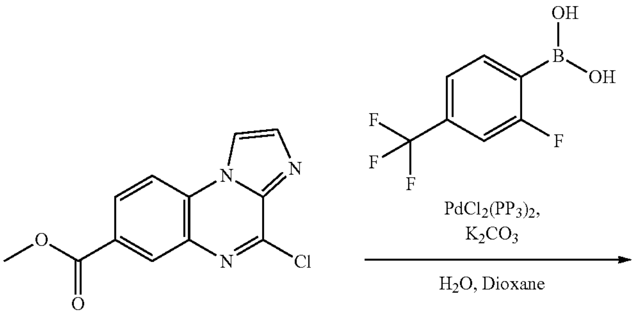

X-1107A3

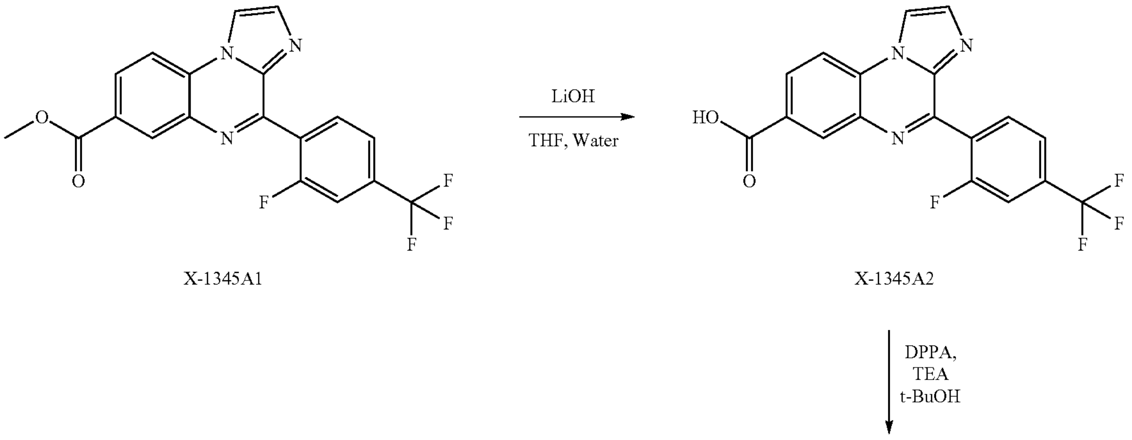

X-1345A1

X-1345A2

-continued

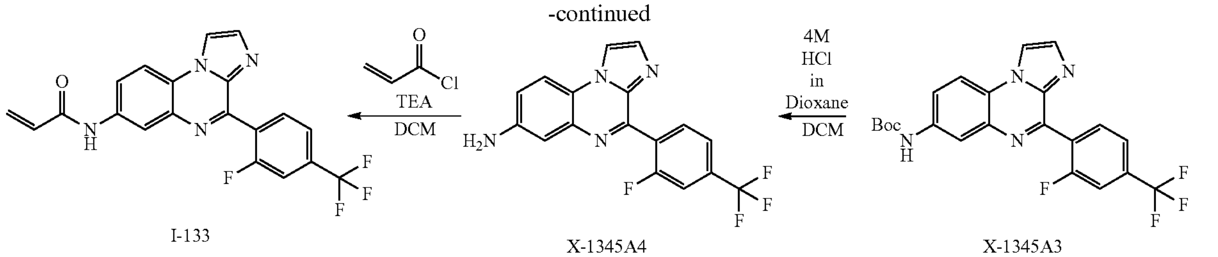

I-133 X-1345A4 X-1345A3

Methyl 4-(2-fluoro-4-(trifluoromethyl)phenyl)imidazo[1,2-a]quinoxaline-7-carboxylate (X-1345A1). To a stirred solution of methyl 4-chloroimidazo[1,2-a]quinoxaline-7-carboxylate (X-1345A1) (2.50 g, 9.5 mmol) in 1,4-dioxane-water (3:1, 40 mL) were added (2-fluoro-4-(trifluoromethyl)phenyl)boronic acid (2.6 g, 12.40 mmol) and $K_2CO_3$ (4.0 g, 28.80 mmol) at room temperature under nitrogen. Reaction mixture was degassed (purging with nitrogen) for 30 min followed by the addition $PdCl_2(PPh_3)_2$ (2.00 g, 0.30 mmol) at the same temperature and the resulting mixture was heated at 100° C. for 1 h. After cooling to room temperature, reaction mixture was diluted with water (150 mL) and was extracted with ethyl acetate (100×3). The organic extracts were combined, dried over anhydrous $Na_2SO_4$ and solvents were distilled off under reduced pressure. The crude mass was purified by silica gel column chromatography, using ethyl acetate-hexane=2:3→1:1 as gradient, to afford methyl 4-(2-fluoro-4-(trifluoromethyl)phenyl)imidazo[1,2-a]quinoxaline-7-carboxylate (X-1345A1) (3.20 g, 86%) as a yellow solid. MS: $[MH]^+$ 390.1.

4-(2-Fluoro-4-(trifluoromethyl)phenyl)imidazo[1,2-a]quinoxaline-7-carboxylic acid (X-1345A2). To a stirred solution of methyl 4-(2-fluoro-4-(trifluoromethyl)phenyl)imidazo[1,2-a]quinoxaline-7-carboxylate (X-1345A1) (3.20 g, 8.20 mmol) in a mixture of THF-water-methanol (2:1:0.1; 46 mL) was added lithium hydroxide monohydrate (1.00 g, 24.60 mmol) at room temperature under nitrogen and the resulting reaction mixture was heated at 60° C. for 3 h. After cooling to room temperature, the reaction mixture was concentrated under reduced pressure, diluted with water (100 mL) and was extracted with ethyl acetate (50×2 mL) to remove unwanted organic impurities. The aqueous layer was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 4-(2-fluoro-4-(trifluoromethyl)phenyl)imidazo[1,2-a]quinoxaline-7-carboxylic acid (X-1345A2) (2.50 g, 84%) as an off-white solid. MS: $[MH]^+$ 376.2.

tert-Butyl (4-(2-fluoro-4-(trifluoromethyl)phenyl)imidazo[1,2-a]quinoxalin-7-yl)carbamate (X-1345A3). Triethylamine (1.70 g, 13.30 mmol) and DPPA (1.80 g, 6.60 mmol) was added to a stirred suspension of 4-(2-fluoro-4-(trifluoromethyl)phenyl)imidazo[1,2-a]quinoxaline-7-carboxylic acid (X-1345A2) (2.50 g, 6.60 mmol) in t-BuOH (220 mL) at room temperature and the resulting solution was stirred at 100° C. for 16 h. The reaction mixture was cooled to room temperature, diluted with water (200 mL) and was extracted with ethyl acetate (150 mL×3). The combined organic extracts were washed with brine (50 mL), dried over anhydrous $Na_2SO_4$ and concentrated under reduced pressure. Obtained crude was purified by silica gel column chromatography, using ethyl acetate-hexane=2:3→1:1 as gradient, to afford tert-butyl (4-(2-fluoro-4-(trifluoromethyl)phenyl)imidazo[1,2-a]quinoxalin-7-yl)carbamate (X-1345A3) (0.350 g, 12%) as a yellow solid. MS: $[M]^+$ 446.2.

4-(2-Fluoro-4-(trifluoromethyl)phenyl)imidazo[1,2-a]quinoxalin-7-amine (X-1345A4). To a stirred solution of tert-butyl (4-(2-fluoro-4-(trifluoromethyl)phenyl)imidazo[1,2-a]quinoxalin-7-yl)carbamate (X-1345A3) (0.300 g, 0.67 mmol) in DCM (5 mL) was added 4M HCl in dioxane (3 mL) at 0° C. and reaction was stirred at room temperature for 1 h. Reaction mixture was concentrated under reduced pressure to afford 4-(2-fluoro-4-(trifluoromethyl)phenyl)imidazo[1,2-a]quinoxalin-7-amine (X-1345A4) [0.2 g, 86% (crude)] as an off-white solid, which was used in next step without further purification. MS: $[MH]^+$ 347.0.

N-(4-(2-fluoro-4-(trifluoromethyl)phenyl)imidazo[1,2-a]quinoxalin-7-yl)acrylamide (I-133). To a stirred solution of 4-(2-fluoro-4-(trifluoromethyl)phenyl)imidazo[1,2-a]quinoxalin-7-amine (X-1345A4) (0.150 g, 0.43 mmol) in DCM (4 mL) were added triethylamine (0.24 g, 1.73 mmol) and acryloyl chloride (0.070 g, 0.52 mmol) respectively at 0° C. under nitrogen and stirring was continued for 30 min at the same temperature. The reaction mixture was diluted with water (10 mL) and was extracted with ethyl acetate (20 mL×3). The organic extracts were combined and dried over anhydrous $Na_2SO_4$. The solvent was removed under reduced pressure. The crude product was purified by silica gel column chromatography, using ethyl acetate-hexane=2:3→1:1 as gradient, to afford N-(4-(2-fluoro-4-(trifluoromethyl)phenyl)imidazo[1,2-a]quinoxalin-7-yl)acrylamide (I-133) (0.100 g, 43%) as an off white solid. $^1H$ NMR (400 MHz, DMSO-$d_6$) δ 10.58 (s, 1H), 8.87 (s, 1H), 8.55-8.54 (d, J=2.0 Hz, 1H), 8.45-8.43 (d, J=8.8 Hz, 1H), 8.15-8.11 (t, J=7.2 Hz, 1H), 8.03-8.00 (dd, J=8.8, 2.4 Hz, 1H), 7.95-7.92 (d, J=10 Hz, 2H), 7.85 (s, 1H), 7.82-7.80 (d, J=7.6 Hz, 1H), 6.50-6.46 (dd, J=16.8, 10.0 Hz, 1H), 6.36-6.32 (dd, J=16.8, 1.6 Hz, 1H), 5.85-5.82 (dd, J=10.0, 1.6 Hz, 1H). MS: [MH]401.1.

Example 1.57. Synthesis of N-(4-(4-(tert-butyl)phenyl)imidazo[1,2-a]quinoxalin-7-yl)propionamide (I-134)

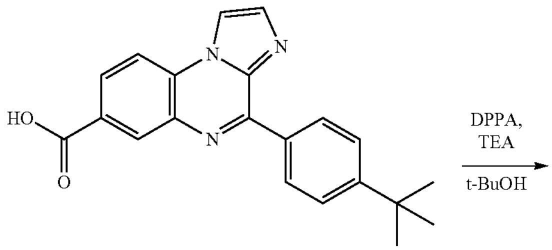

I-58

-continued

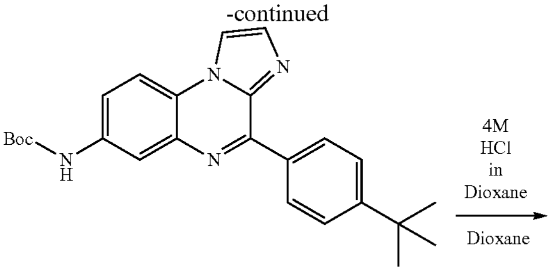

X-1353A1

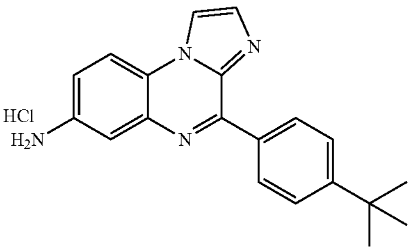

X-1353A2

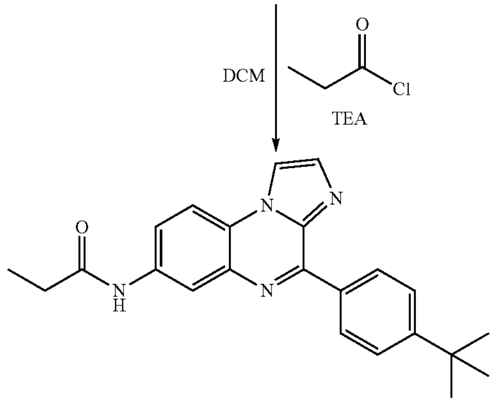

I-134 tert-Butyl (4-(4-(tert-butyl)phenyl)imidazo[1,2-a]quinoxalin-7-yl)carbamate (X-1353A1). Triethylamine (0.900 g, 8.60 mmol) and DPPA (2.400 g, 8.60 mmol) was added to a stirred suspension of methyl 4-(4-(tert-butyl)phenyl) imidazo[1,2-a]quinoxaline-7-carboxylic acid (I-58) (2.00 g, 5.80 mmol) in t-BuOH (110 mL) at room temperature under nitrogen and the resulting mixture stirred at 100° C. for 16 h. Reaction mixture was cooled to room temperature, reaction mixture was slowly poured into water (100 mL) and was extracted with ethyl acetate (100 mL×3). Combined organic extracts were washed with brine (50 mL), dried over anhydrous $Na_2SO_4$ and concentrated under reduced pressure. The crude product was purified by silica gel column chromatography, using ethyl acetate-hexane=1:94→3:7 as gradient, to afford tert-butyl (4-(4-(tert-butyl)phenyl)imidazo[1,2-a]quinoxalin-7-yl)carbamate (X-1353A1) (1.400 g, 58%) as a yellow solid. MS: $[MH]^+$ 417.2.

4-(4-(tert-Butyl)phenyl)imidazo[1,2-a]quinoxalin-7-amine hydrochloride (X-1353A2). To a stirred solution of tert-butyl (4-(4-(tert-butyl)phenyl)imidazo[1,2-a]quinoxalin-7-yl)carbamate (X-1353A1) (0.500 g, 1.20 mmol) in 1,4-dioxane (2 mL) was added 4M HCl in dioxane (10 mL) at 0° C. and the reaction was stirred at room temperature 4 h. Volatiles were distilled off under reduced pressure, obtained crude was triturated with n-hexanes to afford 4-(4-(tert-butyl)phenyl)imidazo[1,2-a]quinoxalin-7-amine hydrochloride (X-1353A2) (4.50 g, 83%) as an off-white solid. MS: $[MH]^+$ 317.1.

N-(4-(4-(tert-butyl)phenyl)imidazo[1,2-a]quinoxalin-7-yl)propionamide (I-134). To a stirred solution of 4-(4-(tert-butyl)phenyl)imidazo[1,2-a]quinoxalin-7-amine hydrochloride (X-1353A2) (0.250 g, 0.79 mmol) in DCM (5 mL) were added triethylamine (0.239 g, 2.37 mmol) and propionyl chloride (0.087 g, 0.940 mmol) respectively at 0° C. under nitrogen and stirring was continued for 10 min. Reaction mixture was diluted with water (30 mL) and the resulting precipitate was collected by filtration. Solid residue was washed with n-hexane (50 mL) and dried in vacuo to afford N-(4-(4-(tert-butyl)phenyl)imidazo[1,2-a]quinoxalin-7-yl) propionamide (I-134) (0.180 g, 62%) as an off-white solid. $^1H$ NMR (400 MHz, DMSO-$d_6$) δ 10.26 (s, 1H), 8.82-8.81 (d, J=0.8 Hz, 1H), 8.71-8.69 (d, J=8.4 Hz, 2H), 8.48-8.47 (d, J=2.0 Hz, 1H), 8.34-8.32 (d, J=8.8 Hz, 1H), 7.88-7.83 (m, 2H), 7.62-7.60 (d, J=8.4 Hz, 2H), 2.43-2.38 (q, J=7.6 Hz, 2H), 1.36 (s, 9H), 1.15-1.11 (t, J=7.6 Hz, 3H). MS: $[MH]^+$ 373.2.

Example 1.58. Synthesis of N-(4-(4-(tert-butyl)phenyl)imidazo[1,2-a]quinoxalin-7-yl)acetamide (I-135)

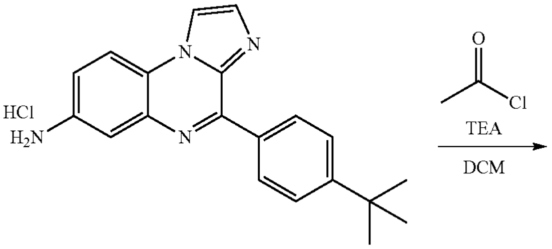

X-1353A2

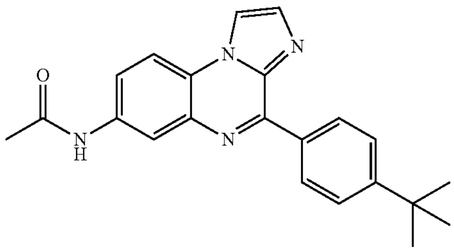

I-135

To a stirred solution of 4-(4-(tert-butyl)phenyl)imidazo[1,2-a]quinoxalin-7-amine hydrochloride (X-1353A2) (0.250 g, 0.79 mmol) in DCM (5 mL) were added TEA (0.239 g, 2.37 mmol) and acetyl chloride (0.074 g, 0.94 mmol) respectively at 0° C. under nitrogen and stirring was continued for 10 min. Reaction mixture was diluted with water (30 mL) and the resulting precipitate was collected by filtration. Solid residue was washed with n-hexane (50 mL) and dried in vacuo to yield N-(4-(4-(tert-butyl)phenyl)imidazo[1,2-a]quinoxalin-7-yl)acetamide (I-135) (0.100 g, 35%) as a white solid. $^1H$ NMR (400 MHz, DMSO-$d_6$) δ 10.32 (s, 1H), 8.81 (s, 1H), 8.72-8.70 (d, J=8.8 Hz, 2H), 8.47-8.46 (d, J=2.0 Hz, 1H), 8.35-8.32 (d, J=8.8 Hz, 1H), 7.88 (s, 1H), 7.83-7.80 (dd, J=8.8, 2.0 Hz, 1H), 7.62-7.60 (d, J=8.4 Hz, 2H), 2.13 (s, 3H), 1.36 (s, 9H). MS: $[MH]^+$ 359.2.

Example 1.59. Synthesis of 1-(5-(4-(Trifluoromethyl)phenyl)-3,4-dihydroisoquinolin-2(1H)-yl)prop-2-en-1-one (I-136)

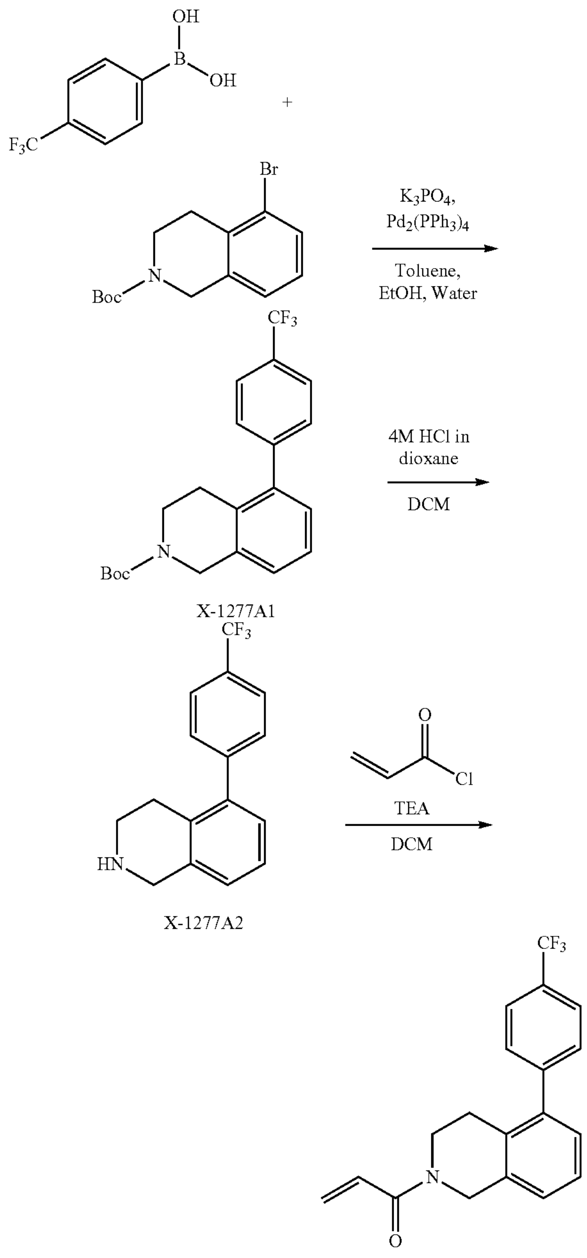

X-1277A1

X-1277A2

I-136 tert-Butyl5-(4-(trifluoro-15-methyl)phenyl)-3,4-dihydroisoquinoline-2(1H)-carboxylate (X-1277A1). To a stirred solution of tert-butyl 5-bromo-3,4-dihydroisoquinoline-2(1H)-carboxylate (1.00 g, 3.20 mmol) in a mixture of toluene-ethanol-water (2:2:1, 50 mL) were added (4-(trifluoro-15-methyl)phenyl)boronic acid (0.670 g, 3.52 mmol) and potassium phosphate tribasic (1.40 g, 6.41 mmol) at room temperature under nitrogen. The reaction mixture was degassed (purging with nitrogen) for 15 min followed by the addition of $Pd_2(PPh_3)_4$ (0.197 g, 0.16 mmol) and the resulting mixture was heated at 100° C. for 1 h. After cooling to room temperature, reaction mixture was diluted with water (300 mL) and was extracted with ethyl acetate (300 mL×2). Combined organic extracts were washed with brine (100 mL), dried over anhydrous $Na_2SO_4$ and concentrated under reduced pressure. The crude product was combined with an identically prepared two more batches and the combined batches were purified by silica gel column chromatography, using ethyl acetate-hexane=0:1→1:4 as gradient, to afford tert-butyl 5-(4-(trifluoro-15-methyl)phenyl)-3,4-dihydroisoquinoline-2(1H)-carboxylate (X-1277A1) (2.50 g, 70%) as a white solid. MS: $[MH-56]^+$ 322.0.

5-(4-(Trifluoro-15-methyl)phenyl)-1,2,3,4-tetrahydroisoquinoline (X-1277A2). A 4M HCl in dioxane (4 mL) was added to a stirred solution of tert-butyl5-(4-(trifluoro-15-methyl)phenyl)-3,4-dihydroisoquinoline-2(1H)-carboxylate (X-1277A2) (0.300 g, 0.79 mmol) in DCM (2 mL) at 0° C. and stirred for 30 min at the same temperature. Reaction mixture was concentrated under reduced pressure to afford 5-(4-(trifluoro-15-methyl) phenyl)-1,2,3,4-tetrahydroisoquinoline (X-1277A2) [0.225 g, quantitative (crude)] as an off-white solid. Obtained crude was taken to the next step without further purification. MS: $[MH]^+$ 278.0.

1-(5-(4-(Trifluoromethyl)phenyl)-3,4-dihydroisoquinolin-2(1H)-yl)prop-2-en-1-one (I-136). Acryloyl chloride (0.067 g, 0.73 mmol) and triethylamine (0.298 g, 2.90 mmol) were added sequentially to a stirred solution of 5-(4-(trifluoro-15-methyl) phenyl)-1,2,3,4-tetrahydroisoquinoline (X-1277A2) (0.205 g, 0.73 mmol) in DCM (3 mL) at 0° C. under nitrogen and stirred for 30 min at the same temperature. The reaction mixture was diluted with water (30 mL) and was extracted with DCM (30 mL×2). Combined organic extracts dried over anhydrous $Na_2SO_4$ and concentrated under reduced pressure. The crude product was purified by reverse phase (C-18) silica gel column chromatography, using acetonitrile-water=0:1→1:0 as gradient, to afford 1-(5-(4-(trifluoromethyl)phenyl)-3,4-dihydroisoquinolin-2(1H)-yl)prop-2-en-1-one (I-136) (0.080 g, 32%) as an off-white solid. $^1H$ NMR (400 MHz, DMSO-$d_6$) δ 7.81-7.79 (d, J=8.0 Hz, 2H), 7.60-7.58 (d, J=8.0 Hz, 2H), 7.35-7.27 (m, 2H), 7.18-7.17 (m, 1H), 6.96-6.79 (m, 1H), 6.18-6.14 (d, J=16.4 Hz, 1H), 5.75-5.69 (m, 1H), 4.85 (s, 1H), 4.74 (s, 1H), 3.71-3.62 (m, 2H), 2.73-2.68 (m, 2H). MS: $[MH]^+$ 332.1.

Example 1.60. Synthesis of 4-Methoxy-3-methyl-1-(5-(4-(trifluoromethyl)phenyl)-3,4-dihydroisoquinolin-2(1H)-yl)butan-1-one (I-137)

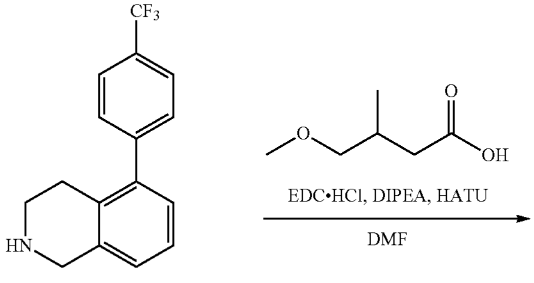

X-1277A2

-continued

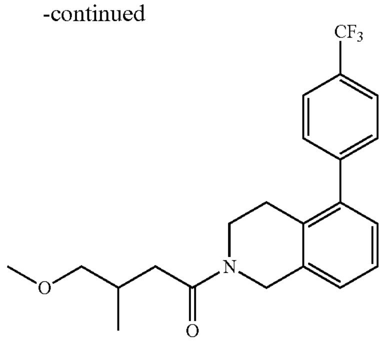

I-137

5-(4-(Trifluoromethyl)phenyl)-1,2,3,4-tetrahydroisoquinoline (X-1277A2) (0.150 g, 0.54 mmol) was added to a stirred solution of 4-methoxy-3-methylbutanoic acid (0.142 g, 1.08 mmol) in DMF (2 mL) at 0° C. temperature under nitrogen. After 5 min of stirring at the same temperature, were added DIPEA (0.349 g, 2.70 mmol) and HATU (0.411 g, 1.08 mmol) into the reaction solution and stirring was continued for 1 h at room temperature. Reaction mixture was slowly poured into ice water (50 mL) and was extracted with ethyl acetate (50 mL×3). Combined organic extracts were washed with brine (20 mL), dried over anhydrous $Na_2SO_4$ and concentrated under reduced pressure to get a crude mass, which was purified by reverse phase (C-18) silica gel column chromatography, using acetonitrile-water=0:1→1:0 as gradient, to afford 4-methoxy-3-methyl-1-(5-(4-(trifluoromethyl)phenyl)-3,4-dihydroisoquinolin-2(1H)-yl)butan-1-one (I-137) (0.090 g, 52%) as a white solid. $^1$H NMR (400 MHz, DMSO-$d_6$) δ 7.81-7.79 (d, J=7.6 Hz, 2H), 7.60-7.56 (m, 2H), 7.35-7.29 (m, 2H), 7.17-7.16 (br. m, 1H), 4.72 (s, 1H; 1×C$\underline{H}_2$), 4.67 (s, 1H; 1×C$\underline{H}_2$), 3.58-3.55 (t, J=5.6 Hz, 2H), 3.23 (s, 3H), 3.21-3.13 (m, 2H), 2.73-2.70 (t, J=5.6 Hz, 1H; 1×C$\underline{H}_2$), 2.65-2.62 (t, J=5.6 Hz, 1H; 1×C$\underline{H}_2$), 2.44-2.39 (m, 1H), 2.26-2.14 (m, 2H), 0.90-0.85 (m, 3H). MS: $[MH]^+$ 392.0.

Example 1.61. Synthesis of 6-(6-Azaspiro[2.5]octan-6-yl)pyrido[3,2-e]pyrrolo[1,2-a]pyrazine-3-carboxylic acid (I-138)

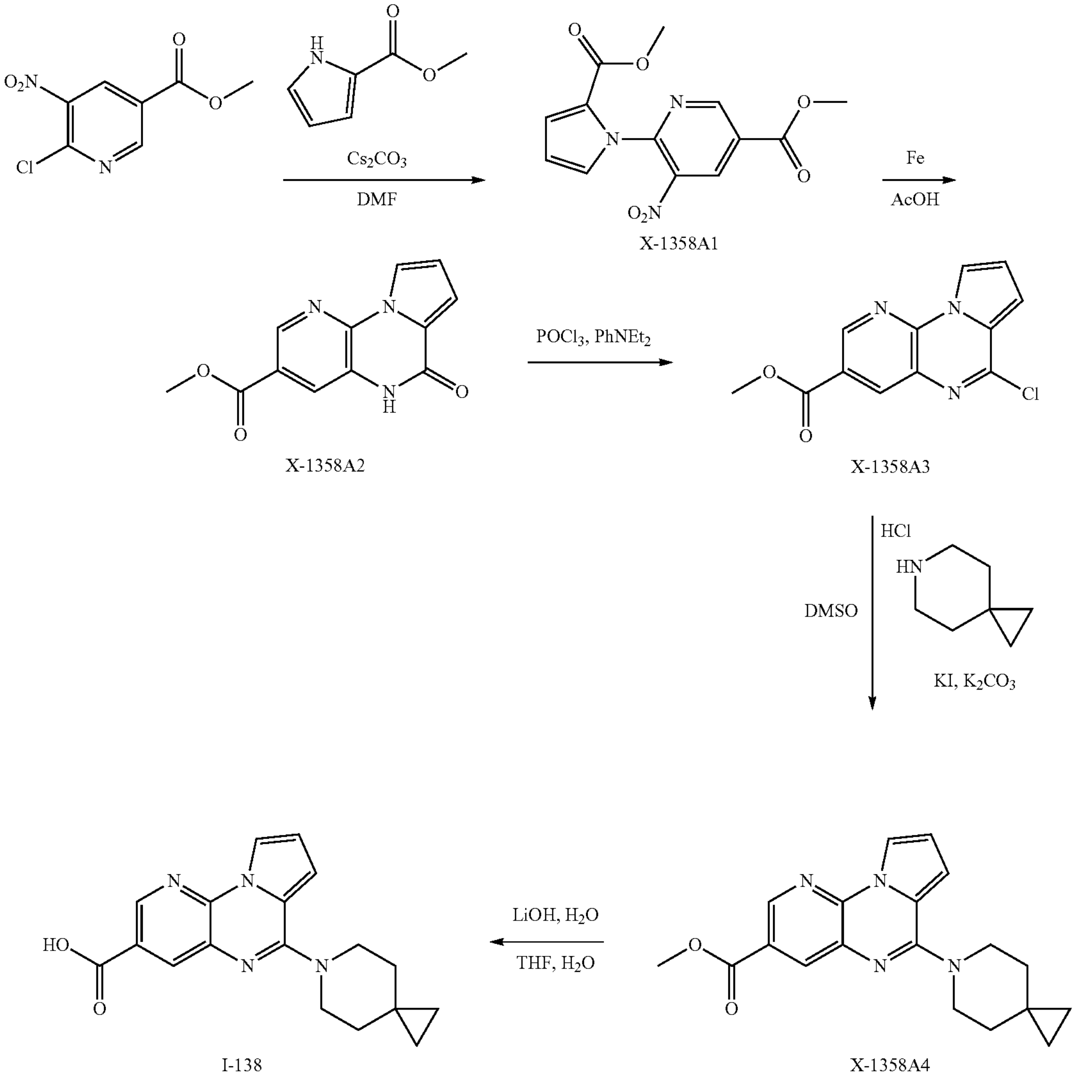

I-138

Methyl 6-(2-(methoxycarbonyl)-1H-pyrrol-1-yl)-5-nitronicotinate (X-1358A1). To a stirred solution of methyl 6-chloro-5-nitronicotinate (5.0 g, 23.25 mmol) in DMF (50 mL) were added cesium carbonate (15.11 g, 58.13 mmol) and methyl 1H-pyrrole-2-carboxylate (3.40 g, 27.90 mmol) at room temperature under nitrogen and the resulting mixture was heated at 90° C. for 5 h. Reaction mixture was cooled to room temperature, diluted with water (100 mL) and was extracted with ethyl acetate (150 mL×3). Combined organic extracts were washed with brine (100 mL), dried over anhydrous $Na_2SO_4$ and concentrated in vacuo. The crude product was purified by reverse phase (C-18) silica gel column chromatography, using formic acid:acetonitrile=0:1→0.1:9.9 as gradient, to afford methyl 6-(2-(methoxycarbonyl)-1H-pyrrol-1-yl)-5-nitronicotinate (X-1358A1) (3.00 g, 42%) as a yellow solid. MS: $[MH]^+$ 306.0.

Methyl 6-oxo-5,6-dihydropyrido[3,2-e]pyrrolo[1,2-a]pyrazine-3-carboxylate (X-1358A2). To a stirred solution of methyl 6-(2-(methoxycarbonyl)-1H-pyrrol-1-yl)-5-nitronicotinate (X-1358A1) (3.00 g, 9.83 mmol) in acetic acid (30 mL) was added Fe-powder (2.00 g, 76.90 mmol) at 0° C. and reaction was allowed to stir at 70° C. for 1 h. After cooling to room temperature, reaction mixture was filtered and the precipitate was washed with water. The precipitate was taken in 10% methanol in dichloromethane, stirred for 30 min and filtered through a celite bed, filtrate was concentrated under reduced pressure to afford methyl 6-oxo-5,6-dihydropyrido[3,2-e]pyrrolo[1,2-a]pyrazine-3-carboxylate (X-1358A2) [2.00 g, 84% (crude)] as a yellow solid, which was taken to the next step without further purification. MS: $[MH]^+$ 244.0.

Methyl 6-chloropyrido[3,2-e]pyrrolo[1,2-a]pyrazine-3-carboxylate (X-1358A3). To a stirred solution of afford methyl 6-oxo-5,6-dihydropyrido[3,2-e]pyrrolo[1,2-a]pyrazine-3-carboxylate (X-1358A2) (2.00 g, 8.23 mmol) in N,N-diethyl aniline (1.0 mL) was added phosphorus oxychloride (20 mL) at 0° C. and resulting mixture was stirred at 110° C. for 2 h. Reaction was diluted with water (50 mL) and was extracted with ethyl acetate (100 mL×2). Combined organic extracts were dried over anhydrous $Na_2SO_4$, filtered and concentrated under reduced pressure to afford methyl 6-chloropyrido[3,2-e]pyrrolo[1,2-a]pyrazine-3-carboxylate (X-1358A3) (1.80 g, 84%) as a yellow solid, which is pure enough to proceed to next step without further purification. MS: $[MH]^+$ 262.0/$[MH+2]^+$263.9.

Methyl 6-(6-azaspiro[2.5]octan-6-yl)pyrido[3,2-e]pyrrolo[1,2-a]pyrazine-3-carboxylate (X-1358A4). To a stirred solution of methyl 6-chloropyrido[3,2-e]pyrrolo[1,2-a]pyrazine-3-carboxylate (X-1358A3) (0.350 g, 1.36 mmol) in DMSO (5 mL) were added potassium carbonate (0.563 g, 4.07 mmol), 6-azaspiro[2.5]octane hydrochloride (0.200 g, 1.36 mmol) and potassium iodide (0.022 g, 0.13 mmol) sequentially at room temperature under nitrogen and the resulting mixture was stirred at 80° C. for 2 h. Reaction mixture was diluted with water (20 mL) and was extracted with ethyl acetate (50 mL×2). Combined organic extracts were dried over anhydrous $Na_2SO_4$, filtered and filtrate was concentrated under reduced pressure. Obtained crude was purified by silica gel column chromatography with using ethyl acetate-hexane=0:1→0.1:9.9 as gradient, to afford methyl 6-(6-azaspiro[2.5]octan-6-yl)pyrido[3,2-e]pyrrolo[1,2-a]pyrazine-3-carboxylate (X-1358A4) (0.340 g, 55%) as an off-white solid. MS: $[MH]^+$ 337.1.

6-(6-Azaspiro[2.5]octan-6-yl)pyrido[3,2-e]pyrrolo[1,2-a]pyrazine-3-carboxylic acid (I-138). To a stirred solution of methyl 6-(6-azaspiro[2.5]octan-6-yl)pyrido[3,2-e]pyrrolo[1,2-a]pyrazine-3-carboxylate (0.340 g, 1.01 mmol) in in a mixture of THF-water (4:1; 10 mL) was added lithium hydroxide monohydrate (0.070 g, 3.00 mmol) at room temperature and the resulting mixture was heated at 70° C. for 2 h. After cooling to room temperature, reaction mixture was concentrated under reduced pressure, acidified (pH~2-3) with an aqueous 1N HCl solution and the resulting precipitate was collected by filtration. Obtained residue was washed with cold water until the pH of the filtrate became neutral (pH~6-7), was triturated with n-Pentane (40 mL) and, finally, dried under reduced pressure to afford 6-(6-azaspiro[2.5]octan-6-yl)pyrido[3,2-e]pyrrolo[1,2-a]pyrazine-3-carboxylic acid (I-138) (0.250 g, 77%) as an off-white solid. $^1H$ NMR (400 MHz, DMSO-$d_6$) 13.40 (br. s, 1H), 8.74 (s, 1H), 8.36 (s, 1H), 8.28 (br. s, 1H), 7.19 (br. s, 1H), 6.92 (s, 1H), 3.92 (s, 4H), 1.54 (s, 4H), 0.40 (s, 4H). MS: $[MH]^+$ 323.2.

Example 1.62. Synthesis of 6-(4-(tert-Butyl)phenyl)pyrido[3,2-e]pyrrolo[1,2-a]pyrazine-3-carboxylic acid (I-139)

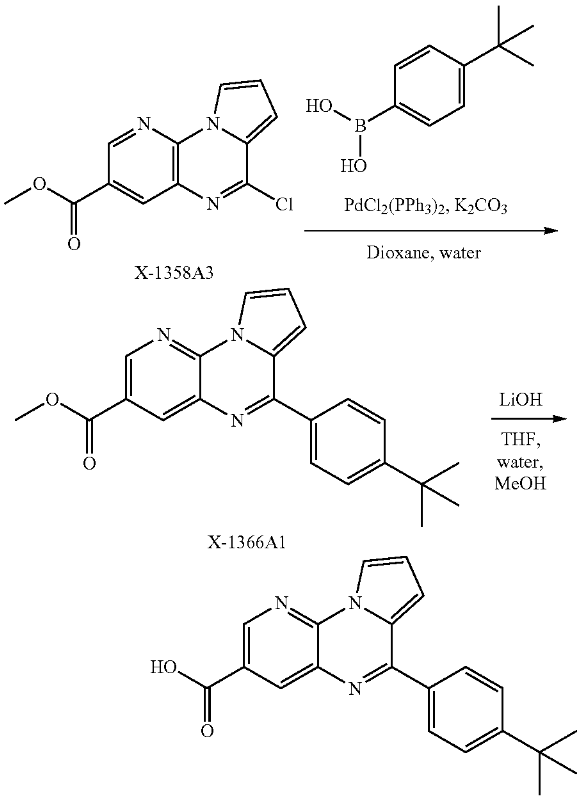

X-1358A3

X-1366A1

I-139

Methyl 6-(4-(tert-butyl)phenyl)pyrido[3,2-e]pyrrolo[1,2-a]pyrazine-3-carboxylate (X-1366A1). To a stirred solution of methyl 6-chloropyrido[3,2-e]pyrrolo[1,2-a]pyrazine-3-carboxylate (X-1358A3) (0.300 g, 1.14 mmol) in a mixture of 1,4-dioxane-water (3:1, 4 mL) were added potassium carbonate (0.475 g, 3.44 mmol) and (4-(tert-butyl)phenyl)boronic acid (0.306 g, 1.72 mmol) at room temperature under nitrogen. The reaction mixture was degassed (purging with nitrogen) for 20 min followed by the addition of $PdCl_2(PPh_3)_2$ (0.024 g, 0.03 mmol) and the reaction mixture was stirred at 90° C. for 1 h. Reaction mixture was cooled to room temperature, diluted with water (20 mL) and was extracted with ethyl acetate (25 mL×3). Combined organic extracts were washed with brine (50 mL), dried over anhydrous $Na_2SO_4$ and concentrated in vacuo. The crude product was purified by silica gel column chromatography, using ethyl acetate:hexane=0:1→3:7 as gradient, to afford methyl 6-(4-(tert-butyl)phenyl)pyrido[3,2-e]pyrrolo[1,2-a]pyrazine-3-carboxylate (X-1366A1) (0.350 g, 85%) as an off-white solid. MS: $[MH]^+$ 360.1.

6-(4-(tert-Butyl)phenyl)pyrido[3,2-e]pyrrolo[1,2-a]pyrazine-3-carboxylic acid (I-139). To a stirred solution of methyl 6-(4-(tert-butyl)phenyl)pyrido[3,2-e]pyrrolo[1,2-a]pyrazine-3-carboxylate (X-1366A1) (0.350 g, 0.97 mmol) in a mixture of THF-water (4:1; 10 mL) was added lithium hydroxide monohydrate (0.070 g, 2.91 mmol) at room temperature and the resulting reaction mixture was heated at 70° C. for 2 h. After cooling to room temperature, the reaction mixture was concentrated under reduced pressure, acidified (pH~2-3) with an aqueous 1N HCl solution and the resulting precipitate was collected by filtration. Obtained residue was washed with cold water until the pH of the filtrate became neutral (pH~6-7) and finally purified by triturated with n-pentane (40 mL) and dried under reduced pressure to afford 6-(4-(tert-butyl)phenyl)pyrido[3,2-e]pyrrolo[1,2-a]pyrazine-3-carboxylic acid (I-139) (0.250 g, 74%) as an off-white solid. $^1H$ NMR (400 MHz, DMSO-$d_6$) 13.60 (br. s, 1H), 9.06-9.05 (d, J=2.0 Hz, 1H), 8.65-8.64 (d, J=1.6 Hz, 1H), 8.56-8.55 (d, J=1.2 Hz, 1H), 7.99-7.97 (d, J=8.4 Hz, 2H), 7.64-7.61 (d, J=8.4 Hz, 2H), 7.22-7.22 (d, J=3.2 Hz, 1H), 7.09-7.08 (t, J=3.2 Hz, 1H), 1.36 (s, 9H). MS: $[MH]^+$ 346.1

Example 1.63. Synthesis of N-((8-(4-(tert-butyl)phenyl)imidazo[1,2-a]pyrazin-6-yl)methyl)acrylamide (I-140)

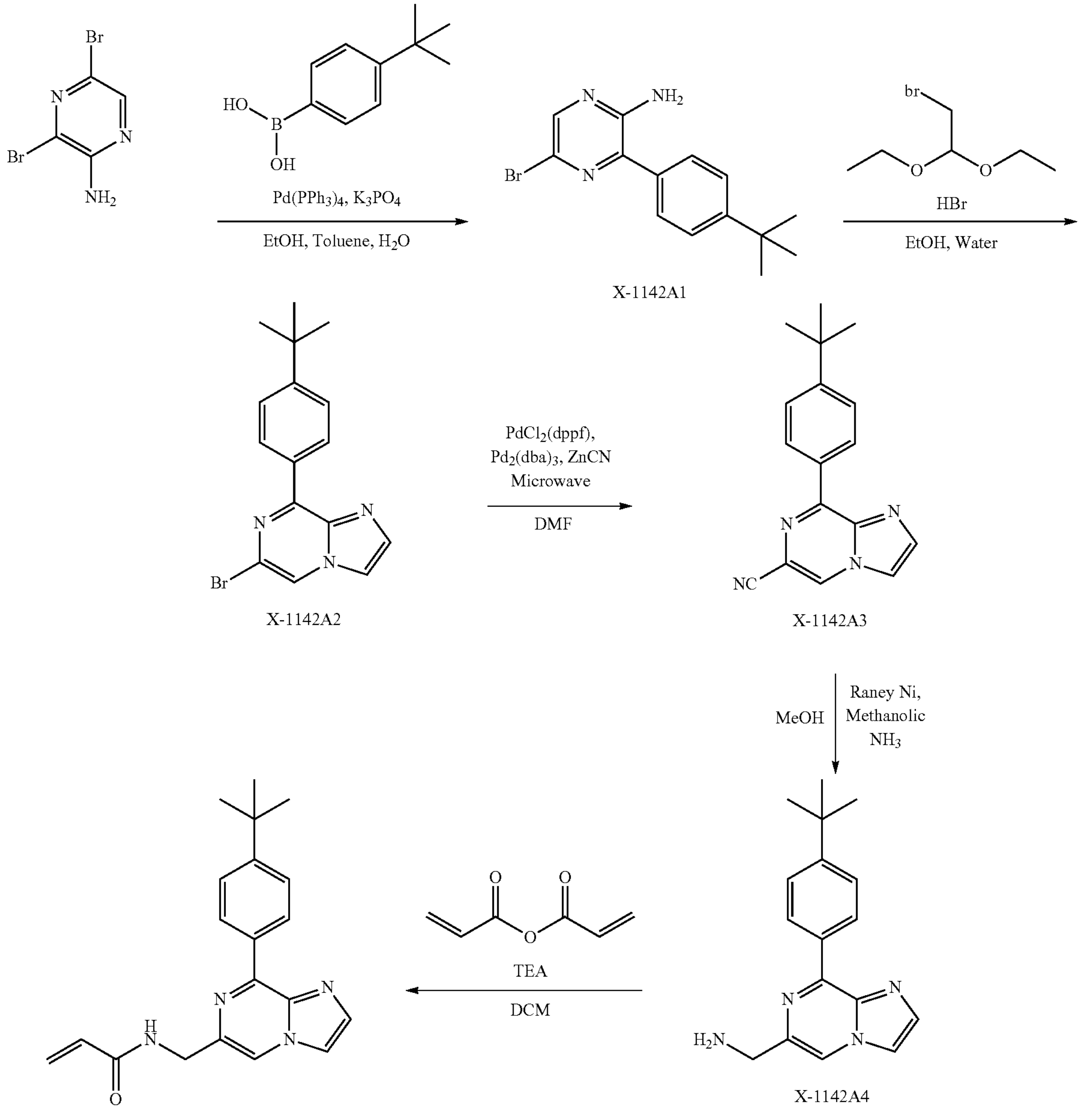

X-1142A1

X-1142A2

X-1142A3

X-1142A4

I-140

5-Bromo-3-(4-(tert-butyl)phenyl)pyrazin-2-amine (X-1142A1). To a stirred solution of 3,5-dibromopyrazin-2-amine (20.0 g, 79.68 mmol) in a mixture of toluene-ethanol-water (7:2:1, 200 mL) were added (4-(tert-butyl)phenyl) boronic acid (14.07 g, 79.68 mmol) and tripotassium phosphate (33.78 g, 159.36 mmol) at room temperature under nitrogen. The reaction mixture was degassed (purging with nitrogen) for 20 min followed by addition of $Pd_2(PPh_3)_4$ (4.60 g, 3.98 mmol) and the resulting suspension was heated at 100° C. for 6 h. Reaction was diluted with water (300 mL) and was extracted with ethyl acetate (300 mL×3). Combined organic extracts were dried over anhydrous $Na_2SO_4$, filtered and concentrated in vacuo to give a crude mass, which was purified by silica gel column chromatography, using ethyl acetate-hexane=0:1→1:4 as gradient, to afford 5-bromo-3-(4-(tert-butyl)phenyl)pyrazin-2-amine (21.0 g, 86%) (X-1142A1) as an off-white solid. MS: $[MH]^+$ 306.2/$[MH+2]^+$ 308.2.

6-Bromo-8-(4-(tert-butyl)phenyl)imidazo[1,2-a]pyrazine (X-1142A2). To a stirred solution of 5-bromo-3-(4-(tert-butyl)phenyl)pyrazin-2-amine (X-1142A1) (20.0 g, 65.50 mmol) in ethanol (200 mL) were added 2-bromo-1,1-diethoxyethane (25.700 g, 131.10 mmol) and HBr (47% in water; 79.00 mL, 458.9 mmol) dropwise, via pressure equalizer dropping funnel, at 0° C. under nitrogen and the resulting solution was slowly heated to 80° C. for 2 h. Reaction was diluted with water (1000 mL), obtained precipitate was filtered through a celite bed, washed the bed with cold water and solid residue was dried under high vacuum to afford 6-bromo-8-(4-(tert-butyl)phenyl)imidazo[1,2-a]pyrazine (X-1142A2) [19.0 g, 84% (crude)] as an off-white solid. MS: $[MH]^+$ 330.1/$[MH+2]^+$332.1.

8-(4-(tert-Butyl)phenyl)imidazo[1,2-a]pyrazine-6-carbonitrile (X-1142A3). To a stirred solution of 6-bromo-8-(4-(tert-butyl)phenyl)imidazo[1,2-a]pyrazine (X-1142A2) (1.00 g, 3.03 mmol) in DMF (10 mL) were added zinc cyanide (0.890 g, 7.60 mmol) under nitrogen at room temperature. The reaction mixture was degassed (purging with nitrogen) for 20 min followed by addition of $PdCl_2$(dppf) (0.111 g, 0.15 mmol) and $Pd_2(dba)_3$ (0.139 g, 0.15 mmol) at the same temperature and the reaction was heated at 120° C. under microwave irradiation for 1 h. Reaction mixture was diluted with ice-water (50 mL) and was extracted with ethyl acetate (50 mL×2). Combined organic extracts were dried over anhydrous $Na_2SO_4$, filtered and concentrated under reduced pressure to get a crude mass, which was combined with an identically prepared 18 batches. Obtained crude mass was purified by silica gel column chromatography using ethyl acetate:hexane=0:1→5:5 as gradient, to afford 8-(4-(tert-butyl)phenyl)imidazo[1,2-a]pyrazine-6-carbonitrile (X-1142A3) (15.000 g, 94%) as an off-white solid. MS: $[MH]^+$ 277.0.

(8-(4-(tert-butyl)phenyl)imidazo[1,2-a]pyrazin-6-yl) methanamine (X-1142A4). To a degassed (by purging nitrogen) solution of 8-(4-(tert-butyl)phenyl)imidazo[1,2-a]pyrazine-6-carbonitrile (X-1142A3) (4.00 g, 1.44 mmol) in methanol (50 mL) were added activated Raney Ni (2.00 g, 34.07 mmol) and $NH_3$ (7N in methanol; 20 mL) respectively at room temperature and the resulting mixture was hydrogenated in a Parr autoclave under 200 psi at 60° C. for 5 h. Reaction was allowed to come to room temperature, filtered off the residue through a celite bed, washed the bed with methanol and collected filtrates were concentrated under reduced pressure to provide a crude mass, which triturated with n-pentane (100 mL) and dried under high vacuum to afford (8-(4-(tert-butyl)phenyl)imidazo[1,2-a]pyrazin-6-yl) methanamine (X-1142A4) (3.80 g, 55%) as an off-white solid. MS: $[MH]^+$ 281.1.

N-((8-(4-(tert-butyl)phenyl)imidazo[1,2-a]pyrazin-6-yl) methyl)acrylamide (I-140). To a stirred solution of (8-(4-(tert-butyl)phenyl)imidazo[1,2-a]pyrazin-6-yl)methanamine (X-1142A4) (3.80 g, 13.57 mmol) in dichloromethane (20 mL) was added triethylamine (4.61 g, 45.64 mmol) at 0° C. under nitrogen. After 5 min of stirring at the same temperature, was added acryloyl chloride (1.40 g, 11.11 mmol) into the reaction solution and stirred for 30 min at 0° C. Reaction mixture was diluted with water (100 mL) and was extracted with dichloromethane (200 mL×3). Combined organic extracts were dried over anhydrous $Na_2SO_4$ and concentrated in vacuo. Obtained crude mass was purified by C-18 silica gel column chromatography using acetonitrile:water=0:1→5:5 as gradient, to afford N-((8-(4-(tert-butyl)phenyl)imidazo[1,2-a]pyrazin-6-yl) methyl)acrylamide (I-140) (2.500 g, 55%) as a white solid. $^1H$ NMR (400 MHz, DMSO-$d_6$) 8.77 (br. s, 1H), 8.70-8.68 (d, J=8.0 Hz, 2H), 8.47 (s, 1H), 8.23 (s, 1H), 7.85 (s, 1H), 7.59-7.57 (d, J=8.4 Hz, 2H), 6.38-6.31 (d, J=16.8, 10.0 Hz, 1H), 6.18-6.14 (d, J=16.8 Hz, 1H), 5.67-5.64 (d, J=10.0 Hz, 1H), 4.52-4.50 (d, J=5.6 Hz, 2H), 1.35 (s, 9H). MS: $[MH]^+$ 335.2.

Example 1.64. Synthesis of N-((8-(4-(tert-Butyl) phenyl)imidazo[1,2-a]pyrazin-6-yl)methyl)ethenesulfonamide (I-141)

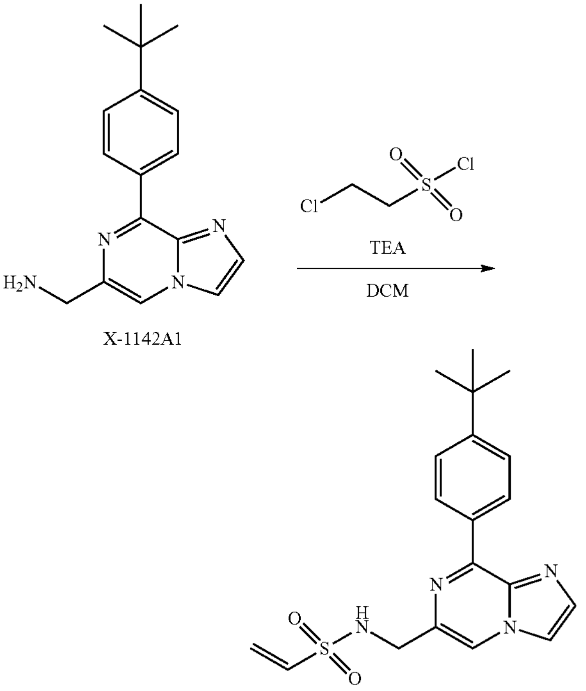

X-1142A1

I-141

To a stirred solution of (8-(4-(tert-butyl)phenyl)imidazo [1,2-a]pyrazin-6-yl)methanamine (X-1142A1) (0.200 g, 0.71 mmol) in DCM (5 mL) were added triethylamine (0.2 mL, 1.42 mmol) followed by acryloyl chloride (0.077 g, 0.85 mmol) at 0° C. under nitrogen and the resulting mixture was stirred at room temperature for 30 min. Reaction mixture was slowly poured into water (50 mL) and was extracted with DCM (50 mL×3). Combined organic extracts were dried over anhydrous $Na_2SO_4$ and concentrated in vacuo. The resulting crude was purified by reverse phase (C-18) silica gel column chromatography using acetonitrile-water=0:141:0 as gradient, to afford N-((8-(4-(tert-butyl)phenyl)imidazo[1,2-a]pyrazin-6-yl)methyl)ethenesulfonamide (I-141) (0.070 g, 22%) as a white solid. $^1$H NMR (400 MHz, DMSO-$d_6$) δ8.72-8.70 (d, J=8.8 Hz, 2H). 8.56 (s, 1H), 8.26 (s, 1H), 8.02 (s, 1H), 7.86 (s, 1H), 759-57 (d, J=8.4 Hz, 2H), 6.83-6.76 (d, J=16.4, 10.0 Hz, 1H), 6.10-6.06 (d, J=16.41 Hz, 1H), 5.98-5.95 (d, J=10.0 Hz, 1H), 4.23-4.22 (d, J=44 Hz, 2H), 1.34 (s, 9H). MS: $[MH]^+$ 371.1.

Example 1.65. Synthesis of N-(1-(8-(4-(tert-butyl)phenyl)imidazo[1,2-a]pyrazin-6-yl)ethyl)acrylamide (I-142)

8-(4-(tert-butyl)phenyl)-N-methoxy-N-methylimidazo[1,2-a]pyrazine-6-carboxamide (X-1272A2). To a stirred solution of 8-(4-(tert-butyl)phenyl)imidazo[1,2-a]pyrazine-6-carboxylic acid (X-1272A1) (4.20 g, 14.23 mmol) in DMF (10 mL) were added N,N-diisopropylethylamine (7.36 g, 56.94 mmol), 1-(3-Dimethylaminopropyl)-3-ethylcarbodiimide hydrochloride (3.540 g, 18.5 mmol) and Hydroxybenzotriazole (2.61 g, 17.08 mmol) simultaneously at 0° C. under nitrogen. After 15 min of stirring at the same temperature, was added N, O-dimethyl hydroxylamine hydrochloride (1.38 g, 14.23 mmol) and stirring was continued at room temperature for 16 h. Reaction mixture was diluted with water (150 mL) and was extracted with ethyl acetate (150 mL×3). Combined organic extracts were washed with brine (50 mL), dried over anhydrous $Na_2SO_4$ and concentrated in vacuo. Obtained solid mass was purified by silica gel column chromatography, using ethyl acetate-hexane=0:1→4 2:8 as gradient, to afford 8-(4-(tert-butyl)phenyl)-N-

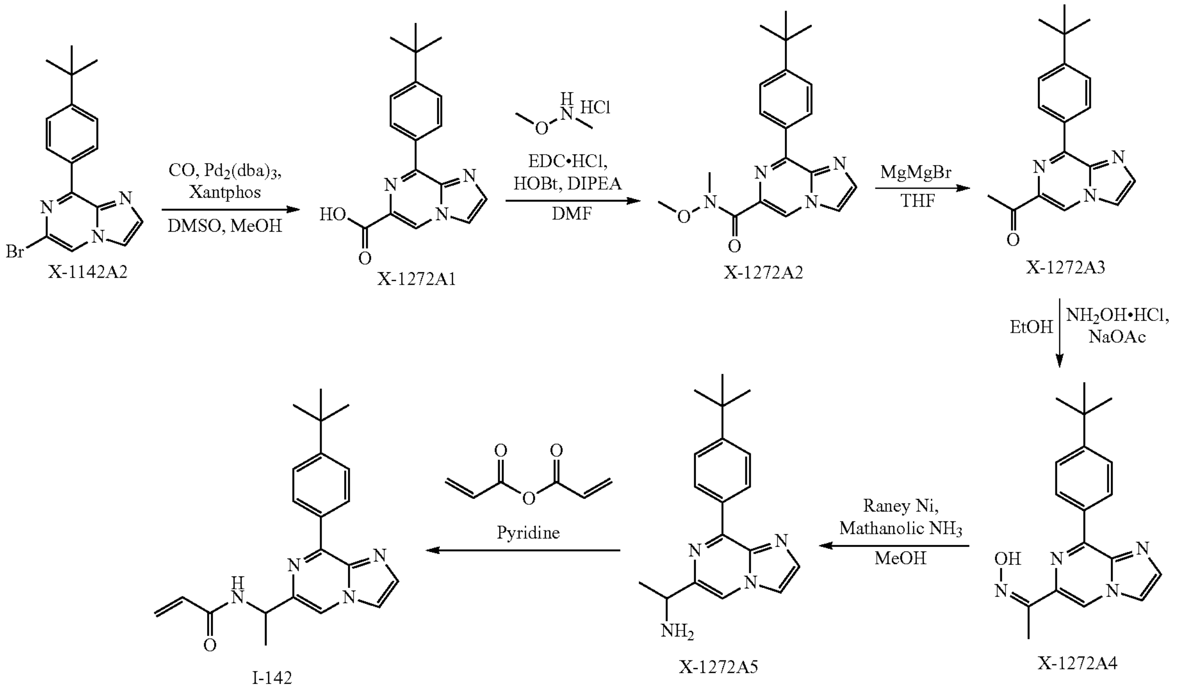

X-1142A2 X-1272A1 X-1272A2 X-1272A3 X-1272A4 X-1272A5 I-142

8-(4-(tert-butyl)phenyl)imidazo[1,2-a]pyrazine-6-carboxylic acid (X-1272A1). To a stirred solution of 6-bromo-8-(4-(tert-butyl)phenyl)imidazo[1,2-a]pyrazine (X-1142A2) (6.20 g, 18.80 mmol) in a mixture of DMSO-methanol (9:1; 30 mL), was added potassium acetate (5.50 g, 56.53 mmol) at room temperature under nitrogen. The reaction mixture was degassed (purging with nitrogen) for 20 min followed by addition of xantphos (1.08 g, 1.88 mol) and $Pd_2(dba)_3$ (5.50 g, 1.88 mmol) sequentially at room temperature and the resulting mixture was stirred under $CO_{(g)}$ for 1 h at the same temperature followed by heating at 90° C. for 2 h. Reaction mixture was cooled to room temperature, diluted with water (150 mL) and was extracted with ethyl acetate (200 mL×3). Combined organic extracts were dried over anhydrous $Na_2SO_4$ and concentrated in vacuo. The crude product was purified by silica gel column chromatography, using ethyl acetate-hexane=0:1→1:9 as gradient, to afford 8-(4-(tert-butyl)phenyl)imidazo[1,2-a]pyrazine-6-carboxylic acid (X-1272A1) (4.20 g, 75%) as an off-white solid. MS: $[MH]^+$ 296.1.

methoxy-N-methylimidazo[1,2-a]pyrazine-6-carboxamide (X-1272A2) (1.50 g, 31%) as a brown solid. MS: $[MH]^+$ 339.1.

1-(8-(4-(tert-butyl)phenyl)imidazo[1,2-a]pyrazin-6-yl)ethan-1-one (X-1272A3). To a stirred solution of 8-(4-(tert-butyl)phenyl)-N-methoxy-N-methylimidazo[1,2-a]pyrazine-6-carboxamide (X-1272A2) (1.50 g, 4.43 mmol) in THE (20 mL), was added methyl magnesium bromide (3.0 M in diethyl ether; 6.40 mL, 22.18 mmol) at 0° C. under nitrogen and stirred for 2 h at the same temperature. Reaction mixture was quenched with with an aqueous solution of saturated $NH_4Cl$ (100 mL) and was extracted with ethyl acetate (100 mL×2). Combined organic extracts were dried over anhydrous $Na_2SO_4$ and concentrated in vacuo. Obtained crude mass was purified by silica gel column chromatography, using ethyl acetate:hexane=0:1→1:9 as gradient, to afford 1-(8-(4-(tert-butyl)phenyl)imidazo[1,2-a]

pyrazin-6-yl)ethan-1-one (X-1272A3) (0.730 g, 56%) as a white solid. MS: $[MH]^+$ 294.1.

(E/Z)-1-(8-(4-(tert-butyl)phenyl)imidazo[1,2-a]pyrazin-6-yl)ethan-1-one oxime (X-1272A4). To a stirred solution of 1-(8-(4-(tert-butyl)phenyl)imidazo[1,2-a]pyrazin-6-yl)ethan-1-one (X-1272A3) (0.730 g, 2.49 mmol) in ethanol (5 mL) were added hydroxylamine hydrochloride (0.340 g, 4.97 mmol) and sodium acetate (0.610 g, 7.46 mmol) sequentially at room temperature and the resulting mixture was heated at 70° C. for 1 h. Reaction mixture was cooled to room temperature, diluted with water (100 mL) and was extracted with ethyl acetate (100 mL×2). Combined organic extracts were dried over anhydrous $Na_2SO_4$ and concentrated in vacuo to afford an isomeric mixture of (E/Z)-1-(8-(4-(tert-butyl)phenyl)imidazo[1,2-a]pyrazin-6-yl)ethan-1-one oxime (X-1272A4) [0.550 g, 71% (crude)] as an off-white solid, which was carried forward to the next step without further purification. MS: $[MH]^+$ 309.1.

1-(8-(4-(tert-Butyl)phenyl)imidazo[1,2-a]pyrazin-6-yl)ethan-1-amine (X-1272A5). To a stirred solution of (Z)-1-(8-(4-(tert-butyl)phenyl)imidazo[1,2-a]pyrazin-6-yl)ethan-1-one oxime (X-1272A4) (0.400 g, 1.29 mmol) in methanol (5 mL) were added activated Raney Ni (0.300 g, 5.03 mmol) and $NH_3$ (7N in methanol; 5 mL) respectively at room temperature and the resulting mixture was hydrogenated in a Parr autoclave under 200 psi at 70° C. for 5 h. Reaction was allowed to come to room temperature, filtered off the residue through a celite bed, washed the bed with methanol and collected filtrates were concentrated under reduced pressure to provide a crude mass, which triturated with n-pentane (100 mL) and dried under high vacuum to afford 1-(8-(4-(tert-butyl)phenyl)imidazo[1,2-a]pyrazin-6-yl)ethan-1-amine (X-1272A5) (0.250 g, 65%) as an off-white solid, which was carried forward to the next step without further purification. MS: $[MH]^+$ 295.1.

N-(1-(8-(4-(tert-butyl)phenyl)imidazo[1,2-a]pyrazin-6-yl)ethyl)acrylamide (I-142). To a stirred solution of 1-(8-(4-(tert-butyl)phenyl)imidazo[1,2-a]pyrazin-6-yl)ethan-1-amine (X-1272A5) (0.250 g, 0.85 mmol) in pyridine (3 mL) was added acrylic anhydride (0.321 g, 2.54 mmol) at 0° C. and stirred for 10 min at the same temperature. Reaction mixture was diluted with water (50 mL) and was extracted with ethyl acetate (50 mL×2). Combined organic extracts were dried over anhydrous $Na_2SO_4$ and concentrated in vacuo. The crude product was purified by reverse phase (C-18) silica gel column chromatography, using acetonitrile-0.1% formic acid in water=0:1→1:1 as gradient, to afford N-(1-(8-(4-(tert-butyl)phenyl)imidazo[1,2-a]pyrazin-6-yl)ethyl)acrylamide (I-142) (0.050 g, 16%) as an off white solid. $^1H$ NMR (400 MHz, DMSO-$d_6$) δ 8.72-8.70 (d, J=8.8 Hz, 2H), 8.62-8.60 (d, J=7.6 Hz, 1H), 8.47 (s, 1H), 8.21 (s, 1H), 7.84 (s, 1H), 7.59-7.57 (d, J=8.4 Hz, 2H), 6.39-6.33 (dd, J=, 17.2, 10.4 Hz, 1H), 6.13-6.09 (dd, J=17.2, 2.0 Hz, 1H), 5.63-5.60 (dd, J=10.0, 2.0 Hz, 1H), 5.11-5.08 (quin, J=3.2 Hz, 1H), 1.55-1.53 (d, J=7.2 Hz, 3H), 1.34 (s, 9H). MS: $[MH]^+$ 349.1.

Example 1.66. Synthesis of 8-(4-(tert-Butyl)phenyl)-N-methylimidazo[1,2-a]pyrazine-6-carboxamide (I-143)

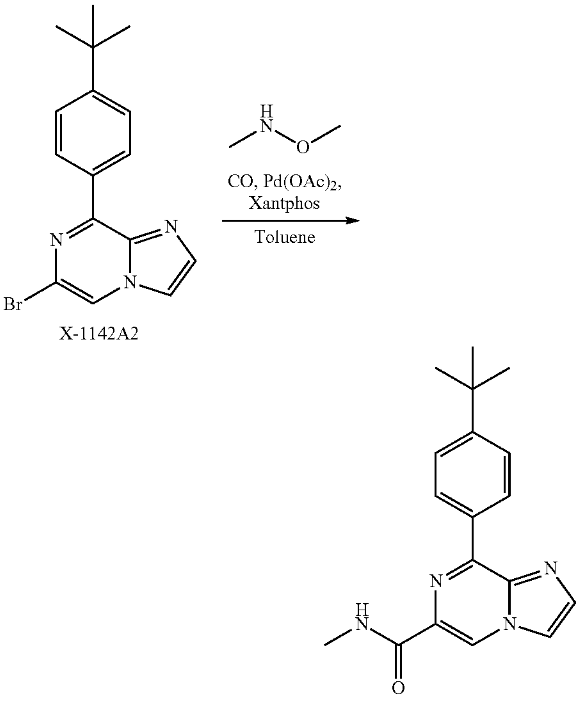

X-1142A2

I-143

To a stirred solution of 6-bromo-8-(4-(tert-butyl)phenyl)imidazo[1,2-a]pyrazine (0.100 g, 0.30 mmol) in toluene (2 mL) was added N,O-dimethylhydroxylamine (0.270 g, 0.45 mmol) at room temperature under nitrogen and the resulting solution was degassed (purging with nitrogen) for 20 min. $Pd(OAc)_2$ (0.013 g, 0.06 mmol) and xantphos (0.034 g, 0.06 mmol) were added sequentially into the reaction mixture, the mixture was purged with $CO_{(g)}$ for 30 min at the same temperature and subjected to heating at 90° C. for 6 h under CO pressure. After cooling to room temperature, reaction mixture was diluted with water (30 mL) and was extracted with ethyl acetate (30 mL×3). Combined organic extracts were dried over anhydrous $Na_2SO_4$ and concentrated under reduced pressure. The crude product was purified by reverse phase (C-18) silica gel column chromatography, using acetonitrile-water=0:1→0:1 as gradient, to afford 8-(4-(tert-butyl)phenyl)-N-methylimidazo[1,2-a]pyrazine-6-carboxamide (I-143) (0.015 g, 16%) as an off-white solid. $^1H$ NMR (400 MHz, DMSO-$d_6$) δ 9.22 (s, 1H), 8.92-8.90 (d, J=8.4 Hz, 2H), 8.82-8.81 (d, J=4.8 Hz, 1H), 8.34 (s, 1H), 7.93 (s, 1H), 7.60-7.58 (d, J=8.4 Hz, 2H), 2.91-2.90 (d, J=4.8 Hz, 3H), 1.35 (s, 9H). MS: $[MH]^+$ 309.1.

Example 1.67. Synthesis of 1-(4-(tert-Butyl)phenyl)imidazo[1,5-a]pyridine-6-carboxylic acid (I-144)

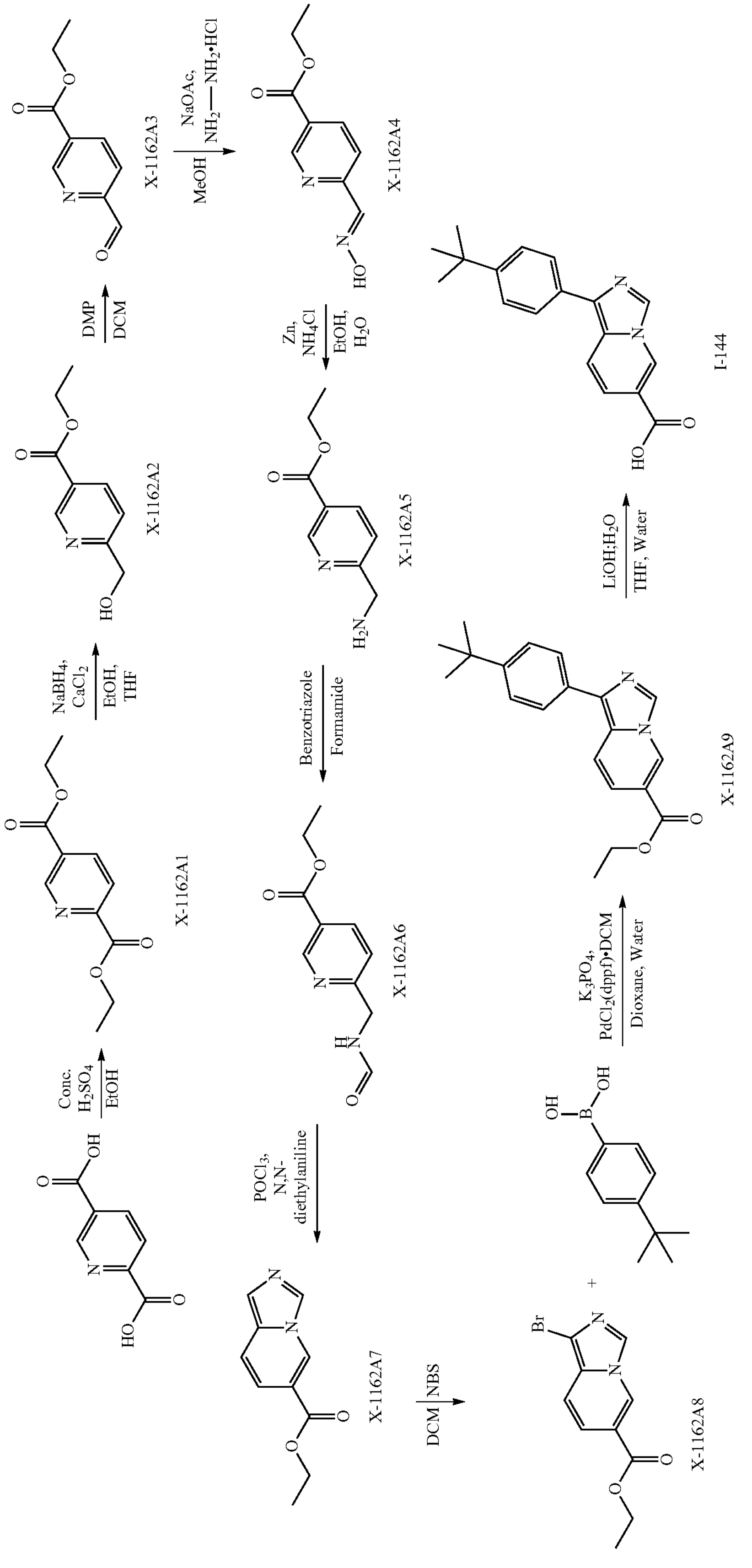
Conc. $H_2SO_4$
EtOH
X-1162A1
$NaBH_4$, $CaCl_2$
EtOH, THF
X-1162A2
DMP
DCM
X-1162A3
MeOH
NaOAc, $NH_2$—$NH_2$•HCl
X-1162A4
Zn, $NH_4Cl$
EtOH, $H_2O$
X-1162A5
Benzotriazole
Formamide
X-1162A6
$POCl_3$, N,N-diethylaniline
X-1162A7
DCM
NBS
X-1162A8
$K_3PO_4$, $PdCl_2$(dppf)•DCM
Dioxane, Water
X-1162A9
LiOH;$H_2O$
THF, Water
I-144

Diethyl pyridine-2,5-dicarboxylate (X-1162A1). Concentrated $H_2SO_4$ (6.41 mL) was added dropwise to a stirred solution of pyridine-2,5-dicarboxylic acid (5.080 g, 30.41 mmol) in ethanol (55 mL) at 0° C. and the resulting mixture was heated at 85° C. for 16 h. Reaction mixture was concentrated in vacuo, obtained crude diluted with water (50 mL) and basifed (pH~8-9) with an aqueous solution of saturated $NaHCO_3$ and was extracted with ethyl acetate (200 mL×2). Combined organic layers were dried over $Na_2SO_4$ and concentrated under reduced pressure to afford diethyl pyridine-2,5-dicarboxylate (X-1162A1) [5.10 g, 76% (crude)] as an off-white solid, which was used in next step without further purification. MS: $[MH]^+$ 224.1.

Ethyl 6-(hydroxymethyl)nicotinate (X-1162A2). To a stirred solution of diethyl pyridine-2,5-dicarboxylate (X-1162A1) (5.10 g, 22.76 mmol) in a mixture of ethanol-THF (2:1; 50 mL) were added calcium chloride (3.75 g, 34.09 mmol) and Sodium borohydride (1.26 g, 34.05 mmol) at 0° C. under nitrogen and stirred at room temperature for 2 h. Reaction mixture was diluted with water (100 mL) and was extracted with ethyl acetate (150 mL×2). Combined organic extracts were dried over anhydrous $Na_2SO_4$ and concentrated under reduced pressure to afford ethyl 6-(hydroxymethyl)nicotinate (X-1162A2) [3.60 g, 88% (crude)] as an off-white solid. Obtained crude was pure enough to proceed to the next step without further purification. MS: $[MH]^+$ 182.4.

Ethyl 6-formylnicotinate (X-1162A3). To a stirred solution of ethyl 6-(hydroxymethyl)nicotinate (X-1162A2) (3.60 g, 19.88 mmol) in dichloromethane (40 mL) was added Dess-Martin periodinane (12.68 g, 29.90 mmol) at 0° C. under nitrogen and stirred at room temperature for 1 h. Reaction mixture was diluted with 50% solution of sodium bicarbonate (100 mL) and was extracted with dichloromethane (200 mL×2). The combined organic extracts were dried over anhydrous $Na_2SO_4$, filtered and concentrated in vacuo. The crude was purified by silica gel column chromatography with using ethyl acetate:hexane=0:1→1:9 as gradient to afford ethyl 6-formylnicotinate (X-1162A3) (2.90 g, 81%) as a white solid. $^1H$ NMR (400 MHz, DMSO-$d_6$) δ 10.06 (s, 1H), 9.28 (s, 1H), 8.52-8.50 (d, J=8.0 Hz, 1H), 8.07-8.05 (d, J=8.0 Hz, 1H), 4.40-4.39 (q, J=7.2 Hz, 2H), 1.38-1.34 (t, J=7.2 Hz, 3H).

Ethyl (E)-6-((hydroxyimino)methyl)nicotinate (X-1162A4). To a stirred solution of ethyl 6-formylnicotinate (X-1162 A3) (2.90 g, 16.20 mmol) in methanol (35 mL) were added sodium acetate (1.990 g, 24.26 mmol) and ammonium hydroxide hydrochloride (1.670 g, 24.20 mmol) sequentially at room temperature under nitrogen and the resulting reaction mixture was heated at 80° C. for 1 h. Reaction mixture was concentrated under reduced pressure, the residue was diluted with water (100 mL) and was extracted with ethyl acetate (100 mL×2). Combined organics were dried over anhydrous $Na_2SO_4$ and concentrated under reduced pressure, to afford ethyl (E)-6-((hydroxyimino) methyl)nicotinate (X-1162A4) [2.60 g, 84% (crude)] as an off-white solid. MS: $[MH]^+$ 195.3.

Ethyl 6-(aminomethyl)nicotinate (X-1162A5). To a stirred solution of ethyl (E)-6-((hydroxyimino)methyl)nicotinate (X-1162A4) (2.60 g, 13.33 mmol) in a mixture of ethanol-water (9:1; 20 mL) were added Zinc powder (4.33 g, 66.61 mmol) and ammonium chloride (3.530 g, 66.60 mmol) sequentially at room temperature under nitrogen and the resulting mixture was heated at 80° C. for 1 h. Reaction mixture was filtered through celite bed, filtrate was concentrated in vacuo, resulting crude was diluted with water (100 mL) and was extracted with 10% methanol in dichloromethane (200 mL×2). Collected organic extracts were dried over anhydrous $Na_2SO_4$ and concentrated under reduced pressure to afford ethyl 6-(aminomethyl)nicotinate (X-1162A5) (1.60 g, 67%) as an off-white solid, which was carried forward to the next step without further purification. MS: $[MH]^+$ 181.3.

Ethyl 6-(formamidomethyl)nicotinate (X-1162A6). To a stirred solution of ethyl 6-(aminomethyl)nicotinate (X-1162A5) (1.60 g, 8.88 mmol) in formamide (16 mL) was added benzotriazole (0.105 g, 0.88 mmol) at room temperature under nitrogen and the resulting mixture was heated at 110° C. for 3 h. Reaction mixture was diluted with water (50 mL) and was extracted with 10% methanol in dichloromethane (50 mL×3). Combined organic extracts were dried over anhydrous $Na_2SO_4$ and concentrated in vacuo. The crude was purified by reverse phase (C-18) silica gel column chromatography using with water-acetonitrile=1:0→5:5 as a gradient to afford ethyl 6-(formamidomethyl)nicotinate (x-1162A6) (1.20 g, 65%) as an off-white solid. MS: $[MH]^+$ 209.4.

Ethyl imidazo[1,5-a]pyridine-6-carboxylate (X-1162A7). To a stirred solution of ethyl 6-(formamidomethyl)nicotinate (X-1162A6) (1.20 g, 5.76 mmol) in N,N-diethyl aniline (1.84 ml, 11.53 mmol) was added phosphorus oxychloride (10 mL) slowly at 0° C. under nitrogen and the resulting mixture was stirred at room temperature for 1 h. Reaction was cooled at 0° C. and basified basifed (pH~8-9) with an aqueous solution of saturated $NaHCO_3$ and was extracted with 10% methanol-dichloromethane (100 mL×2). Combined organic extracts were dried over anhydrous $Na_2SO_4$ and concentrated in vacuo to afford ethyl imidazo[1,5-a] pyridine-6-carboxylate (X-1162A7) [0.850 g, 77% (crude)] as a white solid, which was pure enough to proceed to the next step without further purification. MS: $[MH]^+$ 191.1.

Ethyl 1-bromoimidazo[1,5-a]pyridine-6-carboxylate (X-1162A8). To a stirred solution of ethyl imidazo[1,5-a] pyridine-6-carboxylate (X-1162A7) (0.820 g, 4.31 mmol) in dichloromethane (10 mL) was added n-bromosuccinimide (0.763 g, 4.31 mmol) at −78° C. under nitrogen and allowed stirred at −78° C. to −20° C. during 1 h. Reaction mixture was diluted with an aqueous saturated solution of $Na_2S_2O_4$ (30 mL) and was extracted with dichloromethane (100 mL×2). Combined extracts were dried over anhydrous $Na_2SO_4$ and concentrated in vacuo. The crude was purified by silica gel column chromatography with using ethyl acetate-hexane=0:1→1:4 to afford ethyl 1-bromoimidazo[1, 5-a]pyridine-6-carboxylate (X-1162A8) (0.450 g, 41%) as an off-white solid. MS: $[MH]^+$ 269.0: $[MH+2]^+$269.0.

Ethyl 1-(4-(tert-butyl)phenyl)imidazo[1,5-a]pyridine-6-carboxylate (X-1162A9). To a stirred solution of ethyl 1-bromoimidazo[1,5-a]pyridine-6-carboxylate (X-1162A8) (0.250 g, 0.93 mmol) in mixture of 1,4-dioxane-water (3:1, 6 mL) were added (4-(tert-butyl)phenyl)boronic acid (0.249 g, 1.39 mmol) and tripotassium phosphate (0.494 g, 2.33 mmol) at room temperature under nitrogen. The reaction mixture was degassed (purging with nitrogen) for 20 min followed by addition of $PdCl_2$(dppf). DCM (0.076 g, 0.09 mmol) and the resulting mixture was heated at 100° C. for 2 h. Reaction was diluted with water (50 mL) and was extracted with ethyl acetate (100 mL×2). Combined extracts were dried over anhydrous $Na_2SO_4$ and concentrated in vacuo. Obtained crude was purified by silica gel column chromatography, using ethyl acetate:hexane=0:1→2:8 as gradient, to afford ethyl 1-(4-(tert-butyl)phenyl)imidazo[1, 5-a]pyridine-6-carboxylate (X-1162A9) (0.150 g, 67%) as an off-white solid. MS: $[MH]^+$ 323.1.

1-(4-(tert-butyl)phenyl)imidazo[1,5-a]pyridine-6-carboxylic acid (I-144). To a stirred solution of ethyl 1-(4-(tert-butyl)phenyl)imidazo[1,5-a]pyridine-6-carboxylate (X-1162A9) (0.150 g, 0.46 mmol) in a mixture of THF-water (3:1; 5 mL) was added lithium hydroxide monohydrate (0.039 g, 0.92 mmol) at room temperature and stirred for 2 h at the same temperature. Volatiles were distilled off under reduced pressure, obtained crude was taken in water (100 mL) and was extracted with ethyl acetate (50 mL×2) to remove unwanted organic impurities. The aqueous layer was acidified (pH~2-3) with an aqueous solution of 1N HCl and the resulting precipitate was collected by filtration. Solid residue was washed with cold water until the pH of the filtrate became neutral (pH~6-7). Obtained solid was triturated with ethyl acetate (30 mL) and concentrated in vacuo to afford 1-(4-(tert-butyl)phenyl)imidazo[1,5-a]pyridine-6-carboxylic acid (I-144) (0.055 g, 32%) as a Yellow solid. $^1$H NMR (400 MHz, DMSO-$d_6$) δ 13.26 (br, 1H), 9.09 (s, 1H), 8.61 (s, 1H) 7.93-7.91 (d, J=9.6 Hz, 1H), 7.83-7.81 (d, J=8.4 Hz, 2H), 7.48-7.46 (d, J=8.4 Hz, 2H), 7.21-7.18 (d, J=9.6 Hz, 1H), 1.31 (s, 9H). MS: $[MH]^+$ 295.1.

Example 1.68. Synthesis of 3-(4-(tert-Butyl)phenyl)imidazo[1,5-a]pyridine-6-carboxylic acid (I-145)

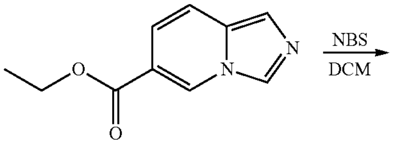

X-1162A7

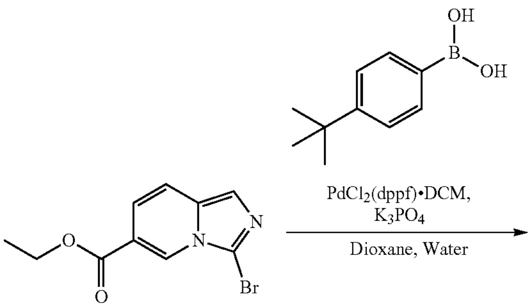

X-1162A8

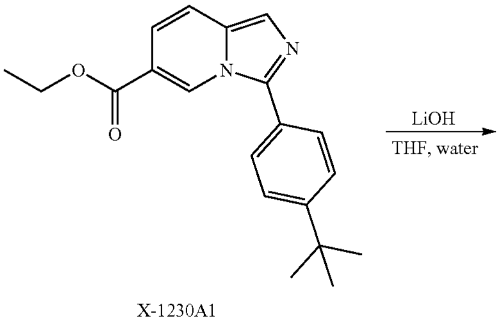

X-1230A1

-continued

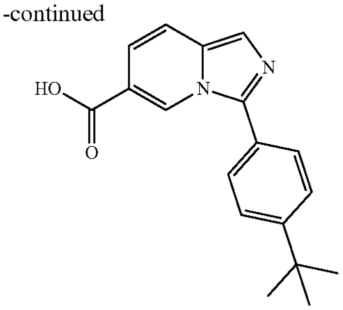

I-145

Ethyl 3-bromoimidazo[1,5-a]pyridine-6-carboxylate (X-1162A8). To a stirred solution of ethyl imidazo[1,5-a]pyridine-6-carboxylate (0.850 g, 4.47 mmol) in dichloromethane (10 mL) was added n-bromosuccinimide (0.763 g, 4.31 mmol) at −78° C. After completion of addition of NBS, the reaction temperature was brought to −20° C. and stirred for 1 h at the same temperature. Reaction was diluted with an aqueous solution of saturated $Na_2S_2O_4$ (50 mL) and was extracted with ethyl acetate (50 mL×3). Combined organic extracts were dried over anhydrous $Na_2SO_4$ and concentrated in vacuo. Obtained crude mass was purified by silica gel column chromatography, using ethyl acetate:hexane=0:1→1:4 as gradient, to afford ethyl 3-bromoimidazo[1,5-a]pyridine-6-carboxylate (X-1162A8) (0.195 g, 16%) as an off-white solid. MS: $[MH]^+$ 269.0/$[MH+2]^+$ 271.0.

Ethyl 3-(4-(tert-butyl)phenyl)imidazo[1,5-a]pyridine-6-carboxylate (X-1230A1). To a stirred solution of ethyl 3-bromoimidazo[1,5-a]pyridine-6-carboxylate (X-1162A8) (0.170 g, 0.634 mmol) in 1,4-dioxane-water (3:1, 6 mL) was added (4-(tert-butyl)phenyl)boronic acid (0.169 g, 0.94 mmol) and tripotassium phosphate (0.336 g, 1.58 mmol) at room temperature under nitrogen. The reaction mixture was degassed (purging with nitrogen) for 15 min followed by the addition of $PdCl_2$ (dppf). DCM (0.051 g, 0.06 mmol) and the resulting suspension was heated at 90° C. for 2 h. Reaction was diluted with water (30 mL) and was extracted with ethyl acetate (30 mL×2). Collected organic parts were dried over anhydrous $Na_2SO_4$ and concentrated in vacuo. Obtained crude residue was purified by silica gel column chromatography, using ethyl acetate:hexane=0:1→1:4 as gradient, to afford ethyl 3-(4-(tert-butyl)phenyl)imidazo[1,5-a]pyridine-6-carboxylate (X-1230A1) (0.140 g, 43%) as a white solid. MS: $[MH]^+$ 323.1.

3-(4-(tert-Butyl)phenyl)imidazo[1,5-a]pyridine-6-carboxylic acid (I-145). To a stirred solution of ethyl 3-(4-(tert-butyl)phenyl)imidazo[1,5-a]pyridine-6-carboxylate (X-1230A1) (0.140 g, 0.43 mmol) in a mixture of THE-water (3:1; 5 mL) was added lithium hydroxide monohydrate (0.036 g, 0.85 mmol) at room temperature and the resulting mixture was heated at 70° C. for 2 h. After cooling to room temperature, the reaction mixture was concentrated under reduced pressure, diluted with water (20 mL), and was extracted with ethyl acetate (30 mL×2) to remove unwanted organic impurities. The aqueous layer was acidified (pH~2-3) with aqueous 1N HCl and the resulting precipitate was collected by filtration. Solid residue was washed with cold water until the pH of the filtrate became neutral (pH~6-7). Obtained solid was dried under high vacuum to afford 3-(4-(tert-butyl)phenyl)imidazo[1,5-a]pyridine-6-carboxylic acid (I-145) (0.070 g, 43%) as an off-white solid. $^1$H NMR (400 MHz, DMSO-$d_6$) δ 13.33 (br, 1H), 8.86 (s, 1H), 7.77-7.75 (d, J=8.4 Hz, 2H), 7.69-7.67 (d, J=8.8 Hz, 1H), 7.64-7.61 (d, J=8.4 Hz, 2H), 7.60 (s, 1H), 7.18-7.15 (d, J=9.2 Hz, 1H), 1.35 (s, 9H). MS: $[MH]^+$ 295.11.

Example 1.69. Synthesis of N-(8-(4-(tert-Butyl)phenyl)imidazo[1,2-a]pyrazin-6-yl)acrylamide (I-146)

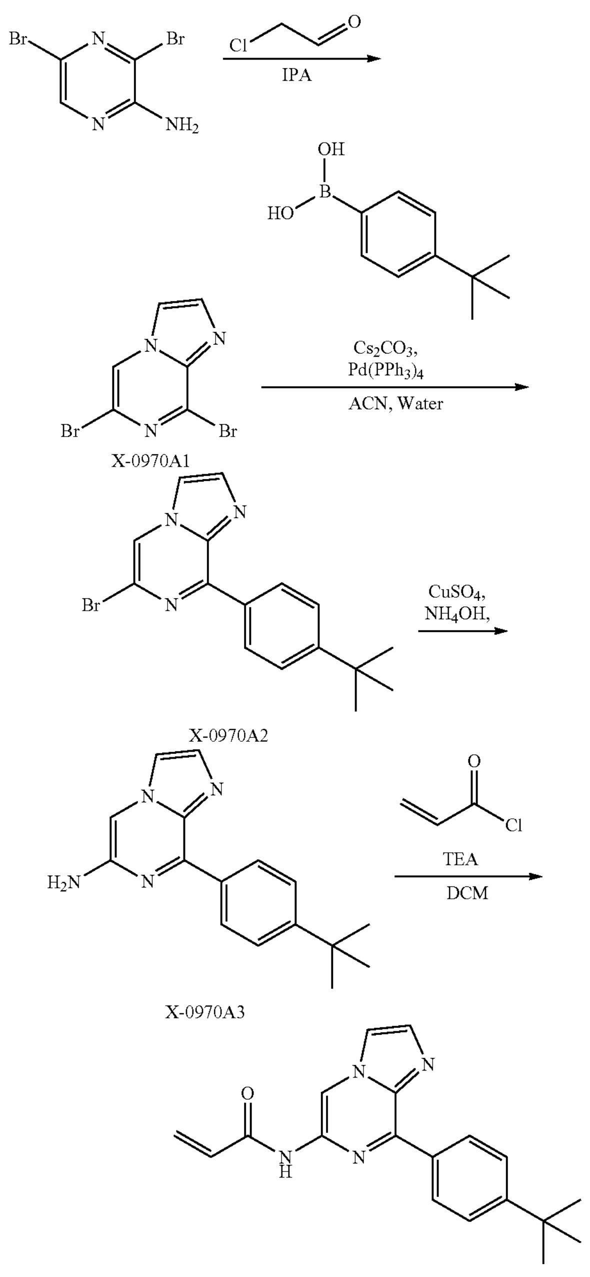

X-0970A1
X-0970A2
X-0970A3
I-146

6,8-Dibromoimidazo[1,2-a]pyrazine (X-0970A1). 2-chloroacetaldehyde (5.00 g, 63.70 mmol) was added to the stirred solution of 3,5-dibromopyrazin-2-amine (4.00 g, 15.93 mmol) in isopropanol (30 mL) at room temperature under nitrogen and the resulting mixture was heated at 110° C. for 16 h. After cooling to room temperature, reaction mixture was diluted with DCM (200 mL) and triethylamine (20 mL) and concentrated under reduced pressure. The crude product was purified by trituration, using n-pentane & diethyl ether to afford 6,8-dibromoimidazo[1,2-a]pyrazine (X-0970A1) [7.50 g, quant. (crude)] as a yellow solid, which was used in next step without further purification. MS: $[MH]^+$ 276.1.

6-Bromo-8-(4-(tert-butyl)phenyl)imidazo[1,2-a]pyrazine (X-0970A2). To a stirred solution of 6,8-dibromoimidazo[1,2-a]pyrazine (X-0970A1) (7.00 g, 25.43 mmol) and (4-(tert-butyl)phenyl)boronic acid (2.70 g, 15.24 mmol) in a mixture of acetonitrile-water (2.5:1, 35 mL) was added cesium carbonate (20.60 g, 63.60 mmol) at room temperature under nitrogen. The reaction mixture was degassed (purging with nitrogen) for 30 min followed by the addition of $Pd(PPh_3)_4$ (1.40 g, 1.27 mmol) at the same temperature and subjected to heat at 90° C. for 16 h. Reaction mixture was cooled to room temperature, crude mass was diluted with water (100 mL), filtered through a celite bed and the filtrate was extracted with ethyl acetate (100 mL×3). Combined organic extracts were dried over anhydrous $Na_2SO_4$ and concentrated under reduced pressure. Obtained crude was purified by reverse phase (C-18) silica gel column chromatography, using acetonitrile-water=0:1→1:0 as gradient, to afford 6-bromo-8-(4-(tert-butyl)phenyl)imidazo[1,2-a]pyrazine (X-0970A2) (2.00 g, 24%) as a white solid. MS: $[MH]^+$330.4/$[MH+2]^+$332.4.

8-(4-(tert-Butyl)phenyl)imidazo[1,2-a]pyrazin-6-amine (X-0970A3). Copper sulfate (0.291 g, 1.82 mmol) was added to a stirred suspension of 6-bromo-8-(4-(tert-butyl)phenyl)imidazo[1,2-a]pyrazine (X-0970A2) (0.400 g, 1.21 mmol) in $NH_4OH$ (40 mL) at room temperature under nitrogen in Parr Autoclave and the reaction mixture hydrogenated under 50 psi at 120° C. for 16 h. After cooling to room temperature, reaction mixture was diluted with water (50 mL) and was extracted with ethyl acetate (50 mL×3). Combined organic extracts were dried over anhydrous $Na_2SO_4$ and concentrated under reduced pressure to afford 8-(4-(tert-butyl)phenyl)imidazo[1,2-a]pyrazin-6-amine (X-0970A3) [0.500 g, quant. (crude)] as a yellow sticky solid. Isolated product was taken to the next step without further purification. MS: $[MH]^+$267.5.

N-(8-(4-(tert-butyl)phenyl)imidazo[1,2-a]pyrazin-6-yl)acrylamide (I-146). Acryloyl chloride (0.186 g, 2.06 mmol) and triethylamine (0.280 g, 2.81 mmol) were added sequentially to a stirred solution of 8-(4-(tert-butyl)phenyl)imidazo[1,2-a]pyrazin-6-amine (X-0970A3) (0.500 g, 1.87 mmol) in DCM (5 mL) at 0° C. under nitrogen and the reaction mixture was stirred at the same temperature for 15 min. Reaction mixture was quenched with water (50 mL) and was extracted with DCM (50 mL×3). Combined organic extracts were dried over anhydrous $Na_2SO_4$ and concentrated under reduced pressure. The crude was mass was purified by reverse phase (C-18) silica gel column chromatography, using acetonitrile-water=0:1→1:0 as gradient, to give N-(8-(4-(tert-butyl)phenyl)imidazo[1,2-a]pyrazin-6-yl)acrylamide (I-146) (0.040 g, 7%) as a yellow solid. $^1H$ NMR (400 MHz, DMSO-$d_6$) δ 11.02 (S, 1H), 9.47 (s, 1H), 8.49-8.47 (m, 3H), 8.03 (s, 1H), 7.64-7.62 (d, J=8.4 Hz, 2H), 6.74-6.67 (dd, J=16.8, 10.0 Hz, 1H), 6.38-6.34 (d, J=16.8 Hz, 1H), 5.85-5.83 (d, J=10.8 Hz, 1H), 1.36 (s, 9H). MS: $[MH]^+$ 321.4.

Example 1.70. Synthesis of 8-(4-(tert-Butyl)phenyl) imidazo[1,2-a]pyrazine-6-carboxylic acid (I-147)

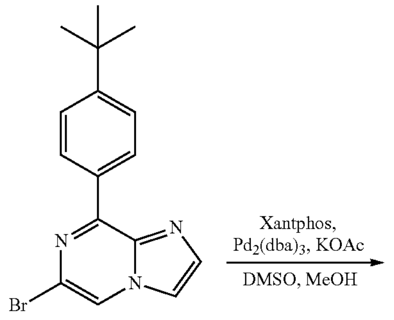

X-0970A2

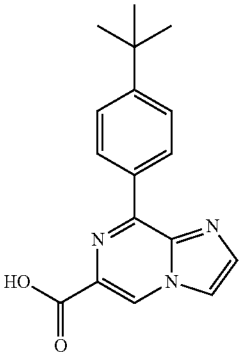

I-147

To a stirred solution of 6-bromo-8-(4-(tert-butyl)phenyl) imidazo[1,2-a]pyrazine (X-0972A2) (0.250 g, 0.75 mmol) in a mixture of DMSO-methanol (4:1; 8 mL) was added potassium acetate (0.223 g, 2.27 mmol) at room temperature under nitrogen. To this reaction mixture $CO_{(g)}$ was purged for 10 min followed by addition of Xantphos (0.030 g, 0.08 mmol) and $Pd_2(dba)_3$ (0.070 g, 0.07 mmol) at the same temperature and the resulting mixture was stirred under $CO_{(g)}$ for 1 h followed by heating at 120° C. for an additional 4 h. Reaction mixture was diluted with water (20 mL) and was extracted with dichloromethane (30 mL×2). Combined organic extracts were dried over anhydrous $Na_2SO_4$ and concentrated under reduced pressure. Obtained crude was purified by reverse phase (C-18) silica gel column chromatography with using acetonitrile-water=0:1→7:3 as gradient, to afford 8-(4-(tert-butyl)phenyl)imidazo[1,2-a]pyrazine-6-carboxylic acid (I-147) (0.030 g, 14%) as an off white solid. $^1H$ NMR (400 MHz, DMSO-$d_6$) 13.31 (br. s, 1H), 9.36 (s, 1H), 8.75-8.73 (d, J=8.4 Hz, 2H), 8.33 (s, 1H), 7.96 (s, 1H), 7.62-7.60 (d, J=8.4 Hz, 2H), 1.35 (s, 9H). MS: $[MH]^+$ 296.4.

Example 1.71. Synthesis of 8-(4-(tert-Butyl)phenyl) imidazo[1,2-a]pyrazin-6-ol (I-148)

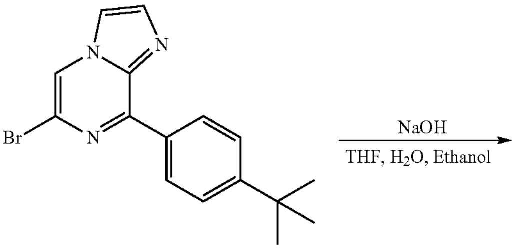

X-0970A2

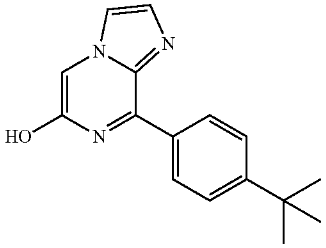

I-148

Sodium hydroxide (0.072 g, 1.82 mmol) was added to a stirred solution of 6-bromo-8-(4-(tert-butyl)phenyl)imidazo [1,2-a]pyrazine (X-0970A2) (0.300 g, 0.91 mmol) in a mixture of THF-ethanol-water (2:2:1, 5 mL) at room temperature and the resulting suspension was heated at 90° C. under microwave irradiation for 3 h. After cooling to room temperature, reaction mixture was diluted with water (20 mL) and was extracted with ethyl acetate (25 mL×3). Combined organic extracts were dried over anhydrous $Na_2SO_4$ and concentrated under reduced pressure. The crude product was purified by triturating with n-pentane & diethyl ether to afford 8-(4-(tert-butyl)phenyl)imidazo[1,2-a] pyrazin-6-ol (I-148) (0.014 g, 6%) as a yellow solid. $^1H$ NMR (400 MHz, DMSO-$d_6$) δ 13.28 (br. s, 1H), 7.97 (s, 1H), 7.82-7.80 (m, 3H), 7.53-7.51 (d, J=8.0 Hz, 2H), 7.14 (br. s, 1H), 1.33 (s, 9H). MS: $[MH]^+$ 268.4.

Example 1.72. Synthesis of 8-(4-(tert-Butyl)phenyl)-6-methoxyimidazo[1,2-a]pyrazine (I-149) and 8-(4-(tert-Butyl)phenyl)-5-methoxyimidazo[1,2-a] pyrazine (I-150)

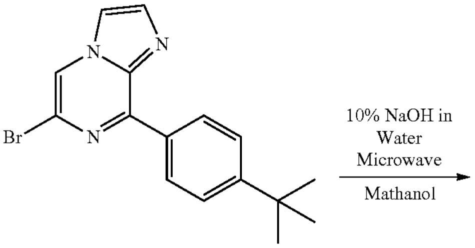

X-0970A2

-continued

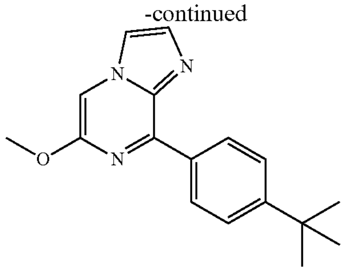

+

I-149

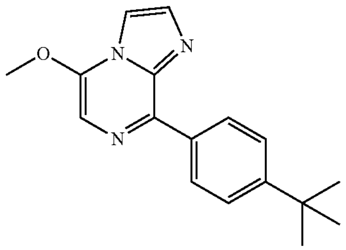

I-150

An aqueous solution of 10% NaOH (w/v; 4 mL) was added to a stirred solution of 6-bromo-8-(4-(tert-butyl)phenyl)imidazo[1,2-a]pyrazine (X-0970A2) (0.250 g, 0.76 mmol) in MeOH (12 mL) at room temperature and the resulting mixture was heated at 100° C. under microwave irradiation for 2 h. After cooling to room temperature, reaction mixture was diluted with water (50 mL) and was extracted with ethyl acetate (50 mL×3). Combined organic extracts were dried over anhydrous $Na_2SO_4$ and concentrated under reduced pressure. The product mass was combined with an identically prepared one more batch and the combined batches was purified by silica gel column chromatography using, ethyl acetate-hexane=1:9→1:1 as gradient to get rid of unwanted non-polar organic impurities followed by re-purification by reverse phase (C-18) silica gel column chromatography, using, acetonitrile-water=0:1→1:0 as gradient, to afford 8-(4-(tert-butyl)phenyl)-6-methoxyimidazo[1,2-a]pyrazine (I-149) (0.015 g) as an off-white & 8-(4-(tert-butyl)phenyl)-5-methoxyimidazo[1,2-a]pyrazine (I-150) (0.035 g) as a white solid (11%).

(I-149)$^1$H NMR (400 MHz, DMSO-$d_6$) δ 8.75-8.73 (d, J=8.4 Hz, 2H), 8.23 (s, 1H), 8.12 (s, 1H), 7.84 (s, 1H), 7.60-7.58 (d, J=8.4 Hz, 2H), 3.94 (s, 3H), 1.35 (s, 9H). MS: $[MH]^+$282.4.

(I-150)$^1$H NMR (400 MHz, DMSO-$d_6$) δ 8.63-8.61 (d, J=8.4 Hz, 2H), 8.05 (s, 1H), 7.86 (s, 1H), 7.72 (s, 1H), 7.56-7.54 (d, J=8.4 Hz, 2H), 4.22 (s, 3H), 1.34 (s, 9H); MS: $[MH]^+$ 282.5.

Example 1.73. Synthesis of Methyl (E)-3-(8-(4-(tert-butyl)phenyl)imidazo[1,2-a]pyrazin-6-yl)acrylate (I-151) and (E)-3-(8-(4-(tert-butyl)phenyl)imidazo[1,2-a]pyrazin-6-yl)acrylic acid (I-152)

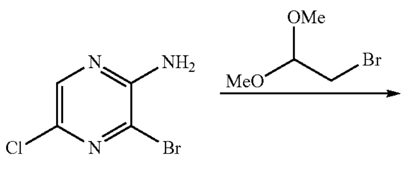

-continued

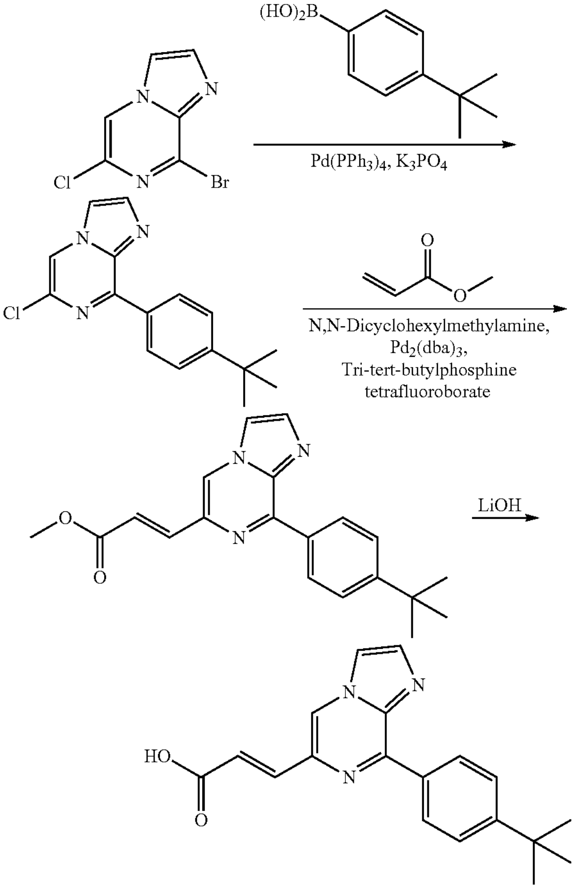

8-Bromo-6-chloroimidazo[1,2-a]pyrazine (LL-0913-062). To a solution of 3-bromo-5-chloropyrazin-2-amine (850 mg, 4.08 mmol) in ACN (15 mL) at room temperature was added 2-bromo-1,1-dimethoxyethane (690 mg, 4.08 mmol). The mixture was then heated in a microwave at 130° C. for 2 h. The mixture was filtered and the filtrate concentrated to afford 8-bromo-6-chloroimidazo[1,2-a]pyrazine (670 mg, 70%) as a white solid. $^1$H NMR (400 MHz, DMSO-$d_6$) δ 8.96 (s, 1H), 8.26 (d, J=1.2 Hz, 1H), 7.93 (d, J=1.2 Hz, 1H).

8-(4-(tert-Butyl)phenyl)-6-chloroimidazo[1,2-a]pyrazine (LL-0913-065). A mixture of 8-bromo-6-chloroimidazo[1,2-a]pyrazine (50 mg, 0.215 mmol), (4-(tert-butyl)phenyl) boronic acid (57 mg, 0.322 mmol), Pd(dppf)C12 (25 mg, 0.021 mmol), $K_3PO_4$ (91 mg, 0.430 mmol) in 1,4-dioxane (2 mL) was heated at reflux under $N_2$ for 6 hours. The mixture was diluted with water (10 mL) and extracted with EtOAc (30 mL×2). The combined organic layers were washed with brine, dried over $Na_2SO_4$, filtered and concentrated. The residue was purified by prep-TLC (DCM) to afford 8-(4-(tert-butyl)phenyl)-6-chloroimidazo[1,2-a]pyrazine (55 mg, 90% yield) as a white solid. $^1$H NMR (400 MHz, DMSO-$d_6$) δ 8.89 (d, J=2.0 Hz, 1H), 8.71-8.65 (m, 2H), 8.22 (dd, J=1.8, 1.0 Hz, 1H), 7.94 (d, J=1.0 Hz, 1H), 7.63-7.57 (m, 2H), 1.34 (s, 9H). LCMS m/z=286.0 $[M+H]^+$.

Methyl (E)-3-(8-(4-(tert-butyl)phenyl)imidazo[1,2-a]pyrazin-6-yl)acrylate (I-151). A mixture of 8-(4-(tert-butyl)phenyl)-6-chloroimidazo[1,2-a]pyrazine (500 mg, 1.75 mmol), methyl acrylate (226 mg, 2.62 mmol), N,N-Dicyclohexylmethylamine (342 mg, 0.174), $Pd_2(dba)_3$ (160 mg, 1.75 mmol), tri-tert-butylphosphine tetrafluoroborate (51 mg, 0.174 mmol) and 1,4-dioxane (5 mL) was heated at 120° C. under $N_2$ for 16 hours. The mixture was diluted with water (30 mL) and extracted with EtOAc (50 mL×3). The combined organic layers were washed with brine, dried over $Na_2SO_4$, filtered and concentrated. The residue was purified by column chromatography on silica gel (eluent: Pet. Ether: EtOAc=5:1) to afford methyl (E)-3-(8-(4-(tert-butyl)phenyl)imidazo[1,2-a]pyrazin-6-yl)acrylate (160 mg, 27% yield) as a yellow solid. $^1H$ NMR (400 MHz, DMSO-$d_6$) δ 8.91 (s, 1H), 8.74 (d, J=8.6 Hz, 2H), 8.24 (d, J=1.2 Hz, 1H), 7.89 (d, J=1.2 Hz, 1H), 7.78 (d, J=15.2 Hz, 1H), 7.61 (d, J=8.6 Hz, 2H), 6.99 (d, J=15.4 Hz, 1H), 3.77 (s, 3H), 1.35 (s, 9H). LCMS m/z=336.1 $[M+H]^+$.

(E)-3-(8-(4-(tert-Butyl)phenyl)imidazo[1,2-a]pyrazin-6-yl)acrylic acid (Example 19) (I-152). To a solution of methyl (E)-3-(8-(4-(tert-butyl)phenyl)imidazo[1,2-a]pyrazin-6-yl)acrylate (60 mg, 0.178 mmol) in a mixture of THF (2 mL), MeOH (0.5 mL) and water (0.5 mL) was added lithium hydroxide monohydrate (9 mg, 0.357 mmol). The reaction was heated at 40° C. for 4 h then diluted with water (20 mL) and extracted with EtOAc (30 mL). The aqueous layer was collected and acidified with 1M HCl to pH~2 then extracted with EtOAc (50 mL×3). The combined organic layers were washed with brine, dried over $Na_2SO_4$, filtered and concentrated. The crude product was purified by prep-HPLC to afford (E)-3-(8-(4-(tert-butyl)phenyl)imidazo[1,2-a]pyrazin-6-yl)acrylic acid (5 mg, 8%) as a yellow solid. $^1H$ NMR (400 MHz, DMSO-$d_6$) δ 8.87 (s, 1H), 8.75-8.69 (m, 2H), 8.22 (d, J=1.2 Hz, 1H), 7.88 (d, J=1.2 Hz, 1H), 7.68 (d, J=15.2 Hz, 1H), 7.62-7.57 (m, 2H), 6.92 (d, J=15.2 Hz, 1H), 1.35 (s, 9H). LCMS m/z=322.0 $[M+H]^+$.

Example 1.74. Synthesis of 3-(8-(4-(tert-Butyl)phenyl)imidazo[1,2-a]pyrazin-6-yl)propanoic acid (I-153)

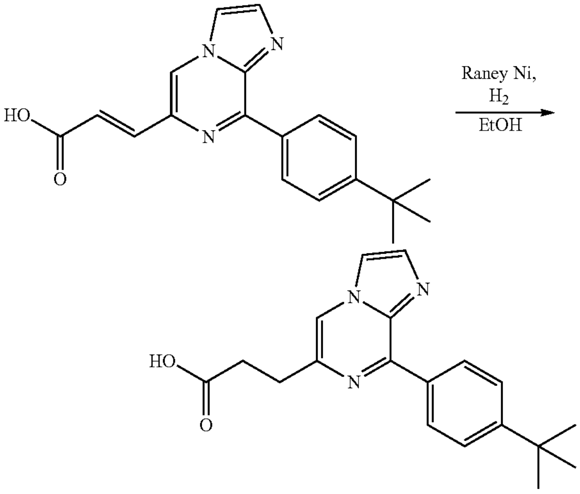

To a solution of (E)-3-(8-(4-(tert-butyl)phenyl)imidazo[1,2-a]pyrazin-6-yl)acrylic acid (60 mg, 0.186 mmol) in EtOH (1 mL) at room temperature was added Raney nickel (6 mg). The mixture was stirred under $H_2$ for 16 h at room temperature. The mixture was filtered, the filtrate concentrated and the crude product purified by prep-HPLC to afford 3-(8-(4-(tert-butyl)phenyl)imidazo[1,2-a]pyrazin-6-yl)propanoic acid (I-153) (10 mg, 16%) as a white solid. $^1H$ NMR (400 MHz, DMSO-$d_6$) δ 8.68 (d, J=8.4 Hz, 2H), 8.45 (s, 1H), 8.14 (s, 1H), 7.84 (s, 1H), 7.57 (d, J=8.4 Hz, 2H), 3.00 (t, J=7.2 Hz, 2H), 2.75 (t, J=7.2 Hz, 2H), 1.35 (s, 9H). LCMS m/z=324.1 $[M+H]^+$.

Example 1.75. Synthesis of (E)-3-(8-(4-(tert-Butyl)phenyl)imidazo[1,2-a]pyrazin-6-yl)acrylonitrile (I-154)

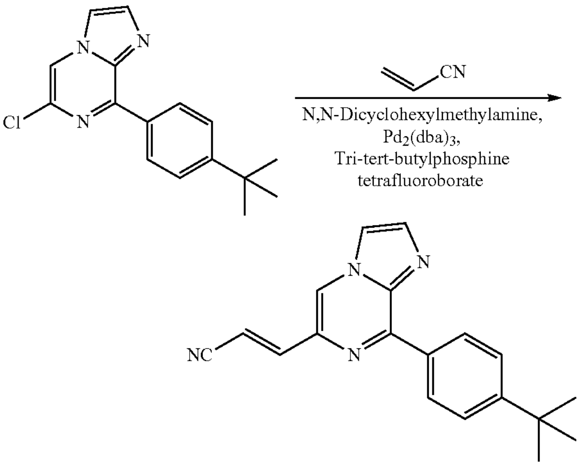

(E)-3-(8-(4-(tert-butyl)phenyl)imidazo[1,2-a]pyrazin-6-yl)acrylonitrile was synthesized from 8-(4-(tert-butyl)phenyl)-6-chloroimidazo[1,2-a]pyrazine according to the procedures outlined for methyl (E)-3-(8-(4-(tert-butyl)phenyl)imidazo[1,2-a]pyrazin-6-yl)acrylate (I-152) using the appropriate commercially available reagents. $^1H$ NMR (400 MHz, DMSO-$d_6$) δ 8.79 (s, 1H), 8.77-8.74 (m, 2H), 8.30 (d, J=1.2 Hz, 1H), 7.90 (d, J=1.2 Hz, 1H), 7.85-7.77 (m, 1H), 7.61-7.56 (m, 2H), 6.76 (dd, J=15.8, 0.5 Hz, 1H), 1.35 (s, 9H). LCMS m/z=303.0 $[M+H]^+$.

Example 1.76. Synthesis of (E)-6-(2-(1H-tetrazol-5-yl)vinyl)-8-(4-(tert-butyl)phenyl)imidazo[1,2-a]pyrazine (I-155)

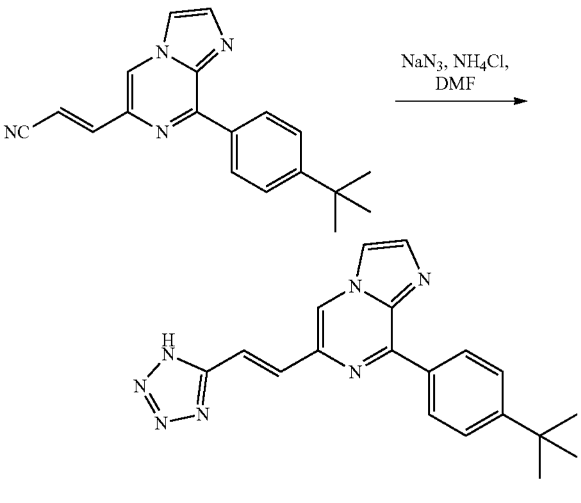

(E)-6-(2-(1H-tetrazol-5-yl)vinyl)-8-(4-(tert-butyl)phenyl)imidazo[1,2-a]pyrazine was synthesized from (E)-3-(8-(4-

(tert-butyl)phenyl)imidazo[1,2-a]pyrazin-6-yl)acrylonitrile according to the procedures outlined for 4-(4-(tert-butyl)phenyl)-7-(1H-tetrazol-5-yl)imidazo[1,2-a]quinoxaline (I-76) using the appropriate commercially available reagents. $^1$H NMR (400 MHz, DMSO-$d_6$) δ 8.85 (s, 1H), 8.77 (d, J=8.2 Hz, 2H), 8.25-8.22 (m, 1H), 7.89-7.87 (m, 1H), 7.75 (s, 2H), 7.62 (d, J=8.4 Hz, 2H), 1.36 (s, 9H). LCMS m/z=346.1 $[M+H]^+$.

Example 1.77. Synthesis of 6-(2-(1H-tetrazol-5-yl)ethyl)-8-(4-(tert-butyl)phenyl)imidazo[1,2-a]pyrazine (I-156)

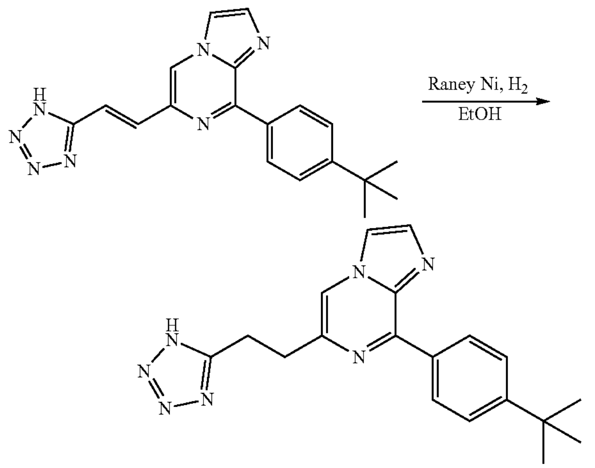

To a solution of (E)-6-(2-(1H-tetrazol-5-yl)vinyl)-8-(4-(tert-butyl)phenyl)imidazo[1,2-a]pyrazine (110 mg, 0.318 mmol) in EtOH (4 mL) at room temperature was added Raney nickel (22 mg). The mixture was stirred under $H_2$ for 16 h at room temperature. The mixture was filtered, the filtrate concentrated and the residue purified by prep-HPLC to afford 6-(2-(1H-tetrazol-5-yl)ethyl)-8-(4-(tert-butyl)phenyl)imidazo[1,2-a]pyrazine (5 mg, 4%) as a white solid. $^1$H NMR (400 MHz, DMSO-$d_6$) δ 8.64 (d, J=8.2 Hz, 2H), 8.43 (s, 1H), 8.12 (s, 1H), 7.82 (s, 1H), 7.56 (d, J=8.0 Hz, 2H), 3.43-3.34 (m, 2H), 3.25-3.16 (m, 2H), 1.35 (s, 9H). LCMS m/z=348.2 $[M+H]^+$.

Example 1.78. Synthesis of 3-(4-(tert-Butyl)phenyl)quinoxaline-6-carboxylic acid (I-157

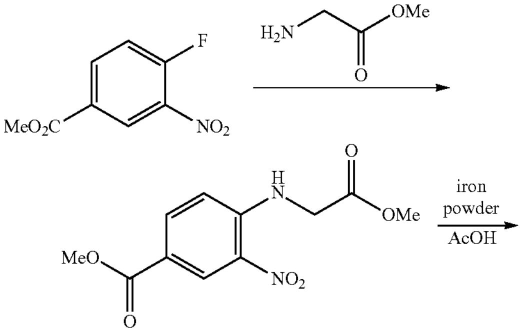

-continued

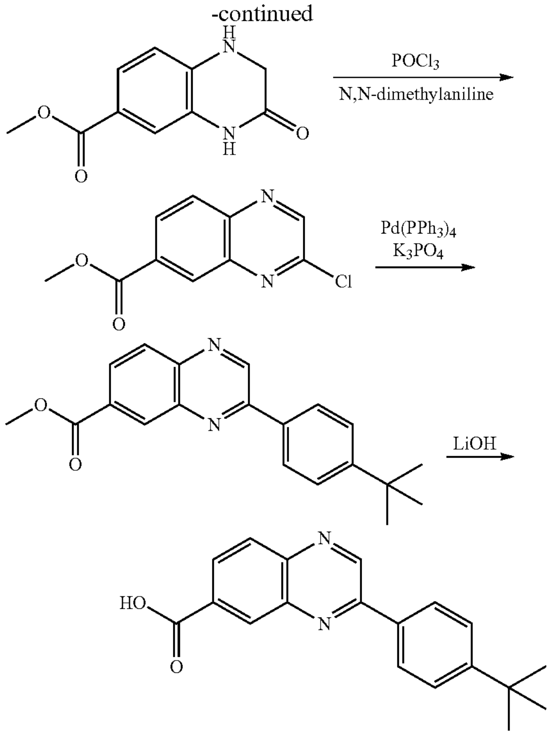

Methyl 4-((2-methoxy-2-oxoethyl)amino)-3-nitrobenzoate. To a solution of methyl 4-fluoro-3-nitrobenzoate (4 g, 0.02 mol) in ACN (40 mL) was added DIEA (13 g, 0.1 mol) and methyl glycinate (1.8 g, 0.02 mol). The reaction mixture was heated at 60° C. overnight. The mixture was diluted with water (100 mL) and extracted with EtOAc (150 mL×2). The combined organic layers were washed with brine, dried over $Na_2SO_4$, filtered and concentrated to afford methyl 4-((2-methoxy-2-oxoethyl)amino)-3-nitrobenzoate (2.3 g, 43%) as a yellow solid. $^1$H NMR (400 MHz, DMSO-$d_6$) δ 8.75 (t, J=5.8 Hz, 1H), 8.64 (d, J=2.0 Hz, 1H), 7.97 (dd, J=9.0, 2.0 Hz, 1H), 7.04 (d, J=9.0 Hz, 1H), 4.36 (d, J=5.8 Hz, 2H), 3.83 (s, 3H), 3.71 (s, 3H). LCMS m/z=269.1 $[M+H]^+$.

Methyl 3-oxo-1,2,3,4-tetrahydroquinoxaline-6-carboxylate. To a solution of methyl 4-((2-methoxy-2-oxoethyl)amino)-3-nitrobenzoate (1 g, 3.7 mmol) in AcOH (10 mL) was added iron powder (900 mg, 14.9 mmol). The reaction mixture was heated at reflux for 3 h. The mixture was diluted with water (30 mL) and extracted with EtOAc (50 mL×2). The combined organic layers were washed with brine, dried over $Na_2SO_4$, filtered and concentrated to afford methyl 3-oxo-1,2,3,4-tetrahydroquinoxaline-6-carboxylate (450 mg, 59%) as a yellow solid. $^1$H NMR (400 MHz, DMSO-$d_6$) δ 10.40 (s, 1H), 7.39 (dd, J=8.2, 1.8 Hz, 1H), 7.33 (d, J=1.8 Hz, 1H), 6.74 (s, 1H), 6.64 (d, J=8.2 Hz, 1H), 3.87 (s, 2H), 3.74 (s, 3H). LCMS m/z=207.1 $[M+H]^+$.

Methyl 3-chloroquinoxaline-6-carboxylate. To a solution of methyl 3-oxo-1,2,3,4-tetrahydroquinoxaline-6-carboxylate (450 mg, 2.18 mmol) in DMA (5 mL) was added $POCl_3$ (2.3 g, 15.2 mmol). The reaction mixture heated at reflux for 1 h. The mixture was diluted with water (20 mL) and extracted with EtOAc (30 mL×2). The combined organic layers were washed with brine, dried over $Na_2SO_4$, filtered and concentrated. The residue was purified by prep-TLC (Pet. Ether:EtOAc=5:1) to afford methyl 3-chloroquinoxaline-6-carboxylate (280 mg, 57%) as a yellow solid. $^1$H NMR (400 MHz, DMSO-$d_6$) δ 9.12 (s, 1H), 8.54 (dd, J=1.8, 0.6 Hz, 1H), 8.34 (dd, J=8.8, 1.8 Hz, 1H), 8.27 (d, J=8.8 Hz, 1H), 3.96 (s, 3H). LCMS m/z=223.1 $[M+H]^+$.

Methyl 3-(4-(tert-butyl)phenyl)quinoxaline-6-carboxylate. To a solution of methyl 3-chloroquinoxaline-6-carboxylate (280 mg, 1.25 mmol) in 1,4-dioxane (5 mL) was added (4-(tert-butyl)phenyl)boronic acid (340 mg, 1.88 mmol), $K_3PO_4$ (530 mg, 2.5 mmol) and $Pd(PPh_3)_4$ (150 mg, 0.125 mmol). The reaction mixture was heated at reflux under $N_2$ overnight. The mixture was diluted with water (30 mL) and extracted with EtOAc (50 mL×2). The combined organic layers were washed with brine, dried over $Na_2SO_4$, filtered and concentrated. The residue obtained was purified by prep-TLC (Pet. Ether:EtOAc=20:1) to afford methyl 3-(4-(tert-butyl)phenyl)quinoxaline-6-carboxylate (150 mg, 37%) as a yellow solid. $^1H$ NMR (400 MHz, DMSO-$d_6$) δ 9.68 (s, 1H), 8.66 (dd, J=1.8, 0.6 Hz, 1H), 8.31 (d, J=1.8 Hz, 1H), 8.30-8.28 (m, 1H), 8.26 (d, J=1.8 Hz, 1H), 8.23 (d, J=0.6 Hz, 1H), 7.64 (d, J=8.4 Hz, 2H), 3.97 (s, 3H), 1.36 (s, 9H). LCMS m/z=321.2 $[M+H]^+$.

3-(4-(tert-Butyl)phenyl)quinoxaline-6-carboxylic acid (I-157). To a solution of methyl 3-(4-(tert-butyl)phenyl) quinoxaline-6-carboxylate (150 mg, 0.46 mmol) in a mixture of THE and $H_2O$ (8 mL/2 mL) was added LiOH (80 mg). The reaction mixture was stirred at room temperature for 2 h then diluted with water (30 mL) and extracted with ether (50 mL). The aqueous layer was collected, acidified to pH~2 with 1M HCl and extracted with EtOAc (50 mL×3). The combined organic layers were washed with brine, dried over $Na_2SO_4$, filtered and concentrated to afford 3-(4-(tert-butyl)phenyl)quinoxaline-6-carboxylic acid (80 mg, 57%) as a white solid. $^1H$ NMR (400 MHz, DMSO-$d_6$) δ 13.49 (s, 1H), 9.66 (s, 1H), 8.64 (d, J=1.6 Hz, 1H), 8.32-8.24 (m, 3H), 8.19 (d, J=8.6 Hz, 1H), 7.66-7.62 (m, 2H), 1.36 (s, 9H). LCMS m/z=307.2 $[M+H]^+$.

Example 1.79. Synthesis of 3-(4-(tert-Butyl)phenyl) quinoxaline-6-carboxamide (I-158)

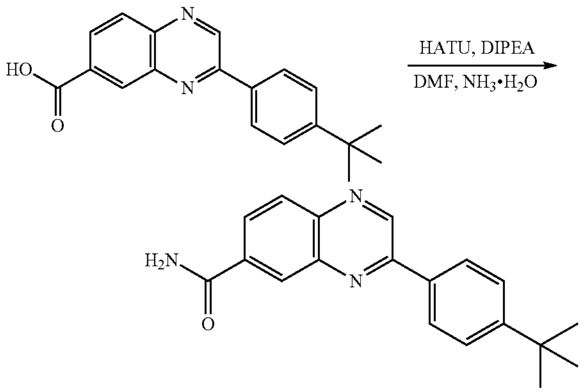

3-(4-(tert-butyl)phenyl)quinoxaline-6-carboxamide was synthesized from 3-(4-(tert-butyl)phenyl)quinoxaline-6-carboxylic acid according to the procedures outlined for 4-(4-(tert-butyl)phenyl)imidazo[1,2-a]quinoxaline-7-carboxamide (I-73) using the appropriate commercially available reagents. $^1H$ NMR (400 MHz, DMSO-$d_6$) δ 9.63 (s, 1H), 8.67 (d, J=1.8 Hz, 1H), 8.38 (s, 1H), 8.32-8.22 (m, 3H), 8.16 (d, J=8.6 Hz, 1H), 7.70-7.59 (m, 3H), 1.36 (s, 9H). LCMS m/z=306.3 $[M+H]^+$.

Example 1.80. Synthesis of 3-(4-(tert-butyl)phenyl) quinoxaline-6-carbonitrile (I-159)

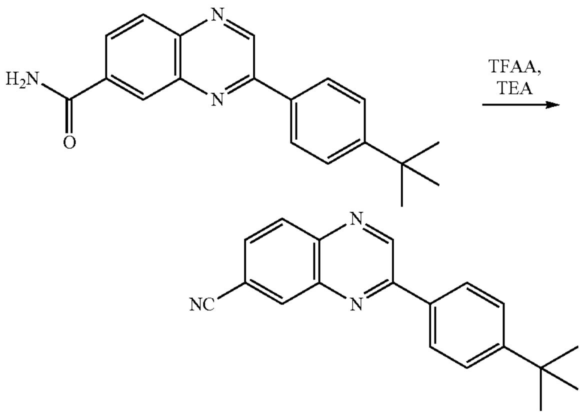

3-(4-(tert-butyl)phenyl)quinoxaline-6-carbonitrile was synthesized from 3-(4-(tert-butyl)phenyl)quinoxaline-6-carboxamide according to the procedures outlined for 4-(4-(tert-butyl)phenyl)imidazo[1,2-a]quinoxaline-7-carbonitrile (I-75) using the appropriate commercially available reagents. $^1H$ NMR (400 MHz, DMSO-$d_6$) δ 9.72 (s, 1H), 8.73 (d, J=1.6 Hz, 1H), 8.29 (dd, J=12.4, 8.4 Hz, 3H), 8.13 (dd, J=8.4, 1.8 Hz, 1H), 7.65 (d, J=8.2 Hz, 2H), 1.36 (s, 9H). LCMS m/z=288.3 $[M+H]^+$.

Example 1.81. Synthesis of 2-(4-(tert-Butyl)phenyl)-7-(1H-tetrazol-5-yl)quinoxaline (I-160)

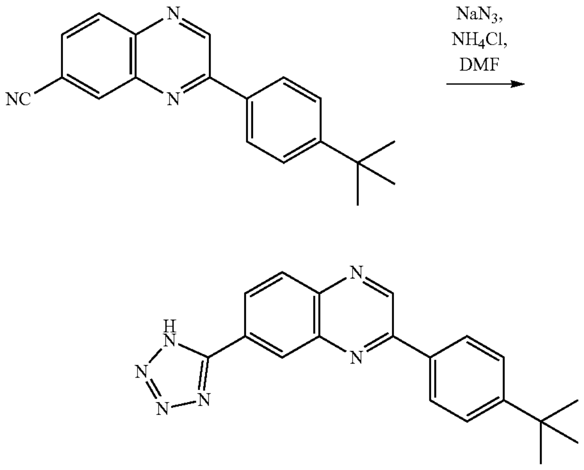

2-(4-(tert-butyl)phenyl)-7-(1H-tetrazol-5-yl)quinoxaline was synthesized from 3-(4-(tert-butyl)phenyl)quinoxaline-6-carbonitrile according to the procedures outlined for 4-(4-(tert-butyl)phenyl)-7-(1H-tetrazol-5-yl)imidazo[1,2-a]quinoxaline (I-76) using the appropriate commercially available reagents. $^1H$ NMR (400 MHz, DMSO-$d_6$) δ 9.66 (s, 1H), 8.79 (d, J=1.8 Hz, 1H), 8.45 (dd, J=8.6, 1.8 Hz, 1H), 8.32 (dd, J=8.6, 1.8 Hz, 3H), 7.66 (d, J=8.6 Hz, 2H), 1.36 (s, 9H). LCMS m/z=331.2 $[M+H]^+$.

Example 1.82. Synthesis of 4-methoxy-2-(4-(trifluoromethyl)phenyl)quinoline-7-carboxylic acid (I-181)

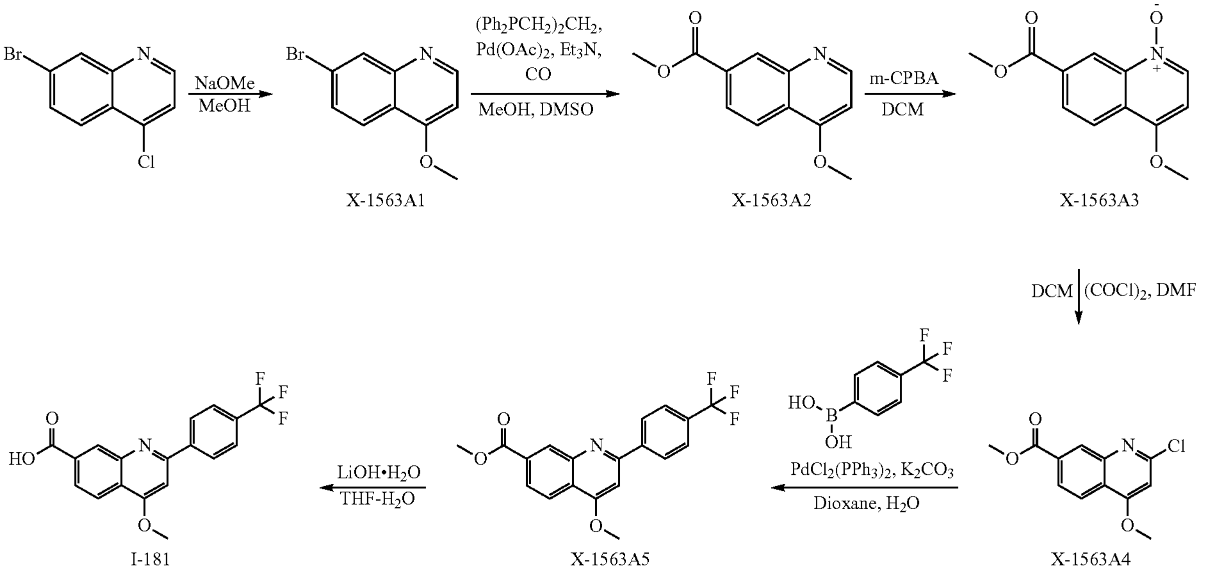

7-bromo-4-methoxyquinoline (X-1563A1). To a stirred solution of 7-bromo-4-chloroquinoline (20.0 g, 83.02 mmol) in methanol (200 mL) was added sodium methoxide (13.3 g, 24.7 mmol) portion wise over the period of 30 min at 0° C. under nitrogen. After 10 min of stirring at room temperature, the reaction mixture was stirred to 65° C. for 6 h. The reaction mixture was cooled to room temperature and solvent was distilled off under reduced pressure. The obtained crude residue was taken in water (500 mL), stirred for 20 min at room temperature, and filtered over a Buchner funnel. The residue was washed with water (100 mL) and dried under high vacuum to afford 7-bromo-4-methoxyquinoline (X-1563A1) (18.0 g, 91.5% (crude)) as an off-white solid. MS: $[MH]^+$ 237.9.

Methyl 4-methoxyquinoline-7-carboxylate (X-1563A2). Triethylamine (105 mL, 75.90 mmol) was added to a stirred solution of 7-bromo-4-methoxyquinoline (X-1563A1) (18.0 g, 75.94 mmol) in a mixture of MeOH-DMSO (1:1; 864 mL) at room temperature in a Parr autoclave, and the resulting solution was degassed with nitrogen for 20 min. To this degassed solution were added 1,3-bis(diphenylphosphino) propane (6.26 g, 15.19 mmol) and $Pd(OAc)_2$ (3.39 g, 15.20 mmol) sequentially and the resulting mixture was heated at 70° C. under pressure under carbon monoxide at 200 psi for 16 h. After cooling to room temperature, reaction mixture was concentrated under reduced pressure, and the obtained crude was diluted with water (500 mL) and was extracted with ethyl acetate (300 mL×3). Combined organic layers were washed with water (100 mL×2), dried over $Na_2SO_4$, and concentrated under reduced pressure. The resulting crude was purified by silica gel (100-200 mesh) column chromatography, using ethyl acetate-hexane=3:17 as gradient, to afford methyl 4-methoxyquinoline-7-carboxylate (X-1563A2) (13.5 g, 81.9%) as an off white solid. MS: $[MH]^+$ 217.9.

4-methoxy-7-(methoxycarbonyl)quinoline 1-oxide (X-1563A3). To a stirred solution of methyl 4-methoxyquinoline-7-carboxylate (X-1563A2) (13.5 g, 62.21 mmol) in DCM (272 mL) was added m-CPBA (21.6 g, 125.14 mmol) portion-wise at 0° C. under nitrogen and stirred for 4 h at room temperature. The reaction mixture was diluted with water (500 mL), stirred for 20 min and was extracted with DCM (100 mL×2). Combined organic extracts were dried over anhydrous $Na_2SO_4$ and concentrated under reduced pressure. Combined organic extracts were washed with water, an aqueous solution of saturated $NaHCO_3$ (200 mL), dried over anhydrous $Na_2SO_4$, and concentrated in vacuo. The obtained residue was triturated with n-hexane (100 mL×2) followed by 2% ethyl acetate in n-hexanes (100 mL) and filtered over a Buchner funnel. Obtained solid was further dried under high vacuum to afford 4-methoxy-7-(methoxycarbonyl)quinoline 1-oxide (X-1563A3) (11.0 g, 75.8%) as a yellow solid. MS: $[MH]^+$233.9.

Methyl 2-chloro-4-methoxyquinoline-7-carboxylate (X-1563A4). A solution of oxalyl chloride (18 g, 141.84 mmol) in DCM (83 mL) was added drop-wise to a stirred solution of 4-methoxy-7-(methoxycarbonyl)quinoline 1-oxide (X-1563A3) (11.0 g, 47.21 mmol) in DMF (165 mL) at 0° C. under nitrogen, and the resulting reaction mixture was heated to 50° C. for 2 h. After cooling to room temperature, the reaction mixture was quenched in ice-water (200 mL) and was extracted with DCM (100 mL×2). Combined organic extracts were washed with water (200 mL×2) followed by an aqueous solution of saturated $NaHCO_3$ (200 mL), dried over anhydrous $Na_2SO_4$, and concentrated under reduced pressure. The resulting crude was purified by silica gel (100-200 mesh) column chromatography, using ethyl acetate-hexane=03:97 as gradient, to afford methyl 2-chloro-4-methoxyquinoline-7-carboxylate (X-1563A4) (8.0 g, 67.5%) as an off white solid. MS: $[MH]^+$ 251.9.

Methyl 4-methoxy-2-(4-(trifluoromethyl)phenyl)quinoline-7-carboxylate (X-1563A5). To a stirred solution of methyl 2-chloro-4-methoxyquinoline-7-carboxylate (X-1563A4) (8.0 g, 31.87 mmol) in a mixture of 1,4-ioxanewater (10:1; 165 mL) were added (4-(trifluoromethyl)phenyl)boronic acid (13.3 g, 70.11 mmol) and $K_2CO_3$ (13.2 g, 95.61 mmol) at room temperature, and the resulting suspension was degassed with nitrogen for 30 min. $PdCl_2(PPh_3)_2$ (2.23 g, 3.18 mmol) was added to the reaction mixture, and the resulting suspension was stirred at 100° C. for 2 h. The reaction mixture was quenched with water (200 mL) and was extracted with ethyl acetate (200 mL×3). Combined organic extracts were dried over anhydrous $Na_2SO_4$ and concentrated under reduced pressure. The resulting crude was purified by silica gel (100-200 mesh) column chromatography, using ethyl acetate-hexane=1:49 as gradient, to afford methyl 4-methoxy-2-(4-(trifluoromethyl)phenyl)quinoline-7-carboxylate (X-1563A5) (8.0 g, 69.5%) as an off-white solid. MS: $[MH]^+$ 361.9.

4-methoxy-2-(4-(trifluoromethyl)phenyl)quinoline-7-carboxylic acid (I-181). A solution of LiOH·$H_2O$ (1.86 g, 44.32) in water (80 mL) was added to a stirred solution of methyl 4-methoxy-2-(4-(trifluoromethyl)phenyl)quinoline-7-carboxylate (X-1563A5) (8 g, 22.16 mmol) in THE (80 mL) and stirred for 16 h at room temperature. The reaction mixture was concentrated under reduced pressure to get rid of THF, aqueous part was extracted ethyl acetate (50 mL×2). Organic part was discarded and aqueous part was acidified (pH~2) with an aqueous solution of 1N HCl, during which a solid mass was precipitated out, which was filtered over a Buchner funnel. Residue was washed with n-hexanes (50 mL) and dried under high vacuum to afford 4-methoxy-2-(4-(trifluoromethyl)phenyl)quinoline-7-carboxylic acid (I-181) (6.5 g, 84.5%) as a white solid. $^1H$ NMR (400 MHz, DMSO-$d_6$)-δ 13.36 (s, 1H), 8.56-8.56 (d, J=1.2 Hz, 1H), 8.53-8.51 (d, J=8.0 Hz, 2H), 8.23-8.21 (d, J=8.8 Hz, 1H), 8.04-8.02 (dd, J=8.4 Hz, 1.6 Hz, 1H), 7.93-7.91 (d, J=8.0 Hz, 2H), 7.72 (s, 1H), 4.20 (s, 3H). MS: $[MH]^+$ 347.9.

Example 1.83. Synthesis of 4-(4-(2,2,2-Trifluoroethyl)piperidin-1-yl)pyrrolo[1,2-a]quinoxaline-7-carboxylic acid (I-182)

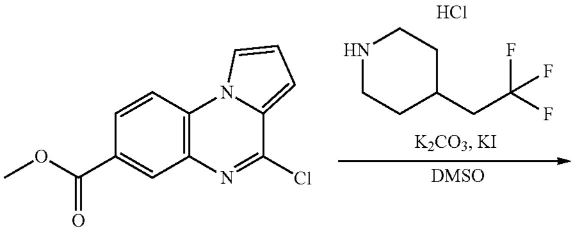

X-1109A3

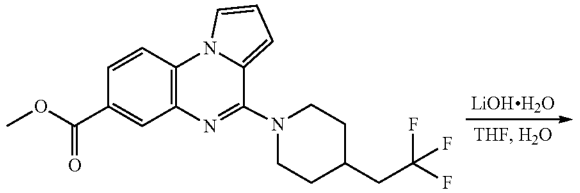

X-1249A1

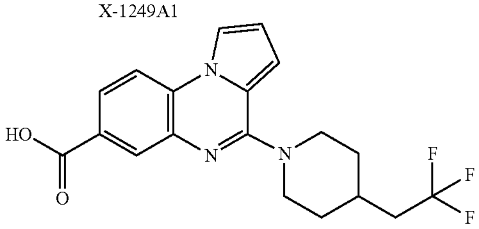

I-182

Methyl 4-chloropyrrolo[1,2-a]quinoxaline-7-carboxylate (X-1109A3) prepared as described in Example 1.2

Methyl 4-(4-(2,2,2-trifluoroethyl)piperidin-1-yl)pyrrolo[1,2-a]quinoxaline-7-carboxylate (X-1249A1). To a stirred solution of methyl 4-chloropyrrolo[1,2-a]quinoxaline-7-carboxylate (X-1109A3) (0.200 g, 0.76 mmol) in DMSO (3 mL) were added potassium carbonate (0.310 g, 2.30 mmol), potassium iodide (0.025 g, 0.15 mmol) and 4-(2,2,2-trifluoroethyl)piperidine hydrochloride (0.150 g, 0.76 mmol) sequentially at room temperature under nitrogen and the resulting mixture was heated at 100° C. for 16 h. Reaction mixture was cooled to room temperature, quenched with water (100 mL) and was extracted with ethyl acetate (75 mL×3). Collected organics were washed with brine (150 mL), dried over anhydrous $Na_2SO_4$ and concentrated in vacuo. The resulting crude was purified by silica gel column chromatography, using ethyl acetate-hexane=0:141:9 as gradient, to afford methyl 4-(4-(2,2,2-trifluoroethyl)piperidin-1-yl)pyrrolo[1,2-a]quinoxaline-7-carboxylate (X-1249A1) (0.290 g, 96%) as a yellow solid. MS: [MH]+ 392.27.

4-(4-(2,2,2-Trifluoroethyl)piperidin-1-yl)pyrrolo[1,2-a]quinoxaline-7-carboxylic acid (I-182). To a stirred solution of methyl 4-(4-(2,2,2-trifluoroethyl)piperidin-1-yl)pyrrolo[1,2-a]quinoxaline-7-carboxylate (X-1249A1) (0.290 g, 0.74 mmol) in a mixture of THF-water (3:1; 4.0 mL) was added lithium hydroxide monohydrate (0.093 g, 2.22 mmol) at room temperature and the resulting mixture was stirred at 70° C. for 1 h. Reaction mixture was concentrated under reduced pressure, obtained crude was acidified (pH~2-3) with an aqueous solution of 1N HCl and extracted with ethyl acetate (50 mL×2). Combined organic extracts were dried over anhydrous $Na_2SO_4$ and concentrated in vacuo. The resulting crude was purified by reverse phase column chromatography, using acetonitrile-water=0:144:6 as gradient, to afford 4-(4-(2,2,2-trifluoroethyl)piperidin-1-yl)pyrrolo[1,2-a]quinoxaline-7-carboxylic acid (I-182) (0.200 g, 70%) as a white solid. $^1H$ NMR (400 MHz, DMSO-$d_6$) δ 8.23-8.23 (d, J=2.0 Hz, 1H), 8.04-8.04 (d, J=1.6 Hz, 1H), 7.94-7.92 (d, J=8.4 Hz, 1H), 7.80-7.78 (dd, J=8.4, 1.6 Hz, 1H), 6.85-6.84 (d, J=3.2 Hz, 1H), 6.78-6.77 (t, J=2.8 Hz, 1H), 4.39-4.36 (d, J=13.2 Hz, 2H), 3.05-2.99 (t, J=11.6 Hz, 2H), 2.35-2.24 (m, 2H), 1.96-1.85 (m, 3H), 1.53-1.44 (m, 2H). (Acid proton missing due to moisture content in DMSO-$d_6$) MS: $[MH]^+$ 378.12.

Example 1.84. Synthesis of 4-(8-azabicyclo[3.2.1]octan-8-yl)pyrrolo[1,2-a]quinoxaline-7-carboxylic acid (I-183)

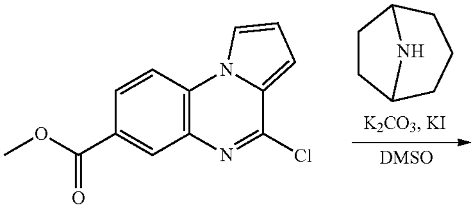

X-1109A3

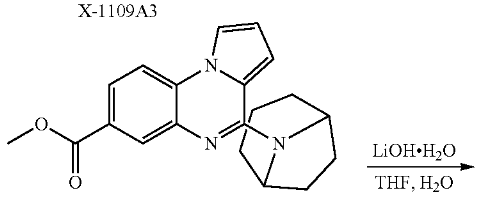

X-1338A1

-continued

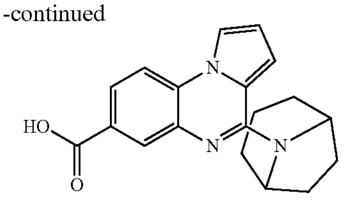

I-183

The following compound was prepared in a manner analogous to the procedures described above for 4-(4-(2,2,2-trifluoroethyl)piperidin-1-yl)pyrrolo[1,2-a]quinoxaline-7-carboxylic acid (I-182):

4-(8-azabicyclo[3.2.1]octan-8-yl)pyrrolo[1,2-a]quinoxaline-7-carboxylic acid (I-183) (0.089 g, 52%) as an off-white solid. $^1$H NMR (400 MHz, DMSO-$d_6$) δ 13.37 (br. s, 1H), 12.04 (br. s, 1H), 8.67 (br. s, 2H), 8.31 (s, 1H), 7.90 (s, 1H), 7.74 (br. s, 1H), 7.06 (s, 1H), 5.46 (br. s, 1H), 5.25 (br. s, 1H), 2.09-1.57 (m, 10H). MS: $[MH]^+$ 322.21

Example 1.85. Synthesis of 7-(1H-tetrazol-5-yl)-4-(4-(trifluoromethyl)phenyl)pyrrolo[1,2-a]quinoxaline (I-184)

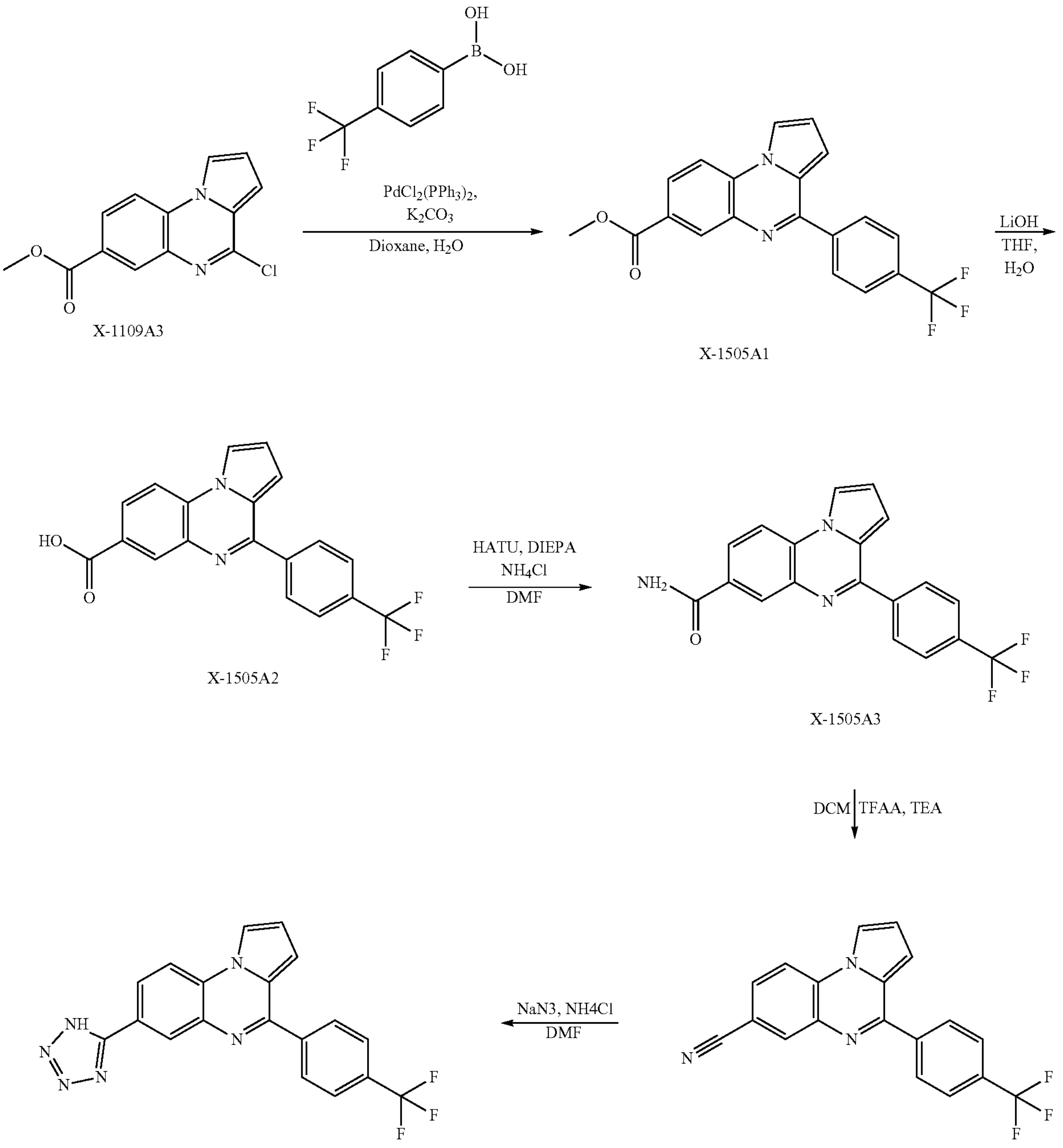

X-1109A3

X-1505A1

X-1505A2

X-1505A3

X-1505A4

I-184

Methyl 4-(4-(trifluoromethyl)phenyl)pyrrolo[1,2-a]quinoxaline-7-carboxylate (X-1505A1). To a stirred solution of methyl 4-chloropyrrolo[1,2-a]quinoxaline-7-carboxylate (X-1109A3) (1.0 g, 3.84 mmol) in a mixture of dioxane: water (26:6, 32 mL) were added (4-(trifluoromethyl)phenyl) boronic acid (0.95 g, 5.00 mmol) and $K_2CO_3$ (1.59 g, 11.53 mmol) at room temperature. The reaction mixture was degassed (purging with nitrogen) for 20 min followed by addition of Pd $(PPh_3)_4$ (0.13 g, 0.19 mmol) and the reaction mixture was heated at 110° C. for 3 h. The reaction mixture was cooled to room temperature, quenched with water (100 mL) and was extracted with ethyl acetate (300 mL×2). The combined organic extracts were dried over anhydrous $Na_2SO_4$ and concentrated under reduced pressure. The crude product was purified by silica gel column chromatography, using ethyl acetate-Hexane=0:1-42:8 as gradient, to afford methyl 4-(4-(trifluoromethyl)phenyl)pyrrolo[1,2-a]quinoxaline-7-carboxylate (X-1505A1) (1.2 g, 85%) as an off-white solid. MS: $[MH]^+$ 371.0

4-(4-(Trifluoromethyl)phenyl)pyrrolo[1,2-a]quinoxaline-7-carboxylic acid (X-1505A2). To a stirred solution of methyl 4-(4-(trifluoromethyl)phenyl)pyrrolo[1,2-a]quinoxaline-7-carboxylate (X-1505A1) (1.10 g, 2.97 mmol) in a mixture of THF-water (8:5; 13 mL) was added lithium hydroxide monohydrate (0.37 g, 8.91 mmol) at room temperature under nitrogen and the resulting reaction mixture was heated at 70° C. for 1 h. After cooling to room temperature, the reaction mixture was concentrated under reduced pressure, crude mass was diluted with water (200 mL) and was extracted with ethyl acetate (100×2 mL) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was dried in vacuo to afford 4-(4-(trifluoromethyl)phenyl)pyrrolo[1,2-a]quinoxaline-7-carboxylic acid (X-1505A2) (1.0 g, 86%) as a white solid. MS: $[MH]^+$ 357.0

4-(4-(Trifluoromethyl)phenyl)pyrrolo[1,2-a]quinoxaline-7-carboxamide (X-1505A3). To a stirred solution of 4-(4-(trifluoromethyl)phenyl)pyrrolo[1,2-a]quinoxaline-7-carboxylic acid (X-1505A2) (0.50 g, 1.40 mmol) in DMF (7.0 mL) were added diisopropylethylamine (0.54 g, 4.21 mmol), HATU (0.91 g, 2.38 mmol) and ammonium chloride (0.100 g, 1.82 mmol) sequentially at 0° C. under nitrogen and the resulting mixture was stirred at room temperature for 3 h. The reaction mixture was slowly poured into ice-water (20 mL) and the resulting precipitate was collected by filtration. Obtained solid was dried in vacuo to afford 4-(4-(trifluoromethyl)phenyl)pyrrolo[1,2-a]quinoxaline-7-carboxamide (X-1505A3) (0.480 g, 96%) as a white solid. MS: $[MH]^+$ 356.1

4-(4-(Trifluoromethyl)phenyl)pyrrolo[1,2-a]quinoxaline-7-carbonitrile (X-1505A4). To a stirred solution of 4-(4-(trifluoromethyl)phenyl)pyrrolo[1,2-a]quinoxaline-7-carboxamide (X-1505A4) (0.40 g, 1.12 mmol) in DMF (5 mL) were added TEA (0.34 g, 3.38 mmol) and TFAA (0.70 g, 3.38 mmol) sequentially at 0° C. under nitrogen and the resulting mixture was stirred at room temperature for 1 h. The Reaction mixture was poured into ice-water (20 mL) and was extracted with ethyl acetate (100 mL×3). The combined organic extracts were dried over anhydrous $Na_2SO_4$ and concentrated in vacuo. The crude product was purified by silica gel column chromatography, using ethyl acetate-hexane=0:1→1:9 as gradient, to afford 4-(4-(trifluoromethyl)phenyl)pyrrolo[1,2-a]quinoxaline-7-carbonitrile (X-1505A4) (0.270 g, 59%) as a white solid. MS: $[MH]^+$ 338.1.

7-(1H-tetrazol-5-yl)-4-(4-(trifluoromethyl)phenyl)pyrrolo[1,2-a]quinoxaline (I-184). To a stirred solution of 4-(4-(trifluoromethyl)phenyl)pyrrolo[1,2-a]quinoxaline-7-carboxamide (X-1505A4) (0.25 g, 0.74 mmol) in DCM (5.0 mL) were added ammonium chloride (0.39 g, 7.41 mmol) and sodium azide (0.29 g, 4.45 mmol) sequentially at room temperature and resulting reaction mixture was heated at 120° C. for 5 h. The reaction mixture was slowly poured into ice-water (30 mL) and the resulting precipitate was collected by filtration. Obtained solid residue was dried in vacuo, the crude product was purified by reverse phase (C-18) silica gel column chromatography, using acetonitrile-water=0:1→1:0 as gradient, to afford 7-(1H-tetrazol-5-yl)-4-(4-(trifluoromethyl)phenyl)pyrrolo[1,2-a]quinoxaline (I-184) (0.150 g, 50%) as a yellow solid. $^1H$ NMR (400 MHz, DMSO-$d_6$) δ 8.63-8.63 (d, J=1.6 Hz, 1H), 8.55-8.54 (d, J=1.2 Hz, 1H), 8.46-8.44 (d, J=8.4 Hz, 1H), 8.26-8.24 (d, J=7.6 Hz, 3H), 7.98-7.96 (d, J=8.4 Hz, 2H), 7.10-7.09 (d, J=4.0 Hz, 1H), 7.05-7.03 (t, J=2.8 Hz, 1H). MS: $[MH]^+$ 381.0.

Example 1.86. Synthesis of 4-(4-(tert-butyl)phenyl)-N-(2-hydroxyethyl)pyrrolo[1,2-a]quinoxaline-7-carboxamide (I-185)

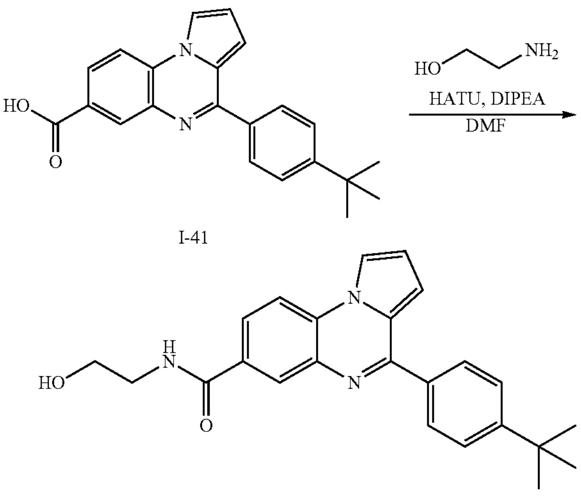

I-41

I-185

To a solution of 4-(4-(tert-butyl)phenyl)pyrrolo[1,2-a]quinoxaline-7-carboxylic acid (I-41) (0.250 g, 0.72 mmol) in DMF (2 mL) was added HATU (0.470 g, 1.23 mmol). The mixture was stirred at room temperature for 30 min. Ammonium hydroxide (28%, 2 mL) and DIPEA (0.468 g, 3.63 mmol) were added and the reaction mixture was stirred at room temperature for 2 h. The mixture was diluted with water (150 mL) and extracted with EtOAc (100 mL×2). The combined organic layers were washed with brine, dried over $Na_2SO_4$, filtered and concentrated. The crude product was purified by reverse phase (C-18) silica gel column chromatography, using acetonitrile-water=0:1→6:4 as gradient, to afford 4-(4-(tert-butyl)phenyl)-N-(2-hydroxyethyl)pyrrolo[1,2-a]quinoxaline-7-carboxamide (I-185) (0.090 g, 32%) as a white solid. $^1H$ NMR (400 MHz, DMSO-$d_6$) δ 8.69-8.67 (m, 1H), 8.60 (d, J=1.2 Hz, 1H), 8.47 (d, J=1.6 Hz, 1H), 8.41-8.38 (d, J=8.4 Hz, 1H), 8.09-8.06 (dd, J=8.8, 1.6 Hz, 1H), 7.99-7.96 (d, J=8.4 Hz, 2H), 7.63-7.61 (d, J=8.4 Hz, 2H), 7.11-7.10 (d, J=3.6 Hz, 1H), 7.03-7.02 (t, J=2.8 Hz, 1H), 4.78-4.75 (t, J=5.6 Hz, 1H), 3.58-3.53 (m, 2H), 3.40-3.32 (m, 2H), 1.36 (s, 9H): MS: $[MH]^+$388.2

Example 1.87. Synthesis of 4-(4-(tert-butyl)phenyl)-N-(1-hydroxypropan-2-yl)pyrrolo[1,2-a]quinoxaline-7-carboxamide (I-186

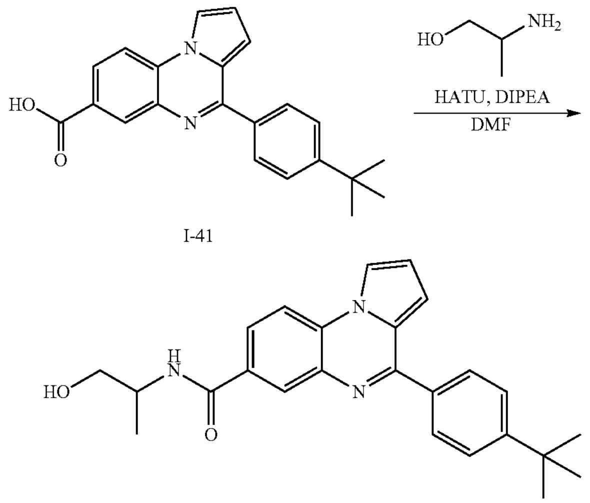

I-41

I-186

The following compound was prepared in a manner analogous to the procedures described above for 4-(4-(tert-butyl)phenyl)-N-(2-hydroxyethyl)pyrrolo[1,2-a]quinoxaline-7-carboxamide (I-185):

4-(4-(tert-butyl)phenyl)-N-(1-hydroxypropan-2-yl)pyrrolo[1,2-a]quinoxaline-7-carboxamide (1-186). (0.060 g, 34%) as a white solid. $^1$H NMR (400 MHz, DMSO-$d_6$) δ 8.61-8.61 (d, J=1.6 Hz, 1H), 8.50 (d, J=1.2 Hz, 1H), δ 8.40-8.36 (m, 2H), 8.09-8.07 (dd, J=8.4 Hz, 1.6 Hz, 1H), δ 7.99-7.98 (d, J=8.4 Hz, 2H), 7.63-7.61 (d, J=8.4 Hz, 2H), 7.12-7.11 (d, J=3.6 Hz, 1H), 7.03-7.02 (t, J=2.8 Hz, 1H), 4.79-4.76 (t, J=5.6 Hz, 1H), 4.11-4.04 (m, 1H), 3.54-3.48 (m, 1H), 3.41-3.33 (m, 1H), 1.36 (s, 9H), 1.18-1.16 (d, J=6.8 Hz, 3H) MS: $[MH]^+$ 402.2

Example 1.88 Synthesis of 4-(4-(tert-butyl)phenyl) pyrrolo[1,2-a]quinoxaline-7-carboxamide (I-166)

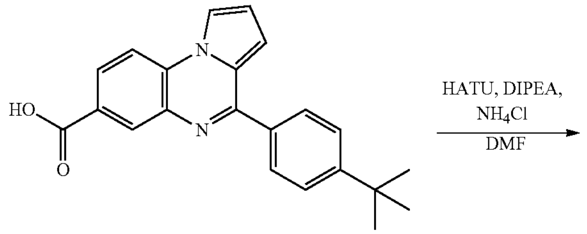

I-41

-continued

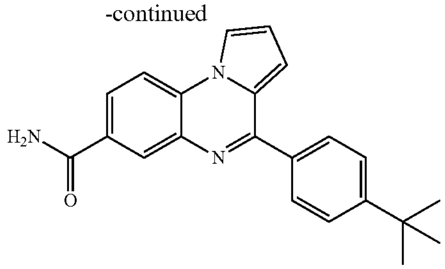

I-166

The following compound was prepared in a manner analogous to the procedures described above for 4-(4-(tert-butyl)phenyl)-N-(2-hydroxyethyl)pyrrolo[1,2-a]quinoxaline-7-carboxamide (I-185):

4-(4-(tert-butyl)phenyl)pyrrolo[1,2-a]quinoxaline-7-carboxamide (I-166) (0.040 g, 17%) as an off-white solid. $^1$H NMR (400 MHz, DMSO-$d_6$) δ 8.61 (s, 1H), 8.48 (s, 1H), 8.40-8.38 (d, J=8.4 Hz, 1H), 8.21 (s, 1H), 8.10-8.08 (d, J=8.4 Hz, 1H), 7.98-7.96 (d, J=8.0 Hz, 2H), 7.63-7.61 (d, J=8.0 Hz, 2H), 7.51 (s, 1H), 7.11-7.10 (m, 1H), 7.03 (br. s, 1H), 1.37 (s, 9H). MS: $[MH]^+$ 344.2

Example 1.89. Synthesis of 4-(4-(tert-butyl) phenyl)-N-(2-(dimethylamino) ethyl)pyrrolo[1,2-a]quinoxaline-7-carboxamide (I-188)

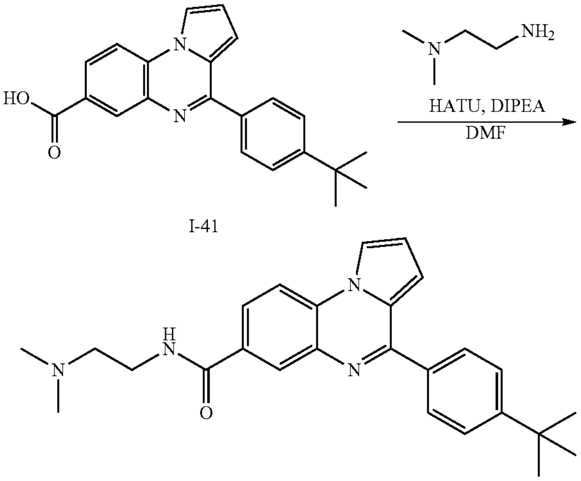

I-41

I-188

The following compound was prepared in a manner analogous to the procedures described above for 4-(4-(tert-butyl)phenyl)-N-(2-hydroxyethyl)pyrrolo[1,2-a]quinoxaline-7-carboxamide (I-185):

4-(4-(tert-butyl) phenyl)-N-(2-(dimethylamino) ethyl) pyrrolo[1,2-a]quinoxaline-7-carboxamide (I-188) (0.20 g, 55%) as an off-white solid. $^1$H NMR (400 MHz, DMSO-$d_6$) δ 8.74-7.57 (m, 1H), 8.61 (d, J=1.6 Hz, 1H), 8.47-8.47 (d, J=1.6 Hz, 1H), 8.42-8.40 (d, J=8.4 Hz, 1H), 8.08-8.06 (dd, J=8.8, 1.6 Hz, 1H), 7.99-7.97 (d, J=8.4 Hz, 2H), 7.63-7.61 (d, J=8.4 Hz, 2H), 7.12-7.11 (d, J=3.2 Hz, 1H), 7.04-7.03 (t, J=6.8 Hz, 1H), 3.51-3.49 (d, J=5.6 Hz, 2H), 2.71-2.75 (m, 2H), 2.42 (s, 6H), 1.37 (s, 9H), MS: $[MH]^+$ 415.2

Example 1.90. Synthesis of 5-(4-(4-(tert-butyl)phenyl)pyrrolo[1,2-a]quinoxalin-7-yl)-1,3,4-oxadiazol-2-amine (I-189)

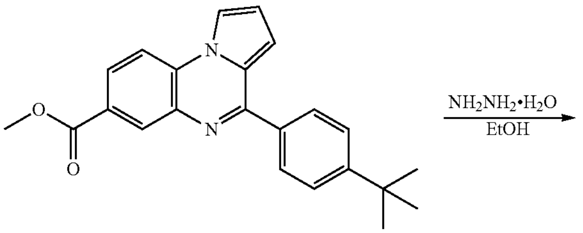

X-1109A4

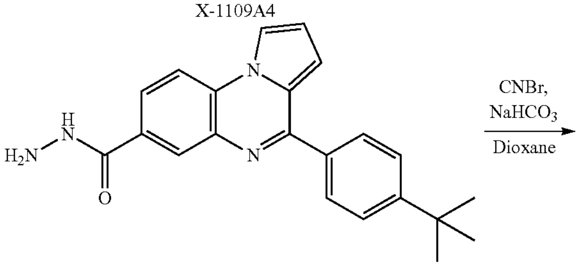

X-1520A1

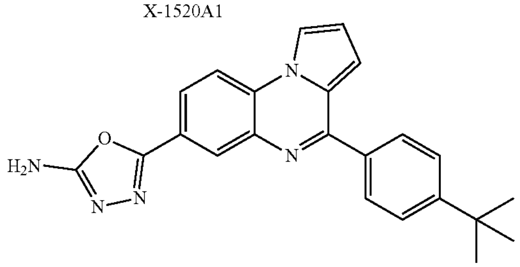

I-189

4-(4-(tert-Butyl)phenyl)pyrrolo[1,2-a]quinoxaline-7-carbohydrazide (X-1520A1). To a solution of methyl 4-(4-(tert-butyl)phenyl)pyrrolo[1,2-a]quinoxaline-7-carboxylate (X-1109A4) (2.00 g, 55.8 mmol) in EtOH (20 mL) was added $N_2H_4·H_2O$ (6.0 ml, 83.7 mmol) at room temperature and the resulting mixture was stirred at 90° C. for 24 h. The reaction mixture was diluted with water (150 mL) and extracted with ethyl acetate (200 mL×2). Combined organic extracts were washed with brine (40 mL), dried over anhydrous $Na_2SO_4$ and concentrated under reduced pressure. The crude product was purified by C-18 silica gel column chromatography, using acetonitrile-water=0:1→4:6 to afford 4-(4-(tert-butyl)phenyl)pyrrolo[1,2-a]quinoxaline-7-carbohydrazide (X-1520A1) (1.4 g, 70%) as a white solid. MS: $[MH]^+$ 359.17.

5-(4-(4-(tert-Butyl)phenyl)pyrrolo[1,2-a]quinoxalin-7-yl)-1,3,4-oxadiazol-2-amine (I-189). To a solution of methyl 4-(4-(tert-butyl)phenyl)pyrrolo[1,2-a]quinoxaline-7-carbohydrazide (X-1520A1) (0.200 g, 55.8 mmol) in 1,4-Dioxane (5 mL) were added $NaHCO_3$ solution in water (0.460 g, 55.8 mmol) and CNBr (0.590 g, 55.8 mmol) and the resulting mixture was stirred at for 4 h. Reaction mixture was poured into water (50 mL) and was filtered through Buckner and dried under high vacuo. Solid was triturated by ether and n-pentane, to afford 5-(4-(4-(tert-butyl)phenyl)pyrrolo[1,2-a]quinoxalin-7-yl)-1,3,4-oxadiazol-2-amine (I-189) (0.038 g, 15%). $^1H$ NMR (400 MHz, DMSO-$d_6$) δ 8.61 (d, J=1.6 Hz, 1H), 8.48-8.46 (d, J=8.8 Hz 1H), 8.21 (d, J=2.0 Hz, 1H), 8.00-7.97 (m, 3H), 7.63-7.61 (d, J=8.0 Hz, 2H), 7.33 (s, 2H), 7.12-7.11 (d, J=4.0 Hz, 1H), 7.04-7.03 (t, J=2.8 Hz, 1H), 1.37 (s, 9H), MS: $[MH]^+$ 384.17.

Example 1.91. Synthesis of (S)-4-(4-(tert-butyl)phenyl)-N-(1-hydroxypropan-2-yl)pyrrolo[1,2-a]quinoxaline-7-carboxamide (I-190)

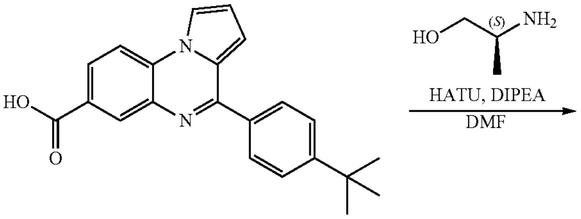

I-41

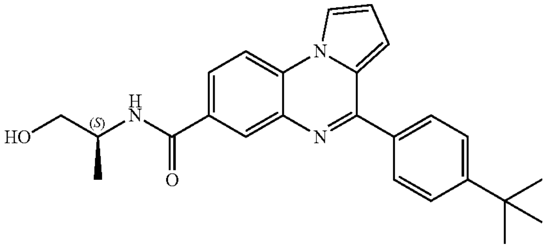

I-190

The following compound was prepared in a manner analogous to the procedures described above for 4-(4-(tert-butyl)phenyl)-N-(2-hydroxyethyl)pyrrolo[1,2-a]quinoxaline-7-carboxamide (I-185):

(S)-4-(4-(tert-butyl) phenyl)-N-(1-hydroxypropan-2-yl) pyrrolo[1,2-a]quinoxaline-7-carboxamide (I-190) (0.050 g, 21%) as an off-white solid. $^1H$ NMR (400 MHz, DMSO-$d_6$) δ 8.61 (s, 1H), 8.50 (s, 1H), 8.40-8.35 (m, 2H), 8.08-8.07 (d, J=7.2 Hz, 1H), 7.99-7.97 (d, J=8.4 Hz, 2H), 7.63-7.61 (d, J=8.4 Hz, 2H), 7.12-7.11 (d, J=3.6 Hz, 1H), 7.04-7.02 (t, J=6.4 Hz, 1H), 4.77-4.74 (t, J=11.6 Hz, 1H), 4.11-4.04 (m, 1H). 3.52-3.49 (m, 1H), 3.40-3.37 (m, 1H), 1.37 (s, 9H), 1.17-1.16 (d, J=6.4 Hz, 3H). MS: $[MH]^+$ 402.1

Example 1.92. (R)-4-(4-(tert-butyl) phenyl)-N-(1-hydroxypropan-2-yl)pyrrolo[1,2-a]quinoxaline-7-carboxamide (I-191)

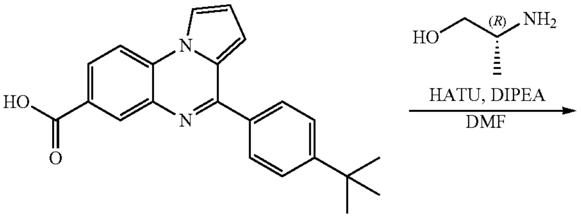

I-41

-continued

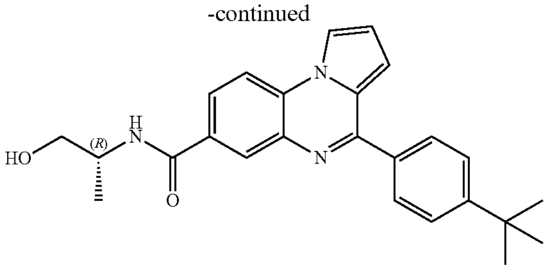

I-191

The following compound was prepared in a manner analogous to the procedures described above for 4-(4-(tert-butyl)phenyl)-N-(2-hydroxyethyl)pyrrolo[1,2-a]quinoxaline-7-carboxamide (I-185):

(R)-4-(4-(tert-butyl) phenyl)-N-(1-hydroxypropan-2-yl) pyrrolo[1,2-a]quinoxaline-7-carboxamide (I-191) (0.040 g, 17%) as an off-white solid. $^1$H NMR (400 MHz, DMSO-$d_6$) δ 8.61-8.61 (d, J=2.0 Hz, 1H), 8.50-8.50 (d, J=1.6 Hz 1H), 8.40-8.36 (m, 2H), 8.09-8.06 (dd, J=8.8, 1.6 Hz, 1H), 7.99-7.97 (d, J=8.4 Hz, 2H), 7.63-7.61 (d, J=8.4 Hz, 2H), 7.12-7.11 (d, J=4.0 Hz, 1H), 7.04-7.02 (t, J=3.6 Hz, 1H), 4.78-4.75 (t, J=6.0 Hz, 1H), 4.10-4.01 (m, 1H), 3.53-3.48 (m, 1H), 3.40-3.31 (m, 1H), 1.36 (s, 9H), 1.17-1.16 (d, J=3.6 Hz, 3H) MS: $[MH]^+$ 402.1.

Example 1.93. Synthesis of 4-(4-(trifluoromethoxy) phenyl)pyrrolo[1,2-a]quinoxaline-7-carboxylic acid (I-192

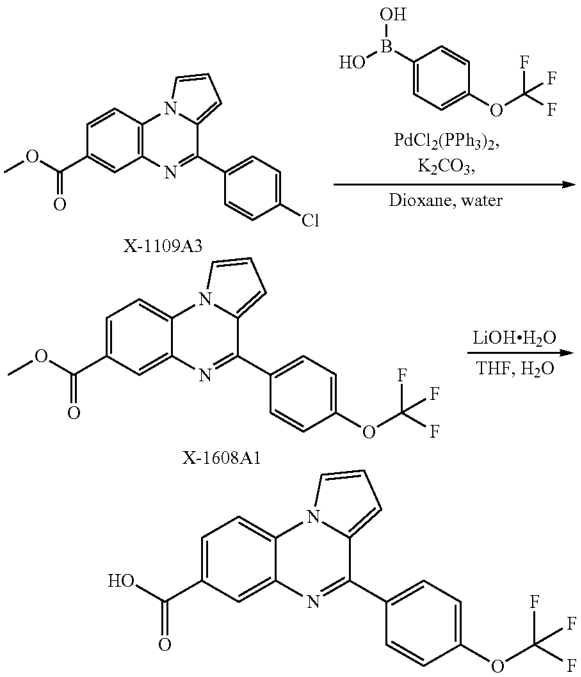

X-1109A3

X-1608A1

I-192

Methyl 4-(4-(trifluoromethoxy)phenyl)pyrrolo[1,2-a]quinoxaline-7-carboxylate (X-1608A1). To a stirred solution of methyl 4-chloropyrrolo[1,2-a] quinoxaline-7-carboxylate-carboxylate (X-1109A3) (0.5 g, 1.92 mmol) in a mixture of 1,4-dioxane-water (8:2, 10 mL) were added $K_2CO_3$ (0.796 g, 5.76 mmol) and (4-(trifluoromethoxy)phenyl)boronic acid (0.594 g, 2.88 mmol) at room temperature under nitrogen. The reaction mixture was degassed (purging with nitrogen) for 20 min followed by the addition of $PdCl_2(PPh_3)_2$ (0.067 g, 0.09 mmol) and the reaction mixture was heated at 100° C. for 2 h. The reaction mixture was cooled to room temperature, diluted with water (50 mL) and was extracted with ethyl acetate (100 mL×2). Combined organic extracts were dried over anhydrous $Na_2SO_4$, filtered and concentrated under reduced pressure. Obtained crude was purified by silica gel column chromatography, using ethyl acetate-hexane=0:1→1:9 as gradient, to afford methyl 4-(4-(trifluoromethoxy)phenyl)pyrrolo[1,2-a]quinoxaline-7-carboxylate (X-1608A1) (0.500 g, 67%) as an off-white solid. MS: [MH]+ 386.92.

4-(4-(Trifluoromethoxy)phenyl)pyrrolo[1,2-a]quinoxaline-7-carboxylic acid (I-192). To a stirred solution of methyl 4-(4-(trifluoromethoxy)phenyl)pyrrolo[1,2-a]quinoxaline-7-carboxylate (X-1608A1) (0.300 g, 0.77 mmol) in a mixture of THF-water (4:1; 3 mL), was added lithium hydroxide monohydrate (0.098 g, 2.33 mmol) at room temperature and the resulting reaction mixture was heated at 70° C. for 3 h. After cooling to room temperature, the reaction mixture was concentrated under reduced pressure. Obtained crude was diluted with water (50 mL) and was extracted with ethyl acetate (60 mL×2) to remove unwanted organic impurities. Aqueous part was acidified (pH~2-3) with an aqueous solution of 1N HCl and the resulting precipitate was collected by filtration. Obtained crude residue was washed with cold water until pH of the filtrate became neutral (pH~6-7). Obtained solid was dried under reduced pressure to afford 4-(4-(trifluoromethoxy)phenyl) pyrrolo[1,2-a]quinoxaline-7-carboxylic acid (I-192) (0.130 g, 45%) as an off-white solid. $^1$H NMR (400 MHz, DMSO-$d_6$) δ 13.29 (brs, 1H), 8.63 (s, 1H), 8.46 (s, 1H), 8.41-8.38 (d, J=8.4 Hz, 1H), 8.16-8.13 (m, 3H), 7.59-7.57 (d, J=8.4 Hz, 2H), 7.11-7.10 (d, 3.6 Hz, 1H), 7.06-7.05 (d, 2.8 Hz, 1H). MS: $[MH]^+$ 372.87.

Example 1.94. Synthesis of 4-(4-(difluoromethoxy) phenyl)pyrrolo[1,2-a]quinoxaline-7-carboxylic acid (I-193)

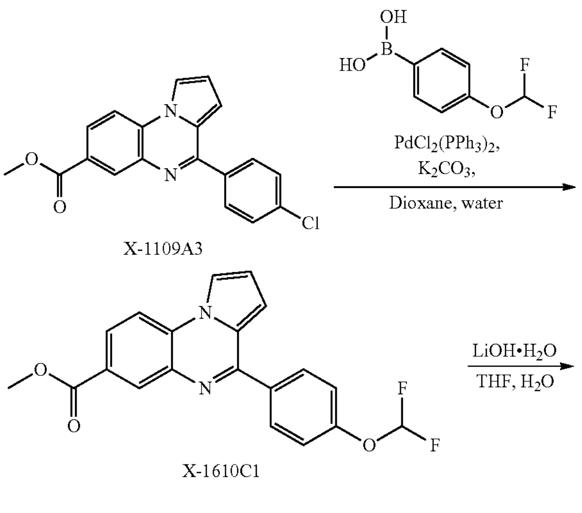

X-1109A3

X-1610C1

-continued

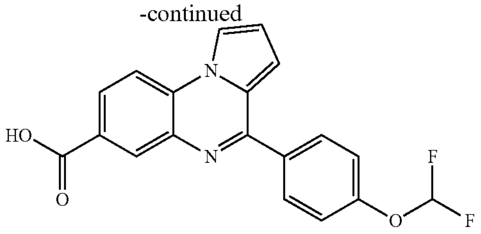

I-193

The following compound was prepared in a manner analogous to the procedures described above for 4-(4-(trifluoromethoxy)phenyl)pyrrolo[1,2-a]quinoxaline-7-carboxylic acid (I-192):

4-(4-(difluoromethoxy)phenyl)pyrrolo[1,2-a]quinoxaline-7-carboxylic acid (I-193) (0.120 g, 50%) as an off-white solid. $^1$H NMR (400 MHz, DMSO-$d_6$) δ 13.21 (br. s, 1H), 8.64 (s, 1H), 8.43 (s, 1H), 8.41 (s, 1H), 8.12-8.08 (m, 3H), 7.59-7.22 (m, 3H), 7.12-7.11 (d, J=0.3.6 Hz, 1H), 7.07-7.06 (d, J=3.6 Hz, 1H). MS: $[MH]^+$ 355.02.

Example 1.95. Synthesis of 4-(4-((trifluoromethyl)thio)phenyl)pyrrolo[1,2-a]quinoxaline-7-carboxylic acid (I-194

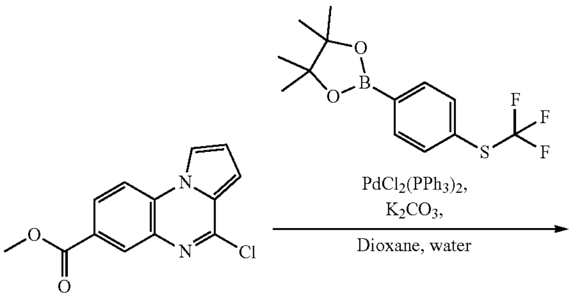

X-1109A3

-continued

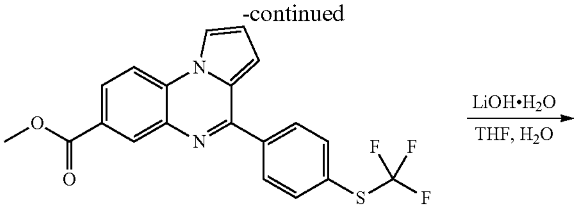

X-1611A2

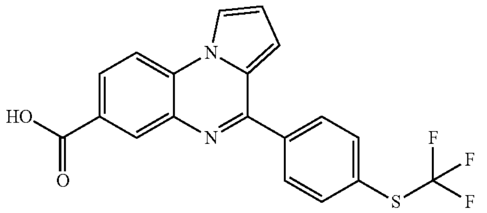

I-194

The following compound was prepared in a manner analogous to the procedures described above for 4-(4-(trifluoromethoxy)phenyl)pyrrolo[1,2-a]quinoxaline-7-carboxylic acid (1-192):

4-(4-((trifluoromethyl)thio)phenyl)pyrrolo[1,2-a]quinoxaline-7-carboxylic acid (I-194) (0.080 g, 52%) as an off-white solid. $^1$H NMR (400 MHz, DMSO-$d_6$) δ 13.20 (brs, 1H), 8.68-8.68 (d, J=1.6 Hz, 1H), 8.47-8.45 (m, 2H), 8.18-8.13 (m, 3H), 7.95-7.93 (d, J=8.0 Hz, 2H), 7.14-7.13 (d, J=3.6 Hz, 1H), 7.09-7.08 (t, J=3.6 Hz, 1H). MS: $[MHl]^+$ 389.33.

Example 1.96. Synthesis of 4-(4-(1,1,1-trifluoropropan-2-yl)phenyl)pyrrolo[1,2-a]quinoxaline-7-carboxylic acid (I-195)

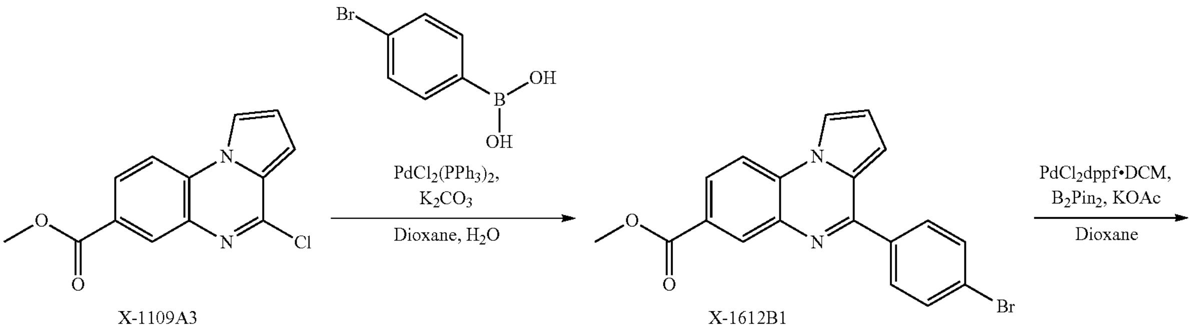

X-1109A3

X-1612B1

-continued

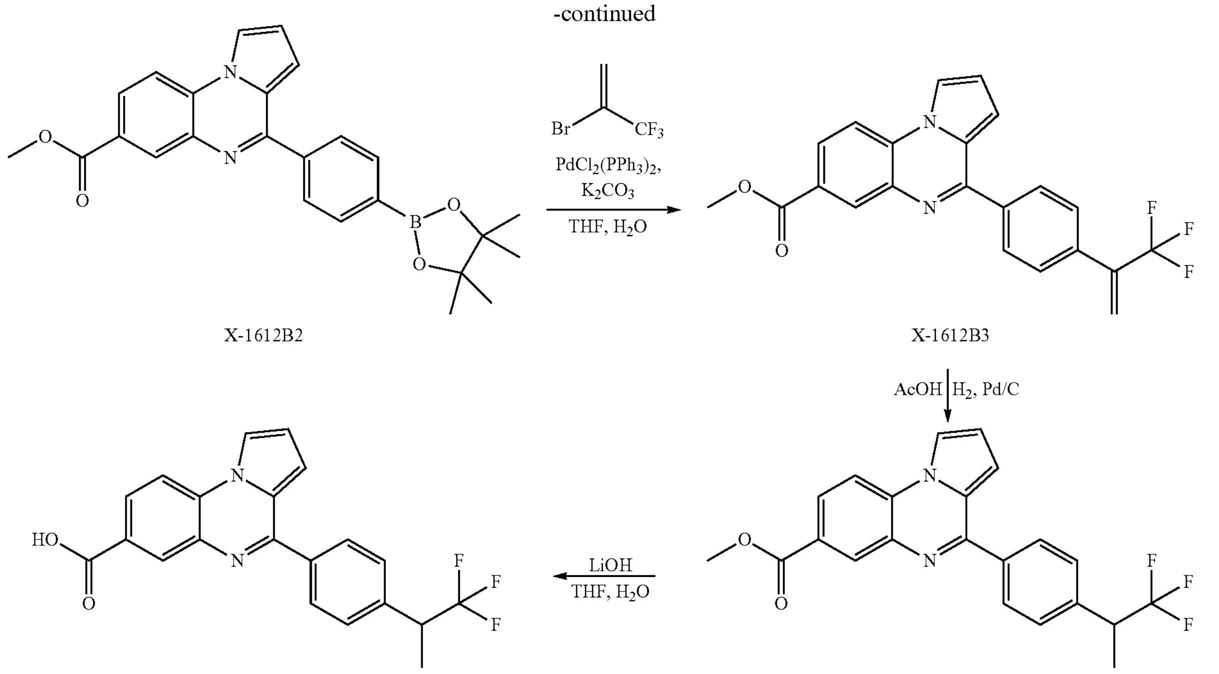

X-1612B2 X-1612B3 X-1612B4 I-195

Methyl 4-(4-bromophenyl)pyrrolo[1,2-a]quinoxaline-7-carboxylate (X-1612B1). To a stirred solution of methyl 4-chloropyrrolo[1,2-a]quinoxaline-7-carboxylate (X-1109A3) (1.20 g, 4.61 mmol) in a mixture of dioxane: water (16:4, 20 mL) were added (4-bromophenyl)boronic acid (1.84 g, 9.23 mmol) and $K_2CO_3$ (1.91 g, 13.8 mmol) at room temperature. The reaction mixture was degassed (purging with nitrogen) for 20 min followed by addition of $PdCl_2(PPh_3)_2$ (0.25 g, 0.36 mmol) and the reaction mixture was heated at 110° C. for 2 h. The reaction mixture was cooled to room temperature, quenched with water (200 mL) and was extracted with ethyl acetate (300 mL×2). The combined organic extracts were dried over anhydrous $Na_2SO_4$ and concentrated in vacuo. The crude product was purified by silica gel column chromatography, using ethyl acetate-Hexane=0:1→1:9 as gradient, to afford methyl 4-(4-bromophenyl)pyrrolo[1,2-a]quinoxaline-7-carboxylate (X-1612B1) (0.85 g, 37%) as an off-white solid. MS: $[MH]^+$ 380.9.

Methyl 4-(4-(4,4,5,5-tetramethyl-1,3,2-dioxaborolan-2-yl)phenyl)pyrrolo[1,2-a]quinoxaline-7-carboxylate (X-1612B2). To a stirred solution of methyl 4-(4-bromophenyl)pyrrolo[1,2-a]quinoxaline-7-carboxylate (0.85 g, 2.23 mmol) in Dioxane (10 mL) were added Bis(pinacolato) diboron (0.73 g, 2.90 mmol) and KOAc (0.65 g, 6.71 mmol) at room temperature under nitrogen. The reaction mixture was degassed (purging with nitrogen) for 20 min followed by the addition of $PdCl_2$(dppf)DCM (0.27 g, 0.33 mmol) and the resulting mixture was heated at 110° C. for 1 h. Reaction mixture was cooled to room temperature, quenched with water (100 mL) and was extracted with ethyl acetate (100 mL×2), and dried over anhydrous $Na_2SO_4$ and concentrated in vacuo. The resulting crude was purified by silica gel column chromatography, using ethyl acetate-hexane=0: 1→1:9 as gradient, to afford methyl 4-(4-(4,4,5,5-tetramethyl-1,3,2-dioxaborolan-2-yl)phenyl)pyrrolo[1,2-a]quinoxaline-7-carboxylate (X-1612B2). (0.55 g, 75%) as an off-white solid. MS: $[MH]^+$ 429.1

Methyl 4-(4-(3,3,3-trifluoroprop-1-en-2-yl)phenyl)pyrrolo[1,2-a]quinoxaline-7-carboxylate (X-1612B3). To a stirred solution of methyl 4-(4-(4,4,5,5-tetramethyl-1,3,2-dioxaborolan-2-yl)phenyl)pyrrolo[1,2-a]quinoxaline-7-carboxylate (X-1612B2) (0.54 g, 1.26 mmol) in a mixture of THF-water (8:2, 10 mL) were added 2-bromo-3,3,3-trifluoroprop-1-ene (0.44 g, 2.52 mmol) and $K_2CO_3$ (0.435 g, 3.15 mmol) at room temperature. The reaction mixture was degassed (purging with nitrogen) for 20 min followed by addition of $PdCl_2(PPh_3)_2$ (0.026 g, 0.037 mmol) and the reaction mixture was heated at 85° C. for 1 h. The reaction mixture was cooled to room temperature, quenched with water (100 mL) and was extracted with ethyl acetate (200 mL×2). The combined organic extracts were dried over anhydrous $Na_2SO_4$ and concentrated in vacuo. The crude product was purified by silica gel column chromatography, using ethyl acetate-Hexane=0:1→1:9 as gradient, to afford methyl 4-(4-(3,3,3-trifluoroprop-1-en-2-yl)phenyl)pyrrolo[1,2-a]quinoxaline-7-carboxylate (X-1612B3) (0.240 g, 48%) as an off-white solid. MS: $[MH]^+$ 397.1.

Methyl 4-(4-(1,1,1-trifluoropropan-2-yl)phenyl)pyrrolo[1,2-a]quinoxaline-7-carboxylate (X-1612B4). 10% Pd inactivated carbon (0.200 g) was added carefully to a stirred solution of methyl 4-(4-(3,3,3-trifluoroprop-1-en-2-yl)phenyl)pyrrolo[1,2-a]quinoxaline-7-carboxylate (X-1612B3) (0.24 g, 0.60 mmol) in acetic acid (3 mL) at room temperature under nitrogen and the resulting mixture was hydrogenated under balloon pressure at the same temperature. The reaction mixture was filtered through a celite bad, washed the bed with methanol (50 mL) and collected filtrates were concentrated under reduced pressure and The reaction mixture was basify using Sat. bicarbonate (50 mL) and was extracted with ethyl acetate (100 mL×2). The crude mass was purified by reverse phase (C-18) silica gel column chromatography, using acetonitrile-water=0:1→5:5 as gradient, to afford methyl 4-(4-(1,1,1-trifluoropropan-2-yl)phenyl)pyrrolo[1,2-a]quinoxaline-7-carboxylate (X-1612B4) (0.040 g, 17%) as an off-white solid. MS: $[MH]^+$ 399.1.

4-(4-(1,1,1-Trifluoropropan-2-yl)phenyl)pyrrolo[1,2-a]quinoxaline-7-carboxylic acid (I-195). To a stirred solution of methyl 4-(4-(1,1,1-trifluoropropan-2-yl)phenyl)pyrrolo[1,2-a]quinoxaline-7-carboxylate (X-1612B4) (0.04 g, 0.10 mmol) in a mixture of THF-water (2:0.4; 2.4 mL) was added lithium hydroxide monohydrate (0.012 g, 0.30 mmol) at room temperature under nitrogen and the resulting reaction mixture was heated at 60° C. for 1 h. After cooling to room temperature, the reaction mixture was concentrated under reduced pressure, crude mass was diluted with water (200 mL) and was extracted with ethyl acetate (100×2 mL) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The crude mass was purified by reverse phase (C-18) silica gel column chromatography, using acetonitrile-water=0:1→2:8 as gradient, afford 4-(4-(1,1,1-trifluoropropan-2-yl)phenyl)pyrrolo[1,2-a]quinoxaline-7-carboxylic acid (I-195) (0.020 g, 52%) as an off-white solid. $^1$H NMR (400 MHz, DMSO-$d_6$) δ 13.24 (s, 1H), 8.65 (s, 1H), 8.45-8.43 (d, J=10.4 Hz, 2H), 8.15-8.13 (d, J=7.6 Hz, 1H), 8.07-8.05 (d, J=8.4 Hz, 2H), 7.65-7.63 (d, J=8.0 Hz, 2H), 7.14-7.13 (d, J=3.6 Hz, 1H), 7.07 (brs, 1H), 4.00-3.96 (m, 1H), 1.55-1.53 (d, J=7.2 Hz, 3H). MS: $[MH]^+$ 384.96.

Example 1.97. Synthesis of 4-(4-(1-(trifluoromethyl)cyclopropyl)phenyl)pyrrolo[1,2-a]quinoxaline-7-carboxylic acid (I-196)

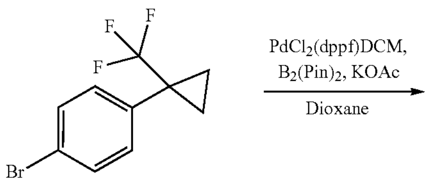

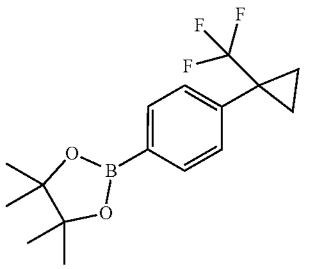

+

X-1613B1

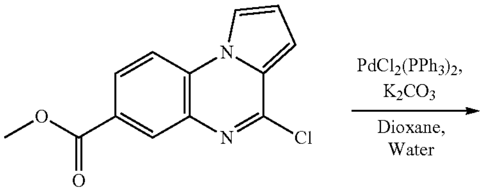

X-1109A3

-continued

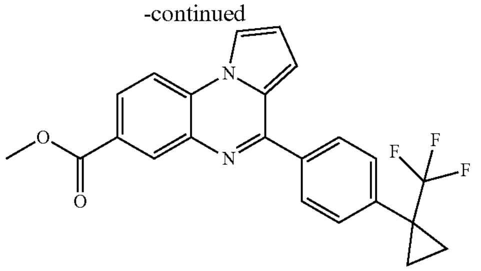

X-1613A2

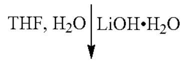

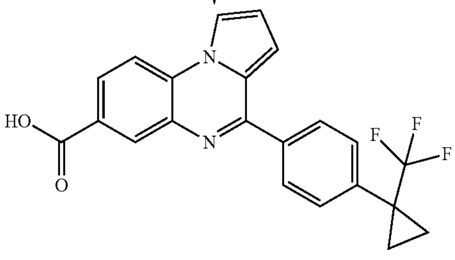

I-196

4,4,5,5-tetramethyl-2-(4-(1-(trifluoromethyl)cyclopropyl)phenyl)-1,3,2-dioxaborolane (X-1613B1). To a stirred solution of 1-bromo-4-(1-(trifluoromethyl)cyclopropyl)benzene (0.800 g, 3.03 mmol) in dioxane (5 mL) were added Bis(pinacolato)diboron (1.15 g, 4.54 mmol) and KOAc (0.890 g, 9.09 mmol) at room temperature under nitrogen. The reaction mixture was degassed (purging with nitrogen) for 20 min followed by the addition of $PdCl_2$(dppf).DCM (0.24 g, 0.30 mmol) and the resulting mixture was heated at 90° C. for 2 h. Reaction mixture was cooled to room temperature, quenched with water (100 mL) and was extracted with ethyl acetate (100 mL×2), and dried over anhydrous $Na_2SO_4$ and concentrated in vacuo. The resulting crude was purified by silica gel column chromatography, using ethyl acetate-hexane=0:1→0:1 as gradient, to afford 4,4,5,5-tetramethyl-2-(4-(1-(trifluoromethyl)cyclopropyl)phenyl)-1,3,2-dioxaborolane (X-1613B1). (0.600 g, 63%) as a white solid. LCMS was not supported. $^1$H NMR (400 MHz, DMSO-$d_6$) δ 7.69-7.67 (d, J=8.0 Hz, 2H), 7.47-7.45 (d, J=7.6 Hz, 2H), 1.36-1.33 (t, J=5.6 Hz, 2H), 1.28 (s, 12H), 1.11 (s, 2H).

Methyl 4-(4-(1-(trifluoromethyl)cyclopropyl)phenyl)pyrrolo[1,2-a]quinoxaline-7-carboxylate (X-1613A2). To a stirred solution of methyl 4-chloropyrrolo[1,2-a]quinoxaline-7-carboxylate (X-1109A3) (0.150 g, 0.57 mmol) in dioxane-water (3:1, 4 mL) were added 4,4,5,5-tetramethyl-2-(4-(1-(trifluoromethyl)cyclopropyl)phenyl)-1,3,2-dioxaborolane (X-1613B1) (0.260 g, 0.86 mmol), Potassium carbonate (0.238 g, 1.73 mmol), at room temperature under nitrogen. The reaction mixture was degassed (purging with nitrogen) for 20 min followed by the addition of $PdCl_2(PPh_3)_2$ (0.020 g, 0.02 mmol) and the resulting mixture was heated at 90° C. for 1 h. Reaction mixture was cooled to room temperature, quenched with water (20 mL) and was extracted with ethyl acetate (30 mL×2), dried over anhydrous $Na_2SO_4$ and concentrated in vacuo. The resulting crude was purified by silica gel column chromatography, using ethyl acetate-hexane=0:1→1:9 as gradient, to afford methyl 4-(4-(1-(trifluoromethyl)cyclopropyl)phenyl)pyrrolo[1,2-a]quinoxaline-7-carboxylate (X-1613A2) (0.200 g, 56%) as a white solid. MS: $[MH]^+$ 411.06.

4-(4-(1-(Trifluoromethyl)cyclopropyl)phenyl)pyrrolo[1,2-a]quinoxaline-7-carboxylic acid (I-196). To a stirred solution of methyl 4-(4-(1-(trifluoromethyl)cyclopropyl)phenyl)pyrrolo[1,2-a]quinoxaline-7-carboxylate (X-1613A2) (0.15 g, 0.36 mmol) in a mixture of THF-water (2:1; 3.0 mL) was added lithium hydroxide monohydrate (0.046 g, 1.09 mmol) at room temperature and the resulting mixture was stirred at 70° C. for 1 h. Reaction mixture was concentrated under reduced pressure, diluted with water (100 mL), and extracted with ethyl acetate (50×2 mL) to remove unwanted organic impurities. The aqueous layer was acidified (pH~2-3) with aqueous 1N HCl, and the resulting precipitate was collected by filtration, and washed with cold water until the pH of the filtrate became neutral (pH~6-7). The obtained solid was triturated by diethyl ether & n-pentane and dried in vacuo, to afford 4-(4-(1-(trifluoromethyl)cyclopropyl)phenyl)pyrrolo[1,2-a]quinoxaline-7-carboxylic acid (I-196) (0.060 g, 41%) as an off-white solid. $^1H$ NMR (400 MHz, DMSO-$d_6$) δ 13.22 (brs, 1H), 8.65 (s, 1H), 8.44-8.43 (m, 2H), 8.13-8.11 (d, J=8.4 Hz, 1H), 8.05-8.03 (d, J=8.0 Hz, 2H), 7.69-7.67 (d, J=7.6 Hz, 2H), 7.11 (s, 1H), 7.06 (s, 1H), 1.42 (brs, 2H), 1.23 (brs, 2H). MS: $[MH]^+$ 397.0.

Example 1.98. Synthesis of 4-(4-(2-hydroxypropan-2-yl)phenyl)pyrrolo[1,2-a]quinoxaline-7-carboxylic acid (I-197)

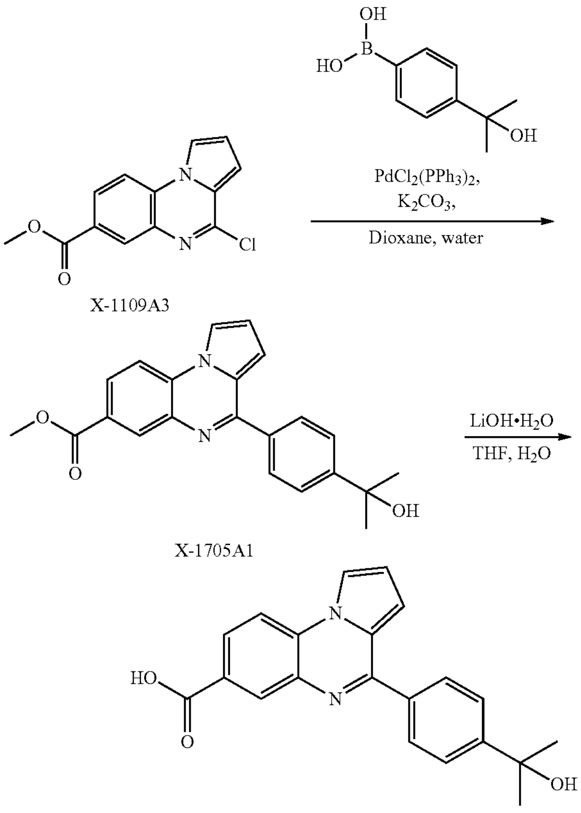

X-1109A3

X-1705A1

I-197

The following compound was prepared in a manner analogous to the procedures described above for 4-(4-(trifluoromethoxy)phenyl)pyrrolo[1,2-a]quinoxaline-7-carboxylic acid (I-192):

4-(4-(2-hydroxypropan-2-yl)phenyl)pyrrolo[1,2-a]quinoxaline-7-carboxylic acid (I-197) (0.070 g, 29%) as an off-white solid. $^1H$ NMR (400 MHz, DMSO-$d_6$) δ 13.17 (brs, 1H), 8.63-8.63 (d, J=1.6 Hz, 1H), 8.44 (s, 1H), 8.42 (d, J=8.4 Hz, 1H), 8.13-8.10 (dd, J=8.4, 1.6 Hz, 1H), 7.99-7.97 (d, J=8.4 Hz, 2H), 7.70-7.68 (d, J=8.4 Hz, 2H), 7.13-7.12 (d, J=3.6 Hz, 1H), 7.06-7.05 (t, J=3.2 Hz, 1H), 5.17 (s, 1H), 1.51 (s, 6H). MS: $[MH]^+$ 347.32.

Example 1.99. Synthesis of 4-(5-(trifluoromethyl)pyrazin-2-yl)pyrrolo[1,2-a]quinoxaline-7-carboxylic acid (I-198

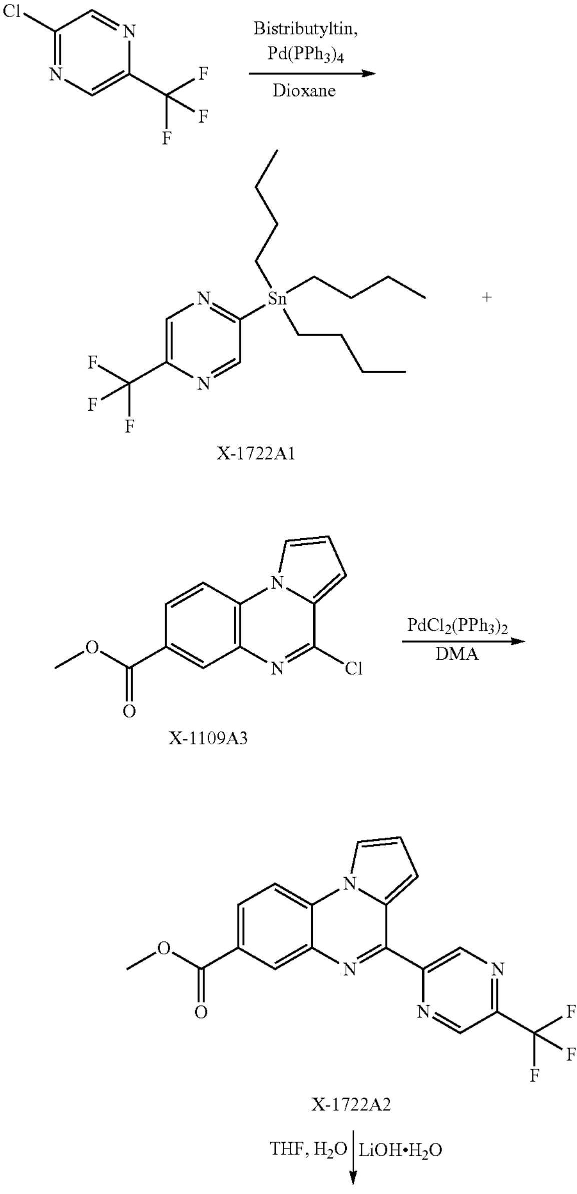

X-1722A1

X-1109A3

X-1722A2

-continued

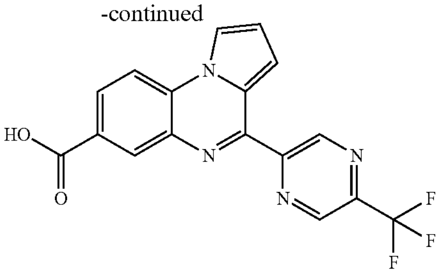

I-198

2-(Tributylstannyl)-5-(trifluoromethyl)pyrazine (X-1722A1). To a stirred solution of 2-chloro-5-(trifluoromethyl)pyrazine (0.500 g, 2.74 mmol) in 1,4-Dioxane (5 mL) were added Bistributyltin (1.90 g, 3.29 mmol) at room temperature under nitrogen. The reaction mixture was degassed (purging with nitrogen) for 20 min followed by the addition of $Pd(PPh_3)_4$ (0.310 g, 0.27 mmol) and the resulting mixture was heated at 110° C. for 1 h. Reaction mixture was directly concentrated under reduced pressure to afford 2-(tributylstannyl)-5-(trifluoromethyl)pyrazine (X-1722A1). (0.85 g, quantitative yield) as a colorless oil. The crude was directly used for next step without further purification. MS: $[MH]^+$ 439.1.

Methyl 4-(5-(trifluoromethyl)pyrazin-2-yl)pyrrolo[1,2-a]quinoxaline-7-carboxylate (X-1722A2). To a stirred solution of methyl 4-chloropyrrolo[1,2-a]quinoxaline-7-carboxylate (X-1109A3) (0.250 g, 0.95 mmol) in DMA (4 mL) were added 2-(tributylstannyl)-5-(trifluoromethyl)pyrazine (0.839 g, 1.91 mmol) at room temperature under nitrogen. The reaction mixture was degassed (purging with nitrogen) for 20 min followed by the addition of $PdCl_2(PPh_3)_4$ (0.110 g, 0.09 mmol) and the resulting mixture was heated at 130° C. for 1 h in microwave. Reaction mixture was cooled to room temperature, quenched with water (100 mL) and was extracted with ethyl acetate (75 mL×3), and washed with brine (50 mL×2), dried over anhydrous $Na_2SO_4$ and concentrated in vacuo. The resulting crude was purified by silica gel column chromatography, using ethyl acetate-hexane=0:1→2:8 as gradient, to afford methyl 4-(5-(trifluoromethyl)pyrazin-2-yl)pyrrolo[1,2-a]quinoxaline-7-carboxylate (X-1722A2) (0.110 g, 30%) as an yellow solid. MS: $[MH]^+$ 373.0.

4-(5-(Trifluoromethyl)pyrazin-2-yl)pyrrolo[1,2-a]quinoxaline-7-carboxylic acid (I-198). To a stirred solution of methyl 4-(5-(trifluoromethyl)pyrazin-2-yl)pyrrolo[1,2-a]quinoxaline-7-carboxylate (X-1722A2) (0.11 g, 0.29 mmol) in a mixture of THF-water (3:1; 4.0 mL) was added lithium hydroxide monohydrate (0.037 g, 0.88 mmol) at room temperature and the resulting mixture was stirred at 70° C. for 1 h. Reaction mixture was concentrated under reduced pressure, diluted with water (100 mL), and extracted with ethyl acetate (50×2 mL) to remove unwanted organic impurities. The aqueous layer was acidified (pH~2-3) with aqueous 1N HCl, and the resulting precipitate was collected by filtration, and washed with cold water until the pH of the filtrate became neutral (pH~6-7). The obtained solid was dried under high vacuum to afford 4-(5-(trifluoromethyl)pyrazin-2-yl)pyrrolo[1,2-a]quinoxaline-7-carboxylic acid (I-198) (0.030 g, 28%) as a yellow solid. $^1H$ NMR (400 MHz, DMSO-$d_6$) δ 9.87 (s, 1H), 9.42 (s, 1H), 8.73-8.73 (d, J=1.6 Hz, 1H), 8.59-8.58 (d, J=1.6 Hz, 1H), 8.52-8.50 (d, J=8.8 Hz, 1H), 8.23-8.20 (dd, J=8.8, 2.0 Hz, 1H), 7.87-7.86 (dd, J=4.0, 3.2 Hz, 1H), 7.17-7.15 (m, 1H). MS: $[MH]^+$ 359.3.

Example 1.100. Synthesis of 4-(2,4-bis(trifluoromethyl)phenyl)pyrrolo[1,2-a]quinoxaline-7-carboxylic acid (I-199)

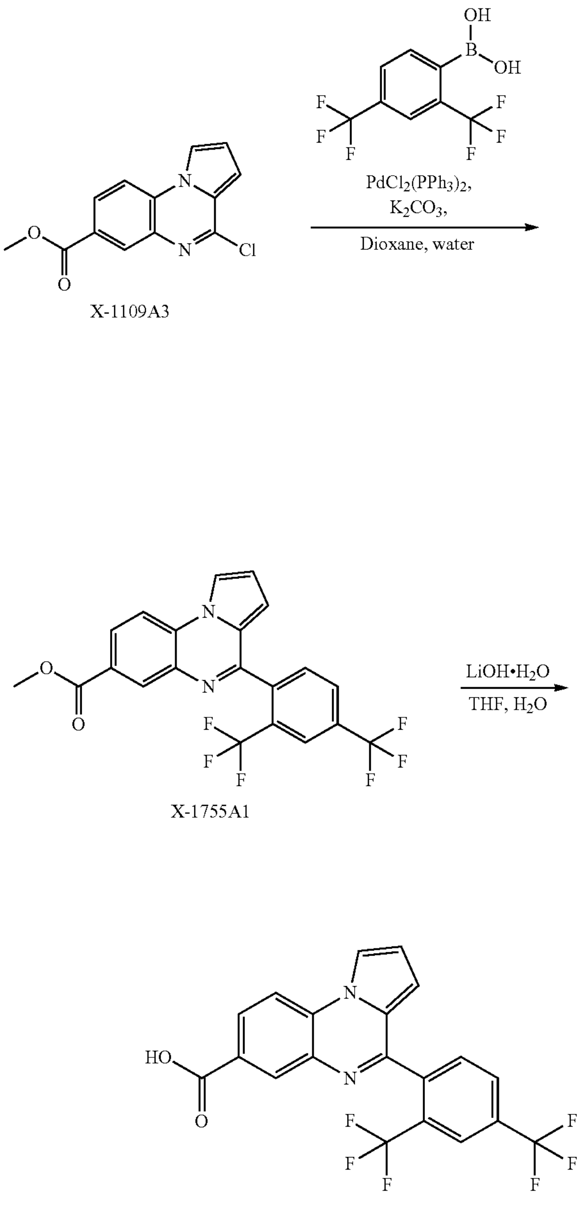

X-1109A3

X-1755A1

I-199

The following compound was prepared in a manner analogous to the procedures described above for 4-(4-(trifluoromethoxy)phenyl)pyrrolo[1,2-a]quinoxaline-7-carboxylic acid (I-192):

4-(2,4-bis(trifluoromethyl)phenyl)pyrrolo[1,2-a]quinoxaline-7-carboxylic acid (I-199) (0.100 g, 34%) as a white solid. $^1H$ NMR (400 MHz, DMSO-$d_6$) δ 8.67-8.66 (d, J=1.6 Hz, 1H), 8.48-8.46 (d, J=8.4 Hz, 1H), 8.39-8.39 (d, J=1.6 Hz, 1H), 8.32 (s, 1H), 8.28-8.26 (d, J=8.4 Hz, 1H), 8.20-8.18 (dd, J=8.4, 1.6 Hz, 1H), 8.05-8.03 (d, J=8.0 Hz, 1H), 7.03-7.01 (m, 1H), 6.64-6.63 (dd, J=4.0, 0.8 Hz, 1H). MS: $[MH]^+$ 425.38.

Example 1.101. Synthesis of 4-(2-methoxy-4,6-bis(trifluoromethyl)phenyl)pyrrolo[1,2-a]quinoxaline-7-carboxylic acid (I-200)

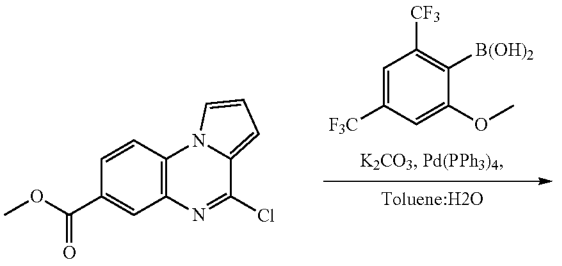

X-1109A3

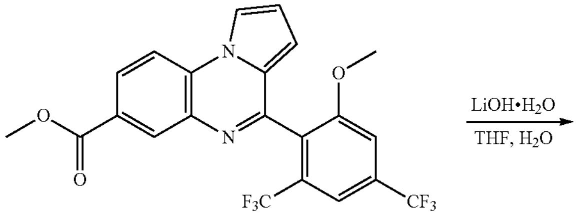

X-1756A1

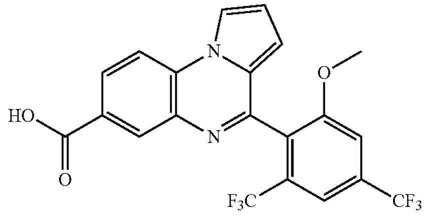

I-200

The following compound was prepared in a manner analogous to the procedures described above for 4-(4-(trifluoromethoxy)phenyl)pyrrolo[1,2-a]quinoxaline-7-carboxylic acid (I-192):

4-(2-methoxy-4,6-bis(trifluoromethyl)phenyl)pyrrolo[1,2-a]quinoxaline-7-carboxylic acid (I-200) (0.090 g, 37%) as an off-white solid. $^1$H NMR (400 MHz, DMSO-$d_6$) δ 8.61-8.60 (m, 1H), 8.49-8.46 (d, J=8.8 Hz, 1H), 8.38-8.37 (d, J=2.0 Hz, 1H), 8.20-8.17 (dd, J=8.8, 2.0 Hz, 1H), 7.89 (s, 1H), 7.83 (s, 1H), 6.97-6.96 (m, 1H), 6.56-6.55 (dd, J=4.0, 1.2 Hz, 1H), 3.82 (s, 3H).

Example 1.102. Synthesis of 4-(2,6-Dichloro-4-(trifluoromethyl)phenyl)pyrrolo[1,2-a]quinoxaline-7-carboxylic acid (I-201)

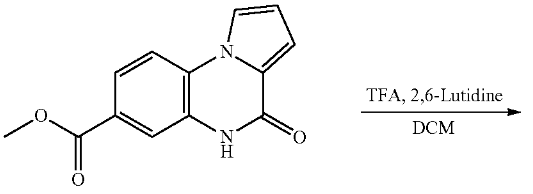

X-1109A2

-continued

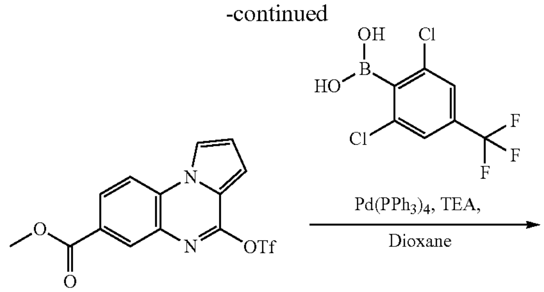

X-1757B1

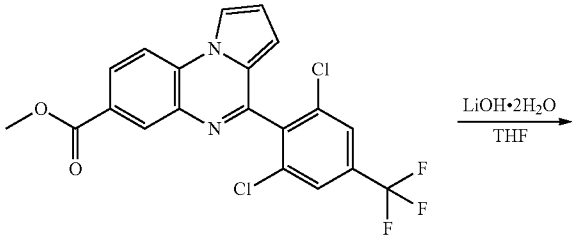

X-1757B2

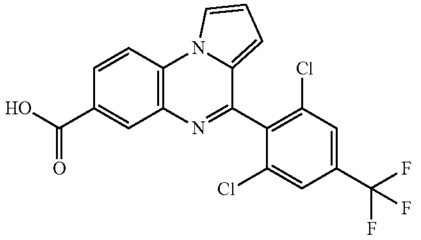

I-201

Methyl 4-oxo-4,5-dihydropyrrolo[1,2-a]quinoxaline-7-carboxylate was prepared as described in Example 1.2

Methyl 4-(((trifluoromethyl)sulfonyl)oxy)pyrrolo[1,2-a]quinoxaline-7-carboxylate (X-1757B1). To a stirred solution of methyl 4-oxo-4,5-dihydropyrrolo[1,2-a]quinoxaline-7-carboxylate (X-1109A2) (1.0 g, 4.13 mmol) in DCM (20 mL) were added 2,6-Lutidine (0.83 g, 8.26 mmol) drop-wise at room temperature under nitrogen and then add TFA (2.3 g, 8.26 mmol) and resulting mixture was stirred at room temperature for 3 h. Reaction mixture was cooled to room temperature, diluted with water (100 mL) and was extracted with ethyl acetate (150 mL×3). Combined organic extracts were dried over anhydrous $Na_2SO_4$ and concentrated under reduce pressure to afford methyl 4-(((trifluoromethyl)sulfonyl)oxy)pyrrolo[1,2-a]quinoxaline-7-carboxylate (X-1757B1) (0.800 g, 38%) as an off-white solid. MS: $[MH]^+$ 375.28.

Methyl 4-(2,6-dichloro-4-(trifluoromethyl)phenyl)pyrrolo[1,2-a]quinoxaline-7-carboxylate (X-1757B2). To a stirred solution of methyl 4-(((trifluoromethyl)sulfonyl)oxy)pyrrolo[1,2-a]quinoxaline-7-carboxylate (X-1757B1) (0.100 g, 0.26 mmol) in 1,4-dioxane (3 ml) were added triethylamine (0.1 ml, 0.66 mmol) and (2,6-dichloro-4-(trifluoromethyl)phenyl)boronic acid (0.08 g, 0.31 mmol) sequentially at room temperature under nitrogen. The reaction mixture was degassed (purging with nitrogen) for 20 min followed by the addition of $Pd(PPh_3)_4$ (0.014 g, 0.013 mmol) and the resulting mixture was heated at 100° C. for 2 h. Reaction mixture was cooled to room temperature, diluted with water (30 mL) and was extracted with ethyl acetate (30 mL×3). Combined organic extracts were dried over anhydrous $Na_2SO_4$ and concentrated under reduce pressure to afford crude mass, which was purified by silica gel CombiFlash column chromatography, using ethyl acetate-hexane=2:8→3:7 as gradient, to afford methyl 4-(2,6-dichloro-4-(trifluoromethyl)phenyl)pyrrolo[1,2-a]quinoxaline-7-carboxylate (X-1757B2) (0.060 g, 50%) as an white solid. MS: $[MH]^+$ 439.28.

4-(2,6-Dichloro-4-(trifluoromethyl)phenyl)pyrrolo[1,2-a]quinoxaline-7-carboxylic acid (I-201). To a stirred solution of methyl 4-(2,6-dichloro-4-(trifluoromethyl)phenyl)pyrrolo[1,2-a]quinoxaline-7-carboxylate (X-1757) (0.060 g, 0.13 mmol) in a mixture of THF-water (2:1; 4.0 mL) was added lithium hydroxide monohydrate (0.011 g, 0.27 mmol) at room temperature and the resulting mixture was heated at 70° C. for 1 h. After cooling to room temperature, the reaction mixture was concentrated under reduced pressure, obtained crude was diluted with water (10 mL) and was extracted with ethyl acetate (10 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was triturated by using n-pentane and dried under high vacuum to afford to afford 4-(2,6-dichloro-4-(trifluoromethyl)phenyl)pyrrolo[1,2-a]quinoxaline-7-carboxylic acid (I-201) (0.030 g, 62%) as an off-white solid. $^1H$ NMR (400 MHz, DMSO-$d_6$) 8.69-8.68 (d, J=2.0 Hz, 1H), 8.51-8.48 (d, J=8.8 Hz, 1H), 8.44 (d, J=2.0 Hz, 1H), 8.23-8.20 (m, 3H), 7.03-7.02 (m, 1H), 6.70-6.69 (dd, J=2.8, 4.0 Hz, 1H). (Acid proton missing due to moisture content in DMSO-$d_6$). MS: $[MH]^+$ 425.29

Example 1.103. Synthesis of N-(4-(5-(trifluoromethyl)pyridin-2-yl)pyrrolo[1,2-a]quinoxalin-7-yl)acrylamide (I-202)

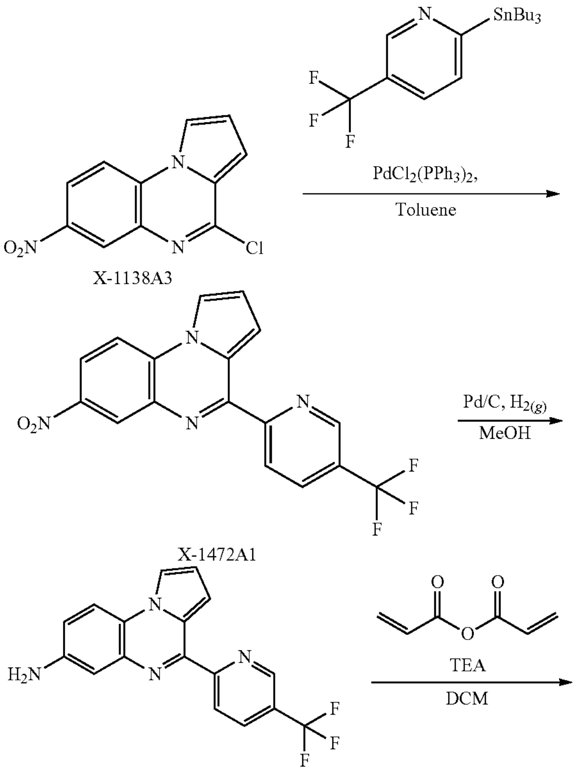

X-1138A3
X-1472A1
X-1472A2

-continued

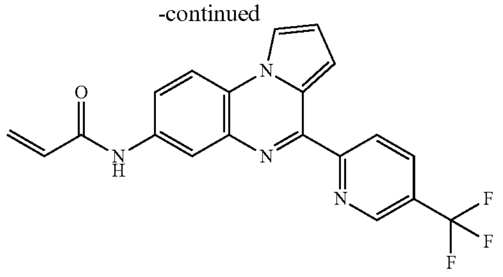

I-202

7-Nitro-4-(5-(trifluoromethyl)pyridin-2-yl)pyrrolo[1,2-a]quinoxaline (X-1472A1). 2-(Tributylstannyl)-5-(trifluoromethyl)pyridine (0.573 g, 1.315 mmol) was added to a stirred solution of 4-chloro-7-nitropyrrolo[1,2-a]quinoxaline (X-1138A3) (0.250 g, 1.012 mmol) in toluene (5 mL) at room temperature under nitrogen. Reaction mixture was degassed (purging with nitrogen) for 15 min followed by the addition of $PdCl_2(PPh_3)_2$ (0.021 g, 0.03 mmol) and the resulting mixture was heated at 140° C. for 2 h. After cooling to room temperature, reaction mixture was diluted with water (50 mL) and was extracted by ethyl acetate (50 mL×3). Combined organic extracts were dried over anhydrous $Na_2SO_4$ and concentrated under reduced pressure. The crude product was purified by silica gel column chromatography, ethyl acetate-hexane=0:1→1:9 as gradient, to afford 7-nitro-4-(5-(trifluoromethyl)pyridin-2-yl)pyrrolo[1,2-a]quinoxaline (X-1472A1) (0.120 g, 55%) as a white solid. MS: $[MH]^+$ 359.0

4-(5-(Trifluoromethyl)pyridin-2-yl)pyrrolo[1,2-a]quinoxalin-7-amine (X-1472A2). To a stirred solution of 7-nitro-4-(5-(trifluoromethyl)pyridin-2-yl)pyrrolo[1,2-a]quinoxaline (X-1472A1) (0.200 g 0.61 mmol) in MeOH (2 mL) was added 10% Pd on activated Carbon (0.380 g, 8.06 mmol) at room temperature. The resulting reaction mixture was hydrogenated under balloon pressure at room temperature for 30 min. The reaction mixture was filtered through celite bed, washed the bed with methanol (50 mL) and collected filtrates were concentrated under reduced pressure. Obtained crude was triturated with n-pentane (100 mL) and dried under high vacuum to afford 4-(5-(trifluoromethyl)pyridin-2-yl)pyrrolo[1,2-a]quinoxalin-7-amine (X-1472A2) (0.180 g, quant.; crude) as an off-white solid, which was carried forward to the next step without further purification.

N-(4-(5-(Trifluoromethyl)pyridin-2-yl)pyrrolo[1,2-a]quinoxalin-7-yl)acrylamide (I-202). This compound was prepared in a manner analogous to the procedures described below for N-(4-(4-(tert-butyl)phenyl)pyrrolo[1,2-a]quinoxalin-7-yl)-2-hydroxyacetamide (I-203): N-(4-(5-(Trifluoromethyl)pyridin-2-yl)pyrrolo[1,2-a]quinoxalin-7-yl)acrylamide (I-202) (0.040 g, 17%) as a white solid. $^1H$ NMR (400 MHz, DMSO-$d_6$) δ 10.47 (s, 1H), 9.22 (s, 1H), 8.72-8.70 (d, J=8.4 Hz, 1H), 8.55 (s, 1H), 8.50-8.50 (dd, J=Hz, 1H), 8.45-8.43 (dd, J=8.0, 1.6 Hz, 1H), 8.36-8.34 (d, J=8.8 Hz, 1H), 7.87-7.83 (m, 2H), 7.04-7.02 (t, J=2.8 Hz, 1H), 6.53-6.46 (m, 1H), 6.35-6.31 (dd, J=16.8, 1.6 Hz, 1H), 5.84-5.81 (dd, J=10.0, 1.2 Hz, 1H). MS: $[MH]^+$ 383.1.

Example 1.104. Synthesis of N-(4-(4-(tert-butyl)phenyl)pyrrolo[1,2-a]quinoxalin-7-yl)-2-hydroxyacetamide (I-203)

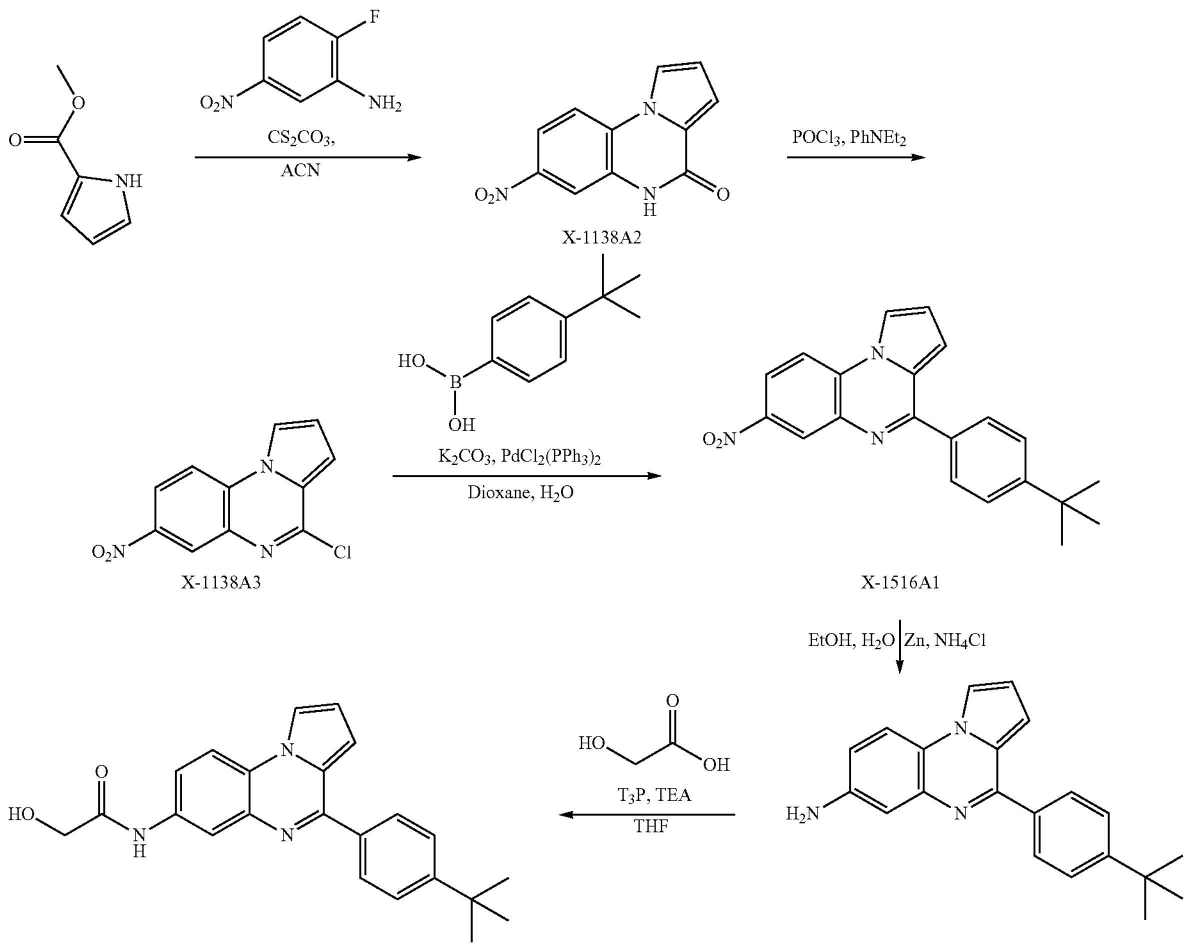

7-Nitropyrrolo[1,2-a]quinoxalin-4(5H)-one (X-1138A2). To a stirred solution of methyl 1H-pyrrole-2-carboxylate (100 g, 799 mmol) in anhydrous $CH_3CN$ (1000 mL) were added 2-fluoro-5-nitroaniline (124.7 g, 799 mmol) and $Cs_2CO_3$ (519.7 g, 1599 mmol) sequentially at room temperature and stirring was continued for 16 h at 80° C. temperature. Completion of reaction was confirmed by TLC (EtOAc:Hex=7:3) A second batch reaction was performed with same 100 g of SM in parallel and observed similar results. Both batches were combined together prior to work-up. Reaction mixture was poured into water (5000 mL), product was precipitated out which was filtered through Buchner funnel, solid material obtained was sticky in nature so we suspended in water and water was concentrated under reduced pressure to get crude (400 g), which was suspended in 10% citric acid solution stirred at room temperature for 30 minute then suspension was filtered through Buckner funnel to afford 7-nitropyrrolo[1,2-a]quinoxalin-4(5H)-one (X-1138A2) (200 g, 54%; crude) as a dark grey solid, which was used further step without any purification. MS: $[MH]^+$ 229.9

4-Chloro-7-nitropyrrolo[1,2-a]quinoxaline (X-1138A3). $POCl_3$ (1000 mL) was added slowly to a stirred solution of 7-nitropyrrolo[1,2-a]quinoxalin-4(5H)-one (X-1138A2) (100 g, 436.68 mmol) in $PhN(CH_3)_2$ (200 mL) at 0° C. Then the reaction was stirred at 100° C. temperature for 2 h. Reaction mixture was slowly poured into ice with continuous stirring, during which solid was precipitated out (black color). The reaction mixture was filtered through Buchner funnel, residue was washed with water, dried under reduced pressure at 50° C. to get the crude product. The crude product was purified by silica gel column chromatography, using DCM=100%, to afford 4-chloro-7-nitropyrrolo[1,2-a]quinoxaline (X-1138A3) (122 g, 30%) as a light pink floppy solid. $^1H$ NMR (400 MHz, DMSO-$d_6$) δ 8.76 (s, 1H), 8.58-8.54 (m, 2H), 8.47-8.44 (dd, J=2.0, 9.2 Hz, 1H), 7.23-7.22 (d, J=4.0 Hz, 1H), 7.13-7.12 (m, 1H). MS: $[MH]^+$ 247.9.

4-(4-(tert-Butyl)phenyl)-7-nitropyrrolo[1,2-a]quinoxaline (X-1516A1). To a stirred solution of 4-chloro-7-nitropyrrolo[1,2-a]quinoxaline (X-1138A3) (3.0 g, 12.14 mmol) in a mixture of 1,4-dioxane-water (1:1; 30 mL) were added (4-(tert-butyl)phenyl)boronic acid (2.80 g, 15.78 mmol) and $K_2CO_3$ (5.0 g, 36.43 mmol) at room temperature under nitrogen. The reaction mixture was degassed (purging with nitrogen) for 20 min followed by the addition of $PdCl_2(PPh_3)_2$ (0.850 g, 1.21 mmol) and the resulting mixture was heated at 90° C. for 2 h. Reaction mixture was cooled to room temperature, diluted with water (150 mL) and was extracted with ethyl acetate (150 mL×3). Combined organic extracts were washed with brine (100 mL), dried over anhydrous $Na_2SO_4$ and concentrated in vacuo. The crude product was purified by silica gel column chromatography, using ethyl acetate-hexane=1:19→1:9 as gradient, to afford 4-(4-(tert-butyl)phenyl)-7-nitropyrrolo[1,2-a]quinoxaline (X-1516A1) (3.20 g, 76%) as a yellow solid. MS: $[MH]^+$ 346.22.

4-(4-(tert-Butyl)phenyl)pyrrolo[1,2-a]quinoxalin-7-amine (X-1516A2). To a stirred solution of 4-(4-(tert-butyl)phenyl)-7-nitropyrrolo[1,2-a]quinoxaline (X-1516A1) (3.20 g, 9.27 mmol) in a mixture of EtOH—$H_2O$ (7:3; 30 mL) were added Zn dust (3.61 g, 55.65 mmol) and ammonium chloride (3.0 g, 55.95 mmol) at room temperature and stirred at 70° C. for 1 h. Reaction mixture was filtered through a celite bed and residue was washed with ethyl acetate (200 mL). Combined filtrates were washed with water (150 mL), dried over anhydrous $Na_2SO_4$ and concentrated under reduce pressure to afford 4-(4-(tert-butyl)phenyl)pyrrolo[1,2-a]quinoxalin-7-amine (X-1516A2) (2.80 g, quant.; crude) as a yellow solid, which was used in next step without further purification. MS: $[MH]^+$ 316.2

N-(4-(4-(tert-Butyl)phenyl)pyrrolo[1,2-a]quinoxalin-7-yl)-2-hydroxyacetamide (I-203). To a stirred solution of 4-(4-(tert-butyl)phenyl)pyrrolo[1,2-a]quinoxalin-7-amine (X-1516A2) (0.200 g, 0.65 mmol) in THE (3.0 mL) were added triethylamine (0.199 g, 1.92 mmol), 2-hydroxyacetic acid (0.050 g, 0.65 mmol) and propylphosphonic anhydride (0.627 g, 1.97 mmol) sequentially at 0° C. under nitrogen and the resulting mixture was stirred at room temperature for 1 h. Reaction mixture was diluted with water (100 mL) and was extracted with ethyl acetate (150 mL×3). Combined organic extracts were dried over anhydrous $Na_2SO_4$ and concentrated under reduce pressure to provide a crude mass, which was purified by reverse phase (C-18) silica gel column chromatography using acetonitrile-water=0:1→3:2 as gradient, to afford N-(4-(4-(tert-butyl)phenyl)pyrrolo[1,2-a]quinoxalin-7-yl)-2-hydroxyacetamide (I-203) (0.040 g, 17%) as a yellow solid. $^1H$ NMR (400 MHz, DMSO-$d_6$) δ 9.96 (s, 1H), 8.48-8.37 (dd, J=1.2 Hz, 1H), 8.40-8.39 (d, J=2.0 Hz, 1H), 8.27-8.24 (d, J=9.2 Hz, 1H), 7.96-7.94 (d, J=8.4 Hz, 2H), 7.91-7.88 (dd, J=2.0, 8.8 Hz, 1H), 7.61-7.59 (d, J=8.4 Hz, 1H), 7.03-7.02 (d, J=3.2 Hz, 1H), 6.95-6.94 (t, J=2.8 Hz, 1H), 5.76-5.73 (t, J=6.0 Hz, 1H), 4.06-4.04 (d, J=5.6 Hz, 2H), 1.36 (s, 9H). MS: $[MH]^+$ 374.2.

Example 1.105. Synthesis of N-(4-(4-(tert-Butyl)phenyl)pyrrolo[1,2-a]quinoxalin-7-yl)-2-hydroxypropanamide (I-204)

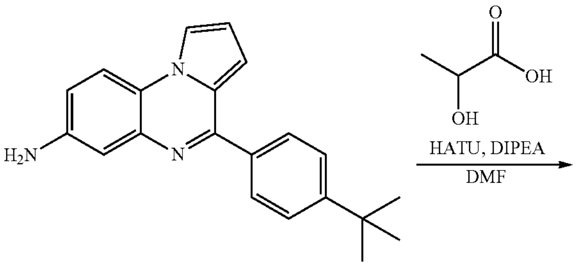

X-1516A2

-continued

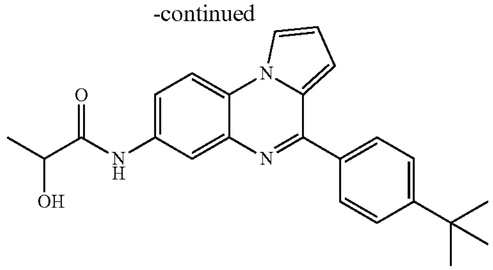

I-204

This compound was prepared in a manner analogous to the procedures described above for N-(4-(4-(tert-butyl)phenyl)pyrrolo[1,2-a]quinoxalin-7-yl)-2-hydroxyacetamide (I-203):

N-(4-(4-(tert-Butyl)phenyl)pyrrolo[1,2-a]quinoxalin-7-yl)-2-hydroxypropanamide (I-204) (0.080 g, 13%) as an off-white solid. $^1H$ NMR (400 MHz, DMSO-$d_6$) δ 9.94 (s, 1H), 8.47-8.47 (d, J=1.6 Hz, 1H), 8.41-8.40 (d, J=2.0 Hz, 1H) 8.26-8.24 (d, J=9.2 Hz, 1H), 7.95-7.90 (m, 3H), 7.61-7.59 (d, J=8.4 Hz, 2H), 7.02-7.01 (d, J=3.2 Hz, 1H), 6.95-6.94 (t, J=2.8 Hz, 1H), 5.83-5.81 (d, J=5.2 Hz, 1H), 4.21-4.18 (m, 1H), 1.36-1.31 (m, 12H). MS: [M-]-388.2.

Example 1.106. Synthesis of N-(4-(4-(tert-butyl)phenyl)pyrrolo[1,2-a]quinoxalin-7-yl)-2-(dimethylamino)acetamide (I-205)

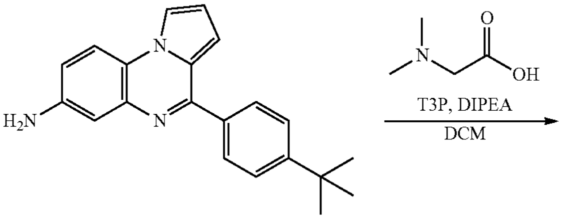

X-1516A2

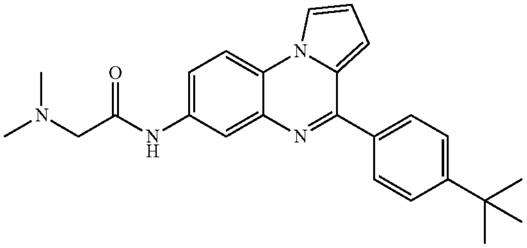

I-205

This compound was prepared in a manner analogous to the procedures described above for N-(4-(4-(tert-butyl)phenyl)pyrrolo[1,2-a]quinoxalin-7-yl)-2-hydroxyacetamide (I-203):

N-(4-(4-(tert-butyl)phenyl)pyrrolo[1,2-a]quinoxalin-7-yl)-2-(dimethylamino)acetamide (I-205) (0.080 g, 31%) as a white solid. $^1H$ NMR (400 MHz, DMSO-$d_6$) δ 10.12 (s, 1H), 8.47-8.47 (d, J=1.6 Hz, 1H), 8.35-8.35 (d, J=2.0 Hz, 1H), 8.26-8.24 (d, J=9.2 Hz, 1H), 7.96-7.94 (d, J=8.0 Hz, 2H), 7.85-7.82 (dd, J=8.8 Hz, 2.0 Hz, 1H), 7.61-7.59 (d, J=8.4 Hz, 2H), 7.03-7.02 (d, J=3.2 Hz, 1H), 6.95-6.94 (t, J=2.8 Hz, 1H), 3.14 (s, 2H), 2.31 (s, 6H), 1.36 (s, 9H). MS: $[MH]^+$ 401.3.

Example 1.107. Synthesis of 2-amino-N-(4-(4-(tert-butyl)phenyl)pyrrolo[1,2-a]quinoxalin-7-yl)acetamide

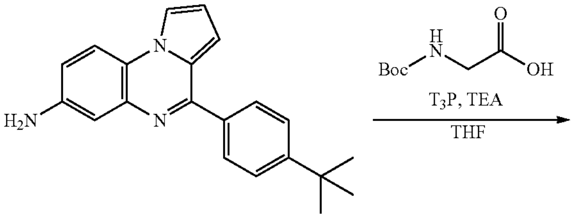

X-1516A2

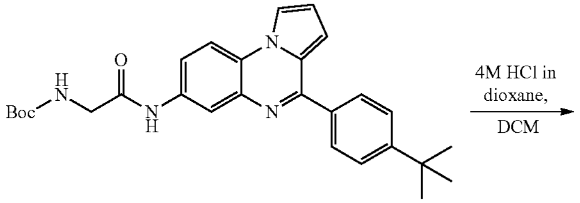

X-1519A1

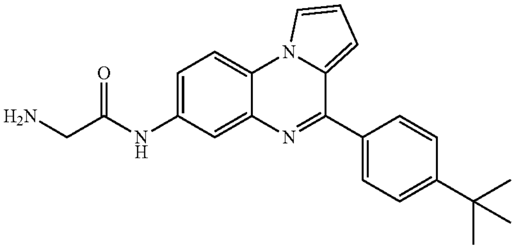

I-206 tert-Butyl (2-((4-(4-(tert-butyl)phenyl)pyrrolo[1,2-a]quinoxalin-7-yl)amino)-2-oxoethyl)carbamate. (X-1519A1). This compound was prepared in a manner analogous to the procedures described above for N-(4-(4-(tert-butyl)phenyl)pyrrolo[1,2-a]quinoxalin-7-yl)-2-hydroxyacetamide (I-203): (0.180 g, 40%) as a white solid. MS: $[MH-100]^+$ 373.2

2-Amino-N-(4-(4-(tert-butyl)phenyl)pyrrolo[1,2-a]quinoxalin-7-yl)acetamide (I-206). To a stirred solution of tert-butyl (2-((4-(4-(tert-butyl)phenyl)pyrrolo[1,2-a]quinoxalin-7-yl)amino)-2-oxoethyl)carbamate (X-1519A1) (0.180 g, 0.38 mmol) in DCM (2 mL) was added 4M HCl in 1,4-dioxane (2 mL) at 0° C. under nitrogen and the resulting reaction mixture was stirred at room temperature for 1 h. Reaction mixture was concentrated under reduced pressure, obtained crude was triturated with diethyl ether (2×10 mL) and dried under reduced pressure to afford 2-amino-N-(4-(4-(tert-butyl)phenyl)pyrrolo[1,2-a]quinoxalin-7-yl)acetamide (I-206) (0.120 g, 85%) as an off-white solid. $^1H$ NMR (400 MHz, DMSO-$d_6$) δ: 10.89 (brs, 1H), 8.60 (brs, 1H), 8.37-8.35 (d, J=9.6 Hz, 2H), 8.19 (br, 2H), 7.96-7.94 (d, J=8.4 Hz, 2H), 7.77-7.75 (d, J=8.4 Hz, 1H), 7.65-7.63 (d, J=8.4 Hz, 2H), 7.16 (brs, 1H), 7.05 (brs, 1H), 3.87-3.86 (d, J=5.6 Hz, 2H), 1.37 (s, 9H). MS: $[MH]^+$ 373.2

Example 1.108. Synthesis of N-(4-(4-(tert-butyl)phenyl)pyrrolo[1,2-a]quinoxalin-7-yl)picolinamide (I-207)

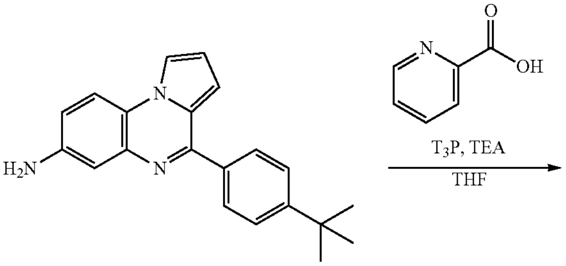

X-1516A2

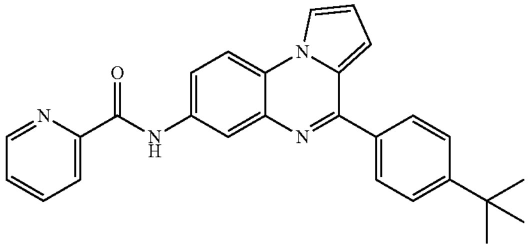

I-207

This compound was prepared in a manner analogous to the procedures described above for N-(4-(4-(tert-butyl)phenyl)pyrrolo[1,2-a]quinoxalin-7-yl)-2-hydroxyacetamide (I-203):

N-(4-(4-(tert-butyl)phenyl)pyrrolo[1,2-a]quinoxalin-7-yl)picolinamide (I-207) (0.080 g, 30%) as off-white solid. $^1H$ NMR (400 MHz, DMSO-$d_6$) δ: 10.95 (s, 1H), 8.78-8.77 (d, J=4.4 Hz, 1H), 8.61-8.61 (d, J=2.4 Hz, 1H), 8.51-8.50 (d, J=1.6 Hz, 1H), 8.33-8.31 (d, J=8.8 Hz, 1H), 8.22-8.20 (d, J=7.6 Hz 1H), 8.13-8.08 (m, 2H), 7.97-7.95 (d, J=8.4, 2H), 7.72-7.69 (m, 1H) 7.62-7.60 (d, J=8.4 Hz, 2H), 7.04-7.03 (d, J=3.2 Hz, 1H) 6.97-6.95 (t, J=6.4 Hz, 1H) 1.36 (s, 9H). MS: $[MH]^+$ 421.2

Example 1.109. Synthesis of (4-(4-(tert-butyl)phenyl)pyrrolo[1,2-a]quinoxalin-7-yl)(imino)(methyl)-16-sulfanone (I-208, I-209)

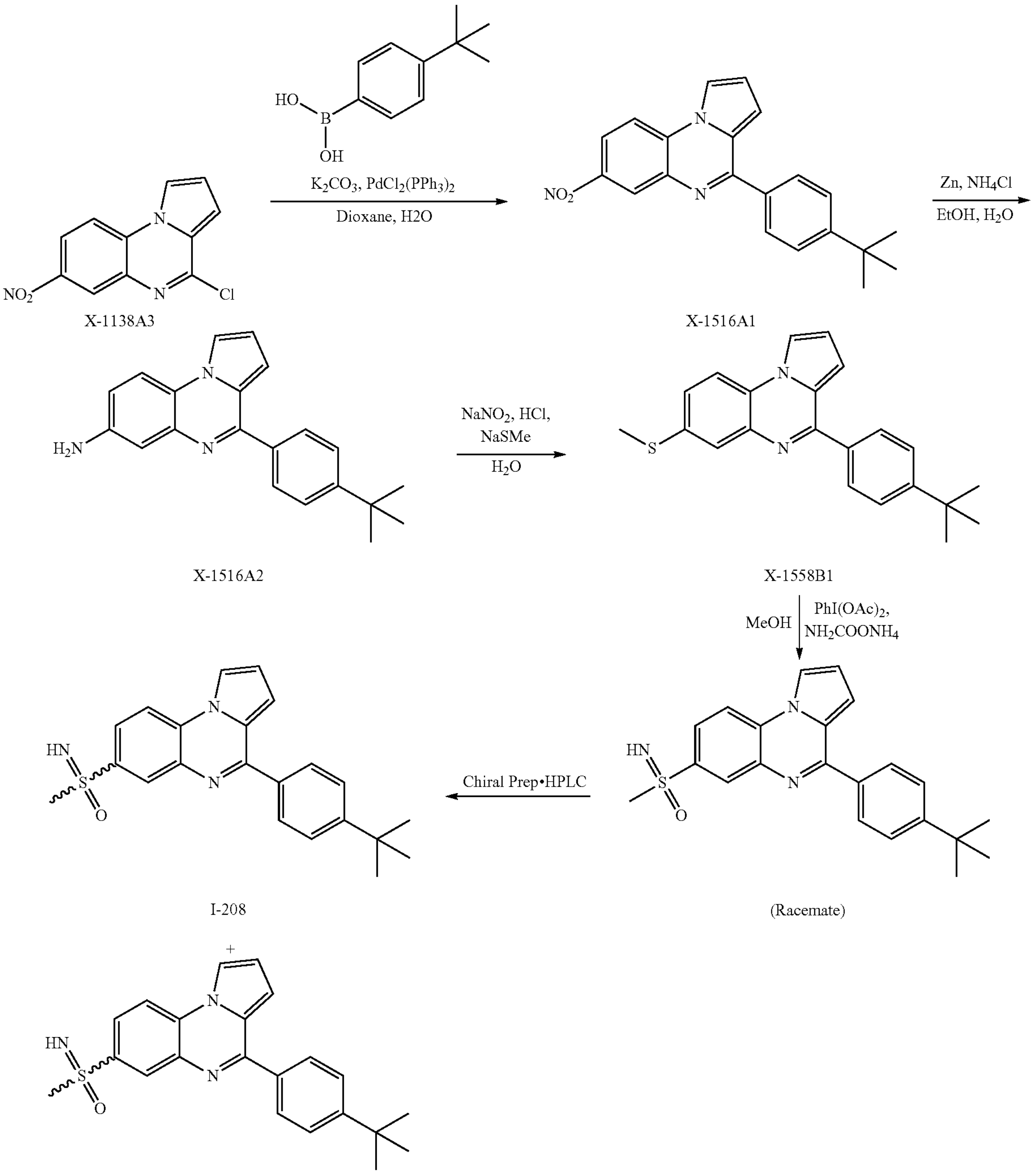

X-1138A3

X-1516A1

X-1516A2

X-1558B1

(Racemate)

I-208

+

I-209

4-(4-(tert-Butyl)phenyl)-7-nitropyrrolo[1,2-a]quinoxaline (X-1516A1) and 4-(4-(tert-Butyl)phenyl)pyrrolo[1,2-a]quinoxalin-7-amine (X-1516A2). Experimental details are mentioned under N-(4-(4-(tert-butyl)phenyl)pyrrolo[1,2-a]quinoxalin-7-yl)-2-hydroxyacetamide (I-203).

4-(4-(tert-Butyl)phenyl)-7-(methylthio)pyrrolo[1,2-a]quinoxaline (X-1558B1). To a stirred solution of 4-(4-(tert-butyl)phenyl)pyrrolo[1,2-a]quinoxalin-7-amine (X-1516A2) (2.0 g, 6.34 mmol) in HCl (0.012 g, 0.0126 mmol) and $H_2O$ was added the solution of $NaNO_2$ (0.430 g, 6.34 mmol) in $H_2O$ and NaSMe (0.440 g, 6.34 mmol) sequentially at 0° C. temperature under nitrogen and stirred at the same temperature for 1 h. The resulting reaction mixture was diluted with water (150 mL) and was extracted with ethyl acetate (150 mL×3) and concentrate under reduce pressure. The crude product was purified by flash column chromatography using ethyl acetate-hexane=1:941:5 as gradient, to afford 4-(4-(tert-butyl)phenyl)-7-(methylthio)pyrrolo[1,2-a]quinoxaline (X-1558B1) (0.930 g, 42%) as a yellow solid. MS: $[MH]^+$ 347.0.

(4-(4-(tert-Butyl)phenyl)pyrrolo[1,2-a]quinoxalin-7-yl)(imino)(methyl)-16-sulfanone. To a stirred solution of 4-(4-(tert-butyl)phenyl)-7-(methylthio)pyrrolo[1,2-a]quinoxaline (X-1558B1) (0.930 g, 2.68 mmol) in methanol (15 mL) were added ammonium carbamate (0.310 g, 4.02 mmol) and $PhI(OAc)_2$ (1.99 g, 6.1 mmol) at room temperature under nitrogen and the reaction mixture was stirred at the same temperature for 30 min. The reaction mixture was directly concentrated under reduce pressure. Obtained crude was purified by reverse phase (C-18) silica gel column chromatography with using acetonitrile-water=0:147:3 as gradient, to afford (4-(4-(tert-butyl)phenyl)pyrrolo[1,2-a]quinoxalin-7-yl)(imino)(methyl)-16-sulfanone (0.15 g, 14%) as an off white solid.

The enantiomers were separated by semi-preparative chiral chromatography and each fraction was labeled by its elution order as first eluting isomer and second eluting isomer. The absolute stereochemistry was not assigned. Instrument: Agilent Column: REPACK-AD (250*30 mm, 10 m). Mobile phase: MeOH/IPA=97/3 at 40 ml/min. Isocratic gradient for 25 min. Detector (UV: 210 nm, 260 nm)

(4-(4-(tert-Butyl)phenyl)pyrrolo[1,2-a]quinoxalin-7-yl)(imino)(methyl)-16-sulfanone, first eluting isomer (I-208): (0.032 g, 3%) as an off-white solid. $^1H$ NMR (400 MHz, DMSO-$d_6$) δ 8.67-8.67 (d, J=1.6 Hz, 1H), 8.54-8.52 (d, J=8.4 Hz, 1H), 8.40-8.40 (d, J=1.6 Hz, 1H), 8.09-8.07 (d, J=8.8 Hz, 1H), 8.00-7.98 (d, J=8.0 Hz, 2H), 7.63-7.61 (d, J=8.4 Hz, 2H), 7.16-7.15 (d, J=3.2 Hz, 1H), 7.07-7.06 (t, J=2.8 Hz, 1H), 4.40 (s, 1H), 3.32 (s, 3H), 1.36 (s, 9H). MS: $[MH]^+$ 377.9.

(4-(4-(tert-Butyl)phenyl)pyrrolo[1,2-a]quinoxalin-7-yl)(imino)(methyl)-16-sulfanone, second eluting isomer (1-209): (0.018 g, 2%) as an off-white solid. $^1H$ NMR (400 MHz, DMSO-$d_6$) δ 8.67-8.67 (d, J=1.6 Hz, 1H), 8.54-8.52 (d, J=8.8 Hz, 1H), 8.40-8.40 (d, J=2.0 Hz, 1H), 8.09-8.07 (dd, J=8.4, 1.6 Hz, 1H), 8.00-7.98 (d, J=8.4 Hz, 2H), 7.63-7.61 (d, J=8.4 Hz, 2H), 7.16-7.15 (d, J=3.6 Hz, 1H), 7.07-7.06 (t, J=3.2 Hz, 1H), 4.39 (brs, 1H), 3.32 (s, 3H), 1.36 (s, 9H). MS: $[MH]^+$ 377.9.

Example 1.110. Synthesis of N-(4-(4-(trifluoromethyl)phenyl)pyrrolo[1,2-a]quinoxalin-7-yl)methanesulfonamide (1-210)

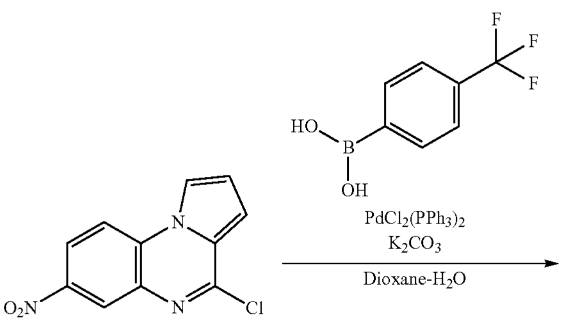

X-1138A3

-continued

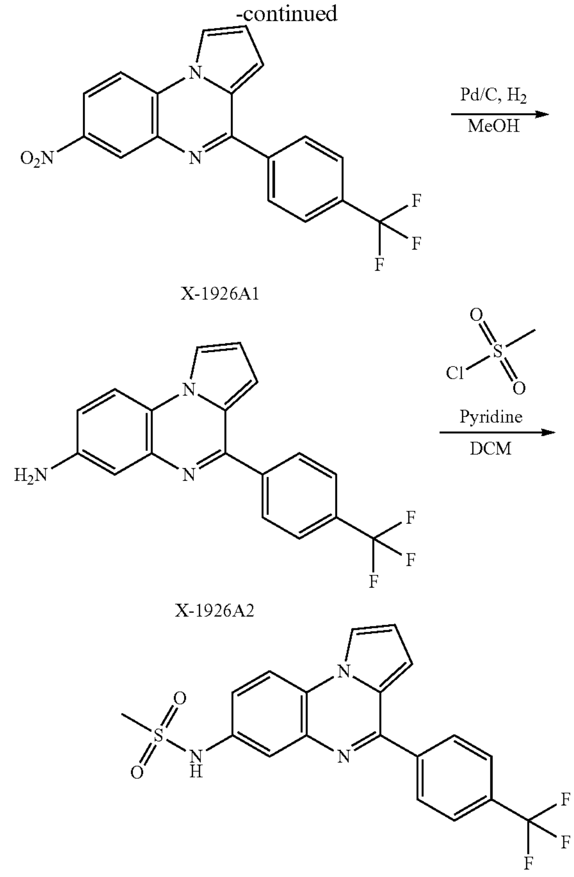

X-1926A1

X-1926A2

I-210

7-Nitro-4-(4-(trifluoromethyl)phenyl)pyrrolo[1,2-a]quinoxaline (X-1926A1). To a stirred solution of 4-chloro-7-nitropyrrolo[1,2-a]quinoxaline (X-1138A3) (1.0 g, 4.04 mmol) in a mixture of 1,4-dioxane-water (9:1; 50 mL) were added (4-(trifluoromethyl)phenyl)boronic acid (1.15 g, 6.07 mmol) and $K_2CO_3$ (1.39 g, 10.10 mmol) sequentially at room temperature under nitrogen. The reaction mixture was degassed (purging with nitrogen) for 20 min followed by the addition of $PdCl_2(PPh_3)_2$ (0.080 g, 0.40 mmol) and the resulting mixture was heated at 80° C. for 2 h. Reaction mixture was cooled to room temperature, diluted with water (250 mL) and was extracted with ethyl acetate (250 mL×2). Combined organic extracts were dried over anhydrous $Na_2SO_4$ and concentrated under reduce pressure to afford crude mass, which was purified by silica gel column chromatography, using ethyl acetate-hexane=0:1→1:3 as eluent, to afford 7-nitro-4-(4-(trifluoromethyl)phenyl)pyrrolo[1,2-a]quinoxaline (X-1926A1) (1.20 g, 83%) as an off-white solid. MS: $[MH]^+$ 358.3.

4-(4-(Trifluoromethyl)phenyl)pyrrolo[1,2-a]quinoxalin-7-amine (X-1926A2). To a stirred solution of 7-nitro-4-(4-(trifluoromethyl)phenyl)pyrrolo[1,2-a]quinoxaline (X-1926A1) (0.600 g, 1.68 mmol) in methanol (25 mL) was added 10% Pd in activated carbon (0.150 g) at room temperature under nitrogen and the resulting mixture was hydrogenated under balloon pressure at the same temperature. The reaction mixture was filtered through a celite bad, washed the bed with methanol (300 mL) and collected filtrates were concentrated under reduced pressure to afford crude mass, which was purified by trituration using n-pentane (50 mL), to afford 4-(4-(trifluoromethyl)phenyl)pyrrolo

[1,2-a]quinoxalin-7-amine (X-1926A2). (0.45 g, 81%) as a yellow solid. MS: $[MH]^+$ 337.3.

N-(4-(4-(trifluoromethyl)phenyl)pyrrolo[1,2-a]quinoxalin-7-yl)methanesulfonamide (I-210). To a stirred solution of 4-(4-(trifluoromethyl)phenyl)pyrrolo[1,2-a]quinoxalin-7-amine (X-1926A2) (0.250 g, 0.76 mmol) in DCM (10 mL) were added pyridine (0.150 g, 1.91 mmol) and methanesulfonyl chloride (0.08 g, 0.76 mmol) sequentially at 0° C. under nitrogen and the resulting reaction mixture was stirred at room temperature for 2 h. Reaction mixture was diluted with water (50 mL) and was extracted with ethyl acetate (50 mL×2). Organic extracts were combined, dried over anhydrous $Na_2SO_4$ and concentrated under reduced pressure to afford crude mass, which was purified by reverse phase (C-18) silica gel column chromatography, using acetonitrile-water=0:1→2:3 as gradient, to afford N-(4-(4-(trifluoromethyl)phenyl)pyrrolo[1,2-a]quinoxalin-7-yl)methanesulfonamide (I-210) (0.080 g, 25.8%) as a pale yellow solid. $^1$H NMR (400 MHz, DMSO-$d_6$) δ: 10.02 (s, 1H), 8.57-8.56 (dd, J=1.2 Hz, 1.2 Hz, 1H), 8.36-8.33 (d, J=9.2 Hz, 1H), 8.24-8.22 (d, J=8.0 Hz, 2H), 7.96-7.94 (d, J=8.0 Hz, 2H), 7.80-7.79 (d, J=2.4 Hz, 1H), 7.49-7.46 (dd, J=9.2 Hz, 2.4 Hz, 1H), 7.08-7.07 (dd, J=0.8 Hz, 1.2 Hz, 1H), 7.02-7.01 (m, 1H), 3.05 (s, 3H). MS: $[MH]^+$ 406.3.

-continued

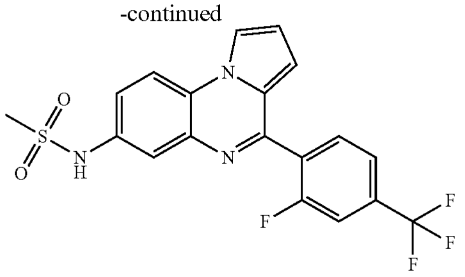

I-211

This compound was prepared in a manner analogous to the procedures described above for N-(4-(4-(trifluoromethyl)phenyl)pyrrolo[1,2-a]quinoxalin-7-yl)methanesulfonamide (I-210):

N-(4-(2-fluoro-4-(trifluoromethyl)phenyl)pyrrolo[1,2-a]quinoxalin-7-yl)methanesulfonamide (I-211) (0.350 g, 63.44%) as a yellow solid. $^1$H NMR (400 MHz, DMSO-$d_6$) δ: 10.03 (s, 1H), 8.56-8.54 (m, 1H), 8.38-8.36 (d, J=8.8 Hz, 1H), 8.01-7.94 (m, 2H), 7.81-7.79 (d, J=8.0 Hz, 1H), 7.77-7.77 (d, J=2.4 Hz, 1H), 7.53-7.7.50 (dd, J=8.8 Hz, 2.4 Hz, 1H), 6.98-6.97 (m, 1H), 6.76-6.75 (t, J=1.6 Hz, 1H), 3.06 (s, 3H). MS: $[MH]^+$ 424.4.

Example 1.111. Synthesis of N-(4-(2-fluoro-4-(trifluoromethyl)phenyl)pyrrolo[1,2-a]quinoxalin-7-yl) methanesulfonamide (I-211)

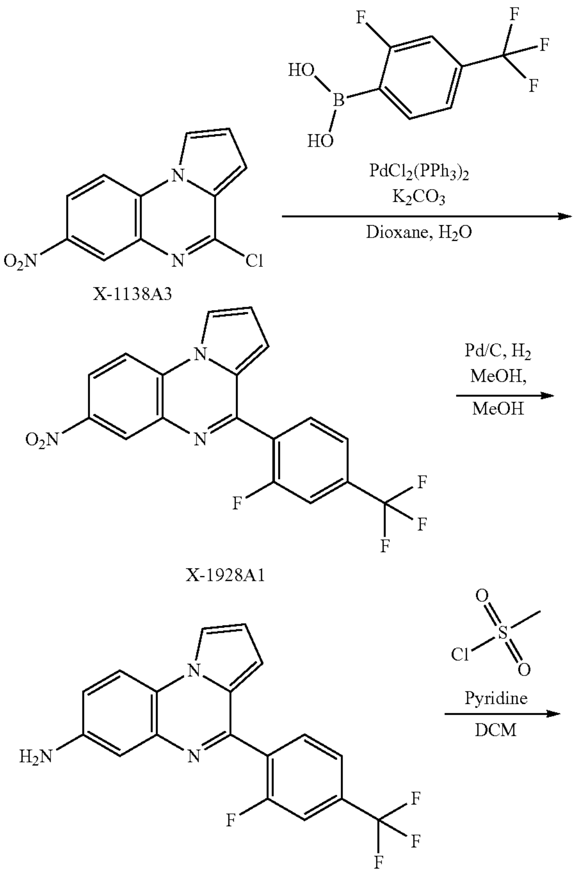

X-1138A3

X-1928A1

X-1928A2

Example 1.112. Synthesis of N-((8-(4-(trifluoromethyl)phenyl)imidazo[1,2-a]pyrazin-6-yl)methyl) nicotinamide (I-212)

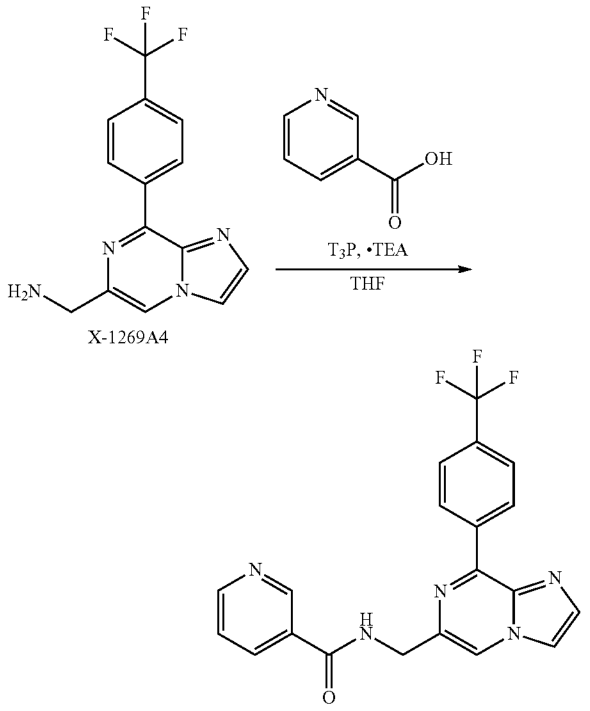

X-1269A4

I-212

Synthetic procedures of (8-(4-(trifluoromethyl)phenyl) imidazo[1,2-a]pyrazin-6-yl)methanamine (CEN2-X-1269A4) described in Example 1.132.

N-((8-(4-(trifluoromethyl)phenyl)imidazo[1,2-a]pyrazin-6-yl)methyl)nicotinamide (I-212). To a solution of (8-(4-(trifluoromethyl)phenyl)imidazo[1,2-a]pyrazin-6-yl)methanamine (0.095 g, 0.32 mmol) in THE (4 mL) were added nicotinic acid (0.060 g, 0.48 mmol) and triethylamine (0.131 g, 1.13 mmol). and propylphosphonic anhydride (0.175 g, 1.07 mmol) sequentially at 0° C. under nitrogen and the resulting mixture was stirred at room temperature for 10 min. Reaction mixture was poured into ice-water (20 mL) and was extracted with ethyl acetate (20 mL×3). Combined organic extracts were washed with brine (30 mL), dried over anhydrous $Na_2SO_4$ and concentrated under reduced pressure. The resulting crude was purified by reverse phase (C-18) silica gel column chromatography, using acetonitrile-water=0:1→8:2 as gradient, to afford N-((8-(4-(trifluoromethyl)phenyl)imidazo[1,2-a]pyrazin-6-yl)methyl)nicotinamide (I-212) (0.075 g, 58%) as a white solid. 1H NMR (400 MHz, DMSO-$d_6$) δ 9.44-9.41 (t, J=6.0 Hz, 1H), 9.12-9.11 (d, J=1.6 Hz, 1H), 9.03-9.01 (d, J=8.0 Hz, 2H), 8.74-8.73 (d, J=3.6 Hz, 1H), 8.67 (s, 1H), 8.29-8.27 (m, 2H), 7.96-7.94 (d, J=8.4 Hz, 2H), 7.91 (s, 1H), 7.56-7.53 (m, 1H), 4.71-4.69 (d, J=5.6 Hz, 2H). MS: $[MH]^+$ 398.20.

Example 1.112. 2-Fluoro-N-((8-(4-(trifluoromethyl)phenyl)imidazo[1,2-a]pyrazin-6-yl)methyl)acrylamide (I-178)

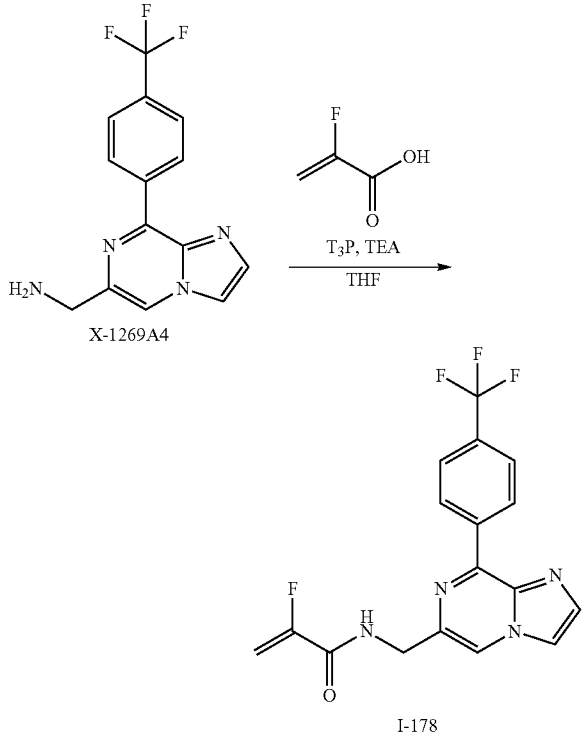

X-1269A4

I-178

The following compound was synthesized in a manner analogous to the procedures described above for N-((8-(4-(trifluoromethyl)phenyl)imidazo[1,2-a]pyrazin-6-yl)methyl)nicotinamide (I-212):

2-Fluoro-N-((8-(4-(trifluoromethyl)phenyl)imidazo[1,2-a]pyrazin-6-yl)methyl)acrylamide (I-178) (0.030 g, 24%) as a white solid. $^1H$ NMR (400 MHz, DMSO-$d_6$) δ 9.23-9.20 (t, J=10.8 Hz, 1H), 9.01-8.99 (d, J=8.0 Hz, 2H), 8.60 (s, 1H), 8.29 (s, 1H), 7.96-7.94 (d, J=8.4 Hz, 2H), 7.91 (s, 1H), 5.67-5.54 (dd, J=48.0, 3.6 Hz, 1H), 5.36-5.31 (dd, J=15.6, 3.6 Hz, 1H), 4.57-4.56 (d, J=5.6 Hz, 2H). MS: $[MH]^+$ 365.09.

Example 1.113. (R)-2-hydroxy-N-((3-(4-(trifluoromethyl)phenyl)imidazo[1,2-a]pyrimidin-2-yl)methyl)propanamide (I-213)

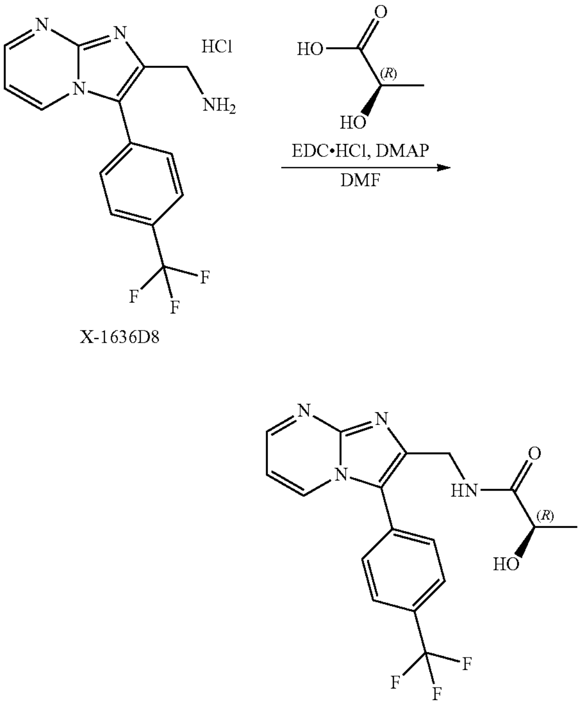

X-1636D8

I-213

Synthesis of of (3-(4-(trifluoromethyl)phenyl)imidazo[1,2-a]pyrimidin-2-yl)methanamine hydrochloride (X-1636D8) provided below for N-((6-(4-(trifluoromethyl)phenyl)imidazo[1,5-a]pyrimidin-8-yl)methyl)acrylamide (I-410)

(R)-2-hydroxy-N-((3-(4-(trifluoromethyl)phenyl)imidazo[1,2-a]pyrimidin-2-yl)methyl)propanamide (I-213). To a stirred solution of (R)-2-hydroxypropanoic acid (0.110 g, 1.23 mmol)) in DMF (1.5 mL) were added 4-dimethylaminopyridine (0.15 g, 1.23 mmol) and EDC·HCl (0.118 g, 0.610 mmol) sequentially at 0° C. under nitrogen. After 30 min of stirring at the same temperature, was added a solution of (3-(4-(trifluoromethyl)phenyl)imidazo[1,2-a]pyrimidin-2-yl)methanamine hydrochloride (X-1636D8) (0.12 g, 0.410 mmol) in DMF (1.5 mL) slowly at 0° C. to the reaction mixture and stirring was continued for 3 h at room temperature. Reaction mixture was diluted with water (10 mL) and was extracted with ethyl acetate (30 mL×3). Combined organic extracts were dried over anhydrous $Na_2SO_4$ and concentrated under reduce pressure to afford crude mass, which was purified by reverse phase column chromatography, using acetonitrile:water (0.1% formic acid)=0:1→2:3 as gradient, to afford (R)-2-hydroxy-N-((3-(4-(trifluoromethyl)phenyl)imidazo[1,2-a]pyrimidin-2-yl)methyl)propanamide (I-213) (0.022 g, 21.8%) as an off-white solid. $^1H$ NMR (400 MHz, DMSO-$d_6$) δ 8.84-8.81 (dd, J=7.2 Hz, 2.0 Hz, 1H), 8.62-8.60 (m, 1H), 8.07-8.06 (t, J=4.8 Hz, 1H), 7.95-7.91 (m 4H), 7.10-7.08 (m, 1H), 5.58-5.57 (d, J=4.8 Hz, 1H), 4.48-4.47 (d, J=5.6 Hz, 2H), 3.99-3.94 (m, 1H), 1.17-1.15 (d, J=6.4 Hz, 3H). MS: $[MH]^+$ 365.4.

Example 1.114. Synthesis of (S)-2-hydroxy-N-((3-(4-(trifluoromethyl)phenyl)imidazo[1,2-a]pyrimidin-2-yl)methyl)propanamide (I-187

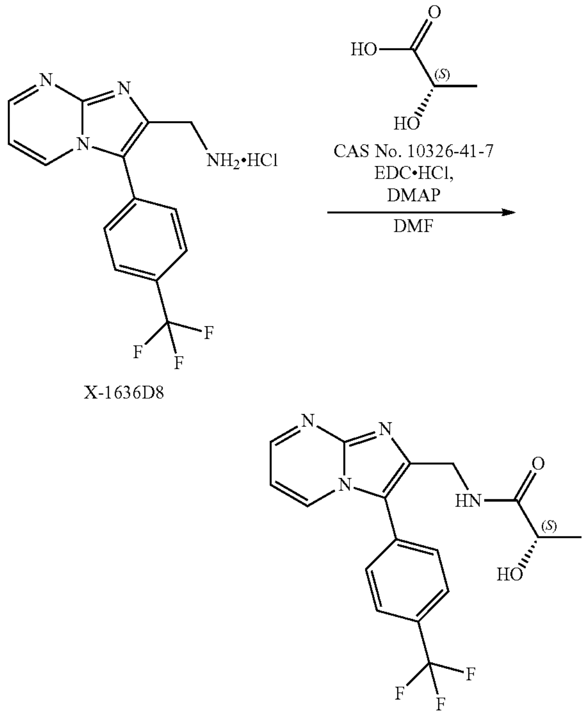

X-1636D8

I-187

The following compound was prepared in a manner analogous to the procedures described above for (R)-2-hydroxy-N-((3-(4-(trifluoromethyl)phenyl)imidazo[1,2-a]pyrimidin-2-yl)methyl)propanamide (I-213):

(S)-2-hydroxy-N-((3-(4-(trifluoromethyl)phenyl)imidazo[1,2-a]pyrimidin-2-yl)methyl)propanamide (I-187) (0.022 g, 15%) as an off-white solid. $^1$H NMR (400 MHz, DMSO-$d_6$) δ 8.84-8.81 (dd, J=6.8 Hz, 1.6 Hz, 1H), 8.62-8.60 (m, 1H), 8.08-8.06 (t, J=5.20 Hz, 1H), 7.95-7.91 (m, 4H), 7.10-7.08 (dd, J=6.8 Hz, 4.0 Hz, 1H), 5.56 (brs, 1H), 4.48-4.47 (d, J=5.2 Hz, 2H), 3.99-3.94 (q, J=6.8 Hz, 1H), 1.19-1.15 (d, J=6.8 Hz, 3H) MS: $[MH]^+$ 365.4.

Example 1.115. Synthesis of (E)-4-fluoro-N-((8-(4-(trifluoromethyl)phenyl)imidazo[1,2-a]pyrazin-6-yl)methyl)but-2-enamide (I-214)

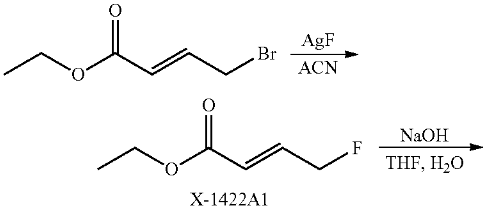

X-1422A1

-continued

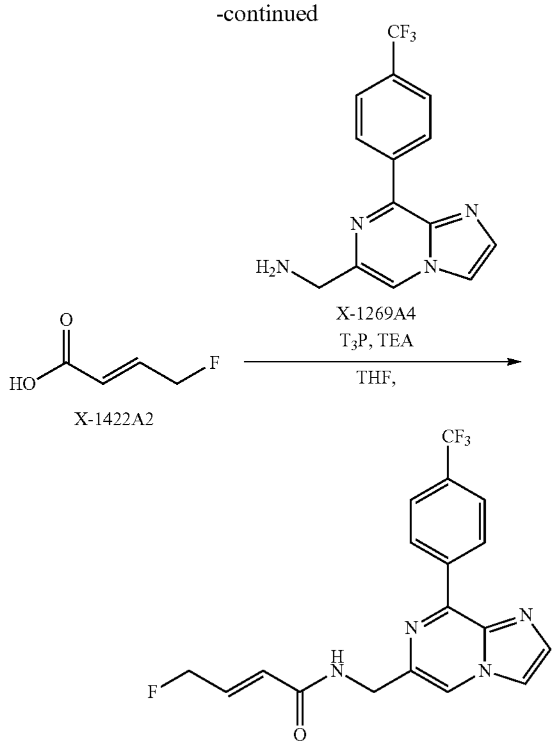

X-1269A4

X-1422A2

I-214

Ethyl (E)-4-fluorobut-2-enoate (X-1422A1). To a solution of ethyl (E)-4-bromobut-2-enoate (0.500 g, 2.60 mmol) in ACN (5 mL) was added AgF (0.98 mL, 7.81 mmol) at room temperature. The resulting reaction mixture was stirred at room temperature for 16 h. Reaction mixture was poured into water (50 mL) and was extracted with ethyl acetate (50×2 mL) Combined extracts were dried over anhydrous $Na_2SO_4$ and concentrated in vacuo. The crude was purified by silica gel column chromatography with using ethyl acetate-hexane=0:1→2:8 as gradient, to afford Ethyl (E)-4-fluorobut-2-enoate (X-1422A1) (0.300 g, 72%) as an colorless oil. $^1$H NMR (400 MHz, DMSO-$d_6$) δ: 7.01-6.84 (m, 1H), 6.04-6.00 (dd, J=1.6, 15.6 Hz, 1H), 5.21-5.19 (m, 1H), 5.09-5.08 (m, 1H), 4.17-4.10 (m, 2H), 1.27-1.13 (m, 3H).

(E)-4-Fluorobut-2-enoic acid (X-1422A2). To a stirred solution of Ethyl (E)-4-fluorobut-2-enoate (X-1422A1) (0.200 g, 1.51 mmol) in a mixture of THF-water (3:1; 4 mL) was added sodium hydroxide monohydrate (0.180 g, 4.53 mmol) at room temperature and stirred at room temperature for 2 h. The reaction mixture was concentrated under reduced pressure, crude mass was diluted with water (10 mL) and was extracted with ethyl acetate (20 mL×2) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was dried in vacuo to afford (E)-4-fluorobut-2-enoic acid (X-1422A2) (0.090 g, 57%) as a white solid. $^1$H NMR (400 MHz, DMSO-$d_6$) δ: 12.44 (br. s, 1H), 6.93-6.82 (m, 1H), 5.97-5.93 (dd, J=2.0, 16.0 Hz, 1H), 5.19-5.17 (m, 1H), 5.07-5.06 (m, 1H).

(E)-4-Fluoro-N-((8-(4-(trifluoromethyl)phenyl)imidazo[1,2-a]pyrazin-6-yl)methyl)but-2-enamide (I-214). To a solution of (E)-4-fluorobut-2-enoic acid (X-1422A2) (0.090 g, 0.86 mmol)) in THE (3 mL) were added TEA (0.3 mL, 2.58 mmol) and T3P (0.550 g, 1.73 mmol) at 0° C. The resulting reaction mixture was stirred at 0° C. for 10 min. (8-(4-(trifluoromethyl)phenyl)imidazo[1,2-a]pyrazin-6-yl) methanamine (X-1269A4) (0.320 g, 1.12 mmol) was added at 0° C. and the resulting reaction mixture was stirred at room temperature for 2 h. Reaction mixture was poured into ice water (30 mL) was extracted with ethyl acetate (30×2 mL) Combined extracts were dried over anhydrous $Na_2SO_4$ and concentrated in vacuo. The crude was purified by silica gel column chromatography with using ethyl acetate-hexane=0:1→5:5 as gradient, to afford (E)-4-fluoro-N-((8-(4-(trifluoromethyl)phenyl)imidazo[1,2-a]pyrazin-6-yl) methyl)but-2-enamide (I-214) (0.035 g, 5%) as an off-white solid. $^1$H NMR (400 MHz, DMSO-$d_6$) δ: 9.02-9.00 (d, J=8.0 Hz, 2H), 8.87-8.84 (t, J=5.2 Hz, 1H), 8.59 (s, 1H), 8.29 (s, 1H), 7.96-7.94 (d, J=8.4 Hz, 2H), 7.91 (s, 1H), 6.83-6.71 (m, 1H), 6.29-6.25 (dd, J=1.6, 15.2 Hz, 1H), 5.19-5.18 (d, J=1.6 Hz, 1H), 5.07 (d, 1.6 Hz, 1H), 4.55-4.54 (d, J=5.6 Hz, 2H). MS: $[MH]^+$ 379.1.

Example 1.116. Synthesis of N-methyl-N-((8-(4-(trifluoromethyl)phenyl)imidazo[1,2-a]pyrazin-6-yl) methyl)acrylamide (I-177)

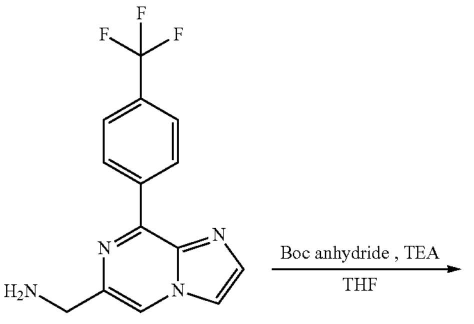

X-1269A4

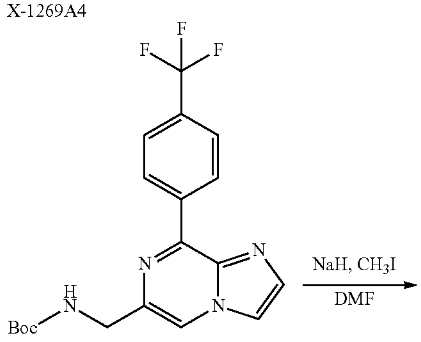

X-1423A1

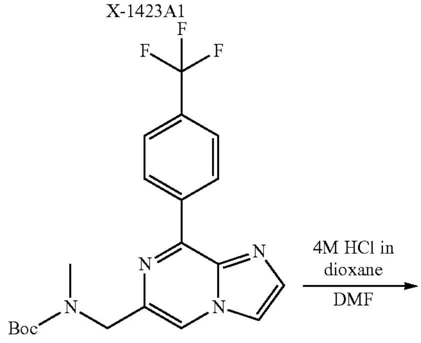

X-1423A2

-continued

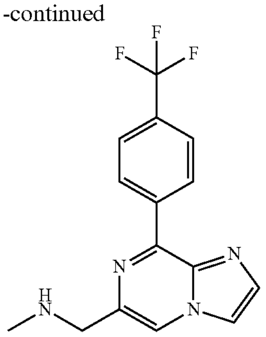

X-1423A3

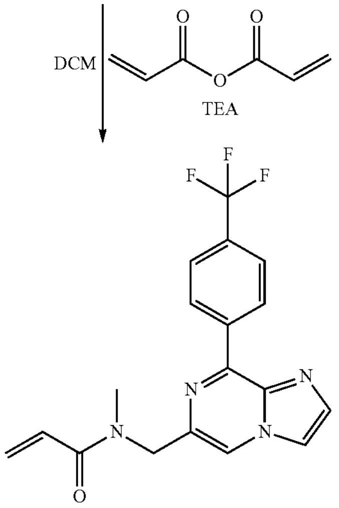

I-177 tert-Butyl ((8-(4-(trifluoromethyl)phenyl)imidazo[1,2-a] pyrazin-6-yl)methyl)carbamate (X-1423A1). To a solution of (8-(4-(trifluoromethyl)phenyl)imidazo[1,2-a]pyrazin-6-yl)methanamine (0.400 g, 1.36 mmol)) in THE (5 mL) was added TEA (0.5 mL, 4.08 mmol) at room temperature. The resulting reaction mixture was stirred at room temperature for 10 min. Boc-anhydride (0.440 g, 2.04 mmol) was added at room temperature and the resulting reaction mixture was stirred at room temperature for 2 h. Reaction mixture was poured into water (50 mL) and was extracted with ethyl acetate (50 mL×2) Combined extracts were dried over anhydrous $Na_2SO_4$ and concentrated in vacuo. The crude was purified by silica gel column chromatography with using ethyl acetate-hexane=0:1→3:7 as gradient, to afford tert-butyl ((8-(4-(trifluoromethyl)phenyl)imidazo[1,2-a] pyrazin-6-yl)methyl)carbamate (X-1423A1) (0.300 g, 57%) as an off-white solid. MS: $[MH]^+$ 393.22.

tert-Butyl methyl((8-(4-(trifluoromethyl)phenyl)imidazo [1,2-a]pyrazin-6-yl)methyl)carbamate (X-1423A2). To a stirred solution of tert-butyl ((8-(4-(trifluoromethyl)phenyl) imidazo[1,2-a]pyrazin-6-yl)methyl)carbamate (X-1423A1) (0.300 g, 0.76 mmol) in DMF (3 mL) was added dried NaH (washed with n-hexane) (0.036 g, 1.52 mmol) at 0° C. and stirred for 15 min at same temperature. MeI (0.160 g, 1.14 mmol) was added at 0° C. and the resulting reaction mixture was stirred at room temperature for 2 h. Reaction mixture was poured into water (50 mL) and was extracted with ethyl acetate (50 mL×2) Combined extracts were dried over anhydrous $Na_2SO_4$ and concentrated in vacuo. The crude was purified by silica gel column chromatography with using ethyl acetate-hexane=0:1→3:7 as gradient, to afford (tert-butyl methyl((8-(4-(trifluoromethyl)phenyl)imidazo[1,2-a]pyrazin-6-yl)methyl)carbamate (X-1423A2) (0.260 g, 84%) as a white solid. MS: $[MH]^+$ 407.12.

N-Methyl-1-(8-(4-(trifluoromethyl)phenyl)imidazo[1,2-a]pyrazin-6-yl)methanamine (X-1423A3). To a solution of (tert-butyl methyl((8-(4-(trifluoromethyl)phenyl)imidazo[1,2-a]pyrazin-6-yl)methyl)carbamate (X-1422A2) (0.250 g, 0.61 mmol)) in DCM (4 mL) was added 4M HCl in 1,4 Dioxane (3.0 mL) at 0° C. under nitrogen and the resulting reaction mixture was stirred at room temperature for 2 h. Reaction mixture was concentrated under reduced pressure. Obtained crude was triturated with diethyl ether (10 mL×2), dried over high vacuum to afford N-methyl-1-(8-(4-(trifluoromethyl)phenyl)imidazo[1,2-a]pyrazin-6-yl)methanamine (X-1423A3) (0.200 g, 92%) as an off-white solid. MS: $[MH]^+$ 307.0

N-Methyl-N-((8-(4-(trifluoromethyl)phenyl)imidazo[1,2-a]pyrazin-6-yl)methyl)acrylamide (I-177). To a stirred solution of N-methyl-1-(8-(4-(trifluoromethyl)phenyl)imidazo[1,2-a]pyrazin-6-yl)methanamine (X-1423A3) (0.180 g, 0.58 mmol) in DCM (5 mL) was added TEA (0.2 mL, 1.76 mmol) at 0° C. under nitrogen atmosphere and stirred for 15 min at same temperature. Acrylic anhydride (0.15 mL, 1.17 mmol) was added at 0° C. and the resulting reaction mixture was stirred at room temperature for 1 h. Reaction mixture was diluted with water (50 mL) and was extracted with DCM (50 mL×2). Combined organic extracts were dried over anhydrous $Na_2SO_4$ and concentrated in vacuo. Obtained crude mass was purified by C-18 silica gel column chromatography with using acetonitrile:water=0:1→6:4 as gradient, to afford N-methyl-N-((8-(4-(trifluoromethyl)phenyl)imidazo[1,2-a]pyrazin-6-yl)methyl)acrylamide (I-177) (0.150 g, 71%) as a Brown solid. $^1H$ NMR (400 MHz, DMSO-$d_6$) δ: 9.0-8.97 (t, J=7.2 Hz, 2H), 8.65 (s, 0.5H), 8.57 (s, 0.5H), 8.28-8.26 (d, J=8.4 Hz, 1H), 7.95-7.91 (m, 3H), 7.1-7.0 (dd, J=10.4, 16.8 Hz, 0.5H), 6.90-6.83 (dd, J=10.4, 16.8 Hz, 0.5H), 8.29 (s, 1H), 6.24-6.16 (m, 1H), 5.76-5.70 (m, 1H), 4.82 (s, 0.5H), 4.74 (m, 0.5H), 3.25 (s, 1.5H), 2.99 (s, 1.5H). MS: $[MH]^+$ 361.02.

Example 1.117. Synthesis of 3-bromo-5-(8-(4-(trifluoromethyl)phenyl)imidazo[1,2-a]pyrazin-6-yl)-4,5-dihydroisoxazole (I-176)

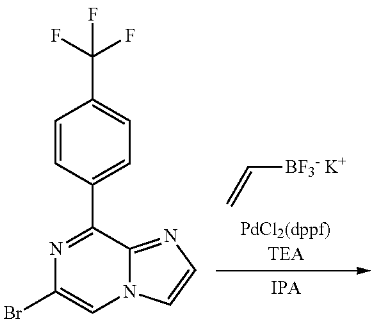

X1269A2

-continued

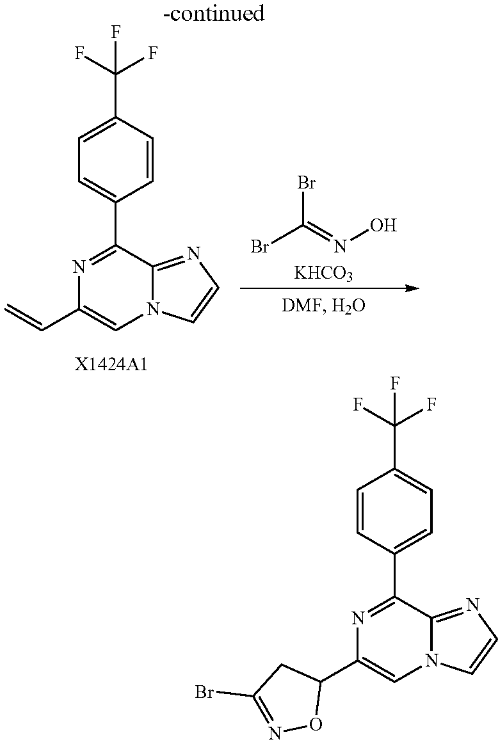

X1424A1

I-176

8-(4-(Trifluoromethyl)phenyl)-6-vinylimidazo[1,2-a]pyrazine (X-1424A1). To a stirred solution of 6-bromo-8-(4-(trifluoromethyl)phenyl)imidazo[1,2-a]pyrazine (X-1269A2) (0.500 g, 1.46 mmol) in a IPA (10 mL), were added triethylamine (0.6 mL g, 4.39 mmol) and potassium vinyltrifluoroborate (0.400 g, 2.98 mmol) at room temperature under nitrogen atmosphere. Resulting mixture was degassed (purging with nitrogen) for 20 min followed by the addition of $PdCl_2$ (dppf) (0.106 g, 0.14 mmol) and was heated at 70° C. for 16 h. Reaction mixture was cooled to room temperature, diluted with water (50 mL) and was extracted with ethyl acetate (100 mL×2). Combined organic extracts were washed with brine (100 mL), dried over anhydrous $Na_2SO_4$ and concentrated in vacuo. Obtained crude product was purified by silica gel column chromatography, using ethyl acetate-hexane: 0:1→4 2:3 as a gradient, to afford 8-(4-(trifluoromethyl)phenyl)-6-vinylimidazo[1,2-a]pyrazine (X-1424A1) (0.600 g, 70%) as an off white solid. MS: $[MH]^+$ 289.91.

3-Bromo-5-(8-(4-(trifluoromethyl)phenyl)imidazo[1,2-a]pyrazin-6-yl)-4,5-dihydroisoxazole (I-176). To a stirred solution of 8-(4-(trifluoromethyl)phenyl)-6-vinylimidazo[1,2-a]pyrazine (X-1424A1) (0.300 g, 1.03 mmol) in DMF-water (9:1; 5 mL) was added $KHCO_3$ (0.250 g, 2.50 mmol) and hydroxycarbonimidic dibromide (0.200 g, 0.99 mmol) at room temperature and stirred at same temperature for 16 h. Reaction mixture was poured into water (50 mL) and was extracted with ethyl acetate (50 mL×2). Combined extracts were dried over anhydrous $Na_2SO_4$ and concentrated in vacuo. Obtained crude mass was purified by reverse phase (C-18) silica gel column chromatography using acetonitrile-water=0:1→2:3 as a gradient, to afford 3-bromo-5-(8-(4-(trifluoromethyl)phenyl)imidazo[1,2-a]pyrazin-6-yl)-4,5-dihydroisoxazole (I-176) (0.100 g, 42%) as a white solid. $^1H$ NMR (400 MHz, DMSO-$d_6$) δ: 8.97-8.95 (d, J=8.0 Hz, 2H), 8.82 (s, 1H), 8.30 (s, 1H), 7.97-7.95 (d, J=6.0 Hz, 2H), 7.95 (s, 1H), 5.94-5.89 (m, 1H), 3.90-3.83 (m, 1H), 3.74-3.68 (m, 1H). MS: $[MH]^+$ 412.82.

Example 1.118 Synthesis of N-((1-(4-(tert-butyl) phenyl)isoquinolin-3-yl)methyl)-2-fluoroacrylamide (I-215)

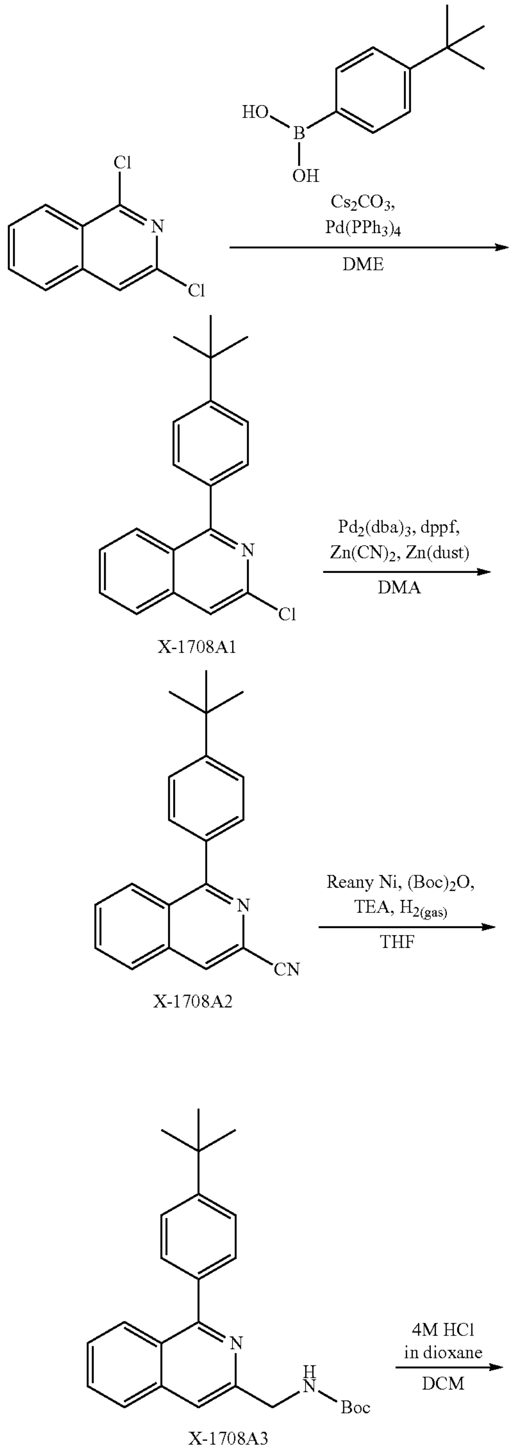

X-1708A1

X-1708A2

X-1708A3

-continued

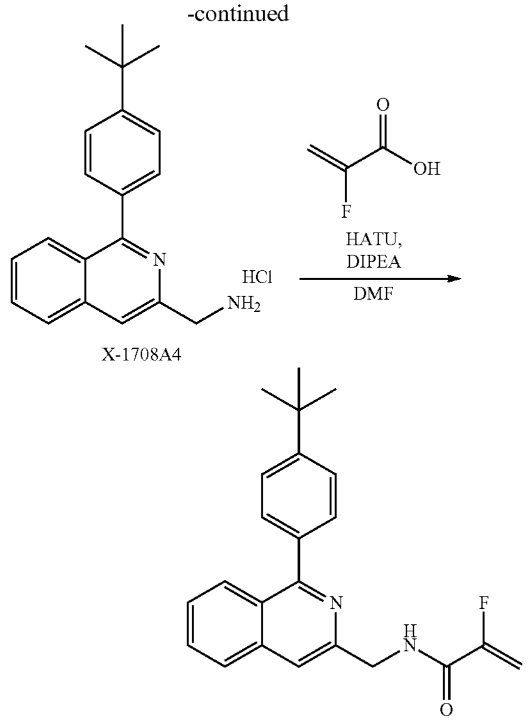

X-1708A4

I-215

1-(4-(Tert-butyl)phenyl)-3-chloroisoquinoline (X-1708A1). To a stirred solution of 1,3-dichloroisoquinoline (1.0 g, 5.07 mmol) in a mixture of DME (10 mL), were added (4-(tert-butyl)phenyl)boronic acid (1.0 g, 6.01 mmol) and $Cs_2CO_3$ (3.3 g, 10.1 mmol) sequentially at room temperature under nitrogen. The reaction mixture was degassed (purging with nitrogen) for 20 min followed by the addition of $Pd(pph_3)_4$ (0.175 g, 0.15 mmol) the resulting mixture was heated at 80° C. for 5 h. Reaction mixture was cooled to room temperature, diluted with water (300 mL) and was extracted with ethyl acetate (300 mL×3). Combined organic extracts were dried over anhydrous $Na_2SO_4$ and concentrated under reduce pressure to afford crude mass, which was purified by silica gel column chromatography, using ethyl acetate-hexane=0:1→1:9 as eluent, to afford 1-(4-(tert-butyl)phenyl)-3-chloroisoquinoline (X-1708A1) (1.0 g, 66%) as an white solid. MS: $[MH]^+$ 295.8.

1-(4-(Tert-butyl)phenyl)isoquinoline-3-carbonitrile (X-1708A2). To a stirred solution of 1-(4-(tert-butyl)phenyl)-3-chloroisoquinoline (X-1708A1) (1.5 g, 5.08 mmol) in a DMA (15 mL) were added $Zn(CN)_2$ (1.1 g, 10.1 mmol) and Zn (0.498 g, 7.62 mmol), under nitrogen. The reaction mixture was degassed (purging with nitrogen) for 20 min followed by the addition of $Pd(dba)_3$ (0.139 g, 1.52 mmol) and dppf (1.6 g, 3.04 mmol) the resulting mixture was heated under microwave irradiation at 150° C. for 2 h. Reaction mixture was cooled to room temperature, diluted with water (300 mL) and was extracted with ethyl acetate (200 mL×3). Combined organic extracts were dried over anhydrous $Na_2SO_4$ and concentrated under reduce pressure. Obtained crude product was purified by silica gel flash column chromatography, using ethyl acetate-hexane=0:1→1:9 as gradient, to afford 1-(4-(tert-butyl)phenyl)isoquinoline-3-carbonitrile (X-1708A2) (0.6 g, 41%) as an white solid. MS: $[MH]^+$ 286.8.

tert-butyl ((1-(4-(tert-butyl)phenyl)isoquinolin-3-yl) methyl)carbamate (X-1708A3). To a stirred solution of 1-(4-(tert-butyl)phenyl)isoquinoline-3-carbonitrile (X-1708A2) (0.350 g, 1.22 mmol) in THE (5 mL) were added activated Raney Ni (0.2 g), Boc anhydride (0.522 g, 2.44 mmol) and methanolic ammonia (7N, 0.1 mL) sequentially in an autoclave at room temperature under nitrogen and the resulting suspension was hydrogenated under 25 psi at same temperature for 1 h. reaction mixture was filtered through celite, residue was washed with MeOH (50 mL) and collected filtrates were concentrated under reduced pressure. Obtained crude product was purified by silica gel flash column chromatography using ethyl acetate-hexane=0: 1→2:8 as gradient, to afford tert-butyl ((1-(4-(tert-butyl) phenyl)isoquinolin-3-yl)methyl)carbamate(X-1708A3) (0.200 g, 42%) as an white solid. MS: $[MH]^+$ 391.1.

(1-(4-(Tert-butyl)phenyl)isoquinolin-3-yl)methanamine (X-1708A4). To a stirred solution of tert-butyl ((1-(4-(tert-butyl)phenyl)isoquinolin-3-yl)methyl)carbamate (X-1708A3) (0.100 g, 0.25 mmol) in DCM (1 mL) was added 4M HCl in dioxane (1.5 mL) at 0° C. and stirred at room temperature for 2 h. The reaction mixture was concentrated under reduced pressure and the obtained crude product was purified by using n-pentane, to afford (1-(4-(tert-butyl)phenyl)isoquinolin-3-yl)methanamine (X-1708A4) (0.070 g, 83%) as a brown solid. MS: $[MH]^+$ 291.1

N-((1-(4-(tert-butyl)phenyl)isoquinolin-3-yl)methyl)-2-fluoroacrylamide (I-215). To a stirred solution of (1-(4-(tert-butyl)phenyl)isoquinolin-3-yl)methanamine (X-1708A4) (0.07 g, 0.24 mmol) in DMF (5 mL) were added 2-fluoroacrylic acid (0.048 g, 0.54 mmol), DIPEA (0.14 g, 1.44 mmol) and HATU (0.246 g, 0.64 mmol) at room temperature and stirred for 2 h at the same temperature. Reaction mixture was diluted with water (10 mL) and was extracted with ethyl acetate (40 mL×2). Organic extracts were combined, dried over anhydrous $Na_2SO_4$ and concentrated under reduced pressure. Obtained crude product was purified by silica gel flash column chromatography using ethyl acetate-hexane=0: 1→3:7 as gradient, to afford N-((1-(4-(tert-butyl)phenyl) isoquinolin-3-yl)methyl)-2-fluoroacrylamide (I-215) (0.030 g, 38%) as a sticky solid. $^1H$ NMR (400 MHz, DMSO-$d_6$) δ 9.23-9.20 (t, J=5.6 Hz, 1H), 8.05-8.02 (dd, J=8.0, 2.4 Hz, 2H, 0.79-0.77 (t. J=7.6 Hz 1H), 7.66 (s, 1H), 7.63-7.59 (m, 5H), 5.68-5.67 (d, J=48.0, 3.2 Hz, 1H), 5.36-5.31 (dd, J=15.6, 3.2 Hz, 1H), 4.65-4.64 (d, J=6.0 Hz, 1H) 1.38 (s, 9H), MS: $[MH]^+$ 363.4.

Example 1.119. Synthesis of 2-Fluoro-N-((1-(4-(2-hydroxypropan-2-yl)phenyl)isoquinolin-3-yl)methyl) acrylamide (I-216)

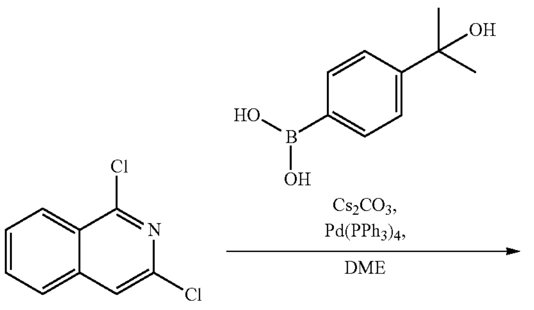

-continued

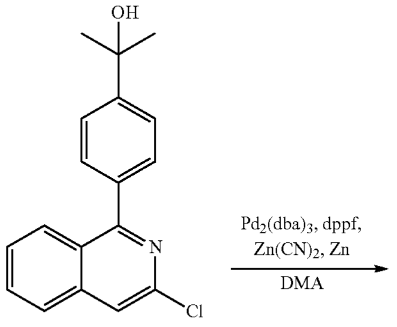

X-1709A1

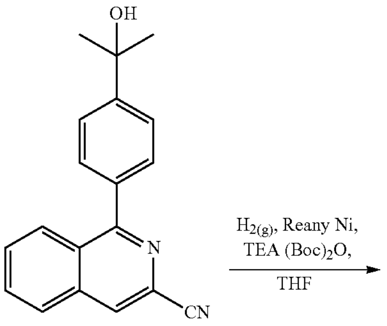

X-1709A2

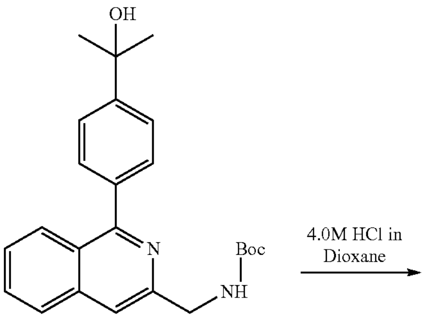

X-1709A3

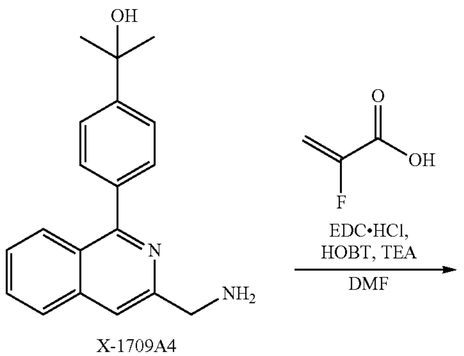

X-1709A4

-continued

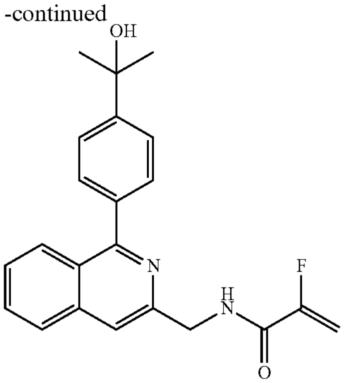

I-216

2-(4-(3-Chloroisoquinolin-1-yl)phenyl)propan-2-ol (X-1709A1). To a stirred solution of 1,3-dichloroisoquinoline (1.0 g, 5.0 mmol) in a mixture of DME (10 mL) were added $Cs_2CO_3$ (3.3 g, 10 mmol) and (4-(2-hydroxypropan-2-yl)phenyl)boronic acid (1.0 g, 6.0 mmol) at room temperature under nitrogen. The reaction mixture was degassed (purging with nitrogen) for 20 min followed by the addition of $Pd(PPh_3)_4$ (0.175 g, 0.7 mmol) and the reaction mixture was heated at 80° C. for 4 h. The reaction mixture was cooled to room temperature, diluted with water (50 mL) and was extracted with ethyl acetate (100 mL×2). Combined organic extracts were dried over anhydrous $Na_2SO_4$, filtered and concentrated under reduced pressure. Obtained crude was purified by silica gel column chromatography, using ethyl acetate-hexane=0:1→1:9 as gradient, to afford 2-(4-(3-chloroisoquinolin-1-yl)phenyl)propan-2-ol (X-1709A1) (1.4 g, 93%) as an off-white solid. MS: $[MH]^+$ 297.7.

1-(4-(2-hydroxypropan-2-yl)phenyl)isoquinoline-3-carbonitrile (X-1709A2). To a stirred solution of 2-(4-(3-chloroisoquinolin-1-yl)phenyl)propan-2-ol (1.4 g, 4.7 mmol) in DMA (10 mL) was added $Zn(CN)_2$ (0.82 g, 7.0 mmol) at room temperature under nitrogen. The reaction mixture was degassed (purging with nitrogen) for 10 min followed by the sequential addition of $Pd_2(dba)_3$ (1.2 g, 1.41 mmol) and $PdCl_2(dppf)$ (1.5 g, 2.8 mmol) and the resulting mixture was heated at 150° C. in Microwave for 2 h. Reaction mixture was cooled to room temperature, diluted with water (15 mL) and was extracted with ethyl acetate (25 mL×3). Combined organic extracts were dried over anhydrous $Na_2SO_4$ and concentrated under reduce pressure. The crude product was purified by silica gel column chromatography, using ethyl acetate-hexane=1:9→2:8 as eluent, to afford 1-(4-(2-hydroxypropan-2-yl)phenyl)isoquinoline-3-carbonitrile (X-1709A2) (1.0 g, 100%) as an off-white solid. MS: $[MH]^+$ 288.13.

Tert-butyl ((1-(4-(2-hydroxypropan-2-yl)phenyl)isoquinolin-3-yl)methyl)carbamate (X-1709A3). To a stirred solution of 1-(4-(2-hydroxypropan-2-yl)phenyl)isoquinoline-3-carbonitrile (X-1709A2) (0.5 g, 1.73 mmol) in THE (5 mL) were added TEA (1.0 ml) and Raney Nickel (0.5 g) and $(Boc)_2O$ (0.75 g, 3.4 mmol) at room temperature, the resulting mixture was hydrogenated in Parr Autoclave at rt under 200 psi for 2 h. Reaction mixture was filtered over a celite bed, washed the bed with MeOH (100 mL) and collected filtrates were concentrated under reduced pressure to give crude, The crude product was purified by silica gel column chromatography, using ethyl acetate-hexane=0: 1→1:0 as gradient, to afford tert-butyl (1-(4-(2-hydroxypropan-2-yl)phenyl)isoquinolin-3-yl)methyl)carbamate (X-1709A3) (45.0 g, 66%) as a yellow solid. MS: $[MH]^+$ 392.2.

2-(4-(3-(aminomethyl)isoquinolin-1-yl)phenyl)propan-2-ol (X-1709A4). A 4M HCl in dioxane (4 mL) was added to a stirred solution of tert-butyl ((1-(4-(2-hydroxypropan-2-yl)phenyl)isoquinolin-3-yl)methyl)carbamate (X-1709A3) (0.45 g, 1.14 mmol) in DCM (4 mL) at 0° C. and stirred at room temperature for 1 h. Reaction mixture was concentrated under reduced pressure. Obtained crude was triturated with Diethyl ether (2×50 mL), dried over high vacuum to afford 2-(4-(3-(aminomethyl)isoquinolin-1-yl)phenyl)propan-2-ol (X-1709A4) (0.45 g, 86%) as a white solid. MS: $[MH]^+$ 313.1.

2-Fluoro-N-((1-(4-(2-hydroxypropan-2-yl)phenyl)isoquinolin-3-yl)methyl)acrylamide (I-216). To a stirred solution of 2-(4-(3-(aminomethyl)isoquinolin-1-yl)phenyl)propan-2-ol (X-1709A4) (0.29 g, 0.8 mmol) in DMF (8 mL) were added 2-fluoroacrylic acid (0.4 g, 4.4 mmol), TEA (1.8 mL, 13.3 mmol) and HOBt (0.87 g, 6.4 mmol) were added EDC·HCl (1.27 g, 6.6 mmol) at room temperature and stirred at the same temperature for 10 h. Reaction mixture was diluted with water (10 mL) and was extracted with ethyl acetate (40 mL×2). Organic extracts were combined, dried over anhydrous $Na_2SO_4$ and concentrated under reduced pressure. Obtained crude was purified by normal phase column chromatography silica gel, using ethyl-hexane=0: 1→4:6 as gradient, to afford 2-fluoro-N-((1-(4-(2-hydroxypropan-2-yl)phenyl)isoquinolin-3-yl)methyl)acrylamide (I-216) (0.34 g, 9%) as a yellow solid. $^1H$ NMR (400 MHz, DMSO-$d_6$) δ 9.22 (m, 1H), 8.05-8.03 (t, J=7.6 Hz, 2H), 7.79-7.77 (t, J=7.6 Hz, 1H), 7.67-7.60 (m, 6H), 5.68-5.55 (d, 48.0, 3.6 Hz, 1H), 5.36-5.31 (dd, J=3.6 Hz, 1H), 5.14 (s, 1H), 4.65-4.64 (d, J=: 5.6 Hz, 2H), 1.52 (s, 61). MS: $[MH]^+$ 365.4

Example 1.120. Synthesis of 2-(8-(4-(trifluoromethyl)phenyl)imidazo[1,2-a]pyrazin-6-yl)acetic acid (I-217)

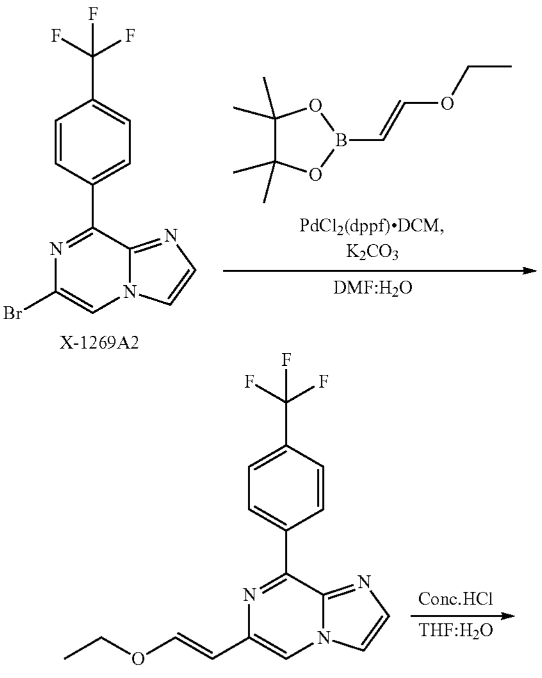

X-1269A2

X-1426A1

-continued

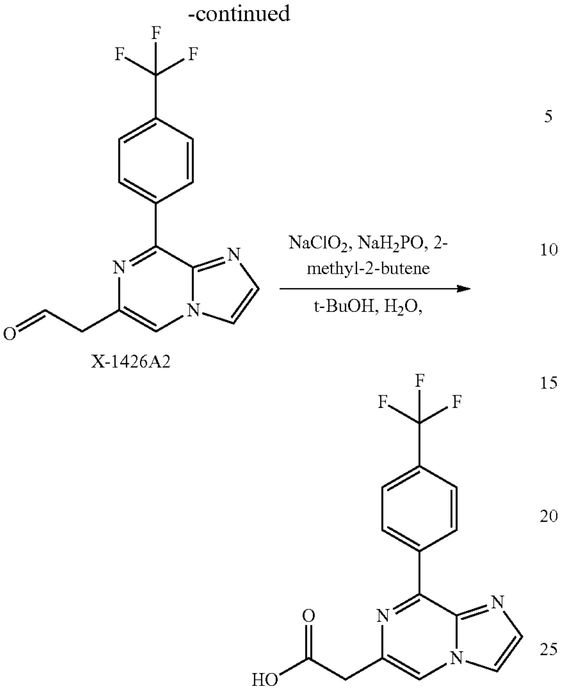

X-1426A2

I-217

(E)-6-(2-Ethoxyvinyl)-8-(4-(trifluoromethyl)phenyl)imidazo[1,2-a]pyrazine (X-1426A1). To a stirred solution of 6-bromo-8-(4-(trifluoromethyl)phenyl)imidazo[1,2-a]pyrazine (X-1269A2) (1.0 g, 2.93 mmol) in DMF (10 mL) were added (E)-2-(2-ethoxyvinyl)-4,4,5,5-tetramethyl-1,3,2-dioxaborolane (1.450 g, 7.33 mmol) and $K_2CO_3$ (1M solution in $H_2O$) (6.25 mL; 6.25 mmol) sequentially at room temperature under nitrogen atmosphere. The reaction mixture was degassed (purging with nitrogen) for 20 min followed by the addition of $PdCl_2$(dppf). DCM (0.239 g, 0.29 mmol) and heated at 90° C. for 2 h. Reaction mixture was cooled to room temperature, diluted with water (100 mL) and was extracted with ethyl acetate (100 mL×3). Combined organic extracts were dried over anhydrous $Na_2SO_4$ and concentrated under reduce pressure. Obtained crude product was purified by silica gel column chromatography, using with ethyl acetate-hexane: 0:1→1:4 as a gradient, to afford (E)-6-(2-ethoxyvinyl)-8-(4-(trifluoromethyl)phenyl)imidazo[1,2-a]pyrazine (X-1426A1) (1.5 g, 77%) as an off-white solid. MS: $[MH]^+$ 334.17.

2-(8-(4-(Trifluoromethyl)phenyl)imidazo[1,2-a]pyrazin-6-yl)acetaldehyde (X-1426A2). To a stirred solution of (E)-6-(2-ethoxyvinyl)-8-(4-(trifluoromethyl)phenyl)imidazo[1,2-a]pyrazine (X-1426A1) (1.5 g, 4.50 mmol) in a mixture of THF—$H_2O$ (20 mL) was added Conc. HCl (8 mL) at 0° C. and the resulting reaction mixture stirred at room temperature for 1 h. Reaction mixture was diluted with water (150 mL) and was extracted with ethyl acetate (150 mL×2). Combined organic extracts were dried over anhydrous $Na_2SO_4$ and concentrated under reduce pressure. Obtained crude product was purified by silica gel column chromatography, using ethyl acetate-hexane: 0:1→1:4 as a gradient, to afford 2-(8-(4-(trifluoromethyl)phenyl)imidazo[1,2-a]pyrazin-6-yl)acetaldehyde (X-1426A2) (0.200 g, 77%) as an off-white solid. MS: $[MH]^+$ 306.0

2-(8-(4-(Trifluoromethyl)phenyl)imidazo[1,2-a]pyrazin-6-yl)acetic acid (I-217). To a stirred solution of 2-(8-(4-(trifluoromethyl)phenyl)imidazo[1,2-a]pyrazin-6-yl)acetaldehyde (X-1426A2) (0.200 g, 0.65 mmol) in a mixture of t-BuOH, $H_2O$, 2-methyl-2-butene (8.8 mL) were added $NaClO_2$ (0.296 g, 3.27 mmol), $NaH_2PO$ (0.298 g, 2.49 mmol) at 0° C. the resulting reaction mixture was stirred at room temperature for 1 h. Reaction mixture was quenched with aq. $NaHCO_3$ solution (50 mL) and was extracted with ethyl acetate (50 mL×3) to remove unwanted organic impurities. Aqueous part was acidified by 1N HCl and was extracted with ethyl acetate (50 mL×3). Combined organic extracts were dried over anhydrous $Na_2SO_4$ and concentrated under reduce pressure. Obtained crude mass was triturated using diethyl ether (10 mL×2) to afford 2-(8-(4-(trifluoromethyl)phenyl)imidazo[1,2-a]pyrazin-6-yl)acetic acid (I-217) (0.020 g, 9%) as an off-white solid. $^1H$ NMR (400 MHz, DMSO-$d_6$) δ 12.61 (br. s, 1H), 8.98-8.96 (d, J=5.2 Hz, 2H), 8.65 (s, 1H), 8.28 (s, 1H) 7.95-7.93 (d, J=8.0 Hz, 2H), 7.93 (s, 1H), 3.85 (s, 2H). MS: $[MH]^+$ 322.01.

Example 1.121. Synthesis of N-((8-(4-(trifluoromethyl)phenyl)imidazo[1,2-a]pyrazin-6-yl)methyl) methanesulfonamide (I-218)

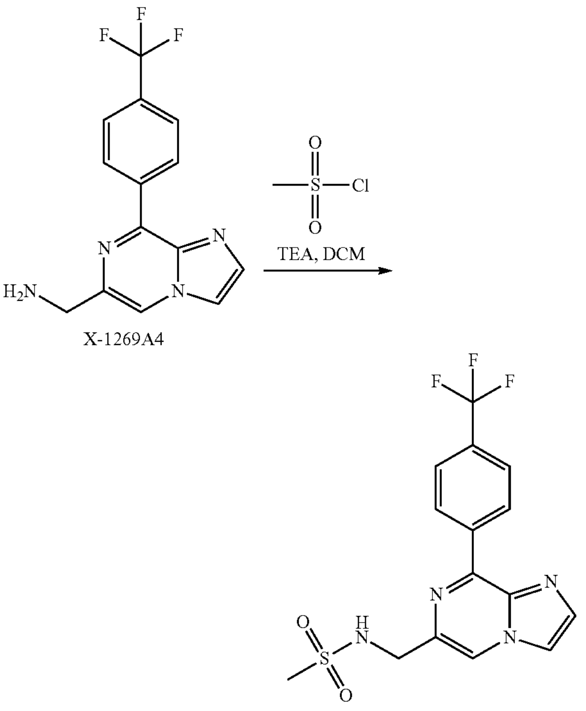

X-1269A4

I-218

Methane sulfonyl chloride (0.037 g, 0.32 mmol) was added to a stirred solution of (8-(4-(trifluoromethyl)phenyl)imidazo[1,2-a]pyrazin-6-yl)methanamine (X-1269A4) (0.095 g, 0.32 mmol) and triethyl amine (0.039 g, 0.39 mmol) in DCM (3 mL) at 0° C. temperature under nitrogen. The reaction mixture was stirred for 30 min at same temperature. The reaction mixture was poured in water (50 mL) and was extracted with DCM (25 mL×2). Combined organic extracts were dried over anhydrous $Na_2SO_4$ and concentrated under reduced pressure. The crude product was purified by reverse phase (C-18) silica gel column chromatography, using acetonitrile-water=0:1→1:0 as gradient, to afford N-((8-(4-(trifluoromethyl)phenyl)imidazo[1,2-a]pyrazin-6-yl)methyl)methane sulfonamide (I-218) (0.060 g, 58%) as a white solid. $^1$H NMR (400 MHz, DMSO-$d_6$) δ 9.04-9.02 (d, J=8.0 Hz, 2H), 8.69 (s, 1H), 8.33 (s, 1H), 7.97-7.93 (d, J=8.0 Hz, 3H), 7.78 (br. s, 1H), 4.39-4.38 (d, J=4.8 Hz, 2H), 3.00 (s, 3H). MS: $[MH]^+$ 371.0.

Example 1.122. Synthesis of (E)-4-methoxy-N-((8-(4-(trifluoromethyl)phenyl)imidazo[1,2-a]pyrazin-6-yl)methyl)but-2-enamide (I-219)

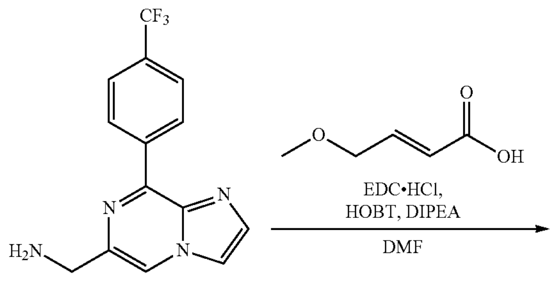

X-1269A4

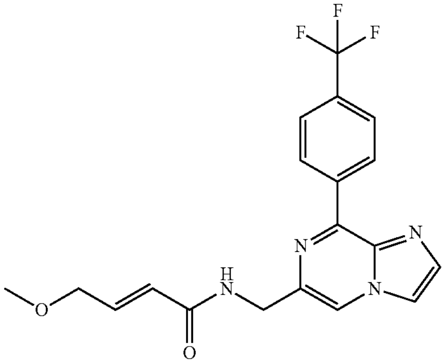

I-219

To a solution of (E)-4-methoxybut-2-enoic acid (0.25 g, 2.15 mmol) in DMF (3 mL) were added DIPEA (0.832 g, 6.45 mmol), EDC·HCl (0.50 g, 3.22 mmol), HOBT (0.436 g, 3.22 mmol) and (8-(4-(trifluoromethyl)phenyl)imidazo[1,2-a]pyrazin-6-yl)methanamine (X-1269A4) (0.314 g, 1.07 mmol) subsequently at 0° C. under nitrogen and the resulting mixture was stirred at room temperature for 1 h. Reaction was slowly poured into ice cold water (30 mL) and the resulting precipitate was collected by filtration. Obtained solid residue was washed with water (20 mL), dried under high vacuum. The resulting crude was purified by reverse phase (C-18) silica gel column chromatography, using acetonitrile-water=0:1→6:4 as gradient, to afford (E)-4-methoxy-N-((8-(4-(trifluoromethyl)phenyl)imidazo[1,2-a]pyrazin-6-yl)methyl)but-2-enamide (I-219) (0.05 g, 17%) as a yellow solid. 1H NMR (400 MHz, DMSO-$d_6$) δ 9.02-9.00 (d, J=8.0 Hz, 2H), 8.75-8.72 (t, J=5.6 Hz, 1H), 8.56 (s, 1H), 8.28 (s, 1H), 7.96-7.94 (d, J=8.4 Hz, 2H), 7.91 (s, 1H), 6.72-6.62 (m, 1H), 6.23-6.20 (d, J=15.6 Hz, 1H), 4.54-4.52 (d, J=5.6 Hz, 2H), 4.05-4.04 (d, J=2.8 Hz, 2H), 3.29 (s, 3H). MS: $[MH]^+$ 390.9.

Example 1.123 Synthesis of 2-Hydroxy-N-((8-(4-(trifluoromethyl)phenyl)imidazo[1,2-a]pyrazin-6-yl)methyl)acetamide (I-220

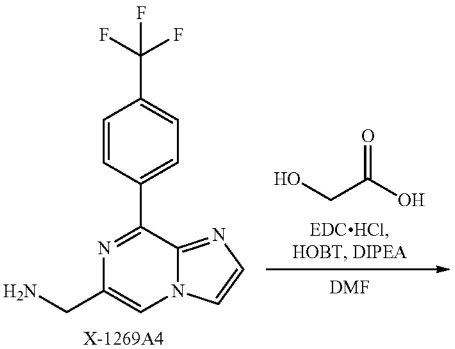

X-1269A4

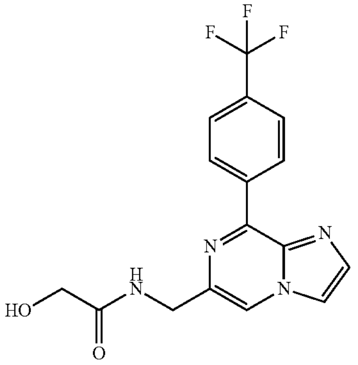

I-220

The following compound was prepared in a manner analogous to the procedures described above for (E)-4-methoxy-N-((8-(4-(trifluoromethyl)phenyl)imidazo[1,2-a]pyrazin-6-yl)methyl)but-2-enamide (I-219):

2-Hydroxy-N-((8-(4-(trifluoromethyl)phenyl)imidazo[1,2-a]pyrazin-6-yl)methyl)acetamide (I-220) (0.04 g, 6%) as a white solid. $^1$H NMR (400 MHz, DMSO-$d_6$) δ 9.02-9.00 (d, J=8.0 Hz, 2H), 8.53 (s, 1H), 8.45-8.49 (m, 1H), 8.27 (s, 1H), 7.96-7.94 (d, J=8.4 Hz, 2H), 7.91 (s, 1H), 5.64 (br, 1H), 4.52-4.51 (d, J=6.0 Hz, 2H), 3.93 (s, 2H). MS: $[MH]^+$ 351.0.

Example 1.124. 2-Methoxy-N-((8-(4-(trifluoromethyl)phenyl)imidazo[1,2-a]pyrazin-6-yl)methyl)acetamide (I-221)

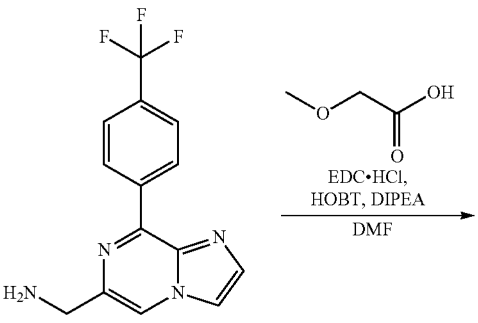

X-129A4

-continued

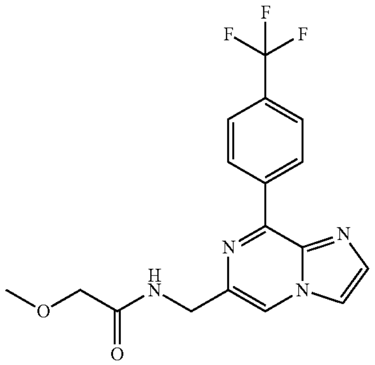

I-221

The following compound was prepared in a manner analogous to the procedures described above for (E)-4-methoxy-N-((8-(4-(trifluoromethyl)phenyl)imidazo[1,2-a]pyrazin-6-yl)methyl)but-2-enamide (I-219):

2-Methoxy-N-((8-(4-(trifluoromethyl)phenyl)imidazo[1,2-a]pyrazin-6-yl)methyl)acetamide (I-221) (0.040 g, 16%) as a white solid. 1H NMR (400 MHz, DMSO-$d_6$) δ 9.02-9.00 (d, J=8.0 Hz, 2H), 8.53 (s, 1H), 8.51-8.49 (t, J=6.0 Hz, 1H), 8.28 (s, 1H), 7.96-7.94 (d, J=8.0 Hz, 2H), 7.91 (s, 1H), 4.51-4.50 (d, J=6.0 Hz, 2H), 3.92 (s, 2H), 3.36 (s, 3H). MS: $[MH]^+$365.1.

Example 1.125. Synthesis of 6-(pyrrolidin-1-ylmethyl)-8-(4-(trifluoromethyl)phenyl)imidazo[1,2-a]pyrazine (I-222)

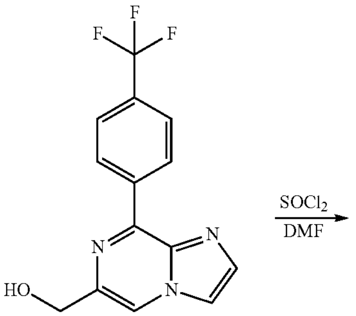

I-243

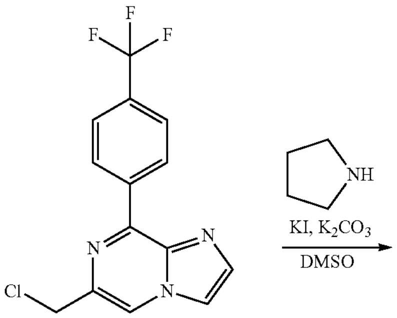

X-1432A3

-continued

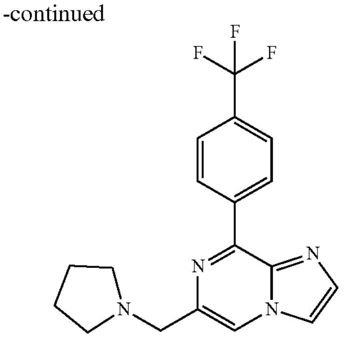

I-222

6-(Chloromethyl)-8-(4-(trifluoromethyl)phenyl)imidazo[1,2-a]pyrazine (X-1432A3). To a stirred solution of (8-(4-(trifluoromethyl)phenyl)imidazo[1,2-a]pyrazin-6-yl)methanol (I-243) (2.0 g, 9.14 mmol) in DCM (25 mL) were added thionyl chloride (4.78 mL, 64.84 mmol) dropwise at 0° C. and the resulting mixture was stirred at room temperature for 2 h. The reaction mixture was quenched with $NaHCO_3$ solution (100 mL) at 0° C. and was extracted with ethyl acetate (100 mL×2). Combined organic extracts were dried over anhydrous $Na_2SO_4$ and concentrated under reduce pressure. The crude product was purified by silica gel column chromatography, using ethyl acetate-hexane=0:1-+3:7 as gradient, to afford 6-(chloromethyl)-8-(4-(trifluoromethyl)phenyl)imidazo[1,2-a]pyrazine (X-1432A3) (1.2 g, 57%) as a yellow solid. MS: $[MH]^+$ 311.9.

6-(Pyrrolidin-1-ylmethyl)-8-(4-(trifluoromethyl)phenyl)imidazo[1,2-a]pyrazine (I-222). To a stirred solution of 6-(chloromethyl)-8-(4-(trifluoromethyl)phenyl)imidazo[1,2-a]pyrazine (X-1432A3) (0.200 g, 0.64 mmol) in DMSO (2 mL) were added potassium carbonate (0.221 g, 1.60 mmol), pyrrolidine (0.054 g, 0.77 mmol) and potassium iodide (0.010 g, 0.006 mmol) sequentially at room temperature under nitrogen and the resulting mixture was stirred at 80° C. for 1.5 h. The reaction mixture was cooled to room temperature, reaction mixture was diluted with water (50 mL) and was extracted with ethyl acetate (50 mL×2). The combined organic extracts were washed with brine (400 mL), and dried over anhydrous $Na_2SO_4$ and concentrated under reduce pressure. The crude was purified by silica gel column chromatography, using methanol-dichloromethane=0:1-41:9 as gradient, to afford 4-(6-azaspiro[2.5]octan-6-yl)pyrazolo[1,5-a]quinoxaline-7-carboxylate (I-222) (0.085 g, 38%) as an off-white solid. $^1H$ NMR (400 MHz, DMSO-$d_6$) δ 9.01-8.89 (d, J=8.4 Hz, 2H), 8.64 (s, 1H), 8.24 (s, 1H), 7.95-7.93 (d, J=8.4 Hz, 2H), 7.89 (s, 1H), 3.83 (s, 2H), 2.61 (brs, 4H), 1.74 (brs, 4H). MS: $[MH]^+$ 346.1.

Example 1.126. Synthesis of 6-((4-methylpiperazin-1-yl)methyl)-8-(4-(trifluoromethyl)phenyl)imidazo[1,2-a]pyrazine (I-223)

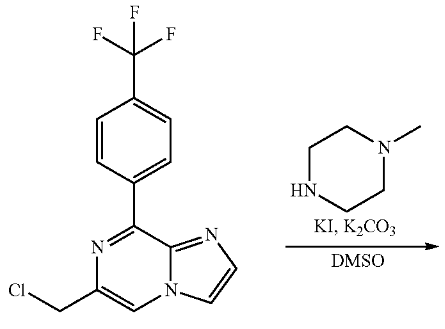

X-1432A3

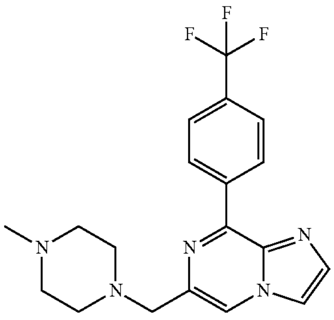

I-223

The following compound was prepared in a manner analogous to the procedures described above for 4-(6-azaspiro[2.5]octan-6-yl)pyrazolo[1,5-a]quinoxaline-7-carboxylate (I-222):

6-((4-methylpiperazin-1-yl)methyl)-8-(4-(trifluoromethyl)phenyl)imidazo[1,2-a]pyrazine (I-223) (0.150 g, 38%) as an off-white solid. $^1$H NMR (400 MHz, DMSO-$d_6$) δ 9.00-8.98 (d, J=8.4 Hz, 2H), 8.63 (s, 1H), 8.26 (s, 1H), 7.95-7.93 (d, J=8.4 Hz, 2H), 7.89 (s, 1H), 3.71 (s, 2H), 2.53 (s, 4H), 2.42-2.32 (br, 4H), 2.16 (s, 3H). MS: $[MH]^+$ 376.0.

Example 1.127. Synthesis of 6-(4-methylpiperazin-1-yl)-8-(4-(trifluoromethyl)phenyl)imidazo[1,2-a]pyrazine morpholine (I-224)

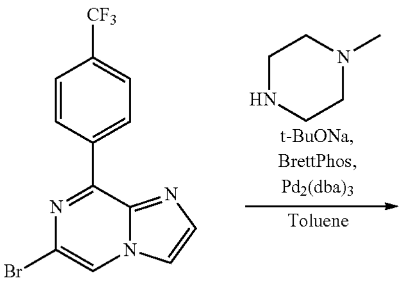

X-1269A2

-continued

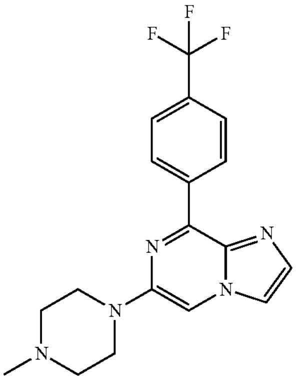

I-224

The following compound was prepared in a manner analogous to the procedures described above for 4-(6-azaspiro[2.5]octan-6-yl)pyrazolo[1,5-a]quinoxaline-7-carboxylate (I-222):

6-(4-methylpiperazin-1-yl)-8-(4-(trifluoromethyl)phenyl)imidazo[1,2-a]pyrazine morpholine (I-224) (0.035 g, 11%) as a yellow solid. $^1$H NMR (400 MHz, $CDCl_3$) δ 8.88-8.86 (d, J=8.0 Hz, 2H), 7.78-7.77 (m, 3H), 7.67 (s, 1H), 3.52 (s, 4H), 2.75 (s, 4H), 2.47 (s, 3H). MS: $[MH]^+$362.07.

Example 1.128. Synthesis of 6-(Piperazin-1-yl)-8-(4-(trifluoromethyl)phenyl)imidazo[1,2-a]pyrazine (I-225)

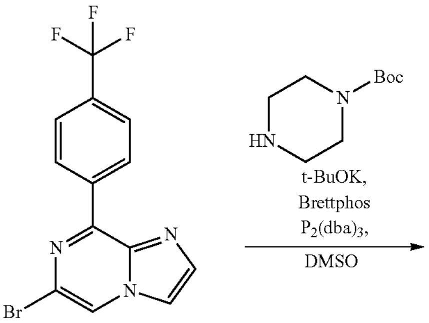

X-1269A2

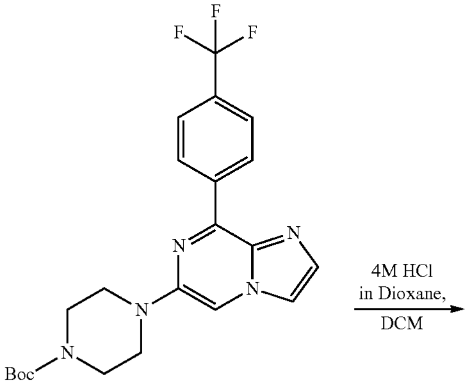

X-1435A1

-continued

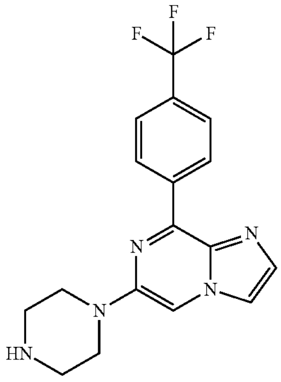

I-225 tert-Butyl 4-(8-(4-(trifluoromethyl)phenyl)imidazo[1,2-a]pyrazin-6-yl)piperazine-1-carboxylate (X-1435A1). The following compound was prepared in a manner analogous to the procedures described above for 4-(6-azaspiro[2.5]octan-6-yl)pyrazolo[1,5-a]quinoxaline-7-carboxylate (I-222) (0.190 g, 37%) as an off-white solid. MS: $[MH]^+$ 448.07.

6-(Piperazin-1-yl)-8-(4-(trifluoromethyl)phenyl)imidazo[1,2-a]pyrazine (I-225). To a stirred solution of tert-butyl 4-(8-(4-(trifluoromethyl)phenyl)imidazo[1,2-a]pyrazin-6-yl)piperazine-1-carboxylate (X-1435A1) (0.170 g, 0.38 mmol) in DCM (5 mL) was added 4M HCl in 1,4-dioxane (2 mL) at 0° C. and stirred at room temperature for 2 h. The reaction mixture was concentrated under reduced pressure and the obtained crude product was purified by using n-pentane to afford 6-(piperazin-1-yl)-8-(4-(trifluoromethyl)phenyl)imidazo[1,2-a]pyrazine (I-225) (0.140 g, 88%) as a yellow solid. $^1H$ NMR (400 MHz, DMSO-$d_6$) δ 9.26 (br. s, 2H), 8.93-8.91 (d, J=8.4 Hz, 2H) 8.30 (s, 1H), 8.14 (s, 1H), 7.95-7.93 (d, J=8.4 Hz, 2H), 7.91 (s, 1H), 3.65 (br. s, 2H), 3.29 (br. s, 2H). MS: $[MH]^+$ 347.9

Example 1.129. Synthesis of 4-((8-(4-(trifluoromethyl)phenyl)imidazo[1,2-a]pyrazin-6-yl)methyl)morpholine (I-226)

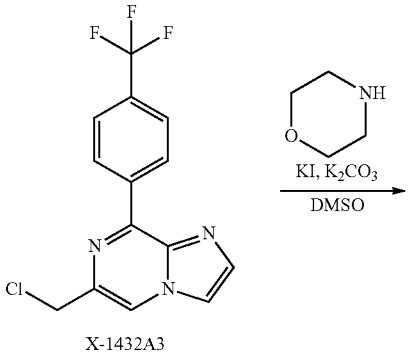

X-1432A3

-continued

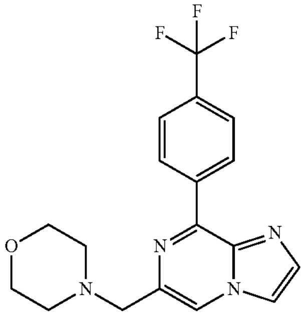

I-226

The following compound was prepared in a manner analogous to the procedures described above for 4-(6-azaspiro[2.5]octan-6-yl)pyrazolo[1,5-a]quinoxaline-7-carboxylate (I-222):

4-((8-(4-(trifluoromethyl)phenyl)imidazo[1,2-a]pyrazin-6-yl)methyl)morpholine (I-226) (0.130 g, 56%) as an off-white solid. $^1H$ NMR (400 MHz, DMSO-$d_6$) δ 9.00-8.98 (d, J=8.0 Hz, 2H), 8.66 (s, 1H), 8.25 (s, 1H), 7.95-7.93 (d, J=8.0 Hz, 2H), 7.90 (s, 1H), 3.72 (s, 2H), 3.62 (brs, 4H), 2.53 (4H, merged with DMSO-$d_6$ peak). MS: $[MH]^+$ 363.1.

Example 1.130. Synthesis of N-(1-(8-(4-(trifluoromethyl)phenyl)imidazo[1,2-a]pyrazin-6-yl)pyrrolidin-3-yl)acrylamide (I-227)

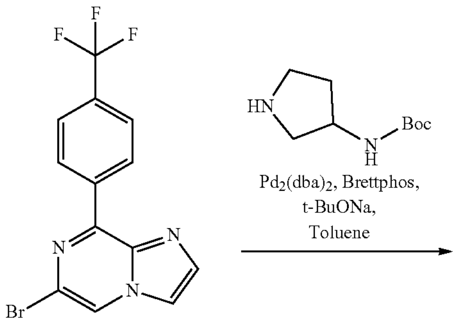

X-1269A2

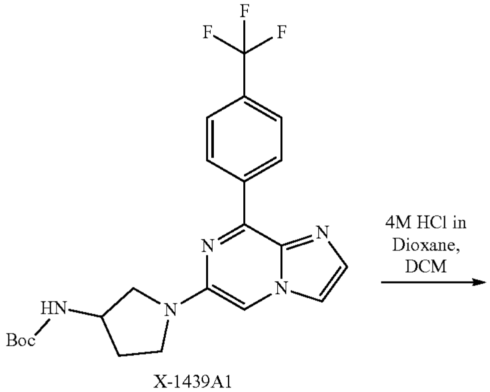

X-1439A1

-continued

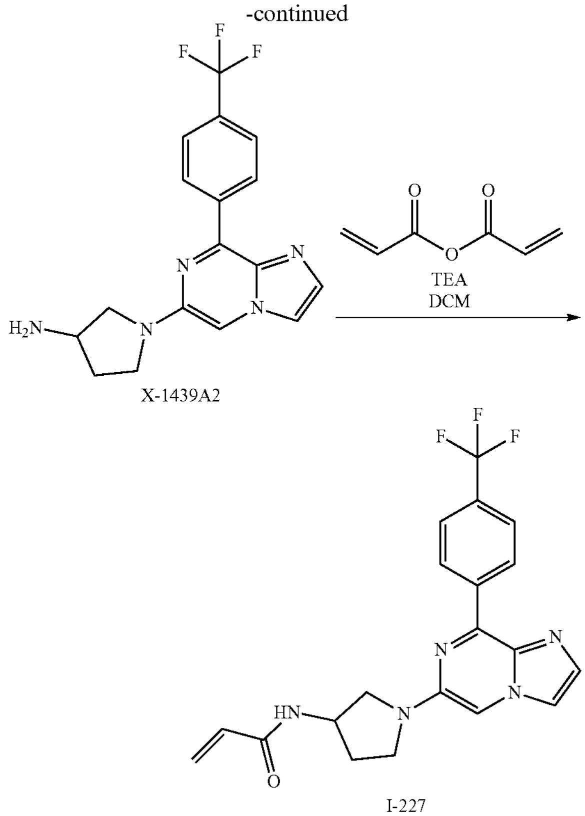

X-1439A2

I-227 tert-Butyl (1-(8-(4-(trifluoromethyl)phenyl)imidazo[1,2-a]pyrazin-6-yl)pyrrolidin-3-yl)carbamate (X-1439A1). To a stirred solution of 6-bromo-8-(4-(trifluoromethyl)phenyl)imidazo[1,2-a]pyrazine (X-1269A2) (1.50 g, 4.30 mmol) in a toluene (10 mL) were added tert-butyl pyrrolidin-3-ylcarbamate (4.09 g, 21.5 mmol), t-BuONa (0.042 g, 0.43 mmol) and Brettphos (0.235 g, 0.43 mmol) sequentially at room temperature under nitrogen. The reaction mixture was degassed (purging with nitrogen) for 20 min followed by the addition of $Pd_2(dba)_3$ (0.033 g, 8.7 mmol) and the resulting mixture was heated at 100° C. for 1 h. Reaction mixture was cooled to room temperature, diluted with water (300 mL) and was extracted with ethyl acetate (200 mL×3). Combined organic extracts were dried over anhydrous $Na_2SO_4$ and concentrated under reduce pressure. Obtained crude product was purified by silica gel column chromatography, using ethyl acetate-hexane=0:1→3:7 as gradient, to afford tert-butyl (1-(8-(4-(trifluoromethyl)phenyl)imidazo[1,2-a]pyrazin-6-yl)pyrrolidin-3-yl)carbamate (X-1439A1) (1.2 g, 61%) as an off-white solid. MS: $[MH]^+$ 448.07.

1-(8-(4-(Trifluoromethyl)phenyl)imidazo[1,2-a]pyrazin-6-yl)pyrrolidin-3-amine (X-1439A2). To a stirred solution of tert-butyl (1-(8-(4-(trifluoromethyl)phenyl)imidazo[1,2-a]pyrazin-6-yl)pyrrolidin-3-yl)carbamate (X-1439A1) (0.600 g, 1.3 mmol) in DCM (10 mL) was added 4M HCl in 1,4-dioxane (5 mL) at 0° C. and stirred at room temperature for 2 h. The reaction mixture was concentrated under reduced pressure and the obtained crude product was purified by using n-pentane, to afford 1-(8-(4-(trifluoromethyl)phenyl)imidazo[1,2-a]pyrazin-6-yl)pyrrolidin-3-amine (X-1439A2) (0.600 g, 96%) as a white solid. MS: $[MH]^+$ 348.07

N-(1-(8-(4-(trifluoromethyl)phenyl)imidazo[1,2-a]pyrazin-6-yl)pyrrolidin-3-yl)acrylamide (I-227). Acrylic anhydride (0.108 g, 0.86 mmol) was added to a stirred solution of 1-(8-(4-(trifluoromethyl)phenyl)imidazo[1,2-a]pyrazin-6-yl)pyrrolidin-3-amine (X-1439A2) (0.250 g, 0.72 mmol) and triethylamine (0.043 g, 3.60 mmol) in DCM (3 mL) at 0° C. temperature under nitrogen. The reaction mixture was stirred for 30 min at same temperature. The reaction mixture was poured in water (50 mL) and was extracted with DCM (25 mL×2). Combined organic extracts were dried over anhydrous $Na_2SO_4$ and concentrated under reduced pressure. The crude product was purified by reverse phase (C-18) silica gel column chromatography, using acetonitrile-water=0:1→1:0 as gradient, to afford N-(1-(8-(4-(trifluoromethyl)phenyl)imidazo[1,2-a]pyrazin-6-yl)pyrrolidin-3-yl)acrylamide (I-227) (0.010 g, 3%) as a yellow solid. $^1H$ NMR (400 MHz, DMSO-$d_6$) δ 9.07-9.05 (d, J=8.0 Hz, 2H), 8.46-8.44 (d, J=6.4 Hz, 1H), 8.04 (s, 1H), 7.94-7.92 (d, J=8.0 Hz, 2H), 7.84 (s, 1H), 7.76 (s, 1H), 6.28-6.21 (m, 1H), 6.13-6.09 (d, J=16.8 Hz, 1H), 5.61-5.59 (d, J=10.0 Hz, 1H), 4.49 (brs, 1H), 3.74-3.70 (m, 1H), 3.57-3.53 (m, 1H), 3.47-3.46 (m, 1H), 3.33 (1H. proton merged with DMSO-$d_6$ moisture peak), 2.32-2.26 (m, 1H), 1.99-1.97 (m, 1H). MS: $[MH]^+$ 402.2.

Example 1.131. Synthesis of N-(1-(8-(4-(trifluoromethyl)phenyl)imidazo[1,2-a]pyrazin-6-yl)piperidin-3-yl)acrylamide (I-228)

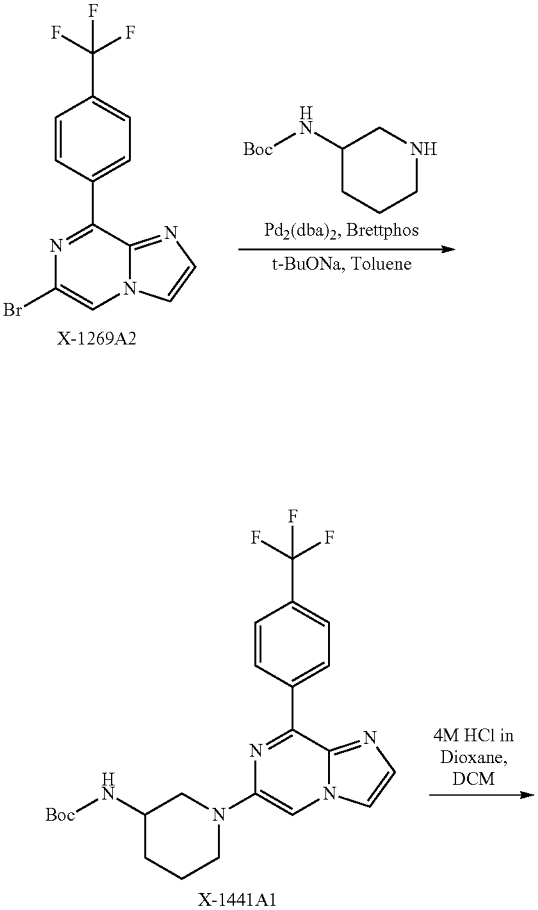

X-1269A2

X-1441A1

-continued

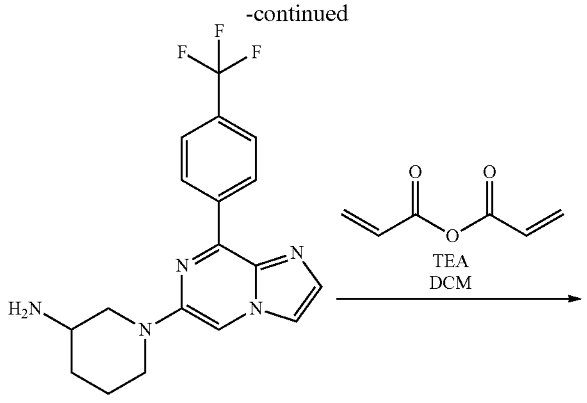

X-1441A2

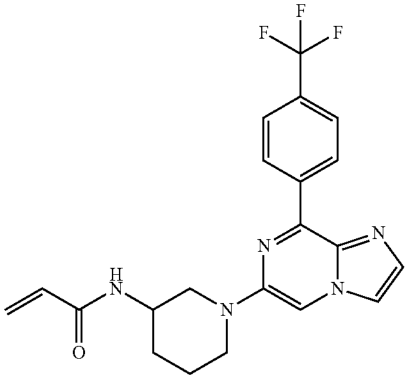

I-228

The following compound was prepared in a manner analogous to the procedures described above for N-(1-(8-(4-(trifluoromethyl)phenyl)imidazo[1,2-a]pyrazin-6-yl)pyrrolidin-3-yl)acrylamide (I-227):

N-(1-(8-(4-(trifluoromethyl)phenyl)imidazo[1,2-a]pyrazin-6-yl)piperidin-3-yl)acrylamide (I-228) (0.140 g, 23%) as a yellow solid. 1H NMR (400 MHz, DMSO-$d_6$) δ 9.01-8.99 (d, J=8.4 Hz, 2H), 8.22-8.20 (d, J=7.6 Hz, 1H), 8.13 (s, 1H), 8.05 (s, 1H), 7.94-7.92 (d, J=8.4 Hz, 2H), 7.78 (s, 1H), 6.31-6.24 (m, 1H), 6.14-6.09 (dd, J=2.0, 16.8 Hz, 1H), 5.61-5.58 (dd, J=2.0, 10.0 Hz, 1H), 3.96-385 (m, 3H), 2.99-2.94 (t, J=10.0 Hz, 1H), 2.80-2.77 (t, J=8.0 Hz, 1H), 1.91-1.85 (m, 2H), 1.69-1.66 (m, 1H), 1.52-1.48 (m, 1H). MS: $[MH]^+$ 416.12.

Example 1.132. N-((8-(4-(trifluoromethyl)phenyl)imidazo[1,2-a]pyrazin-6-yl)methyl)picolinamide (I-229)

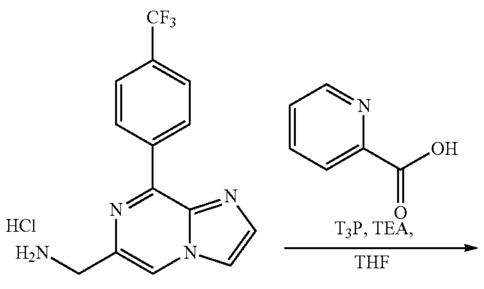

X-1269A4

-continued

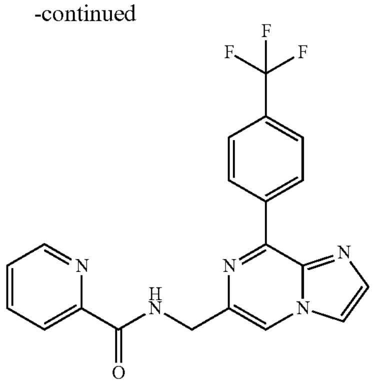

I-229

The following compound was synthesized in a manner analogous to the procedures described above for N-((8-(4-(trifluoromethyl)phenyl)imidazo[1,2-a]pyrazin-6-yl)methyl)nicotinamide (I-212):

N-((8-(4-(trifluoromethyl)phenyl)imidazo[1,2-a]pyrazin-6-yl)methyl)picolinamide (I-229) (0.06 g, 17%) as an off white solid. $^1$H NMR (400 MHz, DMSO-$d_6$) δ 9.50-9.48 (t, J=5.6 Hz, 1H), 9.02-9.00 (d, J=8.0 Hz, 2H), 8.70-8.69 (d, J=4.4 Hz, 1H), 8.57 (s, 1H), 8.27 (s, 1H), 8.11-8.09 (d, J=7.6 Hz, 1H), 8.05-8.01 (t, J=7.6 Hz, 1H), 7.96-7.94 (d, J=8.4 Hz, 2H), 7.66-7.63 (t, J=5.2 Hz, 1H), 4.73-4.72 (d, J=6.0 Hz, 2H). MS: $[MH]^+$ 398.12.

Example 1.333. Synthesis of 1-isopropyl-N-((8-(4-(trifluoromethyl)phenyl)imidazo[1,2-a]pyrazin-6-yl)methyl)-1H-imidazole-5-carboxamide (I-230)

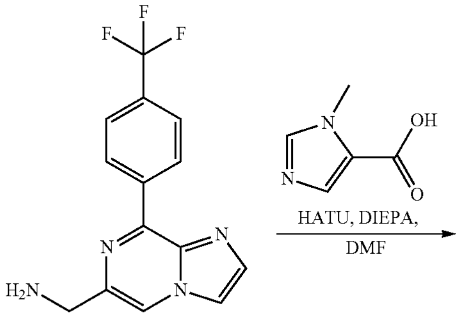

X-1269A4

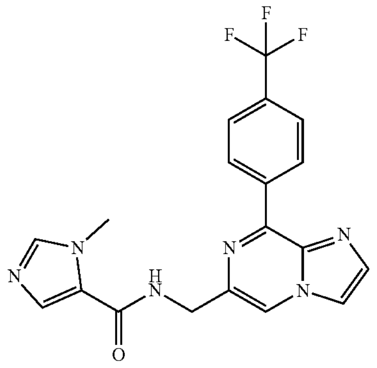

I-230

To a stirred solution of 1-methyl-1H-imidazole-5-carboxylic acid (0.100 g, 0.78 mmol) in DMF (4 mL) were added DIPEA (0.2 g, 1.54 mmol) and HATU (0.6 g, 1.57 mmol) at 0° C. The resulting reaction mixture was stirred at room temperature for 10 min. (8-(4-(trifluoromethyl)phenyl)imidazo[1,2-a]pyrazin-6-yl)methanamine (X-1269A4) (0.200 g, 0.68 mmol) was added at 0° C. and the resulting reaction mixture was stirred at room temperature for 2 h. The resulting mixture was diluted with water (100 mL) and was extracted with ethyl acetate (150 mL×3). The resulting crude was purified by reverse phase (C-18) silica gel column chromatography, using acetonitrile-water=0:1→7:3 as gradient, to afford 1-isopropyl-N-((8-(4-(trifluoromethyl)phenyl)imidazo[1,2-a]pyrazin-6-yl)methyl)-1H-imidazole-5-carboxamide (I-230) (0.030 g, 11%) as an off-white solid. $^1$H NMR (400 MHz, DMSO-$d_6$) δ 9.02-9.00 (m, 3H), 8.61 (s, 1H), 8.29 (s, 1H), 7.96-7.94 (d, J=8.4 Hz, 2H), 7.91 (s, 1H), 7.78 (s, 1H), 7.71 (s, 1H), 4.62-4.60 (d, J=5.6 Hz, 2H), 3.83 (s, 3H). MS: [MH]+ 401.13.

Example 1.334. N-((8-(4-(Trifluoromethyl)phenyl)imidazo[1,2-a]pyrazin-6-yl)methyl)-1H-imidazole-5-carboxamide (I-231

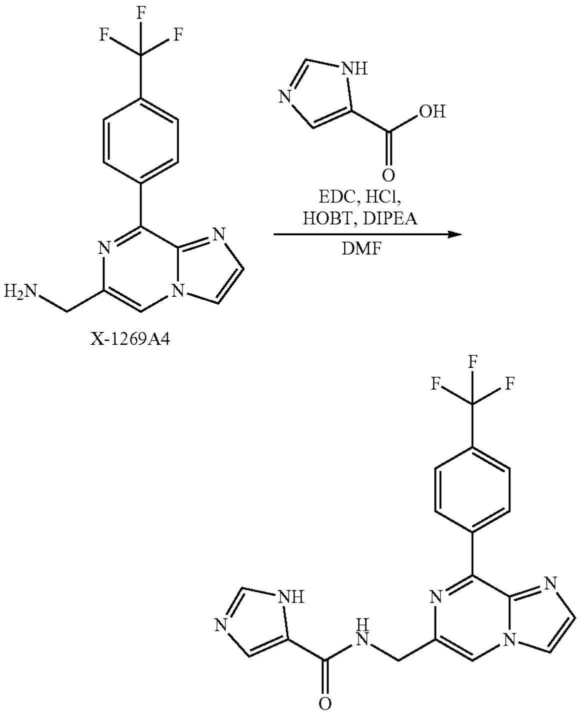

X-1269A4

I-231

The following compound was prepared in a manner analogous to the procedures described above for (E)-4-methoxy-N-((8-(4-(trifluoromethyl)phenyl)imidazo[1,2-a]pyrazin-6-yl)methyl)but-2-enamide (I-219):

N-((8-(4-(Trifluoromethyl)phenyl)imidazo[1,2-a]pyrazin-6-yl)methyl)-1H-imidazole-5-carboxamide (I-231) (0.04 g, 11%) as an off-white solid. $^1$H NMR (400 MHz, DMSO-$d_6$) δ 12.52 (s, 1H), 9.03-9.01 (d, J=8.0 Hz, 2H), 8.62-8.61 (t, J=5.6 Hz, 1H), 8.51 (s, 1H), 8.30 (s, 1H), 7.96-7.94 (d, J=8.0 Hz, 2H), 7.89 (s, 1H), 7.77 (m, 1H), 7.69 (s, 1H), 4.65-4.63 (d, J=6.0 Hz, 2H). MS: $[MH]^+$ 387.0.

Example 1.135. 1-Methyl-N-((8-(4-(trifluoromethyl)phenyl)imidazo[1,2-a]pyrazin-6-yl)methyl)-1H-imidazole-4-carboxamide (I-232)

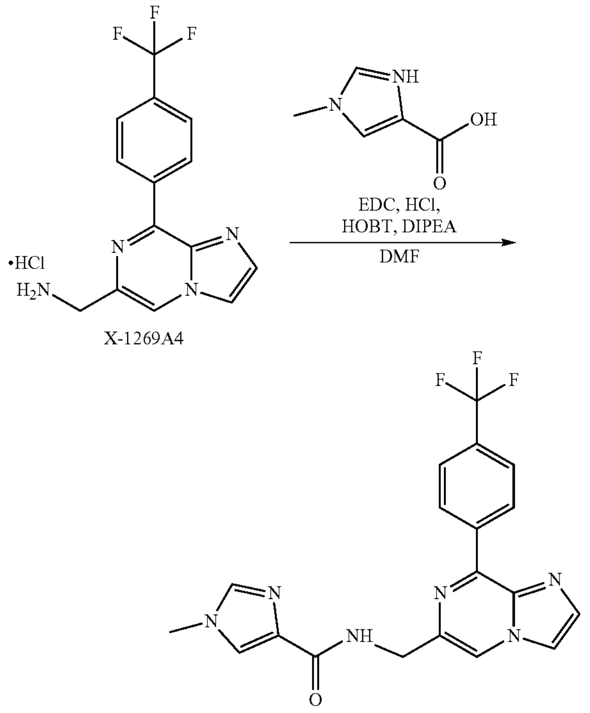

X-1269A4

I-232

The following compound was prepared in a manner analogous to the procedures described above for (E)-4-methoxy-N-((8-(4-(trifluoromethyl)phenyl)imidazo[1,2-a]pyrazin-6-yl)methyl)but-2-enamide (I-219):

1-Methyl-N-((8-(4-(trifluoromethyl)phenyl)imidazo[1,2-a]pyrazin-6-yl)methyl)-1H-imidazole-4-carboxamide (I-232) (0.115 g, 47%) as a white solid. $^1$H NMR (400 MHz, DMSO-$d_6$) δ 9.02-9.00 (d, J=8.0 Hz, 2H), 8.62-8.58 (m, 1H), 8.49 (s, 1H), 8.30 (s, 1H), 7.96-7.94 (d, J=8.4 Hz, 2H), 7.89 (s, 1H), 7.70-7.69 (d, J=3.6 Hz, 2H), 4.63-4.61 (d, J=6.0 Hz, 2H), 3.70 (s, 3H). MS: $[MH]^+$ 401.1.

Example 1.136. Synthesis of (8-(4-(trifluoromethyl)phenyl)imidazo[1,2-a]pyrazin-6-yl)glycine (1-233)

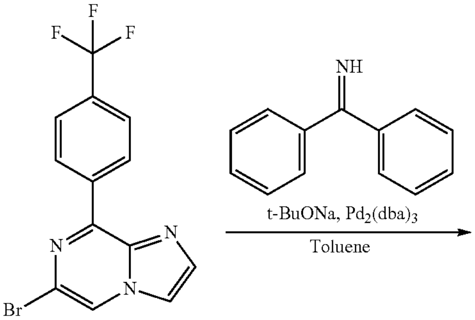

X-1269A4

-continued

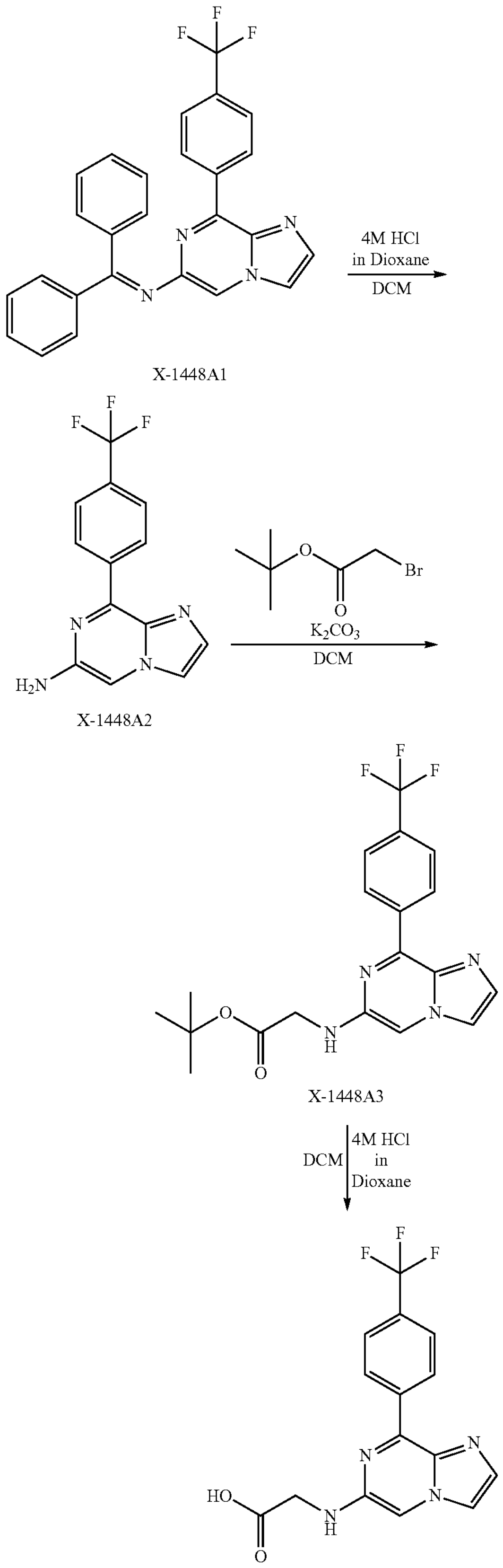

X-1448A1

X-1448A2

X-1448A3

I-233

1,1-Diphenyl-N-(8-(4-(trifluoromethyl)phenyl)imidazo[1,2-a]pyrazin-6-yl)methanimine (X-1448A1). To a stirred solution of 6-bromo-8-(4-(trifluoromethyl)phenyl)imidazo[1,2-a]pyrazine (X-1269A2) (1.5 g, 4.39 mmol) in a toluene (10 mL) were added sodium tert-butoxide (0.630 g, 6.59 mmol) and diphenylmethanimine (0.790 g, 4.39 mmol) at room temperature under nitrogen atmosphere and the resulting mixture was degassed (purging with nitrogen) for 20 min followed by the addition of $Pd_2(dba)_3$ (0.080 g, 0.08 mmol) and BINAP (0.210 g, 0.35 mmol) and the resulting mixture was heated at 100° C. for 3 h. Reaction mixture was cooled to room temperature, diluted with water (150 mL) and was extracted with ethyl acetate (100 mL×2). Combined organic extracts were washed with brine (100 mL), dried over anhydrous $Na_2SO_4$ and concentrated in vacuo. Obtained crude product was purified by silica gel column chromatography, using ethyl acetate-hexane: 0:1→1:9 as a gradient, to afford 1,1-diphenyl-N-(8-(4-(trifluoromethyl)phenyl)imidazo[1,2-a]pyrazin-6-yl)methanimine (X-1448A1) (1.7 g, 52%) as an brown solid. MS: $[MH]^+$ 443.07.

8-(4-(Trifluoromethyl)phenyl)imidazo[1,2-a]pyrazin-6-amine (X-1448A2). To a stirred solution of 1,1-diphenyl-N-(8-(4-(trifluoromethyl)phenyl)imidazo[1,2-a]pyrazin-6-yl)methanimine (X-1448A1) (1.0 g, 2.20 mmol) in DCM (10 mL), was added 4M HCl in 1,4 Dioxane (10 mL) at 0° C. under nitrogen and the resulting reaction mixture was stirred at room temperature for 2 h. Reaction mixture was concentrated under reduced pressure. Obtained crude was triturated with diethyl ether (15 mL×2), dried over high vacuum to afford 8-(4-(trifluoromethyl)phenyl)imidazo[1,2-a]pyrazin-6-amine (X-1448A2) (1.2 g, quant; crude) as a brown solid. MS: $[MH]^+$ 278.96 tert-Butyl (8-(4-(trifluoromethyl)phenyl)imidazo[1,2-a]pyrazin-6-yl)glycinate (X-1448A3). To a stirred solution of 8-(4-(trifluoromethyl)phenyl)imidazo[1,2-a]pyrazin-6-amine (X-1448A2) (0.650 g, 0.23 mmol) in DMF (10 mL) were added $K_2CO_3$ (0.483 g, 0.35 mmol) and tert-butyl 2-bromoacetate (1.130 g, 0.57 mmol) at room temperature and stirred at 80° C. for 3 h. Reaction mixture was cooled to room temperature, poured into water (100 mL) and was extracted with ethyl acetate (100 mL×2). Combined extracts were dried over anhydrous $Na_2SO_4$ and concentrated in vacuo. The crude product was purified by reverse phase (C-18) silica gel column chromatography using acetonitrile-water=0:1→7:3 as gradient, to tert-butyl (8-(4-(trifluoromethyl)phenyl)imidazo[1,2-a]pyrazin-6-yl)glycinate (X-1448A3) (0.100 g, 42%) as an white solid. MS: $[NM]^+$ 393.12.

(8-(4-(Trifluoromethyl)phenyl)imidazo[1,2-a]pyrazin-6-yl)glycine (I-233). To a stirred solution of tert-butyl (8-(4-(trifluoromethyl)phenyl)imidazo[1,2-a]pyrazin-6-yl)glycinate (X-1448A3) (0.150 g, 0.38 mmol) in DCM (4 mL) was added 4M HCl in 1,4-dioxane (1.5 mL) at 0° C. under nitrogen and the resulting reaction mixture was stirred at room temperature for 3 h. Reaction mixture was concentrated under reduced pressure. Obtained crude was triturated with diethyl ether (30 mL×2), dried over high vacuum afford (8-(4-(trifluoromethyl)phenyl)imidazo[1,2-a]pyrazin-6-yl)glycine (I-233) (0.035 g, 27%) as an off-white solid. $^1H$ NMR (400 MHz, DMSO-$d_6$) δ 12.63 (brs, 1H), 8.80-8.78 (d, J=6.0 Hz, 2H), 8.15 (s, 1H), 7.96-7.88 (m, 4H), 4.01 (s, 2H). MS: $[MH]^+$ 336.97.

Example 1.137. Synthesis of 1-(8-(4-(Trifluoromethyl)phenyl)imidazo[1,2-a]pyrazin-6-yl)pyrrolidine-3-carboxylic acid (I-234)

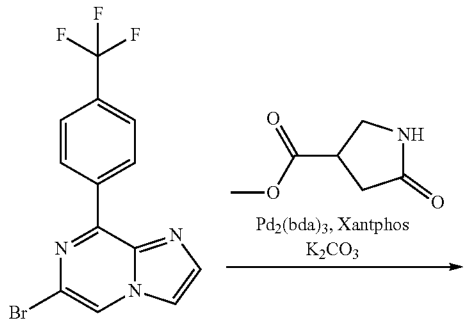

X-1269A2

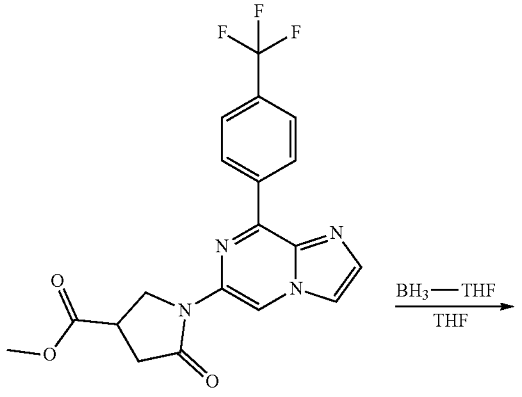

X-1449B1

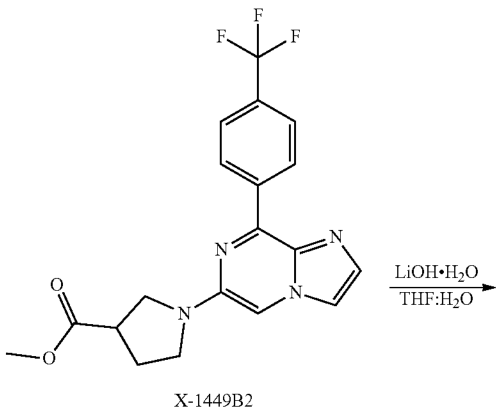

X-1449B2

-continued

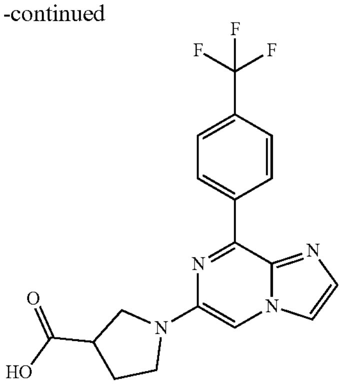

I-234

Methyl 5-xo-1-(8-(4-(trifluoromethyl)phenyl)imidazo[1,2-a]pyrazin-6-yl)pyrrolidine-3-carboxylate (X-1449A1). To a stirred solution of 6-bromo-8-(4-(trifluoromethyl)phenyl)imidazo[1,2-a]pyrazine (X-1269A2) (2.0 g, 5.86 mmol) in a 1,4 dioxane (20 mL) were added $K_2CO_3$ (2.42 g, 17.59 mmol) and methyl 5-oxopyrrolidine-3-carboxylate (1.67 g, 11.73 mmol) at room temperature under nitrogen. The resulting mixture was degassed (purging with nitrogen) for 20 min followed by the addition of $Pd_2(dba)_3$ (0.536 g, 0.58 mmol) and Xanthphos (0.336 g, 0.58 mmol) and the mixture was heated at 100° C. for 5 h. Reaction mixture was cooled to room temperature, diluted with water (150 mL) and was extracted with ethyl acetate (100 mL×3). Combined organic extracts were washed with brine (100 mL), dried over anhydrous $Na_2SO_4$ and concentrated in vacuo. Obtained crude product was purified by silica gel column chromatography, using ethyl acetate-hexane: 3:7→1:3 as a gradient, to afford methyl 5-oxo-1-(8-(4-(trifluoromethyl)phenyl)imidazo[1,2-a]pyrazin-6-yl)pyrrolidine-3-carboxylate (X-1449B1) (0.800 g, 33%) as a yellow solid. MS: $[MH]^+$ 404.91.

Methyl 1-(8-(4-(trifluoromethyl)phenyl)imidazo[1,2-a]pyrazin-6-yl)pyrrolidine-3-carboxylate (X-1449B2). To a stirred solution of methyl 5-oxo-1-(8-(4-(trifluoromethyl)phenyl)imidazo[1,2-a]pyrazin-6-yl)pyrrolidine-3-carboxylate (X-1449B1) (0.200 g, 0.49 mmol) in THF (5 mL) was added $BH_3$-THF (1.0 mL, 1.0 M in THF, 0.99 mmol) at 0° C. under nitrogen and the resulting reaction mixture was stirred at 0° C. for 5 h. Reaction mixture slowly poured into aq. $NH_4C1$ solution (20 mL) and was extracted with ethyl acetate (50 mL×2). Combined extracts were dried over anhydrous $Na_2SO_4$ and concentrated in vacuo. Obtained crude product was purified by silica gel column chromatography, using ethyl acetate-hexane: 4:6→5:5 as a gradient, to afford methyl 1-(8-(4-(trifluoromethyl)phenyl)imidazo[1,2-a]pyrazin-6-yl)pyrrolidine-3-carboxylate (X-1449B2) (0.130 g, 67%) as a yellow solid. MS: $[MH]^+$ 391.1

1-(8-(4-(Trifluoromethyl)phenyl)imidazo[1,2-a]pyrazin-6-yl)pyrrolidine-3-carboxylic acid (I-234). To a stirred solution of methyl 1-(8-(4-(trifluoromethyl)phenyl)imidazo[1,2-a]pyrazin-6-yl)pyrrolidine-3-carboxylate (X-1449B2) (0.130 g, 0.33 mmol) in a mixture of THE-water (3:1; 3 mL) was added lithium hydroxide monohydrate (0.042 g, 0.99 mmol) at room temperature and stirred at 70° C. for 2 h. The reaction mixture was concentrated under reduced pressure, crude mass was diluted with water (3 mL) and was acidified (pH~2-3) with an aqueous 1N HCl, and the resulting precipitate was collected by filtration. Obtained residue was washed with cold water until the pH of the filtrate became neutral (pH~6-7). The obtained solid was triturated in diethyl ether (5 mL×3) and dried in vacuo to afford 1-(8-(4-(trifluoromethyl)phenyl)imidazo[1,2-a]pyrazin-6-yl)pyrrolidine-3-carboxylic acid (I-234) (0.080 g, 63%) as a green solid. $^{1}$H NMR (400 MHz, DMSO-d6) δ: 12.53 (br s, 1H), 9.07-9.05 (d, J=8.4 Hz, 2H), 8.04 (s, 1H), 7.94-7.92 (d, J=8.4 Hz, 2H), 7.84 (s, 1H), 7.77 (s, 1H), 3.70-3.60 (m, 1H), 3.53-3.40 (m, 2H), 3.27-3.17 (m, 2H), 2.33-2.26 (m, 2H). MS: $[MH]^+$ 377.06.

Example 1.138. Synthesis of N-((3-fluoro-8-(4-(trifluoromethyl)phenyl)imidazo[1,2-a]pyrazin-6-yl)methyl)acrylamide (I-235

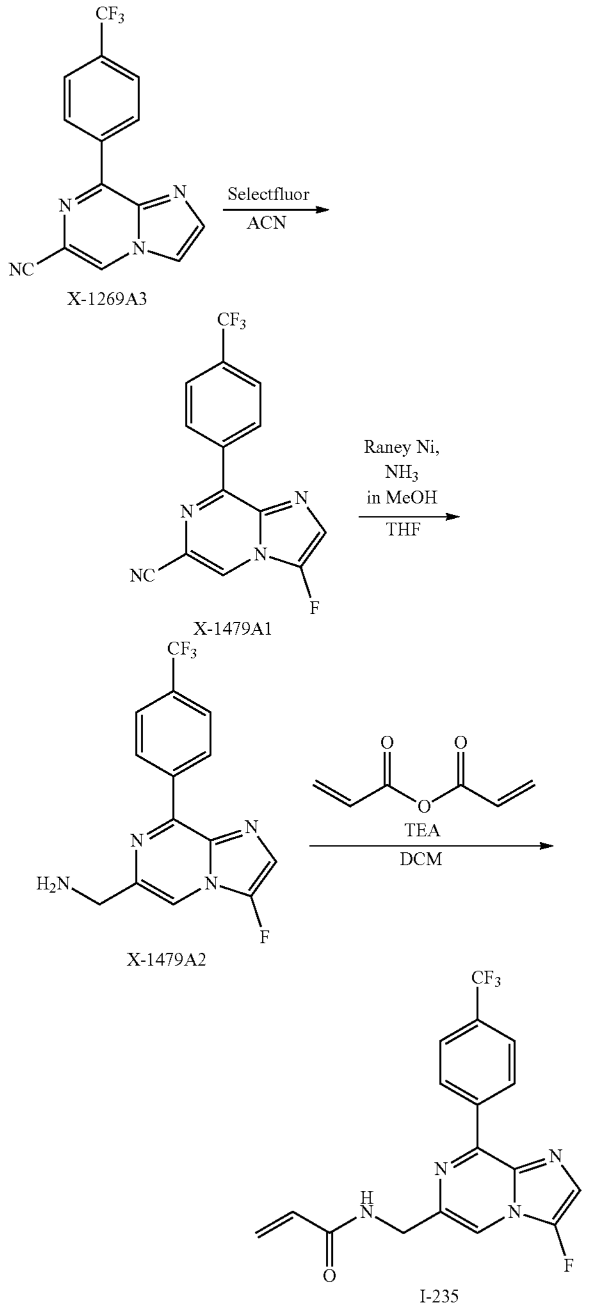

3-Fluoro-8-(4-(trifluoromethyl)phenyl)imidazo[1,2-a]pyrazine-6-carbonitrile (X-1479A1). To a stirred solution 8-(4-(trifluoromethyl)phenyl)imidazo[1,2-a]pyrazine-6-carbonitrile (X-1269A3) (0.500 g, 1.73 mmol) in ACN (6 mL) was added select flour (0.221 g, 1.90 mmol) at 0° C. portion wise under nitrogen. The reaction mixture was heated to 70° C. for 48 h. Reaction mixture was cooled to room temperature, slowly poured into water (100 mL) and was extracted with ethyl acetate (100 mL×3), dried over anhydrous $Na_2SO_4$ and concentrated under reduce pressure. Isolated crude was combined with an identical prepared one more batch (0.5 g) and the combined crude were purified by silica gel column chromatography using ethyl acetate-hexane=0:1→2:8 as gradient, to afford 3-fluoro-8-(4-(trifluoromethyl)phenyl)imidazo[1,2-a]pyrazine-6-carbonitrile (X-1479A1) (0.44 g, 41%) as a yellow solid. MS: $[MH]^+$ 307.01.

(3-Fluoro-8-(4-(trifluoromethyl)phenyl)imidazo[1,2-a]pyrazin-6-yl)methanamine (X-1479A2). To a stirred solution of 3-fluoro-8-(4-(trifluoromethyl)phenyl)imidazo[1,2-a]pyrazine-6-carbonitrile (X-1479A1) (0.400 g, 1.32 mmol) in THE (4 mL) were added Raney Nickel (0.400 g) and ammonia in MeOH (4 mL) at room temperature and the resulting mixture was hydrogenated in Parr Autoclave at room temperature under 200 psi for 2 h. Reaction mixture was cooled to room temperature, filtered over a celite bed, washed the bed with MeOH (100 mL) and collected filtrates were concentrated under reduced pressure. The resulting crude was purified by reverse phase (C-18) silica gel column chromatography using acetonitrile-0.1% formic acid in water=0:142:8 as gradient to give (3-fluoro-8-(4-(trifluoromethyl)phenyl)imidazo[1,2-a]pyrazin-6-yl)methanamine (X-1479A2) (0.180 g, 44%) as a yellow solid. MS: $[MH]^+$ 311.01.

N-((3-Fluoro-8-(4-(trifluoromethyl)phenyl)imidazo[1,2-a]pyrazin-6-yl)methyl)acrylamide (I-235). To a stirred solution of (3-fluoro-8-(4-(trifluoromethyl)phenyl)imidazo[1,2-a]pyrazin-6-yl)methanamine (X-1479A2) (0.180 g, 0.58 mmol) in DCM (5 mL) were added TEA (0.175 g, 1.70 mmol) followed by acrylic anhydride (0.073 g, 0.58 mmol) at 0° C. under nitrogen and the reaction mixture stirred for 30 min at room temperature. The reaction mixture was slowly poured into water (30 mL) and was extracted with DCM (30 mL×3), dried over anhydrous $Na_2SO_4$ and concentrated under reduced pressure. The resulting crude was purified by reverse phase (C-18) silica gel column chromatography using acetonitrile-0.1% formic acid in water=0:145:5 as gradient, to afford N-((3-fluoro-8-(4-(trifluoromethyl)phenyl)imidazo[1,2-a]pyrazin-6-yl)methyl)acrylamide (I-235) (0.035 g, 17%) as an off-white solid. $^{1}$H NMR (400 MHz, DMSO-$d_6$) δ 8.95-8.93 (d, J=8.0 Hz, 2H), 8.78-8.76 (t, J=5.2 Hz, 1H), 8.35 (s, 1H), 7.97-7.95 d, J=8.4 Hz, 2H), 7.78-7.76 (d, J=7.2 Hz, 1H), 6.37-6.31 (m, 1H), 6.17-6.12 (dd, J=9.2, 2.0 Hz, 1H), 5.66-5.63 (dd, J=10.0 Hz, 2.0 Hz, 1H), 4.56-4.55 (d, J=5.6 Hz, 2H). MS: $[MH]^+$ 365.0.

Example 1.139. Synthesis of N-((8-(4-(Trifluoromethyl)phenyl)-[1,2,4]triazolo[1,5-a]pyrazin-6-yl)methyl)acrylamide (I-236)

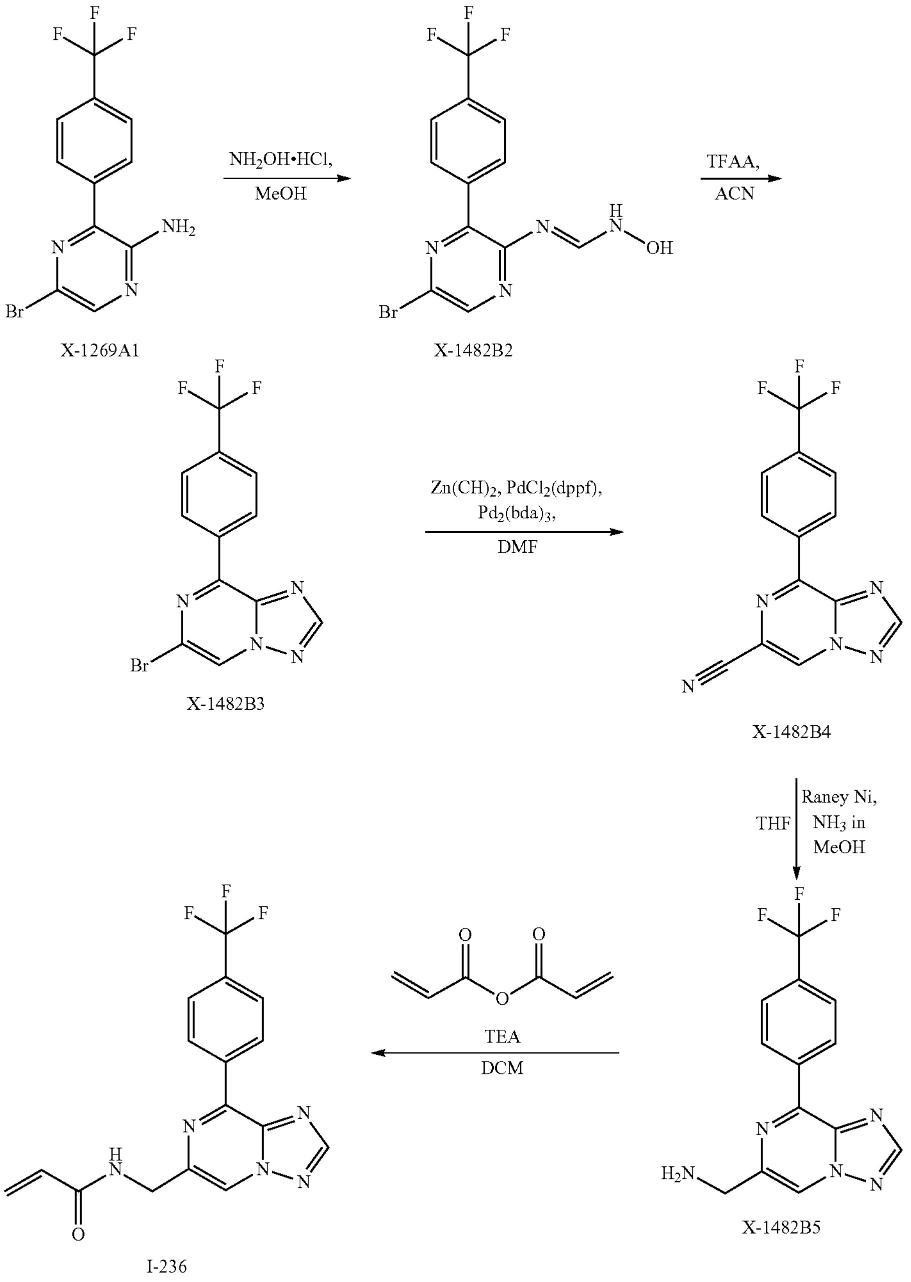

(E)-N'-(5-Bromo-3-(4-(trifluoromethyl)phenyl)pyrazin-2-yl)-N-hydroxyformimidamide (X-1482B2). To a stirred solution of 5-bromo-3-(4-(trifluoromethyl)phenyl)pyrazin-2-amine (X-1269A1) (4.5 g, 14.19 mmol) in N, N-dimethylformamide dimethyl acetal (5.06 mL, 42.58 mmol) was heated at 100° C. for 2 h. The reaction mixture was concentrated in vacuo. The crude was dissolved methanol and treated with Hydroxylamine Hydrochloride (1.48 g, 21.28 mmol). The resulting reaction mixture was stirred at 100° C. for 5 h. Reaction mixture was cooled to room temperature, diluted with water (200 mL) and the resulting precipitate was filtered and washed with water (50 mL×3) and dried under reduced pressure, to afford (E)-N'-(5-bromo-3-(4-(trifluoromethyl)phenyl)pyrazin-2-yl)-N-hydroxyformimidamide (X-1482B2) (6.0 g, Quantitative yield) as a brown gummy solid. MS: $[MH]^+$ 360.92

6-Bromo-8-(4-(trifluoromethyl)phenyl)-[1,2,4]triazolo[1,5-a]pyrazine (X-1482B3). To a stirred solution of (E)-N'-(5-bromo-3-(4-(trifluoromethyl)phenyl)pyrazin-2-yl)-N-hydroxyformimidamide (X-1482B2) (6.0 g, 16.66 mmol) in Acetonitrile (30 mL) was added Trifluoroacetic anhydride (5.29 g, 24.99 mmol) at 0° C. and stirred at room temperature for 3 h. The reaction mixture was concentrated under reduced pressure. Obtained crude mass was purified by silica gel column chromatography, using ethyl acetate-hexane: 0:1→1:9 as a gradient, to afford 6-bromo-8-(4-(trifluoromethyl)phenyl)-[1,2,4]triazolo[1,5-a]pyrazine (X-1482B3) (2.30 g, 40%) as an off-white solid. MS: $[MH]^+$ 344.82

8-(4-(Trifluoromethyl)phenyl)-[1,2,4]triazolo[1,5-a]pyrazine-6-carbonitrile (X-1482B4). To a stirred solution of 6-bromo-8-(4-(trifluoromethyl)phenyl)-[1,2,4]triazolo[1,5-a]pyrazine (X-1482B3) (1.5 g, 4.38 mmol) in DMF (8 mL), was added $Zn(CN)_2$ (1.53 g, 13.15 mmol) at room temperature under nitrogen. The resulting mixture was degassed (purging with nitrogen) for 40 min followed by the addition of $PdCl_2$(dppf) (0.32 g, 0.43 mmol) and $Pd_2(dba)_3$ (0.4 g, 0.43 mmol) the resulting mixture was heated at 130° C. for 1 h in microwave irradiation. Reaction mixture was cooled to room temperature, diluted with water (250 mL) and was extracted with ethyl acetate (200 mL×3). Combined organic extracts were washed with brine (200 mL), dried over anhydrous $Na_2SO_4$ and concentrated in vacuo. The crude product was purified by silica gel column chromatography, using ethyl acetate-hexane: 0:1→3:7 as a gradient, to afford 8-(4-(trifluoromethyl)phenyl)-[1,2,4]triazolo[1,5-a]pyrazine-6-carbonitrile (X-1482B4) (0.800 g, 41%) as an brown white solid. $^1H$ NMR (400 MHz, DMSO-$d_6$) δ: 10.14 (s, 1H), 9.08 (s, 1H), 8.91-8.89 (d, J=8.0 Hz, 2H), 8.03-8.01 (d, J=8.4 Hz, 2H).

(8-(4-(Trifluoromethyl)phenyl)-[1,2,4]triazolo[1,5-a]pyrazin-6-yl)methanamine (X-1482B5). To a stirred solution of 8-(4-(trifluoromethyl)phenyl)-[1,2,4]triazolo[1,5-a]pyrazine-6-carbonitrile (X-1482B4) (0.400 g, 1.38 mmol) in THE (8 mL) were added Raney Nickel (~0.49 g) and 7M Ammonia in methanol (3.0 mL) at room temperature. The resulting reaction mixture was hydrogenated in Parr Autoclave at 60° C. under 200 psi pressure for 2 h. After completion of the reaction was Cooled to room temperature, filtered over celite bed and washed with methanol (20 mL×3) and collected filtrates were concentrated in vacuo, to afford (8-(4-(trifluoromethyl)phenyl)-[1,2,4]triazolo[1,5-a]pyrazin-6-yl)methanamine (X-1482B5) (0.2 g, crude) as a brown sticky solid. Which was used to next step without further purification. MS: $[MH]^+$ 293.96

N-((8-(4-(trifluoromethyl)phenyl)-[1,2,4]triazolo[1,5-a]pyrazin-6-yl)methyl)acrylamide (I-236). To a stirred solution of (8-(4-(trifluoromethyl)phenyl)-[1,2,4]triazolo[1,5-a]pyrazin-6-yl)methanamine (X-1482B5) (0.20 g, 0.68 mmol) in DCM (5 mL) was added TEA (0.29 mL, 2.04 mmol) at 0° C. under nitrogen atmosphere and stirred for 15 min at same temperature. Acrylic anhydride (0.085 g, 0.68 mmol) was added at 0° C. and the resulting reaction mixture was stirred at room temperature for 1 h. Reaction mixture was diluted with water (50 mL) and was extracted with DCM (50 mL×2). Combined organic extracts were dried over anhydrous $Na_2SO_4$ and concentrated in vacuo. Obtained crude mass purified by silica gel column chromatography, using ethyl acetate-hexane: 0:1→4 7:3 as a gradient, to afford N-((8-(4-(trifluoromethyl)phenyl)-[1,2,4]triazolo[1,5-a]pyrazin-6-yl)methyl)acrylamide (I-236) (0.035 g, 15%) as an off white. 1H NMR (400 MHz, DMSO-$d_6$) δ: 9.02 (s, 1H), 8.98-8.96 (d, J=8.0 Hz, 2H), 8.86 (s, 1H), 8.84-8.83 (t, J=5.6 Hz, 1H), 8.02-8.00 (d, J=8.4 Hz, 2H), 6.37-6.31 (m, 1H), 6.17-6.13 (dd, J=1.6, 17.2 Hz, 1H), 5.67-5.64 (dd, J=1.6, 10.0 Hz, 1H), 4.65-4.64 (d, J=5.6 Hz, 2H). MS: $[MH]^+$ 348.02.

Example 1.140. Synthesis of N-(1-(8-(4-(trifluoromethyl)phenyl)imidazo[1,2-a]pyrazin-6-yl)cyclopropyl)acrylamide (I-237)

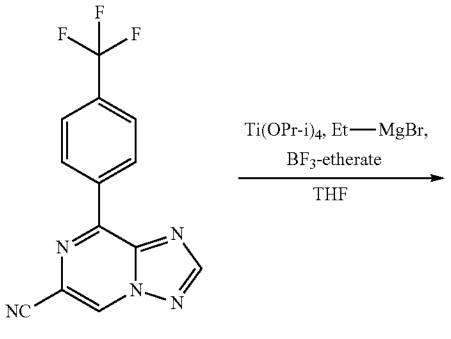

X-1269A3

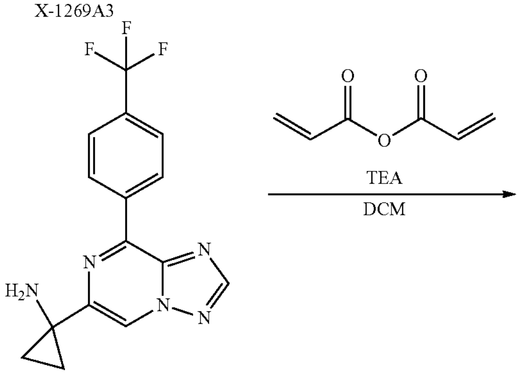

X-1484A1

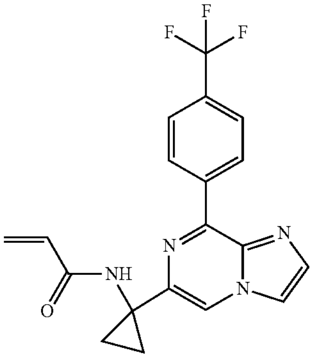

I-237

1-(8-(4-(trifluoromethyl)phenyl)imidazo[1,2-a]pyrazin-6-yl)cyclopropan-1-amine (X-1484A1). To a stirred solution of 8-(4-(trifluoromethyl)phenyl)imidazo[1,2-a]pyrazine-6-carbonitrile (X-1269A3) (0.700 g, 2.43 mmol) in THE (20 mL), was added Titanium(IV) isopropoxide (0.82 g, 2.91 mmol) at room temperature under nitrogen and stirred at same temperature for 1 h. Ethyl magnesium bromide (1M in THF) (6.07 mL, 6.07 mmol) was added slowly at −30° C. The resulting mixture was stirred at room temperature for 2 h. Reaction mixture was cooled to 0° C. and $BF_3$—OEt (1.10 g, 6.07 mmol) was added. The resulting reaction mixture was stirred at 0° C. for 30 min. Reaction mixture was diluted with water (200 mL) and was extracted with ethyl acetate (100 mL×3). Combined organic extracts were washed with brine (100 mL), dried over anhydrous $Na_2SO_4$ and concentrated in vacuo. The crude product was purified by neutral alumina column chromatography, using ethyl acetate-hexane: 0:1→4:6 as a gradient, to afford 1-(8-(4-(trifluoromethyl)phenyl)imidazo[1,2-a]pyrazin-6-yl)cyclopropan-1-amine (X-1484A1) (0.220 g, 28%) as an yellow solid. MS: $[MH]^+$ 318.96

N-(1-(8-(4-(trifluoromethyl)phenyl)imidazo[1,2-a]pyrazin-6-yl)cyclopropyl)acrylamide (I-237). To a stirred solution of 1-(8-(4-(trifluoromethyl)phenyl)imidazo[1,2-a]pyrazin-6-yl)cyclopropan-1-amine (X-1484A1) (0.150 g, 0.47 mmol) in DCM (5 mL) was added TEA (0.20 mL, 1.41 mmol) at 0° C. under nitrogen atmosphere and stirred for 15 min at same temperature. Acrylic anhydride (0.059 g, 0.47 mmol) was added at 0° C. and the resulting reaction mixture was stirred at room temperature for 1 h. Reaction mixture was diluted with water (50 mL) and was extracted with dichloromethane (50 mL×2). Combined organic extracts were dried over anhydrous $Na_2SO_4$ and concentrated in vacuo. Obtained crude mass purified by C-18 silica gel column chromatography using acetonitrile:water=0:1→3:7 as gradient, to afford N-(1-(8-(4-(trifluoromethyl)phenyl)imidazo[1,2-a]pyrazin-6-yl)cyclopropyl)acrylamide (I-237) (0.095 g, 54%) as an off white. $^1H$ NMR (400 MHz, DMSO-$d_6$) δ: 9.01 (s, 1H), 8.96-8.94 (d, J=8.40 Hz, 2H), 8.49 (s, 1H), 8.28 (s, 1H), 7.95-7.92 (d, J=8.40 Hz, 2H), 7.88 (s, 1H), 6.38-6.31 (m, 1H), 6.19-6.15 (d, J=17.2 Hz, 1H), 5.70-5.67 (d, J=10.40 Hz, 1H), 1.62-1.59 (m, 2H), 1.21-1.18 (m, 2H). MS: $[MH]^+$ 372.97

Example 1.141. Synthesis of N-((8-(4-(Trifluoromethyl)phenyl)imidazo[1,2-a]pyrazin-6-yl)methyl)cyanamide (I-238)

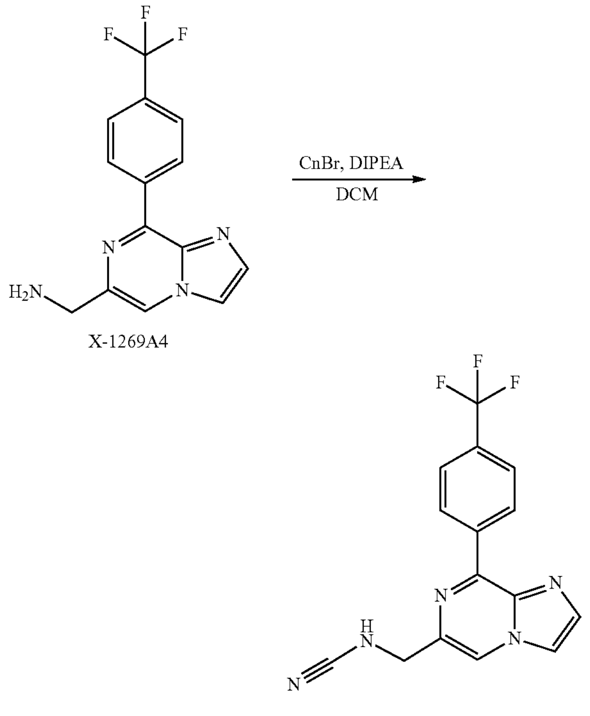

X-1269A4

I-238

To a stirred solution of (8-(4-(trifluoromethyl)phenyl)imidazo[1,2-a]pyrazin-6-yl)methanamine (X-1269A4) (0.100 g, 0.34 mmol) in DCM (5 mL) were added N,N-Diisopropylethylamine (0.088 g, 0.68 mmol) and CNBr (0.036 g, 0.34 mmol) at 0° C. under nitrogen atmosphere and stirred for 15 min at same temperature. Reaction mixture was diluted with water (30 mL) and was extracted with dichloromethane (50 mL×2). Combined organic extracts were dried over anhydrous $Na_2SO_4$ and concentrated in vacuo. Obtained crude mass purified by silica gel column chromatography using ethyl acetate:Hexane=0:1→5:5 as gradient, to afford N-((8-(4-(trifluoromethyl)phenyl)imidazo[1,2-a]pyrazin-6-yl)methyl)cyanamide (I-238) (0.015 g, 14%) as an light brown solid. $^1H$ NMR (400 MHz, DMSO-$d_6$) δ: 9.06-9.04 (d, J=8.0 Hz, 2H), 8.74 (s, 1H), 8.33 (s, 1H), 7.97-7.95 (d, J=8.4 Hz, 2H), 7.95 (s, 1H), 7.48 (s, 1H), 4.31-4.30 (d, J=5.6 Hz, 2H), MS: $[MH]^+$ 317.96.

Example 1.142. Synthesis of N-methyl-N-((8-(4-(trifluoromethyl)phenyl)imidazo[1,2-a]pyrazin-6-yl)methyl)cyanamide (I-239)

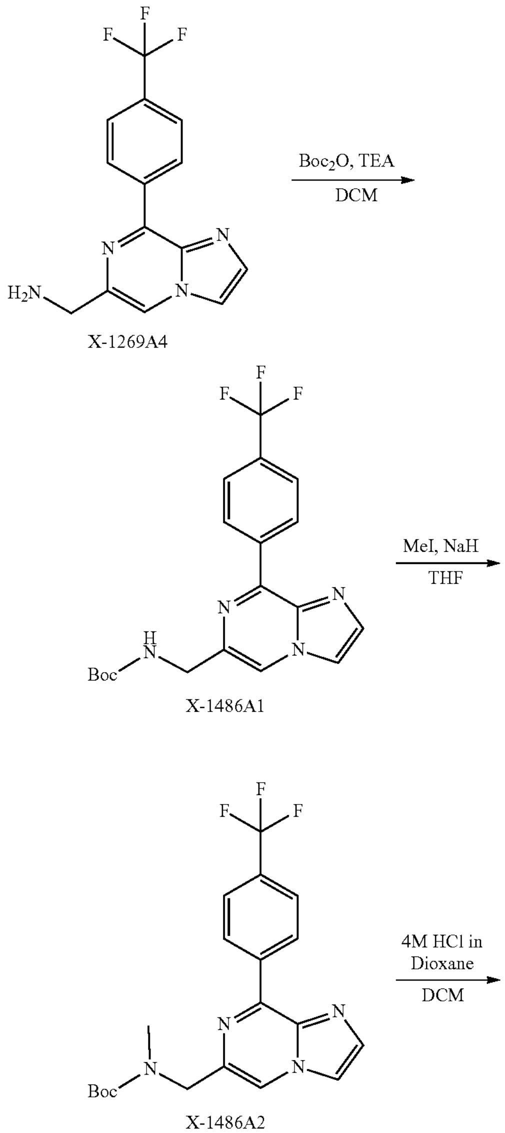

X-1269A4

X-1486A1

X-1486A2

-continued

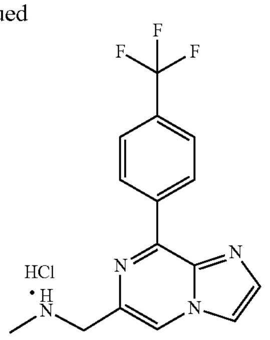

X-1486A3

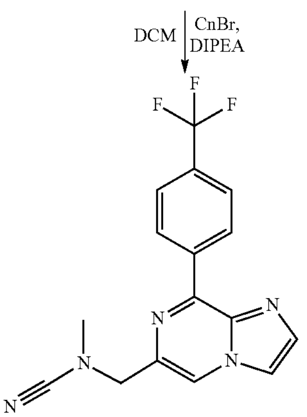

I-239 tert-Butyl ((8-(4-(trifluoromethyl)phenyl)imidazo[1,2-a]pyrazin-6-yl)methyl)carbamate (X-1486A1). To a stirred solution of (8-(4-(trifluoromethyl)phenyl)imidazo[1,2-a]pyrazin-6-yl)methanamine (X-1269A4) (0.050 g, 0.17 mmol) in DCM (2 mL) were added N, N-diisopropylethylamine (0.060 g, 0.51 mmol) at room temperature under nitrogen atmosphere and stirred for 15 min at same temperature. Di-tert-butyl bicarbonate (0.108 g, 0.34 mmol) was added at room temperature and stirred at same temperature for 2 h. Reaction mixture was diluted with water (20 mL) and was extracted with dichloromethane (20 mL×2). Combined organic extracts were dried over anhydrous $Na_2SO_4$ and concentrated in vacuo. Obtained crude mass was triturated in n-pentane (5 mL×2) and dried in vacuo. to afford tert-butyl ((8-(4-(trifluoromethyl)phenyl)imidazo[1,2-a]pyrazin-6-yl)methyl)carbamate (X-1486A1) (0.045 g, 67%) as an off white solid. MS: $[MH]^+$ 393.12 tert-Butyl methyl((8-(4-(trifluoromethyl)phenyl)imidazo[1,2-a]pyrazin-6-yl)methyl)carbamate (X-1486A2). To a stirred solution of tert-butyl ((8-(4-(trifluoromethyl)phenyl)imidazo[1,2-a]pyrazin-6-yl)methyl)carbamate (X-1486A1) (0.020 g, 0.05 mmol) in THE (1 mL) was added dried NaH (washed with n-hexane) (0.007 g, 0.15 mmol) at 0° C. and stirred for 15 min at same temperature. MeI (0.013 g, 0.056 mmol) was added at 0° C. and the resulting reaction mixture was stirred at room temperature for 1 h. Reaction mixture was poured into water (10 mL) and was extracted with ethyl acetate (10 mL×2). Combined extracts were dried over anhydrous $Na_2SO_4$ and concentrated in vacuo. Obtained crude mass was triturated in n-pentane (3 mL×2) and dried in vacuo. to afford tert-butyl methyl((8-(4-(trifluoromethyl)phenyl)imidazo[1,2-a]pyrazin-6-yl)methyl)carbamate (X-1486A2) (0.020 g, 96%) as an off-white solid. MS: $[MH]^+$ 407.12

N-Methyl-1-(8-(4-(trifluoromethyl)phenyl)imidazo[1,2-a]pyrazin-6-yl)methanamine (X-1486A3). To a solution of tert-butyl methyl((8-(4-(trifluoromethyl)phenyl)imidazo[1,2-a]pyrazin-6-yl)methyl)carbamate (X-1486A2) (0.020 g, 0.049 mmol)) in DCM (1 mL) was added 4 M HCl in 1,4-Dioxane (0.2 mL) at 0° C. under nitrogen and the resulting reaction mixture was stirred at room temperature for 2 h. Reaction mixture was concentrated under reduced pressure. Obtained crude was triturated with diethyl ether (5 mL), dried under reduced pressure, to afford N-methyl-1-(8-(4-(trifluoromethyl)phenyl)imidazo[1,2-a]pyrazin-6-yl)methanamine (X-1486A3) (0.025 g, Quantitative yield) as a brown solid. MS: $[MH]^+$ 307.06

N-Methyl-N-((8-(4-(trifluoromethyl)phenyl)imidazo[1,2-a]pyrazin-6-yl)methyl)cyanamide (I-239). To a stirred solution of N-methyl-1-(8-(4-(trifluoromethyl)phenyl)imidazo[1,2-a]pyrazin-6-yl)methanamine (X-1486A3) (0.025 g, 0.04 mmol) in DCM (2 mL) were added N,N-diisopropylethylamine (0.012 g, 0.09 mmol) and CNBr (0.007 g, 0.48 mmol) at 0° C. under nitrogen atmosphere and stirred for 15 min at same temperature. Reaction mixture was diluted with water (30 mL) and was extracted with dichloromethane (50 mL×2). Combined organic extracts were dried over anhydrous $Na_2SO_4$ and concentrated in vacuo. Obtained crude was triturated with diethyl ether (5 mL), to afford N-((8-(4-(trifluoromethyl)phenyl)imidazo[1,2-a]pyrazin-6-yl)methyl)cyanamide (I-239) (0.015 g, 55%) as a light grey solid. $^1H$ NMR (400 MHz, DMSO-$d_6$) δ: 9.06-9.04 (d, J=8.0 Hz, 2H), 8.76 (s, 1H), 8.32 (s, 1H), 7.98-7.96 (d, J=6.8 Hz, 2H), 7.96 (s, 1H), 4.38 (s, 2H), 2.92 (s, 3H). MS: $[MH]^+$ 332.12

Example 1.143. Synthesis of (E)-4-(Dimethylamino)-N-((8-(4-(trifluoromethyl)phenyl)imidazo[1,2-a]pyrazin-6-yl)methyl)but-2-enamide (I-240)

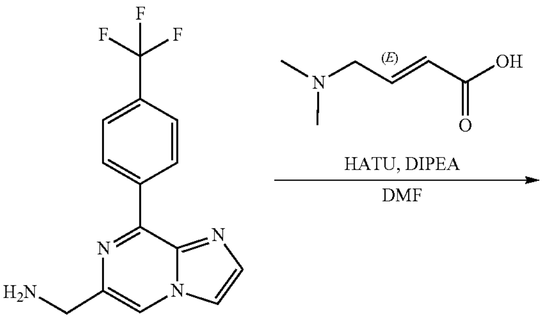

X-1269A4

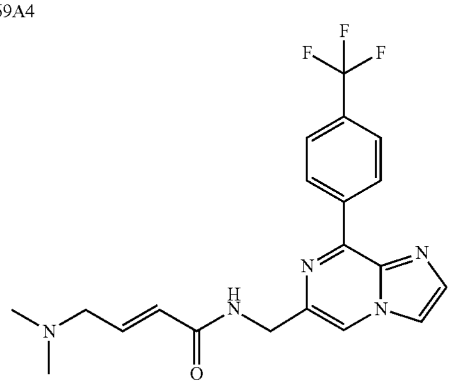

I-240

The following compound was prepared in a manner analogous to the procedures described above for 1-isopropyl-N-((8-(4-(trifluoromethyl)phenyl)imidazo[1,2-a]pyrazin-6-yl)methyl)-1H-imidazole-5-carboxamide (I-230):

(E)-4-(Dimethylamino)-N-((8-(4-(trifluoromethyl)phenyl)imidazo[1,2-a]pyrazin-6-yl)methyl)but-2-enamide (I-240) (0.025 g, 9%) as an off-white solid. $^1$H NMR (400 MHz, DMSO-$d_6$) δ 9.02-9.00 (d, J=8.0 Hz, 2H), 8.72-8.69 (t, J=5.6 Hz, 1H), 8.57 (s, 1H), 8.29 (s, 1H), 7.96-7.94 (d, J=8.4 Hz, 2H), 7.91 (s, 1H), 6.66-6.59 (m, 1H), 6.17-6.13 (d, J=15.6 Hz, 1H), 4.53-4.52 (d, J=5.6 Hz, 2H), 3.00-2.99 (d, J=6.0 Hz, 2H), 2.14 (s, 6H). MS: [MH]+ 404.16.

Example 1.144. Synthesis of N-((2-methyl-8-(4-(trifluoromethyl)phenyl)imidazo[1,2-a]pyrazin-6-yl)methyl)acrylamide (I-241)

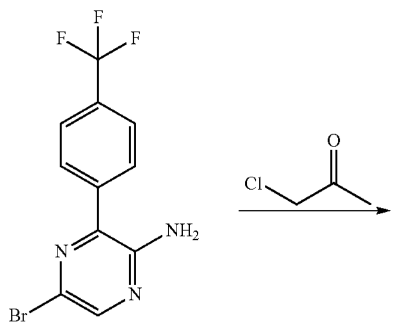

X-1269A1

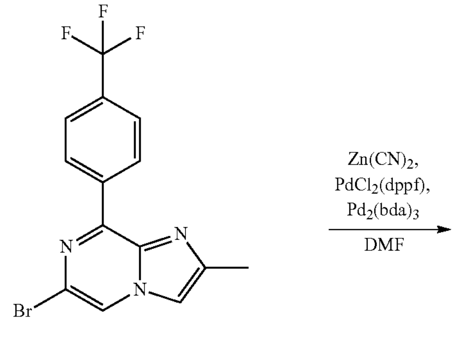

X-1489A1

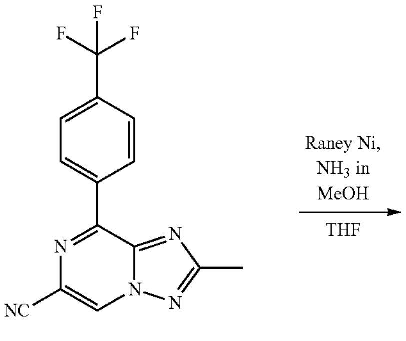

X-1489A2

-continued

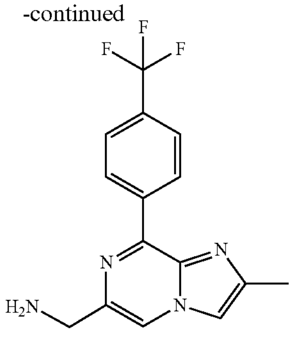

X-1489A3

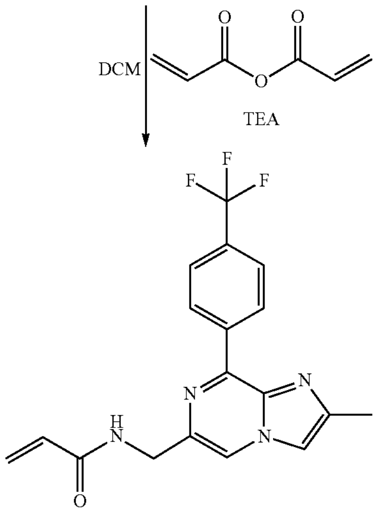

I-241

6-Bromo-2-methyl-8-(4-(trifluoromethyl)phenyl)imidazo[1,2-a]pyrazine (X-1489A1). A mixture of 5-bromo-3-(4-(trifluoromethyl)phenyl)pyrazin-2-amine (X-1269A1) (2.0 g, 6.28 mmol) in 1-chloropropan-2-one (20 mL) was heated at 90° C. for 16 h. After cooling to room temperature, reaction mixture was quenched with an aqueous solution of saturated $NaHCO_3$ (130 mL) and was extracted with ethyl acetate (50 mL×3). Corrected organic extracts were dried over anhydrous $Na_2SO_4$ and concentrated under reduce pressure. The crude product was purified by silica gel column chromatography, ethyl acetate-hexane=0:1→1:4 as gradient, to afford 6-bromo-2-methyl-8-(4-(trifluoromethyl)phenyl)imidazo[1,2-a]pyrazine (X-1489A1) (0.900 g, 40%) as a yellow solid. MS: $[MH]^+$ 355.9/$[MH+2]^+$ 357.9.

2-Methyl-8-(4-(trifluoromethyl)phenyl)imidazo[1,2-a]pyrazine-6-carbonitrile (X-1489A2). To a stirred solution of 6-bromo-2-methyl-8-(4-(trifluoromethyl)phenyl)imidazo[1,2-a]pyrazine (X-1489A1) (0.700 g, 1.97 mmol) in DMF (7 mL) was added zinc cyanide (0.578 g, 4.92 mmol) at room temperature under nitrogen. The reaction mixture was degassed (by purging nitrogen) for 30 min followed by the addition of $PdCl_2$(dppf) (0.288 g, 0.39 mmol), $Pd_2(dba)_3$ (0.360 g, 0.39 mmol) and the resulting mixture was heated at 130° C. under microwave irradiation for 30 min. Reaction mixture was cooled to room temperature, slowly poured into water (120 mL) and was extracted with ethyl acetate (100 mL×2). The combined organic extracts were washed with brine (50 mL), dried over anhydrous $Na_2SO_4$ and concentrated under reduce pressure. The crude product was purified by silica gel column chromatography, using ethyl acetate-hexane=0:1→3:7 as gradient, to afford 2-methyl-8-(4-(trifluoromethyl)phenyl)imidazo[1,2-a]pyrazine-6-carbonitrile (X-1489A2) (0.400 g, 67%) as a brown solid. MS: $[MH]^+$ 302.9.

(2-Methyl-8-(4-(trifluoromethyl)phenyl)imidazo[1,2-a]pyrazin-6-yl)methanamine (X-1489A3). To a stirred solution of 2-methyl-8-(4-(trifluoromethyl)phenyl)imidazo[1,2-a]pyrazine-6-carbonitrile (X-1489A2) (0.4 g, 1.32 mmol) in THE (5 mL) were added Raney Nickel (0.400 g) and methanolic ammonia (7N, 5 mL) at room temperature and the resulting mixture was hydrogenated in Parr Autoclave at same temperature under 200 psi for 3 h. Reaction mixture was cooled to room temperature, filtered over a celite bed, washed the bed with MeOH (100 mL) and collected filtrates were concentrated under reduced pressure, to afford (2-methyl-8-(4-(trifluoromethyl)phenyl)imidazo[1,2-a]pyrazin-6-yl)methanamine (X-1489A3) (0.400 g, 99%) as a yellow solid. MS: $[MH]^+$ 307.01.

N-((2-methyl-8-(4-(trifluoromethyl)phenyl)imidazo[1,2-a]pyrazin-6-yl)methyl)acrylamide (I-241). To a stirred solution of (2-methyl-8-(4-(trifluoromethyl)phenyl)imidazo[1,2-a]pyrazin-6-yl)methanamine (X-1489A3) (0.4 g, 1.28 mmol) in DCM (4 mL) were added TEA (0.390 g, 3.86 mmol) followed by acrylic anhydride (0.162 g, 1.28 mmol) at 0° C. under nitrogen and the reaction mixture stirred for 30 min at room temperature. The reaction mixture was slowly poured into water (30 mL) and was extracted with DCM (30 mL×3), dried over anhydrous $Na_2SO_4$ and concentrated under reduced pressure. The resulting crude was purified by reverse phase (C-18) silica gel column chromatography using acetonitrile-water=0:1→4:6 as gradient, to afford N-((2-methyl-8-(4-(trifluoromethyl)phenyl)imidazo[1,2-a]pyrazin-6-yl)methyl)acrylamide (I-241) (0.190 g, 40%) as an off-white solid. $^1H$ NMR (400 MHz, DMSO-$d_6$) δ 8.99-8.97 (d, J=8.0 Hz, 2H), 8.79-8.77 (t, J=5.2 Hz, 1H), 8.50 (s, 1H), 8.03 (s, 1H), 7.95-7.93 (d, J=8.4 Hz, 2H), 6.37-6.30 (m, 1H), 6.17-6.13 (dd, J=16.8, 1.6 Hz, 1H), 5.66-5.63 (dd, J=10.4, 2.0 Hz, 1H), 4.52-4.51 (d, J=6.0 Hz, 2H), 2.46 (s, 3H). MS: $[MH]^+$ 361.1.

Example 1.145. Synthesis of (Z)-2-cyano-N,N-dimethyl-3-(8-(4-(trifluoromethyl)phenyl)imidazo[1,2-a]pyrazin-6-yl)acrylamide (I-242

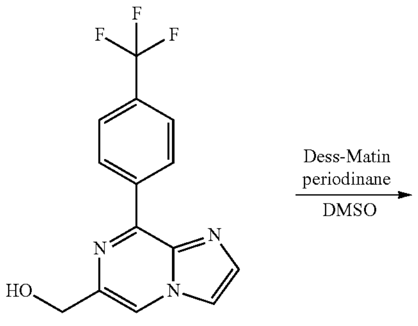

I-243

-continued

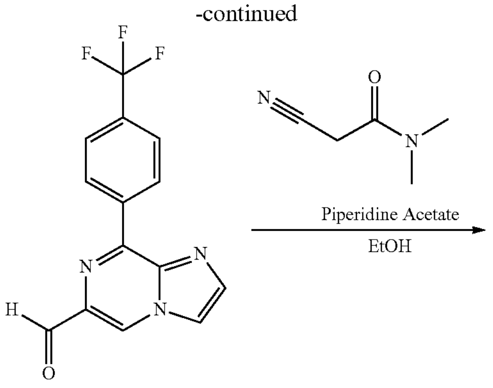

X-1491A3

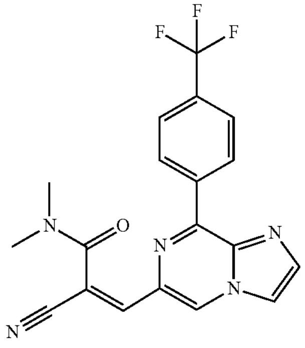

I-242

8-(4-(Trifluoromethyl)phenyl)imidazo[1,2-a]pyrazine-6-carbaldehyde (X-1491A3). To a stirred solution of (8-(4-(trifluoromethyl)phenyl)imidazo[1,2-a]pyrazin-6-yl) methanol (I-243) (1.0 g, 3.41 mmol) in DMSO (10 mL) were added Dess-Martin periodinane (2.89 g, 6.82 mmol) at 0° C. and the resulting reaction mixture was stirred at room temperature for 2 h. The reaction mixture was quenched with $NH_4C1$ solution (100 mL) and was extracted with ethyl acetate (100 mL×3). The combined organic extracts were washed with brine (100 mL), dried over anhydrous $Na_2SO_4$ and concentrated under reduce pressure. The crude was purified by silica gel column chromatography, using ethyl acetate-hexane=0:1→1:9 as gradient, to afford 8-(4-(trifluoromethyl)phenyl)imidazo[1,2-a]pyrazine-6-carbaldehyde (X-1491A3) (0.800 g, 81%) as an off white solid. MS: $[MH]^+$ 291.96.

(Z)-2-Cyano-N,N-dimethyl-3-(8-(4-(trifluoromethyl)phenyl)imidazo[1,2-a]pyrazin-6-yl)acrylamide (I-242). To a stirred solution of 8-(4-(trifluoromethyl)phenyl)imidazo[1,2-a]pyrazine-6-carbaldehyde (X-1491A3) (0.350 g, 1.20 mmol) in EtOH (4 mL) were added 2-cyano-N,N-dimethylacetamide (0.269 g, 2.40 mmol) and piperidine acetate (0.2 ML) at room temperature and the resulting mixture was heated at 60° C. for 1.5 h. The reaction mixture was quenched by water (70 mL) and was extracted with ethyl acetate (50 mL×3). Collected organic extracts were dried over anhydrous $Na_2SO_4$ and concentrated under reduced pressure, isolated crude was purified by reverse phase (C-18) silica gel column chromatography using acetonitrile-water=0:1→1:1 as gradient, to afford (Z)-2-cyano-N,N-dimethyl-3-(8-(4-(trifluoromethyl)phenyl)imidazo[1,2-a]pyrazin-6-yl)acrylamide (I-242) (0.045 g, 31%) as an off-white solid. $^1H$ NMR (400 MHz, DMSO-$d_6$) δ 8.99 (s, 1H), 8.88-8.86 (d, J=8.0 Hz, 2H), 8.42-8.42 (d, J=1.2 Hz, 1H), 7.99-7.98 (m, 3H), 7.78 (s, 1H), 2.98 (s, 3H), 2.89 (s, 3H). MS: $[MH]^+$ 386.0.

Example 1.146. Synthesis of (8-(4-(Trifluoromethyl)phenyl)imidazo[1,2-a]pyrazin-6-yl)methanol (I-243)

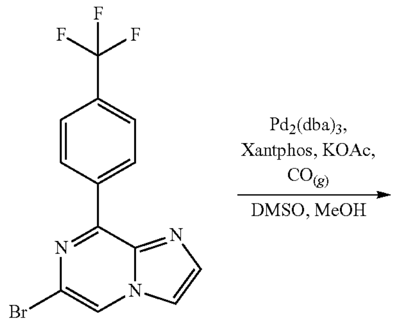

X-1269A2

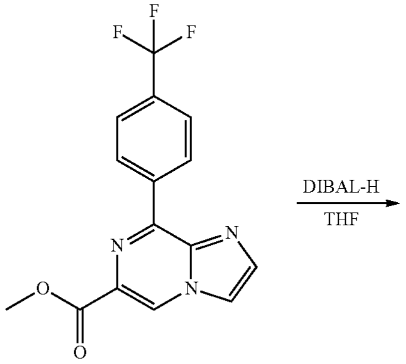

X-1432A1

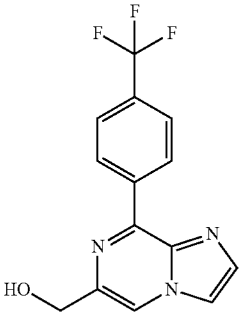

I-243

Methyl 8-(4-(trifluoromethyl)phenyl)imidazo[1,2-a]pyrazine-6-carboxylate (X-1432A1). To a stirred solution of 6-bromo-8-(4-(trifluoromethyl)phenyl)imidazo[1,2-a]pyrazine (X-1269A2) (10.0 g, 29.32 mmol) in DMSO-MeOH (3:7, 100 mL) were added potassium acetate (8.62 g, 87.97 mmol) at room temperature. The reaction mixture was degassed (by purging with nitrogen) for 20 min followed by the addition of $Pd_2(dba)_3$ (2.68 g, 2.93 mmol) and xanthphos (1.69 g, 2.93 mmol) and the resulting mixture was subjected to caboxylation under carbon monoxide atmosphere in a Parr Autoclave at 85° C. for 2 h. Reaction mixture was cooled to room temperature, reaction mixture was filtered through celite, diluted with water (300 mL) and was extracted with ethyl acetate (200 mL×3). Combined organic extracts were washed with brine (300 mL), dried over anhydrous $Na_2SO_4$ and concentrated under reduce pressure. The crude was purified by silica gel column chromatography, using ethyl acetate-hexane=0:1→2:8 as gradient, to afford methyl 8-(4-(trifluoromethyl)phenyl)imidazo[1,2-a]pyrazine-6-carboxylate (X-1432A1) (6.5 g, 69%) as a brown solid. MS: $[MH]^+$321.9.

(8-(4-(Trifluoromethyl)phenyl)imidazo[1,2-a]pyrazin-6-yl)methanol (I-243). To a stirred solution of methyl 8-(4-(trifluoromethyl)phenyl)imidazo[1,2-a]pyrazine-6-carboxylate (X-1432A1) (0.300 g, 0.93 mmol) in THE (5 mL) at −78° C. was added DIBAL-H (0.663 g, 4.67 mmol) dropwise under nitrogen. The mixture was then stirred at same temperature for 1 h. The mixture was quenched aqueous solution of saturated $NH_4Cl$ (20 mL) and extracted with ethyl acetate (30 mL×2). The combined organic layers were washed with brine, dried over $Na_2SO_4$, filtered and concentrated in vacuo. The crude product was purified flash column chromatography, using methanol-dichloromethane=0:1→1:19 as gradient, to afford (8-(4-(trifluoromethyl)phenyl)imidazo[1,2-a]pyrazin-6-yl)methanol (I-243) (0.120 g, 43%) as an off-white solid. $^1H$ NMR (400 MHz, DMSO-$d_6$) δ 9.01-8.99 (d, J=8.0 Hz, 2H), 8.63 (s, 1H), 8.29 (s, 1H), 7.95-7.93 (d, J=8.0 Hz, 2H), 7.90 (s, 1H), 5.63-5.60 (t, J=5.6 Hz, 1H), 4.72-4.70 (d, J=5.6 Hz, 2H), MS: $[MH]^+$ 294.1.

Example 1.147. Synthesis of (1-(8-(4-(Trifluoromethyl)phenyl)imidazo[1,2-a]pyrazin-6-yl)pyrrolidin-2-yl)methanol (I-244)

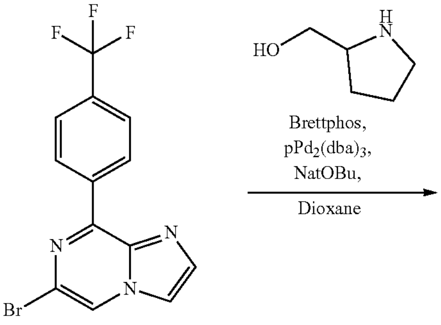

X-1269A2

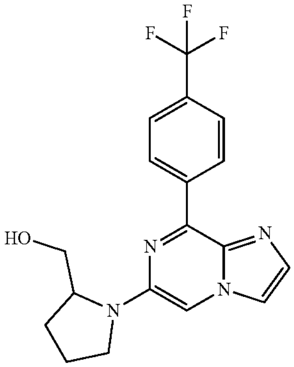

I-244

To a stirred solution of 6-bromo-8-(4-(trifluoromethyl)phenyl)imidazo[1,2-a]pyrazine (X-1269A2) (0.300 g, 0.87 mmol) in 1,4-Dioxane (15 mL) were added pyrrolidin-2-ylmethanol (0.266 g, 2.61 mmol), t-BuONa (0.253 g, 2.52 mmol) and Brettphos (0.094 g, 0.17 mmol) sequentially at room temperature under nitrogen. The reaction mixture was degassed (purging with nitrogen) for 20 min followed by the addition of $Pd_2(dba)_3$ (0.080 g, 0.08 mmol) and the resulting mixture was heated at 120° C. for 3 h. Reaction mixture was cooled to room temperature, diluted with water (100 mL) and was extracted with ethyl acetate (100 mL×3). Combined organic extracts were dried over anhydrous $Na_2SO_4$ and concentrated under reduce pressure. Obtained crude product was purified by silica gel column chromatography, using ethyl acetate-hexane=0:1→3:7 as gradient, to afford (1-(8-(4-(trifluoromethyl)phenyl)imidazo[1,2-a]pyrazin-6-yl)pyrrolidin-2-yl)methanol (I-244) (0.020 g, 6%) as a yellow solid. $^1$H NMR (400 MHz, DMSO-$d_6$) δ 9.06-9.04 (d, J=8.4 Hz, 2H), 8.04 (s, 1H), 7.93-7.91 (d, J=8.4 Hz, 2H), 7.81 (s, 1H), 7.75 (s, 1H), 4.79-4.76 (t, J=5.6 Hz, 1H), 4.07-4.06 (m, 1H), 3.73-3.69 (m, 1H), 3.46-3.43 (m, 1H), 3.37-3-33 (m, 1H; merged with DMSO-d6 moisture peak), 3.19-3.18 (m, 1H), 2.07-2.05 (m, 2H), 1.97-1.91 (m, 2H). MS: $[NM]^+$ 363.1.

Example 1.148. Synthesis of 1-(3-(8-(4-(Trifluoromethyl)phenyl)imidazo[1,2-a]pyrazin-6-yl)azetidin-1-yl)prop-2-en-1-one (I-245)

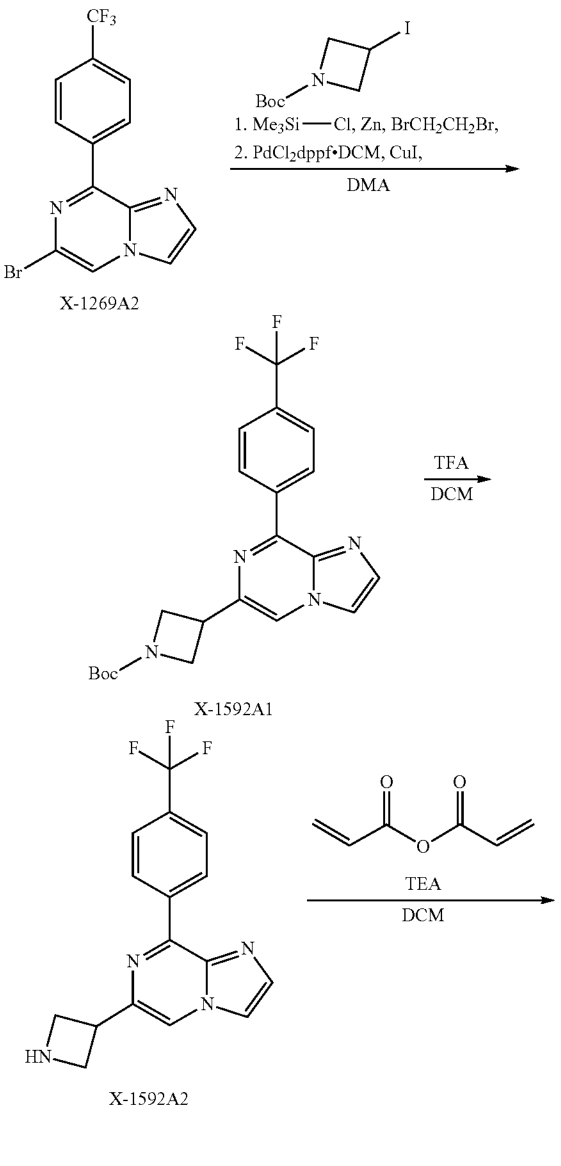

X-1269A2
X-1592A1
X-1592A2

-continued

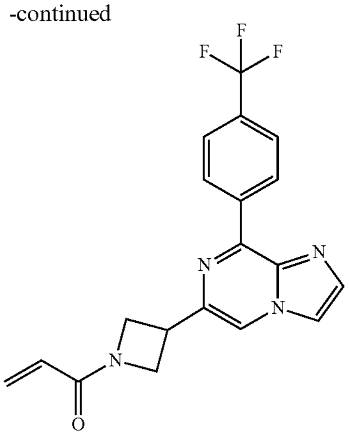
I-245 tert-Butyl 3-(8-(4-(trifluoromethyl)phenyl)imidazo[1,2-a]pyrazin-6-yl)azetidine-1-carboxylate (X-1592A1). To a stirred solution of Zn dust (0.76 g, 11.7 mmol) in DMA (5 mL) were added 1,2-Dibromoethane (0.050 mL, 8.82 mmol) and TMS-Cl (0.095 g, 0.88 mmol) at room temperature and stirred the reaction mixture at same temperature for 30 min. Tert-butyl 3-iodoazetidine-1-carboxylate (2.48 g, 8.82 mmol) was added at room temperature and stirred at same temperature for another 1 h. In an another reaction vessel, a stirred solution of 6-bromo-8-(4-(trifluoromethyl)phenyl)imidazo[1,2-a]pyrazine (X-1269A2) (1.0 g, 2.93 mmol) in DMA (10 mL) was added CuI (0.06 g, 0.35 mmol) at room temperature under nitrogen atmosphere and the reaction mixture was degassed (purged with nitrogen) for 10 min. $PdCl_2$(dppf).DCM (0.14 g, 0.17 mmol), and above solution was added sequentially into the reaction mixture. The resulting reaction mixture was heated at 80° C. for 1 h. Cooling to room temperature, reaction mixture was diluted with cold water (50 mL) and was extracted with ethyl acetate (100 mL×3). Combined organic extracts were washed with brine (50 mL), dried over anhydrous $Na_2SO_4$ and concentrated under reduced pressure. Obtained crude product was purified by silica gel column chromatography, using ethyl acetate-hexane: 1:9→2:8 as a gradient, to afford tert-butyl 3-(8-(4-(trifluoromethyl)phenyl)imidazo[1,2-a]pyrazin-6-yl)azetidine-1-carboxylate (X-1592A1) (0.550 g, 46%) as an brown solid. MS: $[MH]^+$ 419.01

6-(Azetidin-3-yl)-8-(4-(trifluoromethyl)phenyl)imidazo[1,2-a]pyrazine (X-1592A2). To a stirred solution of tert-butyl 3-(8-(4-(trifluoromethyl)phenyl)imidazo[1,2-a]pyrazin-6-yl)azetidine-1-carboxylate (X-1592A1) (0.250 g, 0.59 mmol) in DCM (6 mL) was added Trifluoroacetic acid (0.45 mL, 0.59 mmol) at 0° C. under nitrogen atmosphere, resulting reaction mixture was stirred at room temperature for 6 h. Reaction mixture was concentrated under reduced pressure. Obtained crude was triturated with n-pentane (15 mL×3), dried under reduced pressure, to afford 6-(azetidin-3-yl)-8-(4-(trifluoromethyl)phenyl)imidazo[1,2-a]pyrazine (X-1592A2) (0.130 g, 68%) as a brown solid. MS: $[MH]^+$ 318.94

1-(3-(8-(4-(trifluoromethyl)phenyl)imidazo[1,2-a]pyrazin-6-yl)azetidin-1-yl)prop-2-en-1-one (I-245). To a stirred solution of 6-(azetidin-3-yl)-8-(4-(trifluoromethyl)phenyl)imidazo[1,2-a]pyrazine (X-1592A2) (0.100 g, 0.31 mmol) in DCM (5 mL) were added triethyl amine (0.12 mL, 0.94 mmol) at 0° C. under nitrogen atmosphere and stirred for 15 min at same temperature. Acrylic anhydride (0.059 g, 0.46 mmol) was added at 0° C. and the resulting reaction mixture was stirred at room temperature for 1 h. Reaction mixture was diluted with water (30 mL) and was extracted with dichloromethane (50 mL×2). Combined organic extracts were dried over anhydrous $Na_2SO_4$ and concentrated in vacuo. Obtained crude product was purified by silica gel column chromatography, using methanol-dichloromethane: 0:1→4 0.5:9.5 as a gradient, to afford 1-(3-(8-(4-(trifluoromethyl)phenyl)imidazo[1,2-a]pyrazin-6-yl)azetidin-1-yl)prop-2-en-1-one (I-245) (0.102 g, 87%) as a white solid. $^1H$ NMR (400 MHz, DMSO-$d_6$) δ 9.01-8.99 (d, J=8.4 Hz, 2H), 8.69 (s, 1H), 8.21 (s, 1H), 7.96-7.92 (d, J=8.4 Hz, 2H), 7.92 (s, 1H), 6.45-6.38 (m, 1H), 6.19-6.15 (dd, J=2.4, 17.2 Hz, 1H), 5.73-5.70 (dd, J=2.4, 10.4 Hz, 1H), 4.67-4.63 (t, J=8.8 Hz, 1H), 4.49-4.45 (t, J=6.0 Hz, 1H), 4.37-4.32 (t, J=9.2 Hz, 1H) 4.24-4.20 (m, 1H), 4.15-4.07 (m, 1H). MS: $[MH]^+$ 373.0

Example 1.149. Synthesis of N-((3-(trifluoromethyl)-8-(4-(trifluoromethyl)phenyl)imidazo[1,2-a]pyrazin-6-yl)methyl)acrylamide (I-246)

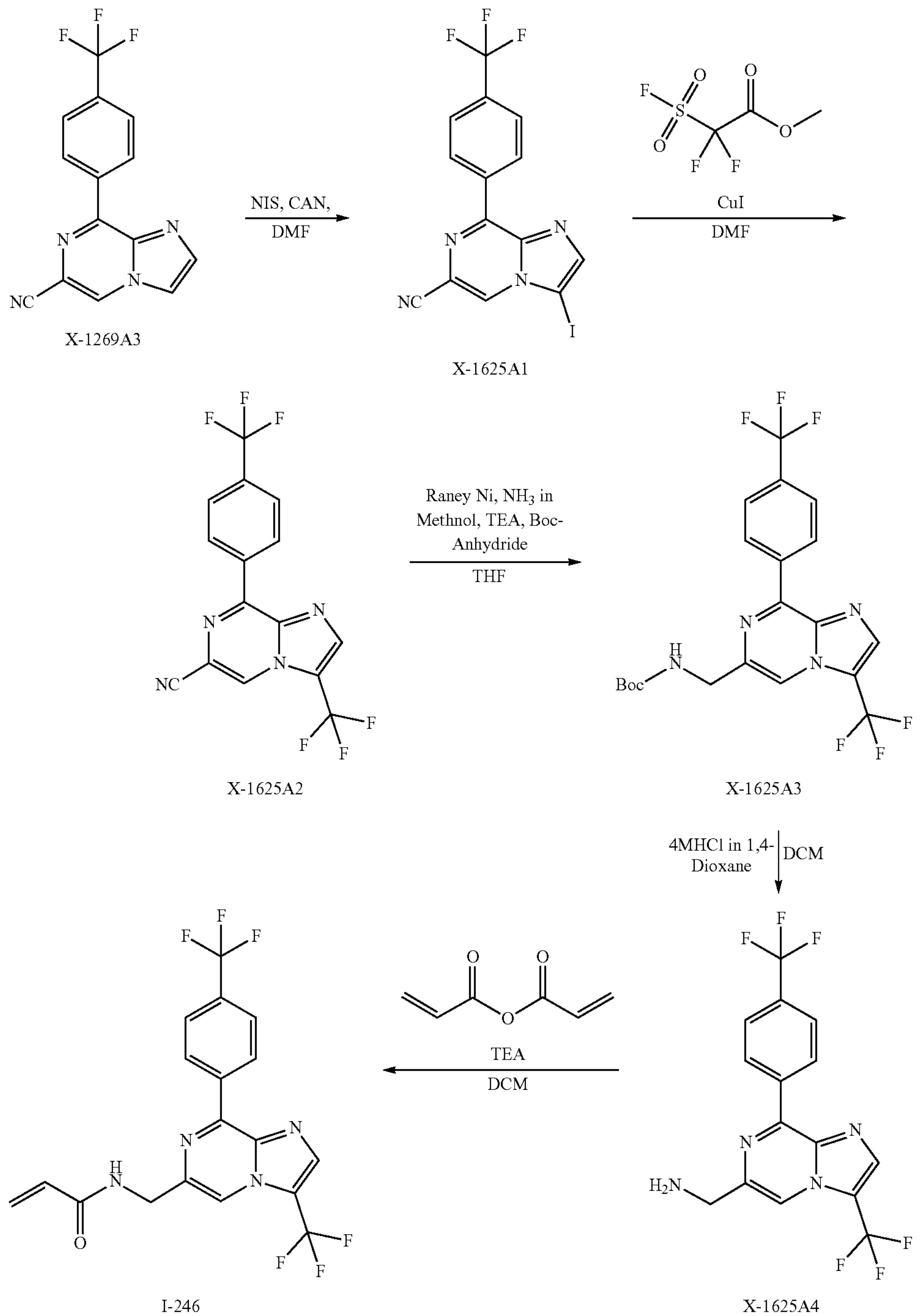

X-1269A3

X-1625A1

X-1625A2

X-1625A3

X-1625A4

I-246

3-iodo-8-(4-(trifluoromethyl)phenyl)imidazo[1,2-a]pyrazine-6-carbonitrile (X-1625A1). A stirred solution of 8-(4-(trifluoromethyl)phenyl)imidazo[1,2-a]pyrazine-6-carbonitrile (X-1269A3) (1.8 g, 6.25 mmol) in DMF (40 mL), were added N-iodosuccinamide (2.89 g, 12.4 mmol) and Ceric Ammonium Nitrate (0.680 g, 1.25 mmol) at room temperature and stirred at 40° C. for 16 h. Reaction mixture was cooled to room temperature, poured in water (200 mL) and was extracted with ethyl acetate (200 mL×3). Combined organic extracts were washed with brine (200 mL), dried over anhydrous $Na_2SO_4$ and concentrated under reduced pressure. Obtained crude product was purified by silica gel column chromatography, using ethyl acetate-hexane: 0:1→1:9 as a gradient, to afford 3-iodo-8-(4-(trifluoromethyl)phenyl)imidazo[1,2-a]pyrazine-6-carbonitrile (X-1625A1) (2.0 g, 69%) as a brown solid. MS: $[MH]^+$ 415.29

3-(trifluoromethyl)-8-(4-(trifluoromethyl)phenyl)imidazo[1,2-a]pyrazine-6-carbonitrile (X-1625A2). To a stirred solution of 3-iodo-8-(4-(trifluoromethyl)phenyl)imidazo[1,2-a]pyrazine-6-carbonitrile (X-1625A1) (2.0 g, 4.83 mmol) in DMF (30 mL) were added CuI (3.34 g, 17.54 mmol) and methyl 2,2-difluoro-2-(fluorosulfonyl)acetate (6.0 g, 31.21 mmol) at room temperature and stirred at 80° C. for 16 h. Reaction mixture was cooled to room temperature, filtered over celite bed and washed with ethyl acetate (200 mL×3), filtrate was collected and washed with water (200 mL×2). Combined organic extracts were washed with brine (200 mL), dried over anhydrous $Na_2SO_4$ and concentrated under reduced pressure. Obtained crude mass was purified by silica gel column chromatography, using ethyl acetate-hexane: 0:1→1:9 as a gradient, to afford 3-(trifluoromethyl)-8-(4-(trifluoromethyl)phenyl)imidazo[1,2-a]pyrazine-6-carbonitrile (X-1625A2) (1.2 g, 69%) as an light brown solid. MS: $[MH]^+$ 357.25 tert-butyl ((3-(trifluoromethyl)-8-(4-(trifluoromethyl)phenyl)imidazo[1,2-a]pyrazin-6-yl)methyl)carbamate (X-1625A3). To a stirred solution of 3-(trifluoromethyl)-8-(4-(trifluoromethyl)phenyl)imidazo[1,2-a]pyrazine-6-carbonitrile (X-1625A2) (1.1 g, 3.08 mmol) in THE (10 mL) were added Di-tert-butyl bicarbonate (1.7 g, 7.79 mmol), TEA (0.94 g, 9.36 mmol), Raney Nickel (~1.1 g) and ammonia in methanol (2.0 mL) at room temperature the resulting reaction mixture was hydrogenated in Parr Autoclave at 70° C. under 200 psi pressure for 16 h. Cooled reaction mixture to room temperature, filtered over celite bed, washed celite bed with methanol (50 mL×3) and collected filtrates were concentrated under reduced pressure. Obtained crude mass was purified by silica gel column chromatography, using ethyl acetate-hexane=2:8→3:7 as a gradient, to afford tert-butyl ((3-(trifluoromethyl)-8-(4-(trifluoromethyl)phenyl)imidazo[1,2-a]pyrazin-6-yl)methyl)carbamate (X-1625A3) (0.600 g, crude) as a brown sticky solid. Which was used to next step without further purification. MS: $[MH]^+$ 461.0

(3-(trifluoromethyl)-8-(4-(trifluoromethyl)phenyl)imidazo[1,2-a]pyrazin-6-yl)methanamine (X-1625A4). To a solution of tert-butyl ((3-(trifluoromethyl)-8-(4-(trifluoromethyl)phenyl)imidazo[1,2-a]pyrazin-6-yl)methyl)carbamate (X-1625A3) (0.550 g, 1.38 mmol) in DCM (4 mL) was added 4M HCl in 1,4-dioxane (3.0 mL) at 0° C. under nitrogen and the resulting reaction mixture was stirred at room temperature for 3 h. Reaction mixture was concentrated under reduced pressure. Obtained crude was triturated with diethyl ether (10 mL×3), dried over reduced pressure, to afford (3-(trifluoromethyl)-8-(4-(trifluoromethyl)phenyl)imidazo[1,2-a]pyrazin-6-yl)methanamine (X-1625A4) (0.400 g, crude) as a brown solid. MS: $[MH]^+$ 361.0

N-((3-(trifluoromethyl)-8-(4-(trifluoromethyl)phenyl)imidazo[1,2-a]pyrazin-6-yl)methyl)acrylamide (I-246). To a stirred solution of (3-(trifluoromethyl)-8-(4-(trifluoromethyl)phenyl)imidazo[1,2-a]pyrazin-6-yl)methanamine (X-1625A4) (0.400 g, 1.01 mmol) in DCM (7 mL) was added TEA (0.410 g, 4.05 mmol) at 0° C. under nitrogen atmosphere and stirred for 15 min at same temperature. Acrylic anhydride (0.140 g, 1.1 mmol) was added at 0° C. and the resulting reaction mixture was stirred at room temperature for 1 h. Reaction mixture was diluted with water (100 mL) and was extracted with DCM (50 mL×3). Combined organic extracts were dried over anhydrous $Na_2SO_4$ and concentrated under reduced pressure, Obtained crude mass was purified by (C-18) silica gel column chromatography using acetonitrile:water=0:1→4:6 as a gradient, to afford N-((3-(trifluoromethyl)-8-(4-(trifluoromethyl)phenyl)imidazo[1,2-a]pyrazin-6-yl)methyl)acrylamide (I-246) (0.150 g, 35%) as an off-white. $^1H$ NMR (400 MHz, DMSO-$d_6$) δ: 8.93-8.91 (d, J=8.0 Hz, 2H), 8.84-8.81 (t, J=5.6 Hz, 1H), 8.53 (d, J=3.2 Hz, 2H), 8.00-7.98 (d, J=8.4 Hz, 2H), 6.37-6.30 (m, 1H), 6.18-6.13 (dd, J=2.0, 17.2 Hz, 1H), 5.68-5.65 (dd, J=2.4, 10.4 Hz, 1H), 4.65-4.64 (d, J=6.0 Hz, 2H). MS: [MH]+415.01

Example 1.150. Synthesis of N-((2-(trifluoromethyl)-8-(4-(trifluoromethyl)phenyl)imidazo[1,2-a]pyrazin-6-yl)methyl)acrylamide (I-247

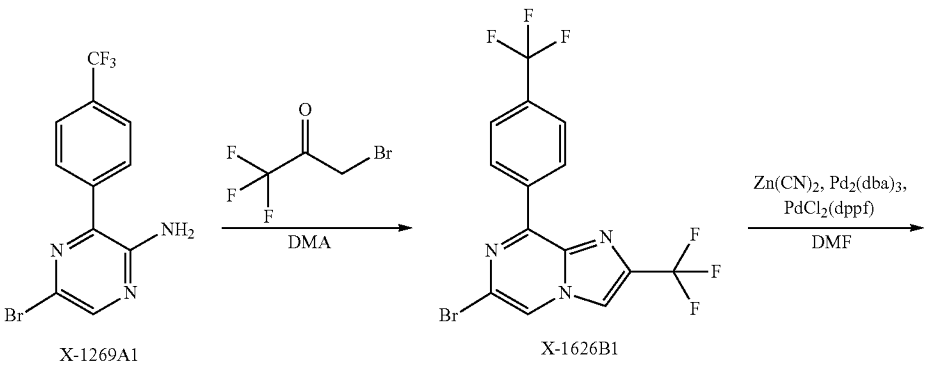

X-1269A1

X-1626B1

-continued

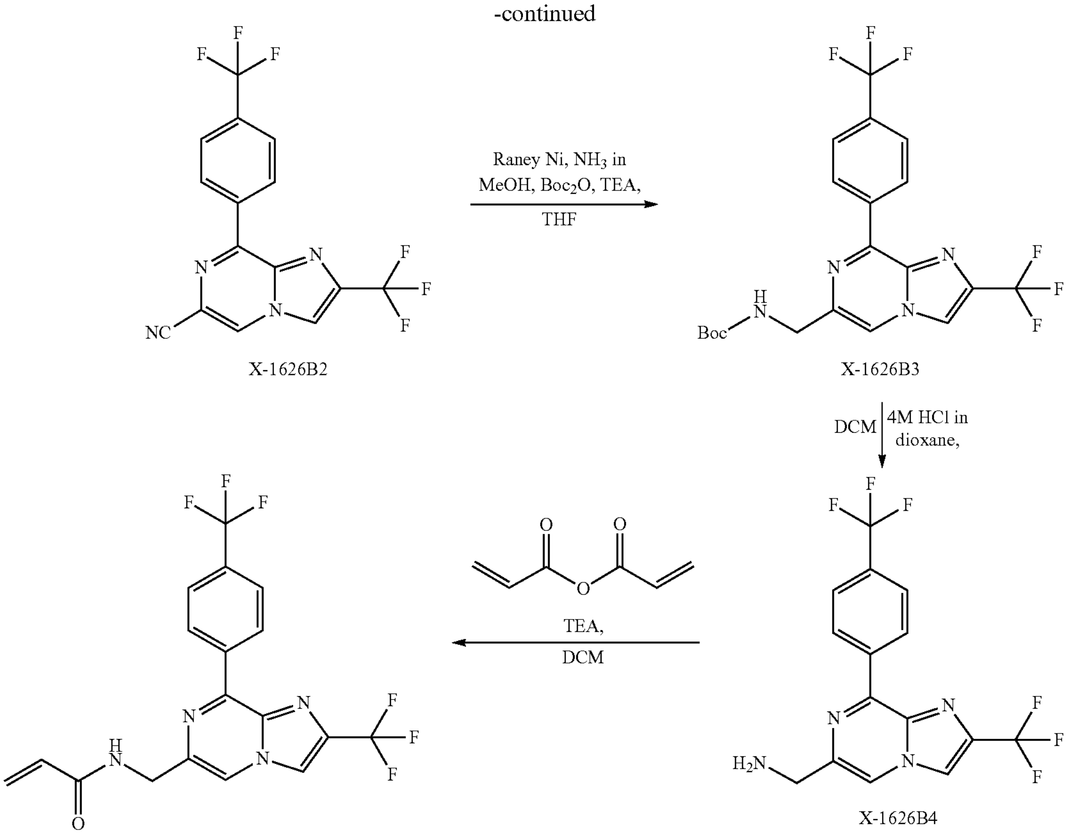

X-1626B2

X-1626B3

X-1626B4

I-247

6-Bromo-2-(trifluoromethyl)-8-(4-(trifluoromethyl)phenyl)imidazo[1,2-a]pyrazine (X-1626B1). This intermediate was prepared in a manner analogous to the procedures described for N-((2-methyl-8-(4-(trifluoromethyl)phenyl)imidazo[1,2-a]pyrazin-6-yl)methyl)acrylamide (I-241). (1.1 g, 57%) as a yellow solid. $^1$H NMR (400 MHz, DMSO-$d_6$) δ 9.05 (s, 1H), 8.83-8.81 (d, J=8.4 Hz, 2H), 8.75 (s, 1H), 8.02-8.00 (d, J=8.4 Hz, 2H 2-(trifluoromethyl)-8-(4-(trifluoromethyl)phenyl)imidazo[1,2-a]pyrazine-6-carbonitrile (X-1626B2). This intermediate was prepared in a manner analogous to the procedures described for N-((2-methyl-8-(4-(trifluoromethyl)phenyl)imidazo[1,2-a]pyrazin-6-yl)methyl)acrylamide (I-241) (0.860 g, 89%) as a brown solid. MS: $[MH]^+$ 357.32.

tert-Butyl ((2-(trifluoromethyl)-8-(4-(trifluoromethyl)phenyl)imidazo[1,2-a]pyrazin-6-yl)methyl)carbamate (X-1626B3). This intermediate was prepared in a manner analogous to the procedures described for N-((3-(trifluoromethyl)-8-(4-(trifluoromethyl)phenyl)imidazo[1,2-a]pyrazin-6-yl)methyl)acrylamide (I-246). (0.66 g, quant.; crude) as a yellow solid. MS: $[MH]^+$ 461.08.

(2-(Trifluoromethyl)-8-(4-(trifluoromethyl)phenyl)imidazo[1,2-a]pyrazin-6-yl)methanamine (X-1626B4). This intermediate was prepared in a manner analogous to the procedures described for N-((3-(trifluoromethyl)-8-(4-(trifluoromethyl)phenyl)imidazo[1,2-a]pyrazin-6-yl)methyl)acrylamide (I-246). (0.370 g, 72%) as an off-white solid. MS: $[MH]^+$ 361.1.

N-((2-(trifluoromethyl)-8-(4-(trifluoromethyl)phenyl)imidazo[1,2-a]pyrazin-6-yl)methyl)acrylamide (I-247). This intermediate was prepared in a manner analogous to the procedures described for N-((3-(trifluoromethyl)-8-(4-(trifluoromethyl)phenyl)imidazo[1,2-a]pyrazin-6-yl)methyl)acrylamide (I-246)

N-((2-(trifluoromethyl)-8-(4-(trifluoromethyl)phenyl)imidazo[1,2-a]pyrazin-6-yl)methyl)acrylamide (I-247). (0.130 g, 30%) as a white solid. $^1$H NMR (400 MHz, DMSO-$d_6$) δ8.88-8.86 (m, 4H), 8.58 (s, 1H), 8.01-7.99 (d, J=8.4 Hz, 2H), 6.38-6.31 (m, 1H), 6.19-6.14 (dd, J=2.0, 17.2 Hz, 1H), 5.69-5.66 (dd, J=10.4, 2.0 Hz, 1H), 4.58-4.57 (d, J=5.6 Hz, 2H). MS: $[MH]^+$ 415.1.

Example 1.151. Synthesis of (E)-4-fluoro-N-((2-methyl-8-(4-(trifluoromethyl)phenyl)imidazo[1,2-a]pyrazin-6-yl)methyl)but-2-enamide (I-248)

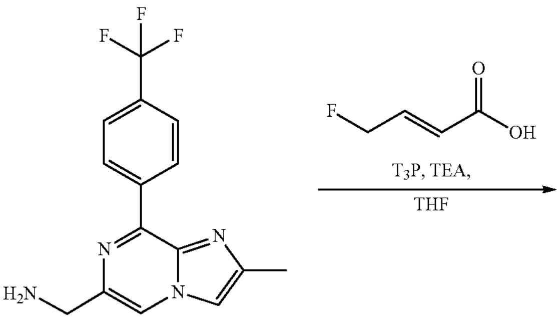

X-1489A3

-continued

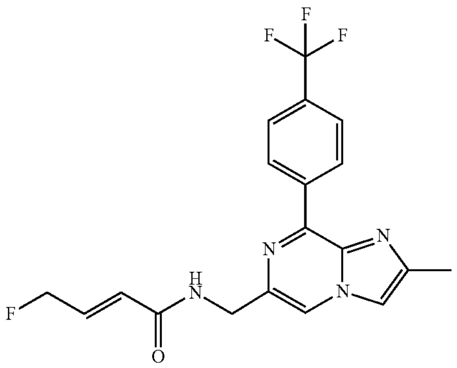

I-248

-continued

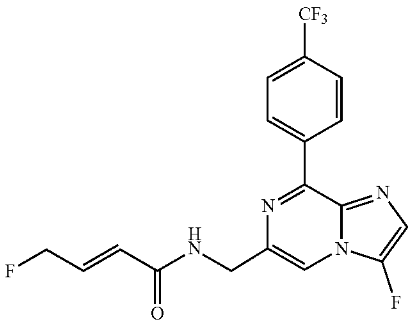

I-249

To a stirred solution of (2-methyl-8-(4-(trifluoromethyl)phenyl)imidazo[1,2-a]pyrazin-6-yl)methanamine (X-1489A3) (0.294 g, 0.96 mmol) in THE (5.0 mL) were added (E)-4-fluorobut-2-enoic acid (0.10 g, 0.96 mmol), triethylamine (0.1 mL) and propylphosphonic anhydride (0.360 g, 1.15 mmol) sequentially at 0° C. under nitrogen and the resulting mixture was stirred at room temperature for 1 h. Reaction mixture was poured into ice-water (50 mL) and was extracted with ethyl acetate (20 mL×3). Combined organic extracts were washed with brine (30 mL), dried over anhydrous $Na_2SO_4$ and concentrated under reduced pressure. The resulting crude was purified by silica gel column chromatography, using ethyl acetate-hexane=0:1→3:2 as gradient, to afford (E)-4-fluoro-N-((2-methyl-8-(4-(trifluoromethyl)phenyl)imidazo[1,2-a]pyrazin-6-yl)methyl)but-2-enamide (I-248) (0.070 g, 48%) as an off-white solid. $^1H$ NMR (400 MHz, DMSO-$d_6$) δ 8.99-8.97 (d, J=8.4 Hz, 2H), 8.84-8.81 (t, J=5.6 Hz, 1H), 8.50 (s, 1H), 8.04 (s, 1H), 7.96-7.94 (d, J=8.4 Hz, 1H), 6.81-6.71 (m, 1H), 6.28-6.24 (d, J=16.0 Hz, 2H), 5.18-5.06 (d, J=6.0 Hz, 2H), 4.53-4.51 (d, J=5.6 Hz, 2H), 2.49 (3H, merged with DMSO-$d_6$). MS: $[MH]^+$ 393.1.

Example 1.152. Synthesis of (E)-4-Fluoro-N-((3-fluoro-8-(4-(trifluoromethyl)phenyl)imidazo[1,2-a]pyrazin-6-yl)methyl)but-2-enamide (I-249)

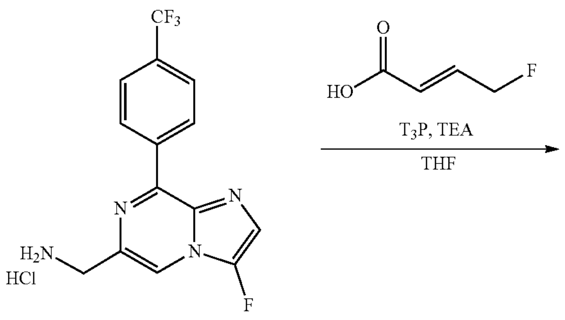

X-1479A2

To a stirred solution of (3-fluoro-8-(4-(trifluoromethyl)phenyl)imidazo[1,2-a]pyrazin-6-yl)methanamine hydrochloride (X-1479A2) (2.38 g, 7.69 mmol) in THE (20 mL) were added (E)-4-fluorobut-2-enoic acid (2.0 g, 19.23 mmol), triethylamine (5.82 g, 57.6 mmol) and propylphosphonic anhydride (9.17 g, 28.8 mmol) sequentially at 0° C. under nitrogen and the resulting mixture was stirred at room temperature for 1 h. Reaction mixture was poured into ice-water (600 mL) and was extracted with ethyl acetate (100 mL×3), dried over anhydrous $Na_2SO_4$ and concentrated under reduced pressure. Isolated crude was combined with an identical prepared one more batch (1.0 g) and the combined crude product was purified reverse phase (C-18) silica gel column chromatography, using acetonitrile-water=0:143:7 as gradient, to afford (E)-4-fluoro-N-((2-methyl-8-(4-(trifluoromethyl)phenyl)imidazo[1,2-a]pyrazin-6-yl)methyl)but-2-enamide (I-249) (1.9 g, 50%) as an off-white solid. $^1H$ NMR (400 MHz, DMSO-$d_6$) δ 8.96-8.94 (d, J=8.0 Hz, 2H), 8.81-8.78 (t, J=5.60 Hz, 1H), 8.36 (s, 1H), 7.98-7.96 (d, J=8.4 Hz, 2H), 7.78-7.76 (d, J=7.2 Hz, 1H), 6.83-6.71 (m, 1H), 6.31-6.26 (m, 1H), 5.19-5.18 (m, 1H), 5.08-5.06 (m, 1H), 4.58-4.57 (d, J=5.60 Hz, 2H). MS: $[MH]^+$397.01.

Example 1.153. Synthesis of N-(2-(8-(4-(trifluoromethyl)phenyl)imidazo[1,2-a]pyrazin-6-yl)allyl)acrylamide (I-250)

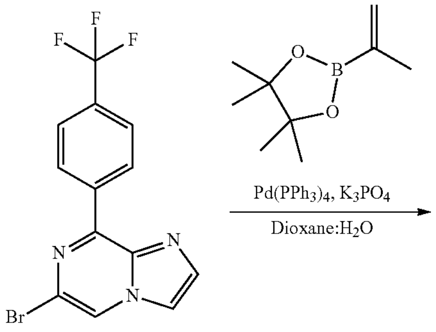

X-1269A2

-continued

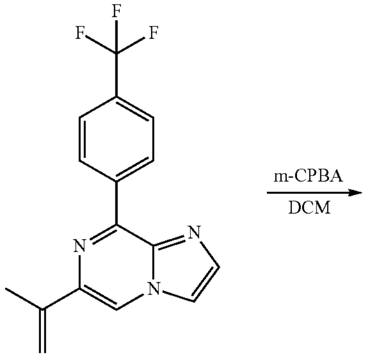

X-1593B1

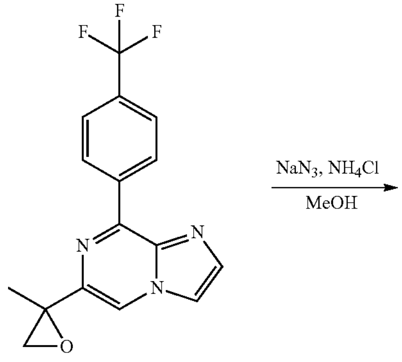

X-1593B2

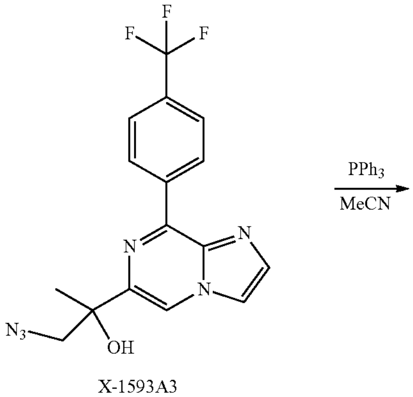

X-1593A3

-continued

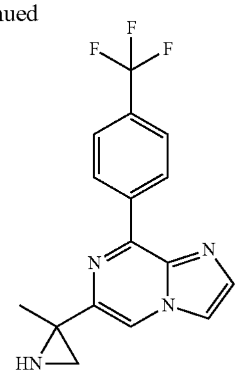

X-1593A4

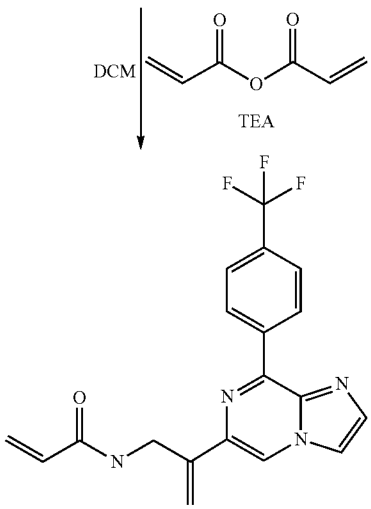

I-250

6-(Prop-1-en-2-yl)-8-(4-(trifluoromethyl)phenyl)imidazo[1,2-a]pyrazine (X-1593B1). To a stirred solution of 6-bromo-8-(4-(trifluoromethyl)phenyl)imidazo[1,2-a]pyrazine (X-1269A2) (3.00 g, 8.31 mmol) in a mixture 1,4-dioxane:$H_2O$ (3:1, 40 mL) were added 4,4,5,5-tetramethyl-2-(prop-1-en-2-yl)-1,3,2-dioxaborolane (2.79 g, 16.62 mmol), potassium phosphate (4.40 g, 20.77 mmol) at room temperature. The reaction mixture was degassed (purging with nitrogen) for 20 min followed by addition of $Pd(PPh_3)_4$ (0.926 g, 0.83 mmol) and the reaction mixture was heated at 100° C. for 2.5 h. The reaction mixture was cooled to room temperature, diluted with water (150 mL) and was extracted with ethyl acetate (200 mL×3). The combined organic extracts were dried over anhydrous $Na_2SO_4$ and concentrated under reduce pressure. Obtained crude product was purified by silica gel column chromatography, using ethyl acetate-hexane 3:7→5:5 as a gradient, to afford 6-(prop-1-en-2-yl)-8-(4-(trifluoromethyl)phenyl)imidazo[1,2-a]pyrazine (X-1593B1) (2.4 g, 90%) as an white solid. MS: $[MH]^+$ 303.84

6-(2-Methyloxiran-2-yl)-8-(4-(trifluoromethyl)phenyl)imidazo[1,2-a]pyrazine (X-1593B2). To a stirred solution of 6-(prop-1-en-2-yl)-8-(4-(trifluoromethyl)phenyl)imidazo[1,2-a]pyrazine (X-1593B1) (1.9 g, 6.20 mmol) in DCM (25 mL) was added m-CPBA (1.40 g, 8.15 mmol) portion wise at 0° C. The resulting reaction mixture was stirred at 0° C. for 2 h. Reaction mixture was quenched with water (100 mL) and was extracted with DCM (200 mL×2). Collected organics were washed with saturated aqueous $NaHCO_3$ solution (150 mL), dried over anhydrous $Na_2SO_4$ and concentrated under reduced pressure. Obtained crude mass was purified by (C-18) silica gel column chromatography using acetonitrile:water=1:9→2:8 as a gradient, to afford 6-(2-methyloxiran-2-yl)-8-(4-(trifluoromethyl)phenyl)imidazo[1,2-a]pyrazine (X-1593B2) (0.900 g, 45%) as an off white solid. MS: $[MH]^+$ 320.16

1-Azido-2-(8-(4-(trifluoromethyl)phenyl)imidazo[1,2-a]pyrazin-6-yl)propan-2-ol (X-1593A3). To a stirred solution of 6-(2-methyloxiran-2-yl)-8-(4-(trifluoromethyl)phenyl)imidazo[1,2-a]pyrazine (X-1593B2) (0.500 g, 1.56 mmol) in MeOH (5 mL) were added ammonium chloride (0.107 g, 2.02 mmol) and sodium azide at room temperature under nitrogen the resulting mixture was stirred at 75° C. for 4 h. After cooling to room temperature, reaction mixture was poured into water (20 mL) and the resulting precipitate was collected by filtration. Obtained solid residue was washed with water (20 mL×4), dried under high vacuum. Obtained crude product was purified by silica gel column chromatography, using ethyl acetate-hexane=1:9→2:8 as a gradient, to afford 1-azido-2-(8-(4-(trifluoromethyl)phenyl)imidazo[1,2-a]pyrazin-6-yl)propan-2-ol (X-1593A3) (0.440 g, 78%) as a white solid. MS: $[MH]^+$ 362.85

6-(2-Methylaziridin-2-yl)-8-(4-(trifluoromethyl)phenyl)imidazo[1,2-a]pyrazine (X-1593A4). Two reaction of same scale were performed in parallel. To a stirred solution of 1-azido-2-(8-(4-(trifluoromethyl)phenyl)imidazo[1,2-a]pyrazin-6-yl)propan-2-ol (X-1593A3) (0.230 g, 0.63 mmol) in ACN (4 mL) was added triphenyl phosphine (0.665 g, 1.27 mmol) at room temperature under nitrogen and the resulting mixture was heated at 60° C. for 5 h. After cooling to room temperature, the reaction mixture was diluted with water (20 mL) and acidified (pH~2-3) with an aqueous solution of 1N HCl and was extracted with ethyl acetate (50 mL×2) to remove unwanted organic impurities. Aqueous part was basified (pH~7-8) with an aqueous solution of sodium bicarbonate and extracted with ethyl acetate (50 mL×2). The combined organic extracts were dried over anhydrous $Na_2SO_4$ and concentrated under reduce pressure, to afford to afford 6-(2-methylaziridin-2-yl)-8-(4-(trifluoromethyl)phenyl)imidazo[1,2-a]pyrazine (X-1593A4) (0.260 g, 68%) as an off-white solid. MS: $[MH]^+$ 318.59.

N-(2-(8-(4-(Trifluoromethyl)phenyl)imidazo[1,2-a]pyrazin-6-yl)allyl)acrylamide (I-250). To a stirred solution of 6-(2-methylaziridin-2-yl)-8-(4-(trifluoromethyl)phenyl)imidazo[1,2-a]pyrazine (X-1593A4) (0.150 g, 0.47 mmol) in DCM (4 mL) were added TEA (0.13 mL, 0.94 mmol) and Acrylic anhydride (0.152 g, 0.70 mmol) sequentially at 0° C. under nitrogen and the reaction mixture was stirred at room temperature for 30 min. The reaction mixture was diluted with water (20 mL) and was extracted with DCM (30 mL×2). Combined organic extracts were dried over anhydrous $Na_2SO_4$ and concentrated under reduced pressure. Obtained crude was mixed with the crude of an identically prepared batch of (0.110 g) and purified by prep HPLC using acetonitrile-Water and lyophilized, to afford N-(2-(8-(4-(trifluoromethyl)phenyl)imidazo[1,2-a]pyrazin-6-yl)allyl)acrylamide (I-250) (0.006 g, 1.9%) as a white solid. $^1$H NMR (400 MHz, DMSO-$d_6$) δ 9.08-9.06 (d, J=8.0 Hz, 2H), 8.91 (s, 1H), 8.50-8.49 (t, J=8.0 Hz, 1H), 8.24 (s, 1H), 7.97-7.95 (d, J=8.4 Hz, 2H), 7.93 (s, 1H), 6.36-6.29 (m, 1H), 6.20 (s, 1H), 6.18-6.13 (dd, J=2.0 & 17.2 Hz, 1H), 5.65-5.62 (dd, J=2.0 & 10.0 Hz, 1H), 5.42 (s, 1H), 4.40-4.38 (d, J=5.6 Hz, 2H). MS: $[MH]^+$ 373.33.

Example 1.154. Synthesis of N-(1-hydroxy-2-(8-(4-(trifluoromethyl)phenyl)imidazo[1,2-a]pyrazin-6-yl)propan-2-yl)acrylamide (I-251

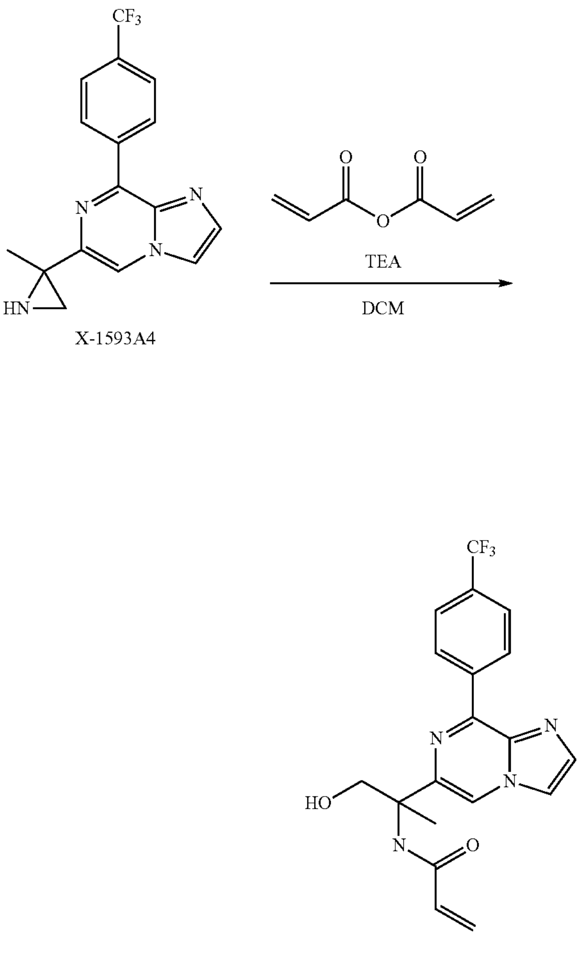

X-1593A4

I-251

To a stirred solution of 6-(2-methylaziridin-2-yl)-8-(4-(trifluoromethyl)phenyl)imidazo[1,2-a]pyrazine (X-1593A4) (0.150 g, 0.47 mmol) in DCM (4 mL) was added TEA (0.13 mL, 0.94 mmol) at 0° C. under nitrogen atmosphere and stirred for 15 min at same temperature. Acrylic anhydride (0.152 g, 0.70 mmol) was added at 0° C. and the resulting reaction mixture was stirred at room temperature for 1 h. Reaction mixture was diluted with water (30 mL) and was extracted with DCM (50 mL×2). Combined organic extracts were dried over anhydrous $Na_2SO_4$ and concentrated under reduced pressure, obtained crude was mixed with the crude of an identically prepared batch of (0.110 g). Obtained crude was purified by preparative HPLC, to afford N-(1-hydroxy-2-(8-(4-(trifluoromethyl)phenyl)imidazo[1,2-a]pyrazin-6-yl)propan-2-yl)acrylamide (I-251) (0.026 g, 8.1%) as a white solid. $^1$H NMR (400 MHz, DMSO-$d_6$) 9.05-9.03 (d, J=8.4 Hz, 2H), 8.73 (s, 1H), 8.32 (s, 1H), 7.97-7.95 (d, J=8.4 Hz, 3H), 7.90 (s, 1H), 6.29-6.22 (m, 1H), 6.04-5.99 (dd, J=2.4, 17.2 Hz, 1H), 5.75 (br. s, 1H), 5.53-5.50 (dd, J=2.4, 10.4 Hz, 1H), 3.80-3.75 (m, 1H), 3.60-3.55 (m, 1H), 1.56 (s, 3H). MS: $[MH]^+$391.33.

Example 1.155. Synthesis of N-(4-methyl-2-(5-(trifluoromethyl)pyridin-2-yl)quinolin-7-yl)acrylamide (I-252

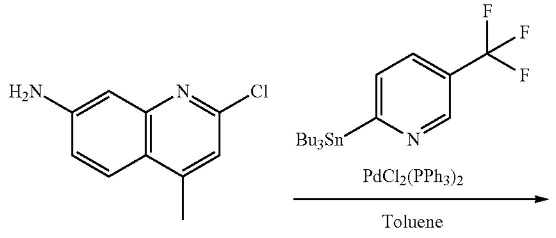

X-1283B4

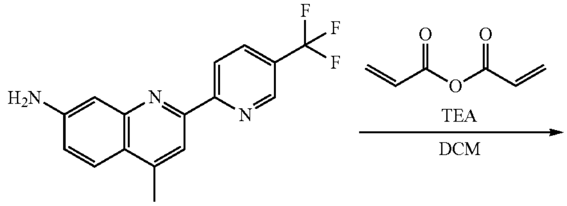

X-1471A1

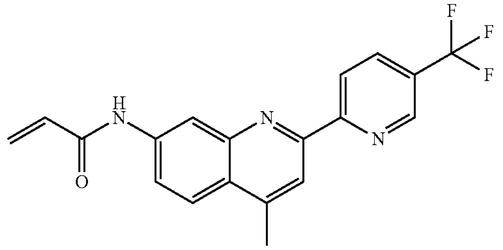

I-252

4-methyl-2-(5-(trifluoromethyl)pyridin-2-yl)quinolin-7-aminecarboxylate (X-1471A1) 2-(tributylstannyl)-5-(trifluoromethyl)pyridine (0.738 g, 1.69 mmol) was added to a stirred solution of 2-chloro-4-methylquinolin-7-amine (X-1283B4) (0.250 g, 1.30 mmol) in toluene (6 mL) at room temperature under nitrogen. Reaction mixture was degassed (purging with nitrogen) for 15 min followed by the addition of $PdCl_2(PPh_3)_2$ (0.273 g, 0.39 mmol) and the resulting mixture was heated at 120° C. for 16 h in seal tube. After cooling to room temperature, reaction mixture was diluted with water (50 mL) and was extracted by ethyl acetate (50 mL×3). Combined organic extracts were dried over anhydrous $Na_2SO_4$ and concentrated under reduced pressure. The crude product was purified by silica gel column chromatography, using ethyl acetate-Hexane=1:9→2:8 as gradient, to afford 4-methyl-2-(5-(trifluoromethyl)pyridin-2-yl)quinolin-7-aminecarboxylate (X-1471A1) (0.040 g, 10.16%) as an pale yellow solid. MS: $[MH]^+$ 304.0.

N-(4-methyl-2-(5-(trifluoromethyl)pyridin-2-yl)quinolin-7-yl)acrylamide (I-252). To a stirred solution of 4-methyl-2-(5-(trifluoromethyl)pyridin-2-yl)quinolin-7-aminecarboxylate (X-1471A1) (0.040 g, 0.1 mmol) in DCM (3 mL) were added triethylamine (0.05 mL, 0.34 mmol) and acryloyl anhydride (0.021 g, 0.17 mmol) sequentially at 0° C. under nitrogen and the reaction mixture was stirred at room temperature for 16 h. The reaction mixture was diluted with water (20 mL) and was extracted with DCM (25 mL×2). Combined organic extracts were dried over anhydrous $Na_2SO_4$ and concentrated under reduced pressure. The crude product was purified by reverse phase (C-18) silica gel column chromatography, using acetonitrile-water=2:3→3:2 as gradient, to afford N-(4-methyl-2-(5-(trifluoromethyl)pyridin-2-yl)quinolin-7-yl)acrylamide (I-252) (0.09 g, 29.10%) as a white solid. $^1H$ NMR (400 MHz, DMSO-$d_6$) 10.56 (s, 1H), 9.12 (s, 1H), 8.80-8.78 (d, J=8.4 Hz, 1H), 8.68 (s, 1H), 8.40-8.38 (d, J=8.0 Hz, 1H), 8.36 (s, 1H), 8.14-8.12 (d, J=9.2 Hz, 1H), 7.81-7.79 (d, J=8.8 Hz, 1H), 6.56-6.50 (m, 1H), 6.38-6.33 (d, J=16.8 Hz 1H), 5.86-5.83 (d, J=10.4 Hz 1H), 2.77 (s, 3H). MS: $[MH]^+$ 358.2.

Example 1.156. Synthesis of (S)-6-methoxy-N-(1-methoxypropan-2-yl)-8-(4-(2,2,2-trifluoroethyl)piperidin-1-yl)quinoline-3-carboxamide (I-253)

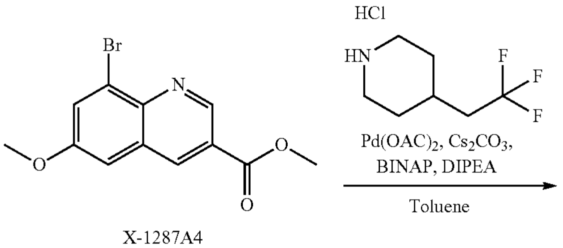

X-1287A4

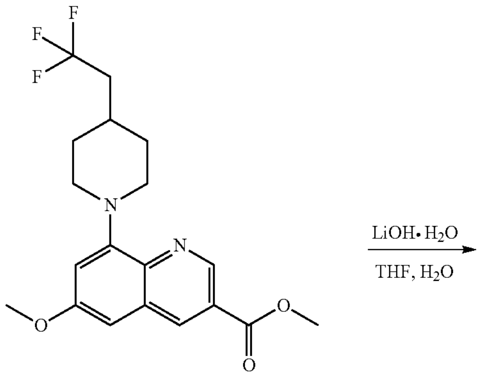

X-1494A1

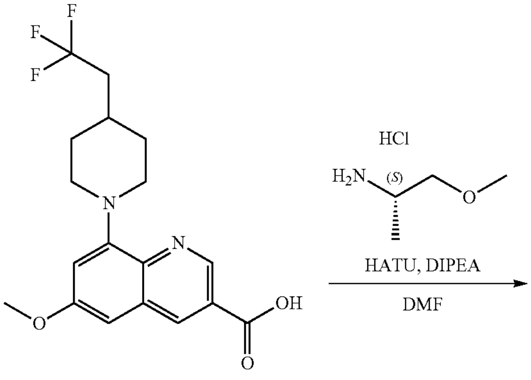

X-1494A2

-continued

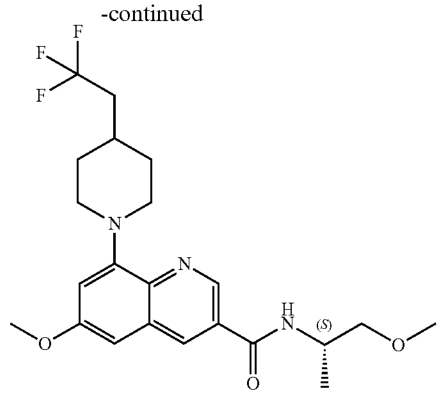

I-253

Methyl 6-methoxy-8-(4-(2,2,2-trifluoroethyl)piperidin-1-yl)quinoline-3-carboxylate (X-1494A1). To a stirred solution of methyl 8-bromo-6-methoxyquinoline-3-carboxylate (X-1287A4) (0.363 g, 1.23 mmol) in toluene (3 mL) were added cesium carbonate (2.81 g, 8.62 mmol), 4-(2,2,2-trifluoroethyl)piperidine hydrochloride (0.25 g, 1.23 mmol) and DIPEA (0.4 mL) and BINAP (0.153 g, 0.24 mmol) sequentially at room temperature under nitrogen. The reaction mixture was degassed (purging with nitrogen) for 20 min followed by the addition of $Pd(OAc)_2$ (0.028 g, 0.12 mmol) and the resulting mixture was heated at 100° C. for 16 h. Reaction mixture was cooled to room temperature, crude mass diluted with water (20 mL) and was extracted with ethyl acetate (20 mL×2). Combined organic extracts were dried over anhydrous $Na_2SO_4$, dried under reduced pressure. The crude product was purified by silica gel column chromatography, using ethyl acetate-hexane=0:1→1:4 as gradient, to afford methyl 6-methoxy-8-(4-(2,2,2-trifluoroethyl)piperidin-1-yl)quinoline-3-carboxylate (X-1494A1) (0.215 g, 66%) as an yellow solid. MS: [MH]+ 383.07.

6-Methoxy-8-(4-(2,2,2-trifluoroethyl)piperidin-1-yl)quinoline-3-carboxylic acid (X-1494A2). To a stirred solution of methyl 6-methoxy-8-(4-(2,2,2-trifluoroethyl)piperidin-1-yl)quinoline-3-carboxylate (X-1494A1) (0.210 g, 0.54 mmol) in a mixture of THF-water (2:1; 3 mL), was added lithium hydroxide monohydrate (0.069 g, 1.64 mmol) at room temperature and the resulting reaction mixture was heated at 70° C. for 1 h. After cooling to room temperature reaction mixture was concentrated under reduced pressure, crude was acidified (pH~2-3) with an aqueous solution of 1N HCl and was extracted with ethyl acetate (30 mL×3). Combined organic extracts were dried over anhydrous $Na_2SO_4$, dried under reduced pressure, to afford 6-methoxy-8-(4-(2,2,2-trifluoroethyl)piperidin-1-yl)quinoline-3-carboxylic acid (X-1494A2) (0.21 g, quant.; crude) as an off-white solid. MS: $[MH]^+$369.17.

(S)-6-methoxy-N-(1-methoxypropan-2-yl)-8-(4-(2,2,2-trifluoroethyl)piperidin-1-yl)quinoline-3-carboxamide (I-253). To a stirred solution of 6-methoxy-8-(4-(2,2,2-trifluoroethyl)piperidin-1-yl)quinoline-3-carboxylic acid (X-1494A2) (0.21 g, 0.57 mmol)) in DMF (3 mL) were added DIPEA (0.5 mL, 2.56 mmol) and HATU (0.32 g, 0.85 mmol) at 0° C. After stirring for 10 min at the same temperature, was added (S)-1-methoxypropan-2-amine hydrochloride (0.14 g, 1.14 mmol) and stirring was continued at the same temperature for 1 h. The reaction mixture was poured into ice water (50 mL) and was extracted with ethyl acetate (30 mL×3). Combined organic extracts were dried over anhydrous $Na_2SO_4$, dried under reduced pressure. The crude product was purified by (C-18) silica gel column chromatography, using acetonitrile-water=0:1 4:6 as gradient, to afford (S)-6-methoxy-N-(1-methoxypropan-2-yl)-8-(4-(2,2,2-trifluoroethyl)piperidin-1-yl)quinoline-3-carboxamide (I-253) (0.110 g, 46%) as an yellow solid. $^1H$ NMR (400 MHz, DMSO-$d_6$) δ 9.02-9.01 (d, J=2.0 Hz, 1H), 8.58-8.58 (d, J=2.0 Hz, 1H), 8.51-8.49 (d, J=8.0 Hz, 1H), 6.98-6.98 (d, J=2.0 Hz, 1H), 6.76-6.76 (d, J=2.4 Hz, 1H), 4.28-4.21 (m, 1H), 3.92-3.89 (d, J=12.0 Hz, 2H), 3.86 (s, 3H), 3.46-3.42 (m, 1H), 3.38-3.33 (1H, merge with DMSO-$d_6$ moisture peak), 3.28 (s, 3H), 2.75-2.69 (t, J=11.6 Hz, 2H), 2.38-2.28 (m, 2H), 1.86-1.83 (m, 3H), 1.65-1.60 (m, 2H), 1.18-1.16 (d, J=6.4 Hz, 3H). MS: $[MH]^+$440.2. Chiral HPLC: 94.90%.

Example 1.157. 4-Methyl-7-(1H-tetrazol-5-yl)-2-(4-(trifluoromethyl)phenyl)quinoline (I-254)

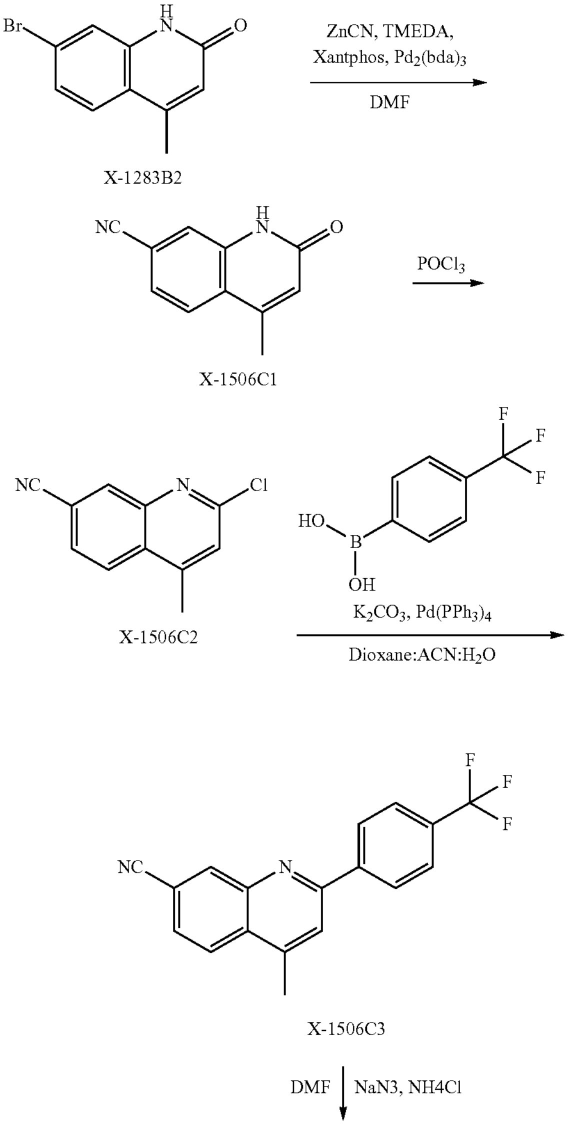

X-1283B2

X-1506C1

X-1506C2

X-1506C3

-continued

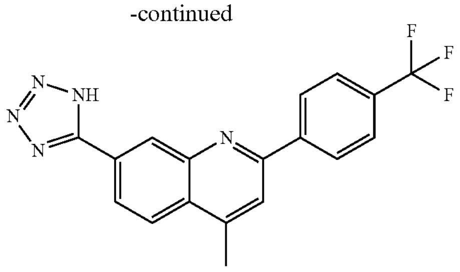

I-254

4-Methyl-2-oxo-1,2-dihydroquinoline-7-carbonitrile (X-1506C1). To a stirred solution of methyl 7-bromo-4-methylquinolin-2(1H)-one (X-1283B2) (0.500 g, 2.10 mmol) in DMF (8 mL) were added ZnCN (0.140 g, 1.26 mmol) and TMEDA (0.070 g, 0.63 mmol) sequentially at room temperature under nitrogen. The reaction mixture was degassed (purging with nitrogen) for 10 min followed by the addition of $Pd_2(dba)_3$ (0.090 g, 0.10 mmol) and xanthphos (0.060 g, 0.10 mmol), the resulting mixture was heated at 160° C. microwave irradiation for 25 min. Reaction mixture was cooled to room temperature, reaction mixture was slowly poured into ice-water (200 mL), solid product was precipitated which was collected by filtration, dried under reduced pressure. The resulting crude material was triturated with diethyl ether (20 mL×2), dried over high vacuum, to afford 4-methyl-2-oxo-1,2-dihydroquinoline-7-carbonitrile (X-1506C1) (0.400 g, 86%) as a yellow solid. MS: $[MH]^+$ 185.0.

2-Chloro-4-methylquinoline-7-carbonitrile (X-1506C2). A solution of 4-methyl-2-oxo-1,2-dihydroquinoline-7-carbonitrile (X-1506C1) (0.300 g, 1.63 mmol) in $POCl_3$ (3 mL) was heated at 90° C. for 2 h. Reaction mixture was cooled to room temperature, reaction mixture was slowly poured into an aqueous solution of saturated $NaHCO_3$ (100 mL) and product was extracted with ethyl acetate (60 mL×3), dried over anhydrous $Na_2SO_4$ and concentrated under reduce pressure, to afford 2-chloro-4-methylquinoline-7-carbonitrile (X-1506C2) (0.230 g, 52%) as a brown solid. MS: $[MH]^+$ 203.0.

2-(4-(Difluoromethyl)phenyl)-4-methylquinoline-7-carbonitrile (X-1506C3). To a stirred solution of 2-chloro-4-methylquinoline-7-carbonitrile (X-1506C2) (0.200 g, 0.99 mmol) in a mixture dioxane-acetonitrile-$H_2O$ (3:2:1, 6 mL) were added (4-(trifluoromethyl)phenyl)boronic acid (0.370 g, 1.98 mmol), potassium carbonate (0.270 g, 1.98 mmol) at room temperature. The reaction mixture was degassed (purging with nitrogen) for 10 min followed by addition of $Pd(PPh_3)_4$ (0.110 g, 0.09 mmol) and the reaction mixture was heated at 100° C. for 2 h. The reaction mixture was cooled to room temperature, diluted with water (50 mL) and was extracted with ethyl acetate (100 mL×2). The combined organic extracts were dried over anhydrous $Na_2SO_4$ and concentrated under reduce pressure. The crude product was purified by silica gel column chromatography, using ethyl acetate-hexane=0:1→2:8 as gradient, to afford 2-(4-(difluoromethyl)phenyl)-4-methylquinoline-7-carbonitrile (X-1506C3) (0.220 g, 71%) as a yellow solid. MS: $[MH]^+$ 313.06.

4-Methyl-7-(1H-tetrazol-5-yl)-2-(4-(trifluoromethyl)phenyl)quinoline (I-254). To a stirred solution of 2-(4-(difluoromethyl)phenyl)-4-methylquinoline-7-carbonitrile (X-1506C3) (0.210 g, 0.67 mmol) in DMF (5 mL) were added $NH_4Cl$ (0.35 g, 6.73 mmol) and $NaN_3$ (0.26 g, 4.03 mmol) at 0° C. under nitrogen and the reaction mixture was heated at 110° C. for 16 h. The reaction mixture was cooled to room temperature, diluted with water (30 mL) and was extracted with EtOAc (50 mL×2). Combined organic extracts were washed with brine (100 mL), dried over anhydrous $Na_2SO_4$ and concentrated under reduced pressure. The crude product was purified by reverse phase (C-18) silica gel column chromatography, using acetonitrile-water=0:1→3:7 as gradient, as gradient afford 4-methyl-7-(1H-tetrazol-5-yl)-2-(4-(trifluoromethyl)phenyl)quinoline (I-254) (0.060 g, 25%) as an off-white solid. $^1H$ NMR (400 MHz, DMSO-$d_6$) δ 8.78 (s, 1H) 8.54-8.52 (d, J=8.4 Hz, 2H), 8.36-8.34 (d, J=8.4 Hz, 1H), 8.29-8.27 (d, J=10.0 Hz, 1H), 8.24 (s, 1H), 7.96-7.94 (d, J=8.4, 2H), 2.83 (s, 3H). MS: $[MH]^+$356.1.

Example 1.158. Synthesis of (R)—N-(1-hydroxypropan-2-yl)-4-methyl-2-(4-(trifluoromethoxy)phenyl)quinoline-7-carboxamide (I-255)

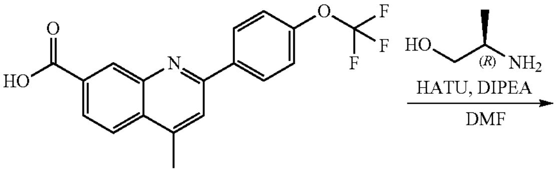

I-256

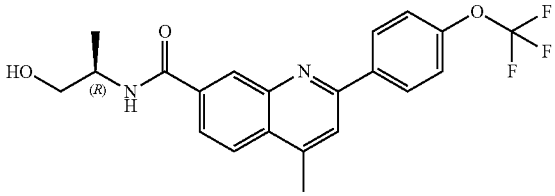

I-255

To a solution of 4-methyl-2-(4-(trifluoromethoxy)phenyl) quinoline-7-carboxylic acid (I-256) (0.200 g, 0.57 mmol)) in DMF (3 mL) were added DIPEA (0.300 mL, 1.71 mmol) and HATU (0.320 g, 0.85 mmol) at 0° C. After stirring for 10 min at the same temperature, was added (R)-2-amino-propan-1-ol (0.051 g, 0.69 mmol) and stirring was continued at the same temperature for 1 h. Reaction mixture was poured into ice water (150 mL), solid product was precipitated which was collected by filtration, dried under reduced pressure. The resulting crude material was triturated with n-pentane (20 mL×2), dried over high vacuum, to afford (R)—N-(1-hydroxypropan-2-yl)-4methyl-2-(4-(trifluoromethoxy)phenyl)quinoline-7-carboxamide (I-255) (0.150 g, 65%) as a white solid. $^1H$ NMR (400 MHz, DMSO-$d_6$) δ 8.62 (s, 1H), 8.50-8.48 (d, J=7.6 Hz, 1H), 8.43-8.41 (d, J=8.8 Hz, 2H), 8.18-8.15 (m, 2H), 8.05-8.03 (d, J=9.2 Hz, 1H), 7.57-7.55 (d, J=8.4 Hz, 2H), 4.79-4.76 (t, J=6.0 Hz, 1H), 4.10-4.07 (m, 1H), 3.54-3.49 (m, 1H), 3.42-3.38 (m, 1H), 2.79 (s, 3H), 1.18-1.17 (d, J=6.4 Hz, 3H). MS: $[MH]^+$ 405.0. Chiral HPLC=100%

Example 1.159. Synthesis of 4-methyl-2-(4-(trifluoromethoxy)phenyl)quinoline-7-carboxylic acid (I-256

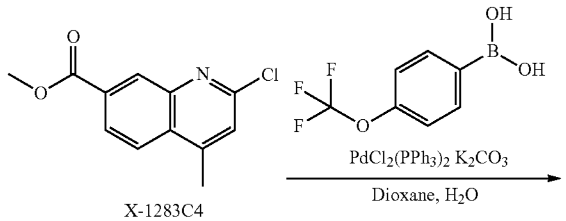

X-1283C4

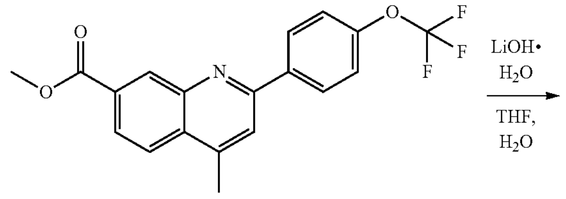

X-1583A1

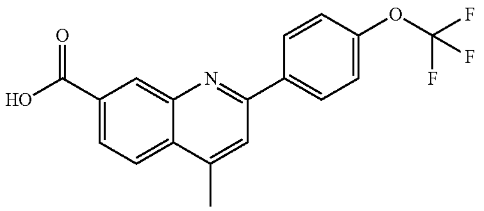

I-256

Methyl 4-methyl-2-(4-(trifluoromethoxy)phenyl)quinoline-7-carboxylate (X-1516A1). To a stirred solution of methyl 2-chloro-4-methylquinoline-7-carboxylate (X-1283C4) (0.500 g, 2.21 mmol) in a mixture of 1,4-dioxane-water (1:1, 5 mL) were added (4-(trifluoromethoxy) phenyl)boronic acid (0.874 g, 6.36 mmol). and $K_2CO_3$ (0.878 g, 6.36 mmol) at room temperature under nitrogen. The reaction mixture was degassed (purging with nitrogen) for 20 min followed by the addition of $PdCl_2(PPh_3)_2$ (0.149 g, 0.21 mmol) and the resulting mixture was heated at 90° C. for 2 h. The reaction mixture was cooled to room temperature, diluted with water (200 mL) and was extracted with ethyl acetate (50 mL×2). Combined organic extracts were washed with brine (50 mL), dried over anhydrous $Na_2SO_4$ and concentrated in vacuo. The crude product was purified by silica gel column chromatography, using ethyl acetate-hexane=1:19→2:8 as a gradient, to methyl 4-methyl-2-(4-(trifluoromethoxy)phenyl)quinoline-7-carboxylate (X-1583A1) (0.550 g, 72%) as a white solid. MS: $[MH]^+$ 361.97.

4-Methyl-2-(4-(trifluoromethoxy)phenyl)quinoline-7-carboxylic acid (I-256). To a stirred solution of methyl 4-methyl-2-(4-(trifluoromethoxy)phenyl)quinoline-7-carboxylate (X-1583A1) (0.550 g, 1.52 mmol) in THF—$H_2O$ (4:1; 5 mL), was added LiOH·$H_2O$ (0.191 g, 4.57 mmol) at room temperature and the mixture was stirred at 60° C. for 1 h. Reaction mixture was concentrated under reduced pressure and crude was acidified (pH~2-3) with an aqueous solution of 1N HCl and the resulting precipitate was collected by filtration. Isolated solid was washed with cold water until the pH became neutral (pH~6-7). The solid product was triturated by using n-pentane (20 mL×2) to afford 4-methyl-2-(4-(trifluoromethoxy)phenyl)quinoline-7-carboxylic acid (I-256) (0.450 g, 85%) as an off white solid. $^1H$ NMR (400 MHz, DMSO-$d_6$) δ 13.35 (s, 1H), 8.61 (s, 1H), 8.43-8.40 (dd, J=2.0, 8.8 Hz, 2H), 8.22-8.19 (m, 2H), 8.09-8.06 (dd, J=1.6, 8.8 Hz, 1H), 7.56-7.54 (d, J=8.0 Hz, 2H), 2.79 (s, 3H). MS: $[MH]^+$347.9.

Example 1.160. Synthesis of N-(8-(4-(tert-butyl) phenyl)-2-methylimidazo[1,2-a]pyrazin-3-yl)acrylamide (1-257)

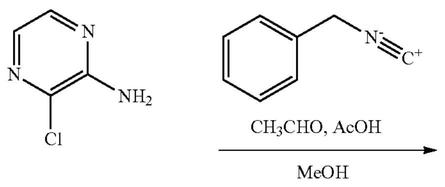

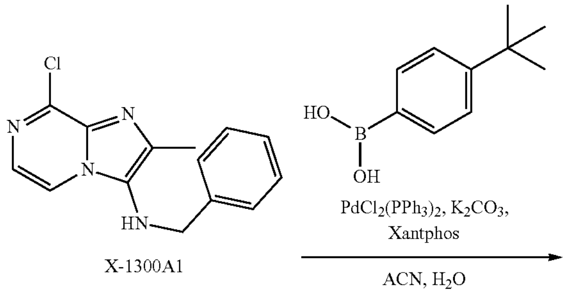

X-1300A1

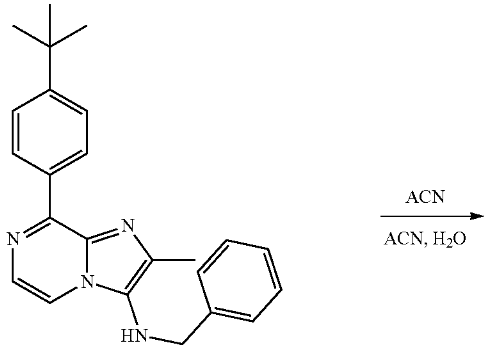

X-1300A2

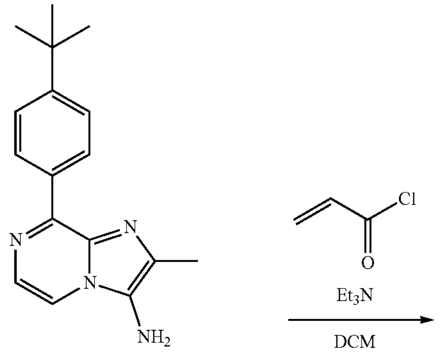

X-1300A3

-continued

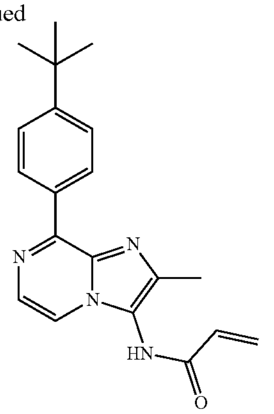

I-257

N-Benzyl-8-chloro-2-methylimidazo[1,2-a]pyrazin-3-amine (X-1300A1) To a stirred solution of 3-chloropyrazin-2-amine (1.0 g, 7.75 mmol) in methanol (10 mL) were added acetaldehyde (0.510 g, 11.62 mmol) and acetic acid (0.69 g, 15.50 mmol) at 0° C. The resulting reaction mixture was stirred at 0° C. for 30 min. Benzyl isocyanide (1.360 g, 11.62 mmol) was added at 0° C. and stirred at room temperature for 4 h. The reaction mixture was poured into water (100 mL) and was extracted with ethyl acetate (100 mL×2). Combined organic extracts were dried over anhydrous $Na_2SO_4$ and concentrated under reduced pressure. Obtained crude was mixed with the crude of an identically prepared batch of (1.0 g) and purified by reverse phase (C-18) silica gel column chromatography using acetonitrile:water=3:7→2:3 as gradient, to afford N-benzyl-8-chloro-2-methylimidazo[1,2-a]pyrazin-3-amine (X-1300A1) (1.20 g, 28%) as an off white solid. MS: $[MH]^+$ 273.0

N-Benzyl-8-(4-(tert-butyl)phenyl)-2-methylimidazo[1,2-a]pyrazin-3-amine (X-1300A2). To a stirred solution of N-benzyl-8-chloro-2-methylimidazo[1,2-a]pyrazin-3-amine (X-1300A1) (0.300 g, 1.10 mmol) in a mixture acetonitrile-$H_2O$ (8:1; 9 mL) were added (4-(tert-butyl)phenyl)boronic acid (0.216 g, 1.21 mmol), potassium carbonate (0.3 g, 2.20 mmol) at room temperature. The reaction mixture was degassed (purging with nitrogen) for 20 min followed by addition of $PdCl_2(PPh_3)_2$ (0.023 g, 0.03 mmol) and Xanthphos (0.038 g, 0.06 mmol) the reaction mixture was heated at 150° C. under microwave irradiation for 1 h. The reaction mixture was cooled to room temperature, diluted with water (50 mL) and was extracted by ethyl acetate (50 mL×3). The combined organic extracts were dried over anhydrous $Na_2SO_4$ and concentrated under reduce pressure. Obtained crude was mixed with the crude of an identically prepared batch of (0.330 g) and purified by reverse phase (C-18) silica gel column chromatography using acetonitrile-water=3:7→1:1 as a gradient, to afford N-benzyl-8-(4-(tert-butyl)phenyl)-2-methylimidazo[1,2-a]pyrazin-3-amine (X-1300A2) (0.360 g, 42%) as an brown solid. MS: $[MH]^+$ 371.27

8-(4-(tert-butyl)phenyl)-2-methylimidazo[1,2-a]pyrazin-3-amine (X-1300A3) To a stirred solution of N-benzyl-8-(4-(tert-butyl)phenyl)-2-methylimidazo[1,2-a]pyrazin-3-amine (X-1300A2) (0.160 g, 0.43 mmol) in a mixture of acetonitrile and water (10 mL) was added ceric ammonium nitrate (0.118 g, 0.34 mmol) at 0° C. and stirred at same temperature for 2 h. Reaction mixture was poured into water (20 mL) and was extracted with ethyl acetate (30 mL×2). Combined organic extracts were dried over anhydrous $Na_2SO_4$ and concentrated under reduced pressure. Obtained crude was mixed with the crude of an identically prepared batch of (0.200 g) and purified by reverse phase (C-18) silica gel column chromatography using acetonitrile:water=1:1→3:2 as gradient, to afford 8-(4-(tert-butyl)phenyl)-2-methylimidazo[1,2-a]pyrazin-3-amine (X-1300A3) (0.090 g, 37%) as an yellow solid. MS: $[MH]^+$ 281.11

N-(8-(4-(tert-butyl)phenyl)-2-methylimidazo[1,2-a]pyrazin-3-yl)acrylamide (I-257). To a stirred solution of 8-(4-(tert-butyl)phenyl)-2-methylimidazo[1,2-a]pyrazin-3-amine (X-1300A3) (0.050 g, 0.17 mmol) in dichloromethane (3 mL) were added triethylamine (0.540 g, 0.53 mmol) and acryloyl chloride (0.020 g, 0.25 mmol) sequentially at 0° C. under nitrogen and the reaction mixture was stirred at same temperature for 30 min. The reaction mixture was diluted with water (20 mL) and was extracted with dichloromethane (30 mL×2). Combined organic extracts were dried over anhydrous $Na_2SO_4$ and concentrated under reduced pressure. Obtained crude was purified by preparative HPLC, using acetonitrile and water as gradient, to afford N-(8-(4-(tert-butyl)phenyl)-2-methylimidazo[1,2-a]pyrazin-3-yl)acrylamide (I-257) (0.012 g, 20%) as a white solid. $^1H$ NMR (400 MHz, DMSO-$d_6$) δ: 10.40 (s, 1H), 8.64-8.62 (d, J=8.4 Hz, 2H), 7.98 (s, 2H), 7.59-7.57 (d, J=8.4 Hz, 2H), 6.59-6.52 (m, 1H), 6.36-6.32 (d, J=16.8 Hz, 1H), 5.92-5.89 (d, J=10.8 Hz, 1H), 2.36 (s, 3H), 1.35 (s, 9H). MS: $[MH]^+$335.22

Example 1.160. Synthesis of 4-Methyl-2-(4-(trifluoromethyl)phenyl)quinoline-7-carboxamide (I-258

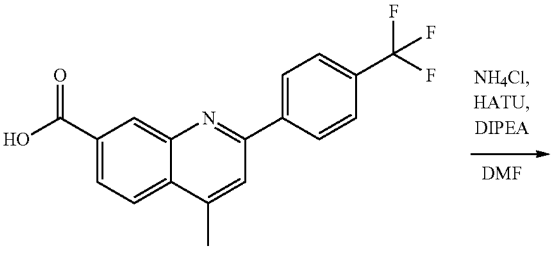

I-89

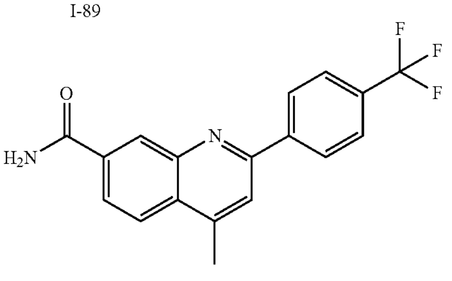

I-258

Synthesis of 4-methyl-2-(4-(trifluoromethyl)phenyl)quinoline-7-carboxylic acid provided in Example 1.14

To a stirred solution of 4-methyl-2-(4-(trifluoromethyl)phenyl)quinoline-7-carboxylic acid (I-89) (0.250 g, 0.75 mmol)) in DMF (6 mL) were added DIPEA (0.52 mL, 3.0 mmol) and HATU (0.573 g, 1.50 mmol) at 0° C. under nitrogen. After 10 min of stirring at room temperature was added a solution of ammonium chloride (0.120 g, 2.25 mmol) in DMF (2 mL) drop-wise at the same temperature and the resulting reaction mixture was stirred at room temperature for 1 h. Reaction mixture was diluted with water (30 mL) and was extracted with ethyl acetate (30 mL×3). Combined organic layers were washed with brine, dried over $Na_2SO_4$, filtered and concentrated under reduced pressure. Obtained crude was purified by reverse phase (C-18) silica gel column chromatography, using acetonitrile-water=0: 1→3:2 as gradient, to afford (4-methyl-2-(4-(trifluoromethyl)phenyl)quinoline-7-carboxamide (I-258) (0.015 g, 6%) as a white solid. $^1$H NMR (400 MHz, DMSO-$d_6$) δ: 8.65 (s, 1H), 8.52-8.50 (d, J=8.0 Hz, 2H), 8.34 (s, 1H), 8.22 (s, 1H) 8.22-8.21 (d, J=8.8 Hz, 1H), 8.10-8.07 (dd, J=1.2, 8.4 Hz, 1H), 7.95-7.93 (d, J=8.0 Hz, 2H), 7.62 (s, 1H), 2.81 (s, 3H), MS: [MH]$^+$331.1.

Example 1.161. Synthesis of N-(2-hydroxyethyl)-4-methyl-2-(4-(trifluoromethyl)phenyl)quinoline-7-carboxamide (I-259)

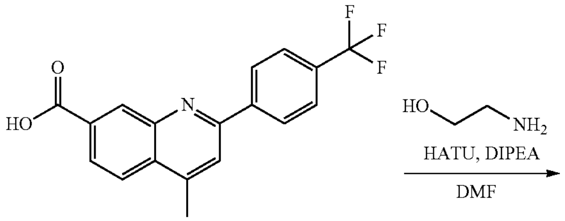

I-89

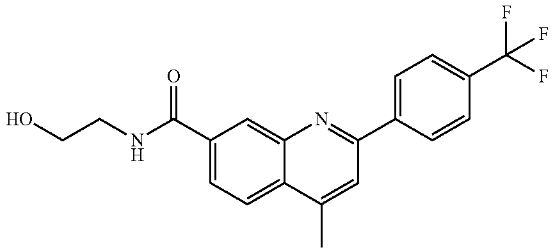

I-259

The following compound was prepared in a manner analogous to the procedures described above for (4-methyl-2-(4-(trifluoromethyl)phenyl)quinoline-7-carboxamide (I-258):

N-(2-hydroxyethyl)-4-methyl-2-(4-(trifluoromethyl)phenyl)quinoline-7-carboxamide (I-259) (0.060 g, 53%) as a white solid. $^1$H NMR (400 MHz, DMSO-d) δ:8.85-8.79 (m, 1H), 8.64 (s, 1H), 8.52-8.50 (d, J=8.0 Hz, 2H), 8.21 (s, 1H) 8.21-8.19 (d, J=9.2 Hz, 1H), 8.08-8.06 (d, J=8.8 Hz, 1H), 7.95-7.93 (d, J=8.0 Hz, 2H), 4.81-4.78 (t, J=5.6 Hz, 1H), 3.59-3.55 (m, 2H), 3.42-3.38 (m, 2H), 2.80 (s, 3H). MS: [MH]$^+$ 375.1.

Example 1.162. Synthesis of N-(1-hydroxypropan-2-yl)-4-methyl-2-(4-(trifluoromethyl)phenyl)quinoline-7-carboxamide (I-260

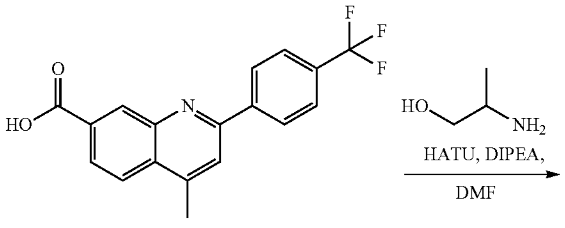

I-89

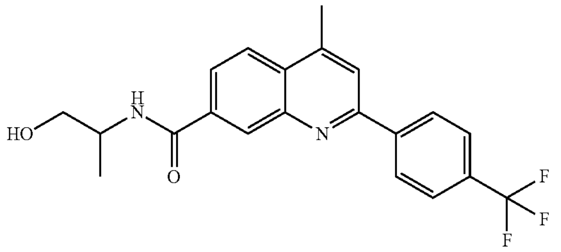

I-260

The following compound was prepared in a manner analogous to the procedures described above for (4-methyl-2-(4-(trifluoromethyl)phenyl)quinoline-7-carboxamide (I-258):

N-(1-hydroxypropan-2-yl)-4-methyl-2-(4-(trifluoromethyl)phenyl)quinoline-7-carboxamide (I-260) (0.050 g, 43%) as an off-white solid. $^1$H NMR (400 MHz, DMSO-$d_6$) δ: 8.66 (s, 1H), 8.52-8.50 (d, J=7.6 Hz, 3H), 8.21 (s, 1H), 8.19-8.18 (d, J=2.8 Hz, 1H), 8.08-8.06 (d, J=8.4 Hz, 1H), 7.95-7.93 (d, J=7.2 Hz, 2H), 4.78-4.78 (d, J=1.6 Hz, 1H) 4.10-4.07 (t, J=6.4 Hz, 1H), 352-350 (t, J=4.8 Hz, 1H), 3.41-3.37 (m, 1H), 2.82-2.81 (d, J=2.4 Hz 3H) 1.22-1.17 (m, 3H). MS: [MH]$^+$389.1.

Example 1.163. Synthesis of (R)—N-(1-hydroxypropan-2yl)-4-methyl-2-(4-(trifluoromethyl)phenyl) quinoline-7-carboxamide (I-261)

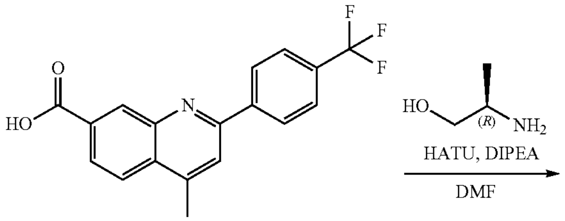

I-89

-continued

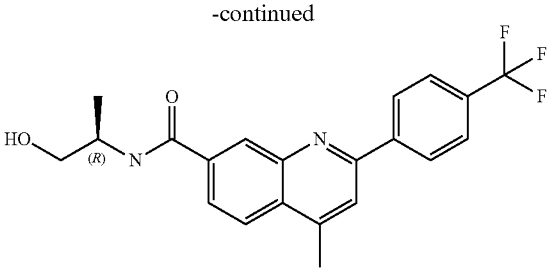

I-261

The following compound was prepared in a manner analogous to the procedures described above for (4-methyl-2-(4-(trifluoromethyl)phenyl)quinoline-7-carboxamide (I-258):

(R)—N-(1-hydroxypropan-2-yl)-4-methyl-2-(4-(trifluoromethyl)phenyl)quinoline-7-carboxamide (I-261) (1.8 g, 51%) as an off-white solid. 1H NMR (400 MHz, DMSO-$d_6$) δ 8.66 (s, 1H), 8.53-8.50 (m, 3H), 8.22-8.19 (m, 2H), 8.08-8.06 (dd, J=8.0 Hz, 1.6 Hz, 1H), 7.96-7.93 (d, J=8.4 Hz, 2H), 4.79-4.76 (t, J=4.0-Hz, 1H), 4.13-4.06 (m, 1H), 3.55-3.50 (m, 1H), 3.43-3.36 (m, 1H), 2.81 (s, 3H), 1.19-1.17 (d, J=8.0 Hz, 3H). MS: $[MH]^+$388.97. Chiral HPLC purity is 100%.

Example 1.164. Synthesis of (S)—N-(1-hydroxypropan-2-yl)-4-methyl-2-(4-(trifluoromethyl)phenyl)quinoline-7-carboxamide (I-262)

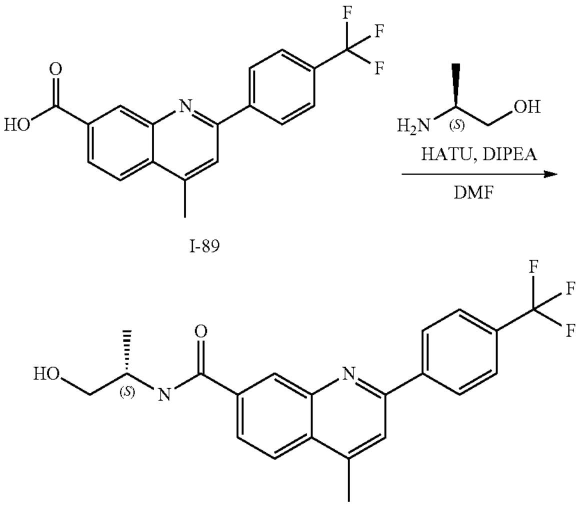

I-89

I-262

The following compound was prepared in a manner analogous to the procedures described above for (4-methyl-2-(4-(trifluoromethyl)phenyl)quinoline-7-carboxamide (I-258):

(S)—N-(1-hydroxypropan-2-yl)-4-methyl-2-(4-(trifluoromethyl)phenyl)quinoline-7-carboxamide (I-262) (2.70 g, 77%) as an off-white solid. $^1$H NMR (400 MHz, DMSO-$d_6$) δ: 8.65 (s, 1H), 8.53-8.49 (m, 3H), 8.22 (s, 1H), 8.21-8.19 (d, J=8.8 Hz, 1H), 8.08-8.59 (dd, J=1.6, 8.8 Hz, 1H), 7.95-7.93 (d, J=8.4 Hz, 2H), 4.79-4.76 (t, J=6.0 Hz, 1H), 4.11-4.07 (m, 1H), 3.55-3.49 (m, 1H), 3.42-3.36 (m, 1H), 2.81 (s, 3H), 1.19-1.17 (d, J=6.8 Hz, 3H). MS: $[MH]^+$388.97, Chiral HPLC=100%

Example 1.165. Synthesis of (S)—N-(1-methoxypropan-2-yl)-4-methyl-2-(4-(trifluoromethyl)phenyl)quinoline-7-carboxamide (I-263

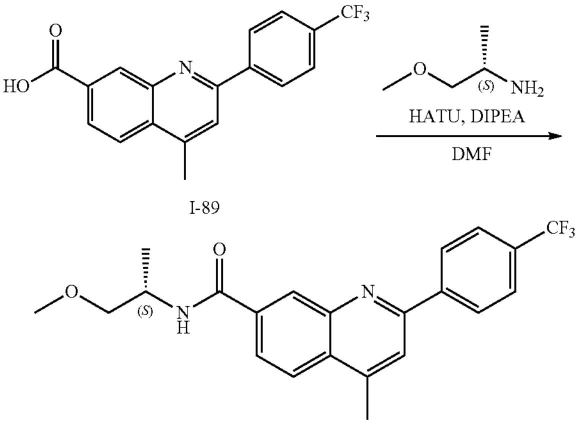

I-89

I-263

The following compound was prepared in a manner analogous to the procedures described above for (4-methyl-2-(4-(trifluoromethyl)phenyl)quinoline-7-carboxamide (I-258):

(S)—N-(1-methoxypropan-2-yl)-4-methyl-2-(4-(trifluoromethyl)phenyl)quinoline-7-carboxamide (I-263) (0.055 g, 22%) as an off-white solid. $^1$H NMR (400 MHz, DMSO-$d_6$) δ: 8.65-8.63 (d, J=8.0 Hz, 2H), 8.53-8.51 (d, J=8.0 Hz, 2H), 8.21 (s, 1H) 8.21-8.19 (d, J=8.0 Hz, 1H), 8.08-8.05 (dd, J=1.6, 8.4 Hz, 1H), 7.95-7.93 (d, J=8.0 Hz, 2H), 4.31-4.25 (m, 1H), 3.50-3.46 (m, 1H), 3.30 (s, 3H), 2.81 (s, 3H), 1.20-1.18 (d, J=8.0 Hz, 3H). MS: $[MH]^+$402.97, Chiral HPLC=100%

Example 1.166. Synthesis of (S)-4-methyl-N-(1-(trifluoromethoxy)propan-2-yl)-2-(4-(trifluoromethyl)phenyl)quinoline-7-carboxamide (I-264

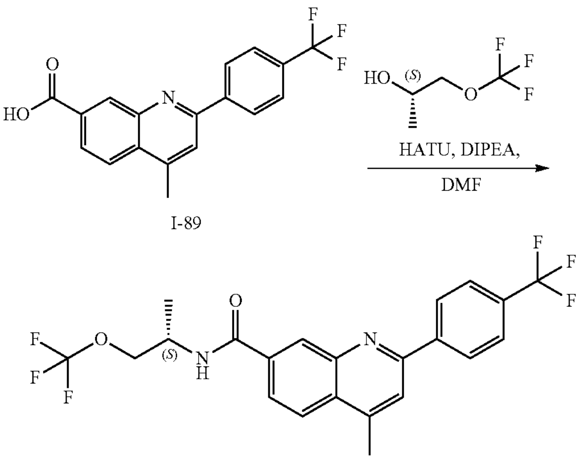

I-89

I-264

The following compound was prepared in a manner analogous to the procedures described above for for (4-methyl-2-(4-(trifluoromethyl)phenyl)quinoline-7-carboxamide (I-258):

(S)-4-methyl-N-(1-(trifluoromethoxy)propan-2-yl)-2-(4-(trifluoromethyl)phenyl)quinoline-7-carboxamide (I-264) (0.180 g, 65%) as a white solid. $^1$H NMR (400 MHz, DMSO-$d_6$) δ: 8.85-8.83 (d, J=8.0 Hz, 1H), 8.65 (s, 1H), 8.52-8.50 (d, J=8.0 Hz, 2H), 8.23 (s, 1H) 8.23-8.21 (d, J=8.0 Hz, 1H), 8.07-8.05 (d, J=8.4 Hz, 1H), 7.95-7.93 (d, J=8.0 Hz, 2H), 4.41-4.38 (m, 1H), 4.17-4.15 (m, 2H), 2.18 (s, 3H), 1.27-1.26 (d, J=6.8 Hz, 3H), MS: $[MH]^+$456.90, Chiral HPLC=99.08%

Example 1.167 Synthesis of (R)—N-(1-hydroxybutan-2-yl)-4-methyl-2-(4-(trifluoromethyl)phenyl) quinoline-7-carboxamide (I-265

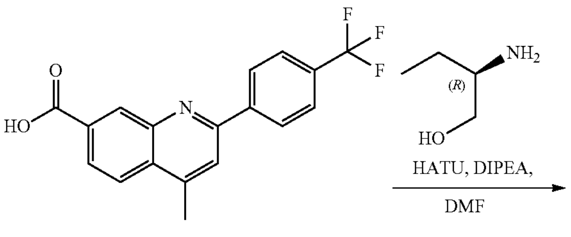

I-89

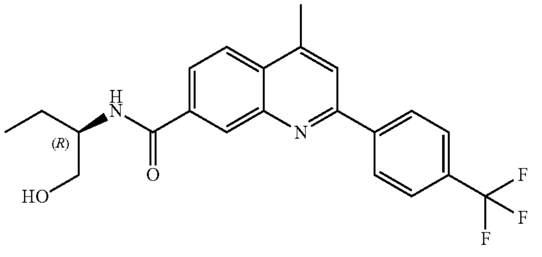

I-265

The following compound was prepared in a manner analogous to the procedures described above for (4-methyl-2-(4-(trifluoromethyl)phenyl)quinoline-7-carboxamide (I-258):

(R)—N-(1-hydroxybutan-2-yl)-4-methyl-2-(4-(trifluoromethyl)phenyl)quinoline-7-carboxamide (I-265) (0.200 g, 55%) as a white solid. $^1$H NMR (400 MHz, DMSO-$d_6$) δ: 8.68-8.67 (d, J=1.6 Hz, 1H), 8.53-8.51 (d, J=8.0 Hz, 2H), 8.42-8.40 (d, J=8.4 Hz, 1H), 8.21 (s, 1H) 8.21-8.19 (d, J=8.8 Hz, 1H), 8.09-8.06 (dd, J=1.6, 8.4 Hz, 1H), 7.95-7.93 (d, J=8.4 Hz, 2H), 4.73-4.70 (t, J=6.0 Hz, 1H), 3.98-3.93 (m, 1H), 3.56-3.50 (m, 1H), 3.48-3.43 (m, 1H), 2.82 (s, 3H), 1.75-1.68 (m, 1H), 1.56-1.48 (m, 1H), 0.94-0.90 (t, J=7.2 Hz, 3H), MS: $[MH]^+$ 403.1, Chiral HPLC=98.24%

Example 1.168. Synthesis of (4-methyl-2-(4-(trifluoromethyl)phenyl)quinoline-7-carbonyl)-D-alanine (I-266

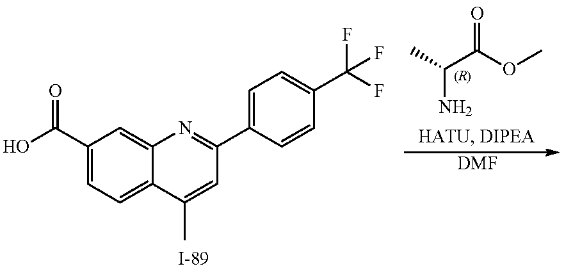

I-89

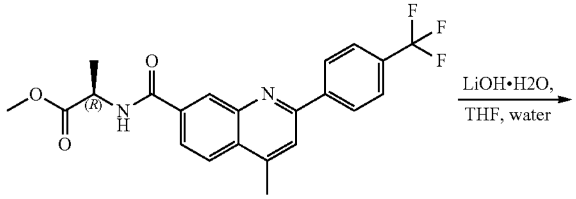

X-1792A1

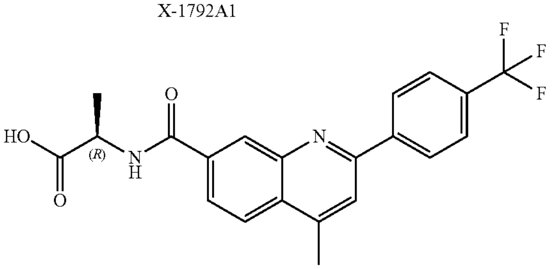

I-266

Methyl (4-methyl-2-(4-(trifluoromethyl)phenyl)quinoline-7-carbonyl)-D-alaninate (X-1792A1). This compound was prepared in a manner analogous to the procedures described above for (4-methyl-2-(4-(trifluoromethyl)phenyl)quinoline-7-carboxamide (I-258). Methyl (4-methyl-2-(4-(trifluoromethyl)phenyl)quinoline-7-carbonyl)-D-alaninate (0.300 g, 66%) as an off-white solid. MS: $[MH]^+$ 417.46.

(4-methyl-2-(4-(trifluoromethyl)phenyl)quinoline-7-carbonyl)-D-alanine (I-266). To a stirred solution of methyl (4-methyl-2-(4-(trifluoromethyl)phenyl)quinoline-7-carbonyl)-D-alaninate (X-1792A1) (0.200 g, 0.48 mmol) in a mixture of THF-water (3:1; 4 mL) was added lithium hydroxide monohydrate (0.080 g, 1.92 mmol) at room temperature and stirred at room temperature for 2 h. The reaction mixture was concentrated under reduced pressure, crude mass was diluted with water (20 mL) and was extracted with ethyl acetate (30×2 mL) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was dried in vacuo to afford (4-methyl-2-(4-(trifluoromethyl)phenyl)quinoline-7-carbonyl)-D-alanine (I-266) (0.150 g, 77%) as a white solid. $^1$H NMR (400 MHz, DMSO-$d_6$) δ: 12.48 (brs, 1H), 9.06-9.05 (d, J=6.8 Hz, 1H), 8.72-8.71 (d, J=1.6 Hz, 1H), 8.54-8.52 (d, J=8.0 Hz, 2H), 8.24 (s, 1H), 8.24-8.22 (d, J=8.4 Hz, 1H), 8.10-8.07 (dd, J=1.6, 8.8 Hz, 1H), 7.96-7.94 (d, J=8.4 Hz, 2H), 4.52-4.45 (m, 1H), 2.82 (s, 3H), 1.47-1.45 (d, J=7.6 Hz, 3H). MS: $[MH]^+$ 403.4, Chiral HPLC=100%

Example 1.169. Synthesis of (S)-3-(1-(4-methyl-2-(4-(trifluoromethyl)phenyl)quinoline-7-carboxamido)ethyl)benzoic acid (I-267)

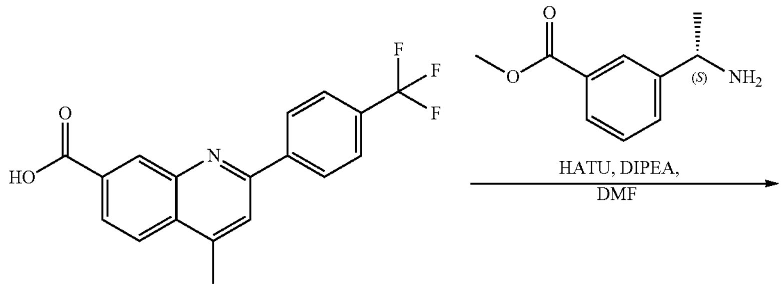

I-89

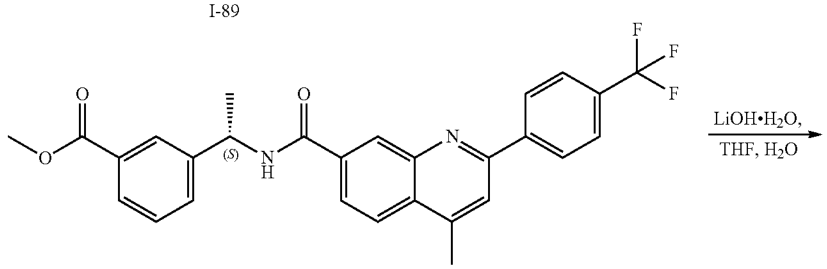

X-1793A1

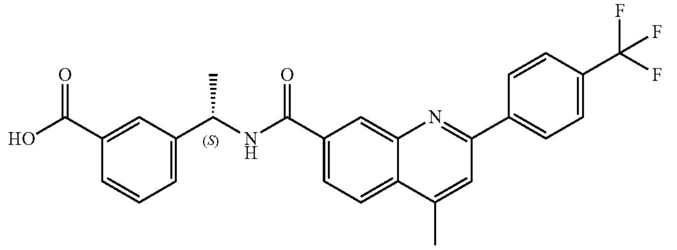

I-267

The following compound was prepared in a manner analogous to the procedures described above for (4-methyl-2-(4-(trifluoromethyl)phenyl)quinoline-7-carbonyl)-D-alanine (I-266):

(S)-3-(1-(4-methyl-2-(4-(trifluoromethyl)phenyl)quinoline-7-carboxamido)ethyl)benzoic acid (I-267) (0.040 g, 27%) as a white solid. $^1H$ NMR (400 MHz, DMSO-$d_6$) δ: 13.40 (br. s, 1H), 9.31-9.29 (d, J=7.6 Hz, 1H), 8.73 (s, 1H), 8.53-8.51 (d, J=8.0 Hz, 2H), 8.21 (s, 1H), 8.21-8.18 (d, J=12.8 Hz, 1H), 8.08-8.06 (d, J=9.2 Hz, 2H), 7.94-7.92 (d, J=8.4 Hz, 2H), 7.82-7.80 (d, J=8.0 Hz, 1H), 7.56-7.54 (d, J=6.8 Hz, 1H), 7.39-7.35 (t, J=7.6 Hz, 1H), 5.31-5.24 (m, 1H), 2.80 (s, 3H), 1.56-1.54 (d, J=7.2 Hz, 3H). MS: $[MH]^+$ 479.4, Chiral HPLC=99.50%

Example 1.170. Synthesis of (S)—N-(1-(3-methoxyphenyl)ethyl)-4-methyl-2-(4-(trifluoromethyl)phenyl)quinoline-7-carboxamide (I-268)

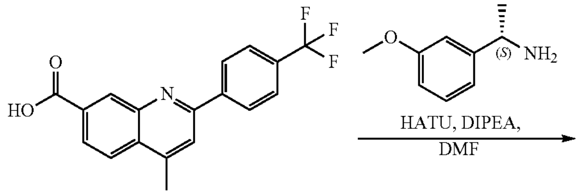

I-89

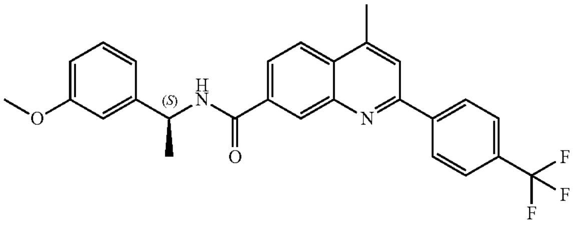

I-268

The following compound was prepared in a manner analogous to the procedures described above for (4-methyl-2-(4-(trifluoromethyl)phenyl)quinoline-7-carboxamide (I-258):

(S)—N-(1-(3-methoxyphenyl)ethyl)-4-methyl-2-(4-(trifluoromethyl)phenyl)quinoline-7-carboxamide (I-268) (0.100 g, 50%) as a white solid. $^1$H NMR (400 MHz, DMSO-$d_6$) δ: 9.21-9.19 (d, J=8.0 Hz, 1H), 8.73-8.72 (d, J=1.6 Hz, 1H), 8.54-8.52 (d, J=8.4 Hz, 2H), 8.23 (s, 1H) 8.23-8.20 (d, J=10.8 Hz, 1H), 8.09-8.06 (dd, J=1.60, 8.8 Hz, 1H), 7.96-7.94 (d, J=8.4 Hz, 2H), 7.29-7.24 (t, J=8.0 Hz, 1H), 7.04-7.02 (m, 2H), 6.83-6.80 (dd, J=8.0, 7.6 Hz, 1H), 5.24-5.20 (m, 1H), 3.75 (s, 3H), 2.82 (s, 3H), 1.54-1.52 (d, J=7.2 Hz, 3H), MS: $[MH]^+$465.4, Chiral HPLC=100%

Example 1.171. Synthesis of (S)—N-(1-(3-hydroxyphenyl)ethyl)-4-methyl-2-(4-(trifluoromethyl)phenyl)quinoline-7-carboxamide (I-269

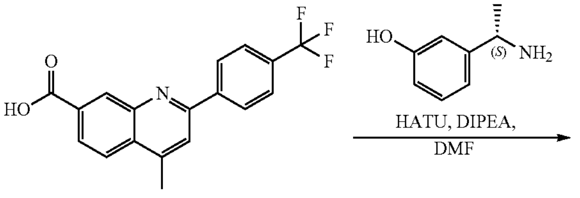

I-89

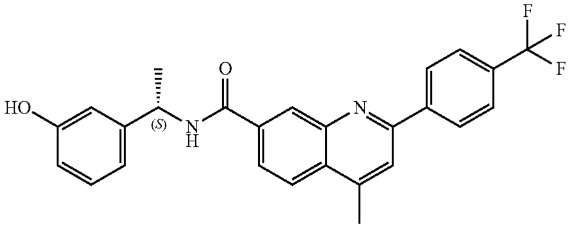

I-269

The following compound was prepared in a manner analogous to the procedures described above for (4-methyl-2-(4-(trifluoromethyl)phenyl)quinoline-7-carboxamide (I-258):

(S)—N-(1-(3-hydroxyphenyl)ethyl)-4-methyl-2-(4-(trifluoromethyl)phenyl)quinoline-7-carboxamide (I-269) (0.145 g, 36%) as a white solid. $^1$H NMR (400 MHz, DMSO-$d_6$) δ: 9.42-9.40 (br. s, 1H), 9.19-9.17 (d, J=8.4 Hz, 1H), 8.74-8.73 (d, J=1.6 Hz, 1H), 8.54-8.52 (d, J=8.0 Hz, 2H), 8.23 (s, 1H) 8.22-8.20 (d, J=8.8 Hz, 1H), 8.10-8.07 (dd, J=1.6, 8.8 Hz, 1H), 7.96-7.94 (d, J=8.0 Hz, 2H), 7.14-7.10 (t, J=4.0 Hz, 1H), 6.87-6.85 (m, 2H), 6.64-6.62 (dd, J=1.6, 8.4 Hz, 1H), 5.19-5.12 (m, 1H), 2.82 (s, 3H), 1.52-1.50 (d, J=7.2 Hz, 3H), MS: $[MH]^+$451.4, Chiral HPLC=100%

Example 1.172. Synthesis of 4-(methoxymethyl)-2-(4-(trifluoromethyl)phenyl)quinoline-7-carboxylic acid (I-270

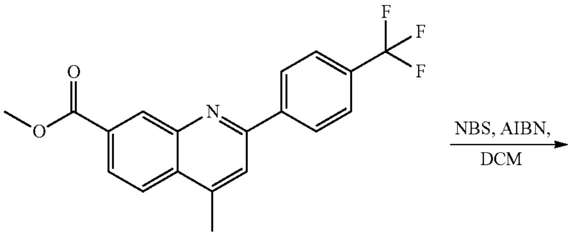

X-1310A1

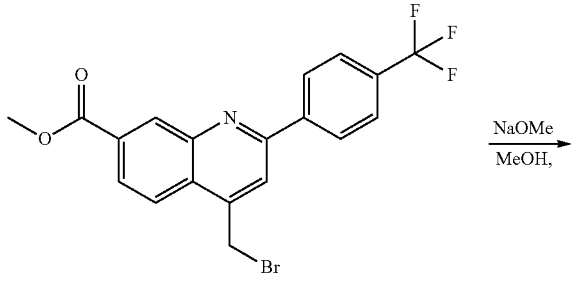

X-1860B1

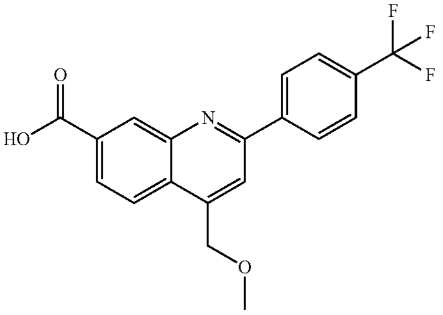

I-270

Methyl 4-methyl-2-(4-(trifluoromethyl)phenyl)quinoline-7-carboxylate (X-1310A1) was prepared in a manner analogous to the procedures described above in Example 1.14

Synthesis of methyl 4-(bromomethyl)-2-(4-(trifluoromethyl)phenyl)quinoline-7-carboxylate (X-1860B1). To a stirred solution of methyl 4-methyl-2-(4-(trifluoromethyl)phenyl)quinoline-7-carboxylate (X-1310A1) (1.0 g, 2.89 mmol) in dichloromethane (10 mL) were added N-bromosuccinimide (1.0 g, 6.08 mmol) and AIBN (0.095 g, 0.57 mmol) at room temperature under nitrogen atmosphere and resulting reaction mixture was heated at 50° C. for 16 h. Reaction mixture was diluted with water (150 mL) was extracted with dichloromethane (100 mL×2). Combined extracts were dried over anhydrous $Na_2SO_4$ and concentrated in vacuo. The crude was purified by silica gel column chromatography with using ethyl acetate-hexane=0:1→1:4 to afford methyl 4-(bromomethyl)-2-(4-(trifluoromethyl)phenyl)quinoline-7-carboxylate (X-1860B1) (0.900 g, 75%) as an off-white solid. MS: $[MH]^+$424.3, $[MH]^{+2}$ 426.3.

4-(Methoxymethyl)-2-(4-(trifluoromethyl)phenyl)quinoline-7-carboxylic acid (I-270). To a stirred solution of methyl 4-(bromomethyl)-2-(4-(trifluoromethyl)phenyl)quinoline-7-carboxylate (X-1860B1) (0.500 g, 1.18 mmol) in methanol (5 mL) was added NaOMe (25% in MeOH) (0.9 mL, 3.54 mmol) at room temperature under nitrogen atmosphere and resulting reaction mixture was heated at 80° C. for 4 h. The reaction mixture was concentrated under reduced pressure, crude mass was diluted with water (20 mL) and was acidified (pH~2-3) with an aqueous 1N HCl, and the resulting precipitate was collected by filtration. Obtained residue was washed with cold water until the pH of the filtrate became neutral (pH~6-7). The obtained solid was dried in vacuo to afford 4-(methoxymethyl)-2-(4-(trifluoromethyl)phenyl)quinoline-7-carboxylic acid (I-270) (0.270 g, 64%) as an off white solid. $^1$H NMR (400 MHz, DMSO-$d_6$) δ: 8.63 (s, 1H), 8.48-8.46 (d, J=8.0 Hz, 2H), 8.18 (s, 1H), 8.16-8.15 (d, J=4.0 Hz, 1H), 8.00-7.98 (d, J=8.4 Hz, 1H), 7.92-7.90 (d, J=8.0 Hz, 2H), 5.01 (s, 2H), 3.47 (s, 3H), MS: $[MH]^+$ 362.32.

Example 1.173. Synthesis of (R)—N-(1-hydroxypropan-2-yl)-4-(methoxymethyl)-2-(4-(trifluoromethyl)phenyl)quinoline-7-carboxamide (I-271)

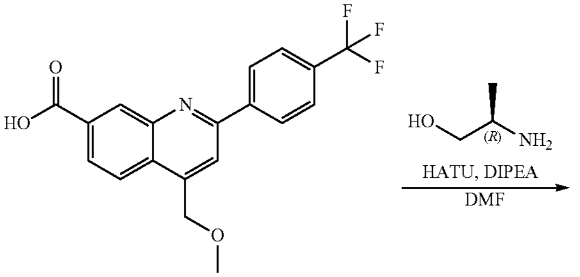

I-270

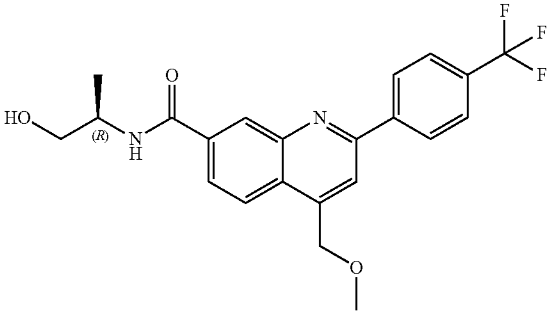

I-271

The following compound was prepared in a manner analogous to the procedures described above for (4-methyl-2-(4-(trifluoromethyl)phenyl)quinoline-7-carboxamide (I-258):

(R)—N-(1-hydroxypropan-2-yl)-4-(methoxymethyl)-2-(4-(trifluoromethyl)phenyl)quinoline-7-carboxamide (I-271) (0.100 g, 59%) as an off-white solid. $^1$H NMR (400 MHz, DMSO-$d_6$) δ: 8.69 (s, 1H), 8.52-8.50 (d, J=8.0 Hz, 2H), 8.50 (s, 1H), 8.26 (s, 1H), 8.18-8.16 (d, J=8.8 Hz, 1H), 8.09-8.06 (dd, J=1.2, 8.4 Hz, 1H), 7.97-7.95 (d, J=8.4 Hz, 2H), 5.05 (s, 2H), 4.80-4.77 (t, J=6.0 Hz, 1H), 4.12-4.08 (m, 1H), 3.56-3.52 (m, 1H), 3.49 (s, 3H), 3.43-3.37 (m, 1H), 1.20-1.18 (d, J=6.8 Hz, 3H). MS: $[MH]^+$ 419.4, Chiral HPLC=100%

Example 1.174. Synthesis of: 4-(3-(trifluoromethyl)bicyclo[1.1.1]pentan-1-yl)pyrrolo[1,2-a]quinoxaline-7-carboxylic acid (I-272)

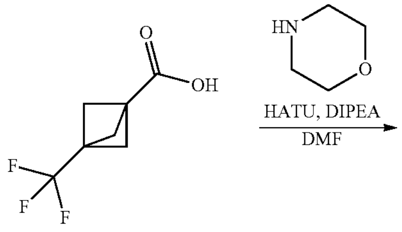

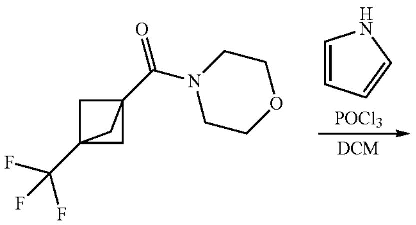

X-1311A1

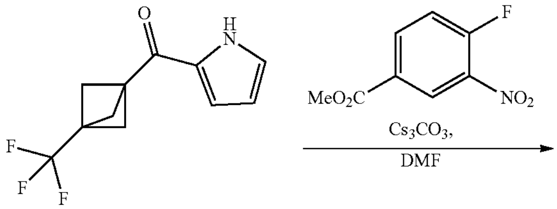

X-1311A2

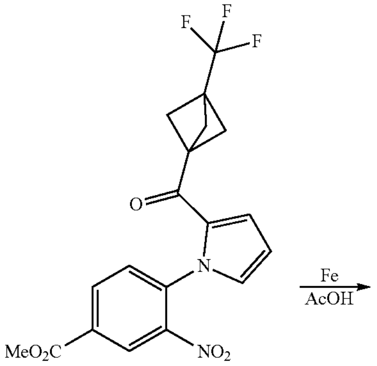

X-1311A3

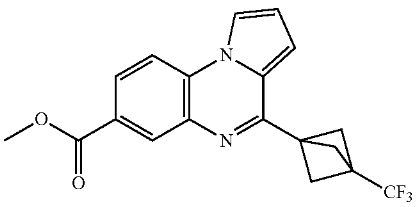

X-1311A4

THF, $H_2O$ LiOH:$H_2O$

-continued

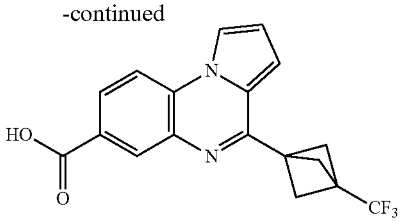

I-272

Morpholino(3-(trifluoromethyl)bicyclo[1.1.1]pentan-1-yl)methanone (X-1311A1). To a stirred solution of 3-(trifluoromethyl)bicyclo[1.1.1]pentane-1-carboxylic acid (0.600 g, 3.33 mmol)) in DMF (8 mL) were added DIPEA (1.2 mL, 9.99 mmol) and HATU (2.5 g, 6.66 mmol) at 0° C. After 15 min of stirring at the same temperature, was added a solution of morpholine (0.652 g, 7.50 mmol) in DMF (2 mL) drop-wise and the resulting reaction mixture was stirred at room temperature for 2 h. Reaction mixture was poured into ice water (150 mL) and was extracted by ethyl acetate (50 mL×3). The combined organic extracts were washed with brine (100 mL) and dried over anhydrous $Na_2SO_4$ and concentrated under reduce pressure. to afford morpholino (3-(trifluoromethyl)bicyclo[1.1.1]pentan-1-yl)methanone (X-1311A1) (0.600 g, 72%) as a brown semi-solid. MS: $[MH]^+$ 250.0.

1H-pyrrol-2-yl) (3-(trifluoromethyl)bicyclo[1.1.1]pentan-1-yl)methanone (X-1311A2). To a stirred solution of morpholino(3-(trifluoromethyl)bicyclo[1.1.1]pentan-1-yl) methanone (X-1311A1) (0.600 g, 2.40 mmol) in dichloromethane (5 mL) was added $POCl_3$ (1.1 g, 7.20 mmol) at room temperature and stirred at same temperature for 16 h. 1H-pyrrole (0.322 g, 4.81 mmol) was added into reaction solution at room temperature and stirring was continued for another 4 h at the same temperature. Reaction mixture was poured into ice cold solution of aqueous sodium bicarbonate (100 mL) and was extracted by ethyl acetate (50 mL×3). The combined organic extracts were dried over anhydrous $Na_2SO_4$ and concentrated under reduce pressure. Obtained crude product was purified by silica gel column chromatography, using, ethyl acetate-hexane=1:9→1:4 as a gradient, to afford (1H-pyrrol-2-yl)(3-(trifluoromethyl)bicyclo[1.1.1]pentan-1-yl)methanone (X-1311A2) (0.300 g, 54%) as an brown solid. MS: $[MH]^+$ 230.0

Methyl 3-nitro-4-(2-(3-(trifluoromethyl)bicyclo[1.1.1]pentane-1-carbonyl)-1H-pyrrol-1-yl)benzoate (X-1311A3) To a stirred solution of (1H-pyrrol-2-yl) (3-(trifluoromethyl)bicyclo[1.1.1]pentan-1-yl)methanone (X-1311A2) (0.300 g, 1.31 mmol) and methyl 4-fluoro-3-nitrobenzoate (0.390 g, 1.96 mmol) in DMF (10 mL) was added cesium carbonate (0.850 g, 2.62 mmol) at room temperature and stirred for 2 h. The reaction mixture was slowly poured into ice water (150 mL) and was extracted with ethyl acetate (50 mL×3). The combined organic extracts were dried over anhydrous $Na_2SO_4$ and concentrated under reduce pressure. Obtained crude product was purified by silica gel column chromatography using, ethyl acetate-hexane=1:9-1:4 as a gradient, to afford methyl 3-nitro-4-(2-(3-(trifluoromethyl)bicyclo[1.1.1]pentane-1-carbonyl)-1H-pyrrol-1-yl)benzoate (X-1311A3) (0.260 g, 48%) as a yellow solid. MS: [MH]- 407.3

Methyl 4-(3-(trifluoromethyl)bicyclo[1.1.1]pentan-1-yl) pyrrolo[1,2-a]quinoxaline-7-carboxylate (X-1311A4). To a stirred solution of methyl 3-nitro-4-(2-(3-(trifluoromethyl) bicyclo[1.1.1]pentane-1-carbonyl)-1H-pyrrol-1-yl)benzoate (X-1311A3) (0.250 g, 0.61 mmol) in acetic acid (3 mL) was added Fe powder (0.342 g, 6.12 mmol) at room temperature and stirred at 90° C. for 1 h. After cooling to room temperature, reaction mixture was filtered and the precipitate was washed with water. The precipitate was taken in 10% methanol in dichloromethane, stirred for 30 min and filtered through a celite bed and filtrate was concentrated under reduced pressure, to afford methyl 4-(3-(trifluoromethyl) bicyclo[1.1.1]pentan-1-yl)pyrrolo[1,2-a]quinoxaline-7-carboxylate (X-1311A4) (0.200 g, 87%; crude) as a brown solid, which was used in next step without further purification. MS: $[MH]^+$361.1.

4-(3-(Trifluoromethyl)bicyclo[1.1.1]pentan-1-yl)pyrrolo [1,2-a]quinoxaline-7-carboxylic acid (I-272). To a stirred solution of methyl 4-(3-(trifluoromethyl)bicyclo[1.1.1]pentan-1-yl)pyrrolo[1,2-a]quinoxaline-7-carboxylate (X-1311A4) (0.200 g, 0.55 mmol) in a mixture of THE-water (3:1; 4 mL) was added lithium hydroxide monohydrate (0.071 g, 1.66 mmol) at room temperature under nitrogen and the resulting reaction mixture was heated at 60° C. for 2 h. After cooling to room temperature, the reaction mixture was concentrated under reduced pressure, crude mass was diluted with water (5 mL) and was extracted with ethyl acetate (10 mL×2) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was dried reduced pressure and triturated with diethyl ether (5 mL×2), to afford 4-(3-(trifluoromethyl) bicyclo[1.1.1]pentan-1-yl)pyrrolo[1,2-a]quinoxaline-7-carboxylic acid (I-272) (0.085 g, 45%) as a brown solid. $^1H$ NMR (400 MHz, DMSO-$d_6$) δ 13.17 (br. s, 1H), 8.56 (s, 1H), 8.39-8.35 (m, 2H), 8.09-8.07 (d, J=8.4 Hz, 1H), 7.30-7.29 (d, J=4.0 Hz, 1H), 7.02-7.01 (d, J=3.2 Hz, 1H), 2.56 (s, 6H). MS: $[MH]^+$ 347.02.

Example 1.175. Synthesis of 4-(4-(tert-butyl)phenyl)-2-methoxypyrrolo[1,2-a]quinoxaline-7-carboxylic acid (I-180)

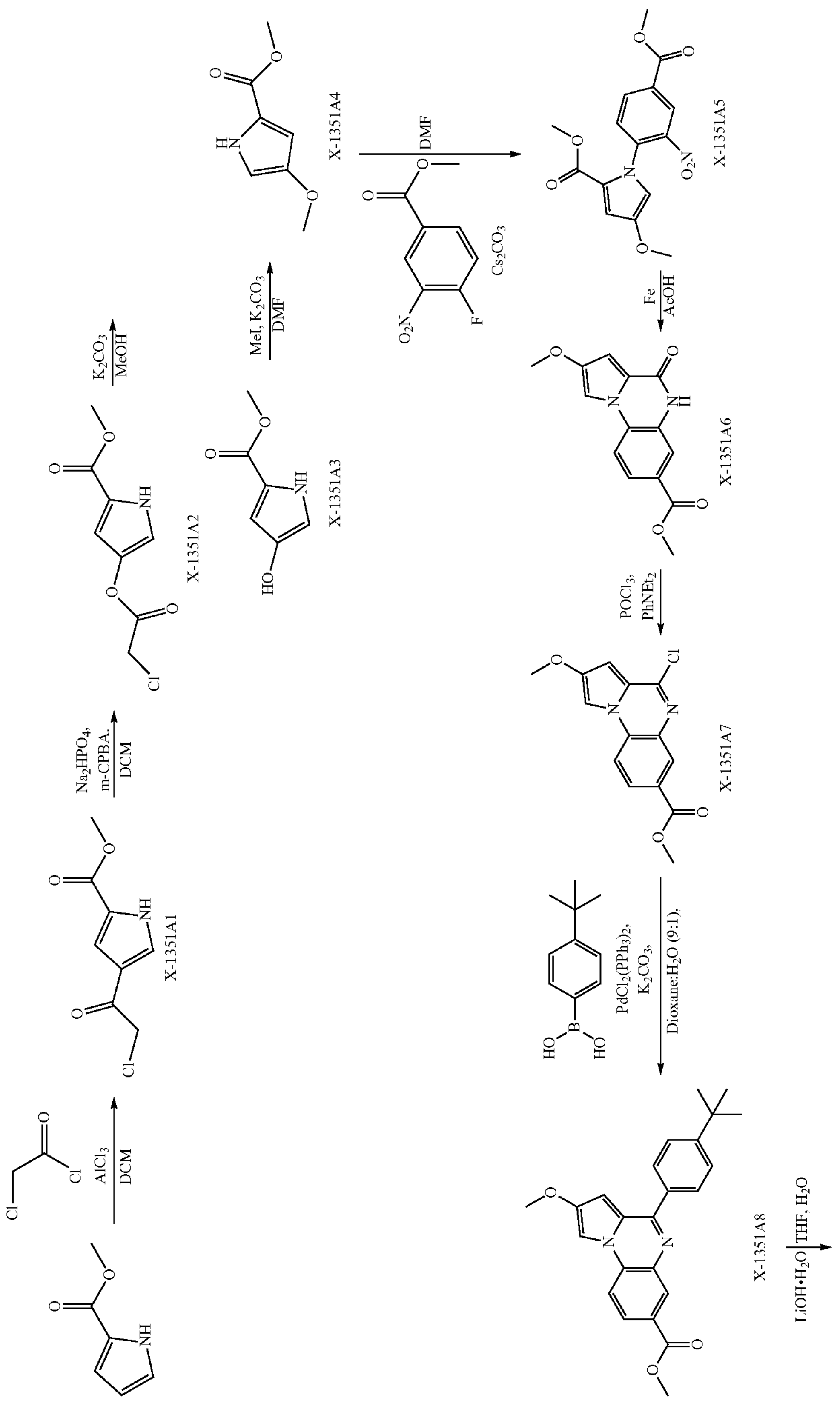
X-1351A1
X-1351A2
X-1351A3
X-1351A4
X-1351A5
X-1351A6
X-1351A7
X-1351A8

-continued
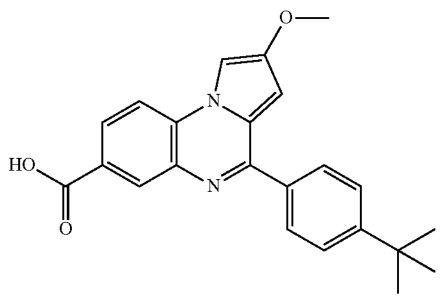
I-180

Methyl 4-(2-chloroacetyl)-1H-pyrrole-2-carboxylate (X-1351A1). To a stirred suspension of $AlCl_3$ (163.8 g, 1232.00 mmol) in DCM (800 mL) was added 2-chloroacetyl chloride (146 g, 1310.00 mmol) dropwise at 0° C. and stirred at same temperature for 15 min. Methyl 1H-pyrrole-2-carboxylate (35 g, 280.00 mmol) was added at 0° C. under nitrogen and the resulting mixture was stirred at room temperature for 2 h. Reaction mixture was slowly quenched with water (2 L) and was extracted with DCM (2 L×3). Combined organic extracts were washed with aqueous sodium bicarbonate solution (2 L), dried over anhydrous $Na_2SO_4$ and concentrated under reduced pressure, to afford methyl 4-(2-chloroacetyl)-1H-pyrrole-2-carboxylate (X-1351A1) (47.0 g, 83%; crude) as an off-white solid. MS: $[MH]^+$ 202.03.

Methyl 4-(2-chloroacetoxy)-1H-pyrrole-2-carboxylatenitronicotinate (X-1351A2). To a stirred solution of methyl 4-(2-chloroacetyl)-1H-pyrrole-2-carboxylate (X-1351A1) (42.0 g, 208.95 mmol) in DCM (1 L) were added $Na_2HPO_4$ (118.6 g, 835.82 mmol) and m-CPBA (143.7 g, 835.82 mmol) at 0° C. under nitrogen and the resulting mixture was stirred at room temperature for 6 h. Reaction mixture was quenched with water (2 L) and was extracted with DCM (2 L×3). Combined organic extracts were washed with brine (2 L), dried over anhydrous $Na_2SO_4$ and concentrated under reduced pressure. The crude product was purified by silica gel column chromatography, using ethyl acetate-hexane=0:1→2:8 as a gradient, to afford methyl 4-(2-chloroacetoxy)-1H-pyrrole-2-carboxylate (X-1351A2) (30.0 g, 66%) as a yellow solid. MS: $[MH]^+$ 218.29.

Methyl 4-hydroxy-1H-pyrrole-2-carboxylate (X-1351A3). To a stirred solution of methyl 4-(2-chloroacetoxy)-1H-pyrrole-2-carboxylate (X-1351A2) (10.0 g, 46.08 mmol) in mixture of MeOH—$H_2O$ (8:2, 185 mL) was added potassium carbonate (31.7 g, 230.41 mmol) at room temperature and reaction was stirred at same temperature for 1 h. Reaction mixture was concentrated under reduced pressure and obtained crude was diluted with water (500 mL) and was extracted with ethyl acetate (500 mL×3). Combined organic extracts were dried over anhydrous $Na_2SO_4$ and concentrated under reduced pressure. Obtained crude was mixed with the crude of an identically prepared batch of (5.0 g), triturated with n-hexanes to afford methyl 4-hydroxy-1H-pyrrole-2-carboxylate (X-1351A3) (5.0 g, 51%; crude) as a brown solid, which was taken to the next step without further purification. MS: $[MH]^+$ 142.01.

Methyl 4-methoxy-1H-pyrrole-2-carboxylate (X-1351A4). To a stirred solution of methyl 4-hydroxy-1H-pyrrole-2-carboxylate (X-1351A3) (5.0 g, 35.46 mmol) in DMF (50 mL) was added potassium carbonate (9.70 g, 70.92 mmol) at room temperature. After 30 min of stirring at same temperature was added methyl iodide (5.0 g, 35.46 mmol) and the resulting mixture was stirred for 16 h at room temperature. Reaction was diluted with water (200 mL) and was extracted with ethyl acetate (250 mL×2). Combined organic extracts were dried over anhydrous $Na_2SO_4$, and concentrated under reduced pressure to give crude. Obtained crude was purified by silica gel column chromatography with using ethyl acetate-hexane=0:1→1:9 as a gradient, to afford Methyl 4-methoxy-1H-pyrrole-2-carboxylate (X-1351A4) (2.30 g, 42%) as an off-white solid. MS: $[MH]^+$ 156.01.

Methyl 4-methoxy-1-(4-(methoxycarbonyl)-2-nitrophenyl)-1H-pyrrole-2-carboxylate (X-1351A5). To a stirred solution of Methyl 4-methoxy-1H-pyrrole-2-carboxylate (X-1351A4) (2.3 g, 14.83 mmol) DMF (20 mL) were added cesium carbonate (9.6 g, 29.67 mmol) and methyl 4-fluoro-3-nitrobenzoate (2.95 g, 14.83 mmol) sequentially at room temperature under nitrogen and the resulting mixture was stirred at 80° C. for 16 h. Reaction mixture was cooled to room temperature and poured into water (200 mL) and was extracted with ethyl acetate (200 mL×2). Combined organic extracts were dried over anhydrous $Na_2SO_4$, and was concentrated under reduced pressure. Obtained crude was purified by silica gel column chromatography with using ethyl acetate-hexane=2:8→:3.7 as gradient, to afford Methyl 4-methoxy-1-(4-(methoxycarbonyl)-2-nitrophenyl)-1H-pyrrole-2-carboxylate (X-1351A5) (4.5 g, 91%) as a yellow solid. MS: $[MH]^+$ 335.02.

Methyl 2-methoxy-4-oxo-4,5-dihydropyrrolo[1,2-a]quinoxaline-7-carboxylate (X-1351A6). To a stirred solution of methyl 4-methoxy-1-(4-(methoxycarbonyl)-2-nitrophenyl)-1H-pyrrole-2-carboxylate (X-1351A5) (1.0 g, 2.99 mmol) in acetic acid (10 mL) was added Fe-powder (0.622 g, 23.95 mmol) at 0° C. and reaction was allowed to stirred at 70° C. for 1 h. Reaction mixture cooled to room temperature, filtered over a Buchner funnel and the precipitate was washed with water. The precipitate was taken in 50% methanol in DCM, stirred for 30 min and filtered through a celite bed, filtrate was concentrated under reduced pressure, to afford methyl 2-methoxy-4-oxo-4,5-dihydropyrrolo[1,2-a]quinoxaline-7-carboxylate (X-1351A6) (0.600 g (crude), 74%) as a yellow solid, which was taken to the next step without further purification. MS: $[MH]^+$ 272.95

Methyl 4-chloro-2-hydroxypyrrolo[1,2-a]quinoxaline-7-carboxylate (X-1351A7). N, N-diethyl aniline (0.3 mL) was added to a stirred suspension of methyl 2-methoxy-4-oxo-4,5-dihydropyrrolo[1,2-a]quinoxaline-7-carboxylate (X-1351A6) (0.600 g, 2.20 mmol) in $POCl_3$ (12 mL) at 0° C. and the resulting mixture was heated at 80° C. for 16 h. Reaction was cooled room temperature and slowly poured ice water (150 mL) and was extracted with ethyl acetate (100 mL×2). Combined organic extracts were dried over anhydrous $Na_2SO_4$, and concentrated under reduced pressure to afford Methyl 4-chloro-2-hydroxypyrrolo[1,2-a]quinoxaline-7-carboxylate (X-1351A7) (0.600 g, quant.; crude) as a yellow solid, which is proceed to next step without further purification. MS: $[MH]^+$ 290.96

Methyl 4-(4-(tert-butyl)phenyl)-2-methoxypyrrolo[1,2-a]quinoxaline-7-carboxylate (X-1351A8). To a stirred solution of methyl 4-chloro-2-hydroxypyrrolo[1,2-a]quinoxaline-7-carboxylate (X-1351A7) (0.300 g, 1.03 mmol) in a mixture of 1,4-dioxane-water (3:1, 10 mL) were added (4-(tert-butyl)phenyl)boronic acid (0.276 g, 1.55 mmol) and $K_2CO_3$ (0.428 g, 3.10 mmol) at room temperature. The reaction mixture was degassed (purging with nitrogen) for 20 min followed by addition of $PdCl_2(PPh_3)_2$ (0.021 g, 0.03 mmol) and the reaction mixture was heated at 90° C. for 2 h. The reaction mixture was cooled to room temperature, diluted with water (100 mL) and was extracted with ethyl acetate (50 mL×3). The combined organic extracts were dried over anhydrous $Na_2SO_4$ and concentrated under reduce pressure. The crude product was purified by silica gel column chromatography, using ethyl acetate-Hexane=1:9→2:8 as a gradient, to afford methyl 4-(4-(tert-butyl)phenyl)-2-methoxypyrrolo[1,2-a]quinoxaline-7-carboxylate (X-1351A8) (0.200 g, 50%) as an off-white solid. MS: [MH]+ 389.17.

4-(4-(tert-butyl)phenyl)-2-methoxypyrrolo[1,2-a]quinoxaline-7-carboxylic acid (I-180). To a stirred solution of Methyl 4-(4-(tert-butyl)phenyl)-2-methoxypyrrolo[1,2-a]quinoxaline-7-carboxylate (X-1351A8) (0.200 g, 0.51 mmol) in in a mixture of THF-water (4:1; 4.2 mL) was added lithium hydroxide monohydrate (0.042 g, 1.54 mmol) at room temperature and the resulting mixture was heated at 70° C. for 2 h. After cooling to room temperature, reaction mixture was concentrated under reduced pressure and diluted with water (5 mL), acidified (pH 2-3) with an aqueous 1N HCl solution and the resulting precipitate was collected by filtration. Obtained residue was washed with cold water until the pH of the filtrate became neutral (pH~6-7), triturated with n-Pentane (20 mL×2), dried under reduced pressure to afford 4-(4-(tert-butyl)phenyl)-2-methoxypyrrolo[1,2-a]quinoxaline-7-carboxylic acid (I-180) (0.120 g, 62%) as an off-white solid. $^1$H NMR (400 MHz, DMSO-$d_6$) δ: 13.26 (br. s, 1H), 8.77 (s, 1H), 8.61 (s, 1H), 8.47-8.45 (d, J=8.4 Hz, 1H), 8.20-8.18 (d, J=8.4 Hz, 1H), 7.99-7.97 (d, J=8.0 Hz, 2H), 7.71-7.69 (d, J=8.4 Hz, 2H), 7.09 (s, 1H), 3.93 (s, 3H), 1.37 (s, 9H). MS: $[MH]^+$ 375.17.

Example 1.176. Synthesis of N-(2-(1-(4-(trifluoromethyl)phenyl)isoquinolin-3-yl)propan-2-yl)acrylamide (I-273)

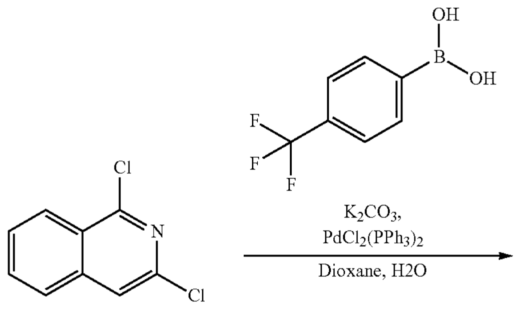

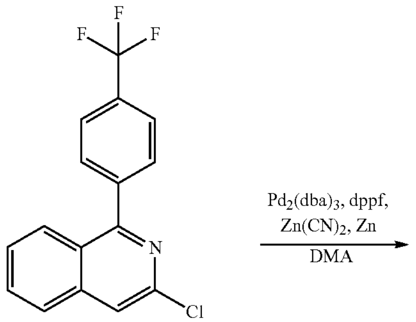

X-1652A1

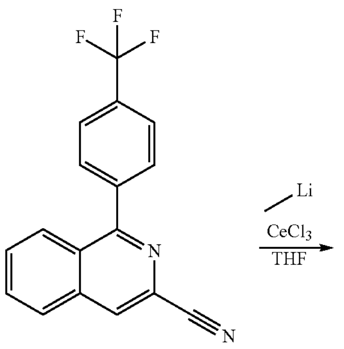

X-1652A2

-continued

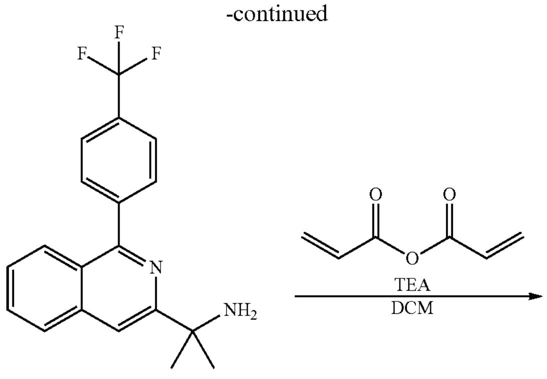

X-1652A3

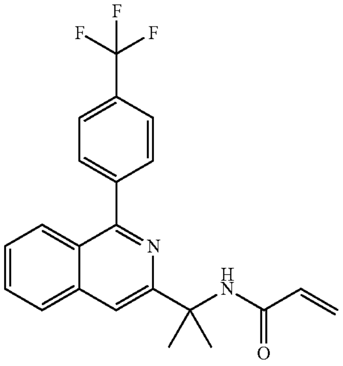

I-273

3-Chloro-1-(4-(trifluoromethyl)phenyl)isoquinoline (X-1652A1). To a stirred solution of 1,3-dichloroisoquinoline (5.0 g, 25.33 mmol) in a mixture of dioxane-water (4:1, 25 mL) were added (4-(trifluoromethyl)phenyl)boronic acid (4.8 g, 25.33 mmol) and $K_2CO_3$ (10.50 g, 76.14 mmol) at room temperature. The reaction mixture was degassed (purging with nitrogen) for 20 min followed by addition of $PdCl_2(PPh_3)_2$ (1.42 g, 2.03 mmol) and the reaction mixture was heated at 110° C. for 2 h. The reaction mixture was cooled to room temperature, diluted with water (200 mL) and was extracted with ethyl acetate (300 mL×3). The combined organic extracts were dried over anhydrous $Na_2SO_4$ and concentrated under reduce pressure. The crude product was purified by silica gel column chromatography, using ethyl acetate-Hexane=2:8→4:6 as gradient, to afford 3-chloro-1-(4-(trifluoromethyl)phenyl)isoquinoline (X-1652A1) (5.5 g, 70%) as an off-white solid. $[MH]^+$ 308.0.

1-(4-(Trifluoromethyl)phenyl)isoquinoline-3-carbonitrile (X-1652A2). To a stirred solution of 3-chloro-1-(4-(trifluoromethyl)phenyl)isoquinoline (X-1652A1) (5.5 g, 17.91 mmol) in a DMF (10 mL) were added zinc cyanide (6.28 g, 53.74 mmol) and Zn dust (3.49 g, 53.74 mmol) at room temperature. The reaction mixture was degassed (purging with nitrogen) for 20 min followed by addition of dppf (0.79 g, 1.43 mmol) and $Pd_2(dba)_3$ (1.31 g, 1.43 mmol) and the reaction mixture was heated at 130° C. under microwave irradiation for 1 h. The reaction mixture was cooled to room temperature, diluted with water (100 mL) and was extracted with ethyl acetate (300 mL×3). The combined organic extracts were dried over anhydrous $Na_2SO_4$ and concentrated under reduce pressure. The crude product was purified by silica gel column chromatography, using ethyl acetate-hexane=4:646:4 as gradient, to afford 1-(4-(trifluoromethyl)

phenyl)isoquinoline-3-carbonitrile (X-1652A2) (3.0 g, 56%) as a yellow solid. [MH]$^+$ 298.9.

2-(1-(4-(Trifluoromethyl)phenyl)isoquinolin-3-yl)propan-2-amine (X-1652A3). To a stirred solution of 1-(4-(trifluoromethyl)phenyl)isoquinoline-3-carbonitrile (X-1652A2) (1.5 g, 5.03 mmol) in THE (10 mL) was added CeCl3 (3.71 g, 15.10 mmol) at −78° C. under nitrogen, resulting mixture was stirred at −78° C. to room temperature for 30 min and MeLi (16.23 g, 50.33 mmol) at −78° C. under nitrogen. The reaction mixture stirred at at −78° C. to room temperature for 16 h. The reaction mixture was diluted by sodium hydroxide to $P^H$~8. The reaction mixture was cooled to room temperature, diluted with water (100 mL) and was extracted with ethyl acetate (300 mL×3). The combined organic extracts were dried over anhydrous $Na_2SO_4$ and concentrated under reduce pressure, to afford 2-(1-(4-(trifluoromethyl)phenyl)isoquinolin-3-yl)propan-2-amine (X-1652A3) (0.6 g, Quantitative) as a Yellow solid. Crude was used in next step without purification. MS: [MH]$^+$ 331.2

N-(2-(1-(4-(trifluoromethyl)phenyl)isoquinolin-3-yl)propan-2-yl)acrylamide (I-273). To a stirred solution of 2-(1-(4-(trifluoromethyl)phenyl)isoquinolin-3-yl)propan-2-amine (X-1652A3) (0.6 g, 1.81 mmol) in DCM (10 mL) were added tri ethylamine (0.55 g, 5.45 mmol) and Acrylic anhydride (0.34 g, 2.72 mmol) at 0° C. and reaction mixture was stirred at rt for 30 min. The reaction mixture was diluted with aqueous $NaHCO_3$ (10 mL) and was extracted by ethyl acetate (30 mL×3). The combined organic extracts were dried over anhydrous $Na_2SO_4$ and concentrated under reduce pressure. The crude product was purified by Prep HPLC, to afford N-(2-(1-(4-(trifluoromethyl)phenyl)isoquinolin-3-yl)propan-2-yl)acrylamide (I-273) (0.014 g, 2%) as an off white solid. $^1$H NMR (400 MHz, DMSO-$d_6$) δ 8.44 (s, 1H), 8.07-8.05 (d, J=8.0 Hz, 1H), 8.00-7.90 (m, 5H), 7.82 (s, 1H), 7.80-7.76 (t, J=7.2 Hz, 1H), 7.64-7.62 (t, J=7.2 Hz, 1H), 6.46-6.39 (m, 1H), 6.02-5.98 (dd, J=17.2, 2.4 Hz, 1H), 5.57-5.54 (dd, J=10.0, 2.4 Hz, 1H), 1.74 (s, 6H). [MH]$^+$ 385.1.

Example 1.177. Synthesis of 4-(4-(tert-butyl)phenyl)-2-(difluoromethoxy)pyrrolo[1,2-a]quinoxaline-7-carboxylic acid (I-274)

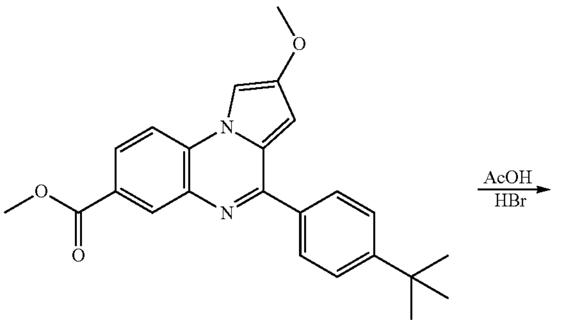

X-1351A8

-continued

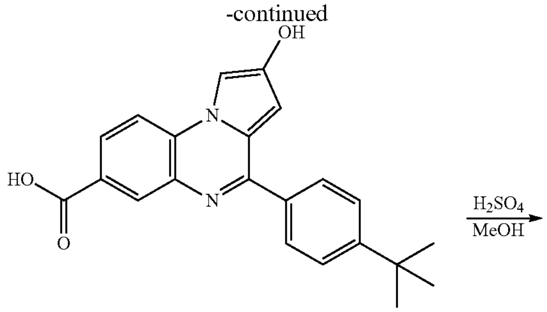

X-1616B1

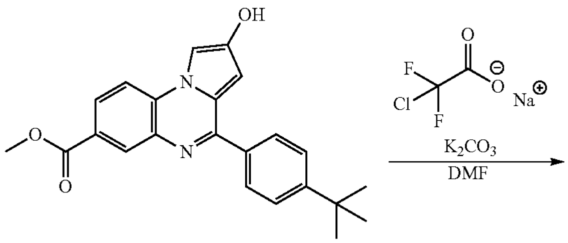

X-1616B2

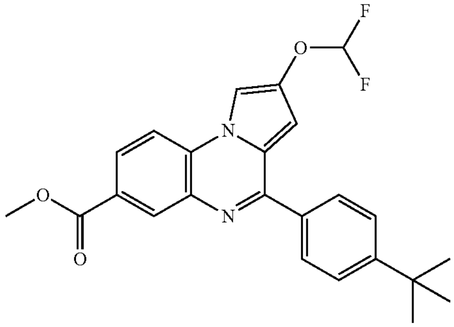

X-1616B3

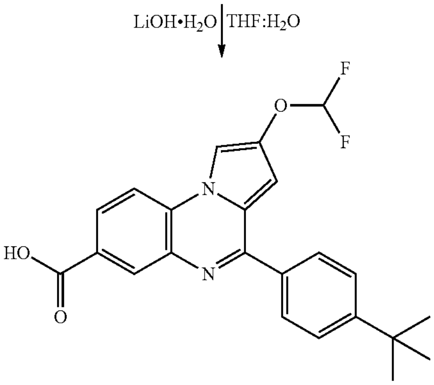

I-274

Synthesis of 4-(4-(tert-Butyl)phenyl)-2-methoxypyrrolo[1,2-a]quinoxaline-7-carboxylate (X-1351A8) provided above in Example 1.175

4-(4-(tert-Butyl)phenyl)-2-hydroxypyrrolo[1,2-a]quinoxaline-7-carboxylic acid (X-1616B1). To a stirred solution of 4-(4-(tert-Butyl)phenyl)-2-methoxypyrrolo[1,2-a]quinoxaline-7-carboxylate (X-1351A8) (0.300 g, 0.77 mmol) in acetic acid (6 mL) was added 33% HBr in acetic acid (22 mL) at room temperature under nitrogen and the resulting reaction mixture was heated at 120° C. for 48 h in sealed tube. After completion of reaction, reaction mixture was cooled to room temperature, reaction mixture was slowly poured into ice-water (50 mL) and the resulting precipitate was collected by filtration. Obtained solid residue was washed with water (50 mL), dried under high vacuum to afford 4-(4-(tert-butyl)phenyl)-2-hydroxypyrrolo[1,2-a]quinoxaline-7-carboxylic acid (X-1616B1) (0.220 g, 79%) as a white solid. MS: $[MH]^+$ 361.07.

Methyl 4-(4-(tert-butyl)phenyl)-2-hydroxypyrrolo[1,2-a]quinoxaline-7-carboxylate (X-1616B2). Concentrated H2$SO_4$ (1 mL) was added to a stirred solution of 4-(4-(tert-butyl)phenyl)-2-hydroxypyrrolo[1,2-a]quinoxaline-7-carboxylic acid (X-1616B1) (0.220 g, 0.611 mmol) in a methanol (3 mL) at room temperature and the resulting mixture was heated at 70° C. for 16 h. After completion of reaction, reaction mixture was cooled to room temperature, was slowly poured into an aqueous solution of saturated $NaHCO_3$ (50 mL) and was extracted with ethyl acetate (50 mL×3). Combined organic extracts were dried over anhydrous $Na_2SO_4$ and concentrated under reduced pressure. Obtained crude was purified by silica gel column chromatography, using ethyl acetate-hexane=0:1→4 5:5 as gradient, to afford methyl 4-(4-(tert-butyl)phenyl)-2-hydroxypyrrolo[1,2-a]quinoxaline-7-carboxylate (X-1616B2) (0.180 g, 78%) as an off-white. MS: $[MH]^+$ 375.1.

Methyl 4-(4-(tert-butyl)phenyl)-2-(difluoromethoxy)pyrrolo[1,2-a]quinoxaline-7-carboxylate (X-1616B3). To a solution of methyl 4-(4-(tert-butyl)phenyl)-2-hydroxypyrrolo[1,2-a]quinoxaline-7-carboxylate (X-1616B2) (0.180 g, 0.481 mmol) in a DMF (4.5 mL) were added $K_2CO_3$ (0.398 g, 2.88 mmol) and 2-chloro-2,2-difluoroacetate (0.365 g, 2.40 mmol). The reaction mixture was stirred at 80° C. for 3.5 h. After completion of reaction, reaction mixture was cooled to room temperature, was diluted with water (50 mL) and was extracted with ethyl acetate (50 mL×3). The combined organic extracts were dried over anhydrous $Na_2SO_4$ and concentrated under reduce pressure. Obtained crude was purified by silica gel column chromatography, using ethyl acetate-hexane=0:1→6:4 as gradient to afford methyl 4-(4-(tert-butyl)phenyl)-2-(difluoromethoxy)pyrrolo[1,2-a]quinoxaline-7-carboxylate (X-1616B3) (0.050 g, 25%) as an off-white solid MS: $[MH]^+$ 425.1.

4-(4-(tert-Butyl)phenyl)-2-(difluoromethoxy)pyrrolo[1,2-a]quinoxaline-7-carboxylic acid (I-274). To a stirred solution methyl 4-(4-(tert-butyl)phenyl)-2-(difluoromethoxy)pyrrolo[1,2-a]quinoxaline-7-carboxylate (X-1616B3) (0.050 g, 0.141 mmol) in THE-water (3:1; 2.6 mL) was added lithium hydroxide monohydrate (0.017 g, 0.424 mmol) at room temperature under nitrogen and the resulting mixture was heated at 70° C. for 1 h. After completion of reaction, reaction mixture was cooled to room temperature, was concentrated under reduced pressure, obtained crude was diluted with water (30 mL) and was acidified (pH~2-3) with an aqueous solution of 1N HCl and then extracted with ethyl acetate. Organic layer was washed with cold water until the pH of the filtrate became neutral (pH~6-7). Combined organic extracts were dried over anhydrous $Na_2SO_4$ and concentrated under reduced pressure. Obtained solid was triturated using n-pentane and dried under high vacuum to afford 4-(4-(tert-butyl)phenyl)-2-(difluoromethoxy)pyrrolo[1,2-a]quinoxaline-7-carboxylic acid (I-274) (0.020 g, 41%) as a yellow solid. MS: $[MH]^+$ 411.07. $^1H$ NMR (400 MHz, DMSO-$d_6$) δ 13.22 (s, 1H), 8.66 (s, 1H), 8.43 (s, 1H), 8.40-8.37 (dd, J=8.8, 2.4 Hz, 1H), 8.13-38.11 (d, J=8.4 Hz, 1H), 7.95-7.94 (d, J=6.4 Hz, 2H), 7.63-7.61 (d, J=6.4 Hz, 2H), 7.51-7.13 (m, 1H), 7.02 (s, 1H), 1.367-1.362 (d, J=2.0 Hz, 9H).

Example 1.178. Synthesis of 2-(difluoromethoxy)-4-(4-(trifluoromethyl)phenyl)pyrrolo[1,2-a]quinoxaline-7-carboxylic acid (I-275)

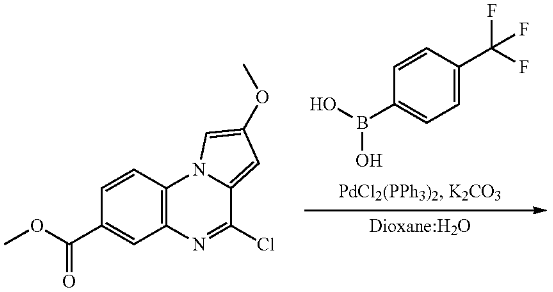

X-1351A7

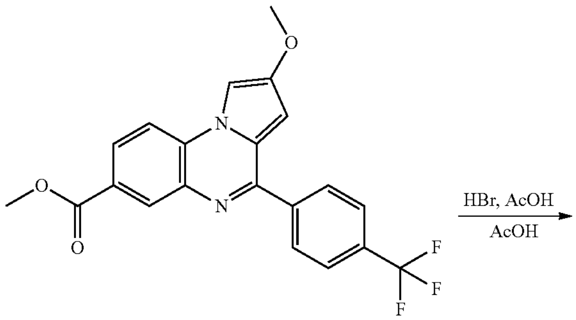

X-1728D1

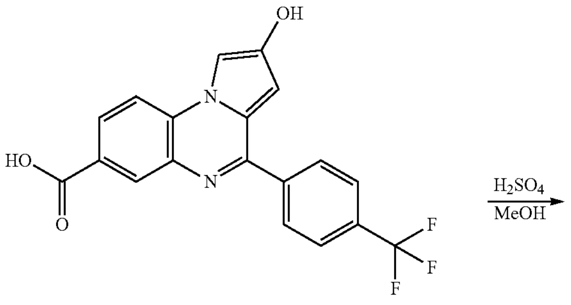

X-1728D2

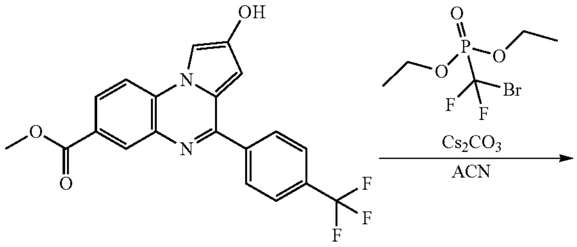

X-1728D3

-continued

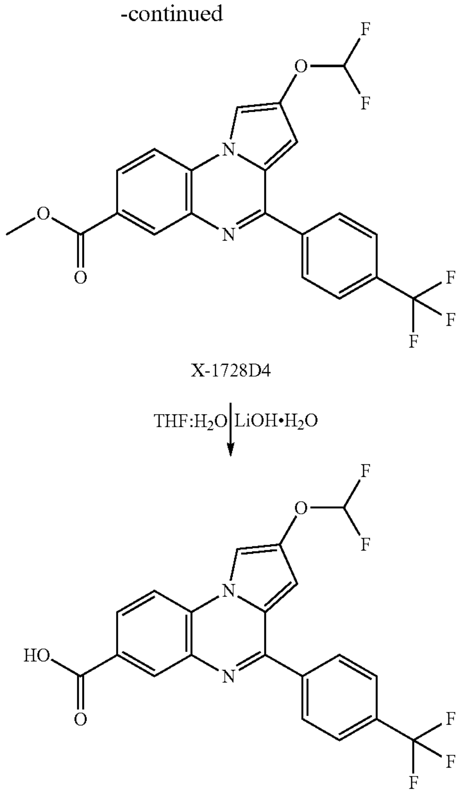

X-1728D4

I-275

Synthesis of methyl 4-chloro-2-hydroxypyrrolo[1,2-a]quinoxaline-7-carboxylate (X-1351A7) provided above target in Example 1.175

Methyl 2-methoxy-4-(4-(trifluoromethyl)phenyl)pyrrolo[1,2-a]quinoxaline-7-carboxylate (X-1728D1). To a stirred solution of methyl 4-chloro-2-hydroxypyrrolo[1,2-a]quinoxaline-7-carboxylate (X-1351A7) (2.5 g, 8.62 mmol) in a mixture of 1,4-dioxane-water (3:1, 40 mL) were added (4-(trifluoromethyl)phenyl)boronic acid (2.45 g, 12.93 mmol) and potassium carbonate (3.56 g, 25.80 mmol) sequentially at room temperature under nitrogen. The reaction mixture was degassed (purging with nitrogen) for 20 min followed by addition of $PdCl_2(PPh_3)_2$ (0.241 g, 0.34 mmol) and the resulting mixture was heated at 100° C. for 1 h. The reaction mixture was cooled to room temperature, diluted with water (150 mL) and was extracted with ethyl acetate (100 mL×2). The combined organic extracts were dried over anhydrous $Na_2SO_4$ and concentrated under reduce pressure to afford crude mass, which was purified by silica gel column chromatography, using ethyl acetate-Hexane=0:1→3:7 as eluent, to afford methyl 2-methoxy-4-(4-(trifluoromethyl)phenyl)pyrrolo[1,2-a]quinoxaline-7-carboxylate (X-1728D1) (3.26 g, 79%) as an off-white solid. MS: [MH]+ 401.40.

2-Hydroxy-4-(4-(trifluoromethyl)phenyl)pyrrolo[1,2-a]quinoxaline-7-carboxylic acid (X-1728D2). To a stirred solution of methyl 2-methoxy-4-(4-(trifluoromethyl)phenyl)pyrrolo[1,2-a]quinoxaline-7-carboxylate (X-1728D1) (2.0 g, 5.00 mmol) in acetic acid (15 mL) was added 37% HBr in acetic acid (5.3 mL, 20.00 mmol) at room temperature under nitrogen and the resulting mixture was heated at 120° C. for 48 h in a sealed tube. Reaction mixture was cooled to room temperature and was slowly poured into ice-water (100 mL). Resulting precipitate was collected by filtration and washed with water (80 mL) and dried under high vacuum to afford 2-hydroxy-4-(4-(trifluoromethyl)phenyl)pyrrolo[1,2-a]quinoxaline-7-carboxylic (X-1728D2) (2.20 g, 94%) as a white solid. MS: $[MH]^+$ 373.37.

Methyl 2-hydroxy-4-(4-(trifluoromethyl)phenyl)pyrrolo[1,2-a]quinoxaline-7-carboxylate (X-1728D3). To a stirred solution of 2-hydroxy-4-(4-(trifluoromethyl)phenyl)pyrrolo[1,2-a]quinoxaline-7-carboxylic (X-1728D2) (1.00 g, 2.68 mmol) in a methanol (10 mL) was added concentrated $H_2SO_4$ (0.28 mL) at room temperature and the resulting reaction mixture was heated at 70° C. for 4 h. After cooling to room temperature the reaction mixture was poured into ice-water (50 mL) and the resulting precipitate was collected by filtration. Obtained solid mass was washed with water (60 mL), dried under high vacuum to afford methyl 2-hydroxy-4-(4-(trifluoromethyl)phenyl)pyrrolo[1,2-a]quinoxaline-7-carboxylate (X-1728D3) (0.530 g, 51.08%) as a white solid. MS: $[MH]^+$ 386.96.

Methyl 2-(difluoromethoxy)-4-(4-(trifluoromethyl)phenyl)pyrrolo[1,2-a]quinoxaline-7-carboxylate (X-1728D4). To a stirred solution of methyl 2-hydroxy-4-(4-(trifluoromethyl)phenyl)pyrrolo[1,2-a]quinoxaline-7-carboxylate (X-1728D3) (0.400 g, 1.03 mmol) in acetonitrile (5 mL) were added cesium carbonate (1.01 g, 3.10 mmol) and diethyl (bromodifluoromethyl)phosphonate (0.415 g, 1.55 mmol) sequentially at room temperature under nitrogen and the resulting reaction mixture was heated at 80° C. for 3 h. After cooling to room temperature reaction mixture was poured into ice-water (50 mL) and was extracted with ethyl acetate (75 mL×2). Combined organic extracts were dried over anhydrous $Na_2SO_4$ and concentrated under reduced pressure to afford crude mass, which was purified by silica gel column chromatography, using ethyl acetate-hexane=0:1→1:4 as gradient, to afford methyl 2-(difluoromethoxy)-4-(4-(trifluoromethyl)phenyl)pyrrolo[1,2-a]quinoxaline-7-carboxylate (X-1728D4) (0.110 g, 31%) as a white solid. MS: $[MH]^+$ 437.35

2-(Difluoromethoxy)-4-(4-(trifluoromethyl)phenyl)pyrrolo[1,2-a]quinoxaline-7-carboxylic acid (I-275). To a stirred solution of methyl 2-(difluoromethoxy)-4-(4-(trifluoromethyl)phenyl)pyrrolo[1,2-a]quinoxaline-7-carboxylate (X-1728D4) (0.110 g, 0.252 mmol) in a mixture of THF-water (3:1; 4.0 mL) was added lithium hydroxide monohydrate (0.020 g, 0.50 mmol) at room temperature and the resulting mixture was heated at 60° C. for 3 h. After cooling to room temperature, reaction mixture was concentrated under reduced pressure, acidified (pH~2-3) with an aqueous 1N HCl solution and the resulting precipitate was collected by filtration. Obtained solid residue was washed with cold water until the pH (~6-7) to afford crude mass, which was purified by trituration with n-Pentane (40 mL) and dried under reduced pressure to afford 2-(difluoromethoxy)-4-(4-(trifluoromethyl)phenyl)pyrrolo[1,2-a]quinoxaline-7-carboxylic acid (I-275) (0.050 g, 46.9%) as an off-white solid. $^1H$ NMR (400 MHz, DMSO-$d_6$) 13.25 (s, 1H), 8.73 (s, 1H), 8.48-8.48 (d, J=1.6 Hz, 1H), 8.44-8.42 (d, J=8.4 Hz, 1H), 8.23-8.21 (d, J=8.0 Hz, 2H), 8.18-8.16 (dd, J=8.8 Hz, 1.6 Hz, 1H), 7.99-7.97 (d, J=8.0 Hz, 2H), 7.50-7.13 (t, J=74 Hz, H), 7.06 (s, 1H). MS: $[MH]^+$ 423.37.

Example 1.179. Synthesis of 2-hydroxy-4-(4-(trifluoromethyl)phenyl)pyrrolo[1,2-a]quinoxaline-7-carboxylic acid (I-276)

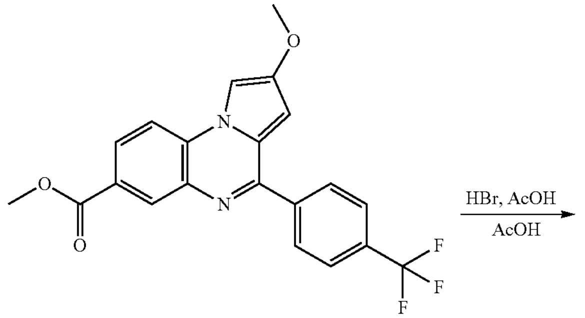

X-1728D1

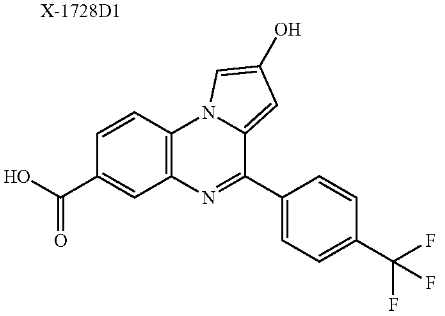

I-276

To a stirred solution of methyl 2-methoxy-4-(4-(trifluoromethyl)phenyl)pyrrolo[1,2-a]quinoxaline-7-carboxylate (X-1728D1) (0.500 g, 1.25 mmol) in acetic acid (4 mL) was added 33% HBr in acetic acid (1.3 mL, 5.00 mmol) at room temperature under nitrogen and the resulting solution was heated at 120° C. for 48 h in a sealed tube. After cooling to room temperature, reaction mixture was slowly poured into ice-water (100 mL) and the resulting precipitate was collected by filtration. Obtained solid residue was washed with water (80 mL), dried under high vacuum and finally, purified by prep HPLC using ACN-MeOH-IPA (65:25:10) and 0.05% $NH_3$ in water to afford 2-hydroxy-4-(4-(trifluoromethyl)phenyl)pyrrolo[1,2-a]quinoxaline-7-carboxylic (I-276) (0.050 g, 10.7%) as a yellow solid. $^1H$ NMR (400 MHz, DMSO-$d_6$) δ: 13.10 (br. s, 1H), 9.96 (br. s, 1H), 8.45 (br. s, 1H), 8.30-8.27 (d, J=8.4 Hz, 1H), 8.21-8.19 (d, J=8.0 Hz, 2H), 8.12 (s, 2H), 7.97-7.95 (d, J=8.0 Hz, 2H), 6.58 (s, 1H). MS: $[MH]^+$ 373.4

Example 1.180. Synthesis of 4-(6-azaspiro[2.5]octan-6-yl)pyrazolo[1,5-a]quinoxaline-7-carboxylic acid (I-277)

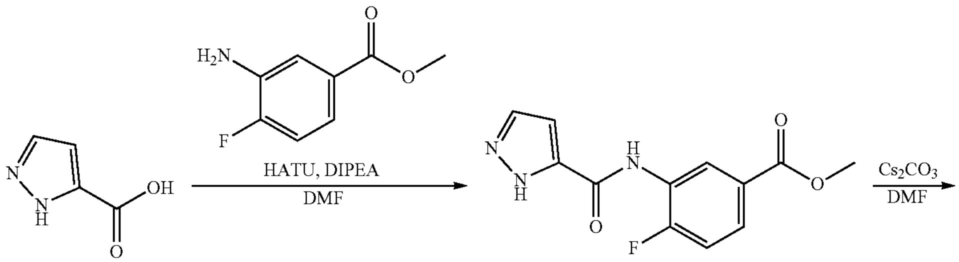

X-1355A1

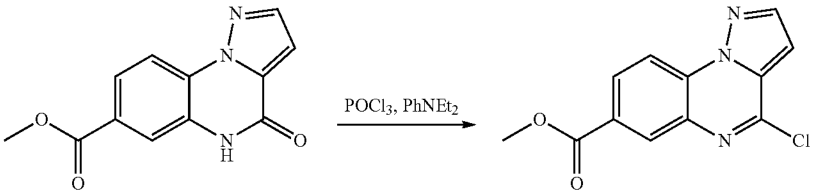

X-1355A2 X-1355A3

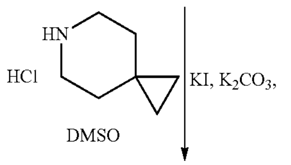

-continued

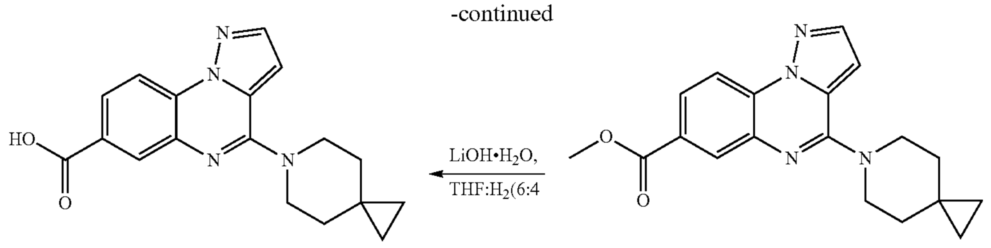

I-277

X-1355A4

Methyl 4-(2-chloroacetyl)-1H-pyrrole-2-carboxylate (X-1351A1). To a solution of 1H-pyrazole-5-carboxylic acid (2.00 g, 17.85 mmol) in DMF (25 mL) were added N, N-diisopropylethylamine (7.63 mL, 44.64 mmol) and HATU (10.18 g, 26.78 mmol) at 0° C. After 10 min of stirring at the same temperature, was added methyl 3-amino-4-fluorobenzoate (2.11 g, 12.49 mmol) and the resulting reaction mixture was stirred at 110° C. for 6 h. Reaction mixture was cooled to room temperature, diluted with water (100 mL) and was extracted with ethyl acetate (150 mL×3). The combined organic layers were washed with brine (100 mL), dried over $Na_2SO_4$, and concentrated under reduced pressure. Obtained crude product was purified by reverse phase (C-18) silica gel column chromatography using acetonitrile: water=3:7→4:6 as a gradient, to afford methyl 4-(2-chloroacetyl)-1H-pyrrole-2-carboxylate (X-1351A1) (2.0 g, 43%) as an off-white solid. MS: $[MH]^+$ 263.95

Methyl 4-oxo-4,5-dihydropyrazolo[1,5-a]quinoxaline-7-carboxylate (X-1355A2). To a stirred solution of methyl 4-fluoro-3-(1H-pyrazole-5-carboxamido)benzoate (X-1355A1) (2.0 g, 7.60 mmol) in DMF (25 mL) was added cesium carbonate (6.17 g, 19.02 mmol) at room temperature under nitrogen and the resulting mixture was stirred at 110° C. for 6 h. Reaction mixture was cooled to room temperature and slowly poured in to ice-cold water (100 mL) and the resulting precipitate was collected by filtration, washed with water (50 mL×3) and dried under reduced pressure, to afford methyl 4-oxo-4,5-dihydropyrazolo[1,5-a]quinoxaline-7-carboxylate (X-1355A2) (1.2 g, 67%) as a light brown solid. MS: $[MH]^+$ 244.

Methyl 4-chloropyrazolo[1,5-a]quinoxaline-7-carboxylate (X-1355A3). To a stirred suspension of methyl 4-oxo-4,5-dihydropyrazolo[1,5-a]quinoxaline-7-carboxylate (X-1355A2) (1.2 g, 4.93 mmol) in N, N-diethyl aniline (0.78 mL, 49.38 mmol) was added $POCl_3$ (12 mL) at 0° C. under nitrogen and the resulting mixture was heated at 110° C. for 4 h. After cooling to room temperature, reaction mixture was slowly poured into ice-water (50 mL) and the resulting precipitate was collected by filtration. Obtained solid residue was washed with cold water until the pH of the filtrate became neutral (pH~6-7) and dried under reduced pressure, to afford methyl 4-chloropyrazolo[1,5-a]quinoxaline-7-carboxylate (X-1355A3) (1.0 g, 77%; crude) as a yellow solid. MS: $[MH]^+$ 262.02.

Methyl 4-(6-azaspiro[2.5]octan-6-yl)pyrazolo[1,5-a]quinoxaline-7-carboxylate (X-1355A4). To a stirred solution of methyl 4-chloropyrazolo[1,5-a] quinoxaline-7-carboxylate (X-1355A3) (0.400 g, 1.53 mmol) in DMSO (5 mL) were added $K_2CO_3$ (0.52 g, 3.83 mmol), 6-azaspiro[2.5]octane (0.270 g, 1.83 mmol) and KI (0.025 g, 0.153 mmol) at room temperature under nitrogen and the resulting mixture was stirred at 110° C. for 2 h. Reaction mixture was cooled to room temperature, crude was diluted with ice-water (100 mL) and was resulting precipitate was collected by filtration. Isolated solid was washed with cold water (20 mL×3), dried under reduced pressure, to afford 4-(6-azaspiro[2.5]octan-6-yl)pyrazolo[1,5-a]quinoxaline-7-carboxylate (X-1355A4) (0.090 g, 10%) as an off-white solid. MS: $[MH]^+$ 337.17.

4-(6-azaspiro[2.5]octan-6-yl)pyrazolo[1,5-a]quinoxaline-7-carboxylic acid (I-277). To a stirred solution of methyl 4-(6-azaspiro[2.5]octan-6-yl)pyrazolo[1,5-a]quinoxaline-7-carboxylate (X-1355A4) (0.090 g, 0.26 mmol) in a mixture of THF-water (4:1; 3 mL) and methanol (0.5 mL) was added lithium hydroxide monohydrate (0.033 g, 0.80 mmol) at room temperature and the resulting reaction mixture was heated at 70° C. for 2 h. After cooling to room temperature, concentrated under reduced pressure, diluted with water (3 mL) and was acidified (pH~2-3) with an aqueous solution of 1N HCl and the resulting precipitate was collected by filtration. Isolated solid was washed with cold water until the pH of the filtrate became neutral (pH~6-7). Obtained solid was triturated with diethyl ether (10 mL×2) and the resulting residue was dried under reduced pressure to afford 4-(4-(tert-butyl)phenyl)pyrazolo[1,5-a]quinoxaline-7-carboxylic acid (I-277) (0.050 g, 58%) as an off-white solid. $^1H$ NMR (400 MHz, DMSO-$d_6$) δ: 12.92 (br. s, 1H), 8.34-8.30 (m, 3H), 7.96-7.93 (dd, J=1.6, 8.8 Hz, 1H), 7.37 (s, 1H), 3.98 (d, J=4.4 Hz, 4H), 1.58-1.55 (t, J=4.8 Hz, 4H), 0.42 (s, 4H). MS: $[MH]^+$ 323.2

Example 1.181. Synthesis of 9-(hydroxymethyl)-4-(6-azaspiro[2.5]octan-6-yl)pyrrolo[1,2-a]quinoxaline-7-carboxylic acid (I-278)

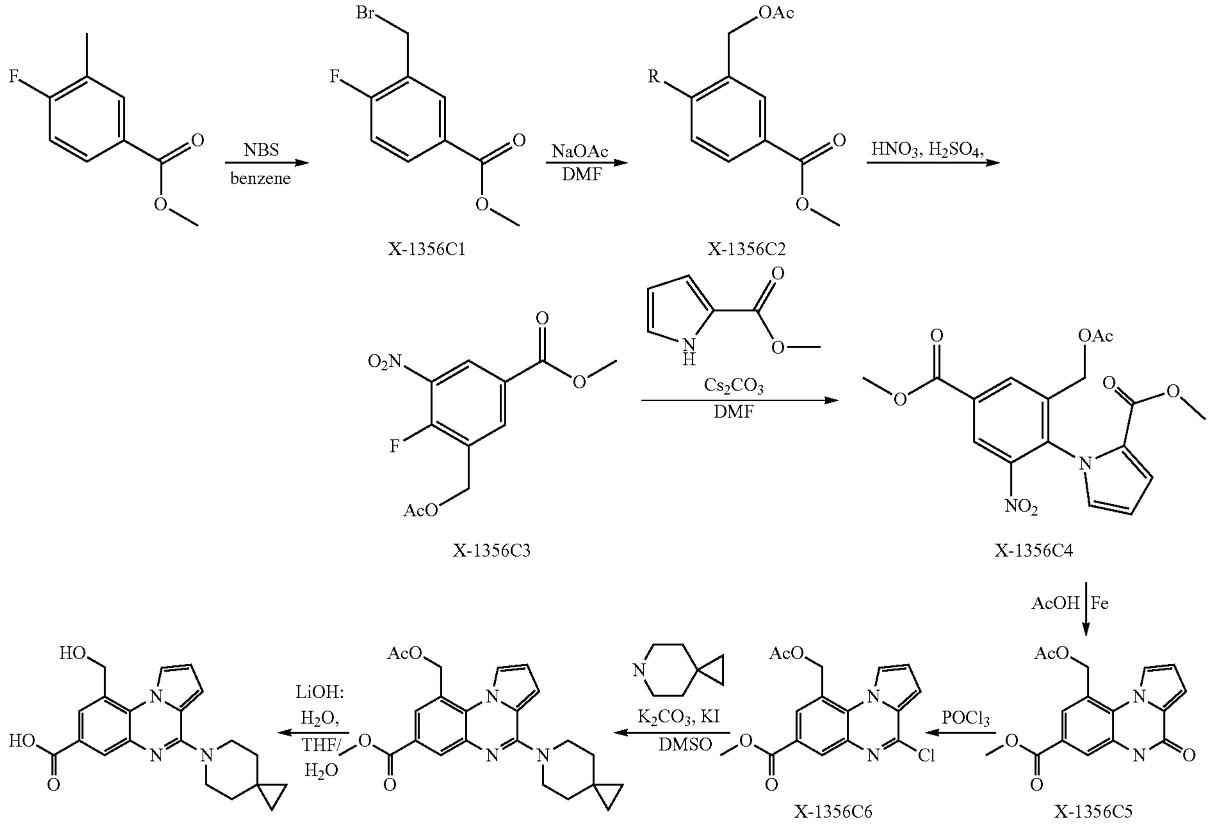

X-1356C1

X-1356C2

X-1356C3

X-1356C4

X-1356C6

X-1356C5

I-278

X-1356C7

Methyl 3-(bromomethyl)-4-fluorobenzoate (X-1356C1). To a stirred solution of methyl 4-fluoro-3-methylbenzoate (10.0 g, 59.52 mmol) in benzene (100 mL) were added benzyl peroxide (1.296 g, 5.35 mmol) and N-bromosuccinimide (11.60 g, 59.52 mmol) portion wise at 0° C. under nitrogen and the resulting mixture was stirred at 80° C. for 3 h. Reaction mixture was cooled to room temperature, quenched with water (200 mL) and was extracted with ethyl acetate (250 mL×3). Combined organic extracts were dried over anhydrous $Na_2SO_4$ and concentrated under reduced pressure, to afford methyl 3-(bromomethyl)-4-fluorobenzoate (X-1356C1) (11.5 g, 78%; crude), which was used further for next without any purification. $^1$H NMR (400 MHz, DMSO-$d_6$) δ: 8.19-8.17 (d, J=6.8 Hz, 1H), 7.98 (s, 1H), 7.42-7.37 (t, J=8.0, 9.6 Hz, 1H), 4.78 (s, 2H), 3.85 (s, 3H).

Methyl 3-(acetoxymethyl)-4-fluorobenzoate (X-1356C2). To a stirred solution of methyl 3-(bromomethyl)-4-fluorobenzoate (X-1356C1) (11.50 g, 46.74 mmol) in DMF (110 mL) was added sodium acetate (11.40 g, 140.22 mmol) at room temperature under nitrogen then resulting reaction mixture was stirred at room temperature for 4 h. Reaction mixture was quenched with water (200 mL) and was extracted with ethyl acetate (250 mL×2). Combined organic extracts were dried over anhydrous $Na_2SO_4$ and concentrated under reduced pressure. The crude product was purified by silica gel column chromatography, using ethyl acetate-hexane=1:9→2:8 as a gradient, to afford methyl 3-(acetoxymethyl)-4-fluorobenzoate (X-1356C2) (5.5 g, 52%) as an yellow solid. $^1$H NMR (400 MHz, DMSO-$d_6$) δ: 8.08-8.06 (dd, J=1.6, 6.8 Hz, 1H), 8.02-7.98 (m, 1H), 7.83 (s, 1H), 7.42-67.37 (t, J=8.8, 9.2 Hz, 1H), 5.16 (s, 2H), 3.85 (s, 3H), 2.06 (s, 3H).

Methyl 3-(acetoxymethyl)-4-fluoro-5-nitrobenzoate (X-1356C3). To a stirred solution of methyl 3-(acetoxymethyl)-4-fluorobenzoate (X-1356C2) (5.50 g, 46.74 mmol) in $H_2SO_4$ (2 mL) was added nitrating mixture of $H_2SO_4$ (5 mL) in $HNO_3$ (4 mL) dropwise at 0° C. Resulting reaction mixture was stirred at 0° C. for 10 min, and then at room temperature for 30 min. Reaction mixture was poured in to ice water (200 mL) and basified (pH~7-8) with aqueous $NaHCO_3$, extracted with ethyl acetate (250 mL×2). Combined organic extracts were dried over anhydrous $Na_2SO_4$ and concentrated under reduced pressure to afford methyl 3-(acetoxymethyl)-4-fluoro-5-nitrobenzoate (X-1356C3) (5.6 g, 86%; crude), which was used further for next step without any purification.

Methyl 1-(2-(acetoxymethyl)-4-(methoxycarbonyl)-6-nitrophenyl)-1H-pyrrole-2-carboxylate (X-1356C4). To a stirred solution of methyl 3-(acetoxymethyl)-4-fluoro-5-nitrobenzoate (X-1356C3) (5.60 g, 20.66 mmol) in DMF (60 mL) were added cesium carbonate (13.47 g, 41.32 mmol) and methyl 1H-pyrrole-2-carboxylate (2.58 g, 20.66 mmol) sequentially at room temperature under nitrogen and the resulting mixture was stirred at room temperature for 36 h. Reaction mixture was poured into water (200 mL) and was extracted with ethyl acetate (250 mL×2), Combined organic extracts were dried over anhydrous $Na_2SO_4$ and concentrated under reduced pressure. The crude product was purified by silica gel column chromatography, using ethyl acetate:Hexane=0:1→3:7 as a gradient, to afford methyl 1-(2-(acetoxymethyl)-4-(methoxycarbonyl)-6-nitrophenyl)-1H-pyrrole-2-carboxylate (X-1356C4) (0.60 g, 8%) as a white solid. MS: $[MH]^+$ 377.09.

Methyl 9-(acetoxymethyl)-4-oxo-4,5-dihydropyrrolo[1,2-a]quinoxaline-7-carboxylate (X-1356C5). To a stirred solution of methyl 1-(2-(acetoxymethyl)-4-(methoxycarbonyl)-6-nitrophenyl)-1H-pyrrole-2-carboxylate (X-1356C4) (0.600 g, 1.59 mmol) in acetic acid (12 mL) was added Fe powder (0.446 g, 7.97 mmol) at room temperature and reaction stirred at room temperature for 16 h. Filtered reaction mixture over celite bed and washed with ethyl acetate (50 mL×3), combined filtrate was collected and concentrated under reduced pressure, diluted with ethyl acetate (100 mL) and washed with water (100 mL), Combined organic extracts were dried over anhydrous $Na_2SO_4$ and concentrated under reduced pressure, to afford methyl 9-(acetoxymethyl)-4-oxo-4,5-dihydropyrrolo[1,2-a]quinoxaline-7-carboxylate (X-1356C5) (0.380 g, 75%) as a white solid. MS: $[MH]^+$ 315.06.

Methyl 9-(acetoxymethyl)-4-chloropyrrolo[1,2-a]quinoxaline-7-carboxylate (X-1356C6). To a stirred solution of methyl 9-(acetoxymethyl)-4-oxo-4,5-dihydropyrrolo[1,2-a]quinoxaline-7-carboxylate (X-1356C5) (0.380 g, 1.21 mmol) in $POCl_3$ (8 mL) was heated at 80° C. for 1.5 h. After completion of reaction, reaction mixture was slowly poured into ice-water (100 mL) and was extracted with ethyl acetate (100 mL×2). Combined organic extracts was washed with aqueous saturated $NaHCO_3$ solution (100 mL×2). Combined organic extracts were dried over anhydrous $Na_2SO_4$ and concentrated under reduce pressure to afford methyl 9-(acetoxymethyl)-4-chloropyrrolo[1,2-a]quinoxaline-7-carboxylate (X-1356C6) (0.280 g, 70%) as a white solid. MS: $[MH]^+$ 333.07.

Methyl 9-(acetoxymethyl)-4-(6-azaspiro[2.5]octan-6-yl)pyrrolo[1,2-a]quinoxaline-7-carboxylate (X-1356C7). To a stirred solution of 9-(acetoxymethyl)-4-chloropyrrolo[1,2-a]quinoxaline-7-carboxylate (X-1356C6) (0.150 g, 0.45 mmol) in DMSO (4 mL) were added 6-azaspiro[2.5]octane (0.133 g, 0.90 mmol), potassium carbonate (0.156 g, 1.12 mmol) and potassium iodide (0.015 g, 0.09 mmol) sequentially at room temperature under nitrogen and the resulting mixture was heated at 100° C. for 1 h. Reaction mixture was cooled to room temperature, slowly poured in ice water (30 mL) and was extracted with ethyl acetate (50 mL×3). Combined organic extracts were washed with brine (50 mL), dried over anhydrous $Na_2SO_4$ and concentrated. The crude product was purified by silica gel column chromatography, using ethyl acetate-hexane=1:9→2:8 as a gradient, to afford Methyl 9-(acetoxymethyl)-4-(6-azaspiro[2.5]octan-6-yl)pyrrolo[1,2-a]quinoxaline-7-carboxylate (X-1356C7) (0.068 g, 37%) as an off-white solid. MS: $[MH]^+$ 408.17.

9-(hydroxymethyl)-4-(6-azaspiro[2.5]octan-6-yl)pyrrolo[1,2-a]quinoxaline-7-carboxylic acid (I-278). To a stirred solution of Methyl 9-(acetoxymethyl)-4-(6-azaspiro[2.5]octan-6-yl)pyrrolo[1,2-a]quinoxaline-7-carboxylate (X-1356C7) (0.065 g, 0.15 mmol) in a mixture of THF-water (3:1; 5 mL) was added lithium hydroxide monohydrate (0.032 g, 0.798 mmol) at room temperature under nitrogen and the resulting mixture was heated at 60° C. for 3 h. Reaction mixture was concentrated under reduced pressure, obtained crude was diluted with water (20 mL) and was extracted with ethyl acetate (25 mL×2) to remove unwanted organic impurities. Aqueous part was acidified (pH~2-3) with an aqueous solution of 1N HCl and extracted with 10% methanol:dichloromethane (25 mL×2). Combined organic extracts dried over anhydrous $Na_2SO_4$ and concentrated. The resulting crude was purified by reverse phase (C-18) silica gel column chromatography, using acetonitrile-water=3:7→4:6 as a gradient, to afford 9-(hydroxymethyl)-4-(6-azaspiro[2.5]octan-6-yl)pyrrolo[1,2-a]quinoxaline-7-carboxylic acid (I-278) (0.025 g, 43%) as an white solid. $^1H$ NMR (400 MHz, DMSO-$d_6$) δ: 8.44-8.42 (d, J=5.2 Hz, 3H), 8.01 (s, 1H), 7.83 (s, 1H), 6.92-6.91 (d, J=4.0 Hz, 1H), 6.82 (s, 1H), 4.89 (s, 2H), 3.71 (s, 4H), 1.52 (s, 4H), 0.37 (s, 4H). MS: $[MH]^+$ 352.2

Example 1.182. Synthesis of 4-(4-(tert-butyl)phenyl)-9-(hydroxymethyl)pyrrolo[1,2-a]quinoxaline-7-carboxylic acid (1-279)

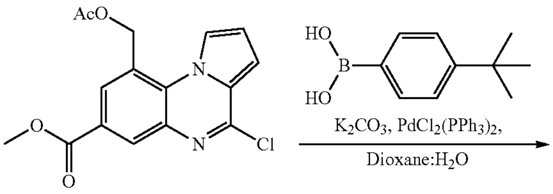

X-1356C6

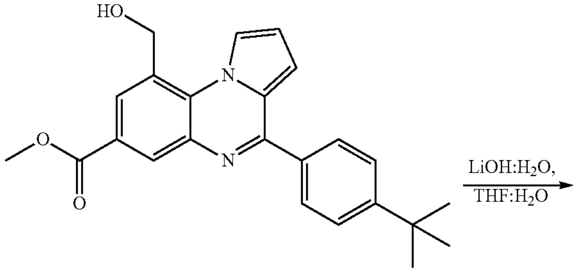

X-1364B1

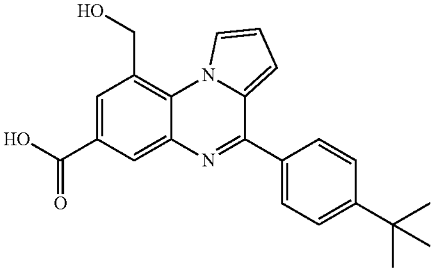

I-279

Methyl 4-(4-(tert-butyl)phenyl)-9-(hydroxymethyl)pyrrolo[1,2-a]quinoxaline-7-carboxylate (X-1364B1). To a stirred solution of methyl 9-(acetoxymethyl)-4-chloropyrrolo[1,2-a]quinoxaline-7-carboxylate (X-1357C6) (0.100 g, 0.30 mmol) in a mixture 1,4-Dioxane:$H_2O$ (4:1, 5 mL) were added (4-(tert-butyl)phenyl)boronic acid (0.070 g, 0.39 mmol), potassium carbonate (0.104 g, 0.75 mmol) at room temperature. The reaction mixture was degassed (purging with nitrogen) for 15 min followed by addition of $PdCl_2(PPh_3)_2$ (0.021 g, 0.03 mmol) and the reaction mixture was heated at 100° C. for 1 h. The reaction mixture was cooled to room temperature, diluted with water (50 mL) and was extracted with ethyl acetate (75 mL×2). The combined organic extracts were dried over anhydrous $Na_2SO_4$ and concentrated under reduce pressure. The crude product was purified by silica gel column chromatography, using ethyl acetate-hexane=1:9→2:8 as a gradient, to afford methyl 4-(4-(tert-butyl)phenyl)-9-(hydroxymethyl)pyrrolo[1,2-a]quinoxaline-7-carboxylate (X-1364B1) (0.080 g, 69%) as an yellow solid. MS: $[MH]^+$ 389.12

4-(4-(tert-Butyl)phenyl)-9-(hydroxymethyl)pyrrolo[1,2-a]quinoxaline-7-carboxylic acid (I-279). To a stirred solution of 4-(4-(tert-butyl)phenyl)-9-(hydroxymethyl)pyrrolo[1,2-a]quinoxaline-7-carboxylate (X-1364B1) (0.080 g, 0.20 mmol) in a mixture of THE-water (3:1; 4 mL) was added lithium hydroxide monohydrate (0.016 g, 0.41 mmol) at room temperature under nitrogen and the resulting mixture was heated at 60° C. for 2 h. After cooling to room temperature, the reaction mixture was concentrated under reduced pressure, obtained crude was diluted with water (10 mL) and was extracted with ethyl acetate (15 mL×2) to remove unwanted organic impurities. Aqueous part was acidified (pH~2-3) with an aqueous solution of 1N HCl and extracted with 10% MeOH:DCM (25 mL×2). The combined organic extracts were dried over anhydrous $Na_2SO_4$ and concentrated under reduce pressure to afford 4-(4-(tert-butyl)phenyl)-9-(hydroxymethyl)pyrrolo[1,2-a]quinoxaline-7-carboxylic acid (I-279) (0.025 g, 32%) as a white solid. $^1$H NMR (400 MHz, DMSO-$d_6$) 13.16 (br. s, 1H), 8.64 (s, 1H), 8.38 (s, 1H), 8.16 (s, 1H), 7.96-7.94 (d, J=8.0 Hz, 2H), 7.63-7.61 (d, J=7.6 Hz, 2H), 7.14 (s, 1H), 7.06 (s, 1H), 5.96 (br. s, 1H) 5.06 (br. s, 2H), 1.37 (s, 9H). MS: $[MH]^+$ 375.22.

Example 1.183. Synthesis of 3-fluoro-4-(4-(trifluoromethyl)phenyl)pyrrolo[1,2-a]quinoxaline-7-carboxylic acid (I-280)

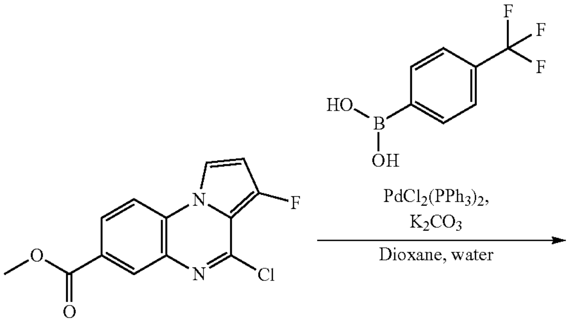

X-1350A3

-continued

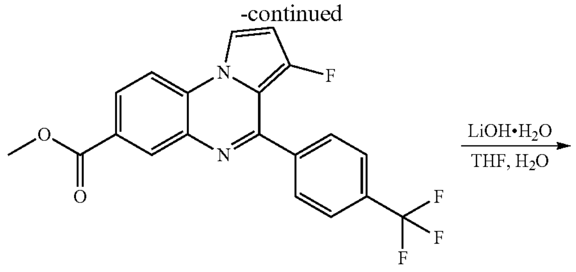

X-1586A1

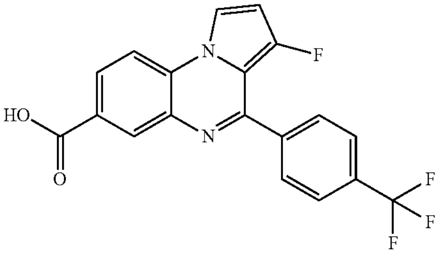

I-280

The following compound was prepared in a manner analogous to the procedures described above for 4-(4-(tert-butyl)phenyl)-9-(hydroxymethyl)pyrrolo[1,2-a]quinoxaline-7-carboxylic acid (I-279):

3-fluoro-4-(4-(trifluoromethyl)phenyl)pyrrolo[1,2-a]quinoxaline-7-carboxylic acid (I-280) (0.070 g, 54%) as an off-white solid. $^1$H NMR (400 MHz, DMSO-$d_6$) δ 13.25 (brs, 1H), 8.58-8.57 (t, J=4.0 Hz, 1H), 8.45-8.43 (d, J=8.4 Hz, 1H), 8.39-8.39 (d, J=2.0 Hz, 1H), 8.15-8.12 (dd, J=8.4, 1.6 Hz, 1H), 8.04-8.02 (dd, J=8.4, 6.0 Hz, 2H), 7.95-7.93 (d, J=8.4 Hz, 2H), 7.03-7.02 (d, J=3.6 Hz, 1H). MS: $[MH]^+$ 374.8.

Example 1.184. Synthesis of 6-(6-azaspiro[2.5]octan-6-yl)pyrido[4,3-e]pyrrolo[1,2-a]pyrazine-3-carboxylic acid (I-281)

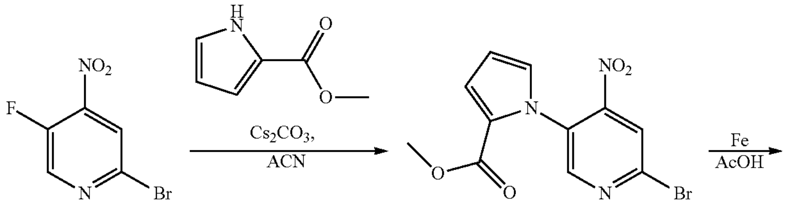

X-1359A1

-continued

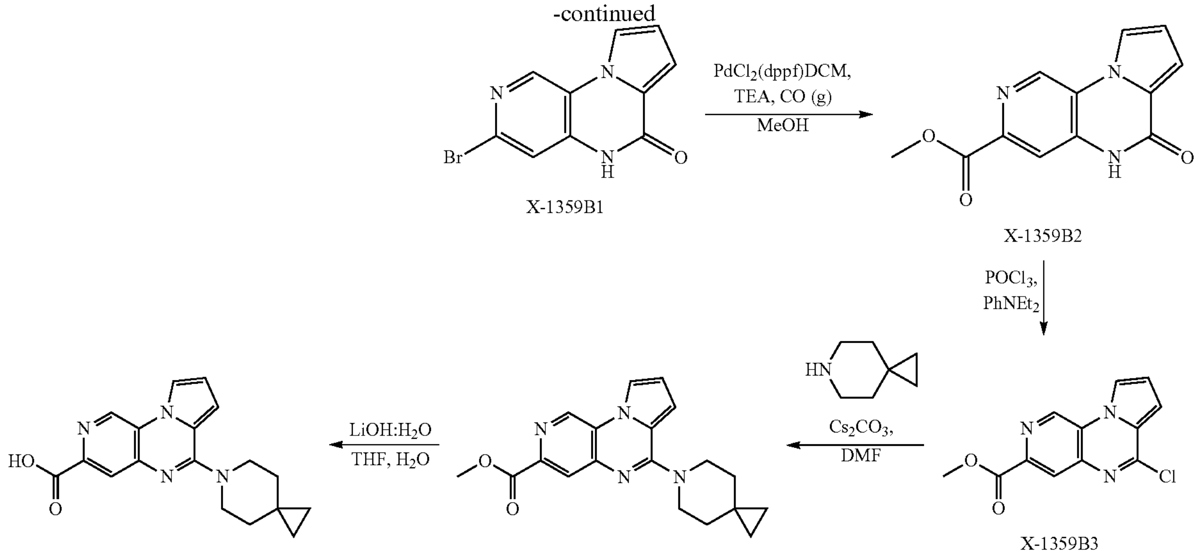

X-1359B1

X-1359B2

X-1359B3

X-1359B4

I-281

Methyl 1-(6-bromo-4-nitropyridin-3-yl)-1H-pyrrole-2-carboxylate (X-1359A1) To a stirred solution of 2-bromo-5-fluoro-4-nitropyridine (0.500 g, 2.27 mmol) and methyl 1H-pyrrole-2-carboxylate (0.286 g, 2.27 mmol) in acetonitrile (10 mL) was added $Cs_2CO_3$ (1.48 g, 4.54 mmol) at room temperature and reaction mixture was stirred at room temperature for 2 h. The reaction mixture was diluted with water (300 mL) and extracted with ethyl acetate (300 mL×3). The combined organic extracts were dried over anhydrous $Na_2SO_4$ and concentrated under reduce pressure. The crude product was combined with identically prepared two batches and purified by silica gel column chromatography, using ethyl acetate-hexane=3:7→5:5 as a gradient, to afford methyl 1-(6-bromo-4-nitropyridin-3-yl)-1H-pyrrole-2-carboxylate (X-1359A1) (0.600 g, 40%) as an off-white solid. $^1H$ NMR (400 MHz, DMSO-$d_6$) δ: 8.77 (s, 1H), 8.49 (s, 1H), 7.40-7.39 (t, J=2.4, 2.0 Hz, 1H), 7.12-7.10 (m, 1H), 6.46-6.44 (t, J=3.2 Hz, 1H), 3.62 (s, 3H).

3-Bromopyrido[4,3-e]pyrrolo[1,2-a]pyrazin-6(5H)-one (X-1359B1). To a stirred solution of methyl 1-(6-bromo-4-nitropyridin-3-yl)-1H-pyrrole-2-carboxylate (X-1359A1) (0.700 g, 2.15 mmol) in acetic acid (7 mL), was added Fe powder (0.482 g, 8.61 mmol) at room temperature and the resulting reaction mixture was stirred at 100° C. for 16 h. Filtered reaction mixture on a celite bed and washed with ethyl acetate (50 mL×3), combined filtrate was collected and concentrated under reduced pressure, diluted with ethyl acetate (100 mL) and washed with water (100 mL). Combined organic extracts were dried over anhydrous $Na_2SO_4$ and concentrated under reduced pressure, to afford 3-bromopyrido[4,3-e]pyrrolo[1,2-a]pyrazin-6(5H)-one (X-1359B1) (0.700 g, crude) as a brown semi solid. MS: $[MH]^+$ 263.9

Methyl 6-oxo-5,6-dihydropyrido[4,3-e]pyrrolo[1,2-a]pyrazine-3-carboxylate (X-1359B2). To a stirred solution of 3-bromopyrido[4,3-e]pyrrolo[1,2-a]pyrazin-6(5H)-one (X-1359B1) (0.500 g, 1.90 mmol) in methanol (10 mL) was added TEA (0.384 g, 3.80 mmol) at room temperature under nitrogen. The reaction mixture was degassed (purging with nitrogen) for 15 min and was added $PdCl_2$(dppf). DCM (0.155 g, 0.19 mmol), The reaction mixture was degassed (purging with carbon monoxide) for 15 min at room temperature, the resulting reaction mixture stirred under $CO_{(g)}$ (balloon pressure) at 80° C. for 4 h. Reaction was cooled to room temperature, concentrate under reduced pressure and diluted with water (150 mL) and extracted with ethyl acetate (200 mL×3). The combined organic extracts were dried over anhydrous $Na_2SO_4$ and concentrated under reduce pressure. The crude product was purified by silica gel column chromatography, using ethyl acetate-Hexane=2:8→3:6 as a gradient, to afford methyl 6-oxo-5,6-dihydropyrido[4,3-e]pyrrolo[1,2-a]pyrazine-3-carboxylate (X-1359B2) (0.3 g, 65%) as a yellow solid. MS: $[MH]^+$ 244.0

Methyl 6-chloropyrido[4,3-e]pyrrolo[1,2-a]pyrazine-3-carboxylate (X-1359B3). N, N-diethyl aniline (0.046 g, 0.31 mmol) was added to a stirred suspension of methyl 6-oxo-5,6-dihydropyrido[4,3-e]pyrrolo[1,2-a]pyrazine-3-carboxylate (X-1359B2) (0.190 g, 0.78 mmol) in $POCl_3$ (5 mL) at 0° C. and the resulting reaction mixture was heated at 80° C. for 16 h. Reaction was cooled to room temperature and slowly poured into ice water (150 mL) and was extracted with ethyl acetate (100 mL×2). Combined organic extracts were dried over anhydrous $Na_2SO_4$, and concentrated under reduced pressure. Obtained crude product was purified by silica gel column chromatography, using ethyl acetate-hexane=2:8→4:6 as a gradient, to afford methyl 6-chloropyrido[4,3-e]pyrrolo[1,2-a]pyrazine-3-carboxylate (X-1359B3) (0.200 g, 98%) as a brown solid. MS: $[MH]^+$ 261.95.

Methyl 6-(6-azaspiro[2.5]octan-6-yl)pyrido[4,3-e]pyrrolo[1,2-a]pyrazine-3-carboxylate (X-1359B4). To a stirred solution of methyl 6-chloropyrido[4,3-e]pyrrolo[1,2-a]pyrazine-3-carboxylate (X-1359B3) (0.090 g, 0.34 mmol) in DMF, (3 mL), were added $Cs_2CO_3$ (0.223 g, 0.68 mmol), and 6-azaspiro[2.5]octane hydrochloride (0.076 g, 0.51 mmol) at room temperature and stirred at same temperature for 2 h. The reaction mixture was diluted with water (100 mL) and extracted with ethyl acetate (100 mL×2). The combined organic extracts were dried over anhydrous $Na_2SO_4$ and concentrated under reduce pressure. Obtained crude was mixed with the crude of an identically prepared batch. The crude product was purified by silica gel column chromatography, using ethyl acetate-Hexane=3:7→4:6 as a gradient, to afford methyl 6-(6-azaspiro[2.5]octan-6-yl)

pyrido[4,3-e]pyrrolo[1,2-a]pyrazine-3-carboxylate (X-1359B4) (0.160 g, 69%) as an off-white solid. MS: $[MH]^+$ 337.17.

6-(6-azaspiro[2.5]octan-6-yl)pyrido[4,3-e]pyrrolo[1,2-a] pyrazine-3-carboxylic acid (I-281). To a stirred solution of methyl 6-(6-azaspiro[2.5]octan-6-yl)pyrido[4,3-e]pyrrolo[1, 2-a]pyrazine-3-carboxylate (X-1359B4) (0.150 g, 0.44 mmol) in a mixture of THF-water (3:1; 4 mL) was added lithium hydroxide monohydrate (0.053 g, 2.20 mmol) at room temperature under nitrogen and the resulting mixture was stirred at same temperature for 3 h. Reaction mixture was concentrated under reduced pressure, obtained crude was diluted with water (10 mL) and was extracted with ethyl acetate (30 mL×2) to remove unwanted organic impurities. Aqueous part was acidified (pH~2-3) with an aqueous solution of 1N HCl and extracted with 10% methanol:DCM (30 mL×2). Combined organic extracts dried over anhydrous $Na_2SO_4$ and concentrated. The resulting crude was purified by reverse phase (C-18) silica gel column chromatography, using acetonitrile-water=3:7→4:6 as gradient to 6-(6-azaspiro[2.5]octan-6-yl)pyrido[4,3-e]pyrrolo[1,2-a] pyrazine-3-carboxylic acid (I-281) (0.040 g, 28%) as an off-white solid. $^1H$ NMR (400 MHz, DMSO-$d_6$) δ: 9.37 (s, 1H), 8.55 (s, 1H), 7.91 (s, 1H), 7.15-7.14 (d, J=3.6 Hz, 1H), 6.91 (s, 1H), 3.99-3.98 (d, J=5.2 Hz, 4H), 1.53-1.50 (t, J=4.8 Hz, 4H), 0.40 (s, 4H), MS: $[MH]^+$ 323.16.

Example 1.185. Synthesis of 6-(4-(tert-butyl)phenyl)pyrido[4,3-e]pyrrolo[1,2-a]pyrazine-3-carboxylic acid (I-282

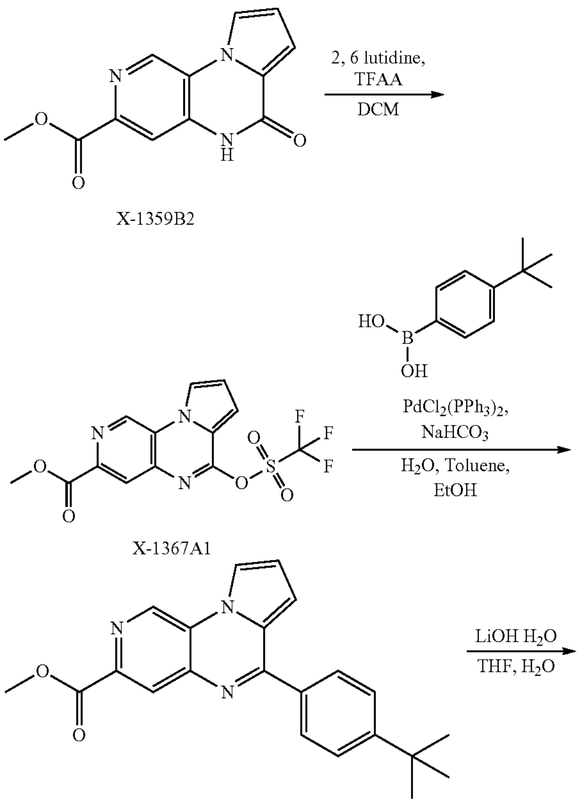

X-1359B2

X-1367A1

X-1367A2

-continued

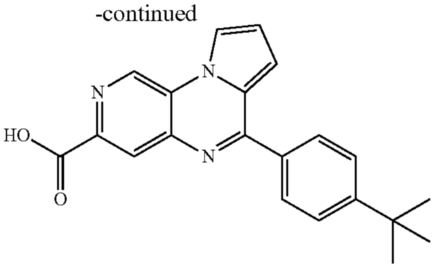

I-282

Methyl 6-(((trifluoromethyl)sulfonyl)oxy)pyrido[4,3-e] pyrrolo[1,2-a]pyrazine-3-carboxylate (X-1367A1). To a stirred solution of methyl 6-oxo-5,6-dihydropyrido[4,3-e] pyrrolo[1,2-a]pyrazine-3-carboxylate (X-1359B2) (0.400 g, 1.64 mmol) in DCM (5 mL) was added 2,6-Lutidine (0.350 g, 3.29 mmol) at room temperature, then reaction mixture was cooled to 0° C. and TFAA (0.789 g, 2.79 mmol) was added. The resulting reaction mixture was stirred at 0° C. for 3 h. Reaction mixture was poured into ice water (200 mL) and was extracted by DCM (200 mL×2) and combined organic extracts were washed with brine (50 mL), dried over anhydrous $Na_2SO_4$ and concentrated under reduced pressure, Isolated crude was combined with an identical prepared one more batch (0.200 g) and the combined crude product, to afford methyl 6-(((trifluoromethyl)sulfonyl)oxy) pyrido[4,3-e]pyrrolo[1,2-a]pyrazine-3-carboxylate (X-1367A1) (0.600 g, quantitative yield) as an off-white solid MS: $[MH]^+$ 376.1

Methyl 6-(4-(tert-butyl)phenyl)pyrido[4,3-e]pyrrolo[1,2-a]pyrazine-3-carboxylate (X-1367A2). To a stirred solution methyl 6-(((trifluoromethyl)sulfonyl)oxy)pyrido[4,3-e]pyrrolo[1,2-a]pyrazine-3-carboxylate (X-1367A1) (0.600 g, 1.60 mmol) in toluene-EtOH-water (7 mL) were added (4-(tert-butyl)phenyl)boronic acid (0.569 g, 3.20 mmol) and sodium bicarbonate (0.403 g, 4.80 mmol) sequentially at room temperature under nitrogen. The resulting mixture was degassed (purged with nitrogen) for 20 min followed by the addition of $PdCl_2(PPh_3)_4$ (0.112 g, 0.16 mmol), was heated at 90° C. for 30 min. After cooling to room temperature, reaction mixture was diluted with water (100 mL) and was extracted by ethyl acetate (100 mL×3). Combined organic extracts were dried over anhydrous $Na_2SO_4$ and concentrated under reduce pressure. The crude product was purified by silica gel column chromatography, using ethyl acetate-hexane=0:1→2:8 as a gradient, to afford methyl 6-(4-(tert-butyl)phenyl)pyrido[4,3-e]pyrrolo[1,2-a]pyrazine-3-carboxylate (X-1367A2) as an white solid (0.200 g, 34%). MS: $[MH]^+$ 360.6

6-(4-(tert-butyl)phenyl)pyrido[4,3-e]pyrrolo[1,2-a]pyrazine-3-carboxylic acid (I-282). To a stirred solution of methyl 6-(4-(tert-butyl)phenyl)pyrido[4,3-e]pyrrolo[1,2-a] pyrazine-3-carboxylate (X-1367A2) (0.180 g, 0.50 mmol) in a mixture of THF-water (3:1; 5.0 mL) was added lithium hydroxide monohydrate (0.042 g, 1.00 mmol) at room temperature. Reaction mixture was stirred at room temperature for 2 h, After completion of reaction the reaction mixture was concentrated under reduced pressure, obtained crude was acidified (pH~2-3) with an aqueous solution of 1N HCl and the resulting precipitate was collected by filtration. Crude residue was washed with cold water until the pH of the filtrate became neutral (pH~6-7). Obtained solid was dried under reduced pressure and triturated with using n-pentane (5 mL), to afford 6-(4-(tert-butyl)phenyl) pyrido[4,3-e]pyrrolo[1,2-a]pyrazine-3-carboxylic acid (I-282) (0.090 g, 52%) as an off white solid. $^1$H NMR (400 MHz, DMSO-$d_6$) δ: 9.56 (s, 1H), 8.83 (s, 1H), 8.30 (s, 1H), 7.99-7.97 (d, J=8.4 Hz, 2H), 7.64-7.62 (d, J=8.0 Hz, 2-1), 7.20 (s, 1H), 7.06 (s, 1H), 1.36 (s, 9H) MS: $[MH]^+$ 345.9.

Example 1.186. Synthesis of 6-(6-azaspiro[2.5]octan-6-yl)pyrido[2,3-e]pyrrolo[1,2-a]pyrazine-3-carboxylic acid (I-283)

mL×3). The combined organic extracts were washed with brine (100 mL) and dried over anhydrous $Na_2SO_4$ and concentrated under reduced pressure, crude was combined with another identically prepare (2.0 g & 7.5 g) reactions. Obtained crude was purified by silica gel column chromatography with using ethyl acetate-hexane=0:1→1:9 as a gradient, to afford 6-bromo-3-(1H-pyrrol-1-yl)pyridin-2-amine (X-1360B2) (10.5 g, 75%) as a yellow solid, MS: $[MH]^+$ 237.9; MS: $[MH]^+$ 239.9

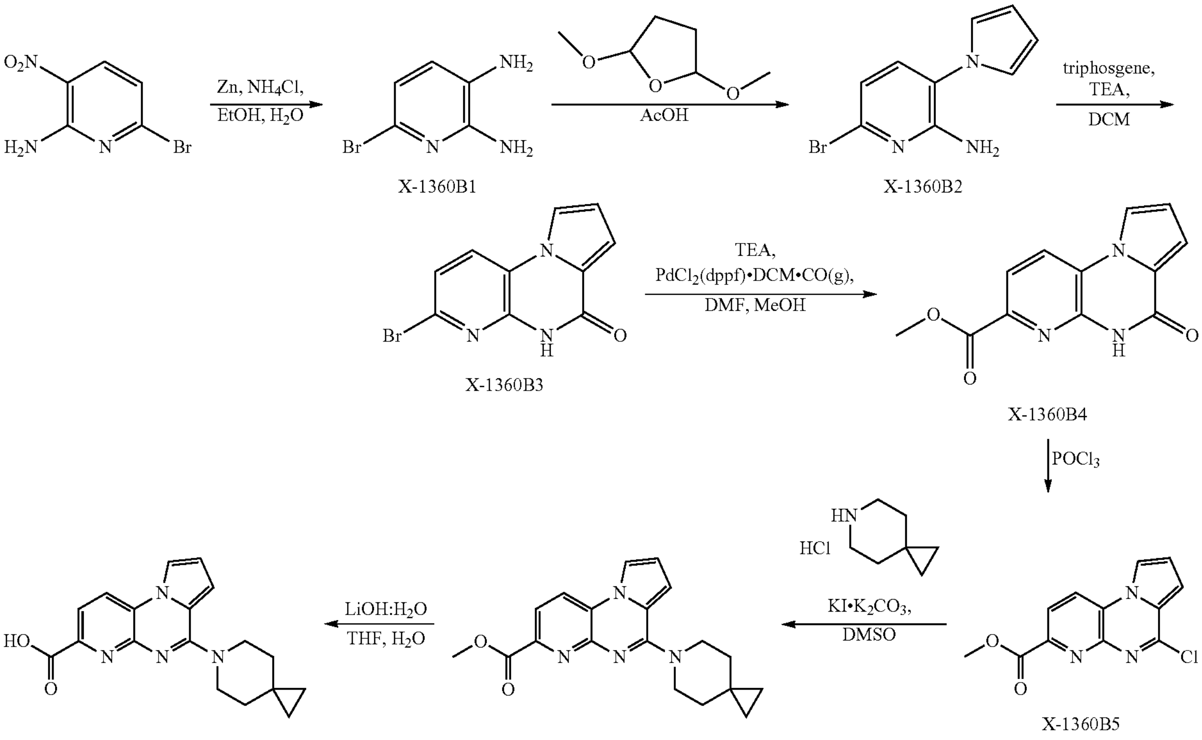

X-1360B1 X-1360B2 X-1360B3 X-1360B4 X-1360B5 X-1360B6 I-283

6-Bromopyridine-2,3-diamine (X-1360B1). To a stirred solution of 6-bromo-3-nitropyridin-2-amine (10.0 g, 45.87 mmol) in a mixture of ethanol-water (7:2, 120 mL) were added $NH_4Cl$ (19.5 g, 366.97 mmol) and Zinc dust (23.9 g, 366.97 mmol) at room temperature under nitrogen and the resulting mixture was heated at 80° C. for 3 h. Reaction mixture was cooled to room temperature, filtered over celite bed and washed with ethyl acetate (100 mL×2), filtrate was concentrated under reduced pressure, diluted with ethyl acetate (500 mL), washed with water (200 mL), The combined organic extracts were dried over anhydrous $Na_2SO_4$ and concentrated under reduced pressure, crude was combined with another identically prepare (15.0 g) reaction. The crude was purified by silica gel column chromatography with using ethyl acetate-hexane=0:1→4 1:9 as a gradient, to afford 6-bromopyridine-2,3-diamine (X-1360B1) (11.0 g, 51%) as a brown solid. MS: $[MH]^+$187.9, MS: $[MH]^+$ 189.8

6-Bromo-3-(1H-pyrrol-1-yl)pyridin-2-amine (X-1360B2). To a stirred solution of 6-bromopyridine-2,3-diamine (X-1361B1) (1.5 g, 8.02 mmol) in acetic acid (6 mL) was added 2,5-dimethoxytetrahydrofuran (1.05 g, 8.02 mmol) at room temperature and reaction was allowed to stir at 110° C. for 1 h. After cooling to room temperature, reaction mixture was quenched by saturated $NaHCO_3$ aqueous solution (80 mL) and was extracted by ethyl acetate (100

3-Bromopyrido[2,3-e]pyrrolo[1,2-a]pyrazin-6(5H)-one (X-1360B3). To the stirred solution of 6-bromo-3-(1H-pyrrol-1-yl)pyridin-2-amine (X-1360B2) (8.8 g, 37.13 mmol) in DCM (80 mL) were added triethylamine (15.5 mL, 111.39 mmol) and triphosgene (14.2 g, 81.68 mmol) sequentially at 0° C. under nitrogen, resulting reaction mixture was stirred at room temperature for 16 h. Reaction mixture was poured into ice-water (100 mL) and basified with aqueous ammonia solution (10 mL) and was extracted by ethyl acetate (100 mL×3), The combined organic extracts were dried over anhydrous $Na_2SO_4$ and concentrated under reduced pressure, crude was combined with another identically prepare (2.2 g) reaction. The crude product was triturated with n-hexane (50 mL×2), to afford 3-bromopyrido[2,3-e]pyrrolo[1,2-a]pyrazin-6(5H)-one (X-1360B3) (9.5 g, 82%) as a brown solid MS: $[MH]^+$ 265.88.

Methyl 6-oxo-5,6-dihydropyrido[2,3-e]pyrrolo[1,2-a]pyrazine-3-carboxylate (X-1360B4). To a stirred solution of 3-bromopyrido[2,3-e]pyrrolo[1,2-a]pyrazin-6(5H)-one (X-1360B3) (2.5 g, 9.50 mmol) in a mixture of methanol-DMSO-DCM (7:2:1, 100 ml), was added triethylamine (13.2 mL, 95.05 mmol) at room temperature. The reaction mixture was degassed (by purging with carbon monoxide) for 20 min followed by the addition of $Pd_2Cl_2$(dppf). DCM (0.390 g, 0.47 mmol) at room temperature. The resulting reaction mixture was heated in Parr autoclave in 150 psi pressure at 80° C. for 16 h. The reaction mixture was cooled to room temperature, filtered through celite bed and washed with DCM (50 mL×3), filtrate was collected and washed with water (100 mL), The combined organic extracts were washed with brine (200 mL), dried over anhydrous $Na_2SO_4$ and concentrated under reduced pressure, crude was combined with another identically prepare (2.5 g×2) reactions. Obtained crude product was purified by silica gel column chromatography, using ethyl acetate-hexane=1:9→2:8 as a gradient, to afford methyl 6-oxo-5,6-dihydropyrido[2,3-e]pyrrolo[1,2-a]pyrazine-3-carboxylate (X-1360B4) (3.0 g, 34%) as a yellow solid. MS: $[MH]^+$ 243.93

Methyl 6-chloropyrido[2,3-e]pyrrolo[1,2-a]pyrazine-3-carboxylate (X-1360B5). To a stirred solution of methyl 6-oxo-5,6-dihydropyrido[2,3-e]pyrrolo[1,2-a]pyrazine-3-carboxylate (X-1360B4) (0.500 g, 2.05 mmol) in $POCl_3$ (5 mL) was heated at 100° C. for 1 h. After cooling to room temperature, reaction mixture was slowly poured in ice water (100 mL) and basified with aqueous ammonia solution (30 mL) and was extracted by ethyl acetate (50 mL×3), The combined organic extracts were dried over anhydrous $Na_2SO_4$ and concentrated under reduced pressure. Obtained crude product was purified by silica gel column chromatography, using ethyl acetate-hexane=1:9→2:8 as a gradient, to afford methyl 6-chloropyrido[2,3-e]pyrrolo[1,2-a]pyrazine-3-carboxylate (X-1360B5) (0.090 g, 17%) as a yellow solid. MS: $[MH]^+$ 261.9

Methyl 6-(6-azaspiro[2.5]octan-6-yl)pyrido[2,3-e]pyrrolo[1,2-a]pyrazine-3-carboxylate (X-1360B6). To a stirred solution of methyl 6-chloropyrido[2,3-e]pyrrolo[1,2-a]pyrazine-3-carboxylate (X-1360B5) (0.090 g, 0.34 mmol) in DMSO (2 mL), were added $K_2CO_3$ (0.095 g, 0.68 mmol), potassium iodide (0.005 g, 0.0344 mmol), and 6-azaspiro[2.5]octane (0.061 g, 0.47 mmol) at room temperature under nitrogen and the resulting reaction mixture was stirred at 90° C. for 1 h. Reaction mixture was cooled to room temperature and diluted with water (50 mL) and was extracted by ethyl acetate (50 mL×3). The combined organic layers were washed with brine (10 mL), dried over $Na_2SO_4$, and concentrated under reduced pressure. Obtained crude product was purified by silica gel column chromatography using ethyl acetate:hexane=1:9→2:8 as a gradient, to afford methyl 6-(6-azaspiro[2.5]octan-6-yl)pyrido[2,3-e]pyrrolo[1,2-a]pyrazine-3-carboxylate (X-1360B6) (0.040 g, 15%) as an off-white solid. MS: $[MH]^+$ 336.95

6-(6-Azaspiro[2.5]octan-6-yl)pyrido[2,3-e]pyrrolo[1,2-a]pyrazine-3-carboxylic acid (I-283). To a stirred solution of methyl 6-(6-azaspiro[2.5]octan-6-yl)pyrido[2,3-e]pyrrolo[1,2-a]pyrazine-3-carboxylate (X-1360B6) (0.040 g, 0.11 mmol) in a mixture of THF-water-methanol (6:3:1, 2 mL), was added lithium hydroxide monohydrate (0.015 g, 0.35 mmol) at room temperature under nitrogen and the resulting mixture was stirred at room temperature for 2 h. The reaction mixture was concentrated under reduced pressure, crude mass was diluted with water (5 mL) and was extracted with ethyl acetate (10×2 mL) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was triturated in n-hexane (10 mL×2), dried under reduced pressure to afford 6-(6-azaspiro[2.5]octan-6-yl)pyrido[2,3-e]pyrrolo[1,2-a]pyrazine-3-carboxylic acid (I-283) (0.010 g, 26%) as a yellow solid. $^1H$ NMR (400 MHz, DMSO-$d_6$) δ: 8.61-8.59 (d, J=8.4 Hz, 1H), 8.45-8.44 (d, J=2.0 Hz, 1H), 7.88-7.86 (d, J=8.0 Hz, 1H), 7.13-7.12 (d, J=3.6 Hz, 1H), 6.91-6.90 (t, J=3.2 Hz, 1H), 4.01-3.98 (t, =5.2 Hz, 4H), 1.55-1.52 (t, J=5.2 Hz, 4H), 0.42 (s, 4H). MS: [MH]-323.0.

Example 1.187. Synthesis of 6-(6-azaspiro[2.5]octan-6-yl)pyrrolo[1,2-f]pteridine-3-carboxylic acid (I-284)

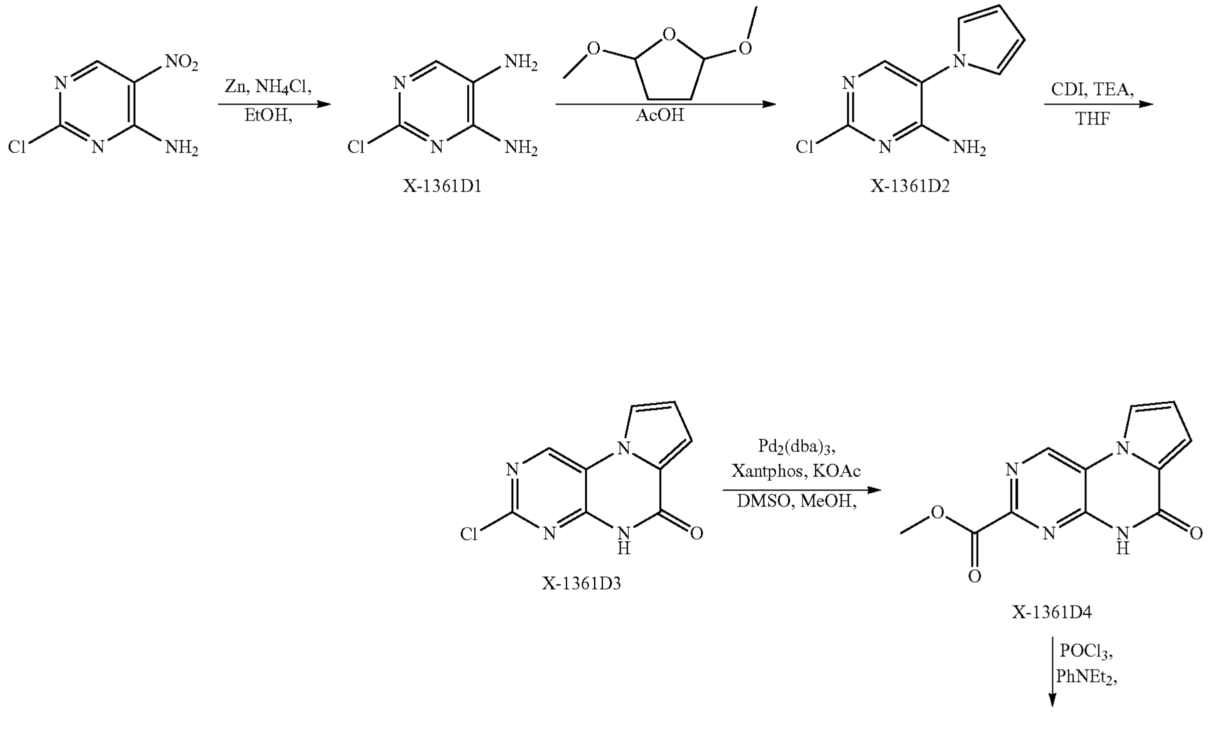

X-1361D1

X-1361D2

X-1361D3

X-1361D4

-continued

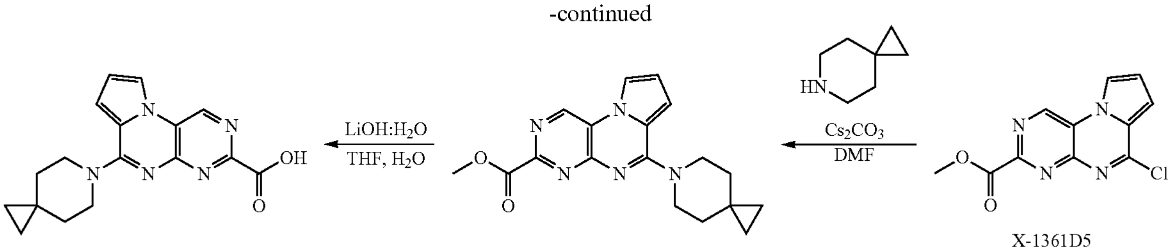

I-284 X-1361D6 X-1361D5

2-Chloropyrimidine-4,5-diamine (X-1361D1). To a stirred solution of 2-chloro-5-nitropyrimidin-4-amine (5.0 g, 28.73 mmol) in ethanol (300 mL) were added $NH_4Cl$ (7.6 g, 143.67 mmol) and Zinc dust (9.3 g, 143.67 mmol) at room temperature under nitrogen and the resulting mixture was heated at 80° C. for 1 h. Reaction mixture was cooled to room temperature, diluted with water (100 mL) and was extracted with ethyl acetate (150 mLx3). Dried over anhydrous $Na_2SO_4$ and concentrated under reduced pressure. The crude was purified by silica gel column chromatography with using ethyl acetate-hexane=1:1→6:4 as a gradient, to afford 2-chloropyrimidine-4,5-diamine (X-1361D1) (2.3 g, 56%) as a yellow solid. MS: $[MH]^+$ 144.87.

2-Chloro-5-(1H-pyrrol-1-yl)pyrimidin-4-amine (X-1361D2). To a stirred solution of 2-chloropyrimidine-4,5-diamine (X-1361D1) (1.0 g, 6.94 mmol) in acetic acid (30 mL) was added 2,5-dimethoxytetrahydrofuran (0.916 g, 6.94 mmol) at room temperature and stirred at 110° C. for 1 h. After cooling to room temperature, reaction mixture was filtered and the precipitate was washed with water (20 mLx2). The precipitate was taken in 10% methanol in dichloromethane, stirred for 30 min and filtered through a celite bed, filtrate was concentrated under reduced pressure, Obtained crude was mixed with the crude of an identically prepared batch of (1.0 g) and purified by silica gel column chromatography, using ethyl acetate-hexane=0:1→5:5 as gradient, to afford 2-chloro-5-(1H-pyrrol-1-yl)pyrimidin-4-amine (X-1361D2) (3.2 g, 59%) as a white solid. MS: $[MH]^+$ 194.88

3-chloropyrrolo[1,2-f]pteridin-6(5H)-one (X-1361D3). To a stirred solution of 2-chloro-5-(1H-pyrrol-1-yl)pyrimidin-4-amine (X-1361D2) (1.4 g, 7.21 mmol) in THE (10 mL) were added triethylamine (1.45 g, 14.43 mmol) and 1,1'-Carbonyldiimidazole (1.75 g, 10.82 mmol) sequentially at 0° C. under nitrogen, resulting reaction mixture was stirred at 70° C. for 16 h. Reaction mixture was poured into ice-water (100 mL) and was extracted by DCM (100 mLx3), The combined organic extracts were washed with brine (100 mL), dried over anhydrous $Na_2SO_4$ and concentrated under reduced pressure, The crude product was purified by silica gel column chromatography, using ethyl acetate-hexane=0:1→1:0 as a gradient, to afford 3-chloropyrrolo[1,2-f]pteridin-6(5H)-one (X-1361D3) (1.0 g, 93%) as a white solid MS: $[MH]^+$220.9.

Methyl 6-oxo-5,6-dihydropyrrolo[1,2-f]pteridine-3-carboxylate (X-1361D4). To a stirred solution of 3-chloropyrrolo[1,2-f]pteridin-6(5H)-one (X-1361D3) (0.200 g, 0.90 mmol) in DMSO and methanol (6 mL) was added potassium acetate (0.178 g, 1.81 mmol) at room temperature. The reaction mixture was degassed (by purging with nitrogen) for 30 min followed by the addition of $Pd_2(dba)_3$ (0.083 g, 0.09 mmol) and Xanthphos (0.052 g, 0.09 mmol) at the same temperature and the resulting mixture was purged with carbon monoxide gas for 30 min. The reaction mixture was heated at 80° C. for 16 h. The reaction mixture was cooled to room temperature, reaction mixture was slowly poured in ice water (100 mL), and extracted with ethyl acetate (100 mL). The combined organic extracts were washed with brine (200 mL), dried over anhydrous $Na_2SO_4$ and concentrated under reduced pressure. Obtained crude was mixed with the crude of an identically prepared batch of (0.200 gx4) and purified by silica gel column chromatography, using ethyl acetate-hexane=0:1→1:0 as gradient, to afford methyl 6-oxo-5,6-dihydropyrrolo[1,2-f]pteridine-3-carboxylate (X-1361D4) (0.300 g, 27%) as a white solid. MS: $[MH]^+$ 244.93.

Methyl 6-chloropyrrolo[1,2-f]pteridine-3-carboxylate (X-1361D5). To a stirred solution of methyl 6-oxo-5,6-dihydropyrrolo[1,2-f]pteridine-3-carboxylate (X-1361D4) (0.100 g, 0.40 mmol) in N, N-diethyl aniline (1.0 mL), was added $POCl_3$ (5 mL) at 0° C. under nitrogen and the resulting mixture was heated at 100° C. for 10 h. After cooling to room temperature, reaction mixture was slowly poured in ice water (100 mL), and was extracted with ethyl acetate (100 mLx3). The combined organic extracts were washed with brine (200 mL), dried over anhydrous $Na_2SO_4$ and concentrated under reduced pressure. Obtained crude was mixed with the crude of an identically prepared batch of (0.100 gx2). to afford methyl 6-chloropyrrolo[1,2-f]pteridine-3-carboxylate (X-1361D5) (0.200 g (crude), 93%) as a brown solid, which was taken to the next step without further purification. MS: $[MH]^+$ 262.93

Methyl 6-(6-azaspiro[2.5]octan-6-yl)pyrrolo[1,2-f]pteridine-3-carboxylate (X-1361D6). To a stirred solution of methyl 6-chloropyrrolo[1,2-f]pteridine-3-carboxylate) (X-1361D5) (0.100 g, 0.38 mmol) in DMF (3.0 mL), were added $Cs_2CO_3$ (0.370 g, 1.14 mmol) and 6-azaspiro[2.5]octane (0.093 g, 0.76 mmol) at room temperature under nitrogen and the resulting mixture was stirred at 110° C. for 2 h. Reaction mixture was cooled to room temperature and was diluted with water (50 mL) and was extracted with ethyl acetate (50 mLx3). The combined organic layers were washed with brine (10 mL), dried over $Na_2SO_4$, and concentrated under reduced pressure Obtained crude was mixed with the crude of an identically prepared batch of (0.080 g) and purified by silica gel column chromatography using ethyl acetate-hexane=1:9→2:8 as a gradient, to afford methyl 6-(6-azaspiro[2.5]octan-6-yl)pyrrolo[1,2-f]pteridine-3-carboxylate (X-1361D6) (0.070 g, 30%) as a white solid. MS: $[MH]^+$ 337.90

6-(6-azaspiro[2.5]octan-6-yl)pyrrolo[1,2-f]pteridine-3-carboxylic acid (I-284). To a stirred solution of methyl 6-(6-azaspiro[2.5]octan-6-yl)pyrrolo[1,2-f]pteridine-3-carboxylate (X-1361D6) (0.070 g, 0.20 mmol) in a mixture of THF-water-methanol (7:2:1, 5 ml), was added lithium hydroxide monohydrate (0.025 g, 0.62 mmol) at room temperature under nitrogen and the resulting mixture was stirred at room 60° C. for 2 h. the reaction mixture was cooled to room temperature and concentrated under reduced pressure, crude mass was diluted with water (20 mL) and was extracted with ethyl acetate (20 mL×2) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was triturated in n-hexane (10 mL×2), dried under reduced pressure to afford 6-(6-azaspiro[2.5]octan-6-yl)pyrrolo[1,2-f]pteridine-3-carboxylic acid (I-284) (0.025 g, 37%) as an off-white solid. $^1H$ NMR (400 MHz, DMSO-$d_6$) δ: 13.06 (br. s, 1H), 9.44 (s, 1H), 8.55 (s, 1H), 7.24-7.23 (d, J=4.0 Hz, 1H), 6.94-6.92 (t, J=3.2 Hz, 1H), 4.13-4.10 (m, 4H), 1.54 (m, 4H), 0.43 (m, 4H). MS: $[MH]^+$ 324.18

Example 1.188. Synthesis of 4-(6-azaspiro[2.5]octan-6-yl)-[1,2,4]triazolo[1,5-a]quinoxaline-7-carboxylic acid (I-285

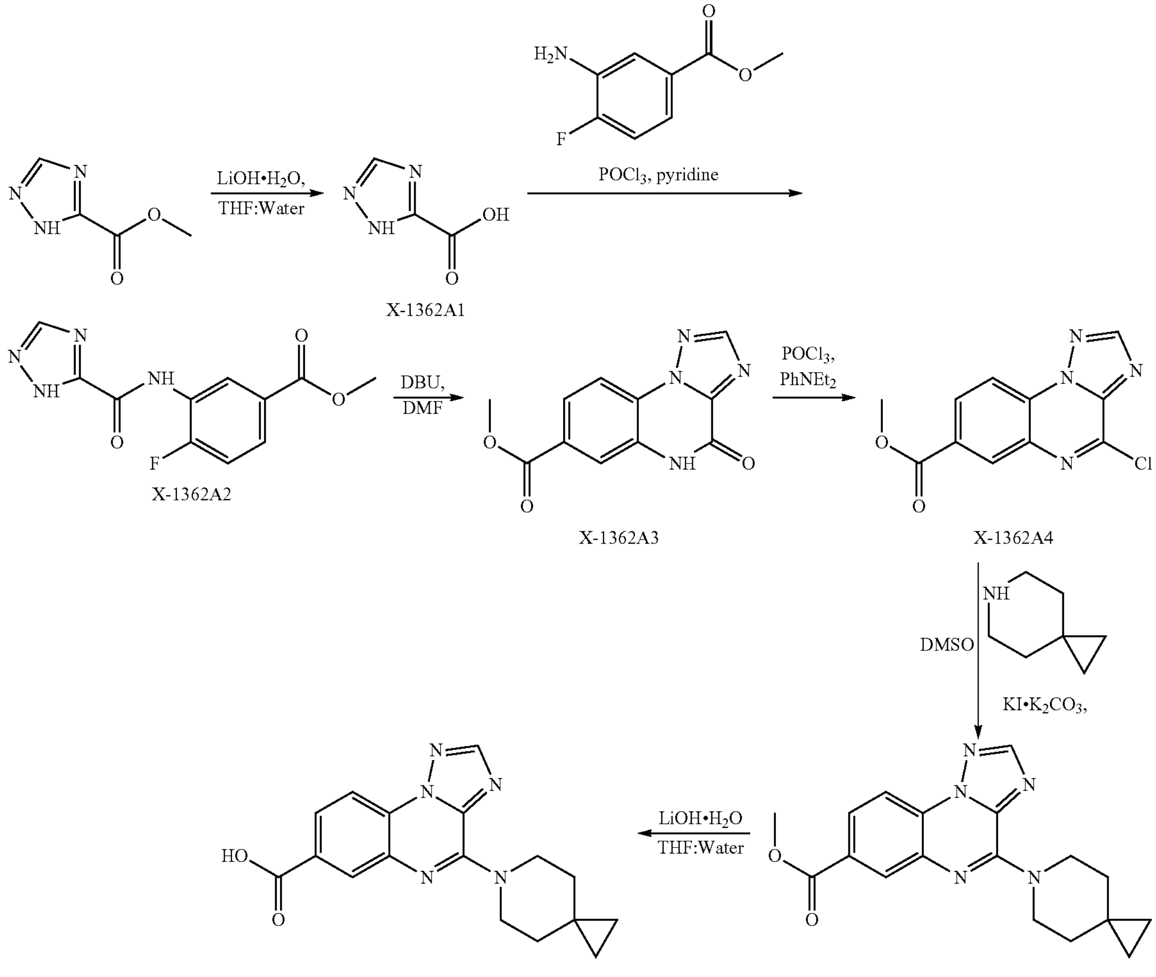

X-1362A1
X-1362A2
X-1362A3
X-1362A4
X-1362A5
I-285

1H-1,2,4-triazole-5-carboxylic acid (X-1362A1). To a stirred solution of methyl 1H-1,2,4-triazole-5-carboxylate (5.0 g, 39.37 mmol) in a mixture of THF-water (3:1; 30 mL) was added lithium hydroxide monohydrate (2.8 g, 118.11 mmol) at room temperature under nitrogen and the resulting mixture was stirred at 60° C. for 2 h. The reaction mixture was cooled to room temperature and concentrated under reduced pressure, crude mass was diluted with water (50 mL) and was extracted with ethyl acetate (50 mL×2) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was triturated in n-hexane (10 mL×2), dried under reduced pressure, to afford 1H-1,2,4-triazole-5-carboxylic acid (X-1362A1) (4.0 g, 90%) as a white solid. MS: $[MH]^+$ 113.92

Methyl 4-fluoro-3-(1H-1,2,4-triazole-5-carboxamido) benzoate (X-1362A2). To a stirred solution of 1H-1,2,4-triazole-5-carboxylic acid (X-1362A1) (3.5 g, 30.97 mmol) and methyl 3-amino-4-fluorobenzoate (6.3 g, 37.16 mmol) in pyridine (35 mL) was added $POCl_3$ (5.8 mL, 61.94 mmol) at 0° C., resulting reaction mixture was stirred at room temperature for 1 h. Reaction mixture was poured into cold water (150 mL) and extracted with ethyl acetate (100 mL×3). The combined organic extracts were washed with brine (200 mL), dried over anhydrous $Na_2SO_4$ and concentrated under reduced pressure. Obtained crude was mixed with the crude of an identically prepared batch of (0.500 g)

and triturated in n-pentane, dried under reduced pressure, to afford methyl 4-fluoro-3-(1H-1,2,4-triazole-5-carboxamido) benzoate (X-1362A2) (4.5 g, 48%) as an off-white solid. MS: $[MH]^+$ 265.0

Methyl 4-oxo-4,5-dihydro-[1,2,4]triazolo[1,5-a]quinoxaline-7-carboxylate (X-1362A3). To a stirred solution of methyl 4-fluoro-3-(1H-1,2,4-triazole-5-carboxamido)benzoate (X-1362A2) (1.5 g, 5.68 mmol) in DMF (15 mL) was added 1,8-Diazabicyclo[5.4.0]undec-7-ene (2.59 g, 17.04 mmol) at room temperature. The reaction mixture was heated at 110° C. for 16 h. reaction mixture was slowly poured in ice water (200 mL), obtained precipitates were filtered and the residue was washed with water (50 mL×2). Obtained crude was mixed with the crude of an identically prepared batch of (1.0 g & 0.500 g) and the combined batches were dried under high vacuum, to afford methyl 4-oxo-4,5-dihydro-[1,2,4]triazolo[1,5-a]quinoxaline-7-carboxylate (X-1362A3) (1.5 g, 54%) as a white solid, MS: $[MH]^+$ 244.95

Methyl 4-chloro-[1,2,4]triazolo[1,5-a]quinoxaline-7-carboxylate (X-1362A4). To a stirred solution of methyl 4-oxo-4,5-dihydro-[1,2,4]triazolo[1,5-a]quinoxaline-7-carboxylate (X-1362A3) (1.5 g, 6.14 mmol) in N, N-diethyl aniline (0.7 mL), was added $POCl_3$ (15 mL) at 0° C. under nitrogen and the resulting mixture was heated at 100° C. for 10 h. After cooling to room temperature, reaction mixture was slowly poured into ice-water (50 mL) and the resulting precipitate was collected by filtration. Obtained solid residue was washed with cold water until the pH of the filtrate became neutral (pH~6-7) and dried under reduced pressure, The crude product was purified by silica gel column chromatography, using ethyl acetate-hexane=6:448:2 as a gradient, to afford methyl 4-chloro-[1,2,4]triazolo[1,5-a]quinoxaline-7-carboxylate (X-1362A4) (0.500 g, 31%) as a yellow solid. MS: $[MH]^+$ 262.95

Methyl 4-(6-azaspiro[2.5]octan-6-yl)-[1,2,4]triazolo[1,5-a]quinoxaline-7-carboxylate (X-1362A5). To a stirred solution of methyl 4-chloro-[1,2,4]triazolo[1,5-a]quinoxaline-7-carboxylate (X-1362A4) (0.200 g, 0.76 mmol) in DMSO (5 mL) were added $K_2CO_3$ (0.263 g, 1.90 mmol), 6-azaspiro[2.5]octane (0.135 g, 0.91 mmol) and KI (0.012 g, 0.076 mmol) at room temperature under nitrogen and the resulting mixture was stirred at 110° C. for 2 h. Reaction mixture was cooled to room temperature and diluted with water (50 mL) and was extracted with ethyl acetate (50 mL×3). The combined organic layers were washed with brine (10 mL), dried over $Na_2SO_4$, and concentrated under reduced pressure. Obtained crude product was purified by silica gel column chromatography using ethyl acetate-hexane=1:9→2:8 as a gradient, to afford methyl 4-(6-azaspiro[2.5]octan-6-yl)-[1,2,4]triazolo[1,5-a]quinoxaline-7-carboxylate (X-1362A5) (0.230 g, 89%) as an brown solid. MS: $[MH]^+$ 338.22

4-(6-azaspiro[2.5]octan-6-yl)-[1,2,4]triazolo[1,5-a]quinoxaline-7-carboxylic acid (I-285). To a stirred solution of methyl 4-(6-azaspiro[2.5]octan-6-yl)-[1,2,4]triazolo[1,5-a]quinoxaline-7-carboxylate (X-1362A5) (0.200 g, 0.59 mmol) in a mixture of THF-water (3:1; 5 mL) was added lithium hydroxide monohydrate (0.074 g, 1.78 mmol) at room temperature under nitrogen and the resulting mixture was stirred at 60° C. for 2 h. The reaction mixture was concentrated under reduced pressure, crude mass was diluted with water (50 mL) and was extracted with ethyl acetate (20 mL×2) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was triturated in n-hexane (10 mL×2), dried under reduced pressure, to afford 4-(6-azaspiro[2.5]octan-6-yl)-[1,2,4]triazolo[1,5-a]quinoxaline-7-carboxylic acid (I-285) (0.130 g, 68%) as a white solid. 1H NMR (400 MHz, DMSO-$d_6$) δ: 13.24 (br. s, 1H), 8.74 (s, 1-1), 8.23-8.20 (d, J=8.40 Hz, 1H), 8.17 (s, 1H), 7.93-7.91 (d, J=8.40 Hz, 1H), 435 (in, 4H), 1.50 (m, 4H), 0.40 (m, 4H), MS: $[MH]^+$ 324.11.

Example 1.189. Synthesis of 6-(4-(tert-butyl)phenyl)pyrido[2,3-e]pyrrolo[1,2-a]pyrazine-3-carboxylic acid (I-286)

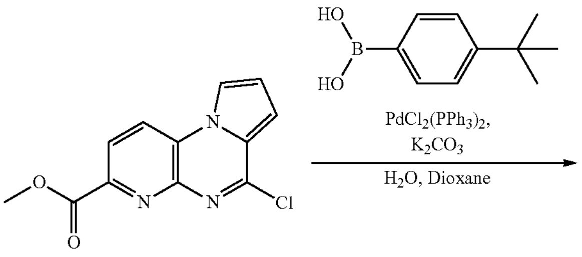

X-1360B5

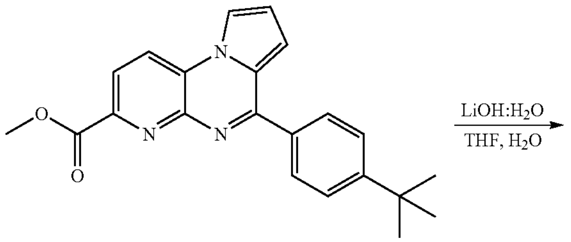

X-1368A1

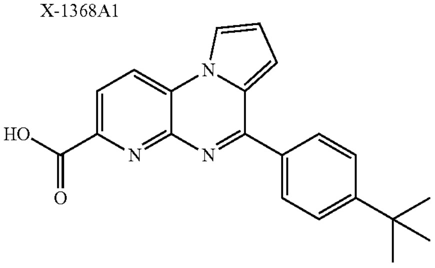

I-286

Synthesis of methyl 6-chloropyrido[2,3-e]pyrrolo[1,2-a]pyrazine-3-carboxylate (X-1360B5) provided above in Example 1.186

Methyl 6-(4-(tert-butyl)phenyl)pyrido[2,3-e]pyrrolo[1,2-a]pyrazine-3-carboxylate (X-1368A1). To a stirred solution of methyl 6-chloropyrido[2,3-e]pyrrolo[1,2-a]pyrazine-3-carboxylate (X-1360B5) (0.300 g, 1.49 mmol) in a mixture 1,4-dioxane:$H_2O$ (4:1, 9 mL) were added (4-(tert-butyl)phenyl)boronic acid (0.204 g, 1.72 mmol), potassium carbonate (0.411 g, 2.98 mmol) at room temperature. The reaction mixture was degassed (purging with nitrogen) for 15 min followed by addition of $PdCl_2(PPh_3)_2$ (0.052 g, 0.074 mmol) and the reaction mixture was heated at 100° C. for 1 h. The reaction mixture was cooled to room temperature, diluted with water (100 mL) and was extracted with ethyl acetate (100 mL×2). The combined organic extracts were dried over anhydrous $Na_2SO_4$ and concentrated under reduce pressure. The crude product was purified by silica gel column chromatography, using ethyl acetate-hexane=3:7→4:6 as a gradient, to afford methyl 6-(4-(tert-butyl)phenyl)pyrido[2,3-e]pyrrolo[1,2-a]pyrazine-3-carboxylate (X-1368A1) (0.300 g, 43%) as an off-white solid. MS: $[MH]^+$ 360.15

6-(4-(tert-Butyl)phenyl)pyrido[2,3-e]pyrrolo[1,2-a]pyrazine-3-carboxylic acid (I-286). To a stirred solution of methyl 6-(4-(tert-butyl)phenyl)pyrido[2,3-e]pyrrolo[1,2-a]pyrazine-3-carboxylate (X-1368A1) (0.280 g, 0.77 mmol) in a mixture of THF-water (3:1; 4 mL) was added lithium hydroxide monohydrate (0.098 g, 2.33 mmol) at room temperature under nitrogen and the resulting mixture was stirred at room temperature for 2 h. The reaction mixture was concentrated under reduced pressure, crude mass was diluted with water (10 mL) and was extracted with ethyl acetate (20 mL×2) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was triturated in n-hexane (10 mL×2), dried under reduce pressure, to afford 6-(4-(tert-butyl)phenyl)pyrido[2,3-e]pyrrolo[1,2-a]pyrazine-3-carboxylic acid (I-286) (0.200 g, 69%) as a white solid. $^1$H NMR (400 MHz, DMSO-$d_6$) δ: 8.85-8.83 (d, J=8.4 Hz, 1H), 8.67 (s, 1H), 8.18-8.16 (d, J=8.4 Hz, 1H), 8.01-7.99 (d, J=8.0 Hz, 2H), 7.64-7.62 (d, J=8.0 Hz, 2H), 7.17-7.16 (d, J=3.2 Hz, 1H), 7.07-7.06 (t, J=2.8 Hz, 1H), 1.37 (s, 9H), MS: $[MH]^+$ 346.1.

Example 1.90. Synthesis of 4-(4-(tert-butyl)phenyl)-[1,2,4]triazolo[1,5-a]quinoxaline-7-carboxylic acid (I-287)

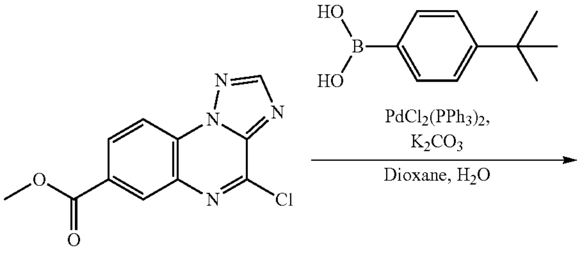

X-1362A4

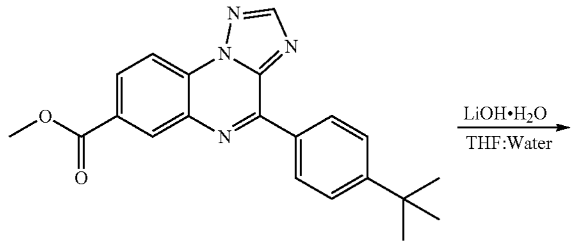

X-1370A1

-continued

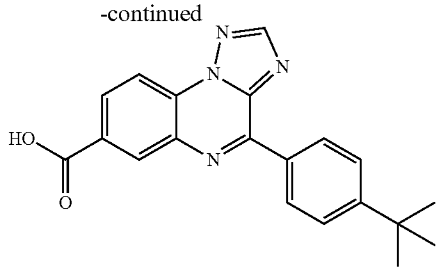

I-287

The following compound was prepared in a manner analogous to the procedures described above for 6-(4-(tert-butyl)phenyl)pyrido[2,3-e]pyrrolo[1,2-a]pyrazine-3-carboxylic acid (I-286):

4-(4-(tert-butyl)phenyl)-[1,2,4]triazolo[1,5-a]quinoxaline-7-carboxylic acid (I-287) (0.130 g, 59%) as a white solid. 1H NMR (400 MHz, DMSO-$d_6$) S: 13.53 (s, 1H), 8.96 (s, 1H), 8.78-8.76 (d, J=8.4 Hz, 2H), 8.71-8.71 (d, J=0.2 Hz, 1H), 8.53-8.51 (d, J=8.8 Hz, 1H), 8.37-8.34 (dd, J=1.2, 8.4 Hz, 1H), 7.69-7.66 (d, J=8.4 Hz, 2H), 1.37 (s, 9H), MS: $[MH]^+$ 347.07.

Example 1.190. Synthesis of 4-(4-(tert-butyl)phenyl)-9-(hydroxymethyl)pyrrolo[1,2-a]quinoxaline-7-carboxylic acid (I-288)

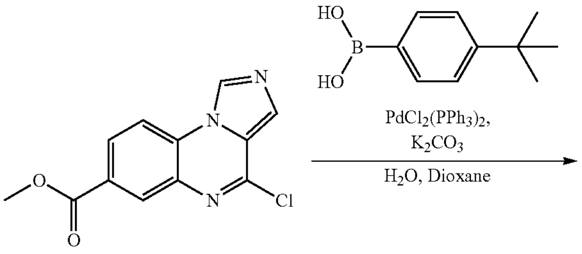

X-1357A3

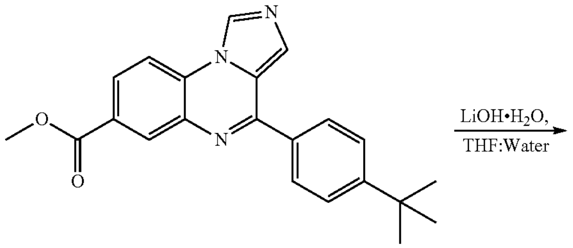

X-1365A1

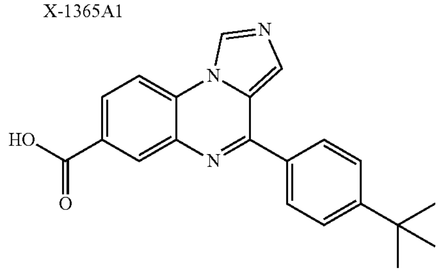

I-288

Methyl 4-(4-(tert-butyl)phenyl)imidazo[1,5-a]quinoxaline-7-carboxylate (X-1365A1). To a stirred solution of methyl 4-chloroimidazo[1,5-a]quinoxaline-7-carboxylate (X-1357A3) (0.230 g, 0.88 mmol) in a mixture 1,4-Dioxane: $H_2O$ (4:1, 6 mL) were added (4-(tert-butyl)phenyl)boronic acid (0.188 g, 1.05 mmol), potassium carbonate (0.364 g, 2.64 mmol) at room temperature. The reaction mixture was degassed (purging with nitrogen) for 15 min followed by addition of $PdCl_2(PPh_3)_2$ (0.018 g, 0.026 mmol) and the reaction mixture was heated at 90° C. for 1 h. The reaction mixture was cooled to room temperature, diluted with water (100 mL) and was extracted with ethyl acetate (100 mL×2). The combined organic extracts were dried over anhydrous $Na_2SO_4$ and concentrated under reduce pressure. The crude product was purified by silica gel column chromatography, using ethyl acetate-hexane=3:7→4:6 as a gradient, to afford methyl 4-(4-(tert-butyl)phenyl)imidazo[1,5-a]quinoxaline-7-carboxylate (X-1365A1) (0.140 g, 44%) as an off white solid. MS: $[MH]^+$ 360.17

4-(4-(tert-butyl)phenyl)imidazo[1,5-a]quinoxaline-7-carboxylic acid (I-288). To a stirred solution of methyl 4-(4-(tert-butyl)phenyl)imidazo[1,5-a]quinoxaline-7-carboxylate (X-1365A1) (0.130 g, 0.36 mmol) in a mixture of THE-water (3:1; 4 mL) was added lithium hydroxide monohydrate (0.046 g, 1.08 mmol) at room temperature under nitrogen and the resulting mixture was heated at 60° C. for 2 h. The reaction mixture was concentrated under reduced pressure, crude mass was diluted with water (10 mL) and was extracted with ethyl acetate (20 mL×2) to remove unwanted organic impurities. The aqueous layer was acidified (pH~2-3) with an aqueous 1N HCl, and the resulting precipitate was collected by filtration. Obtained residue was washed with cold water until the pH of the filtrate became neutral (pH~6-7). The obtained solid was triturated in n-hexane (10 mL×2), dried under reduced pressure, to afford 4-(4-(tert-butyl)phenyl)imidazo[1,5-a]quinoxaline-7-carboxylic acid (I-288) (0.050 g, 45%) as a white solid. 11-NMR (400 MHz, DMSO-$d_6$) δ: 933 (s, 1H), 8.42 (s, 1H), 8.30-8.28 (d, J=8.0 Hz, 1H), 8.13-8.11 (d, J=8.0 Hz, 1H), 8.06-8.04 (d, J=8.0 Hz, 2H), 7.99 (s, 1H), 7.64-7.62 (d, J=8.4 Hz, 2H), 1.36 (s, 9H) (MS: $[MH]^+$ 345.17.

Example 1.191. Synthesis of —N-(1-(8-(4-(trifluoromethyl)phenyl)imidazo[1,2-a]pyrazin-6-yl)ethyl) acrylamide (I-172)

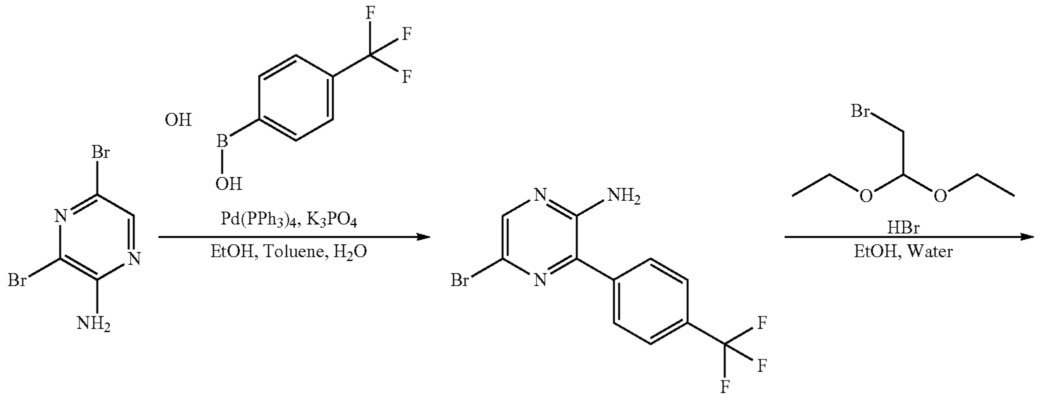

X-1421A1

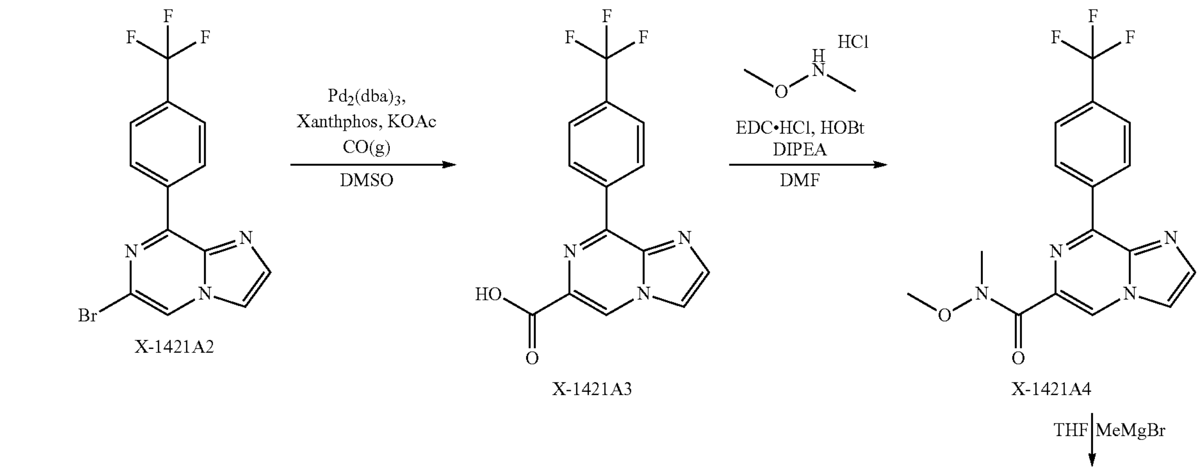

X-1421A2

X-1421A3

X-1421A4

-continued

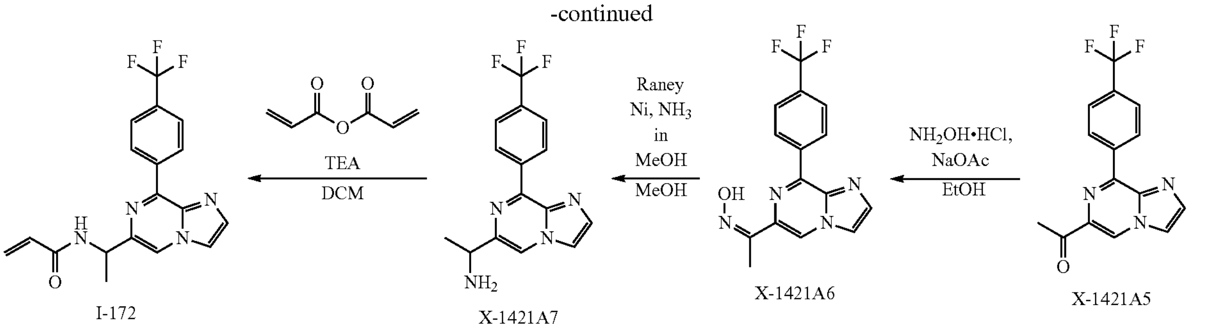

I-172 X-1421A7 X-1421A6 X-1421A5

5-Bromo-3-(4-(trifluoromethyl)phenyl)pyrazin-2-amine (X-1421A1). To a stirred solution of 3,5-dibromopyrazin-2-amine (25.0 g, 98.81 mmol) in a mixture of toluene-ethanol-water (8:1:1, 200 mL), were added potassium phosphate (41.91 g, 197.62 mmol) and (4-(trifluoromethyl)phenyl) boronic acid (22.52 g, 118.57 mmol) at room temperature under nitrogen. The resulting mixture was degassed (purging with nitrogen) for 50 min followed by the addition of $Pd(PPh_3)_4$ (5.71 g, 4.94 mmol) and the resulting mixture was heated at 80° C. for 6 h. Reaction mixture was cooled to room temperature, diluted with water (2 L) and was extracted with ethyl acetate (500 mL×3). Combined organic extracts were washed with brine (1 L), dried over anhydrous $Na_2SO_4$ and concentrated under reduced pressure. Another one identical batch (25.0 g) was performed parallel and workup done together. The crude product was purified by silica gel column chromatography, using ethyl acetate-hexane: 0:1→2:8 as a gradient, to afford 5-bromo-3-(4-(trifluoromethyl)phenyl)pyrazin-2-amine (X-1421A1) (40.0 g, 64%) as an off-white solid. MS: $[MH]^+$ 318.0 $[M+2H]^+$ 319.9

6-Bromo-8-(4-(trifluoromethyl)phenyl)imidazo[1,2-a]pyrazine (X-1421A2). To a stirred solution of 5-bromo-3-(4-(trifluoromethyl)phenyl)pyrazin-2-amine (X-1421A1) (40.0 g, 126.18 mmol) in ethanol (300 mL) were added 2-bromo-1,1-diethoxyethane (42.6 g, 252.36 mmol) and HBr in $H_2O$ (48%; 152.2 mL, 883.26 mmol) sequentially at room temperature under nitrogen at 0° C. and resulting mixture was heated at 80° C. for 2 h. Reaction mixture was cooled to room temperature, slowly poured into water (1 L) and precipitated solid was collected by filtration and dried under high vacuum to afford 6-bromo-8-(4-(trifluoromethyl)phenyl)imidazo[1,2-a]pyrazine (X-1421A2) (35 g, 81%; crude) as an off white solid. MS: $[MH]^+$ 341.9 $[M+2H]^+$ 343.9

8-(4-(Trifluoromethyl)phenyl)imidazo[1,2-a]pyrazine-6-carboxylic acid (X-1421A3). To a stirred solution of 6-bromo-8-(4-(trifluoromethyl)phenyl)imidazo[1,2-a]pyrazine (7.0 g, 20.58 mmol) in DMSO (70 mL) was added potassium acetate (6.05 g, 61.76 mmol) at room temperature. The reaction mixture was degassed (by purging with nitrogen) for 30 min followed by the addition of $Pd_2(dba)_3$ (1.88 g, 2.05 mmol) and xanthphos (1.18 g, 2.05 mmol) at the same temperature and the resulting mixture carboxylated by purging with carbon monoxide gas in a Parr Autoclave and the reaction mixture was heated at 80° C. for 16 h. The reaction mixture was cooled to room temperature, slowly poured in ice water (200 mL) and obtained precipitates were filtered. The residue was washed with water (150 mL×2) and dried under high vacuum to afford 8-(4-(trifluoromethyl)phenyl)imidazo[1,2-a]pyrazine-6-carboxylic acid (X-1421A3) [5.7 g, (crude)] as a brown solid, which was used in next step without further purification. MS: $[MH]^+$ 307.96

N-Methoxy-N-methyl-8-(4-(trifluoromethyl)phenyl)imidazo[1,2-a]pyrazine-6-carboxamide (X-1421A4). To a stirred solution of 8-(4-(trifluoromethyl)phenyl)imidazo[1,2-a]pyrazine-6-carboxylic acid (X-1421A3) (5.7 g, 18.56 mmol) in DMF (50 mL) were added DIPEA (9.5 mL, 74.26 mmol), EDC-HCl (4.62 g, 24.13 mmol) and HOBt (3.40 g, 22.28 mmol) at ° C. under nitrogen atmosphere and stirred at same temperature for 15 min. N,O-dimethylhydroxylamine (1.81 g, 18.56 mmol) was added at 0° C. under nitrogen and stirred at room temperature for 16 h. Reaction mixture was poured into cold water (200 mL) and was extracted with ethyl acetate (200 mL×3). The combined organic extracts were washed with brine (200 mL), dried over anhydrous $Na_2SO_4$ and concentrated under reduced pressure. Obtained crude product was purified by silica gel column chromatography, using ethyl acetate-hexane=0:1→1:0 as gradient, to afford N-methoxy-N-methyl-8-(4-(trifluoromethyl)phenyl)imidazo[1,2-a]pyrazine-6-carboxamide (X-1421A4) (3.2 g, 49%) as a yellow solid. MS: $[MH]^+$ 351.02

1-(8-(4-(Trifluoromethyl)phenyl)imidazo[1,2-a]pyrazin-6-yl)ethan-1-one (X-1421A5). To a stirred solution of N-methoxy-N-methyl-8-(4-(trifluoromethyl)phenyl)imidazo[1,2-a]pyrazine-6-carboxamide (X-1421A4) (3.2 g, 9.14 mmol) in THF (32 mL) was added methyl magnesium bromide (3.0M in diethyl ether) (18.2 mL, 54.85 mmol) dropwise at 0° C. and the resulting mixture was stirred at room temperature for 2 h. The reaction mixture was quenched with aqueous $NH_4Cl$ solution (100 mL) at 0° C. and was extracted with ethyl acetate (200×2). Combined organic extracts dried over anhydrous $Na_2SO_4$ and concentrated under reduced pressure. The crude product was purified by silica gel column chromatography, using ethyl acetate-hexane=0:1→2:8 as gradient, to afford 1-(8-(4-(trifluoromethyl)phenyl)imidazo[1,2-a]pyrazin-6-yl)ethan-1-one (X-1421A5) (1.5 g, 54%) as a yellow solid. MS: $[MH]^+$ 305.86

(Z)-1-(8-(4-(trifluoromethyl)phenyl)imidazo[1,2-a]pyrazin-6-yl)ethan-1-one oxime (X-1421A6). To a stirred solution of 1-(8-(4-(trifluoromethyl)phenyl)imidazo[1,2-a]pyrazin-6-yl)ethan-1-one (X-1421A5) (1.5 g, 4.91 mmol) in ethanol (20 mL) were added hydroxylamine hydrochloride (0.67 g, 9.83 mmol) and sodium acetate (1.20 g, 14.75 mmol) at room temperature and resulting reaction mixture stirred at 70° C. for 1 h. The reaction mixture was slowly poured into water (50 mL), obtained precipitates were collected by filtration, washed with water (50 mL×2) and dried under high vacuum, to afford (Z)-1-(8-(4-(trifluoromethyl)phenyl)imidazo[1,2-a]pyrazin-6-yl)ethan-1-one oxime (X-1421A6) [1.2 g, (crude)] as a white solid, which was used in next step without further purification. MS: $[MH]^+$ 320.91.

1-(8-(4-(trifluoromethyl)phenyl)imidazo[1,2-a]pyrazin-6-yl)ethan-1-amine (X-1421A7). To a stirred solution of (Z)-1-(8-(4-(trifluoromethyl)phenyl)imidazo[1,2-a]pyrazin-6-yl)ethan-1-one oxime (X-1421A6) (0.500 g, 1.56 mmol) in methanol (5 mL) were added Raney Nil (~0.500 g) and ammonia in methanol (7N, 5 mL) at room temperature and the resulting mixture was hydrogenated in Parr Autoclave at same temperature under 200 psi for 16 h. Reaction mixture was filtered over a celite bed, washed the bed with methanol (100 mL) and collected filtrates were concentrated under reduced pressure. Obtained crude product was purified by neutral alumina gel column chromatography, using methanol-DCM=0:1→1:9 as gradient, to afford 1-(8-(4-(trifluoromethyl)phenyl)imidazo[1,2-a]pyrazin-6-yl)ethan-1-amine (X-1421A7) (0.15 g, 13%) as a yellow solid. MS: $[MH]^+$ 307.06.

N-(1-(8-(4-(trifluoromethyl)phenyl)imidazo[1,2-a]pyrazin-6-yl)ethyl)acrylamide (I-172). Acrylic anhydride (0.061 g, 0.49 mmol) was added to a stirred solution of 1-(8-(4-(trifluoromethyl)phenyl)imidazo[1,2-a]pyrazin-6-yl)ethan-1-amine (X-1421A7) (0.15 g, 0.49 mmol) and TEA (0.148 g, 1.47 mmol) in DCM (5 mL) at 0° C. under nitrogen and the resulting reaction mixture was stirred at same temperature for 30 min. The reaction mixture was poured in water (50 mL) and was extracted with DCM (50 mL×3). Combined organic extracts were dried over anhydrous $Na_2SO_4$ and concentrated under reduced pressure. The crude product was purified by reverse phase (C-18) silica gel column chromatography, using acetonitrile-water=0:1→1:0 as gradient, to afford N-(1-(8-(4-(trifluoromethyl)phenyl)imidazo[1,2-a]pyrazin-6-yl)ethyl)acrylamide (I-172) (0.05 g, 28%) as a white solid. $^1H$ NMR (400 MHz, DMSO-$d_6$) δ 9.04-9.02 (d, J=8.0 Hz, 2H), 8.66-8.84 (d, J=7.20 Hz, 1H), 8.60 (s, 1H), 8.28 (s, 1H), 7.96-7.94 (d, J=8.0 Hz, 2H), 7.91 (s, 1H), 6.37-6.32 (m, 1H), 6.14-6.09 (dd, J=17.2, 2.0 Hz, 1H), 5.63-5.60 (dd, J=10.40, 2.0 Hz, 1H), 5.14 (m, 1H), 1.57-1.55 (d, J=7.2 Hz, 3H). MS: $[MH]^+$ 361.2.

Example 1.192. Synthesis of N-((8-(2-fluoro-4-(trifluoromethyl)phenyl)imidazo[1,2-a]pyrazin-6-yl)methyl)acrylamide (I-175)

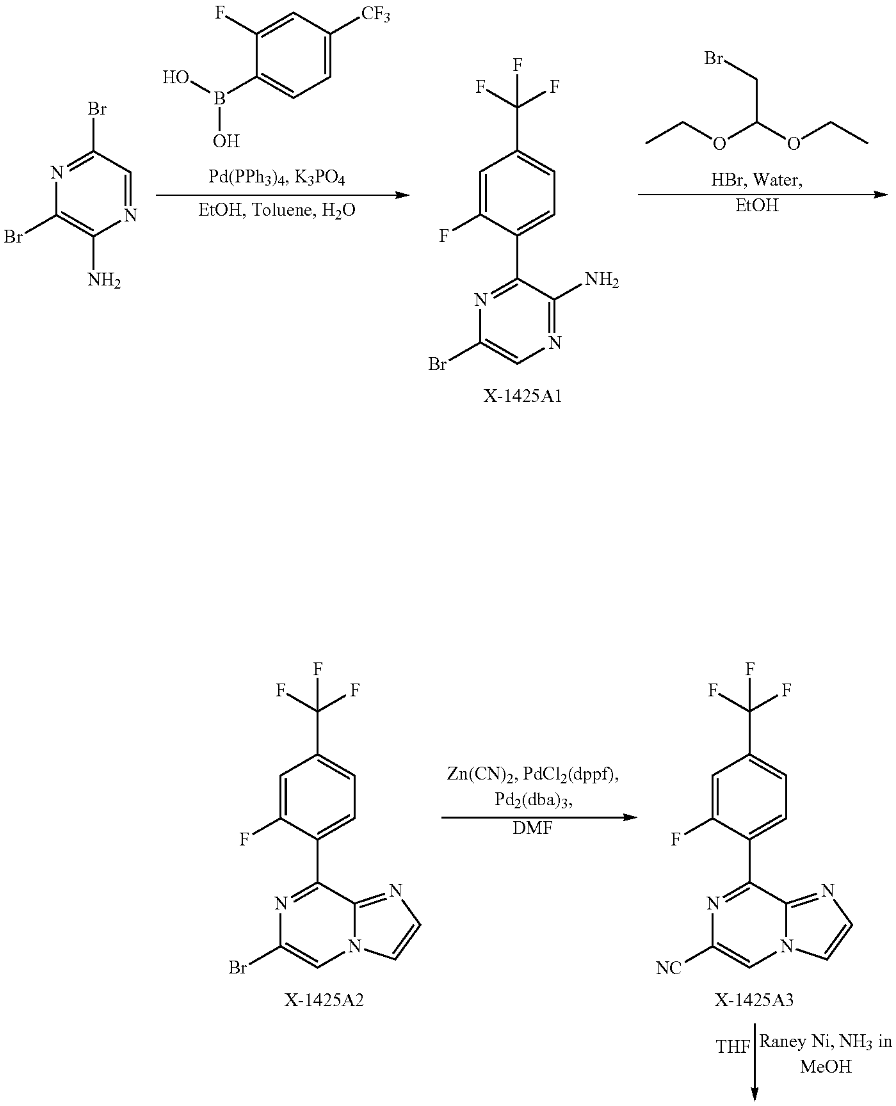

X-1425A1

X-1425A2

X-1425A3

-continued

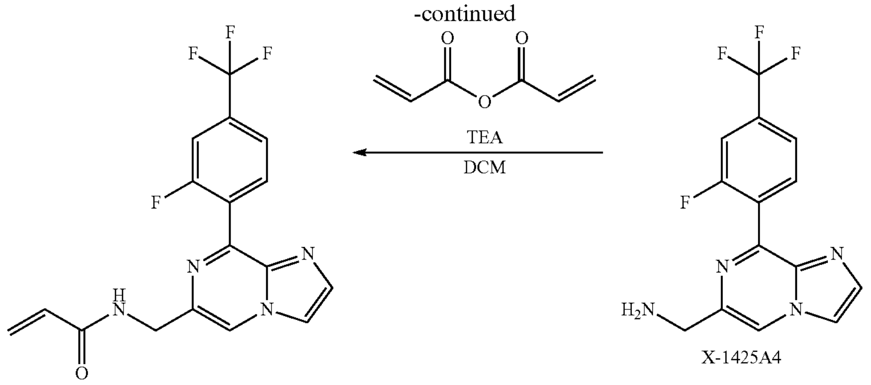

I-175

X-1425A4

5-Bromo-3-(2-fluoro-4-(trifluoromethyl)phenyl)pyrazin-2-amine (X-1425A1). To a stirred solution of 3,5-dibromopyrazin-2-amine (5.0 g, 19.76 mmol) in a mixture of toluene-ethanol-water (50 mL), were added Potassium phosphate (12.59 g, 59.28 mmol) and (2-fluoro-4-(trifluoromethyl)phenyl)boronic acid (8.22 g, 39.52 mmol) at room temperature under nitrogen. The resulting mixture was degassed (purging with nitrogen) for 40 min followed by the addition of $Pd(PPh_3)_4$ (1.14 g, 0.98 mmol) and the resulting mixture was heated at 100° C. for 3 h. Reaction mixture was cooled to room temperature, diluted with water (1 L) and was extracted with ethyl acetate (500 mL×3). Combined organic extracts were washed with brine (500 mL), dried over anhydrous $Na_2SO_4$ and concentrated under reduced pressure. The crude product was purified by silica gel column chromatography, using ethyl acetate-hexane: 0:1→4 2:8 as a gradient, to afford 5-bromo-3-(2-fluoro-4-(trifluoromethyl)phenyl)pyrazin-2-amine (X-1425A1) (5.0 g, 75%) as an off-white solid. MS: $[MH]^+$ 335.9 $[MH+2]^+$337.9.

6-Bromo-8-(2-fluoro-4-(trifluoromethyl)phenyl)imidazo[1,2-a]pyrazine (X-1425A2). To a stirred solution of 5-bromo-3-(2-fluoro-4-(trifluoromethyl)phenyl)pyrazin-2-amine (X-1425A1) (5.0 g, 14.92 mmol) in ethanol (10 mL) was added 2-bromo-1,1-diethoxyethane (5.04 g, 29.85 mmol) at room temperature under nitrogen, HBr in $H_2O$ (48%) (8.46 g, 104.37 mmol) was added at 0° C., and resulting mixture was heated at 80° C. for 2 h. Reaction mixture was cooled to room temperature, slowly poured into water (250 mL) and was extracted with ethyl acetate (200 mL×3). The combined organic extracts were washed with brine (100 mL), dried over anhydrous $Na_2SO_4$ and concentrated under reduced pressure. The crude product was purified by silica gel column chromatography, using ethyl acetate-hexane=0:1→1:0 as gradient, 6-bromo-8-(2-fluoro-4-(trifluoromethyl)phenyl)imidazo[1,2-a]pyrazine (X-1425A2) (2.5 g, 47%) as an off white solid. MS: $[MH]^+$ 360.0 $[MH^+2]$=362.0.

8-(2-Fluoro-4-(trifluoromethyl)phenyl)imidazo[1,2-a]pyrazine-6-carbonitrile (X-1425A3). To a stirred solution of 6-bromo-8-(2-fluoro-4-(trifluoromethyl)phenyl)imidazo[1,2-a]pyrazine (X-1425A2) (1.0 g, 2.78 mmol) in DMF (10 mL) was added zinc cyanide (0.890 g, 6.96 mmol) at room temperature under nitrogen. The reaction mixture was degassed (by purging nitrogen) for 30 min followed by the addition of $PdCl_2(dppf)$ (0.111 g, 0.13 mmol) and $Pd_2(dba)_3$ (0.140 g, 0.13 mmol) and resulting mixture was heated at 120° C. under microwave irradiation for 1 h. Reaction mixture was cooled to room temperature, slowly poured into water (120 mL) and was extracted with ethyl acetate (100 mL×3). The combined organic extracts were washed with brine (50 mL), dried over anhydrous $Na_2SO_4$ and concentrated under reduced pressure. Another one 0.5 g and one identical batch (1.0 g) was performed and workup done together. The crude product was purified by silica gel column chromatography, using ethyl acetate-hexane=0:1→1:0 as gradient, to afford 8-(2-fluoro-4-(trifluoromethyl)phenyl)imidazo[1,2-a]pyrazine-6-carbonitrile (X-1425A3) (2.5 g, crude) as a brown solid. MS: $[MH]^+$ 307.01.

8-(2-Fluoro-4-(trifluoromethyl)phenyl)imidazo[1,2-a]pyrazin-6-yl)methanamine (X-1425A4). To a stirred solution of 8-(2-fluoro-4-(trifluoromethyl)phenyl)imidazo[1,2-a]pyrazine-6-carbonitrile (X-1425A3) (0.400 g, 1.30 mmol) in THF (8 mL) were added Raney Nickel (~0.2 g) and ammonia in MeOH (4 mL) at room temperature and the resulting mixture was hydrogenated in Parr Autoclave at 70° C. under 150 psi for 2 h. Reaction mixture was cooled to room temperature, filtered over a celite bed, washed the bed with MeOH (50 mL×3) and collected filtrates were concentrated under reduced pressure to give (8-(2fluoro4(trifluoromethyl)phenyl)imidazo[1,2-a]pyrazin-6-yl)methanamine (X-1425A4) (0.250 g, 61%) as a yellow sticky solid. MS: $[MH]^+$ 310.96.

N-((8-(2-Fluoro-4-(trifluoromethyl)phenyl)imidazo[1,2-a]pyrazin-6-yl)methyl)acrylamide (I-175). To a stirred solution of (8-(2fluoro4(trifluoromethyl)phenyl)imidazo[1,2-a]pyrazin-6-yl)methanamine (X-1425A4) (0.200 g, 0.64 mmol) in DCM (8 mL) were added TEA (0.130 g, 1.29 mmol) followed by Acrylic anhydride (0.081 g, 0.64 mmol) at 0° C. under nitrogen and the reaction mixture stirred for 30 min at 0° C. The reaction mixture was slowly poured into water (50 mL) and was extracted with DCM (50 mL×3). The combined organic extracts were washed with brine (30 mL), dried over anhydrous $Na_2SO_4$ and concentrated in under reduced pressure. The resulting crude was purified by reverse phase (C-18) silica gel column chromatography using acetonitrile-water=0:1→1:0 as gradient, to afford N-((8-(2-fluoro-4-(trifluoromethyl)phenyl)imidazo[1,2-a]pyrazin-6-yl)methyl)acrylamide (I-175) (0.050 g, 20%) as a white solid. $^1H$ NMR (400 MHz, DMSO-$d_6$) δ 8.82-8.79 (t, J=5.60 Hz, 1H), 8.61 (s, 1H), 8.28 (s, 1H), 8.07-8.04 (t, J=7.20 Hz, 1H), 7.92-7.89 (d, J=10.0 Hz, 1H), 7.83 (s, 1H), 7.79-7.77 (d, J=8.0 Hz, 1H), 6.35-6.28 (m, 1H), 6.17-6.12 (dd, J=17.20, 1.60 Hz, 1H), 5.66-5.63 (dd, J=10.0, 1.60 Hz, 1H), 4.50-4.49 (d, J=5.6 Hz, 2H) MS: $[MH]^+$ 365.0.

Example 1.193. Synthesis of N-((8-fluoro-1-(4-(trifluoromethyl)phenyl)isoquinolin-3-yl)methyl) acrylamide (I-289)

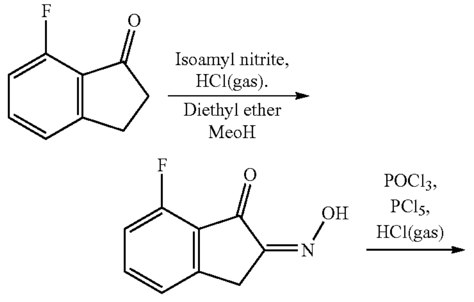

X-1651A1

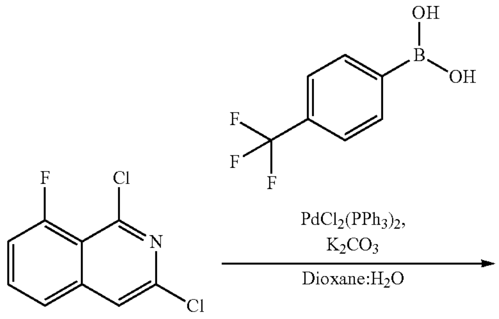

X-1651A2

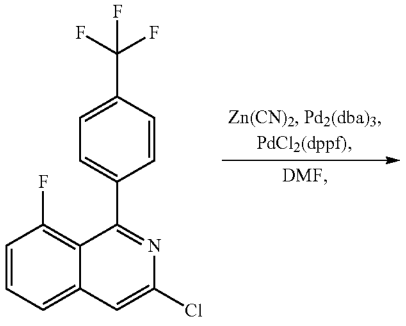

X-1651A3

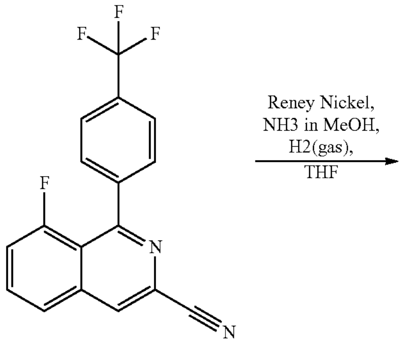

X-1651A4

-continued

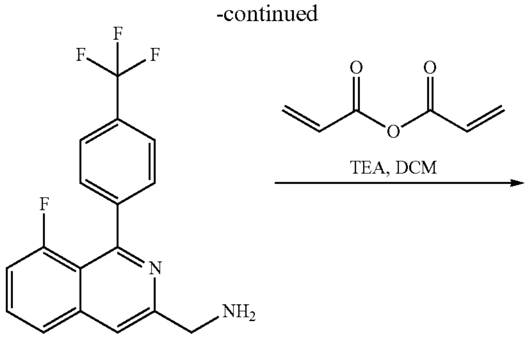

X-1651A5

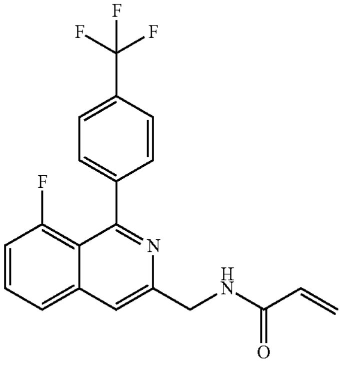

I-289

(Z)-7-fluoro-2-(hydroxyimino)-2,3-dihydro-1H-inden-1-one (X-1651A1). Freshly prepared methanolic HCl was added to the solution of 7-fluoro-2,3-dihydro-1H-inden-1-one (3.00 g, 20.0 mmol) in diethyl ether at 0° C. dropwise followed by isoamyl nitrile (3.5 g, 30.0 mmol) under nitrogen and the resulting mixture was stirred same temperature for 30 min. After cooling to room temperature, solid precipitated was collected by filtration, wash with diethyl ether to afford (Z)-7-fluoro-2-(hydroxyimino)-2,3-dihydro-1H-inden-1-one (X-1651A1) (2.40 g, 68%) as a yellow solid which was used in next step without further purification. MS: $[MH]^+$ 179.88.

1,3-dichloro-8-fluoroisoquinoline (X-1651A2). $PCl_5$ (4.1 g, 20.1 mmol) was added to a stirred solution of (Z)-7-fluoro-2-(hydroxyimino)-2,3-dihydro-1H-inden-1-one (X-1651A1) (2.4 g, 13.4 mmol)) in $POCl_3$ (30 mL) at 0° C. under nitrogen and heated 60° C. for 2 h. Reaction mixture was cooled to room temperature and was slowly poured into ice-water. The resulting precipitate was filtered and the residue was washed with cold water until the pH of the filtrate became neutral (pH~6-7) and dried in vacuo, to afford 1,3-dichloro-8-fluoroisoquinoline (X-1651A2) (1.8 g, 64%) as a yellow solid, which was used in next step without further purification. MS: $[MH]^+$ 215.88

3-Chloro-8-fluoro-1-(4-(trifluoromethyl)phenyl)isoquinoline (X-1651A3). To a stirred solution of 1,3-dichloro-8-fluoroisoquinoline (0.650 g, 2.89 mmol) in a mixture of dioxane-water (12:2 mL), were added (4-(trifluoromethyl) phenyl)boronic acid (0.460 g, 2.41 mmol) and $K_2CO_3$ (0.834 g, 6.046 mmol) sequentially at room temperature under nitrogen. The reaction mixture was degassed (purging with nitrogen) for 20 min followed by the addition of $PdCl_2(PPh_3)_2$ (0.106 g, 0.15 mmol) the resulting mixture was heated at 100° C. for 30 min. Reaction mixture was cooled to room temperature, diluted with water (100 mL) and was extracted with ethyl acetate (100 mL×3). Combined organic extracts were dried over anhydrous $Na_2SO_4$ and concentrated under reduce pressure, Isolated crude was combined with an identical prepared one more batch (1.2 g) and the combined crude product was purified by reverse phase (C-18) silica gel column chromatography, using acetonitrile-water=0:1→1:0 as gradient, to afford 3-chloro-8-fluoro-1-(4-(trifluoromethyl)phenyl)isoquinoline (X-1651A3) (2.0 g, 62%) as a white solid. MS: $[MH]^+$ 325.85.

8-Fluoro-1-(4-(trifluoromethyl)phenyl)isoquinoline-3-carbonitrile (X-1651A4). To a stirred solution of 3-chloro-8-fluoro-1-(4-(trifluoromethyl)phenyl)isoquinoline (X-1651A3) (1.0 g, 3.07 mmol) in a DMF (10 mL) were added $Zn(CN)_2$ (2.15 g, 18.46 mmol) under nitrogen. The reaction mixture was degassed (purging with nitrogen) for 20 min followed by the addition of $PdCl_2$(dppf) (0.112 g, 0.15 mmol) and of $Pd_2(dba)_3$ (0.140 g, 0.15 mmol) resulting mixture was heated in microwave at 160° C. for 45 min. Reaction mixture was cooled to room temperature, diluted with water (300 mL) and was extracted with ethyl acetate (200 mL×3). Combined organic extracts were dried over anhydrous $Na_2SO_4$ and concentrated under reduce pressure, to afford 8-fluoro-1-(4-(trifluoromethyl)phenyl)isoquinoline-3-carbonitrile (X-1651A4) (0.5 g, 51%) as an yellow solid. which was carried forward to next step.

8-Fluoro-1-(4-(trifluoromethyl)phenyl)isoquinolin-3-yl)methanamine (X-1651A5). To a stirred solution of 8-fluoro-1-(4-(trifluoromethyl)phenyl)isoquinoline-3-carbonitrile (X-1651A4) (0.500 g, 1.5 mmol) in THE (5 mL) were added activated Raney Ni (0.1 g) and methanolic ammonia (0.1 mL) sequentially at room temperature the resulting suspension was hydrogenated under $H_{2(gas)}$ 25 psi at rt for 4 h. After cooling to room temperature, reaction mixture was filtered through celite, residue was washed with MeOH (100 mL) and collected filtrates were concentrated under reduced pressure. to afford 8-fluoro-1-(4-(trifluoromethyl)phenyl)isoquinolin-3-yl)methanamine (X-1651A5) 0.250 g, 69% (crude)] as an off-white solid. MS: $[MH]^+$ 320.99.

N-((8-fluoro-1-(4-(trifluoromethyl)phenyl)isoquinolin-3-yl)methyl)acrylamide (I-289). Acrylic anhydride (0.108 g, 0.85 mmol) was added to a stirred solution of 8-fluoro-1-(4-(trifluoromethyl)phenyl)isoquinolin-3-yl)methanamine (X-1651A5) (0.250 g, 0.78 mmol) and tri-ethyl amine (0.145 g, 1.44 mmol) in DCM (5 mL) at 0° C. temperature under nitrogen. The reaction mixture was stirred for 30 min at same temperature. The reaction mixture was poured in water (50 mL) and was extracted with DCM (50 mL×2). Combined organic extracts were dried over anhydrous $Na_2SO_4$ and concentrated under reduced pressure. The crude product was triturate with n-pentane to afford N-((8-fluoro-1-(4-(trifluoromethyl)phenyl)isoquinolin-3-yl)methyl)acrylamide (I-289) (0.100 g, 34%) as a white solid. $^1H$ NMR (400 MHz, DMSO-$d_6$) δ 8.86-8.84 (t, J=6.0, 1H), 7.96-7.94 (d, J=8.4 Hz, 1H), 7.86-7.77 (m, 6H), 7.43-7.38 (m, 1H), 6.41-6.35 (m, 1H), 6.20-6.15 (dd, J=17.2, 2.4 Hz, 1H), 5.69-5.66 (dd, J=10.4, 2.4 Hz, 1H), 4.64-4.63 (d, J=6.0 Hz, 2H). MS: $[MH]^+$ 375.1.

Example 1.194. Synthesis of N-((6-(4-(trifluoromethyl)phenyl)imidazo[1,2-b]pyridazin-8-yl)methyl)acrylamide (I-290)

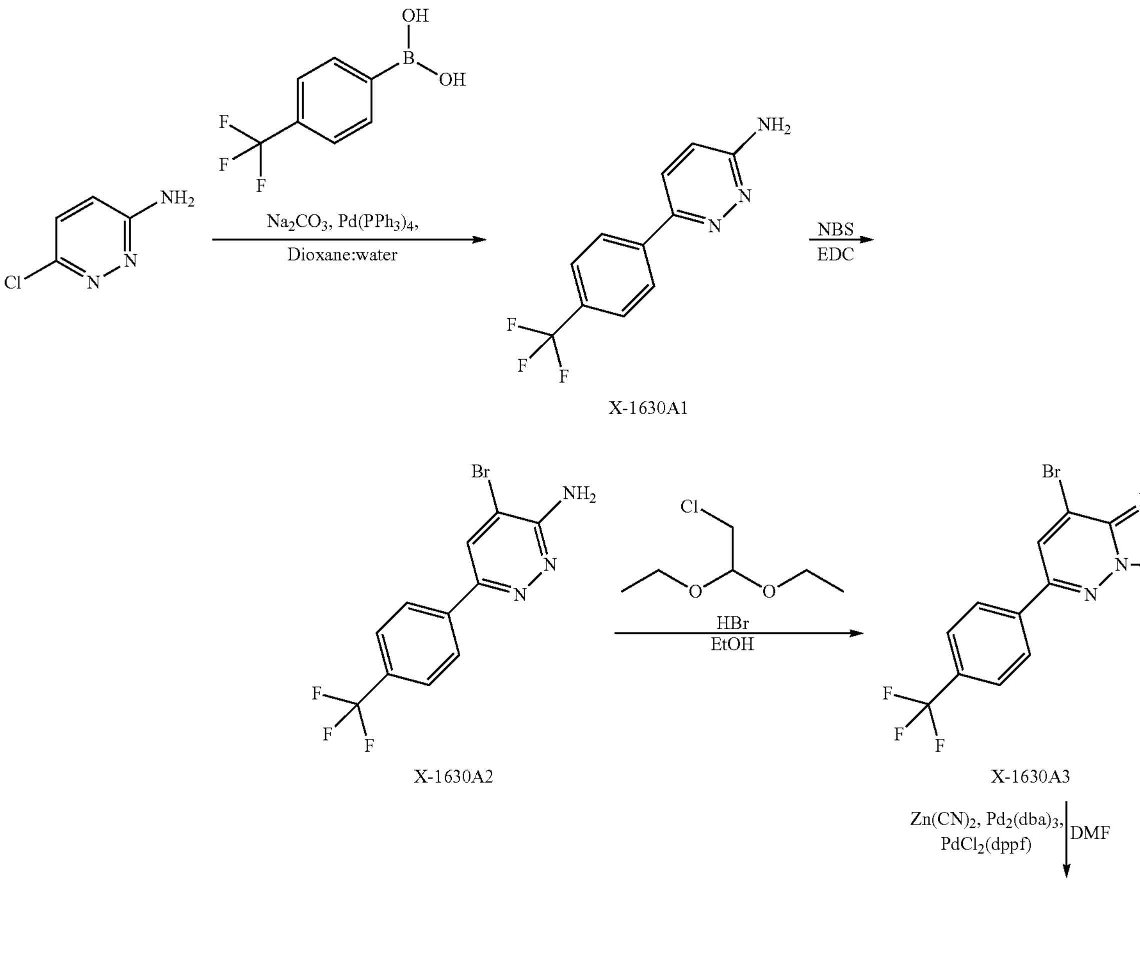

X-1630A1

X-1630A2

X-1630A3

-continued

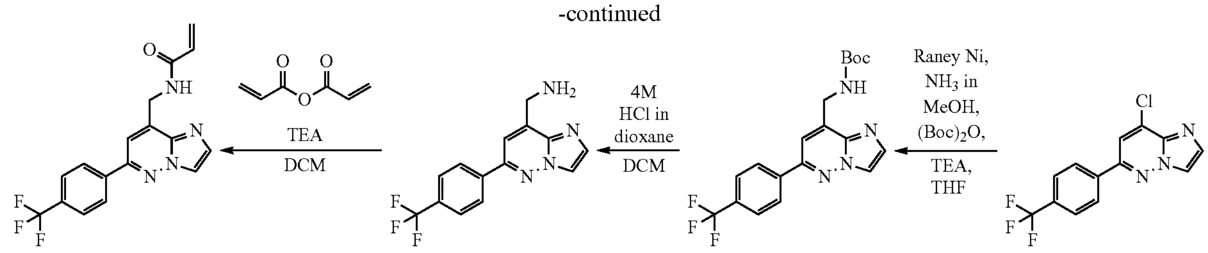

I-290 X-1630A6 X-1630A5 X-1630A4

6-(4-(Trifluoromethyl)phenyl)pyridazin-3-amine (X-1630A1). To a stirred solution of 6-chloropyridazin-3-amine (5.0 g, 38.07 mmol) in a mixture of dioxane-$H_2O$ (3:1, 30 mL) were added (4-(trifluoromethyl)phenyl)boronic acid (13.25 g, 69.7 mmol) and $Na_2CO_3$ (12.32 g, 116 mmol) at room temperature. The reaction mixture was degassed (purging with nitrogen) for 20 min followed by addition of $Pd(PPh_3)_4$ (2.23 g, 1.93 mmol) and the reaction mixture was heated at 110° C. for 2 h. The reaction mixture was cooled to room temperature, diluted with water (300 mL) and was extracted with ethyl acetate (300 mL×3). The combined organic extracts were dried over anhydrous $Na_2SO_4$ and concentrated under reduce pressure. The crude product was purified by silica gel column chromatography, using ethyl acetate-hexane=0:1→4:6 as gradient, to afford 6-(4-(trifluoromethyl)phenyl)pyridazin-3-amine (X-1630A1) (4.0 g, 43%) as an off-white solid. MS: $[MH]^+$ 240.0.

4-Bromo-6-(4-(trifluoromethyl)phenyl)pyridazin-3-amine (X-1630A2). To a stirred solution of 6-(4-(trifluoromethyl)phenyl)pyridazin-3-amine (X-1630A1) (4.00 g, 16.73 mmol) in ethylene dichloride (15 mL) was added N-Bromosuccinimide (5.9 g, 33.47 mmol) at 0° C. under nitrogen and the resulting mixture was stirred at room temperature for 16 h. The reaction mixture was diluted with water (200 mL) and was extracted with ethyl acetate (300 mL×3). The combined organic extracts were dried over anhydrous $Na_2SO_4$ and concentrated under reduce pressure. The crude product was purified by silica gel column chromatography, using ethyl acetate-hexane=0:1→8:2 as gradient, to afford 4-bromo-6-(4-(trifluoromethyl)phenyl)pyridazin-3-amine (X-1630A2) (2.0 g, 37%) as a brown solid. MS: $[MH]^+$ 317.9.

8-Bromo-6-(4-(trifluoromethyl)phenyl)imidazo[1,2-b]pyridazine (X-1630A3). To a stirred solution of 4-bromo-6-(4-(trifluoromethyl)phenyl)pyridazin-3-amine (X-1630A2) (2.0 g, 6.30 mmol) in ethanol (7 mL) were added 2-chloro-1,1-diethoxyethane (1.19 g, 12.61 mmol) and HBr in water (5 mL) at 0° C. under nitrogen and the resulting mixture was stirred at 80° C. for 16 h. After cooling to room temperature, the reaction mixture was quenched with an aqueous solution of saturated $NaHCO_3$ (250 mL) and was extracted with ethyl acetate (50 mL×3). The combined organic extracts were washed with brine (50 mL), dried over anhydrous $Na_2SO_4$ and concentrated in vacuo. The crude product was purified by reverse phase (C-18) silica gel column chromatography, using acetonitrile-water=0:1→6:4 as gradient, to afford 8-bromo-6-(4-(trifluoromethyl)phenyl)imidazo[1,2-b]pyridazine (X-1630A3) (0.400 g, 19%) as a brown solid. MS: $[MH]^+$ 341.8

6-(4-(Trifluoromethyl)phenyl)imidazo[1,2-b]pyridazine-8-carbonitrile (X-1630A4). To a stirred solution of 8-bromo-6-(4-(trifluoromethyl)phenyl)imidazo[1,2-b]pyridazine (X-1630A3) (0.400 g, 1.17 mmol) in a DMF (5 mL) was added zinc cyanide (0.820 g, 7.05 mmol) at room temperature. The reaction mixture was degassed (purging with nitrogen) for 20 min followed by addition of $PdCl_2$ (dppf) (0.042 g, 0.050 mmol) and $Pd_2$ $(dba)_3$ (0.053 g, 0.05 mmol) and the reaction mixture was heated at 150° C. under microwave irradiation for 1 h. The reaction mixture was cooled to room temperature, diluted with water (100 mL) and was extracted with ethyl acetate (100 mL×3). The combined organic extracts were dried over anhydrous $Na_2SO_4$ and concentrated under reduce pressure. The crude product was purified by silica gel column chromatography, using ethyl acetate-hexane=0:1→8:2 as gradient, to afford 6-(4-(trifluoromethyl)phenyl)imidazo[1,2-b]pyridazine-8-carbonitrile (X-1630A4) (0.21 g, 60%) as an orange solid. MS: $[MH]^+$ 289.0.

tert-Butyl ((6-(4-(trifluoromethyl)phenyl)imidazo[1,2-b]pyridazin-8-yl)methyl)carbamate (X-1630A5). To a stirred solution of 6-(4-(trifluoromethyl)phenyl)imidazo[1,2-b]pyridazine-8-carbonitrile (X-1630A4) (0.210 g, 0.69 mmol) in THE (5 mL) were added methanolic ammonia (7N, 1 mL) and di-tert-butyl dicarbonate (0.300 g, 1.38 mmol), TEA (1 ml) and Raney Ni (0.160 g, 2.77 mmol) sequentially at room temperature under nitrogen and the resulting mixture was hydrogenated under balloon pressure at the same temperature for 16 h. The reaction mixture was filtered through a celite bad, washed the bed with ethyl acetate (50 mL) and collected filtrates were concentrated under reduced pressure. Isolated crude was purified by silica gel column chromatography, using ethyl acetate-hexane=6:4→8:2 as gradient, to afford tert-butyl ((6-(4-(trifluoromethyl)phenyl)imidazo[1,2-b]pyridazin-8-yl)methyl)carbamate (X-1630A5) (0.15 g, 77%) as a colorless liquid. MS: $[MH]^+$ 393.0.

(6-(4-(Trifluoromethyl)phenyl)imidazo[1,2-b]pyridazin-8-yl)methanamine (X-1630A6). To a stirred solution of tert-butyl ((6-(4-(trifluoromethyl)phenyl)imidazo[1,2-b]pyridazin-8-yl)methyl)carbamate (X-1630A5) (0.15 g, 0.38 mmol) in DCM (2 mL) were added 4M HCl in dioxane (2.5 mL) at 0° C. to room temperature under nitrogen and the resulting mixture was stirred at room temperature for 1 h. Precipitate fall out was collected by filtration, washed the residue by n-pentane and dried to afford (6-(4-(trifluoromethyl)phenyl)imidazo[1,2-b]pyridazin-8-yl)methanamine (X-1630A6) (0.11 g, 98%) as a white solid. MS: $[MH]^+$ 292.9.

N-((6-(4-(trifluoromethyl)phenyl)imidazo[1,2-b]pyridazin-8-yl)methyl)acrylamide (I-290). To a stirred solution of (6-(4-(trifluoromethyl)phenyl)imidazo[1,2-b]pyridazin-8-yl)methanamine (X-1630A5) (0.110 g, 0.28 mmol) in DCM (3 mL) were added triethylamine (0.085 g, 0.84 mmol) and acrylic anhydride (0.03 g, 0.30 mmol) at 0° C. and reaction mixture was stirred at room temperature for 30 min. The reaction mixture was diluted with aqueous $NaHCO_3$ (10 mL) and was extracted by ethyl acetate (30 mL×3). The combined organic extracts were dried over anhydrous $Na_2SO_4$ and concentrated under reduce pressure. The crude product was purified by (C-18) silica gel column chromatography, using acetonitrile-water=0:1→6:4 as gradient, to N-((6-(4-(trifluoromethyl)phenyl)imidazo[1,2-b] pyridazin-8-yl)methyl)acrylamide (I-290) (0.030 g, 23%) as an off-white solid. $^1$H NMR (400 MHz, DMSO-$d_6$) δ 8.85-8.86 (m, 1H), 8.44 (s, 1H), 8.23-8.21 (d, J=8.0 Hz, 2H), 7.97-7.95 (d, J=8.0 Hz, 2H), 7.86 (s, 1H), 7.61 (s, 1H), 6.42-6.35 (m, 1H), 6.19-6.15 (d, J=16.8 Hz, 1H), 5.71-5.68 (d, J=10.4 Hz, 1H), 4.84-4.83 (d, J=5.6 Hz, 2H). MS: $[MH]^+$347.1.

Example 1.195. Synthesis of (E)-4-fluoro-N-((8-(2-fluoro-4-(trifluoromethyl)phenyl)imidazo[1,2-a] pyrazin-6-yl)methyl)but-2-enamide (I-291)

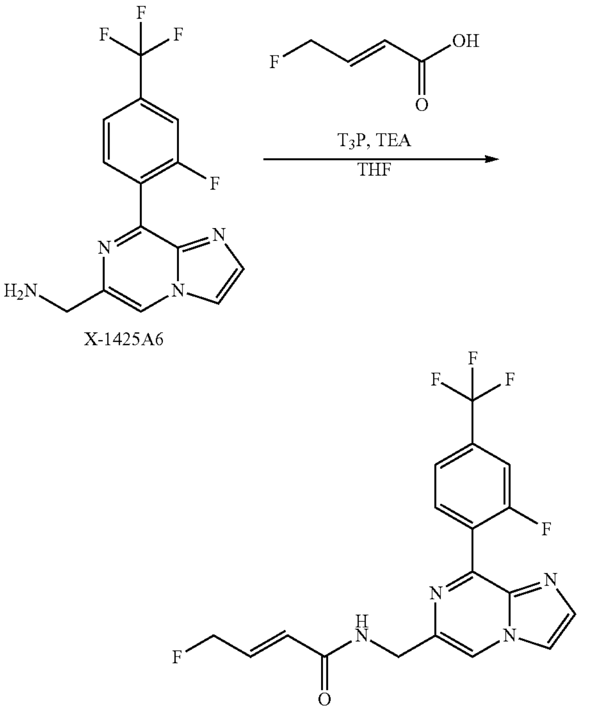

X-1425A6

I-291

To a solution of (8-(2-fluoro-4-(trifluoromethyl)phenyl) imidazo[1,2-a]pyrazin-6-yl)methanamine (0.298 g, 0.960 mmol) in THE (5 mL) were added (E)-4-fluorobut-2-enoic acid (0.100 g, 0.960 mmol) and TEA (0.485 g, 4.80 mmol). The mixture was stirred at room temperature for 5 min after that $T_3P$ (0.458 g, 1.44 mmol) was added dropwise and the resulting mixture was stirred at room temperature for 1 h. The resulting mixture was diluted with water (100 mL) and was extracted with dichloromethane (150 mL×3) The resulting crude was purified by reverse phase (C-18) silica gel column chromatography, using acetonitrile-water=0:147:3 as gradient, to afford (E)-4-fluoro-N-((8-(2-fluoro-4-(trifluoromethyl)phenyl)imidazo[1,2-a]pyrazin-6-yl)methyl) but-2-enamide (I-291) (0.040 g, 11%) as an off-white solid. $^1$H NMR (400 MHz, DMSO-$d_6$) δ 8.85-8.83 (t, J=5.6 Hz, 1H), 8.61 (s, 1H), 8.28 (s, 1H), 8.07-8.04 (t, J=7.2 Hz, 1H), 7.91-7.89 (d, J=10.0 Hz, 1H), 7.82 (s, 1H), 7.79-7.77 (d, J=8.0 Hz 1H), 6.81-6.71 (m, 1H), 6.27-6.23 (dd, J=15.6, 2.0 Hz, 1H), 5.18-5.17 (d, J=1.6 Hz, 1H), 5.067-5.063 (d, J=1.6 Hz, 1H), 4.50-4.49 (d, J=5.6 Hz, 2H) MS: $[MH]^+$ 397.3.

Example 1.196. Synthesis of—N-((8-(4-(trifluoromethyl)phenoxy)imidazo[1,2-a]pyrazin-6-yl)methyl) acrylamide (1-174)

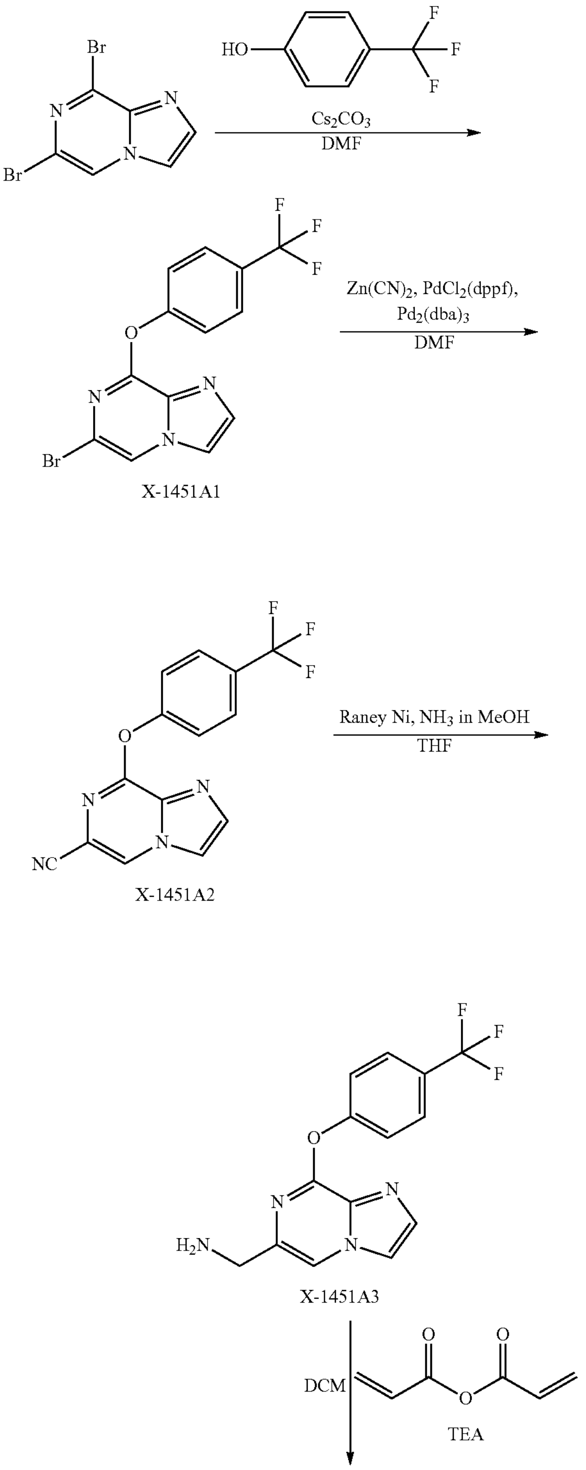

X-1451A1

X-1451A2

X-1451A3

-continued

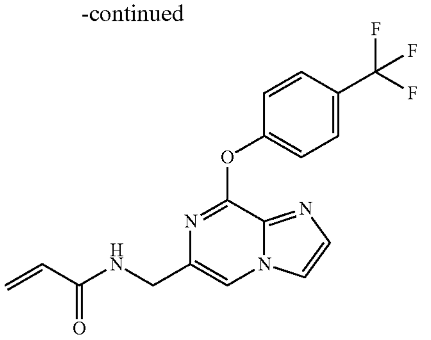

I-174

6-Bromo-8-(4-(trifluoromethyl)phenoxy)imidazo[1,2-a]pyrazine (X-1451A1). To a stirred solution of 6,8-dibromo-imidazo[1,2-a]pyrazine (0.500 g, 1.82 mmol) in DMF (5 mL) were added cesium carbonate (1.180 g, 3.64 mmol) and 4-(trifluoromethyl)phenol (0.295 g, 1.82 mmol) at room temperature under nitrogen and the resulting mixture was stirred at same temperature for 1 h. The reaction mixture was slowly poured into ice-water (20 mL) and the resulting precipitate was collected by filtration. Obtained residue was washed with water, crude solid residue was dried under reduced pressure, to afford 6-bromo-8-(4-(trifluoromethyl)phenoxy)imidazo[1,2-a]pyrazine (X-1451A1) (0.530 g, 82%) as an off-white solid, which was used in the next step without further purification. MS: $[MH]^+$ 357.9.

8-(4-(trifluoromethyl)phenoxy)imidazo[1,2-a]pyrazine-6-carbonitrile (X-1451A2). To a stirred solution of 6-bromo-8-(4-(trifluoromethyl)phenoxy)imidazo[1,2-a]pyrazine (X-1451A1) (0.450 g, 1.26 mmol) in DMF (10 mL) was added zinc cyanide (0.445 g, 3.79 mmol) at room temperature under nitrogen. The reaction mixture was degassed (by purging nitrogen) for 30 min followed by the addition of $PdCl_2$(dppf) (0.092 g, 0.12 mmol), $Pd_2(dba)_3$ (0.115 g, 0.12 mmol) and resulting mixture was heated at 120° C. under microwave irradiation for 1 h. Reaction mixture was cooled to room temperature, slowly poured into water (120 mL) and was extracted with ethyl acetate (100 mL×3). The combined organic extracts were washed with brine (50 mL), dried over anhydrous $Na_2SO_4$ and concentrated under reduced pressure. The crude product was purified by silica gel column chromatography, using ethyl acetate-hexane=0:1→1:0 as a gradient, to afford 8-(4-(trifluoromethyl)phenoxy)imidazo[1,2-a]pyrazine-6-carbonitrile (X-1451A2) (0.300 g, 78%) as a brown solid. MS: $[MH]^+$ 304.96.

8-(4-(trifluoromethyl)phenoxy)imidazo[1,2-a]pyrazin-6-yl)methanamine (X-1451A3). To a stirred solution of 8-(4-(trifluoromethyl)phenoxy)imidazo[1,2-a]pyrazine-6-carbonitrile (X-1451A2) (0.300 g, 0.98 mmol) in THE (5 mL) were added Raney Nickel (~0.3 g) and solution of ammonia in MeOH (7N, 5 mL) at room temperature and the resulting mixture was hydrogenated in Parr Autoclave under 200 psi at 60° C. for 3 h. Reaction mixture was cooled to room temperature, filtered over a celite bed, washed the bed with MeOH (50 mL×3) and collected filtrates were concentrated under reduced pressure to give (8-(4-(trifluoromethyl)phenoxy)imidazo[1,2-a]pyrazin-6-yl)methanamine (X-1451A3) (0.280 g, 92%) as a yellow solid. MS: $[MH]^+$ 308.91.

N-((8-(4-(trifluoromethyl)phenoxy)imidazo[1,2-a]pyrazin-6-yl)methyl)acrylamide (I-174). To a stirred solution of (8-(4-(trifluoromethyl)phenoxy)imidazo[1,2-a]pyrazin-6-yl)methanamine (X-1451A3) (0.280 g, 0.90 mmol) in DCM (5 mL) were added TEA (0.275 g, 2.72 mmol) followed by acrylic anhydride (0.114 g, 0.90 mmol) at 0° C. under nitrogen and the reaction mixture stirred for 10 min at room temperature. The reaction mixture was slowly poured into water (30 mL) and was extracted with DCM (30 mL×3). The combined organic extracts were washed with brine (30 mL), dried over anhydrous $Na_2SO_4$ and concentrated under reduced pressure. The resulting crude was purified by reverse phase (C-18) silica gel column chromatography using acetonitrile-water=0:1→1:0 as a gradient, to afford N-((8-(4-(trifluoromethyl)phenoxy)imidazo[1,2-a]pyrazin-6-yl)methyl)acrylamide (I-174) (0.090 g, 27%) as a white solid. $^1H$ NMR (400 MHz, DMSO-$d_6$) δ 8.61-8.59 (t, J=5.6 Hz, 1H), 8.25-8.21 (d, J=14.0 Hz, 2H), 7.84-7.82 (d, J=8.4 Hz, 2H), 7.76 (s, 1H), 7.57-7.54 (d, J=8.4 Hz, 2H), 6.30-6.23 (m, 1H), 6.13-6.08 (dd, J=2.0, 17.2 Hz, 1H), 5.64-5.61 (dd, J=10.0, 1.6 Hz, 1H), 4.20-4.19 (d, J=5.6 Hz, 2H). MS: $[MH]^+$ 362.92.

Example 1.197. Synthesis of N-((7-methyl-4-(4-(trifluoromethyl)phenyl)-7H-pyrrolo[2,3-d]pyrimidin-2-yl)methyl)acrylamide (1-292)

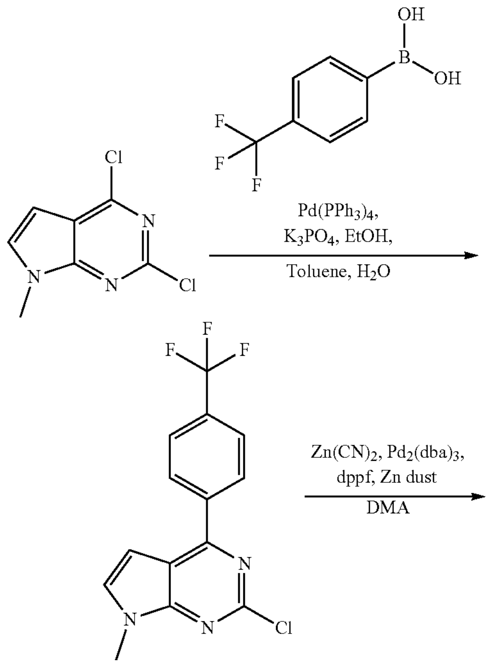

X-1631A1

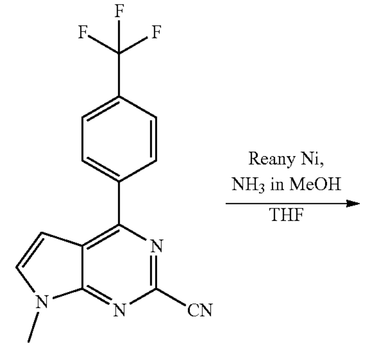

X-1631A2

-continued

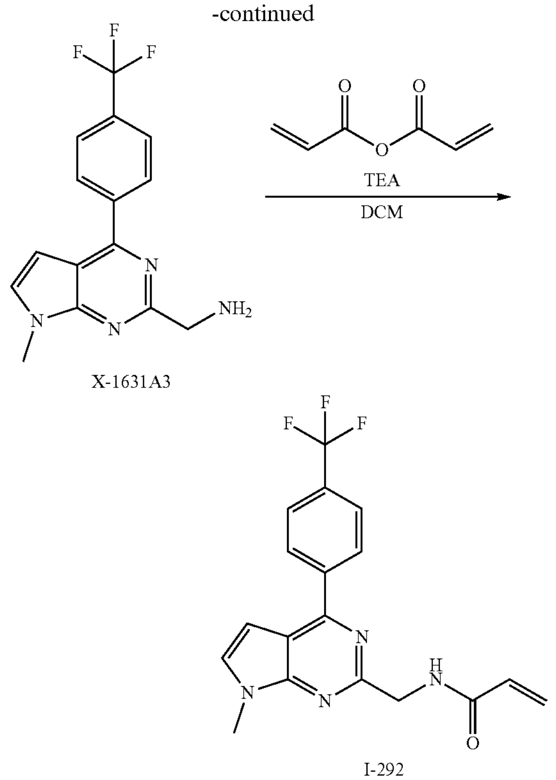

X-1631A3

I-292

2-Chloro-7-methyl-4-(4-(trifluoromethyl)phenyl)-7H-pyrrolo[2,3-d]pyrimidine (X-1631A1). To a stirred solution of 2,4-dichloro-7-methyl-7H-pyrrolo[2,3-d]pyrimidine (3.0 g, 14.9 mmol) in a mixture of Toluene-water (25:10 mL), EtoH (10 mL) were added (4-(trifluoromethyl)phenyl)boronic acid (2.83 g, 14.9 mmol) and $K_3PO_4$ (6.31 g, 29.8 mmol) sequentially at room temperature under nitrogen. The reaction mixture was degassed (purging with nitrogen) for 20 min followed by the addition of $Pd(PPh_3)_4$ (0.863 g, 0.74 mmol) and the resulting mixture was heated at 90° C. for 2 h. Reaction mixture was cooled to room temperature, diluted with water (300 mL) and was extracted with ethyl acetate (300 mL×3). Combined organic extracts were dried over anhydrous $Na_2SO_4$ and concentrated under reduce pressure to afford crude mass, which was purified by silica gel Flash column chromatography, using ethyl acetate-hexane=0: 1→1:9 as eluent, to afford 2-chloro-7-methyl-4-(4-(trifluoromethyl)phenyl)-7H-pyrrolo[2,3-d]pyrimidine (X-1631A1) (3.2 g, 68%) as an off-white solid. MS: $[MH]^+$ 312.0.

N-((7-methyl-4-(4-(trifluoromethyl)phenyl)-7H-pyrrolo[2,3-d]pyrimidin-2-yl)methyl)acrylamide (I-292). The remaining steps, starting with 2-chloro-7-methyl-4-(4-(trifluoromethyl)phenyl)-7H-pyrrolo[2,3-d]pyrimidine (X-1631A1) were prepared in a manner analogous to the procedures described below for N-((4-(4-(trifluoromethyl)phenyl)-5H-pyrrolo[3,2-d]pyrimidin-2-yl)methyl)acrylamide (I-450)

N-((7-methyl-4-(4-(trifluoromethyl)phenyl)-7H-pyrrolo[2,3-d]pyrimidin-2-yl)methyl)acrylamide (I-292). (0.230 g, 49%) as a white solid. $^1$H NMR (400 MHz, DMSO-$d_6$) δ 8.73-8.70 (t, J=5.2 Hz, 1H), 8.40-8.38 (d, J=8.0 Hz, 2H), 7.95-7.93 (d, J=8.4 Hz, 2H), 7.73-7.72 (d, J=3.2 Hz, 1H), 6.94-6.93 (d, J=3.6 Hz, 1H), 6.46-6.39 (m, 1H), 6.16-6.11 (dd, J=17.2, 2.0 Hz, 1H), 5.65-5.62 (dd, J=10.4, 2.0 Hz, 1H), 4.69-4.67 (d, J=5.6 Hz, 2H) 3.85 (s, 3H). MS: $[MH]^+$361.1.

Example 1.198. Synthesis of N-((8-((4-(trifluoromethyl) benzyl) oxy) imidazole[1,2-a] pyrazin-6-yl) methyl) acrylamide (1-293)

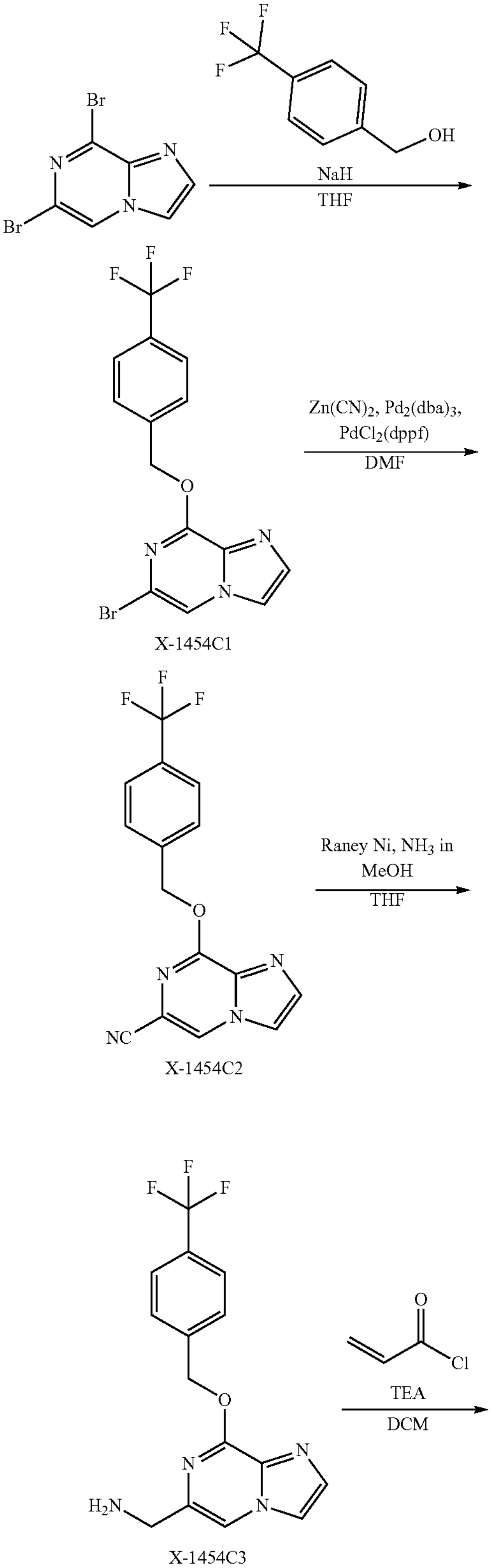

X-1454C1

X-1454C2

X-1454C3

-continued

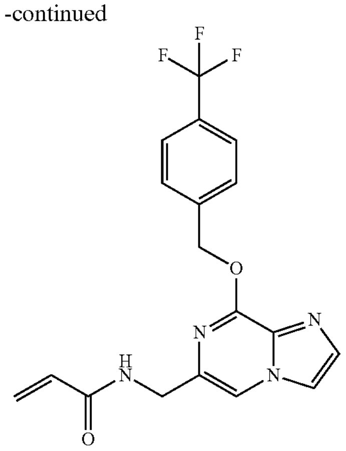

I-293

6-Bromo-8-((4-(trifluoromethyl) benzyl) oxy) imidazole [1,2-a] pyrazine (X-1454A1). To a stirred solution of (4-(trifluoromethyl) phenyl) methanol (2.83 g, 10.83 mmol) in THE (30 mL) was added NaH (60% dispersion in mineral oil; 0.380 g, 16.24 mmol) at 0° C. under nitrogen. After stirring for 30 min at the same temperature, was added methyl 6,8-dibromoimidazo[1,2-a] pyrazine (3.0 g, 10.80 mmol) into the reaction solution and the resulting mixture was stirred at 80° C. for 1 h. Reaction was cooled to room temperature, diluted with water (150 mL) and was extracted with ethyl acetate (150 mL×2). Combined organic extracts were dried over anhydrous $Na_2SO_4$ and concentrated under reduce pressure. Obtained crude product was purified by silica gel column chromatography, using ethyl acetate-hexane 0:1→1:9 as a gradient, to afford 6-bromo-8-((4-(trifluoromethyl) benzyl) oxy) imidazole[1,2-a] pyrazine (X-1454A1) (2.0 g, 49%) as an off-white solid. MS: $[MH]^+$ 372.2/374.1

8-((4-(Trifluoromethyl) benzyl) oxy) imidazo[1,2-a] pyrazine-6-carbonitrile (X-1454A2). To a stirred solution of 6-bromo-8-((4-(trifluoromethyl) benzyl) oxy) imidazole[1, 2-a] pyrazine (X-1454A1) (2.0 g, 3.65 mmol) in DMF (8 mL) was added zinc cyanide (1.07 g, 9.22 mmol) at room temperature under nitrogen. The reaction mixture was degassed (purged with nitrogen) for 20 min followed by the addition of $Pd_2(dba)_3$ (0.337 g, 0.36 mmol) and $PdCl_2(dppf)$ (0.269 g, 0.37 mmol) and the resulting suspension was heated at 120° C. under microwave irradiation for 1 h. After cooling to room temperature, reaction mixture was diluted with water (100 mL) and was extracted with ethyl acetate (50 mL×3). Combined organic extracts were dried over $Na_2SO_4$ and concentrated under reduce pressure. Isolated crude was purified by silica gel column chromatography, using ethyl acetate-hexane 3:7→3:2 as gradient, to afford 8-(4-fluorophenyl)imidazo[1,2-a]pyrazine-6-carbonitrile (X1454A2) (1.0 g, 58%) as a yellow solid. MS: $[MH]^+$ 318.9.

8-((4-(trifluoromethyl) benzyl) oxy) imidazo[1,2-a] pyrazin-6-yl) methoxamine (X-1454A3). To a stirred solution of 8-(4-fluorophenyl) imidazole[1,2-a] pyrazine-6-carbonitrile (X1454A2) (1.0 g, 3.10 mmol) in methanol (10 mL) were added Raney Ni (0.300 g) and $NH_3$ (7N in methanol; 6 mL) respectively in a Parr Autoclave and the resulting mixture was hydrogenated under 200 psi at 60° C. for 1 h. Reaction mixture was cooled to room temperature, filtered through a celite bed and the collected filtrate was concentrated in vacuum to afford (8-((4-(trifluoromethyl) benzyl) oxy) imidazo[1,2-a] pyrazin-6-yl) methoxamine (X-1454A3) (0.250 g, 24% crude) as an off white solid. Isolated crude was taken to the next step without further purification. MS: $[MH]^+$ 322.9.

N-((8-((4-(trifluoromethyl) benzyl) oxy) imidazo[1,2-a] pyrazin-6-yl) methyl) acrylamide (I-293). To a stirred solution of 8-((4-(trifluoromethyl) benzyl) oxy) imidazo[1,2-a] pyrazin-6-yl) methoxamine (X-1454A3) (0.200 g, 0.62 mmol) in DCM (5 mL) were added trimethylamine (0.188 g, 1.86 mmol) and acryloyl chloride (0.078 g, 0.61 mmol) sequentially at 0° C. under nitrogen and stirred for 15 min at the same temperature. The reaction mixture was diluted with water (50 mL) and was extracted with ethyl acetate (50 mL×2). Combined organic extracts were washed with brine (50 mL), dried over anhydrous $Na_2SO_4$ and concentrated under reduce pressure. The crude product was purified by reverse phase (C-18) silica gel column chromatography, using acetonitrile-0.1% formic acid in water as gradient, to afford N-((8-((4-(trifluoromethyl) benzyl) oxy) imidazo[1, 2-a] pyrazin-6-yl) methyl) acrylamide (I-293) (0.080 g, 27%) as an off white solid. 1H NMR (400 MHz, DMSO-$d_6$) δ 8.61 (br, 1H), 8.11-8.09 (d, J=7.6 Hz, 2H), 7.76 (s, 4H), 7.62 (s, 1H), 6.35-6.28 (m, 1H), 6.16-6.12 (d, J=16.0 Hz, 1H), 5.64 (s, 3H), 4.32-4.31 (d, J=5.6 Hz, 2H). MS: $[MH]^+$ 377.2.

Example 1.199. Synthesis of N-((8-((3-(trifluoromethyl) benzyl) oxy) imidazo[1,2-a] pyrazin-6-yl) methyl) acrylamide (I-294)

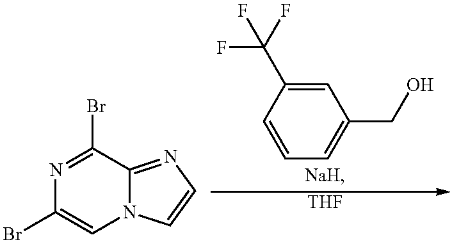

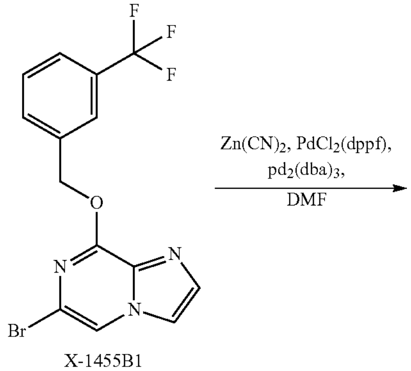

X-1455B1

-continued

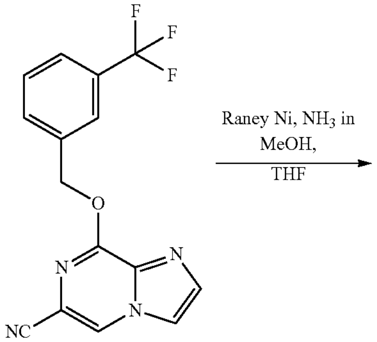

X-1455B2

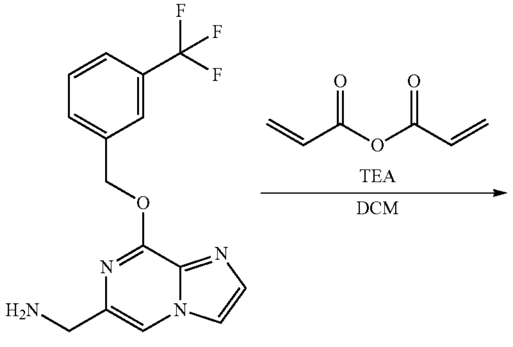

X-1455B3

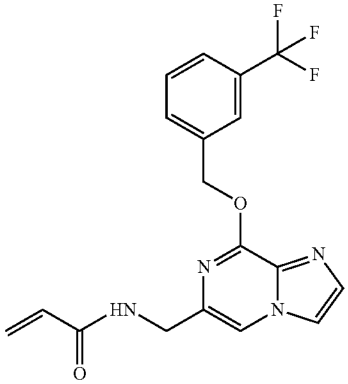

I-294

The following compound was prepared in a manner analogous to the procedures described above for N-((8-((4-(trifluoromethyl) benzyl) oxy) imidazo[1,2-a] pyrazin-6-yl) methyl) acrylamide (I-293):

N-((8-((3-(trifluoromethyl) benzyl) oxy) imidazo[1,2-a] pyrazin-6-yl) methyl) acrylamide (I-294) (0.040 g, 17%) as an off white solid. $^1H$ NMR (400 MHz, DMSO-$d_6$) δ 8.65-8.63 (t, J=5.6 Hz, 1H), 8.10-8.09 (d, J=6.4 Hz, 2H), 7.92 (s, 1H), 7.87-7.85 (d, J=7.6 Hz, 1H), 7.74-7.72 (d, J=7.6 Hz, 1H), 7.66-7.64 (d, J=8.4 Hz, 1H), 7.62 (s, 1H), 6.36-6.29 (dd, J=17.2 Hz, 10.4 Hz, 1H), 6.17-6.16 (dd, J=17.2 Hz, 2.0 Hz, 1H), 5.67-5.66 (d, J=2.0 Hz, 1H), 5.64 (s, 2H), 4.34-4.32 (d, J=5.6 Hz, 2H). MS: $[MH]^+$ 377.2.

Example 1.200. Synthesis of N-((7-fluoro-1-(4-(trifluoromethyl)phenyl)isoquinolin-3-yl)methyl) acrylamide (I-295)

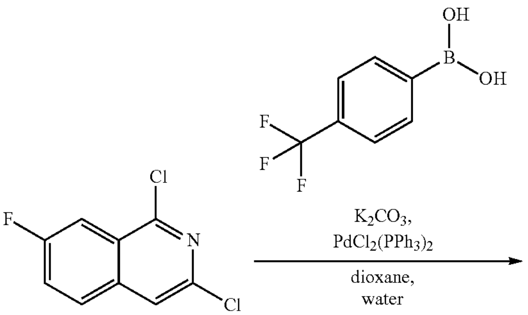

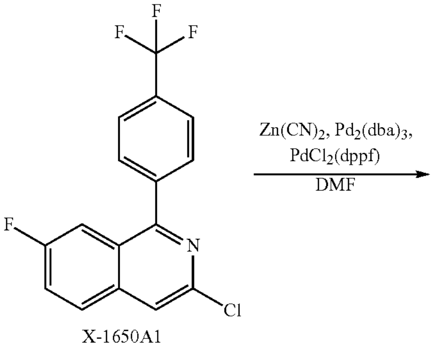

X-1650A1

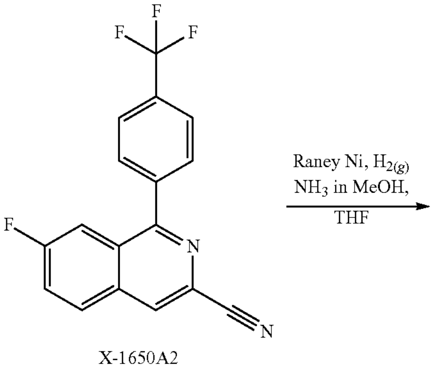

X-1650A2

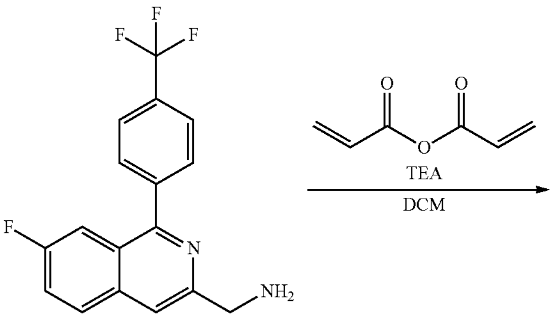

X-1650A3

-continued

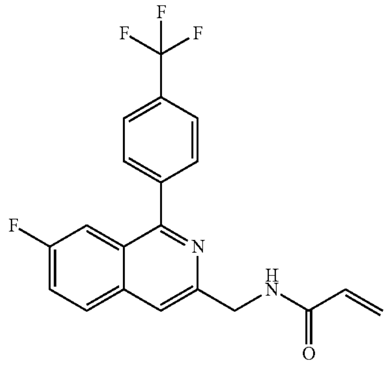

I-295

The following target was prepared in a manner analogous to the procedures described below for N-((4-(4-(trifluoromethyl)phenyl)-5H-pyrrolo[3,2-d]pyrimidin-2-yl)methyl) acrylamide (I-450):

N-((7-fluoro-1-(4-(trifluoromethyl)phenyl)isoquinolin-3-yl)methyl)acrylamide (I-295) (0.07 g, 33%) as a white solid. $^{1}H$ NMR (400 MHz, DMSO-$d_6$) δ 8.85-8.84 (t, J=5.6 Hz, 1H), 8.24-8.21 (m, 1H), 7.97-7.92 (m, 4H), 7.83-7.75 (m, 2H), 7.64-7.62 (d, J=8.8 Hz, 1H), 6.41-6.34 (m, 1H), 6.19-6.14 (dd, J=17.2, 1.6 Hz, 1H), 5.68-5.65 (dd, J=10.0, 1.6 Hz, 1H), 4.65-4.66 (d, J=5.6 Hz, 2H). MS: $[MH]^+$ 375.0.

Example 1.201. Synthesis of N-((8-((3-(trifluoromethyl) phenyl) amino) imidazo[1,2-a] pyrazin-6-yl) methyl) acrylamide (I-169)

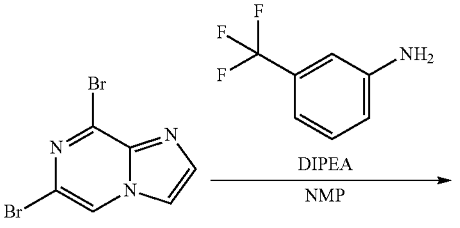

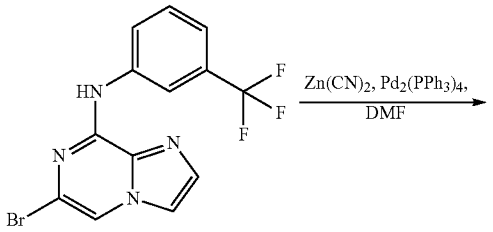

X-1456A1

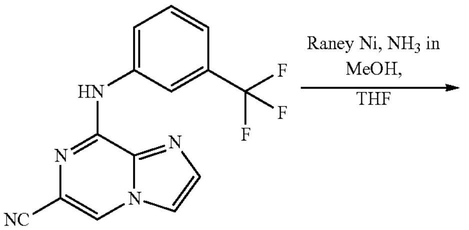

X-1456A2

-continued

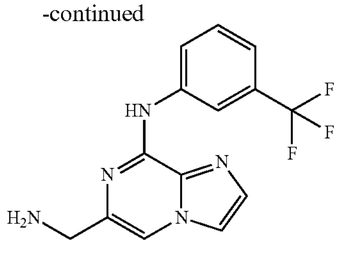

X-1456A3

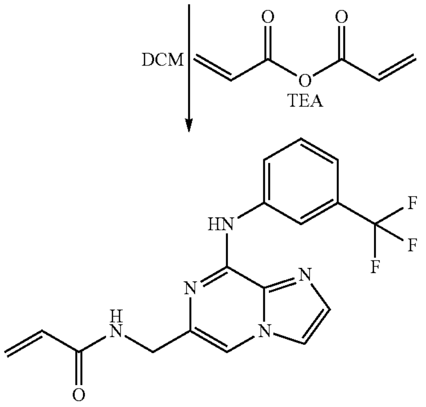

I-169

6-bromo-N-(3-(trifluoromethyl) phenyl) imidazo[1,2-a] pyrazin-8-amine (X-1456A1) 3-(trifluoromethyl) aniline (0.580 g, 3.61 mmol) in NMP (10 mL) and DIPEA (0.931 g, 7.20 mmol) were added to a stirred solution of 6,8-dibromoimidazo[1,2-a] pyrazine (1.0 g, 3.61 mmol) at room temperature under nitrogen and reaction mixture was stirred at 120° C. under microwave irradiation for 30 min. After cooling to room temperature, reaction mixture was diluted with water (50 mL) and was extracted by ethyl acetate (50 ml×3). Combined organic extracts were dried over $Na_2SO_4$ and concentrated under reduced pressure. The crude product was purified silica gel column chromatography, using ethyl acetate-hexane 5:0→5:0 as gradient, to afford 6-bromo-N-(3-(trifluoromethyl) phenyl) imidazo[1,2-a] pyrazin-8-amine (X-1456A1) (0.700 g, 54%) as an off-whitesolid. MS: $[NM]^+$356.9.

8-((3-(trifluoromethyl) phenyl) amino) imidazo[1,2-a] pyrazine-6-carbonitrile (X-1456A2) To a stirred solution of 6-bromo-N-(3-(trifluoromethyl) phenyl) imidazo[1,2-a] pyrazin-8-amine (X-1456A1) (0.700 g, 1.56 mmol) in DMF (5 mL) was added zinc cyanide (0.578 g, 94.91 mmol) at room temperature under nitrogen. The reaction mixture was degassed (purged with nitrogen) for 20 min followed by the addition of $Pd_2$ $(pph_3)_4$ (0.454 g, 0.39 mmol) and the resulting suspension was heated at 120° C. for 1 h under microwave irradiation. After cooling to room temperature, reaction mixture was diluted with water (100 mL) and was extracted with ethyl acetate (50 mL×2). Combined organic extracts were dried over $Na_2SO_4$ and concentrated under reduce pressure. Crude product was purified by silica gel column chromatography, using ethyl acetate-hexane 3.7→7.3 as gradient, to afford 8-((3-(trifluoromethyl) phenyl) amino) imidazo[1,2-a] pyrazine-6-carbonitrile (X-1456A2) (0.500 g, 67%) as a yellow solid. MS: [MH]+ 304.0.

6-(amino methyl)-N-(3-(trifluoromethyl) phenyl) imidazo [1,2-a] pyrazin-8-amine (X-1456A3) To stirred solution of 8-((3-(trifluoromethyl) phenyl) amino) imidazo[1,2-a]pyrazine-6-carbonitrile (X-1456A2) (0.400 g, 1.32 mmol) in THF (5 mL) were added Raney Ni (0.200 g) and $NH_3$ (7N in methanol; 3 mL) respectively in a Parr Autoclave and the resulting mixture was hydrogenated under 200 psi at 60° C. for 1 h. Reaction mixture was cooled to room temperature, filtered through a celite bed and the collected filtrate was concentrated in vacuum to afford 6-(amino methyl)-N-(3-(trifluoromethyl) phenyl) imidazo[1,2-a] pyrazin-8-amine (X-1456A3) (0.300 g, 74%) as an off white solid. Isolated crude was taken to the next step without further purification. MS: $[MH]^+$ 308.0.

N-((8-((3-(trifluoromethyl) phenyl) amino) imidazo[1,2-a] pyrazin-6-yl) methyl) acrylamide (I-169) To a stirred solution of 6-(amino methyl)-N-(3-(trifluoromethyl) phenyl) imidazo[1,2-a] pyrazin-8-amine (X-1456A3) (0.300 g, 0.97 mmol) in DCM (3 mL) were added trimethylamine (0.296 g, 2.93 mmol) and acrylic anhydride (0.123 g, 0.57 mmol) sequentially at 0° C. under nitrogen and stirred for 15 min at the same temperature. The reaction mixture was diluted with water (50 mL) and was extracted with ethyl acetate (50 mL×2). Combined organic extracts were washed with brine (50 mL), dried over anhydrous $Na_2SO_4$ and concentrated under reduce pressure. The crude product was purified by reverse phase (C-18) silica gel column chromatography, using acetonitrile in water 3:0→7:0 as gradient, to afford N-((8-((3-(trifluoromethyl) phenyl) amino) imidazo[1,2-a] pyrazin-6-yl) methyl) acrylamide (I-169) (0.120 g, 34.02%) as an off white solid. 1H NMR (400 MHz, DMSO-$d_6$) δ 10.04 (s, 1H), 8.62-8.58 (m, 2H), 8.44-8.42 (d, J=8.4 Hz, 1H), 8.04 (s, 1H), 7.94 (s, 1H), 7.64 (s, 1H), 7.53-7.49 (t, J=7.6 Hz 1H), 7.32-7.303 (d, J=7.6 Hz 1H), 6.32-6.29 (m, 1H), 6.17-6.13 (d, J=16.8 Hz 1H), 5.65-5.63 (d, J=10.4 Hz 1H), 4.34-4.33 (d, J=5.6 Hz 2H) MS: [MH]+ 362.0.

Example 1.202. Synthesis of N-((8-((3-(trifluoromethyl) benzyl) amino) imidazo[1,2-a] pyrazin-6-yl) methyl) acrylamide (I-296)

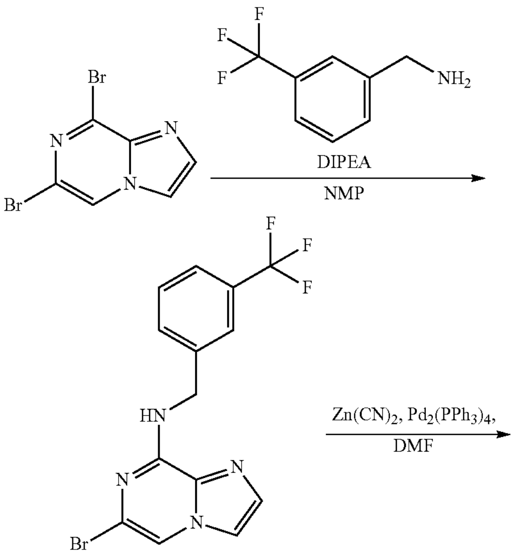

X-1457A1

-continued

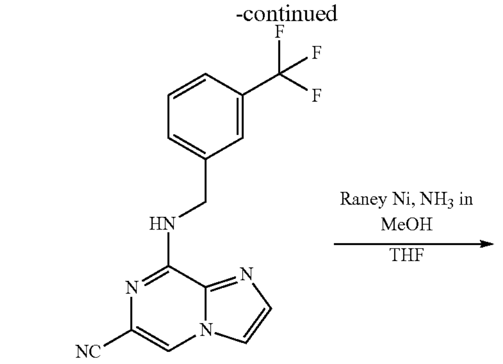

X-1457A2

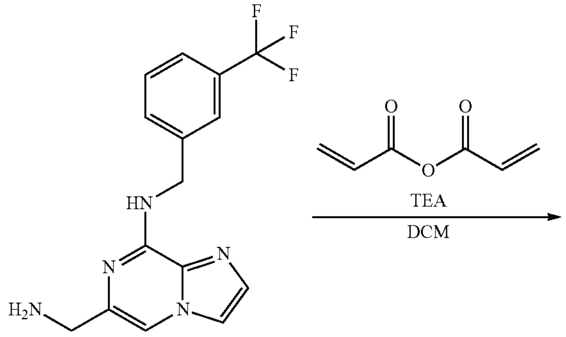

X-1457A3

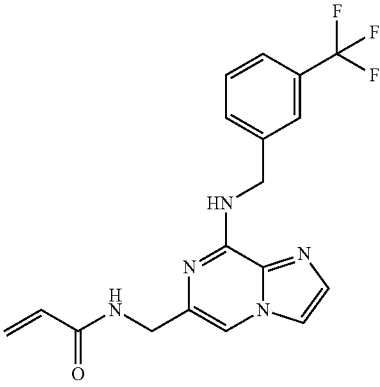

I-296

The following compound was prepared in a manner analogous to the procedures described above for N-((8-((3-(trifluoromethyl) phenyl) amino) imidazo[1,2-a] pyrazin-6-yl) methyl) acrylamide (I-169):

N-((8-((3-(trifluoromethyl) benzyl) amino) imidazo[1,2-a] pyrazin-6-yl) methyl) acrylamide (I-296) (0.090 g, 39%) as an off white solid. $^1H$ NMR (400 MHz, DMSO-$d_6$) δ 8.50-8.47 (t, J=5.6 Hz, 1H), 8.26-8.23 (t, J=6.0 Hz, 1H), 7.89 (s, 1H), 7.64-7.58 (m, 5H), 7.94 (s, 1H), 6.32-6.25 (dd, J=2 Hz, J=17.2 Hz, 10.4 Hz, 1H), 6.13-6.09 (dd, J=17.2 Hz, 2.0 Hz 1H), 5.63-5.60 (dd, J=10.0 Hz, 2.0 Hz 1H), 4.72-4.71 (d, J=6.0 Hz 2H), 4.18-4.16 (d, J=5.6 Hz 1H); MS: $[MH]^+$ 376.2.

Example 1.203. Synthesis of N-((8-((4-(trifluoromethyl) benzyl) amino) imidazo[1,2-a] pyrazin-6-yl) methyl) acrylamide (I-297)

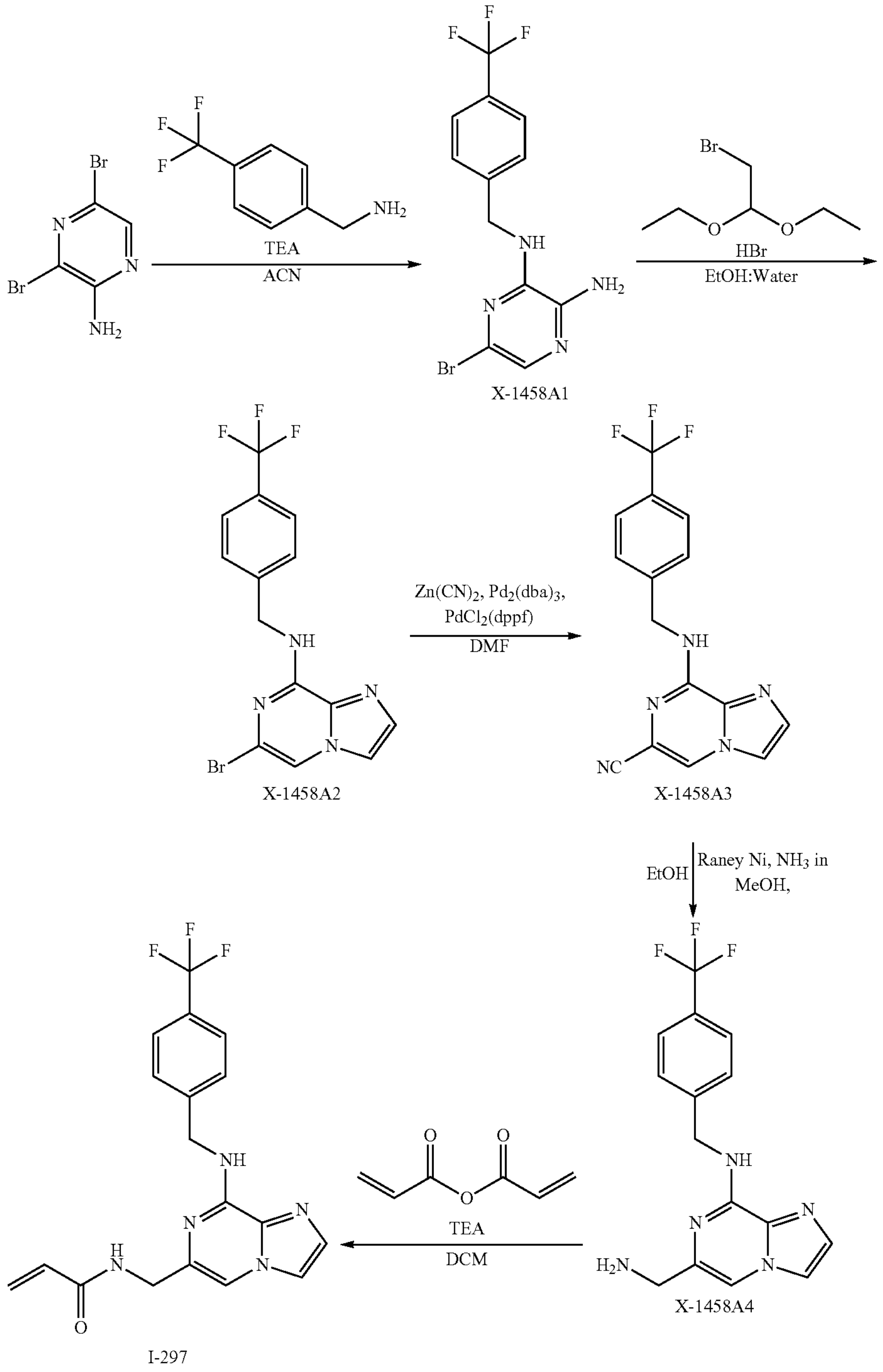

X-1458A1

X-1458A2

X-1458A3

X-1458A4

I-297

6-bromo-N²-(4-(trifluoromethyl) benzyl) pyrazine-2,3-diamine (X-1458A1) To a stirred solution of 3,5-dibromopyrazin-2-amine (X-1458A1) (3.0 g, 11.86 mmol) in ACN. (10 mL) was added (4-(trifluoromethyl) phenyl) methoxamine (4.6 g, 26.09 mmol) and TEA (3.5 gm, 35.5 mmol) at room temperature under nitrogen and the resulting mixture was heated at 180° C. under microwave irradiation for 3 h. Reaction mixture was cooled to room temperature, slowly poured into water (60 mL) and was extracted with ethyl acetate (100 mL×2). The combined organic extracts were washed with brine (50 mL), dried over anhydrous $Na_2SO_4$ and concentrated in vacuum. The crude was purified by silica gel column chromatography, using ethyl acetate-hexane=0:1→1:0 as gradient, to afford 6-bromo-N2-(4-(trifluoromethyl) benzyl) pyrazine-2,3-diamine (X-1458A1) (3.0 g, 73%) as a white solid. MS: $[MH]^+$ 346.9. MS: $[MH]^2$+ 348.8.

6-bromo-N-(4-(trifluoromethyl) benzyl) imidazo[1,2-a] pyrazin-8-amine (X-1458A2). To a stirred solution 6-bromo-$N^2$-(4-(trifluoromethyl) benzyl) pyrazine-2,3-diamine (X-1458A1) (3.0 g, 8.67 mmol) in EtOH—$H_2O$ (1:1, 25 mL) was added solution of 2-bromo-1,1-diethoxyethane (3.3 g, 17.34 mmol) in EtOH (30 mL) at room temperature under nitrogen followed by the addition of HBr (4.9 mL, 60.70 mmol) dropwise at 0° C. and resulting mixture was heated at 80° C. for 24 h. After cooling to room temperature, reaction mixture was slowly poured into ice-water (120 mL) and was extracted with ethyl acetate (100 mL×3). Combined organic extracts were washed with brine (50 mL), dried over anhydrous $Na_2SO_4$ and concentrated in vacuo. The crude product was purified by silica gel column chromatography, using ethyl acetate-hexane=0:1→1:0 as gradient, to afford 6-bromo-N-(4-(trifluoromethyl)benzyl)imidazo[1,2-a] pyrazin-8-amine (X-1458A2) (1.3 g, 41%) as a white solid. MS: $[MH]^+$ 370.9$[MH]^2$+372.8.

8-((4-(trifluoromethyl) benzyl) amino) imidazo[1,2-a] pyrazine-6-carbonitrile (X-1458A3). To a stirred solution 6-bromo-N-(4-(trifluoromethyl) benzyl) imidazo[1,2-a] pyrazin-8-amine (X-1458A2) (1.3 g, 3.51 mmol) in DMF (10 mL) was added zinc cyanide (1.03 g, 8.78 mmol) at room temperature under nitrogen. The reaction mixture was degassed (by purging nitrogen) for 30 min followed by the addition of $PdCl_2$(dppf) (0.257 g, 0.35 mmol), $Pd_2(dba)_3$ (0.321 g, 0.35 mmol) and the resulting mixture was heated at 120° C. under microwave irradiation for 1 h. Reaction mixture was cooled to room temperature, slowly poured into ice-water (120 mL) and was extracted with ethyl acetate (100 mL×3). Combined organic extracts were washed with brine (50 mL), dried over anhydrous $Na_2SO_4$ and concentrated in vacuo. The crude product was purified by silica gel column chromatography, using ethyl acetate-hexane=0: 1→1:0 as gradient, to afford 8-((4-(trifluoromethyl)benzyl) amino)imidazo[1,2-a]pyrazine-6-carbonitrile (X-1458A3) (0.850 g, 77%) as a white solid. MS: $[MH]^+$ 317.09.

6-(amino methyl)-N-(4-(trifluoromethyl) benzyl) imidazo [1,2-a] pyrazin-8-amine (X-1458A4). To a stirred solution of 8-((4-(trifluoromethyl)benzyl)amino)imidazo[1,2-a]pyrazine-6-carbonitrile (X-1458A3) (0.500 g, 1.58 mmol) in THF (5 mL) were added activated Raney Ni (0.300 g, 5.03 mmol) and $NH_3$ (7N in methanol; 5 mL) respectively at room temperature and the resulting mixture was hydrogenated in a Parr autoclave under 200 psi at 70° C. for 2 h. Reaction was allowed to come to room temperature, filtered off the residue through a celite bed, washed the bed with methanol and collected filtrates were concentrated under reduced pressure to provide a crude mass, which triturated with n-pentane (100 mL) and dried under high vacuum to afford 6-(aminomethyl)-N-(4-(trifluoromethyl)benzyl)imidazo[1,2-a]pyrazin-8-amine (X-1458A4) (0.500 g, 100%) as an off-white solid, which was carried forward to the next step without further purification. MS: $[MH]^+$ 321.9.

N-((8-((4-(trifluoromethyl) benzyl) amino) imidazo[1,2-a] pyrazin-6-yl) methyl) acrylamide (I-297). To a stirred solution of 6-(amino methyl)-N-(4-(trifluoromethyl) benzyl) imidazo[1,2-a] pyrazin-8-amine (X-1458A4) (0.250 g, 0.778 mmol) in DCM (3 mL) were added triethylamine (0.315 g, 3.11 mmol) followed by acryloyl chloride (0.118 g, 0.93 mmol) at 0° C. under nitrogen and the reaction mixture stirred for 30 min at room temperature. The reaction mixture was slowly poured into water (30 mL) and was extracted with DCM (30 mL×3). Combined organic extracts were washed with brine (30 mL), dried over anhydrous $Na_2SO_4$ and concentrated in vacuo. The resulting crude was purified by reverse phase (C-18) silica gel column chromatography using acetonitrile-water=0:1→1:0 as gradient, to afford N-((8-((4-(trifluoromethyl)benzyl)amino)imidazo[1,2-a]pyrazin-6-yl)methyl)acrylamide (I-297) (0.120 g, 29%) as a white solid. $^1H$ NMR (400 MHz, DMSO-$d_6$) δ 8.48-8.45 (t, J=5.2 Hz, 1H), 8.24-8.21 (t, J=6.0 Hz, 1H), 7.89 (s, 1H), 7.63-7.59 (m, 5H), 7.49 (s, 1H), 6.32-6.25 (dd, J=17.2 Hz, 10.4 Hz, 1H), 6.13-6.09 (dd, J=17.2 Hz, 2.0 Hz, 1H), 5.63-5.60 (dd, J=10.4 Hz, 2.0 Hz, 1H), 4.73-4.71 (d, J=6.0 Hz, 2H), 4.183-4.169 (d, J=6.4 Hz, 2H), MS: $[MH]^+$ 376.3.

Example 1.204. Synthesis of N-((8-(methyl(3-trifluoromethyl)phenyl)amino)imidazol[1,2-a]pyrazin-6-yl)methyl)acrylamide (I-298)

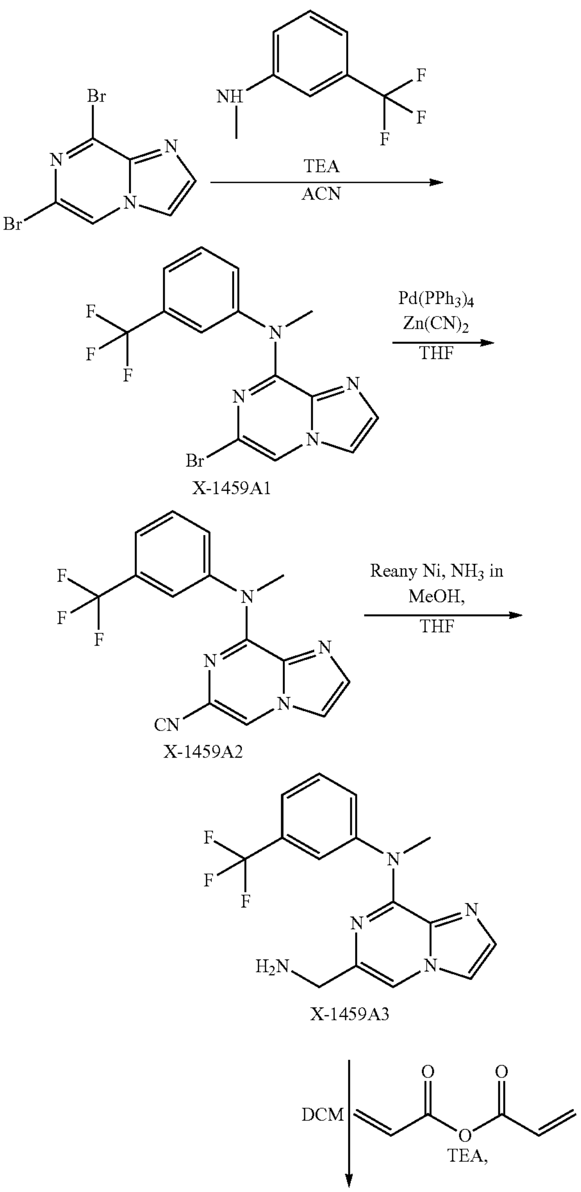

-continued

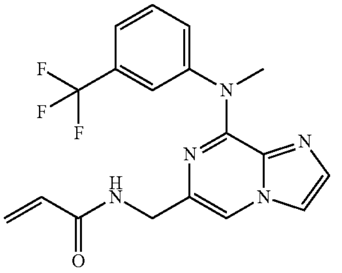

I-298

The following compound was prepared in a manner analogous to the procedures described above for N-((8-((3-(trifluoromethyl) phenyl) amino) imidazo[1,2-a] pyrazin-6-yl) methyl) acrylamide (I-169):

N-((8-(methyl(3-(trifluoromethyl)phenyl)amino)imidazo[1,2-a]pyrazin-6-yl)methyl)acrylamide (I-298) (0.030 g, 18.34%) as an off white solid. $^1$H NMR (400 MHz, DMSO-$d_6$) δ8.59 (s, 1H), 8.34 (s, 1H), 7.96 (s, 2H), 7.55 (s, 1H), 7.49 (s, 2H), 7.41 (s, 1H), 6.32 (m, 1H), 6.15-6.11 (d, J=16 Hz, 1H), 5.65-5.62 (d, J=10.8 Hz, 1H), 4.28-4.27 (d, J=5.6 Hz, 2H), 3.70 (s, 3H). MS: $[MH]^+$ 376.2.

Example 1.205. Synthesis of N-((6-fluoro-1-(4-(trifluoromethyl)phenyl)isoquinolin-3-yl)methyl) acrylamide (I-299)

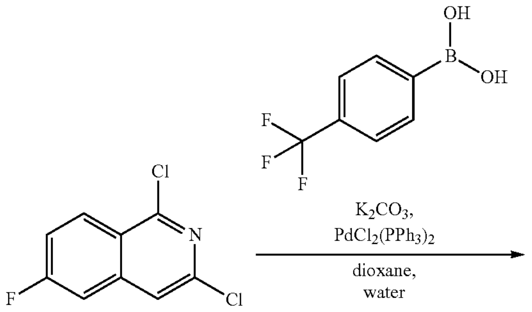

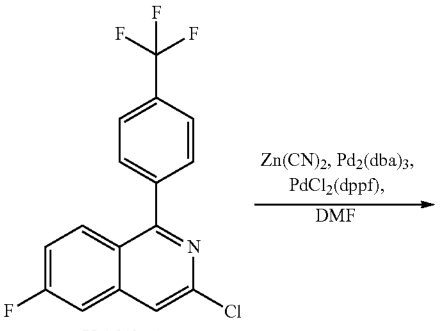

X-1649A1

-continued

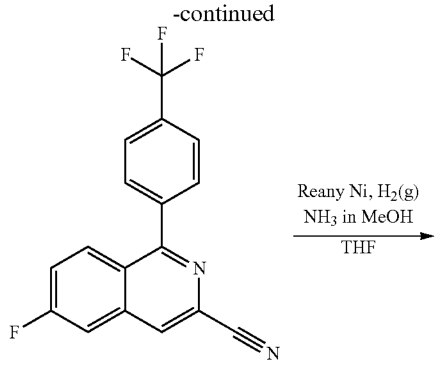

X-1649A2

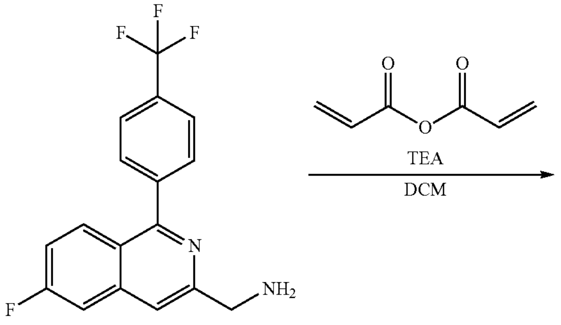

X-1649A3

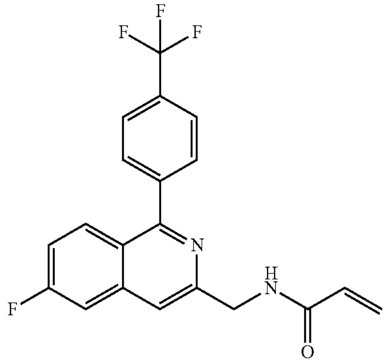

I-299

The following target was prepared in a manner analogous to the procedures described below for N-((4-(4-(trifluoromethyl)phenyl)-5H-pyrrolo[3,2-d]pyrimidin-2-yl)methyl) acrylamide (I-450):

N-((6-fluoro-1-(4-(trifluoromethyl)phenyl)isoquinolin-3-yl)methyl)acrylamide (I-299) (0.07 g, 30%) as a white solid. $^1$H NMR (400 MHz, DMSO-$d_6$) δ 8.87 (br, 1H), 8.05-8.02 (m, 1H), 7.96-7.89 (m, 5H), 7.76 (s, 1H), 7.54-7.50 (t, J=7.6 Hz, 1H), 6.41-6.35 (m, 1H), 6.19-6.15 (d, J=17.2 Hz 1H), 5.68-5.65 (m, J=10.0 Hz 1H), 4.64-4.63 (d, J=5.2 Hz, 1H). MS: $[MH]^+$ 375.1.

Example 1.206. Synthesis of N-((8-((5-(trifluoromethyl)pyridin-2-yl)amino)imidazo[1,2-a]pyrazin-6-yl)methyl)acrylamide (I-170)

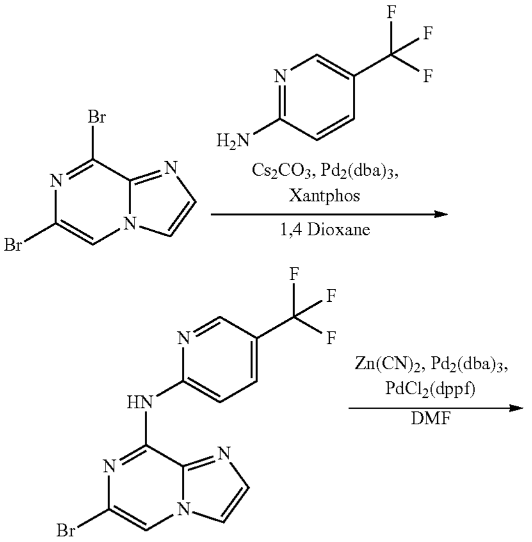

X-1460A1

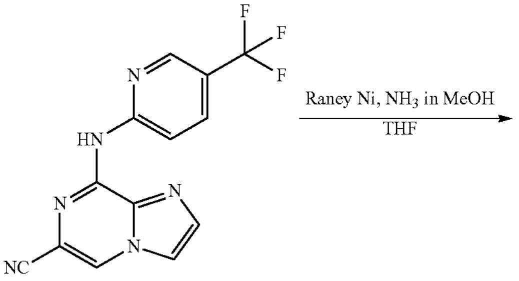

X-1460A2

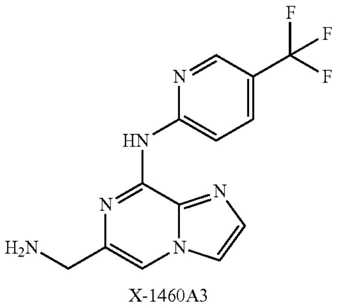

X-1460A3

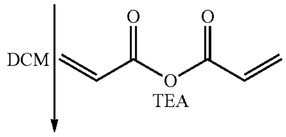

-continued

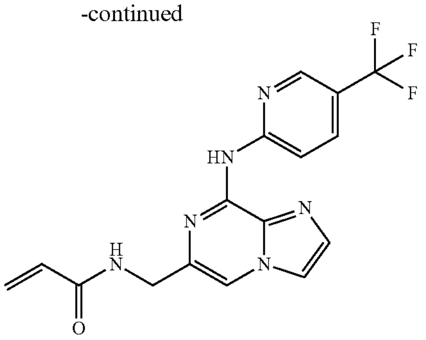

I-170

6-Bromo-N-(5-(trifluoromethyl)pyridin-2-yl)imidazo[1,2-a]pyrazin-8-amine (X-1460A1). To a stirred solution of 6,8-dibromoimidazo[1,2-a]pyrazine (2.0 g, 7.21 mmol) in 1,4-Dioxane (20 mL) was added 5-(trifluoromethyl)pyridin-2-amine (1.18 g, 7.21 mmol) and $Cs_2CO_3$ (5.86 g, 18.05 mmol) and Xanthphos (0.418 g, 0.72 mmol) at room temperature under nitrogen. The reaction mixture was degassed (purged with nitrogen) for 30 min followed by the addition of $Pd_2(dba)_3$ (0.66 g, 0.72 mmol) and reaction mixture was heated at 120° C. for 1 h under microwave irradiation. After cooling to room temperature, reaction mixture was diluted with water (100 mL) and was extracted with ethyl acetate (100 mL×3). Combined organic extracts were dried over $Na_2SO_4$ and concentrated under reduce pressure. Crude product was purified by silica gel column chromatography, using ethyl acetate-hexane 2:8→3:7 as gradient, to afford 6-bromo-N-(5-(trifluoromethyl)pyridin-2-yl)imidazo[1,2-a]pyrazin-8-amine (X-1460A1) (1.8 g, 70%) as a yellow solid. MS: $[MH^{+}2]^{+}$ 358.0, $[MH+2]^{2+}$ 356.0

8-((5-(Trifluoromethyl)pyridin-2-yl)amino)imidazo[1,2-a]pyrazine-6-carbonitrile (X-1460A2). To a stirred solution of 6-bromo-N-(5-(trifluoromethyl)pyridin-2-yl)imidazo[1,2-a]pyrazin-8-amine (X-1460A1) (1.8 g, 5.04 mmol) in DMF (20 mL) was added zinc cyanide (1.47 g, 12.60 mmol) at room temperature under nitrogen. The reaction mixture was degassed (purged with nitrogen) for 30 min followed by the addition of $Pd_2(dba)_3$ and (0.461 g, 0.50 mmol) and $PdCl_2$(dppf) and (0.368 g, 0.50 mmol) the resulting suspension was heated at 180° C. for 30 min under microwave irradiation. After cooling to room temperature, reaction mixture was diluted with water (50 mL) and was extracted with ethyl acetate (50 mL×3). Combined organic extracts were dried over $Na_2SO_4$ and concentrated under reduce pressure. Crude product was purified by silica gel column chromatography, using ethyl acetate-hexane=5:0→5:0 as gradient, to afford 8-((5-(trifluoromethyl)pyridin-2-yl)amino)imidazo[1,2-a]pyrazine-6-carbonitrile (X-1460A2) (1.2 g, 78%) as an off-white solid. MS: $[MH]^+$ 305.0.

6-(Aminomethyl)-N-(5-(trifluoromethyl)pyridin-2-yl)imidazo[1,2-a]pyrazin-8-amine (X-1460A3). To a stirred solution of 8-((5-(trifluoromethyl)pyridin-2-yl)amino)imidazo[1,2-a]pyrazine-6-carbonitrile (X-1460A2) (0.500 g, 1.64 mmol) in THE (5 mL) were added Raney Ni (0.250 g) and $NH_3$ (7N in methanol; 1 mL) respectively in a Parr Autoclave and the resulting mixture was heated at 60° C. for 3 h. Reaction mixture was cooled to room temperature, filtered through a celite bed and the collected filtrate was concentrated in vacuo to afford 6-(aminomethyl)-N-(5-(trifluoromethyl)pyridin-2-yl)imidazo[1,2-a]pyrazin-8-amine (X-1460A3) (0.450 g, 88.82%) as an off white solid. MS: $[MH]^+$ 309.04.

N-((8-((5-(trifluoromethyl)pyridin-2-yl)amino)imidazo[1,2-a]pyrazin-6-yl)methyl)acrylamide (I-170). To a stirred solution of 6-(aminomethyl)-N-(5-(trifluoromethyl)pyridin-2-yl)imidazo[1,2-a]pyrazin-8-amine (X-1460A3) (0.200 g, 0.64 mmol) in DCM (4 mL) were added triethylamine (0.327 g, 3.24 mmol) and acrylic anhydride (0.081 g, 0.64 mmol) sequentially at 0° C. under nitrogen and stirred for 10 min. The reaction mixture was diluted with water (50 mL) and was extracted with ethyl acetate (50 mL×2). Combined organic extracts were washed with brine (50 mL), dried over anhydrous $Na_2SO_4$ and concentrated under reduce pressure. The crude product was purified by reverse phase (C-18) silica gel column chromatography, using acetonitrile in water 6:5→3:5 as gradient, to afford N-((8-((5-(trifluoromethyl)pyridin-2-yl)amino)imidazo[1,2-a]pyrazin-6-yl)methyl)acrylamide (I-170) (0.030 g, 13%) as an off white solid. $^1H$ NMR (400 MHz, DMSO-$d_6$) δ 9.307 (s, 1H), 8.773-8.751 (d, J=8.8 Hz 1H), 8.715 (s, 1H), 8.156-8.102 (m, 3H), 7.702 (s, 1H), 6.377-6.309 (m, 1H), 6.197-6.192 (dd, J=2 Hz, 1H), 5.679-5.674 (d, J=2 Hz, 1H), 4.410-4.395 (d, J=6 Hz, 2H). MS: $[MH]^+$363.0.

Example 1.207. Synthesis of N-((8-(methyl(4-(trifluoromethyl)benzyl)amino)imidazo[1,2-a]pyrazin-6-yl)methyl)acrylamide (I-300)

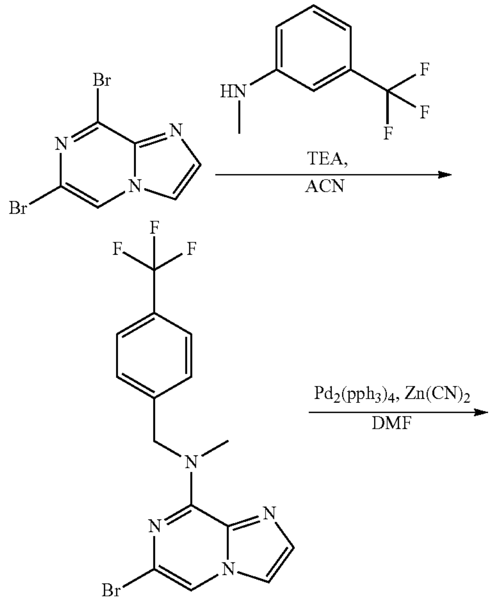

X-1461A1

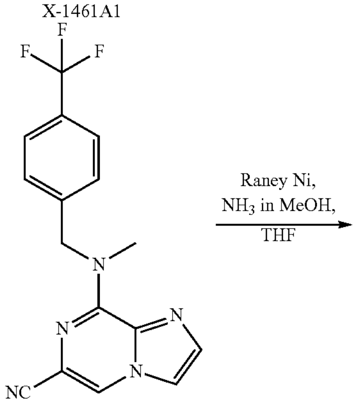

X-1461A2

-continued

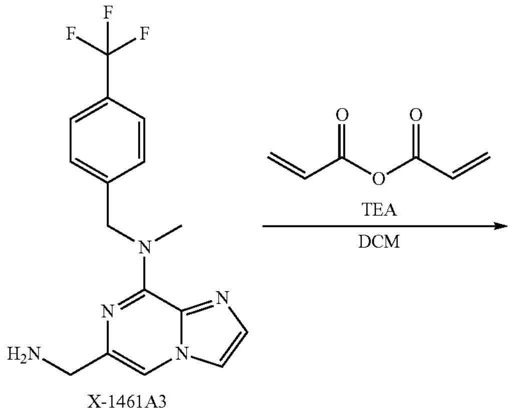

X-1461A3

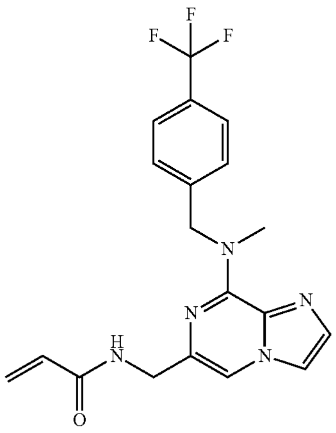

I-300

The following compound was prepared in a manner analogous to the procedures described above for N-((8-((3-(trifluoromethyl) phenyl) amino) imidazo[1,2-a] pyrazin-6-yl) methyl) acrylamide (I-169):

N-((8-(methyl(4-(trifluoromethyl)benzyl)amino)imidazo[1,2-a]pyrazin-6-yl)methyl)acrylamide (I-300) (0.120 g, 34%) as an off white solid. $^1H$ NMR (400 MHz, DMSO-$d_6$) δ8.53 (s, 1H), 7.96 (s, 1H), 7.48-7.66 (m, 3H), 7.50-7.48 (s, 3H), 6.34-6.27 (m, 1H), 6.14-6.10 (d, J=17.2 HZ 1H), 5.63-5.56 (m, 3H), 4.23-4.22 (d, J=5.2 HZ 2H). MS: $[MH]^+$ 390.2.

Example 1.208. Synthesis of N-((1-(2-fluoro-4-(trifluoromethyl)phenyl)isoquinolin-3-yl)methyl) acrylamide (I-301)

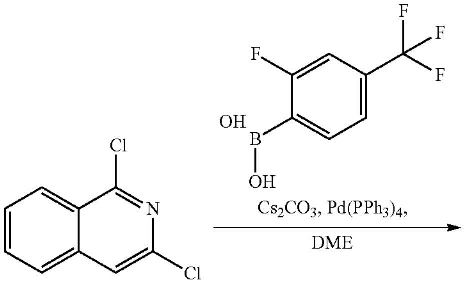

-continued

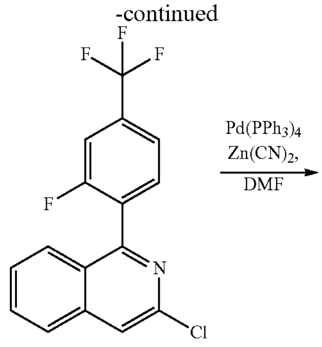

X-1463A1

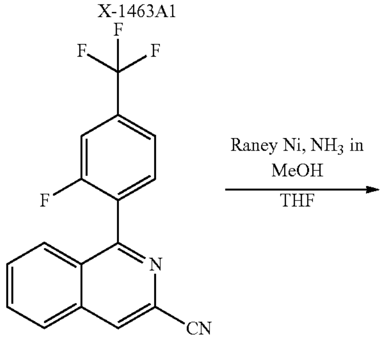

X-1463A2

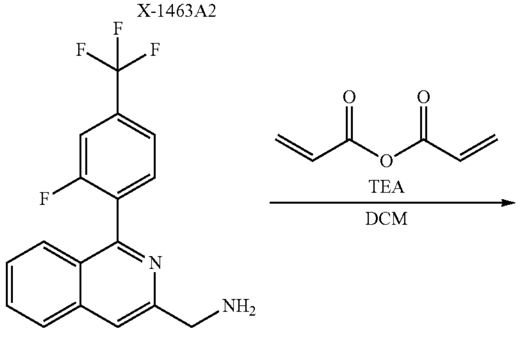

X-1463A3

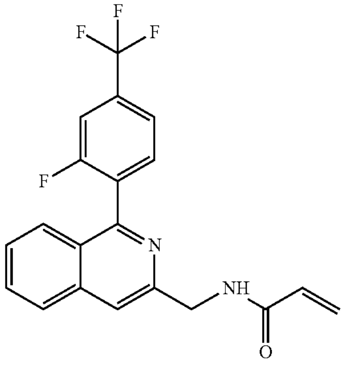

I-301

3-Chloro-1-(2-fluoro-4-(trifluoromethyl) phenyl) isoquinoline (X-1463A1). To a stirred solution of 1,3-dichloroisoquinoline (3.0 g, 15.23 mmol) in a DME (20 mL) were added (2-fluoro-4-(trifluoromethyl)phenyl)boronic acid (3.8 g, 18.27 mmol) and $Cs_2CO_3$ (16.12 g, 45.70 mmol) at room temperature. The reaction mixture was degassed (purging with nitrogen) for 20 min followed by addition of $Pd(PPh_3)_4$ (1.76 g, 1.52 mmol) and the reaction mixture was heated at 80° C. for 16 h. The reaction mixture was cooled to room temperature, diluted with water (100 mL) and was extracted with ethyl acetate (100 mL×3). The combined organic layer extracts were dried over anhydrous $Na_2SO_4$ and concentrated under reduce pressure. The crude product was purified by silica gel column chromatography, using ethyl acetate-Hexane 0:1→9:9 as gradient, to afford 3-chloro-1-(2-fluoro-4-(trifluoromethyl)phenyl)isoquinoline (X-1463A1) (1.7 g, 34%) as an off-white solid. MS: $[MH]^+$ 326.1.

1-(2-Fluoro-4-(trifluoromethyl)phenyl)isoquinoline-3-carbonitrile (X-1463A2). To a stirred solution 3-chloro-1-(2-fluoro-4-(trifluoromethyl)phenyl)isoquinoline (X-1463A1) (0.5 g, 1.54 mmol) in DMF (5 mL) was added zinc cyanide (0.540 g, 4.61 mmol) at room temperature under nitrogen. The reaction mixture was degassed (by purging nitrogen) for 30 min followed by the addition of $Pd(pph_3)_4$ (0.711 g, 0.61 mmol) resulting mixture was heated at 160° C. under microwave irradiation for 1 h. Reaction mixture was cooled to room temperature, slowly poured into water (40 mL) and was extracted with ethyl acetate (40 mL×3). The combined organic extracts were washed with brine (50 mL), dried over anhydrous $Na_2SO_4$ and concentrated in vacuo. The crude product was purified by silica gel column chromatography, using ethyl acetate-hexane 0.1→9.9 as gradient, to afford 1-(2-fluoro-4-(trifluoromethyl)phenyl)isoquinoline-3-carbonitrile (X-1463A2) (0.4 g, 82.39%) as a white solid. MS: $[MH]^+$ 317.0.

(1-(2-Fluoro-4-(trifluoromethyl)phenyl)isoquinolin-3-yl) methanamine (X-1463A3). To a stirred solution of 1-(2-fluoro-4-(trifluoromethyl)phenyl)isoquinoline-3-carbonitrile (X-1463A2) (0.400 g, 1.26 mmol) in THE (5 mL) were added activated Raney Ni (0.150 g) and $NH_3$ (7N in methanol 4 mL) respectively at room temperature and the resulting mixture was hydrogenated in a Parr autoclave under 200 psi at 60° C. for 2 h. Reaction was allowed to come to room temperature, filtered off the residue through a celite bed, washed the bed with methanol and collected filtrates were concentrated under reduced pressure to provide a crude product. and dried under high vacuum to afford (1-(2-fluoro-4-(trifluoromethyl)phenyl)isoquinolin-3-yl)methanamine (X-1463A3) (0.350 g, 86%) as an off-white solid, which was carried forward to the next step without further purification. MS: $[MH]^+$ 321.

N-((1-(2-Fluoro-4-(trifluoromethyl)phenyl)isoquinolin-3-yl)methyl)acrylamide (I-301). To a stirred solution of (1-(2-fluoro-4-(trifluoromethyl)phenyl)isoquinolin-3-yl) methanamine (X-1463A3) (0.200 g, 0.62 mmol) in DCM (3 mL) were added triethylamine (0.189 g, 1.87 mmol) followed by acrylic anhydride (0.95 g, 0.75 mmol) at 0° C. under nitrogen and the reaction mixture stirred at 0° C. for 30 min at room temperature. The reaction mixture was dilute with water (50 mL) and was extracted with DCM (50 mL×3). The combined organic layer extracts were washed with brine (50 mL), dried over anhydrous $Na_2SO_4$ and concentrated in vacuo. The resulting crude was purified by silica gel column chromatography using ethyl acetate-hexane 2:8→3:7 as gradient, to afford N-((1-(2-fluoro-4-(trifluoromethyl)phenyl)isoquinolin-3-yl)methyl)acrylamide (I-301) (0.060 g, 26%) as a white solid. $^1H$ NMR (400 MHz, DMSO-$d_6$) δ 8.84 (s, 1H) 8.09-8.07 (d, J=8 Hz, 1H), 7.94-7.92 (d, J=9.6 Hz, 1H), 7.81 (s, 4H), 7.66-7.62 (t, J=16.4 Hz, 2H), 6.40 6.34 (q, J=27.2 Hz, 1H), 6.18-6.14 (d, J=10.4 Hz, 1H), 5.67-5.65 (d, J=10.4 Hz, 1H), 4.64-4.63 (d, J=5.2 Hz, 2H), MS: $[MH]^+$ 375.2.

Example 1.209. Synthesis of N-((1-(6-(trifluoromethyl)pyridin-3-yl)isoquinolin-3-yl)methyl)acrylamide (I-302)

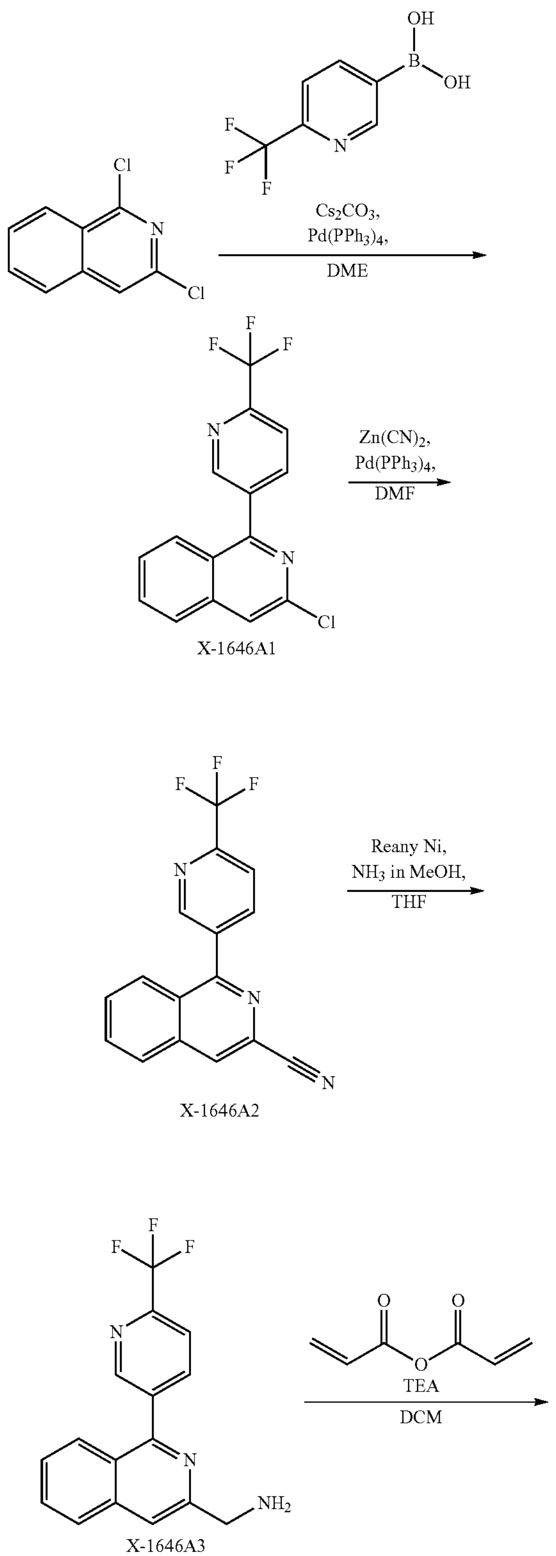

X-1646A1

X-1646A2

X-1646A3

-continued

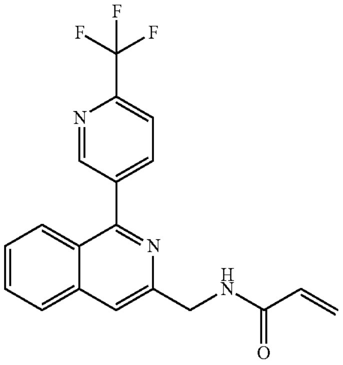

I-302

The following compound was prepared in a manner analogous to the procedures described below for N-((4-(4-(trifluoromethyl)phenyl)-5H-pyrrolo[3,2-d]pyrimidin-2-yl)methyl)acrylamide (I-450):

N-((1-(6-(trifluoromethyl)pyridin-3-yl)isoquinolin-3-yl)methyl)acrylamide (I-302) (0.07 g, 30%) as a white solid. $^1$H NMR (400 MHz, DMSO-d$_6$) δ 9.09 (s, 1H), 8.86-8.84 (t, J=5.6 Hz, 1H), 8.44-8.42 (d, J=7.6 Hz, 1H), 8.14-8.10 (t, J=8.4 Hz, 2H), 8.00-7.98 (d, J=8.4 Hz, 1H), 7.86-7.82 (m, 2H), 7.69-7.65 (t, J=7.2 Hz, 1H), 6.42-6.35 (m, 1H), 6.19-6.15 (dd, J=17.2, 1.6 Hz, 1H), 5.68-5.66 (dd, J=10.4 Hz, 1.6 Hz, 1H), 4.67-4.66 (d, J=5.6 Hz, 2H) MS: [MH]$^+$ 358.1

Example 1.210. Synthesis of N-((4-(2-fluoro-4-(trifluoromethyl)phenyl)quinazolin-2-yl)methyl)acrylamide (I-303)

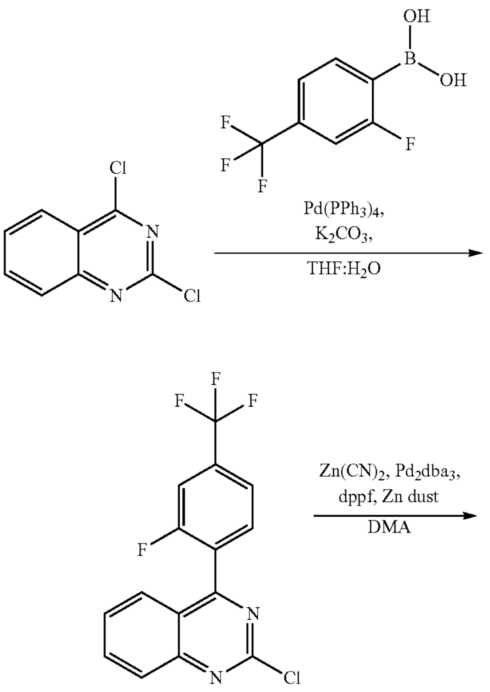

X-1647A1

-continued

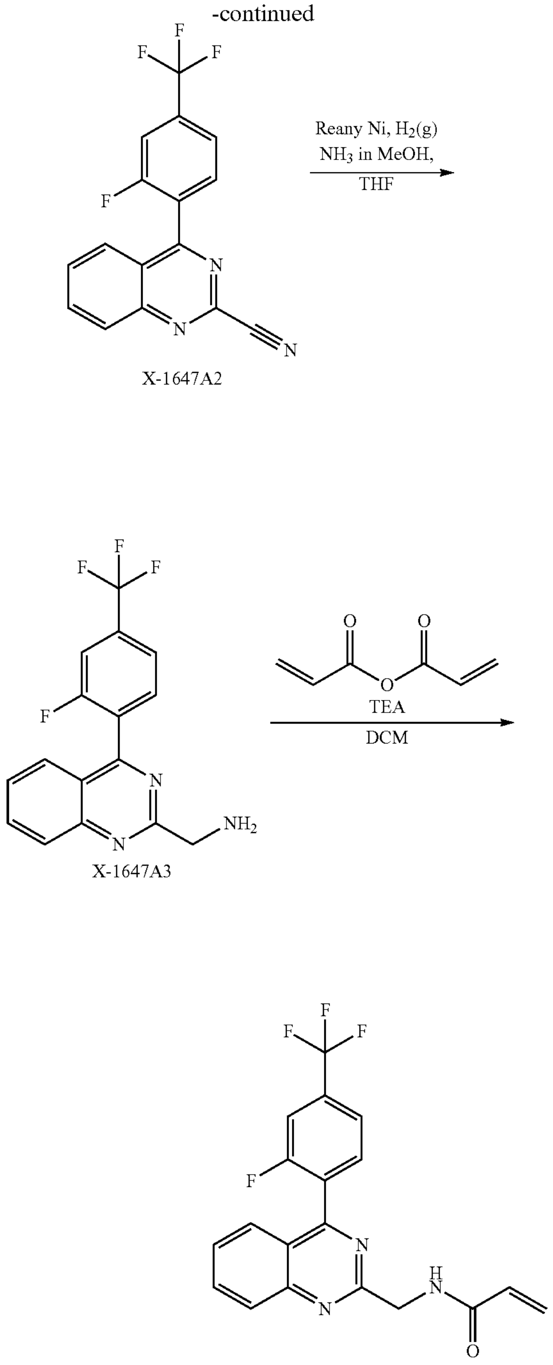

X-1647A2

X-1647A3

I-303

The following compound was prepared in a manner analogous to the procedures described below for N-((4-(4-(trifluoromethyl)phenyl)-5H-pyrrolo[3,2-d]pyrimidin-2-yl)methyl)acrylamide (I-450):

N-((4-(2-fluoro-4-(trifluoromethyl)phenyl)quinazolin-2-yl)methyl)acrylamide (I-303) (0.080 g, 27%) as a white solid. $^1$H NMR (400 MHz, DMSO-$d_6$) δ 8.87-8.84 (t, J=5.6 Hz, 1H), 8.10-8.07 (m, 2H), 8.02-8.00 (d, J=10.0 Hz, 1H), 7.93-7.86 (m, 2H), 7.79-7.77 (m, 1H), 7.73-7.70 (m, 1H), 6.44-6.37 (m, 1H), 6.15-6.10 (m, 1H), 5.66-5.63 (dd, J=1.6 Hz, J=10.0 Hz, 1H), 4.78-4.76 (d, J=6.0 Hz, 2H) MS: [MH]$^+$ 376.12

Example 1.211. Synthesis of 2-fluoro-N-((1-(4-(trifluoromethyl)phenyl)isoquinolin-3-yl)methyl)acrylamide (I-168)

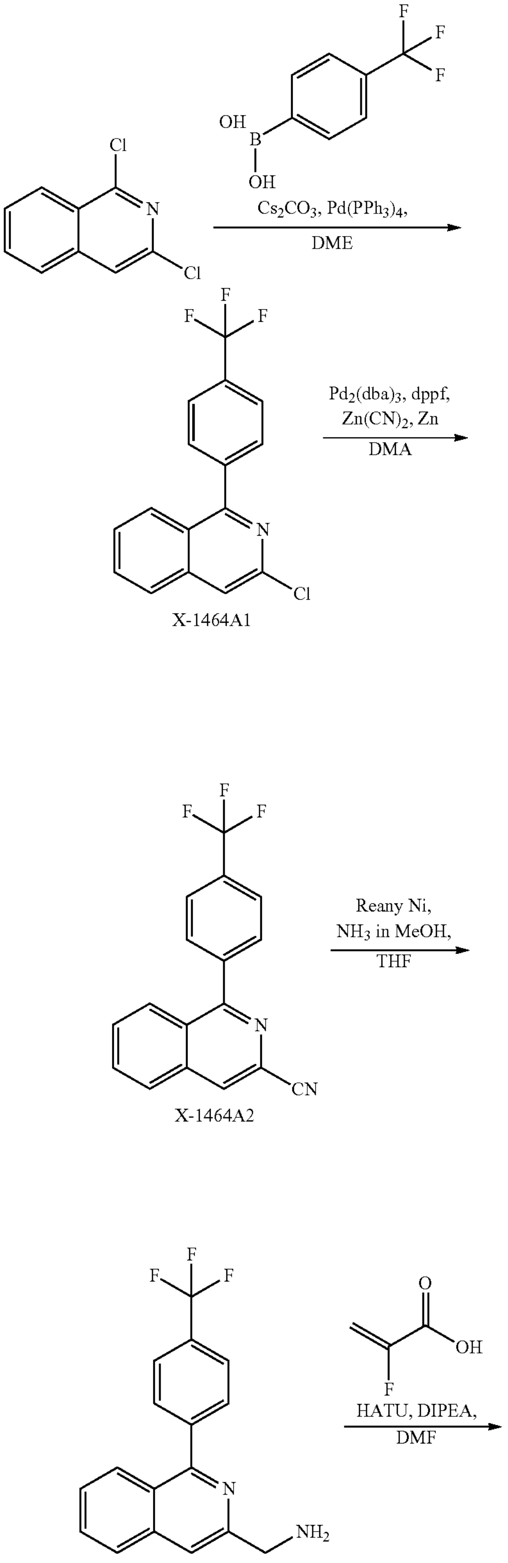

X-1464A1

X-1464A2

X-1464A3

-continued

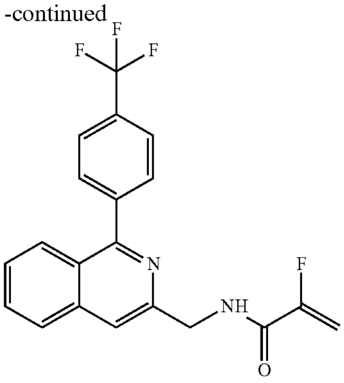

I-168

3-Chloro-1-(4-(trifluoromethyl)phenyl)isoquinoline (X-1464A1). To a stirred solution of 1,3-dichloroisoquinoline (3.0 g, 15.15 mmol) in a DME (30 mL) were added (2-fluoro-4-(trifluoromethyl)phenyl)boronic acid (3.45 g, 18.18 mmol) and $Cs_2CO_3$ (9.87 g, 30.30 mmol) at room temperature. The reaction mixture was degassed (purging with nitrogen) for 20 min followed by addition of $Pd(PPh_3)_4$ (0.524 g, 0.45 mmol) and the reaction mixture was heated at 80° C. for 5 h. The reaction mixture was cooled to room temperature, diluted with water (100 mL) and was extracted with ethyl acetate (100 mL×3). The combined organic layer extracts were dried over anhydrous $Na_2SO_4$ and concentrated under reduce pressure. The crude product was purified by silica gel column chromatography, using ethyl acetate-Hexane 4:8-45:2 as gradient, to afford 3-chloro-1-(4-(trifluoromethyl)phenyl)isoquinoline (X-1464A1) (3.5 g, 75%) as an off-white solid. MS: $[MH]^+$ 307.09.

1-(4-(Trifluoromethyl)phenyl)isoquinoline-3-carbonitrile (X-1464A2). To a stirred solution 3-chloro-1-(4-(trifluoromethyl)phenyl)isoquinoline (X-1464A1) (1.5 g, 4.88 mmol) in DMA (10 mL) was added zinc cyanide (0.342 g, 2.93 mmol) and Zn dust (0.634 g, 9.76 mml) at room temperature under nitrogen. The reaction mixture was degassed (by purging nitrogen) for 30 min followed by the addition of $Pd_2(dba)_3$ (1.3 g, 1.46 mmol) and dppf (1.66 g, 2.52 mml) resulting mixture was heated at 130° C. under microwave irradiation for 1.5 h. Reaction mixture was cooled to room temperature, slowly poured into water (100 mL) and was extracted with ethyl acetate (100 mL×3). Combined extracts were dried over anhydrous $Na_2SO_4$ and concentrated in vacuo. The crude product was purified by silica gel column chromatography, using ethyl acetate-hexane 0.1→9.9 as gradient, to afford 1-(4-(trifluoromethyl)phenyl)isoquinoline-3-carbonitrile (X-1464A2) (1.2 g, 82%) as a white solid. MS: $[MH]^+$ 298.9.

(1-(4-(Trifluoromethyl)phenyl)isoquinolin-3-yl)methanamine (X-1464A3). To a stirred solution of 1-(4-(trifluoromethyl)phenyl)isoquinoline-3-carbonitrile (X-1464A2) (0.500 g, 1.67 mmol) in THE (5 mL) were added activated Raney Ni (0.200 g) and $NH_3$ (7N in methanol 3 mL) respectively at room temperature and the resulting mixture was hydrogenated in a Parr autoclave under 200 psi at 60° C. for 2 h. Reaction was allowed to come to room temperature, filtered off the residue through a celite bed, washed the bed with methanol and collected filtrates were concentrated under reduced pressure to provide a crude product. and dried under high vacuum to afford (1-(4-(trifluoromethyl)phenyl) isoquinolin-3-yl) methanamine (X-1464A3) (0.350 g, 69%) as an off-white solid, which was carried forward to the next step without further purification. MS: $[MH]^+$ 303.0.

2-Fluoro-N-((1-(4-(trifluoromethyl)phenyl)isoquinolin-3-yl)methyl)acrylamide (I-168). To a stirred solution of 2-fluoroacrylic acid (0.200 g, 2.23 mmol) in DMF (4 mL) were added DIPEA (0.86 g, 6.69 mmol), HATU (1.27 g, 3.34 mmol) &(1-(4-(trifluoromethyl) phenyl) isoquinolin-3-yl) methanamine (X-1464A3) (0.33 g, 1.12 mmol) at 0° C. under nitrogen and the resulting mixture was stirred at room temperature for 1 h. Reaction mixture diluted with water (50 mL) and was extracted with ethyl acetate (50 mL×3). Combined organic layer extracts, dried over anhydrous $Na_2SO_4$ and concentrated in vacuo. The resulting crude product was purified by silica gel column chromatography, using ethyl acetate-hexane 0.3→9.7 as gradient, to afford 2-fluoro-N-((1-(4-(trifluoromethyl)phenyl)isoquinolin-3-yl)methyl)acrylamide (I-168) (0.150 g, 61%) an off white solid. $^1H$ NMR (400 MHz, DMSO-$d_6$) δ 9.25 (s, 1H) 8.10-8.08 (d, J=8 Hz, 1H), 7.97-7.89 (m, 1H), 7.82-7.78 (t, 1H), 7.75 (s, 1H), 7.65-7.61 (t, 1H), 5.67 (s, 1H) 5.55 (s, 1H), 5.36-5.35, 5.32-5.31 (dd, J=3.2 Hz, J=15.6 Hz 2H), 4.66-4.665 (d, J=6 Hz, 2H), MS: $[MH]^+$ 375.1. MS: $[MH]^+$ 374.10.

Example 1.212. Synthesis of N-((4-(4-(trifluoromethyl)phenyl)quinazolin-2-yl)methyl)acrylamide (I-167)

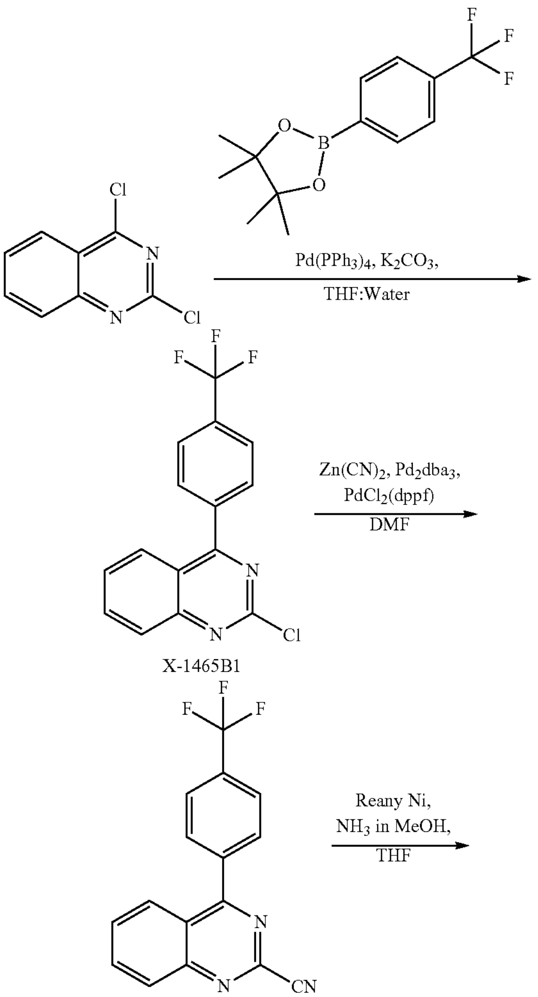

X-1465B1

X-1465B2

-continued

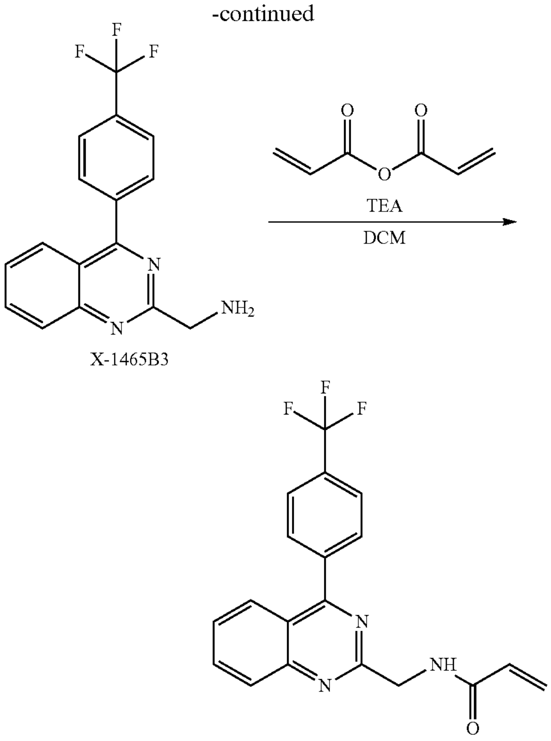

X-1465B3

I-167

The following compound was prepared in a manner analogous to the procedures described above for N-((1-(2-fluoro-4-(trifluoromethyl)phenyl)isoquinolin-3-yl)methyl) acrylamide (I-301):

N-((4-(4-(trifluoromethyl)phenyl)quinazolin-2-yl) methyl)acrylamide (I-167) (0.100 g, 42.44%) as an off white solid. $^1$H NMR (400 MHz, DMSO-$d_6$) δ 8.82 (s, 1H), 8.07-8.00 (m, 7H), 7.74-7.70 (t, 1H), 6.45-6.38 (m, 1H), 6.15-6.11 (d, J=17.2 Hz 1H), 6.65-6.63 (d, J=10.4 Hz, 1H), 4.77-4.76 (d, J=5.6 Hz, 1H). MS: $[MH]^+$ 358.1.

Example 1.213. Synthesis of N-((4-(4-(trifluoromethyl)phenyl)pyrido[2,3-d]pyrimidin-2-yl) methyl) acrylamide (I-304)

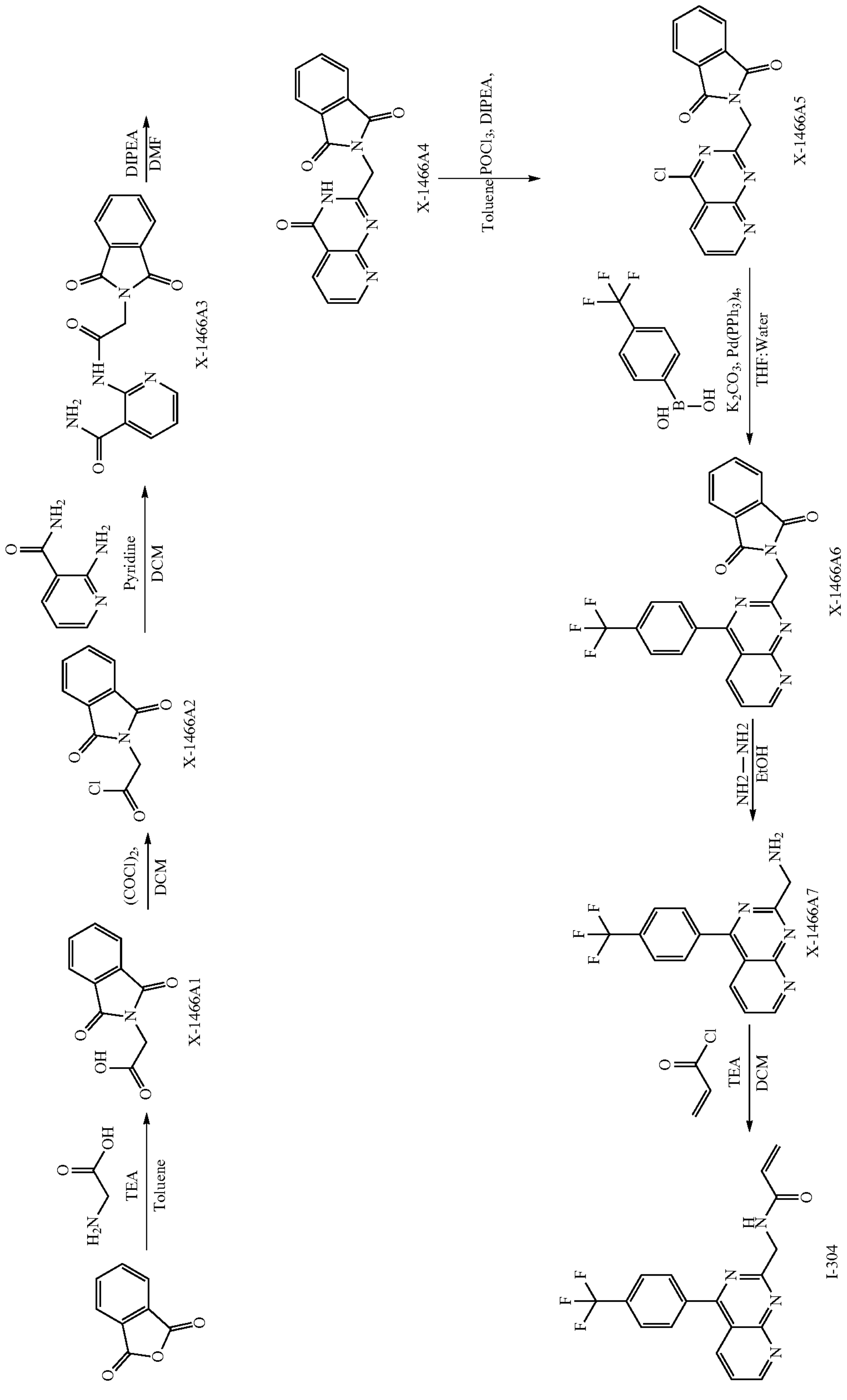
TEA
Toluene
X-1466A1
(COCl)2,
DCM
X-1466A2
Pyridine
DCM
X-1466A3
DIPEA
DMF
X-1466A4
Toluene POCl3, DIPEA,
X-1466A5
K2CO3, Pd(PPh3)4,
THF:Water
X-1466A6
NH2—NH2
EtOH
X-1466A7
TEA
DCM
I-304

2-(1,3-Dioxoisoindolin-2-yl)acetic acid (X-1466A1). To a stirred solution of Iisobenzofuran-1,3-dione (23.6 g, 159.45 mmol) in toluene (60 mL) were added triethylamine (20 mL) and glycine (10.0 g, 133.33 mmol) at room temperature under nitrogen and the resulting mixture was heated at 110° C. for 16 h. Reaction mixture was cooled to room temperature, reaction mixture was slowly poured into ice-water (500 mL) and was extracted with ethyl acetate (500 mL×3). Collected organics were washed with an aqueous 1N HCl (150 mL), dried over anhydrous $Na_2SO_4$ and concentrated in vacuo to afford 2-(1,3-Dioxoisoindolin-2-yl)acetic acid (X-1466A1) (28.0 g g, quant; crude) as an off-white solid. MS: [MH]-203.6.

2-(1,3-Dioxoisoindolin-2-yl)acetyl chloride (X-1466A2). To a stirred solution of 2-(1,3-dioxoisoindolin-2-yl)acetic acid (X-1466A1) (3.0 g, 14.60 mmol) in DCM (30 mL) was added oxalyl chloride (2.8 g, 21.95 mmol) at 0° C. under nitrogen and was stirred for 1 h. Reaction mixture was concentrated under reduce pressure under nitrogen to afford 2-(1,3-dioxoisoindolin-2-yl)acetyl chloride (X-1466A2) (3.0 g, quant; crude) as a light yellow oil. MS: [MH]-222.7.

2-(2-(1,3-Dioxoisoindolin-2-yl) acetamido) nicotinamide (X-1466A3). To a stirred solution of 2-(1,3-dioxoisoindolin-2-yl)acetyl chloride (X-1466A2) (3.0 g, 13.45 mmol) in DCM (30 mL) were added pyridine and (3.2 g, 40.35 mmol) and 2-aminonicotinamide (1.8 g, 13.45 mmol) at 0° C. under nitrogen and the resulting mixture was stirred at room temperature for 1 h, during which a solid was precipitated out. Reaction mixture filtered, solid precipitate was washed with water and dried in vacuo to afford 2-(2-(1,3-Dioxoisoindolin-2-yl)acetamido)nicotinamide (X-1466A3) (2.0 g, 45.97%) as an off white solid. MS: $[MH]^+$ 325.10.

2-((4-Oxo-3,4-dihydropyrido[2,3-d]pyrimidin-2-yl) methyl)isoindoline-1,3-dione (X-1466A4). To a stirred solution of 2-(2-(1,3-dioxoisoindolin-2-yl) acetamido) nicotinamide (X-1466A3) (2.0 g, 3.08 mmol) in DMF (6 mL) was added diisopropylethylamine (1.2 g, 9.25 moll) at room temperature. The reaction mixture was heated at 130°o. for 16 h. The reaction mixture was cooled to room temperature, diluted with water (50 mL) and product was precipitated out. Solid product was filtered and dried in vacuum to afford 2-((4-oxo-3,4-dihydropyrido[2,3-d] pyrimidin-2-yl) methyl) isoindoline-1,3-dione (X-1466A4) (1.0 g, 53.0%; crude) as an off-white solid. MS: $[MH]^+$307.0.

2-((4-Chloropyrido[2,3-d]pyrimidin-2-yl)methyl)isoindoline-1,3-dione (X-1466A5). To a stirred solution of 2-((4-oxo-3,4-dihydropyrido[2,3-d]pyrimidin-2-yl)methyl)isoindoline-1,3-dione (X-1466A4) (1.0 g, 1.63 mmol) in toluene (5 mL) were added diisopropylethylamine (0.6 g, 4.90 mmol) and $POCl_3$ (0.5 g, 3.26 mmol) at 0° C. The reaction mixture was heated at 70° C. for 16 h. After cooling to room temperature, reaction mixture was poured in to ice-water (200 mL), basified (pH~7-8) with an aqueous solution of saturated $NaHCO_3$ and was extracted with ethyl acetate (50 ml×3). Combined organic extracts were dried over $Na_2SO_4$ and concentrated under reduced pressure to afford 2-((4-Chloropyrido[2,3-d]pyrimidin-2-yl)methyl)isoindoline-1,3-dione (X-1466A5) (0.8 g, 80%; crude) as an off-white solid. MS: $[MH]^+$325.3.

2-((4-(4-(Trifluoromethyl)phenyl)pyrido[2,3-d]pyrimidin-2-yl)methyl)isoindoline-1,3-dione (X-1466A6). To a stirred solution of 2-((4-Chloropyrido[2,3-d]pyrimidin-2-yl)methyl)isoindoline-1,3-dione (X-1466A5) (0.800 g, 2.47 mmol) in a mixture of THE-water (5:1.5, 7 mL) were added (4-(trifluoromethyl)phenyl)boronic acid (0.457 g, 2.40 mmol) and $K_2CO_3$ (0.766 g, 5.55 mmol) at room temperature. The reaction mixture was degassed (purging with nitrogen) for 20 min followed by addition of Pd $(PPh_3)_4$ (0.106 g, 0.09 mmol) and the resulting mixture was heated at 110° C. for 1 h. Reaction mixture was cooled to room temperature, diluted with water (50 mL) and was extracted with ethyl acetate (50 mL×3). Combined organic extracts were dried over anhydrous $Na_2SO_4$ and concentrated under reduce pressure. The crude product was purified by silica gel column chromatography, using ethyl acetate-hexane=1:1→3:2 as gradient, to afford 2-((4-(4-(trifluoromethyl)phenyl)pyrido[2,3-d]pyrimidin-2-yl)methyl)isoindoline-1,3-dione (X-1466A6) (0.6 g, 60%) as an off-white solid. MS: $[MH]^+$ 434.9.

(4-(4-(Trifluoromethyl)phenyl)pyrido[2,3-d]pyrimidin-2-yl)methanamine (X-1466A7). To a stirred solution of 2-((4-(4-(trifluoromethyl)phenyl)pyrido[2,3-d] pyrimidin-2-yl) methyl) isoindoline-1,3-dione (X-1466A6) (0.400 g, 0.92 mmol) in EtOH (5 mL) was added $NH_2$—$NH_2 \cdot H_2O$ (0.090 g, 1.84 mmol) at room temperature and the resulting mixture was heated at 80° C. for 2 h. The reaction mixture was cooled to room temperature, diluted with EtOH (50 mL) and was filtered through Buckner funnel. Filtrate was concentrated under reduce pressure and the crude was purified by reverse phase (C-18) silica column chromatography, using acetonitrile-water=3:7→1:1 as gradient, to afford (4-(4-(Trifluoromethyl)phenyl)pyrido[2,3-d]pyrimidin-2-yl)methanamine (X-1466A7) (0.100 g, 35%) as an off-white solid. MS: $[MH]^+$ 305.3.

N-((4-(4-(trifluoromethyl)phenyl)pyrido[2,3-d]pyrimidin-2-yl) methyl)acrylamide (1-304). To a stirred solution of (4-(4-(Trifluoromethyl) phenyl)pyrido[2,3-d]pyrimidin-2-yl) methanamine (X-1466A7) (0.100 g, 0.32 mmol) in DCM (3 mL) were added triethylamine (0.096 g, 0.98 mmol) and acryloyl chloride (0.04 g, 0.39 mmol) at 0° C. and the reaction mixture was stirred at room temperature for 30 min. Reaction mixture was diluted with aqueous $NaHCO_3$ (20 mL) and was extracted by ethyl acetate (30 mL×3). Combined organic extracts were dried over anhydrous $Na_2SO_4$ and concentrated under reduce pressure. The crude was purified by Prep-HPLC, using acetonitrile-water=1:9→3:7 as gradient, to afford N-((4-(4-(trifluoromethyl)phenyl) pyrido[2,3-d]pyrimidin-2-yl)methyl)acrylamide (1-304) (0.012 g, 10%) as an off-white solid. $^1H$ NMR (400 MHz, DMSO-$d_6$) δ 9.30-9.29 (d, J=2.4 Hz, 1H), 8.92-8.89 (t, J=5.6 Hz, 1H), 8.50-8.48 (d, J=6.8 Hz, 1H), 8.02 (s, 4H), 7.75-7.72 (dd, J=12.4, 4.4 Hz, 1H), 6.48-6.41 (m, 1H), 6.16-6.11 (dd, J=17.2, 1.6 Hz, 1H), 5.69-5.66 (dd, J=17.2, 1.6 Hz, 2H), 4.80 (s, 2H). MS: $[MH]^+$ 359.0.

Example 1.214. Synthesis of N-((4-(4-(trifluoromethyl)phenyl)pyrido[3,2-d]pyrimidin-2-yl)methyl) acrylamide (I-305)

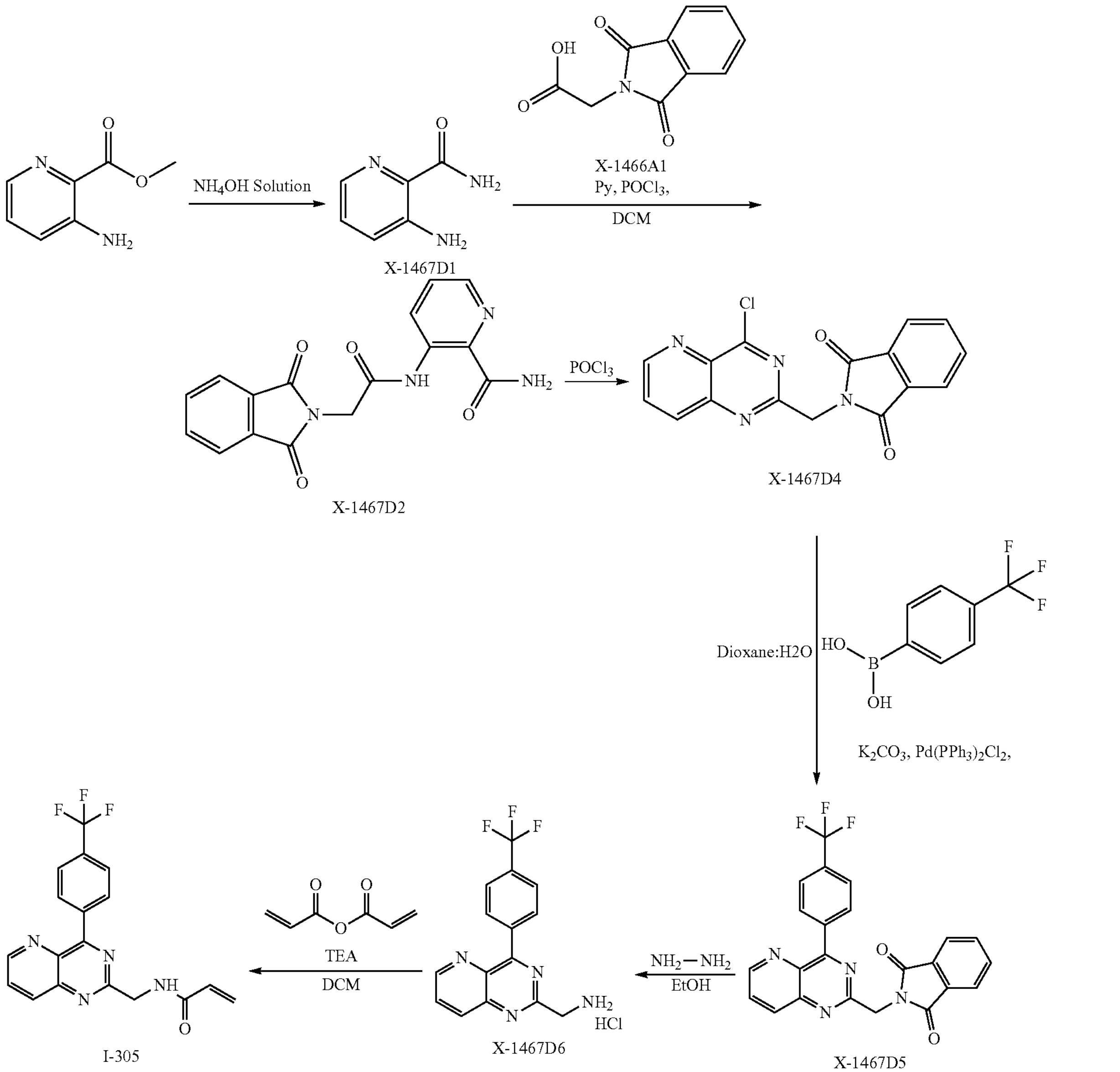

3-Aminopicolinamide (X-1467D1). A suspension of methyl 3-aminopicolinate (20.0 g, 65.76 mmol) in aqueous ammonia solution (150 mL) in a Parr Autoclave was heated at 70° C. for 16 h. Obtained solid precipitate was filtered over Buchner funnel, washed the solid residue with water (300 mL) and dried under high vacuum to afford 3-aminopicolinamide (X-1467D1) [13.7 g, 76% (crude)] as an off-white solid. MS: $[MH]^+$ 137.9.

3-(2-(1,3-Dioxoisoindolin-2-yl)acetamido)picolinamide (X-1467D2). To a stirred suspension of 3-aminopicolinamide (X-1467D1) (11.8 g, 86.13 mmol) and 2-(1,3-dioxoisoindolin-2-yl)acetic acid (X-1467A1) (17.6 g, 86.13 mmol) in DCM (118 mL) were added pyridine (68.04 g, 861.31 mmol) and $POCl_3$ (26.4 g, 172.26 mmol) sequentially at 0° C. under nitrogen and stirred for 1 h at room temperature. The reaction mixture was filtered over Buchner funnel, washed the residue with DCM (50 mL) and dried under vacuum. Thus obtained solid product was triturated with methanol-dichloromethane (0.5:9.5) and dried under vacuum to afford 3-(2-(1,3-dioxoisoindolin-2-yl)acetamido) picolinamide (X-1467D2) [13.0 g, 46% (crude)] as a white solid. MS: $[MH]^+$ 324.8.

2-((4-Chloropyrido[3,2-d]pyrimidin-2-yl)methyl)isoindoline-1,3-dione (X-1467D4). To a stirred solution of 3-(2-(1,3-dioxoisoindolin-2-yl)acetamido)picolinamide (X-1467D2) (12.0 g, 29.5 mmol) in $POCl_3$ (150 mL) was heated at 100° C. for 16 h. After completion of reaction, reaction mixture was slowly poured into crushed ice with vigorous stirring. Solid product precipitated was filtered over Buchner funnel and washed with cold water until pH of filtrate was neutral. The solid product was dried over vacuum, to afford 2-((4-chloropyrido[3,2-d]pyrimidin-2-yl)methyl)isoindoline-1,3-dione (X-1467D4) (7.0 g, 58%) as a brown solid. MS: $[MH]^+$ 324.8.

2-((4-(4-(Trifluoromethyl)phenyl)pyrido[3,2-d]pyrimidin-2-yl)methyl)isoindoline-1,3-dione (X-1467D5). To a stirred solution of 2-((4-chloropyrido[3,2-d]pyrimidin-2-yl)methyl)isoindoline-1,3-dione (X-1467D4) (3 g, 9.25 mmol) in a mixture of 1,4-dioxane-water (5:1; 36 mL) were added (4-(trifluoromethyl)phenyl)boronic acid (3.5 g, 18.5 mmol) and $K_2CO_3$ (3.83 g, 27.77 mmol) and the resulting suspension was degassed with nitrogen gas for 30 min. To the reaction mixture was added $PdCl_2(PPh_3)_2$ (0.650 g, 0.92 mmol) and the reaction mixture was heated to 100° C. for 2 h. Reaction mixture was diluted with water (100 mL) and was extracted with ethyl acetate (70 mL×3). Combined organic layer was dried over $Na_2SO_4$ and concentrated in vacuo. The resulting crude was purified by silica gel column chromatography, using ethyl acetate-hexane=1:9→1:4 as gradient, to 2-((4-(4-(trifluoromethyl)phenyl)pyrido[3,2-d]pyrimidin-2-yl)methyl)isoindoline-1,3-dione (X-1467D5) (4.0 g, 50%) as an off white solid. MS: $[MH]^+$ 434.09.

(4-(4-(Trifluoromethyl)phenyl)pyrido[3,2-d]pyrimidin-2-yl)methanamine hydrochloride (X-1467D6). 2-((4-(4-(trifluoromethyl)phenyl)pyrido[3,2-d]pyrimidin-2-yl)methyl)isoindoline-1,3-dione (X-1467D5) (4.0 g, 9.86 mmol) in ethanol (80 mL) were added hydrazine hydrate (1.38 g, 27.64 mmol) at room temperature and the resulting mixture was heated at 70° C. for 2 h. Reaction mixture was filtered over a Buchner funnel, washed the residue with ethanol and combined filtrates were concentrated under reduced pressure to afford (4-(4-(trifluoromethyl)phenyl)pyrido[3,2-d]pyrimidin-2-yl)methanamine [3.5 g (crude).]. To this crude material in DCM (35 mL) was added 4M HCl in dioxane (10 mL) at 0° C. and reaction mixture was stirred at same temperature for 30 min. Reaction mass was filtered over a Buchner funnel, washed solid material with DCM (50 mL) and dried under vacuum to afford (4-(4-(trifluoromethyl)phenyl)pyrido[3,2-d]pyrimidin-2-yl)methanamine hydrochloride (X-1467D6) (3 g, quant; crude) as off white solid. LCMS was not supported. Crude carried forward to next step without purification.

N-((4-(4-(trifluoromethyl)phenyl)pyrido[3,2-d]pyrimidin-2-yl)methyl)acrylamide (1-305). To a stirred suspension of (4-(4-(trifluoromethyl)phenyl)pyrido[3,2-d]pyrimidin-2-yl)methanamine hydrochloride (X-1467D6) (3.0 g, 9.86 mmol) in DCM (60 mL) was added triethylamine (6.8 mL, 49.34 mmol) at 0° C. After 15 min of stirring at the same temperature, was added acrylic anhydride (0.1.24 g, 9.86 mmol) and stirred for 2 h at room temperature. Reaction mixture was diluted with water (100 mL) and was extracted with dichloromethane (100×3 mL). The combined organic extracts were dried over anhydrous $Na_2SO_4$ and concentrated under reduce pressure. Obtained crude mass was purified by silica gel column chromatography, using methanol-dichloromethane=0:1→1:1 as gradient, to N-((4-(4-(trifluoromethyl)phenyl)pyrido[3,2-d]pyrimidin-2-yl)methyl)acrylamide (I-305) (1.8 g, 57%) as a light yellow solid. $^1H$ NMR (400 MHz, DMSO-$d_6$) δ 9.14-9.13 (m, 1H), 8.89-8.86 (t, J=5.6 Hz, 1H), 8.50-8.47 (m, 3H), 8.06-8.03 (m, 1H), 7.98-7.96 (d, J=8.4 Hz, 2H), 6.47-6.41 (m, 1H), 6.18-6.13 (dd, J=17.2, 2 Hz, 1H), 5.68-5.65 (dd, J=10.4, 2 Hz, 1H), 4.842-4.827 (d, J=6, 2H). MS: $[MH]^+$ 359.0.

Example 1.215. Synthesis of N-((3-(4-(trifluoromethyl)phenyl)imidazo[1,2-a]pyrimidin-2-yl)methyl)acrylamide (I-306)

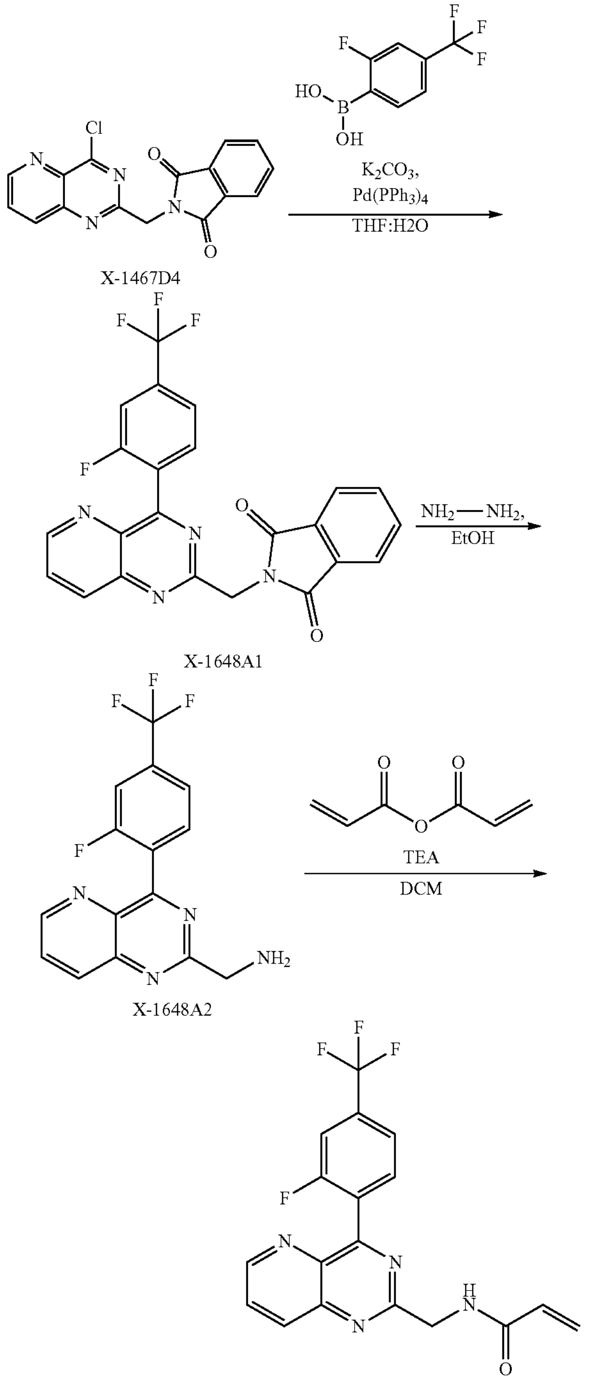

X-1467D4

X-1648A1

X-1648A2

I-306

Synthesis of 2-((4-chloropyrido[3,2-d]pyrimidin-2-yl)methyl)isoindoline-1,3-dione (X-1467D4) provided above and Example 1.214

2-((4-(2-Fluoro-4-(trifluoromethyl)phenyl)pyrido[3,2-d]pyrimidin-2-yl)methyl)isoindoline-1,3-dione (X-1648A1).

To a stirred solution of 2-((4-chloropyrido[3,2-d]pyrimidin-2-yl)methyl)isoindoline-1,3-dione (X-1467D4) (0.600 g, 1.85 mmol) in a mixture of THE-water (6:1 mL; 15 mL) were added (2-fluoro-4-(trifluoromethyl)phenyl)boronic acid (0.770 g, 3.7 mmol) and $K_2CO_3$ (0.766 g, 5.55 mmol) sequentially at room temperature under nitrogen. The reaction mixture was degassed (purging with nitrogen) for 20 min followed by the addition of $Pd(pph_3)_4$ (0.213 g, 0.18 mmol) the resulting mixture was heated at 100° C. for 1 h. Reaction mixture was cooled to room temperature, diluted with water (100 mL) and was extracted with ethyl acetate (100 mL×3). Combined organic extracts were dried over anhydrous $Na_2SO_4$ and concentrated under reduce pressure to afford crude mass, which was purified by silica gel Flash column chromatography, using ethyl acetate-hexane=0: 1→3:7 as eluent, to afford 2-((4-(2-fluoro-4-(trifluoromethyl)phenyl)pyrido[3,2-d]pyrimidin-2-yl)methyl)isoindoline-1,3-dione (X-1648A1) (0.300 g, 35%) as a white solid. MS: $[MH]^+$ 453.0.

(4-(2-Fluoro-4-(trifluoromethyl)phenyl)pyrido[3,2-d]pyrimidin-2-yl)methanamine (X-1648A2). Hydrazine Hydrate (0.116 g, 2.32 mmol) was added to a stirred solution of 2-((4-(2-fluoro-4-(trifluoromethyl)phenyl)pyrido[3,2-d]pyrimidin-2-yl)methyl)isoindoline-1,3-dione (X-1648A1) (0.350 g, 0.77 mmol) in ethanol (4 mL) at room temperature and the resulting mixture was heated at 70° C. for 1 h. Reaction mixture was cooled to room temperature, diluted with water (100 mL) and was extracted with ethyl acetate (100 mL×3). Combined organic extracts were dried over anhydrous $Na_2SO_4$ and concentrated under reduce pressure crude to afford (4-(2-fluoro-4-(trifluoromethyl)phenyl) pyrido[3,2-d]pyrimidin-2-yl)methanamine (X-1648A2) (0.330 g, quant; crude) as a white solid. MS: $[MH]^+$ 322.9

N-((4-(2-fluoro-4-(trifluoromethyl)phenyl)pyrido[3,2-d] pyrimidin-2-yl)methyl)acrylamide (I-306). Acrylic anhydride (0.089 g, 0.71 mmol) was added to a stirred solution of (4-(2-fluoro-4-(trifluoromethyl)phenyl)pyrido[3,2-d]pyrimidin-2-yl)methanamine (X-1644A2) (0.230 g, 0.71 mmol) and triethylamine (0.364 g, 2.13 mmol) in DCM (5 mL) at 0° C. temperature under nitrogen and stirred for 30 min at the same temperature. The reaction mixture was poured in water (50 mL) and was extracted with DCM (25 mL×2). Combined organic extracts were dried over anhydrous $Na_2SO_4$ and concentrated under reduced pressure. The crude product was purified by reverse phase (C-18) silica gel column chromatography, using acetonitrile-water=0:1→2:3 as gradient, to afford N-((4-(2-fluoro-4-(trifluoromethyl) phenyl)pyrido[3,2-d]pyrimidin-2-yl)methyl)acrylamide (I-306) (0.100 g, 37%) as a white solid. $^1H$ NMR (400 MHz, DMSO-$d_6$) δ 9.079-9.072 (d, J=2.8 Hz, 1H), 8.90-8.88 (t, J=6.0 Hz, 1H), 8.53-8.51 (d, J=7.6 Hz, 1H), 8.08-8.04 (m, 1H), 7.95-7.93 (m, 2H), 7.84-7.82 (d, J=8.0 Hz, 1H), 6.45-6.38 (m, 1H), 6.16-6.12 (dd, J=17.6, 1.6 Hz, 1H), 5.67-5.64 (dd, J=10.4, 2.0 Hz, 1H), 4.84-4.76 (d, J=6.0 Hz, 2H) MS: $[MH]^+$ 376.9.

Example 1.216. Synthesis of 2-fluoro-N-((4-(4-(trifluoromethyl)phenyl)pyrido[2,3-d]pyrimidin-2-yl)methyl)acrylamide (I-307)

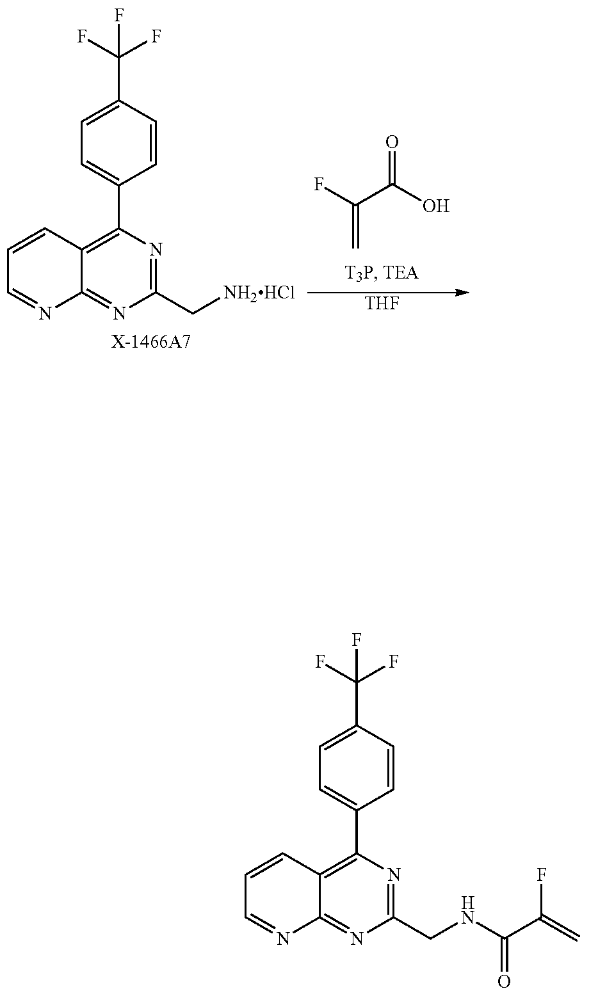

X-1466A7

I-307

To a solution of 2-fluoroacrylic acid (1.68 g, 18.7 mmol) and (4-(4-(trifluoromethyl)phenyl)pyrido[2,3-d]pyrimidin-2-yl)methanamine hydrochloride (1.90 g, 6.25 mmol) in THE (25 mL) were added TEA (3.72 g, 36.88 mmol) and $T_3P$ (5.96 g, 9.37 mmol) sequentially at room temperature under nitrogen and the resulting reaction mixture stirred at 80° C. for 2 h. Reaction mixture was diluted with water (200 mL) and was extracted with ethyl acetate (200 mL×3). Combined organic extracts were dried over anhydrous $Na_2SO_4$ and concentrated under reduced pressure. Obtained crude was purified by reverse phase (C-18) silica gel column chromatography, using acetonitrile-0.1% FA in water=0: 1→3:7 as gradient, to afford 2-fluoro-N-((4-(4-(trifluoromethyl)phenyl)pyrido[2,3-d]pyrimidin-2-yl)methyl)acrylamide (I-307) (1.03 g, 43%) as an off-white solid. $^1H$ NMR (400 MHz, DMSO-$d_6$) δ 9.31-9.30 (dd, J=4.4, 2.0 Hz, 1H), 9.24-9.21 (t, J=6.0 Hz, 1H), 8.52-8.49 (dd, J=8.4, 2.0 Hz, 1H), 8.03 (s, 4H), 7.77-7.74 (m, 1H), 5.67-5.54 (dd, J=48.0, 3.6 Hz, 1H), 5.38-5.33 (dd, J=3.2 Hz, J=15.6 Hz, 1H), 4.83-4.81 (d, J=6.0 Hz, 1H). MS: $[MH]^+$ 377.4

Example 1.217. Synthesis of (E)-4-fluoro-N-((4-(4-(trifluoromethyl)phenyl)pyrido[2,3-d]pyrimidin-2-yl)methyl)but-2-enamide (I-308)

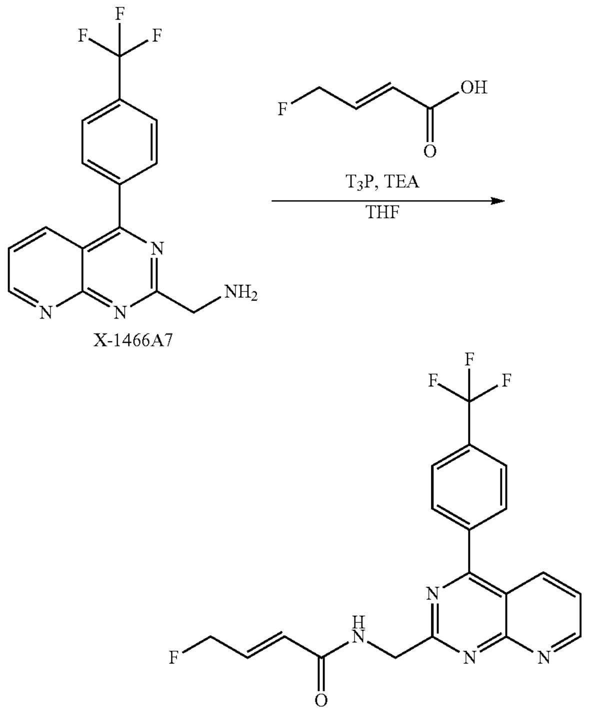

X-1466A7

I-308

The following compound was prepared in a manner analogous to the procedures described above for 2-fluoro-N-((4-(4-(trifluoromethyl)phenyl)pyrido[2,3-d]pyrimidin-2-yl)methyl)acrylamide (I-307):

(E)-4-fluoro-N-((4-(4-(trifluoromethyl)phenyl)pyrido[2,3-d]pyrimidin-2-yl)methyl)but-2-enamide (I-308) (0.025 g, 7%) as a yellow solid. $^1$H NMR (400 MHz, DMSO-$d_6$) δ 9.31-9.30 (dd, J=4.0, 2.0 Hz, 1H), 8.97-8.99 (t, J=7.6 Hz, 1H), 8.51-8.48 (dd, J=2.0 Hz, J=8.4 Hz, 1H), 8.05-8.010 (m, 4H), 7.76-7.73 (m, 1H), 6.80-6.70 (m, 1H), 6.40-6.36 (dd, J=15.6, 2.0 Hz, 1H), 5.21-5.20 (m, 1H), 5.09-5.08 (m, 1H), 4.83-4.82 (d, J=5.6 Hz, 2H). MS: $[MH]^+$ 391.4.

Example 1.218. Synthesis of N-((4-(4-(trifluoromethyl)phenyl)pyrido[3,4-d]pyrimidin-2-yl)methyl) acrylamide (I-309)

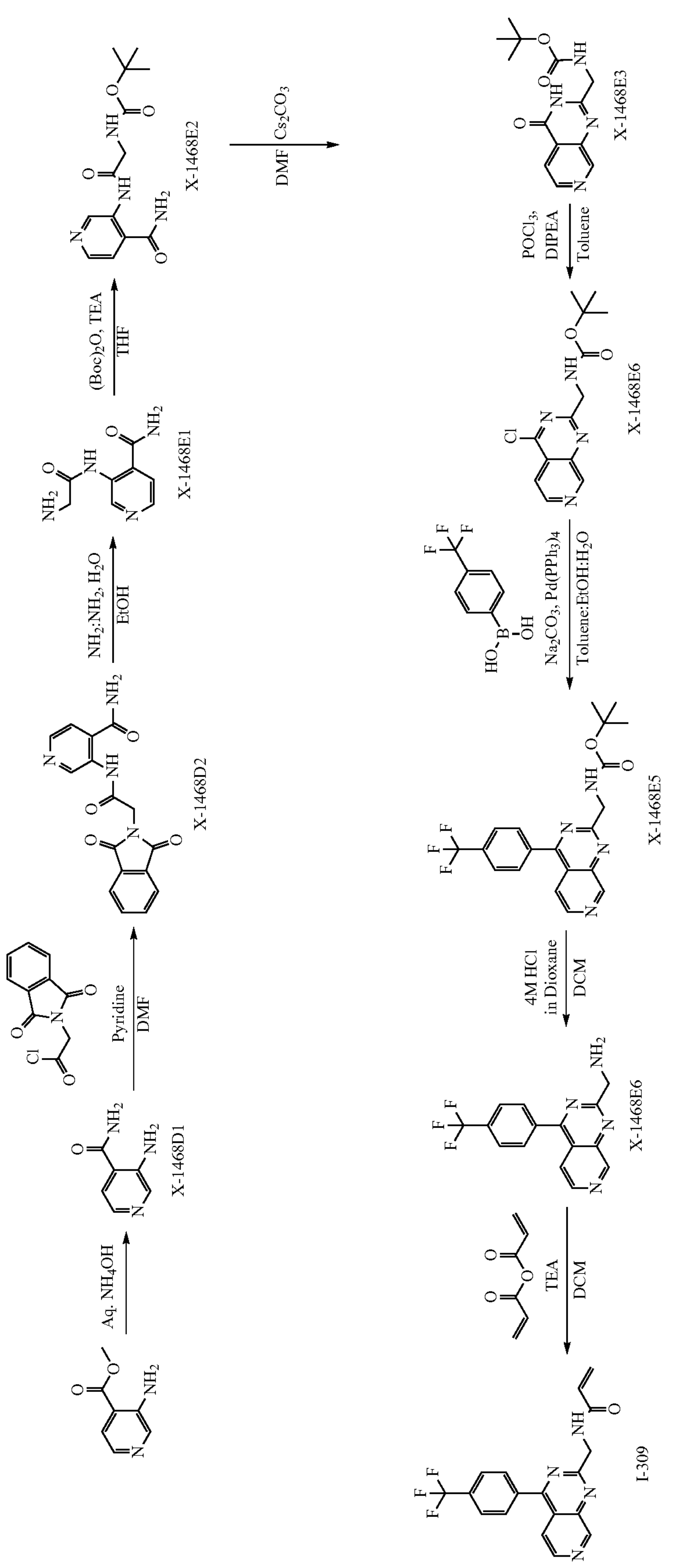
Aq. $NH_4OH$
X-1468D1
Pyridine
DMF
X-1468D2
$NH_2$:$NH_2$, $H_2O$
EtOH
X-1468E1
$(Boc)_2O$, TEA
THF
X-1468E2
DMF $Cs_2CO_3$
X-1468E3
$POCl_3$,
DIPEA
Toluene
X-1468E6
$Na_2CO_3$, $Pd(PPh_3)_4$
Toluene:EtOH:$H_2O$
X-1468E5
4M HCl
in Dioxane
DCM
X-1468E6
TEA
DCM
I-309

3-Aminoisonicotinamide (X-1468D1). To a stirred solution of methyl 3-aminoisonicotinate (10.0 g, 65.78 mmol) in $NH_4OH$ solution (80 mL) was heated at 60° C. for 3 h. Reaction mixture was cooled to room temperature, quenched with water (100 mL) and was extracted with IPA:Chloroform (200 mL×2). Combined organic layer was dried over Na2SO4 and concentrated under reduced pressure to afford 3-aminoisonicotinamide (X-1468D1) (5.2 g, 57%) as a white solid. MS: $[MH]^+$ 138.0.

3-(2-(1,3-Dioxoisoindolin-2-yl)acetamido)isonicotinamide (X-1468D2). To a stirred solution of 2-(1,3-dioxoisoindolin-2-yl) acetyl chloride (3.0 g, 14.63 mmol) in DMF (40 mL) were added pyridine (6.5 ml, 79.90 mmol) and 3-aminoisonicotinamide (X-1468D1) (2.19 g, 15.90 mmol) at 0° C. under nitrogen and the resulting mixture was stirred at room temperature for 1 h. Reaction mixture was poured into ice-water (200 mL) and the resulting precipitate was collected by filtration. Obtained solid residue was washed with water (100 mL), dried under high vacuum to afford 3-(2-(1,3-dioxoisoindolin-2-yl)acetamido)isonicotinamide (X-1468D2) (3.9 g, 55%) as an off white solid. MS: $[MH]^+$ 325.1.

3-(2-Aminoacetamido)isonicotinamide (X-1468E1). To a stirred solution of 3-(2-(1,3-dioxoisoindolin-2-yl)acetamido)isonicotinamide (X-1468D2) (3.0 g, 9.25 mmol) in EtOH (30 mL) was added hydrazine hydrate (1.03 mL, 27.7 mmol) at room temperature and reaction mixture was heated at 80° C. for 1.5 h. The reaction mixture was cooled to room temperature, Solvents were distilled off under reduced pressure, resulting crude was diluted with ice-water (100 mL) and the obtained precipitate was collected by filtration. Isolated residue was triturated with n hexanes (50 mL×2), filtered and solid part was dried under high vacuum to afford 3-(2-aminoacetamido)isonicotinamide (X-1468E1) (1.8 g, 78%) as brown sticky solid. Which was used further for next step without any purification. MS: $[MH]^+$ 195.0.

Tert-butyl (2-((4-carbamoylpyridin-3-yl)amino)-2-oxoethyl)carbamate (X-1468E2). To a stirred solution of 3-(2-aminoacetamido)isonicotinamide (X-1468E1) (1.80 g, 9.27 mmol) in THE (20 mL) were added triethylamine (5.20 mL, 37.1 mmol) and Boc-Anhydride (2.70 mL, 12.0 mmol) sequentially at 0° C. under nitrogen and the resulting mixture was stirred at room temperature for 1 h. The reaction mixture was poured into ice-water (250 mL) and was extracted with DCM (150 mL×3). Combined organic extracts were dried over anhydrous $Na_2SO_4$ and concentrated under reduced pressure to afford tert-butyl (2-((4-carbamoylpyridin-3-yl)amino)-2-oxoethyl)carbamate (X-1468E2)(1.2 g, 44%) as an brown solid. Which was used further for next step without any purification. MS: $[MH]^+$ 295.0.

Tert-butyl ((4-oxo-3,4-dihydropyrido[3,4-d]pyrimidin-2-yl)methyl)carbamate (X-1468E3). To a stirred solution of tert-butyl (2-((4-carbamoylpyridin-3-yl)amino)-2-oxoethyl) carbamate (X-1468E2) (1.20 g, 4.08 mmol) in THE (12 mL) was added $Cs_2CO_3$ (3.80 g, 12.24 mmol) at room temperature and The resulting reaction mixture was heated at 100° C. for 2 h. The Reaction mixture was cooled to room temperature, quenched with water (80 mL) and was extracted with IPA:Chloroform (100 mL×2). Combined organic layer was dried over $Na_2SO_4$ and concentrated under reduced pressure to afford tert-butyl ((4-oxo-3,4-dihydropyrido[3,4-d]pyrimidin-2-yl)methyl)carbamate (X-1468E3) (1.1 g, 98%) as a white solid. MS: $[MH]^+$ : 277.0.

Tert-butyl ((4-chloropyrido[3,4-d]pyrimidin-2-yl)methyl) carbamate (X-1468E4). $POCl_3$ (0.37 mL, 4.07) was added drop wise, via syringe, to a solution of tert-butyl ((4-oxo-3,4dihydropyrido[3,4-d]pyrimidin-2-yl)methyl)carbamate (X-1468E3) (0.750 g, 2.71 mmol) in Toluene (10 mL) were added diisopropylethylamine (0.8 mL, 4.61 mmol) at 0° C. under nitrogen. The reaction mixture was slowly brought to reflux and continued heating at 90° C. for 1 h. Reaction mixture was allowed to cool to room temperature and was slowly poured into ice-water with stirring. Obtained precipitate was filtered and the residue was washed with ice-water until the pH of the filtrate became neutral (pH~6-7). Solid was dried in vacuo to afford tert-butyl ((4-chloropyrido[3,4-d]pyrimidin-2-yl)methyl)carbamate (X-1468E4) (0.75 g, 64%) as a brown sticky solid. MS: $[MH]^+$ 294.9.

Tert-butyl ((4-(4-(trifluoromethyl)phenyl)pyrido[3,4-d]pyrimidin-2-yl)methyl)carbamate (X-1468E5). To a stirred solution of tert-butyl ((4-chloropyrido[3,4-d]pyrimidin-2-yl)methyl)carbamate (X-1468E4) (0.750 g, 2.55 mmol) in a mixture Toluene:EtOH:$H_2O$ (3:1:0.5, 14 mL) were added (4-(trifluoromethyl)phenyl)boronic acid (0.96 g, 5.10 mmol), $Na_2CO_3$ (0.800 g, 7.65 mmol) at room temperature. The reaction mixture was degassed (purging with nitrogen) for 10 min followed by addition of $Pd(PPh_3)_4$ (0.290 g, 0.25 mmol) and the reaction mixture was heated at 100° C. for 30 min. The reaction mixture was cooled to room temperature, diluted with water (100 mL) and was extracted with ethyl acetate (200 mL×3). The combined organic extracts were dried over anhydrous $Na_2SO_4$ and concentrated under reduce pressure. The crude product was purified by silica gel column chromatography, using ethyl acetate-hexane=2:8→3:7 as gradient, to afford tert-butyl ((4-(4-(trifluoromethyl)phenyl)pyrido[3,4-d]pyrimidin-2-yl)methyl)carbamate (X-1468E5) (0.35 g, 33%) as an white solid. MS: $[MH]^+$348.77.

(4-(4-(trifluoromethyl)phenyl)pyrido[3,4-d]pyrimidin-2-yl)methanamine (X-1468E6). To a stirred solution of tert-butyl ((4-(4-(trifluoromethyl)phenyl)pyrido[3,4-d]pyrimidin-2-yl)methyl)carbamate (X-1468E5) (0.35 g, 0.86 mmol) in DCM (10 mL) was added 4 M HCl in Dioxane (2.0 mL) at 0° C. under nitrogen and the resulting reaction mixture was stirred at room temperature for 30 min. Reaction mixture was concentrated under reduced pressure. Obtained crude was triturated with Diethyl ether (2×25 mL), dried over high vacuum to afford (4-(4-(trifluoromethyl)phenyl) pyrido[3,4-d]pyrimidin-2-yl)methanamine (X-1468E6) (0.25 g, 95%) as yellow sticky solid. Which was used further for next without any purification. MS: $[MH]^+$304.9.

N-((4-(4-(trifluoromethyl)phenyl)pyrido[3,4-d]pyrimidin-2-yl)methyl)acrylamide (I-309). To a stirred solution of (4-(4-(trifluoromethyl)phenyl)pyrido[3,4-d]pyrimidin-2-yl) methanamine (X-1468E6) (0.250 g, 0.92 mmol) in DCM (8 mL) were added triethylamine (0.51 mL, 3.68 mmol) at 0° C. under nitrogen acrylic anhydride (0.174 g, 1.38 mmol) and the reaction mixture was stirred at room temperature for 1 h. The reaction mixture was diluted with water (50 mL) and was extracted with DCM (50 mL×2). Combined organic extracts were dried over anhydrous $Na_2SO_4$ and concentrated under reduced pressure. The obtained crude product was purified by reverse phase column chromatography, using ACN:H2O=3:7→4:6 as a gradient to afford N-((4-(4-(trifluoromethyl)phenyl)pyrido[3,4-d]pyrimidin-2-yl) methyl)acrylamide (I-309) (0.070 g, 24%) as a white solid. $^1H$ NMR (400 MHz, DMSO-$d_6$) δ 9.51 (s, 1H), 8.93-8.90 (t, J=5.6 Hz, 1H), 8.78-8.76 (d, J=6.0 Hz, 1H), 8.09-8.02 (m, 4H), 7.95-7.94 (d, J=5.6 Hz, 1H), 6.46-6.39 (m, 1H), 6.16-6.11 (dd, J=1.6, 2.0 Hz, 1H), 5.67-5.64 (dd, J=1.6, 2.0 Hz, 1H), 4.84-4.82 (d, J=6.0 Hz, 2H). MS: $[MH]^+$ 358.9.

Example 1.219. Synthesis of 4-(4-(tert-butyl)phenyl)-N-methylpyrrolo[1,2-a]quinoxaline-7-sulfonamide (I-310)

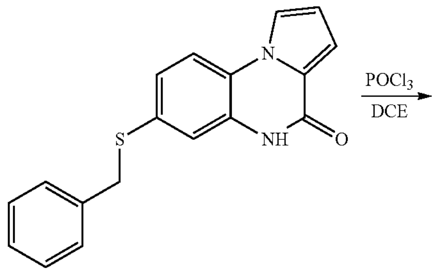

X-1470B3

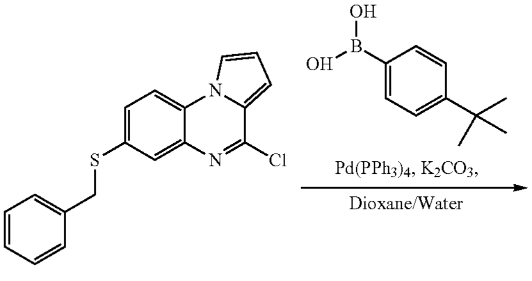

X-1470B4

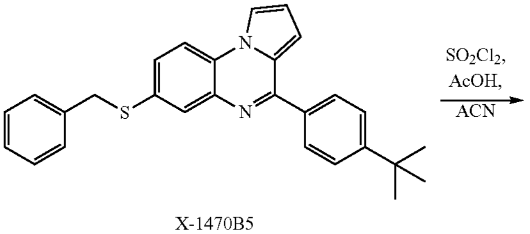

X-1470B5

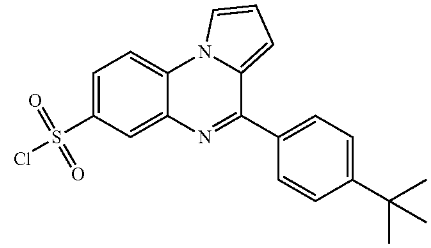

X-1470B6

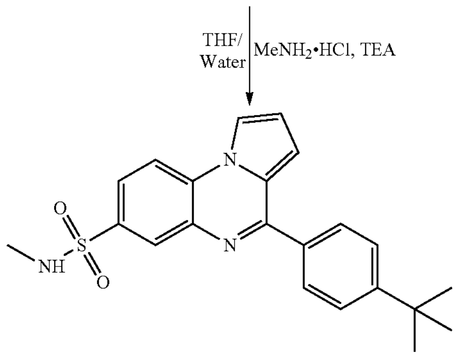

I-310

7-(benzylthio)-4-chloropyrrolo[1,2-a]quinoxaline (X-1470B4) $POCl_3$ (1.21 mL, 13.0 mmol) was added drop wise, via addition funnel, to a solution of 7-(benzylthio) pyrrolo[1,2-a] quinoxalin-4(5H)-one (X-1470B3) (2.0 g, 6.53 mmol) in DCE (20 mL) at 0° C. under nitrogen. and heated 100° C. to reflux for 2 h. Reaction mixture was allowed to cool to room temperature and was slowly poured into ice-water. The resulting precipitate was filtered and the residue was washed with cold water until the pH of the filtrate became neutral (pH~6-7) and dried in vacuo, to afford 7-(benzylthio)-4-chloropyrrolo[1,2-a]quinoxaline (X-1470B4) (2.0 g, 94%) as a brown solid, which was used in next step without further purification. MS: $[MH]^+$ 325.0.

7-(benzylthio)-4-(4-(tert-butyl)phenyl)pyrrolo[1,2-a]quinoxaline (X-1470B5). To a stirred solution of 7-(benzylthio)-4-chloropyrrolo[1,2-a]quinoxaline (X-1470B4) (1.0 g, 3.08 mmol) in a mixture of dioxane-water (3:1, 20 mL) were added (4-(tert-butyl)phenyl)boronic acid (0.549 g, 3.08 mmol) and $K_2CO_3$ (2.09 g, 15.14 mmol) at room temperature under nitrogen. The reaction mixture was degassed (purging with nitrogen) for 20 min followed by addition of $Pd(PPh_3)_4$ (0.356 g, 0.30 mmol) and the reaction mixture was heated at 100° C. for 1 h in microwave irradiation The reaction mixture was cooled to room temperature, diluted with water (100 mL) and was extracted with ethyl acetate (100 mL×3). The combined organic extracts were dried over anhydrous $Na_2SO_4$ and concentrated under reduce pressure. The crude product was purified by silica gel column chromatography, using ethyl acetate-Hexane=1:9→1:3 as gradient, to afford 7-(benzylthio)-4-(4-(tert-butyl)phenyl)pyrrolo [1,2-a]quinoxaline (X-1470B5) (2.2 g, 84%) as an off-white solid. MS: $[MH]^+$ 423.1.

4-(4-(tert-Butyl)phenyl)pyrrolo[1,2-a]quinoxaline-7-sulfonyl chloride (X-1470B6). To a stirred solution of 7-(benzylthio)-4-(4-(tert-butyl)phenyl)pyrrolo[1,2-a]quinoxaline (X-1470B5) (0.5 g, 1.10 mmol) in ACN (12 mL) were added AcOH (0.3 mL) and $H_2O$ (0.3 mL) at 0° C. under nitrogen and then $SO_2Cl_2$ (0.479 g, 3.55 mmol) drop-wise at 0° C. over period of time. The resulting reaction mixture was stirred at room temperature for 1 h. Reaction mixture was diluted with water (50 mL) and extracted with EtOAc (150 mL×2). Organic extract were dried over anhydrous $Na_2SO_4$, filtered and concentrated under reduced pressure, to afford 4-(4-(tert-butyl)phenyl)pyrrolo[1,2-a]quinoxaline-7-sulfonyl chloride (X-1470B6) (0.370 g, 78%) as a yellow solid, which was used in next step without further purification. MS: $[MH]^+$ 399.1.

4-(4-(tert-Butyl)phenyl)-N-methylpyrrolo[1,2-a]quinoxaline-7-sulfonamide (I-310). To a stirred solution of 4-(4-(tert-butyl)phenyl)pyrrolo[1,2-a]quinoxaline-7-sulfonyl chloride (X-1470B6) (0.37 g, 0.92 mmol) in THE (5 mL) were added triethylamine (0.563 g, 5.57 mmol), $MeNH_2$·HCl (0.075 g, 1.11 mmol) and $H_2O$ (1.5 mL) at −35° C. under nitrogen. The resulting reaction mixture was stirred at room temperature for 1 h. Reaction mixture was diluted with water (100 mL) and extracted with EtOAc (100 mL×2). Organic extract were dried over anhydrous $Na_2SO_4$, filtered and concentrated under reduced pressure. Obtained crude was purified by reverse phase (C-18) silica gel column chromatography, using acetonitrile-water=0:1→1:0 as gradient, to afford 4-(4-(tert-butyl)phenyl)-N-methylpyrrolo[1,2-a]quinoxaline-7-sulfonamide (I-310) (0.1 g, 27%) as a white solid. $^1H$ NMR (400 MHz, DMSO-$d_6$) δ 8.66 (s, 1H), 8.56-8.54 (d, J=8.8 Hz, 1H), 8.25-8.24 (d, J=2 HZ, 1H), 7.99-7.93 (d, J=8.4 Hz, 1H), 7.63-7.61 (d, J=8.4 Hz, 3H), 7.17-7.16 (d, J=3.2 Hz, 1H), 7.07-7.06 (d, J=3.6 Hz, 1H), 2.49 (s, 3H), 1.36 (s, 9H). MS: $[MH]^+$ 393.9.

Example 1.220. Synthesis of 4-(4-(tert-butyl)phenyl)pyrrolo[1,2-a]quinoxaline-7-sulfonamide (I-311)

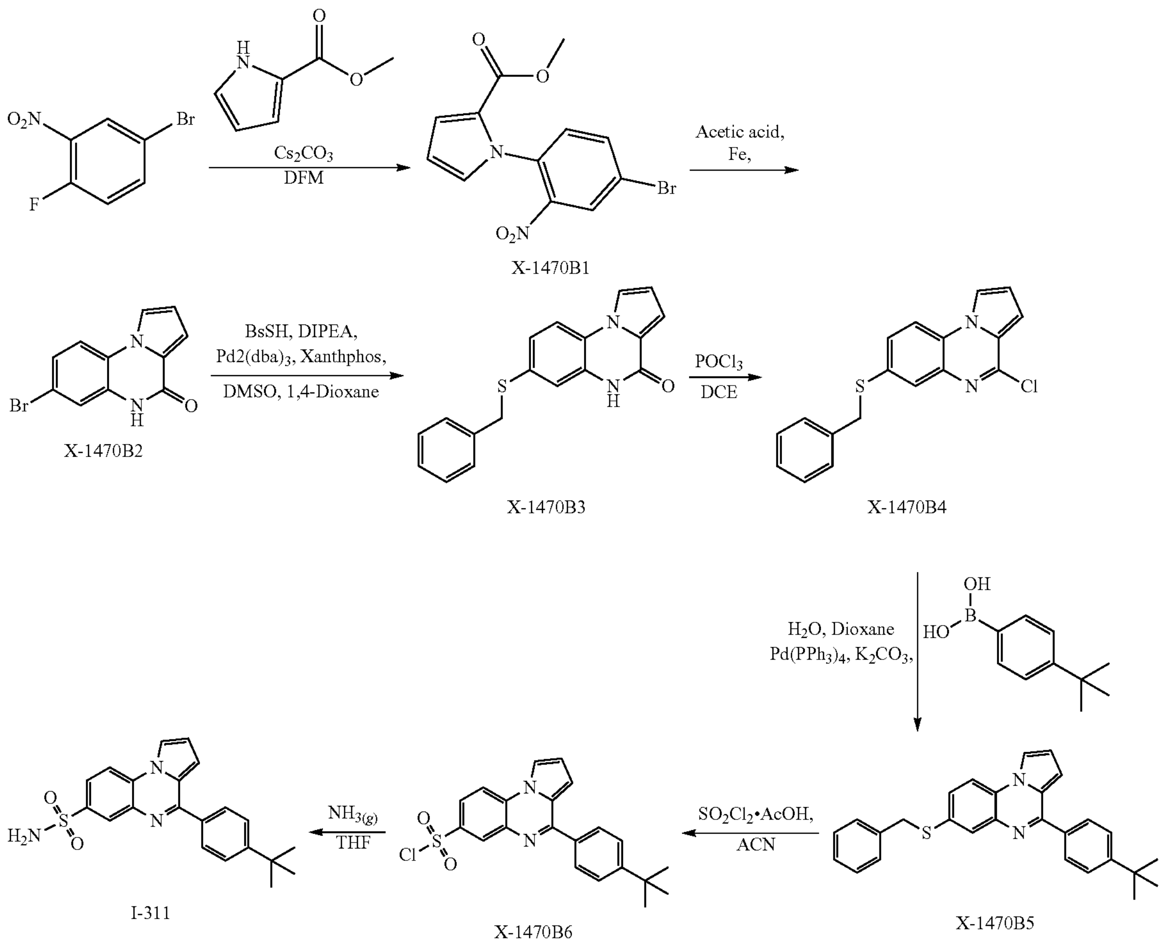

Methyl 1-(4-bromo-2-nitrophenyl)-1H-pyrrole-2-carboxylate (X-1470B1). Cesium carbonate (14.88 g, 45.68 mmol) and methyl methyl 1H-pyrrole-2-carboxylate (3.42 g, 27.4 mmol) were added to a stirred solution of 4-bromo-1-fluoro-2-nitrobenzene (5.00 g, 22.8 mmol) in DMF (50 mL) at room temperature and the reaction mixture was stirred at room temperature for 16 h. After cooling to room temperature, reaction mixture was slowly poured in ice water (200 mL) and resulting precipitates were collected by filtration and dried in vacuo to afford Methyl 1-(4-bromo-2-nitrophenyl)-1H-pyrrole-2-carboxylate (X-1470B1) (7.3 g, 98.79%) as an off-white solid which was used in the next step without further purification. MS: $[MH]^+$ 324.9, $[MH]^{2+}$ 326.9.

7-Bromopyrrolo[1,2-a]quinoxalin-4(5H)-one (X-1470B2). To a stirred solution of methyl 1-(4-bromo-2-nitrophenyl)-1H-pyrrole-2-carboxylate (X-1470B1) (7.3 g, 33.34 mmol) in acetic acid (70 mL) was added Fe powder (6.93 g, 266.78 mmol) was added at −78° C. and resulting reaction mixture was stirred at 100° C. for 1 h. After cooling to room temperature. The reaction mixture was dilute with DCM-MeOH (1:1, 3 L) and filtered through celite. Filtrate was concentrated under reduced pressure to afford 7-bromopyrrolo[1,2-a]quinoxalin-4(5H)-one (X-1470B2) (5.5 g, 93%) as an off white solid, which was used in next step without further purification. MS: $[MH]^+$ 262.9, $[MH]^{2+}$ 262.9, 7-(Benzylthio)pyrrolo[1,2-a]quinoxalin-4(5H)-one (X-1470B3). To a stirred solution of 7-bromopyrrolo[1,2-a]quinoxalin-4(5H)-one (X-1470B2) (1.0 g, 7.63 mmol) in 1,4-dioxane-s DMSO (20 mL) at room temperature and $Pd_2dba_3$ (0.349 g, 0.38 mmol) and Xantphos (0.21 g, 0.38 mmol) were added sequentially to the reaction mixture at room temperature and the resulting mixture was degassed by purging nitrogen through the solution for 15 min. DIPEA (1.97 g, 15.26 mmol) and benzyl mercaptan (1.04 g, 8.30 mmol) were added sequentially to the reaction mixture at the same temperature under nitrogen and the resulting mixture was heated to 110° C. for 16 h. Reaction mixture was brought to room temperature, The reaction mixture was diluted with water (100 mL) and extracted with EtOAc (100 mL×2). Combined organic extracts were dried over anhydrous $Na_2SO_4$, filtered and concentrated under reduced pressure, to afford crude mass, which was purified by silica gel Combi flash column chromatography, using ethyl acetate-hexane=1:9→1:3 as eluent, to afford 7-(benzylthio)pyrrolo[1,2-a]quinoxalin-4(5H)-one (X-1470B3) (4.5 g, 77%) as a yellow solid. MS: $[MH]^+$ 306.9.

7-(Benzylthio)-4-chloropyrrolo[1,2-a]quinoxaline (X-1470B4). $POCl_3$ (0.3 mL) was added drop wise to a solution of 7-(benzylthio)pyrrolo[1,2-a]quinoxalin-4(5H)-one (X-1470B3) (0.3 g, 0.98 mmol) in DCE (3 mL) at 0° C. under nitrogen. After addition of $POCl_3$, the reaction mixture was slowly brought to reflux and continued heating for 2 h. Reaction mixture was brought to room temperature, diluted with water (150 mL) and extracted with ethyl acetate (100 mL×2). Combined organic extracts were dried over anhydrous $Na_2SO_4$, filtered and concentrated under reduced pressure, to afford 7-(benzylthio)-4-chloropyrrolo[1,2-a]quinoxaline (X-1470B4) (0.31 g, 97%) as a brown solid, which was used in next step without further purification. MS: $[MH]^+$ 325.0.

7-(Benzylthio)-4-(4-(tert-butyl)phenyl)pyrrolo[1,2-a]quinoxaline (X-1470B5). To a stirred solution of 7-(benzylthio)-4-chloropyrrolo[1,2-a]quinoxaline (X-1470B4) (0.32 g, 0.98 mmol) in a mixture of dioxane-water (3:1, 13 mL) were added (4-(tert-butyl)phenyl)boronic acid (0.175 g, 0.98 mmol) and potassium carbonate (0.668 g, 4.83 mmol) at room temperature under nitrogen. The reaction mixture was degassed (purging with nitrogen) for 20 min followed by addition of $Pd(PPh_3)_4$ (0.113 g, 0.098 mmol) and the reaction mixture was heated at 100° C. for 1 h. Reaction mixture was slowly poured in to water (50 mL) and was extracted with ethyl acetate (50 mL×3). The combined organic extracts were dried over anhydrous $Na_2SO_4$ and concentrated under reduce pressure. The crude product was purified by silica gel column chromatography, using ethyl acetate-Hexane=1:9→1:3 as gradient, to afford 7-(benzylthio)-4-(4-(tert-butyl)phenyl)pyrrolo[1,2-a]quinoxaline (X-1470B5) (0.3 g, 74%) as an off-white solid.

4-(4-(tert-Butyl)phenyl)pyrrolo[1,2-a]quinoxaline-7-sulfonyl chloride (X-1470B6). To a stirred solution of 7-(benzylthio)-4-(4-(tert-butyl)phenyl)pyrrolo[1,2-a]quinoxaline (X-1470B5) (0.3 g, 0.71 mmol) in ACN (12 mL) were added AcOH (0.05 mL) and $H_2O$ (0.05 mL) at 0° C. and then $SO_2Cl_2$ (0.287 g, 2.13 mmol) drop wise at 0° C. The resulting reaction mixture was stirred at room temperature for 1 h. Reaction mixture was diluted with water (50 mL) and extracted with ethyl acetate (50 mL×2). Organic extract were dried over anhydrous $Na_2SO_4$, filtered and concentrated under reduced pressure, to afford 4-(4-(tert-butyl)phenyl)pyrrolo[1,2-a]quinoxaline-7-sulfonyl chloride (X-1470B6) (0.16 g, 56%) as a yellow solid, which was used in next step without further purification. MS: $[MH]^+$ 399.1.

4-(4-(tert-Butyl)phenyl)pyrrolo[1,2-a]quinoxaline-7-sulfonamide (I-311). To a stirred solution of 4-(4-(tert-butyl)phenyl)pyrrolo[1,2-a]quinoxaline-7-sulfonyl chloride (X-1470B6) (0.16 g, 0.40 mmol) in THE (5 mL), $NH_3$(g) was purged at −35° C. for 30 min. The reaction mixture was stirred at room temperature for 1 h. Reaction mixture was diluted with water (50 mL) and extracted with ethyl acetate (50 mL×2). Organic extract was dried over anhydrous $Na_2SO_4$, filtered and concentrated under reduced pressure. The crude product was triturated using n-pentane and diethyl ether to afford 4-(4-(tert-butyl)phenyl)pyrrolo[1,2-a]quinoxaline-7-sulfonamide (I-311) (0.1 g, 65%) as an off-white solid. $^1H$ NMR (400 MHz, DMSO-$d_6$) δ 8.646-8.641 (d, J=2.0 Hz, 1H), 8.52-8.50 (d, J=8.4 Hz, 1H), 8.328-8.323 (d, J=2.0 HZ, 1H), 7.99-7.77 (d, J=8.0 Hz, 3H), 7.63-7.61 (d, J=8.0 Hz, 2H), 7.530 (s, 2H), 7.16-7.15 (d, J=3.6 Hz, 1H), 7.07-7.05 (t, J=3.2 Hz, 1H), 1.36 (s, 9H). MS: $[MH]^+$ 380.2.

Example 1.221. Synthesis of N-(4-(5-(trifluoromethyl)pyridin-2-yl)imidazo[1,2-a]quinoxalin-7-yl) acrylamide (I-312)

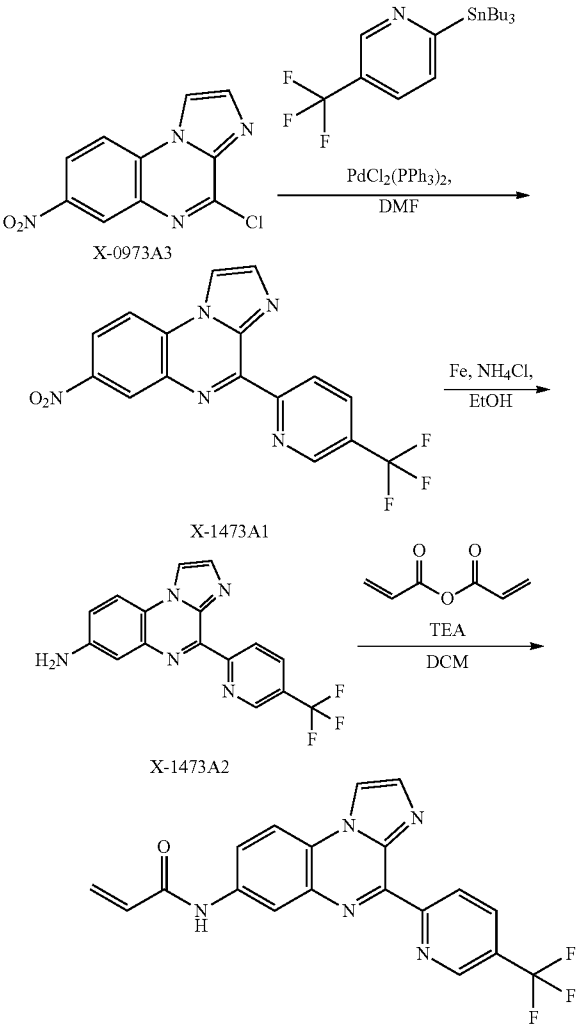

X-0973A3

X-1473A1

X-1473A2

I-312

7-nitro-4-(5-(trifluoromethyl)pyridin-2-yl)imidazo[1,2-a]quinoxaline (X-1473A1). 2-(tributylstannyl)-5-(trifluoromethyl)pyridine (0.528 g, 1.20 mmol) was added to a stirred solution of 4-chloro-7-nitroimidazo[1,2-a]quinoxaline (X-0973A3) (0.25 g, 1.00 mmol) in DMF (5 mL) at room temperature under nitrogen. Reaction mixture was degassed (purging with nitrogen) for 15 min followed by the addition of $PdCl_2(PPh_3)_2$ (0.021 g, 0.03 mmol) and the resulting mixture was heated at 140° C. for 5 h. After cooling to room temperature, reaction mixture was diluted with water (50 mL) and was extracted by ethyl acetate (50 mL×3). Combined organic extracts were dried over anhydrous $Na_2SO_4$ and concentrated under reduced pressure. The crude product was purified by silica gel column chromatography, using ethyl acetate-Hexane=5:0-5:0 as gradient, to afford 7-nitro-4-(5-(trifluoromethyl)pyridin-2-yl)imidazo[1,2-a]quinoxaline (X-1473A1) (0.180 g, 49.83%) as an pale yellow solid. MS: $[MH]^+$ 360.1.

4-(5-(trifluoromethyl)pyridin-2-yl)imidazo[1,2-a]quinoxalin-7-amine (X-1473A2). To a stirred solution of 7-nitro-4-(5-(trifluoromethyl)pyridin-2-yl)imidazo[1,2-a]quinoxaline (X-1473A1) (0.180 g, 0.47 mmol) in ethanol-water (8:2; 10 mL) were added Fe (0.132 g, 2.36 mmol) and ammonium chloride (0.125 g, 2.36 mmol) at room temperature and stirred for 2 h at the same temperature. The reaction mixture was filtered through celite and residue was washed with ethyl acetate (50 mL). Combined filtrates were washed with water (20 mL), dried over anhydrous $Na_2SO_4$ and concentrated under reduce pressure to afford 4-(5-(trifluoromethyl)pyridin-2-yl)imidazo[1,2-a]quinoxalin-7-amine (X-1473A2) [0.120 g, 72.74% (crude)] as a brown solid, which was used in next step without further purification. MS: $[MH]^+$ 330.1.

N-(4-(5-(trifluoromethyl)pyridin-2-yl)imidazo[1,2-a]quinoxalin-7-yl)acrylamide (I-312). To a stirred solution of 4-(5-(trifluoromethyl)pyridin-2-yl)imidazo[1,2-a]quinoxalin-7-amine (X-1473A2) (0.120 g, 0.30 mmol) in DCM (3 mL) were added triethylamine (0.091 mL, 0.90 mmol) and Acrylic Anhydride (0.076 g, 0.60 mmol) sequentially at 0° C. under nitrogen and the reaction mixture was stirred at room temperature for 16 h. The reaction mixture was diluted with water (50 mL) and was extracted with DCM (50 mL×2). Combined organic extracts were dried over anhydrous $Na_2SO_4$ and concentrated under reduced pressure. The crude product was purified by C-18 silica gel column chromatography, using acetonitrile-water=6:0>4:0 as gradient, to afford N-(4-(5-(trifluoromethyl)pyridin-2-yl)imidazo[1,2-a]quinoxalin-7-yl)acrylamide (I-312) (0.030 g, 21.48%) as a white solid. $^1H$ NMR (400 MHz, DMSO-$d_6$) 10.66 (s, 1H), 9.22 (s, 1H), 8.90 (s, 1H), 8.79-8.77 (d, J=8 Hz 1H), 8.61 (s, 1H), 8.50-8.44 (m, 2H), 8.05-8.03 (d, J=8.8 Hz, 1H), 7.91 (s, 1H), 6.56-6.49 (m, 1H), 6.37-6.33 (d, J=16.4 Hz 1H), 5.85-5.82 (d, J=10.4 Hz 1H). MS: $[MH]^+$ 384.1.

Example 1.222. Synthesis of N-((8-(5-(trifluoromethyl)pyridin-2-yl)imidazo[1,2-a]pyrazin-6-yl)methyl)acrylamide (I-313)

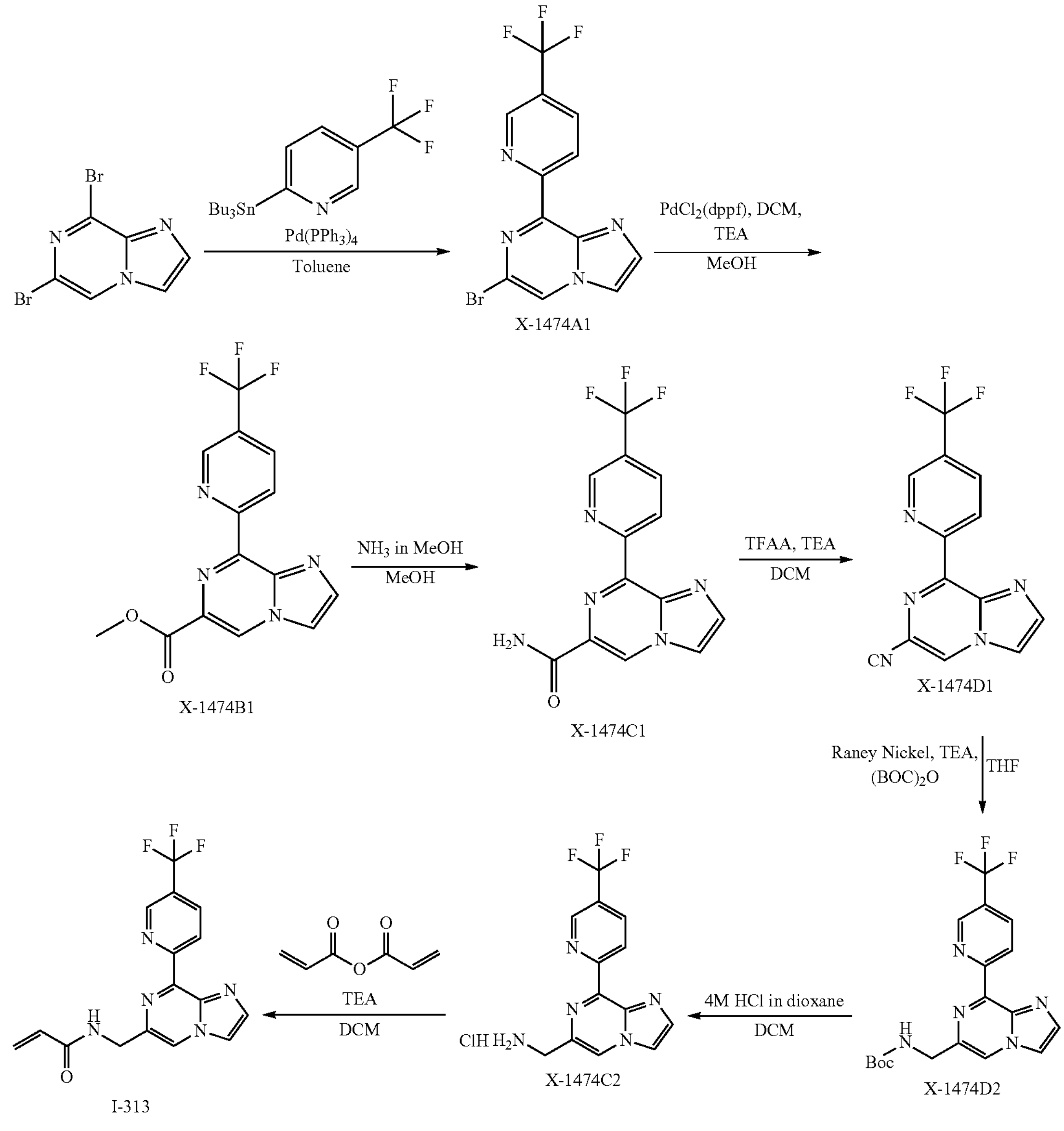

X-1474A1

X-1474B1

X-1474C1

X-1474D1

X-1474D2

X-1474C2

I-313

6-Bromo-8-(5-(trifluoromethyl)pyridin-2-yl)imidazo[1,2-a]pyrazine (X-1474A1). To a stirred solution of 6,8-dibromoimidazo[1,2-a]pyrazine (1.0 g, 3.63 mmol) in a toluene (12 mL) was added 2-(tributylstannyl)-5-(trifluoromethyl)pyridine (1.90 g, 4.36 mmol) at room temperature under nitrogen. The reaction mixture was degassed (purging with nitrogen) for 10 min followed by the addition of $Pd(PPh_3)_4$ (0.20 g, 0.18 mmol) and the resulting mixture was heated at 140° C. for 3 h. After the completion of reaction, reaction mixture was diluted with water (80 mL) and was extracted with ethyl acetate (100 mL×2). Combined organic extracts were washed with brine water (50 mL×2), dried over anhydrous $Na_2SO_4$ and concentrated under reduced pressure. The crude product was purified by silica gel column chromatography, using ethyl acetate-hexane=4:0→6:0 as gradient, to afford 6-bromo-8-(5-(trifluoromethyl)pyridin-2-yl)imidazo[1,2-a]pyrazine (X-1474A1) (0.53 g, 44%) as an yellow solid. MS: $[MH]^+$ 342.8. $[MH]^{2+}$ 344.8.

Methyl 8-(5-(trifluoromethyl)pyridin-2-yl)imidazo[1,2-a]pyrazine-6-carboxylate (X-1474B1). To a stirred solution of 6-bromo-8-(5-(trifluoromethyl)pyridin-2-yl)imidazo[1,2-a]pyrazine (X-1474A1) (0.53 g, 1.55 mmol) in MeOH (8 mL) was added trimethylamine (1.06 mL, 7.77 mmol) and reaction mixture was degassed (purging with nitrogen) for 10 min followed by addition of $PdCl_2$(dppf).DCM (0.12 g, 0.15 mmol) sequentially at room temperature under nitrogen. The resulting reaction mixture was degassed (purging with CO gas) for 15 min and stirred at 85° C. under CO gas pressure for 6 h. The reaction mixture was concentrated under reduced pressure. The obtained crude product was purified by reverse phase column chromatography, using ACN: $H_2O$=6:0→4:0 as a gradient to afford methyl 8-(5-(trifluoromethyl)pyridin-2-yl)imidazo[1,2-a]pyrazine-6-carboxylate (X-1474B1) (0.37 g, 74%) as a white solid. MS: $[MH]^+$ :322.9.

8-(5-(Trifluoromethyl)pyridin-2-yl)imidazo[1,2-a]pyrazine-6-carboxamide. (X-1474C1). To a Stirred solution of methyl 8-(5-(trifluoromethyl) pyridin-2-yl)imidazo[1,2-a]pyrazine-6-carboxylate (X-1474B1) (0.37 g, 1.14 mmol) in MeOH (5 ml) was added $NH_3$ in MeOH (3 ml). The reaction mixture was stirred at 70° C. for 3 h in sealed tube. After completion of the reaction, reaction mixture was diluted with water (15 ml) and product was extracted with 10% MeOH in DCM (100 ml×2). Combined organic layer was dried over $Na_2SO_4$ and concentrated under reduced pressure to give 8-(5-(trifluoromethyl)pyridin-2-yl)imidazo[1,2-a]pyrazine-6-carboxamide (X-1474C1) (0.29 g, 82%) as a white solid. Which was used to next step without any further purification. MS: [MH]+ : 308.4.

8-(5-(Trifluoromethyl)pyridin-2-yl)imidazo[1,2-a]pyrazine-6-carbonitrile (X-1474D1). To a Stirred solution of 8-(5-(trifluoromethyl)pyridin-2-yl)imidazo[1,2-a]pyrazine-6-carboxamide (X-1474C1) (0.29 g, 0.94 mmol) in DCM were added trimethylamine (0.64 mL, 4.72 mmol), TFAA (0.32 ml, 2.36 mmol) at 0° C. and stirred the reaction mixture at room temperature for 3 h. After completion of the reaction, reaction mixture was diluted with water (30 ml) and product was extracted with DCM (100 ml×2). Combined organic layer was dried over $Na_2SO_4$ and concentrated under reduced pressure to give 8-(5-(trifluoromethyl)pyridin-2-yl)imidazo[1,2-a]pyrazine-6-carbonitrile (X-1474D1) (0.21 g, 77%) as a yellow solid. Which was used to next step without any further purification. MS: [MH]+ : 290.3.

tert-Butyl ((8-(5-(trifluoromethyl)pyridin-2-yl)imidazo[1,2-a]pyrazin-6-yl)methyl)carbamate (X-1474D2). To a stirred solution of 8-(5-(trifluoromethyl)pyridin-2-yl)imidazo[1,2-a]pyrazine-6-carbonitrile (X-1474D1) (0.210 g, 0.58 mmol) in THE (8 mL) were added triethylamine (0.40 mL, 2.94 mmol), Raney nickel (~0.25 g) and Boc anhydride (0.26 mL, 1.17 mmol) at room temperature under nitrogen then resulting reaction mixture was hydrogenated in balloon pressure at room temperature for 16 h. After completion of the reaction, reaction mixture was filtered, filtrate was concentrated under reduced pressure. The crude product was purified by silica gel column chromatography, using MeOH-DCM=0.1→1:1 as gradient to afford tert-butyl ((8-(5-(trifluoromethyl)pyridin-2-yl)imidazo[1,2-a]pyrazin-6-yl)methyl)carbamate (X-1474D2) (0.050 g, 18%) as a brown solid. MS: $[MH]^+$ :393.9.

(8-(5-(trifluoromethyl)pyridin-2-yl)imidazo[1,2-a]pyrazin-6-yl)methanamine hydrochloride (X-1474C2). To a stirred solution of tert-butyl ((8-(5-(trifluoromethyl)pyridin-2-yl)imidazo[1,2-a]pyrazin-6-yl)methyl)carbamate (X-1474D2) (0.05 g, 0.17 mmol) in DCM (4 mL) was added 4 M HCl in Dioxane (2 mL) at 0° C. under nitrogen and the resulting reaction mixture was stirred at room temperature for 1 h. Reaction mixture was concentrated under reduced pressure. Obtained crude was triturated with diethyl ether (2×10 mL), dried over high vacuum to afford (8-(5-(trifluoromethyl)pyridin-2-yl)imidazo[1,2-a]pyrazin-6-yl)methanamine hydrochloride (X-1474C2) (0.03 g, 81%) as a brown solid. Which was used further for next without any purification. MS: $[MH]^+$ 293.9.

N-((8-(5-(trifluoromethyl)pyridin-2-yl)imidazo[1,2-a]pyrazin-6-yl)methyl)acrylamide (1-313). To a stirred solution of (8-(5-(trifluoromethyl)pyridin-2-yl)imidazo[1,2-a]pyrazin-6-yl)methanamine hydrochloride (X-1474C2) (0.03 g, 0.10 mmol) in DCM (3 mL) were added Acryllic anhydride (0.02 g, 0.20 mmol) and triethylamine (0.04 g, 0.40 mmol) at 0° C. under nitrogen and the reaction mixture was stirred at room temperature for 1 h. The reaction mixture was diluted with water (30 mL) and was extracted with DCM (50 mL×2). Combined organic extracts were dried over anhydrous $Na_2SO_4$ and concentrated under reduced pressure. The resulting crude was purified by reverse phase (C-18) silica gel column chromatography, using acetonitrile-water=3:7→4:6 as gradient to afford N-((8-(5-(trifluoromethyl)pyridin-2-yl)imidazo[1,2-a]pyrazin-6-yl)methyl)acrylamide (I-313) (0.0045 g, 14.40%) as a white solid. $^1H$ NMR (400 MHz, DMSO-$d_6$) δ 9.19 (s, 1H), 8.85-8.82 (d, J=8.80 Hz, 2H), 8.66 (s, 1H), 8.47-8.45 (d, J=7.20 Hz, 1H), 8.32 (s, 1H), 7.90 (s, 1H), 6.35-6.29 (m, 1H) 6.17-6.12 (d, J=16.8 Hz, 1H), 5.66-5.63 (d, J=10.4 Hz, 1H), 4.54-4.52 (d, J=5.20 Hz, 2H). MS: $[MH]^+$347.8.

Example 1.223. Synthesis of N-((1-(5-(Trifluoromethyl)pyridin-2-yl)pyrrolo[1,2-a]pyrazin-3-yl)methyl)acrylamide (~314)

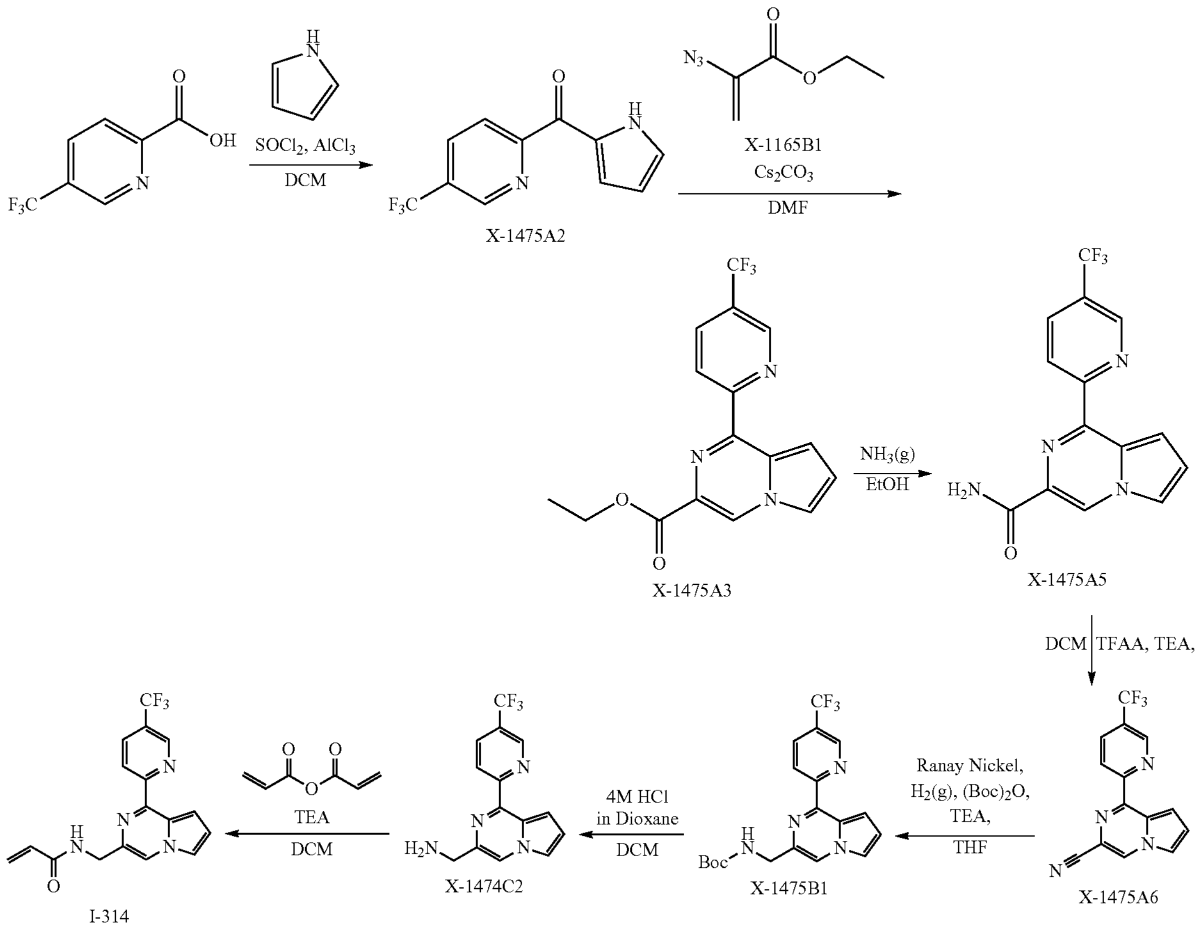

X-1475A2, X-1475A3, X-1475A5, X-1475A6, X-1475B1, X-1474C2, I-314

Ethyl (1H-Pyrrol-2-yl) (5-(trifluoromethyl)pyridin-2-yl) methanone (X-1475A2). A stirred solution of 5-(trifluoromethyl)picolinic acid (6.0 g, 31.41 mmol) in thionyl chloride (51.0 mL, 703.66 mmol) and the resulting mixture was heated at 90° C. for 6 h. After cooling to room temperature, the reaction mixture was concentrated and then reaction mixture was dissolved in dry DCM (100 mL) were added aluminium chloride (6.8 g, 50.49 mmol) portion wise and 1H-pyrrole (5.6 g, 84.81 mmol) and the resulting reaction mixture was stirred at room temperature for 16 h. Reaction mixture was poured into ice water (500 mL) and was extracted with DCM (350 mL×3), dried over anhydrous $Na_2SO_4$ and concentrated under reduced pressure. The crude product was purified by silica gel column chromatography, using ethyl acetate-hexane=0:1→1:9 as gradient, to afford ethyl (1H-Pyrrol-2-yl)(5-(trifluoromethyl)pyridin-2-yl) methanone (X-1475A2) (4.0 g, 53%) as an off-white solid. MS: $[MH]^+$ 240.9.

Synthetic procedure of Ethyl 2-azidoacrylate (X-1165B1) was described under N-(1-(4-(trifluoromethyl)phenyl)pyrrolo[1,2-a]pyrazin-3-yl)acrylamide (I-96)

Ethyl 1-(5-(trifluoromethyl)pyridin-2-yl)pyrrolo[1,2-a]pyrazine-3-carboxylate (X-1475A3). To a stirred solution of ethyl (1H-Pyrrol-2-yl)(5-(trifluoromethyl)pyridin-2-yl) methanone (X-1475A2) (1.0 g, 4.16 mmol) in DMF (10 mL) were added $Cs_2CO_3$ (4.75 g, 14.58 mmol) and Ethyl 2-azidoacrylate (X-1165B1) (0.79 g, 5.66 mmol) at 0° C. under nitrogen and the resulting mixture was stirred at 70° C. for 3 h. After cooling to room temperature, the reaction mixture was diluted with cold water (300 mL) and was extracted with ethyl acetate (200 mL×3). The combined organic extracts were washed with brine (500 mL), dried over anhydrous $Na_2SO_4$ and concentrated under reduce pressure. Isolated crude was combined with an identical prepared three more batch (1 g) and the combined crude were purified by silica gel column chromatography, using ethyl acetate-hexane=0:1→3:7 as gradient, to afford ethyl 1-(5-(trifluoromethyl)pyridin-2-yl)pyrrolo[1,2-a]pyrazine-3-carboxylate (X-1475A3) (2.1 g, 39%) as an off-white solid. MS: $[MH]^+$ 335.87.

1-(5-(Trifluoromethyl)pyridin-2-yl)pyrrolo[1,2-a]pyrazine-3-carboxamide (X-1475A5). To a stirred solution of ethyl 1-(5-(trifluoromethyl)pyridin-2-yl)pyrrolo[1,2-a]pyrazine-3-carboxylate (X-1475A3) (2.1 g, 6.26 mmol) in ethanol (40 mL) purge ammonia gas at −78° C. room temperature and the resulting mixture was hydrogenated in Parr Autoclave at 70° C. under 200 psi for 22 h. After cooling to room temperature, the reaction mixture was diluted with water (500 mL) and was extracted with ethyl acetate (300 mL×3), dried over anhydrous $Na_2SO_4$ and concentrated under reduced pressure. Crude was triturated by methanol: dichloromethane (0.5:9.5) and dried under reduced pressure, to afford 1-(5-(trifluoromethyl)pyridin-2-yl)pyrrolo[1,2-a]pyrazine-3-carboxamide (X-1475A5) (1.50 g, 75%) as an off-white solid. MS: $[MH]^+$ 306.81.

1-(5-(Trifluoromethyl)pyridin-2-yl)pyrrolo[1,2-a]pyrazine-3-carbonitrile (X-1475A6). To a stirred solution of 1-(5-(Trifluoromethyl)pyridin-2-yl)pyrrolo[1,2-a]pyrazine-3-carboxamide (X-1475A5) (1.50 g, 4.90 mmol) in DCM (30 mL) were added TEA (1.48 g, 14.70 mmol) and trifluoroacetic anhydride (2.05 g, 9.80 mmol) at 0° C. under nitrogen and the resulting mixture was stirred at room temperature for 2 h. The reaction mixture was diluted with $NaHCO_3$ solution (300 mL) and was extracted with DCM (300 mL×2). Combined organic extracts were dried over anhydrous $Na_2SO_4$ and concentrated under reduced pressure. Crude was triturated by diethyl ether and dried in vacuo, to afford 1-(5-(trifluoromethyl)pyridin-2-yl)pyrrolo[1,2-a]pyrazine-3-carbonitrile (X-1475A6) (1.40 g, 99%) as an off-white solid. MS: $[MH]^+$ 288.86.

Tert-butyl ((1-(5-(trifluoromethyl)pyridin-2-yl)pyrrolo[1,2-a]pyrazin-3-yl)methyl)carbamate (X-1475B1). To a stirred solution of 1-(5-(trifluoromethyl)pyridin-2-yl)pyrrolo[1,2-a]pyrazine-3-carbonitrile (X-1475A6) (0.7 g, 2.43 mmol) in THE (8 mL) were added TEA (1.22 g, 12.15 mmol), Raney nickel (0.7 g) and $(Boc)_{2}O$ (1.06 g, 4.86 mmol) at room temperature and the resulting mixture was hydrogenated in Parr Autoclave at room temperature under 200 psi for 10 h. Reaction mixture was filtered over a celite bed, washed the bed with MeOH (100 mL) and collected filtrates were concentrated under reduced pressure and reaction mixture was diluted with water (100 mL) and was extracted with ethyl acetate (100 mL×2). The combined organic extracts were dried over anhydrous $Na_2SO_4$ and concentrated under reduce pressure. Isolated crude was combined with an identical prepared one more batch (0.4 g) and the combined crude were purified by $C^{18}$ silica gel column chromatography, using acetonitrile-water=0:1→6:4 as gradient, to afford tert-butyl ((1-(5-(trifluoromethyl)pyridin-2-yl)pyrrolo[1,2-a]pyrazin-3-yl)methyl)carbamate (X-1475B1) (0.25 g, 16%) as a brown solid. MS: $[MH]^+$ :393.07.

(1-(5-(Trifluoromethyl)pyridin-2-yl)pyrrolo[1,2-a]pyrazin-3-yl)methanamine hydrochloride (X-1475A7). To a stirred solution of tert-butyl ((1-(5-(trifluoromethyl)pyridin-2-yl)pyrrolo[1,2-a]pyrazin-3-yl)methyl)carbamate (X-1475B1) (0.25 g, 0.63 mmol) in DCM (3 mL) was added 4 M HCl in dioxane (2 mL) at 0° C. under nitrogen and the resulting reaction mixture was stirred at room temperature for 1 h. Reaction mixture was concentrated under reduced pressure. Obtained crude was triturated with diethyl ether (2×10 mL), dried over reduced pressure, to afford (1-(5-(trifluoromethyl)pyridin-2-yl)pyrrolo[1,2-a]pyrazin-3-yl)methanamine hydrochloride (X-1475A7) (0.2 g, quantitative) as an off-white solid. MS: $[MH]^+$ 292.91.

N-((1-(5-(Trifluoromethyl)pyridin-2-yl)pyrrolo[1,2-a]pyrazin-3-yl)methyl)acrylamide (1-314). To a stirred solution of (1-(5-(trifluoromethyl)pyridin-2-yl)pyrrolo[1,2-a]pyrazin-3-yl)methanamine hydrochloride (X-1475A8) (0.2 g, 0.68 mmol) in DCM (2 mL) were added triethylamine (0.34 g, 3.42 mmol) and acrylic anhydride (0.10 g, 0.82 mmol) at 0° C. under nitrogen and the reaction mixture was stirred at room temperature for 1 h. The reaction mixture was diluted with water (20 mL) and was extracted with DCM (50 mL×2). Combined organic extracts were dried over anhydrous $Na_2SO_4$ and concentrated under reduced pressure. The crude product was purified by (C-18) silica gel column chromatography, using acetonitrile-water=0:1→4:6 as gradient, to afford N-((1-(5-(trifluoromethyl)pyridin-2-yl)pyrrolo[1,2-a]pyrazin-3-yl)methyl)acrylamide (I-314) (0.09 g, 42%) as an yellow solid. MS: $[MH]^+$ 346.9. $^1H$ NMR (400 MHz, DMSO-$d_6$) δ 9.19 (s, 1H), 8.73-8.70 (t, J=5.6 Hz, 1H), 8.65-8.63 (d, J=8.4 Hz, 1H), 8.42-8.40 (dd, J=8.0, 2.0 Hz, 1H), 8.36 (s, 1H), 7.94-7.93 (m, 1H), 7.70-7.69 (d, J=4.4 Hz, 1H), 7.03-7.01 (m, 1H), 6.37-6.30 (m, 1H), 6.17-6.12 (dd, J=17.2, 2.4 Hz, 1H), 5.65-5.62 (dd, J=10.4, 2.4 Hz, 1H), 4.47-4.45 (d, J=5.6 Hz, 2H).

Example 1.224. Synthesis of N-((5-(4-(trifluoromethyl)phenyl)imidazo[1,2-c]pyrimidin-7-yl)methyl)acrylamide (I-315)

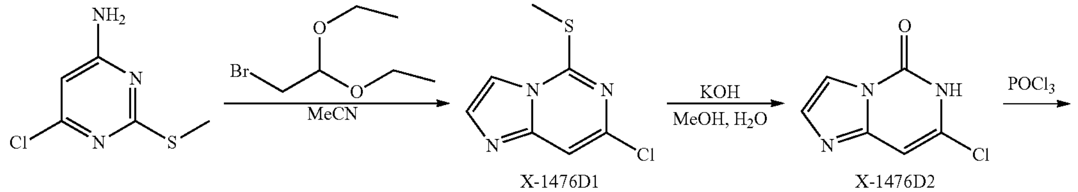

X-1476D1

X-1476D2

-continued

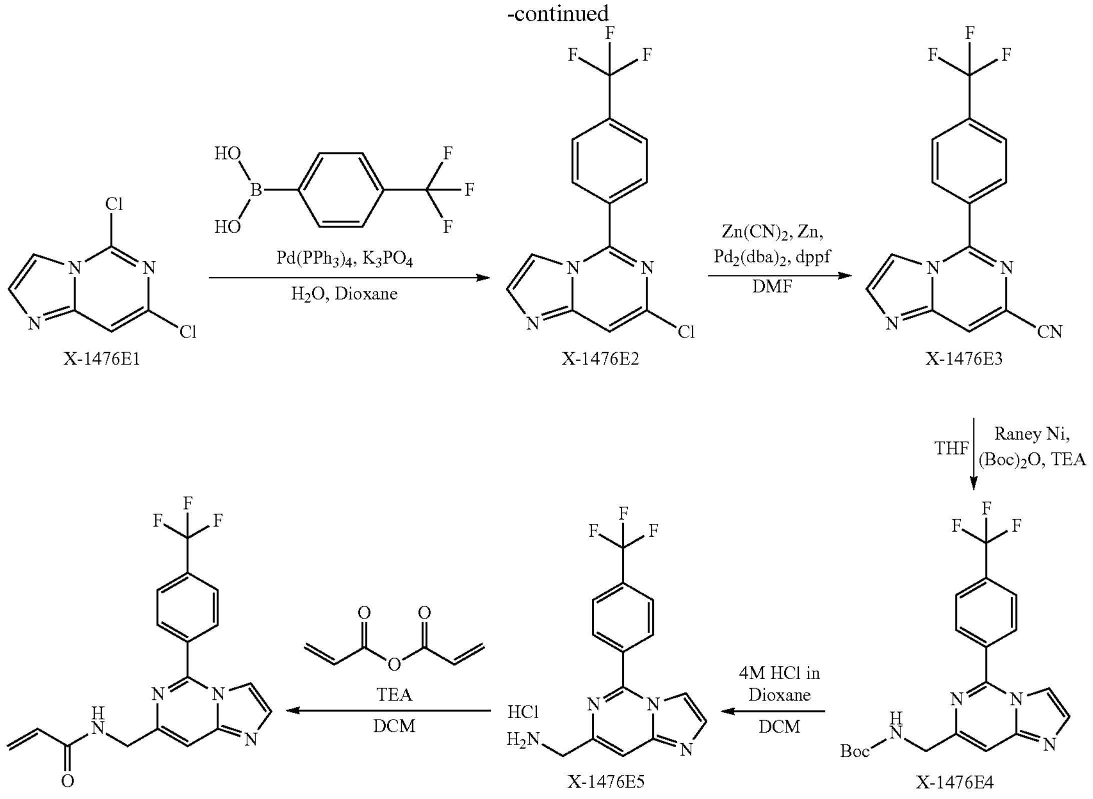

X-1476E1 X-1476E2 X-1476E3 X-1476E4 X-1476E5 I-315

7-Chloro-5-(methylthio)imidazo[1,2-c]pyrimidine (X-1476D1). To a stirred solution of 6-chloro-2-(methylthio)pyrimidin-4-amine (0.75 g, 4.26 mmol) in MeCN (10 mL) was added 2-bromo-1,1-diethoxyethane (6.64 g, 34.09 mmol) at room temperature under nitrogen and the resulting mixture was stirred at 120° C. for 16 h. After completion of reaction, reaction mixture was cooled to room temperature and was diluted with water (500 mL) and extracted with ethyl acetate (500 mL×3), dried over anhydrous $Na_2SO_4$ and concentrated under reduce pressure. Obtained crude was combined with an identical prepared 23 more batch (0.75 g) and was purified by silica gel column chromatography, using ethyl acetate-hexane=0:1→1:4 as a gradient, to afford 7-chloro-5-(methylthio)imidazo[1,2-c]pyrimidine (X-1476D1) (9.5 g, 46%) as an off-white solid. MS: $[MH]^+$ 199.7/$[MH+2]^+$ 201.6.

7-Chloroimidazo[1,2-c]pyrimidin-5(6H)-one (X-1476D2). To a stirred solution of 7-chloro-5-(methylthio)imidazo[1,2-c]pyrimidine (X-1476D1) (3.0 g, 15.07 mmol) in MeOH (12 mL) was added dropwise an aqueous solution of KOH (3.79 g, 67.89 mmol) at room temperature under nitrogen and the resulting mixture was stirred at 100° C. for 2 h. After completion of reaction, reaction mixture was cooled to room temperature and was combined with an identically prepared two more batches (3.0 g) and concentrate under reduced pressure. The reaction mixture was acidified (pH~2-3) with a dil. HCl and the resulting precipitate was collected by filtration. Crude residue was washed with cold water until the pH of the filtrate became neutral (pH~6-7) and concentrated under reduce pressure, to afford 7-chloroimidazo[1,2-c]pyrimidin-5(6H)-one (X-1476D2) (6.0 g, 78%) as an off-white solid. MS: $[MH]^+$ 170.0/$[MH+2]^+$171.9.

5,7-Dichloroimidazo[1,2-c]pyrimidine (X-1476E1). 7-chloroimidazo[1,2-c]pyrimidin-5(6H)-one (X-1476D2) (1.5 g, 8.87 mmol) and $POCl_3$ (15 mL) were mixed at 0° C. under nitrogen and the resulting reaction mixture was heated at 130° C. for 16 h. After completion of reaction, reaction mixture was cooled to room temperature and was combined with an identically prepared one more batch (1.5 g) and the reaction mixture was basified (pH~8-9) with an aqueous solution of saturated $NaHCO_3$ and was extracted with ethyl acetate (500 mL×3), dried over anhydrous $Na_2SO_4$ and concentrated under reduce pressure. Solid residue obtained was triturated by using n-pentane and diethyl ether, to afford 5,7-dichloroimidazo[1,2-c]pyrimidine (X-1476E1) (2.0 g, 60%) as an off-white solid. MS: $[MH]^+$ 188.2/$[MH+2]^+$ 190.2.

7-Chloro-5-(4-(trifluoromethyl)phenyl)imidazo[1,2-c]pyrimidine (X-1476E2). To a stirred solution of 5,7-dichloroimidazo[1,2-c]pyrimidine (X-1476E1) (0.8 g, 4.27 mmol) in a mixture of 1,4-dioxane:water (8:2, 10 mL) were added (4-(trifluoromethyl)phenyl)boronic acid (1.2 g, 6.41 mmol) and Potassium phosphate (2.7 g, 12.83 mmol) at room temperature under nitrogen. The reaction mixture was degassed (purging with nitrogen) for 20 min followed by addition of $Pd(PPh_3)_4$ (0.24 g, 0.21 mmol) and the reaction mixture was heated at 90° C. for 2 h. After completion of reaction, reaction mixture was cooled to room temperature, diluted with water (100 mL) and was extracted with ethyl acetate (100 mL×3). The combined organic extracts were dried over anhydrous $Na_2SO_4$ and concentrated under reduce pressure. Obtained crude was combined with an identical prepared one more batch (0.7 g) and was purified by silica gel column chromatography using, ethyl acetate-hexane=0:1→3:7 as gradient, to afford 7-chloro-5-(4-(trifluoromethyl)phenyl)imidazo[1,2-c]pyrimidine (X-1476E2) (0.6 g, 25%) as an off-white solid. MS: $[MH]^+$ 298.2/$[MH]^{+}$300.2.

5-(4-(Trifluoromethyl)phenyl)imidazo[1,2-c]pyrimidine-7-carbonitrile (X-1476E3). To a stirred solution of 7-chloro-5-(4-(trifluoromethyl)phenyl)imidazo[1,2-c]pyrimidine (X-1476E2) (0.3 g, 1.01 mmol) in a DMF (3 mL) were added zinc cyanide (0.189 g, 1.61 mmol) and Zn dust (0.019 g, 0.30 mmol) at room temperature under nitrogen. The reaction mixture was degassed (purging with nitrogen) for 20 min followed by addition of dppf (0.055 g, 0.10 mmol) and $Pd_2(dba)_3$ (0.092 g, 0.10 mmol) and the reaction mixture was heated at 130° C. for 1 h under microwave irradiation. After completion of reaction, reaction mixture was cooled to room temperature, diluted with water (100 mL) and was extracted with ethyl acetate (100 mL×3). The combined organic extracts were dried over anhydrous $Na_2SO_4$ and concentrated under reduce pressure. Obtained crude was combined with an identical prepared one more batch (0.3 g) and was purified by silica gel column chromatography using, using ethyl acetate-hexane=0:1→2:8 as gradient, to afford 5-(4-(trifluoromethyl)phenyl)imidazo[1,2-c]pyrimidine-7-carbonitrile (X-1476E3) (0.25 g, 43%) as an off-white solid. MS: $[MH]^+$289.2.

tert-Butyl ((5-(4-(trifluoromethyl)phenyl)imidazo[1,2-c]pyrimidin-7-yl)methyl)carbamate (X-1476E4). To a stirred solution of 5-(4-(trifluoromethyl)phenyl)imidazo[1,2-c]pyrimidine-7-carbonitrile (X-1476E3) (0.25 g, 0.86 mmol) in THE (5 mL) were added TEA (0.17 g, 1.73 mmol), Raney nickel (0.15 g) and Boc anhydride (0.227 g, 1.04 mmol) at room temperature and resulting mixture was hydrogenated in Parr Autoclave at room temperature under 200 psi for 2 h. After completion od reaction, reaction mixture was filtered over a celite bed, the bed was washed with MeOH (100 mL) and collected filtrate was concentrated under reduced pressure. Obtained crude was purified by silica gel column chromatography, using methanol-dichloromethane=0:1→4 0.5:9.5 as gradient, to afford tert-Butyl ((5-(4-(trifluoromethyl)phenyl)imidazo[1,2-c]pyrimidin-7-yl)methyl)carbamate (X-1476E4) (0.120 g, 35%) as a brown solid. MS: $[MH]^+$ :393.46.

(5-(4-(Trifluoromethyl)phenyl)imidazo[1,2-c]pyrimidin-7-yl)methanamine hydrochloride (X-1476E5). To a stirred solution of tert-butyl ((5-(4-(trifluoromethyl)phenyl)imidazo[1,2-c]pyrimidin-7-yl)methyl)carbamate (X-1476E4) (0.12 g, 0.30 mmol) in DCM (1 mL) was added 4 M HCl in Dioxane (0.5 mL) at 0° C. under nitrogen and the resulting reaction mixture was stirred at room temperature for 2 h. After completion of reaction, reaction mixture was concentrated under reduced pressure. Obtained crude was triturated with diethyl ether (2×10 mL), dried under reduced pressure, to afford (5-(4-(trifluoromethyl)phenyl)imidazo[1,2-c]pyrimidin-7-yl)methanamine hydrochloride (X-1476E5) (0.09 g, quant; crude) as an off-white solid. MS: $[MH]^+$ 293.29.

N-((5-(4-(trifluoromethyl)phenyl)imidazo[1,2-c]pyrimidin-7-yl)methyl)acrylamide (I-315). To a stirred solution of (5-(4-(trifluoromethyl)phenyl)imidazo[1,2-c]pyrimidin-7-yl)methanamine hydrochloride (X-1476E5) (0.09 g, 0.308 mmol) in DCM (4 mL) were added triethylamine (0.12 g, 1.23 mmol) and acrylic anhydride (0.046 g, 0.36 mmol) at 0° C. under nitrogen and the reaction mixture was stirred at room temperature for 30 min. After completion of reaction, reaction mixture was diluted with water (20 mL) and was extracted with DCM (50 mL×2). Combined organic extracts were dried over anhydrous $Na_2SO_4$ and concentrated under reduced pressure. The crude product was purified by (C-18) silica gel column chromatography, using acetonitrile-water=0:1→4:6 as gradient, to afford N-((5-(4-(trifluoromethyl)phenyl)imidazo[1,2-c]pyrimidin-7-yl)methyl)acryl amide (I-315) (0.035 g, 33%) as an off-white solid. MS: $[MH]^+$ 347.37. $^1H$ NMR (400 MHz, DMSO-$d_6$) δ 8.80-8.77 (t, J=5.6 Hz, 1H), 8.19-8.17 (d, J=8.0 Hz, 2H), 8.02-8.00 (m, 3H), 7.70-7.70 (d, J=1.6 Hz, 1H), 7.42 (s, 1H), 6.41-6.34 (m, 1H), 6.19-6.14 (dd, J=16.8, 2.0 Hz, 1H), 5.69-5.66 (dd, J=10.0, 2.0 Hz, 1H), 4.50-4.49 (d, J=5.6 Hz, 2H).

Example 1.225. Synthesis of N-((4-(4-(trifluoromethyl)phenyl)pyrazolo[1,5-a]pyrazin-6-yl)methyl) acrylamide (I-316)

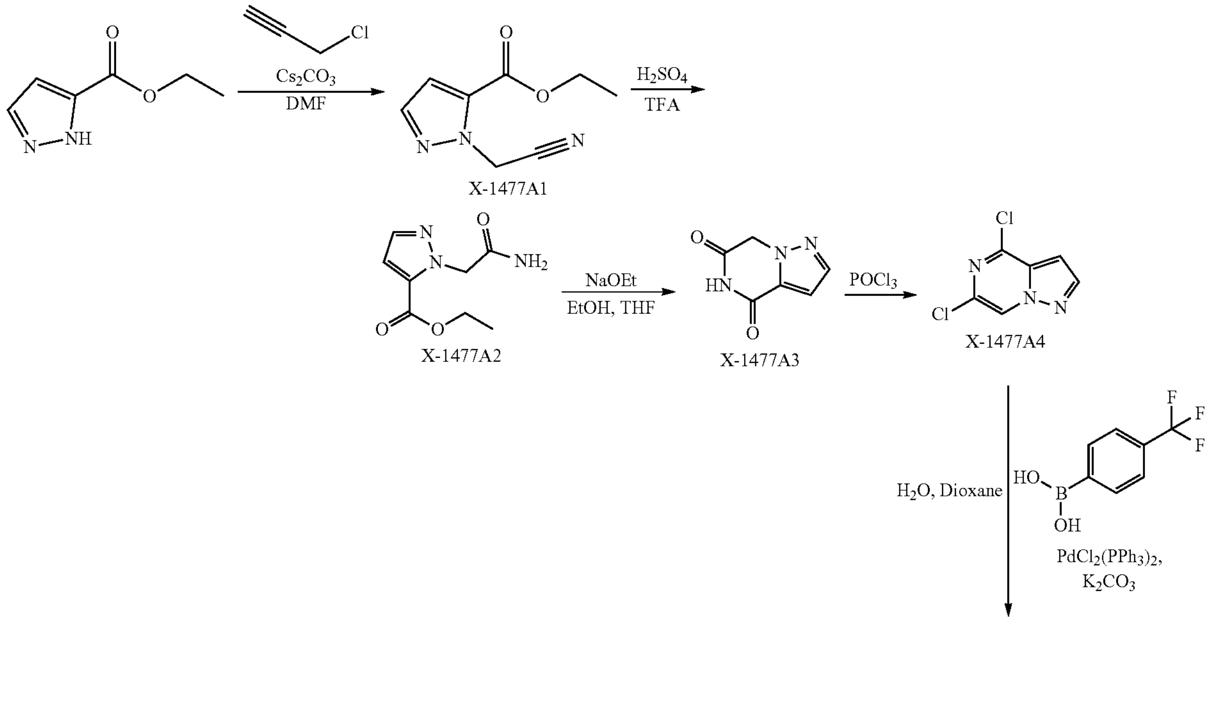

X-1477A1
X-1477A2
X-1477A3
X-1477A4

-continued

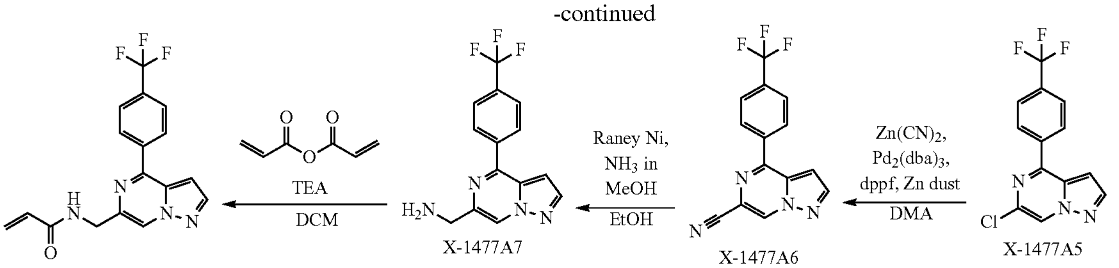

I-316

Ethyl 1-(cyanomethyl)-1H-pyrazole-5-carboxylate (X-1477A1). To a stirred solution of ethyl 1H-pyrazole-5-carboxylate (30.00 g, 214.22 mmol) in DMF (100 mL) were added $Cs_2CO_3$ (24.12 g, 321.42 mmol) and 2-chloroacetonitrile (208.92 g, 642.53 mmol) at 0° C. under nitrogen and the resulting mixture was stirred at room temperature for 16 h. The reaction mixture was diluted with water (2000 mL) and was extracted with ethyl acetate (3000 mL×3). The combined organic extracts were washed with brine (2000 mL), dried over anhydrous $Na_2SO_4$ and concentrated under reduce pressure. The crude product was purified by silica gel column chromatography, using ethyl acetate-Hexane=0:1→4:6 as gradient, to afford ethyl 1-(cyanomethyl)-1H-pyrazole-5-carboxylate (X-1477A1) (8.0 g, 21%) as a colorless liquid. MS: $[MH]^+$ 180.02.

Ethyl 1-(2-amino-2-oxoethyl)-1H-pyrazole-5-carboxylate (X-1477A2). To a stirred solution of ethyl 1-(cyanomethyl)-1H-pyrazole-5-carboxylate (X-1477A1) (8.0 g, 44.69 mmol) in Triflouroacetic acid (25.47 g, 223.46 mmol) was added concentrated $H_2SO_4$ (43.79 g, 446.92 mmol) at 0° C. under nitrogen and the resulting mixture was stirred at room temperature for 16 h. The reaction mixture was basified (pH~8-9) with an aqueous solution of saturated $NaHCO_3$ and was extracted with ethyl acetate (1000 mL×3), dried over anhydrous $Na_2SO_4$ and concentrated under reduce pressure, to afford ethyl 1-(2-amino-2-oxoethyl)-1H-pyrazole-5-carboxylate (X-1477A2) (8.0 g, 90%) as a white solid. MS: $[MH]^+$ 198.05.

Pyrazolo[1,5-a]pyrazine-4,6(5H,7H)-dione (X-1477A3). To a stirred solution of ethyl 1-(2-amino-2-oxoethyl)-1H-pyrazole-5-carboxylate (X-1477A2) (8.0 g, 40.60 mmol) in ethanol-THF (35:17 mL) was added concentrated sodium ethoxide (8.28 g, 121.82 mmol) at 0° C. under nitrogen and the resulting mixture was stirred at 70° C. for 1 h. The reaction mixture was acidified (pH~2-3) with a dil. HCl and the resulting precipitate was collected by filtration. Crude residue was washed with cold water until the pH of the filtrate became neutral (pH~6-7) and concentrated under reduce pressure to afford pyrazolo[1,5-a]pyrazine-4,6(5H,7H)-dione (X-1477A3) (8.0 g, quantitative) as a white solid. MS: $[MH]^+$ 152.37.

4,6-Dichloropyrazolo[1,5-a]pyrazine (X-1477A4). A stirred solution of pyrazolo[1,5-a]pyrazine-4,6(5H,7H)-dione (X-1477A3) (8.0 g, 52.98 mmol) in $POCl_3$ at 0° C. under nitrogen and the resulting mixture was heated at 150° C. for 16 h. After cooling to room temperature, the reaction mixture was basified (pH~8-9) with an aqueous solution of saturated $NaHCO_3$ and was extracted with ethyl acetate (500 mL×3), dried over anhydrous $Na_2SO_4$ and concentrated under reduce pressure, to afford 4,6-dichloropyrazolo[1,5-a]pyrazine (X-1477A4) (0.80 g, 8%) as an off-white solid. MS: $[MH]^+$ 188.3/$[MH+2]^{30}$ 190.3.

6-Chloro-4-(4-(trifluoromethyl)phenyl)pyrazolo[1,5-a]pyrazine (X-1477A5). To a stirred solution of 4,6-dichloropyrazolo[1,5-a]pyrazine (X-1477A4) (0.75 g, 4.27 mmol) in a mixture of 1,4-dioxane-water (4:1, 10 mL) were added (4-(trifluoromethyl)phenyl)boronic acid (0.97 g, 5.13 mmol) and potassium carbonate (1.77 g, 12.83 mmol) at room temperature under nitrogen. The reaction mixture was degassed (purging with nitrogen) for 20 min followed by addition of $PdCl_2$ $(PPh_3)_2$ (0.24 g, 0.34 mmol) and the reaction mixture was heated at 110° C. for 1 h. The reaction mixture was cooled to room temperature, diluted with water (30 mL) and was extracted with ethyl acetate (30 mL×3). The combined organic extracts were dried over anhydrous $Na_2SO_4$ and concentrated under reduce pressure. The crude product was purified by silica gel column chromatography, using ethyl acetate-hexane=0:1→0.3:9.7 as gradient, to afford 6-chloro-4-(4-(trifluoromethyl)phenyl)pyrazolo[1,5-a]pyrazine (X-1477A5) (0.75 g, 63%) as an off-white solid. MS: $[MH]^+$ 298.3

4-(4-(Trifluoromethyl)phenyl)pyrazolo[1,5-a]pyrazine-6-carbonitrile (X-1477A6). To a stirred solution of 6-chloro-4-(4-(trifluoromethyl)phenyl)pyrazolo[1,5-a]pyrazine (X-1477A5) (0.750 g, 2.35 mmol) in a DMA (10 mL) were added zinc cyanide (0.550 g, 4.71 mmol) and Zn dust (0.310 g, 4.71 mmol) at room temperature under nitrogen. The reaction mixture was degassed (purging with nitrogen) for 20 min followed by addition of dppf (0.11 g, 0.18 mmol) and $Pd_2$ $(dba)_3$ (0.17 g, 0.18 mmol) and the reaction mixture was heated at 170° C. for 30 min under microwave irradiation. The reaction mixture was cooled to room temperature, diluted with water (100 mL) and was extracted with ethyl acetate (100 mL×3). The combined organic extracts were dried over anhydrous $Na_2SO_4$ and concentrated under reduce pressure. The crude product was purified by silica gel column chromatography, using ethyl acetate-Hexane=0:1-2:8 as gradient, to afford 4-(4-(trifluoromethyl)phenyl)pyrazolo[1,5-a]pyrazine-6-carbonitrile (X-1477A6) (0.3 g, 41%) as a yellow solid. MS: $[MH]^+$ 288.9

(4-(4-(Trifluoromethyl)phenyl)pyrazolo[1,5-a]pyrazin-6-yl)methanamine (X-1477A7). To a stirred solution of 4-(4-(trifluoromethyl)phenyl)pyrazolo[1,5-a]pyrazine-6-carbonitrile (X-1477A6) (0.300 g, 0.87 mmol) in THF (10 mL) were added Raney Nickel (0.25 g) and ammonia in MeOH (1 mL) at room temperature and the resulting mixture was hydrogenated in Parr Autoclave at room temperature under 200 psi for 16 h. Reaction mixture was cooled to room temperature, filtered over a celite bed, washed the bed with MeOH (100 mL) and collected filtrates were concentrated under reduced pressure. The resulting crude was purified by reverse phase (C-18) silica gel column chromatography using acetonitrile-water=0:144:6 as gradient, to afford (4-(4-(trifluoromethyl)

phenyl)pyrazolo[1,5-a]pyrazin-6-yl)methanamine (X-1477A7) (0.08 g, 26%) as a white solid. MS: $[MH]^+$ 292.9.

N-((4-(4-(trifluoromethyl)phenyl)pyrazolo[1,5-a]pyrazin-6-yl)methyl)acrylamide (I-316). To a stirred solution of (4-(4-(trifluoromethyl)phenyl)pyrazolo[1,5-a]pyrazin-6-yl)methanamine (X-1477A7) (0.080 g, 0.24 mmol) in DCM (10 mL) were added triethylamine (0.070 g, 0.72 mmol) and Acrylic anhydride (0.040 g, 0.29 mmol) at 0° C. and reaction mixture was stirred at rt for 30 min. The reaction mixture was diluted with aqueous $NaHCO_3$ (10 mL) and was extracted by ethyl acetate (30 mL×3). The combined organic extracts were dried over anhydrous $Na_2SO_4$ and concentrated under reduce pressure. The crude product was purified by (C-18) silica gel column chromatography, using acetonitrile-water=0:1→4:6 as gradient, to afford N-((4-(4-(trifluoromethyl)phenyl)pyrazolo[1,5-a]pyrazin-6-yl)methyl)acrylamide (I-316) (0.07 g, 77%) as a white solid. $^1H$ NMR (400 MHz, DMSO-$d_6$) δ 8.76-8.74 (t, J=5.2 Hz, 1H), 8.71 (s, 1H), 8.30-8.27 (m, 3H), 7.97-7.95 (d, J=8.4 Hz, 2H), 7.23-7.22 (d, J=2.0 Hz, 1H), 6.36-6.29 (m, 1H), 6.16-6.12 (dd, J=16.8, 2.0 Hz, 1H), 5.65-5.62 (dd, J=10.0, 2.0 Hz, 1H), 4.55-4.54 (d, J=5.6 Hz, 2H). MS: $[MH]^+$ 347.1.

Example 1.226. Synthesis of N-((8-(4-(trifluoromethyl)phenyl)-[1,2,4]triazolo[4,3-a]pyrazin-6-yl)methyl)acrylamide (I-317)

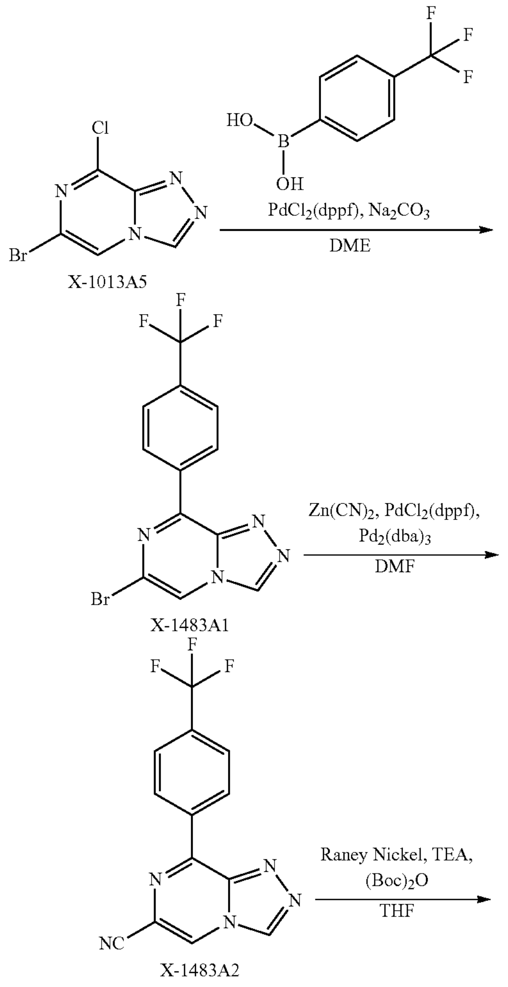

X-1013A5

X-1483A1

X-1483A2

-continued

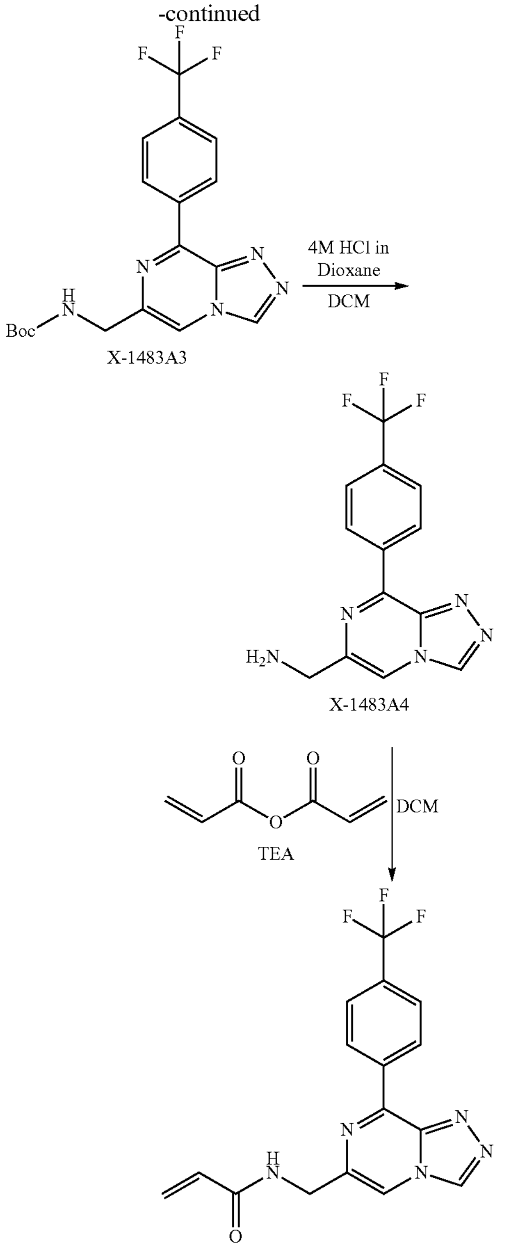

X-1483A3

X-1483A4

I-317

6-Bromo-8-(4-(trifluoromethyl)phenyl)-[1,2,4]triazolo[4,3-a]pyrazine (X-1483A1). To a stirred solution of 6-bromo-8-chloro-[1,2,4]triazolo[4,3-a]pyrazine (X-1013A5) (1.0 g, 4.31 mmol) in DME (7 mL) were added (4-(trifluoromethyl)phenyl)boronic acid (0.97 g, 5.17 mmol) and sodium carbonate (1.37 g, 12.93 mmol) at room temperature under nitrogen. The reaction mixture was degassed (purging with nitrogen) for 20 min followed by addition of $PdCl_2$(dppf) (0.31 g, 0.43 mmol) and the reaction mixture was heated at 60° C. for 1 h. The reaction mixture was cooled to room temperature, diluted with water (400 mL) and was extracted with ethyl acetate (300 mL×2). The combined organic extracts were dried over anhydrous $Na_2SO_4$ and concentrated under reduce pressure. Isolated crude was combined with an identical prepared one more batch (1.0 g) and the combined crude were purified by silica gel column chromatography, using ethyl acetate-hexane=0:1→4:6 as gradient, to afford 6-bromo-8-(4-(trifluoromethyl)phenyl)-[1,2,4]triazolo[4,3-a]pyrazine (X-1483A1) (0.8 g, 27%) as an Off-white solid. MS: $[MH]^+$ 342.7/$[MH+2]^+$344.7.

8-(4-(Brifluoromethyl)phenyl)-[1,2,4]triazolo[4,3-a]pyrazine-6-carbonitrile (X-1483A2). To a stirred solution of 6-bromo-8-(4-(trifluoromethyl)phenyl)-[1,2,4]triazolo[4,3-a]pyrazine (X-1483A1) (0.8 g, 2.33 mmol) in DMF (7 mL) was added Copper cyanide (0.62 g, 7.01 mmol) and the reaction mixture was heated at 170° C. under microwave irradiation for 1 h. The reaction mixture was cooled to room temperature, diluted with water (200 mL) and was extracted with ethyl acetate (300 mL×2). The combined organic extracts were dried over anhydrous $Na_2SO_4$ and concentrated under reduce pressure, the crude was purified by silica gel column chromatography, using ethyl acetate-hexane=0:1→6:4 as gradient, to afford 8-(4-(trifluoromethyl)phenyl)-[1,2,4]triazolo[4,3-a]pyrazine-6-carbonitrile (X-1483A2) (0.23 g, 29%) as an Off-white solid. MS: $[MH]^+$ 290.6.

Tert-butyl((8-(4-(trifluoromethyl)phenyl)-[1,2,4]triazolo[4,3-a]pyrazin-6-yl)methyl)carbamate (X-1483A3). To a stirred solution of 8-(4-(trifluoromethyl)phenyl)-[1,2,4]triazolo[4,3-a]pyrazine-6-carbonitrile (X-1483A2) (0.230 g, 0.79 mmol) in THE (8 mL) were added TEA (0.540 g, 3.97 mmol), Raney nickel (0.25 g) and Boc anhydride (0.33 g, 1.59 mmol) at room temperature and the resulting mixture was hydrogenated in Parr Autoclave at room temperature under 200 psi for 16 h. Reaction mixture was filtered over a celite bed, washed the bed with MeOH (100 mL) and collected filtrates were concentrated under reduced pressure and reaction mixture was diluted with water (100 mL) and was extracted with ethyl acetate (100 mL×2). The combined organic extracts were dried over anhydrous $Na_2SO_4$ and concentrated under reduce pressure, to afford tert-butyl ((8-(4-(trifluoromethyl)phenyl)-[1,2,4]triazolo[4,3-a]pyrazin-6-yl)methyl)carbamate (X-1483A3) (0.150 g, 48%) as a brown sticky solid. Which was used to next step without further purification. MS: $[MH]^+$ 393.9.

(8-(4-(Trifluoromethyl)phenyl)-[1,2,4]triazolo[4,3-a]pyrazin-6-yl)methanamine hydrochloride (X-1483A4). To a stirred solution of tert-butyl ((8-(4-(trifluoromethyl)phenyl)-[1,2,4]triazolo[4,3-a]pyrazin-6-yl)methyl)carbamate (X-1483A3) (0.15 g, 0.38 mmol) in DCM (4 mL) was added 4 M HCl in Dioxane (1 mL) at 0° C. under nitrogen and the resulting reaction mixture was stirred at room temperature for 2 h. Reaction mixture was concentrated under reduced pressure. Obtained crude was triturated with diethyl ether (2×10 mL), dried over reduced pressure, to afford (8-(4-(trifluoromethyl)phenyl)-[1,2,4]triazolo[4,3-a]pyrazin-6-yl)methanamine hydrochloride (X-1483A4) (0.09 g, 81%) as a brown sticky solid. MS: $[MH]^+$ 293.9

N-((8-(4-(trifluoromethyl)phenyl)-[1,2,4]triazolo[4,3-a]pyrazin-6-yl)methyl)acrylamide (1-317). To a stirred solution of (8-(4-(trifluoromethyl)phenyl)-[1,2,4]triazolo[4,3-a]pyrazin-6-yl)methanamine hydrochloride (X-1483A4) (0.090 g, 0.30 mmol) in DCM (5 mL) were added acrylic anhydride (0.050 g, 0.46 mmol) and triethylamine (0.150 g, 1.53 mmol) at 0° C. under nitrogen and the reaction mixture was stirred at room temperature for 1 h. The reaction mixture was diluted with water (20 mL) and was extracted with DCM (50 mL×2). Combined organic extracts were dried over anhydrous $Na_2SO_4$ and concentrated under reduced pressure. The resulting crude was purified by preparative HPLC, using ACN: 0.1% formic acid in water to afford N-((8-(4-(trifluoromethyl)phenyl)-[1,2,4]triazolo[4,3-a]pyrazin-6-yl)methyl)acrylamide (I-317) (0.019 g, 18%) as an yellow solid. MS: $[MH]^+$ 347.9. $^1H$ NMR (400 MHz, DMSO-$d_6$) δ 9.55 (s, 1H), 9.02-9.00 (d, J=8.0 Hz, 2H), 8.86 (br. s, 1H), 8.54 (s, 1H), 8.03-8.01 (d, J=8.0 Hz, 2H), 6.38-6.31 (m, 1H), 6.19-6.15 (d, J=16.8 Hz, 1H), 5.69-5.66 (d, J=10.4 Hz, 1H), 4.57-4.56 (d, J=5.6 Hz, 2H).

Example 1.227. Synthesis of N-((6-Fluoro-1-(4-(trifluoromethyl)phenyl)pyrrolo[1,2-a]pyrazin-3-yl)methyl)acrylamide (I-318)

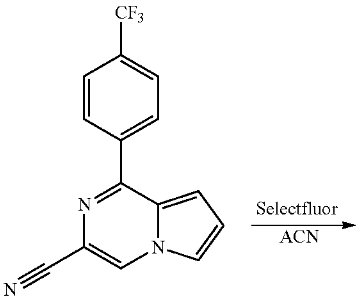

X-1490A6

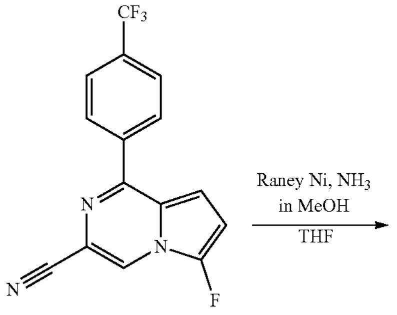

X-1488A1

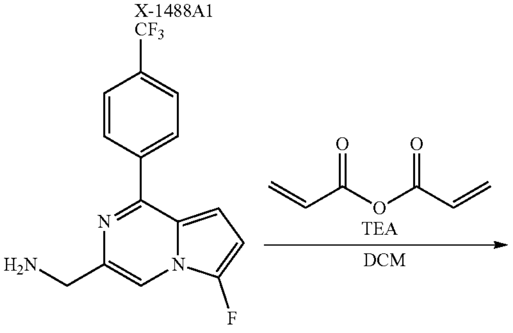

X-1488A2

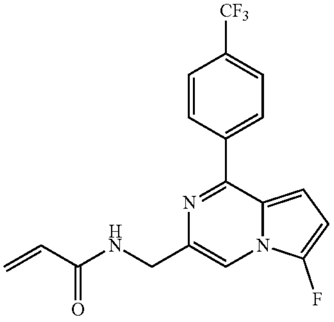

I-318

6-Fluoro-1-(4-(trifluoromethyl)phenyl)pyrrolo[1,2-a]pyrazine-3-carbonitrile (X-1488A1). To a stirred solution 8-(4-(trifluoromethyl)phenyl)imidazo[1,2-a]pyrazine-6-carbonitrile (X-1269A3) (0.500 g, 1.74 mmol) in ACN (5 mL) was added select flour (0.67 g, 1.91 mmol) at 0° C. portion wise under nitrogen. The reaction mixture was stirred at room temperature for 16 h. Reaction mixture dilute with water (100 mL) and was extracted with ethyl acetate (100 mL×3), dried over anhydrous $Na_2SO_4$ and concentrated under reduce pressure. Isolated crude was combined with an identical prepared one more batch (0.5 g) and the combined crude were purified by silica gel column chromatography using ethyl acetate-hexane=0:1→1:9 as gradient, to afford 6-fluoro-1-(4-(trifluoromethyl)phenyl)pyrrolo[1,2-a]pyrazine-3-carbonitrile (X-1488A1) (0.280 g, 26%) as an off-white solid. MS: $[MH]^+$ 305.96.

(6-Fluoro-1-(4-(trifluoromethyl)phenyl)pyrrolo[1,2-a]pyrazin-3-yl)methanamine (X-1488A2). To a stirred solution of 3-fluoro-8-(4-(trifluoromethyl)phenyl)imidazo[1,2-a]pyrazine-6-carbonitrile (X-1479A1) (0.28 g, 0.91 mmol) in THF (2 mL) were added Raney Nickel (0.06 g) and ammonia in MeOH (0.1 mL) at room temperature and the resulting mixture was hydrogenated in Parr Autoclave at room temperature under 200 psi for 16 h, filtered over a celite bed, washed the bed with EtOAc (100 mL) and collected filtrates were concentrated under reduced pressure, to give (6-fluoro-1-(4-(trifluoromethyl)phenyl)pyrrolo[1,2-a]pyrazin-3-yl)methanamine (X-1488A2) (0.20 g, 71%) as a brown solid. MS: $[MH]^+$ 309.96.

N-((6-Fluoro-1-(4-(trifluoromethyl)phenyl)pyrrolo[1,2-a]pyrazin-3-yl)methyl)acrylamide (I-318). To a stirred solution of (6-fluoro-1-(4-(trifluoromethyl)phenyl)pyrrolo[1,2-a]pyrazin-3-yl)methanamine (X-1488A2) (0.200 g, 0.64 mmol) in DCM (3 mL) were added TEA (0.196 g, 1.94 mmol) followed by acrylic anhydride (0.097 g, 0.77 mmol) at 0° C. under nitrogen and the reaction mixture stirred for 30 min at room temperature. The reaction mixture was slowly poured into water (30 mL) and was extracted with DCM (30 mL×3), dried over anhydrous $Na_2SO_4$ and concentrated under reduced pressure. The resulting crude was purified by reverse phase (C-18) silica gel column chromatography using acetonitrile-water=0:1→5:5 as gradient, to afford N-((6-fluoro-1-(4-(trifluoromethyl)phenyl)pyrrolo[1,2-a]pyrazin-3-yl)methyl)acrylamide (I-318) (0.100 g, 43%) as an yellow solid. $^1H$ NMR (400 MHz, DMSO-$d_6$) δ 8.66-8.63 (t, J=5.2 Hz, 1H), 8.19-8.17 (d, J=8.0 Hz, 2H), 7.97 (s, 1H), 7.94-7.91 (d, J=8.4 Hz, 2H), 6.97-6.95 (t, J=4.4 Hz, 1H), 6.75-6.73 (t, J=4.0 Hz, 1H), 6.36-6.29 (m, 1H), 6.15-6.11 (dd, J=17.2, 2.0 Hz, 1H), 5.64-5.61 (dd, J=10.0 Hz, 2.0 Hz, 1H), 4.43-4.42 (d, J=5.2 Hz, 2H). MS: $[MH]^+$ 364.2.

Example 1.228. Synthesis of N-((1-(4-(trifluoromethyl)phenyl)pyrrolo[1,2-a]pyrazin-3-yl)methyl)acrylamide (I-319)

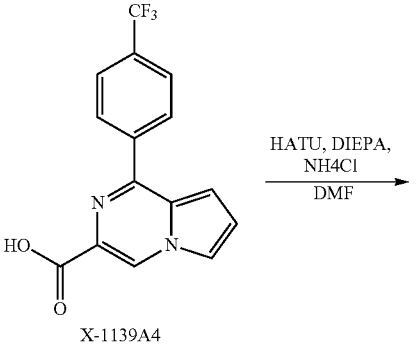

X-1139A4

-continued

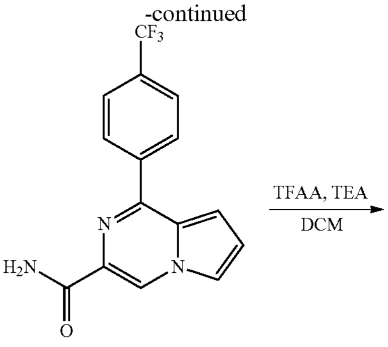

X-1490A5

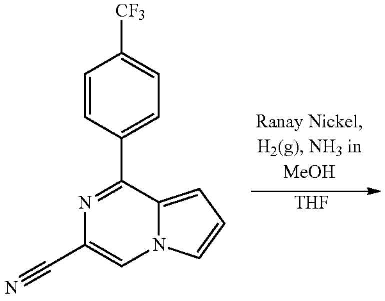

X-1490A6

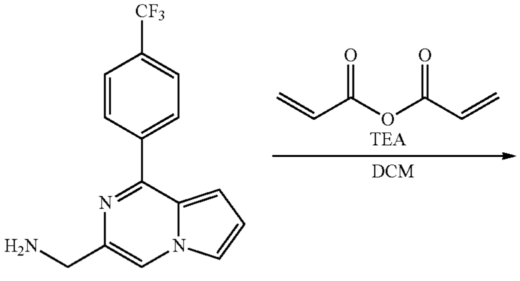

X-1490A7

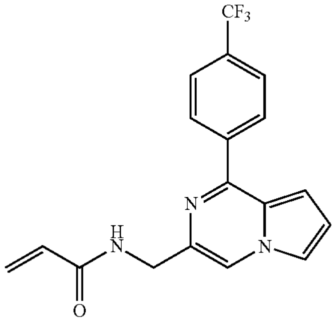

I-319

Compound X-1139A4 was synthesized as disclosed in Example 1.20.

1-(4-(Trifluoromethyl)phenyl)pyrrolo[1,2-a]pyrazine-3-carboxamide (X-1490A5). To a stirred solution of 1-(4-(trifluoromethyl)phenyl)pyrrolo[1,2-a]pyrazine-3-carboxylic acid (X-1139A4) (2.5 g, 8.16 mmol) in a DMF (20 mL) were added DIPEA (5.26 g, 40.84 mmol) and HATU (6.20 g, 16.33 mmol) at room temperature under nitrogen. After 5 min of stirring at the same temperature, was added ammonium chloride (1.29 g, 24.50 mmol) and reaction mixture was allowed to stirred at room temperature for 2 h. After completion of reaction, reaction mixture was slowly poured in cold water (150 mL), obtained precipitates were filtered and the residue was washed with water (100 mL), solid precipitate was dried under reduced pressure. Obtained solid was triturated using n-pentane, to afford 1-(4-(trifluoromethyl)phenyl)pyrrolo[1,2-a]pyrazine-3-carboxamide (X-1490A5) (2.2 g, 91%) as an off-white solid. MS: $[MH]^+$ 306.01.

1-(4-(Trifluoromethyl)phenyl)pyrrolo[1,2-a]pyrazine-3-carbonitrile (X-1490A6). To a stirred solution of 1-(4-(trifluoromethyl)phenyl)pyrrolo[1,2-a]pyrazine-3-carboxamide (X-1490A5) (0.500 g, 1.63 mmol) in DCM (5 mL) were added trimethylamine (0.49 g, 4.91 mmol) and TFAA (1.03 g, 4.91 mmol) at room temperature under nitrogen and reaction mixture was allowed to stirred at room temperature for 2 h. After completion of reaction, reaction mixture was lowly poured into water (200 mL), was extracted with ethyl acetate (200 mL×3), dried over anhydrous $Na_2SO_4$ and concentrated under reduced pressure. Obtained crude was combined with an identical prepared three more batches (0.5 g) and was purified by silica gel column chromatography, using ethyl acetate-hexane=0:1→2:8 as gradient, to afford 1-(4-(trifluoromethyl)phenyl)pyrrolo[1,2-a]pyrazine-3-carbonitrile (X-1490A6) (1.5 g, 80%) as an off-white solid. MS: [MH]+ 287.96.

(1-(4-(Trifluoromethyl)phenyl)pyrrolo[1,2-a]pyrazin-3-yl)methanamine (X-1490A7). To a stirred degassed (purging with nitrogen) solution of 1-(4-(trifluoromethyl)phenyl)pyrrolo[1,2-a]pyrazine-3-carbonitrile (X-1490A6) (0.3 g, 1.04 mmol) in THE (5 mL) were added Raney Nickel (0.068 g) and methanolic ammonia (7N; 0.1 mL) at room temperature and the resulting mixture was hydrogenated in Parr Autoclave at 60° C. under 200 psi for 3 h. Reaction mixture was cooled to room temperature, filtered over a celite bed, the bed washed with EtOAc (100 mL) and collected filtrates were concentrated under reduced pressure, to afford (1-(4-(trifluoromethyl)phenyl)pyrrolo[1,2-a]pyrazin-3-yl)methanamine (X-1490A7) (0.200 g, 66%) as a brown solid. MS: $[MH]^+$ 292.01.

N-((1-(4-(Trifluoromethyl)phenyl)pyrrolo[1,2-a]pyrazin-3-yl)methyl)acrylamide (I-319). To a stirred solution of (1-(4-(trifluoromethyl)phenyl)pyrrolo[1,2-a]pyrazin-3-yl)methanamine (X-1490A7) (0.2 g, 0.68 mmol) in DCM (3 mL) were added triethylamine (0.20 g, 2.06 mmol) and acrylic anhydride (0.10 g, 0.80 mmol) at 0° C. under nitrogen and the reaction mixture was stirred at room temperature for 30 min. Reaction mixture was diluted with water (100 mL) and was extracted with DCM (100 mL×2). Combined organic extracts were dried over anhydrous $Na_2SO_4$ and concentrated under reduced pressure. The crude product was purified by reverse phase (C-18) silica gel column chromatography, using acetonitrile-water=0:1→4:6 as gradient, to afford N-((1-(4-(trifluoromethyl)phenyl)pyrrolo[1,2-a]pyrazin-3-yl)methyl)acrylamide (I-319) (0.070 g, 30%) as a yellow solid. $^1H$ NMR (400 MHz, DMSO-$d_6$) δ 8.69-8.67 (t, J=5.6 Hz, 1H), 8.25 (s, 1H), 8.20-8.18 (d, J=8.0 Hz, 2H), 7.93-7.91 (m, 3H), 6.98-6.97 (d, J=1.6 Hz, 2H), 6.35-6.29 (m, 1H), 6.16-6.11 (dd, J=17.2, 2.0 Hz, 1H), 5.64-5.61 (dd, J=10.0, 2.0 Hz, 1H), 4.41-4.40 (d, J=5.6 Hz, 2H). MS: $[MH]^+$ 346.02.

Example 1.229. Synthesis of N-((1-(4-(trifluoromethyl)phenyl)pyrrolo[1,2-a]pyrazin-3-yl)methyl) methanesulfonamide (I-320)

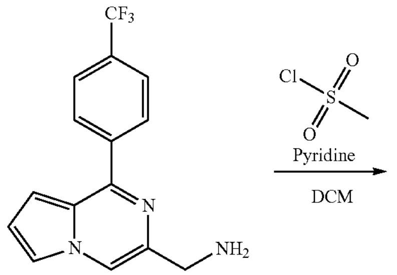

X-1490A7

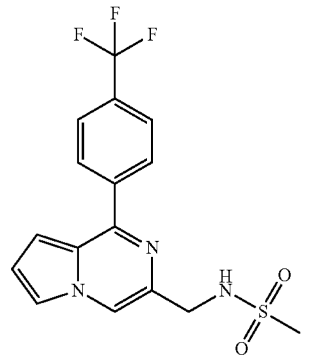

I-320

To a stirred (1-(4-(trifluoromethyl)phenyl)pyrrolo[1,2-a]pyrazin-3-yl)methanamine (X-1490A7) (0.450 g, 1.54 mmol) in DCM (10 mL) were added pyridine (0.244 g, 3.09 mmol) and mesyl chloride (0.176 g, 1.54 mmol) at 0° C. under nitrogen and the resulting mixture was stirred at room temperature for 1 h. The reaction mixture was slowly poured into ice-water (50 mL) and was extracted with ethyl acetate (50 mL×3). The combined organic extracts were washed with brine (100 mL), dried over anhydrous $Na_2SO_4$ and concentrated under reduced pressure. The residue obtained was purified by silica gel column chromatography, using ethyl acetate-hexane=0:1→1:9 as gradient, to afford N-((1-(4-(trifluoromethyl)phenyl)pyrrolo[1,2-a]pyrazin-3-yl)methyl)methanesulfonamide (I-320) (0.060 g, 10%) as a yellow solid. $^1H$ NMR (400 MHz, DMSO-$d_6$) δ 8.35 (s, 1H), 8.23-8.21 (d, J=8.4 Hz, 2H), 7.96-7.92 (m, 3H), 7.64 (brs, 1H), 7.007-7.003 (d, J=1.6 Hz, 2H), 4.25 (s, 2H), 2.99 (s, 3H). MS: $[MH]^+$ 370.3.

Example 1.230. Synthesis of 4-(4-(Tert-butyl)phenyl)-9-methylpyrrolo[1,2-a]quinoxaline-7-carboxylic acid (I-321)

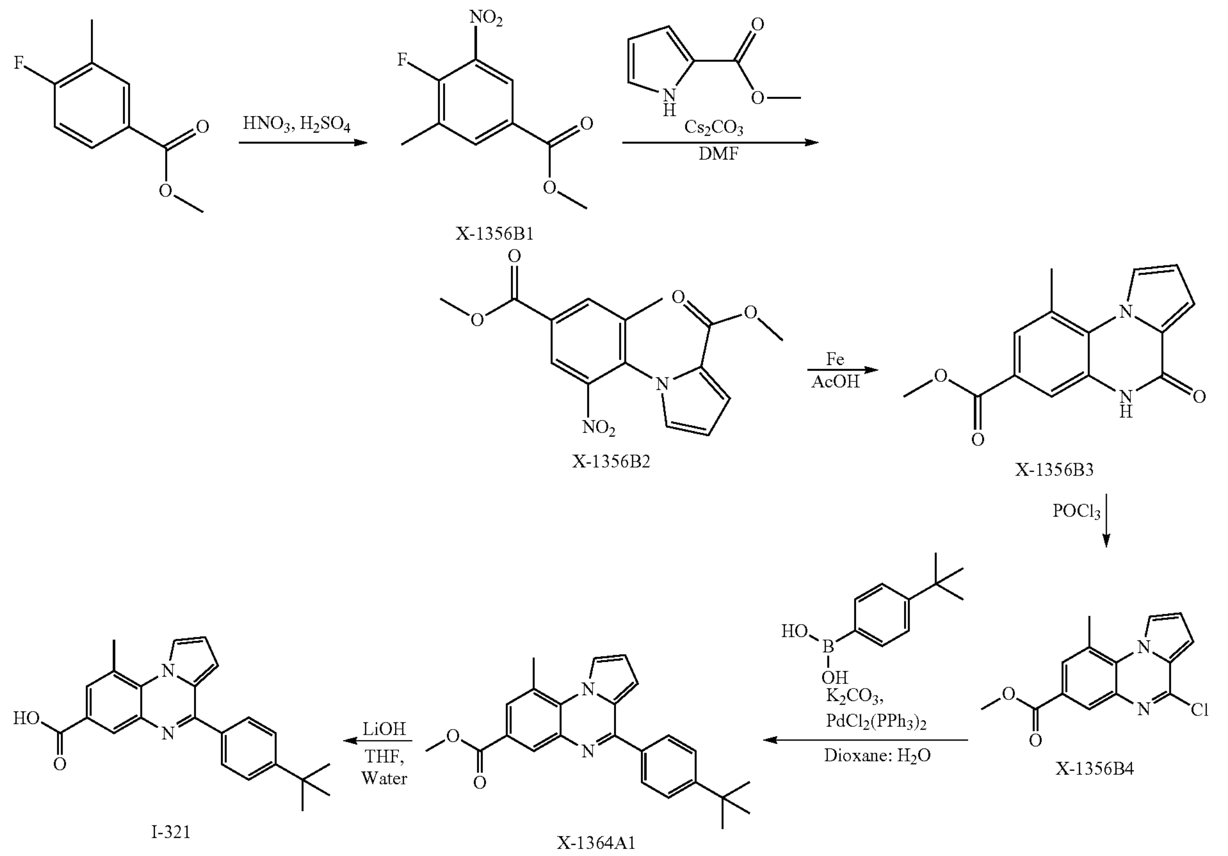

Methyl 4-fluoro-3-methyl-5-nitrobenzoate (X-1356B1). To a stirred solution of methyl 4-fluoro-3-methylbenzoate (10.0 g, 59.52 mmol) in $H_2SO_4$ (12.7 mL) was added nitrating mixture of $H_2SO_4$ (12.7 mL) in $HNO_3$ (10 mL) dropwise at 0° C. and the resulting mixture was stirred at room temperature for 30 min. Reaction mixture was poured into cold water (500 mL) obtained precipitates were filtered and the residue was washed with water (200 mL). Solid precipitate was dried under reduced pressure, to afford methyl 4-fluoro-3-methyl-5-nitrobenzoate (X-1356B1) (10.2 g, 80%). Crude material was carry forward to next step.

Methyl 1-(4-(methoxycarbonyl)-2-methyl-6-nitrophenyl)-1H-pyrrole-2-carboxylate (X-1356B2). To a stirred solution of methyl 4-fluoro-3-methyl-5-nitrobenzoate (X-1356B1) (6.00 g, 28.16 mmol) in DMF (50 mL) were added cesium carbonate (18.30 g, 56.30 mmol) and methyl 1H-pyrrole-2-carboxylate (3.50 g, 28.16 mmol) sequentially at room temperature under nitrogen and the resulting mixture was stirred at room temperature for 2 h. Reaction mixture was quenched with water (500 mL) and was extracted with ethyl acetate (600 mL×2). Combine organic extract was washed with brine (200 mL). Combined organic extracts were dried over anhydrous $Na_2SO_4$ and concentrated under reduce pressure. The crude product was purified by silica gel column chromatography, using EtOAc: Hexane=0:1-42:8 as gradient to afford methyl 1-(4-(methoxycarbonyl)-2-methyl-6-nitrophenyl)-1H-pyrrole-2-carboxylate (X-1356B2) (1.50 g, 16%) as a white solid. MS: [MH]+ :318.91.

Methyl 9-methyl-4-oxo-4,5-dihydropyrrolo[1,2-a]quinoxaline-7-carboxylate (X-1356B3). To a stirred solution of 1-(4-(methoxycarbonyl)-2-methyl-6-nitrophenyl)-1H-pyrrole-2-carboxylate (X-1356B2) (1.50 g, 4.71 mmol) in acetic acid (25 mL) was added Fe powder (1.3 g, 23.50 mmol) at 0° C. and reaction was allowed to stirred at room temperature for 16 h. Reaction mixture was filtered and quenched with $NaHCO_3$ solution (200 mL) and was extracted with IPA-chloroform (300 mL×2). Combined organic extracts were dried over anhydrous $Na_2SO_4$ and concentrated under reduced pressure, to afford methyl 9-methyl-4-oxo-4,5-dihydropyrrolo[1,2-a]quinoxaline-7-carboxylate (X-1356B3) (1.20 g, 99%) as a white solid. MS: [MH]+ :257.00.

Methyl 4-chloro-9-methylpyrrolo[1,2-a]quinoxaline-7-carboxylate (X-1356B4). A solution of 9-methyl-4-oxo-4,5-dihydropyrrolo[1,2-a]quinoxaline-7-carboxylate (X-1356B3) (0.7 g, 2.80 mmol) in $POCl_3$ (5 mL) was heated at 80° C. for 2 h. After cooling to room temperature, reaction mixture was slowly poured into ice-water (100 mL) and was extracted with ethyl acetate (250 mL×2). The Organic layer combined with identically prepared one batches of (0.5 g). Combined organic extracts were washed with sat. $NaHCO_3$, dried over anhydrous $Na_2SO_4$ and concentrated under reduce pressure, to afford methyl 4-chloro-9-methylpyrrolo[1,2-a]quinoxaline-7-carboxylate (X-1356B4) (0.76 g, 63%) as a white solid. MS: $[MH]^+$ 274.90/$[MH+2]^+$ 276.90.

Methyl 4-(4-(tert-butyl)phenyl)-9-methylpyrrolo[1,2-a]quinoxaline-7-carboxylate (X-1364A1). To a stirred solution of methyl 4-chloro-9-methylpyrrolo[1,2-a]quinoxaline-7-carboxylate (X-1356B4) (0.300 g, 1.09 mmol) in a mixture dioxane:$H_2O$ (6:1.5, 7.5 mL) were added (4-(tert-butyl)phenyl)boronic acid (0.253 g, 1.42 mmol) and potassium carbonate (0.377 g, 2.73 mmol) at room temperature. The reaction mixture was degassed (purging with nitrogen) for 10 min followed by addition of $PdCl_2(PPh_3)_2$ (0.076 g, 0.10 mmol) and the reaction mixture was heated at 90° C. for 1 h. The reaction mixture was cooled to room temperature, diluted with water (50 mL) and was extracted with ethyl acetate (250 mL×2). Combined organic extracts were dried over anhydrous $Na_2SO_4$ and concentrated under reduce pressure. The crude product was purified by silica gel column chromatography, using ethyl acetate-hexane=0: 1→1:9 as gradient, to afford methyl 4-(4-(tert-butyl)phenyl)-9-methylpyrrolo[1,2-a]quinoxaline-7-carboxylate (X-1364A1) (0.270 g, 66%) as an white solid. MS: $[MH]^+$ 373.1.

4-(4-(tert-Butyl)phenyl)-9-methylpyrrolo[1,2-a]quinoxaline-7-carboxylic acid (I-321). To a stirred solution of methyl 4-(4-(tert-butyl)phenyl)-9-methylpyrrolo[1,2-a]quinoxaline-7-carboxylate (X-1364A1) (0.150 g, 0.40 mmol) in a mixture of THF-water (4:1; 5 mL) was added lithium hydroxide monohydrate (0.033 g, 0.80 mmol) at room temperature under nitrogen and the resulting mixture was stirred at same temperature for 1.5 h. Reaction mixture was concentrated under reduced pressure, obtained crude was diluted with water (40 mL) and was extracted with ethyl acetate (60 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum, to afford to afford 4-(4-(tert-butyl)phenyl)-9-methylpyrrolo[1,2-a]quinoxaline-7-carboxylic acid (I-321) (0.080 g, 55%) as an off-white solid. MS: $[MH]^+$ 359.2. $^1H$ NMR (400 MHz, DMSO-$d_6$) 13.17 (br, 1H), 8.60-8.59 (d, J=1.2 Hz, 1H), 8.27 (s, 1H), 7.95-7.92 (m, 3H), 7.62-7.60 (d, J=8.4 Hz, 2H), 7.12-7.11 (d, J=4.0 Hz, 1H), 7.03-7.01 (t, J=3.2 Hz, 1H), 2.99 (s, 3H), 1.36 (s, 9H). MS: $[MH]^+$ 359.2.

Example 1.231. Synthesis of N-((7-(4-(Trifluoromethyl)phenyl)imidazo[1,2-c]pyrimidin-5-yl)methyl)acrylamide (I-322)

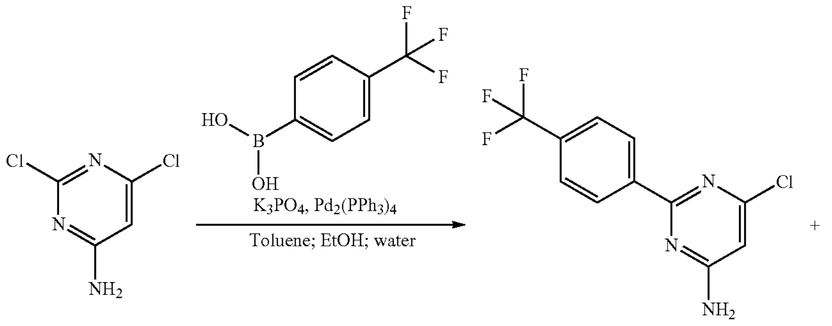

X-1476A1

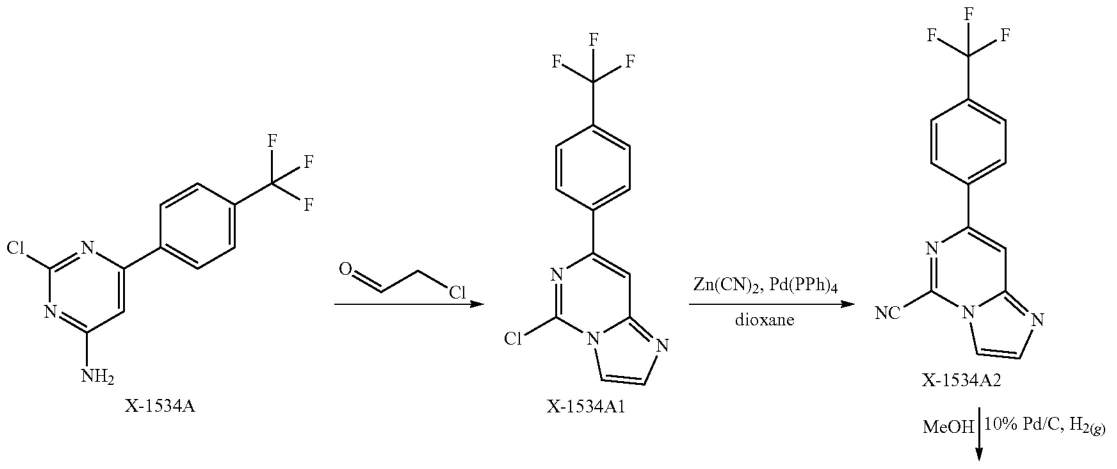

X-1534A X-1534A1 X-1534A2

-continued

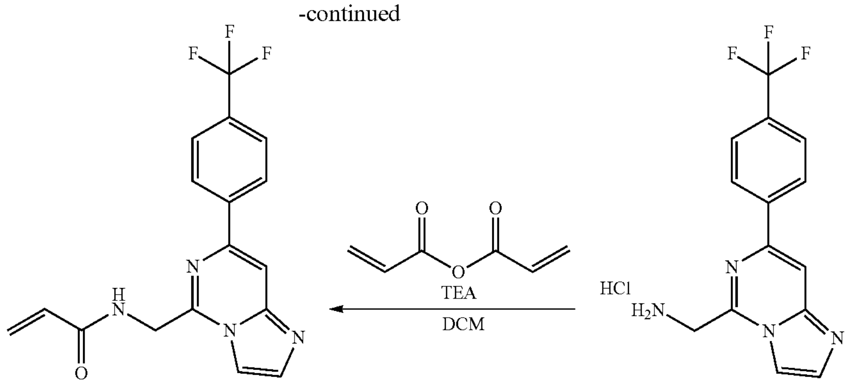

I-322

X-1534A3

2-Chloro-6-(4-(trifluoromethyl)phenyl)pyrimidin-4-amine (X-1534A). To a stirred solution of 2,6-dichloropyrimidin-4-amine (10.0 g, 61.0 mmol) in a mixture of toluene-ethanol-water (140:40:20, 200 mL) were added (4-(trifluoromethyl)phenyl)boronic acid (12.74 g, 67.11 mmol) and Potassium phosphate (38.0 g, 183.03 mmol) at room temperature under nitrogen. The reaction mixture was degassed (purging with nitrogen) for 20 min followed by addition of $Pd(PPh_3)_4$ (3.53 g, 3.05 mmol) and the reaction mixture was heated at 90° C. for 4 h. The reaction mixture was cooled to room temperature, diluted with water (500 mL) and was extracted with ethyl acetate (500 mL×3). The combined organic extracts were dried over anhydrous $Na_2SO_4$ and concentrated under reduce pressure. Isolated crude was combined with an identical prepared two more batch (10.0 g) and the combined crude were purified by silica gel column chromatography using, ethyl acetate-hexane=0:1→3:7 as gradient, both region isomer are separated such as 6-chloro-2-(4-(trifluoromethyl)phenyl)pyrimidin-4-amine (X-1476A1) (4.0 g, 8%) and 2-chloro-6-(4-(trifluoromethyl)phenyl)pyrimidin-4-amine (X-1534A) (15.0 g, 30%) as an off-white solid. MS: $[MH]^+$ 273.9

5-Chloro-7-(4-(trifluoromethyl)phenyl)imidazo[1,2-c]pyrimidine (X-1534A1). A stirred solution of 2-chloro-6-(4-(trifluoromethyl)phenyl)pyrimidin-4-amine (X-1476A) (1.0 g, 3.66 mmol) in 2-chloroacetaldehyde (3.42 g, 43.95 mmol) under nitrogen was heated at 80° C. for 2 h. The reaction mixture was diluted with water (500 mL) and was extracted with ethyl acetate (500 mL×3), dried over anhydrous $Na_2SO_4$ and concentrated under reduce pressure. Isolated crude was combined with an identical prepared eight more batch (1.0 g) and the combined crude were purified by silica gel column chromatography, using ethyl acetate-hexane=0:1→2:8 as gradient, to afford 5-chloro-7-(4-(trifluoromethyl)phenyl)imidazo[1,2-c]pyrimidine (X-1534A1) (4.5 g, 46%) as a white solid. MS: $[MH]^+$ 297.9

7-(4-(Trifluoromethyl)phenyl)imidazo[1,2-c]pyrimidine-5-carbonitrile (X-1534A2). To a stirred solution 5-chloro-7-(4-(trifluoromethyl)phenyl)imidazo[1,2-c]pyrimidine (X-1534A1) (0.500 g, 1.68 mmol) in 1,4-dioxane (4 mL) was added zinc cyanide (0.59 g, 5.05 mmol) at room temperature under nitrogen. The reaction mixture was degassed (purging with nitrogen) for 20 min followed by addition of $Pd(PPh_3)_4$ (0.38 g, 0.33 mmol) and the reaction mixture was heated at 160° C. for 10 min. into Microwave irradiation. The reaction mixture was cooled to room temperature, diluted with water (500 mL) and was extracted with ethyl acetate (500 mL×3). The combined organic extracts were dried over anhydrous $Na_2SO_4$ and concentrated under reduce pressure. Isolated crude was combined with an identical prepared eight more batch (0.5 g) and the combined crude were purified by silica gel column chromatography using, using ethyl acetate-hexane=0:141:9 as gradient, to afford 7-(4-(trifluoromethyl)phenyl)imidazo[1,2-c]pyrimidine-5-carbonitrile (X-1534A2) (4.5 g, quantitative) as a white solid. MS: $[MH]^+$ 289.01.

(7-(4-(Trifluoromethyl)phenyl)imidazo[1,2-c]pyrimidin-5-yl)methanamine (X-1534A3). To a stirred solution of 7-(4-(trifluoromethyl)phenyl)imidazo[1,2-c]pyrimidine-5-carbonitrile (X-1534A2) (0.130 g 0.45 mmol) in MeOH (2 mL) was added 10% Pd/C (0.190 g) at room temperature under nitrogen. The resulting reaction mixture was hydrogenated under balloon pressure at room temperature for 30 min. Reaction mixture was filtered through celite bed, washed the bed with MeOH (100 mL) and collected filtrates were concentrated under reduced pressure, to afford (7-(4-(trifluoromethyl)phenyl)imidazo[1,2-c]pyrimidin-5-yl)methanamine (X-1534A3) (0.120 g, 91%) as an off-white solid, which was carried forward to the next step without further purification. MS: $[MH]^+$ 292.8.

N-((7-(4-(Trifluoromethyl)phenyl)imidazo[1,2-c]pyrimidin-5-yl)methyl)acrylamide (I-322). To a stirred solution of (7-(4-(trifluoromethyl)phenyl)imidazo[1,2-c]pyrimidin-5-yl)methanamine (X-1534A3) (0.130 g, 0.43 mmol) in DCM (1 mL) were added TEA (0.17 g, 1.75 mmol) and acrylic anhydride (0.11 g, 0.52 mmol) at 0° C. under nitrogen and the reaction mixture was stirred at room temperature for 30 min. The reaction mixture was diluted with water (20 mL) and was extracted with DCM (50 mL×2). Combined organic extracts were dried over anhydrous $Na_2SO_4$ and concentrated under reduced pressure. The crude product was purified by (C-18) silica gel column chromatography, using acetonitrile-water=0:1→3:7 as gradient, to afford N-((7-(4-(trifluoromethyl)phenyl)imidazo[1,2-c]pyrimidin-5-yl)methyl)acrylamide (I-322) (0.022 g, 14%) as a yellow solid. $^1H$ NMR (400 MHz, DMSO-$d_6$) δ 8.97 (brs, 1H), 8.43-8.42 (d, J=4.0 Hz, 2H), 8.35 (s, 1H), 8.13 (s, 1H), 7.86-7.85 (d, J=4.0 Hz, 2H), 7.80 (m, 1H), 6.44-6.37 (m, 1H), 6.22-6.18 (d, J=16.0 Hz, 1H), 5.72-5.70 (d, J=8.0 Hz, 1H), 4.92 (s, 2H). MS: $[MH]^+$ 346.9.

Example 1.232. Synthesis of 4-(4-(tert-butyl) phenyl)-7-(methylsulfonyl)pyrrolo[1,2-a]quinoxaline (I-323)

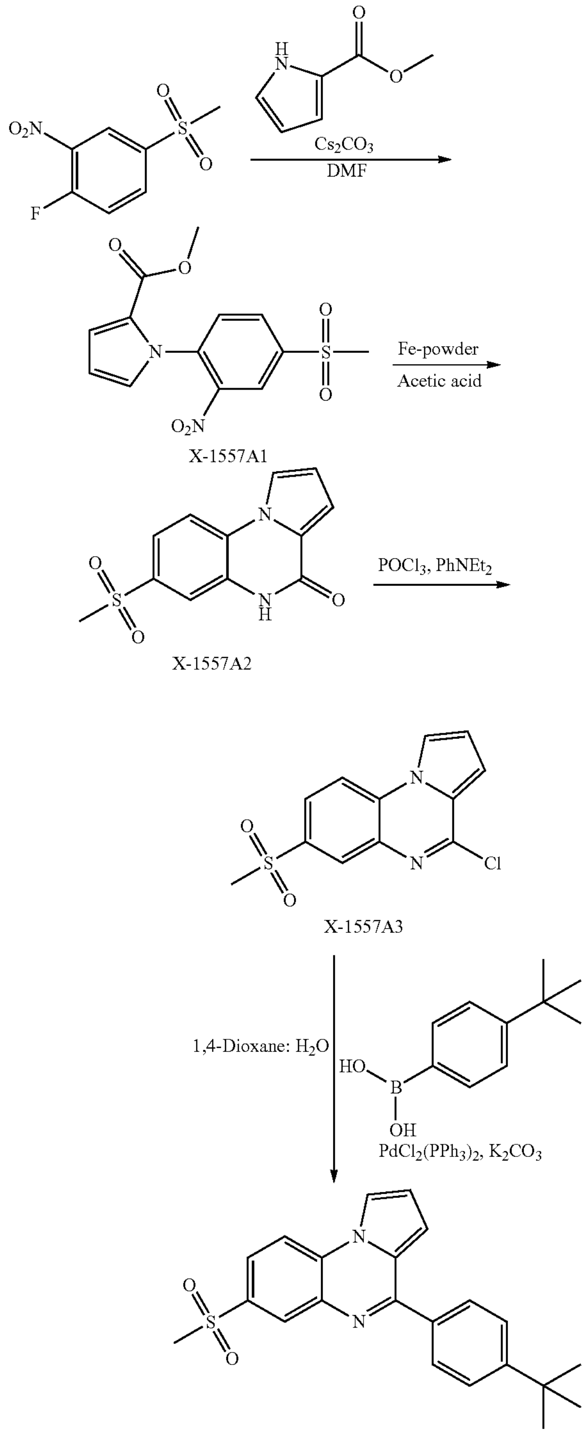

X-1557A1

X-1557A2

X-1557A3

I-323

Methyl 1-(4-(methylsulfonyl)-2-nitrophenyl)-1H-pyrrole-2-carboxylate (X-1557A1). To a stirred solution of 1-fluoro-4-(methylsulfonyl)-2-nitrobenzene (5.0 g, 22.81 mmol) in DMF (30 mL) were added cesium carbonate (14.86 g, 45.62 mmol) and methyl 1H-pyrrole-2-carboxylate (3.42 g, 27.37 mmol) at room temperature under nitrogen and the resulting mixture was stirred at room temperature for 18 h. After completion of reaction, reaction mixture was poured into cold water (500 mL) obtained precipitates were filtered and the residue was washed with water (400 mL). Solid precipitate was triturated by diethyl ether and dried under reduced pressure, to afford methyl 1-(4-(methylsulfonyl)-2-nitrophenyl)-1H-pyrrole-2-carboxylate (X-1557A1) (4.0 g, 48%) as an off-white solid. MS: $[MH]^+$ 324.04.

7-(Methylsulfonyl)pyrrolo[1,2-a]quinoxalin-4(5H)-one (X-1557A2). To a stirred solution of methyl 1-(4-(methylsulfonyl)-2-nitrophenyl)-1H-pyrrole-2-carboxylate (X-1557A1) (5.0 g, 15.43 mmol) in acetic acid (5 mL) was added Fe-powder (6.89 g, 12.34 mmol) at 0° C. and reaction was allowed to stir at 100° C. for 6 h. After completion of reaction, reaction mixture was cooled to room temperature, was filtered and the precipitate was washed with water. The precipitate was dissolved in 10% methanol in dichloromethane, stirred for 30 min and filtered through a celite bed, filtrate was concentrated under reduced pressure to afford 7-(methylsulfonyl)pyrrolo[1,2-a]quinoxalin-4(5H)-one (X-1557A2) (3.5 g, 87%) as an off-white solid. MS: $[MH]^+$ 262.80.

4-Chloro-7-(methylsulfonyl)pyrrolo[1,2-a]quinoxaline (X-1557A3). N,N-diethylaniline (1 mL) was added to a stirred suspension of 7-(methylsulfonyl)pyrrolo[1,2-a]quinoxalin-4(5H)-one (X-1557A2) (0.5 g, 1.90 mmol) in $POCl_3$ (3 mL) at 0° C. and the resulting mixture was heated at 100° C. for 16 h. After completion of reaction, reaction mixture was cooled to room temperature, was diluted with cold water (100 mL), and was extracted with ethyl acetate (200 mL×3). Combined organic extracts were dried over anhydrous $Na_2SO_4$ and concentrated under reduce pressure. The crude product was purified by silica gel column chromatography, using ethyl acetate-hexane=0:1→5:5 as gradient, to afford 4-chloro-7-(methylsulfonyl)pyrrolo[1,2-a]quinoxaline (X-1557A3) (0.5 g, 93%) as an off-white solid. MS: $[MH]^+$ 280.8.

4-(4-(tert-Butyl) phenyl)-7-(methylsulfonyl)pyrrolo[1,2-a]quinoxaline (I-323). To a stirred solution of 4-chloro-7-(methylsulfonyl)pyrrolo[1,2-a]quinoxaline (X-1557A3) (0.5 g, 1.78 mmol) in 1,4-dioxane-water (4:1, 5 mL) were added (4-(tert-butyl)phenyl)boronic acid (0.41 g, 2.32 mmol) and potassium carbonate (0.73 g, 5.35 mmol) at room temperature under nitrogen. The resulting mixture was degassed (purged with nitrogen) for 20 min followed by the addition of $PdCl_2(PPh_3)_2$ (0.03 g, 0.05 mmol) and was heated at 90° C. for 4 h. After completion of reaction, reaction mixture was cooled to room temperature, was diluted with water (100 mL) and was extracted with ethyl acetate (200 mL×3). Combined organic extracts were dried over anhydrous $Na_2SO_4$ and concentrated under reduce pressure. The crude product was purified by $C^{18}$ silica gel column chromatography, using acetonitrile-water=0:1→1:0 as gradient, to afford 4-(4-(tert-butyl)phenyl)-7-(methylsulfonyl)pyrrolo[1,2-a]quinoxaline (I-323) (0.11 g, 16%) as a white solid. MS: $[MH]^+$ 379.87. $^1H$ NMR (400 MHz, DMSO-$d_6$) δ 8.70-8.70 (d, J=1.6 Hz, 1H), 8.60-8.58 (d, J=8.8 Hz, 1H), 8.39-8.38 (d, J=1.6 Hz, 1H), 8.10-8.07 (dd, J=8.4, 1.6 Hz, 1H), 8.00-7.98 (d, J=8.4 Hz, 2H), 7.64-7.61 (d, J=8.4 Hz, 2H), 7.18-7.17 (d, J=3.6 Hz, 1H), 7.09-7.08 (t, J=2.8 Hz, 1H), 3.34-3.33 (d, J=5.2 Hz, 3H), 1.36 (s, 9H).

Example 1.233. Synthesis of (R)—N-(1-hydroxypropan-2-yl)-4-methoxy-2-(4-(trifluoromethyl)phenyl)quinoline-7-carboxamide (I-324)

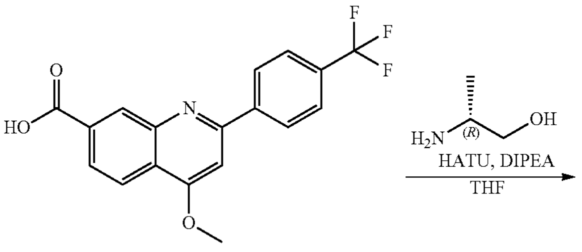

I-181

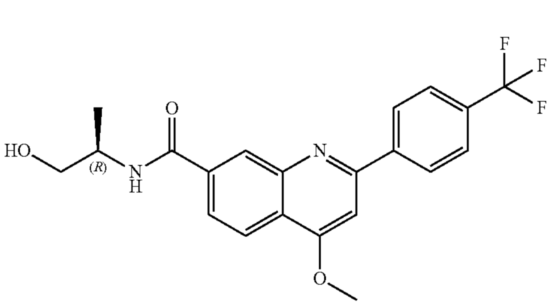

I-324

To a stirred solution of 4-methoxy-2-(4-(trifluoromethyl)phenyl)quinoline-7-carboxylic acid (I-181) (0.300 g, 0.86 mmol) in THE (3 mL) were added DIPEA (0.400 mL, 2.59 mmol) and HATU (0.330 g, 1.29 mmol) at at 0° C. under nitrogen. After 10 min of stirring at the same temperature, was added a solution of (R)-2-aminopropan-1-ol (0.320 g, 4.32 mmol) in THF (1 mL) at 0° C. drop-wise and the resulting reaction mixture was stirred at room temperature for 2 h. Reaction mixture was diluted with water (50 mL) and was extracted with ethyl acetate (60 mL×3). Combined organic extracts were dried over $Na_2SO_4$ and concentrated under reduced pressure. The crude product was purified by reverse phase (C-18) silica gel column chromatography, using acetonitrile-water=0:1→6:4 as gradient, to afford (R)—N-(1-hydroxypropan-2-yl)-4-methoxy-2-(4-(trifluoromethyl)phenyl)quinoline-7-carboxamide (I-324) as an off-white solid, (2.10 g, 78%). $^1H$ NMR (400 MHz, DMSO-$d_6$) δ: 8.59-8.58 (d, J=4.0 Hz, 1H), 8.55-8.53 (d, J=8.0 Hz, 2H), 8.49-8.47 (d, J=8.0 Hz, 1H), 8.21-8.19 (d, J=8.0 Hz, 1H), 8.02-7.99 (dd, J=4.0, 8.0 Hz, 1H), 7.95-7.93 (d, J=8.0 Hz, 2H), 7.72 (s, 1H), 4.79-4.76 (t, J=8.0 Hz, 1H), 4.21 (s, 3H), 4.12-4.05 (m, 1H), 3.54-3.49 (m, 1H), 3.42-3.33 (m, 1H), 1.18-1.17 (d, J=4.0 Hz, 3H). MS: $[MH]^+$ 405.01, Chiral HPLC=99.68%

Example 1.234. Synthesis of (S)—N-(1-hydroxypropan-2-yl)-4-methoxy-2-(4-(trifluoromethyl)phenyl)quinoline-7-carboxamide (I-325)

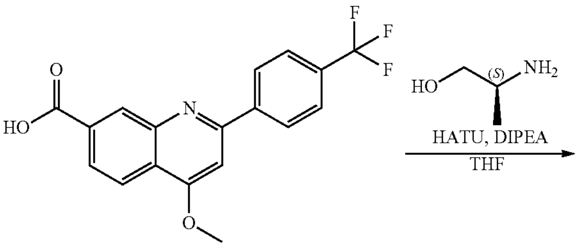

I-181

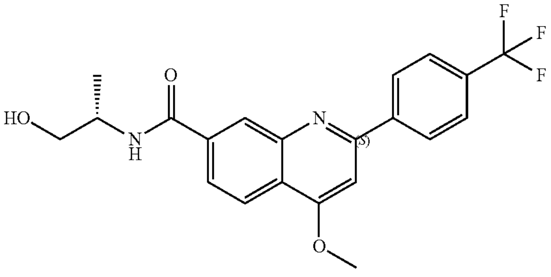

I-325

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(S)—N-(1-hydroxypropan-2-yl)-4-methoxy-2-(4-(trifluoromethyl)phenyl)quinoline-7-carboxamide (I-325) (0.055 g, 22%) as an off-white solid. $^1H$ NMR (400 MHz, DMSO-$d_6$) δ: 8.59-8.58 (d, J=1.2 Hz, 1H), 8.55-8.53 (d, J=8.0 Hz, 2H), 8.93-8.73 (d, J=8.0 Hz, 1H), 8.21-8.19 (d, J=8.8 Hz, 1H), 8.01-7.99 (dd, J=1.2, 8.4 Hz, 1H), 7.94-7.92 (d, J=8.4 Hz, 2H), 7.72 (s, 1H), 4.78-4.75 (t, J=5.6 Hz, 1H), 4.20 (s, 3H), 4.11-4.05 (m, 1H), 3.54-3.48 (m, 1H), 3.41-3.35 (m, 1H), 1.18-1.16 (d, J=6.8 Hz, 3H). MS: $[MH]^+$ 404.97, Chiral HPLC=99.68%

Example 1.235. Synthesis of (R)—N-(1-hydroxybutan-2-yl)-4-methoxy-2-(4-(trifluoromethyl)phenyl)quinoline-7-carboxamide (I-326)

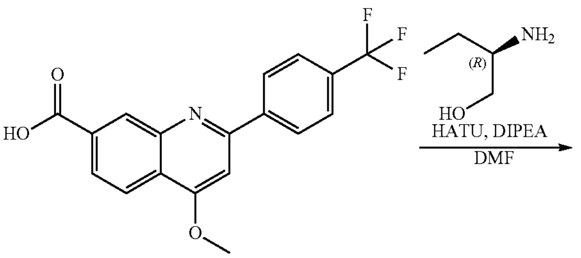

I-181

-continued

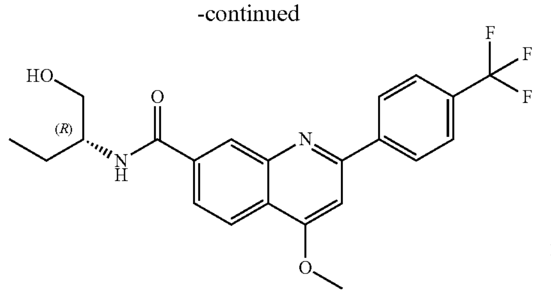

I-326

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(1-hydroxybutan-2-yl)-4-methoxy-2-(4-(trifluoromethyl)phenyl)quinoline-7-carboxamide (I-326) (2.70 g, 77%) as an off-white solid. $^1$H NMR (400 MHz, DMSO-$d_6$) δ: 8.61-8.60 (d, J=1.6 Hz, 1H), 8.56-8.54 (d, J=8.0 Hz, 2H), 8.41-8.39 (d, J=8.4 Hz, 1H), 8.22-8.19 (d, J=8.8 Hz, 1H), 8.02-8.00 (dd, J=1.6, 8.80 Hz, 1H), 7.95-7.93 (d, J=8.0 Hz, 2H), 7.72 (s, 1H), 4.74-4.71 (t, J=5.6 Hz, 1H), 4.21 (s, 3H), 3.96-3.92 (m, 1H), 3.55-3.42 (m, 2H), 1.73-1.67 (m, 1H), 1.55-1.47 (m, 1H) 0.94-0.90 (t, J=7.6 Hz, 3H), MS: [MH]$^+$ 419.1, Chiral HPLC=99.09%

Example 1.236. Synthesis of (S)-4-methoxy-N-(1-(pyridin-2-yl)ethyl)-2-(4-(trifluoromethyl)phenyl)quinoline-7-carboxamide (I-327)

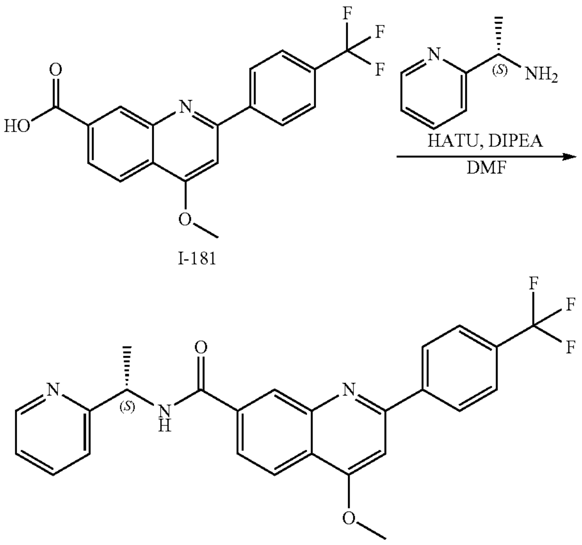

I-181

I-327

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(S)-4-methoxy-N-(1-(pyridin-2-yl)ethyl)-2-(4-(trifluoromethyl)phenyl)quinoline-7-carboxamide (I-327) (0.220 g, 68%) as an off-white solid. $^1$H NMR (400 MHz, DMSO-$d_6$) δ: 9.22-9.20 (d, J=7.6 Hz, 1H), 8.70-8.69 (d, J=1.2 Hz, 1H), 8.58-8.56 (d, J=8.0 Hz, 2H), 8.56 (s, 1H), 8.25-8.23 (d, J=8.4 Hz, 1H), 8.06-8.03 (dd, J=1.6, 8.8 Hz, 1H), 7.96-7.94 (d, J=8.4 Hz, 2H), 7.81-7.77 (m, 1H), 7.75 (s, 1H), 7.50-7.48 (d, J=8.0 Hz, 1H), 7.29-7.26 (m, 1H), 5.29-5.26 (t, J=7.2 Hz, 1H), 4.23 (s, 3H), 1.58-1.57 (d, J=6.8 Hz, 3H). MS: [MH]$^+$ 452, Chiral HPLC=100%

Example 1.237. Synthesis of (R)—N-(1-hydroxypropan-2-yl)-4-methoxy-2-(4-(trifluoromethyl)piperidin-1-yl)quinoline-7-carboxamide (I-328)

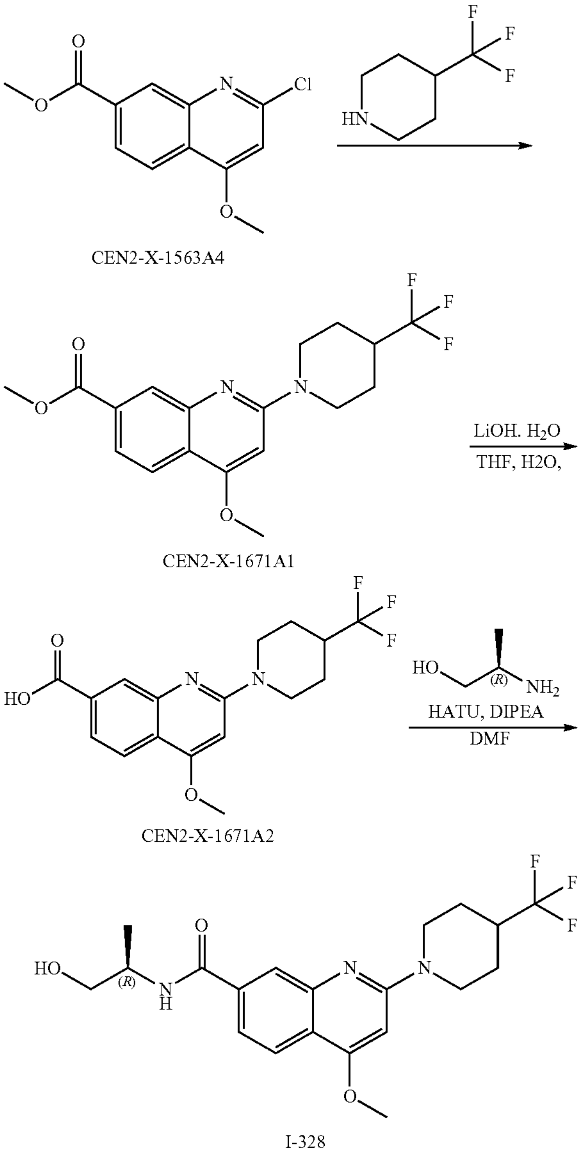

CEN2-X-1563A4

CEN2-X-1671A1

CEN2-X-1671A2

I-328

Methyl 4-methoxy-2-(4-(trifluoromethyl)piperidin-1-yl)quinoline-7-carboxylate (X-1671A1). A solution of methyl 2-chloro-4-methoxyquinoline-7-carboxylate (X-1563A4) (0.500 g, 1.99 mmol) in 4-(trifluoromethyl)piperidine (1.37 g, 8.96 mmol) was heated at 180° C. for 1 h. After cooling to room temperature, reaction mixture was first acidified (pH~1) with an aqueous solution of 1N HCl to remove excess 4-(trifluoromethyl)piperidine. A precipitate occurred, which was extracted with EtOAc (100 mL×2). Combined organic extracts was dried over anhydrous $Na_2SO_4$ and was concentrated under reduced pressure. Obtained solid residue was triturated by n-pentane to afford methyl 4-methoxy-2-(4-(trifluoromethyl)piperidin-1-yl)quinoline-7-carboxylate (X-1671A1) (0.300 g, 40%) as a white solid. MS: $[MH]^+$ 369.0.

4-Methoxy-2-(4-(trifluoromethyl)piperidin-1-yl)quinoline-7-carboxylic acid (X-1671A2). To a stirred solution of methyl 4-methoxy-2-(4-(trifluoromethyl)piperidin-1-yl)quinoline-7-carboxylate (X-1671A1) (0.300 g, 0.81 mmol) in a mixture of THF-water (3:1; 5.0 mL) was added lithium hydroxide monohydrate (0.058 g, 2.44 mmol) at room temperature under nitrogen and the resulting mixture was heated at 60° C. for 1 h. After cooling to room temperature, the reaction mixture was concentrated under reduced pressure, obtained crude was diluted with water (40 mL) and was extracted with ethyl acetate (40 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 4-methoxy-2-(4-(trifluoromethyl)piperidin-1-yl)quinoline-7-carboxylic acid (X-1671A2) (0.150 g, 52%) as an off-white solid. MS: $[MH]^+$ 355.0.

(R)—N-(1-hydroxypropan-2-yl)-4-methoxy-2-(4-(trifluoromethyl)piperidin-1-yl)quinoline-7-carboxamide (I-328). To a stirred solution of 4-methoxy-2-(4-(trifluoromethyl)piperidin-1-yl)quinoline-7-carboxylic acid (X-1671A2) (0.130 g, 0.36 mmol) in DMF (2.5 mL) were added DIPEA (0.230 g, 1.8 mmol) and HATU (0.270 g, 0.73 mmol) at room temperature under nitrogen. After 10 min of stirring at the same temperature, was added (R)-2-aminopropan-1-ol (0.032 g, 0.43 mmol) and the resulting mixture was stirred at room temperature for 30 min. The mixture was diluted with water (60 mL) and extracted with EtOAc (100 mL×2). The combined organic layers were washed with brine, dried over $Na_2SO_4$, filtered and was concentrated under reduced pressure. The crude mass was purified by reverse phase (C-18) silica gel column chromatography, using acetonitrile-water=0:1→3:7 as gradient, to afford (R)—N-(1-hydroxypropan-2-yl)-4-methoxy-2-(4-(trifluoromethyl)piperidin-1-yl)quinoline-7-carboxamide (I-328) (0.030 g, 20%) as an off-white solid. $^1H$ NMR (400 MHz, DMSO-$d_6$) δ 8.32 (br, 1H), 8.14-7.93 (m, 2H), 7.70-7.63 (m, 1H), 6.72 (s, 1H), 4.69-4.60 (m, 3H), 4.10-4.03 (m, 3H), 3.50-3.46 (m, 1H), 3.38 (3H, merged with DMSO-$d_6$ moisture peak), 3.10-2.98 (m, 1H), 2.74-2.59 (m, 1H). 2.99-2.91 (br, 2H), 1.51 (brs, 2H), 1.58-1.41 (d, J=6.8 Hz, 3H). MS: $[MH]^+$ 412.1.

Example 1.238. Synthesis of 1-(4-Methoxy-2-(4-(trifluoromethyl)phenyl)quinolin-7-yl)ethan-1-one (I-329)

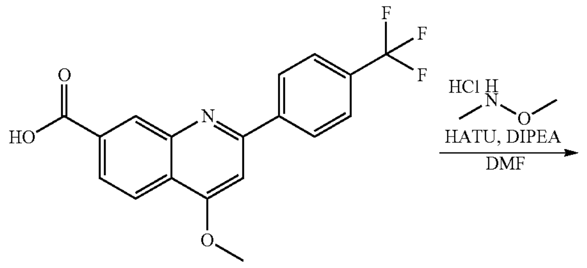

I-181

-continued

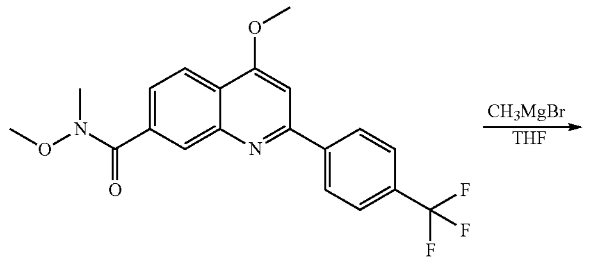

CEN2-X-1694A1

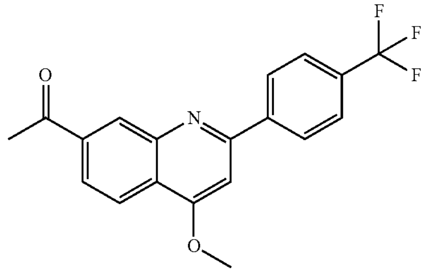

I-329

1,4-Dimethoxy-N-methyl-2-(4-(trifluoromethyl)phenyl)quinoline-7-carboxamide (X-1694A1). To a stirred solution of 4-methoxy-2-(4-(trifluoromethyl)phenyl)quinoline-7-carboxylic acid (I-181) (0.500 g, 1.44 mmol) in DMF (5.0 mL) were added HATU (1.095 g, 2.88 mmol) and DIPEA (0.65 g, 5.04 mmol) at 0° C. under nitrogen. After 10 min of stirring at the same temperature, was added N,O-dimethylhydroxylamine hydrochloride (0.21 g, 2.10 mmol) the resulting mixture was stirred at room temperature for 2 h. The mixture was diluted with water (60 mL) and extracted with EtOAc (100 mL×2). The combined organic layers were washed with brine, dried over $Na_2SO_4$, filtered and concentrated. Obtained crude product was purified by silica gel column chromatography, using ethyl acetate-hexane=0:1→5:5 as gradient, to afford N,4-dimethoxy-N-methyl-2-(4-(trifluoromethyl)phenyl)quinoline-7-carboxamide (X-1694A1) (0.35 g, 62%) as a solid. MS: $[MH]^+$ 369.05.

1-(4-Methoxy-2-(4-(trifluoromethyl)phenyl)quinolin-7-yl)ethan-1-one (I-329). Molecular sieves were added to a 30 ml vial and was dried by heating it, then it was cool to room temperature & charged reaction. To a solution of N,4-dimethoxy-N-methyl-2-(4-(trifluoromethyl)phenyl)quinoline-7-carboxamide (X-1694A1) (0.350 g, 0.89 mmol) in THE (7.0 mL) was added $CH_3MgBr$ (3M in ether, 0.59 mL, 1.79 mmol) slowly dropwise and the resulting mixture was stirred at room temperature for 1 h. The resulting reaction mixture was quenched in cold $NH_4Cl$ solution and then it was extracted with EtOAc (100 mL×2). The combined organic layers, dried over $Na_2SO_4$, filtered and was concentrated under reduced pressure. The crude mass was purified by silica gel column chromatography, using ethyl acetate-hexane=0:1→2:8 as gradient. Obtained solid was dried under high vacuum to afford 1-(4-methoxy-2-(4-(trifluoromethyl)phenyl)quinolin-7-yl)ethan-1-one (I-329) (0.250 g, 81%) as an off-white solid. $^1H$ NMR (400 MHz, DMSO-$d_6$) δ 8.65 (s, 1H), 8.57-8.55 (d, J=8.0 Hz, 2H), 8.26-8.24 (d, J=8.4 Hz, 1H), 8.04-8.02 (dd, J=1.2 Hz, 8.4 Hz, 1H), 7.95-7.93 (d, J=8.4 Hz, 2H), 7.76 (s, 1H), 4.22 (s, 3H). 2.77 (s, 3H). MS: $[MH]^+$ 345.1.

Example 1.239. Synthesis of (R)-4-(difluoromethoxy)-N-(1-hydroxypropan-2-yl)-2-(4-(trifluoromethyl)phenyl)quinoline-7-(I-330)

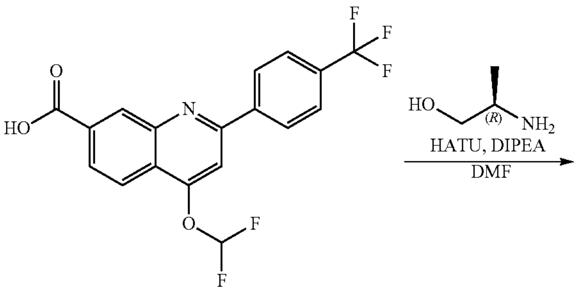

I-331

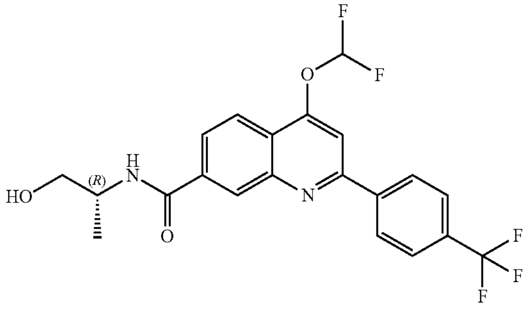

I-330

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)-4-(difluoromethoxy)-N-(1-hydroxypropan-2-yl)-2-(4-(trifluoromethyl)phenyl)quinoline-7-carboxamide (I-330) (0.046 g, 24%) as an off-white solid. $^1$H NMR (400 MHz, DMSO-$d_6$) δ 8.69 (s, 1H), 8.57-8.52 (m, 3H), 8.22-7.90 (m, 6H), 4.79-4.76 (t, J=6.0 Hz, 1H), 4.13-4.08 (m, 1H), 3.54-3.50 (q, 1H), 3.42-3.38 (m, 1H), 1.20-1.18 (d, J=6.4 Hz, 3H). MS: $[MH]^+$ 440.97.

Example 1.240. Synthesis of 4-(Difluoromethoxy)-2-(4-(trifluoromethyl)phenyl)quinoline-7-carboxylic acid (I-331)

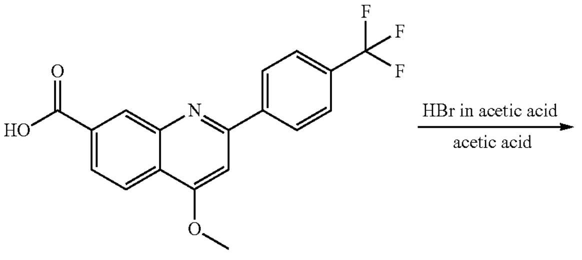

I-181

-continued

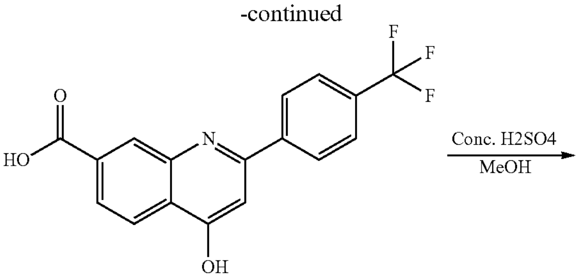

X-1579B1

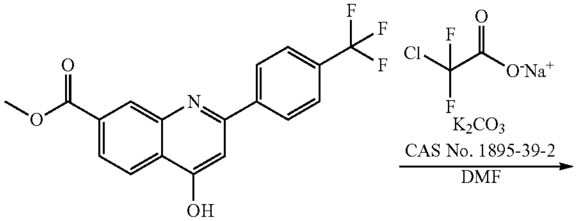

X-1579B2

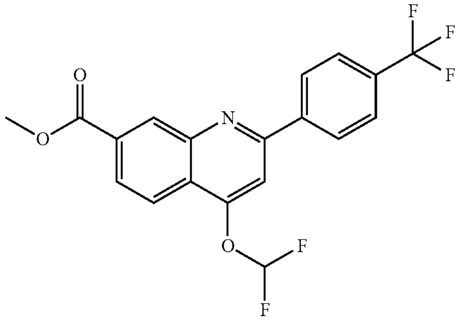

X-1714A1

LiOH. $H_2O$, THF: $H_2O$

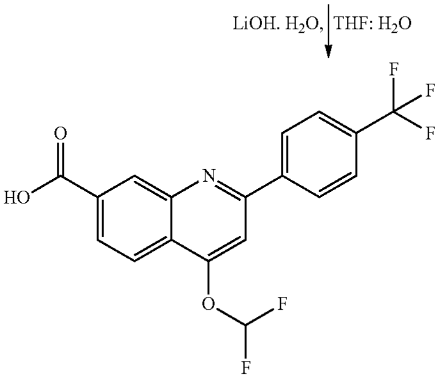

I-331

Synthesis of 4-methoxy-2-(4-(trifluoromethyl)phenyl)quinoline-7-carboxylic acid (I-181) provided in Example 1.82

4-Hydroxy-2-(4-(trifluoromethyl)phenyl)quinoline-7-carboxylic acid (X-1579B1). To a stirred solution of 4-methoxy-2-(4-(trifluoromethyl)phenyl)quinoline-7-carboxylic acid (I-181) (0.500 g, 1.44 mmol) in AcOH (4 mL) was added HBr in acetic acid (0.500 mL, 2.88 mmol) at room temperature under nitrogen and the reaction mixture was heated at 120° C. for 16 h. After cooling to room temperature, reaction mixture was slowly poured into ice-water (40 mL) and solid precipitate fall out was filtered. Obtained solid residue was washed with water (80 mL), dried under high vacuum to afford 4-hydroxy-2-(4-(trifluoromethyl)phenyl)quinoline-7-carboxylic acid (X-1579B1) (0.51 g, Quantitative yield) as a white solid, which was carried forward to next step without further purification. MS: $[MH]^+$ 333.8.

Methyl 4-hydroxy-2-(4-(trifluoromethyl)phenyl)quinoline-7-carboxylate (X-1579B2). Concentrated $H_2SO_4$ (0.1 mL) was added dropwise to a stirred suspension of 4-hydroxy-2-(4-(trifluoromethyl)phenyl)quinoline-7-carboxylic acid (X-1579B1) (0.51 g, 1.53 mmol) in a methanol (6 mL) at room temperature and the resulting mixture was heated at 80° C. for 3 h. After cooling to room temperature the reaction mixture was concentrated under reduced pressure. The resulting mixture was poured into ice-water (30 mL) and the resulting precipitate was collected by filtration. Obtained solid residue was washed with water (60 mL), dried under high vacuum to afford methyl 4-hydroxy-2-(4-(trifluoromethyl)phenyl)quinoline-7-carboxylate (X-1579B2) (0.40 g, 75%) as a white solid. MS: $[MH]^+$ 347.8.

Methyl 4-(difluoromethoxy)-2-(4-(trifluoromethyl)phenyl)quinoline-7-carboxylate (X-1714A1). To a stirred solution of methyl 4-hydroxy-2-(4-(trifluoromethyl)phenyl)quinoline-7-carboxylate (X-1579B2) (0.40 g, 1.15 mmol) in DMF (6 mL) were added potassium carbonate (0.47 g, 3.45 mmol) and sodium 2-chloro-2,2-difluoroacetate (0.26 g, 1.72 mmol) sequentially at room temperature under nitrogen the resulting mixture was stirred at 80° C. for 3 h. The reaction mixture was poured into ice-water (50 mL) and was extracted with ethyl acetate (120 mL×3). Combined organic extracts were dried over anhydrous $Na_2SO_4$ and concentrated under reduced pressure. Obtained crude product was purified by silica gel column chromatography, using ethyl acetate-hexane=2:8→3:7 as gradient, to afford methyl 4-(difluoromethoxy)-2-(4-(trifluoromethyl)phenyl)quinoline-7-carboxylate (X-1714A1) (0.32 g, 70%) as a white solid. MS: $[MH]^+$ 397.9.

4-(Difluoromethoxy)-2-(4-(trifluoromethyl)phenyl)quinoline-7-carboxylic acid (I-331). To a stirred solution of methyl 4-(difluoromethoxy)-2-(4-(trifluoromethyl)phenyl)quinoline-7-carboxylate (X-1714A1) (0.32 g, 0.80 mmof) in a mixture of THF-water (3:1; 8.0 mL) was added lithium hydroxide monohydrate (0.067 g, 1.61 mmol) at room temperature and the resulting mixture was stirred for 2 h at the same temperature. Reaction mixture was concentrated under reduced pressure, crude was diluted with water and Aqueous part was acidified (pH~2-3) with an aqueous solution of 1N HCl. Product was extracted with ethyl acetate (50 mL×2). Organic extracts were combined, dried over anhydrous $Na_2SO_4$ and concentrated under reduced pressure. The resulting crude was purified by reverse phase (C-18) silica gel column chromatography, using acetonitrile-water=3:7→4:6 as gradient, to afford 4-(difluoromethoxy)-2-(4-(trifluoromethyl)phenyl)quinoline-7-carboxylic acid (I-331) (0.270 g, 87%) as a white solid. $^1H$ NMR (400 MHz, DMSO-$d_6$) δ 13.7 (s, 1H), 8.65-8.65 (d, J=0.80 Hz, 1H), 8.54-8.52 (d, J=8.0 Hz, 2H), 8.24-8.22 (d, J=8.8 Hz, 1H), 8.18-8.16 (dd, J=1.6 Hz, J=8.8 Hz, 1H), 8.09 (s, 1H), 7.98-7.96 (d, J=8.4 Hz, 2H), 7.90 (s, 1H). MS: $[MH]^+$ 384.2.

Example 1.241. Synthesis of (R)—N-(1-hydroxybutan-2-yl)-4-methoxy-2-((4-(trifluoromethyl)phenyl)amino)quinoline-7-carboxamide (I-332)

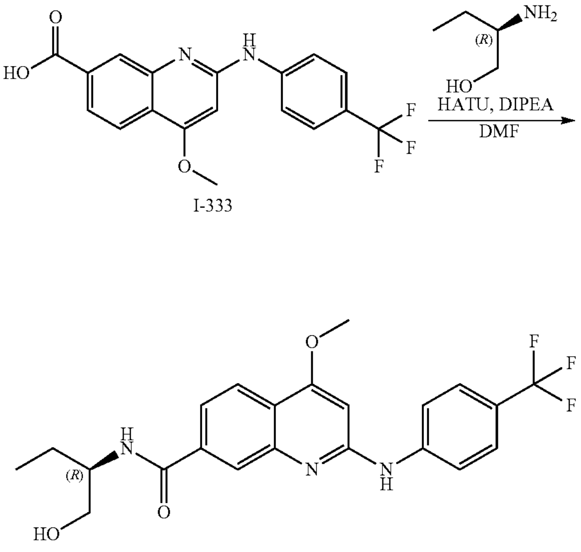

I-333

I-332

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(1-hydroxybutan-2-yl)-4-methoxy-2-((4-(trifluoromethyl)phenyl)amino)quinoline-7-carboxamide (I-332) (0.110 g, 46%) as a white solid. $^1H$ NMR (400 MHz, DMSO-$d_6$) δ 9.83 (S, 1H), 8.28-8.26 (d, J=8.8 Hz, 1H), 8.21-8.20 (m, 3H), 8.00-7.98 (d, J=8.4 Hz, 1H), 7.77-7.74 (dd, J=8.4, 1.6 Hz, 1H), 7.69-7.67 (d, J=8.8 Hz, 2H), 6.61 (s, 1H), 4.72-4.69 (t, J=5.6 Hz, 1H), 4.04 (s, 3H), 3.97-3.88 (m, 1H), 3.53-3.40 (m, 2H), 1.75-1.64 (m, 1H), 1.55-1.44 (m, 1H), 0.90-0.93 (m, 3H). MS: $[MH]^+$ 434.1.

Example 1.242. Synthesis of 4-Methoxy-2-((4-(trifluoromethyl)phenyl)amino)quinoline-7-carboxylic acid (I-333)

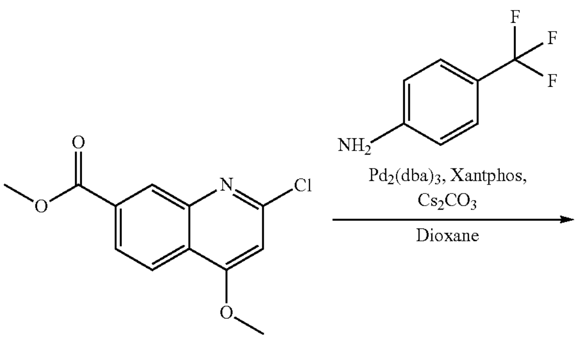

CEN2-X-1563A4

-continued

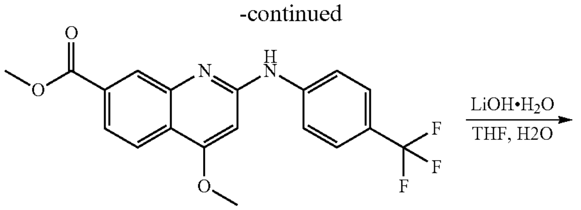

CEN2-X-1730A1

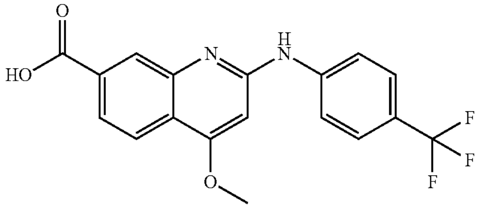

I-333

Methyl 4-methoxy-2-((4-(trifluoromethyl)phenyl)amino) quinoline-7-carboxylate (X-1730A1). To a stirred solution of methyl 2-chloro-4-methoxyquinoline-7-carboxylate (X-1563A4) (0.600 g, 2.39 mmol) in a 1,4-dioxane (6 mL) were added 4-(trifluoromethyl) aniline (0.460 g, 2.86 mmol), cesium carbonate (2.30 g, 7.17 mmol) sequentially at room temperature under nitrogen. The reaction mixture was degassed (purging with nitrogen) for 20 min followed by the addition of $Pd_2(dba)_3$ (0.10 g, 0.11 mmol) and xanthphos (1.38 g, 2.39 mmol) and the resulting mixture was heated at 100° C. for 4 h. Reaction mixture was cooled to room temperature, diluted with water (300 mL), solid precipitate falls out was filtered and dried under high vacuum. Obtained crude product was purified by silica gel column chromatography, using ethyl acetate-hexane=0:1→2:8 as gradient, to afford methyl 4-methoxy-2-((4-(trifluoromethyl)phenyl) amino)quinoline-7-carboxylate (X-1730A1) (0.500 g, 55%) as an solid. MS: $[MH]^+$ 377.11

6-Methoxy-8-(4-(trifluoromethyl)piperidin-1-yl)quinoline-3-carboxylic acid (I-333). To a stirred solution of methyl 4-methoxy-2-((4-(trifluoromethyl)phenyl)amino) quinoline-7-carboxylate (X-1730A1) (0.300 g, 0.79 mmol) in a mixture of THE-water (3:1; 5 mL) was added lithium hydroxide monohydrate (0.100 g, 2.39 mmol) at room temperature and the resulting mixture was heated at 50° C. for 4 h. After cooling to room temperature, the reaction mixture was concentrated under reduced pressure. Aqueous part was acidified (pH~2-3) with an aqueous solution of 1N HCl and the resulting precipitate was collected by filtration. Obtained crude was purified by preparative HPLC using 0.1% Formic acid in water-acetonitrile as gradient to afford 6-methoxy-8-(4-(trifluoromethyl)piperidin-1-yl)quinoline-3-carboxylic acid (I-333) (0.020 g, 7%) as a white solid. $^1H$ NMR (400 MHz, DMSO-$d_6$) δ9.87 (s, 1H), 8.27 (s, 1H), 8.27-8.22 (m, 3H), 8.02-8.00 (d, J=8.8 Hz, 1H), 7.82-7.79 (dd, J=8.4, 1.2 Hz, 1H), 7.70-7.68 (d, J=8.4 Hz, 2H), 6.63 (s, 1H), 4.04 (s, 3H). MS: $[MH]^+$ 363.09

Example 1.243. Synthesis of (R)—N-(1-hydroxybutan-2-yl)-4-methoxy-2-((3-(trifluoromethyl)phenyl) amino)quinoline-7-carboxamide (I-334)

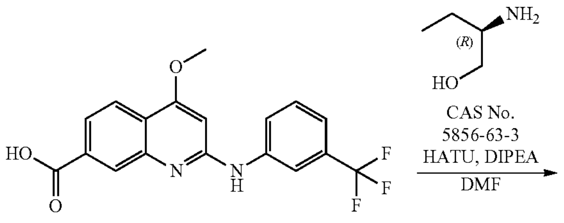

I-335

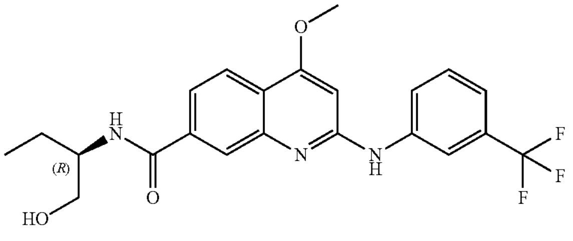

I-334

To a solution of 4-methoxy-2-((3-(trifluoromethyl)phenyl)amino)quinoline-7-carboxylic acid (I-335) (0.1 g, 0.2 mmol)) in DMF (2 mL) were added DIPEA (0.1 mL, 0.8 mmol) and HATU (0.114 g, 0.3 mmol) at 0° C. The resulting reaction mixture was stirred at room temperature for 10 min. (R)-2-aminobutan-1-ol (0.029 g, 0.2 mmol) was added at 0° C. drop-wise and the resulting reaction mixture was stirred at rt for 2 h. Reaction mixture was poured into ice water (50 mL), solid product was precipitated which was collected by filtration, dried under reduced pressure. The resulting crude material was triturated with diethyl ether (30 mL×3), dried over high vacuum to afford (R)—N-(1-hydroxybutan-2-yl)-4-methoxy-2-((3-(trifluoromethyl)phenyl)amino)quinoline-7-carboxamide (I-334) (0.025 g, 20%) as an off-white solid. $^1H$ NMR (400 MHz, DMSO-$d_6$) δ: 9.78 (s, 1H), 8.43 (s, 1H), 8.29-8.28 (t, J=5.2 Hz, 2H), 8.135-8.132 (d, J=1.2 Hz, 1H), 8.00-7.97 (d, J=8.4 Hz, 1H), 7.75-7.72 (dd, J=7.6, 1.6 Hz, 1H), 7.59-7.57 (t, J=8.0 Hz, 1H), 7.29-7.27 (d, J=7.6 Hz, 1H), 6.56 (s, 1H), 4.71-4.68 (t, J=5.6 Hz, 1H), 4.04 (s, 3H), 3.94-3.90 (m, 1H), 3.52-3.38 (m, 2H), 1.74-1.64 (m, 1H), 1.55-1.43 (m, 1H), 0.92-0.90 (t, J=7.6 Hz, 3H). MS: $[MH]^+$ 434.3, Chiral HPLC=92.7%

Example 1.244. Synthesis of 4-methoxy-2-((3-(trifluoromethyl)phenyl)amino)quinoline-7-carboxylic acid (I-335)

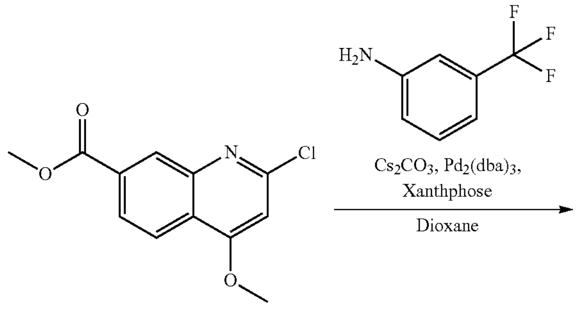

X-1563A4

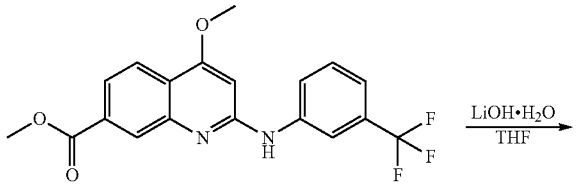

X-1732A1

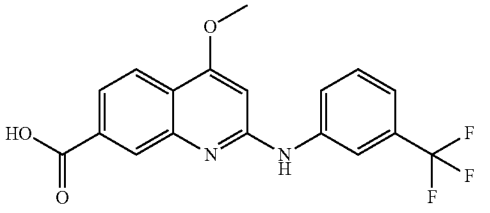

I-335 methyl 4-methoxy-2-((3-(trifluoromethyl)phenyl)amino) quinoline-7-carboxylate (X-1732A1). To a stirred solution of methyl 2-chloro-4-methoxyquinoline-7-carboxylate (1.0 g, 3.9 mmol) in dioxane (10 mL), was added $Cs_2CO_3$ (4.5 g, 13.9 mmol) and added 3-(trifluoromethyl) aniline (0.7 g, 4.7 mmol) at room temperature under nitrogen. The reaction mixture was degassed by purging with $N_{2(g)}$ for 10 min followed by addition of $Pd_2(dba)_3$ (0.18 g, 0.1 mmol) and xanthphos (0.23 g, 0.3 mmol) and the resulting mixture was stirred at 90° C. for 4 h. The reaction mixture was diluted with water (40 mL) and was extracted with DCM (40 mL×3). Combined organic extracts were dried over $Na_2SO_4$ and concentrated under reduced pressure. The crude product was purified by column chromatography (C-18) silica gel column chromatography, using ethyl acetate-hexane=0:1→1:0 as gradient, to afford methyl 4-methoxy-2-((3-(trifluoromethyl)phenyl)amino)quinoline-7-carboxylate (X-1732A1) (1.0 g, 66%) as an off-white solid. MS: $[MH]^+$ 376.1

4-Methoxy-2-((3-(trifluoromethyl)phenyl)amino)quinoline-7-carboxylic acid (I-335). Lithium hydroxide monohydrate (1.6 g, 3.9 mmol) was added to a stirred solution of a mixture of methyl 4 methoxy-2-((3-(trifluoromethyl)phenyl)amino)quinoline-7-carboxylate (X-1732A1) (0.5 g, 1.3 mmol) in of THF-water (2.5:1; 5.0 mL). at room temperature and the resulting reaction mixture was heated at 70° C. for 1 h. After cooling to room temperature, the reaction mixture was concentrated under reduced pressure, diluted with water (30 mL) and extracted with ethyl acetate (30 mL) to remove unwanted organic impurities. The aqueous layer was acidified (pH~2-3) with an aqueous solution of 1N HCl, and the resulting precipitate was collected by filtration. Isolated solid was washed with cold water until the pH of the filtrate became neutral (pH~6-7) and was purified by reverse phase (C-18) silica gel column chromatography, to afford 4-methoxy-2-((3-(trifluoromethyl) phenyl) amino)quinoline-7-carboxylic acid (I-335) (0.3 g, 62%) as a white solid. $^1H$ NMR (400 MHz, DMSO-$d_6$) δ 13.07 (br, 1H), 10.32 (br, 1H), 8.42 (brs, 1H), 8.27 (s, 1H), 8.08 (s, 1H), 8.06-8.02 (m, 1H), 7.87-7.85 (d, J=8.4 Hz, 1H), 7.66-7.62 (t, J=7.6 Hz, 1H), 7.44 (brs, 1H), 6.68 (s, 1H), 4.08 (s, 3H). MS: $[MH]^+$ 363.4

Example 1.245. Synthesis of (R)—N-(1-hydroxybutan-2-yl)-4-methoxy-2-(2-methyl-4-(trifluoromethyl) phenyl)quinoline-7-carboxamide (I-336)

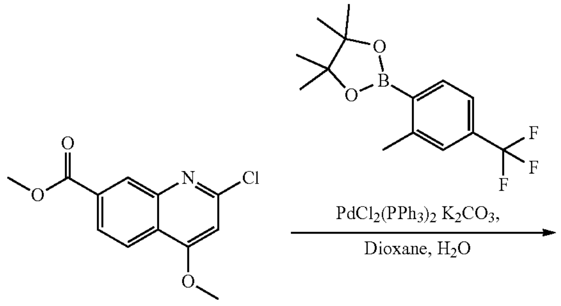

X-1563A4

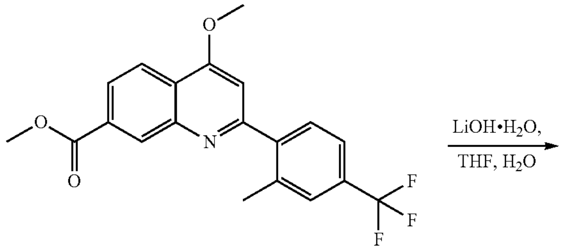

X-1748A1

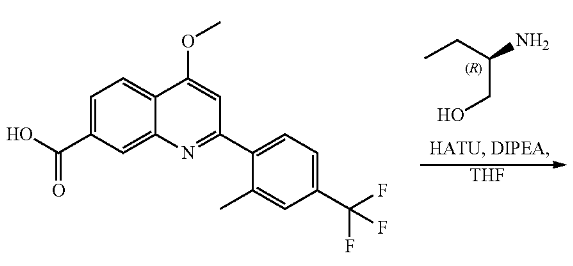

X-1748A2

-continued

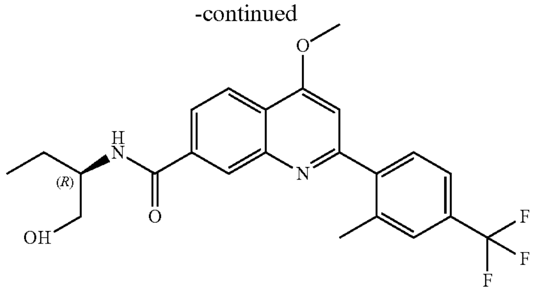

I-336

Methyl 4-methoxy-2-(2-methyl-4-(trifluoromethyl)phenyl)quinoline-7-carboxylate (X-1748A1). To a stirred solution of methyl 2-chloro-4-methoxyquinoline-7-carboxylate (X-1563A4) (0.600 g, 2.30 mmol) in a mixture of 1,4-dioxane-water (7:1, 8 mL) were added 4,4,5,5-tetramethyl-2-(2-methyl-4-(trifluoromethyl)phenyl)-1,3,2-dioxaborolane (1.36 g, 4.7 mmol) and $K_2CO_3$ (0.98 g, 7.10 mmol) sequentially at room temperature under nitrogen. The reaction mixture was degassed (purging with nitrogen) for 20 min followed by the addition of $PdCl_2(PPh_3)_2$ (0.083 g, 0.10 mmol) and the resulting mixture was heated at 100° C. for 3 h. Reaction mixture was cooled to room temperature, diluted with water (200 mL) and was extracted with ethyl acetate (200 mL×3). Combined organic extracts were dried over anhydrous $Na_2SO_4$ and concentrated under reduce pressure to afford crude mass, which was purified by silica gel Combi Flash column chromatography, using ethyl acetate-hexane=0:1→1:3 as eluent, to afford methyl 4-methoxy-2-(2-methyl-4-(trifluoromethyl)phenyl)quinoline-7-carboxylate (X-1748A1) (0.6 g, 67%) as an off-white solid. MS: $[MH]^+$ 376.1.

4-Methoxy-2-(2-methyl-4-(trifluoromethyl)phenyl)quinoline-7-carboxylic acid (X-1748A2). To a stirred solution of methyl 4-methoxy-2-(2-methyl-4-(trifluoromethyl)phenyl)quinoline-7-carboxylate (X-1748A1) (0.400 g, 1.06 mmol) in a mixture of THF-water (2:1; 4.0 mL) was added lithium hydroxide monohydrate (0.076 g, 1.81 mmol) at room temperature and the resulting mixture was stirred at room temperature for 1 h. The reaction mixture was concentrated under reduced pressure, obtained crude was diluted with water (10 mL) and was extracted with ethyl acetate (10 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford 4-methoxy-2-(2-methyl-4-(trifluoromethyl)phenyl)quinoline-7-carboxylic acid (X-1748A2) (0.300 g, 75%) as a white solid. MS: $[MH]^+$ 362.10.

(R)—N-(1-hydroxybutan-2-yl)-4-methoxy-2-(2-methyl-4-(trifluoromethyl)phenyl)quinoline-7-carboxamide (I-336). To a stirred solution of 4-methoxy-2-(2-methyl-4-(trifluoromethyl)phenyl)quinoline-7-carboxylic acid (X-1748A2) (0.280 g, 0.7 mmol) in THE (3 mL) were added DIPEA (0.300 g, 2.30 mmol), HATU (0.440 g, 1.1 mmol) and (R)-2-aminobutan-1-ol (0.442 g, 1.10 mmol) at 0° C. under nitrogen and the resulting mixture was stirred at room temperature for 1 h. Reaction mixture diluted with water (50 mL) and was extracted with ethyl acetate (50 mL×3). Combined organic extracts were washed with brine (40 mL), dried over anhydrous $Na_2SO_4$ and concentrated under reduced pressure. The resulting crude was purified by reverse phase (C-18) silica gel column chromatography, using acetonitrile-water=0:1→5:5 as gradient, to afford (R)—N-(1-hydroxybutan-2-yl)-4-methoxy-2-(2-methyl-4-(trifluoromethyl)phenyl)quinoline-7-carboxamide (I-336) (0.200 g, 71%) as an off-white solid. 1H NMR (400 MHz, DMSO-$d_6$) δ 8.53-8.53 (d, J=1.6 Hz, 1H), 8.39-8.37 (d, J=8.4 Hz, 1H), 8.24-8.22 (d, J=8.8 Hz 1H), 8.05-8.02 (dd, J=8.4, 1.6 Hz, 1H), 7.76-7.70 (m, 3H), 7.27 (s, 1H), 4.75-4.73 (t, J=5.6 Hz, 1H), 4.12 (s, 3H), 3.95-3.90 (m, 1H), 3.53-3.44 (m, 2H), 2.49 (s, 3H), 1.71-1.66 (m, 1H), 1.53-1.46 (m, 1H), 0.92-0.88 (t, J=8.4 Hz, 3H) MS: $[MH]^+$ 433.5.

Example 1.246. Synthesis of (R)-2-(2-fluoro-4-(trifluoromethyl)phenyl)-N-(1-hydroxypropan-2-yl)-4-methoxyquinoline-7-carboxamide (I-337)

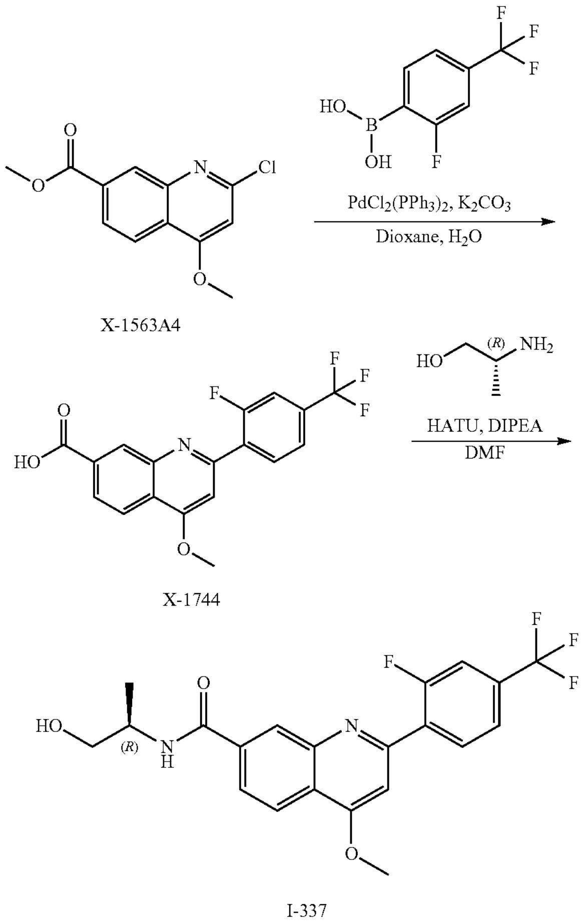

I-337

The following compounds were prepared in a manner analogous to the procedures described above for (R)—N-(1-hydroxybutan-2-yl)-4-methoxy-2-(2-methyl-4-(trifluoromethyl)phenyl)quinoline-7-carboxamide (I-336):

(R)-2-(2-fluoro-4-(trifluoromethyl)phenyl)-N-(1-hydroxypropan-2-yl)-4-methoxyquinoline-7-carboxamide (I-337) (0.280 g, 81%) as an off-white solid. $^1H$ NMR (400 MHz, DMSO-$d_6$) δ 8.60-8.60 (d, J=1.2 Hz, 1H), 8.49-8.47 (d, J=8 Hz, 1H), 8.25-8.21 (m, 2H), 8.07-8.04 (dd, J=1.6 Hz, 8.8 Hz, 1H), 7.93-7.91 (d, J=10.4 Hz, 1H), 7.82-7.80 (d, J=8 Hz, 1H), 7.49-7.49 (d, J=1.6 Hz, 1H), 4.78-4.75 (t, =5.6 Hz, 1H), 4.11 (s, 31H), 4.12-4.07 (m, 1H), 3.54-3.49 (m, 1H), 3.42-3.39 (m, 1H), 1.18-1.17 (d, J=6.8 Hz, 3H). MS: $[MH]^+$ 423.3.

Example 1.247. Synthesis of (R)-2-(2,4-bis(trifluoromethyl)phenyl)-N-(1-hydroxybutan-2-yl)-4-methoxyquinoline-7-carboxamide (I-338)

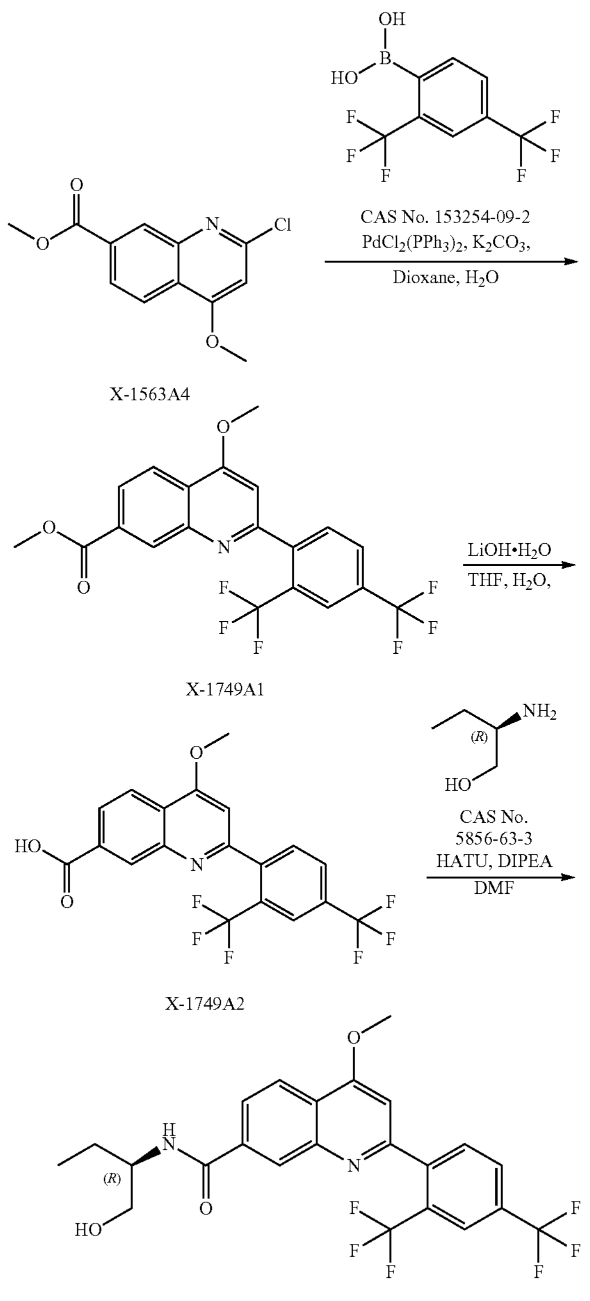

X-1563A4

X-1749A1

X-1749A2

I-338

The following compound was prepared in a manner analogous to the procedures described above for (R)—N-(1-hydroxybutan-2-yl)-4-methoxy-2-(2-methyl-4-(trifluoromethyl)phenyl)quinoline-7-carboxamide (I-336):

(R)-2-(2,4-bis(trifluoromethyl)phenyl)-N-(1-hydroxybutan-2-yl)-4-methoxyquinoline-7-carboxamide (I-338) (0.080 g, 34%) as an off-white solid. $^1H$ NMR (400 MHz, DMSO-$d_6$) δ 8.50 (br. s, 1H), 8.40-8.38 (d, J=8.0 Hz, 1H), 8.25 (br., 3H), 8.07-8.05 (d, J=8.4 Hz, 1H), 7.97-7.95 (d, J=7.6 Hz, 1H), 7.30 (s, 1H), 4.73 (br. s, 1H), 4.10 (s, 3H), 3.92 (br. s, 1H), 3.39-3.37 (m, 2H), 3.38 (2H, merged with DMSO-d6 moisture peak), 1.68-1.47 (m, 2H), 0.92-0.88 (t, J=14.4 Hz, 3H). MS: $[MH]^+$ 487.3

Example 1.248. Synthesis of (R)-2-(2-cyano-4-(trifluoromethyl)phenyl)-N-(1-hydroxybutan-2-yl)-4-methoxyquinoline-7-carboxamide (I-339)

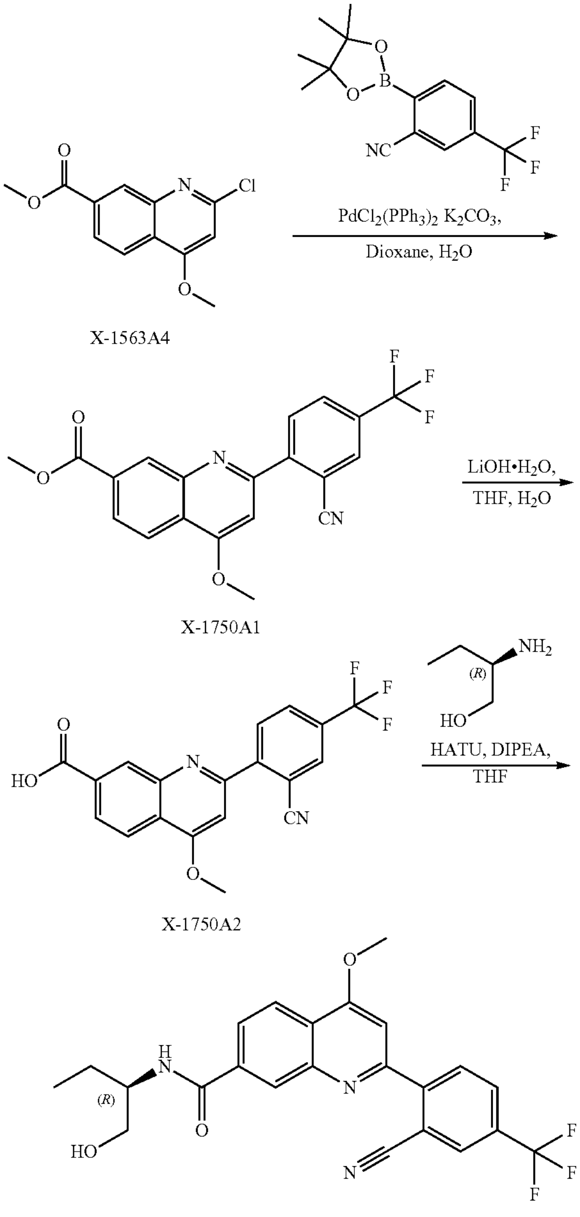

X-1563A4

X-1750A1

X-1750A2

I-339

The following compound was prepared in a manner analogous to the procedures described above for (R)—N-(1-hydroxybutan-2-yl)-4-methoxy-2-(2-methyl-4-(trifluoromethyl)phenyl)quinoline-7-carboxamide (I-336):

(R)-2-(2-cyano-4-(trifluoromethyl)phenyl)-N-(1-hydroxybutan-2-yl)-4-methoxyquinoline-7-carboxamide (I-339) (0.500 g, 22%) as an off-white solid. $^1$H NMR (400 MHz, DMSO-$d_6$) δ 8.59 (s, 1H), 8.54 (s, 1H), 8.45-8.43 (d, J=8.4 Hz, 1H), 8.34-8.26 (m, 3H), 8.11-8.09 (dd, J=8.4 Hz, J=1.2 Hz, 1H), 7.62 (s, 1H), 4.75-4.72 (t, J=5.6 Hz, 1H), 4.19 (s, 3H), 3.96-3.94 (m, 1H), 3.54-3.43 (m, 2H), 1.73-1.67 (m, 1H), 1.58-1.47 (m, 1H), 0.93-0.89 (t, J=7.2 Hz, 3H). MS: $[MH]^+$ 444.40.

Example 1.249. Synthesis of (R)—N-(1-hydroxybutan-2-yl)-4-methoxy-2-(2-methoxy-4,6-bis(trifluoromethyl)phenyl)quinoline-7-carboxamide (I-340)

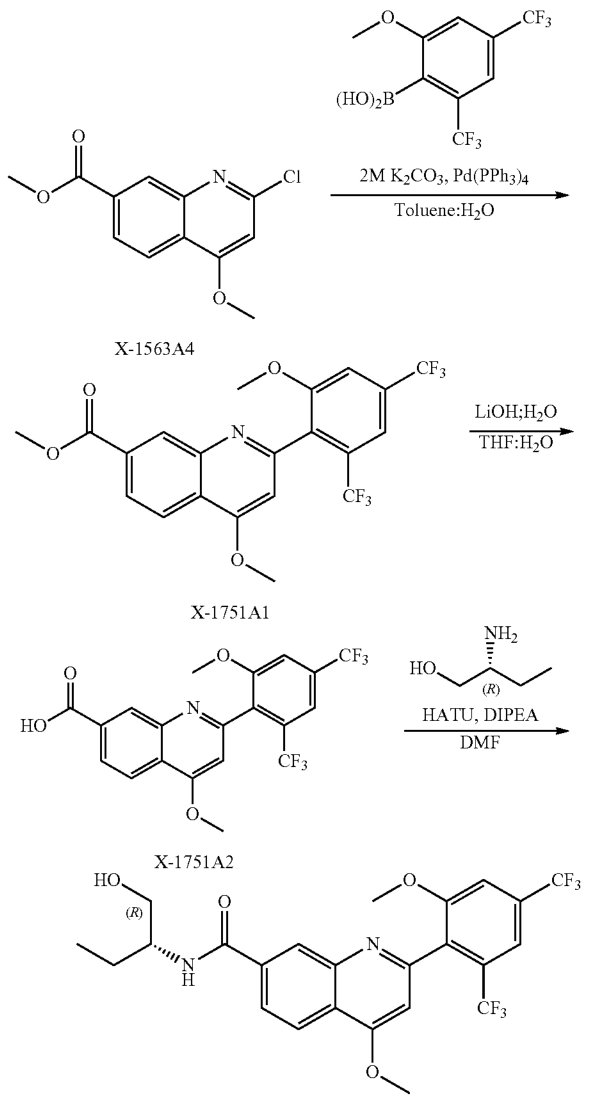

X-1563A4

X-1751A1

X-1751A2

I-340

The following compound was prepared in a manner analogous to the procedures described above for (R)—N-(1-hydroxybutan-2-yl)-4-methoxy-2-(2-methyl-4-(trifluoromethyl)phenyl)quinoline-7-carboxamide (I-336):

(R)—N-(1-hydroxybutan-2-yl)-4-methoxy-2-(2-methoxy-4,6-bis(trifluoromethyl)phenyl)quinoline-7-carboxamide (I-340) (0.06 g, 58%) as an off-white solid. H NMR (400 MHz, DMSO-$d_6$) δ 8.47-8.47 (d, J=1.2 Hz, 1H), 8.38-8.36 (d, J=8.4 Hz, 1H), 8.24-8.22 (d, J=8.4 Hz, 1H), 8.05-8.02 (dd, J=8.4, 1.2 Hz, 1H), 7.83 (s, 1H), 7.77 (s, 1H), 7.17 (s, 1H), 4.70-4.74 (t, J=5.6 Hz, 1H), 4.03 (s, 3H), 3.92-3.87 (m, 1H), 3.84 (s, 3H), 3.52-3.46 (m, 1H), 3.46-3.39 (m, 1H), 1.71-1.65 (m, 1H), 1.51-1.44 (m, 1H), 0.91-0.88 (t, J=7.6 Hz, 3H) MS: $[MH]^+$ 517.4

Example 1.250. Synthesis of (R)-2-(2-chloro-4-(trifluoromethyl)phenyl)-N-(1-hydroxybutan-2-yl)-4-methoxyquinoline-7-carboxamide (I-341)

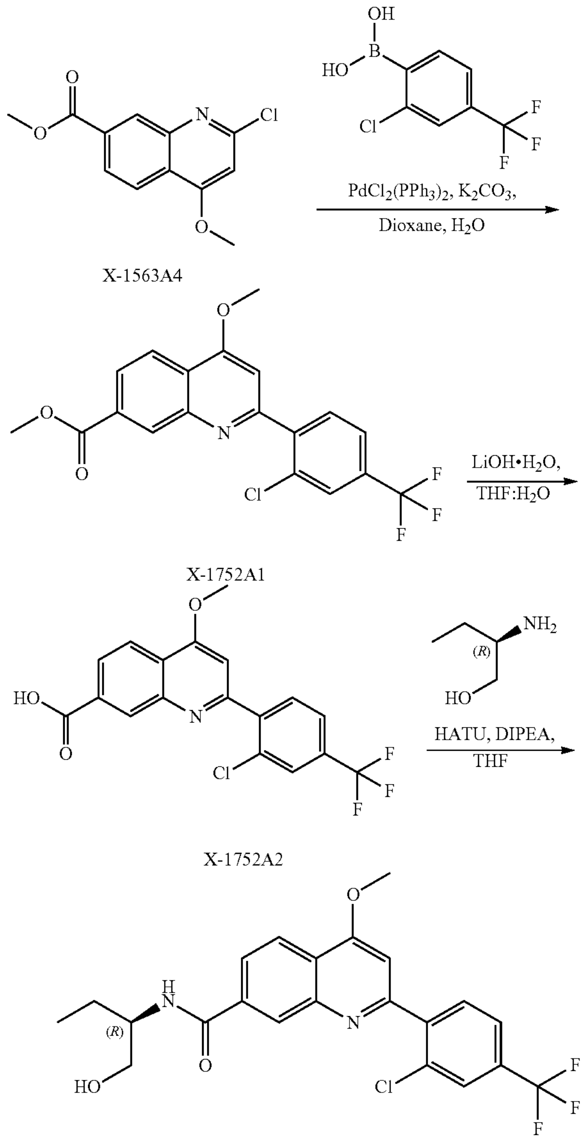

X-1563A4

X-1752A1

X-1752A2

I-341

The following compound was prepared in a manner analogous to the procedures described above for (R)—N-(1-hydroxybutan-2-yl)-4-methoxy-2-(2-methyl-4-(trifluoromethyl)phenyl)quinoline-7-carboxamide (I-336):

(R)-2-(2-chloro-4-(trifluoromethyl)phenyl)-N-(1-hydroxybutan-2-yl)-4-methoxyquinoline-7-carboxamide (I-341) (0.190 g, 52%) as a yellow solid. $^1$H NMR (400 MHz, DMSO-$d_6$) δ 8.57 (d, J=1.2 Hz, 1H), 8.40-8.37 (d, J=8.4 Hz, 1H), 8.26-8.24 (d, J=8.8 Hz, 1H), 8.08-8.05 (m, 2H), 7.91-7.91 (d, J=0.8 Hz, 2H), 7.39 (s, 1H), 4.72 (brs, 1H), 4.12 (s, 3H), 3.96-3.90 (m, 1H), 3.53-3.40 (m, 2H), 1.72-1.66 (m, 1H), 1.53-1.46 (m, 1H), 0.92-0.88 (t, J=8.4 Hz, 3H), MS: $[MH]^+$ 453.4

Example 1.251. (R)—N-(1-hydroxybutan-2-yl)-4-methoxy-2-(2-methoxy-4-(trifluoromethyl)phenyl) quinoline-7-carboxamide (I-342)

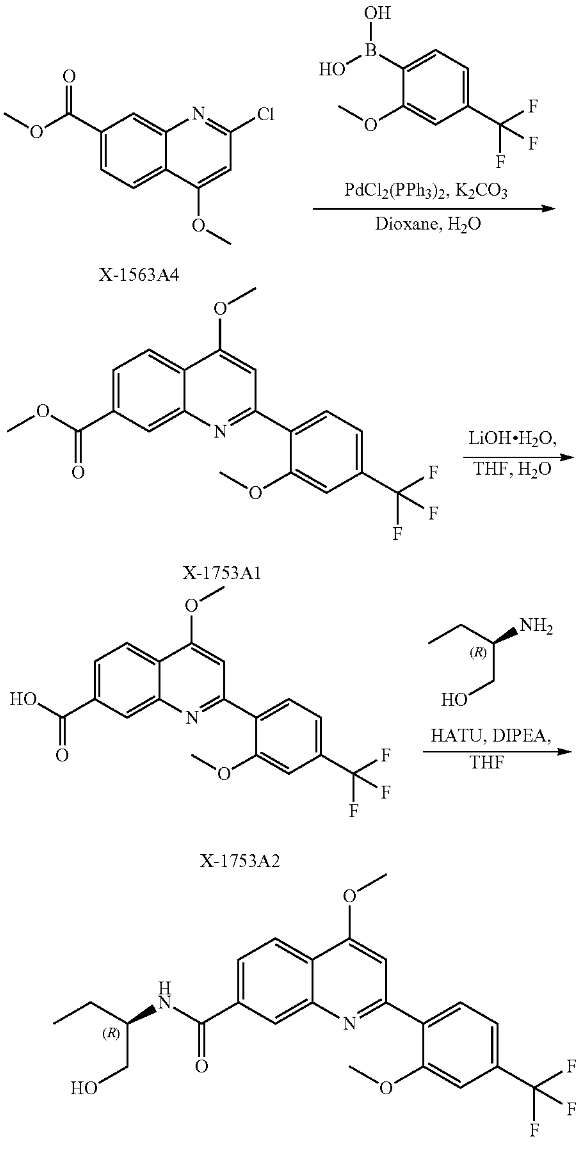

X-1563A4
X-1753A1
X-1753A2
I-342

The following compound was prepared in a manner analogous to the procedures described above for (R)—N-(1-hydroxybutan-2-yl)-4-methoxy-2-(2-methyl-4-(trifluoromethyl)phenyl)quinoline-7-carboxamide (I-336):

(R)—N-(1-hydroxybutan-2-yl)-4-methoxy-2-(2-methoxy-4-(trifluoromethyl)phenyl)quinoline-7-carboxamide (I-342) (0.110 g, 32%) as an off-white solid. $^1$H NMR (400 MHz, DMSO-$d_6$) δ 8.58-8.57 (d, J=0.8 Hz, 1H), 8.38-8.36 (d, J=8.4 Hz, 1H), 8.22-8.19 (d, J=8.4 Hz, 1H), 8.03-8.01 (m, J=8.4, 1.6 Hz, 1H), 7.99-7.97 (d, J=7.6 Hz, 1H), 7.50 (s, 2H), 7.50-7.48 (d, J=6.4 Hz, 1H), 4.72-4.70 (t, J=6.0 Hz, 1H), 4.10 (s, 3H), 3.97 (s, 3H), 3.97-3.92 (m, 1H), 3.52-3.38 (m, 2H), 1.71-1.66 (m, 1H), 1.54-1.48 (m, 1H), 0.93-0.89 (t, J=7.6 Hz, 3H). MS: $[MH]^+$ 449.4.

Example 1.252. Synthesis of (R)—N-(1-hydroxy-3-methylbutan-2-yl)-4-methoxy-2-(4-(trifluoromethyl) phenyl)quinoline-7-carboxamide (I-343)

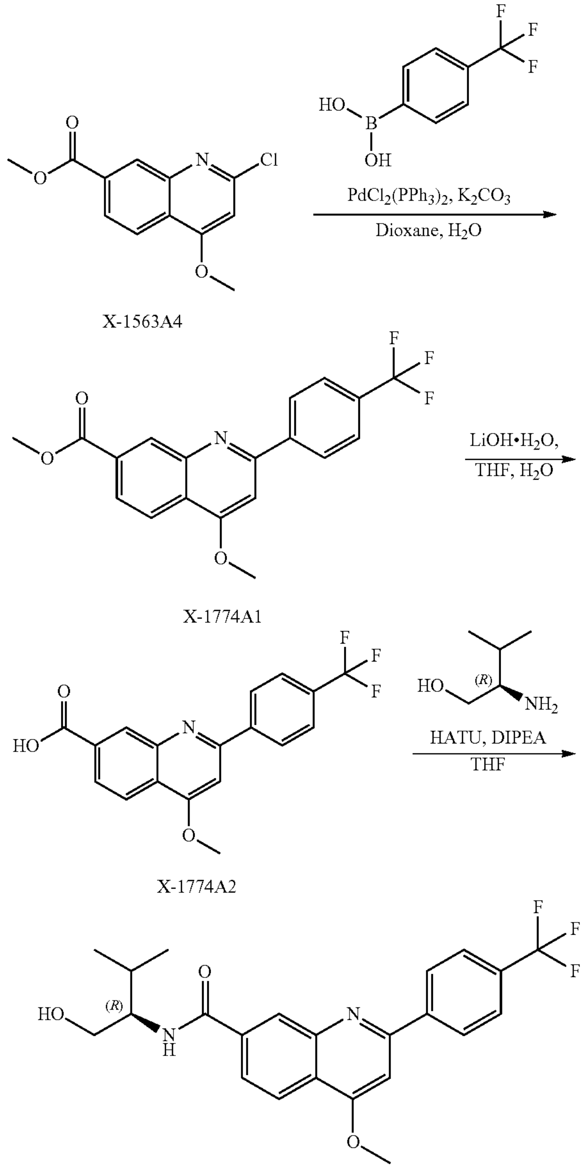

X-1563A4
X-1774A1
X-1774A2
I-343

The following compound was prepared in a manner analogous to the procedures described above for (R)—N-(1-hydroxybutan-2-yl)-4-methoxy-2-(2-methyl-4-(trifluoromethyl)phenyl)quinoline-7-carboxamide (I-336):

(R)—N-(1-hydroxy-3-methylbutan-2-yl)-4-methoxy-2-(4-(trifluoromethyl)phenyl)quinoline-7-carboxamide (I-343) (0.180 g, 36%) as an off-white solid. $^1$H NMR (400 MHz, DMSO-$d_6$) δ 8.61-8.61 (d, J=1.2 Hz, 1H), 8.57-8.55 (d, J=8.0 Hz, 2H), 8.38-8.36 (d, J=8.8 Hz, 1H), 8.22-8.20 (d, J=8.8 Hz, 1H), δ 8.02-8.00 (dd, J=8.8 Hz, J=1.6 Hz 1H), 7.95-7.93 (d, J=8.4 Hz, 2H), 7.73 (s, 1H), 4.64-4.61 (t, J=5.6 Hz, 1H), 4.22 (s, 3H), 3.91-3.86 (m, 1H), 3.60-3.54 (m, 2H), 2.00-1.94 (m, 1H), 0.96-0.92 (t, J=7.2 Hz, 6H) MS: [MH] 433.35.

Example 1.253. Synthesis of (R)—N-(1-cyclopropyl-2-hydroxyethyl)-4-methoxy-2-(4-(trifluoromethyl)phenyl)quinoline-7-carboxamide (I-344)

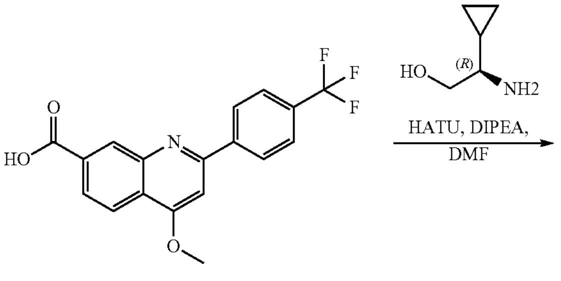

I-181

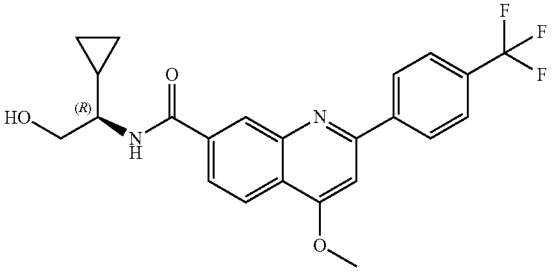

I-344

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(1-cyclopropyl-2-hydroxyethyl)-4-methoxy-2-(4-(trifluoromethyl)phenyl)quinoline-7-carboxamide (I-344) (0.150 g, 60%) as a white solid. $^1$H NMR (400 MHz, DMSO-$d_6$) δ: 8.62-8.61 (d, J=8.0 Hz, 1H), 8.56-8.54 (d, J=8.0 Hz, 2H), 8.54 (s, 1H), 8.22-8.20 (d, J=8.4 Hz, 1H), 8.03-8.00 (dd, J=1.6, 8.8 Hz, 1H), 7.96-7.94 (d, J=8.0 Hz, 2H), 7.73 (s, 1H), 4.74-4.71 (t, J=5.6, 6.0 Hz, 1H), 4.22 (s, 3H), 3.63-3.60 (t, J=11.6 Hz, 2H), 3.57-3.39 (m, 1H), 1.05-1.02 (m, 1H), 0.49-0.25 (m, 4H), MS: [MH]$^+$ 431.4, Chiral HPLC=97.75%

Example 1.254. Synthesis of (R)—N-(2-hydroxy-1-phenylethyl)-4-methoxy-2-(4-(trifluoromethyl)phenyl)quinoline-7-carboxamide (I-345)

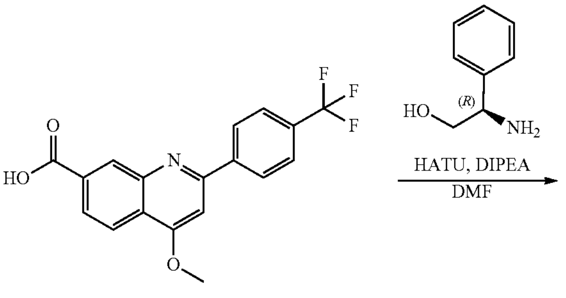

I-181

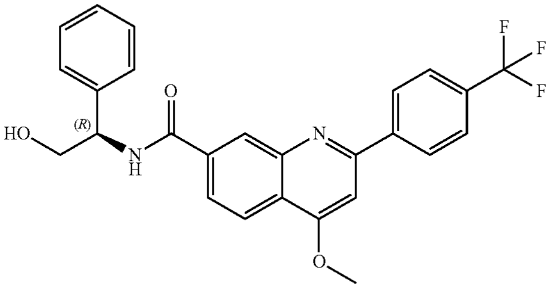

I-345

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(2-hydroxy-1-phenylethyl)-4-methoxy-2-(4-(trifluoromethyl)phenyl)quinoline-7-carboxamide (I-345) (0.100 g, 21%) as a white solid. $^1$H NMR (400 MHz, DMSO-$d_6$) δ: 9.12-9.10 (d, J=8.0 Hz, 1H), 8.70 (s, 1H), 8.57-8.55 (d, J=8.4 Hz, 2H), 8.24-8.21 (d, J=8.8 Hz, 1H), 8.03-8.01 (d, J=8.4 Hz, 1H), 7.96-7.94 (d, J=8.0 Hz, 2H), 7.74 (s, 1H), 7.46-7.44 (d, J=7.2 Hz, 2H), 7.36-7.33 (t, J=7.6 Hz, 2H), 7.27-7.23 (t, J=7.2 Hz, 1H), 5.2-5.12 (m, 1H), 5.02-5.00 (t, J=5.6 Hz, 1H), 4.22 (s, 3H), 3.79-3.76 (m, 1H), 3.72-3.66 (m, 1H). MS: [MH]$^+$ 467.4, Chiral HPLC=99.53%

Example 1.255. Synthesis of (4-methoxy-2-(4-(trifluoromethyl)phenyl)quinoline-7-carbonyl)-D-alanine (I-346)

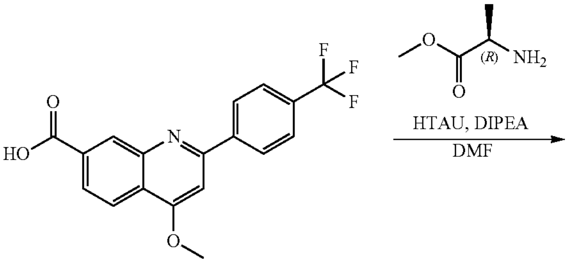

I-181

-continued

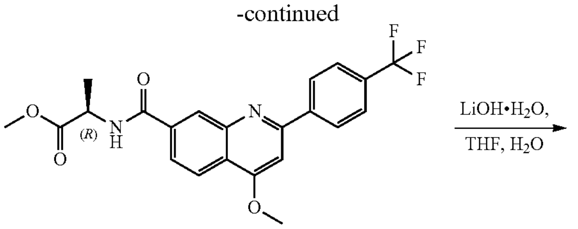

X-1786A1

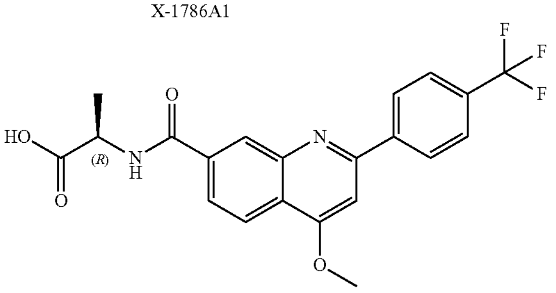

I-346

The following compound was prepared in a manner analogous to the procedures described for (R)-4-(2-hydroxy-1-(4-methoxy-2-(4-(trifluoromethyl)phenyl)quinoline-7-carboxamido)ethyl)benzoic acid (I-364):

(4-methoxy-2-(4-(trifluoromethyl)phenyl)quinoline-7-carbonyl)-D-alanine (I-346) (0.050 g, 32%) as an off-white solid. $^1$H NMR (400 MHz, DMSO-$d_6$) δ: 12.6 (br. s, 1H), 9.05-9.03 (d, J=7.2 Hz, 1H), 8.65-8.64 (d, J=1.2 Hz, 1H), 8.56-8.54 (d, J=8.4 Hz, 2H), 8.24-8.22 (d, J=8.8 Hz, 1H), 8.04-8.01 (dd, J=1.6, 8.8 Hz, 1H), 7.96-7.93 (d, J=8.4 Hz, 2H), 7.74 (s, 1H), 4.52-4.45 (m, 1H), 4.22 (s, 3H), 1.46-1.44 (d, J=7.2 Hz, 3H). MS: $[MH]^+$ 419.4. Chiral HPLC=100.0%

Example 1.256. Synthesis of (S)-3-(1-(4-methoxy-2-(4-(trifluoromethyl)phenyl)quinoline-7-carboxamido)ethyl)benzoic acid (I-347)

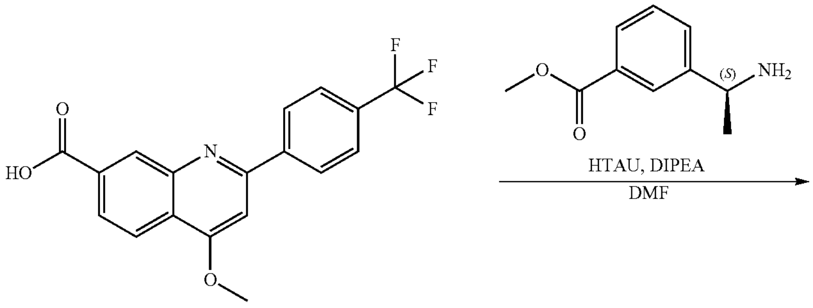

I-181

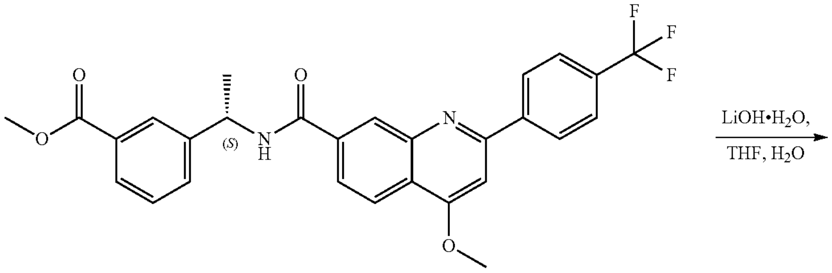

X-1787A1

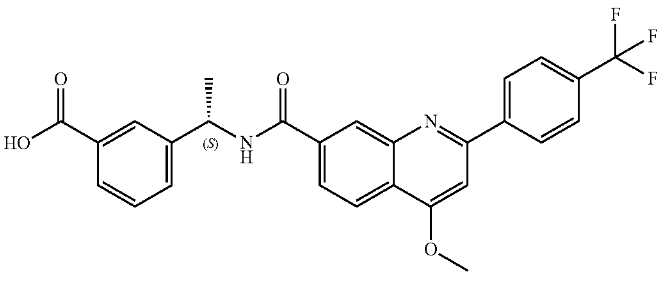

I-347

The following compound was prepared in a manner analogous to the procedures described for (R)-4-(2-hydroxy-1-(4-methoxy-2-(4-(trifluoromethyl)phenyl)quinoline-7-carboxamido)ethyl)benzoic acid (I-364):

(S)-3-(1-(4-methoxy-2-(4-(trifluoromethyl)phenyl)quinoline-7-carboxamido)ethyl)benzoic acid (I-347) (0.055 g, 22%) as an off-white solid. $^1$H NMR (400 MHz, DMSO-$d_6$) δ: 9.32-9.30 (d, J=8.0 Hz, 1H), 8.68-8.68 (d, J=1.6 Hz, 1H), 8.56-8.54 (d, J=8.0 Hz, 2H), 8.25-8.23 (d, J=8.4 Hz, 1H), 8.06-8.02 (m, 2H), 7.97-7.95 (d, J=8.4 HZ 2H), 7.84-7.82 (d, J=7.6 Hz, 1H), 7.75 (s, 1H), 7.71-7.69 (d, J=8.0 Hz, 1H) 8.50-8.47 (t, J=7.6 Hz, 1H), 5.32-5.25 (m, 1H), 4.21 (s, 3H), 1.57-1.55 (d, J=7.2 Hz, 3H). MS: $[MH]^+$ 495.4. Chiral HPLC=99.68%

Example 1.257. Synthesis of (S)-4-methoxy-N-(1-(3-methoxyphenyl)ethyl)-2-(4-(trifluoromethyl)phenyl)quinoline-7-carboxamide (I-348)

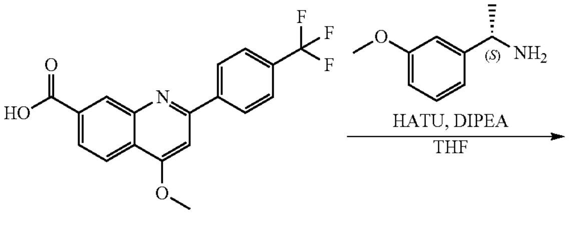

I-181

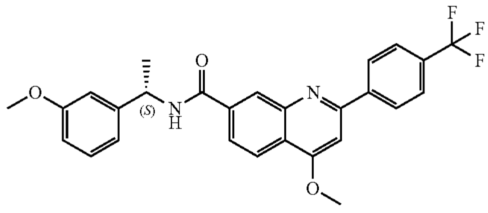

I-348

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(S)-4-methoxy-N-(1-(3-methoxyphenyl)ethyl)-2-(4-(trifluoromethyl)phenyl)quinoline-7-carboxamide (I-348) (0.100 g, 48%) as an off-white solid. $^1$H NMR (400 MHz, DMSO-$d_6$) δ: 9.18-9.16 (d, J=8.0 Hz, 1H), 8.65 (s, 1H), 8.57-8.55 (d, J=8.0 Hz, 2H), 8.23-8.21 (d, J=8.8 Hz, 1H), 8.02-8.00 (dd, J=1.2, 8.4 Hz, 1H), 7.96-7.93 (d, J=8.4 Hz, 2H), 7.73 (s, 1H), 7.28-7.24 (t, J=8.0 Hz, 1H), 7.03-6.98 (m, 2H), 6.82-6.80 (dd, J=1.2, 8.0 Hz, 1H), 5.24-5.17 (m, 1H), 4.21 (s, 3H), 3.79 (s, 3H), 1.53-1.48 (d, J=6.8 Hz, 3H). MS: $[MH]^+$ 404.97, Chiral HPLC=99.68%

Example 1.258. Synthesis of (S)—N-(1-(3-hydroxyphenyl)ethyl)-4-methoxy-2-(4-(trifluoromethyl)phenyl)quinoline-7-carboxamide (I-349)

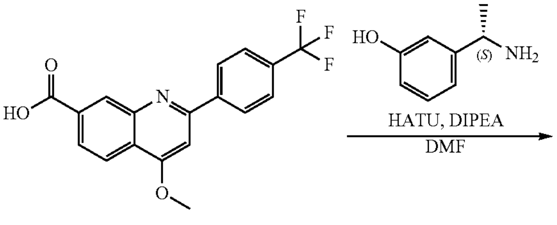

I-181

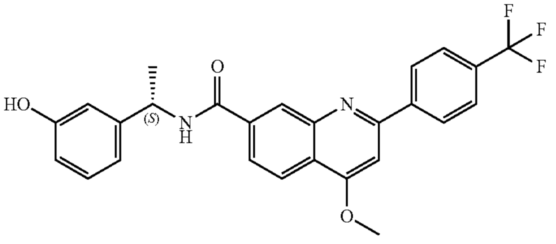

I-349

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(S)—N-(1-(3-hydroxyphenyl)ethyl)-4-methoxy-2-(4-(trifluoromethyl)phenyl)quinoline-7-carboxamide (I-349) (0.030 g, 15%) as a white solid. $^1$H NMR (400 MHz, DMSO-$d_6$) δ: 9.34 (s, 1H), 9.16-9.14 (d, J=8.0 Hz, 1H), 8.66-8.66 (d, J=1.2 Hz, 1H), 8.57-8.55 (d, J=8.4 Hz, 2H), 8.23-8.21 (d, J=8.4 Hz, 1H), 8.03-8.0 (dd, J=1.6, 8.4 Hz, 1H), 7.96-7.94 (d, J=8.0 Hz, 2H), 7.74 (s, 1H), 7.15-7.11 (t, J=8.0, Hz, 1H), 6.87 (s, 1H), 6.87-6.85 (d, J=7.2, Hz, 1H), 6.64-6.61 (m, 1H), 5.18-5.12 (m, 1H), 4.22 (s, 3H), 1.51-1.49 (d, J=6.8 Hz, 3H). MS: $[MH]^+$ 467.4, Chiral HPLC=99.21%

Example 1.259. Synthesis of (S)—N-(1-(3-aminophenyl)ethyl)-4-methoxy-2-(4-(trifluoromethyl)phenyl)quinoline-7-carboxamide (I-350)

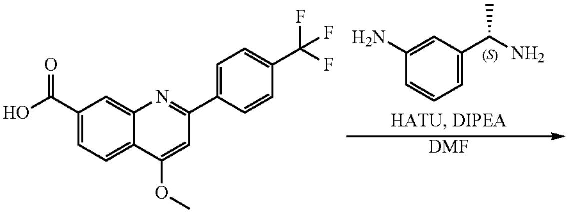

I-181

-continued

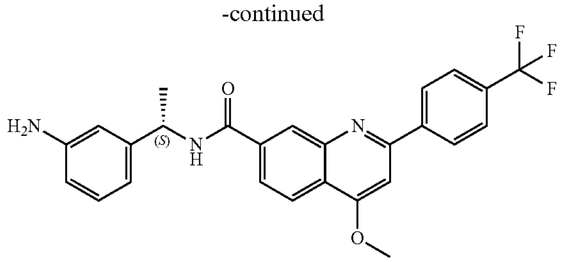

I-350

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(S)—N-(1-(3-aminophenyl)ethyl)-4-methoxy-2-(4-(trifluoromethyl)phenyl)quinoline-7-carboxamide (I-350) (0.050 g, 19%) as a white solid. 1H NMR (400 MHz, DMSO-$d_6$) δ 9.10-9.08 (d, J=8.4 Hz, 1H), 8.66-8.65 (d, J=1.2 Hz, 1H), 8.57-8.55 (d, J=8.4 Hz, 2H), 8.22-8.20 (d, J=8.8 Hz, 1H), 8.03-8.01 (dd, J=1.6, 8.8 Hz, 1H), 7.96-7.93 (d, J=8.4 Hz, 2H) 7.73 (s, 1H), 6.99-6.95 (t, J=8.0 Hz, 1H), 6.63-6.62 (m, 2H), 6.43-6.41 (dd, J=1.2, 7.6 Hz, 1H), 5.11-5.07 (m, 1H), 5.02 (s, 2H), 4.21 (s, 3H), 1.49-1.47 (d, J=6.8 Hz, 3H). MS: $[MH]^+$ 466.4, Chiral HPLC=98.28%

Example 1.260. Synthesis of (S)-4-methoxy-N-(1-phenylethyl)-2-(4-(trifluoromethyl)phenyl)quinoline-7-carboxamide (I-351)

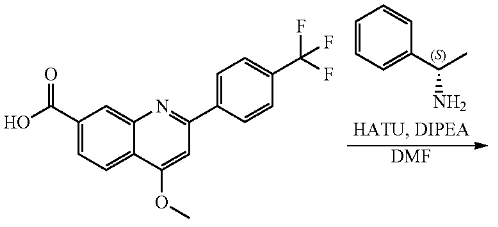

I-181

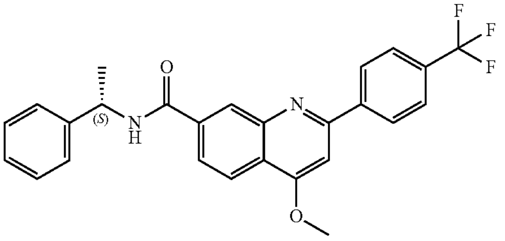

I-351

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(S)-4-methoxy-N-(1-phenylethyl)-2-(4-(trifluoromethyl)phenyl)quinoline-7-carboxamide (I-351) (0.100 g, 51%) as a white solid. 1H NMR (400 MHz, DMSO-$d_6$) δ 9.21-9.19 (d, J=8.0 Hz, 1H), 8.66-8.66 (d, J=1.2 Hz, 1H), 8.57-8.55 (d, J=8.0 Hz, 2H), 8.23-8.20 (d, J=8.8 Hz, 1H), 8.03-8.00 (dd, J=1.6, 8.8 Hz, 1H), 7.95-7.93 (d, J=8.4 Hz, 2H) 7.73 (s, 1H), 7.46-7.45 (d, J=7.6 Hz, 2H), 7.37-7.33 (t, J=7.6 Hz, 2H), 7.26-7.22 (t, J=7.2 Hz, 1H), 5.28-5.20 (m, 1H), 4.21 (s, 3H), 1.54-1.53 (d, J=7.2, Hz, 3H). MS: $[MH]^+$ 451.4, Chiral HPLC=99.12%

Example 1.261. Synthesis of N-(1-hydroxy-2-methylpropan-2-yl)-4-methoxy-2-(4-(trifluoromethyl)phenyl)quinoline-7-carboxamide (I-352)

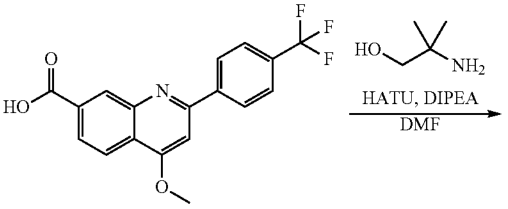

I-181

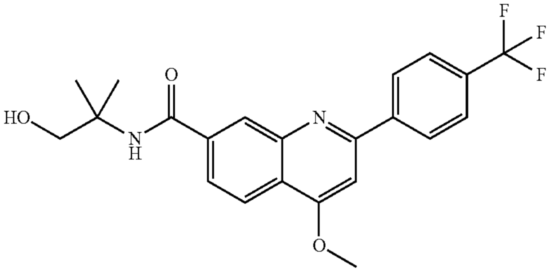

I-352

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

N-(1-hydroxy-2-methylpropan-2-yl)-4-methoxy-2-(4-(trifluoromethyl)phenyl)quinoline-7-carboxamide (I-352) (0.145 g, 36%) as a white solid. $^1H$ NMR (400 MHz, DMSO-$d_6$) δ: 8.56-8.52 (m, 3H), 8.20-8.18 (d, J=8.4 Hz, 1H), 7.95-7.93 (d, J=8.4 Hz, 4H), 7.72 (s, 1H), 4.95-4.92 (t, J=6.4 Hz, 1H), 4.21 (s, 3H), 3.57-3.56 (d, J=6.4 Hz, 2H), 1.37 (s, 6H), MS: $[MH]^+$ 419.4.

Example 1.262. Synthesis of N-(1-(hydroxymethyl)cyclopropyl)-4-methoxy-2-(4-(trifluoromethyl)phenyl)quinoline-7-carboxamide (I-353)

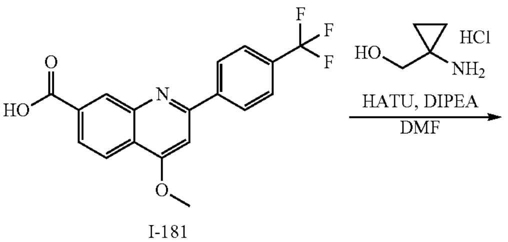

I-181

-continued

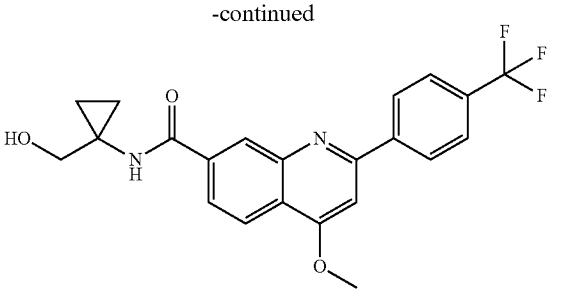

I-353

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

N-(1-(hydroxymethyl)cyclopropyl)-4-methoxy-2-(4-(trifluoromethyl)phenyl)quinoline-7-carboxamide (I-353) (0.015 g, 6%) as a white solid. $^1$H NMR (400 MHz, DMSO-$d_6$) δ: 9.0 (s, 1H), 8.57-8.53 (m, 3H), 8.20-8.18 (d, J=8.4 Hz, 1H), 8.0-7.98 (d, J=8.8 Hz, 1H), 7.95-7.93 (d, J=8.4 Hz, 2H), 7.71 (s, 1H), 4.81-4.78 (t, J=5.6 Hz, 1H), 4.20 (s, 3H), 3.59-3.57 (d, J=5.6 Hz, 2H), 0.79-0.77 (d, J=9.2 Hz, 4H), MS: [MH]417.4.

Example 1.263. Synthesis of N-(tert-butyl)-4-methoxy-2-(4-(trifluoromethyl)phenyl)quinoline-7-carboxamide (I-354)

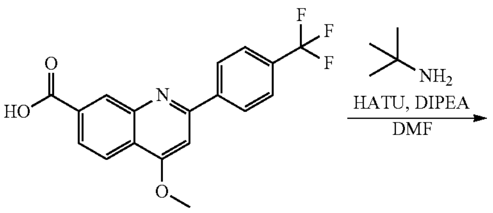

I-181

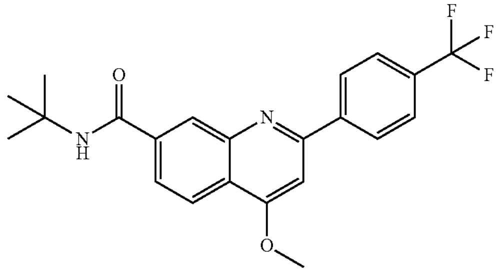

I-354

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

N-(tert-butyl)-4-methoxy-2-(4-(trifluoromethyl)phenyl)quinoline-7-carboxamide (I-354) (0.150 g, 65%) as a white solid. 1H NMR (400 MHz, DMSO-$d_6$) δ 8.56-8.54 (d, J=8.0 Hz, 2H), 8.52-8.51 (d, J=1.2 Hz, 1H), 8.19 (s, 1H), 8.17-816 (d, J=2.8 Hz, 1H), 7.96-7.93 (m, 3H), 7.72 (s, 1H), 4.21 (s, 3H), 1.44 (s, 9H). MS: $[MH]^+$ 403.4.

Example 1.264. Synthesis of 4-methoxy-2-(4-(trifluoromethyl)phenyl)quinoline-7-carbonitrile (I-355)

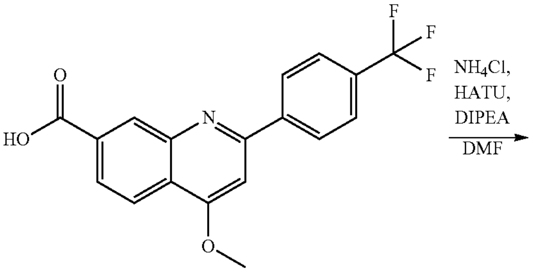

I-181

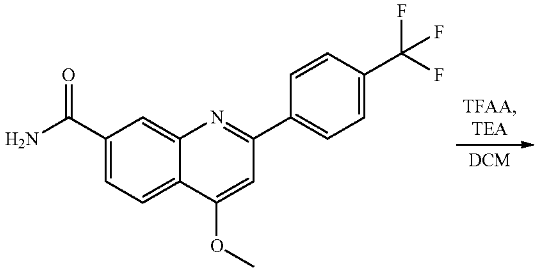

X-1805A1

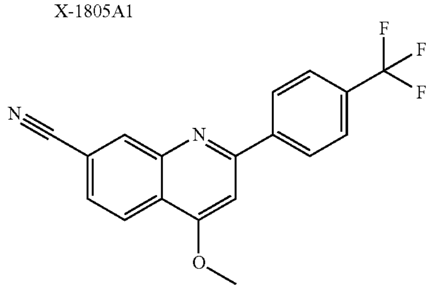

I-355

4-Methoxy-2-(4-(trifluoromethyl)phenyl)quinoline-7-carboxamide (X-1805A1). To a stirred solution of 4-methoxy-2-(4-(trifluoromethyl)phenyl)quinoline-7-carboxylic acid (I-181) (1.00 g, 2.88 mmol) in a DMF (10 mL) were added DIPEA (1.858 g, 14.10 mmol) and HATU (2.190 g, 5.76 mmol) sequentially at 0° C. under nitrogen. After stirring for 10 min at the same temperature, was added ammonium-chloride (0.458 g 8.64 mmol) and stirring was continued at the room temperature for 2 h. Reaction mixture was poured into ice water (100 mL), solid product was precipitated which was collected by filtration, dried under reduced pressure. The resulting crude material was triturated with n-Pentane (10 mL×3) dried over high vacuum to afford 4-methoxy-2-(4-(trifluoromethyl)phenyl)quinoline-7-carboxamide (X-1805A1) (1.0 g, 100%) as an off-white solid. LCMS: $[MH]^+$ 347.2

4-methoxy-2-(4-(trifluoromethyl)phenyl)quinoline-7-carbonitrile (I-355). To a solution of 4-methoxy-2-(4-(trifluoromethyl)phenyl)quinoline-7-carboxamide (X-1805A1) (1.00 g, 2.89 mmol) in DCM (5 mL) at 0° C. was added TEA (0.875 g, 8.67 mmol) and TFAA (2.190 g, 10.11 mmol). The mixture was stirred at room temperature for 16 h. The mixture was diluted with water (60 mL) and extracted with EtOAc (100 mL×2). The combined organic layers were washed with brine, dried over $Na_2SO_4$, filtered and concentrated. The residue obtained was purified by silica gel column chromatography, using ethyl acetate-hexane=0: 1→1:9 as gradient, to afford 4-methoxy-2-(4-(trifluoromethyl)phenyl)quinoline-7-carbonitrile (I-355) (0.800 g, 84%) as a white solid. $^1$H NMR (400 MHz, DMSO-$d_6$) δ 8.573-8.570 (d, J=1.2 Hz, 1H), 8.53-8.51 (d, J=8.0 Hz, 2H), 8.29-8.27 (d, J=8.8 Hz, 1H), 7.95-7.93 (d, J=8.0 Hz, 2H), 7.89-7.86 (dd, =8.8, 2.4 Hz, 1H), 7.79 (s, 1H), 4.22 (s, 3H). MS: [MH]$^+$ 329.3.

Example 1.265. Synthesis of (R)—N-(1-hydroxybutan-2-yl)-4-methoxy-2-((3-(trifluoromethyl)benzyl)amino)quinoline-7-carboxamide (I-356)

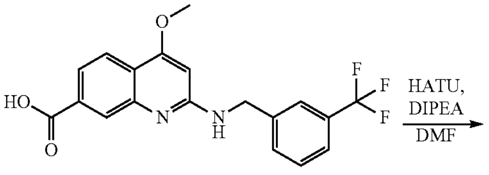

I-359

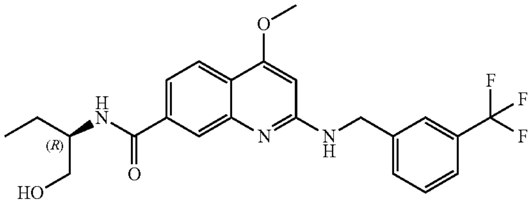

I-356

The following compound was prepared in a manner analogous to the procedures described for (R)—N-(1-hydroxypropan-2-yl)-4-methoxy-2-(4-(trifluoromethyl)phenyl)quinoline-7-carboxamide (I-324):

(R)—N-(1-hydroxybutan-2-yl)-4-methoxy-2-((3-(trifluoromethyl)benzyl)amino)quinoline-7-carboxamide (I-356) (0.060 g, 33%) as an off-white solid. $^1$H NMR (400 MHz, DMSO-$d_6$) δ: 8.16-8.14 (d, J=8.4 Hz, 1H), 7.95 (d, J=1.2 Hz, 1H), 7.87-7.85 (d, J=8.8 Hz, 1H), 7.74 (s, 1H), 7.71-7.69 (d, J=7.2, 1H), 7.61-7.55 (m, 4H), 6.36 (s, 1H), 4.76-4.75 (d, J=5.6 Hz, 2H), 4.67-4.64 (t, J=5.6 Hz, 1H), 3.95 (s, 3H), 3.92-3.85 (m, 1H), 3.49-3.34 (m, 2H), 1.69-1.61 (m, 1H), 1.48-1.41 (m, 1H), 0.88-0.85 (t, J=7.6 Hz, 3H). MS: [MH]$^+$ 448.4, Chiral HPLC=100%

Example 1.266. (R)—N-(1-hydroxybutan-2-yl)-4-methoxy-2-((4-(trifluoromethyl)benzyl)amino)quinoline-7-carboxamide (I-357)

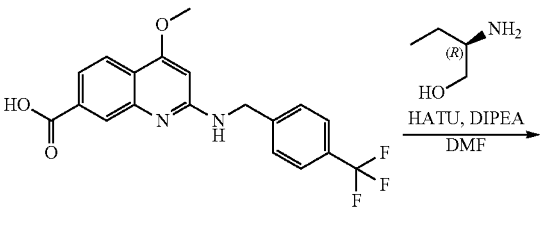

I-360

-continued

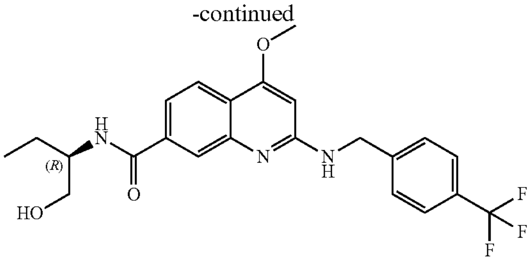

I-357

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(1-hydroxybutan-2-yl)-4-methoxy-2-((4-(trifluoromethyl)benzyl)amino)quinoline-7-carboxamide (I-357) (0.020 g, 17%) as an off-white solid. $^1$H NMR (400 MHz, DMSO-$d_6$) δ 8.15-8.13 (d, J=8.4 Hz, 1H), 7.93-7.93 (d, J=1.2 Hz, 1H), 7.87-7.85 (d, J=8.8 Hz, 1H), 7.70-7.68 (d, J=8.0 Hz, 2H), 7.65-7.56 (m, 4H), 6.36 (s, 1H), 4.77-4.75 (d, J=5.6 Hz, 2H), 4.67-4.65 (t, J=6.0 Hz, 1H), 3.95 (s, 3H), 3.90-3.84 (m, 1H), 3.48-3.34 (m, 2H), 1.68-1.62 (m, 1H), 1.48-1.42 (m, 1H), 0.88-0.86 (t, J=7.2 Hz, 3H). MS: [MH]$^+$ 448.4, Chiral HPLC=100%

Example 1.267. Synthesis of (R)—N-(1-hydroxybutan-2-yl)-4-methoxy-2-(5-(trifluoromethyl)pyridin-2-yl)quinoline-7-carboxamide (I-358)

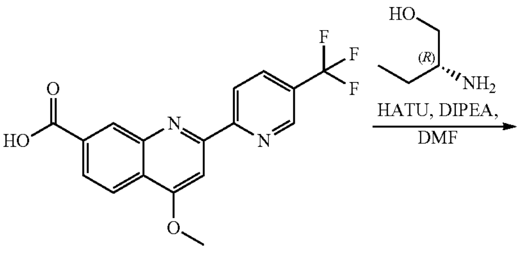

I-361

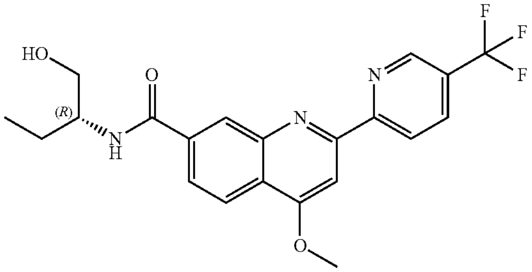

I-358

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(1-hydroxybutan-2-yl)-4-methoxy-2-(5-(trifluoromethyl)pyridin-2-yl)quinoline-7-carboxamide (I-358) (0.055 g, 22%) as an off-white solid. $^1$H NMR (400 MHz, DMSO-$d_6$) δ: 9.18 (s, 1H), 8.83-8.81 (d, J=8.4 Hz, 1H), 8.64 (s, 1H) 8.48-8.43 (t, J=9.6 Hz, 2H), 8.26-8.24 (d, J=8.4 Hz, 1H), 8.12 (s, 1H), 8.07-8.05 (d, J=8.8 Hz, 1H), 4.75-4.74 (t, J=5.6 Hz, 1H), 4.20 (s, 3H), 3.96-3.94 (m, 1H), 3.55-3.49 (m, 1H), 3.47-3.42 (m, 1H), 1.74-1.67 (m, 1H), 1.55-1.47 (m, 1H), 0.94-0.90 (t, J=7.2 Hz, 3H), MS: $[MH]^+$ 420.5, Chiral HPLC=100%

Example 1.268. Synthesis of 4-Methoxy-2-((3-(trifluoromethyl)benzyl)amino)quinoline-7-carboxylic acid (I-359)

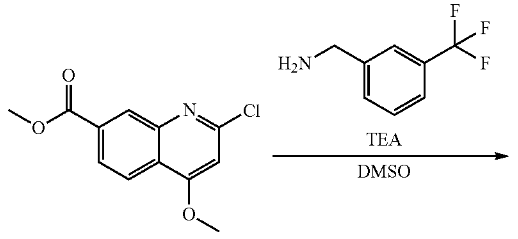

X-1563A4

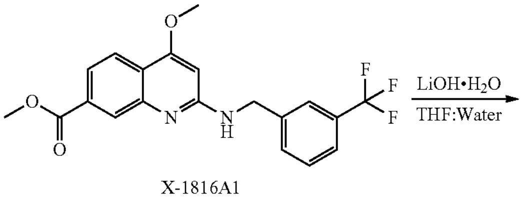

X-1816A1

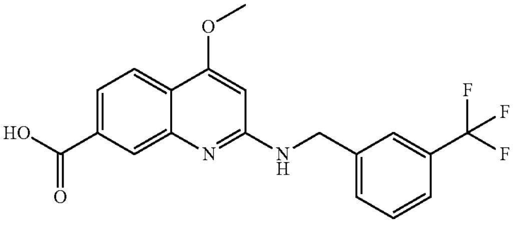

I-359

Methyl 4-methoxy-2-((3-(trifluoromethyl)benzyl)amino) quinoline-7-carboxylate (X-1816A1). To stirred solution of methyl 2-chloro-4-methoxyquinoline-7-carboxylate (X-1563A4) (0.700 g, 2.78 mmol) in DMSO (10 mL). were added TEA (0.846 g, 8.36 mmol) and (3-(trifluoromethyl) phenyl)methanamine (1.95 g, 11.15 mmol) under nitrogen and the resulting mixture was stirred at 100° C. for 16 h. After cooling to room temperature, reaction mixture was poured into ice-water (100 mL) and extracted with ethyl acetate (200 ml×2). Combined organic extracts were washed with brine (200 mL), dried over $Na_2SO_4$ concentrate in vacuo. The resulting crude was purified by column chromatography using ethyl acetate-hexane=0:1→3:7 as gradient to afford methyl 4-methoxy-2-((3-(trifluoromethyl)benzyl) amino)quinoline-7-carboxylate (X-1816A1) (0.30 g, 27%) as a white solid. MS: $[MH^+]$ 391.4.

4-Methoxy-2-((3-(trifluoromethyl)benzyl)amino)quinoline-7-carboxylic acid (I-359). To a stirred solution of methyl 4-methoxy-2-((3-(trifluoromethyl)benzyl)amino) quinoline-7-carboxylate (X-1816A1) (0.300 g, 0.769 mmol) in mixture of THF-water (2.5:1; 5.0 mL) was added lithium hydroxide monohydrate (0.096 g, 2.30 mmol) at room temperature under nitrogen and the resulting mixture was heated at 70° C. for 1 h. After cooling to room temperature, the reaction mixture was concentrated under reduced pressure, diluted with water (30 mL) and extracted with ethyl acetate (30 mL) to remove unwanted organic impurities. The aqueous layer was acidified (pH~2-3) with an aqueous solution of 1N HCl, and the resulting precipitate was collected by filtration. Crude solid was washed with cold water until the pH of the filtrate became neutral (pH~6-7). Obtained solid was purified by reverse phase (C-18) silica gel column chromatography, to afford 4-methoxy-2-((3-(trifluoromethyl)benzyl)amino)quinoline-7-carboxylic acid (I-359) (0.200 g, 69%) as a white solid. 1H NMR (400 MHz, DMSO-$d_6$) δ 13.10 (brs, 1H), 8.15 (br, 1H), 7.97-7.95 (d, J=7.2 Hz, 1H), 7.81 (s, IFI), 7.75-7.73 (d, J=7.2, 2H), 7.64-7.58 (m, 31H) 6.47 (brs, 1H), 4.81 (s, 2H), 4.00 (s, 3H). MS: $[MH^+]$ 377.4.

Example 1.269. Synthesis of 4-Methoxy-2-((4-(trifluoromethyl)benzyl)amino)quinoline-7-carboxylic acid (I-360)

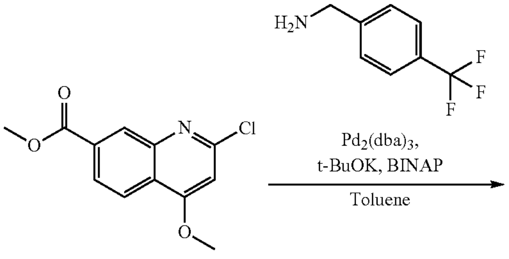

CEN2-X-1563A4

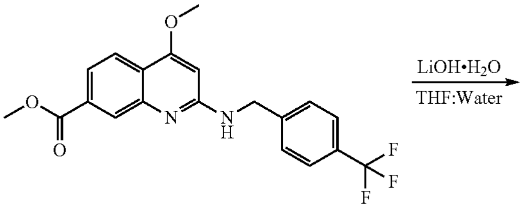

CEN2-X-1817A1

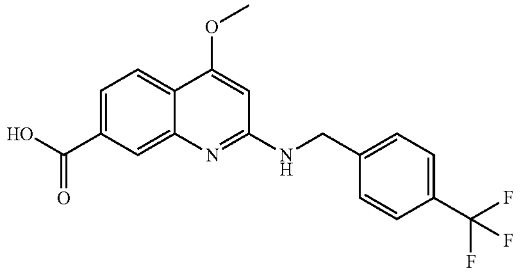

I-360

Methyl 4-methoxy-2-((4-(trifluoromethyl)benzyl)amino) quinoline-7-carboxylate (X-1817A1). To a stirred solution of methyl 2-chloro-4-methoxyquinoline-7-carboxylate (X-1563A4) (0.300 g, 1.19 mmol) in Toluene (10 mL) was added (3-(trifluoromethyl)phenyl)methanamine (0.380 g, 1.4 mmol) and t-BuOK (0.402 g, 3.58 mmol) at room temperature under nitrogen. The reaction mixture was degassed (purging with nitrogen) for 30 min followed by the addition of $Pd_2(dba)_3$ (0.050 g, 0.059 mmol) and BINAP (0.074 g, 0.11 mmol) at room temperature under nitrogen. The reaction mixture was heated at 80° C. under microwave irradiation for 6 h. Reaction mixture was cooled to room temperature, diluted with water (100 mL) and was extracted with ethyl acetate (100 mL×3). Combined organic extracts were dried over $Na_2SO_4$ and concentrated under reduced pressure. The crude product was combined with an identically-prepared four batches and combined crude batches were purified by reverse phase (C-18) silica gel column chromatography, using acetonitrile-water=0:1→1:0 as gradient, to afford 7 methyl 4-methoxy-2-((4-(trifluoromethyl)benzyl)amino)quinoline-7-carboxylate (X-1817A1) (0.380 g, 40%) as a yellow solid. MS: $[MH]^+$ 390.3.

4-Methoxy-2-((4-(trifluoromethyl)benzyl)amino)quinoline-7-carboxylic acid (I-360). To a stirred solution of methyl 4-methoxy-2-((4-(trifluoromethyl)benzyl)amino)quinoline-7-carboxylate (X-1817A1) (0.45 g, 1.15 mmol) in a mixture of THF-water (2.5:1; 5.0 mL) was added Lithium hydroxide monohydrate (0.17 g, 3.46 mmol) at room temperature under nitrogen and the resulting reaction mixture was heated at 70° C. for 1 h. After cooling to room temperature, the reaction mixture was concentrated under reduced pressure, diluted with water (30 mL) and extracted with ethyl acetate (30 mL) to remove unwanted organic impurities. The aqueous layer was acidified (pH~2-3) with an aqueous solution of 1N HCl, and the resulting precipitate was collected by filtration. Isolated solid was washed with cold water until the pH of the filtrate became neutral (pH~6-7). The crude product was purified by reverse phase (C-18) silica gel column chromatography, to afford 4-methoxy-2-((4-(trifluoromethyl)benzyl)amino)quinoline-7-carboxylic acid (I-360) (0.025 g, 43%) as a white solid. $^1H$ NMR (400 MHz, DMSO-$d_6$) δ 13.13-13.09 (br, 1H), 8.23 (brs, 1H), 7.98-7.96 (d, J=8.0 Hz, 1H), 7.80-7.63 (m, 6H), 6.52 (s, 1H), 4.85 (s, 2H), 4.01 (s, 3H). MS: $[MH^+]$ 377.4.

Example 1.270. Synthesis of 4-methoxy-2-(5-(trifluoromethyl)pyridin-2-yl)quinoline-7-carboxylic acid (I-361)

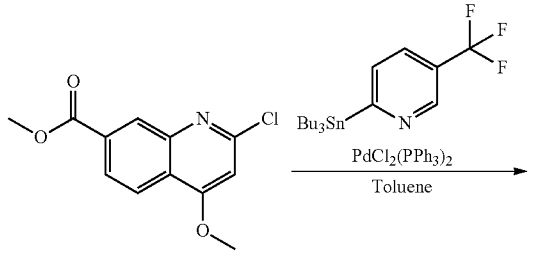

CEN2-X-1563A4

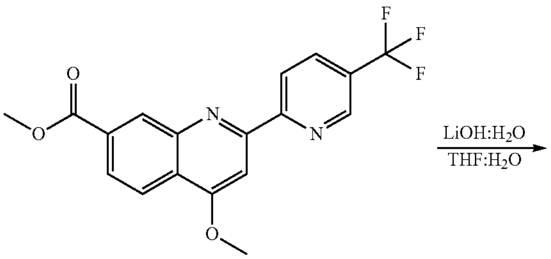

CEN2-X-1818A1

-continued

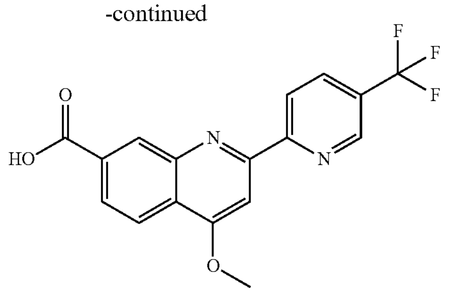

I-361

Methyl 4-methoxy-2-(5-(trifluoromethyl)pyridin-2-yl)quinoline-7-carboxylate (X-1818A1). To a stirred solution of methyl 2-chloro-4-methoxyquinoline-7-carboxylate (0.700 g, 2.78 mmol) in toluene (4 mL) was added 2-(tributylstannyl)-5-(trifluoromethyl)pyridine (1.8 g, 4.18 mmol) stirred at 0° C. under nitrogen. The reaction mixture was degassed (purging with nitrogen) for 30 min followed by the addition of $PdCl_2(PPh_3)_2$ (0.19 g, 0.27 mmol) under nitrogen at same temperature and the resulting mixture was heated at 140° C. for 8 h. After cooling to room temperature, reaction mixture poured into water (50 mL) and was extracted with ethyl acetate (75 mL×3). Combined organic extracts were dried over anhydrous $Na_2SO_4$ and concentrated under reduced pressure. The crude product was purified by Column chromatography using ethyl acetate-hexane=0:1→1:0 as gradient, to afford methyl 4-methoxy-2-(5-(trifluoromethyl)pyridin-2-yl)quinoline-7-carboxylate (X-1818A1) (0.25 g, 25%) as a brown solid. MS: $[MH]^+$ 362.3

4-Methoxy-2-(5-(trifluoromethyl)pyridin-2-yl)quinoline-7-carboxylic acid (I-361). Lithium hydroxide monohydrate (0.087 g, 2.0 mmol) was added to a stirred solution of a mixture of methyl 4-methoxy-2-(5-(trifluoromethyl)pyridin-2-yl)quinoline-7-carboxylate (X-1818A1) (0.25 g, 0.6 mmol) in of THF-water (2.5:1; 5.0 mL). at room temperature and the resulting reaction mixture was heated at 70° C. for 3 h. After cooling to room temperature, the reaction mixture was concentrated under reduced pressure, diluted with water (30 mL) and extracted with ethyl acetate (30 mL) to remove unwanted organic impurities. The aqueous layer was acidified (pH~2-3) with an aqueous solution of 1N HCl, and the resulting precipitate was collected by filtration. Isolated solid was washed with cold water until the pH of the filtrate became neutral (pH 6-7) and was purified by reverse phase (C-18) silica gel column chromatography, to afford 4-methoxy-2-(5-(trifluoromethyl)pyridin-2-yl)quinoline-7-carboxylic acid (I-361) (0.200 g, 83%) as a white solid. MS: $[MH]^+$ 349.3. $^1H$ NMR (400 MHz, DMSO-$d_6$) δ: 9.14 (s, 1H), 8.81-8.79 (d, J=8.0 Hz, 1H), 8.59 (s, 1H), 8.43-8.41 (d, J=8.0 Hz, 1H), 8.13 (s, 2H), 8.05 (s, 1H), 4.17 (s, 3H).

Example 1.271. Synthesis of 4-Methoxy-N-(4,4,4-trifluoro-3-oxobutyl)-2-(4-(trifluoromethyl)phenyl) quinoline-7-carboxamide (I-362)

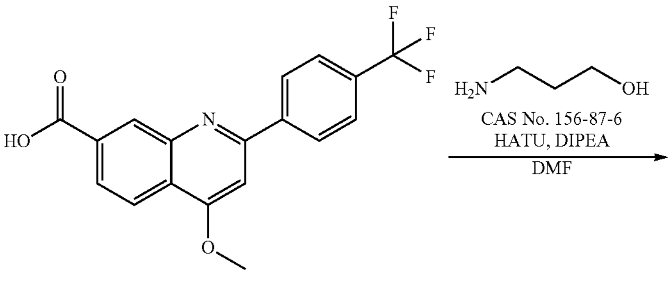

I-181

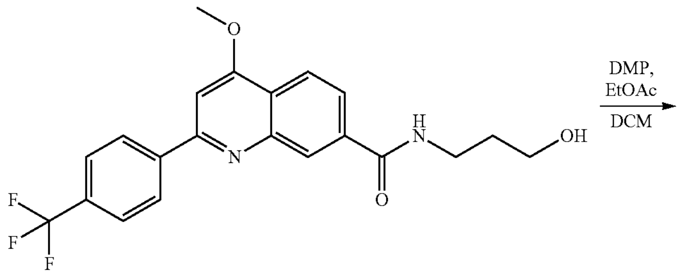

CEN2-X-1827C1

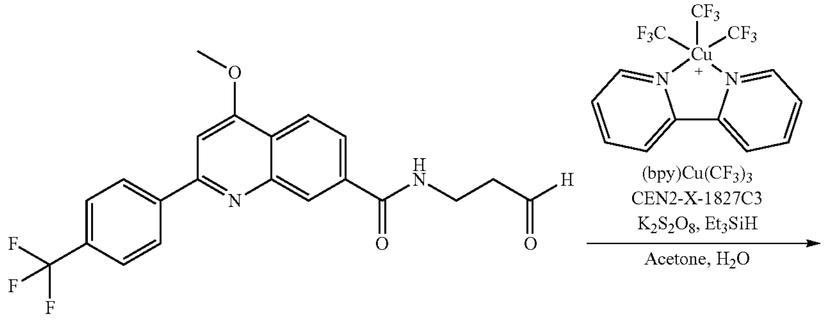

CEN2-X-1827C2

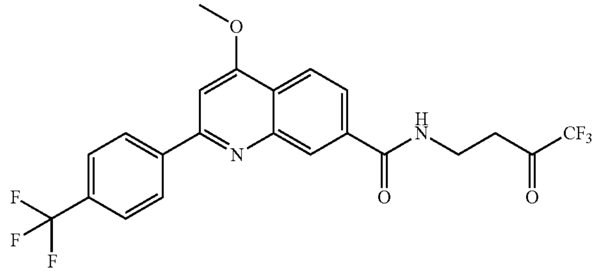

I-362

N-(3-hydroxypropyl)-4-methoxy-2-(4-(trifluoromethyl) phenyl)quinoline-7-carboxamide (X-1827C1). To a solution of 4-methoxy-2-(4-(trifluoromethyl)phenyl)quinoline-7-carboxylic acid (I-181) (1.0 g, 2.5 mmol)) in DMF (10 mL) were added DIPEA (1.0 g, 2.8 mmol) and HATU (2.1 g, 5.6 mmol) at 0° C. under nitrogen. The resulting reaction mixture was stirred at room temperature for 10 min. 3-aminopropan-1-ol (0.32 g, 0.4 mmol) was added at 0° C. drop-wise and the resulting reaction mixture was stirred at room temperature for 2 h. Reaction mixture was poured into ice water (100 mL), solid product was precipitated which was collected by filtration, dried under reduced pressure. The resulting crude material was triturated with diethyl ether (30 mL×3), dried over high vacuum to afford N-(3-hydroxypropyl)-4-methoxy-2-(4-(trifluoromethyl)phenyl)quinoline-7-carboxamide (X-1827C1) (0.9 g, 86%) as an off-white solid. MS: [MH]$^+$ 404.3.

4-Methoxy-N-(3-oxopropyl)-2-(4-(trifluoromethyl)phenyl)quinoline-7-carboxamide (X-1827C2). To a solution of N-(3-hydroxypropyl)-4-methoxy-2-(4-(trifluoromethyl) phenyl)quinoline-7-carboxamide (X-1827C1) in DCM-EtOAc (10:13 mL) was added DMP (1.9 g, 0.4 mmol) at 0° C. under nitrogen and the resulting mixture was stirred at same temperature for 2 h. The reaction mixture was quenched with $NaHCO_3$ (50 mL) & extracted with ethyl acetate (60 mL×3). Combined extracts were dried over anhydrous $Na_2SO_4$ concentrated under reduced pressure. The crude was purified by normal phase column chromatography on silica gel with ethyl acetate-hexane=0:1→4:6 as the eluent to give the pure product 4-methoxy-N-(3-oxopropyl)-2-(4-(trifluoromethyl)phenyl)quinoline-7-carboxamide (X-1800C2) (0.68 g, 62%) as an off-white solid. MS: $[MH]^+$ 403.1

4-Methoxy-N-(4,4,4-trifluoro-3-oxobutyl)-2-(4-(trifluoromethyl)phenyl)quinoline-7-carboxamide (I-362). To a solution of 4-methoxy-N-(3-oxopropyl)-2-(4-(trifluoromethyl)phenyl)quinoline-7-carboxamide (X-1800C2) (0.55 g, 0.13 mmol) in acetone-$H_2O$ (70:5, 75 mL) were added $K_2S208$ (1.47 g, 0.52 mmol) and Et3SiH (0.31 g, 0.2 mmol) at room temperature under nitrogen and the resulting mixture was stirred at room temperature for 32 h. Reaction mixture was diluted with $H_2O$ (100 mL) & extracted with ethyl acetate (100 mL×3). Combined extracts were dried over anhydrous $Na_2SO_4$ and concentrated under reduced pressure. Obtained crude was purified by preparative HPLC using acetonitrile-water=0:1→5:5, to afford 4-methoxy-N-(4,4,4-trifluoro-3-oxobutyl)-2-(4-(trifluoromethyl)phenyl) quinoline-7-carboxamide (I-362) (0.020 g, 3%) as an off-white solid. $^1H$ NMR (400 MHz, DMSO-$d_6$) δ 8.81-8.80 (m, 1H), 8.55-8.53 (m, 2H), 8.23-8.21 (d, J=8.4 Hz, 1H), 8.01-7.98 (dd, J=8.8, 1.6 Hz, 1H), 7.95-7.93 (d, J=8.4 Hz, 1H), 7.73 (s, 1H), 6.96 (s, 2H), 6.54 (s, 2H), 4.21 (s, 3H), 3.56-3.51 (m, 2H), 2.03-2.01 (t, J=8.0 Hz, 2H), MS: $[MH^+$ 18] 489.4.

Example 1.272. Synthesis of (R)—N-(2-hydroxy-1-(4-hydroxyphenyl)ethyl)-4-methoxy-2-(4-(trifluoromethyl)phenyl)quinoline-7 carboxamide (I-363)

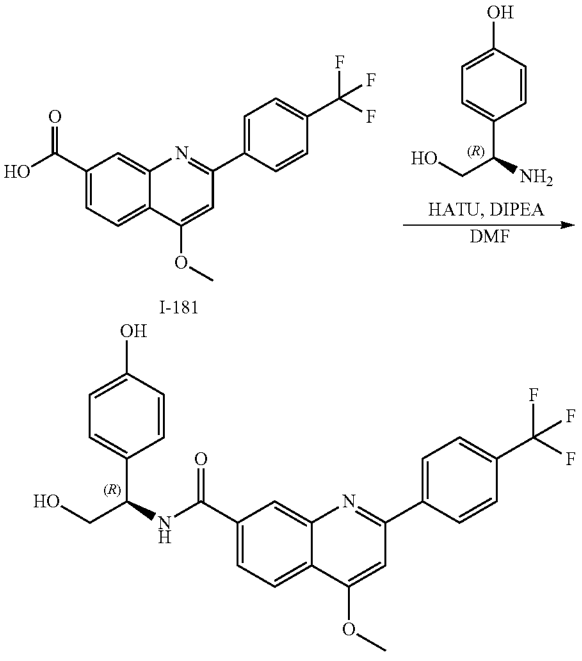

I-181

I-363

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(2-hydroxy-1-(4-hydroxyphenyl)ethyl)-4-methoxy-2-(4-(trifluoromethyl)phenyl)quinoline-7 carboxamide (I-363) (0.060 g, 53%) as a white solid. 41 NMR (400 MHz, DMSO-$d_6$) δ9.03-9.01 (d, J=8.0 Hz, 1H), 8.68-8.67 (d, J=1.2 Hz, 1H), 8.57-8.55 (d, J=8.0 Hz, 2H), 8.47 (s, 1H), 8.22-8.20 (d, J=8.8 Hz, 1H), 8.03-8.0 (dd, J=1.6, 8.8 Hz, 1H), 7.96-7.94 (d, J=8.0 Hz, 2H), 7.73 (s, 1H), 7.24-7.22 (d, J=8.4 Hz, 2H), 6.73-6.71 (d, J=8.4 Hz, 2H), 5.07-5.01 (m, 2H), 4.21 (s, 3H), 3.73-3.71 (m, 1H), 3.63-3.61 (m, 1H). MS: $[MH]^+$ 483.4.

Example 1.273. Synthesis of (R)-4-(2-hydroxy-1-(4-methoxy-2-(4-(trifluoromethyl)phenyl)quinoline-7-carboxamido)ethyl)benzoic acid (I-364)

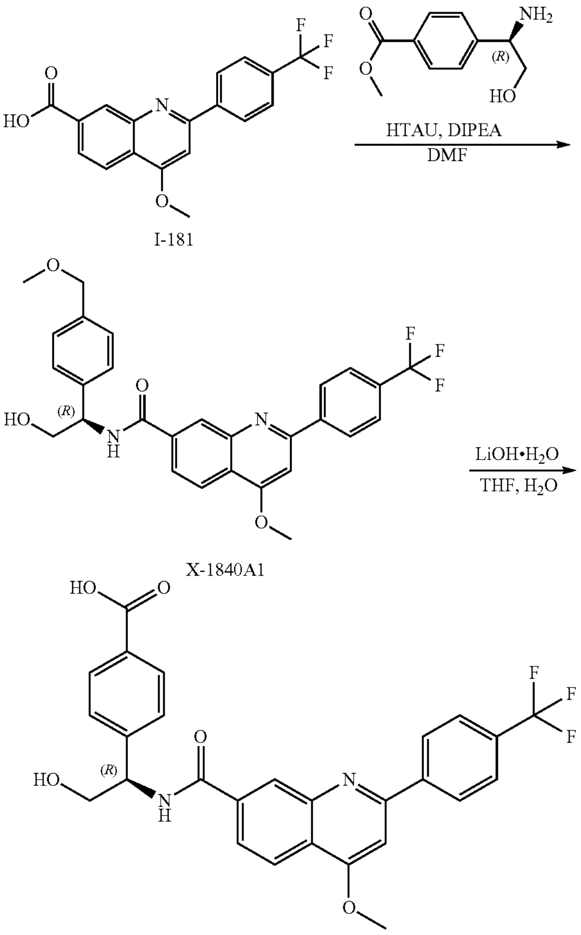

I-181

X-1840A1

I-364

Methyl (R)-4-(2-hydroxy-1-(4-methoxy-2-(4-(trifluoromethyl)phenyl)quinoline-7-carboxamido)ethyl)benzoate (X-1840A1). To a stirred solution of 4-methoxy-2-(4-(trifluoromethyl)phenyl)quinoline-7-carboxylic acid (I-181) (0.250 g, 0.72 mmol) in DMF (5 mL) were added DIPEA (0.37 mL, 2.16 mmol) and HATU (0.540 g, 1.44 mmol) at 0° C. under nitrogen. After 10 min of stirring at the same temperature, was added a solution of methyl (R)-4-(1-amino-2-hydroxyethyl)benzoate (0.190 g, 0.86 mmol) in DMF (2 mL) drop-wise and the resulting reaction mixture was stirred at room temperature for 2 h. Reaction mixture was diluted with water (30 mL) and was extracted with ethyl acetate (30 mL×3). Combined organic layers were washed with brine, dried over $Na_2SO_4$, filtered and concentrated. The crude product was purified by reverse phase (C-18) silica gel column chromatography, using acetonitrile-water=0:1→4:6 as gradient, to afford methyl (R)-4-(2-hydroxy-1-(4-methoxy-2-(4-(trifluoromethyl)phenyl)quinoline-7-carboxamido)ethyl)benzoate (X-1840A1) as an off white solid, (0.250 g, 66%). MS: $[MH]^+$ 525.1

(R)-4-(2-hydroxy-1-(4-methoxy-2-(4-(trifluoromethyl)phenyl)quinoline-7-carboxamido)ethyl)benzoic acid (I-364) To a stirred solution of methyl (R)-4-(2-hydroxy-1-(4-methoxy-2-(4-(trifluoromethyl)phenyl)quinoline-7-carboxamido)ethyl)benzoate (X-1840A1) (0.250 g, 0.47 mmol) in a mixture of THF-water (3:1; 4 mL) was added lithium hydroxide monohydrate (0.060 g, 1.43 mmol) at room temperature under nitrogen and the resulting mixture was heated at 80° C. for 2 h. After cooling to room temperature, the reaction mixture was concentrated under reduced pressure, obtained crude was diluted with water (20 mL) and was extracted with ethyl acetate (30 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was triturated using n-pentane and dried under high vacuum to afford to afford (R)-4-(2-hydroxy-1-(4-methoxy-2-(4-(trifluoromethyl)phenyl)quinoline-7-carboxamido)ethyl)benzoic acid (I-364) (0.089 g, 52%) as a white solid. $^1H$ NMR (400 MHz, DMSO-$d_6$) 9.23-9.21 (d, J=8.0 Hz, 1H), 8.73-8.73 (d, J=1.2 Hz, 1H), 8.56-8.54 (d, J=8.0 Hz, 2H), 8.27-8.25 (d, J=8.4 Hz, 1H), 8.08-8.06 (dd, J=1.2, 8.4 Hz, 1H), 7.99-7.96 (d, J=8.4 Hz, 2H), 7.93-7.91 (d, J=8.0 Hz, 2H), 7.77 (s, 1H), 7.58-7.56 (d, J=8.0 Hz, 2H), 5.22-5.17 (m, 1H), 4.24 (s, 3H), 3.83-3.78 (m, 1H), 3.74-3.70 (m, 1H). MS: $[MH]^+$ 511.4. Chiral HPLC=100%

Example 1.274. Synthesis of (R)—N-(2-hydroxy-1-(pyridin-2-yl)ethyl)-4-methoxy-2-(4-(trifluoromethyl)phenyl)quinoline-7-carboxamide (I-365)

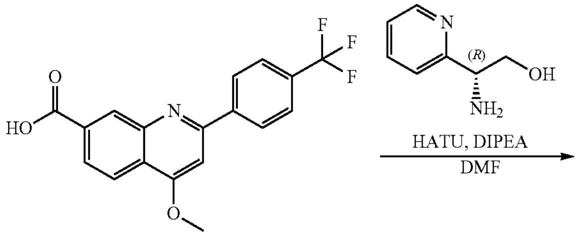

I-181

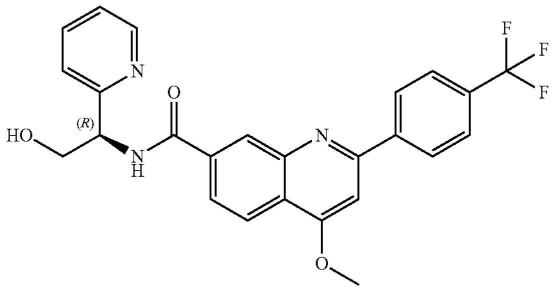

I-365

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(2-hydroxy-1-(pyridin-2-yl)ethyl)-4-methoxy-2-(4-(trifluoromethyl)phenyl)quinoline-7-carboxamide (I-365) (0.050 g, 24%) as a white solid. 1H NMR (400 MHz, DMSO-$d_6$) δ: 9.09-9.07 (d, J=7.6 Hz, 1H), 8.72 (s, 1H), 8.58-8.56 (d, J=8.0 Hz, 2H), 8.55 (s, 1H), 8.25-8.23 (d, J=8.8 Hz, 1H), 8.05-8.03 (dd, J=1.6, 8.8 Hz, 1H), 7.96-7.94 (d, J=8.4 Hz, 2H), 7.80-7.75 (m, 2H), 7.49-7.47 (d, J=8.0, 1H), 7.30-7.27 (m, 1H), 5.25-5.19 (m, 1H), 5.02-4.99 (t, J=6.0 Hz, 1H), 4.22 (s, 3H), 3.90-3.82 (m, 2H). MS: $[MH]^+$ 468.4, Chiral HPLC=98.86%

Example 1.275. (R)—N-(2-hydroxy-1-(pyridin-4-yl)ethyl)-4-methoxy-2-(4-(trifluoromethyl)phenyl)quinoline-7-carboxamide (I-366)

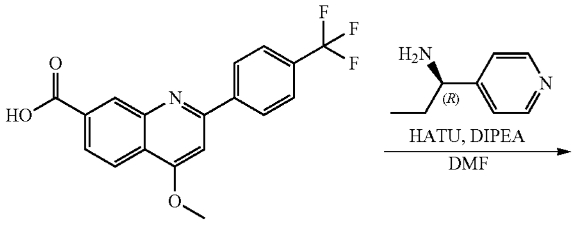

I-181

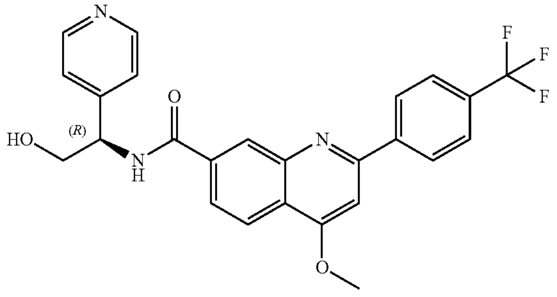

I-366

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(2-hydroxy-1-(pyridin-4-yl)ethyl)-4-methoxy-2-(4-(trifluoromethyl)phenyl)quinoline-7-carboxamide (I-366) (0.018 g, 5%) as a white solid. $^1H$ NMR (400 MHz, DMSO-$d_6$) δ: 9.22-9.20 (d, J=7.6 Hz, 1H), 8.72-8.721 (d, J=1.6 Hz, 1H), 8.58-8.56 (d, J=8.4 Hz, 2H), 8.54-8.52 (dd, J=1.6, 4.4 Hz, 2H), 8.24-8.22 (d, J=8.8 Hz, 1H) 8.04-8.01 (dd, J=2.0, 8.8 Hz, 1H), 7.96-7.94 (d, J=8.4 Hz, 2H), 7.75 (s, 1H), 7.46-7.45 (d, J=6.0 Hz, 2H), 5.17-5.10 (m, 2H), 4.22 (s, 3H), 3.82-3.73 (m, 2H). MS: $[MH]^+$ 468.4, Chiral HPLC=97.87%

Example 1.276. Synthesis of N-(2-hydroxy-1-(tetrahydro-2H-pyran-4-yl)ethyl)-4-methoxy-2-(4-(trifluoromethyl)phenyl)quinoline-7-carboxamide (I-367 & I-368)

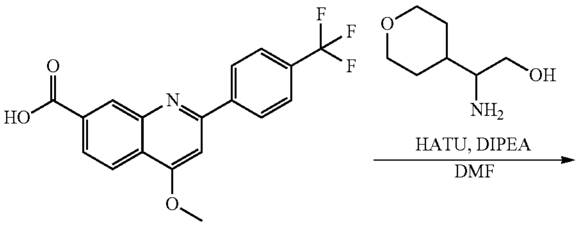

I-181

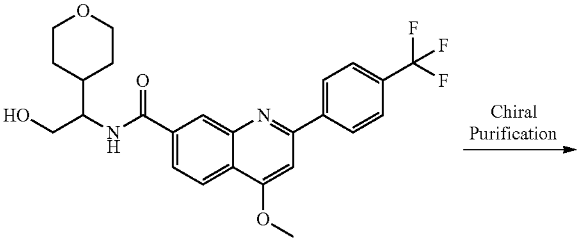

racemate

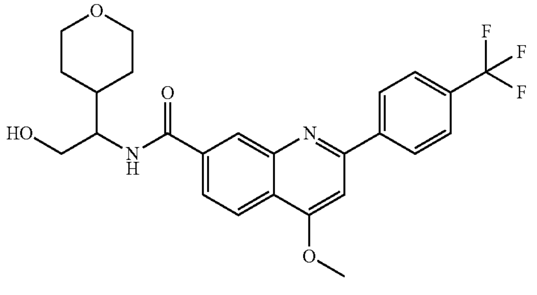

I-367

+

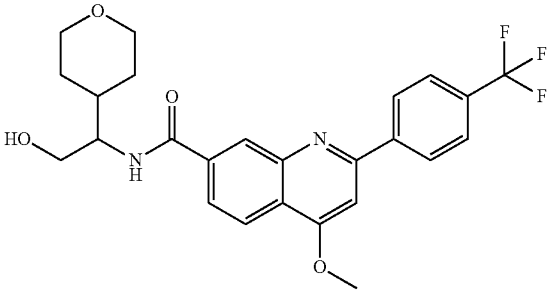

I-368

To a stirred solution of 4-methoxy-2-(4-(trifluoromethyl)phenyl)quinoline-7-carboxylic acid (I-181) (0.200 g, 0.57 mmol) in DMF (5 mL) were added DIPEA (0.30 mL, 1.72 mmol) and HATU (0.328 g, 0.86 mmol) at 0° C. under nitrogen. After 10 min of stirring at the same temperature, was added a solution of 2-amino-2-(tetrahydro-2H-pyran-4-yl)ethan-1-ol (0.100 g, 0.69 mmol) in DMF (2 mL) drop-wise and the resulting reaction mixture was stirred at room temperature for 2 h. Reaction mixture was poured into ice water (20 mL), solid product was precipitated which was collected by filtration, dried under reduced pressure. The resulting crude material was triturated with n-pentane (5 mL×2), dried over high vacuum to obtain a crude.

The enantiomers were separated by SFC chiral chromatography and each fraction was labeled by its elution order as first eluting isomer and second eluting isomer. The absolute stereochemistry was not assigned. Instrument: Waters SFC 350 Column: CHIRALPAK IG 250×50 mm 5 um. Mobile phase: supercritical CO 2/IPA-ACN (50/50) =50/50 at 150 ml/min. Isocratic gradient for 25 min. Detector (UV: 210 nm)

N-(2-hydroxy-1-(tetrahydro-2H-pyran-4-yl)ethyl)-4-methoxy-2-(4-(trifluoromethyl)phenyl)quinoline-7-carboxamide, first eluting isomer (I-367) (0.016 g, 5.8%) as an off-white solid. $^1$H NMR (400 MHz, DMSO-$d_6$) δ: 8.61 (s, 1H), 8.57-8.55 (d, J=8.4 Hz, 2H), 8.44-8.41 (d, J=9.2 Hz, 1H), 8.22-8.20 (d, J=8.8 Hz, 1H) 8.02-8.00 (d, J=8.0 Hz, 1H), 7.95-7.93 (d, J=8.0 Hz, 2H), 7.73 (s, 1H), 4.70-4.68 (m, 1H), 4.21 (s, 3H), 3.89-3.86 (m, 3H), 3.59-3.58 (d, J=4.4 Hz, 2H), 3.28-3.23 (m, 2H), 1.93-1.91 (m, 1H), 1.70-1.68 (m, 2H), 1.36-1.23 (m, 2H). MS: $[MH]^+$ 475.4, Chiral HPLC=100%

N-(2-hydroxy-1-(tetrahydro-2H-pyran-4-yl)ethyl)-4-methoxy-2-(4-(trifluoromethyl)phenyl)quinoline-7-carboxamide, second eluting isomer (I-368) (0.025 g, 9%) as an off-white solid. $^1$H NMR (400 MHz, DMSO-$d_6$) δ: 8.61 (s, 1H), 8.57-8.55 (d, J=8.4 Hz, 2H), 8.44-8.42 (d, J=8.8 Hz, 1H), 8.22-8.20 (d, J=8.8 Hz, 1H) 8.02-8.00 (dd, J=7.2, 8.8 Hz, 1H), 7.95-7.93 (d, J=8.4 Hz, 2H), 7.73 (s, 1H), 4.70-4.68 (t, J=5.6 Hz, 1H), 4.22 (s, 3H), 3.89-3.86 (m, 3H), 3.59-3.57 (m, 2H), 3.28-3.23 (m, 2H), 1.93-1.91 (m, 1H), 1.65-1.63 (m, 2H), 1.36-1.30 (m, 2H). MS: $[MH]^+$ 475.4, Chiral HPLC=100%

Example 1.277. (R)—N-(1-hydroxy-3-phenylpropan-2-yl)-4-methoxy-2-(4-(trifluoromethyl)phenyl)quinoline-7-carboxamide (I-369)

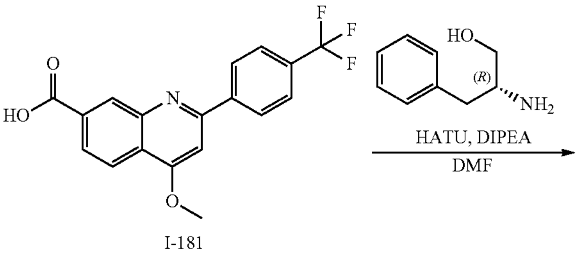

I-181

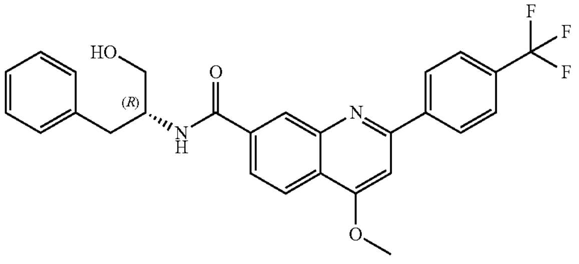

I-369

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(1-hydroxy-3-phenylpropan-2-yl)-4-methoxy-2-(4-(trifluoromethyl)phenyl)quinoline-7-carboxamide (I-369) (0.100 g, 36%) as a white solid. $^1$H NMR (400 MHz, DMSO-d6) δ: 8.58-8.55 (m, 4H), 8.20-8.17 (d, J=8.8 Hz, 1H), 7.95-7.93 (d, J=8.8 Hz, 2H), 7.93 (s, 1H), 7.72 (s, 1H), 7.33-7.24 (m, 4H), 7.17-7.16 (t, J=8.8 Hz, 1H), 4.19-4.88 (t, J=6.0 Hz, 1H), 4.28-4.20 (m, 1H), 4.20 (s, 3H), 3.58-3.52 (m, 1H), 3.49-3.45 (m, 1H), 3.01-2.97 (m, 1H), 2.88-2.82 (m, 1H). MS: $[MH]^+$ 481.4, Chiral HPLC=100.0%

Example 1.278. (R)—N-(1-hydroxy-4-methylpentan-2-yl)-4-methoxy-2-(4-(trifluoromethyl)phenyl)quinoline-7-carboxamide (I-370)

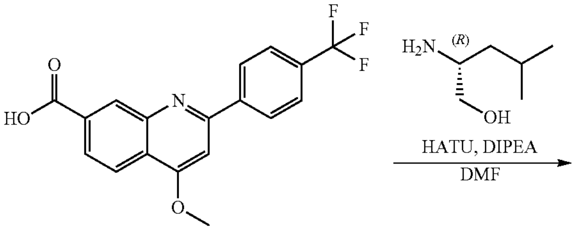

I-181

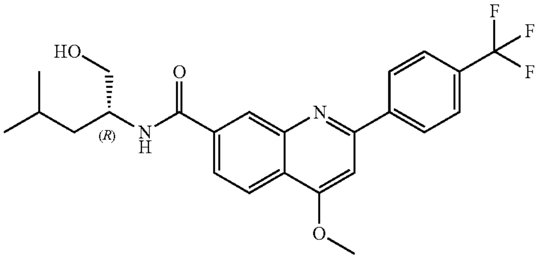

I-370

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)—N-(1-hydroxy-4-methylpentan-2-yl)-4-methoxy-2-(4-(trifluoromethyl)phenyl)quinoline-7-carboxamide (I-370) (0.150 g, 58%) as a white solid. $^1$H NMR (400 MHz, DMSO-$d_6$) δ: 8.59-8.59 (d, J=1.2 Hz, 1H), 8.56-8.54 (d, J=8.0 Hz, 2H), 8.41-8.39 (d, J=8.8 Hz, 1H), 8.22-8.20 (d, J=8.8 Hz, 1H), 8.02-8.02 (dd, J=1.6, 8.8 Hz, 1H), 7.95-7.93 (d, J=8.4 Hz, 2H), 7.73 (s, 1H), 4.75-4.72 (t, J=5.6, Hz, 1H), 4.21 (s, 3H), 4.15-4.11 (m, 1H), 3.50-3.45 (m, 1H), 3.42-3.34 (m, 1H), 1.70-1.66 (m, 1H), 1.53-1.49 (m, 1H), 1.43-1.39 (m, 1H) 0.93-0.88 (m, 6H). MS: $[MH]^+$ 447.5, Chiral HPLC=100.0%

Example 1.279. Synthesis of (R)-(2-(hydroxymethyl)pyrrolidin-1-yl) (4-methoxy-2-(4-(trifluoromethyl)phenyl)quinolin-7-yl)methanone (I-371)

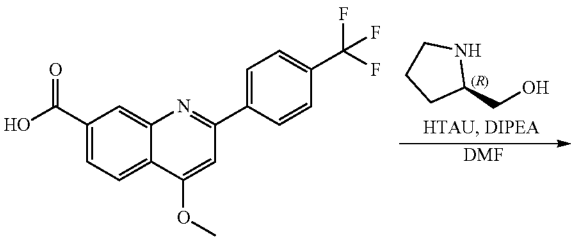

I-181

-continued

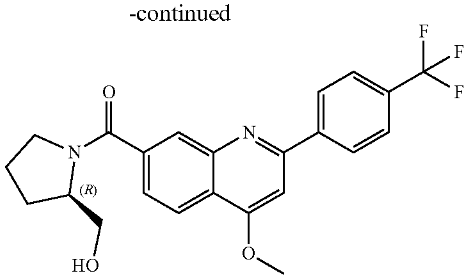

I-371

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324):

(R)-(2-(hydroxymethyl)pyrrolidin-1-yl) (4-methoxy-2-(4-(trifluoromethyl)phenyl)quinolin-7-yl)methanone (I-371) (0.200 g, 81%) as a white solid. $^1$H NMR (400 MHz, DMSO-$d_6$) d: 8.54-8.52 (d, J=8.4 Hz, 2H), 8.21-8.18 (d, J=8.4 Hz, 1H), 8.15 (s, 1H), 7.94-7.92 (d, J=8.4 Hz, 2H), 7.71 (s, 1H), 7.67-7.65 (d, J=8.4 Hz, 1H), 4.87-4.84 (t, J=5.6 Hz 1H), 4.21 (s, 3H), 3.64-3.61 (m, 2H), 3.57-3.49 (m, 1H), 3.05 (s, 1H), 1.98-1.89 (m, 4H), 1.74-1.67 (mu, 1H). MS: $[MH]^+$ 431.4, Chiral HPLC=100.0%

Example 1.280. (2-(hydroxymethyl)azetidin-1-yl) (4-methoxy-2-(4-(trifluoromethyl)phenyl)quinolin-7-yl)methanone (I-372 & I-373)

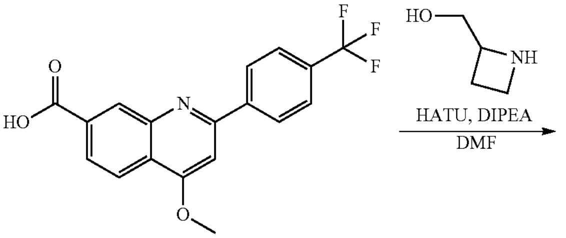

I-181

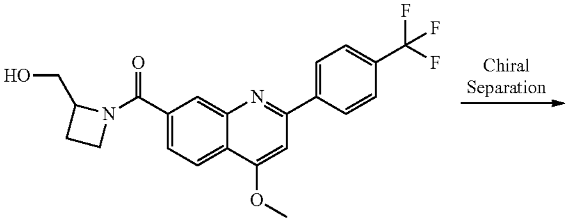

Racemate

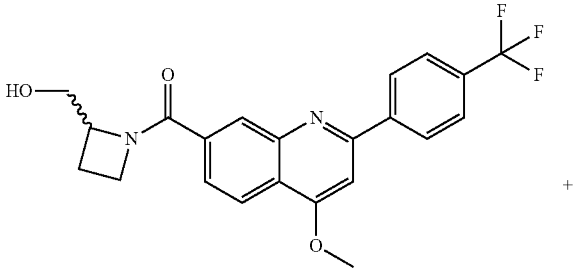

+

I-372

-continued

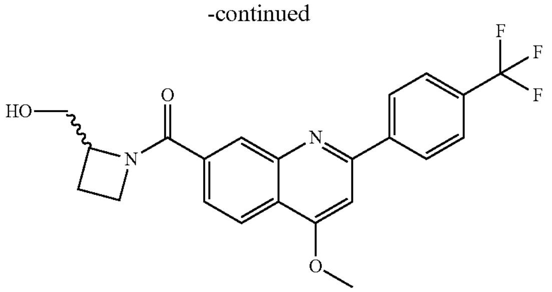

I-373

The following compound was prepared in a manner analogous to the procedures described above for (N-(2-hydroxy-1-(tetrahydro-2H-pyran-4-yl)ethyl)-4-methoxy-2-(4-(trifluoromethyl)phenyl)quinoline-7-carboxamide (I-367 and I-368). The enantiomers were separated by SFC chiral chromatography and each fraction was labeled by its elution order as first eluting isomer and second eluting isomer. The absolute stereochemistry was not assigned. Instrument: Waters SFC 350 Column: CHIRALPAK IG 250×50 mm Sum. Mobile phase: supercritical CO 2/IPA-ACN (70/30)=60/40 at 150 ml/min. Isocratic gradient for 12 min. Detector (UV: 260 nm)

(2-(hydroxymethyl)azetidin-1-yl) (4-methoxy-2-(4-(trifluoromethyl)phenyl)quinolin-7-yl)methanone, first eluting isomer (I-372): (0.010 g, 5.5%) as a white solid. $^1$H NMR (400 MHz, DMSO-$d_6$) δ: 8.54-8.52 (d, J=7.6 Hz, 2H), 8.22-8.20 (d, J=8.0 Hz, 2H) 7.94-7.92 (d, J=8.0 Hz, 2H), 7.78-7.76 (d, J=8.8 Hz, 1H), 7.72 (s, 1H), 5.00-4.88 (m, 1H), 4.71-4.55 (m, 1H), 4.36-4.34 (m, 1H), 4.21 (s, 3H), 4.16-4.12 (s, 1H), 4.01-3.85 (m, 1H), 3.67-3.65 (m, 1H), 3.21-3.19 (m, 1H), 2.21-2.20 (d, J=3.6 Hz, 1H), MS: $[MH]^+$ 416.9. Chiral HPLC=100%

(2-(hydroxymethyl)azetidin-1-yl) (4-methoxy-2-(4-(trifluoromethyl)phenyl)quinolin-7-yl)methanone, second eluting isomer (I-373): (0.010 g, 5.5%) as an off-white solid. $^1$H NMR (400 MHz, DMSO-$d_6$) δ: 8.54-8.52 (d, J=7.6 Hz, 2H), 8.22-8.20 (d, J=8.0 Hz, 2H) 7.94-7.92 (d, J=7.6 Hz, 2H), 7.78-7.76 (d, J=8.0 Hz, 1H), 7.72 (s, 1H), 5.11-4.98 (m, 1H), 4.57-4.55 (m, 1H), 4.37-4.35 (d, J=7.2 Hz, 1H), 4.21 (s, 3H), 4.13-4.11 (d, J=7.2 Hz, 1H), 3.85-3.84 (m, 1H), 3.66-3.60 (s, 2H), 2.22-2.20 (m, 1H). MS: $[MH]^+$ 417.0, Chiral HPLC=100%

Example 1.281. Synthesis of (S)-4-(cyclopropylmethoxy)-N-(1-hydroxypropan-2-yl)-2-(4-(trifluoromethyl)phenyl)quinoline-7-carboxamide (I-374) & 4-(cyclopropylmethoxy)-2-(4-(trifluoromethyl)phenyl)quinoline-7-carboxylic acid (I-375)

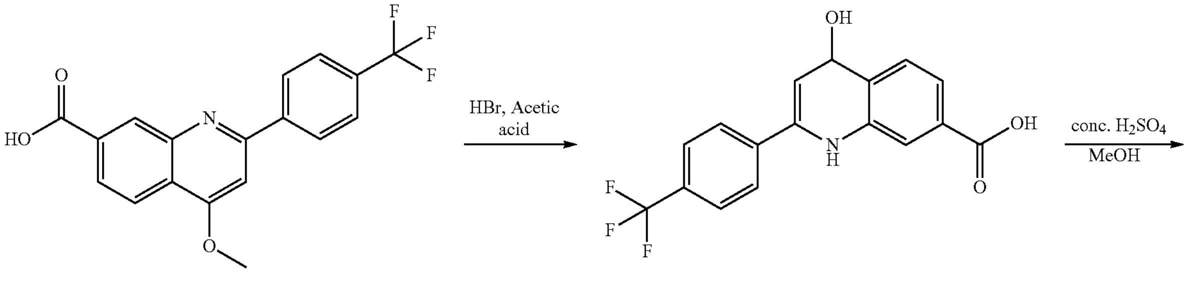

I-181

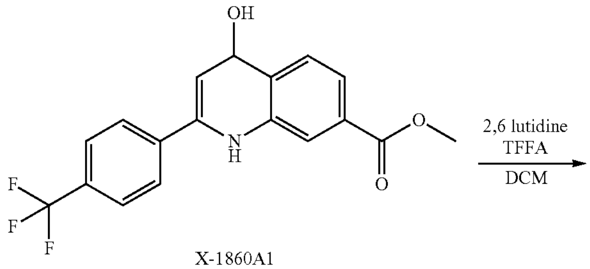

X-1860A1

-continued

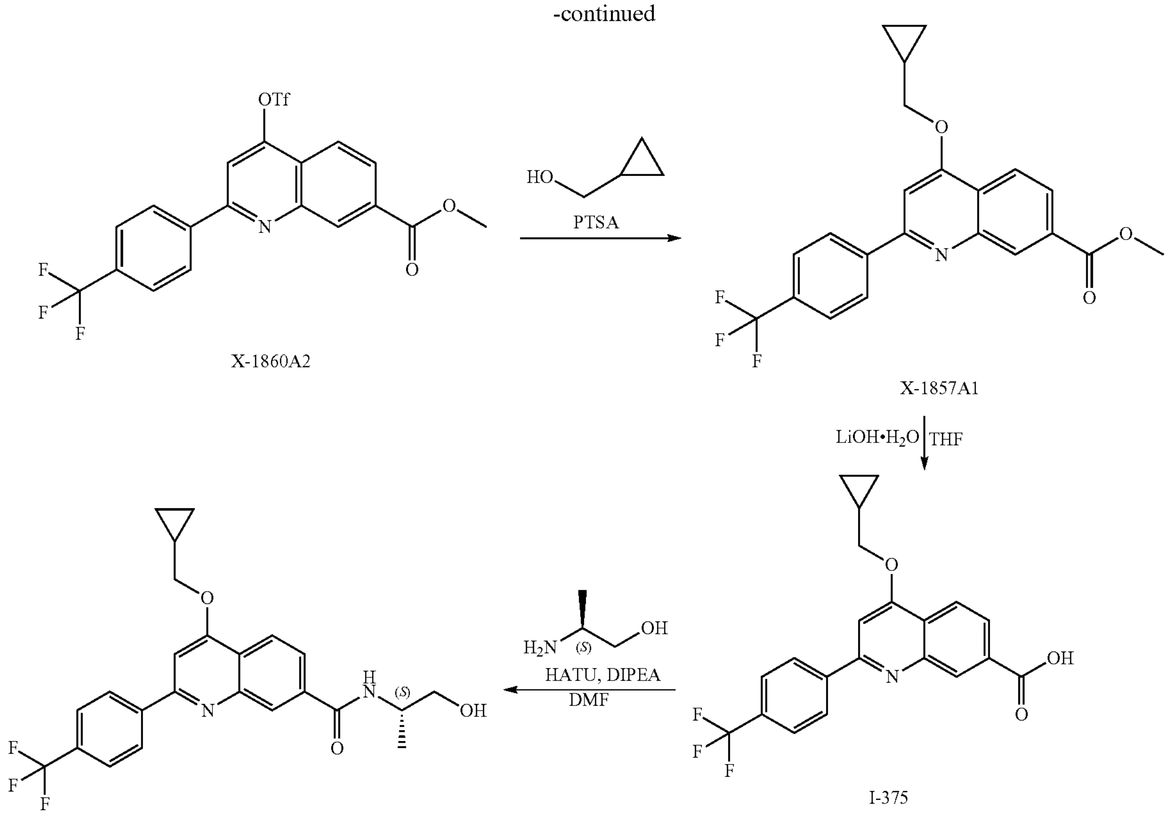

X-1860A2

X-1857A1

I-375

I-374

Synthetic procedure of I-181 provided at Example 1.82.

4-Hydroxy-2-(4-(trifluoromethyl)phenyl)-1,4-dihydroquinoline-7-carboxylic acid. The solution of 4-methoxy-2-(4-(trifluoromethyl)phenyl)quinoline-7-carboxylic acid (I-181) (0.250 g, 0.72 mmol) in HBr in AcOH (3 mL, 12 Vol) was heated at 90° C. for 16 h. Reaction mixture was cooled to room temperature, poured into ice water (200 mL), solid product was precipitated which was collected by filtration, and washed with water, dried under high vacuum to afford 4-hydroxy-2-(4-(trifluoromethyl)phenyl)-1,4-dihydroquinoline-7-carboxylic acid (0.090 g, 37%) as a grey solid. MS: $[MH]^+$ 336.0.

Methyl 4-hydroxy-2-(4-(trifluoromethyl)phenyl)-1,4-dihydroquinoline-7-carboxylate (X-1860A1). Concentrated $H_2SO_4$ (1 mL) was added to a stirred solution of 4-hydroxy-2-(4-(trifluoromethyl)phenyl)-1,4-dihydroquinoline-7-carboxylic acid (0.400 g, 1.19 mmol) in methanol (5 mL) at room temperature and the resulting mixture was heated at 80° C. for 3 h. Reaction mixture was poured into ice water (200 mL), solid product was precipitated which was collected by filtration, and washed with water, dried under high vacuum to afford, methyl 4-hydroxy-2-(4-(trifluoromethyl)phenyl)-1,4-dihydroquinoline-7-carboxylate (X-1860A1) (0.350 g, 84%) as a grey solid. MS: $[MH]^+$ 350.0.

Methyl 2-(4-(trifluoromethyl)phenyl)-4-(((trifluoromethyl)sulfonyl)oxy)quinoline-7-carboxylate (X-1860A2). To a stirred solution of methyl 4-hydroxy-2-(4-(trifluoromethyl)phenyl)-1,4-dihydroquinoline-7-carboxylate (X-1860A1) (0.400 g, 1.17 mmol) in DCM (4 mL) was added 2,6-Lutidine (0.240 g, 2.30 mmol) at room temperature, then reaction mixture was cooled to 0° C. followed by addition of TFAA (0.6 mL, 3.45 mmol). The resulting reaction mixture was stirred at room temperature for 30 min. The reaction mixture was basified (ph~8-9) with an aqueous solution of saturated $NaHCO_3$ (200 mL) and was extracted with dichloromethane (200 mL×2). Combined organic extracts were dried over anhydrous $Na_2SO_4$ and concentrated under reduce pressure to afford, methyl 2-(4-(trifluoromehyl)phenyl)-4-(((trifluoromethyl)sulfonyl)oxy)quinoline-7-carboxylate (X-1860A2) (0.45 g, 84.08%) as brown solid. MS: $[MH]^+$ 480.03.

Methyl 4-(cyclopropylmethoxy)-2-(4-(trifluoromethyl)phenyl)quinoline-7-carboxylate (X-1857A1). To a stirred solution of methyl 2-(4-(trifluoromethyl)phenyl)-4-(((trifluoromethyl)sulfonyl)oxy)quinoline-7-carboxylate (X-1860A2) (0.300 g, 0.62 mmol) in cyclopropylmethanol (3 mL) was added p-Toluenesulfonic acid (0.050 g, 0.31 mmol) portion wise at 0° C. under nitrogen and the resulting mixture was heated at 90° C. for 16 h. Reaction mixture was cooled to room temperature, diluted with water (500 mL) and was extracted with ethyl acetate (500 mL×2). Combined organic extracts were dried over anhydrous $Na_2SO_4$ and concentrated under reduce pressure to afford crude mass, which was purified by silica gel column chromatography, using ethyl acetate-hexane=0:1→3:2 as eluent, to afford, methyl 4-(cyclopropylmethoxy)-2-(4-(trifluoromethyl)phenyl)quinoline-7-carboxylate (X-1857A1) (0.090 g, 36%) as brown solid. MS: $[MH]^+$ 402.1.

4-(cyclopropylmethoxy)-2-(4-(trifluoromethyl)phenyl)quinoline-7-carboxylic acid (I-375). To a stirred solution of methyl 4-(cyclopropylmethoxy)-2-(4-(trifluoromethyl)phenyl)quinoline-7-carboxylate (X-1857A1) (0.080 g, 0.19 mmol) in a mixture of THF-water (3:1; 5.0 mL) was added lithium hydroxide monohydrate (0.014 g, 033 mmol) at room temperature. Reaction mixture was stirred at room temperature for 16 h. After completion of reaction the reaction mixture was concentrated under reduced pressure, obtained crude was acidified (pH 2-3) with an aqueous solution of 1N HCl and the resulting precipitate was collected by filtration. Crude residue was washed with cold water until the pH of the filtrate became neutral (pH~6-7). Obtained solid was dried under reduced pressure and triturated with using n-pentane (5 mL), to afford 4-(cyclopropylmethoxy)-2-(4-(trifluoromethyl)phenyl)quinoline-7-carboxylic acid (I-375) (0.070 g, 90%) as an off white solid $^1H$ NMR (400 MHz, DMSO-$d_6$) δ: 13.37 (br. s, 1H), 8.58-8.58 (d, J=1.6 Hz, 1H), 8.54-8.52 (d, J=8.0 Hz, 2H), 8.30-8.27 (d, J=8.4 Hz, 1H), 8.08-8.06 (dd, J=1.6, 8.4 Hz, 1H), 7.94-7.92 (d, J=8.4 Hz, 2H), 7.71 (s, 1H), 4.33-4.32 (d, J=7.2 Hz, 2H), 1.48-1.42 (m, 1H), 0.72-0.68 (m, 2H), 0.49-0.47 (m, 2H), MS: $[MH]^+$ 388.4.

(S)-4-(Cyclopropylmethoxy)-N-(1-hydroxypropan-2-yl)-2-(4-(trifluoromethyl)phenyl)quinoline-7-carboxamide (I-374). To a stirred solution of 4-(cyclopropylmethoxy)-2-(4-(trifluoromethyl)phenyl)quinoline-7-carboxylic acid (I-375) (0.070 g, 0.18 mmol) in DMF (2 mL) were added (S)-2-aminopropan-1-ol (0.020 g, 0.36 mmol), DIPEA (0.1 mL, 0.5 mmol) and HATU (0.100 g, 0.27 mmol) sequentially at room temperature and stirred for 1 h. Reaction mixture was diluted with water (100 mL) and was extracted with ethyl acetate (100 mL×2). Combined organic extracts were dried over anhydrous $Na_2SO_4$ and concentrated under reduce pressure to afford crude mass, which was purified by silica gel column chromatography, using ethyl acetate-hexane=0:1→7:3 as eluent, to afford, (S)-4-(cyclopropylmethoxy)-N-(1-hydroxypropan-2-yl)-2-(4-(trifluoromethyl)phenyl)quinoline-7-carboxamide (I-374) (0.070 g, 87%) as an off-white solid. 1H NMR (400 MHz, DMSO-$d_6$) 8.59-8.59 (d, J=1.6 Hz, 1H), 8.54-8.52 (d, J=8.4 Hz, 2H), 8.50-8.48 (d, J=8.0 Hz, 1H), 8.24-8.22 (d, J=8.8 Hz, 1H), 8.03-8.00 (dd, J=8.8 Hz, 1.6 Hz, 1H), 7.94-7.92 (d, J=8.0 Hz, 2H), 7.68 (s, 1H), 4.79-4.76 (t, =5.61 Hz, 1H), 432-430 (d, J=7.2 Hz, 21), 4.11-4.05 (m, 1H), 3.55-3.50 (m, 1H), 3.42-3.34 (m, 1H), 1.47-1.43 (m, 1H), 1.19-1.17 (d, J=6.4 Hz, 3H), 0.72-0.68 (m, 2H), 0.49-0.45 (m, 2H). MS: $[MH]^+$ 445.4.

Example 1.282. Synthesis of (R)-3-Hydroxy-N-(4-methoxy-2-(4-(trifluoromethyl)phenyl)quinolin-7-yl)-2-phenylpropanamide (I-376)

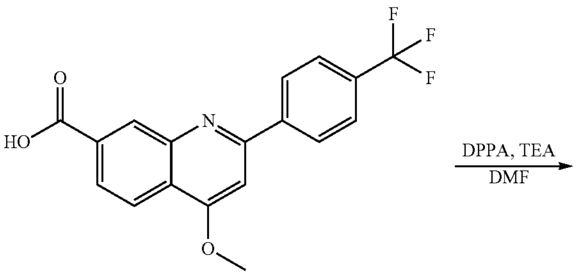

I-181

-continued

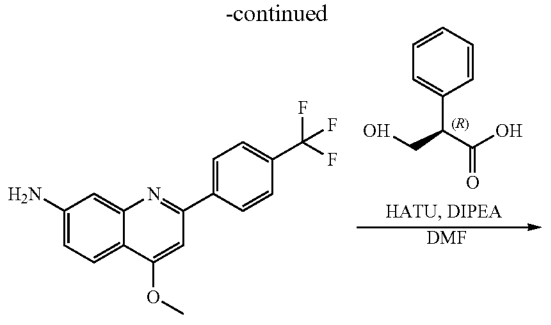

CEN2-X-1866A1

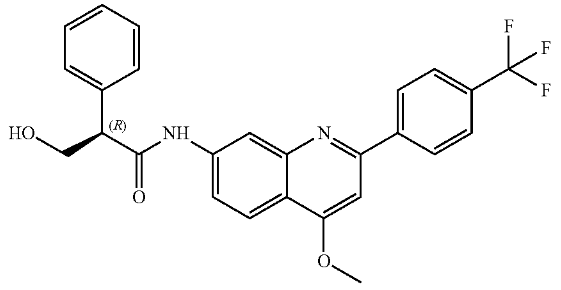

I-376

4-Methoxy-2-(4-(trifluoromethyl)phenyl)quinolin-7-amine (X-1866A1). To a stirred solution of 4-methoxy-2-(4-(trifluoromethyl) phenyl) quinoline-7-carboxylic acid (I-181) (0.800 g, 2.30 mmol) in DMF (12 mL) were added TEA (0.349 g, 3.45 mmol) and DPPA (0.951 g, 1.60 mmol) sequentially at room temperature under nitrogen and reaction mixture was stirred at same temperature for 1 h. After allowing the reaction mixture to stirred for 1 h, water is added and resulting reaction mixture heated at 100° C. for 3 h. After cooling to room temperature, reaction mixture was poured in water, the resulting precipitate was collected by filtration and dried under high vacuum. The resulting crude was purified by reverse phase (C-18) silica gel column chromatography, using acetonitrile-water=0:1→4:6 as gradient, afford 4-methoxy-2-(4-(trifluoromethyl)phenyl)quinolin-7-amine (X-1866A1) (0.250 g, 34%) as an off-white solid. MS: $[MH]^+$ 319.3.

(R)-3-hydroxy-N-(4-methoxy-2-(4-(trifluoromethyl)phenyl)quinolin-7-yl)-2-phenylpropanamide (I-376). To a stirred solution of (R)-3-hydroxy-2-phenylpropanoic acid (0.105 g, 0.632 mmol) in DMF (4 mL) were added DIPEA (0.244 g, 1.89 mmol) and HATU (0.480 g, 1.26 mmol) sequentially at 0° C. under nitrogen. After stirring for 10 min at the same temperature, was added 4-methoxy-2-(4-(trifluoromethyl)phenyl)quinolin-7-amine (X-1866A1) (0.140 g, 0.440 mmol) was added at 0° C. and the resulting reaction mixture was stirred at room temperature for 48 h. After completion of reaction, reaction mixture was slowly poured in ice water (100 mL), obtained precipitates were filtered and the residue was washed with water (100 mL). Solid precipitate was, dried under high vacuum to afford (R)-3-hydroxy-N-(4-methoxy-2-(4-(trifluoromethyl)phenyl)quinolin-7-yl)-2-phenylpropanamide (I-376) (0.020 g, 10%) as an off-white solid. $^1H$ NMR (400 MHz, DMSO-$d_6$) δ 8.51 (s, 1H), 8.50-8.48 (d, J=8.0 Hz, 3H), 8.08-8.06 (d, J=8.8 Hz, 1H), 7.91-7.89 (d, J=8.4 Hz, 2H), 7.68-7.66 (m, 1H), 7.54 (s, 1H), 7.43-7.41 (d, J=7.6 Hz, 2H), 7.37-7.33 (t, J=7.6 Hz, 2H), 7.28-7.26 (d, J=7.2 Hz, 1H), 5.05 (brs, 1H), 4.15-4.10

(m, 3H), 3.10-3.15 (m, 1H), 3.94-3.91 (m, 1H). 3.60-3.59 (m, 1H), MS: $[MH]^+$ 467.4. Chiral HPLC: 100%

Example 1.283. Synthesis of 4-methoxy-N-(methylsulfonyl)-2-(4-(trifluoromethyl)phenyl)quinoline-7-carboxamide (I-377)

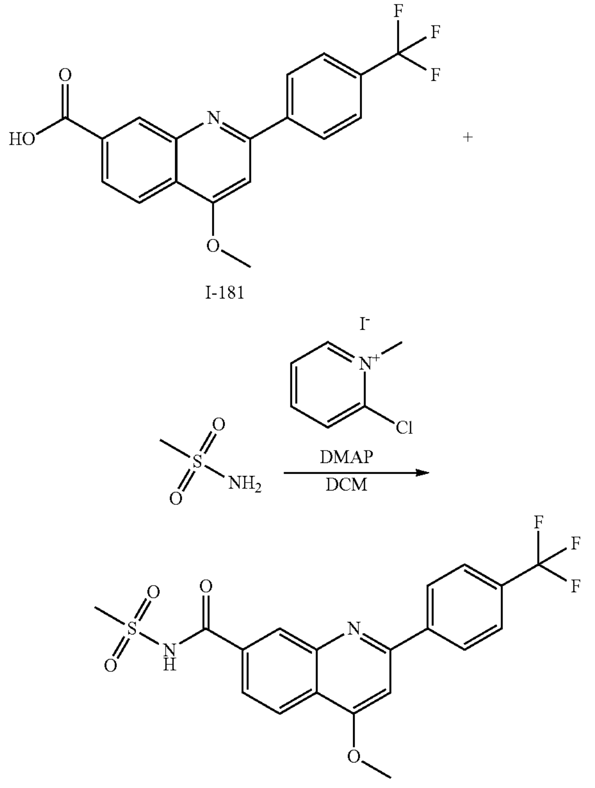

I-181

I-377

To a stirred solution of 4-methoxy-2-(4-(trifluoromethyl) phenyl)quinoline-7-carboxylic acid (I-181) (0.300 g, 0.86 mmol) in DCM (5 mL) were added DMAP (0.005 g, 0.04 mmol) and 2-chloro-1-methylpyridinium iodide (0.260 g, 1.0 mmol) followed by triethylamine (0.26 g, 2.59 mmol) at 0° C. under nitrogen. After 10 min of stirring at the same temperature, was added methanesulfonamide (0.240 g, 2.59 mmol) and reaction mixture was stirred at room temperature for 3 h. Reaction mixture was poured into water (40 mL) and was extracted with DCM (40 mL×3). Combined organic extracts were dried over $Na_2SO_4$ and concentrated under reduced pressure. Obtained crude was purified by reverse phase (C-18) silica gel column chromatography, using acetonitrile-water=0:1→1:0 as gradient, to provide 4-methoxy-N-(methylsulfonyl)-2-(4-(trifluoromethyl)phenyl)quinoline-7-carboxamide (I-377) (0.070 g, 19%) as an off-white solid. $^1H$ NMR (400 MHz, DMSO-$d_6$) δ 12.47 (brs, 1H), 8.684-8.681 (d, J=1.2 Hz, 1H), 8.56-8.54 (d, J=8.4 Hz, 2H), 8.26-8.24 (d, J=8.8 Hz, 1H), 8.05-8.02 (dd, J=8.8, 1.6 Hz, 1H), 7.96-7.94 (d, J=8.0 Hz, 2H), 7.77 (s, 1H), 4.22 (s, 3H), 3.34 (s, 3H). MS: $[MH]^+$ 425.3

Example 1.284. Synthesis of 4-Methoxy-2-(5-(trifluoromethyl)-[1,1'-biphenyl]-2-yl)quinoline-7-carboxylic acid (I-378)

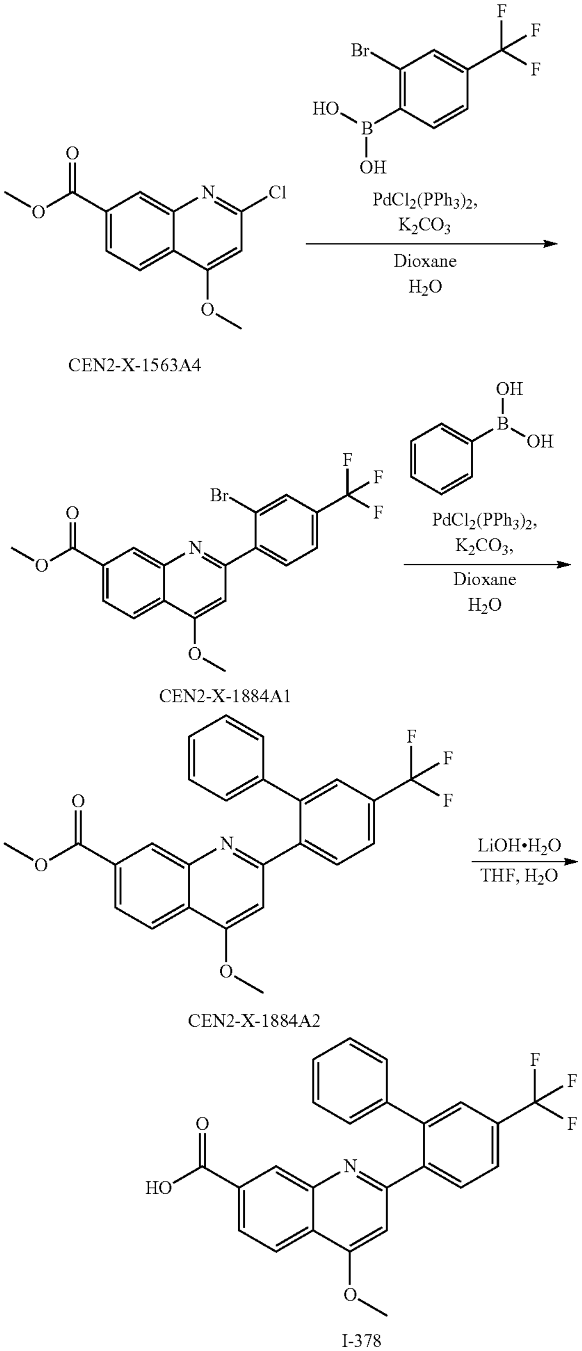

CEN2-X-1563A4

CEN2-X-1884A1

CEN2-X-1884A2

I-378

Methyl 2-(2-bromo-4-(trifluoromethyl)phenyl)-4-methoxyquinoline-7-carboxylate (X-1884A1). To a stirred solution of methyl 2-chloro-4-methoxyquinoline-7-carboxylate (X-1563A4) (0.500 g, 1.99 mmol) in a mixture of 1,4-dioxane-water (4:1, 5 mL) were added (2-bromo-4-(trifluoromethyl)phenyl)boronic acid (0.695 g, 2.58 mmol) and $K_2CO_3$ (1.3 g, 9.95 mmol) sequentially at room temperature under nitrogen. The reaction mixture was degassed (purging with nitrogen) for 20 min followed by the addition of $PdCl_2$(dppf) (0.037 g, 0.09 mmol) and the resulting mixture was heated at 100° C. for 1 h. Reaction mixture was cooled to room temperature, diluted with water (30 mL) and was extracted with ethyl acetate (30 mL×3). Combined organic extracts were dried over anhydrous $Na_2SO_4$ and concentrated under reduce pressure to afford crude mass, which was purified by silica gel Combi-Flash column chromatography, using ethyl acetate-hexane=0:1→2:8 as eluent, to afford methyl 2-(2-bromo-4-(trifluoromethyl)phenyl)-4-methoxyquinoline-7-carboxylate (X-1884A1) (0.250 g, 23%) as an off-white solid. MS: $[MH]^+$ 440.25.

Methyl 4-methoxy-2-(5-(trifluoromethyl)-[1,1'-biphenyl]-2-yl)quinoline-7-carboxylate (X-1884A2). To a stirred solution of methyl 2-(2-bromo-4-(trifluoromethyl)phenyl)-4-methoxyquinoline-7-carboxylate (X-1884A1) (0.200 g, 0.45 mmol) in a mixture of 1,4-dioxane-water (4:1, 5 mL) were added phenylboronic acid (0.066 g, 0.54 mmol) and $K_2CO_3$ (0.248 g, 1.8 mmol) sequentially at room temperature under nitrogen. The reaction mixture was degassed (purging with nitrogen) for 20 min followed by the addition of $PdCl_2$(dppf) (0.018 g, 0.02 mmol) and the resulting mixture was heated at 100° C. for 2 h. Reaction mixture was cooled to room temperature, diluted with water (30 mL) and was extracted with ethyl acetate (30 mL×3). Combined organic extracts were dried over anhydrous $Na_2SO_4$ and concentrated under reduce pressure to afford crude mass, which was purified by silica gel CombiFlash column chromatography, using ethyl acetate-hexane=0:1→1:9 as eluent, to afford methyl 4-methoxy-2-(5-(trifluoromethyl)-[1,1'-biphenyl]-2-yl)quinoline-7-carboxylate (X-1884A2) (0.160 g, 75%) as an off-white solid. MS: $[MH]^+$ 438.37.

4-Methoxy-2-(5-(trifluoromethyl)-[1,1'-biphenyl]-2-yl) quinoline-7-carboxylic acid (I-378). To a stirred solution of methyl 4-methoxy-2-(5-(trifluoromethyl)-[1,1'-biphenyl]-2-yl)quinoline-7-carboxylate (X-1884A2) (0.150 g, 0.34 mmol) in a mixture of THF-water (9:1; 3.0 mL) was added lithium hydroxide monohydrate (0.042 g, 1.02 mmol) at room temperature and the resulting mixture was heated at 70° C. for 2 h. After cooling to room temperature, the reaction mixture was concentrated under reduced pressure, obtained crude was diluted with water (30 mL) and was extracted with ethyl acetate (20 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford to afford 4-methoxy-2-(5-(trifluoromethyl)-[1,1'-biphenyl]-2-yl)quinoline-7-carboxylic acid (I-378) (0.140 g, 32%) as a white solid. $^1H$ NMR (400 MHz, DMSO-$d_6$) δ 13.5 (br., 1H), 8.47-8.47 (d, J=1.6 Hz, 1H), 8.14-8.12 (d, J=8.8 Hz, 1H), 8.08-8.06 (d, J=8.0 Hz, 1H), 8.03-8.00 (dd, J=8.4, 1.6 Hz, 1H), 7.95-7.93 (dd, J=8.4, 1.6 Hz, 1H), 7.83 (s, 1H), 7.32-7.29 (m, 3H), 7.25-7.22 (m, 2H), 6.63 (s, 1H), 3.62 (s, 3H). MS: $[MH]^+$ 424.39.

Example 1.285. Synthesis of 4-Methoxy-2-(2-(4-methyl-1H-imidazol-1-yl)-4-(trifluoromethyl)phenyl)quinoline-7-carboxylic acid (I-379) & 4-methoxy-2-(2-(5-methyl-1H-imidazol-1-yl)-4-(trifluoromethyl)phenyl)quinoline-7-carboxylic acid (I-380)

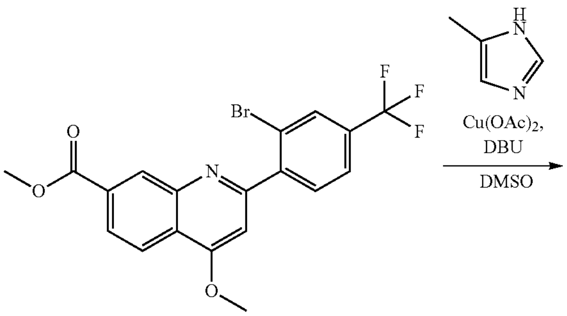

X-1884A1

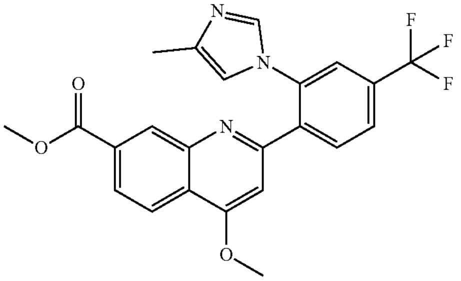

+

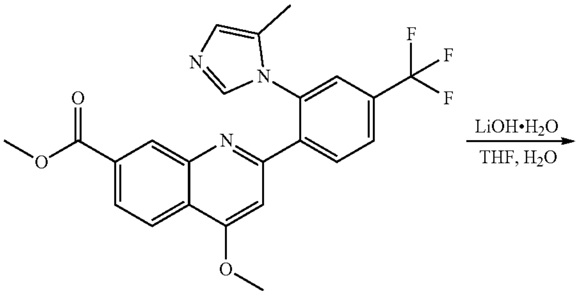

X-1885A1

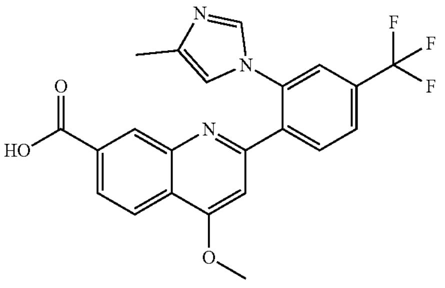

+

I-379

-continued

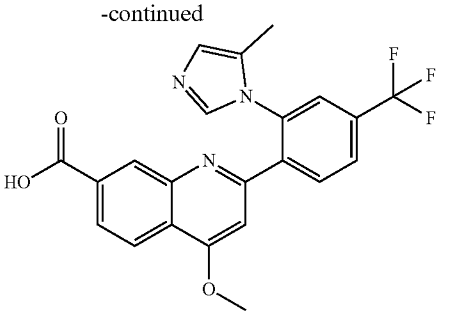

I-380

Methyl 4-methoxy-2-(2-(4-methyl-1H-imidazol-1-yl)-4-(trifluoromethyl)phenyl)quinoline-7-carboxylate (X-1885A1). To a stirred solution of methyl 2-(2-bromo-4-(trifluoromethyl)phenyl)-4-methoxyquinoline-7-carboxylate (X-1884A1) (0.400 g, 0.91 mmol) in a DMSO (5 mL) were added 5-methyl-1H-imidazole (0.110 g, 1.36 mmol), DBU (0.276 g, 1.82 mmol) sequentially at room temperature. The reaction mixture was degassed (purging with nitrogen) for 10 min followed by the addition of $Cu(OAc)_2$ (0.016 g, 0.09 mmol) and the resulting mixture was heated at 130° C. under microwave irradiation for 10 min. Reaction mixture was cooled to room temperature, diluted with water (80 mL) and was extracted with ethyl acetate (50 mL×2). Combined organic extracts were dried over anhydrous $Na_2SO_4$ and concentrated under reduce pressure. Obtained crude product was purified by silica gel column chromatography, using ethyl acetate-hexane=0:1→8:2 as gradient, to afford mixture of two regio-isomer as methyl 4-methoxy-2-(2-(4-methyl-1H-imidazol-1-yl)-4-(trifluoromethyl)phenyl) quinoline-7-carboxylate (X-1885A1) (0.220 g, 50%) MS: $[MH]^+$ 442.38.

4-Methoxy-2-(2-(4-methyl-1H-imidazol-1-yl)-4-(trifluoromethyl)phenyl)quinoline-7-carboxylic acid (I-379) &4-methoxy-2-(2-(5-methyl-1H-imidazol-1-yl)-4-(trifluoromethyl)phenyl)quinoline-7-carboxylic acid (I-380). To a stirred solution of methyl 4-methoxy-2-(2-(4-methyl-1H-imidazol-1-yl)-4-(trifluoromethyl)phenyl)quinoline-7-carboxylate (X-1885A1) (0.200 g, 0.45 mmol) in a mixture of THF-water (9:1; 5 mL) was added lithium hydroxide monohydrate (0.076 g, 1.81 mmol) at room temperature and the resulting mixture was heated at 60° C. for 2 h. After cooling to room temperature, the reaction mixture was concentrated under reduced pressure. Obtained crude was diluted with water (50 mL) and aqueous part was acidified (pH~5-6) with an aqueous solution of 1N HCl and was extracted with ethyl acetate (35 mL×2). Combined organic extracts were dried over anhydrous $Na_2SO_4$ and concentrated under reduce pressure. Obtained crude product was purified by prep HPLC to afford two product mentioned below.

4-methoxy-2-(2-(4-methyl-1H-imidazol-1-yl)-4-(trifluoromethyl)phenyl)quinoline-7-carboxylic acid (I-379) (0.065 g, 34%) as a white solid. $^1H$ NMR (400 MHz, DMSO-$d_6$) δ 13.40 (br, 1H), 8.50-8.50 (d, J=1.2 Hz, 1H), 8.20-8.16 (m, 2H), 8.07-8.00 (m, 3H), 7.53-7.53 (d, J=1.2 Hz, 1H), 7.05 (s, 1H), 6.60 (s, 1H), 3.81 (s, 3H), 2.06 (s, 3H). MS: $[MH]^+$ 428.39.

4-methoxy-2-(2-(5-methyl-1H-imidazol-1-yl)-4-(trifluoromethyl)phenyl)quinoline-7-carboxylic acid (I-380) (0.007 g, 4%) as white solid. $^1H$ NMR (400 MHz, DMSO-$d_6$) δ 8.45 (s, 1H), 8.25-8.23 (d, J=8.0 Hz, 1H), 8.11-8.03 (m, 4H), 7.72 (s, 1H), 6.70 (s, 1H), 6.45 (s, 1H), 3.80 (s, 3H), 1.80 (s, 3H). MS: $[MH]^+$ 428.38.

Example 1.286. Synthesis of 2-(2-(1H-imidazol-1-yl)-4-(trifluoromethyl)phenyl)-4-methoxyquinoline-7-carboxylic acid (I-381)

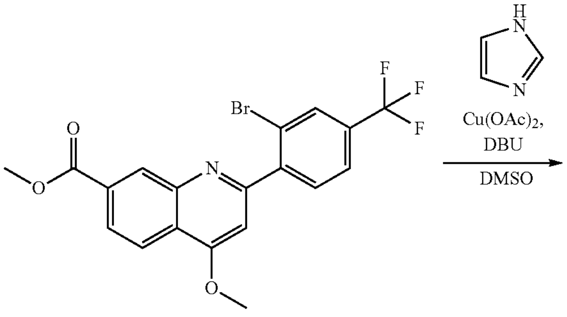

X-1884A1

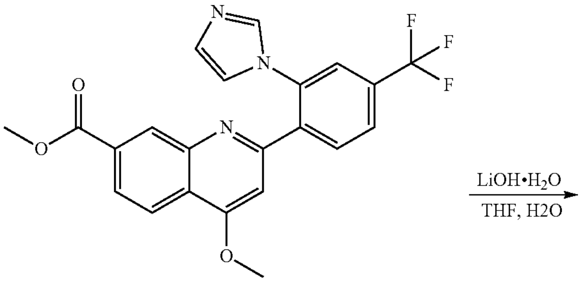

X-1886A1

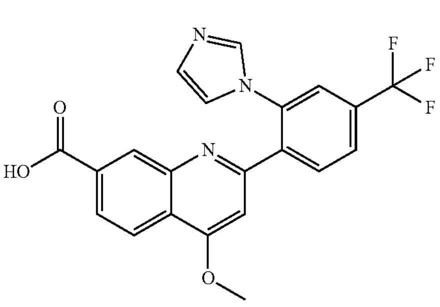

I-381

The following compound was prepared in a manner analogous to the procedures described above for 4-methoxy-2-(2-(4-methyl-1H-imidazol-1-yl)-4-(trifluoromethyl)phenyl)quinoline-7-carboxylic acid (I-379).

2-(2-(1H-imidazol-1-yl)-4-(trifluoromethyl)phenyl)-4-methoxyquinoline-7-carboxylic acid (I-381) (0.100 g, 69%) as a white solid. $^1H$ NMR (400 MHz, DMSO-$d_6$) δ 13.39 (br, 1H), 8.46 (s, 1H), 8.18-8.13 (t, J=8.4 Hz, 3H), 8.06-8.04 (m, 2H), 7.73 (s, 1H), 7.28 (s, 1H), 6.98 (s, 1H), 6.63 (s, 1H). 3.18 (s, 3H). MS: [MH]414.39.

Example 1.287. Synthesis of 4-methoxy-N-(3,3,3-trifluoro-2-hydroxypropyl)-2-(4-(trifluoromethyl)phenyl)quinoline-7-carboxamide (I-382)

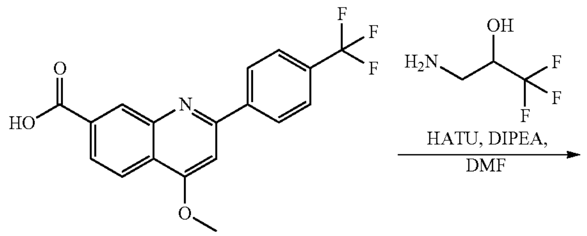

I-181

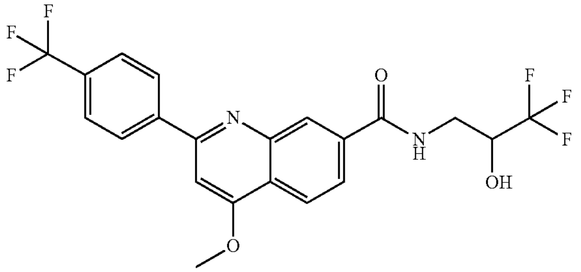

I-382

The following compound was prepared in a manner analogous to the procedures described above for (R)—N-(1-hydroxypropan-2-yl)-4-methoxy-2-(4-(trifluoromethyl)phenyl)quinoline-7-carboxamide (I-324).

4-methoxy-N-(3,3,3-trifluoro-2-hydroxypropyl)-2-(4-(trifluoromethyl)phenyl)quinoline-7-carboxamide (I-382) (0.250 g, 71%) as a white solid. $^1$H NMR (400 MHz, DMSO-$d_6$) δ: 9.08-9.05 (t, J=5.6 Hz, 1H), 8.59-8.59 (d, J=1.6 Hz, 1H), 8.56-8.54 (d, J=8.0 Hz, 2H), 8.24-8.22 (d, J=8.4 Hz, 1H), 8.02-8.00 (dd, J=1.6, 8.4 Hz, 1H), 7.96-7.94 (d, J=8.0 Hz, 2H), 7.74 (s, 1H), 6.56-6.55 (d, J=6.8 Hz, 1H), 4.28-4.26 (m, 1H), 4.21 (s, 3H), 3.69-3.64 (m, 1H), 3.43-3.36 (m, 1H). MS: $[MH]^+$ 459.3.

Example 1.288. Synthesis of N-(4-methoxy-2-(4-(trifluoromethyl)phenyl)quinolin-7-yl)methanesulfonamide (I-383)

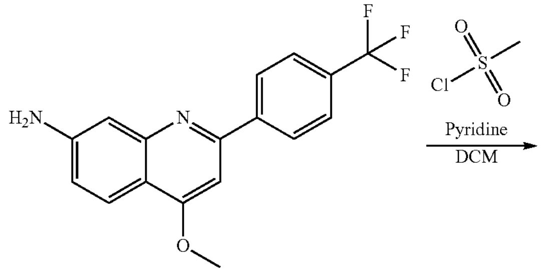

X-1866A1

-continued

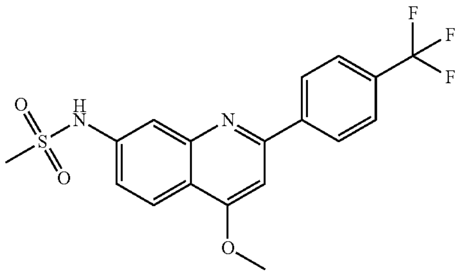

I-383

To a stirred 4-methoxy-2-(4-(trifluoromethyl)phenyl)quinolin-7-amine (X-1866A1) (0.150 g, 0.45 mmol) in DCM (3 mL) were added pyridine (0.071 g, 0.90 mmol) and mesyl chloride (0.052 g, 0.45 mmol) at 0° C. under nitrogen and the resulting mixture was stirred at room temperature for 1 h. The reaction mixture was slowly poured into ice-water (50 mL) and was extracted with ethyl acetate (50 mL×3). The combined organic extracts were washed with brine (100 mL), dried over anhydrous $Na_2SO_4$ and concentrated under reduced pressure. The resulting crude was purified by reverse phase (C-18) silica gel column chromatography using acetonitrile-water=0:1→1:0 as gradient, to afford N-(4-methoxy-2-(4-(trifluoromethyl)phenyl)quinolin-7-yl)methanesulfonamide (I-383) (0.06 g, 42%) as a brown solid. $^1$H NMR (400 MHz, DMSO-$d_6$) δ 10.31 (bs, 1H), 8.52-8.50 (d, J=8.4 Hz, 2H), 8.10-8.08 (d, J=8.8 Hz, 1H), 7.91-7.89 (d, J=8.4 Hz, 2H), 7.80-7.79 (d, J=2.0 Hz, 1H), 7.56 (s, 1H), 7.41-7.38 (dd, J=8.8, 2.0 Hz, 1H), 4.16 (s, 3H), 3.11 (s, 3H). $[MH]^+$ 397.4.

Example 1.289. Synthesis of N-(2-(4-(Tert-butyl)phenyl)-4-methoxyquinolin-7-yl)acrylamide (I-384)

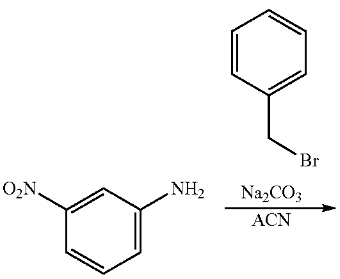

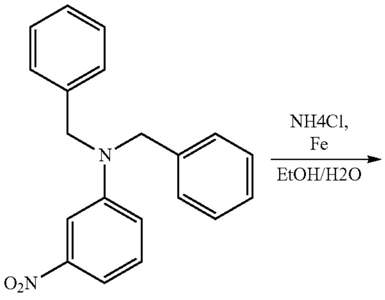

X-1286D1

-continued

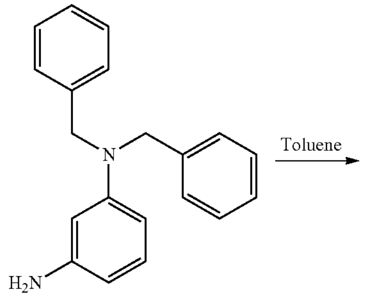

X-1286D2

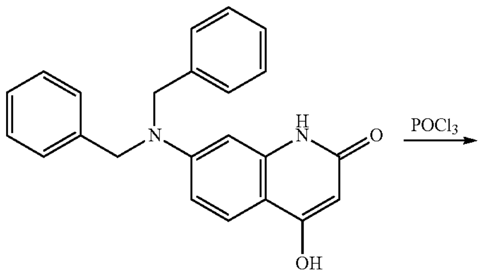

X-1286D3

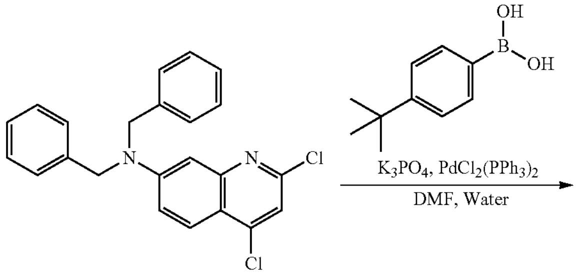

X-1286D4

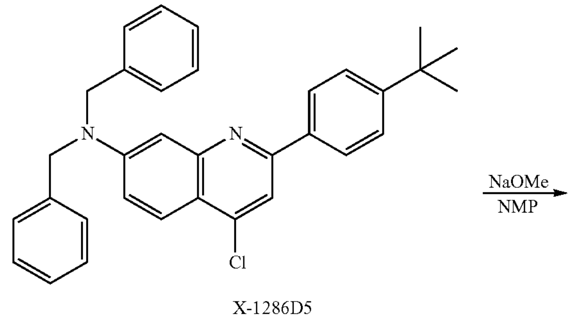

X-1286D5

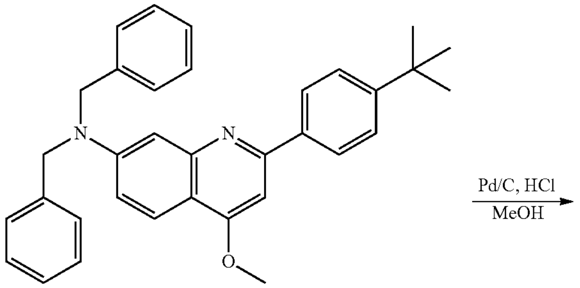

X-1566A1

-continued

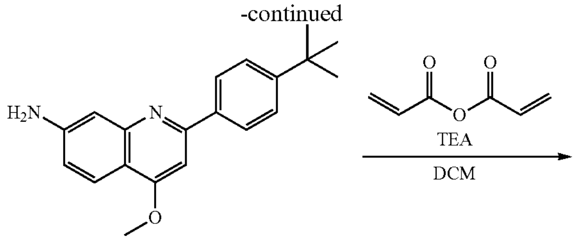

X-1566A2

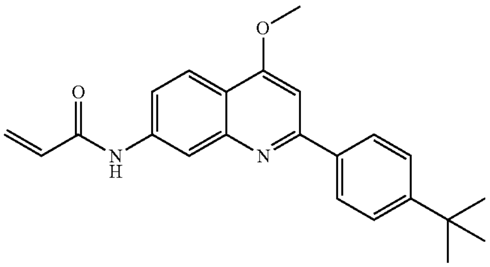

I-384

N,N-Dibenzyl-3-nitroaniline (X-1286D1). To a stirred solution of 3-nitroaniline (7.0 g, 50.67 mmol) in ACN (140 mL) were added sodium carbonate (21.5 g, 202.70 mmol) and (bromomethyl)benzene (18.2 g, 106.42 mmol) at room temperature under nitrogen and the resulting mixture was stirred at 80° C. for 20 h. After cooling to room temperature, reaction mixture was poured into ice water (1000 mL) and was extracted with ethyl acetate (1000 mL×3), dried over anhydrous $Na_2SO_4$ and concentrated under reduced pressure. The crude product was purified by silica gel column chromatography, using ethyl acetate-hexane=0:1→1:9 as gradient, to afford N,N-dibenzyl-3-nitroaniline (X-1286D1) (15.5 g, 96%) as an off-white solid. MS: $[MH]^+$ 319.11.

N1,N1-Dibenzylbenzene-1,3-diamine (X-1286D2). To a stirred solution of N,N-dibenzyl-3-nitroaniline (X-1286D1) (15.5 g, 48.72 mmol) in ethanol water (15:5, 20 mL) were added Fe-powder (13.60 g, 243.60 mmol) and ammonium chloride (13.03 g, 243.60 mmol) at 0° C. and reaction was allowed to stirred at 70° C. for 2 h. After cooling to room temperature, reaction mixture was filtered through a celite, filtrate was diluted with water (500 mL) and was extracted with ethyl acetate (1000 mL×3). Combined organic extracts were dried over anhydrous $Na_2SO_4$ and concentrated under reduced pressure, to afford N1,N1-dibenzylbenzene-1,3-diamine (X-1286D2) (14.0 g, 99%) as an off-white solid, which was taken to the next step without further purification. MS: $[MH]^+$ 289.16.

7-(Dibenzylamino)-4-hydroxyquinolin-2(1H)-one (X-1286D3). To a stirred solution of N1,N1-dibenzylbenzene-1,3-diamine (X-1286D2) (4.0 g, 13.88 mmol) in toluene (16 mL) was added Bis(2,4,6-trichlorophenyl) malonate (6.8 g, 13.88 mmol) at room temperature and reaction was allowed to stirred at 110° C. for 2 h. After cooling to room temperature, the reaction mixture was combined with an identically prepared one more batches (4.0 g) and the reaction mixture filtered and solid was washed with ethyl acetate-hexane and concentrated under reduce pressure, to afford 7-(dibenzylamino)-4-hydroxyquinolin-2(1H)-one (X-1286D3) (3.0 g, 30%) as an off-white solid. MS: $[MH]^+$ 357.12.

N,N-Dibenzyl-2,4-dichloroquinolin-7-amine (X-1286D4). A stirred solution of 7-(dibenzylamino)-4-hydroxyquinolin-2(1H)-one (X-1286D3) (3.0 g, 8.42 mmol) in $POCl_3$ (26 mL) was heated at 110° C. for 4 h. After cooling to room temperature, the reaction mixture was basified (pH~8-9) with an aqueous solution of saturated $NaHCO_3$ and was extracted with ethyl acetate (500 mL×3). Combined organic extracts were dried over anhydrous $Na_2SO_4$ and concentrated under reduce pressure. The crude product was purified by silica gel column chromatography, using ethyl acetate-hexane=0:1→2:8 as gradient, to afford N,N-dibenzyl-2,4-dichloroquinolin-7-amine (X-1286D4) (1.7 g, 51%) as an off-white solid. MS: $[MH]^+$ 393.1

N,N-Dibenzyl-2-(4-(tert-butyl)phenyl)-4-chloroquinolin-7-amine (X-1286D5). To a stirred solution of N,N-dibenzyl-2,4-dichloroquinolin-7-amine (X-1286D4) (1.7 g, 4.33 mmol) in a mixture of DMF-water (3:1, 15 mL) were added (4-(tert-butyl)phenyl)boronic acid (1.07 g, 6.05 mmol) and potassium phosphate (2.29 g, 10.84 mmol) at room temperature under nitrogen. The reaction mixture was degassed (purging with nitrogen) for 20 min followed by addition of $Pd(PPh_3)_4$ (0.24 g, 0.21 mmol) and the reaction mixture was heated at 90° C. for 2 h. The reaction mixture was cooled to room temperature, diluted with water (100 mL) and was extracted with ethyl acetate (100 mL×3). The combined organic extracts were dried over anhydrous $Na_2SO_4$ and concentrated under reduce pressure. The crude product was purified by silica gel column chromatography, using ethyl acetate-hexane=0:1→0.2:9.8 as gradient, to afford N,N-dibenzyl-2-(4-(tert-butyl)phenyl)-4-chloroquinolin-7-amine (X-1286D5) (0.6 g, 28%) as an off-white solid. MS: $[MH]^+$ 491.1.

N,N-Dibenzyl-2-(4-(tert-butyl)phenyl)-4-methoxyquinolin-7-amine (X-1566A1). To a stirred solution of N,N-dibenzyl-2-(4-(tert-butyl)phenyl)-4-chloroquinolin-7-amine (X-1286D5) (0.2 g, 0.40 mmol) in a NMP (15 mL) were added sodium methoxide (2 mL) at 0° C. under nitrogen and the resulting mixture was stirred at room temperature for 20 h. The reaction mixture was cooled to room temperature, diluted with water (100 mL) and was extracted with ethyl acetate (100 mL×3). Combined organic extracts were dried over anhydrous $Na_2SO_4$ and concentrated under reduce pressure. The crude product was purified by (C-18) silica gel column chromatography, using acetonitrile-water=0:1→5:5 as gradient, to afford N,N-dibenzyl-2-(4-(tert-butyl)phenyl)-4-methoxyquinolin-7-amine (X-1566A1) (0.14 g, 71%) as an off-white solid. MS: $[MH]^+$487.27.

2-(4-(Tert-butyl)phenyl)-4-methoxyquinolin-7-amine (X-1566A2). To a stirred solution of N,N-dibenzyl-2-(4-(tert-butyl)phenyl)-4-methoxyquinolin-7-amine (X-1566A1) (0.14 g, 0.28 mmol) in MeOH (5 mL) were added Pd/C (0.14 g) and HCl (14 drops) dropwise in the reaction mixture at room temperature and the resulting mixture was stirred at room temperature for 1 h. reaction mixture was filtered over a celite bed, washed the bed with MeOH (50 mL) and collected filtrates were concentrated under reduced pressure. The reaction mixture was basified (pH~8-9) with an aqueous solution of saturated $NaHCO_3$ and was extracted with ethyl acetate (50 mL×3), dried over anhydrous $Na_2SO_4$ and concentrated under reduce pressure, to afford 2-(4-(tert-butyl)phenyl)-4-methoxyquinolin-7-amine (X-1566A2) (0.05 g, 56%) as a brown solid. MS: $[MH]^+$ :307.47.

N-(2-(4-(Tert-butyl)phenyl)-4-methoxyquinolin-7-yl) acrylamide (I-384). To a stirred solution of 2-(4-(tert-butyl) phenyl)-4-methoxyquinolin-7-amine (X-1566A2) (0.05 g, 0.16 mmol) in DCM (2 mL) were added triethylamine (0.082 g, 0.81 mmol) and acrylic anhydride (0.024 g, 0.19 mmol) at 0° C. under nitrogen and the reaction mixture was stirred at room temperature for 30 min. The reaction mixture was diluted with water (20 mL) and was extracted with DCM (50 mL×2). Combined organic extracts were dried over anhydrous $Na_2SO_4$ and concentrated under reduced pressure. The crude product was purified by $C^{18}$ silica gel column chromatography, using acetonitrile-water=0:1→4:6 as gradient, to afford N-(2-(4-(Tert-butyl)phenyl)-4-methoxyquinolin-7-yl)acrylamide (I-384) (0.035 g, 59%) as an off-white solid. MS: $[MH]^+$ 361.02. $^1H$ NMR (400 MHz, DMSO-$d_6$) δ 10.47 (s, 1H), 8.49 (s, 1H), 8.18-8.16 (d, J=7.6 Hz, 2H), 8.07-8.05 (d, J=8.8 Hz, 1H), 7.68-7.65 (d, J=9.2 Hz, 1H), 7.56-7.54 (d, J=7.6 Hz, 2H), 7.41 (s, 1H), 6.54-6.48 (m, 1H), 6.35-6.31 (d, J=16.8, Hz, 1H), 5.84-5.81 (d, J=10.4 Hz, 1H), 4.13 (s, 3H), 1.34 (s, 9H).

Example 1.290. Synthesis of N-(2-(2-(2-Aminoethoxy)ethoxy)ethyl)-4-(4-(tert-butyl)phenyl)pyrrolo[1,2-a]quinoxaline-7-carboxamide (I-385)

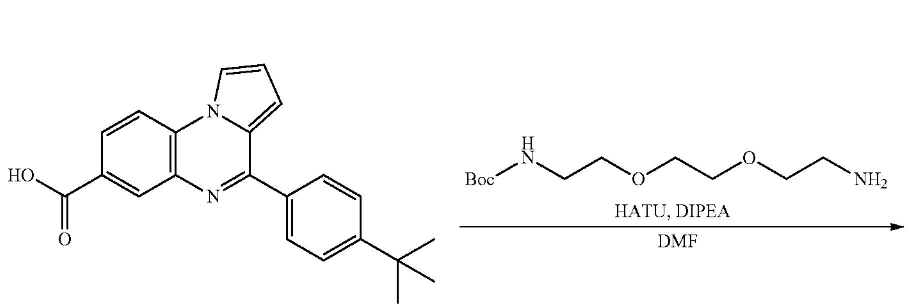

I-41

-continued

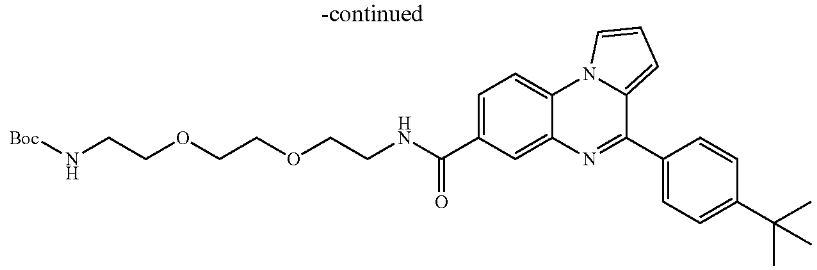

X-1578A1

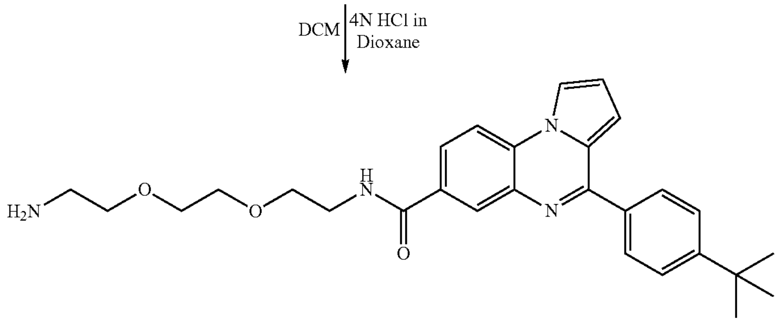

I-385 tert-Butyl(2-(2-(2-(4-(4-(tert-butyl)phenyl)pyrrolo[1,2-a]quinoxaline-7-carboxamido)ethoxy)ethoxy)ethyl) carbamate (X-1578A1). To a solution of 4-(4-(tert-butyl)phenyl)pyrrolo[1,2-a]quinoxaline-7-carboxylic acid (I-41) (0.250 g, 0.72 mmol)) in DMF (6 mL) were added DIPEA (0.370 mL, 2.18 mmol) and HATU (0.410 g, 1.09 mmol) sequentially at room temperature under nitrogen. After stirring for 10 min at the same temperature, tert-butyl (2-(2-(2-aminoethoxy)ethoxy)ethyl)carbamate (0.270 g, 1.09 mmol) was added at 0° C. and the resulting reaction mixture was stirred at room temperature for 30 min. Reaction mixture was poured into ice water (150 mL) and was extracted with ethyl acetate (70 mL×3). Combined organic extracts were washed with brine (70 mL×2), dried over anhydrous $Na_2SO_4$ and concentrated under reduced pressure, to afford tert-butyl (2-(2-(2-(4-(4-(tert-butyl) phenyl)pyrrolo[1,2-a]quinoxaline-7-carboxamido)ethoxy)ethoxy)ethyl)carbamate (X-1578A1) (0.300 g, 72%) as an off-white solid. MS: $[MH]^+$ 575.21.

N-(2-(2-(2-Aminoethoxy)ethoxy)ethyl)-4-(4-(tert-butyl)phenyl)pyrrolo[1,2-a]quinoxaline-7-carboxamide (I-385). To a stirred solution of tert-butyl (2-(2-(2-(4-(4-(tert-butyl)phenyl)pyrrolo[1,2-a]quinoxaline-7-carboxamido)ethoxy)ethoxy)ethyl)carbamate (X-1578A1) (0.300 g, 0.52 mmol) in DCM (4 mL) was added 4 M HCl in dioxane (2 mL) at 0° C. under nitrogen and the resulting reaction mixture was stirred at room temperature for 1 h. Reaction mixture was concentrated under reduced pressure. Obtained crude was triturated with diethyl ether (2×10 mL), dried over reduced pressure, to afford N-(2-(2-(2-aminoethoxy)ethoxy)ethyl)-4-(4-(tert-butyl)phenyl)pyrrolo[1,2-a]quinoxaline-7-carboxamide (I-385) (0.120 g, 48%) as a yellow solid. $^1H$ NMR (400 MHz, DMSO-$d_6$) δ 8.89-8.87 (t, J=4.0 Hz, 1H), 8.76 (s, 1H), 8.52-8.48 (m, 2H), 8.17-8.17 (d, J=8.4 Hz, 1H), 8.00-7.94 (m, 4H), 7.68-7.66 (d, J=8.4 Hz, 2H), 7.26 (brs, 1H), 7.13 (brs, 1H), 3.62-3.60 (m, 6H), 3.56 (s, 2H), 3.51-3.47 (m, 2H), 2.96-2.92 (m, 2H), 1.38 (s, 9H). MS: $[MH]^+$ 475.0.

Example 1.291. Synthesis of (R)-4-cyclopropyl-N-(1-hydroxypropan-2-yl)-2-(4-(trifluoromethyl)phenyl)quinoline-7-carboxamide (I-386)

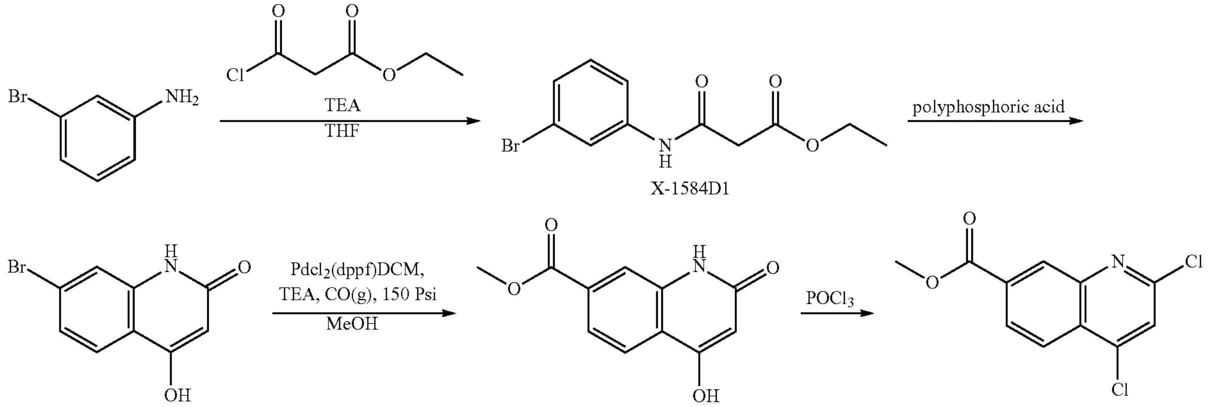

X-1584D1

X-1584D2

X-1584D3

X-1584D4

-continued

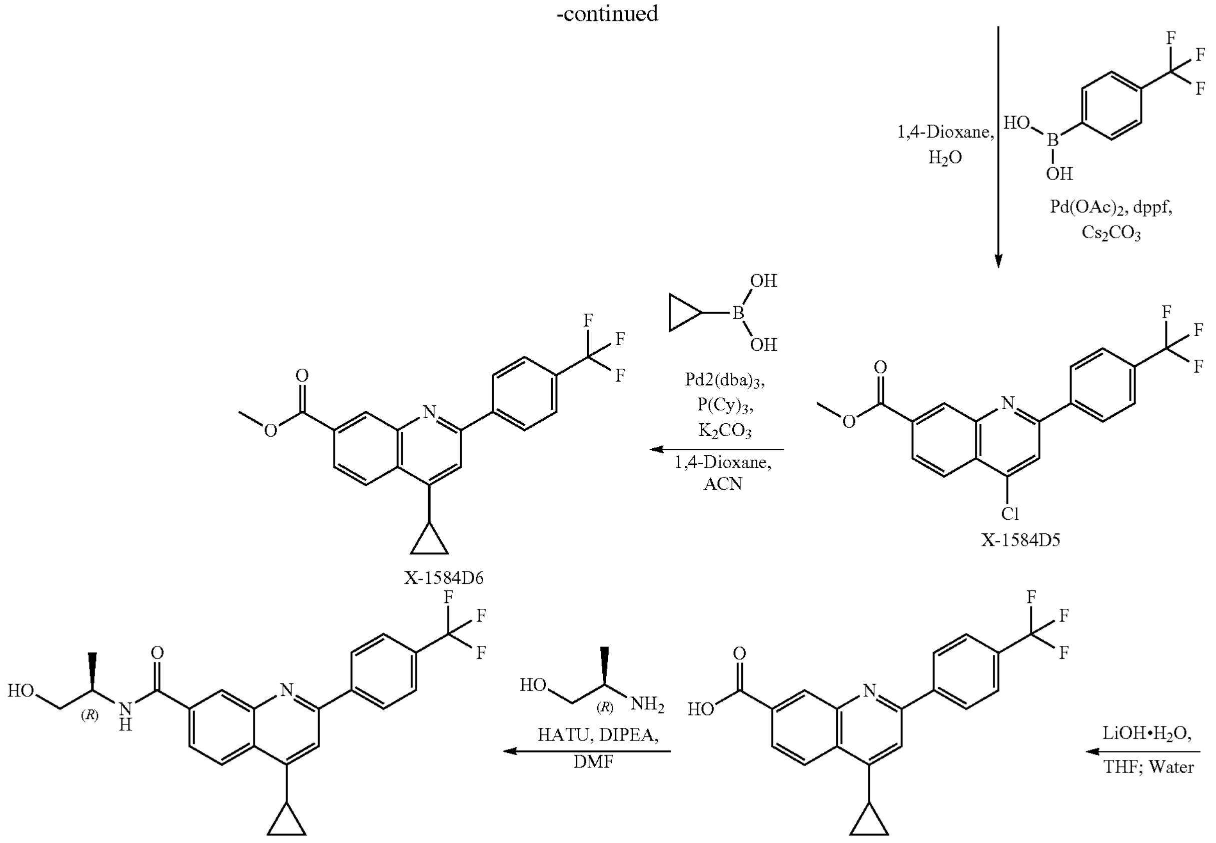

X-1584D5

X-1584D6

I-387

I-386

Ethyl 3-((3-bromophenyl)amino)-3-oxopropanoate (X-1584D1). To a stirred solution of 3-bromoaniline (15.0 g, 87.71 mmol) in THE (200 mL) was added TEA (26.57 g, 263.15 mmol) and stirred at 0° C. for 10 min. Ethyl 3-chloro-3-oxopropanoate (19.07 g, 131.57 mmol) was added at 0° C. and the resulting reaction mixture was stirred at room temperature for 1 h. After completion of reaction, reaction mixture was diluted by $NaHCO_3$ solution (30 mL), was extracted by ethyl acetate (50 mL×2). Combined organic extracts were washed with brine (200 mL), dried over anhydrous $Na_2SO_4$ and concentrated in vacuo. The crude product was purified by silica gel column chromatography, using ethyl acetate-hexane=0:1→2:8 as a gradient, to afford ethyl 3-((3-bromophenyl)amino)-3-oxopropanoate (X-1584D1) (20.0 g, 80%) as a brown liquid. MS: $[MH]^+$ 286.1/$[MH]^+$ 288.1.

7-bromo-4-hydroxyquinolin-2(1H)-one (X-1584D2). To a stirred solution of ethyl 3-((3-bromophenyl)amino)-3-oxopropanoate (X-1584D1) (12.0 g, 42.10 mmol) in polyphosphoric acid (71.0 g, 210.30 mmol). Reaction mixture was stirred at 100° C. for 16 h. After completion of reaction, reaction mixture was poured to crushed ice. precipitate was filtered and dry under reduce pressure, to afford 7-bromo-4-hydroxyquinolin-2(1H)-one (X-1584D2) (9.0 g, 54%) as a yellow solid. MS: $[MH]^+$ 285.8/$[MH]^+$ 287.8 methyl 4-hydroxy-2-oxo-1,2-dihydroquinoline-7-carboxylate (X-1584D3). To a stirred solution of 7-bromo-4-hydroxyquinolin-2(1H)-one (X-1584D2) (7.0 g, 12.98 mmol) in MeOH (100 mL). were added TEA (17.74 g, 175.73 mmol) at room temperature. The reaction mixture was purging with carbon monoxide for 30 min followed by addition of $PdCl_2$(dppf). DCM (0.341 g, 0.41 mmol) at room temperature. the resulting reaction mixture was stirred in a Parr autoclave under CO(g) at 100° C. for 2 h in 150 Psi. Reaction mixture was cooled to room temperature, filtered over a celite bed and washed with methanol. Combined filtrates were concentrated under reduced pressure and diluted by water (300 mL). Precipitate was filtered and dry under reduce pressure, to afford methyl 4-hydroxy-2-oxo-1,2-dihydroquinoline-7-carboxylate (X-1584D3) (8.0 g, Quantitative yield) as an off-white solid. MS: $[MH]^+$ 219.98.

methyl 2,4-dichloroquinoline-7-carboxylate (X-1584D4). To a stirred solution of methyl 4-hydroxy-2-oxo-1,2-dihydroquinoline-7-carboxylate (X-1584D3) (8.0 g, 31.96 mmol) in $POCl_3$ (50 mL). Reaction mixture was stirred at 100° C. for 1 h. After completion of reaction, reaction mixture was poured in to crushed ice water (200 mL) and resulting precipitate was collected by filtration and dry under reduce pressure. The crude product was purified by silica gel column chromatography, using ethyl acetate-hexane=0:1→4 2:8 as a gradient, to afford methyl 2,4-dichloroquinoline-7-carboxylate (X-1584D4) (1.0 g, 11%) as a white solid. MS: $[MH]^+$ 255.9 methyl 4-chloro-2-(4-(trifluoromethyl)phenyl)quinoline-7-carboxylate (X-1584D5). To a stirred solution of methyl 2,4-dichloroquinoline-7-carboxylate (X-1584D4) (1.0 g, 3.92 mmol) in 1,4-Dioxane:water (8:2, 8 mL), were added $Cs_2CO_3$ (3.19 g, 263.15 mmol) and (4-(trifluoromethyl) phenyl)boronic acid (0.745 g, 3.92 mmol) at room temperature. The reaction mixture was degassed (purging with nitrogen) for 30 min followed by the addition of $Pd(OAc)_2$ (0.044 g, 0.19 mmol) and dppf (0.108 g, 0.19 mmol) and resulting mixture was heated at 70° C. for 16 h. After cooling to room temperature, reaction mixture was poured into water (200 mL) and was extracted by ethyl acetate (200 ml×2) and concentrate under reduce pressure. The crude product was purified by silica gel column chromatography, using ethyl acetate-hexane=0:1→4 5:5 as a gradient, to afford methyl 4-chloro-2-(4-(trifluoromethyl)phenyl)quinoline-7-carboxylate (X-1584D5) (0.580 g, 36%) as a white solid. MS: $[MH]^+$ 365.9/$[MH]^+$ 367.9 methyl 4-cyclopropyl-2-(4-(trifluoromethyl)phenyl)quinoline-7-carboxylate (X-1584D6). To a stirred solution of methyl 4-chloro-2-(4-(trifluoromethyl)phenyl)quinoline-7-carboxylate (X-1584D5) (0.520 g, 1.42 mmol) in 1,4-Dioxane:acetonitrile (1:1, 10 mL), were added $K_2CO_3$ (0.590 g, 4.27 mmol) and cyclopropylboronic acid (0.144 g, 2.84 mmol) at room temperature. The reaction mixture was degassed (purging with nitrogen) for 30 min followed by the addition of $Pd_2(dba)_3$ (0.130 g, 0.14 mmol) and $P(Cy)_3$ (0.060 g, 0.21 mmol) and resulting mixture was heated at 120° C. for 2 h. After cooling to room temperature, reaction mixture was poured into water (200 mL) and was extracted by ethyl acetate (200 mL×2) and concentrate under reduce pressure. The crude product was purified by silica gel column chromatography, using ethyl acetate-hexane=0:1→4 5:5 as a gradient, to afford methyl 4-cyclopropyl-2-(4-(trifluoromethyl)phenyl)quinoline-7-carboxylate (X-1584D6) (0.450 g, 85%) as a white solid. MS: $[MH]^+$ 372.0

4-cyclopropyl-2-(4-(trifluoromethyl)phenyl)quinoline-7-carboxylic acid (I-387). To a stirred solution of methyl 4-cyclopropyl-2-(4-(trifluoromethyl)phenyl)quinoline-7-carboxylate (X-1584D6) (0.450 g, 1.21 mmol) in THE (7 mL), was added lithium hydroxide monohydrate (0.254 g, 6.06 mmol) at room temperature and resulting reaction mixture was stirred at 70° C. for 3 h. After cooling to room temperature, the reaction mixture was acidified (pH~2-3) with an aqueous solution of 1N HCl and the resulting precipitate was collected by filtration. Isolated solid was washed with cold water until the pH became neutral (pH~6-7) and precipitate was filtered and dry under reduce pressure, to afford 4-cyclopropyl-2-(4-(trifluoromethyl)phenyl)quinoline-7-carboxylic acid (I-387) (0.290 g, 57%) as an off white solid. MS: $[MH]^+$ 358.0.

(R)-4-cyclopropyl-N-(1-hydroxypropan-2-yl)-2-(4-(trifluoromethyl)phenyl)quinoline-7-carboxamide (I-386). To a stirred solution of 4-cyclopropyl-2-(4-(trifluoromethyl)phenyl)quinoline-7-carboxylic acid (I-387) (0.250 g, 0.70 mmol) in DMF (4.0 mL), were added diisopropylethylamine (0.270 g, 2.10 mmol), HATU (0.399 g, 1.05 mmol) sequentially at 0° C. under nitrogen. After stirring for 10 min at the same temperature, was added (R)-2-aminopropan-1-ol (0.105 g, 1.40 mmol). Reaction mixture was stirred at room temperature for 30 min. Reaction mixture was poured into ice-water (20 mL) and resulting precipitate was filtered and dry under reduce pressure. Obtained solid material was purified by trituration with diethyl ether (5 mL×2), to afford (R)-4-cyclopropyl-N-(1-hydroxypropan-2-yl)-2-(4(trifluoromethyl)phenyl)quinoline-7-carboxamide (I-386) (0.190 g, 65%) as a white solid. $^1H$ NMR (400 MHz, DMSO-$d_6$) δ 8.67-8.66 (d, J=1.6 Hz, 1H), 8.54-8.49 (m, 4H), 8.11-8.08 (dd, J=1.6, 8.8 Hz, 1H), 7.93-7.91 (d, J=8.4 Hz, 2H), 7.80 (s, 1H), 4.80-4.77 (t, J=6.0 Hz, 1H), 4.12-4.09 (m, 1H), 3.55-3.50 (m, 1H), 3.43-3.38 (m, 1H), 2.71-2.68 (m, 1H), 1.26-1.21 (m, 2H), 1.20-1.18 (d, J=6.8 Hz, 3H), 1.13-1.09 (m, 2H). MS: $[MH]^+$ 415.1

Example 1.292. Synthesis of 4-cyclopropyl-2-(4-(trifluoromethyl)phenyl)quinoline-7-carboxylic acid (I-387)

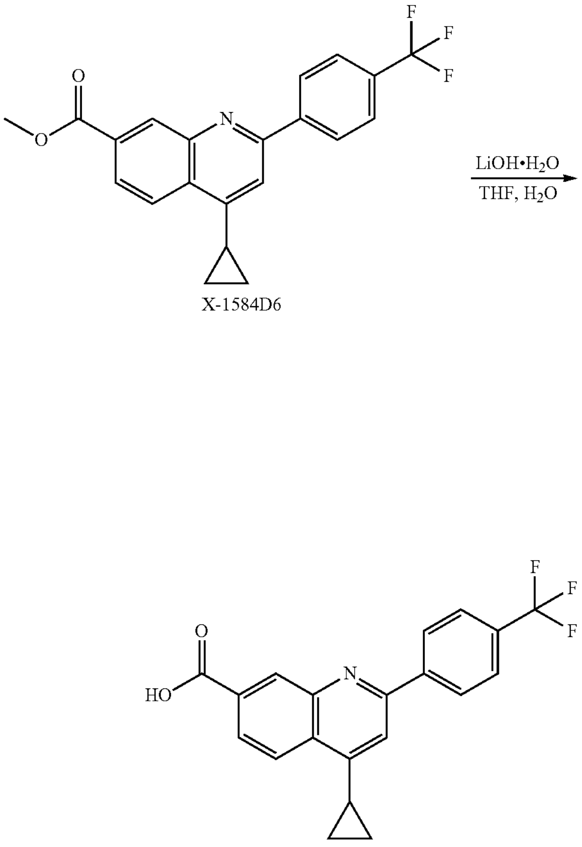

X-1584D6

I-387

To a stirred solution of methyl 4-cyclopropyl-2-(4-(trifluoromethyl)phenyl)quinoline-7-carboxylate (X-1584D6) (0.250 g, 0.67 mmol) in THF (3 mL), was added lithium hydroxide monohydrate (0.141 g, 3.36 mmol) at room temperature. Reaction mixture was stirred at 70° C. for 3 h. After completion of reaction mixture was cooled to room temperature and concentrated under reduced pressure and acidified (pH~2-3) with an aqueous solution of 1N HCl (5 mL) and the resulting precipitate was collected by filtration. Isolated solid was washed with cold water until the pH became neutral (pH~6-7). The solid product was triturated by using n-pentane (5 mL×2) to afford 4-cyclopropyl-2-(4-(trifluoromethyl)phenyl)quinoline-7-carboxylic acid (I-387) (0.150 g, 62%) as an off-white solid. MS: $[MH]^+$ 358.0. $^1H$ NMR (400 MHz, DMSO-$d_6$) δ 13.38 (s, 1H), 8.65-8.65 (d, J=1.6 Hz, 1H), 8.56-8.53 (m, 3H), 8.15-8.12 (dd, J=1.6, 8.8 Hz, 1H), 7.92-7.90 (d, J=8.4 Hz, 2H), 7.85 (s, 1H), 2.72-2.67 (m, 1H), 1.26-1.21 (m, 2H), 1.13-1.109 (m, 2H).

Example 1.293. Synthesis of 4-(1-methyl-1H-imidazol-4-yl)-2-(4-(trifluoromethyl)phenyl)quinoline-7-carboxylic acid (I-388)

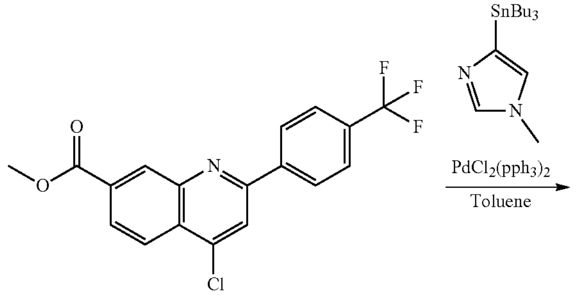

X-1584D5

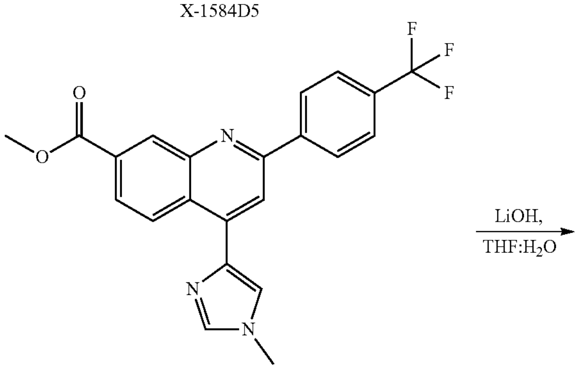

X-1682A1

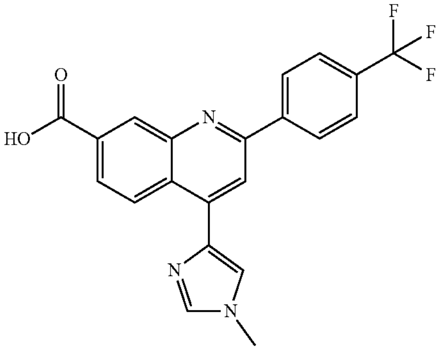

I-388

Methyl 4-(1-methyl-1H-imidazol-4-yl)-2-(4-(trifluoromethyl)phenyl)quinoline-7-carboxylate (X-1682A1). To a stirred solution of methyl 4-chloro-2-(4-(trifluoromethyl)phenyl)quinoline-7-carboxylate (X-1584D5) (0.200 g, 0.54 mmol) in toluene (5 mL) was added 1-methyl-4-(tributylstannyl)-1H-imidazole (0.224 g, 0.60 mmol) at room temperature under nitrogen and reaction mixture was degassed (purging with nitrogen) for 15 min followed by the addition of $PdCl_2(PPh_3)_2$ (0.039 g, 0.05 mmol), and the resulting mixture was heated at 150° C. for 4 h. After cooling to room temperature, reaction mixture was diluted with water (50 mL) and was extracted by ethyl acetate (50 mL×3). Combined organic extracts were dried over anhydrous $Na_2SO_4$ and concentrated under reduced pressure. The crude product was purified by silica gel column chromatography, ethyl acetate-hexane=0:1→5:5 as a gradient, to afford methyl 4-(1-methyl-1H-imidazol-4-yl)-2-(4-(trifluoromethyl)phenyl)quinoline-7-carboxylate (X-1682A1) (0.190 g, 84%) as an off-white solid. MS: $[MH]^+$ 411.9

4-(1-Methyl-1H-imidazol-4-yl)-2-(4-(trifluoromethyl)phenyl)quinoline-7-carboxylic acid (I-388). To a stirred solution of methyl 4-(1-methyl-1H-imidazol-4-yl)-2-(4-(trifluoromethyl)phenyl)quinoline-7-carboxylate (X-1682A1) (0.200 g, 0.48 mmol) in a mixture of THF-water (3:1; 5 mL), was added lithium hydroxide monohydrate (0.081 g, 1.94 mmol) at room temperature. The reaction was heated at 80° C. for 2 h. The reaction was allowed to stirred at room temperature and concentrated under vacuo. The reaction mixture was acidified (pH~2-3) with aqueous 1N HCl, and the resulting precipitate was collected by filtration, washed with cold water until the pH of the filtrate became neutral (pH~6-7). The obtained solid was triturated with hexane (5 mL×2) and dried under vacuo, to afford 4-(1-methyl-1H-imidazol-4-yl)-2-(4-(trifluoromethyl)phenyl)quinoline-7-carboxylic acid (I-388) (0.050 g, 25%) as a yellow solid. $^1H$ NMR (400 MHz, DMSO-$d_6$) δ 13.57 (br. s, 1H), 8.61 (d, J=9.2 Hz, 1H), 8.66 (s, 1H), 8.56-8.54 (d, J=8.4, Hz, 2H), 8.44 (s, 1H), 8.17 (s, 1H), 8.12-8.10 (d, J=8.8 Hz, 1H), 8.96-8.94 (m, 3H), 3.83 (s, 3H). MS: $[MH]^+$ 397.8

Example 1.294. Synthesis of 4-(oxazol-5-yl)-2-(4-(trifluoromethyl)phenyl)quinoline-7-carboxylic acid (I-389)

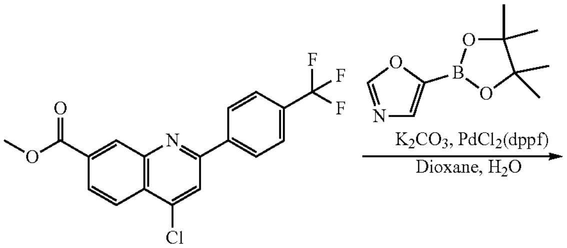

X-1584D5

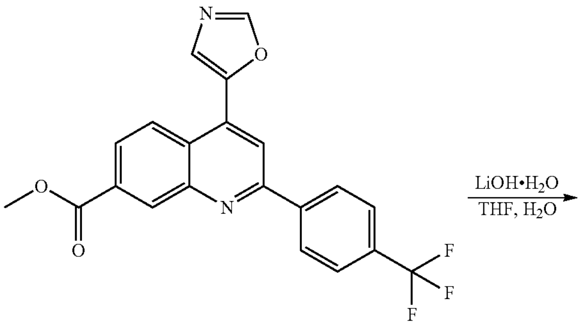

X-1683A1

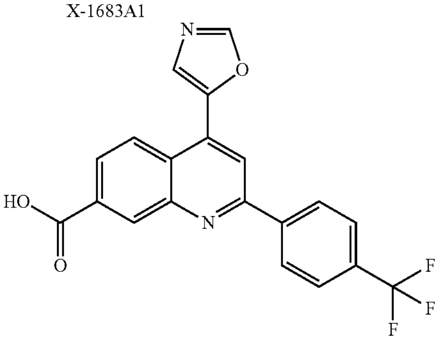

I-389

Methyl 4-(oxazol-5-yl)-2-(4-(trifluoromethyl)phenyl)quinoline-7-carboxylate (X-1683A1). To a stirred solution of methyl 4-chloro-2-(4-(trifluoromethyl) phenyl)quinoline-7-carboxylate (X-1584D5) (0.120 g, 0.32 mmol) in 1,4-dioxane-water (1:1, 6 mL). Were added $K_2CO_3$ (0.09 g, 0.65 mmol) and 5-(4,4,5,5-tetramethyl-1,3,2-dioxaborolan-2-yl) oxazole (0.092 g, 0.82 mmol) at room temperature. The reaction mixture was degassed (purging with nitrogen) for 20 min followed by the addition of $PdCl_2$(dppf) (0.024 g, 0.032 mmol) and the reaction mixture was heated at 100° C. for 3 h. The reaction mixture was cooled to room temperature, diluted with water (60 mL) and was extracted with ethyl acetate (50 mL×3) and concentrate under reduce pressure. The crude product was purified by silica gel column chromatography, using ethyl acetate-hexane=2:8→3:7 as a gradient, to afford methyl 4-(oxazol-5-yl)-2-(4-(trifluoromethyl)phenyl)quinoline-7-carboxylate (X-1683A1) (0.080 g, 61%) as a white solid. MS: $[MH]^+$ 399.41.

4-(Oxazol-5-yl)-2-(4-(trifluoromethyl)phenyl)quinoline-7-carboxylic acid (I-389). To a stirred solution of methyl 4-(oxazol-5-yl)-2-(4-(trifluoromethyl) phenyl)quinoline-7-carboxylate (X-1683A1) (0.070 g, 0.17 mmol) in THF—$H_2O$ (3 mL). was added $LiOH{\cdot}H_2O$ (0.066 g, 0.52 mmol) at room temperature. Reaction mixture was stirred at room temperature for 1 h. After completion of reaction. The reaction mixture was concentrated under reduced pressure and acidified (pH~2-3) with an aqueous solution of 1N HCl (5 mL) and the resulting precipitate was collected by filtration. Isolated solid was washed with cold water until the pH became neutral (pH 6-7). The solid product was triturated by using n-pentane (5 mL×2) to afford 4-(oxazol-5-yl)-2-(4-(trifluoromethyl)phenyl)quinoline-7-carboxylic acid (I-389) (0.040 g, 59.21%) as an off-white solid. $^1H$ NMR (400 MHz, DMSO-$d_6$) δ 8.82 (s, 1H), 8.71 (s, 1H), 8.59-8.57 (d, J=8.8 Hz, 2H), 8.54 (s, 2H), 8.25 (s, 1H), 8.21-8.18 (dd, J=1.2, 8.8 Hz, 1H), 7.97-7.94 (d, J=8.4 Hz, 2H). MS: $[MH]^+$ 385.37.

Example 1.295. Synthesis of 4-(tetrahydro-2H-pyran-4-yl)-2-(4-(trifluoromethyl)phenyl)quinoline-7-carboxylic acid (I-390)

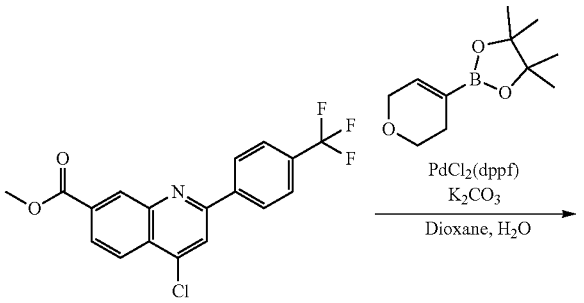

X-1584D5

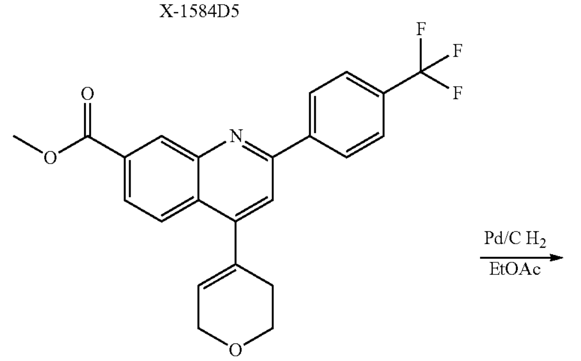

X-1685A1

-continued

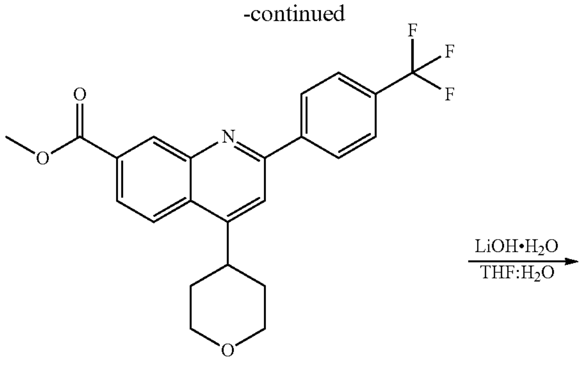

X-1685A2

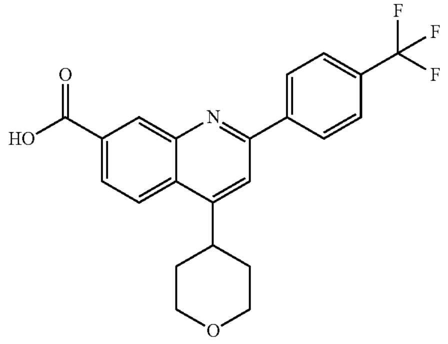

I-390

Methyl 4-(3,6-dihydro-2H-pyran-4-yl)-2-(4-(trifluoromethyl)phenyl)quinoline-7-carboxylate (X-1685A1). To a stirred solution of methyl 4-chloro-2-(4-(trifluoromethyl) phenyl)quinoline-7-carboxylate (X-1584D5) (0.200 g, 0.54 mmol) in 1,4-dioxane-water (3:1, 6 mL) were added 2-(3,6-dihydro-2H-pyran-4-yl)-4,4,5,5-tetramethyl-1,3,2-dioxaborolane (0.133 g, 1.09 mmol) and $K_2CO_3$ (0.226 g, 1.64 mmol) at room temperature under nitrogen. Reaction mixture was degassed (purging with nitrogen) for 30 min followed by the addition $PdCl_2(PPh_3)_2$ (0.039 g, 0.054 mmol) at the same temperature and the resulting mixture was heated at 100° C. for 1 h. After cooling to room temperature, reaction mixture was diluted with water (150 mL) and was extracted with ethyl acetate (100×3). The organic extracts were combined, dried over anhydrous $Na_2SO_4$ and concentration under reduced pressure. The crude mass was purified by silica gel column chromatography, using ethyl acetate-hexane=0:1→5:5 as gradient, to afford methyl 4-(3,6-dihydro-2H-pyran-4-yl)-2-(4-(trifluoromethyl)phenyl)quinoline-7-carboxylate (X-1685A1) (0.200 g, 83%) as a yellow solid. MS: $[MH]^+$ 414.1

Methyl 4-(tetrahydro-2H-pyran-4-yl)-2-(4-(trifluoromethyl)phenyl)quinoline-7-carboxylate (X-1685A2). 10% Pd in activated carbon (0.100 g) was added carefully to a stirred solution of methyl 4-(3,6-dihydro-2H-pyran-4-yl)-2-(4-(trifluoromethyl)phenyl)quinoline-7-carboxylate (X-1685A1) (0.170 g, 0.41 mmol) in a mixture of ethanol (4 mL) at room temperature under nitrogen and the resulting mixture was hydrogenated under balloon pressure at the same temperature. The reaction mixture was filtered through a celite bad, washed the bed with methanol (20 mL) and collected filtrates were concentrated under reduced pressure. The crude mass was purified by reverse phase (C-18) silica gel column chromatography, using acetonitrile-water=0:1→1:0 as gradient, to afford methyl 4-(tetrahydro-2H-pyran-4-yl)-2-(4-(trifluoromethyl)phenyl)quinoline-7-carboxylate (X-1685A2) (0.150 g, 87%) as a yellow solid. MS: $[MH]^+$ 317.4.

4-(Tetrahydro-2H-pyran-4-yl)-2-(4-(trifluoromethyl)phenyl)quinoline-7-carboxylic acid (I-390). To a stirred solution of methyl 4-(tetrahydro-2H-pyran-4-yl)-2-(4-(trifluoromethyl)phenyl)quinoline-7-carboxylate (X-1685A2) (0.100 g, 0.24 mmol) in a mixture of THE-water (3:1; 5 mL), was added lithium hydroxide monohydrate (0.023 g, 0.55 mmol) at room temperature. The reaction mixture was heated at 80° C. for 2 h. The reaction mixture was cooled to room temperature and concentrated and acidified (pH~2-3) with aqueous 1N HCl, and the resulting precipitate was collected by filtration, washed with cold water until the pH of the filtrate became neutral (pH~6-7). The obtained solid was triturated with hexane (15 mL) and dried under reduced pressure, to afford 4-(tetrahydro-2H-pyran-4-yl)-2-(4-(trifluoromethyl)phenyl)quinoline-7-carboxylic acid (I-390) (0.090 g, 93%) as an off-white solid. $^1$H NMR (400 MHz, DMSO-$d_6$) δ 13.47 (br. s, 1H), 8.67 (s, 1H), 8.59-8.57 (d, J=8.4 Hz, 2H), 8.45-8.43 (d, J=8.8 Hz, 1H), 8.18 (s, 1H), 8.12-8.10 (d, J=8.8 Hz, 1H), 7.94-7.92 (d, J=8.0 Hz, 2H), 4.06-4.02 (t, J=8.4, 12.4 Hz, 1H), 3.82-3.76 (t, J=12.4 Hz, 1H), 3.71-3.66 (t, J=11.2, Hz, 2H), 2.08-2.02 (m, 2H), 1.87-1.84 (d, J=8.0 Hz, 2H). MS: $[MH]^+$ 362.12.

Example 1.296. Synthesis of 4-(piperidin-1-yl)-2-(4-(trifluoromethyl)phenyl)quinoline-7-carboxylic acid (I-391)

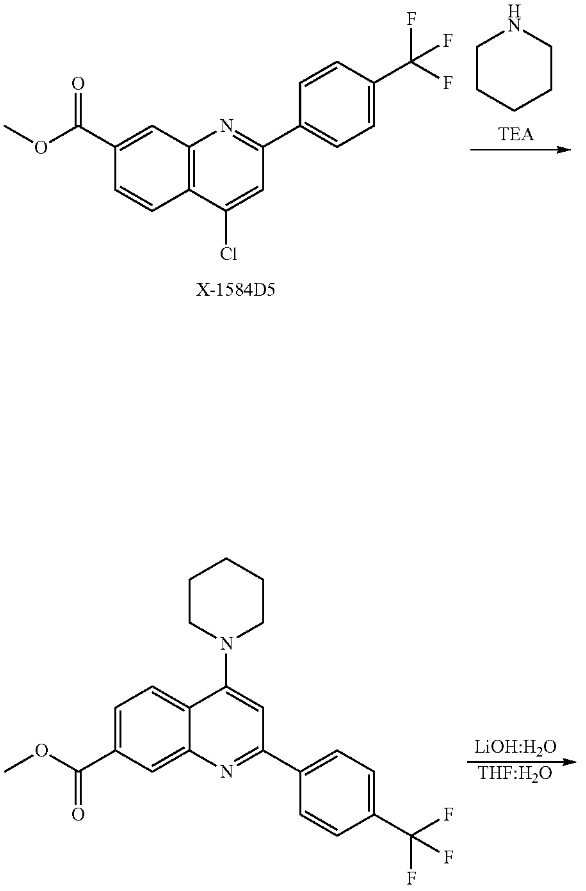

X-1584D5

X-1686A1

-continued

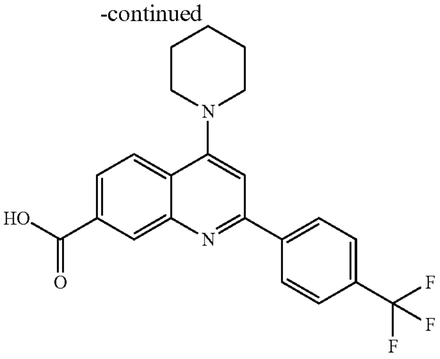

I-391

Methyl 4-(piperidin-1-yl)-2-(4-(trifluoromethyl)phenyl)quinoline-7-carboxylate (X-1686A1). To a stirred solution methyl 4-chloro-2-(4-(trifluoromethyl)phenyl)quinoline-7-carboxylate (0.250 g, 0.68 mmol) in piperidine (4 mL) was added TEA (0.09 mL, 0.68 mmol) and the resulting mixture was heated at 80° C. for 7 h. After cooling to room temperature, reaction mixture was diluted with water (40 mL) and was extracted with dichloromethane (30 mL×2). Combined organic extracts were dried over anhydrous $Na_2SO_4$ and concentrated under reduced pressure. The crude product was purified by silica gel column chromatography, using ethyl acetate-hexane=0:1→2:8 as a gradient, to afford methyl 4-(piperidin-1-yl)-2-(4-(trifluoromethyl)phenyl)quinoline-7-carboxylate (X-1686A1) (0.100 g, 35%) as a yellow solid. MS: $[MH]^+$ 415.17.

4-(piperidin-1-yl)-2-(4-(trifluoromethyl)phenyl)quinoline-7-carboxylic acid (I-391). To a stirred solution of methyl 4-(piperidin-1-yl)-2-(4-(trifluoromethyl)phenyl)quinoline-7-carboxylate (X-1686A1) (0.100 g, 0.24 mmol) in a mixture of THE-water (3:1; 4 mL) was added lithium hydroxide monohydrate (0.030 g, 0.72 mmol) at room temperature under nitrogen and the resulting mixture was heated at 80° C. for 2 h. After cooling to room temperature, the reaction mixture was concentrated and diluted with water (10 mL) and acidified (pH~2-3) with an aqueous solution of 1N HCl and the resulting precipitate was collected by filtration. Crude residue was washed with cold water until the pH of the filtrate became neutral (pH~6-7). Obtained solid was triturated using n-pentane and dried under reduced pressure, to afford to 4-(piperidin-1-yl)-2-(4-(trifluoromethyl)phenyl)quinoline-7-carboxylic acid (I-391) (0.050 g, 51%) as a white solid. $^1$H NMR (400 MHz, DMSO-$d_6$) 8.60 (br. s, 1H), 8.46-8.42 (d, J=8.4 Hz 2H), 8.11-8.08 (d, J=8.4 Hz 1H), 7.96-7.93 (d, J=8.4 Hz 1H), 7.89-7.87 (d, J=8.4 Hz 2H), 7.52 (s, 1H), 3.25 (br. s, 4H), 1.82 (br. s, 4H), 1.68-1.66 (d, J=5.2 Hz, 2H). MS: $[MH]^+$ 401.4.

Example 1.297. Synthesis of 4-(dimethylamino)-2-(4-(trifluoromethyl)phenyl)quinoline-7-carboxylic acid (I-392)

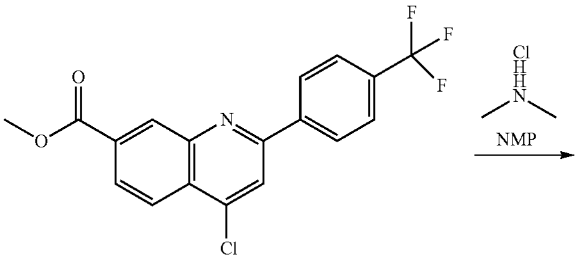

X-1584D5

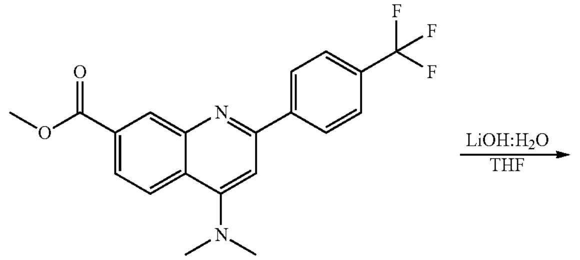

X-1687A1

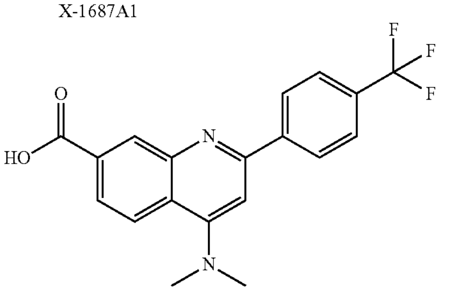

I-392

Methyl 4-(dimethylamino)-2-(4-(trifluoromethyl)phenyl) quinoline-7-carboxylate (X-1687A1). To a stirred solution of methyl 4-chloro-2-(4-(trifluoromethyl)phenyl)quinoline-7-carboxylate (X-1584D5) (0.400 g, 1.69 mmol) in NMP (6 mL) was added dimethylamine hydrochloride (0.519 g, 6.57 mmol) at room temperature and reaction mixture was stirred at 120° C. under microwave irradiation for 40 min. After cooling to room temperature, reaction mixture was diluted with water (50 mL) and was extracted by ethyl acetate (50 mL×3). Combined organic extracts were dried over $Na_2SO_4$ and concentrated under reduced pressure. The crude product was purified silica gel column chromatography, using ethyl acetate-hexane=0:1→4:6 as a gradient, to methyl 4-(dimethylamino)-2-(4-(trifluoromethyl)phenyl)quinoline-7-carboxylate (X-1687A1) (0.070 g, 17%) as an off-white solid. MS: $[MH]^+$ 375.0

4-(dimethylamino)-2-(4-(trifluoromethyl)phenyl)quinoline-7-carboxylic acid (I-392). To a stirred solution of methyl 4-(dimethylamino)-2-(4-(trifluoromethyl)phenyl) quinoline-7-carboxylate (X-1687A1) (0.060 g, 0.16 mmol) in a mixture of THE-water (3:1; 7 mL) was added lithium hydroxide monohydrate (0.026 g, 0.64 mmol) at room temperature. The resulting mixture was heated at 80° C. for 2 h. After cooling to room temperature, the reaction mixture was concentrated under reduced pressure and diluted with water (10 mL) and was acidified (pH~2-3) with an aqueous solution of 1N HCl and the resulting precipitate was collected by filtration. Crude residue was washed with cold water until the pH of the filtrate became neutral (pH~6-7). Obtained solid was triturated using n-pentane and dried under reduced pressure, to afford 4-(dimethylamino)-2-(4-(trifluoromethyl)phenyl)quinoline-7-carboxylic acid (I-392) (0.045 g, 77%) as an off-white solid. $^1H$ NMR (400 MHz, DMSO-$d_6$) δ 13.39 (s, 1H), 8.62 (s, 1H), 8.44-8.42 (d, J=8.0 Hz, 2H), 8.29-8.27 (d, J=8.8 Hz, 1H), 7.99-7.97 (dd, J=1.6, 8.8 Hz, 1H), 7.95-7.93 (d, J=8.0 Hz, 2H), 7.43 (s, 1H), 3.25 (s, 6H). MS: $[MH]^+$ 361.1

Example 1.298. Synthesis of 4-ethoxy-2-(4-(trifluoromethyl)phenyl)quinoline-7-carboxylic acid (I-393)

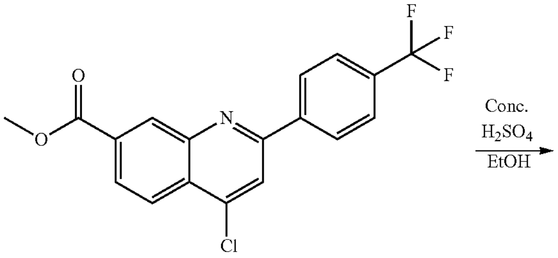

X-1584D5

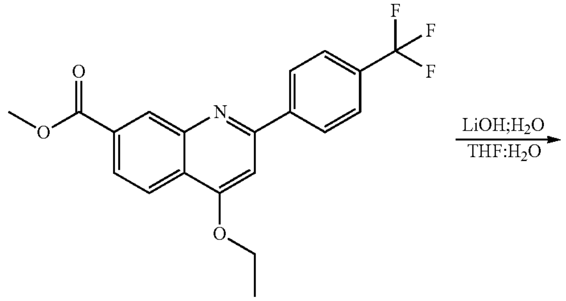

X-1688A1

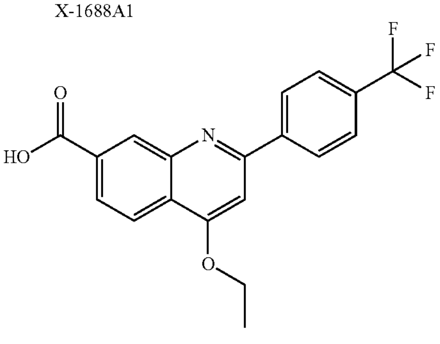

I-393

Ethyl 4-ethoxy-2-(4-(trifluoromethyl)phenyl)quinoline-7-carboxylate (X-1688A1). Concentrated $H_2SO_4$ (0.15 mL, 2.19 mmol) was added dropwise to a stirred solution of methyl 4-chloro-2-(4-(trifluoromethyl)phenyl)quinoline-7-carboxylate (X-15841D5) (0.200 g, 0.54 mmol) in ethanol (6 mL) at 0° C. and the resulting mixture was heated at 90° C. for 3 h. Reaction mixture was concentrated in under reduced pressure, obtained crude diluted with ice cold water (50 mL) and the resulting precipitate was collected by filtration. Crude residue was washed with cold water until the pH of the filtrate became neutral (pH~6-7). Obtained solid was triturated using n-pentane and dried under high vacuum to afford ethyl 4-ethoxy-2-(4-(trifluoromethyl)phenyl)quinoline-7-carboxylate (X-1688A1) (0.230 g, quantitative yield) as an off white solid. MS: [MH]P390.6

4-Ethoxy-2-(4-(trifluoromethyl)phenyl)quinoline-7-carboxylic acid (I-393). To a stirred solution of ethyl 4-ethoxy-2-(4-(trifluoromethyl)phenyl)quinoline-7-carboxylate (X-1688A1) (0.230 g, 0.59 mmol) in a mixture of THF-water (3:1; 5.0 mL) was added lithium hydroxide monohydrate (0.049 g, 1.18 mmol) at room temperature. Reaction mixture was stirred at 70° C. for 2 h. After cooling to room temperature, the reaction mixture was concentrated under reduced pressure, obtained crude was acidified (pH~2-3) with an aqueous solution of 1N HCl and the resulting precipitate was collected by filtration. Crude residue was washed with cold water until the pH of the filtrate became neutral (pH~6-7). Obtained solid was dried under reduced pressure and triturated with using n-pentane (5 mL), to afford 4-ethoxy-2-(4-(trifluoromethyl)phenyl)quinoline-7-carboxylic acid (I-393) (0.600 g, 28%) as an off-white solid. $^1$H NMR (400 MHz, DMSO-$d_6$) δ: 8.52-8.50 (d, J=7.6 Hz, 2H), 8.50 (s, 1H), 8.09 (m, 2H), 7.92-7.89 (d, J=8.4 Hz, 2H), 7.61 (s, 1H), 4.50-4.45 (m, 2H), 1.55-1.51 (t, J=7.2, 6.8 Hz, 3H), MS: [MH]-361.8.

Example 1.299. Synthesis of 4-isopropoxy-2-(4-(trifluoromethyl)phenyl)quinoline-7-carboxylic (I-394)

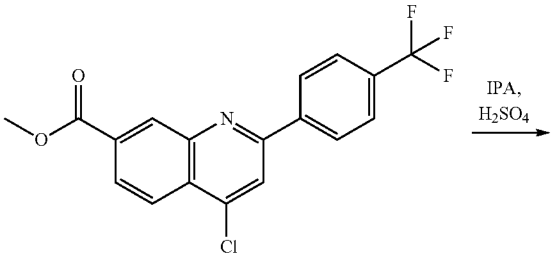

X-1584D5

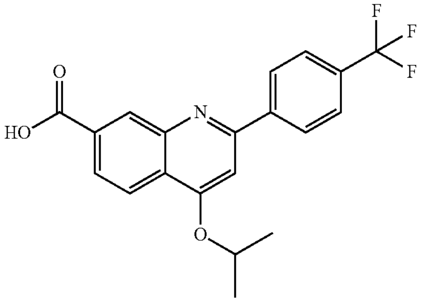

I-394

To a stirred solution of methyl 4-chloro-2-(4-(trifluoromethyl)phenyl)quinoline-7-carboxylate (X-1584D5) (0.200 g, 0.54 mmol) in IPA (5 mL) were added $H_2SO_4$ (3 mL) at 0° C. The reaction mixture was heated at 100° C. for 16 h. The reaction mixture was cooled to room temperature and concentrated under reduce pressure. The solid product was triturated by using n-pentane, to afford 4-isopropoxy-2-(4-(trifluoromethyl)phenyl)quinoline-7-carboxylic acid (I-394) (0.008 g, 9%) as an off-white solid. $^1$H NMR (400 MHz, DMSO-$d_6$) 13.36 (br. s, 1H), 8.56-8.52 (m, 3H), 8.24-8.22 (d, J=8.8 Hz, 1H), 8.05-8.03 (d, J=8.8 Hz 1H), 7.94-7.92 (d, J=8.4 Hz, 2H), 7.74 (s, 1H), 5.30-5.27 (t, J=6.0 Hz, 1H), 1.48-1.47 (d, J=6.0 Hz, 6H). MS: $[MH]^+$ 376.40.

Example 1.300. Synthesis of 4-cyclopropoxy-2-(4-(trifluoromethyl)phenyl)quinoline-7-carboxylic acid (I-395)

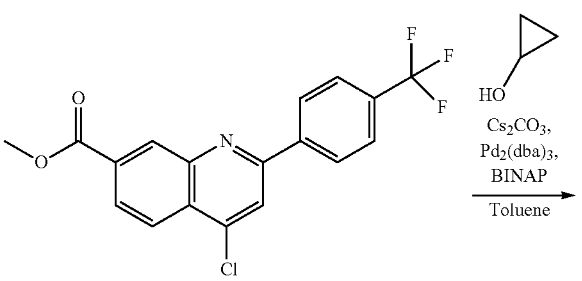

X-1584D5

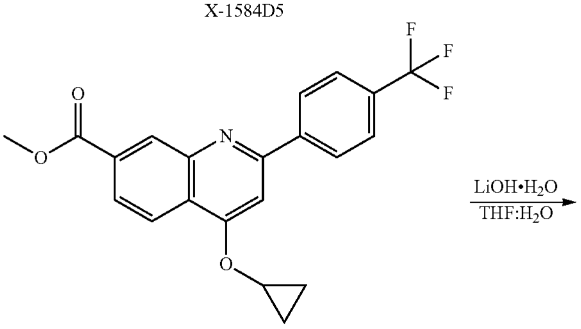

X-1690A1

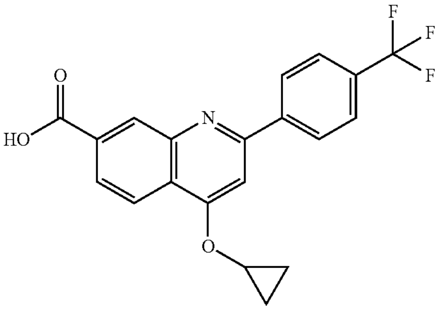

I-395

Methyl 4-cyclopropoxy-2-(4-(trifluoromethyl)phenyl)quinoline-7-carboxylate (X-1690A1). To a stirred solution of methyl 4-chloro-2-(4-(trifluoromethyl)phenyl)quinoline-7-carboxylate (X-1584D5) (0.300 g, 0.82 mmol) and cyclopropanol (0.470 g, 8.20 mmol) in toluene (5 mL) was added cesium carbonate (0.534 g, 1.64 mmol) at room temperature under nitrogen. The reaction mixture was degassed (purging with nitrogen) for 15 min followed by the addition of $Pd_2(dba)_3$ (0.075 g, 0.08 mmol) and BINAP (0.076 g, 0.12 mmol) at room temperature under nitrogen. The reaction mixture was heated at 120° C. for 16 h. Reaction mixture was cooled to room temperature, diluted with water (50 mL) and was extracted with ethyl acetate (60 mL×3). Combined organic extracts were dried over $Na_2SO_4$ and concentrated under reduced pressure. The crude product was combined with an identically-prepared batch (0.300 g) and combined crude batches were purified by silica gel column chromatography, using ethyl acetate-hexane=0:1→1:9 as gradient, to afford methyl 4-cyclopropoxy-2-(4-(trifluoromethyl)phenyl)quinoline-7-carboxylate (X-1690A1). (0.050 g, 8%) as a yellow solid. MS: $[MH]^+$ 388.1.

4-Cyclopropoxy-2-(4-(trifluoromethyl)phenyl)quinoline-7-carboxylic acid (I-395). To a stirred solution of methyl 4-cyclopropoxy-2-(4-(trifluoromethyl)phenyl)quinoline-7-carboxylate (X-1690A1) (0.050 g, 0.12 mmol) in a mixture of THIF-methanol-water (2:2:1; 2.0 mL) was added lithium hydroxide monohydrate (0.010 g, 0.25 mmol) at room temperature. Reaction mixture was stirred at 70° C. for 2 h. After cooling to room temperature, the reaction mixture was concentrated under reduced pressure and acidified (pH~2-3) with an aqueous solution of 1N HCl and the resulting precipitate was collected by filtration. Crude residue was washed with cold water until the pH of the filtrate became neutral (pH~6-7). Obtained solid was dried under reduced pressure the solid product was triturated by using n-pentane (5 ml) to afford 4-cyclopropoxy-2-(4-(trifluoromethyl)phenyl)quinoline-7-carboxylic acid (I-395) (0.010 g, 21%) as an off-white solid. $^1$H NMR (400 MHz, DMSO-$d_6$) δ: 13.40 (brs, 1H), 8.59-8.58 (d, J=1.2 Hz, 1H), 8.52-8.50 (d, J=8.0 Hz, 2H), 8.18-8.15 (d, J=8.8 Hz, 1H), 8.05-8.02 (dd, J=1.6, 8.8 Hz, 1H), 7.98 (s, 1H), 7.96-7.94 (d, J=8.0 Hz, 2H), 4.45-4.41 (m, 1H), 1.03-1.01 (d, J=6.0 Hz, 2H), 0.92-0.91 (d, J=4.0 Hz, 2H). MS: $[MH]^+$ 374.4.

Example 1.301. Synthesis of 4-acetyl-2-(4-(trifluoromethyl)phenyl)quinoline-7-carboxylic acid (I-396)

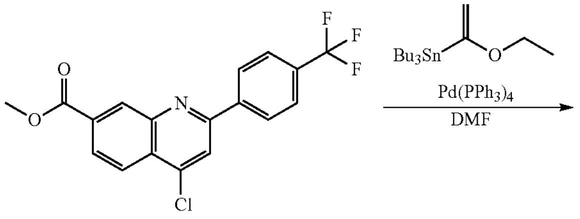

X-1584D5

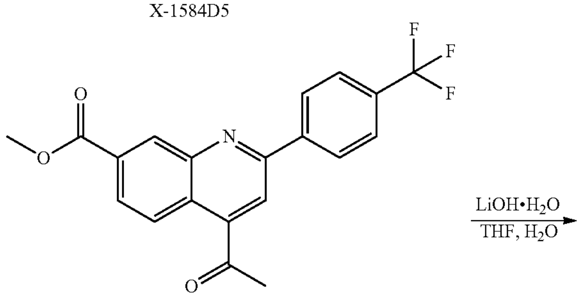

X-1692A1

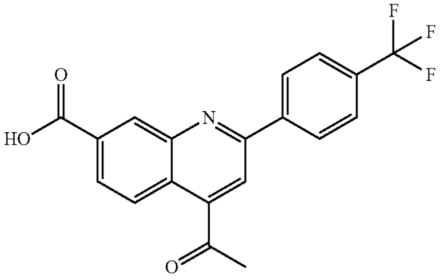

I-396 methyl 4-acetyl-2-(4-(trifluoromethyl)phenyl)quinoline-7-carboxylate (X-1692A1). To a stirred solution of methyl 4-chloro-2-(4-(trifluoromethyl)phenyl)quinoline-7-carboxylate (X-1584D5) (0.350 g, 0.95 mmol) in DMF (5 mL), was added tributyl(1-ethoxyvinyl)stannane (1.380 g, 3.83 mmol) at room temperature. The reaction mixture was degassed (purging with nitrogen) for 30 min followed by the addition of $Pd(PPh_3)_4$ (0.033 g, 0.04 mmol) and resulting mixture was heated at 80° C. for 5 h. After completion of reaction mixture was cool to room temperature. Reaction mixture was diluted with water (50 mL) and was extracted by ethyl acetate (100 mL×2) and concentrate under reduce pressure. The crude product was purified by silica gel column chromatography, using ethyl acetate-hexane=1:9→2:8 as a gradient, to afford methyl 4-acetyl-2-(4-(trifluoromethyl)phenyl)quinoline-7-carboxylate (X-1692A1) (0.180 g, 50%) as a white solid. MS: $[MH]^+$ 374.4.

4-acetyl-2-(4-(trifluoromethyl)phenyl)quinoline-7-carboxylic acid (I-396). To a stirred solution of methyl 4-acetyl-2-(4-(trifluoromethyl)phenyl)quinoline-7-carboxylate (X-1692A1) (0.180 g, 0.48 mmol) in THF—$H_2O$ (7 mL), was added lithium hydroxide monohydrate (0.061 g, 1.44 mmol). Reaction mixture was stirred at room temperature for 1 h. The reaction mixture was concentrated under reduced pressure and acidified (pH~2-3) with an aqueous solution of 1N HCl and the resulting precipitate was collected by filtration. Isolated solid was washed with cold water until the pH became neutral (pH~6-7). The resulting residue was dried under reduced pressure, to afford 4-acetyl-2-(4-(trifluoromethyl)phenyl)quinoline-7-carboxylic acid (I-396) (0.140 g, 67%) as an off white solid. 1H NMR (400 MHz, DMSO-$d_6$) δ 13.50 (s, 1H), 8.71-8.70 (m, 2H), 8.63-8.61 (d, J=8.4 Hz, 2H), 8.47-8.44 (d, J=8.8 Hz, 1H), 8.18-8.15 (d, J=1.6, 8.8 Hz, 1H), 7.99-7.97 (d, J=8.4 Hz, 2H), 2.90 (s, 3H). MS: $[MH]^+$ 360.4

Example 1.302. Synthesis of 4-chloro-2-(4-(trifluoromethyl)phenyl)quinoline-7-carboxylic acid (I-397)

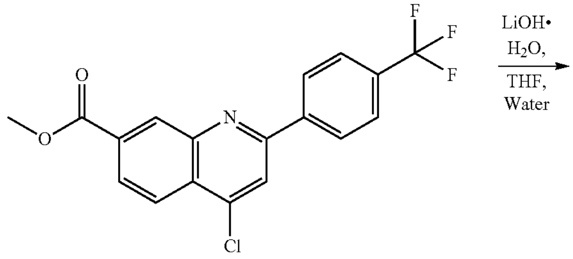

X-1584D5

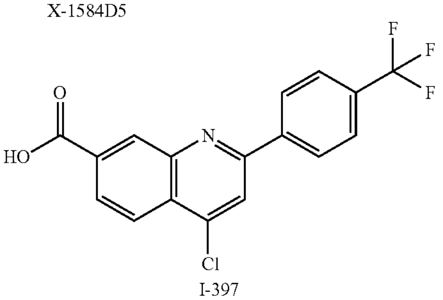

I-397

The following compound was prepared in a manner analogous to the procedures described above for (R)-4-cyclopropyl-N-(1-hydroxypropan-2-yl)-2-(4(trifluoromethyl)phenyl)quinoline-7-carboxamide (I-386):

4-chloro-2-(4-(trifluoromethyl)phenyl)quinoline-7-carboxylic acid (I-397) (0.055 g, 57%) as an off-white solid. MS: $[MH]^+$ 352.3. $^1$H NMR (400 MHz, DMSO-$d_6$) δ 13.62 (br. s, 1H), 8.69 (s, 1H), 8.64 (s, 1H), 8.57-8.55 (d, J=8.0 Hz, 2H), 8.35-8.33 (d, J=8.8 Hz, 1H), 8.24-8.22 (dd, J=1.2, 8.4 Hz, 1H), 7.96-7.94 (d, J=8.4 Hz, 2H).

Example 1.303. Synthesis of (R)-2-(2,6-dichloro-4-(trifluoromethyl)phenyl)-N-(1-hydroxybutan-2-yl)-4-methoxyquinoline-7-carboxamide (I-398)
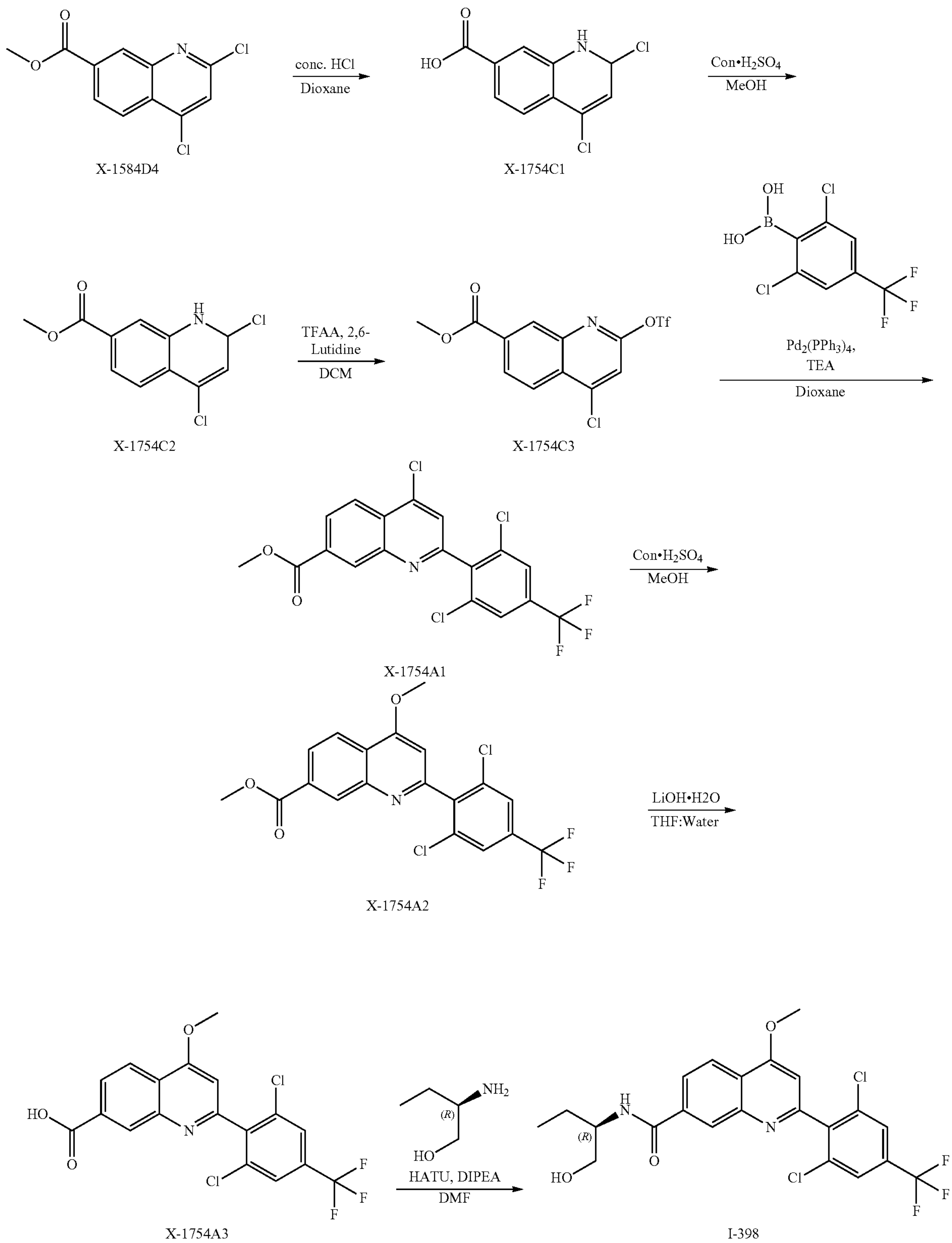
X-1584D4
X-1754C1
X-1754C2
X-1754C3
X-1754A1
X-1754A2
X-1754A3
I-398

4-Chloro-2-oxo-1,2-dihydroquinoline-7-carboxylic acid (X-1754C1). To a stirred solution of methyl 2,4-dichloro-quinoline-7-carboxylate (X-1584D4) (2.0 g, 7.84 mmol) in dioxane (10 mL) was added Conc. HCl (6.8 mL, 62.74 mmol) at 0° C. The resulting reaction mixture was stirred at 110° C. for 16 h. Reaction mixture was poured into ice water (200 mL) and the resulting precipitate was collected by filtration. Crude residue was washed with cold water until the pH of the filtrate became neutral (pH 6-7). Obtained solid was triturated using n-pentane and dried under reduced pressure, to afford 4-chloro-2-oxo-1,2-dihydroquinoline-7-carboxylic acid (X-1754C1) (2.0 g, quantitative yield) as an off-white solid. MS: $[MH]^+$ 224.0

Methyl 4-chloro-2-oxo-1,2-dihydroquinoline-7-carboxylate (X-1754C2). Concentrated $H_2SO_4$ (2.65 mL, 26.09 mmol) was added dropwise to a stirred solution of 4-chloro-2-oxo-1,2-dihydroquinoline-7-carboxylic acid (X-1754C1) (2.0 g, 30.41 mmol) in methanol (20 mL) at 0° C. and the resulting mixture was heated at 90° C. for 3 h. Reaction mixture was concentrated under reduced pressure, obtained crude diluted with ice cold water (50 mL) and the resulting precipitate was collected by filtration. Crude residue was washed with cold water until the pH of the filtrate became neutral (pH~6-7). Obtained solid was triturated using n-pentane and dried under reduced pressure to afford methyl 4-chloro-2-oxo-1,2-dihydroquinoline-7-carboxylate (X-1754C2) (1.5 g, 97%) as an off-white solid. MS: $[MH]^+$ 237.2

Methyl 4-chloro-2-(((trifluoromethyl)sulfonyl)oxy)quinoline-7-carboxylate (X-1754C3). To a stirred solution of methyl 4-chloro-2-oxo-1,2-dihydroquinoline-7-carboxylate (X-1754C2) (1.5 g, 6.32 mmol) in DCM (20 mL) was added 2,6-Lutidine (1.35 gm, 12.65 mmol) at room temperature, then reaction mixture was cooled to 0° C. and TFAA (3.5 gm, 12.65 mmol) was added. The resulting reaction mixture was stirred at 0° C. for 3 h. Reaction mixture was poured into ice water (200 mL) and was extracted by DCM (200 ml×2), combined organic extracts dried over anhydrous $Na_2SO_4$, and concentrate under reduce pressure. Obtained solid was triturated using n-pentane and dried under high vacuum to afford methyl 4-chloro-2-(((trifluoromethyl)sulfonyl)oxy)quinoline-7-carboxylate (X-1754C3) (1.5 g, quantitative yield) as an off-white solid MS: $[MH]^+$ 370.3

Methyl 4-chloro-2-(2,6-dichloro-4-(trifluoromethyl)phenyl)quinoline-7-carboxylate (X-1754A1). To a stirred solution 4-chloro-2-(((trifluoromethyl)sulfonyl)oxy)quinoline-7-carboxylate (X-1754C3) (0.500 g, 1.35 mmol) in 1,4-dioxane (4 mL) were added (2,6-dichloro-4-(trifluoromethyl)phenyl)boronic acid (0.546 g, 2.03 mmol) and triethylamine (0.410 g, 4.65 mmol) sequentially at room temperature under nitrogen. The resulting mixture was degassed (purged with nitrogen) for 20 min followed by the addition of $Pd(PPh_3)_4$ (0.156 g, 0.13 mmol) and was heated at 90° C. for 3 h. After cooling to room temperature, reaction mixture was diluted with water (100 mL) and was extracted with ethyl acetate (100 mL×3). Combined organic extracts were dried over anhydrous $Na_2SO_4$ and concentrated under reduce pressure. The crude product was purified by silica gel column chromatography, using ethyl acetate-hexane=0:1→1:9 as a gradient, to afford methyl 4-chloro-2-(2,6-dichloro-4-(trifluoromethyl)phenyl)quinoline-7-carboxylate (X-1754A1) (0.450 g, 76%) as an white solid. MS: $[MH]^+$ 434.2

Methyl 2-(2,6-dichloro-4-(trifluoromethyl)phenyl)-4-methoxyquinoline-7-carboxylate (X-1754A2). Concentrated $H_2SO_4$ (0.3 mL, 3.11 mmol) was added dropwise to a stirred solution of methyl 4-chloro-2-(2,6-dichloro-4-(trifluoromethyl)phenyl)quinoline-7-carboxylate (X-1754A1) (0.450 g, 1.03 mmol) in methanol (4 mL) at 0° C. and the resulting mixture was heated at 90° C. for 3 h. Reaction mixture was concentrated under reduce pressure, obtained crude diluted with ice cold water (50 mL) and the resulting precipitate was collected by filtration. Crude residue was washed with cold water until the pH of the filtrate became neutral (pH~6-7). Obtained solid was triturated using n-pentane and dried under reduced pressure, to afford methyl 2-(2,6-dichloro-4-(trifluoromethyl)phenyl)-4-methoxyquinoline-7-carboxylate (X-1754A2) (0.380 g, 85%) as an off-white solid. MS: $[MH]^+$ 430.3

2-(2,6-dichloro-4-(trifluoromethyl)phenyl)-4-methoxy-quinoline-7-carboxylic acid (X-1754A3). To a stirred solution of methyl 2-(2,6-dichloro-4-(trifluoromethyl)phenyl)-4-methoxyquinoline-7-carboxylate (X-1754A2) (0.380 g, 0.88 mmol) in a mixture of THF-water (3:1; 5.0 mL) was added lithium hydroxide monohydrate (0.11 g, 2.65 mmol) at room temperature. Reaction mixture was stirred at 70° C. for 2 h. After cooling to room temperature, the reaction mixture was concentrated under reduced pressure, obtained crude was acidified (pH~2-3) with an aqueous solution of 1N HCl and the resulting precipitate was collected by filtration Crude residue was washed with cold water until the pH of the filtrate became neutral (pH~6-7). Obtained solid was dried under reduced pressure and triturated with using n-pentane (5 mL), to afford 2-(2,6-dichloro-4-(trifluoromethyl)phenyl)-4-methoxyquinoline-7-carboxylic acid (X-1754A3) (0.350 g, 95%) as an off-white solid. MS: [MH]-416.3

(R)-2-(2,6-dichloro-4-(trifluoromethyl)phenyl)-N-(1-hydroxybutan-2-yl)-4-methoxyquinoline-7-carboxamide (I-398). To a stirred solution of 2-(2,6-dichloro-4-(trifluoromethyl)phenyl)-4-methoxyquinoline-7-carboxylic acid (X-1754A3) (0.350 g, 0.84 mmol) in a DMF (5 mL) were added DIPEA (0.323 g, 2.52 mmol) and HATU (0.640 g, 1.68 mmol) sequentially at 0° C. under nitrogen. After stirring for 10 min at the same temperature, (R)-2-aminobutan-1-ol (0.150 g, 1.68 mmol) was added at 0° C. and stirred at room temperature for 16 h. The reaction mixture was slowly poured into ice-water (50 mL) and was extracted with ethyl acetate (100 mL×3). The combined organic extracts were washed with brine (100 mL), dried over anhydrous $Na_2SO_4$ and concentrated under reduced pressure. The resulting crude was purified by (C-18) column chromatography, using acetonitrile:water=0:1→4:6 as a gradient, to afford (R)-2-(2,6-dichloro-4-(trifluoromethyl)phenyl)-N-(1-hydroxybutan-2-yl)-4-methoxyquinoline-7-carboxamide (1-398) (0.200 g, 48%) as an off-white solid. $^1H$ NMR (400 MHz, DMSO-$d_6$) δ: 8.53-8.53 (d, J=1.2 Hz, 1H), 8.40-8.38 (d, J=8.8 Hz, 1H), 8.27-8.25 (d, J=8.4 Hz, 1H), 8.14 (s, 2H), 8.07-8.05 (dd, J=2.0, 8.8 Hz, 1H), 7.29 (s, 1H), 4.72-4.69 (t, J=5.6 Hz, 1H), 4.08 (s, 3H), 3.94-3.89 (m, 1H), 3.52-3.46 (m, 1H), 3.44-3.34 (m, 1H) 1.71-1.65 (m, 1H), 1.51-1.44 (m, 1H) 0.92-0.88 (t, J=7.6 Hz, 3H). MS: [MH]-487.3, Chiral HPLC=97.51%.

Example 1.304. Synthesis of (R)-4-cyclopropyl-N-(1-hydroxybutan-2-yl)-2-(4-(trifluoromethyl)phenyl)quinoline-7-carboxamide (I-399)

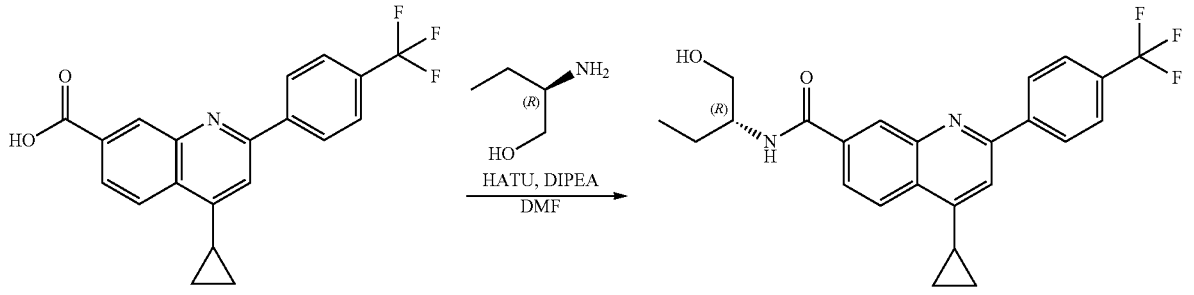

I-387

I-399

To a stirred solution of 4-cyclopropyl-2-(4-(trifluoromethyl)phenyl)quinoline-7-carboxylic acid (I-387) (0.150 g, 0.42 mmol) in a DMF (5 mL) were added DIPEA (0.162 g, 1.26 mmol) and HATU (0.239 g, 0.63 mmol) sequentially at 0° C. under nitrogen. After stirring for 10 min at the same temperature, (R)-2-aminobutan-1-ol (0.112 g, 1.26 mmol) was added and stirring was continued at the room temperature for 16 h. The reaction mixture was slowly poured into ice-water (50 mL) and was extracted with ethyl acetate (100 mL×3). The combined organic extracts were washed with brine (100 mL), dried over anhydrous $Na_2SO_4$ and concentrated under reduced pressure. Obtained solid was triturated with using n-pentane (5 mL), dried under reduced pressure and to afford (R)-4-cyclopropyl-N-(1-hydroxybutan-2-yl)-2-(4-(trifluoromethyl)phenyl)quinoline-7-carboxamide (I-399) (0.150 g, 83%) as an off-white solid. $^1H$ NMR (400 MHz, DMSO-$d_6$) δ: 8.68-8.67 (d, J=1.6 Hz, 1H), 8.55-8.50 (m, 3H), 8.43-8.41 (d, J=8.4 Hz, 1H), 8.11-8.08 (dd, J=2.0, 8.8 Hz, 1H), 7.93-7.91 (d, J=8.4 Hz, 2H), 7.80 (s, 1H), 4.74-4.71 (t, J=5.6, 6.0 Hz, 1H), 3.96-3.95 (m, 1H), 3.55-3.50 (m, 1H), 3.48-3.44 (m, 1H), 2.72-2.67 (m, 1H) 1.73-1.68 (m, 1H), 1.56-1.50 (m, 1H) 1.26-1.21 (m, 2H), 1.13-1.09 (m, 2H), 0.94-0.90 (t, J=7.2 Hz 3H). MS: $[MH]^+$ 429.44.

Example 1.305. Synthesis of (R)-4-ethynyl-N-(1-hydroxybutan-2-yl)-2-(4-(trifluoromethyl)phenyl)quinoline-7-carboxamide (1-400)

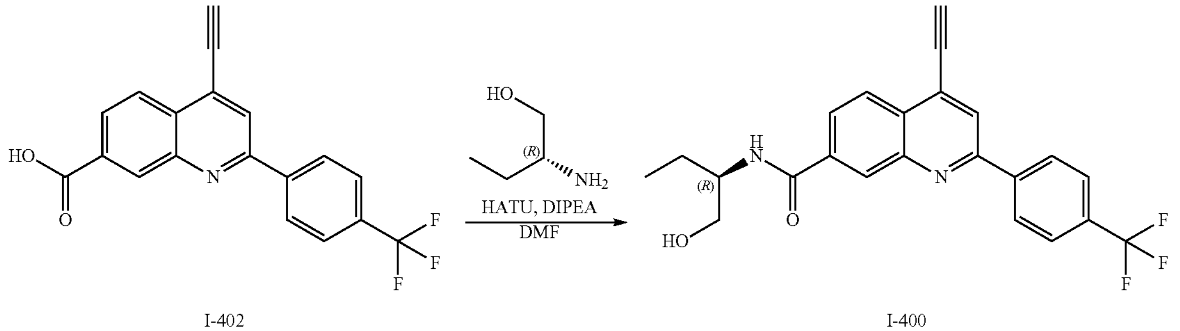

I-402

I-400

The following compound was prepared in a manner analogous to the procedures described above for (R)-4-cyclopropyl-N-(1-hydroxybutan-2-yl)-2-(4-(trifluoromethyl)phenyl)quinoline-7-carboxamide (I-399):

(R)-4-ethynyl-N-(1-hydroxybutan-2-yl)-2-(4-(trifluoromethyl)phenyl)quinoline-7-carboxamide (I-400) (0.080 g, 77%) as an off-white solid. LCMS: $[MH]^+$ 413.44. $^1H$ NMR (400 MHz, DMSO-$d_6$) δ 8.73-8.73 (dd, J=1.2 Hz, 1H), 8.57-8.55 (d, J=8.4 Hz, 2H), 8.51 (s, 1H), 8.49-8.47 (d, J=8.4 Hz, 1H), 8.31-8.29 (d, J=8.8 Hz, 1H), 8.18-8.16 (dd, J=1.6, 8.4 Hz, 1H), 7.96-7.94 (d, J=8.4 Hz, 2H), 5.19 (s, 1H), 4.75-4.72 (t, J=6.0 Hz, 1H), 3.96-3.94 (m, 1H), 3.54-3.50 (m, 1H), 3.48-3.33 (m, 1H) 1.72-1.68 (m, 1H), 1.55-1.50 (m, 1H), 0.94-0.90 (t, J=7.6 Hz, 3H).

Example 1.306. Synthesis of 4-cyano-2-(4-(trifluoromethyl)phenyl)quinoline-7-carboxylic acid (I-401)

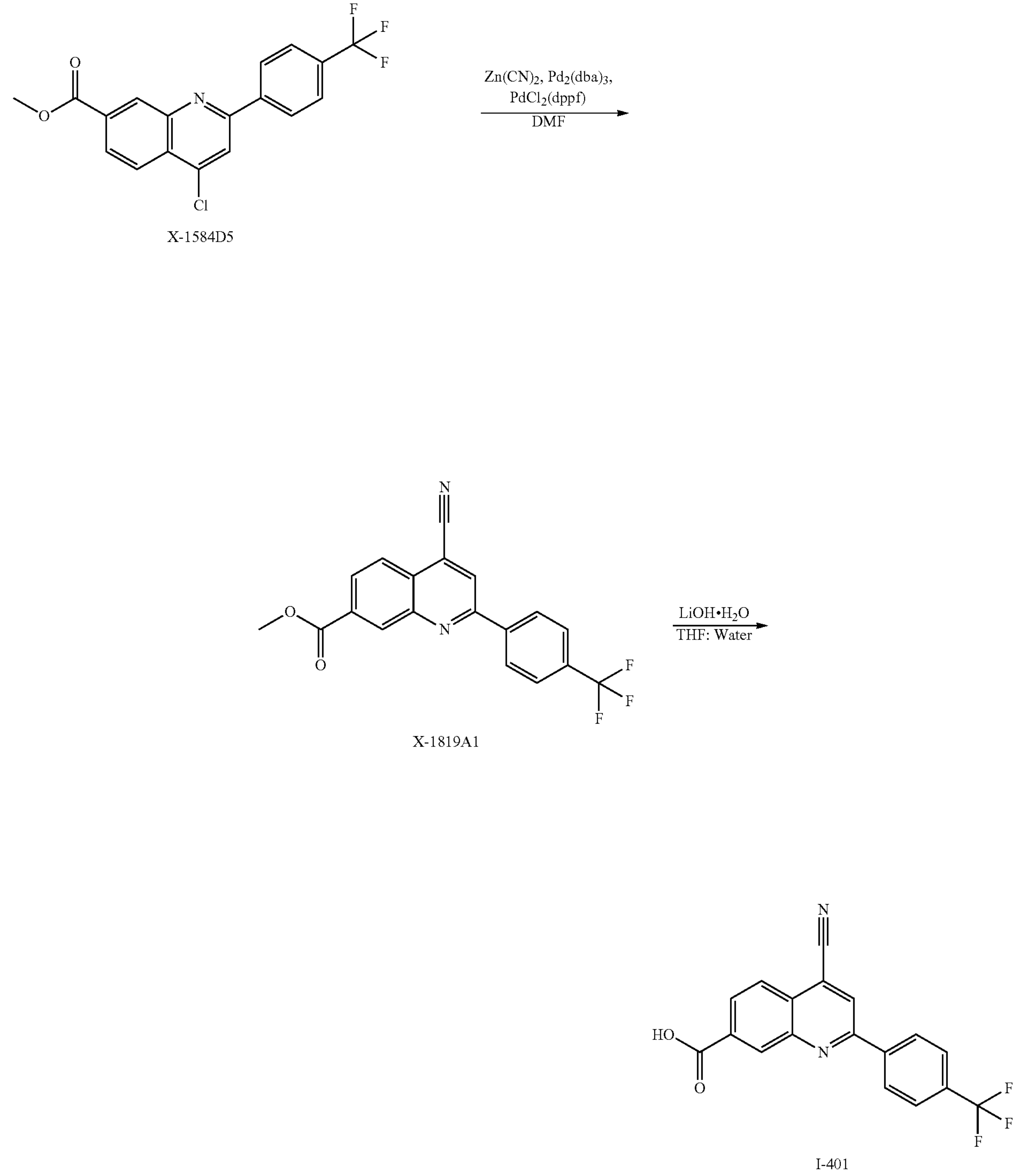

Methyl 4-cyano-2-(4-(trifluoromethyl)phenyl)quinoline-7-carboxylate (X-1819A1). To a stirred solution of methyl 4-chloro-2-(4-(trifluoromethyl)phenyl)quinoline-7-carboxylate (X-1584D5) (0.850 g, 2.32 mmol) in a DMF (8 mL) was added zinc cyanide (0.953 g, 8.14 mmol) and reaction mixture was degassed (purging with nitrogen) for 20 min followed by addition 1,1'-Bis(diphenylphosphino) ferrocene (0.054 g, 0.097 mmol) and $Pd_2$ $(dba)_3$ (0.089 g, 0.097 mmol) and the reaction mixture was heated at 120° C. for 30 min under microwave irradiation. The reaction mixture was cooled to room temperature, diluted with water (100 mL) and was extracted by ethyl acetate (150 mL×2). The combined organic extracts were washed with brine (50 mL), dried over anhydrous $Na_2SO_4$ and concentrated under reduce pressure. The crude product was purified by silica gel column chromatography, using ethyl acetate-Hexane=0: 1→2:8 as a gradient, to afford methyl 4-cyano-2-(4-(trifluoromethyl)phenyl)quinoline-7-carboxylate (X-1819A1) (0.200 g, 24%) as an off-white solid. MS: $[MH]^+$ 357.1.

4-Cyano-2-(4-(trifluoromethyl)phenyl)quinoline-7-carboxylic acid (I-401). To a stirred solution of methyl 4-cyano-2-(4-(trifluoromethyl)phenyl)quinoline-7-carboxylate (X-1819A1) (0.200 g, 0.56 mmol) in a mixture of THF-water (3:1; 5.0 mL) was added lithium hydroxide monohydrate (0.033 g, 0.79 mmol) at room temperature. Reaction mixture was stirred at room temperature for 2 h. After completion of reaction the reaction mixture was concentrated under reduced pressure, obtained crude was acidified (pH~2-3) with an aqueous solution of 1N HCl and the resulting precipitate was collected by filtration. Crude residue was washed with cold water until the pH of the filtrate became neutral (pH~6-7). The crude product was purified by (C-18) silica gel column chromatography, using acetonitrile-water=0:1→6:4 as a gradient, to afford 4-cyano-2-(4-(trifluoromethyl)phenyl)quinoline-7-carboxylic acid (I-401) (0.070 g, 90%) as an off-white solid. $^1H$ NMR (400 MHz, DMSO-$d_6$) δ: 8.92 (s, 1H), 8.68 (s, 1H), 8.57-8.55 (d, J=8.0 Hz, 2H), 8.37-8.34 (dd, J=1.2, 8.4 Hz, 1H), 8.11-8.09 (d, J=8.4 Hz, 1H), 7.97-7.95 (d, J=8.4 Hz, 2H). MS: $[MH]^+$ 343.3

Example 1.307. Synthesis of 4-ethynyl-2-(4-(trifluoromethyl)phenyl)quinoline-7-carboxylic acid (I-402)

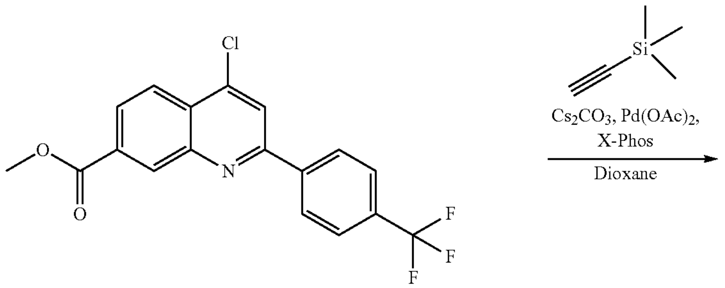

X-1584D5

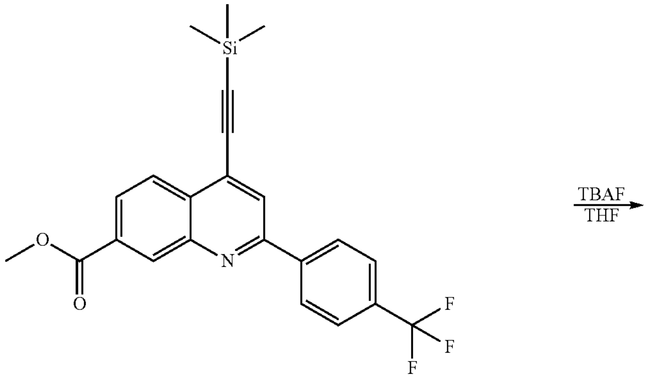

X-1820A1

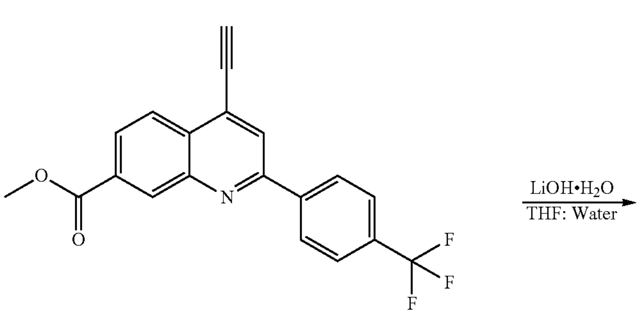

X-1820A2

-continued

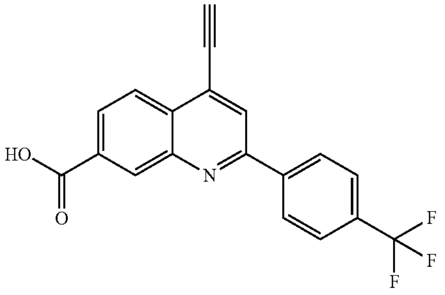

I-402

Methyl 2-(4-(trifluoromethyl)phenyl)-4-((trimethylsilyl)ethynyl)quinoline-7-carboxylate (X-1820A1). To a stirred solution of methyl 4-chloro-2-(4-(trifluoromethyl)phenyl)quinoline-7-carboxylate (X-1584D5) (0.250 g, 6.84 mmol) in 1,4-Dioxane (5 mL) $Cs_2CO_3$ (0.669 g, 20.54 mmol) and ethynyltrimethylsilane (0.336 g, 3.42 mmol) were added at room temperature, The reaction mixture was degassed (purging with nitrogen) for 20 min followed by addition of $Pd(OAc)_2$ (0.0076 g, 0.03 mmol) and X-phos (0.538 g, 0.06 mmol) were added and stirred at 100° C. for 1 hr. Reaction mixture was diluted with water (100 mL) and was extracted with ethyl acetate (100 mL×2), combined organic extracts were dried over anhydrous $Na_2SO_4$ and concentrated under reduce pressure. Isolated crude was combined with an identical prepared one more batch (0.250 g) and the combined crude product was purified by silica gel column chromatography, using ethyl acetate-hexane=0:1→4 3:7 as a gradient, to afford methyl 2-(4-(trifluoromethyl)phenyl)-4-((trimethylsilyl)ethynyl)quinoline-7-carboxylate (X-1820A1) (0.550 g, 94%) as a white solid. MS: $[MH]^+$ 428.0

Methyl 4-ethynyl-2-(4-(trifluoromethyl)phenyl)quinoline-7-carboxylate (X-1820A2). To a stirred solution of methyl 2-(4-(trifluoromethyl)phenyl)-4-((trimethylsilyl)ethynyl)quinoline-7-carboxylate (X-1820A1) (0.500 g, 11.70 mmol) in THE (7 mL) was added TBAF (2.93 mL, 29.27 mmol) at 0° C. Then reaction mixture stirred at room temperature for 1 h. reaction mixture was quenched by aqueous $NaHCO_3$ solution and was extracted by ethyl acetate (100 ml×2), combined organic extracts were dried over anhydrous $Na_2SO_4$ and concentrated under reduce pressure, to afford methyl 4-ethynyl-2-(4-(trifluoromethyl)phenyl)quinoline-7-carboxylate (X-1820A2) (0.270 g, 60%) as an off-white solid. MS: $[MH]^+$ 356.0

4-Ethynyl-2-(4-(trifluoromethyl)phenyl)quinoline-7-carboxylic acid (I-402). To a stirred solution of methyl 4-ethynyl-2-(4-(trifluoromethyl)phenyl)quinoline-7-carboxylate (X-1820A2) (0.300 g, 8.45 mmol) in a mixture of THE-water (8:2; 5.0 mL) was added lithium hydroxide monohydrate (0.106 g, 25.35 mmol) at room temperature. Reaction mixture was stirred at 70° C. for 2 h. After cooling to room temperature, the reaction mixture was concentrated under reduced pressure and acidified (pH~2-3) with an aqueous solution of 1N HCl and the resulting precipitate was collected by filtration. Crude residue was washed with cold water until the pH of the filtrate became neutral (pH~6-7). Obtained solid product was triturated by using n-pentane (5 ml) dried under reduced pressure, to afford 4-ethynyl-2-(4-(trifluoromethyl)phenyl)quinoline-7-carboxylic acid (I-402) (0.180 g, 62%) as an off-white solid. $^1H$ NMR (400 MHz, DMSO-$d_6$) δ: 13.58 (bs, 1H), 8.69 (s, 1H), 8.56-8.54 (d, J=8.0 Hz, 2H), 8.53 (s, 1H), 8.33-8.31 (d, J=8.8 Hz, 1H), 8.23-8.20 (dd, J=1.2, 8.8 Hz, 1H), 7.94-7.92 (d, J=8.4 Hz, 2H), 5.21 (s, 1H). MS: $[MH]^+$342.33

Example 1.308. Synthesis of 2-(4-(trifluoromethyl)phenyl)quinoline-7-carboxylic acid (1-403)

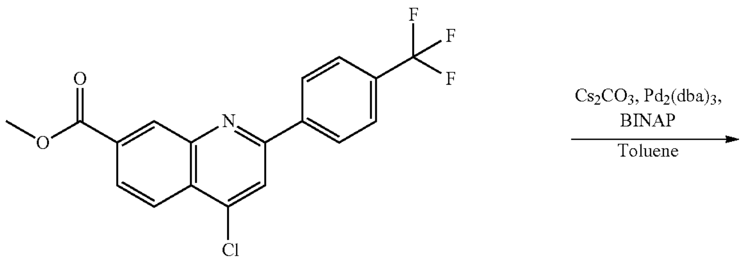

X-1584D5

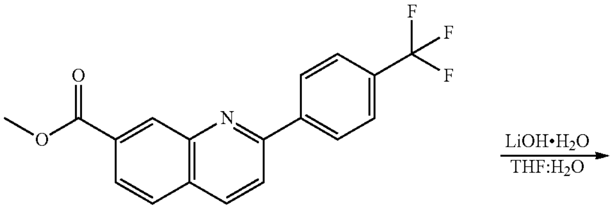

X-1824A1

-continued

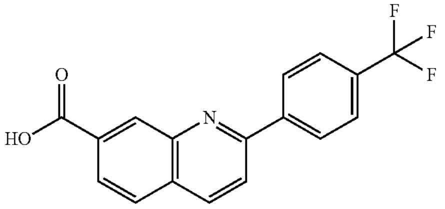

I-403

The following compounds were prepared in a manner analogous to the procedures described above for 4-Cyclopropoxy-2-(4-(trifluoromethyl)phenyl)quinoline-7-carboxylic acid (I-395):

2-(4-(trifluoromethyl)phenyl)quinoline-7-carboxylic acid (1-403) (0.010 g, 11%) as an off-white solid. $^1$H NMR (400 MHz, DMSO-$d_6$) δ: 8.65-8.62 (d, J=9.6 Hz, 1H), 8.60 (s, 1H), 8.54-8.52 (d, J=8.4 Hz 2H), 8.36-8.33 (d, J=8.8 Hz, 1H), 8.11 (s, 2H), 795-7.93 (d, J=8.4 Hz, 2H). MS: $[MH]^+$ 318.3.

Example 1.309. Synthesis of 2-Methyl-4-(4-(trifluoromethyl)phenyl)pyrrolo[1,2-a]quinoxaline-7-carboxylic acid (1-404)

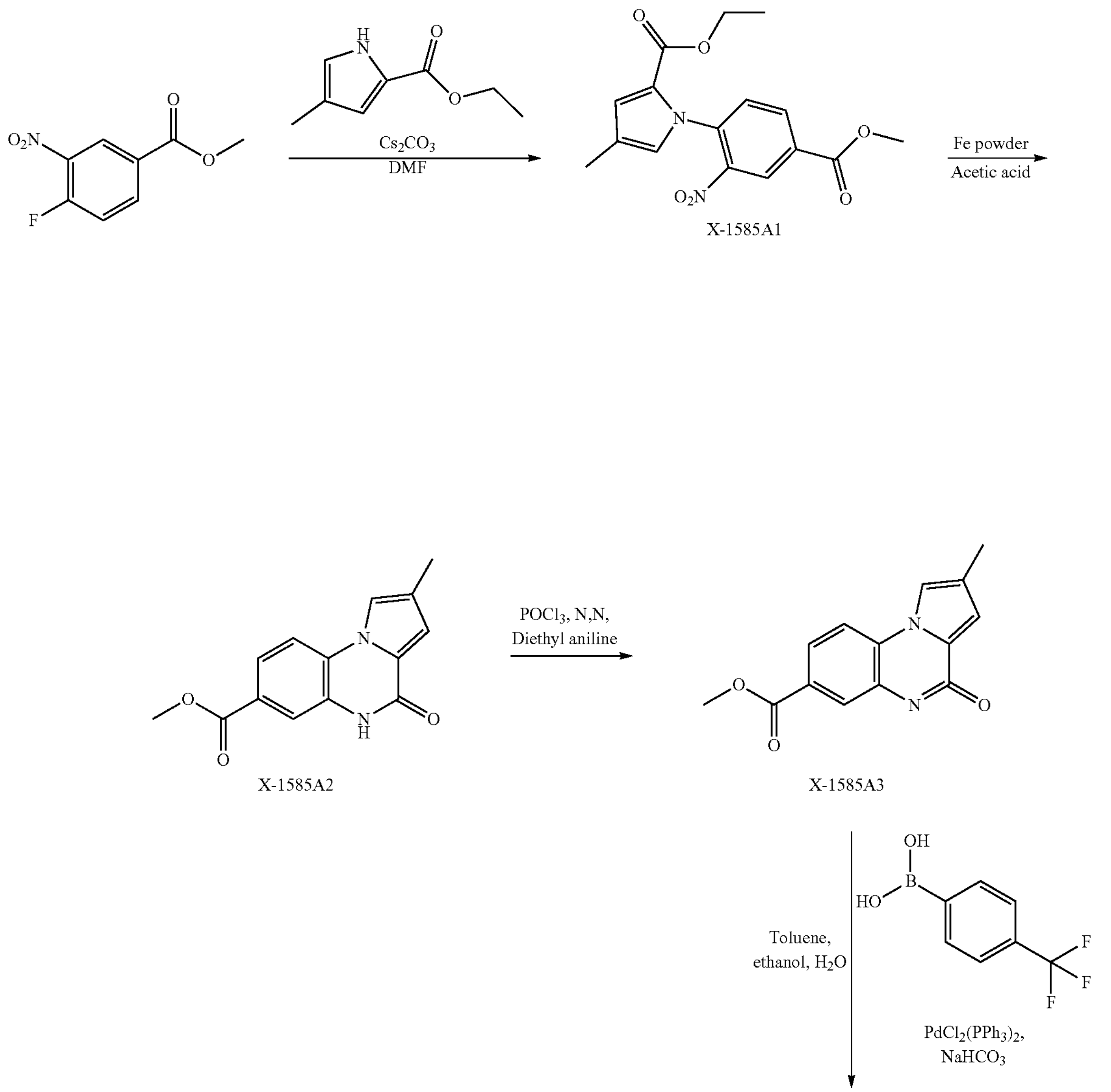

-continued

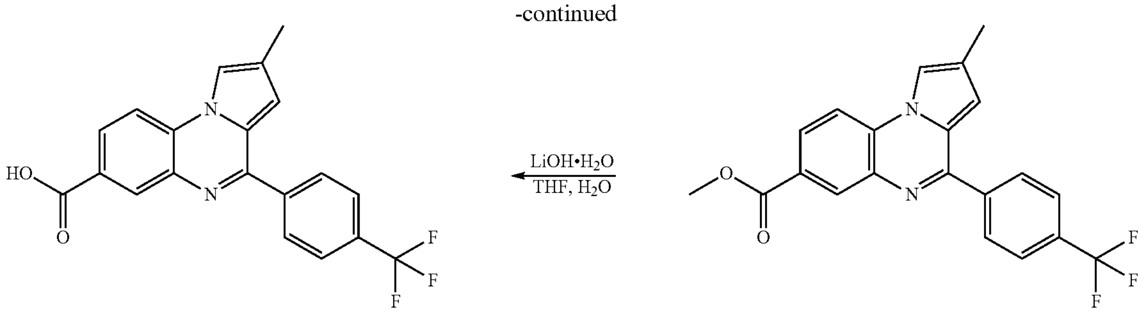

I-404 X-1585A4

Ethyl 1-(4-(methoxycarbonyl)-2-nitrophenyl)-4-methyl-1H-pyrrole-2-carboxylate (X-1585A1). To a stirred solution of methyl 4-fluoro-3-nitrobenzoate (5.0 g, 25.12 mmol) in DMF (15 mL) were added cesium carbonate (17.0 g, 52.32 mmol) and ethyl 4-methyl-1H-pyrrole-2-carboxylate (3.2 g, 20.93 mmol) at room temperature under nitrogen and the resulting mixture was stirred at room temperature for 2 h. Reaction mixture was cooled to room temperature, the reaction mixture was slowly poured into ice water (1000 mL) and was extracted with ethyl acetate (1000 mL×3). Combined organic extracts were washed with brine (500 mL), dried over anhydrous $Na_2SO_4$ and concentrated under reduced pressure. The crude product was purified by silica gel column chromatography, using ethyl acetate-hexane=0: 1→1:9 as gradient to afford ethyl 1-(4-(methoxycarbonyl)-2-nitrophenyl)-4-methyl-1H-pyrrole-2-carboxylate (X-1585A1) (4.0 g, 48%) as an off-white solid. MS: $[MH]^+$ 332.87

Methyl 2-methyl-4-oxo-4,5-dihydropyrrolo[1,2-a]quinoxaline-7-carboxylate (X-1585A2). To a stirred solution of ethyl 1-(4-(methoxycarbonyl)-2-nitrophenyl)-4-methyl-1H-pyrrole-2-carboxylate (X-1585A1) (4.0 g, 12.04 mmol) in acetic acid (15 mL) was added Fe-powder (5.30 g, 96.38 mmol) at 0° C. and reaction was allowed to stir at 70° C. for 3 h. After cooling to room temperature, reaction mixture was filtered and the precipitate was washed with water. The precipitate was taken in 10% methanol in dichloromethane, stirred for 30 min and filtered through a celite bed, filtrate was concentrated under reduced pressure to afford methyl 2-methyl-4-oxo-4,5-dihydropyrrolo[1,2-a]quinoxaline-7-carboxylate (X-1585A2) (3.0 g, 75%) as an off-white solid, which was taken to the next step without further purification. MS: $[MH]^+$ 256.95.

Methyl 4-chloro-2-methylpyrrolo[1,2-a]quinoxaline-7-carboxylate (X-1585A3). N,N-diethylaniline (5 mL) was added to a stirred suspension of methyl 2-methyl-4-oxo-4,5-dihydropyrrolo[1,2-a]quinoxaline-7-carboxylate (X-1585A2) (1.0 g, 3.90 mmol) in $POCl_3$ (10 mL) at 0° C. and the resulting mixture was heated at 110° C. for 3 h. After cooling to room temperature, reaction was diluted with cold water (100 mL), obtained precipitates were filtered and the residue was washed with water (200 mL). Solid precipitate was dried under reduced pressure, to afford methyl 4-chloro-2-methylpyrrolo[1,2-a]quinoxaline-7-carboxylate (X-1585A3) (0.8 g, 57%) as an off-white solid. MS: $[MH]^+$ 274.8/$[MH+2]^+$ 276.8.

Methyl 2-methyl-4-(4-(trifluoromethyl)phenyl)pyrrolo[1,2-a]quinoxaline-7-carboxylate (X-1585A4). To a stirred solution of methyl 4-chloro-2-methylpyrrolo[1,2-a]quinoxaline-7-carboxylate (X-1585A3) (0.300 g, 1.09 mmol) in toluene-ethanol-water (3:1:1, 5 mL) were added (4-(trifluoromethyl)phenyl)boronic acid (0.27 g, 1.42 mmol) and $NaHCO_3$ (0.27 g, 3.27 mmol) sequentially at room temperature under nitrogen. The resulting mixture was degassed (purged with nitrogen) for 20 min followed by the addition of $PdCl_2(PPh_3)_2$ (0.38 g, 0.54 mmol) and was heated at 120° C. for 2 h. After cooling to room temperature, reaction mixture was diluted with water (100 mL) and was extracted with ethyl acetate (200 mL×3). Combined organic extracts were dried over anhydrous $Na_2SO_4$ and concentrated under reduce pressure. The crude product was purified by silica gel column chromatography, using ethyl acetate-hexane=0: 1→3:7 as gradient, to afford methyl 2-methyl-4-(4-(trifluoromethyl)phenyl)pyrrolo[1,2-a]quinoxaline-7-carboxylate (X-1585A4) (0.2 g, 48%) as an off-white solid. MS: $[MH]^+$ 384.87.

2-Methyl-4-(4-(trifluoromethyl)phenyl)pyrrolo[1,2-a]quinoxaline-7-carboxylic acid (I-404). To a stirred solution of methyl 2-methyl-4-(4-(trifluoromethyl)phenyl)pyrrolo[1,2-a]quinoxaline-7-carboxylate (X-1585A4) (0.200 g, 0.52 mmol) in a mixture of THF-water (5:1; 6 mL) was added lithium hydroxide monohydrate (0.065 g, 1.56 mmol) at room temperature under nitrogen and the resulting reaction mixture was heated at 70° C. for 1 h. After cooling to room temperature, the reaction mixture was concentrated under reduced pressure, diluted with water (30 mL), and was extracted with ethyl acetate (30×2 mL) to remove unwanted organic impurities. The aqueous layer was acidified (pH~2-3) with an aqueous solution of 1N HCl and the resulting precipitate was collected by filtration. Obtained crude was washed with cold water until the pH of the filtrate became neutral (pH~6-7) and triturated by n-pentane, dried under reduced pressure, to afford 2-Methyl-4-(4-(trifluoromethyl)phenyl)pyrrolo[1,2-a]quinoxaline-7-carboxylic acid (I-404) (0.090 g, 47%) as an off-white solid. $^1H$ NMR (400 MHz, DMSO-$d_6$) δ 13.16 (brs, 1H), 8.46 (s, 1H), 8.427-8.423 (d, J=1.6 Hz, 1H), 8.33-8.31 (d, J=8.8 Hz, 1H), 8.22-8.20 (d, J=8.0 Hz, 2H), 8.12-8.09 (dd, J=8.4, 1.6 Hz, 1H), 7.95-7.93 (d, J=8.4 Hz, 2H), 6.97 (s, 1H), 2.35 (s, 3H). $[MH]^+$ 371.0.

Example 1.310. Synthesis of 2-Methyl-4-(5-(trifluoromethyl)pyridin-2-yl)pyrrolo[1,2-a]quinoxaline-7-carboxylic acid (1-405)

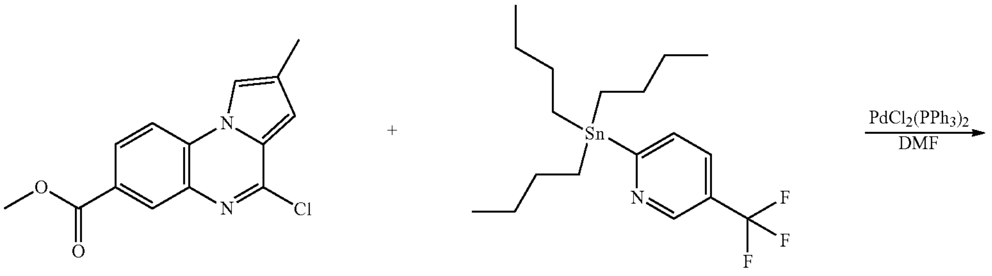

X-1585A3

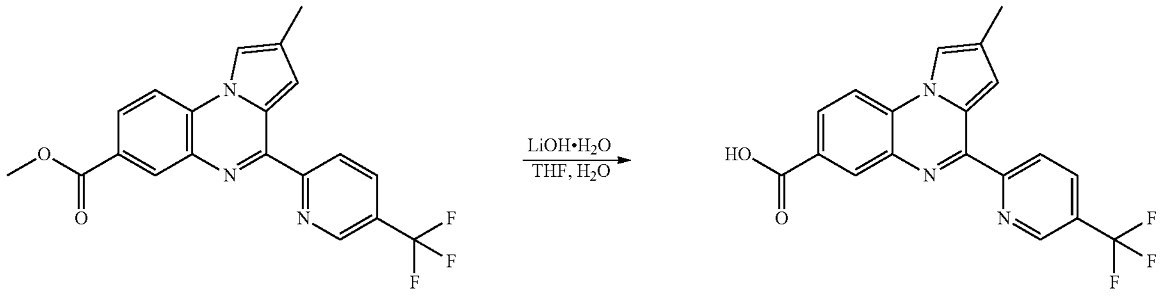

X-1587A1

I-405

Methyl 2-methyl-4-(5-(trifluoromethyl)pyridin-2-yl)pyrrolo[1,2-a]quinoxaline-7-carboxylate (X-1587A1). To a stirred solution of methyl 4-chloro-2-methylpyrrolo[1,2-a]quinoxaline-7-carboxylate (X-1585A3) (0.3 g, 1.09 mmol) in DMF (5 mL) were added 2-(tributylstannyl)-5-(trifluoromethyl)pyridine (0.717 g, 1.64 mmol) at room temperature under nitrogen. The reaction mixture was degassed (purging with nitrogen) for 20 min followed by the addition of $PdCl_2(PPh_3)_4$ (0.074 g, 0.10 mmol) and the resulting mixture was heated at 120° C. for 2 h. After completion of reaction, reaction mixture was cooled to room temperature, diluted with water (100 mL) and was extracted with ethyl acetate (100 mL×3), dried over anhydrous $Na_2SO_4$ and concentrated under reduced pressure. Obtained crude product was purified by $C^{18}$ silica gel column chromatography, using acetonitrile-water=0:1→6:4 as gradient, to afford methyl 2-methyl-4-(5-(trifluoromethyl)pyridin-2-yl)pyrrolo[1,2-a]quinoxaline-7-carboxylate (X-1587A1) (0.2 g, 47%) as an off-white solid. MS: $[MH]^+$ 385.92.

2-Methyl-4-(5-(trifluoromethyl)pyridin-2-yl)pyrrolo[1,2-a]quinoxaline-7-carboxylic acid (I-405). To a stirred solution of methyl 2-methyl-4-(5-(trifluoromethyl)pyridin-2-yl)pyrrolo[1,2-a]quinoxaline-7-carboxylate (X-1587A1) (0.2 g, 0.51 mmol) in a mixture of THF-water (5:2; 7.0 mL) was added lithium hydroxide monohydrate (0.065 g, 1.55 mmol) at room temperature and the resulting mixture was stirred at 70° C. for 1 h. After completion of reaction, reaction mixture was concentrated under reduced pressure, diluted with water (100 mL), and was extracted with ethyl acetate (50×2 mL) to remove unwanted organic impurities. The aqueous layer was acidified (pH~2-3) with aqueous 1N HCl, and the resulting precipitate was collected by filtration, and washed with cold water until the pH of the filtrate became neutral (pH~6-7). Obtained solid was triturated by n-pentane and was dried under reduced pressure, to afford 2-Methyl-4-(5-(trifluoromethyl)pyridin-2-yl)pyrrolo[1,2-a]quinoxaline-7-carboxylic acid (I-405) (0.050 g, 26%) as a yellow solid. MS: $[MH]^+$ 372.02. $^1H$ NMR (400 MHz, DMSO-$d_6$) δ 13.24 (s, 1H), 9.21 (s, 1H), 8.71-8.69 (d, J=8.4 Hz, 1H), 8.49-8.44 (m, 3H), 8.36-8.34 (d, J=8.8 Hz, 1H), 8.15-8.13 (dd, J=8.8, 1.6, Hz, 1H), 7.74 (s, 1H), 2.39 (s, 3H).

Example 1.311. Synthesis of 2-Methyl-4-(4-(trifluoromethyl)piperidin-1-yl)pyrrolo[1,2-a]quinoxaline-7-carboxylic acid (I-406)

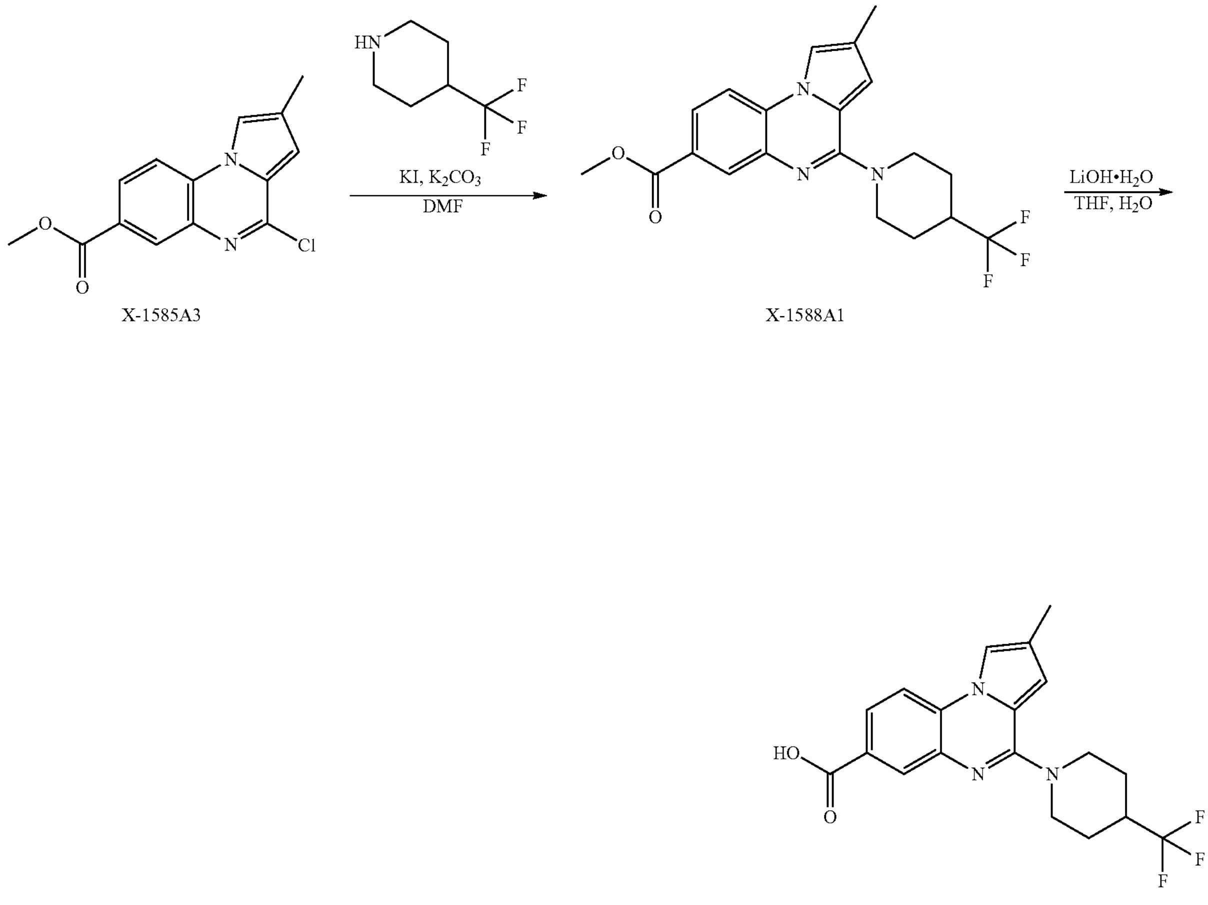

X-1585A3

X-1588A1

I-406

Methyl 2-methyl-4-(4-(trifluoromethyl)piperidin-1-yl) pyrrolo[1,2-a]quinoxaline-7-carboxylate (X-1588A1). To a stirred solution of methyl 4-chloro-2-methylpyrrolo[1,2-a] quinoxaline-7-carboxylate (X-1585A3) (0.4 g, 1.45 mmol) and 4-(trifluoromethyl)piperidine (0.29 g, 1.89 mmol) in DMF (7 mL) were added potassium carbonate (0.60 g, 4.35 mmol) and potassium iodide (0.92 g, 4.35 mmol) at room temperature under nitrogen and the resulting mixture was stirred at 100° C. for 3 h. After completion of reaction, reaction mixture was cooled to room temperature and was poured in ice-water (50 mL) and was extracted with ethyl acetate (50 mL×3). Combined organic extracts were washed with brine (50 mL), dried over anhydrous $Na_2SO_4$ and concentrated under reduced pressure, to afford methyl 2-methyl-4-(4-(trifluoromethyl)piperidin-1-yl)pyrrolo[1,2-a]quinoxaline-7-carboxylate (X-1588A1) (0.41 g, 71%) as an off-white solid. MS: $[MH]^+$ 391.97.

2-Methyl-4-(4-(trifluoromethyl)piperidin-1-yl)pyrrolo[1,2-a]quinoxaline-7-carboxylic acid (1-406). To a stirred solution of methyl 2-methyl-4-(4-(trifluoromethyl)piperidin-1-yl)pyrrolo[1,2-a]quinoxaline-7-carboxylate (X-1588A1) (0.4 g, 1.02 mmol) in a mixture of THE-water (4:1; 5.0 mL) was added lithium hydroxide monohydrate (0.128 g, 3.06 mmol) at room temperature under nitrogen and the resulting mixture was heated at 70° C. for 2 h. After completion of reaction, reaction mixture was cooled to room temperature and was concentrated under reduced pressure. Obtained crude was diluted with water (40 mL) and was extracted with ethyl acetate (40 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was triturated by n-pentane and dried under high vacuum, to afford 2-methyl-4-(4-(trifluoromethyl)piperidin-1-yl)pyrrolo[1,2-a]quinoxaline-7-carboxylic acid (I-406) (0.250 g, 65%) as an off-white solid. $^1H$ NMR (400 MHz, DMSO-$d_6$) δ 12.91 (s, 1H), 8.15 (s, 1H), 8.09-8.07 (d, J=8.4 Hz, 1H), 8.04-8.04 (d, J=1.2 Hz, 1H), 7.81-7.78 (dd, J=8.4, 1.6 Hz, 1H), 6.86 (s, 1H), 4.54-4.51 (d, J=12.8 Hz, 2H), 3.08-3.02 (t, J=12.4 Hz, 2H), 2.69-2.66 (m, 1H), 2.29 (s, 3H), 1.98-1.93 (m, 2H), 1.66-1.60 (m, 2H). MS: $[MH]^+$ 377.92.

Example 1.312. Synthesis of 3-methyl-4-(4-(trifluoromethyl)phenyl)pyrrolo[1,2-a]quinoxaline-7-carboxylic acid (1-407)

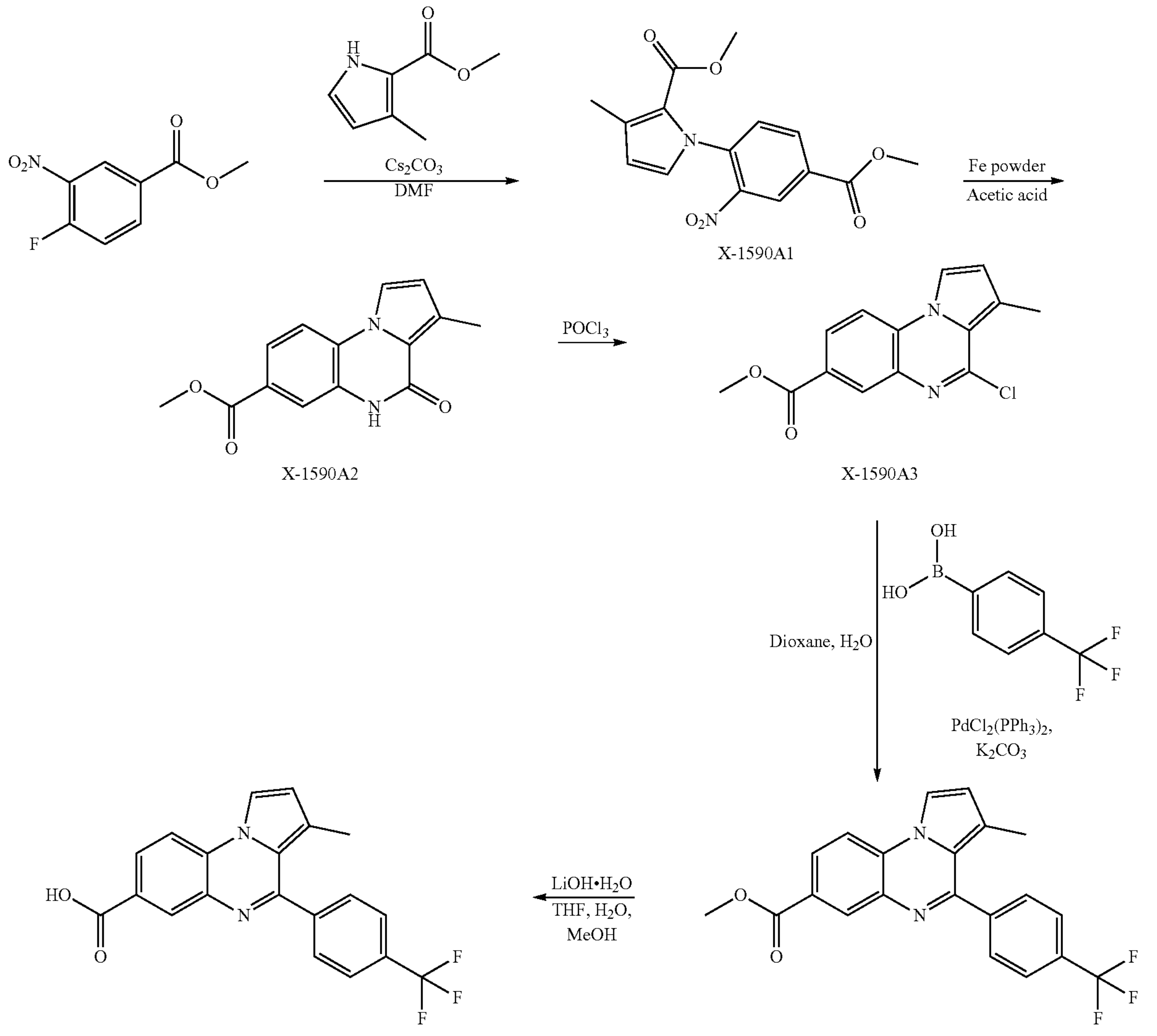

X-1590A1, X-1590A2, X-1590A3, X-1590A4, I-407

Methyl 1-(4-(methoxycarbonyl)-2-nitrophenyl)-3-methyl-1H-pyrrole-2-carboxylate (X-1590A1). To a stirred solution of methyl 4-fluoro-3-nitrobenzoate (3.0 g, 15.07 mmol) in DMF (10 mL) were added cesium carbonate (9.8 g, 30.15 mmol) and methyl 3-methyl-1H-pyrrole-2-carboxylate (2.3 g, 16.58 mmol) at room temperature under nitrogen and the resulting mixture was heated at 60° C. for 2 h. Reaction mixture was cooled to room temperature, poured into cold water (500 mL) obtained precipitates were filtered and the residue was washed with water (200 mL). Solid precipitate was dried under reduced pressure, to afford methyl 1-(4-(methoxycarbonyl)-2-nitrophenyl)-3-methyl-1H-pyrrole-2-carboxylate (X-1590A1) (3.0 g, 68%) as an off-white solid. MS: $[MH]^+$ 318.91.

Methyl 3-methyl-4-oxo-4,5-dihydropyrrolo[1,2-a]quinoxaline-7-carboxylate (X-1590A2). To a stirred solution of methyl 1-(4-(methoxycarbonyl)-2-nitrophenyl)-3-methyl-1H-pyrrole-2-carboxylate (X-1590A1) (3.0 g, 9.14 mmol) in acetic acid (10 mL) was added Fe-powder (4.02 g, 73.17 mmol) at 0° C. and reaction was allowed to stir at 60° C. for 2 h. After cooling to room temperature, reaction mixture was filtered and the precipitate was washed with water. The precipitate was taken in 10% methanol in dichloromethane, stirred for 30 min and filtered through a celite bed, filtrate was concentrated under reduced pressure to afford methyl 3-methyl-4-oxo-4,5-dihydropyrrolo[1,2-a]quinoxaline-7-carboxylate (X-1590A2) (2.0 g, 83%) as an off-white solid, which was taken to the next step without further purification. MS: $[MH]^+$ 256.95.

Methyl 4-chloro-3-methylpyrrolo[1,2-a]quinoxaline-7-carboxylate (X-1590A3). A solution of methyl 3-methyl-4-oxo-4,5-dihydropyrrolo[1,2-a]quinoxaline-7-carboxylate (X-1590A2) (1.0 g, 3.90 mmol) in $POCl_3$ (7 mL, 74.87 mmol) was heated at 110° C. for 1 h. After cooling to room temperature, reaction was diluted with cold water (100 mL), obtained precipitates were filtered and the residue was washed with water (200 mL). Solid precipitate was triturated by n-pentane and dried under reduced pressure, to afford methyl 4-chloro-3-methylpyrrolo[1,2-a]quinoxaline-7-carboxylate (X-1590A3) (0.6 g, 60%) as an off-white solid. MS: $[MH]^+$ 274.9/$[MH^+2]$276.8.

Methyl 3-methyl-4-(4-(trifluoromethyl)phenyl)pyrrolo[1,2-a]quinoxaline-7-carboxylate (X-1590A4). To a stirred solution of methyl 4-chloro-3-methylpyrrolo[1,2-a]quinoxaline-7-carboxylate (X-1590A3) (0.3 g, 1.09 mmol) in 1,4-dioxane-water (8:2, 10 mL) were added (4-(trifluoromethyl)phenyl)boronic acid (0.27 g, 1.42 mmol) and $K_2CO_3$ (0.45 g, 3.28 mmol) sequentially at room temperature under nitrogen. The resulting mixture was degassed (purged with nitrogen) for 20 min followed by the addition of $PdCl_2(PPh_3)_2$ (0.022 g, 0.03 mmol) and was heated at 110° C. for 1 h. After cooling to room temperature, reaction mixture was diluted with water (100 mL) and was extracted with ethyl acetate (200 mL×3). Combined organic extracts were dried over anhydrous $Na_2SO_4$ and concentrated under reduce pressure. The crude product was purified by silica gel column chromatography, using ethyl acetate-hexane=0:1→1:9 as gradient, to afford methyl 3-methyl-4-(4-(trifluoromethyl)phenyl)pyrrolo[1,2-a]quinoxaline-7-carboxylate (X-1590A4) (0.3 g, 71%) as an white solid. MS: $[MH]^+$ 385.02.

3-Methyl-4-(4-(trifluoromethyl)phenyl)pyrrolo[1,2-a]quinoxaline-7-carboxylic acid (1-407). To a stirred solution of methyl 3-methyl-4-(4-(trifluoromethyl)phenyl)pyrrolo[1,2-a]quinoxaline-7-carboxylate (X-1590A4) (0.3 g, 0.78 mmol) in a mixture of THF-water-MeOH (4:1.5:1; 6.5 mL) was added lithium hydroxide monohydrate (0.056 g, 234 mmol) at room temperature under nitrogen and the resulting reaction mixture was heated at 60° C. for 1 h. After cooling to room temperature, the reaction mixture was concentrated under reduced pressure, diluted with water (30 mL), and was extracted with ethyl acetate (30×2 mL) to remove unwanted organic impurities. The aqueous layer was acidified (pH~2-3) with an aqueous solution of 1N HCl and the resulting precipitate was collected by filtration. Obtained crude was washed with cold water until the pH of the filtrate became neutral (pH~6-7) and triturated by n-pentane, dried under reduced pressure, to afford 3-methyl-4-(trifluoromethyl)phenyl)pyrrolo[1,2-a]quinoxaline-7-carboxylic acid (1-407) (0.2 g, 71%) as a white solid. $[MH]^+$ 371.0. $^1H$ NMR (400 MHz, DMSO-$d_6$) δ 13.16 (brs, 1H), 8.57-8.56 (d, J=2.8 Hz, 1H), 8.39-8.36 (d, J=8.8 Hz, 1H), 8.34-8.33 (d, J=1.6 Hz, 1H), 8.10-8.08 (dd, J=8.8, 2.0 Hz, 1H), 7.93-7.91 (d, J=8.4 Hz, 2H), 7.84-7.82 (d, J=8.0 Hz, 2H), 6.88-6.87 (d, J=2.8 Hz, 1H), 1.85 (s, 3H).

Example 1.313. Synthesis of N-((6-(4-(trifluoromethyl)phenyl)imidazo[1,2-a]pyrazin-8-yl)methyl)acrylamide (I-408)

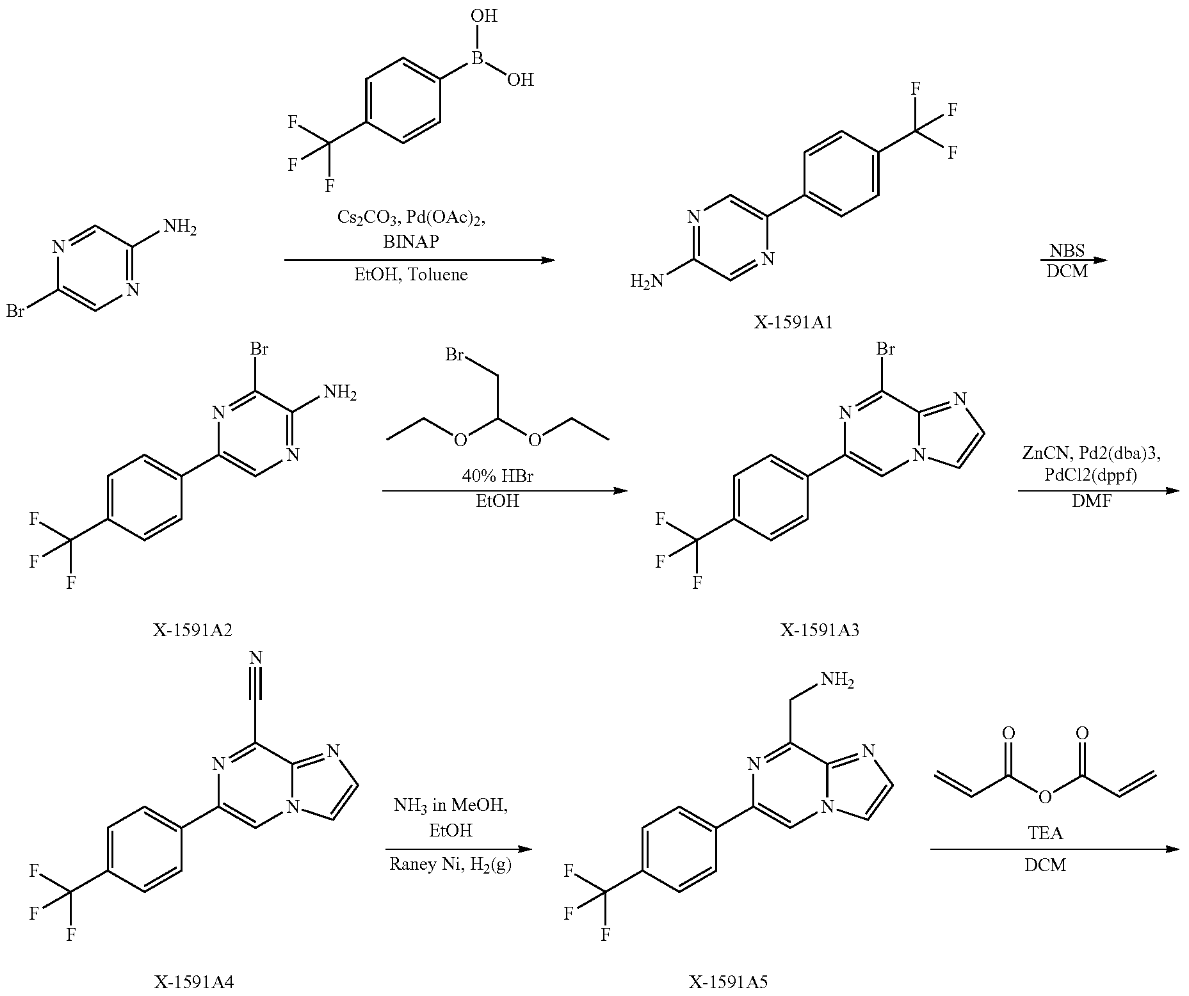

X-1591A1

X-1591A2

X-1591A3

X-1591A4

X-1591A5

-continued

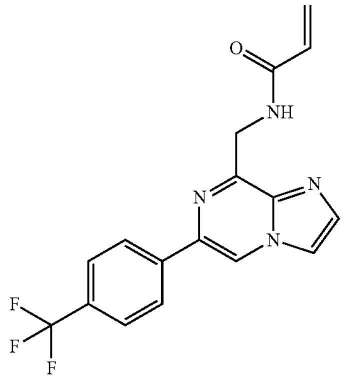

I-408

5-(4-(Trifluoromethyl)phenyl)pyrazin-2-amine (X-1591A1). To a stirred solution of 5-bromopyrazin-2-amine (5.0 g, 28.91 mmol) in a mixture of toluene-ethanol (2:1, 30 mL) were added (4-(trifluoromethyl)phenyl)boronic acid (7.13 g, 37.55 mmol) and $Cs_2CO_3$ (28.2 g, 86.72 mmol) at room temperature. The reaction mixture was degassed (purging with nitrogen) for 20 min followed by addition of Pd $(OAc)_2$ (0.32 g, 1.44) mmol and BINAP (0.90 g, 1.44 mmol) and the reaction mixture was heated at 110° C. for 3 h. The reaction mixture was cooled to room temperature, diluted with water (300 mL) and was extracted with ethyl acetate (300 mL×3). Combined organic extracts were dried over anhydrous $Na_2SO_4$ and concentrated under reduce pressure. The crude product was purified by silica gel column chromatography, using ethyl acetate-hexane=0:1→4:6 as gradient, to afford 5-(4-(trifluoromethyl)phenyl) pyrazin-2-amine (X-1591A1) (5.0 g, 72%) as an off-white solid. MS: $[MH]^+$239.95

3-Bromo-5-(4-(trifluoromethyl)phenyl)pyrazin-2-amine (X-1591A2). To a stirred solution of 5-(4-(trifluoromethyl) phenyl)pyrazin-2-amine (X-1591A1) (2.0 g, 8.36 mmol) in DCM (10 mL) was added N-Bromosuccinimide (1.48 g, 4.18 mmol) at −78° C. under nitrogen and the resulting mixture was stirred at room temperature for 4 h. The reaction mixture was diluted with water (100 mL) and was extracted with ethyl acetate (300 mL×3). The combined organic extracts were dried over anhydrous $Na_2SO_4$ and concentrated under reduce pressure. The crude product was purified by silica gel column chromatography, using ethyl acetate-Hexane=8:2→10:0 as gradient, to afford 3-bromo-5-(4-(trifluoromethyl)phenyl)pyrazin-2-amine (X-1591A2) (1.8 g, 68%) as a brown solid. MS: $[MH]^+$ 317.8

8-Bromo-6-(4-(trifluoromethyl)phenyl)imidazo[1,2-a] pyrazine (X-1591A3). To a stirred solution of 3-bromo-5-(4-(trifluoromethyl)phenyl)pyrazin-2-amine (X-1591A2) (1.80 g, 5.68 mmol) in ethanol (20 mL) were added HBr in water (2.27 g, 28.39 mmol) and 2-bromo-1,1-diethoxy-ethane (2.24 g, 11.35 mmol) at 0° C. under nitrogen and the resulting mixture was stirred at 800° C. for 4 h. After cooling to room temperature, the reaction mixture was quenched with an aqueous solution of saturated $NaHCO_3$ (250 mL) and was extracted with ethyl acetate (50 mL×3). The combined organic extracts were washed with brine (50 mL), dried over anhydrous $Na_2SO_4$ and concentrated under reduce pressure. The crude product was purified by silica gel column chromatography, using methanol-dichloromethane=0:1→1:9 as gradient, to afford 8-bromo-6-(4-(trifluoromethyl)phenyl)imidazo[1,2-a]pyrazine (X-1591A3) (1.2 g, 63%) as a Brown solid. MS: $[MH]^+$ 341.8

6-(4-(Trifluoromethyl)phenyl)imidazo[1,2-a]pyrazine-8-carbonitrile (X-1591A4). To a stirred solution of 8-bromo-6-(4-(trifluoromethyl)phenyl)imidazo[1,2-a]pyrazine (X-1591A3) (1.3 g, 3.81 mmol) in a DMF (10 mL) was added zinc cyanide (1.78 g, 15.25 mmol) at room temperature. The reaction mixture was degassed (purging with nitrogen) for 20 min followed by addition of $PdCl_2$(dppf) (0.22 g, 0.30 mmol) and $Pd_2$ $(dba)_3$ (0.28 g, 0.30 mmol) and the reaction mixture was heated at 150° C. under microwave irradiation for 30 min. The reaction mixture was cooled to room temperature, diluted with water (100 mL) and was extracted with ethyl acetate (100 mL×3). The combined organic extracts were dried over anhydrous $Na_2SO_4$ and concentrated under reduce pressure. The crude product was purified by silica gel column chromatography, using ethyl acetate-hexane=0:1→4 8:2 as gradient, to afford 6-(4-(trifluoromethyl)phenyl)imidazo[1,2-a]pyrazine-8-carbonitrile (X-1591A4) (0.25 g, 23%) as a brown solid. MS: $[MH]^+$ 289.3

(6-(4-(Trifluoromethyl)phenyl)imidazo[1,2-a]pyrazin-8-yl)methanamine (X-1591A5). To a stirred solution of 6-(4-(trifluoromethyl)phenyl)imidazo[1,2-a]pyrazine-8-carbonitrile (X-1591A4) (0.25 g, 0.87 mmol) in THE (8 mL) were added methanolic ammonia (7N, 1 mL) and Raney Nickel (0.25 g) room temperature under nitrogen the resulting mixture was hydrogenated in Parr Autoclave at same temperature under 200 psi for 4 h. The reaction mixture was filtered through celite bad and wash with ethyl acetate. The filtrates were dried over anhydrous $Na_2SO_4$ and concentrated under reduce pressure. The crude product was purified by (C-18) silica gel column chromatography, using acetonitrile-water=0:144:6 as gradient, to afford (6-(4-(trifluoromethyl)phenyl)imidazo[1,2-a]pyrazin-8-yl)methanamine (X-1591A5) (0.045 g, 17%) as a yellow solid. MS: $[MH]^+$ 293.4

N-((6-(4-(trifluoromethyl)phenyl)imidazo[1,2-a]pyrazin-8-yl)methyl)acrylamide (I-408). To a stirred solution of (6-(4-(trifluoromethyl)phenyl)imidazo[1,2-a]pyrazin-8-yl) methanamine (X-1591A5) (0.045 g, 0.15 mmol) in DCM (3 mL) were added triethylamine (0.05 g, 0.46 mmol) and acrylic anhydride (0.025 g, 0.20 mmol) at 0° C. under nitrogen and the reaction mixture stirred for 30 min at same temperature. The reaction mixture was diluted with aqueous $NaHCO_3$ (10 mL) and was extracted by ethyl acetate (30 mL×3). The combined organic extracts were dried over anhydrous $Na_2SO_4$ and concentrated under reduce pressure. The crude product was purified by (C-18) silica gel column chromatography, using acetonitrile-water=0:144:6 as gradient, to afford N-((6-(4-(trifluoromethyl)phenyl)imidazo[1,2-a]pyrazin-8-yl)methyl)acrylamide (I-408) (0.012 g, 18%) as an off-white solid. 1H NMR (400 MHz, DMSO-$d_6$) δ 9.32 (s, 1H), 8.76-8.73 (t, J=5.2 Hz, 1H), 8.28-8.26 (d, J=8.0 Hz, 2H), 8.17 (s, 1H), 7.88-7.84 (m, 3H), 6.48-6.41 (m, 1H), 6.16-6.12 (dd, J=17.2, 1.6 Hz, 1H), 5.67-5.64 (dd, J=1.6 Hz, 10.0 Hz, 1H), 4.95-4.93 (d, J=5.6 Hz, 2H). MS: $[MH]^+$ 347.1.

Example 1.314. Synthesis of N-((1-(4-(tert-butyl)phenyl)-6-fluoropyrrolo[1,2-a]pyrazin-3-yl)methyl)acrylamide (I-409)

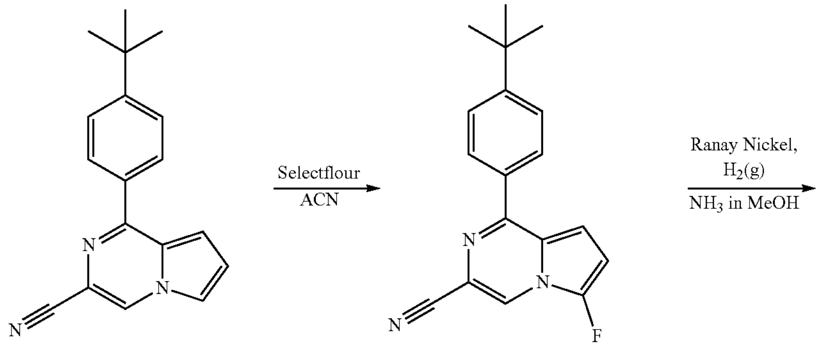

X-1273A6 X-1599A1

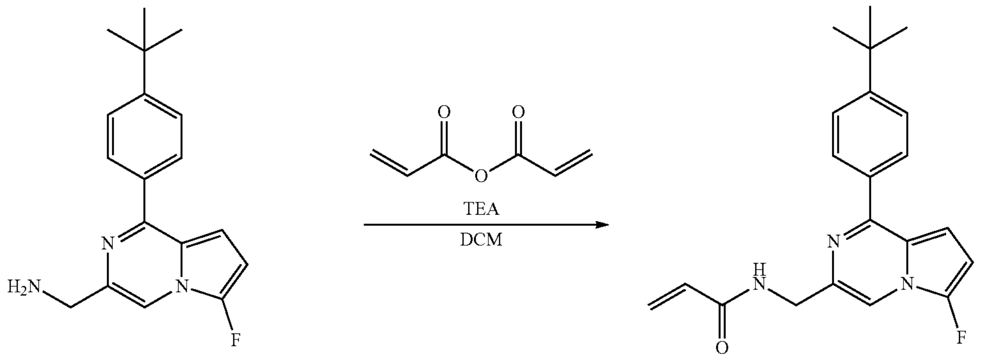

X-1599A2 I-409

3-Fluoro-8-(4-(trifluoromethyl)phenyl)imidazo[1,2-a]pyrazine-6-carbonitrile (X-1599A1). To a stirred solution 1-(4-(tart-butyl)phenyl)pyrrolo[1,2-a]pyrazine-3-carbonitrile (X-1273A6) (0.700 g, 2.54 mmol) in acetonitrile (6 mL) was added select flour (1.0 g, 2.79 mmol) portion wise at 0° C. under nitrogen and the resulting mixture was stirred at room temperature for 16 h. Reaction mixture was diluted in water (100 mL) and was extracted with ethyl acetate (100 mL×3). Collected organic parts were dried over anhydrous $Na_2SO_4$ and concentrated under reduce pressure. The crude was purified by silica gel column chromatography, using ethyl acetate-hexane=0:1→1:9 as gradient, to afford 1-(4-(tert-butyl)phenyl)-6-fluoropyrrolo[1,2-a]pyrazine-3-carbonitrile (X-1599A1) (0.400 g, 54%) as a yellow solid. MS: $[MH]^+$ 294.1.

(1-(4-(tert-Butyl)phenyl)-6-fluoropyrrolo[1,2-a]pyrazin-3-yl)methanamine (X-1599A2). To a stirred solution of 1-(4-(tert-butyl)phenyl)-6-fluoropyrrolo[1,2-a]pyrazine-3-carbonitrile (X-1599A1) (0.400 g, 1.32 mmol) in THE (5 mL) were added Raney Ni (0.400 g) and methanolic ammonia (7N; 2 mL) at room temperature and the resulting mixture was hydrogenated in Parr Autoclave at room temperature under 200 psi for 6 h. Reaction mixture was filtered over a celite bed, the bed was washed with methanol (100 mL) and collected filtrates were concentrated under reduced pressure to afford ((1-(4-(tert-butyl)phenyl)-6-fluoropyrrolo[1,2-a]pyrazin-3-yl)methanamine (X-1599A2) (0.400 g; quant; crude) as a yellow solid. MS: $[MH]^+$ 298.1.

N-((1-(4-(tert-butyl)phenyl)-6-fluoropyrrolo[1,2-a]pyrazin-3-yl)methyl)acrylamide (I-409). To a stirred solution of ((1-(4-(tert-butyl)phenyl)-6-fluoropyrrolo[1,2-a]pyrazin-3-yl)methanamine (X-1599A2) (0.400 g, 1.34 mmol) in DCM (6 mL) were added triethylamine (0.272 g, 2.69 mmol) followed by acrylic anhydride (0.203 g, 1.61 mmol) at 0° C. under nitrogen and the reaction mixture stirred for 30 min at room temperature. Reaction mixture was slowly poured into water (30 mL) and was extracted with DCM (30 mL×3). Combined organic layers were dried over anhydrous $Na_2SO_4$ and concentrated under reduced pressure. Obtained crude was purified by reverse phase (C-18) silica gel column chromatography using acetonitrile-0.1% in water=0:1-7:3 as gradient, to afford N-((1-(4-(tert-butyl)phenyl)-6-fluoropyrrolo[1,2-a]pyrazin-3-yl)methyl)acrylamide (I-409) (0.150 g, 31%) as an off-white solid. $^1H$ NMR (400 MHz, DMSO-$d_6$) δ 8.61 (m, 1H), 7.91-7.87 (d, J=8.0 Hz, 3H), 7.59-7.57 (d, J=8.0 Hz, 2H), 6.92-6.90 (t, J=4.0 Hz, 1H), 6.67-6.66 (t, J=4.0 Hz, 1H), 6.36-6.30 (m, 1H), 6.16-6.11 (m, 1H), 5.64-5.61 (dd, J=12.0 Hz, 1H), 4.41-4.39 (d, J=8.0 Hz, 2H), 1.34 (s, 9H). MS: $[MH]^+$352.0.

Example 1.315. Synthesis of N-((3-(4-(trifluoromethyl)phenyl)imidazo[1,2-a]pyrimidin-2-yl)methyl) acrylamide (I-410)
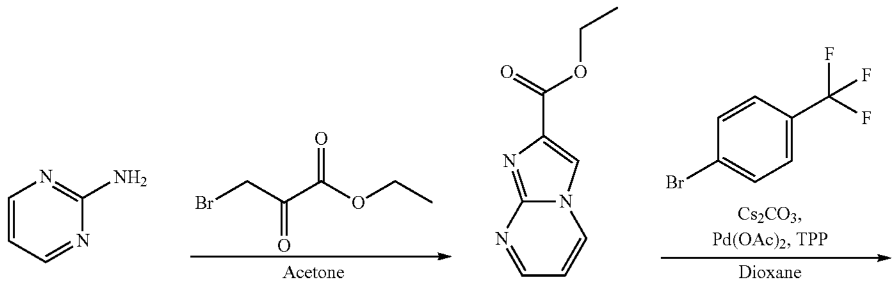
X-1636F1
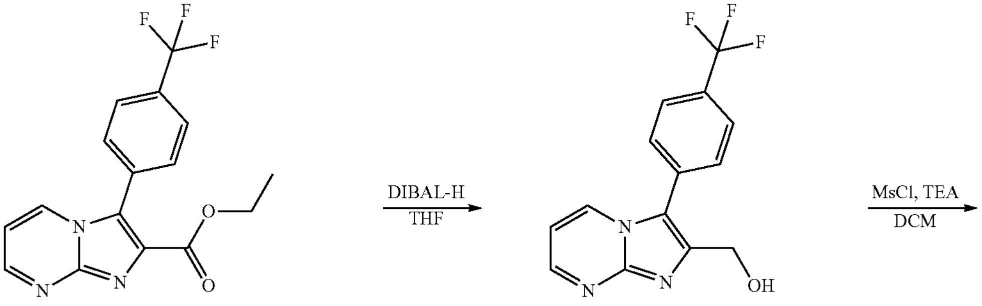
-1636D2
X-1636D3
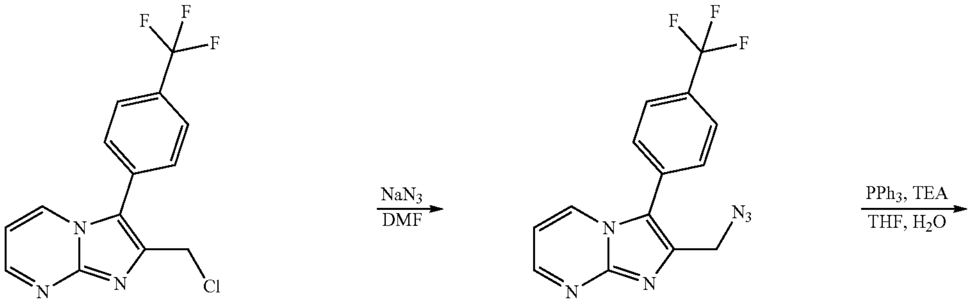
X-1636D4
X-1636D5
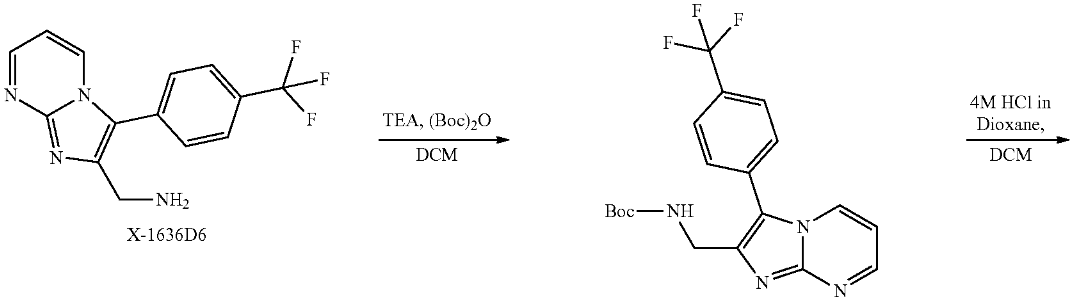
X-1636D6
X-1636D7

-continued

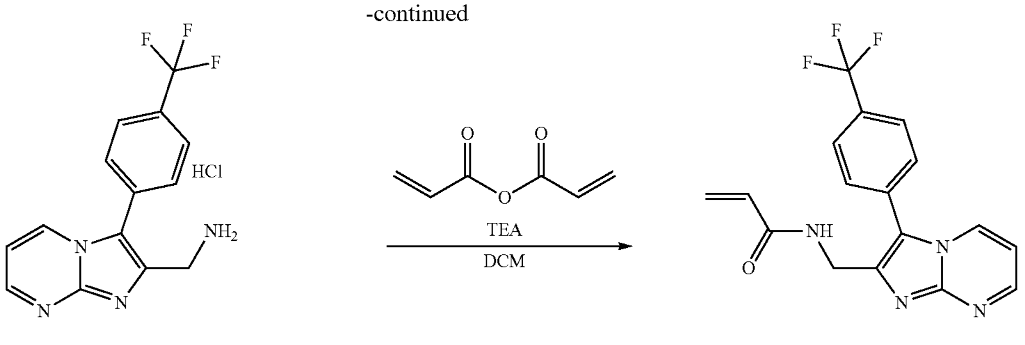

X-1636D8

I-410

Ethyl imidazo[1,2-a]pyrimidine-2-carboxylate (X-1636F1). To a stirred solution of pyrimidin-2-amine (10.0 g, 105.2 mmol) in acetone (250 mL) were added ethyl 3-bromo-2-oxopropanoate (13.5 g, 105.2 mmol) the resulting reaction mixture 60° C. for 1 h. Reaction mixture was cooled to give solid precipitate was filtered and dried in vacuo. Collected solid material was taken in EtOH:$H_2O$ (80:120 mL) and heated at 60° C. until clear the solution. After reaction mix was added $NaHCO_3$ (1 g) and filtered after reaction mixture was diluted with water (500 mL) and was extracted with ethyl acetate (500 mL×2). Organic extracts were combined, dried over anhydrous $Na_2SO_4$ and concentrated under reduced pressure. Obtained crude to afford N-(pyrimidin-2-ylmethyl)-4-(trifluoromethyl)benzamide (X-1636F1) (9.0 g, 45%) as a yellow solid. MS: $[MH]^+$ 192.28.

Ethyl 3-(4-(trifluoromethyl)phenyl)imidazo[1,2-a]pyrimidine-2-carboxylate (X-1637D2). To a stirred solution of ethyl imidazo[1,2-a]pyrimidine-2-carboxylate (X-1636F1) (1.0 g, 5.23 mmol) in a dioxane (10 mL) were added 1-bromo-4-(trifluoromethyl)benzene (1.59 g, 7.32 mmol), cesium carbonate (1.87 g, 5.75 mmol) the reaction mixture was degassed (purging with nitrogen) for 20 min followed by the addition of TPP (0.135 g, 0.52 mmol) and $Pd(OAc)_2$ (0.094 g, 0.41 mmol) and the resulting mixture was heated under microwave irradiation at 140° C. for 1 h. Reaction mixture was cooled to room temperature, diluted with water (300 mL) and was extracted with ethyl acetate (300 mL×3). Combined organic extracts were dried over anhydrous $Na_2SO_4$ and concentrated under reduce pressure. Isolated crude was combined with an identical prepared seven more batch (1 g) and the combined crude were purified by silica gel column chromatography, using ethyl acetate-hexane=0:1→1:0 as gradient, to afford ethyl 3-(4-(trifluoromethyl)phenyl)imidazo[1,2-a]pyrimidine-2-carboxylate (X-1634D2) (6.0 g, 43%) as a yellow solid. MS: $[MH]^+$ 336.3.

(3-(4-(Trifluoromethyl)phenyl)imidazo[1,2-a]pyrimidin-2-yl)methanol (X-1636D3). To a stirred solution of ethyl 3-(4-(trifluoromethyl)phenyl)imidazo[1,2-a]pyrimidine-2-carboxylate (X-1636D2) (2.5 g, 7.46 mmol) in THE (20 mL) were added DIBAL-H (1.0M in THF, 22.3 mL, 22.3 mmol) dropwise at −78° C. The resulting reaction mixture was stirred at −78° C. for 1 h. The reaction mixture was quenched with aqueous solution of saturated $NH_4Cl$ (500 mL) at −78° C. and allowed to maintain room temperature then extracted with ethyl acetate (200 mL×3), dried over anhydrous $Na_2SO_4$ and concentrated under reduce pressure crude product purified by using ethyl acetate-hexane=0:1→1:0 as gradient, to afford (3-(4-(trifluoromethyl)phenyl)imidazo[1,2-a]pyrimidin-2-yl)methanol (X-1634D3) (1.0 g, 46%) as a white solid. MS: $[MH]^+$ 294.4.

2-(Chloromethyl)-3-(4-(trifluoromethyl)phenyl)imidazo[1,2-a]pyrimidine (X-1636D4). To a stirred solution of (3-(4-(trifluoromethyl)phenyl)imidazo[1,2-a]pyrimidin-2-yl)methanol (X-1636D3) (1.0 g, 3.40 mmol) in DCM (10 mL) were added tri-ethylamine (0.75 g, 0.42 mmol) and methane sulfonyl chloride (0.586 g, 4.11 mmol) at 0° C. under nitrogen and stirred rt for 3 h, reaction mixture was diluted with water (100 mL) and was extracted with DCM (75 mL×3). Combined organic extracts dried over anhydrous $Na_2SO_4$ and concentrated in vacuo the crude product to afford 2-(chloromethyl)-3-(4-(trifluoromethyl)phenyl)imidazo[1,2-a]pyrimidine (X-1636D4) (1.2 g, qnt.) as a white solid. MS: $[MH]^+$ 312.28.

2-(Azidomethyl)-3-(4-(trifluoromethyl)phenyl)imidazo[1,2-a]pyrimidine (X-1636D5). To a stirred solution of 2-(chloromethyl)-3-(4-(trifluoromethyl)phenyl)imidazo[1,2-a]pyrimidine (X-1636D4) (1.2 g, 3.85 mmol) in DMF (10 mL) was added $NaN_3$ (0.501 g, 7.71 mmol) at room temperature under nitrogen and the resulting reaction mixture was heated at 50° C. for 3 h. Reaction mixture diluted with water (200 mL) and was extracted with ethyl acetate (200 mL×3). Combined organic extracts were washed with brine (50 mL), dried over anhydrous $Na_2SO_4$ and concentrated under reduced pressure Obtained crude was purified by silica gel flash column chromatography, using ethyl acetate-hexane=0:1→3:7 as gradient, to afford 2-(azidomethyl)-3-(4-(trifluoromethyl)phenyl)imidazo[1,2-a]pyrimidine (X-1636D5) (0.35 g, 28%) as a yellow solid. MS: $[MH]^+$ 319.32.

(3-(4-(Trifluoromethyl)phenyl)imidazo[1,2-a]pyrimidin-2-yl)methanamine (X-1636D6). To a stirred solution of 2-(azidomethyl)-3-(4-(trifluoromethyl)phenyl)imidazo[1,2-a]pyrimidine (X-1636D5) (0.35 g, 1.10 mmol) in a THF:$H_2O$ (5:1 mL) was added TPP (0.432 g, 1.65 mmol) and the resulting mixture was heated at 50° C. for 4 h. Reaction mixture was cooled to room temperature, diluted with water (100 mL) and was extracted with ethyl acetate (100 mL×3). Combined organic extracts were dried over anhydrous $Na_2SO_4$ and concentrated under reduce pressure. Obtained crude product to afford (3-(4-(trifluoromethyl)phenyl)imidazo[1,2-a]pyrimidin-2-yl)methanamine (X-1636D6) (0.77 g, Quantitative) as an off-white solid. MS: $[MH]^+$ 369.1.

Tert-butyl ((6-(4-(trifluoromethyl)phenyl)imidazo[1,5-a]pyrimidin-8-yl)methyl)carbamate (X-1636D7). To a stirred solution of (3-(4-(trifluoromethyl)phenyl)imidazo[1,2-a]pyrimidin-2-yl)methanamine (X-1636D7) (0.77 g, 3.08 mmol) in DCM (10 mL) were added triethylamine (1.24 g, 12.33 mmol) and $(Boc)_{2O}$ (1.15 g, 5.27 mmol) at 0° C. under nitrogen and stirred room temperature for 3 h. Reaction mixture was diluted with water (100 mL) and was extracted with DCM (100 mL×3). Combined organic extracts were dried over anhydrous $Na_2SO_4$ and concentrated under reduced pressure. Obtained crude was purified by silica gel flash column chromatography, using ethyl acetate-hexane=0:1→5:5 as gradient, to afford tert-butyl ((6-(4-(trifluoromethyl)phenyl)imidazo[1,5-a]pyrimidin-8-yl)methyl)carbamate (X-1636D7) (0.25 g, qnt.) as a white solid. MS: $[MH]^+$ 393.43

(3-(4-(Trifluoromethyl)phenyl)imidazo[1,2-a]pyrimidin-2-yl)methanamine (X-1636D8). To a stirred solution tert-butyl ((6-(4-(trifluoromethyl)phenyl)imidazo[1,5-a]pyrimidin-8-yl)methyl)carbamate (X-1636D7) (0.25 g, 0.63 mmol) in DCM (5 mL) was added 4M HCl in dioxane (1 mL) at 0° C. and stirred at room temperature for 2 h. The reaction mixture was concentrated under reduced pressure and the obtained crude product was purified by using n-pentane, to afford (3-(4-(trifluoromethyl)phenyl)imidazo[1,2-a]pyrimidin-2-yl)methanamine (X-1636D8) (0.17 g, 50%) as a white solid. MS: $[MH]^+$ 293.16

N-((6-(4-(trifluoromethyl)phenyl)imidazo[1,5-a]pyrimidin-8-yl)methyl)acrylamide (I-410). Acrylic anhydride (0.073 g, 0.58 mmol) was added to a stirred solution (3-(4-(trifluoromethyl)phenyl)imidazo[1,2-a]pyrimidin-2-yl)methanamine (X-1636D8) (0.17 g, 0.58 mmol) and triethyl amine (0.29 g, 2.9 mmol) in DCM (5 mL) at 0° C. temperature under nitrogen. The reaction mixture was stirred for 2 h at same temperature. The reaction mixture was poured in water (50 mL) and was extracted with DCM (50 mL×2). Combined organic extracts were dried over anhydrous $Na_2SO_4$ and concentrated under reduced pressure. The crude product was purified by Obtained crude was purified by reverse phase (C-18) silica gel column chromatography, using acetonitrile-water=0:1→1:0 as gradient, to afford N-((6-(4-(trifluoromethyl)phenyl)imidazo[1,5-a]pyrimidin-8-yl)methyl)acrylamide (I-410) (0.068 g, 29%) as an off-white solid. $^1H$ NMR (400 MHz, DMSO-$d_6$) δ 8.83-8.81 (dd, J=7.8, 1.6 Hz, 1H), 8.75-8.50 (t, J=4.8 Hz, 1H), 8.62-8.60 (m, 1H), 7.94-7.91 (m, 4H), 7.10-7.07 (m, 1H), 6.32-6.26 (m, 1H), 6.09-6.04 (dd, J=16.8, 2.0 Hz, 1H), 5.59-5.56 (dd, J=10.4, 2.0 Hz, 1H), 4.51-4.50 (d, J=8.0 Hz, 2H) MS: $[MH]^+$ 347.4.

Example 1.316. Synthesis of N-(1-(pyridin-2-yl)ethyl)-5-(4-(trifluoromethyl)phenyl)-3,4-dihydroisoquinoline-2(1H)-carboxamide (I-179)

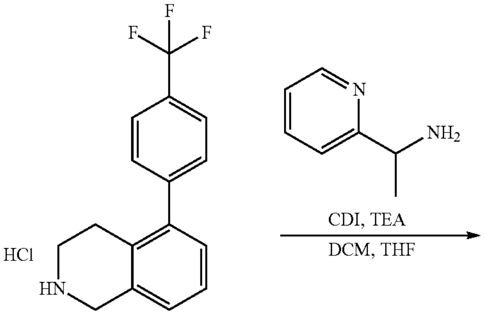

X-1277A2

-continued

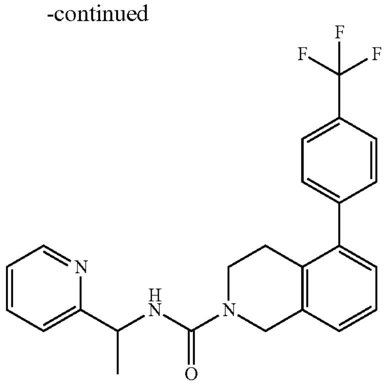

I-179

To the stirred solution of 1-(pyridin-2-yl)ethan-1-amine (0.132 g, 1.08 mmol) in DCM-THF (1:1; 5 mL) were added TEA (0.219 g, 2.16 mmol) and CDI (0.140 g, 0.86 mmol) respectively and stirred at 0° C. for 1 h. The reaction mixture was diluted with water (30 mL) and was extracted with DCM (50 mL×2). Collected organic parts were concentrated under reduce pressure. obtained crude was taken in DCM (5 mL) at 0° C. and 5-(4-(trifluoromethyl)phenyl)-1,2,3,4-tetrahydroisoquinoline hydrochloride (X-1277A2) (0.200 g, 0.72 mmol) was added into it. Stirring was continued at room temperature for 48 h. Reaction mixture was poured into ice-water (20 mL) and was extracted by DCM (50 mL×3). Combined organic layers were dried over anhydrous $Na_2SO_4$ and concentrated under reduced pressure to obtain a crude mass, which was purified by reverse phase (C-18) silica gel column chromatography, using acetonitrile-water=0:1→1:1 as gradient, to afford N-(1-(pyridin-2-yl)ethyl)-5-(4-(trifluoromethyl)phenyl)-3,4-dihydroisoquinoline-2(1H)-carboxamide (I-179) (0.050 g, 16%) as a white solid. $^1H$ NMR (400 MHz, DMSO-$d_6$) δ 8.49-8.48 (d, J=4.4 Hz, 1H), 7.81-7.79 (d, J=8.0 Hz, 2H), 7.74-7.70 (m, 1H), 7.59-7.57 (d, J=8.0 Hz, 2H), 7.37-7.29 (m, 2H), 7.24-7.20 (m, 2H), 7.16-7.14 (d, J=7.2, 1H), 6.87-6.85 (d, J=7.6 Hz, 1H), 4.92-4.88 (t, J=7.2 Hz, 1H), 4.62 (s, 2H), 3.51-3.49 (t, J=5.6 Hz, 2H), 2.68-2.65 (d, J=4.8 Hz, 2H), 1.41-1.39 (d, J=6.8 Hz, 3H). MS: $[MH]^+$ 426.1

Example 1.317. Synthesis of 4-(4-(Tert-butyl)phenyl)-2-((trifluoromethyl)thio)pyrrolo[1,2-a]quinoxaline-7-carboxylic acid (I-411)

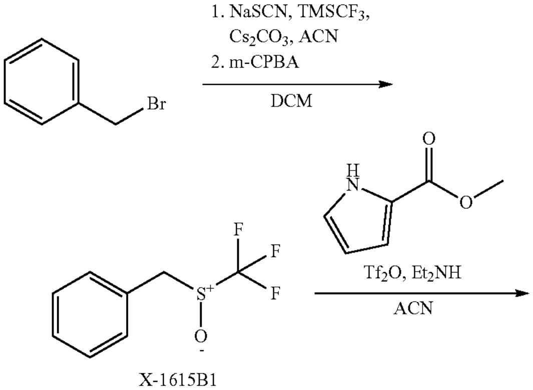

X-1615B1

-continued

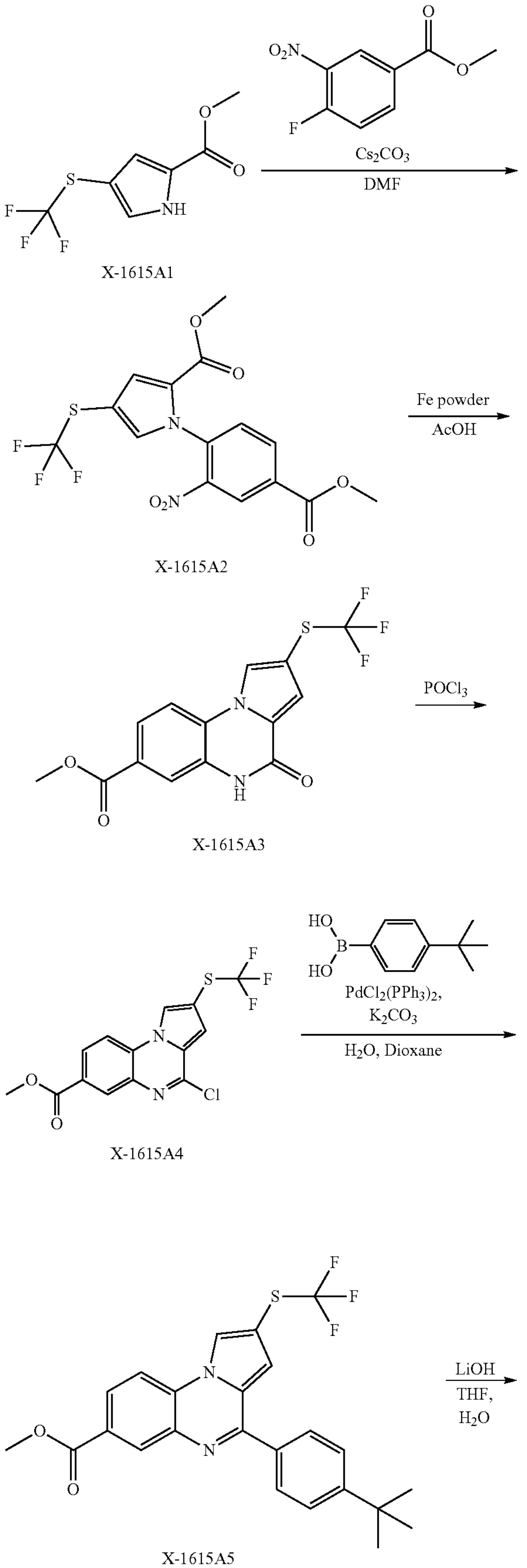

X-1615A1

X-1615A2

X-1615A3

X-1615A4

X-1615A5

-continued

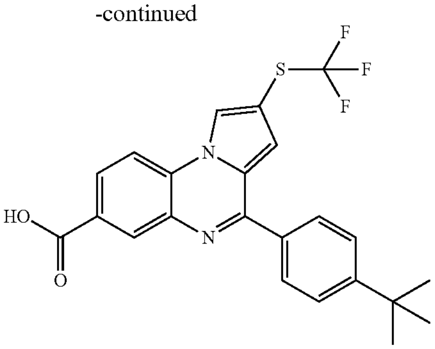

I-411

(((Trifluoromethyl)sulfinyl)methyl)benzene (X-1615B1). To a stirred solution of (bromomethyl)benzene (3.4 g, 0.019 mmol) in ACN (40 mL) was added NaSCN (1.62 g, 0.019 mmol) at room temperature under nitrogen and the resulting mixture was heated at 60° C. for 1 h. After that $Cs_2CO_3$ (6.5 g, 0.019 mmol) and $TMSCF_3$ (5.7 g, 0.039 mmol) was added sequentially at room temperature and resulting mixture was continued to at room temperature for 16 h followed by addition of m-CPBA (3.24 g) was added at room temperature. the resulting reaction mixture was stirred at same temperature for 16 h. Reaction mixture was slowly poured into an aqueous solution of saturated NaHCO3 (60 mL) and was extracted with dichloromethane (60 mL×3). Combined organic extracts were dried over anhydrous $Na_2SO_4$ and concentrated under reduced pressure. The crude product was purified by triturating using n-hexane to afford (((trifluoromethyl)sulfinyl)methyl)benzene (X-1615B1) (1.1 g, 32%) as an off-white solid. Crude 1H-NMR: (400 MHz, DMSO-$d_6$) δ 7.48-7.40 (m, 5H), 4.63-4.60 (d, J=12.8 Hz, 1H), 4.50-4.47 (d, J=12.8 Hz, 1H).

Methyl 4-((trifluoromethyl)thio)-1H-pyrrole-2-carboxylate (X-1615A1). To a stirred solution of (((trifluoromethyl)sulfinyl)methyl)benzene (X-1615B1) (0.900 g, 4.32 mmol) in ACN (5 mL) was added methyl 1H-pyrrole-2-carboxylate (0.812 g, 6.49 mmol) and diethylamine (0.315 gm, 4.326 mmol) sequentially at room temperature under nitrogen. After that at 0° C. trifluoromethanesulfonic anhydride (1.46 g, 5.19 mmol) was added then allowed to stirred at same temperature for 1 h. After cooling to room temperature, reaction mixture was slowly poured into water (50 mL) and was extracted with ethyl acetate (50 mL×3). The combined organic extracts were washed with brine (50 mL), dried over anhydrous $Na_2SO_4$ and concentrated under reduced pressure. The crude product was purified by silica gel column chromatography, using ethyl acetate-hexane=0:1→1:9 as gradient, to afford methyl 4-((trifluoromethyl)thio)-1H-pyrrole-2-carboxylate (X-1615A1) (0.500 g, 51%) as an off-white solid. MS: [MH]-223.9.

Methyl 1-(4-(methoxycarbonyl)-2-nitrophenyl)-4-((trifluoromethyl)thio)-1H-pyrrole-2-carboxylate (X-1615A2). To a stirred solution of methyl 4-fluoro-3-nitrobenzoate (0.370 g, 1.85 mmol) in DMF (3.0 mL) were added methyl 4-((trifluoromethyl)thio)-1H-pyrrole-2-carboxylate (X-1615A1) (0.500 g, 2.66 mmol) and $Cs_2CO_3$ (1.51 g, 4.64 mmol), the resulting mixture was stirred at room temperature for 2 h. The reaction mixture was poured into water, the resulting precipitate was filtered and the residue was washed with water and dried under reduce pressure to afford methyl 1-(4-(methoxycarbonyl)-2-nitrophenyl)-4-((trifluoromethyl)thio)-1H-pyrrole-2-carboxylate (X-1615A2) (0.550 g, 82%) as an off-white solid. MS: $[MH]^+$ 404.9.

Methyl 4-oxo-2-((trifluoromethyl)thio)-4,5-dihydropyrrolo[1,2-a]quinoxaline-7-carboxylate (X-1615A3). To a stirred solution of methyl 4-methoxy-1-(4-(methoxycarbonyl)-2-nitrophenyl)-1H-pyrrole-2-carboxylate (X-1351A5) (0.550 g, 65.86 mmol) in acetic acid (5 mL) was added Fe-powder (0.610 g, 10.891 mmol) at room temperature and resulting mixture was allowed to stirred at 85° C. for 1 h. After cooling to room temperature, reaction mixture was filtered and the precipitate was washed with water. The precipitate was taken in 10% methanol in dichloromethane, stirred for 30 min and filtered through a celite bed, filtrate was concentrated under reduced pressure to afford methyl 4-oxo-2-((trifluoromethyl)thio)-4,5-dihydropyrrolo[1,2-a]quinoxaline-7-carboxylate (X-1615A3) (0.450 g, 96%) as an off-white solid. MS: $[MH]^+$ 342.8.

Methyl 4-chloro-2-((trifluoromethyl)thio)pyrrolo[1,2-a]quinoxaline-7-carboxylate (X-1615A4). $POCl_3$ (1.0 ml) was added dropwise to methyl 4-oxo-2-((trifluoromethyl)thio)-4,5-dihydropyrrolo[1,2-a]quinoxaline-7-carboxylate (X-1615A4) (0.450 g, 1.31 mmol) at 0° C. under nitrogen. After completion of addition of $POCl_3$, the reaction mixture was slowly brought to reflux and continued heating at 100° C. for 1 h. The reaction mixture was poured in ice-water, the resulting precipitate was filtered and the residue was washed with water and dried under reduce pressure to afford methyl 4-chloro-2-((trifluoromethyl)thio)pyrrolo[1,2-a]quinoxaline-7-carboxylate (X-1615A4) (0.380 g, 80%) as an off-white solid. MS: $[MH]^+$ 360.8.

Methyl 4-(4-(tert-butyl)phenyl)-2-((trifluoromethyl)thio)pyrrolo[1,2-a]quinoxaline-7-carboxylate (X-1615A5). To a stirred solution of methyl 4-chloro-2-((trifluoromethyl)thio)pyrrolo[1,2-a]quinoxaline-7-carboxylate (X-1615A4) (0.400 g, 1.111 mmol) in in a mixture of dioxane-water (3:1, 3 mL) were added (4-(tert-butyl)phenyl)boronic acid (0.297 g, 1.66 mmol) and $K_2CO_3$ (0.384 g, 2.77 mmol) sequentially at room temperature. The reaction mixture was degassed (purging with nitrogen) for 20 min followed by addition of $PdCl_2$ $(PPh_3)_2$ (0.078 g, 0.111 mmol) and the reaction mixture was heated at 80° C. for 16 h. After cooling to room temperature, reaction mixture diluted with water (50 mL) and was extracted with ethyl acetate (50 mL×3). The combined organic extracts were dried over anhydrous $Na_2SO_4$ and concentrated under reduce pressure. The crude product was purified by silica gel column chromatography, using ethyl acetate-Hexane=0:1→3:7 as gradient, to afford methyl 4-(4-(tert-butyl)phenyl)-2-((trifluoromethyl)thio)pyrrolo[1,2-a]quinoxaline-7-carboxylate (X-1615A5) (0.200 g, 37%) as an off-white solid. MS: $[MH]^+$ 459.0.

4-(4-(tert-Butyl)phenyl)-2-((trifluoromethyl)thio)pyrrolo[1,2-a]quinoxaline-7-carboxylic acid (I-411). To a stirred solution of methyl 4-(4-(tert-butyl)phenyl)-2-((trifluoromethyl)thio)pyrrolo[1,2-a]quinoxaline-7-carboxylate (X-1615A5) (0.200 g, 0.436 mmol) in a mixture of THF-water (3:1; 2.2 mL) was added lithium hydroxide monohydrate (0.055 g, 1.30 mmol) at room temperature under nitrogen and the resulting mixture was heated at 70° C. for 1 h. After cooling to room temperature, the reaction mixture was concentrated under reduced pressure, obtained crude was diluted with water (30 mL) and was acidified (pH~2-3) with an aqueous solution of 1N HCl and then extracted with ethyl acetate. Ethyl acetate layer was washed with cold water until the pH of the filtrate became neutral (pH~6-7). Combined organic extracts were dried over anhydrous $Na_2SO_4$ and concentrated under reduced pressure. Obtained solid was triturated using n-pentane and dried under high vacuum to afford 4-(4-(tert-butyl)phenyl)-2-((trifluoromethyl)thio)pyrrolo[1,2-a]quinoxaline-7-carboxylic acid (I-411) (0.100 g, 51%) as a white solid. 1H NMR (400 MHz, DMSO-$d_6$) δ 13.38 (s, 1H), 9.15 (s, 1H), 8.56-8.54 (d, J=8.8 Hz, 1H), 8.455-8.450 (d, J=2.0 Hz, 1H), 8.16-8.13 (dd, J=8.4, 1.6 Hz, 1H), 7.98-7.96 (d, J=8.4 Hz, 2H), 7.66-7.64 (d, J=8.4 Hz, 2H), 7.34 (s, 1H), 1.37 (s, 9H). MS: $[MH]^+$ 444.9

Example 1.318. Synthesis of N-(2-(4-(trifluoromethyl)phenyl)-5,6,7,8-tetrahydroquinolin-8-yl)acrylamide (I-412)

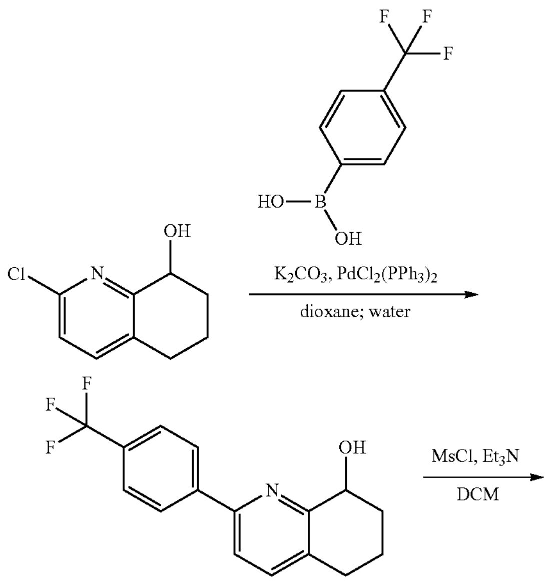

X-1632A1

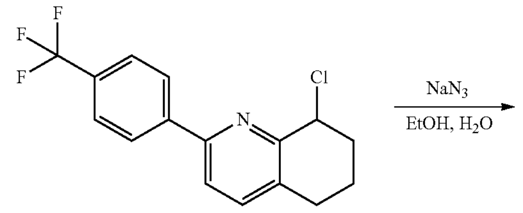

X-1632A2

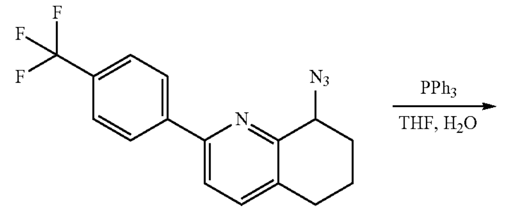

X-1632A3

-continued

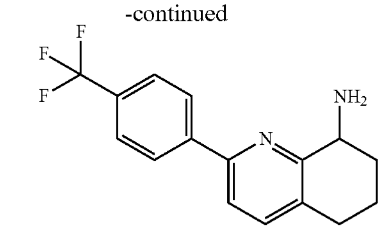

X-1632A4

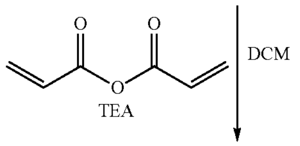

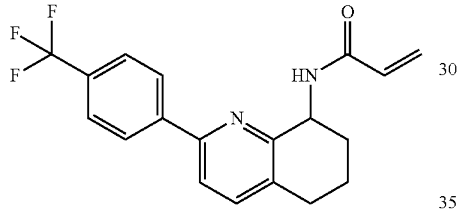

I-412

2-(4-(Trifluoromethyl)phenyl)-5,6,7,8-tetrahydroquinolin-8-ol (X-1632A1). To a stirred solution of 2-chloro-5,6,7,8-tetrahydroquinolin-8-ol (0.600 g, 3.26 mmol) in a mixture of dioxane-water (8:1, 9 mL) were added (4-(trifluoromethyl)phenyl)boronic acid (0.81 g, 4.24 mmol) and $K_2CO_3$ (1.35 g, 9.80 mmol) at room temperature. The reaction mixture was degassed (purging with nitrogen) for 20 min followed by addition of $PdCl_2(PPh_3)_2$ (0.11 g, 0.16 mmol) and the reaction mixture was heated at 110° C. for 1 h. The reaction mixture was cooled to room temperature, diluted with water (80 mL) and was extracted with ethyl acetate (100 mL×3). The combined organic extracts were dried over anhydrous $Na_2SO_4$ and concentrated under reduce pressure. The crude product was purified by silica gel column chromatography, using ethyl acetate-Hexane=1:9→3:7 as gradient, to afford 2-(4-(Trifluoromethyl)phenyl)-5,6,7,8-tetrahydroquinolin-8-ol (X-1632A1) (0.600 g, 62%) as an off-white solid. MS: $[MH]^+$ 294.0.

8-Chloro-2-(4-(trifluoromethyl)phenyl)-5,6,7,8-tetrahydroquinoline (X-1632A2). To a stirred solution of 2-(4-(Trifluoromethyl)phenyl)-5,6,7,8-tetrahydroquinolin-8-ol (X-1632A1) (0.600 g, 2.04 mmol) in a DCM (10 mL) were added triethylamine (0.620 g, 6.14 mmol) and mesyl chloride (0.700 g, 6.14 mmol) at 0° C. The reaction mixture was stirred for 16 h. The reaction mixture was diluted with water (80 mL) and was extracted with ethyl acetate (100 mL×3). The combined organic extracts were dried over anhydrous $Na_2SO_4$ and concentrated under reduce pressure, to afford 8-chloro-2-(4-(trifluoromethyl)phenyl)-5,6,7,8-tetrahydroquinoline (X-1632A2) (1.2 g (crude), Quantitative) as a yellow solid. Crude was used in next step without purification MS: $[MH]^+$ 311.9.

8-Azido-2-(4-(trifluoromethyl)phenyl)-5,6,7,8-tetrahydroquinoline (X-1632A3). To a stirred solution of 8-chloro-2-(4-(trifluoromethyl)phenyl)-5,6,7,8-tetrahydroquinoline (X-1632A2) (1.2 g, 3.85 mmol) in mixture of ethanol-water (9:1, 10 mL) was added sodium azide (0.75 g, 11.57 mmol) at room temperature under nitrogen. The reaction mixture stirred at 100° C. for 5 h. The reaction mixture was diluted by sodium hydroxide to $P^H$~8 The reaction mixture was cooled to room temperature, diluted with water (100 mL) and was extracted with ethyl acetate (300 mL×3). The combined organic extracts were dried over anhydrous $Na_2SO_4$ and concentrated under reduce pressure. The crude product was purified by silica gel column chromatography, using ethyl acetate-Hexane=1:9→3:7 as gradient, to afford 8-azido-2-(4-(trifluoromethyl)phenyl)-5,6,7,8-tetrahydroquinoline (X-1632A3) (0.25 g, 20%) as a white solid. MS: $[MH]^+$ 318.9.

2-(4-(Trifluoromethyl)phenyl)-5,6,7,8-tetrahydroquinolin-8-amine (X-1632A4). To a stirred solution of 8-azido-2-(4-(trifluoromethyl)phenyl)-5,6,7,8-tetrahydroquinoline (X-1632A3) (0.25 g, 0.78 mmol) in mixture of THE-water (9:1, 10 mL) was added Tri-phenyl phosphate (1.23 g, 2.35 mmol) at room temperature under nitrogen. The reaction mixture stirred at 80° C. for 1 h. The reaction mixture was diluted by sodium hydroxide to $P^H$~8 The reaction mixture was cooled to room temperature, diluted with water (100 mL) and was extracted with ethyl acetate (300 mL×3). The combined organic extracts were dried over anhydrous $Na_2SO_4$ and concentrated under reduce pressure, to afford 2-(4-(trifluoromethyl)phenyl)-5,6,7,8-tetrahydroquinolin-8-amine (X-1632A4) (0.200 g, 87%) as a white solid. MS: $[MH]^+$ 293.0.

N-(2-(4-(trifluoromethyl)phenyl)-5,6,7,8-tetrahydroquinolin-8-yl)acrylamide (I-412). To a stirred solution of 2-(4-(trifluoromethyl)phenyl)-5,6,7,8-tetrahydroquinolin-8-amine (X-1632A4) (0.200 g, 0.68 mmol) in DCM (5 mL) were added triethylamine (0.207 g, 2.05 mmol) and acrylic anhydride (0.128 g, 1.02 mmol) at 0° C. and reaction mixture was stirred at room temperature for 30 min. The reaction mixture was diluted with aqueous $NaHCO_3$ (10 mL) and was extracted by ethyl acetate (30 mL×3). Combined organic extracts were dried over anhydrous $Na_2SO_4$ and concentrated under reduce pressure. The crude product was purified by (C-18) silica gel column chromatography, using Acetonitrile-water=7:3→9:1 as gradient, to afford N-(2-(4-(trifluoromethyl)phenyl)-5,6,7,8-tetrahydroquinolin-8-yl)acrylamide (I-412) (0.07 g, 28%) as a white solid. $^1H$ NMR (400 MHz, DMSO-$d_6$) δ 8.52-8.50 (d, J=8.0 Hz, 1H), 8.26-8.24 (d, J=8.0 Hz, 2H), 7.93-7.91 (d, J=8.0 Hz, 1H), 7.84-7.82 (d, J=8.0 Hz, 2H), 7.72-7.70 (d, J=8.0 Hz, 1H), 6.34-6.27 (m, 1H), 6.19-6.14 (dd, J=17.2, 2.4 Hz, 1H), 5.63-5.60 (dd, J=10.0, 2.4 Hz, 1H), 5.08-5.05 (m, 1H), 2.85-2.83 (m, 2H), 2.05-2.03 (m, 2H), 1.88-1.83 (m, 2H). MS: $[MH]^+$ 346.9.

Example 1.319. Synthesis of 4-methoxy-7-(5-methyl-4H-1,2,4-triazol-3-yl)-2-(4-(trifluoromethyl)phenyl)quinolone (I-413)

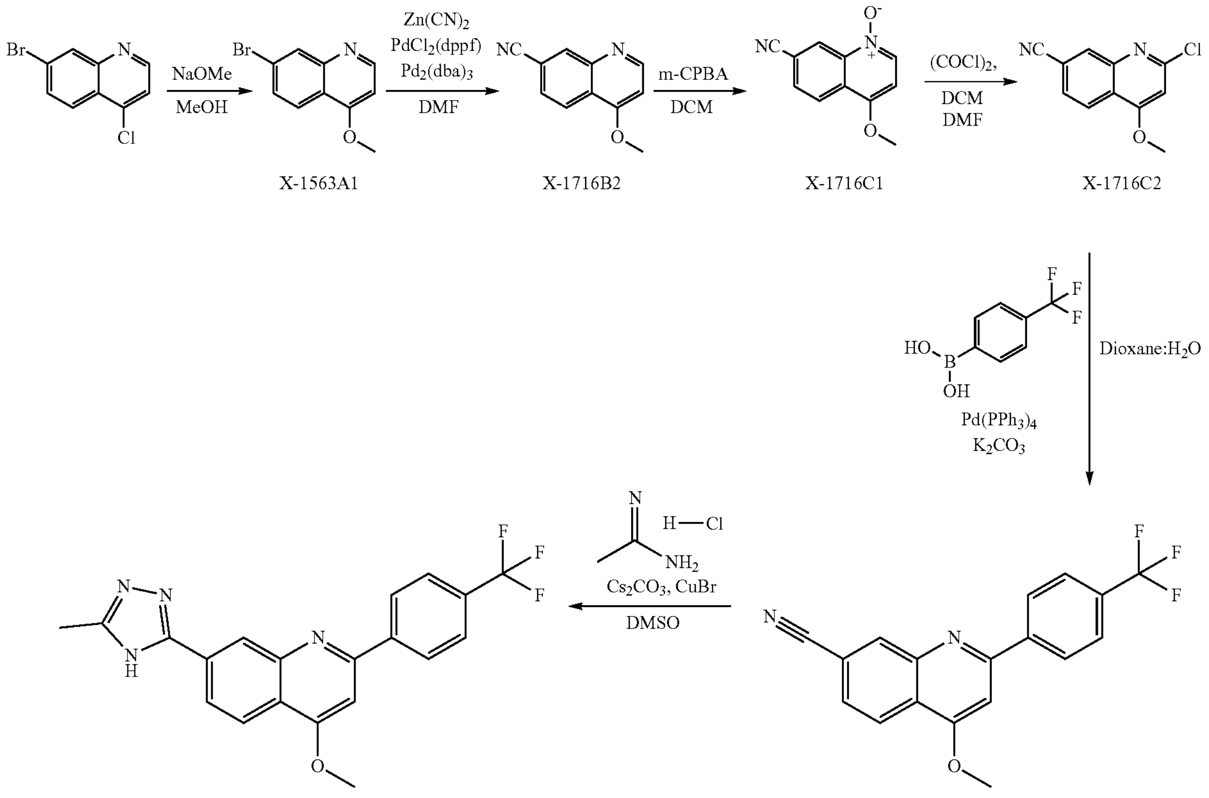

X-1563A1 X-1716B2 X-1716C1 X-1716C2

I-413 X-1803A1

7-Bromo-4-methoxyquinoline (X-1563A1). To a stirred solution of 7-bromo-4-chloroquinoline (10.0 g, 41.66 mmol) in methanol (100 mL) was added sodium methoxide (6.74 g, 124.99 mmol) gradually in portions at 0° C. and stirred the reaction mixture at 70° C. for 6 h. The reaction mixture was concentrated under reduced pressure and the obtained slurry was poured into ice water (500 mL), solid product was precipitated which was collected by filtration, dried under high vacuum. Obtained crude was purified by trituration using n-pentane (100 mL) to afford 7-bromo-4-methoxyquinoline (X-1563A1) (9.50 g, 97%; crude) as yellow solid. MS: $[MH]^+$ 238.2

4-Methoxyquinoline-7-carbonitrile (X-1716B2). To a stirred solution of 7-bromo-4-methoxyquinoline (X-1563A1) (0.700 g, 2.96 mmol) in DMF (8 mL) was added zinc cyanide (1.38 g, 11.86 mmol) at room temperature. The reaction mixture was degassed (purged with nitrogen) for 20 min followed by addition of $PdCl_2$(dppf)(0.210 g, 0.29 mmol) and $Pd_2(dba)_3$ (0.270 g, 0.29 mmol) and the resulting reaction mixture was heated at 150° C. under microwave irradiation for 30 min. The reaction mixture was cooled to room temperature, diluted with water (50 mL) and was extracted by ethyl acetate (50 mL×3). Combined organic extracts were dried over anhydrous $Na_2SO_4$ and concentrated under reduce pressure. The crude mass was purified by silica gel column chromatography, using ethyl acetate-Hexane=0:1→2:3 as gradient, to afford 4-methoxyquinoline-7-carbonitrile (X-1716B2) (0.560 g, 60%) as a brown solid. MS: $[MH]^+$317.8

7-Cyano-4-methoxyquinoline 1-oxide (X-1716C1). To a stirred solution of 4-methoxyquinoline-7-carbonitrile (X-1716B2) (0.550 g, 2.97 mmol) in DCM (8 mL) was added m-CPBA (1.02 g, 5.94 mmol) in portions at 0° C. and stirred the reaction mixture at room temperature for 3 h. The reaction mixture was basified (pH~8-9) with an aqueous solution of saturated $NaHCO_3$ (200 mL) and was extracted with dichloromethane (200 mL×2). Combined organic extracts were dried over anhydrous $Na_2SO_4$ and concentrated under reduce pressure to afford 7-cyano-4-methoxyquinoline 1-oxide (X-1716C1) (0.700 g, crude) as off-white solid. MS: $[MH]^+$ 204.2.

2-Chloro-4-methoxyquinoline-7-carbonitrile (X-1716C2). To a stirred solution of 7-cyano-4-methoxyquinoline 1-oxide (X-1716C1) (0.650 g, 3.25 mmol) in a mixture of DMF-DCM (1:1; 40 mL) was added oxalyl chloride (1.23 g, 9.75 mmol) at 0° C. drop-wise and stirred the reaction mixture at 50° C. for 3 h. Reaction mixture was quenched with an aqueous solution of saturated $NaHCO_3$ (100 mL) and was extracted with dichloromethane (100 mL×2). Combined organic extracts were dried over anhydrous $Na_2SO_4$ and concentrated under reduce pressure to afford 2-chloro-4-methoxyquinoline-7-carbonitrile (X-1716C2) (0.430 g, 60%) as off-white solid. MS: $[MH]^+$ 4-Methoxy-2-(4-(trifluoromethyl)phenyl)quinoline-7-carbonitrile (X-1803A1). To a stirred solution of 2-chloro- 4-methoxyquinoline-7-carbonitrile (X-1716C2) (0.420 g, 1.92 mmol) in a mixture of 1,4-dioxane-water (9:1, 10 mL) were added (4-(trifluoromethyl)phenyl)boronic acid (0.540 g, 2.88 mmol) and $K_2CO_3$ (0.790 g, 5.77 mmol) sequentially at room temperature under nitrogen. The reaction mixture was degassed (purged with nitrogen) for 20 min followed by the addition of $Pd(PPh_3)_4$ (0.110 g, 0.09 mmol) and the resulting mixture was heated at 100° C. for 1 h. Reaction mixture was cooled to room temperature, diluted with water (100 mL) and was extracted with ethyl acetate (100 mL×2). Combined organic extracts were dried over anhydrous $Na_2SO_4$ and concentrated under reduce pressure to afford crude mass, which was purified by silica gel column chromatography, using ethyl acetate-hexane=0:1→0.5:9.5 as eluent, to afford, 4-methoxy-2-(4-(trifluoromethyl)phenyl) quinoline-7-carbonitrile (X-1803A1) (0.400 g, 61%) as a brown solid. MS: $[MH]^+$ 4-Methoxy-7-(5-methyl-4H-1,2,4-triazol-3-yl)-2-(4-(trifluoromethyl)phenyl)quinolone (I-413). To a stirred solution of 4-methoxy-2-(4-(trifluoromethyl)phenyl)quinoline-7-carbonitrile (X-1803A1) (0.050 g, 0.15 mmol) in DMSO (2.5 mL) were added acetamidine hydrochloride (0.020 g, 0.22 mmol) and cesium carbonate (0.140 g, 0.45 mmol) sequentially at room temperature followed by the addition of copper bromide (0.008 g, 0.06 mmol) and the resulting mixture was heated at 120° C. for 7 h. The reaction mixture was basified (ph~8-9) with an aqueous solution of saturated $NaHCO_3$ and was extracted with ethyl acetate (50 mL×2). Combined organic extracts were dried over anhydrous $Na_2SO_4$ and concentrated under reduce pressure to afford crude mass. The crude mass was combined with identically prepared 5 batches (0.05 g) and was purified together by Prep-HPLC using acetonitrile-water=0:1→4:6 as gradient to afford, 4-methoxy-7-(5-methyl-4H-1,2,4-triazol-3-yl)-2-(4-(trifluoromethyl)phenyl)quinolone (I-413) (0.050 g, 10%) as a brown solid. 1H NMR (400 MHz, DMSO-$d_6$) δ 8.59 (s, 1H), 8.55-8.53 (d, J=8.0 Hz, 2H), 8.20-8.19 (d, J=2.0 Hz, 2H), 7.94-7.92 (d, J=Hz, 8.4 Hz, 2H), 7.66 (s, 1H), 4.20 (s, 3H), 2.43 (s, 3H). MS: $[MH]^+$ 385.4

Example 1.320. Synthesis of 4-methoxy-7-(5-methyl-1H-imidazol-2-yl)-2-(4-(trifluoromethyl) phenyl)quinoline (I-414)

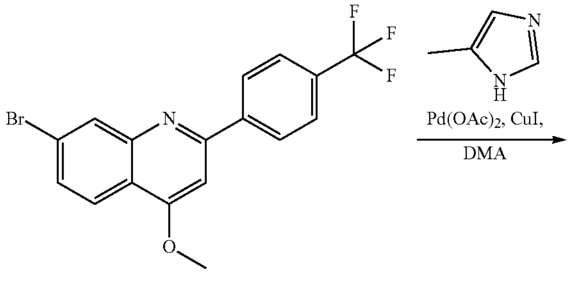

X-1716B1

-continued

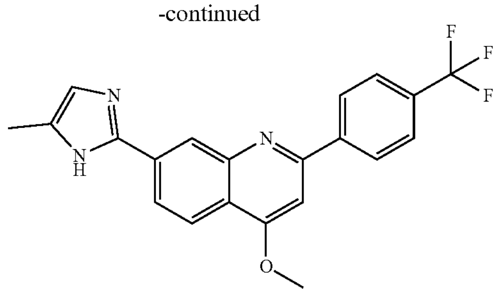

I-414

To a stirred solution of 7-bromo-4-methoxy-2-(4-(trifluoromethyl)phenyl)quinolone (X-1716B1) (0.300 g, 0.787 mmol)) in DMA (3 mL) were added 5-methyl-1H-imidazole (0.161 g, 1.96 mmol) and copper iodide (0.299 g, 1.57 mmol) sequentially at room temperature under nitrogen. The reaction mixture was degassed (purged with nitrogen) for 10 min followed by addition of $Pd(OAc)_2$ (0.017 g, 0.078 mmol). The resulting reaction mixture was heated at 100° C. for 7 h. After cooling to room temperature, reaction mixture was diluted with cold water (50 mL) and ammonium chloride was added and was extracted with ethyl-acetate (50 mL×3). Combined organic extracts were washed with brine (50 mL), and dried over anhydrous $Na_2SO_4$ and concentrated under reduced pressure to afford crude mass, which was purified by reverse phase (C-18) silica gel column chromatography, using acetonitrile-water=0:1→2:8 as gradient, to afford 4-methoxy-7-(5-methyl-1H-imidazol-2-yl)-2-(4-(trifluoromethyl)phenyl)quinoline (I-414) (0.08 g, 27%) as an off-white solid. $^1H$ NMR (400 MHz, DMSO-$d_6$ at 80° C.) δ 12.51 (br, 1H), 8.54 (s, 1H), 8.52-8.50 (d, J=8.0 Hz, 2H), 8.17 (s, 2H), 7.95-7.93 (d, J=8.4 Hz, 2H), 7.64 (s, 1H), 6.87 (br, 1H), 4.21 (s, 3H), 2.26 (s, 3H). MS: $[MH]^+$ 384.17.

Example 1.321. Synthesis of 4-methoxy-7-(methylsulfonyl)-2-(4-(trifluoromethyl)phenyl)quinoline (I-415)

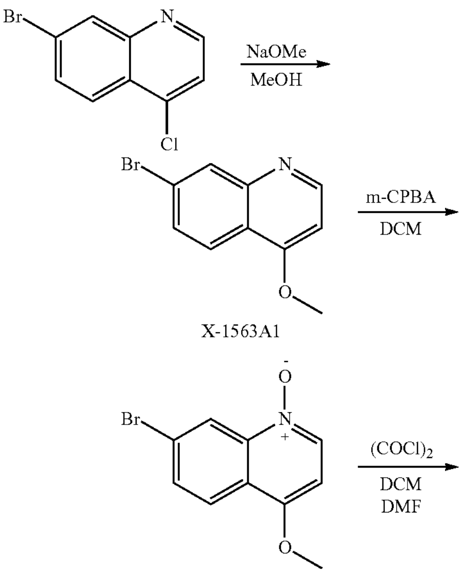

X-1563A1

X-1716A1

-continued

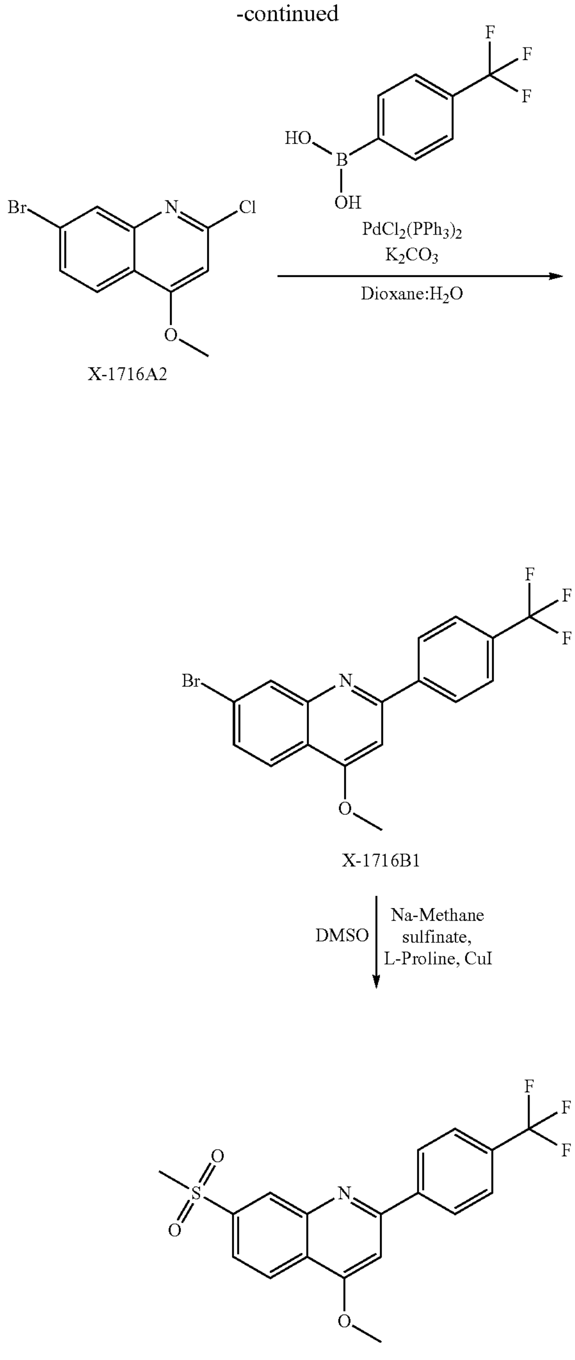

X-1716A2

X-1716B1

I-415

7-Bromo-4-methoxyquinoline (X-1563A1). To a stirred solution of 7-bromo-4-chloroquinoline (20.0 g, 82.64 mmol) in methanol (200 mL) was added sodium methoxide (13.38 g, 247.93 mmol) gradually in portions at 0° C. and stirred the reaction mixture at 70° C. for 6 h. Reaction mixture was concentrated under reduced pressure and the obtained slurry was poured into ice water (500 mL). Solid product was precipitated which was collected by filtration and dried under high vacuum. Obtained crude was purified by trituration using n-pentane (100 mL) to afford 7-bromo-4-methoxyquinoline (X-1563A1) (18.50 g, 94.8%; crude) as yellow solid. MS: $[MH]^+$238.1.

7-Bromo-4-methoxyquinoline 1-oxide (X-1716A1). To a stirred solution of 7-bromo-4-methoxyquinoline (X-1563A1) (18.50 g, 78.05 mmol) in anhydrous DCM (500 mL) was added m-CPBA (26.85 g, 156.11 mmol) in portions at 0° C. and stirred the reaction mixture at room temperature for 4 h. The reaction mixture was basified (ph~8-9) with an aqueous solution of saturated $NaHCO_3$ and was extracted with dichloromethane (500 mL×2). Combined organic extracts were dried over anhydrous $Na_2SO_4$ and concentrated under reduce pressure to afford crude mass. Obtained crude was purified by trituration using mixture of ethyl acetate and hexane (1:1; 20 mL) to afford 7-bromo-4-methoxyquinoline 1-oxide (X-1716A1) (14.50 g, 73.2%) as an off-white solid. MS: $[MH]^+$ 256.1.

7-Bromo-2-chloro-4-methoxyquinoline (X-1716A2). To a stirred solution of 7-bromo-4-methoxyquinoline 1-oxide (X-1716A1) (14.50 g, 57.31 mmol) in a mixture of DMF-DCM (14.5:10.1; 246 mL) was added oxalyl chloride (21.83 g, 171.93 mmol) at 0° C. dropwise and stirred the reaction mixture at 50° C. for 2 h. Reaction mixture was quenched with an aqueous solution of saturated $NaHCO_3$ (500 mL) and was extracted with DCM (500 mL×2). Combined organic extracts were dried over anhydrous $Na_2SO_4$ and concentrated under reduce pressure to a crude mass which was purified by silica gel column chromatography, using ethyl acetate-hexane=0:1→1:9 as eluent, to afford 7-bromo-2-chloro-4-methoxyquinoline (X-1716A2) (10 g, 64.5%) as off-white solid. MS: $[MH]^+$ 272.1.

7-Bromo-4-methoxy-2-(4-(trifluoromethyl)phenyl)quinolone (X-1716B1). To a stirred solution of 7-bromo-2-chloro-4-methoxyquinoline (X-1716A2) (10.0 g, 36.90 mmol) in a mixture of 1,4-dioxane-water (9:1, 50 mL) were added (4-(trifluoromethyl)phenyl)boronic acid (7.01 g, 36.90 mmol) and $K_2CO_3$ (15.27 g, 110.7 mmol) sequentially at room temperature under nitrogen. The reaction mixture was degassed (purged with nitrogen) for 20 min followed by the addition of $PdCl_2(PPh_3)_2$ (1.8 g, 2.58 mmol) and the resulting mixture was heated at 70° C. for 2 h. Reaction mixture was cooled to room temperature, diluted with water (250 mL) and was extracted with ethyl acetate (250 mL×2). Combined organic extracts were dried over anhydrous $Na_2SO_4$ and concentrated under reduce pressure to afford crude mass, which was purified by silica gel column chromatography, using ethyl acetate-hexane=0:1→1:4 as eluent, to afford 7-bromo-4-methoxy-2-(4(trifluoromethyl)phenyl) quinolone (X-1716B1) (3.5 g, 25.1%) as a brown solid. MS: $[MH]^+$ 382.2.

4-Methoxy-7-(methylsulfonyl)-2-(4-(trifluoromethyl) phenyl)quinolone (I-415). To a stirred solution of 7-bromo-4-methoxy-2-(4-(trifluoromethyl)phenyl)quinolone (X-1716B1) (0.300 g, 0.78 mmol) in DMSO (7 mL) were added L-proline and (0.040 g, 0.39 mmol) and sodium methanesulfonate (0.160 g, 1.57 mmol) sequentially at room temperature followed by addition of copper iodide (0.074 g, 0.39 mmol) and the resulting mixture was heated at 130° C. for 6 h. Reaction mixture was cooled to room temperature, diluted with water (50 mL) and was extracted with ethyl acetate (50 mL×2). Combined organic extracts were dried over anhydrous $Na_2SO_4$ and concentrated under reduce pressure to afford crude mass, which was purified by reverse phase (C-18) silica gel column chromatography, using acetonitrile-water=0:1→4:6 as gradient, to afford 4-methoxy-7-(methyl sulfonyl)-2(trifluoromethyl)phenyl) quinolone (I-415) (0.130 g, 43%) as a white solid. $^1H$ NMR (400 MHz, DMSO-$d_6$) δ: 8.59-8.57 (d, J=8.0 Hz, 2H), 8.56 (s, 1H), 8.41-8.39 (d, J=8.8 Hz, 1H), 8.05-8.02 (dd, J=, 8.4 Hz, 1.6 Hz 1H), 7.97-7.95 (d, J=8.4 Hz, 2H), 7.85 (s, 1H), 4.25 (s, 3H), 3.38 (s, 3H). MS: $[MH]^+$ 382.3.

Example 1.322. Synthesis of 4-Methoxy-2-(4-(trifluoromethyl)phenyl)quinoline-7-sulfonamide (I-416)

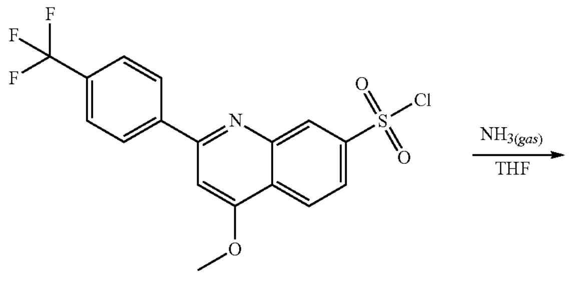

X-1716A5

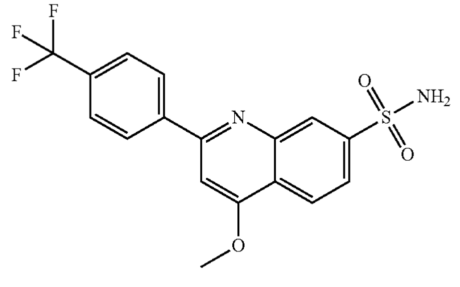

I-416

To a stirred solution of 4-methoxy-2-(4-(trifluoromethyl)phenyl)quinoline-7-sulfonyl chloride (X-1716A5) (0.100 g, 0.24 mmol) in THF (5 mL) the reaction mixture was purged with ammonia gas at room temperature the resulting reaction mixture stirred at room temperature for 30 min. Reaction mixture was concentrated under reduced pressure and the crude product was purified by silica gel column chromatography, using ethyl acetate-hexane=1:9→2:8 as gradient, to afford 4-methoxy-2-(4-(trifluoromethyl)phenyl)quinoline-7-sulfonamide (I-416) (0.030 g, 12%) as an off-white solid. $^1H$ NMR (400 MHz, DMSO-$d_6$) 8.57-8.55 (d, J=8.4 Hz, 2H), 8.46-8.46 (d, J=1.6 Hz, 1H), 8.35-8.33 (d, J=8.8 Hz, 1H), 7.95-7.93 (d, J=8.0 Hz, 3H), 7.79 (s, 1H), 7.63 (s, 2H), 4.23 (s, 3H). MS: $[MH]^+$ 383.33.

Example 1.323. Synthesis of N-ethyl-4-methoxy-2-(4-(trifluoromethyl)phenyl)quinoline-7-sulfonamide (I-417)

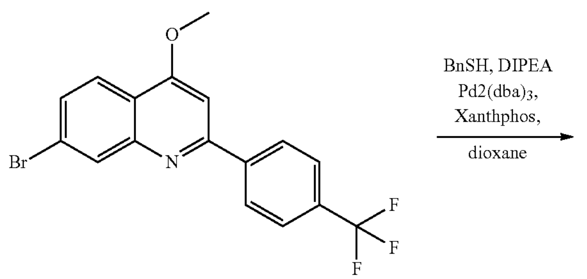

X-1716B1

-continued

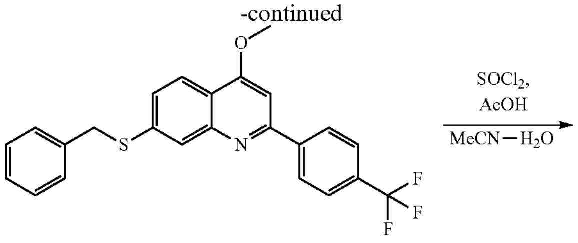

X-1716A4

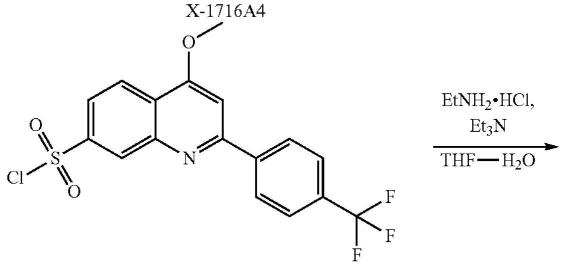

X-1716A5

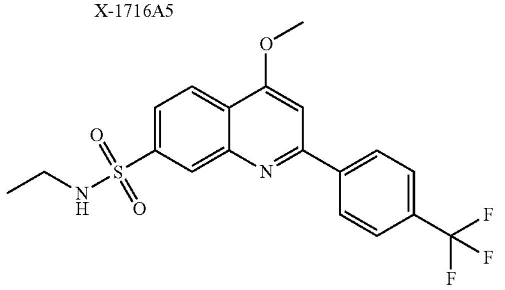

I-417

7-(Benzylthio)-4-methoxy-2-(4-(trifluoromethyl)phenyl)quinolone (1716A4). To a stirred solution of 7-bromo-4-methoxy-2-(4-(trifluoromethyl)phenyl)quinolone (X-1716B1) (1.5 g, 3.93 mmol) in 1,4-dioxane (20 mL) was added DIPEA (1.4 mL, 7.87 mmol) at room temperature under nitrogen and stirred for 5 min. The reaction mixture was degassed (purging with nitrogen) for 20 min followed by the addition of $Pd_2(dba_3)$ (0.18 g, 0.19 mmol), Xanthphos (0.10 g, 0.19 mmol) and BnSH (0.480 g, 3.93 mmol) and the resulting mixture was heated at 100° C. for 1 h. Reaction mixture was cooled to room temperature, diluted with water (500 mL) and was extracted with ethyl acetate (100 mL×2). Combined organic extracts were dried over anhydrous $Na_2SO_4$ and concentrated under reduce pressure to afford crude mass, which was purified by silica gel column chromatography, using ethyl acetate-hexane=0:1→1:4 as eluent to afford 7-(benzylthio)-4-methoxy-2-(4-(trifluoromethyl)phenyl)quinolone (1716A4) (0.750 g, 44.8%) as a brown solid. MS: $[MH]^+$ 426.3.

4-Methoxy-2-(4-(trifluoromethyl)phenyl)quinoline-7-sulfonyl chloride (X-1716A5). To a stirred solution of 7-(benzylthio)-4-methoxy-2-(4-(trifluoromethyl)phenyl)quinolone (1716A4) (0.600 g, 1.41 mmol) in acetonitrile (10 mL) was added sulfuryl chloride (0.280 g, 2.11 mmol) followed by addition of acetic acid (0.1 mL) and catalytic amount of water (0.1 mL) and the resulting mixture was stirred at room temperature for 1 h. Reaction mixture was diluted with water (100 mL) and was extracted with ethyl acetate (100 mL×2). Combined organic extracts were dried over anhydrous $Na_2SO_4$ and concentrated under reduce pressure to afford, 4-methoxy-2-(4-(trifluoromethyl)phenyl)quinoline-7-sulfonyl chloride (X-1716A5) (0.500 g, 88%; crude) as an off-white solid. MS: $[MH]^+$ 402.02.

N-Ethyl-4-methoxy-2-(4-(trifluoromethyl)phenyl)quinoline-7-sulfonamide (I-417). To a stirred solution of 4-methoxy-2-(4-(trifluoromethyl)phenyl)quinoline-7-sulfonyl chloride (X-1716A5) (0.250 g, 6.23 mmol) in THE (4 mL) was added triethylamine (0.190 g, 1.86 mmol) followed by addition of ethylamine·hydrochloride in water (0.100 g, 1.24 mmol) sequentially at −40° C. under nitrogen and the resulting reaction mixture was stirred at room temperature for 30 min. Reaction mixture was diluted with water (50 mL) and was extracted with ethyl acetate (50 mL×3). Organic extracts were combined, dried over anhydrous $Na_2SO_4$ and concentrated under reduced pressure to afford crude mass, which was purified by silica gel column chromatography, using ethyl acetate-hexane=0:1→1:4 as gradient, to afford N-ethyl-4-methoxy-2-(4-(trifluoromethyl)phenyl)quinoline-7-sulfonamide (I-417) (0.10 g, 39.1%) as an off-white solid. $^1$H NMR (400 MHz, DMSO-$d_6$) δ: 8.57-8.55 (d, J=8.4 Hz, 2H), 8.41-8.41 (d, J=1.6 Hz, 1H), 8.37-8.35 (d, J=8.8 Hz, 1H), 7.95-7.93 (d, J=8.4 Hz, 2H), 7.91-7.88 (dd, J=8.8 Hz, 2 Hz, 1H), 7.85-7.82 (t, J=5.6 Hz, 1H), 7.80 (s, 1H), 4.23 (s, 3H), 2.89-2.82 (m, 2H), 1.00-0.96 (t, J=7.2 Hz, 3H). MS: [MH]$^+$ 411.4.

Example 1.324. Synthesis of 4-Methoxy-7-(pyridin-2-yl)-2-(4-(trifluoromethyl)phenyl)quinoline (I-418)

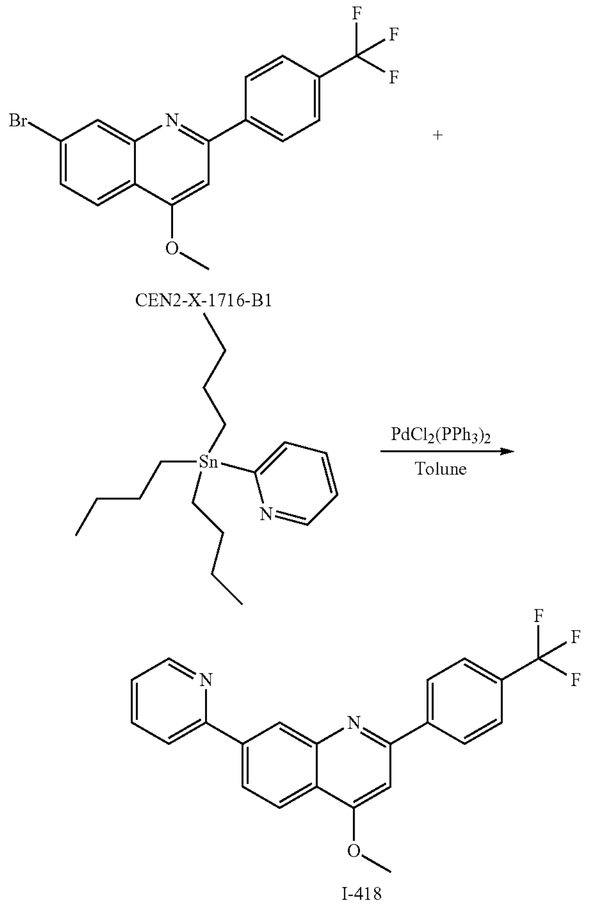

CEN2-X-1716-B1

I-418

To a stirred solution of 7-bromo-4-methoxy-2-(4-(trifluoromethyl)phenyl)quinoline (X-1716B1) (0.150 g, 0.390 mmol) in toluene (2 mL) were added 2-(tributylstannyl)pyridine (0.217 g, 0.590 mmol) at room temperature under nitrogen. The reaction mixture was degassed (purging with nitrogen) for 30 min followed by addition of $PdCl_2(PPh_3)_2$ (0.013 g, 0.019 mmol) and the reaction mixture was heated at 100° C. for 3 h. After cooling to room temperature, reaction mixture diluted with water (50 mL) and was extracted with ethyl acetate (50 mL×3). Combined organic extracts were dried over anhydrous $Na_2SO_4$ and concentrated under reduce pressure. The crude product was purified by silica gel column chromatography, using ethyl acetate-hexane=0:1→2:8 as gradient, to afford 4-methoxy-7-(pyridin-2-yl)-2-(4-(trifluoromethyl)phenyl)quinoline (I-418) (0.070 g, 47%) as an off-white solid. $^1$H NMR (400 MHz, DMSO-$d_6$) δ 8.77-8.76 (d, J=3.6 Hz, 1H), 8.734-8.731 (d, J=1.2 Hz, 1H), 8.57-8.55 (d, J=8.0 Hz, 2H), 8.37-8.35 (dd, J=8.8, 1.6 Hz, 1H), 8.27-8.24 (m, 2H), 7.98-7.93 (m, 3H), 7.69 (s, 1H), 7.46-7.43 (m, 1H), 4.22 (s, 3H). MS: [MH]$^+$ 381.4.

Example 1.325. Synthesis of 3-(4-methoxy-2-(4-(trifluoromethyl)phenyl)quinolin-7-yl)oxetan-3-ol-methanesulfonamide (I-419)

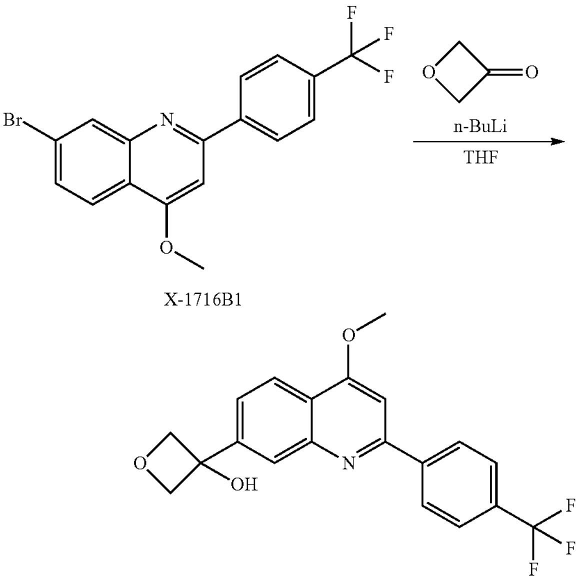

X-1716B1

I-419

To a stirred 7-bromo-4-methoxy-2-(4-(trifluoromethyl)phenyl)quinoline (X-1716B1) (0.300 g, 0.78 mmol) in anhydrous THE (2 mL) was added n-BuLi (2.5 M in n-hexane; 0.62 mL, 1.57 mmol) −78° C. under nitrogen and the resulting mixture was stirred at same temperature for 1 h. Oxetan-3-one (0.170 g, 2.36 mmol) was added into the reaction mixture at −78° C. and resulting mixture was stirred at room temperature for 5 h. The reaction mixture was slowly quenched with methanol (10 mL) and concentrated under reduced pressure. Obtained crude was combined with another identically prepare (0.300 g) reaction and the combined batches were purified by silica gel column chromatography, using ethyl acetate-hexane=3:7→4:6 as gradient, to afford 3-(4-methoxy-2-(4-(trifluoromethyl)phenyl)quinolin-7-yl)oxetan-3-ol (I-419) (0.280 g, 47%) as a white solid. $^1$H NMR (400 MHz, DMSO-$d_6$) δ 8.55-8.53 (d, J=8.0 Hz, 2H), 8.22-8.20 (m, 2H), 7.93-7.81 (d, J=8.4 Hz, 2H), 7.88-

7.85 (dd, J=1.6, 8.8 Hz, 1H), 7.66 (s, 1H), 6.62 (s, 1H), 4.89-4.82 (dd, J=6.8 Hz, 4H), 4.20 (s, 3H), $[MH]^+$ 376.40.

Example 1.326. Synthesis of N,4-dimethyl-2-(4-(trifluoromethyl)phenyl)quinoline-7-sulfonamide (I-420)

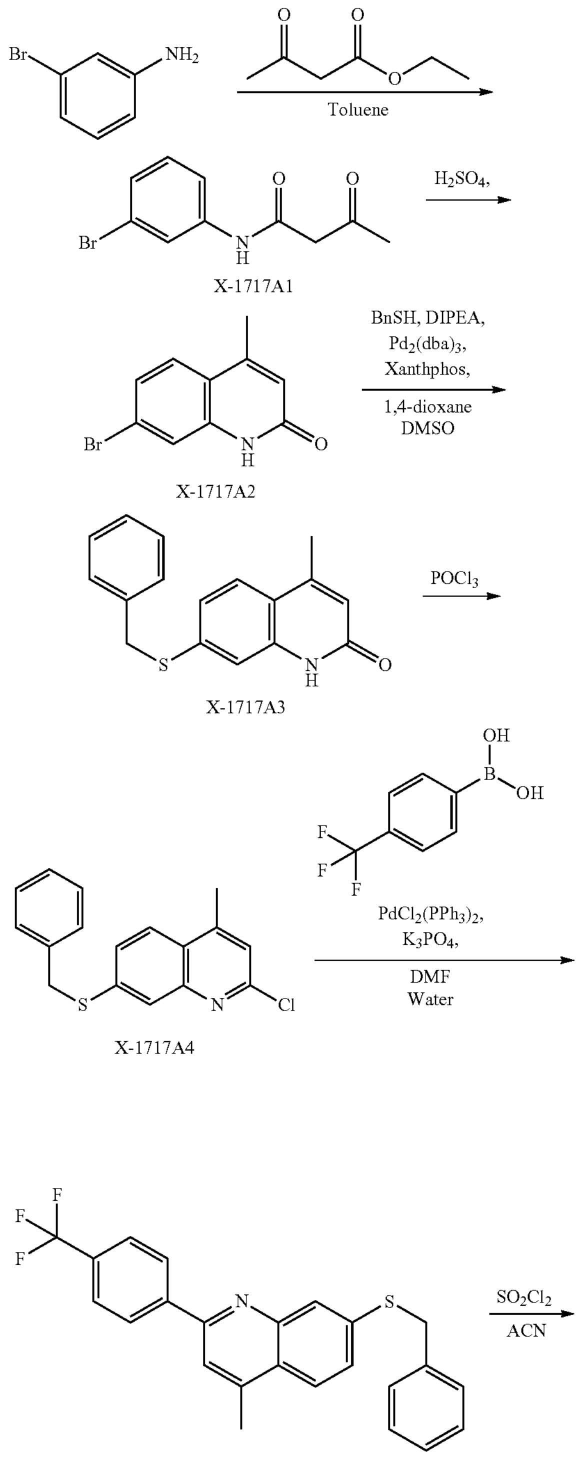

X-1717A1

X-1717A2

X-1717A3

X-1717A4

X-1717A5

-continued

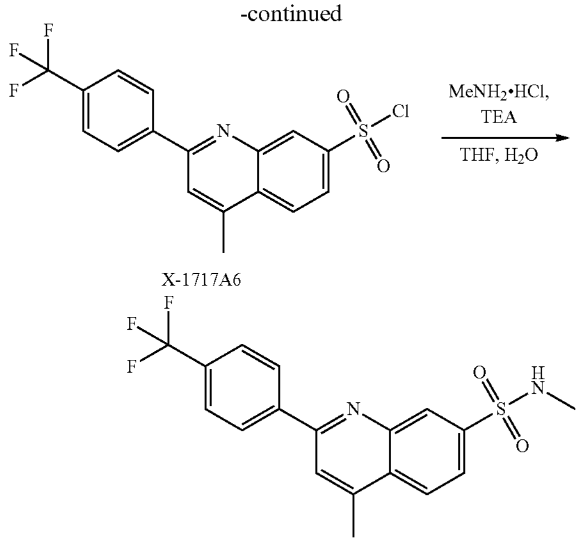

X-1717A6

I-420

N-(3-bromophenyl)-3-oxobutanamide (X-1717A1). To a solution of 3-bromoaniline (10.0 g, 58.4 mmol)) in toluene (150 mL) were added ethyl 3-oxobutanoate (15.2 g, 111.6 mmol) at 0° C. under nitrogen and the resulting reaction mixture was stirred at 110° C. for 16 h. The reaction mixture was cooled to room temperature, diluted with water (5000 mL) and was extracted with ethyl acetate (1000 mL×2). Combined organic extracts were dried over anhydrous $Na_2SO_4$, filtered and concentrated under reduced pressure. Obtained crude was purified by silica gel column chromatography, using ethyl acetate-hexane=2:8→3:7 as gradient, to afford N-(3-bromophenyl)-3-oxobutanamide (X-1709A1) (6.5 g, 43%) as an off-white solid. MS: $[MH]^+$257.8.

7-Bromo-4-methylquinolin-2(1H)-one (X-1717A2). To a solution of N-(3-bromophenyl)-3-oxobutanamide (6.5 g, 1.95 mmol)) in $H_2SO_4$ (60 mL) at 0° C. The resulting reaction mixture was stirred at 100° C. for 2 h. The reaction mixture was poured into ice water (100 mL), solid product was precipitated which was collected by filtration, dried under reduced pressure. The resulting crude material was wash with water, dried over high vacuum to afford 7-bromo-4-methylquinolin-2(1H)-one (X-1717A2) (4.5 g, 74%) as an off-white solid. MS: $[MH]^+$239.63

7-(Benzylthio)-4-methylquinolin-2(1H)-one (X-1717A3). To a stirred solution of 7-bromo-4-methylquinolin-2(1H)-one (3.3 g, 13.8 mmol) in mixture of DMSO-dioxane (20:20 mL) was added DIPEA (5.17 g, 40.1 mmol) and phenylmethanethiol (1.88 g, 15.1 mmol) under nitrogen. The reaction mixture was degassed purging with $N_{2(gas)}$ for 30 min followed by addition of $Pd_2(dba)_3$ (0.630 g, 0.69 mmol) and X-phos (0.4 g, 0.69 mmol) and the reaction mixture was heated at 100° C. for 4 h. Reaction mixture was cooled to room temperature, diluted with water (500 mL) and was extracted with ethyl acetate (500 mL×2). Combined organic extracts were dried over anhydrous $Na_2SO_4$, filtered and concentrated under reduced pressure. Obtained crude was purified by silica gel column chromatography, using ethyl acetate-hexane=2:8→3:7 as gradient, to afford 7-(benzylthio)-4-methylquinolin-2(1H)-one (X-1717A3) (1.5 g, 38%) as an off-white solid. MS: $[MH]^+$ 281.7.

7-(Benzylthio)-2-chloro-4-methylquinoline (X-1717A4). A solution of $POCl_3$ (20 mL) in 7-(benzylthio)-4-methylquinolin-2(1H)-one (X-1717A3) (1.5 g, 5.3 mmol) was slowly brought to reflux and continued heating at 100° C. for 2 h. Reaction mixture was allowed to cool to room temperature and was slowly poured into ice-water with stirring. After cooling to room temperature, the reaction mixture was quenched with an aqueous solution of saturated $NaHCO_3$ (500 mL) and was extracted with ethyl acetate (500 mL×3). Combined organic extracts were dried over anhydrous $Na_2SO_4$, filtered and concentrated under reduced pressure. Obtained crude to afford 7-(benzylthio)-2-chloro-4-methylquinoline (X-1717A4) (1.4 g, 88%) as a yellow solid. MS: [MH]+ 299.5. crude which was carried forward to next step.

7-(Benzylthio)-4-methyl-2-(4-(trifluoromethyl)phenyl)quinoline (X-1717A5). To a stirred solution of 7-(benzylthio)-2-chloro-4-methylquinoline (2.3 g, 7.6 mmol) in a mixture of DMF:water (15:5 mL), were added (4-(trifluoromethyl)phenyl)boronic acid (1.60 g, 8.4 mmol) and $K_3PO_4$ (4.0 g, 18.8 mmol) sequentially at room temperature under nitrogen. The reaction mixture was degassed (purging with nitrogen) for 20 min followed by the addition of $PdCl_2(PPh_3)_2$ (1.06 g, 1.42 mmol) the resulting mixture was heated at 100° C. for 3 h. Reaction mixture was cooled to room temperature, diluted with water (300 mL) and was extracted with ethyl acetate (300 mL×3). Combined organic extracts were dried over anhydrous $Na_2SO_4$ and concentrated under reduce pressure to afford crude mass, which was purified by silica gel Flash column chromatography, using ethyl acetate-hexane=5:546:4 as eluent, to afford 7-(benzylthio)-4-methyl-2-(4-(trifluoromethyl)phenyl)quinoline (X-1717A5) (2.8 g, 89%) as an white solid. MS: $[MH]^+$ 409.81.

4-Methyl-2-(4-(trifluoromethyl)phenyl)quinoline-7-sulfonyl chloride (X-1717A6). To a solution of 7-(benzylthio)-4-methyl-2-(4-(trifluoromethyl)phenyl)quinolone (X-1717A5) (0.600 g, 1.22 mmol)) in ACN (10 mL) was added $SO_2C1_2$ (0.49 g, 3.6 mmol) at 0° C. under nitrogen and the resulting reaction mixture was stirred at room temperature for 1 h. Reaction mixture was poured into ice water (100 mL) was extracted with ethyl acetate (200 mL×3). Combined organic extracts were dried over anhydrous $Na_2SO_4$, filtered and concentrated under reduced pressure to afford 4-methyl-2-(4-(trifluoromethyl)phenyl)quinoline-7-sulfonyl chloride (X-1717A6) (0.450 g, 80%) crude which was carried forward to next step.

N,4-dimethyl-2-(4-(trifluoromethyl)phenyl)quinoline-7-sulfonamide (I-420). To a stirred solution of 4-methyl-2-(4-(trifluoromethyl)phenyl)quinoline-7-sulfonyl chloride (X-1717A6) (0.45 g, 1.16 mmol) in a THE (5 mL), was added TEA (0.353 g, 3.50 mmol) and $MeNH_2\cdot HCl$ (0.120 g, 1.51 mmol) sequentially at room temperature under nitrogen and the resulting mixture stirred at room temperature for 2 h. Reaction mixture was cooled to room temperature, diluted with water (100 mL) and was extracted with ethyl acetate (100 mL×3). Combined organic extracts were dried over anhydrous $Na_2SO_4$ and concentrated under reduce pressure to afford crude Obtained crude was purified by silica gel column chromatography, using ethyl acetate-hexane=2:843:7 as gradient, to afford N,4-dimethyl-2-(4-(trifluoromethyl)phenyl)quinoline-7-sulfonamide (I-420) (0.1 g, 25%) as an white solid. $^1H$ NMR (400 MHz, DMSO-$d_6$) δ 8.55-8.53 (d, J=8.0 Hz, 2H), 8.47-8.46 (d, J=1.6 Hz, 1H), 8.39-8.37 (d, J=8.8 Hz, 1H), 8.32 (s, 1H), 7.96-7.93 (m, 3H), 7.74 (brs, 1H), 2.84 (s, 3H), 2.51-2.49 (m, 3H). MS: $[MH]^+$ 381.3.

Example 1.327. Synthesis of 5-(4-(trifluoromethyl)phenyl)pyrrolo[1,2-a]quinazoline-2-carboxylic acid (I-421)

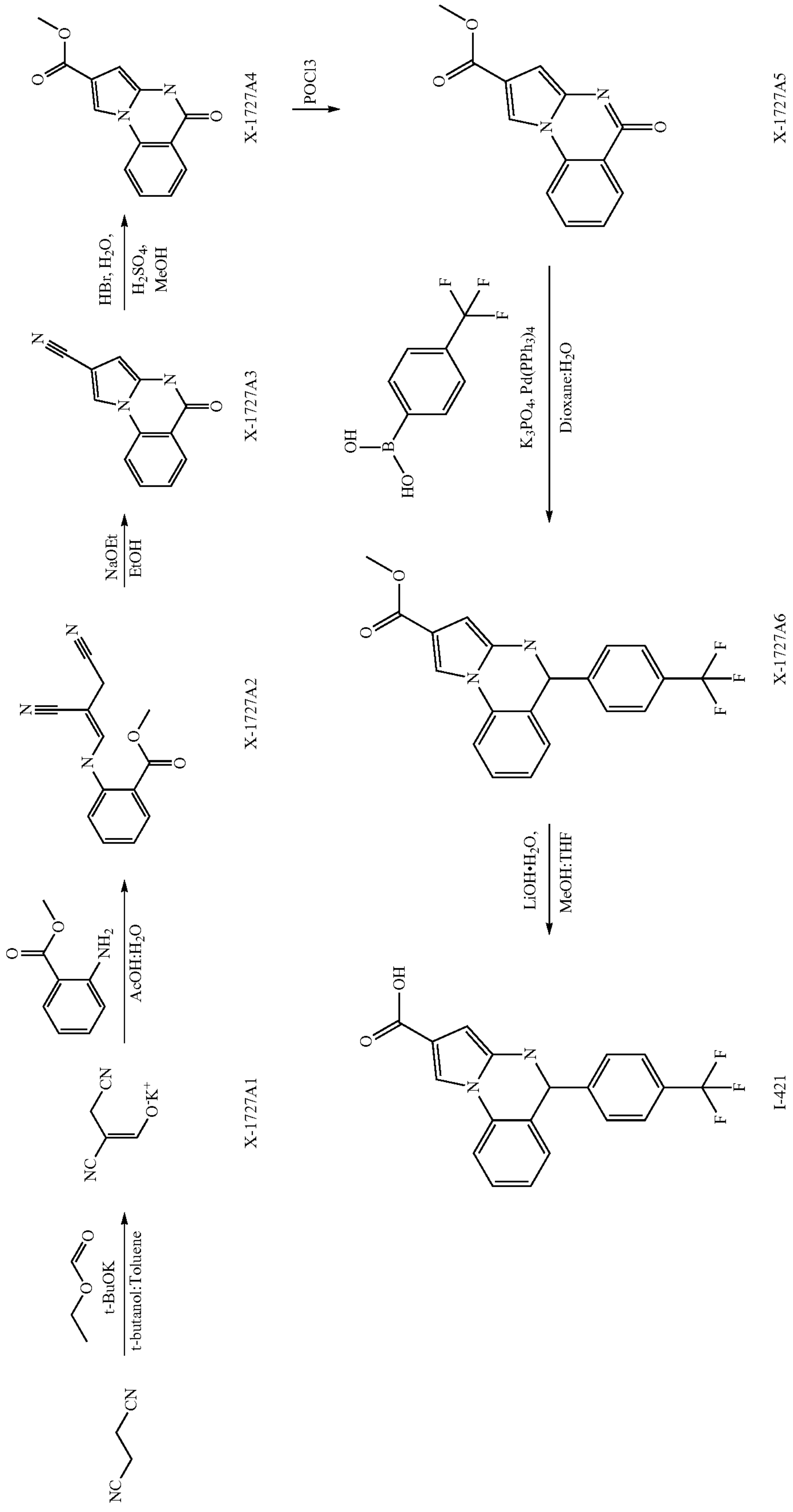
X-1727A1
X-1727A2
X-1727A3
X-1727A4
X-1727A5
X-1727A6
I-421

Potassium (E)-2,3-Dicyanoprop-1-en-1-olate (X-1727A1). To a stirred solution of succinonitrile (10.0 g, 125 mmol) and ethylformate (11.09 g, 150 mmol) in toluene (100 mL) was added a solution of potassium tert-butoxide (15.40 g, 137 mmol) in t-butanol (25 mL) and resulting reaction mixture was stirred at room temperature for 3 h. Reaction mixture was filtered through a Buchner funnel and residue was washed with a solution of diethyl ether-ethanol (1:1; 160 mL). Residue was collected and dried under high vacuum to afford as an isomeric mixture (2:1) (E/Z)-2,3-dicyanoprop-1-en-1-olate (X-1727A1) (11.8 g, 65.1%) as a brown solid. $^1$H NMR (400 MHz, DMSO-$d_6$) δ 8.57 (s, 0.33H), 8.27 (s, 0.66H), 3.06 (s, 2H).

Methyl (Z)-2-((2,3-dicyanoprop-1-en-1-yl)amino)benzoate (X-1727A2). To a stirred solution of an isomeric mixture (2:1) of potassium (E/Z)-2,3-dicyanoprop-1-en-1-olate (X-1727A1) (10.0 g, 68.96 mmol) and methyl 2-aminobenzoate (13.85 g, 91.70 mmol) in water (55 mL) was added acetic acid (55 mL) at room temperature under nitrogen and the resulting mixture was heated at 100° C. for 1 h. Reaction mixture was cooled to room temperature, solid precipitate was filtered and washed the residue with diethyl ether and ethanol. Obtained solid was dried under high vacuum to afford an isomeric mixture (7:3) of methyl (Z/E)-2-((2,3-dicyanoprop-1-en-1-yl)amino)benzoate (X-1727A2) (12.0 g, 72.2%; crude) as brown solid. MS: $[MH]^-$ 240.12.

5-Oxo-4,5-dihydropyrrolo[1,2-a]quinazoline-2-carbonitrile (X-1727A3). To a stirred solution of an isomeric mixture (7:3) of methyl (Z/E)-2-((2,3-dicyanoprop-1-en-1-yl)amino)benzoate (X-1727A2) (5.0 g, 20.74 mmol) in ethanol (80 mL) was added a solution of sodium ethoxide in ethanol (3.52 g, 51.86 mmol) at 0° C. and resulting reaction mixture was stirred at room temperature for 3 h. Reaction mixture was filtered and residue was washed with ethanol (20 mL). Residue was collected and dried under high vacuum to afford 5-oxo-4,5-dihydropyrrolo[1,2-a]quinazoline-2-carbonitrile (X-1727A3) (4.2 g, 96.8%; crude) as an off-white solid. MS: $[MH]^+$ 210.24.

Methyl 5-oxo-4,5-dihydropyrrolo[1,2-a]quinazoline-2-carboxylate (X-1727A4). A solution of 47% HBr in water (10 mL, 20V) was added to methyl 5-oxo-4,5-dihydropyrrolo[1,2-a]quinazoline-2-carbonitrile (X-1727A3) (0.500 g, 2.39 mmol) under nitrogen and the resulting reaction mixture was heated at 110° C. for 5 h. Reaction mixture was filtered and washed with water. Collected residue was dissolved in methanol (15 mL) followed by addition of conc. $H_2SO_4$ (1 mL) and the resulting suspension was refluxed for 12 h. Reaction mixture was filtered in a Buchner funnel, residue was washed with water (500 mL) and dried under high vacuum to afford methyl 5-oxo-4,5-dihydropyrrolo[1,2-a]quinazoline-2-carboxylate (X-1727A4) (0.450 g, 77.7%; crude) as a light brown solid. MS: $[MH]^+$ 243.3.

Methyl 5-chloropyrrolo[1,2-a]quinazoline-2-carboxylate (X-1727A5). Phosphorus oxychloride (3 mL, 10V) was added to methyl 5-oxo-4,5-dihydropyrrolo[1,2-a]quinazoline-2-carboxylate (X-1727A4) (0.300 g, 1.23 mmol) at 0° C. under nitrogen and the resulting reaction mixture was heated at 100° C. for 3 h. Reaction mixture was slowly poured in cold aqueous solution of saturated $NaHCO_3$ solution (50 mL) till pH becomes neutral (Ph-9) and was extracted with ethyl-acetate (50 mL×3). Combined organic extracts were dried over anhydrous $Na_2SO_4$ and concentrated under reduce pressure to afford methyl 5-chloropyrrolo[1,2-a]quinazoline-2-carboxylate (X-1727A5) (0.180 g, 55.8%) as an off-white solid. MS: $[MH]^+$ 261.20

Methyl 5-(4-(trifluoromethyl)phenyl)pyrrolo[1,2-a]quinazoline-2-carboxylate (X-1727A6). To a stirred solution of methyl 5-chloropyrrolo[1,2-a]quinazoline-2-carboxylate (X-1727A5) (0.080 g, 0.30 mmol) in a 1,4-dioxane-water (1:0.5, 1.5 mL) were added (4-(trifluoromethyl)phenyl)boronic acid (0.087 g, 0.461 mmol) and $K_3PO_4$ (0.19 g, 0.922 mmol) sequentially at room temperature. The reaction mixture was degassed (purging with nitrogen) for 20 min followed by addition of $Pd(PPh_3)_4$ (0.017 g, 0.015 mmol) and the resulting reaction mixture was heated at 120° C. for 1 h. Reaction mixture was cooled to room temperature, diluted with water (20 mL) and was extracted with ethyl acetate (30 mL×3). The combined organic extracts were dried over anhydrous $Na_2SO_4$ and concentrated under reduce pressure to afford crude mass, which was purified by silica gel column chromatography, using ethyl acetate-Hexane=0:1→3:7 as eluent, to afford methyl 5-(4-(trifluoromethyl)phenyl)pyrrolo[1,2-a]quinazoline-2-carboxylate (X-1727A6) (0.080 g, 70.2%) as an off-white solid. MS: $[MH]^+$ 371.39.

5-(4-(trifluoromethyl)phenyl)pyrrolo[1,2-a]quinazoline-2-carboxylic acid (I-421). To a stirred solution of methyl 5-(4-(trifluoromethyl)phenyl)pyrrolo[1,2-a]quinazoline-2-carboxylate (X-1727A6) (0.080 g, 0.21 mmol) in a mixture of THF-water (1:1; 7 mL) was added lithium hydroxide monohydrate (0.182 g, 1.29 mmol) at room temperature and the resulting mixture was heated at 45° C. for 4 h. After cooling to room temperature, the reaction mixture was concentrated under reduced pressure. Obtained crude was diluted with water (10 mL) and was acidified (pH~2-3) with an aqueous solution of 1N HCl and the resulting precipitate was collected by filtration and washed with water till the pH became neutral (pH~6-7) and dried under high vacuum to afford, 5-(4-(trifluoromethyl)phenyl)pyrrolo[1,2-a]quinazoline-2-carboxylic acid (I-421) (0.045 g, 58.4%) as a white solid. $^1$H NMR (400 MHz, DMSO-$d_6$) δ 12.61 (br, 1H), 8.80-8.79 (d, J=1.6 Hz, 1H), 8.57-8.55 (d, J=8.4 Hz, 1H), 7.97-7.94 (m, 5H), 7.83-7.81 (dd, J=8.0 Hz, 0.8 Hz, 1H), 7.56-7.52 (t, J=7.6 Hz, 1H), 6.98-6.98 (d, J=1.2 Hz, 1H). MS: $[MH]^+$ 357.35.

Example 1.328. Synthesis of 2-methyl-3-(4-(trifluoromethyl)phenyl)quinoxaline-6-carboxylic acid (I-422)

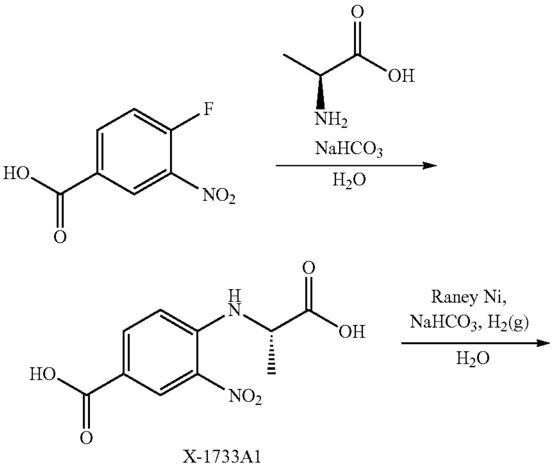

X-1733A1

-continued

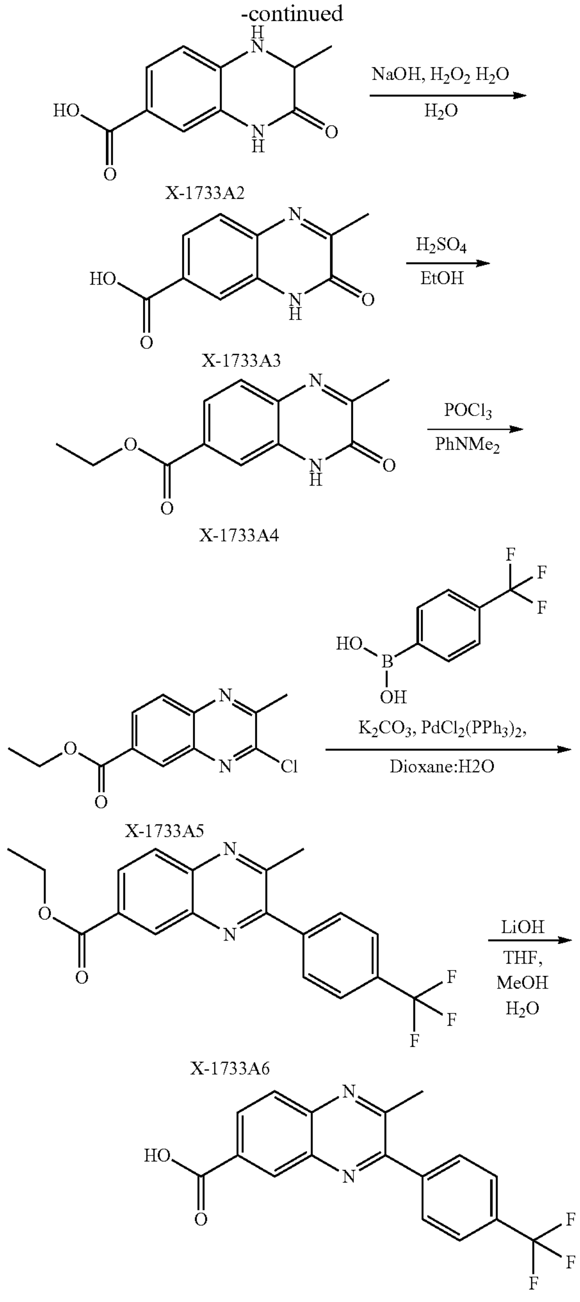

X-1733A2

X-1733A3

X-1733A4

X-1733A5

X-1733A6

I-422

(S)-4-((1-Carboxyethyl)amino)-3-nitrobenzoic acid (X-1733A1). To a stirred solution of 4-fluoro-3-nitrobenzoic acid (15 g, 81.1 mmol) in water (150 mL) were added sodium bicarbonate (20.4 g, 243.0 mmol) and L-alanine (14.4 g, 162.10 mmol) sequentially at room temperature under nitrogen and the reaction mixture was heated at 100° C. for 20 h. The reaction mixture was cooled to room temperature and diluted with water (500 mL), acidified (pH~2-3) with an aqueous solution of 3N HCl and the resulting precipitate was collected by filtration. Residue was washed with water until the pH became neutral (pH~6-7) and obtained solid was dried under high vacuum to afford (S)-4-((1-carboxyethyl)amino)-3-nitrobenzoic acid (X-1733A1) (16.00 g, 77.6%; crude) as a yellow solid. MS: $[MH]^+$ 252.88.

2-Methyl-3-oxo-1,2,3,4-tetrahydroquinoxaline-6-carboxylic acid (X-1733A2). To a stirred solution of (S)-4-((1-carboxyethyl)amino)-3-nitrobenzoic acid (X-1733A1) (8.0 g, 31.40 mmol) in water (80 mL) were added sodium bicarbonate (7.9 g, 94.40 mmol) and Raney Ni (6.0 g (wet)) sequentially at room temperature under nitrogen and the resulting mixture was hydrogenated in a Parr Autoclave under 60 psi at room temperature for 48 h. Reaction mixture was filtered through celite bed and concentrated under reduce pressure to afford 2-methyl-3-oxo-1,2,3,4-tetrahydroquinoxaline-6-carboxylic acid (X-1733A2) (6.4 g, quant.; crude) as a brown solid. MS: $[MH]^+$ 207.30.

2-Methyl-3-oxo-3,4-dihydroquinoxaline-6-carboxylic acid (X-1733A3). Sodium hydroxide (6.20 g, 155.30 mmol) and hydrogen peroxide (6.40 mL) were added a stirred solution of 2-methyl-3-oxo-1,2,3,4-tetrahydroquinoxaline-6-carboxylic acid (X-1733A2) (6.40 g, 31.00 mmol) in water (60 mL) and the resulting mixture was stirred at 100° C. for 70 h. The reaction mixture was cooled to room temperature, acidified (pH~2-3) with an aqueous solution of 3N HCl and the resulting precipitate was collected by filtration. Obtained residue was washed with water until the pH of the filtrate became neutral (pH~6-7) and finally triturated using diethyl ether (50×2 mL) and dried under high vacuum to afford (2-methyl-3-oxo-3,4-dihydroquinoxaline-6-carboxylic acid (X-1733A3) (3.2 g, 50.4%) as a brown solid. MS: $[MH]^+$ 205.26.

Ethyl 2-methyl-3-oxo-3,4-dihydroquinoxaline-6-carboxylate (X-1733A4). Concentrated $H_2SO_4$ (0.26 mL) was added to a stirred solution of (2-methyl-3-oxo-3,4-dihydroquinoxaline-6-carboxylic acid (X-1733A3) (0.500 g, 2.45 mmol) in ethanol (3 ml) at room temperature and the resulting mixture was heated at 100° C. for 16 h. Reaction mixture was cooled to room temperature, and it was slowly poured into an aqueous solution of saturated $NaHCO_3$ (50 mL) and was extracted with ethyl acetate (50 mL×3). Combined organic extracts were dried over anhydrous $Na_2SO_4$ and concentrated under reduced pressure, to afford, ethyl 2-methyl-3-oxo-3,4-dihydroquinoxaline-6-carboxylate (X-1733A4) (0.300 g, 52.76%) as an off-white solid. MS: $[MH]^+$ 233.3.

ethyl 3-chloro-2-methylquinoxaline-6-carboxylate (X-1733A5). Phosphorus oxychloride (10 mL) was added to ethyl 2-methyl-3-oxo-3,4-dihydroquinoxaline-6-carboxylate (X-1733A4) (0.800 g, 3.44 mmol) under nitrogen at 0° C. and the resulting reaction mixture was heated at 100° C. for 2 h. After cooling to room temperature, reaction mass was slowly poured into an aqueous solution of saturated $NaHCO_3$ (100 mL) and was extracted by ethyl acetate (100 mL×2). Collected organic parts were dried over anhydrous $Na_2SO_4$ and concentrated under reduce pressure to afford ethyl 3-chloro-2-methylquinoxaline-6-carboxylate (X-1733A5) (0.400 g, 46.4%) as a white solid. MS: $[MH]^+$ 251.17.

Ethyl 2-methyl-3-(4-(trifluoromethyl)phenyl)quinoxaline-6-carboxylate (X-1733A6). To a stirred solution of ethyl 3-chloro-2-methylquinoxaline-6-carboxylate (X-1733A6) (0.500 g, 2.00 mmol) in 1,4-dioxane-water (9:1, 10 mL) were added $K_2CO_3$ (0.790 g, 6.00 mmol) and (4-(trifluoromethyl)phenyl)boronic acid (0.710 g, 2.40 mmol) sequentially at room temperature under nitrogen. The reaction mixture was degassed (purged with nitrogen) for 20 min followed by the addition of $PdCl_2(PPh_3)_2$ (0.140 g, 0.20 mmol) and the resulting mixture was heated at 120° C. for 3 h. Reaction mixture was cooled to room temperature, diluted with water (200 mL) and was extracted with ethyl acetate (200 mL×2). Combined organic extracts were dried over anhydrous $Na_2SO_4$ and concentrated under reduce pressure to get a crude mass, which was purified by silica gel column chromatography, using methanol:DCM=1:49→1:9 as eluent, to afford ethyl 2-methyl-3-(4-(trifluoromethyl)phenyl)quinoxaline-6-carboxylate (X-1733A6) (0.110 g, 15.2%) as a brown solid MS: $[MH]^+$ 251.17.

2-Methyl-3-(4-(trifluoromethyl)phenyl)quinoxaline-6-carboxylic acid (I-422). To a stirred solution of ethyl 2-methyl-3-(4-(trifluoromethyl)phenyl)quinoxaline-6-carboxylate (X-1733A6) (0.100 g, 0.277 mmol) in a mixture of THF-water (1:1; 4.0 mL) was added lithium hydroxide monohydrate (0.023 g, 0.55 mmol) at room temperature and the resulting mixture was heated at 100° C. for 1 h. After cooling to room temperature, reaction mixture was concentrated under reduced pressure, acidified (pH~2-3) with an aqueous 1N HCl solution to obtain crude, which was diluted with water (40 mL) and was extracted with ethyl acetate (40 mL×2). Combined organic extracts were dried over anhydrous $Na_2SO_4$ and concentrated under reduce pressure to afford 2-methyl-3-(4-(trifluoromethyl)phenyl)quinoxaline-6-carboxylic acid (I-422) (0.030 g, 32.5%) as an off-white solid. $^1H$ NMR (400 MHz, DMSO-$d_6$) δ 8.55 (s, 1H), 8.37-8.35 (d, J=8.8 Hz, 1H), 8.00-7.91 (m, 5H), 2.70 (s, 3H). MS: $[MH]^+$ 333.3.

Example 1.329. Synthesis of (R)—N-(1-hydroxybutan-2-yl)-2-methyl-3-(4-(trifluoromethyl)phenyl)quinoxaline-6-carboxamide (I-423)

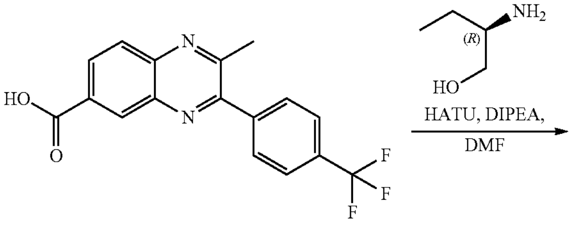

I-422

-continued

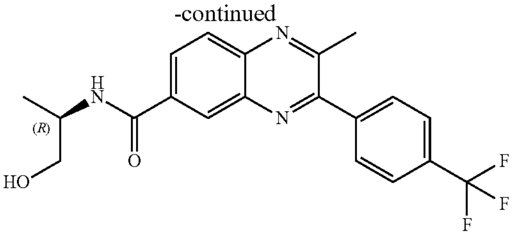

I-423

To a stirred solution of 2-methyl-3-(4-(trifluoromethyl)phenyl)quinoxaline-6-carboxylic acid (I-422) (0.090 g, 0.27 mmol) in DMF (3 mL) were added DIPEA (0.30 mL, 0.54 mmol) and HATU (0.380 g, 0.40 mmol) sequentially at 0° C. under nitrogen. After stirring for 10 min at the same temperature, was added a solution of (R)-2-aminobutan-1-ol (0.048 g, 0.54 mmol) in DMF (1 mL) into the reaction mass and stirred for an additional 1 h at room temperature. Reaction mixture was diluted with water (30 mL) and was extracted with ethyl acetate (50 mL×2). Organic extracts were combined, dried over anhydrous $Na_2SO_4$ and concentrated under reduced pressure to afford crude mass, which was purified by silica gel column chromatography, using ethyl acetate-hexane=0:1→3:7 as gradient, to afford (R)—N-(1-hydroxybutan-2-yl)-2-methyl-3-(4-(trifluoromethyl)phenyl)quinoxaline-6-carboxamide (I-423) (0.020 g, 16%) as an off-white solid. $^1H$ NMR (400 MHz, DMSO-$d_6$) δ 8.66-8.66 (d, J=1.6 Hz, 1H), 8.43-8.41 (d, J=8 Hz, 1H), 8.29-8.26 (dd, J=8.8 Hz, 2.0 Hz, 1H), 8.15-8.13 (d, J=8.8 Hz, 1H), 8.03-8.01 (d, J=8.4 Hz, 2H), 7.96-7.94 (d, J=8.4 Hz, 2H), 4.74-4.71 (t, J=5.6 Hz, 1H), 3.94-3.90 (m, 1H), 3.52-3.50 (m, 1H), 3.48-3.44 (m, 1H), 1.73-1.68 (m, 1H), 2.75 (s, 3H), 1.73-1.66 (m, 1H) 1.54-1.46 (m, 1H) 0.93-0.89 (t, J=7.6 Hz, 3H). MS: $[MH]^+$ 404.4.

Example 1.330. Synthesis of 1-oxo-3-(4-(trifluoromethyl)phenyl)-1,2-dihydroisoquinoline-6-carboxylic acid (I-424)

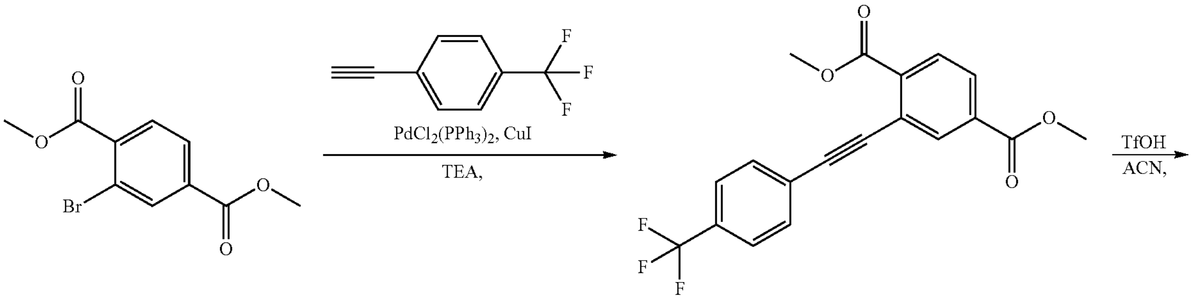

X-1815A1

-continued

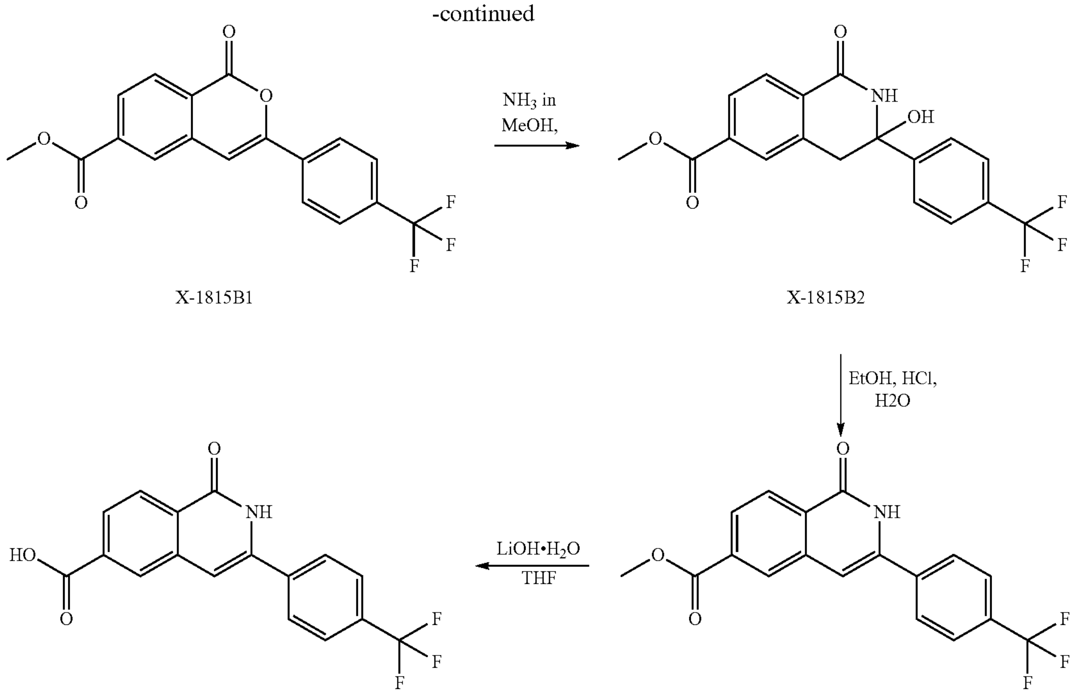

X-1815B1 X-1815B2

I-424 X-1815B3

Dimethyl 2-((4-(trifluoromethyl)phenyl)ethynyl)terephthalate (X-1815A1). To a stirred solution of dimethyl 2-bromoterephthalate (10.0 g, 36.63 mmol) in TEA (100 mL) was added 1-ethynyl-4-(trifluoromethyl)benzene (9.34 g, 54.90 mmol) and reaction mixture was degassed (purged with nitrogen) for 20 min followed by the addition of copper iodide (0.130 g, 0.73 mmol) and $PdCl_2(PPh_3)_2$ (0.510 g, 0.73 mmol) sequentially at room temperature under nitrogen and the resulting mixture was heated at 80° C. for 16 h. Reaction mixture was cooled to room temperature, diluted with water (250 mL) and was extracted with DCM (250 mL×2). Combined organic extracts were dried over anhydrous $Na_2SO_4$ and concentrated under reduce pressure to afford crude mass, which was purified by reverse phase (C-18) silica gel column chromatography, using acetonitrile-water=0:1→7:3 as gradient to afford dimethyl 2-((4-(trifluoromethyl)phenyl)ethynyl)terephthalate (X-1815A1) (8.5 g, 64%) as a brown solid. MS: $[MH]^+$ 363.08.

Methyl 1-oxo-3-(4-(trifluoromethyl)phenyl)-1H-isochromene-6-carboxylate (X-1815B1). To a stirred solution of dimethyl 2-((4-(trifluoromethyl)phenyl)ethynyl)terephthalate (X-1815A1) (4.30 g, 11.87 mmol) in acetonitrile (50 mL) was added triflic acid (3.91 g, 26.13 mmol) at 0° C. and stirred the reaction mixture at 90° C. for 16 h. Reaction mixture was cooled to room temperature, diluted with ice water (250 mL) and was extracted with DCM (50 mL×3). Combined organic extracts were dried over anhydrous $Na_2SO_4$ and concentrated under reduce pressure to afford crude mass, which was purified by silica gel column chromatography, using ethyl acetate-hexane=0:1→1:4 as eluent, to afford, methyl 1-oxo-3-(4-(trifluoromethyl)phenyl)-1H-isochromene-6-carboxylate (X-1815B1) (3.10 g, 75%) as a yellow solid. MS: $[MH]^+$ 349.0.

Methyl 3-hydroxy-1-oxo-3-(4-(trifluoromethyl)phenyl)-1,2,3,4-tetrahydroisoquinoline-6-carboxylate (X-1815B2). To a stirred solution of ammonia in methanol (7N, 45 mL) was added methyl 1-oxo-3-(4-(trifluoromethyl)phenyl)-1H-isochromene-6-carboxylate (X-1815B1) (3.0 g, 8.59 mmol) in a sealed tube and stirred the reaction mixture at room temperature for 2 h. Obtained crude was concentrated under reduced pressure, which was purified by silica gel column chromatography, using methanol-dichloromethane=0:1→1:4 as eluent, to afford, methyl 3-hydroxy-1-oxo-3-(4(trifluoromethyl)phenyl)-1,2,3,4-tetrahydroisoquinoline-6-carboxylate (X-1815B2) (2.0 g, 64%) as a yellow solid. MS: $[MH]^+$366.01.

Methyl 1-oxo-3-(4-(trifluoromethyl)phenyl)-1,2-dihydroisoquinoline-6-carboxylate (X-1815B3). To a stirred solution of methyl 3-hydroxy-1-oxo-3-(4(trifluoromethyl)phenyl)-1,2,3,4-tetrahydroisoquinoline-6-carboxylate (X-1815B2) (2.0 g, 5.40 mmol) in mixture of ethanol-water (25:6; 31 mL) was added conc HCl (6 mL) slowly at 0° C. and stirred at room temperature for 2 h. Reaction mixture was cooled to room temperature, diluted with ice water (250 mL) and was extracted with EtOAc (50 mL×3). Combined organic extracts were dried over anhydrous $Na_2SO_4$ and concentrated under reduce pressure to afford, methyl 1-oxo-3-(4-(trifluoromethyl)phenyl)-1,2-dihydroisoquinoline-6-carboxylate (X-1815B3) (1.8 g, 94%; crude) as off-white solid. MS: $[MH]^+$ 348.2.

1-oxo-3-(4-(trifluoromethyl)phenyl)-1,2-dihydroisoquinoline-6-carboxylic acid (I-424). To a stirred solution of methyl 1-oxo-3-(4-(trifluoromethyl)phenyl)-1,2-dihydroisoquinoline-6-carboxylate (X-1815B3) (0.700 g, 2.01 mmol) in a mixture of THF-water (15:1; 64 mL) was added lithium hydroxide monohydrate (0.250 g, 6.05 mmol) at room temperature and the resulting mixture was stirred at 70° C. for 5 h. After cooling to room temperature, the reaction mixture was concentrated under reduced pressure, obtained crude was diluted with water (40 mL) and was extracted with ethyl acetate (40 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford crude mass which was purified by Prep-HPLC to afford 1-oxo-3-(4 (trifluoromethyl)phenyl)-1,2-dihydroisoquinoline-6-carboxylic acid (I-424) (0.080 g, 13%) as a white solid. $^1H$ NMR (400 MHz, DMSO-$d_6$) δ: 11.59 (s, 1H), 8.20 (s, 1H), 8.14-8.12 (d, J=8.0 Hz, 1H), 8.04-8.02 (d, J=8.4 Hz, 2H), 8.00-7.98 (dd, J=8.4 Hz, 1.2 Hz, 2H), 7.86-7.84 (d, J=8.4 Hz, 2H), 7.09 (s, 1H). MS: $[MH]^+$ 334.3. MS: $[MH]^+$ 334.06.

Example 1.331. Synthesis of 4-isopropyl-2-(4-(trifluoromethyl)phenyl)quinoline-7-carboxylic acid (I-425)

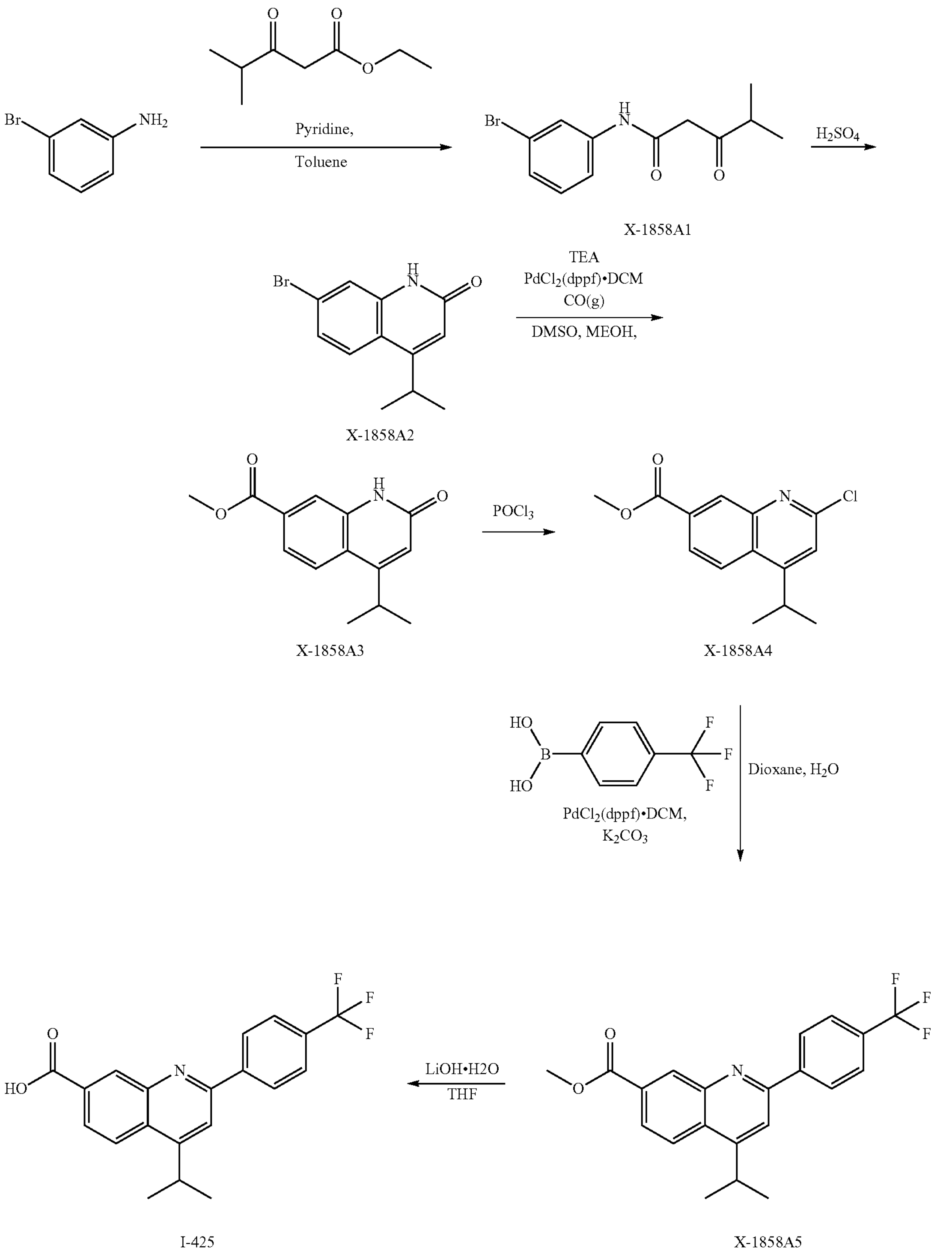

X-1858A1

X-1858A2

X-1858A3

X-1858A4

I-425

X-1858A5

N-(3-bromophenyl)-4-methyl-3-oxopentanamide (X-1858A1). To a stirred solution of 3-bromoaniline (5.0 g, 18.45 mmol) in toluene (20 mL) were added pyridine (5 mL) and ethyl 4-methyl-3-oxopentanoate (4.37 g, 27.67 mmol) sequentially at room temperature under nitrogen and the resulting reaction mixture was heated at 80° C. for 16 h. Reaction mixture was cooled to room temperature, diluted with water (500 mL) and was extracted with ethyl acetate (500 mL×3). Combined organic extracts were dried over anhydrous $Na_2SO_4$ and concentrated under reduce pressure to afford crude mass, which was purified by silica gel column chromatography, using ethyl acetate-hexane=0:1→1:4 as eluent, to afford, N-(3-bromophenyl)-4-methyl-3-oxopentanamide (X-1858A1) (2.5 g, 48%) as a brown liquid. MS: $[MH]^+$ 285.02.

7-bromo-4-isopropylquinolin-2(1H)-one (X-1858A2). A solution of N-(3-bromophenyl)-4-methyl-3-oxopentanamide (X-1858A1) (2.5 g, 8.83 mmol) in $H_2SO_4$ (30 mL) was heated at 100° C. for 1.5 h. Reaction mixture was cooled to room temperature and slowly poured into ice water (500 mL), solid product was precipitated which was collected by filtration, washed with cold water and dried under high vacuum to afford, 7-bromo-4-isopropylquinolin-2(1H)-one (X-1858A2) (1.1 g, 48%) as yellow solid. MS: $[MH]^+$ 267.1

Methyl 4-isopropyl-2-oxo-1,2-dihydroquinoline-7-carboxylate (X-1858A3). To a stirred solution of, 7-bromo-4-isopropylquinolin-2(1H)-one (X-1858A2) (1.10 g, 4.13 mmol) in DMSO (40 mL) were added methanol (30 mL) and triethylamine (2.9 mL, 20.67 mmol) sequentially at room temperature under nitrogen. The reaction mixture was degassed (purged with nitrogen) for 45 min followed by addition of $PdCl_2$(dppf).DCM (0.330 g, 0.41 mmol) at room temperature under nitrogen. The resulting reaction mixture was degassed (purged with nitrogen) for 20 min and kept for carboxylation under CO in a Parr Autoclave heated at 100° C. at 200 psi for 16 h. Reaction mixture was cooled to room temperature, diluted with water (200 mL) and was extracted with ethyl acetate (100 mL×3). Combined organic extracts were dried over anhydrous $Na_2SO_4$ and concentrated under reduce pressure to afford crude mass, which was purified by silica gel column chromatography, using ethyl acetate-hexane=0:1→2:3 as eluent, to afford methyl 4-isopropyl-2-oxo-1,2-dihydroquinoline-7-carboxylate (X-1858A3) (0.55 g, 54%) as brown solid. MS: $[MH]^+$ 246.2.

Methyl 2-chloro-4-isopropylquinoline-7-carboxylate (X-1858A4). A solution of methyl 4-isopropyl-2-oxo-1,2-dihydroquinoline-7-carboxylate (X-1858A3) (0.550 g, 2.24 mmol) in $POCl_3$ (4 mL) was heated at 90° C. for 2 h. Reaction mixture was cooled to room temperature and slowly poured in ice water (100 mL) and basified (pH~7-8) with slow addition of an aqueous solution of saturated $NaHCO_3$ and was extracted with ethyl acetate (50 mL×2). Combined organic extracts were dried over anhydrous $Na_2SO_4$ and concentrated under reduce pressure to afford, methyl 2-chloro-4-isopropylquinoline-7-carboxylate (X-1858A4) (0.420 g, 71%; crude) as an off-white solid. MS: $[MH]^+$ 264.07.

Methyl 4-isopropyl-2-(4-(trifluoromethyl)phenyl)quinoline-7-carboxylate (X-1858A5). To a stirred solution of methyl 2-chloro-4-isopropylquinoline-7-carboxylate (X-1858A4) (0.420 g, 1.59 mmol) in a mixture of 1,4-dioxane-water (2:1; 6 mL) were added (4-(trifluoromethyl)phenyl)boronic acid (0.300 g, 1.59 mmol) and $K_2CO_3$ (0.660 g, 4.79 mmol) sequentially at room temperature under nitrogen. The reaction mixture was degassed (purging with nitrogen) for 25 min followed by the addition of $PdCl_2$(dppf).DCM (0.050 g, 0.079 mmol) and the resulting mixture was heated at 100° C. for 2 h. Reaction mixture was cooled to room temperature, diluted with water (50 mL) and was extracted with ethyl acetate (50 mL×2). Combined organic extracts were dried over anhydrous $Na_2SO_4$ and concentrated under reduce pressure to afford crude mass, which was purified by silica gel column chromatography, using ethyl acetate-hexane=0:1→1:9 as eluent, to afford, methyl 4-isopropyl-2-(4-(trifluoromethyl)phenyl)quinoline-7-carboxylate (X-1858A5) (0.450 g, 76%) as a brown solid. MS: $[MH]^+$ 374.2.

4-isopropyl-2-(4-(trifluoromethyl)phenyl)quinoline-7-carboxylic acid (I-425). To a stirred solution of methyl 4-isopropyl-2-(4-(trifluoromethyl)phenyl)quinoline-7-carboxylate (X-1858A5) (0.450 g, 1.20 mmol) in a mixture of THF-water (5:4; 9 mL) was added lithium hydroxide monohydrate (0.28 g, 3.61 mmol) at room temperature and the resulting mixture was stirred at 70° C. for 3 h. After cooling to room temperature, the reaction mixture was concentrated under reduced pressure, obtained crude was diluted with water (40 mL). The reaction mixture was acidified (pH~2-3) with an aqueous solution of 1N HCl and was extracted with ethyl acetate (40 mL×2). Combined organic extracts were dried over anhydrous $Na_2SO_4$ and concentrated under reduce pressure to afford crude mass, which was purified by trituration using diethyl ether, to afford 4-isopropyl-2-(4-(trifluoromethyl)phenyl)quinoline-7-carboxylic acid (I-425) (0.350 g, 81%) as a white solid. 1H NMR (400 MHz, DMSO-$d_6$) δ 13.37 (s, 1H), 8.66-8.66 (d, J=1.6 Hz, 1H), 8.55-8.53 (d, J=8.4 Hz, 21H), 8.38-8.36 (d, J=8.8 Hz, 1H), 8.17 (s, 14H), 8.12-8.09 (dd, J=8.8 Hz, 1.6 Hz, 1H), 7.95-7.92 (d, J=8.4 Hz, 2H), 3.91-3.84 (m, 1H), 1.46-1.44 (d, J=6.8 Hz, 6H). MS: $[MH]^+$ 360.4.

Example 1.332. Synthesis of (R)—N-(1-hydroxypropan-2-yl)-4-isopropyl-2-(4-(trifluoromethyl)phenyl)quinoline-7-carboxamide (I-426)

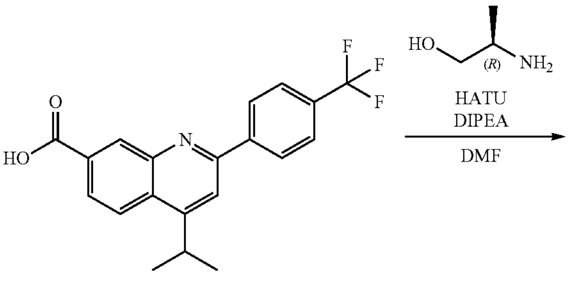

I-425

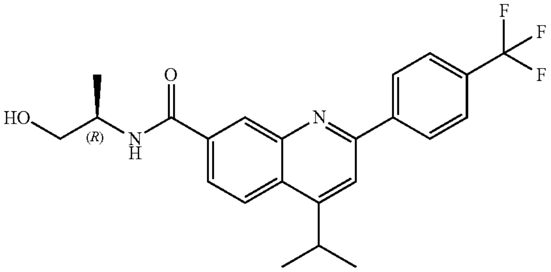

I-426

To a stirred solution of 4-isopropyl-2-(4-(trifluoromethyl)phenyl)quinoline-7-carboxylic acid (I-425) (0.250 g, 0.69 mmol) in DMF (4 mL) were added DIPEA (0.24 mL, 2.08 mmol) and HATU (0.530 g, 1.39 mmol) followed by addition of (R)-2-aminopropan-1-ol (0.070 g, 1.04 mmol), at room temperature and stirred for 1 h at the same temperature. Reaction mixture was diluted with water (50 mL) and was extracted with ethyl acetate (50 mL×2). Organic extracts were combined, dried over anhydrous $Na_2SO_4$ and concentrated under reduced pressure. Obtained crude was purified by trituration using diethyl ether to afford, (R)—N-(1-hydroxypropan-2-yl)-4-isopropyl-2-(4-(trifluoromethyl)phenyl)quinoline-7-carboxamide (I-426) (0.200 g, 69%) as an off-white solid. 1H NMR (400 MH z, DMSO-$d_6$) δ 8.68-8.67 (d, J=1.6 Hz, 1H), 8.55-8.53 (d, J=8.4 Hz, 21H), 8.51-8.49 (d, J=8.0 Hz, 1H), 8.34-8.32 (d, J=8.8 Hz, 1H), 8.13 (s, 1H), 8.09-8.06 (dd, J=8.8 Hz, 1.6 Hz, 1H), 7.95-7.93 (d, J=8.4 Hz, 2H), 4.79-4.76 (t, J=5.6 Hz, 1H), 4.12-4.08 (m, 1H), 3.89-3.86 (m, 1H), 3.55-3.50 (m, 1H), 3.43-3.40 (m, 1H), 1.45-1.44 (d, J=6.8 Hz, 6H), 1.19-1.18 (d, J=6.8 Hz, 311). MS: $[MH]^+$ 417.

Example 1.333. Synthesis of (R)—N-(1-hydroxypropan-2-yl)-2-(4-(trifluoromethyl)phenyl)quinoline-7-carboxamide (I-427)

(0.27 g, 1.20 mmol) sequentially at room temperature under nitrogen. The resulting reaction mixture was kept for carboxylation under CO gas pressure 220 psi at 70° C. in a Parr Autoclave for 16 h. Reaction mixture was cooled to room temperature, diluted with water (500 mL) and was extracted with ethyl acetate (250 mL×2). Combined organic extracts were dried over anhydrous $Na_2SO_4$ and concentrated under reduce pressure to afford crude mass, which was purified by silica gel column chromatography, using ethyl acetate-hexane=0:1→1:9 as eluent, to afford methyl quinoline-7-carboxylate (X-1865A1) (5.0 g, 78%) as brown solid. MS: $[MH]^+$ 188.2.

7-(methoxycarbonyl)quinoline 1-oxide (X-1865A2). To a stirred solution of methyl quinoline-7-carboxylate (X-1865A1) (5.0 g, 26.73 mmol) in DCM (100 mL) was added m-CPBA (9.7 g, 56.39 mmol) portion-wise at 0° C. under nitrogen and stirred the reaction mixture at room temperature for 3 h. The reaction mixture was basified (ph~8-9) with an aqueous solution of saturated $NaHCO_3$ and was extracted with ethyl acetate (200 mL×2). Combined organic extracts were dried over anhydrous $Na_2SO_4$ and concentrated under reduce pressure to afford crude mass.

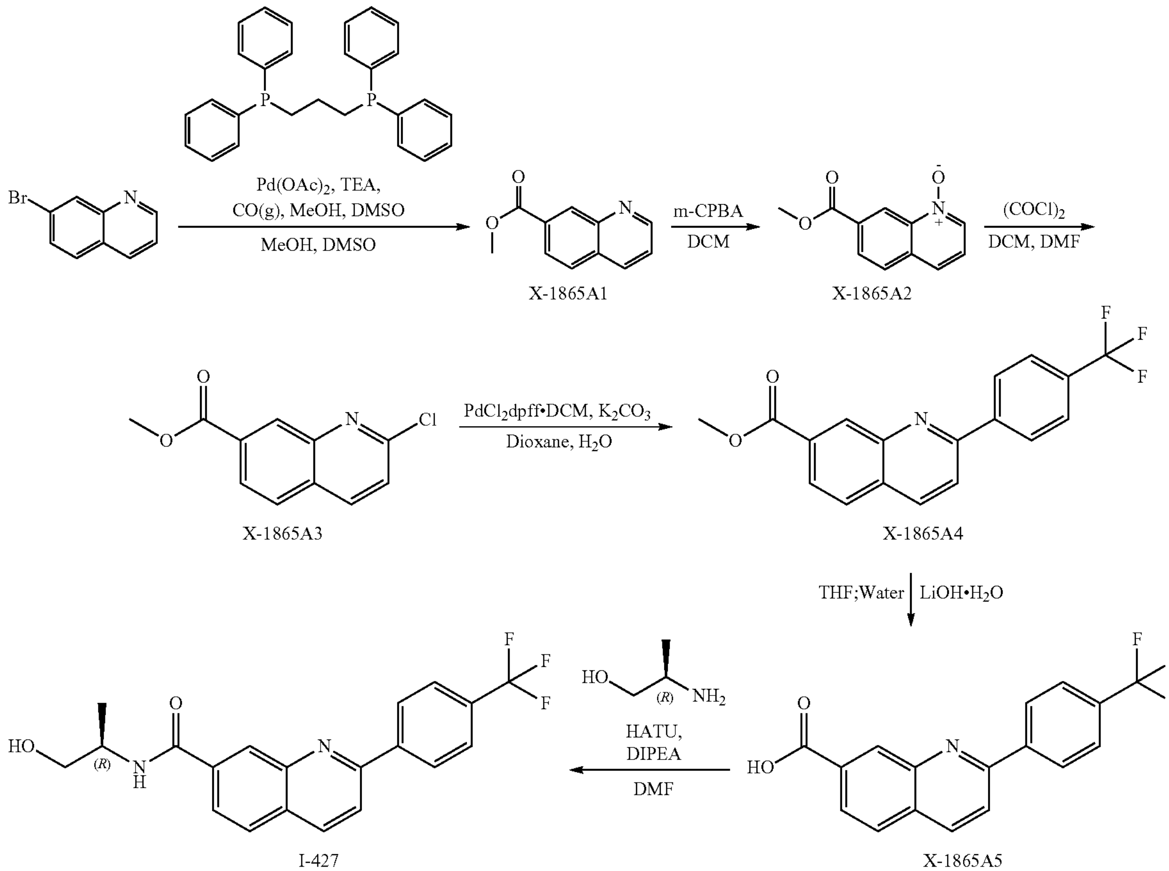

Methyl quinoline-7-carboxylate (X-1865A1). To a stirred solution of 7-bromoquinoline (5.0 g, 24.03 mmol) in DMSO (25 mL) were added methanol (25 mL) and trimethylamine (33 mL, 0.24 mmol) sequentially at room temperature under nitrogen and reaction mixture was degassed (purged with nitrogen) for 10 min followed by addition of 1,3-Bis(diphenylphosphino)propane (1.98 g, 4.80 mmol) and $Pd(OAc)_2$ Obtained crude was purified by trituration using mixture of ethyl acetate and hexane (1:1; 20 mL×3) to afford, 7-(methoxycarbonyl)quinoline 1-oxide (X-1865A2) (4.5 g, 82%) as off-white solid. MS: $[MH]^+$ 204.2.

Methyl 2-chloroquinoline-7-carboxylate (X-1865A3). To a stirred solution of 7-(methoxycarbonyl)quinoline 1-oxide (X-1865A2) (4.50 g, 22.16 mmol) in a mixture of DMF- DCM (1:1; 90 mL) was added oxalyl chloride (8.44 g, 66.48 mmol) at 0° C. drop-wise and the reaction mixture was heated at 50° C. for 2 h. Reaction mixture was quenched with an aqueous solution of saturated $NaHCO_3$ (100 mL) and was extracted with dichloromethane (200 mL×2). Combined organic extracts were dried over anhydrous $Na_2SO_4$ and concentrated under reduce pressure to afford crude mass which was purified by silica gel column chromatography, using ethyl acetate-hexane=0:1→1:9 as eluent, to afford methyl 2-chloroquinoline-7-carboxylate (X-1865A3) (1.8 g, 36%) as off-white solid. MS: $[MH]^+$ 222.2.

Methyl 2-(4-(trifluoromethyl)phenyl)quinoline-7-carboxylate (X-1865A4). To a stirred solution of methyl 2-chloroquinoline-7-carboxylate (X-1865A3) (1.80 g, 8.14 mmol) in a mixture of 1,4-dioxane-water (9:1, 50 mL) were added (4-(trifluoromethyl)phenyl)boronic acid (3.59 g, 18.94 mmol) and $K_2CO_3$ (3.59 g, 26.06 mmol) sequentially at room temperature under nitrogen. The reaction mixture was degassed (purging with nitrogen) for 20 min followed by the addition of $PdCl_2(PPh_3)_2$ (1.32 g, 1.62 mmol) and the resulting mixture was heated at 80° C. for 2 h. Reaction mixture was cooled to room temperature, diluted with water (200 mL) and was extracted with ethyl acetate (200 mL×2). Combined organic extracts were dried over anhydrous $Na_2SO_4$ and concentrated under reduce pressure to afford crude mass, which was purified by silica gel column chromatography, using ethyl acetate-hexane=0:1→1:4 as eluent, to afford methyl 2-(4-(trifluoromethyl)phenyl)quinoline-7-carboxylate (X-1865A4) (2.3 g, 85%) as a light brown solid. MS: $[MH]^+$ 332.3.

2-(4-(trifluoromethyl)phenyl)quinoline-7-carboxylic acid (X-1865A5). To a stirred solution of methyl 2-(4-(trifluoromethyl)phenyl)quinoline-7-carboxylate (X-1865A4) (1.30 g, 3.92 mmol) in a mixture of THF-water (9:1; 20 mL) was added lithium hydroxide monohydrate (0.680 g, 16.19 mmol) at room temperature and the resulting mixture was stirred at 60° C. for 1 h. After cooling to room temperature, the reaction mixture was concentrated under reduced pressure, obtained crude was diluted with water (40 mL) and was extracted with ethyl acetate (40 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under high vacuum to afford, 2-(4-(trifluoromethyl)phenyl)quinoline-7-carboxylic acid (X-1865A5) (1.0 g, 80%) as a white solid. MS: $[MH]^+$ 318.3.

(R)—N-(1-hydroxypropan-2-yl)-2-(4-(trifluoromethyl)phenyl)quinoline-7-carboxamide (I-427). To a stirred solution of 2-(4-(trifluoromethyl)phenyl)quinoline-7-carboxylic acid (X-1865A5) (0.220 g, 0.69 mmol) in DMF (4 mL) were added (R)-2-aminopropan-1-ol (0.200 g, 2.66 mmol), DIPEA (0.42 mL, 2.35 mmol) and HATU (0.400 g, 1.11 mmol) at room temperature and stirred for 2 h at the same temperature. Reaction mixture was poured into ice water (100 mL), solid product was precipitated which was collected by filtration, dried under reduced pressure. Obtained crude was purified by reverse phase (C-18) silica gel column chromatography, using acetonitrile-water=0:1→2:3 as gradient, to afford (R)—N-(1-hydroxypropan-2-yl)-2-(4-(trifluoromethyl)phenyl)quinoline-7-carboxamide (I-427) (0.070 g, 29%) as a white solid. $^1H$ NMR (400 MHz, DMSO-$d_6$) δ 9.08-9.07 (d, J=4.4 Hz, 1H), 8.68-8.67 (d, J=1.6 Hz, 1H), 8.53-8.51 (d, J=8.0 Hz, 1H), 8.05-8.02 (dd, J=8.8 Hz, 1.6 Hz, 1H), 7.99-7.97 (d, J=8.0 Hz, 2H), 7.89-7.86 (d, J=8.8 Hz, 1H), 7.83-7.81 (d, J=8.4 Hz, 2H), 7.61-7.60 (d, J=4.4 Hz, 1H), 4.79-4.76 (t, J=5.6 Hz, 1H), 4.10-4.07 (m, 1H), 3.53-3.49 (m, 1H), 3.42-3.33 (m, 1H), 1.19-1.17 (d, J=6.8 Hz, 3H). MS: $[MH]^+$ 375.4.

Example 1.334. Synthesis of (R)—N-(2-hydroxy-1-phenylethyl)-2-(4-(trifluoromethyl)phenyl)quinoline-7-carboxamide (I-428)

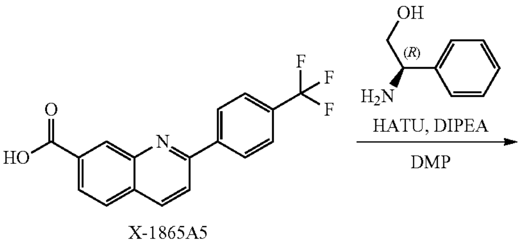

X-1865A5

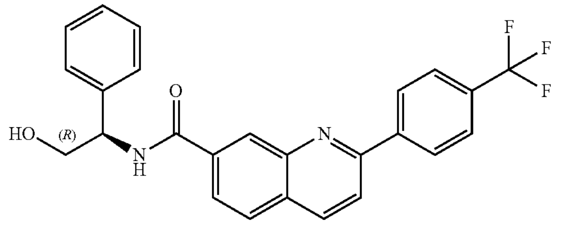

I-428

Synthesis of 2-(4-(trifluoromethyl)phenyl)quinoline-7-carboxylic acid (X-1865A5) disclosed above in Example 1.333

(R)—N-(2-hydroxy-1-phenylethyl)-2-(4-(trifluoromethyl)phenyl)quinoline-7-carboxamide (I-428). To a stirred solution of 2-(4-(trifluoromethyl)phenyl)quinoline-7-carboxylic acid (X-1865A5) (0.200 g, 0.63 mmol) in a DMF (5 mL) were added DIPEA (0.244 g, 1.89 mmol) and HATU (0.359 g, 0.94 mmol) sequentially at 0° C. under nitrogen. After stirring for 10 min at the same temperature, was added (R)-2-amino-2-phenylethan-1-ol (0.207 g, 0.94 mmol) and stirring was continued at the room temperature for 16 h. Reaction mixture was poured into ice water (100 mL), solid product was precipitated which was collected by filtration, dried under reduced pressure. The resulting crude material was triturated with n-Pentane (10 mL×3) dried over high vacuum to afford (R)—N-(2-hydroxy-1-phenylethyl)-2-(4-(trifluoromethyl)phenyl)quinoline-7-carboxamide (I-428) (0.200 g, 72%) as an off-white solid. $^1H$ NMR (400 MHz, DMSO-$d_6$) δ 9.15-9.13 (d, J=8.4 Hz, 1H), 9.10-9.09 (d, J=4.0 Hz, 1H), 8.786-8.782 (d, J=1.6 Hz, 1H), 8.06-8.03 (dd, J=8.8, 2.0 Hz, 1H), 7.99-7.97 (d, J=8.4 Hz, 2H), 7.90-7.88 (d, J=8.8 Hz, 1H), 7.84-7.82 (d, J=8.0 Hz, 2H), 7.63-7.62 (d, J==4.4 Hz, 1H), 7.45-7.43 (d, J=7.2 Hz, 2H). 7.36-7.32 (t, J=7.6 Hz, 2-1), 7.27-7.23 (m, 1H), 5.17-5.11 (m, 1H), 5.02-5.00 (t, J=6.0 Hz, 1H), 3.82-3.75 (m, 1H), 3.72-3.66 (m, 1H). MS: $[MH]^+$ 437.4.

Example 1.335. Synthesis of 1-Isopropyl-3-(2-(4-(trifluoromethyl)phenyl)quinolin-7-yl)urea (I-429)

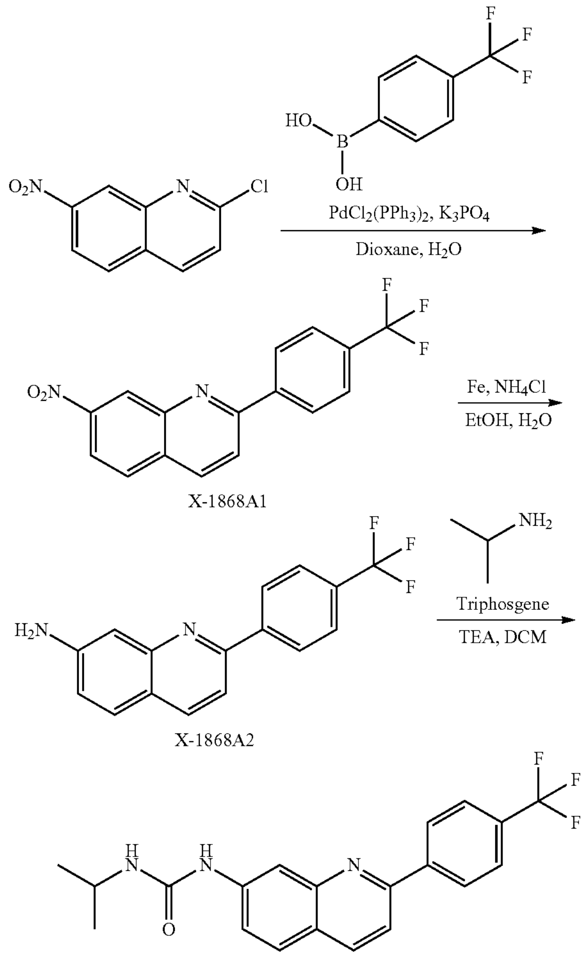

X-1868A1

X-1868A2

I-429

7-Nitro-2-(4-(trifluoromethyl)phenyl)quinoline (X-1868A1). To a stirred solution of 2-chloro-7-nitroquinoline (0.500 g, 2.40 mmol) in a mixture of dioxane-water (3:1, 7.0 mL) were added (4-(trifluoromethyl)phenyl)boronic acid (0.548 g, 2.88 mmol) and $K_3PO_4$ (1.50 g, 7.21 mmol) sequentially at room temperature. The reaction mixture was degassed (purging with nitrogen) for 30 min followed by addition of $PdCl_2$ $(PPh_3)_2$ (0.843 g, 0.120 mmol) and the reaction mixture was heated at 100° C. for 1 h. After cooling to room temperature, reaction mixture diluted with water (50 mL) and was extracted with ethyl acetate (50 mL×3). The combined organic extracts were dried over anhydrous $Na_2SO_4$ and concentrated under reduce pressure. The crude product was purified by silica gel column chromatography, using ethyl acetate-Hexane=0:1→1:9 as gradient, to afford 7-nitro-2-(4-(trifluoromethyl)phenyl)quinoline (X-1868A1) (0.800 g, Quantitate) as an off-white solid. MS: $[MH]^+$ 319.3.

2-(4-(Trifluoromethyl)phenyl)quinolin-7-amine (X-1868A2). Fe powder (0.704 g, 12.57 mmol) and $NH_4Cl$ (0.662 g, 10.4 mmol) were sequentially added to a stirred solution of 7-nitro-2-(4-(trifluoromethyl)phenyl)quinoline (X-1868A1) (0.500 g, 1.57 mmol) in EtOH:water (10 mL) at room temperature under nitrogen and the resulting suspension was heated at 90° C. temperature for 1 h. After cooling to room temperature, reaction mixture was filtered through a celite, filtrate was diluted with water (50 mL) and was extracted with ethyl acetate (50 mL×3). Combined organic extracts were dried over anhydrous $Na_2SO_4$ and concentrated under reduced pressure to afford 2-(4-(trifluoromethyl)phenyl)quinolin-7-amine (X-1868A2) (0.390 g, 86%) as a yellow solid, which is pure enough to proceed to next step without further purification. MS: $[MH]^+$ 289.2.

1-Isopropyl-3-(2-(4-(trifluoromethyl)phenyl)quinolin-7-yl)urea (I-429). To a stirred solution of 2-(4-(trifluoromethyl)phenyl)quinolin-7-amine (X-1868A2) (0.350 g, 1.21 mmol) in DCM (10.0 mL) were added triethylamine (0.613 g, 6.07 mmol) and triphosgene (0.216 g, 0.729 mmol) sequentially at 0° C. under nitrogen and the reaction mixture was stirred at room temperature for 4 h. Reaction mixture was diluted with water (30 mL) and was extracted with DCM (50 mL×2). Combined organic extracts were dried over anhydrous $Na_2SO_4$ and concentrated under reduced pressure. The crude product was purified by $C^{18}$ silica gel column chromatography, using acetonitrile-water=0:1→6:4 as gradient, 1-isopropyl-3-(2-(4-(trifluoromethyl)phenyl)quinolin-7-yl)urea (I-429) (0.240 g, 53%) as an white solid. $^1H$ NMR (400 MHz, DMSO-$d_6$) δ 9.23 (s, 1H), 8.48-8.46 (d, J=8.0 Hz, 2H), 8.36-8.34 (d, J=8.4 Hz, 1H), 8.284-8.281 (d, J=1.2 Hz, 1H), 8.02-8.00 (d, J=8.4 Hz, 1H), 7.90-7.85 (m, 3H), 7.57-7.54 (dd, J=8.8, 2.0 Hz, 1H), 6.54-6.52 (d, J=7.6 Hz, 1H), 3.86-3.77 (m, 1H), 1.14-1.12 (d, J=6.8 Hz, 6H). MS: [MH]+374.4.

Example 1.336. Synthesis of 4-Methoxy-3-methyl-2-(4-(trifluoromethyl)phenyl)quinoline-7-carboxylic acid (I-430)

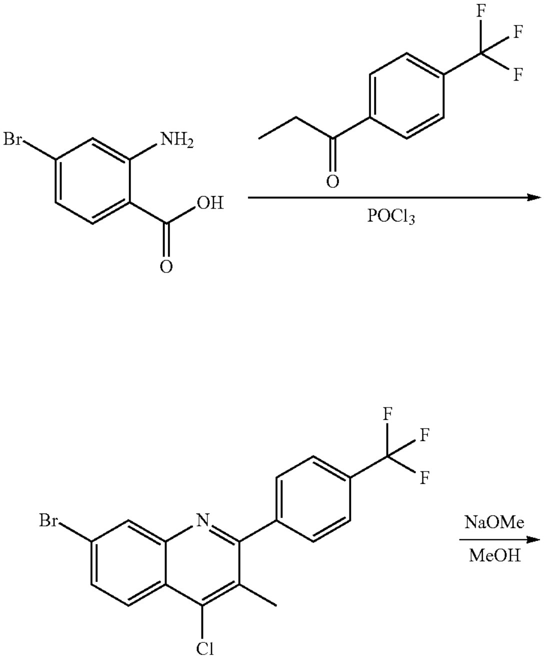

X-1872A1

-continued

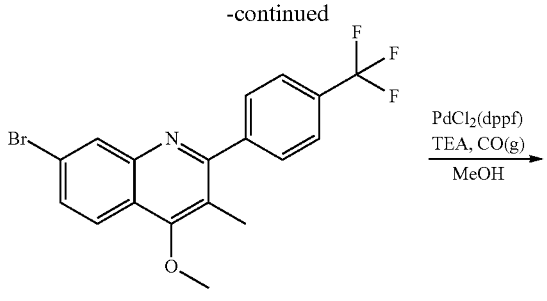

X-1872A2

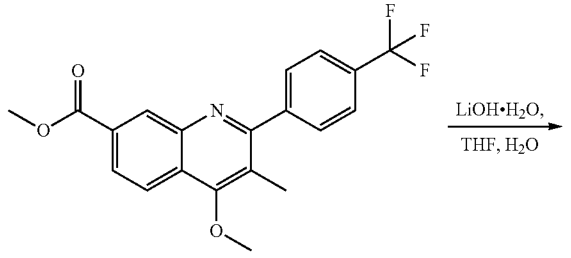

X-1872A3

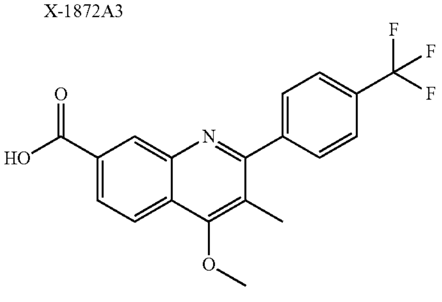

I-430

7-Bromo-4-chloro-3-methyl-2-(4-(trifluoromethyl)phenyl)quinoline (X-1872A1). $POCl_3$ (50 ml) was added dropwise via additional funnel to a mixture of 1-(4-(trifluoromethyl)phenyl)propan-1-one (5.0 g, 24.75 mmol) and methyl 2-amino-4-bromobenzoic acid (8.0 g, 37.12 mmol) at 0° C. under nitrogen. After complete addition of $POCl_3$, the reaction mixture was slowly brought to reflux and continued heating at 80° C. for 16 h. After cooling to room temperature, reaction mixture was slowly quenched with an aqueous solution of saturated $NaHCO_3$ and was extracted with ethyl acetate (200 mL×3). Combined organic extracts were dried over anhydrous $Na_2SO_4$ and concentrated under reduce pressure. The crude product was purified by silica gel column chromatography, using ethyl acetate-hexane=0:1→1:9 as gradient to afford 7-bromo-4-chloro-3-methyl-2-(4-(trifluoromethyl)phenyl)quinoline (X-1872A1) (3.5 g, 35%) as a Brown solid. MS: $[MH]^+$ 400.3/$[MH+2]^+$ 402.2.

7-Bromo-4-methoxy-3-methyl-2-(4-(trifluoromethyl)phenyl)quinoline (X-1872A2). To a stirred solution of 7-bromo-4-chloro-3-methyl-2-(4-(trifluoromethyl)phenyl)quinoline (X-1872A2) (3.0 g, 75.20 mmol) in MeOH (50 mL) were added sodium methoxide (1.62 g, 30.08 mmol) and the resulting mixture was heated at 85° C. for 16 h. After cooling to room temperature, reaction mixture was directly concentrated after that reaction mixture was diluted with water (50 mL) and was extracted with ethyl acetate (50 mL×3). Combined organic extracts were dried over anhydrous $Na_2SO_4$ and concentrated under reduce pressure to afford methyl 7-bromo-4-methoxy-3-methyl-2-(4-(trifluoromethyl)phenyl)quinoline (X-1872A2) (1.5 g, 50%) as an off-white solid. MS: $[MH]^+$ 396.3/$[MH+2]^+$ 398.3.

Methyl 4-methoxy-3-methyl-2-(4-(trifluoromethyl)phenyl)quinoline-7-carboxylate (X-1872A3). To a stirred solution of methyl 7-bromo-4-methoxy-3-methyl-2-(4-(trifluoromethyl)phenyl)quinoline (X-1872A2) (0.400 g, 1.01 mmol) in MeOH (6 mL) was added TEA (1.02 g, 10.12 mmol) at room temperature under nitrogen. The reaction mixture was degassed [purging with $CO_{(g)}$] for 20 min followed by addition of $PdCl_2$(dppf)DCM (0.165 g, 0.202 mmol), the reaction mixture was heated at 80° C. under $CO_{(g)}$ for 2 h. After cooling to room temperature, reaction mixture diluted with water (100 mL) and was extracted with ethyl acetate (150 mL×3). The combined organic extracts were dried over anhydrous $Na_2SO_4$ and concentrated under reduced pressure, Isolated crude was combined with an identical prepared two more batch (0.400 g) and the combined crude product was purified by silica gel column chromatography, using ethyl acetate-hexane=0:1→2:8 as gradient, to afford methyl 4-methoxy-3-methyl-2-(4-(trifluoromethyl)phenyl)quinoline-7-carboxylate (X-1872A3) (1.0 g, 87%) as a white solid. MS: $[MH]^+$ 376.3.

4-Methoxy-3-methyl-2-(4-(trifluoromethyl)phenyl)quinoline-7-carboxylic acid (I-430). To a stirred solution of methyl 4-methoxy-3-methyl-2-(4-(trifluoromethyl)phenyl)quinoline-7-carboxylate (X-1872A1) (0.500 g, 1.33 mmol) in a mixture of THE-water (3:1; 5.5 mL) was added lithium hydroxide monohydrate (0.167 g, 3.99 mmol) at room temperature and the resulting mixture was stirred at 70° C. for 1 h. Reaction mixture was concentrated under reduced pressure, crude was diluted with water and aqueous part was acidified (pH~2-3) with an aqueous solution of 1N HCl and the resulting precipitate was collected by filtration. The crude product was triturated using n-pentane to afford 4-methoxy-3-methyl-2-(4-(trifluoromethyl)phenyl)quinoline-7-carboxylic acid (I-430) (0.450 g, 93%) as an off-white. $^1H$ NMR (400 MHz, DMSO-$d_6$) δ 13.41-13.36 (br, 1H), 8.557-8.555 (d, J=0.8 Hz, 1H), 8.22-8.19 (d, J=8.8 Hz, 1H), 8.12-8.09 (dd, J=8.8, 1.6 Hz, 1H), 7.90 (s, 4H), 4.04 (s, 3H), 2.37 (s, 3H). MS: $[MH]^+$ 362.3.

Example 1.337. Synthesis of (R)—N-(1-hydroxypropan-2-yl)-4-methoxy-3-methyl-2-(4-(trifluoromethyl)phenyl)quinoline-7-carboxamide (I-431)

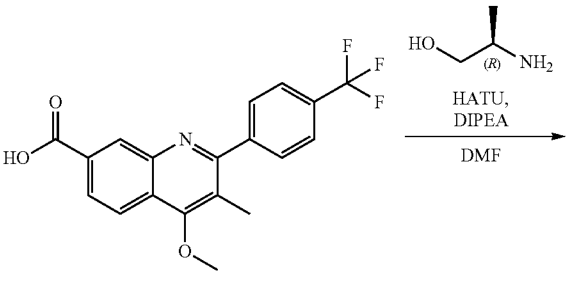

I-430

-continued

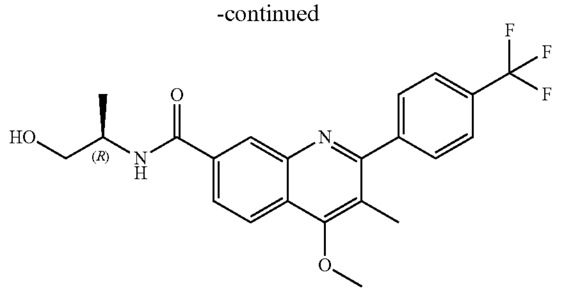

I-431

To a stirred solution of 4-methoxy-3-methyl-2-(4-(trifluoromethyl)phenyl)quinoline-7-carboxylic acid (I-430) (0.250 g, 0.692 mmol) in DMF (3.5 mL) were added DIPEA (0.357 g, 2.76 mmol) and HATU (0.394 g, 10.38 mmol) sequentially at 0° C. under nitrogen. After stirring for 30 min at the same temperature, was added (R)-2-aminopropan-1-ol (0.155 g, 2.07 mmol) was added at 0° C. and the resulting reaction mixture was stirred at room temperature for 48 h. After completion of reaction, reaction mixture was slowly poured in ice water (100 mL), obtained precipitates were filtered and the residue was washed with water (100 mL). Solid precipitate was, dried under high vacuum to afford (R)—N-(1-hydroxypropan-2-yl)-4-methoxy-3-methyl-2-(4-(trifluoromethyl)phenyl)quinoline-7-carboxamide (I-431) (0.230 g, 79%) as an off-white solid. 1H NMR (400 MHz, DMSO-$d_6$) δ 8.60-8.59 (d, J=1.2 Hz, 1H), 8.45-8.43 (d, J=8.0 Hz, 1H), 8.17-8.15 (d, J=8.4 Hz, 1H), 8.08-8.05 (dd, J=8.8, 1.6 Hz, 1H), 7.92-7.88 (m, 4H), 4.78-4.75 (t, J=6.0 Hz, 1H), 4.11-4.04 (m, 1H), 4.04 (s, 3H) 3.53-3.48 (m, 1H), 3.41-3.34, 1H), 2.37 (s, 3H), 1.17-1.16 (d, J=6.4 Hz, 3H), MS: $[MH]^+$419.4. Chiral HPLC: 100%.

Example 1.338. Synthesis of 4-ethoxy-2-(4-(trifluoromethyl)phenyl)quinazoline-7-carboxylic acid (I-432)

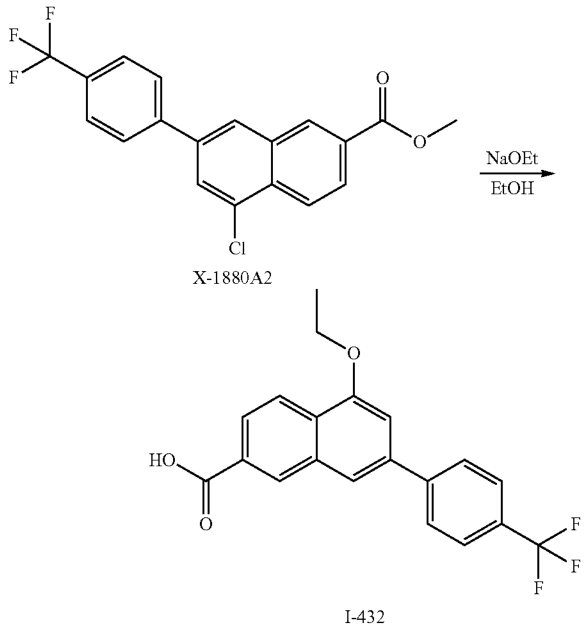

X-1880A2

I-432

To a stirred solution of methyl 4-chloro-2-(4-(trifluoromethyl)phenyl)quinazoline-7-carboxylate (X-1880A2) (0.200 g, 0.56 mmol) in ethanol (7 mL) was added NaOEt (0.074 g, 1.09 mmol) at 0° C. under nitrogen and stirred at 80° C. for 2 h. Reaction mixture was concentrated under reduced pressure, obtained crude was acidified (pH~2-3) with an aqueous solution of 1N HCl and the resulting precipitate was collected by filtration. Crude residue was washed with cold water until the pH of the filtrate became neutral (pH~6-7). Obtained crude was purified by reverse phase (C-18) silica gel column chromatography, using acetonitrile-water=0:1→4:6 as a gradient, to afford 4-ethoxy-2-(4-(trifluoromethyl)phenyl)quinazoline-7-carboxylic acid (I-432) (0.100 g, 57%) as a yellow solid. $^1H$ NMR (400 MHz, DMSO-$d_6$) δ 13.69 (br. s, 1H), 8.70-8.68 (d, J=8.4 Hz, 2H), 8.47-8.46 (d, J=1.2 Hz, 1H), 8.25-8.23 (d, J=8.4 Hz, 1H), 8.13-8.11 (dd, J=1.6 Hz, J=8.8 Hz, 1H), 7.93-7.91 (d, J=8.0 Hz, 2H), 4.80-4.75 (m, 2H), 1.55-1.51 (t, J=7.2 Hz, 3H). MS: $[MH]^+$ 363.4

Example 1.339. Synthesis of 4-methoxy-2-(4-(trifluoromethyl)phenyl)quinazoline-7-carboxylic acid (I-433)

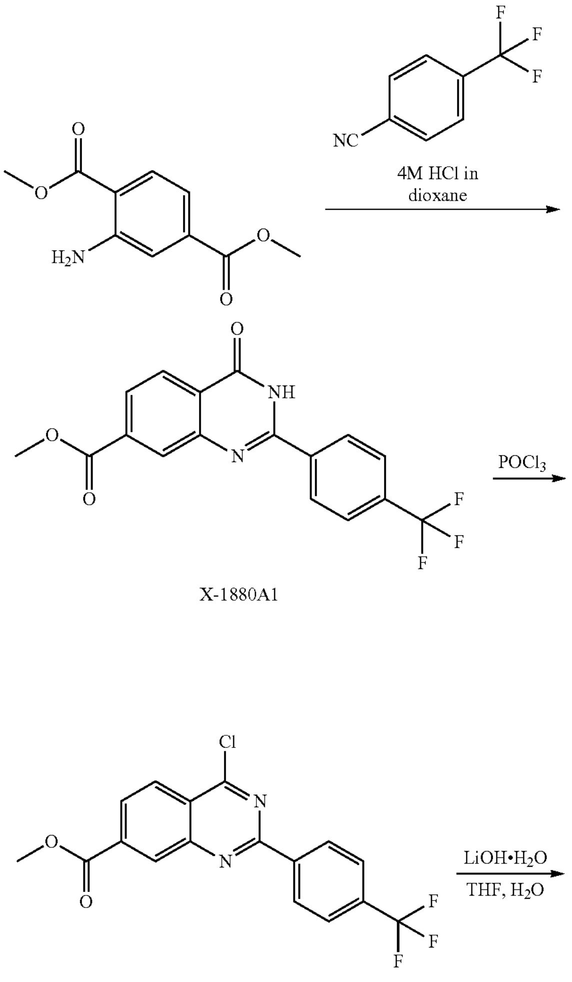

X-1880A1

X-1880A2

-continued

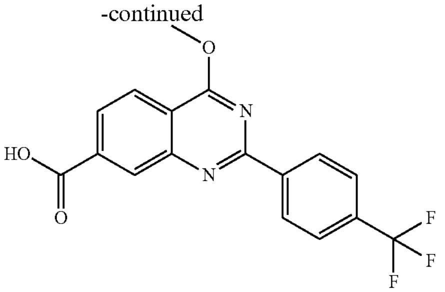

I-433

Methyl 4-oxo-2-(4-(trifluoromethyl)phenyl)-3,4-dihydroquinazoline-7-carboxylate (X-1880A1). 4-(Trifluoromethyl) benzonitrile (0.440 g, 2.63 mmol) was added to a stirred suspension of dimethyl 2-aminoterephthalate (0.500 g, 2.39 mmol) in 4M HCl in 1,4-dioxane (8 mL) in a pressure vial at room temperature and the resulting mixture was heated at 110° C. for 16 h. After cooling to room temperature, reaction mixture was slowly poured into ice water (100 mL) and was extracted with ethyl acetate (100 mL×3). Combined organic extracts were dried over anhydrous $Na_2SO_4$ and concentrated in under reduced pressure, to afford methyl 4-oxo-2-(4-(trifluoromethyl)phenyl)-3,4-dihydroquinazoline-7-carboxylate (X-1880A1) (0.480 g, 69%) as a white solid. MS: $[MH]^+$ 349.30.

Methyl 4-chloro-2-(4-(trifluoromethyl)phenyl)quinazoline-7-carboxylate (X-1880A2). A solution of methyl 4-oxo-2-(4-(trifluoromethyl)phenyl)-3,4-dihydroquinazoline-7-carboxylate (X-1880A1) (0.500 g, 1.43 mmol) in $POCl_3$ (10 mL) was heated at 120° C. for 16 h. After cooling to room temperature, reaction mixture was slowly poured in ice water (200 mL), basified (pH~7-8) with slow addition of an aqueous solution of saturated $NaHCO_3$ and was extracted by ethyl acetate (100 mL×3). Combined organic extracts were dried over anhydrous $Na_2SO_4$ and concentrated under reduced pressure. The crude product was product was purified by silica gel column chromatography, using ethyl acetate-hexane=0:1→1:9 as a gradient, to afford methyl 4-chloro-2-(4-(trifluoromethyl)phenyl)quinazoline-7-carboxylate (X-1880A2) (0.320 g, 60%) as a white solid. MS: $[MH]^+$ 367.28.

4-Methoxy-2-(4-(trifluoromethyl)phenyl)quinazoline-7-carboxylic acid (I-433). To a stirred solution of methyl 4-chloro-2-(4-(trifluo methyl)phenyl)quinazoline-7-carboxylate (X-1880A2) (0.200 g, 0.54 mmol) in a mixture of THF-Methanol-water (2:2:1; 5.0 mL) was added lithium hydroxide monohydrate (0.127 g, 3.03 mmol) at room temperature. Reaction mixture was stirred at 70° C. for 2 h. After cooling to room temperature, the reaction mixture was concentrated under reduced pressure and acidified (pH~2-3) with an aqueous solution of 1N HCl and the resulting precipitate was collected by filtration. Crude residue was washed with cold water until the pH of the filtrate became neutral (pH~6-7). Obtained solid was dried under reduced pressure and the resulting crude was purified by (C-18) silica gel column chromatography, using acetonitrile:water=0:1→3:7 as gradient, to afford 4-methoxy-2-(4-(trifluoromethyl)phenyl)quinazoline-7-carboxylic acid (I-433) (0.050 g, 26%) as an off-white solid. $^1H$ NMR (400 MHz, DMSO-$d_6$) δ: 8.74-8.72 (d, J=8.0 Hz, 2H), 8.47 (s, 1H), 8.23-8.21 (d, J=8.4 Hz, 1H), 8.15-8.13 (dd, J=1.2 & 8.4 Hz, 1H), 7.95-7.92 (d, J=8.4 Hz, 2H), 4.30 (s, 3H). MS: $[MH]^+$ 349.33.

Example 1.340. Synthesis of (R)—N-(1-hydroxypropan-2-yl)-4-methoxy-2-(4-(trifluoromethyl)phenyl)quinazoline-7-carboxamide (I-434)

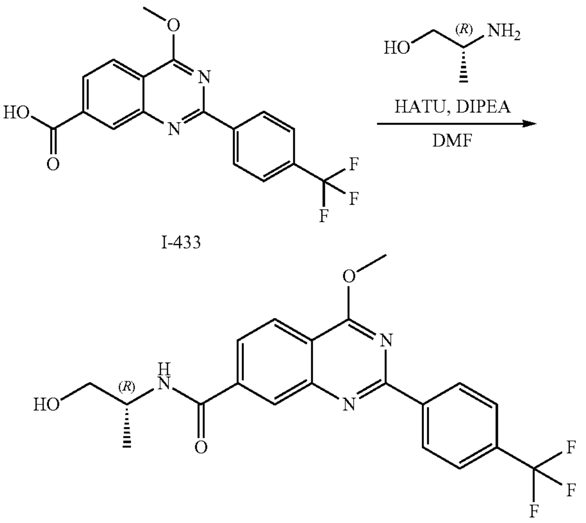

I-433

I-434

To a stirred solution of 4-methoxy-2-(4-(trifluoromethyl) phenyl)quinazoline-7-carboxylic acid (I-433) (0.400 g, 1.19 mmol) in a DMF (5 mL) were added DIPEA (0.444 g, 3.44 mmol) and HATU (0.873 g, 2.29 mmol) sequentially at 0° C. under nitrogen. After stirring for 10 min at the same temperature, was added (R)-2-aminopropan-1-ol (0.172 g, 2.29 mmol) into the reaction solution and stirring was continued at the room temperature for 16 h. Reaction mixture was slowly poured into ice-water (200 mL) and was extracted with ethyl acetate (100 mL×3). Combined organic extracts were washed with brine (100 mL), dried over anhydrous $Na_2SO_4$ and concentrated in vacuo. Obtained crude was purified by reverse phase (C-18) silica gel column chromatography, using acetonitrile:water=0:1→4:6 as a gradient, to afford (R)—N-(1-hydroxypropan-2-yl)-4-methoxy-2-(4-(trifluoromethyl)phenyl)quinazoline-7-carboxamide (I-434) (0.250 g, 53%) as an off-white solid. 1 NMR (400 MHz, DMSO-$d_6$) δ: 8.75-8.73 (d, J=8.4 Hz, 2H), 8.58-8.56 (d, J=8.0 Hz, 1H), 8.52 (d, J=1.2 Hz 1H), 8.26-8.24 (d, J=8.4 Hz, 1H), 8.10-8.08 (dd, J=1.6, 8.4 Hz, 1H), 7.97-7.95 (d, J=8.4 Hz, 2H), 4.80-4.77 (t, J=6.0, 5.6 Hz, 1H), 4.31 (s, 3H), 4.12-4.05 (m, 1H), 3.54-3.49 (m, 1H), 3.41-3.33 (m, 1H), 1.19-1.17 (d, J=6.8 Hz, 3H) MS: $[MH]^+$ 406.4.

Example 1.341. Synthesis of 4-methyl-2-(4-(trifluoromethyl)phenyl)quinazoline-7-carboxylic acid (I-435)

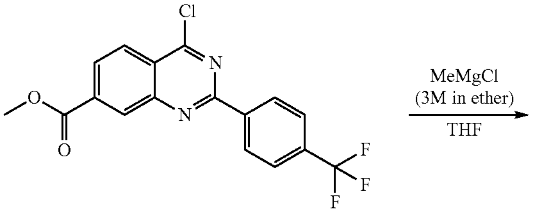

X-1880A2

-continued

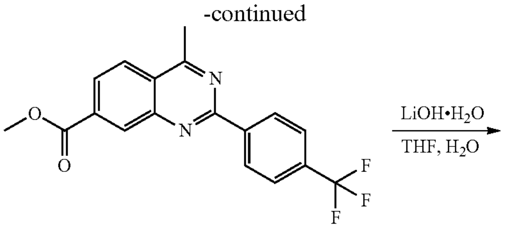

X-1882A1

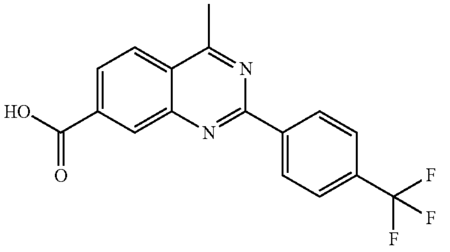

I-435

Methyl 4-methyl-2-(4-(trifluoromethyl)phenyl)quinazoline-7-carboxylate (X-1882A1). To a stirred solution of methyl 4-chloro-2-(4-(trifluoromethyl)phenyl)quinazoline-7-carboxylate (X-1880A2) (0.650 g, 1.77 mmol) in dry THF (10 mL) was added iron (III) acetylacetonate (0.087 g, 0.24 mmol) at room temperature. The reaction mixture was cooled at −10° C. and methyl magnesium bromide (3.0M in diethyl ether) (0.024 g, 12.43 mmol) was added at same temperature and reaction mixture was stirred at −10° C. for 15 min. Reaction mixture was quenched with a saturated aqueous $NH_4Cl$ solution (100 mL) and was extracted by ethyl acetate (100 mL×2). Combined organic extracts were dried over anhydrous $Na_2SO_4$ and concentrate under reduce pressure. The crude product was purified by silica gel column chromatography, using ethyl acetate-hexane=0:1→3:7 as a gradient, to afford methyl 4-methyl-2-(4-(trifluoromethyl)phenyl)quinazoline-7-carboxylate (X-1882A1) (0.350 g, 74%) as a yellow solid. MS: $[MH]^+$ 347.32.

4-Methyl-2-(4-(trifluoromethyl)phenyl)quinazoline-7-carboxylic acid (I-435). To a stirred solution of methyl 4-methyl-2-(4-(trifluoromethyl)phenyl)quinazoline-7-carboxylate (X-1882A1) (0.350 g, 1.01 mmol) in a mixture of THF-water (3:1; 5.0 nL) was added lithium hydroxide monohydrate (0.127 g, 3.03 mmol) at room temperature. Reaction mixture was stirred at 70° C. for 2 h. After cooling to room temperature, the reaction mixture was concentrated under reduced pressure, obtained crude was diluted with water (40 mL) and was extracted with ethyl acetate (40 mL×2) to remove unwanted organic impurities. Aqueous part was acidified (pH~2-3) with an aqueous solution of 1N HCl and the resulting precipitate was collected by filtration. Crude residue was washed with cold water until the pH of the filtrate became neutral (pH~6-7). Obtained solid was dried under reduced pressure, to afford 4-methyl-2-(4-(trifluoromethyl)phenyl)quinazoline-7-carboxylic acid (I-435) (0.280 g, 75%) as an off-white solid. $^1H$ NMR (400 MHz, DMSO-$d_6$) δ: 13.85 (bs, 1H), 8.76-8.74 (d, J=8.0 Hz, 2H), 8.55 (d, J=0.8 Hz, 1H), 8.42-8.39 (d, J=8.4 Hz, 1H), 8.19-8.16 (dd, J=1.2, 8.8 Hz, 1H), 7.95-7.93 (d, J=8.4 Hz, 2H), 3.05 (s, 3H). MS: $[MH]^+$ 333.3.

Example 1.342. Synthesis of (R)—N-(1-hydroxypropan-2-yl)-4-methyl-2-(4-(trifluoromethyl)phenyl)quinazoline-7-carboxamide (I-436)

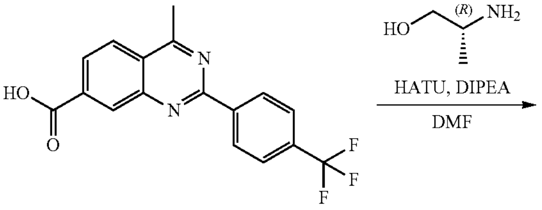

I-435

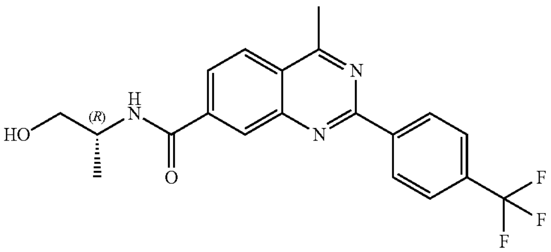

I-436

The following compound was synthesized in a manner analogous to the procedures described above for (R)—N-(1-hydroxypropan-2-yl)-4-methoxy-2-(4-(trifluoromethyl)phenyl)quinazoline-7-carboxamide (I-434):

(R)—N-(1-hydroxypropan-2-yl)-4-methyl-2-(4-(trifluoromethyl)phenyl)quinazoline-7-carboxamide (I-436) (0.150 g, 65%) as an off-white solid. $^1H$ NMR (400 MHz, DMSO-$d_6$) δ: 8.77-8.75 (d, J=8.0 Hz, 1H), 8.62-8.59 (m, 2H), 8.41-8.39 (d, J=8.4 Hz, 1H), 8.15-8.12 (dd, J=1.2, 8.4 Hz, 1H), 7.97-7.95 (d, J=8.4 Hz, 2H), 4.81-7.78 (t, J=6.0 Hz, 1H), 4.13-4.06 (m, 1H), 3.55-3.50 (m, 1H), 3.44-333 (m, 1H), 3.061 (s, 3H), 1.22-1.28 (t, J=11.6 Hz, 3H), MS: $[MH]^+$ 390.4.

Example 1.343. Synthesis of—N-((8-(6-azaspiro[2.5]octan-6-yl)imidazo[1,2-a]pyrazin-6-yl)methyl)acrylamide (I-437)

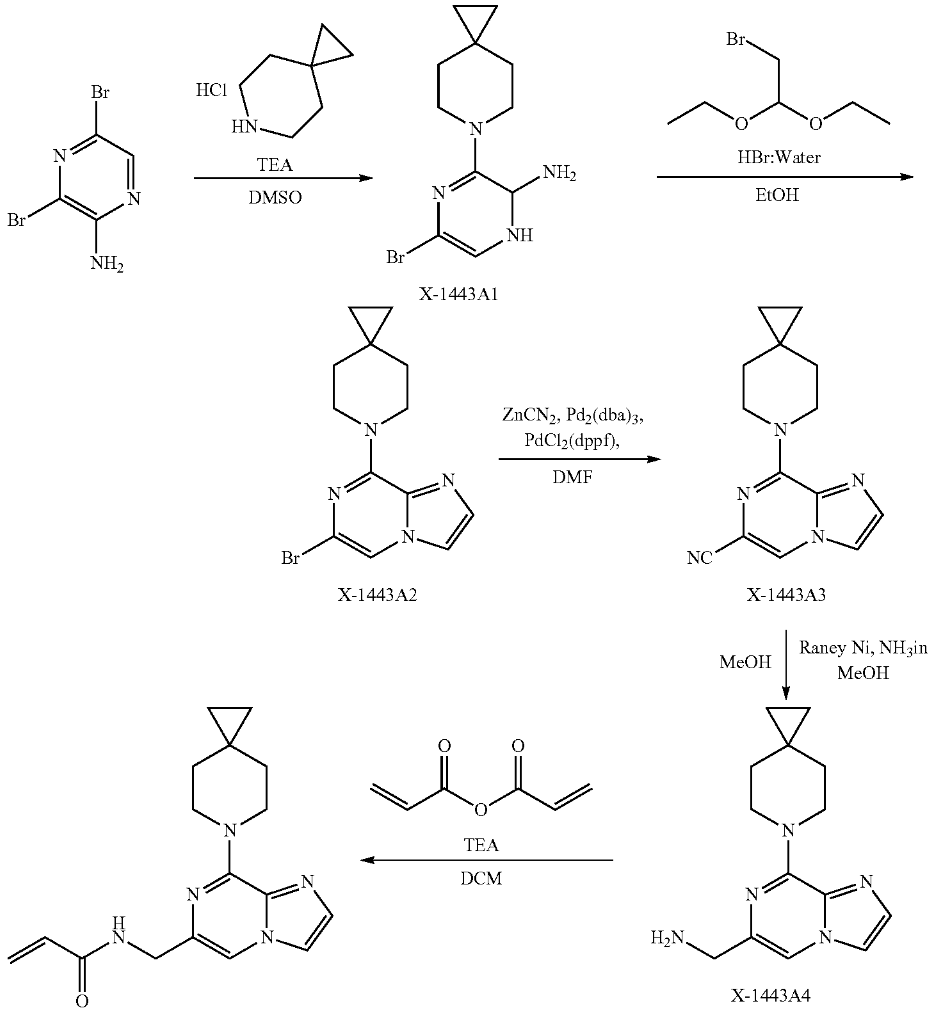

X-1443A1

X-1443A2

X-1443A3

X-1443A4

I-437

5-Bromo-3-(6-azaspiro[2.5]octan-6-yl)-1,2-dihydropyrazin-2-amine (X-1443A1). To a stirred solution of 3,5-dibromopyrazin-2-amine (5.6 g, 22.40 mmol) in DMSO (25 mL) were added TEA (9.8 mL, 167.20 mmol) and 6-azaspiro[2.5]octane (3.3 g, 22.40 mmol) at room temperature under nitrogen and the resulting mixture was stirred at 120° C. for 16 h. The reaction mixture was slowly poured into ice-water (150 mL), solid product was precipitated which was collected by filtration, dried under reduced pressure. to afford 5-bromo-3-(6-azaspiro[2.5]octan-6-yl)-1,2-dihydropyrazin-2-amine (X-1443A1) (4.5 g, 71%) as a yellow solid. MS: $[MH]^+$ 283.0/$[MH+2]^+$ 284.9.

6-Bromo-8-(6-azaspiro[2.5]octan-6-yl)imidazo[1,2-a]pyrazine (X-1443A2). To a stirred solution of 5-bromo-3-(6-azaspiro[2.5]octan-6-yl)-1,2-dihydropyrazin-2-amine (X-1443A1) (1.1 g, 3.87 mmol) in ethanol (10 mL) was added 2-bromo-1,1-diethoxyethane (1.51 g, 7.74 mmol) at room temperature under nitrogen, HBr in $H_2O$ (48%) (2.19 g, 27.09 mmol) was added at 0° C., and resulting mixture was heated at 80° C. for 3 h. Reaction mixture was cooled to room temperature, slowly poured into water (100 mL) and was extracted with ethyl acetate (100 mL×3). The combined organic extracts were washed with brine (50 mL), dried over anhydrous $Na_2SO_4$ and concentrated under reduced pressure. Another 3 identical batches (1.1 g) performed and workup done together. The crude product was purified by silica gel column chromatography, using ethyl acetate-hexane=0:1→1:9 as gradient, to afford 6-bromo-8-(6-azaspiro[2.5]octan-6-yl)imidazo[1,2-a]pyrazine (X-1443A2) (0.800 g, 17%) as a brown solid. MS: $[MH]^+$ 306.9 $[M+H]/[M+2H]^+$ 308.8

8-(6-Azaspiro[2.5]octan-6-yl)imidazo[1,2-a]pyrazine-6-carbonitrile (X-1443A3). To a stirred solution of 6-bromo-8-(6-azaspiro[2.5]octan-6-yl)imidazo[1,2-a]pyrazine (X-1443A2) (0.600 g, 1.96 mmol) in DMF (6 mL) was added zinc cyanide (0.690 g, 5.88 mmol) at room temperature under nitrogen. The reaction mixture was degassed (by purging nitrogen) for 30 min followed by the addition of $PdCl_2(dppf)$ (0.071 g, 0.098 mmol) and $Pd_2(dba)_3$ (0.089 g, 0.098 mmol) and resulting mixture was heated at 120° C.

under microwave irradiation for 1 h. Reaction mixture was cooled to room temperature, slowly poured into water (120 mL) and was extracted with ethyl acetate (100 mL×3). The combined organic extracts were washed with brine (50 mL), dried over anhydrous $Na_2SO_4$ and concentrated under reduced pressure. The crude product was purified by silica gel column chromatography, using ethyl acetate-hexane=0:1→4 3:7 as gradient, 8-(6-azaspiro[2.5]octan-6-yl)imidazo[1,2-a]pyrazine-6-carbonitrile (X-1443A3) (0.200 g, 40%) as a brown solid. MS: $[MH]^+$ 253.80.

(8-(6-Azaspiro[2.5]octan-6-yl)imidazo[1,2-a]pyrazin-6-yl)methanamine (X-1443A4). To a stirred solution of 8-(6-azaspiro[2.5]octan-6-yl)imidazo[1,2-a]pyrazine-6-carbonitrile (X-1443A3) (0.200 g, 0.79 mmol) in THE (8 mL) were added Raney Nickel (~0.150 g) and ammonia in MeOH (4 mL) at room temperature and the resulting mixture was hydrogenated in Parr Autoclave at 70° C. under 200 psi for 3 h. Reaction mixture was cooled to room temperature, filtered over a celite bed, washed the bed with MeOH (50 mL×2) and collected filtrates were concentrated under reduced pressure to give (8-(6-azaspiro[2.5]octan-6-yl)imidazo[1,2-a]pyrazin-6-yl)methanamine (X-1443A4) [0.200 g, (crude)] as a yellow sticky solid. MS: $[MH]^+$ 258.10.

N-((8-(6-Azaspiro[2.5]octan-6-yl)imidazo[1,2-a]pyrazin-6-yl)methyl)acrylamide (I-437). To a stirred solution of (8-(6-azaspiro[2.5]octan-6-yl)imidazo[1,2-a]pyrazin-6-yl)methanamine (X-1443A4) (0.200 g, 0.77 mmol) in DCM (8 mL) were added TEA (0.157 g, 1.55 mmol) followed by acrylic anhydride (0.117 g, 0.92 mmol) at 0° C. under nitrogen and the reaction mixture stirred for 30 min at same temperature. The reaction mixture was slowly poured into water (50 mL) and was extracted with DCM (50 mL×3). The combined organic extracts were washed with brine (30 mL), dried over anhydrous $Na_2SO_4$ and concentrated in under reduced pressure. The resulting crude was purified by reverse phase (C-18) silica gel column chromatography using acetonitrile-water=0:1→3:7 as gradient, N-((8-(6-azaspiro[2.5]octan-6-yl)imidazo[1,2-a]pyrazin-6-yl)methyl)acrylamide (I-437) (0.070 g, 29%) as an off white solid. 1H NMR (400 MHz, DMSO-$d_6$) δ 8.54 (m, 1H), 7.92 (s, 1H), 7.71 (s, 1H), 7.50 (s, 1H), 6.35-6.28 (m, 1H), 6.14-6.09 (dd, J=16.8, 2.0 Hz, 1H), 5.64-5.61 (dd, J=10.0, 2.0 Hz, 1H), 4.26 (brs, 4H), 4.21-4.19 (d, J=5.6 Hz, 2H), 1.43-1.40 (t, J=5.2 Hz, 4H), 0.36 (s, 4H), MS: $[MH]^+$ 312.21.

Example 1.344. Synthesis of N-((6-(4-(trifluoromethyl)phenyl)imidazo[1,5-a]pyrimidin-8-yl)methyl) acrylamide (I-438)

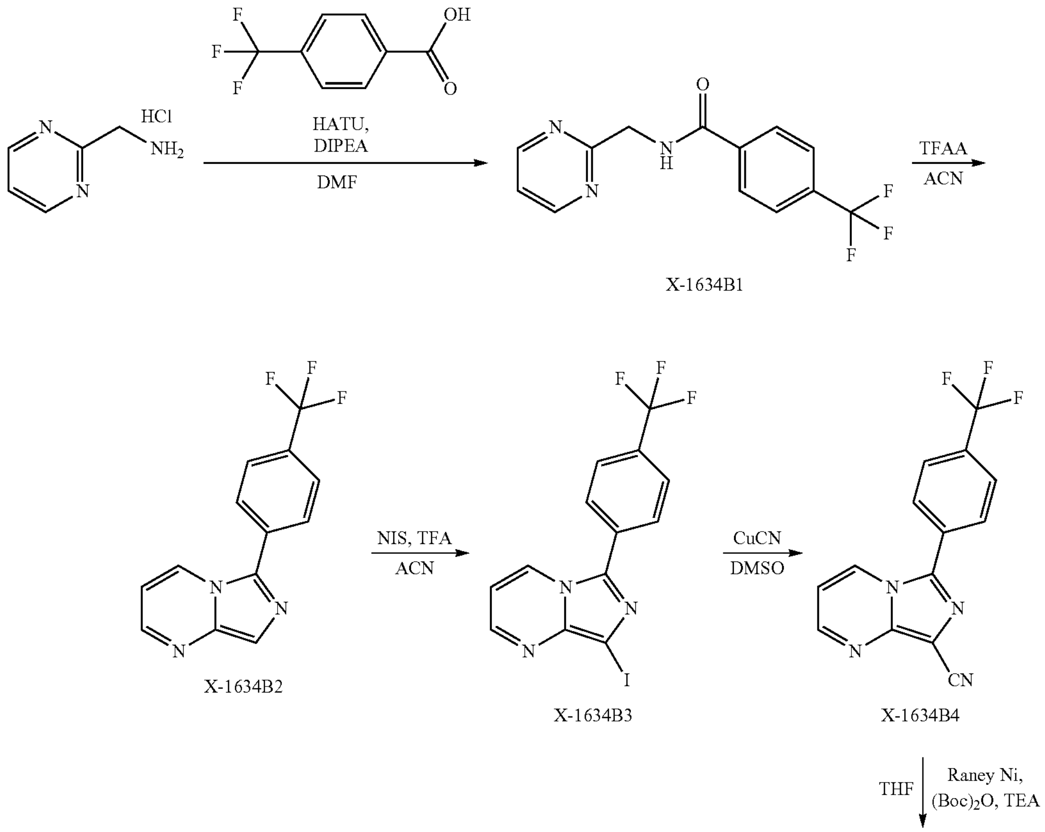

X-1634B1
X-1634B2
X-1634B3
X-1634B4

-continued

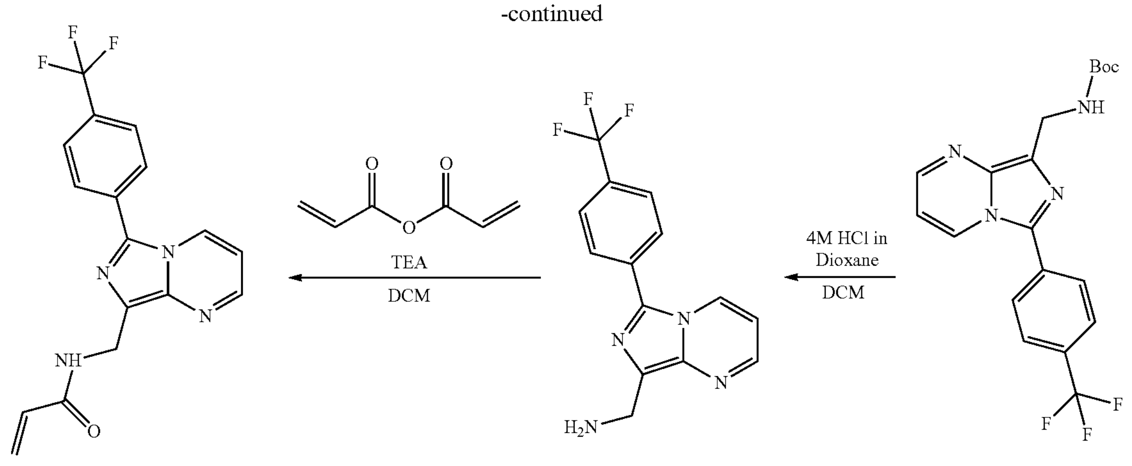

I-438 X-1634B6 X-1634B5

N-(pyrimidin-2-ylmethyl)-4-(trifluoromethyl)benzamide (X-1634B1). To a stirred solution of 4-(trifluoromethyl) benzoic acid (4.0 g, 21 mmol) in DMF (15 mL) were added DIPEA (8.14 g, 63 mmol) and HATU (11.9 g, 31.5 mmol) at room temperature. After sti and stirred for 30 min after to add pyrimidin-2-ylmethanamine (3.07 g, 21.0 mmol) at the same temperature. Reaction mixture was diluted with water (500 mL) and was extracted with ethyl acetate (500 mL×2). Organic extracts were combined, dried over anhydrous $Na_2SO_4$ and concentrated under reduced pressure. Obtained crude was purified by silica gel flash column chromatography, using using ethyl acetate-hexane=0:1→1:0 as gradient, to afford N-(pyrimidin-2-ylmethyl)-4-(trifluoromethyl)benzamide (X-1634B1) (3.5 g, 60%) as a yellow solid. MS: $[MH]^+$ 281.9.

6-(4-(Trifluoromethyl)phenyl)imidazo[1,5-a]pyrimidine (X-1634B2). To a stirred solution of N-(pyrimidin-2-ylmethyl)-4-(trifluoromethyl)benzamide (X-1634B1) (4.5 g, 14.2 mmol) in a ACN (10 mL) was added TFAA (4 mL, 21.3 mmol) at 0° C. dropwise and stirred at room temperature for 30 min. The reaction mixture was concentrated under reduced pressure and the obtained crude product was purified by using n-pentane, to afford 6-(4-(Trifluoromethyl) phenyl)imidazo[1,5-a]pyrimidine (X-1634B2) (4.0 g, 95%) as an colorless oil. MS: $[MH]^+$ 263.93.

8-Iodo-6-(4-(trifluoromethyl)phenyl)imidazo[1,5-a]pyrimidine (X-1634B3). A stirred solution of 6-(4-(trifluoromethyl)phenyl)imidazo[1,5-a]pyrimidine (X-1634B2) (3.5 g, 12.5 mmol) in ACN (10 mL) was added NIS (3.29 g, 14.6 mmol) portion wise at 0° C. under nitrogen and were added TFA (0.30 g, 2.6 mmol) the resulting mixture was stirred at room temperature for 15 min. diluted with $NaHSO_4$ soln. (500 mL) and was extracted with ethyl acetate (500 mL×2). Organic extracts were combined, dried over anhydrous $Na_2SO_4$ and concentrated under reduced pressure. Obtained crude was purified by silica gel flash column chromatography, using using ethyl acetate-hexane=0:1-1:0 as gradient, to afford 8-iodo-6-(4-(trifluoromethyl)phenyl)imidazo[1,5-a] pyrimidine (X-1634B3) (3.5 g, 68%) as a yellow solid. MS: $[MH]^+$ 389.9.

6-(4-(Trifluoromethyl)phenyl)imidazo[1,5-a]pyrimidine-8-carbonitrile (X-1634B4). To a stirred solution of 8-iodo-6-(4-(trifluoromethyl)phenyl)imidazo[1,5-a]pyrimidine (X-1634B4) (3.5 g, 8.99 mmol) in DMSO (10 mL) was added CuCN (1.21 g, 13.4 mmol) at room temperature under nitrogen and the resulting mixture was allowed to stir at 150° C. for 1 h. After cooling to room temperature, reaction mixture was poured in to water (200 mL) and was extracted with ethyl acetate (500 mL×3). Combined organic extracts were dried over anhydrous $Na_2SO_4$ and concentrated under reduced pressure. Obtained crude was purified by silica gel flash column chromatography, using ethyl acetate-hexane=0:1→7:3 as gradient, to afford 6-(4-(trifluoromethyl)phenyl)imidazo[1,5-a]pyrimidine-8-carbonitrile (X-1634B4) (2.5 g, 96%) as a yellow solid. MS: $[MH]^+$ 288.9.

Tert-butyl ((6-(4-(trifluoromethyl)phenyl)imidazo[1,5-a] pyrimidin-8-yl)methyl)carbamate (X-1634B5). To a stirred solution of 6-(4-(trifluoromethyl)phenyl)imidazo[1,5-a]pyrimidine-8-carbonitrile (X-1634B4) (1.0 g, 3.47 mmol) in THE (10 mL) were added activated Raney Nickel (1.0 g), Boc anhydride (1.51 g, 6.94 mmol) and TEA (1.75 g, 17.35 mmol) at room temperature under nitrogen and the resulting mixture was hydrogenated in a Parr autoclave under 200 psi at same temperature for 16 h. reaction mixture was filtered through celite bed, bed was washed with MeOH (100 mL) and collected filtrates were concentrated under reduced pressure. The crude product was purified by silica gel flash column chromatography, using methanol-dichloromethane=0:1→2:8 as to afford tert-butyl ((6-(4-(trifluoromethyl) phenyl)imidazo[1,5-a]pyrimidin-8-yl)methyl)carbamate (X-1634B5) [0.500 g, 42%] as an Colorless oil. MS: $[MH]^+$ 393.01.

(6-(4-(Trifluoromethyl)phenyl)imidazo[1,5-a]pyrimidin-8-yl)methanamine (X-1634B6). To a stirred solution of tert-butyl ((6-(4-(trifluoromethyl)phenyl)imidazo[1,5-a]pyrimidin-8-yl)methyl)carbamate (X-1634B5) (0.400 g, 1.15 mmol) in DCM (5 mL) was added 4M HCl in dioxane (5 mL) at 0° C. and stirred at room temperature for 2 h. The reaction mixture was concentrated under reduced pressure and the obtained crude product was purified by using n-pentane, to afford (6-(4-(trifluoromethyl)phenyl)imidazo [1,5-a]pyrimidin-8-yl)methanamine (X-1634B6) [0.4 g, quantitative] as a white solid. MS: $[MH]^+$ 294.9

N-((6-(4-(trifluoromethyl)phenyl)imidazo[1,5-a]pyrimidin-8-yl)methyl)acrylamide (I-438). Acrylic anhydride (0.179 g, 1.36 mmol) was added to a stirred solution of (6-(4-(trifluoromethyl)phenyl)imidazo[1,5-a]pyrimidin-8-yl)methanamine (X-1634B6) (0.400 g, 1.36 mmol) and tri-ethyl amine (0.412 g, 4.08 mmol) in DCM (5 mL) at 0°

C. temperature under nitrogen. The reaction mixture was stirred for 30 min at same temperature. The reaction mixture was poured in water (50 mL) and was extracted with DCM (50 mL×2). Combined organic extracts were dried over anhydrous $Na_2SO_4$ and concentrated under reduced pressure. The crude product was purified by silica gel flash column chromatography, using ethyl acetate-hexane=0:1→1:0 as to afford N-((6-(4-(trifluoromethyl)phenyl)imidazo[1,5-a]pyrimidin-8-yl)methyl)acrylamide (I-438) (0.12 g, 25%) as an White solid. $^1$H NMR (400 MHz, DMSO-$d_6$) δ 8.96-8.94 (dd, J=7.2, 1.6 Hz, 1H), 8.51-8.50 (m, 1H), 8.31-8.29 (dd, J=3.6, 1.6 Hz, 1H), 8.13-8.10 (d, J=8.4 Hz, 2H), 7.92-7.90 (d, J=8.0 Hz, 2H), 6.91-6.88 (m, 1H), 6.33-6.26 (m, 1H), 6.14-6.09 (dd, J=17.2, 2.4 Hz, 1H), 5.59-5.56 (dd, J=10.0, 2.0 Hz, 1H), 4.72-4.71 (d, J=5.2 Hz, 2H). MS: $[MH]^+$ 346.9.

Example 1.345. Synthesis N-((7-methyl-6-(4-(trifluoromethyl)phenyl)-7H-purin-2-yl)methyl)acrylamide (I-439)

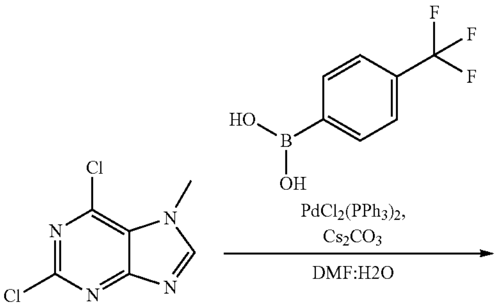

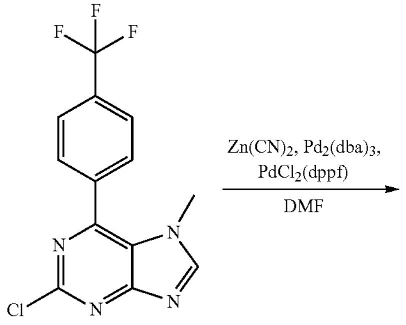

X-1623A1

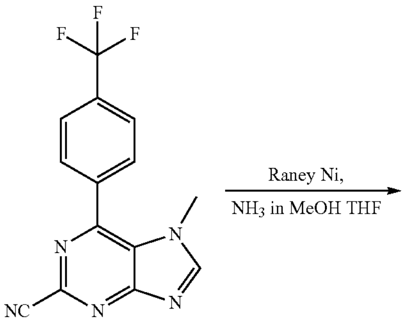

X-1623A2

-continued

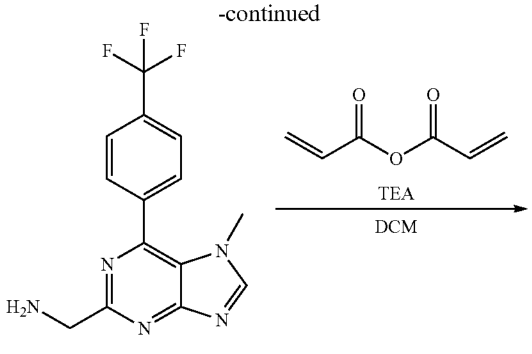

X-1623A3

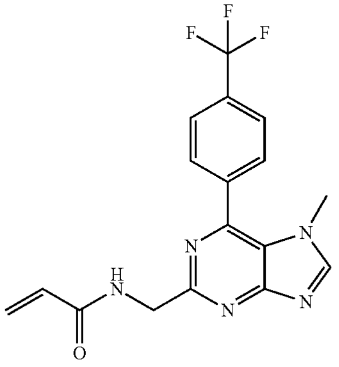

I-439

The following compound was prepared in a manner analogous to the procedures described below for N-((4-(4-(trifluoromethyl)phenyl)-5H-pyrrolo[3,2-d]pyrimidin-2-yl)methyl)acrylamide (I-450):

N-((7-methyl-6-(4-(trifluoromethyl)phenyl)-7H-purin-2-yl)methyl)acrylamide (I-439) (0.100 g, 56%) as an off-white solid. $^1$H NMR (400 MHz, DMSO-$d_6$) δ 8.76-8.71 (m, 2H), 7.98 (brs, 4H), 6.46-6.40 (m, 1H), 6.16-6.11 (d, J=16.8 Hz, 1H), 5.66-5.63 (d, J=10.0 Hz, 1H), 4.70-4.69 (d, J=5.2 Hz, 2H), 3.61 (s, 3H). MS: $[MH]^+$ 362.0

Example 1.346. Synthesis of N-((8-(3-(trifluoromethyl)phenoxy)imidazo[1,2-a]pyrazin-6-yl)methyl)acrylamide (I-171)

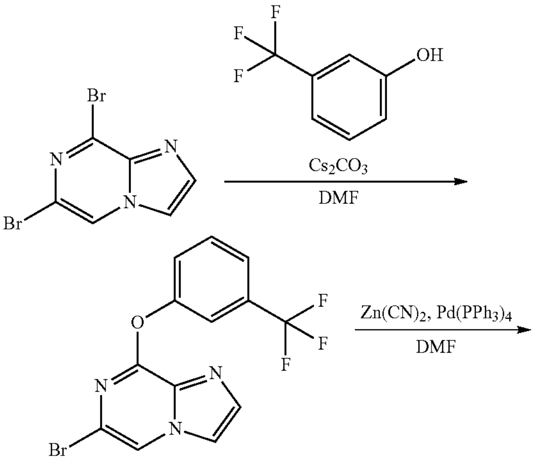

X-1452A1

-continued

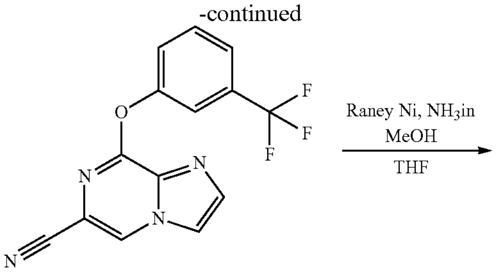

X-1452A2

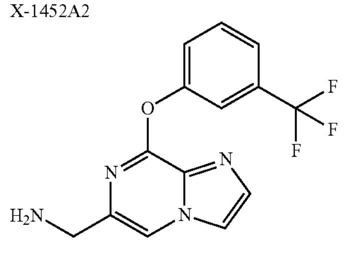

X-1452A3

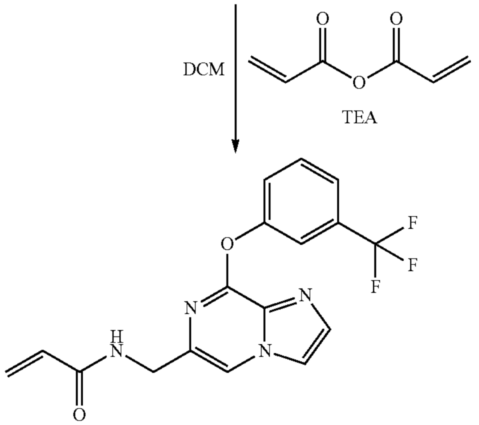

I-171

6-Bromo-8-(3-(trifluoromethyl)phenoxy)imidazo[1,2-a]pyrazine (X-1452A1). To a stirred solution of 6,8-dibromo-imidazo[1,2-a]pyrazine (1.5 g, 5.41 mmol) in DMF (15 mL) were added cesium carbonate (4.5 g, 13.53 mmol) and 3-(trifluoromethyl)phenol (1.0 g, 6.10 mmol) at room temperature under nitrogen and the resulting mixture was stirred at 90° C. for 16 h. The reaction mixture was slowly poured into ice-water (150 mL) and was extracted with ethyl acetate (100 mL×3). The combined organic extracts were washed with brine (100 mL), dried over anhydrous $Na_2SO_4$ and concentrated under reduced pressure. The crude product was purified by silica gel column chromatography, using ethyl acetate-hexane=0:1→1:0 as a gradient, to afford 6-bromo-8-(3-(trifluoromethyl)phenoxy)imidazo[1,2-a]pyrazine (X-1452A1) (1.0 g, 51%) as an off-white solid. MS: $[MH]^+$ 357.7, MS: $[MH]^{+2}$ 359.9

N-((8-(3-(trifluoromethyl)phenoxy)imidazo[1,2-a]pyrazin-6-yl)methyl)acrylamide (I-171). The remaining steps, starting with 6-bromo-8-(3-(trifluoromethyl)phenoxy)imidazo[1,2-a]pyrazine (X-1452A1) were prepared in a manner analogous to the procedures described above for N-((8-(6-azaspiro[2.5]octan-6-yl)imidazo[1,2-a]pyrazin-6-yl)methyl)acrylamide (I-437):

N-((8-(3-(trifluoromethyl)phenoxy)imidazo[1,2-a]pyrazin-6-yl)methyl)acrylamide (I-171) (0.050 g, 14%) as a white solid. $^1H$ NMR (400 MHz, DMSO-$d_6$) δ 8.59 (m, 1H), 8.24-8.21 (d, J=10.8 Hz, 2H), 7.76 (s, 2H), 7.72-7.66 (m, 3H), 6.28-6.22 (m, 1H), 6.12-6.07 (dd, J=17.2, 1.6 Hz, 1H), 5.63-5.60 (dd, J=10.0, 1.6 Hz, 1H), 4.18-4.16 (d, J=5.6 Hz, 2H). MS: $[MH]^+$ 363.2

Example 1.347. Synthesis of N-((8-(4-(trifluoromethoxy)phenyl)imidazo[1,2-a]pyrazin-6-yl)methyl)acrylamide (I-173)

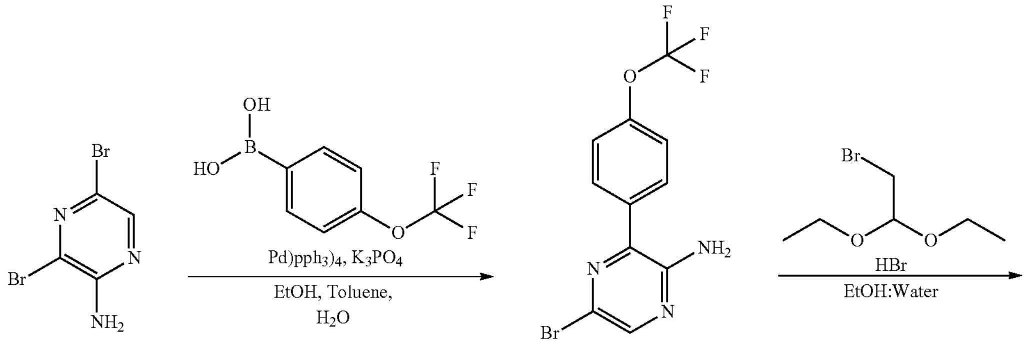

X-1453A1

-continued

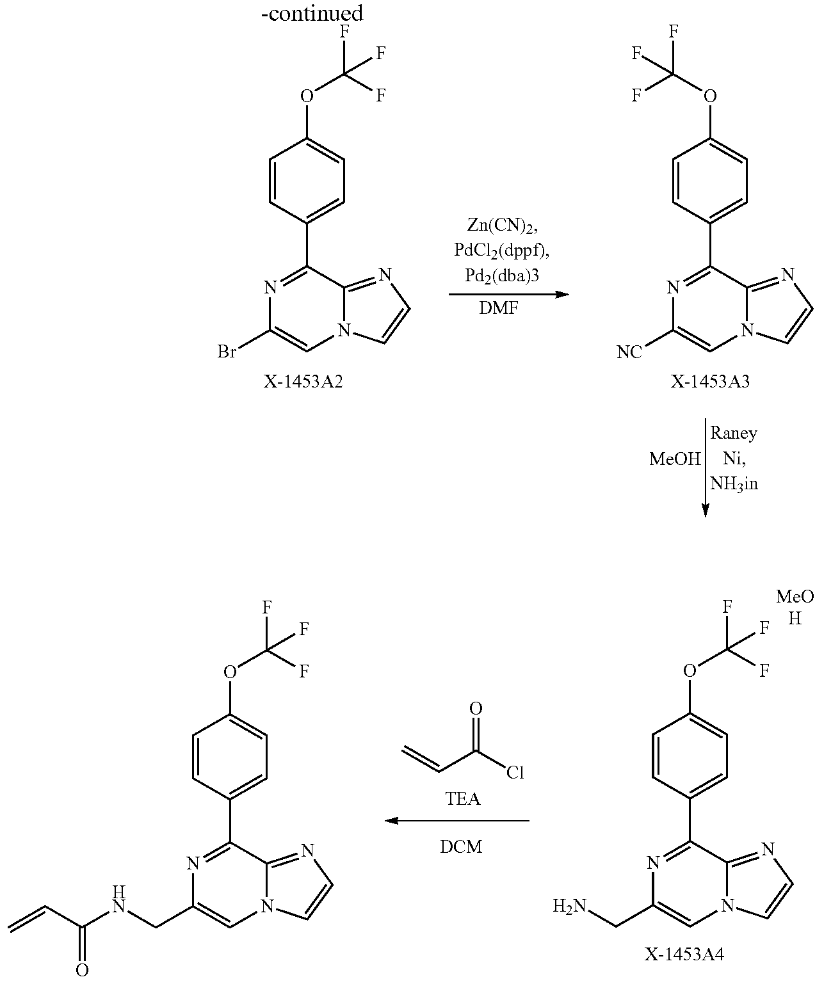

X-1453A2

X-1453A3

X-1453A4

I-173

5-Bromo-3-(4-(trifluoromethoxy)phenyl)pyrazin-2-amine (X-1453A1). To a stirred solution of 3,5-dibromopyrazin-2-amine (3.0 g, 11.85 mmol) in a mixture of toluene-ethanol-water (7:2:1; 30 mL), were added Potassium phosphate (7.50 g, 35.57 mmol) and (4-(trifluoromethoxy) phenyl)boronic acid (2.93 g, 14.20 mmol) at room temperature under nitrogen. The resulting mixture was degassed (purging with nitrogen) for 40 min followed by the addition of $Pd(PPh_3)_4$ (0.412 g, 0.35 mmol) and the resulting mixture was heated at 100° C. for 2 h. Reaction mixture was cooled to room temperature, diluted with water (200 L) and was extracted with ethyl acetate (300 mL×3). Combined organic extracts were washed with brine (200 mL), dried over anhydrous $Na_2SO_4$ and concentrated under reduced pressure. The crude product was purified by silica gel column chromatography, using ethyl acetate-hexane: 0:1→2:8 as a gradient, to afford 5-bromo-3-(4-(trifluoromethoxy)phenyl) pyrazin-2-amine (X-1453A1) (2.8 g, 99%) as an off-white solid. MS: [MH]1333.9, MS: $[NM]^{12}$ 335.8

6-Bromo-8-(4-(trifluoromethoxy)phenyl)imidazo[1,2-a] pyrazine (X-1453A2). To a stirred solution of 5-bromo-3-(4-(trifluoromethoxy)phenyl)pyrazin-2-amine (X-1453A1) (3.0 g, 9.03 mmol) in ethanol (5 mL) was added 2-bromo-1,1-diethoxyethane (3.05 g, 18.07 mmol) at room temperature under nitrogen, HBr (47% in $H_2O$) (5.12 g, 63.21 mmol) was added at 0° C., and resulting mixture was heated at 80° C. for 2 h. Reaction mixture was cooled to room temperature, slowly poured into water (100 mL) and was extracted with ethyl acetate (100 mL×3). The combined organic extracts were washed with brine (50 mL), dried over anhydrous $Na_2SO_4$ and concentrated under reduced pressure. The crude product was purified by silica gel column chromatography, using ethyl acetate-hexane=0:1→1:0 as a gradient, 6-bromo-8-(4-(trifluoromethoxy)phenyl)imidazo[1,2-a] pyrazine (X-1453A2) (1.9 g, 59%) as a brown solid. MS: $[MH]^+$ 357.9, MS: $[MH]^+$ 359.9

N-((8-(4-(trifluoromethoxy)phenyl)imidazo[1,2-a] pyrazin-6-yl)methyl)acrylamide (I-173). The remaining steps, starting with 6-bromo-8-(4-(trifluoromethoxy)phenyl) imidazo[1,2-a]pyrazine (X-1453A2) were prepared in a manner analogous to the procedures described above for N-((8-(6-azaspiro[2.5]octan-6-yl)imidazo[1,2-a]pyrazin-6-yl)methyl)acrylamide (I-437).

N-((8-(4-(trifluoromethoxy)phenyl)imidazo[1,2-a] pyrazin-6-yl)methyl)acrylamide (I-173) (0.050 g, 10%) as a white solid. $^1H$ NMR (400 MHz, DMSO-$d_6$) δ 8.93-8.91 (d, J=8.8 Hz, 2H), 8.79 (m, 1H), 8.54 (s, 1H), 8.27 (s, 1H), 7.89 (s, 1H), 7.58-7.56 (d, J=8.0 Hz, 2H), 6.33-6.30 (m, 1H), 6.17-6.13 (d, J=17.2 Hz, 1H), 5.67-5.64 (d, J=10.4 Hz, 1H), 4.53-4.51 (d, J=5.6 Hz, 2H). MS: $[MH]^+$ 363.0

Example 1.348. Synthesis of N-((6-(4-(trifluoromethyl)phenyl)imidazo[1,2-a]pyrazin-8-yl)methyl) acrylamide (I-440)

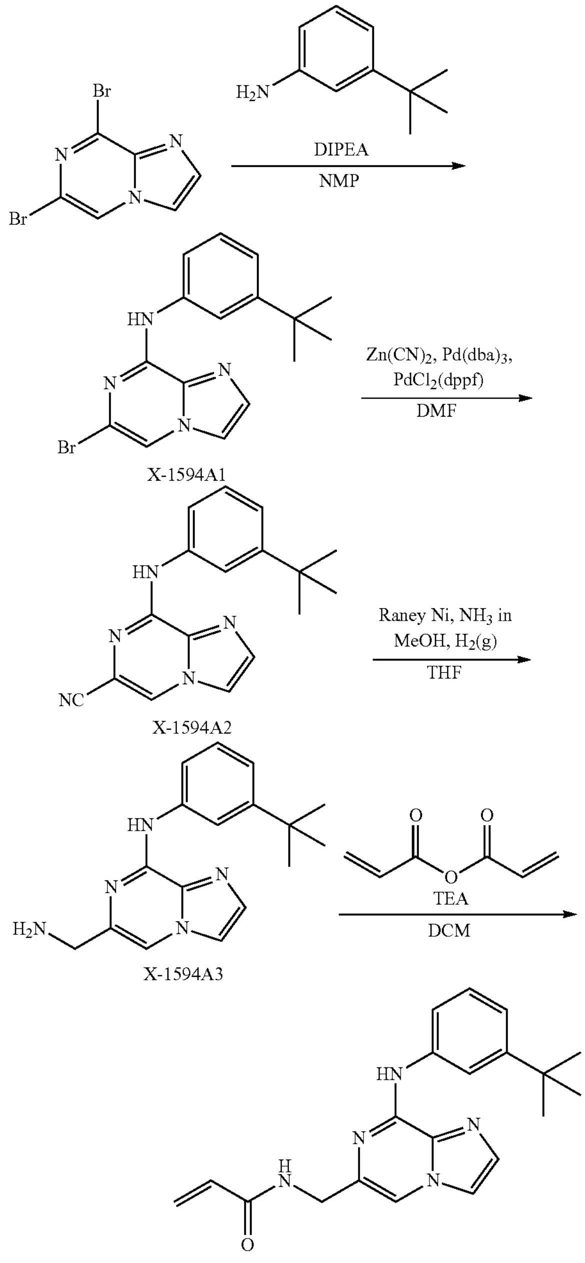

X-1594A1
X-1594A2
X-1594A3

I-440

The following compound was prepared in a manner analogous to the procedures described above for N-((8-(6-azaspiro[2.5]octan-6-yl)imidazo[1,2-a]pyrazin-6-yl)methyl) acrylamide (I-437):

N-((6-(4-(trifluoromethyl)phenyl)imidazo[1,2-a]pyrazin-8-yl)methyl)acrylamide (I-440) (0.070 g, 17%) as an off-white solid. $^1H$ NMR (400 MHz, DMSO-$d_6$) δ 9.48 (s, 1H), 8.60-8.57 (t, J=6.0 Hz, 1H), 8.21 (s, 1H), 8.00 (s, 1H), 7.92-7.89 (d, J=8.8 Hz, 1H), 7.85 (s, 1H), 7.60 (s, 1H), 7.22-7.18 (t, J=8.0 Hz, 1H), 7.03-7.01 (d, J=8.0 Hz, 1H), 6.36-6.29 (m, 1H), 6.17-6.12 (dd, J=17.2, 2.4 Hz, 1H), 5.65-5.62 (dd, J=10.2, 2.4 Hz, 1H), 4.31-4.30 (d, J=5.6 Hz, 2H), 1.28 (s, 9H). MS: $[MH]^+$ 349.9.

Example 1.349. Synthesis of N-((8-(3-(tert-butyl) phenoxy)imidazo[1,2-a]pyrazin-6-yl)methyl)acrylamide (I-441)

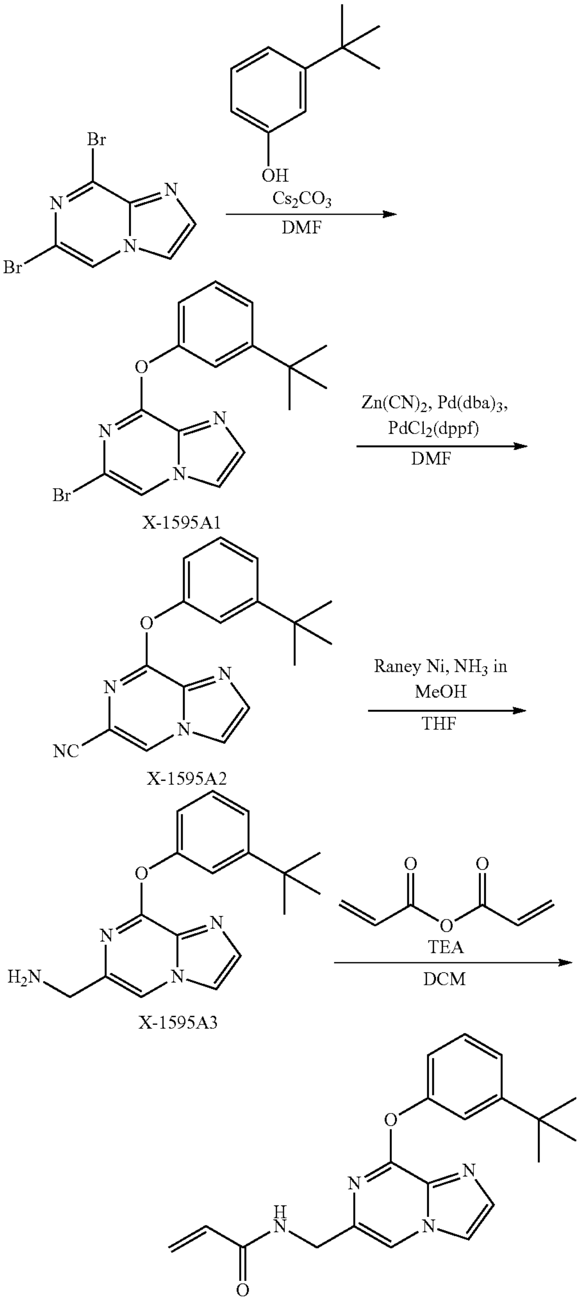

X-1595A1
X-1595A2
X-1595A3

I-441

The following compound was prepared in a manner analogous to the procedures described above for 6-bromo-8-(3-(trifluoromethyl)phenoxy)imidazo[1,2-a]pyrazine (X-1452A1) (for Step-1) and N-((8-(6-azaspiro[2.5]octan-6-yl)imidazo[1,2-a]pyrazin-6-yl)methyl)acrylamide (I-437):

N-((8-(3-(tert-butyl)phenoxy)imidazo[1,2-a]pyrazin-6-yl)methyl)acrylamide (I-441) (0.030 g, 7%) as a white solid.

$^1$H NMR (400 MHz, DMSO-$d_6$) δ 8.58-8.56 (t, J=5.6 Hz, 1H), 8.19-8.18 (dd, J=4.8 Hz, 5.2 Hz, 2H), 7.734-7.732 (d, J=0.8 Hz, 1H) 7.38-7.34 (t J=8.0 Hz, 1H), 7.30-7.27 (m, 2H), 7.13-7.11 (dd, J=1.2 Hz, 7.6 Hz, 1H), 6.28-6.22 (m, 1H), 6.12-6.07 (dd, J=2.0 Hz, 17.2 Hz, 1H), 5.63-5.60 (dd, J=10.4, 2.4 Hz, 1H), 4.17-4.16 (d, J=5.6 Hz, 2H), 1.29 (s, 9H). MS: $[MH]^+$ 351.1.

Example 1.350. Synthesis of N-((8-((3-(trifluoromethoxy)phenyl)amino)imidazo[1,2-a]pyrazin-6-yl)methyl)acrylamide (I-442)

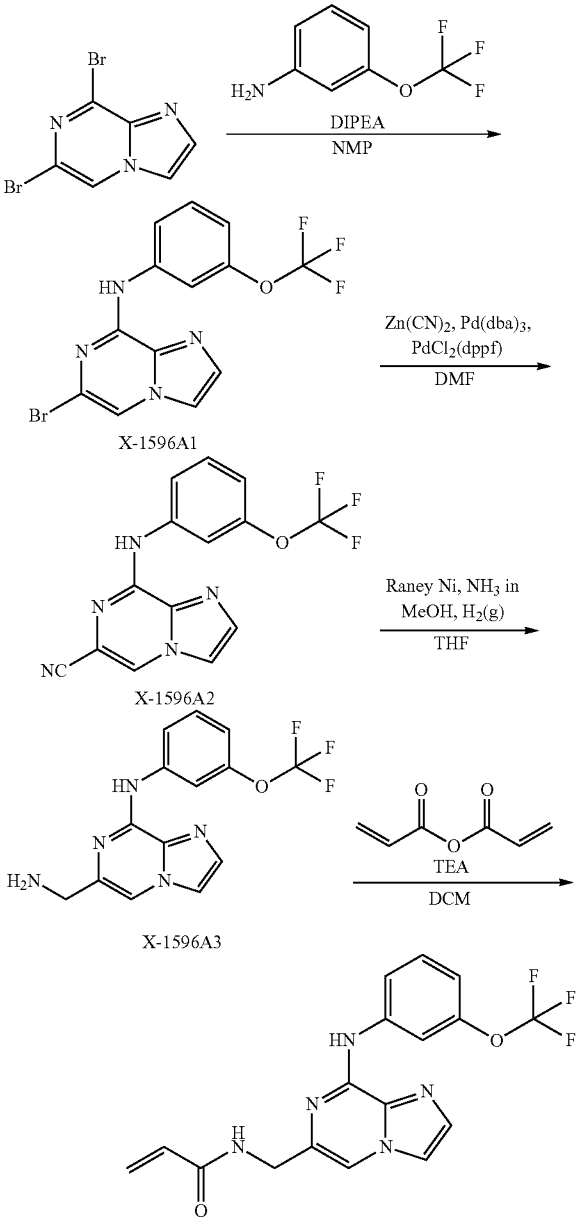

I-442

The following compound was prepared in a manner analogous to the procedures described above for N-((8-(6-azaspiro[2.5]octan-6-yl)imidazo[1,2-a]pyrazin-6-yl)methyl)acrylamide (I-437).

N-((8-((3-(trifluoromethoxy)phenyl)amino)imidazo[1,2-a]pyrazin-6-yl)methyl)acrylamide (I-442) (0.022 g, 15%) as an off-white solid. $^1$H NMR (400 MHz, DMSO-$d_6$) δ9.99 (s, 1H), 8.62-8.60 (t, J=5.6 Hz, 1H), 8.32 (s, 1H), 8.10-8.08 (dd, J=8.4, 1.2 Hz, 1H), 8.045-8.043 (d, J=0.8 Hz, 1H), 7.93 (s, 1H), 7.643-7.641 (d, J=0.8 Hz, 1H), 7.41-7.37 (t, J=8.4 Hz, 1H), 6.95-6.93 (d, J=8.0 Hz, 1H), 6.36-6.29 (m, 1H), 6.18-6.13 (dd, J=17.2, 2.4 Hz, 1H), 5.65-5.62 (dd, J=10.2, 2.0 Hz, 1H), 4.33-4.32 (d, J=5.6 Hz, 2H), 1.28 (s, 9H). MS: $[MH]^+$ 378.1.

Example 1.351. Synthesis of N-((6-(4-(trifluoromethyl)phenyl)imidazo[1,2-a]pyrazin-8-yl)methyl)acrylamide (I-443)

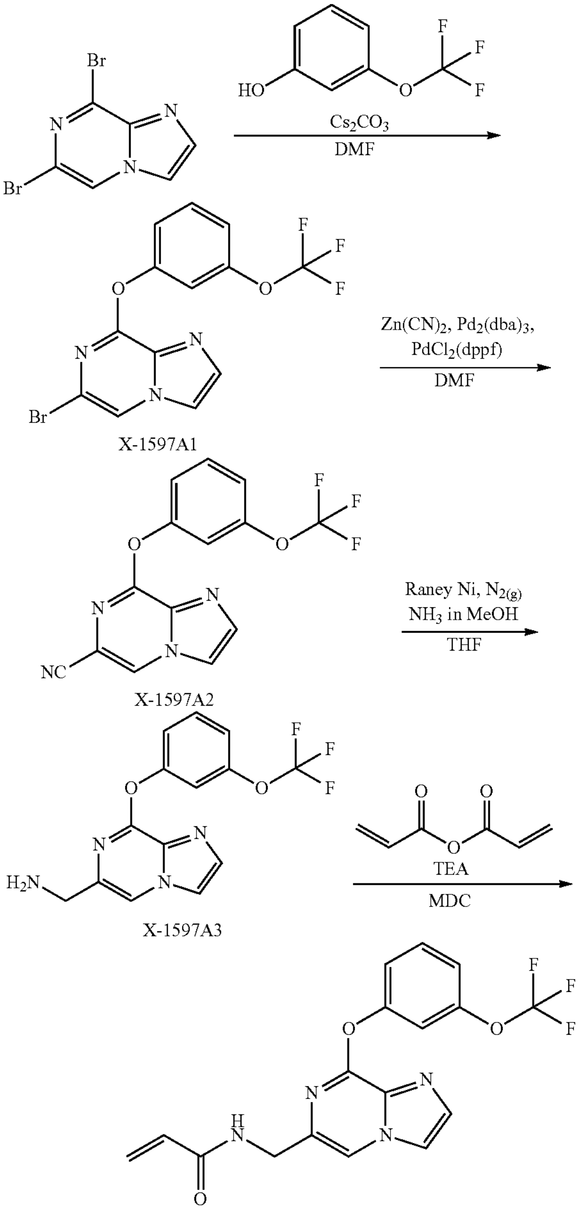

I-443

The following compound was prepared in a manner analogous to the procedures described above for 6-bromo- 8-(3-(trifluoromethyl)phenoxy)imidazo[1,2-a]pyrazine (X-1452A1) (for Step-1) and N-((8-(6-azaspiro[2.5]octan-6-yl)imidazo[1,2-a]pyrazin-6-yl)methyl)acrylamide (I-437):

N-((6-(4-(trifluoromethyl)phenyl)imidazo[1,2-a]pyrazin-8-yl)methyl)acrylamide (I-443) (0.040 g, 11%) as an off-white solid. $^{1}$H NMR (400 MHz, DMSO-$d_6$) δ 8.61-8.58 (t, J=5.6 Hz, 1H), 8.23-8.20 (d, J=10.0 Hz, 2H), 7.75 (s, 1H), 7.61-7.57 (t, J=8.0 Hz, 1H), 7.45 (s, 1H), 7.40-7.38 (d, J=8.4 Hz, 1H), 7.30-7.28 (d, J=8.0 Hz, 1H), 6.29-6.22 (m, 1H), 6.13-6.08 (dd, J=17.2, 2.0 Hz, 1H), 5.64-5.61 (dd, J=10.2, 2.0 Hz, 1H), 4.19-4.17 (d, J=5.6 Hz, 2H). MS: [MH]+379.1.

Example 1.352. Synthesis of N-((8-((2-(trifluoromethyl)pyridin-4-yl)amino)imidazo[1,2-a]pyrazin-6-yl)methyl)acrylamide (I-444)

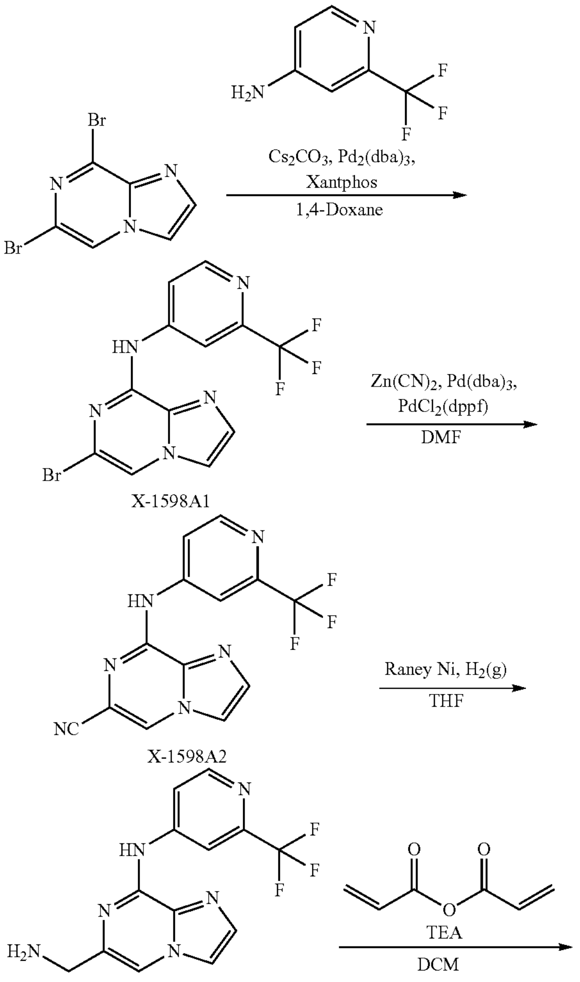

X-1598A1
X-1598A2
X-1598A3

-continued

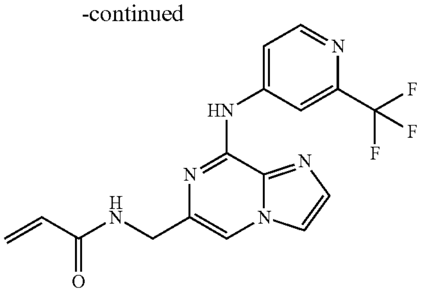

I-444

6-Bromo-N-(2-(trifluoromethyl)pyridin-4-yl)imidazo[1,2-a]pyrazin-8-amine (X-1598A1). To a stirred solution of 6,8-dibromoimidazo[1,2-a]pyrazine (1.0 g, 3.61 mmol) 1,4-dioxane (5 mL) were added 2-(trifluoromethyl)pyridin-4-amine (0.584 g, 3.61 mmol) cesium carbonate (2.94 g, 9.02 mmol) sequentially at room temperature under nitrogen. The reaction mixture was degassed (purging with nitrogen) for 20 min followed by the addition of $Pd_2(dba)_3$ (0.330 g, 0.361 mmol) and Xanthphos (0.209 g, 0.361 mmol) and the resulting mixture was heated at 120° C. under microwave irradiation for 1 h. Reaction mixture was cooled to room temperature, slowly poured into water (120 mL) and was extracted with ethyl acetate (100 mL×3). The combined organic extracts were washed with brine (50 mL), dried over anhydrous $Na_2SO_4$ and concentrated under reduced pressure, Isolated crude was combined with an identical prepared two more batch (1.0 g) and the combined crude product was purified by silica gel column chromatography, using ethyl acetate-hexane=0:1→4:6 as gradient, to afford to afford 6-bromo-N-(2-(trifluoromethyl)pyridin-4-yl)imidazo[1,2-a]pyrazin-8-amine (X-1598A1) (3.0 g, 77%) as an solid. MS: $[MH]^+$ 357.9.

N-((8-((2-(trifluoromethyl)pyridin-4-yl)amino)imidazo[1,2-a]pyrazin-6-yl)methyl)acrylamide (I-444). The remaining steps, starting with 6-bromo-N-(2-(trifluoromethyl)pyridin-4-yl)imidazo[1,2-a]pyrazin-8-amine (X-1598A1) were prepared in a manner analogous to the procedures described above for N-((8-(6-azaspiro[2.5]octan-6-yl)imidazo[1,2-a]pyrazin-6-yl)methyl)acrylamide (I-437)

N-((8-((2-(trifluoromethyl)pyridin-4-yl)amino)imidazo[1,2-a]pyrazin-6-yl)methyl)acrylamide (I-444) (0.060 g, 13%) as an off-white solid. $^{1}$H NMR (400 MHz, DMSO-$d_6$) δ8.58-8.56 (t, J=5.6 Hz, 1H), 8.19-8.18 (m, 2H), 7.734-7.732 (d, J=0.8 Hz, 1H), 7.38-7.34 (t, J=8.0 Hz, 1H), 7.30-7.27 (m, 2H), 7.13-7.11 (dd, J=1.2, 7.6 Hz, 1H), 6.28-6.22 (m, 1H), 6.12-6.07 (dd, J=2.0, 17.2 Hz, 1H), 5.63-5.60 (dd, J=2.4 Hz, 10.4 Hz, 1H), 4.17-4.16 (d, J=5.6 Hz, 2H), 1.29 (s, 9H). MS: $[MH]^+$ 351.0.

Example 1.353. Synthesis of N-((7-fluoro-4-(4-(trifluoromethyl)phenyl)quinazolin-2-yl)methyl)acrylamide (I-445)

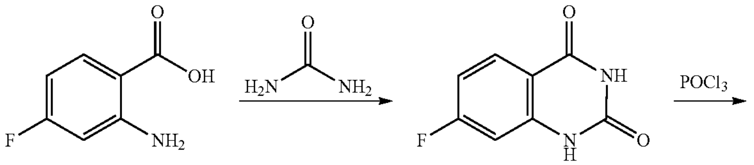

CAS No. 446-32-2
X-1600C1

-continued

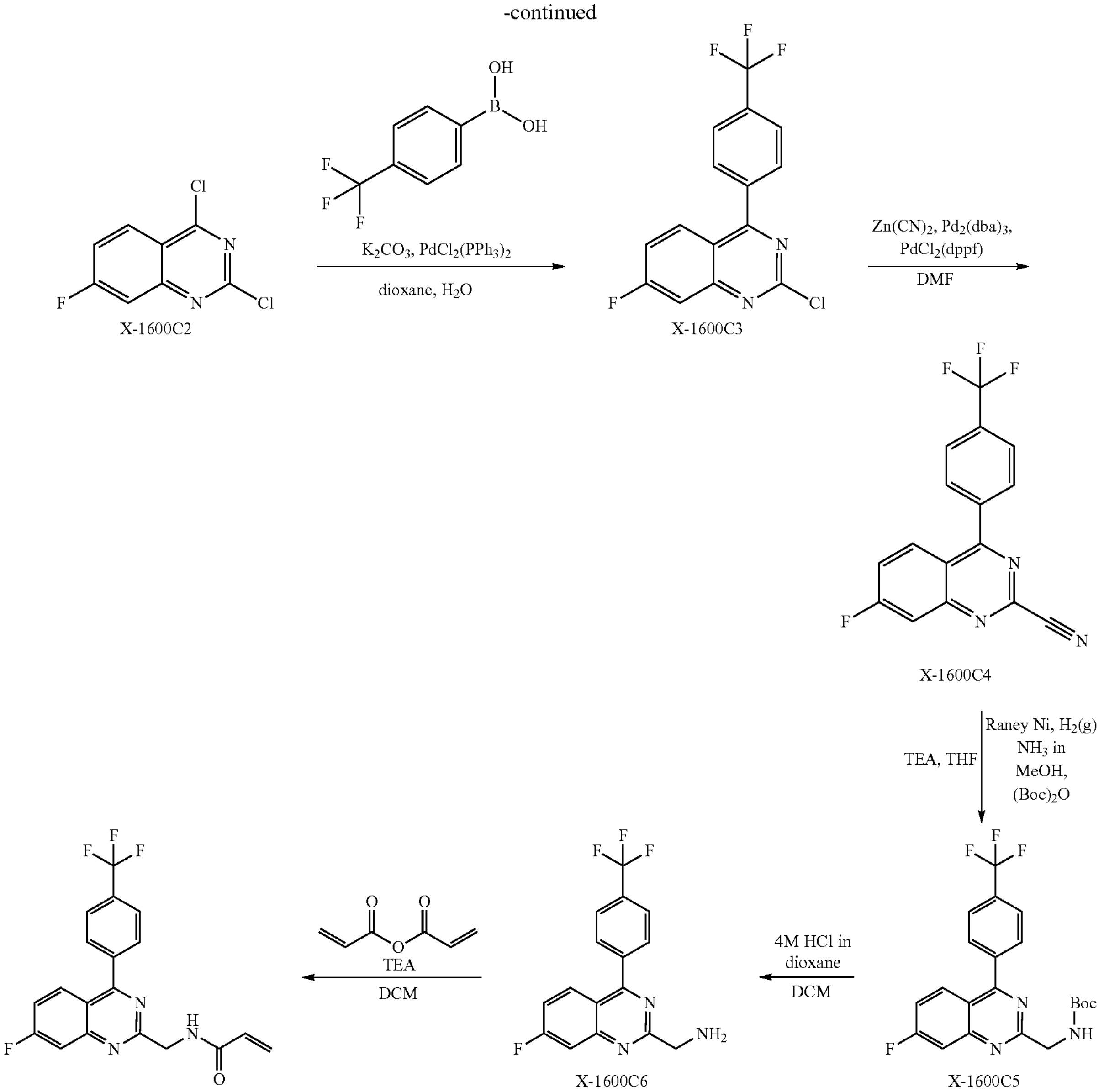

7-Fluoroquinazoline-2,4(1H,3H)-dione (X-1600C1). A mixture of 2-amino-4-fluorobenzoic acid (15.0 g, 96.77 mmol) and urea (16.80 g, 280.64 mmol) was heated under stirring at 220° C. for 2 h. After cooling to room temperature, reaction mixture was poured in water (300 mL) and the resulting precipitate was collected by filtration. Obtained residue was washed with water and was dried under high vacuum to afford 7-fluoroquinazoline-2,4(1H,3H)-dione (X-1600C1) (11.80 g, 68%; crude) as a yellow solid, which was used in next step without further purification. MS: [MH]-179.03.

2,4-Dichloro-7-fluoroquinazoline (X-1600C2). $POCl_3$ (50 mL) was added drop wise, via additional funnel, to 7-fluoroquinazoline-2,4(1H,3H)-dione (X-1600C1) (5.0 g, 27.77 mmol) at 0° C. under nitrogen and resulting mixture was heated at 110° C. for 5 days. After cooling to room temperature, reaction mixture was slowly poured into ice, the resulting precipitate was filtered, the residue was washed with cold water until the pH of the filtrate became neutral (pH 6-7) and dried under high vacuum to afford 2,4-dichloro-7-fluoroquinazoline (X-1600C2) (4.5 g, 75%; crude) as an off-white solid, which was used in next step without further purification. $^1H$ NMR [crude and not very clean] (400 MHz, DMSO-$d_6$) δ 8.45-8.41 (m, 1H), 7.96-7.93 (m, 1H), 7.87-7.82 (m, 1H).

2-Chloro-7-fluoro-4-(4-(trifluoromethyl)phenyl)quinazoline (X-1600C3). To a stirred solution of 2,4-dichloro-7-fluoroquinazoline (X-1600C2) (1.00 g, 4.63 mmol) in mixture of 1,4-dioxane-$H_2O$ (9:1, 15 mL) were added (4-(trifluoromethyl)phenyl)boronic acid (0.879 g, 4.63 mmol) and $K_2CO_3$ (1.27 g, 9.26 mmol) sequentially at room temperature. The reaction mixture was degassed (purging with nitrogen) for 20 min followed by addition of $PdCl_2(PPh_3)_2$ (0.162 g, 0.230 mmol) and the reaction mixture was heated at 90° C. for 2 h. The reaction mixture was cooled to room temperature, diluted with water (150 mL) and was extracted with ethyl acetate (150 mL×2). The combined organic extracts were dried over anhydrous $Na_2SO_4$ and concentrated under reduce pressure. Isolated crude was combined with an identical prepared one more batch (0.250 g) and the combined crude product was purified by silica gel column chromatography, using ethyl acetate-hexane=0:1→2:8 as gradient, to afford 2-chloro-7-fluoro-4-(4-(trifluoromethyl)phenyl)quinazoline (X-1600C3) (1.2 g, 64%) as a yellow solid. MS: $[MH]^+$ 326.8.

7-Fluoro-4-(4-(trifluoromethyl)phenyl)quinazoline-2-carbonitrile (X-1600C4). To a stirred solution of 2-chloro-7-fluoro-4-(4-(trifluoromethyl)phenyl)quinazoline (X-1600C3) (1.20 g, 3.68 mmol) in DMF (15 mL) was added zinc cyanide (1.29 g, 11.04 mmol) sequentially at room temperature under nitrogen. The reaction mixture was degassed (by purging nitrogen) for 20 min followed by the addition of $PdCl_2(dppf)$ (0.134 g, 0.184 mmol), $Pd_2(dba)_3$ (0.168 g, 0.184 mmol) and resulting mixture was heated at 150° C. for 30 min. Reaction mixture was cooled to room temperature, slowly poured into water (120 mL) and was extracted with ethyl acetate (100 mL×2). The combined organic extracts were washed with brine (50 mL), dried over anhydrous $Na_2SO_4$ and concentrated under reduce pressure. The crude product was purified by silica gel column chromatography, using ethyl acetate-hexane=0:1→4 3:7 as gradient, to afford 7-fluoro-4-(4-(trifluoromethyl)phenyl)quinazoline-2-carbonitrile (X-1600C4) (0.800 g, 68%) as a yellow solid. MS: $[MH]^+$ 317.9.

tert-Butyl ((7-fluoro-4-(4-(trifluoromethyl)phenyl)quinazolin-2-yl)methyl)carbamate (X-1600C5). To a stirred solution of 7-fluoro-4-(4-(trifluoromethyl)phenyl)quinazoline-2-carbonitrile (X-1600C4) (0.400 g, 1.26 mmol) in THE (5 mL) were added Raney Nickel (0.400 g) and TEA (0.637 g, 6.30 mmol), and di-tert-butyl dicarbonate (0.550 g, 2.52 mmol) sequentially at room temperature and the resulting reaction mixture was hydrogenated in Parr Autoclave at 70° C. under 200 psi for 3 h. Reaction mixture was filtered over a celite bed, washed the bed with MeOH (100 mL) and collected filtrates were concentrated under reduced pressure to give crude. The crude product was purified by silica gel column chromatography, using ethyl acetate-hexane=0:1→2:8 as gradient, to afford tert-butyl ((7-fluoro-4-(4-(trifluoromethyl)phenyl)quinazolin-2-yl)methyl)carbamate (X-1600C5) (0.400 g, 75%) as a yellow solid. MS: [MH]+ 422.0.

(7-Fluoro-4-(4-(trifluoromethyl)phenyl)quinazolin-2-yl)methanamine (X-1600C6). To a stirred solution of tert-butyl ((7-fluoro-4-(4-(trifluoromethyl)phenyl)quinazolin-2-yl)methyl)carbamate (X-1600C5) (0.400 g, 0.950 mmol) in DCM (4 mL) was added 4 M HCl in dioxane (4 mL) at 0° C. under nitrogen and the reaction mixture stirred for 30 min at room temperature. The reaction mixture was concentrated under reduced pressure to give crude, the obtained crude product was purified by triturated using ethyl acetate to remove impurities and to afford (7-fluoro-4-(4-(trifluoromethyl)phenyl)quinazolin-2-yl)methanamine (X-1600C6) (0.340 g, quant; crude) as an off-white solid. MS: [MH]+ 422.1.

N-((7-fluoro-4-(4-(trifluoromethyl)phenyl)quinazolin-2-yl)methyl)acrylamide (I-445). To a stirred solution of (7-fluoro-4-(4-(trifluoromethyl)phenyl)quinazolin-2-yl)methanamine (X-1600C6) (0.340 g, 1.05 mmol) in DCM (5 mL) were added triethylamine (0.534 g, 5.29 mmol) followed by the addition of acrylic anhydride (0.133 g, 1.05 mmol) at 0° C. under nitrogen and the reaction mixture stirred for 10 min at same temperature. The reaction mixture was slowly poured into water (50 mL) and was extracted with DCM (50 mL×3). The combined organic extracts were washed with brine (50 mL), dried over anhydrous $Na_2SO_4$ and concentrated under reduced pressure. The crude product was purified by silica gel column chromatography, using ethyl acetate-hexane=0:1→7:3 as gradient, to afford N-((7-fluoro-4-(4-(trifluoromethyl)phenyl)quinazolin-2-yl)methyl)acrylamide (I-445) (0.19 g, 48%) as an off-white solid. $^1H$ NMR (400 MHz, DMSO-$d_6$) δ 8.84 (m, 1H), 8.15-8.11 (m, 1H), 8.01 (s, 4H), 8.01 (s, 4H), 7.88-7.85 (dd, J=9.6, 2.4 Hz, 1H), 7.67-7.62 (m, 1H), 6.45-6.38 (m, 1H), 6.16-6.11 (dd, J=17.2, 2.0 Hz, 1H), 5.67-5.64 (dd, J=10.4, 2.4 Hz, 1H), 4.77-4.76 (d, J=6.0 Hz, 2H). MS: $[MH]^+$ 376.0.

Example 1.354. Synthesis of N-((4-(4-(tert-butyl)phenyl)-7-fluoroquinazolin-2-yl)methyl)acrylamide (I-446)

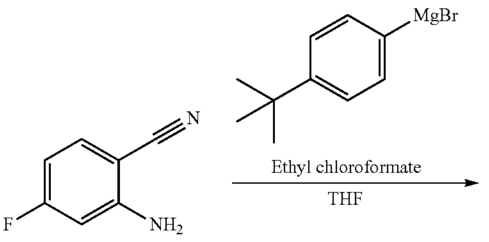

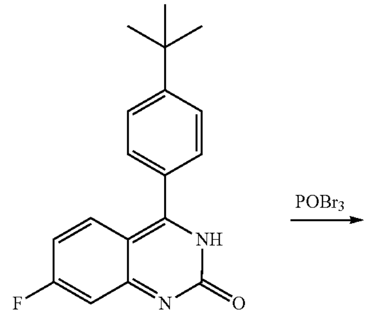

X-1601A1

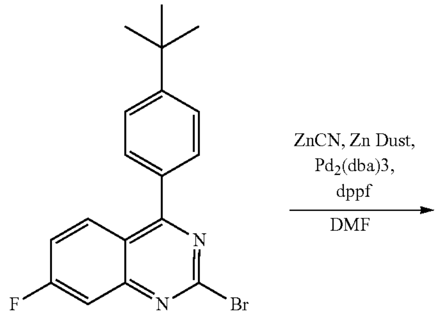

X-1601A2

-continued

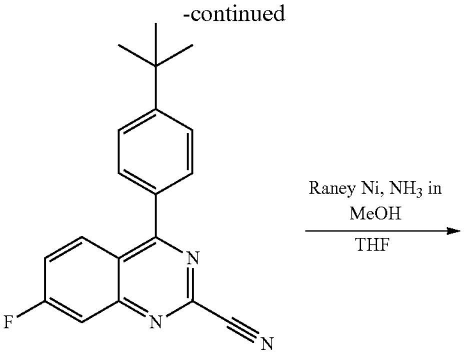

X-1601A3

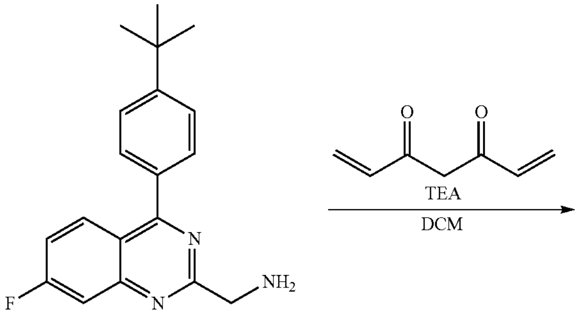

X-1601A4

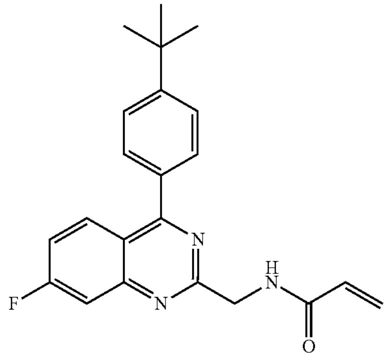

I-446

4-(4-(tert-butyl)phenyl)-7-fluoroquinazolin-2(3H)-one (X-1601A1). To a stirred solution of 2-amino-4-fluorobenzonitrile (3.0 g, 22.05 mmol) in THE (40 mL) was added (4-(tert-butyl)phenyl)magnesium bromide (66.00 mL, 132.0 mmol) at 0° C. under nitrogen and the reaction mixture was heated at 80° C. for 1 h. The reaction mixture was cooled and ethyl chloroformate (2.70 mL, 28.60 mmol) was added and again stirred at room temperature for 2 h. After completion of reaction, the resulting mixture was slowly poured into aqueous solution of saturated $NH_4Cl$ and was extracted with ethyl acetate (250 mL×2). Combined organic extracts were dried over anhydrous $Na_2SO_4$ and concentrated under reduce pressure. The crude product was triturated using diethyl ether (100×2) and dried under high vacuum to afford 4-(4-(tert-butyl)phenyl)-7-fluoroquinazolin-2(3H)-one (X-1601A1) (3.00 g, 46%) as an white solid. MS: $[MH]^+$ 297.4.

2-Bromo-4-(4-(tert-butyl)phenyl)-7-fluoroquinazoline (X-1601A2). The mixture of 4-(4-(tert-butyl)phenyl)-7-fluoroquinazolin-2(3H)-one (X-1601A1) (3.00 g, 10.10 mmol) and $POBr_3$ (8.700 g, 30.40 mmol) was heated at 130° C. for 3 h. After completion of reaction, reaction mixture was slowly poured into ice-water (100 mL) and was extracted with ethyl acetate (150 mL×3). Combined organic layer was washed with saturated solution of aqueous $NaHCO_3$ and dried over anhydrous $Na_2SO_4$ and concentrated under reduce pressure to get crude. The crude product was purified by silica gel column chromatography, using ethyl acetate-hexane=0:1→2:8 as gradient, to afford 2-bromo-4-(4-(tert-butyl)phenyl)-7-fluoroquinazoline (X-1601A2) (2.20 g, 61%) as off white solid. MS: $[MH]^+$ 359.3.

N-((4-(4-(tert-butyl)phenyl)-7-fluoroquinazolin-2-yl)methyl)acrylamide (I-446). Remaining steps, starting with 2-bromo-4-(4-(tert-butyl)phenyl)-7-fluoroquinazoline (X-1601A2) were prepared in a manner analogous to the procedures described above for N-((8-(6-azaspiro[2.5]octan-6-yl)imidazo[1,2-a]pyrazin-6-yl)methyl)acrylamide (I-437):

N-((4-(4-(tert-butyl)phenyl)-7-fluoroquinazolin-2-yl)methyl)acrylamide (I-446) (0.100 g, 28%) as a white solid. $^1H$ NMR (400 MHz, DMSO-$d_6$) δ 8.82-8.80 (t, J=5.6 Hz, 1H), 8.21-8.17 (m, 1H), 7.81-7.78 (dd, J=9.6, 2.0 Hz, 1H), 7.74-7.72 (d, J=8.0 Hz, 2H), 7.66-7.58 (m, 3H), 6.45-6.38 (m, 1H), 6.15-6.10 (d, J=17.2 Hz, 1H), 5.65-5.63 (d, J=10.4 Hz, 1H), 4.73-4.72 (d, J=5.6 Hz, 2H), 1.36 (s, 9H). MS: $[MH]^+$ 364.4.

Example 1.355. Synthesis of N-((4-(4-(tert-butyl)phenyl)-7-fluoroquinazolin-2-yl)methyl)acrylamide (I-447)

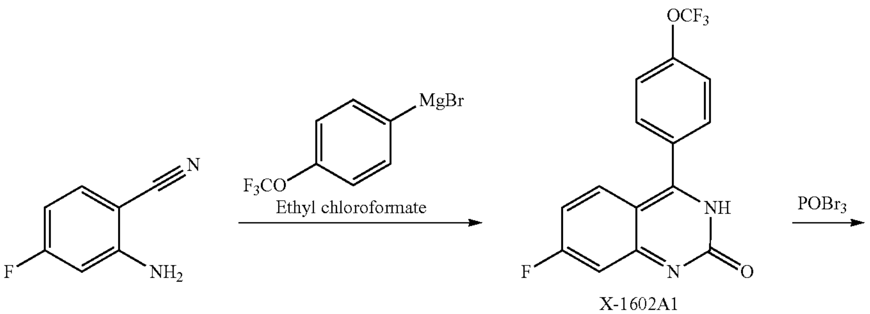

X-1602A1

-continued

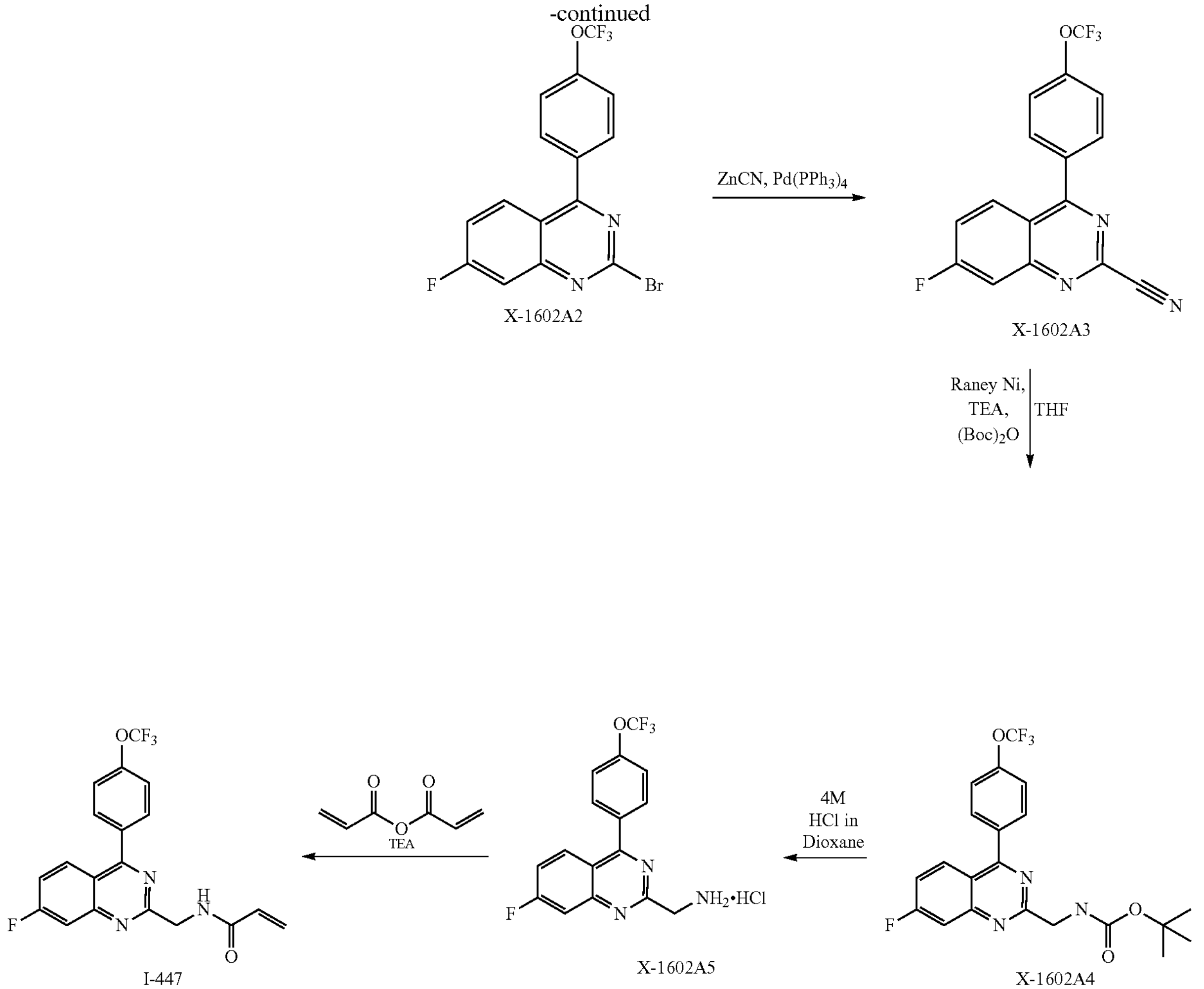

X-1602A2 X-1602A3 X-1602A4 X-1602A5 I-447

7-Fluoro-4-(4-(trifluoromethoxy)phenyl)quinazolin-2(3H)-one (X-1602A1). To a stirred solution of 2-amino-4-fluorobenzonitrile (0.900 g, 6.61 mmol) in THE (10 mL) was added (4-(trifluoromethoxy)phenyl)magnesium bromide (0.5 M in THF, 79.0 mL, 39.70 mmol), at 0° C. under nitrogen and the reaction mixture was heated at 80° C. for 2 h. The reaction mixture was cooled and ethyl chloroformate (1.44 g, 13.20 mmol) was added and again stirred at room temperature for 2 h. After completion of reaction, the resulting mixture was slowly poured into aqueous solution of saturated $NH_4Cl$ and was extracted with ethyl acetate (250 mL×2). Combined organic extracts were dried over anhydrous $Na_2SO_4$ and concentrated under reduce pressure. The crude product was purified by silica gel column chromatography, using ethyl acetate-hexane=0:1→9:1 as gradient, to afford 7-fluoro-4-(4-(trifluoromethoxy)phenyl)quinazolin-2(3H)-one (X-1602A1) (0.75 g, 35%) as an white solid. MS: $[MH]^+$ 325.2.

2-Bromo-7-fluoro-4-(4-(trifluoromethoxy)phenyl)quinazoline (X-1602A2). The mixture of 7-fluoro-4-(4-(trifluoromethoxy)phenyl)quinazolin-2(3H)-one (X-1602A1) (0.100 g, 0.30 mmol) and $POBr_3$ (0.265 g, 0.92 mmol) was heated at 130° C. for 2 h. After completion of reaction, The resulting mixture was slowly poured into ice-water (100 mL) and was extracted with ethyl acetate (150 mL×3). Combined organic layer was washed with saturated solution of aqueous $NaHCO_3$ and dried over anhydrous $Na_2SO_4$ and concentrated under reduce pressure to get crude. Isolated crude was combined with an identical prepared three more batch (0.1 g) and the combined crude product was purified by silica gel column chromatography, using ethyl acetate-hexane=0:1→2:8 as gradient, to afford 2-bromo-7-fluoro-4-(4-(trifluoromethoxy)phenyl)quinazoline (X-1602A2) (0.370 g, 78%) as off white solid. MS: $[MH]^+$ 386.9.

N-((7-fluoro-4-(4-(trifluoromethoxy)phenyl)quinazolin-2-yl)methyl)acrylamide (I-447). The remaining steps, starting with 2-bromo-7-fluoro-4-(4-(trifluoromethoxy)phenyl)quinazoline (X-1602A2) were prepared in a manner analogous to the procedures described above for N-((7-fluoro-4-(4-(trifluoromethyl)phenyl)quinazolin-2-yl)methyl)acrylamide (I-445).

N-((4-(4-(tert-butyl)phenyl)-7-fluoroquinazolin-2-yl)methyl)acrylamide (I-447) (0.035 g, 37%) as a white solid. $^1H$ NMR (400 MHz, DMSO-$d_6$) δ 8.84 (brs, 1H), 8.18-8.14 (m, 1H), 7.95-7.92 (d, J=8.4 Hz, 2H), 7.86-7.84 (dd, J=10.0, 2.4 Hz, 1H), 7.65-7.63 (m, 3H), 6.45-6.38 (m, 1H), 6.16-6.12 (d, J=17.2, 1.6 Hz, 1H), 5.67-5.64 (d, J=10.0, 2.4 Hz, 1H), 4.76-4.75 (d, J=5.6 Hz, 2H), MS: $[MH]^+$ 392.0.

Example 1.356. Synthesis of N-((8-(4-((trifluoromethyl)thio)phenyl)imidazo[1,2-a]pyrazin-6-yl) methyl) acrylamide (I-448)

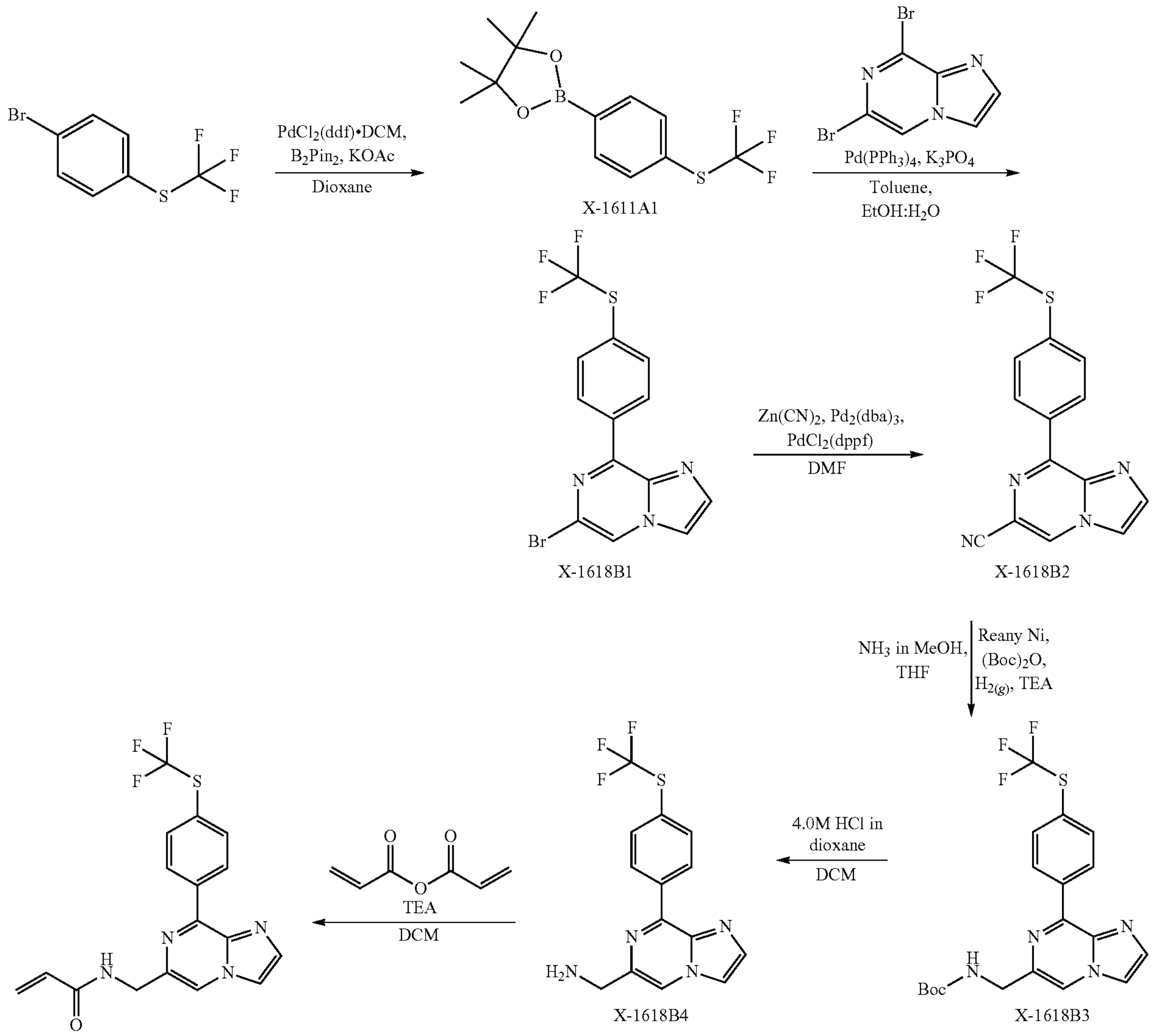

4,4,5,5-Tetramethyl-2-(4-((trifluoromethyl)thio)phenyl)-1,3,2-dioxaborolane (X-1611A1). To a stirred solution of (4-bromophenyl)(trifluoromethyl)sulfane (2.0 g, 3.89 mmol) in dioxane (10 mL) were added Bis(pinacolato)diboron (1.19 g, 4.67 mmol) and KOAc (2.29 g, 2.33 mmol) at room temperature. The reaction mixture was degassed (purging with nitrogen) for 30 min followed by addition of $PdCl_2$(dppf).DCM (0.635 g, 0.770 mmol) and the reaction mixture was heated at 90° C. for 5 h. After completion of reaction, reaction mixture was cooled to room temperature, was diluted with water (50 mL) and was extracted with ethyl acetate (50 mL×3). The combined organic extracts were dried over anhydrous $Na_2SO_4$ and concentrated under reduce pressure. The crude product was purified by silica gel column chromatography, using ethyl acetate-hexane=0:1→1:9 as gradient, to afford 4,4,5,5-tetramethyl-2-(4-((trifluoromethyl)thio)phenyl)-1,3,2-dioxaborolane (X-1611A1) (1.5 g, 62%) as a brown liquid. MS: $[MH]^+$ 305.0.

6-Bromo-8-(4-((trifluoromethyl)thio)phenyl)imidazo[1,2-a]pyrazine (X-1618B1). To a stirred solution of (4-bromophenyl)(trifluoromethyl)sulfane (X-1611A1) (0.82 g, 3.89 mmol) in EtOH:toluene:water (6 mL) were added 6,8-dibromoimidazo[1,2-a]pyrazine (0.500 g, 1.80 mmol) and $K_3PO_4$ (1.14 g, 5.41 mmol) at room temperature. The reaction mixture was degassed (purging with nitrogen) for 30 min followed by addition of $Pd(PPh_3)_4$ (0.104 g, 0.900 mmol) and the reaction mixture was heated at 90° C. for 19 h. After completion of reaction, reaction mixture was cooled to room temperature, was diluted with water (50 mL) and was extracted with ethyl acetate (50 mL×3). The combined organic extracts were dried over anhydrous $Na_2SO_4$ and concentrated under reduce pressure. Obtained crude was combined with an identical prepared one more batch (1.0 g) and was purified by silica gel column chromatography, using ethyl acetate-hexane=0:1→2:8 as gradient, to afford 6-bromo-8-(4-((trifluoromethyl)thio)phenyl)imidazo[1,2-a]pyrazine (X-1618B1) (0.800 g, 39%) as a white solid. MS: $[MH]^+$ 373.9/[MH+2]+ 374.9.

N-((8-(4-((trifluoromethyl)thio)phenyl)imidazo[1,2-a]pyrazin-6-yl)methyl)acrylamide (I-448). The remaining steps, starting with 6-bromo-8-(4-((trifluoromethyl)thio)phenyl)imidazo[1,2-a]pyrazine (X-1618B1) were prepared in a manner analogous to the procedures described above for N-((7-fluoro-4-(4-(trifluoromethyl)phenyl)quinazolin-2-yl)methyl)acrylamide (I-445)

N-((8-(4-((trifluoromethyl)thio)phenyl)imidazo[1,2-a]pyrazin-6-yl)methyl) acrylamide (I-448) (0.060 g, 29%) as a white solid. MS: $[MH]^+$ 378.9. $^1$H NMR (400 MHz, DMSO-$d_6$) δ 8.93-8.91 (d, J=8.4 Hz, 2H), 8.79-8.78 (t, J=6.0 Hz, 1H), 8.58 (s, 1H), 8.29 (s, 1H), 7.94-7.91 (m, 3H), 6.38-6.31 (m, 1H), 6.18-6.14 (d, J=16.8 Hz, 1H), 5.68-5.65 (d, J=10.0 Hz, 1H), 4.55-4.53 (d, J=5.6 Hz, 2H).

Example 1.357. Synthesis of 4-(4-(Tert-butyl)phenyl)-2-(difluoromethoxy)pyrrolo[1,2-a]quinoxaline-7-carboxylic acid (I-449)

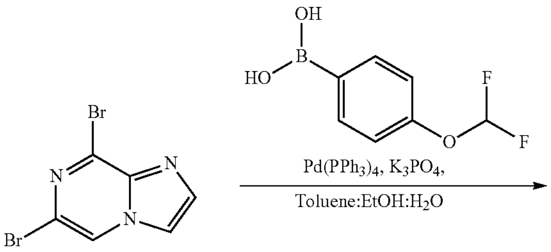

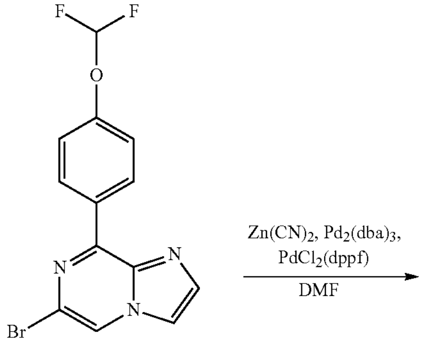

X-1619C1

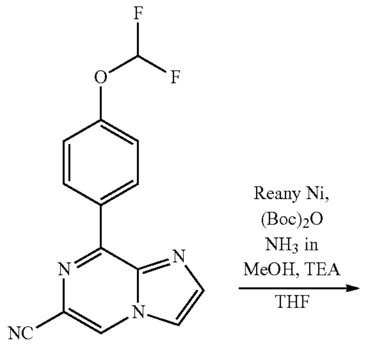

X-1619C2

-continued

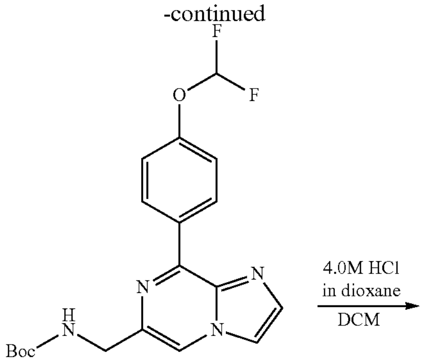

X-1619C3

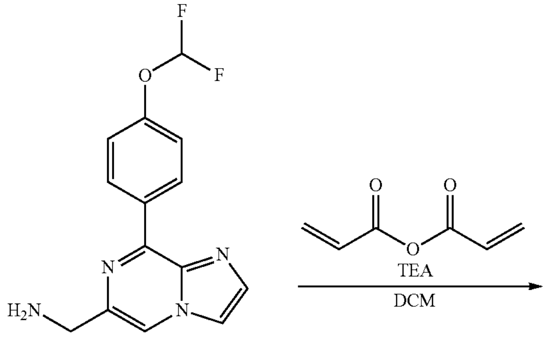

X-1619C4

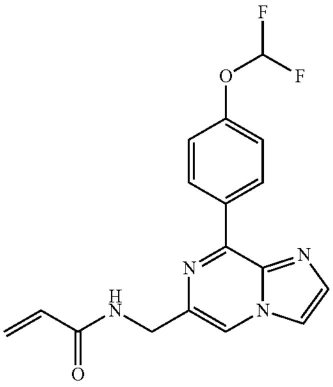

I-449

The following compound was prepared in a manner analogous to the procedures described above for N-((7-fluoro-4-(4-(trifluoromethyl)phenyl)quinazolin-2-yl)methyl)acrylamide (I-445):

4-(4-(Tert-butyl)phenyl)-2-(difluoromethoxy)pyrrolo[1,2-a]quinoxaline-7-carboxylic acid (I-449) (0.140 g, 39%) as an off-white solid. $^1$H NMR (400 MHz, DMSO-$d_6$) δ 8.89-8.87 (d, J=8.4 Hz, 2H), 8.79-8.76 (t, J=5.6 Hz, 1H), 8.50 (s, 1H), 8.24 (s, 1H), 7.87 (s, 1H), 7.57-7.20 (m, 3H), 7.39-7.35 (m, 2H), 7.20 (s, 1H), 6.37-6.30 (m, 1H), 6.17-6.13 (d, J=17.2 Hz, 1H), 5.67-5.64 (dd, J=10.0, 1.6 Hz, 1H), 4.52-4.50 (d, J=6.0 Hz, 2H). MS: $[MH]^+$ 345.3

Example 1.358. Synthesis of N-((4-(4-(trifluoromethyl)phenyl)-5H-pyrrolo[3,2-d]pyrimidin-2-yl)methyl) acrylamide (I-450)

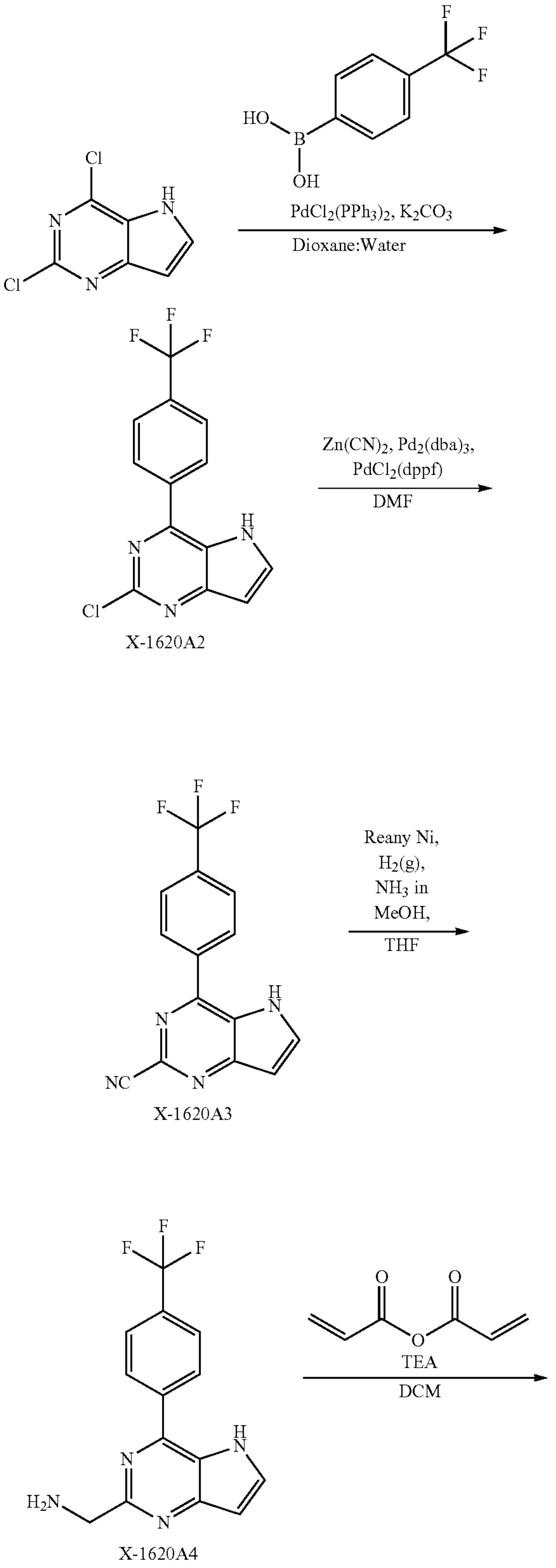

-continued

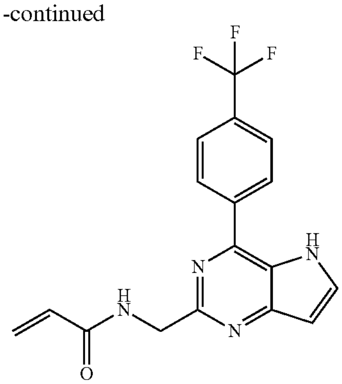

I-450

2-Chloro-4-(4-(trifluoromethyl)phenyl)-5H-pyrrolo[3,2-d]pyrimidine (X-1620A2). To a stirred solution of 2,4-dichloro-5H-pyrrolo[3,2-d]pyrimidine (4.00 g, 21.27 mmol) in dioxane:water (2:1 26 mL) were added (4-(trifluoromethyl)phenyl)boronic acid (6.06 g, 31.91 mmol) and potassium carbonate (7.34 g, 53.19 mmol) at room temperature under nitrogen. The reaction mixture was degassed (purging with nitrogen) for 20 min followed by the addition of $PdCl_2(PPh_3)_2$ (0.746 g, 1.06 mmol) and the resulting mixture was heated at 80° C. for 2 h. After completion of reaction, reaction mixture was cooled to room temperature, slowly poured into water (120 mL) and was extracted with ethyl acetate (100 mL×3), dried over anhydrous $Na_2SO_4$ and concentrated under reduced pressure. Obtained crude was purified by silica gel column chromatography, using ethyl acetate-hexane=0:1→4 2:8 as gradient, to afford 2-chloro-4-(4-(trifluoromethyl)phenyl)-5H-pyrrolo[3,2-d]pyrimidine (X-1620A2) (4.7 g, 74%) as an off-white solid. MS: $[MH]^+$ 298.3/[MH+2]+ 300.3.

4-(4-(Trifluoromethyl)phenyl)-5H-pyrrolo[3,2-d]pyrimidine-2-carbonitrile (X-1620A3). To a stirred solution of 2-chloro-4-(4-(trifluoromethyl)phenyl)-5H-pyrrolo[3,2-d]pyrimidine (X-1620A2) (2.00 g, 6.73 mmol) in DMF (3 mL) was added zinc cyanide (4.72 g, 40.40 mmol) at room temperature under nitrogen. The reaction mixture was degassed (by purging nitrogen) for 15 min followed by the addition of $PdCl_2(dppf)$ (0.246 g, 0.336 mmol), $Pd_2(dba)_3$ (0.308 g, 0.336 mmol) and resulting mixture was heated at 150° C. under microwave irradiation for 1 h. After completion of reaction, reaction mixture was cooled to room temperature, slowly poured into water (120 mL) and was extracted with ethyl acetate (100 mL×3). The combined organic extracts were washed with brine (50 mL), dried over anhydrous $Na_2SO_4$ and concentrated under reduced pressure. Obtained crude was purified by silica gel column chromatography, using ethyl acetate-hexane=0:1→4:6 as gradient, to afford 4-(4-(trifluoromethyl)phenyl)-5H-pyrrolo[3,2-d]pyrimidine-2-carbonitrile (X-1623A2) (0.50 g, 26%) as an brown solid. MS: $[MH]^+$ 289.0.

(4-(4-(trifluoromethyl)phenyl)-5H-pyrrolo[3,2-d]pyrimidin-2-yl)methanamine (X-1620A4). To a stirred solution of 4-(4-(trifluoromethyl)phenyl)-5H-pyrrolo[3,2-d]pyrimidine-2-carbonitrile (X-1620A2) (0.500 g, 1.73 mmol) in THF (9 mL) were added Raney Nickel (0.124 g) and methanolic ammonia (0.1 mL) at room temperature and the resulting mixture was hydrogenated in Parr Autoclave at room temperature under 200 psi for 24 h. After completion of reaction, reaction mixture was filtered over a celite bed, washed the bed with EtOAc (100 mL) and collected filtrate was concentrated under reduced pressure, to afford (4-(4-

(trifluoromethyl)phenyl)-5H-pyrrolo[3,2-d]pyrimidin-2-yl) methanamine (X-1620A4) (0.450 g, 88%) as a yellow solid. MS: $[MH]^+$ 293.4.

N-((4-(4-(trifluoromethyl)phenyl)-5H-pyrrolo[3,2-d]pyrimidin-2-yl)methyl)acrylamide (I-450). To a stirred solution of (4-(4-(trifluoromethyl)phenyl)-5H-pyrrolo[3,2-d]pyrimidin-2-yl)methanamine (X-1620A3) (0.200 g, 0.684 mmol) in DCM (5.0 mL) were added triethylamine (0.345 g, 3.42 mmol) followed by acrylic anhydride (0.086 g, 0.684 mmol) at −78° C. under nitrogen and the reaction mixture stirred for 10 min at same temperature. After completion of reaction, reaction mixture was diluted with water (30 mL) and was extracted with DCM (50 mL×2). Combined organic extracts were dried over anhydrous $Na_2SO_4$ and concentrated under reduced pressure. The crude product was purified by $C^{18}$ silica gel column chromatography, using acetonitrile-water=0:1→4:6 as gradient, N-((4-(4-(trifluoromethyl) phenyl)-5H-pyrrolo[3,2-d]pyrimidin-2-yl)methyl) acrylamide (I-450) (0.06 g, 25%) as an off-white solid. $^1H$ NMR (400 MHz, DMSO-$d_6$) δ 12.08 (s, 1H), 8.70-8.68 (t, J=5.6 Hz, 1H), 8.29-8.27 (d, J=8.0 Hz, 2H), 7.98-7.96 (m, 3H), 6.70-6.70 (d, J=2.8 Hz, 1H), 6.45-6.39 (m, 1H), 6.14-6.10 (dd, J=16.8, 2.0 Hz, 1H), 5.63-5.60 (dd, J=10.0, 2.0 Hz, 1H), 4.67-4.66 (d, J=5.5 Hz, 2H). MS: $[MH]^+$ 347.3.

Example 1.359. Synthesis of N-((5-methyl-4-(4-(trifluoromethyl)phenyl)-5H-pyrrolo[3,2-d]pyrimidin-2-yl)methyl)acrylamide (I-451)

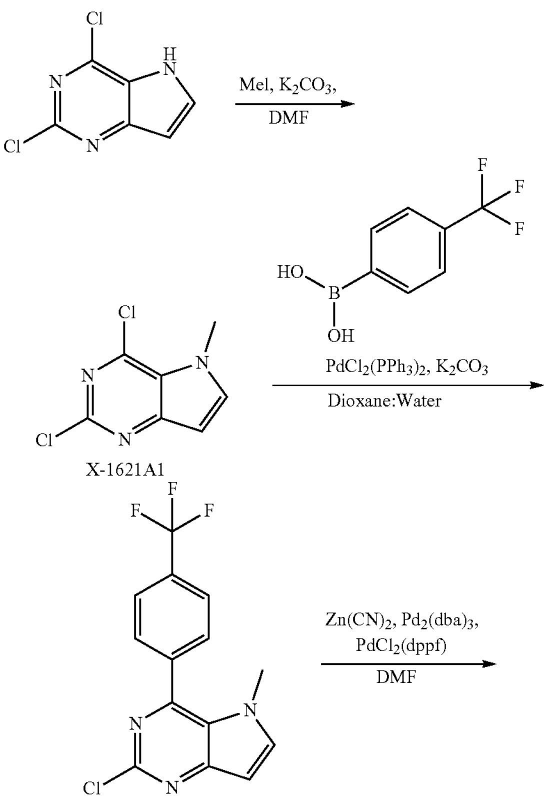

X-1621A1

X-1621A2

-continued

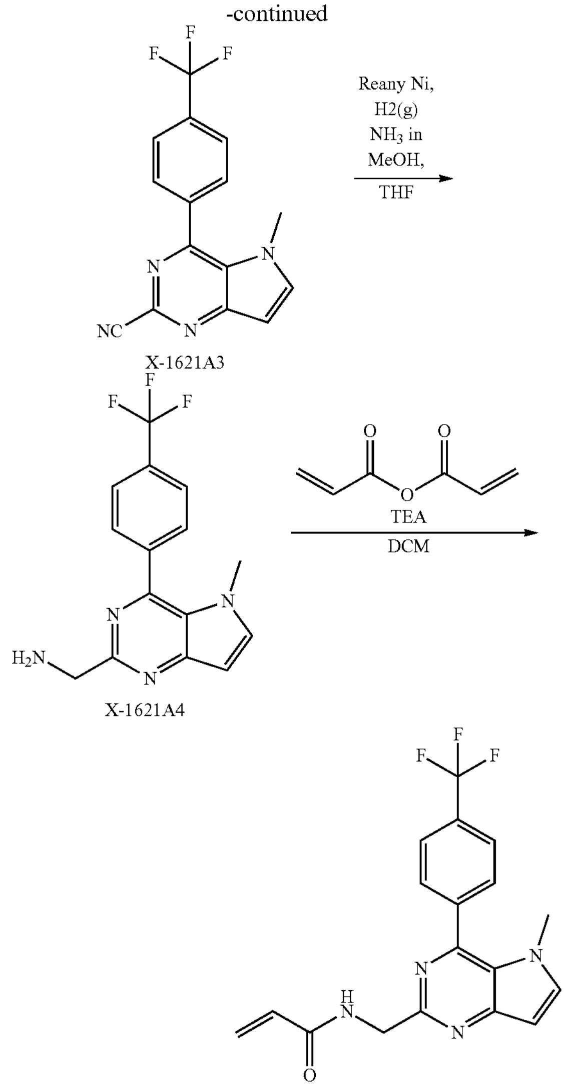

X-1621A3

X-1621A4

I-451

2,4-dichloro-5-methyl-5H-pyrrolo[3,2-d]pyrimidine (X-1621A1). To a stirred solution of 2,4-dichloro-5H-pyrrolo[3,2-d]pyrimidine (3.0 g, 16.04 mmol) in DMF (13 mL) were added $K_2CO_3$ (6.64 g, 48.12 mmol) and methyliodide (2.70 g, 19.25 mmol) at 0° C. under nitrogen. The reaction mixture was stirred at room temperature for 1 h. Reaction mixture was poured into water, resulting precipitate was filtered and dried under reduced pressure, to afford 2,4-dichloro-5-methyl-5H-pyrrolo[3,2-d]pyrimidine (X-1621A1) (3.0 g, 93%) as an off-white solid. MS: $[MH]^+$ 202.9/$[MH+2]^+$ 204.9.

N-((5-methyl-4-(4-(trifluoromethyl)phenyl)-5H-pyrrolo [3,2-d]pyrimidin-2-yl)methyl)acrylamide (I-451). The remaining steps, starting with 2,4-dichloro-5-methyl-5H-pyrrolo[3,2-d]pyrimidine (X-1621A1) were prepared in a manner analogous to the procedures described above for N-((4-(4-(trifluoromethyl)phenyl)-5H-pyrrolo[3,2-d]pyrimidin-2-yl)methyl)acrylamide (I-450)

N-((5-methyl-4-(4-(trifluoromethyl)phenyl)-5H-pyrrolo [3,2-d]pyrimidin-2-yl)methyl)acrylamide (I-451) (0.100 g, 43%) as an off-white solid. $^1H$ NMR (400 MHz, DMSO-$d_6$) δ8.68-8.65 (t, J=5.6 Hz, 1H), 7.93-7.87 (m, 5H), 6.688-6.681 (d, J=2.8 Hz, 1H), 6.43-6.36 (m, 1H), 6.13-6.08 (dd, J=17.2, 2.0 Hz, 1H), 5.62-5.59 (dd, J=10.0, 2.0 Hz, 1H), 4.63-4.62 (d, J=6.0 Hz, 2H), 3.47 (s, 3H). MS: $[MH]^+$ 361.1.

Example 2. TEAD Compound Displacement and Proliferation Assays

Compound Displacement Assay.

A TEAD1 lipid pocket displacement assay was carried out according to the following protocol. Purified His-tagged TEAD1 protein (YAP Binding Domain) was pre-mixed with a Cy5-probe (Cy5-conjugated to a small molecule that binds in the TEAD1 lipid pocket) and Terbium-labeled anti-His antibody (Cisbio Cat 61H12TLB). The binding of the Cy5-probe to anti-His-Tb/His-tag TEAD1 complex yielded a TR-FRET signal. Addition of compounds that are TEAD1 lipid pocket binders resulted in the displacement of the Cy5-probe from TEAD1 and a decrease in the TR-FRET signal. After 60 minutes incubation at room temperature of compounds with the His-TEAD1/anti-His-Tb/Cy5-probe complex, the plate was read on a plate reader (BMG ClarioStar Cat 430-1300) using TR-FRET mode with wavelengths of 665 nm/620 nm. The potency of compounds as TEAD1 lipid pocket binders was determined by IC50 value generated using a non-linear 4 parameter curve fit.

72H TEAD Proliferation Assay.

The effect of TEAD inhibition on cell proliferation was assayed using Cell Titer Glo (CTG) 2.0 to measure response in mesothelioma cell lines NCI-H226 (ATCC, #CRL-5826) and NCI-H28 (ATCC, #CRL-5820).

Description

The 72H TEAD Proliferation assay utilizes Cell Titer-Glo 2.0 (Promega, #G9243) to measure the proliferation of cells in the presence or absence of compound. Cell Titer-Glo 2.0 determines the amount of viable cells by quantifying ATP (an indication of metabolically active cells). It utilizes the conversion of Luciferin to Oxyluciferin and a luminescent signal with the use of ATP to report the quantity of viable cells in culture. Within cells that are continually growing, ATP is being synthesized to meet their metabolic demands, meanwhile the opposite is true for cells that are dying or slowing down their proliferation and either no longer using ATP or are using less, respectively. The NF2-deficient NCI-H226 has been genetically validated as a cell line that is sensitive to TEAD inhibition. The NF2-wild type NCI-H28 has been genetically validated as a cell line that is not sensitive to TEAD inhibition and grows independently of TEAD activity.

Application

Monitor for any effects on proliferation with compound treatment.

Compounds were screened against the responsive NCI-H226 cell line to assess the compounds' ability to inhibit TEAD and cell growth. Compounds were also screened against the non-responsive NCI-H28 cell line to ascertain whether the inhibition of cell growth was due to inhibition of the target TEAD or whether the inhibition was due to off-target cytotoxicity.

General Culture Conditions

Thaw Medium 1/Growth Medium 1: RPMI 1640 with GlutaMAX supplement medium (Gibco, #61870036) with 10% FBS (Gibco, #A3160402))

Assay Medium 1: RPMI 1640 medium with L-Glutamine, no phenol red (Gibco, #11835030) with 10% FBS (Gibco, #A3160402)

Both NCI-H226 and NCI-H28 cells were grown at 37° C. with 5% CO2 using Growth Medium 1.

To recover the cells, frozen stock was thawed quickly in a 37° C. water-bath after removal from liquid nitrogen, transferred to a tube containing 1 ml of pre-warmed Thaw Medium 1, spun down, resuspended with 1 ml of pre-warmed Growth Medium 1 and added into a T75 with 9 ml of Growth Medium 1. The cell culture was grown in an incubator at 37° C. with 5% CO2. At first passage, cells were transferred into a T150 with 15 mL Growth Medium 1 to allow the cells to continue growing. Cells were split before they reached complete confluency and were not used past passage number 20.

The cells were passaged by first rinsing them with phosphate buffered saline (PBS), and then detaching them from the flask with TrypLE Express (1×) (Gibco, #12604013). Growth Medium 1 was added and the cell suspension was transferred to a tube. The cells were counted and the volume was reduced to get 1M cells was added to another tube. The cells were spun down and resuspended in 2 mL of fresh Growth Medium 1. 1 ml of the cell suspension was added into a new T150 with 14 mL of Growth Medium 1. Sub-cultivation ratio: 500,000 cells in a T150 weekly.

The cells were frozen by rinsing them with phosphate buffered saline (PBS), and detaching them from the flask with TrypLE Express (1×) (Gibco, #12604013). Growth Medium 1 was added and the cell suspension was transferred to a tube. The cells were spun down and resuspended in freezing medium (95% FBS+5% DMSO). The cells were then added to cryovials and stored at −80° C. overnight then transferred to liquid nitrogen the next day.

Functional Validation and Assay Performance

The following assays were designed for 384-well format. Performing the assay in different tissue culture formats will need the cell number and reagent volume to be scaled up appropriately.

Materials

- Thaw Medium 1/Growth Medium 1 (Gibco, #61870036)+10% FBS (Gibco #A3160402)
- Assay Medium 1 (Gibco, #11835030) with 10% FBS (Gibco #A3160402)
- Phosphate Buffered Saline (Gibco, #10010023)
- TrypLE Express (Gibco, #12604013)
- Trypan Blue 0.4% (Invitrogen, #T10282)
- Countess II FL Automated Cell Counter (ThermoFisher Scientific, #AMQAF1000)
- Multidrop Combi Reagent Dispenser (ThermoFisher Scientific, #5840300)
- 384-well Low Flange Black Flat Bottom Polystyrene TC-treated Microplates (Corning 3571)
- Echo (Beckman)
- CTG 2.0 (Promega, #G9243)
- Bravo Liquid Handler (Agilent)
- EnVision Multilabel Plate Reader (PerkinElmer)

*Mycoplasma* Testing of NCI-H226 and NCI-H28 Cell Lines

The 2 cell lines were tested for *Mycoplasma* by IDEXX BioAnalytics using PCR-based *Mycoplasma* detection and confirmed to be negative.

Anti-Proliferative Effect of Compounds that Inhibits TEAD Activity Measured by CTG 1) Assay ready plates (ARPs) were prepared by Echo acoustic liquid handler. For each compound, duplicate of 10-point half-log dilution series were dispensed in a 384-well microplate (Corning 3571).
2) Each well had 50 nl of compound and had a final DMSO of 0.1% after cell plating.
3) Before use, ARPs were allowed to warm up to room temperature for 30 min.

4) ARPs were spun for 5 minutes at 1500 RPM before removing the plate seals.

5) NCI-H226 or NCI-H28 cells were harvested from culture in Assay Medium 1 and the multidrop Combi reagent dispenser was used to seed cells at 500 cells per 50 ul in each well of the ARPs and one Corning 3571 plate without compounds for Time 0 (TO) readout.

6) The T0 plate was incubated for 2 hours at 37° C. with 5% $CO_2$ to allow cells to settle, then the CTG Assay was performed.

7) All ARPs were incubated for 72 hours at 37° C. with 5% $CO_2$, then the CTG Assay was performed for Time 72H (T72) readout.

8) CTG Assay: Bravo liquid handler (Agilent) was used to add 25 ul of CTG 2.0 to all columns of the plate except for Column 24, which was used to subtract out the background. After CTG addition, plates were placed on shaker at 800 RPM for 15 minutes at room temperature and kept in the dark. Luminescence was measured using EnVision multilabel plate reader with ultra-sensitive detection module.

9) Data Analysis: First background luminescence (no CTG wells) was subtracted from luminescence reading of all wells, then TO luminescence was subtracted from T72 luminescence. To compare anti-proliferative effect of compounds, $GI_{50}$ was obtained by fitting dose response curves with nonlinear regression curve fit.

Results are presented in Table 1. Corn pounds having an $IC_{50}$ less than or equal to 250 nM are represented as "A"; compounds having an $IC_{50}$ greater than 250 nM but less than or equal to 500 nM are represented as "B"; compounds having an $IC_{50}$ greater than 500 nM but less than or equal to 1 μM are represented as "C"; and compounds having an $IC_{50}$ greater than 1 μM are represented as "D". Compounds having a $GI_{50}$ less than or equal to 1 μM are represented as "A"; compounds having a $GI_{50}$ greater than 1 μM but less than or equal to 5 μM are represented as "B"; compounds having a $GI_{50}$ greater than 5 μM but less than or equal to 10 μM are represented as "C"; and compounds having a $GI_{50}$ greater than 10 μM are represented as "D".

TABLE 1

| Compound | CDA $IC_{50}$ | $GI_{50}$ |
|---|---|---|
| I-1 | B | D |
| I-2 | D | D |
| I-3 | B | B |
| I-4 | B | A |
| I-5 | D | D |
| I-6 | A | A |
| I-7 | B | D |
| I-8 | A | A |
| I-9 | B | B |
| I-10 | D | B |
| I-11 | D | D |
| I-12 | A | B |
| I-13 | D | D |
| I-14 | B | D |
| I-15 | D | D |
| I-16 | B | B |
| I-17 | B | B |
| I-18 | C | B |
| I-19 | D | B |
| I-20 | D | D |
| I-21 | B | D |
| I-22 | C | B |
| I-23 | A | A |
| I-24 | A | B |
| I-25 | A | C |
| I-26 | D | C |
| I-27 | C | B |
| I-28 | A | B |
| I-29 | D | D |
| I-30 | B | B |
| I-31 | B | D |
| I-32 | A | B |
| I-33 | B | C |
| I-34 | C | D |
| I-35 | D | B |
| I-36 | A | A |
| I-37 | A | D |
| I-38 | A | D |
| I-39 | A | D |
| I-40 | D | B |
| I-41 | A | A |
| I-42 | A | A |
| I-43 | A | D |
| I-44 | B | D |
| I-45 | B | D |
| I-46 | B | D |
| I-47 | C | D |
| I-48 | B | D |
| I-49 | B | D |
| I-50 | A | A |
| I-51 | B | B |
| I-52 | A | B |
| I-53 | A | B |
| I-54 | B | C |
| I-55 | D | C |
| I-56 | B | D |
| I-57 | | D |
| I-58 | C | C |
| I-59 | D | B |
| I-60 | A | B |
| I-61 | A | B |
| I-62 | D | D |
| I-63 | | D |
| I-64 | D | D |
| I-65 | D | D |
| I-66 | D | C |
| I-67 | B | D |
| I-68 | D | D |
| I-69 | D | D |
| I-70 | D | D |
| I-71 | D | D |
| I-72 | A | C |
| I-73 | D | B |
| I-74 | D | C |
| I-75 | D | D |
| I-76 | D | D |
| I-77 | | D |
| I-78 | B | A |
| I-79 | B | B |
| I-80 | A | A |
| I-81 | B | B |
| I-82 | B | B |
| I-83 | B | B |
| I-84 | A | A |
| I-85 | A | A |
| I-86 | A | A |
| I-87 | A | A |
| I-88 | | B |
| I-89 | | A |
| I-90 | A | A |
| I-91 | A | A |
| I-92 | A | B |
| I-93 | D | D |
| I-94 | D | D |
| I-95 | D | D |
| I-96 | A | A |
| I-97 | D | D |
| I-98 | C | A |
| I-99 | D | D |
| I-100 | C | C |
| I-101 | C | D |
| I-102 | B | A |
| I-103 | D | D |
| I-104 | B | D |
| I-105 | D | B |

TABLE 1-continued

| Compound | CDA $IC_{50}$ | $GI_{50}$ |
|---|---|---|
| I-106 | B | B |
| I-107 | D | D |
| I-108 | C | B |
| I-109 | A | A |
| I-110 | D | B |
| I-111 | A | A |
| I-112 | | B |
| I-113 | D | D |
| I-114 | A | A |
| I-115 | | A |
| I-116 | D | D |
| I-117 | B | B |
| I-118 | B | D |
| I-119 | A | A |
| I-120 | A | A |
| I-121 | D | B |
| I-122 | B | B |
| I-123 | D | D |
| I-124 | B | D |
| I-125 | C | D |
| I-126 | D | D |
| I-127 | C | B |
| I-128 | A | B |
| I-129 | D | B |
| I-130 | A | D |
| I-131 | B | D |
| I-132 | A | A |
| I-133 | | A |
| I-134 | C | B |
| I-135 | A | B |
| I-136 | B | A |
| I-137 | C | B |
| I-138 | A | B |
| I-139 | A | A |
| I-140 | A | A |
| I-141 | B | B |
| I-142 | D | A |
| I-143 | D | D |
| I-144 | C | D |
| I-145 | D | D |
| I-146 | A | B |
| I-147 | D | D |
| I-148 | D | D |
| I-149 | A | D |
| I-150 | D | D |
| I-151 | B | D |
| I-152 | B | B |
| I-153 | D | D |
| I-154 | D | B |
| I-155 | B | D |
| I-156 | D | D |
| I-157 | D | D |
| I-158 | D | D |
| I-159 | D | D |
| I-160 | D | D |
| I-161 | | D |
| I-162 | | |
| I-163 | | |
| I-164 | C | D |
| I-165 | | |
| I-166 | A | A |
| I-167 | A | A |
| I-168 | A | A |
| I-169 | A | A |
| I-170 | D | A |
| I-171 | B | A |
| I-172 | A | A |
| I-173 | A | A |
| I-174 | A | A |
| I-175 | B | A |
| I-176 | A | A |
| I-177 | A | A |
| I-178 | A | A |
| I-179 | A | A |
| I-180 | A | A |
| I-181 | A | A |
| I-182 | B | |
| I-183 | D | |

TABLE 1-continued

| Compound | CDA $IC_{50}$ | $GI_{50}$ |
|---|---|---|
| I-184 | A | C |
| I-185 | C | B |
| I-186 | C | B |
| I-187 | D | |
| I-188 | B | B |
| I-189 | D | C |
| I-190 | B | B |
| I-191 | A | A |
| I-192 | A | A |
| I-193 | A | B |
| I-194 | A | A |
| I-195 | B | B |
| I-196 | B | B |
| I-197 | B | |
| I-198 | A | B |
| I-199 | C | B |
| I-200 | A | |
| I-201 | D | C |
| I-202 | A | A |
| I-203 | A | B |
| I-204 | C | B |
| I-205 | B | B |
| I-206 | D | B |
| I-207 | A | C |
| I-208 | A | B |
| I-209 | B | C |
| I-210 | A | |
| I-211 | A | |
| I-212 | D | |
| I-213 | A | |
| I-214 | A | A |
| I-215 | A | A |
| I-216 | D | |
| I-217 | D | |
| I-218 | D | |
| I-219 | D | B |
| I-220 | A | |
| I-221 | C | |
| I-222 | A | |
| I-223 | D | |
| I-224 | D | |
| I-225 | A | |
| I-226 | A | |
| I-227 | D | A |
| I-228 | D | |
| I-229 | D | |
| I-230 | A | |
| I-231 | D | |
| I-232 | A | |
| I-233 | B | |
| I-234 | D | C |
| I-235 | A | A |
| I-236 | A | A |
| I-237 | D | |
| I-238 | B | B |
| I-239 | B | B |
| I-240 | D | |
| I-241 | A | A |
| I-242 | D | |
| I-243 | A | |
| I-244 | B | |
| I-245 | A | A |
| I-246 | A | A |
| I-247 | A | A |
| I-248 | B | A |
| I-249 | A | A |
| I-250 | A | A |
| I-251 | A | A |
| I-252 | A | A |
| I-253 | A | B |
| I-254 | A | C |
| I-255 | A | B |
| I-256 | A | B |
| I-257 | A | C |
| I-258 | A | B |
| I-259 | A | A |
| I-260 | B | A |
| I-261 | A | A |

TABLE 1-continued

| Compound | CDA $IC_{50}$ | $GI_{50}$ |
|---|---|---|
| I-262 | A | A |
| I-263 | A | A |
| I-264 | A | B |
| I-265 | A | A |
| I-266 | B | |
| I-267 | A | A |
| I-268 | A | A |
| I-269 | B | A |
| I-270 | A | A |
| I-271 | A | B |
| I-272 | A | B |
| I-273 | D | |
| I-274 | A | A |
| I-275 | A | A |
| I-276 | C | |
| I-277 | A | B |
| I-278 | C | B |
| I-279 | A | B |
| I-280 | A | A |
| I-281 | B | B |
| I-282 | C | B |
| I-283 | A | |
| I-284 | D | |
| I-285 | A | B |
| I-286 | D | |
| I-287 | A | B |
| I-288 | D | |
| I-289 | A | A |
| I-290 | A | A |
| I-291 | C | A |
| I-292 | A | A |
| I-293 | A | |
| I-294 | D | B |
| I-295 | A | A |
| I-296 | A | |
| I-297 | A | |
| I-298 | D | |
| I-299 | A | A |
| I-300 | A | A |
| I-301 | A | A |
| I-302 | A | A |
| I-303 | A | A |
| I-304 | B | A |
| I-305 | A | A |
| I-306 | B | A |
| I-307 | A | A |
| I-308 | C | A |
| I-309 | D | A |
| I-310 | B | B |
| I-311 | B | B |
| I-312 | C | A |
| I-313 | D | B |
| I-314 | A | A |
| I-315 | D | A |
| I-316 | A | A |
| I-317 | A | B |
| I-318 | A | A |
| I-319 | A | A |
| I-320 | A | B |
| I-321 | A | B |
| I-322 | C | A |
| I-323 | A | B |
| I-324 | A | A |
| I-325 | A | A |
| I-326 | A | A |
| I-327 | A | A |
| I-328 | A | B |
| I-329 | A | |
| I-330 | A | A |
| I-331 | A | A |
| I-332 | D | |
| I-333 | D | |
| I-334 | D | |
| I-335 | C | |
| I-336 | B | A |
| I-337 | A | A |
| I-338 | C | B |
| I-339 | D | |

TABLE 1-continued

| Compound | CDA $IC_{50}$ | $GI_{50}$ |
|---|---|---|
| I-340 | B | |
| I-341 | A | A |
| I-342 | D | B |
| I-343 | A | A |
| I-344 | A | A |
| I-345 | A | A |
| I-346 | B | |
| I-347 | A | C |
| I-348 | A | A |
| I-349 | A | A |
| I-350 | A | A |
| I-351 | A | A |
| I-352 | A | B |
| I-353 | B | B |
| I-354 | D | |
| I-355 | B | |
| I-356 | D | |
| I-357 | A | |
| I-358 | A | A |
| I-359 | D | |
| I-360 | D | |
| I-361 | A | B |
| I-362 | B | B |
| I-363 | A | A |
| I-364 | A | |
| I-365 | A | A |
| I-366 | A | A |
| I-367 | A | |
| I-368 | C | B |
| I-369 | A | A |
| I-370 | A | B |
| I-371 | D | C |
| I-372 | C | B |
| I-373 | A | A |
| I-374 | A | B |
| I-375 | A | A |
| I-376 | C | B |
| I-377 | A | |
| I-378 | D | |
| I-379 | D | |
| I-380 | A | |
| I-381 | A | |
| I-382 | B | B |
| I-383 | A | B |
| I-384 | A | A |
| I-385 | B | C |
| I-386 | A | A |
| I-387 | A | A |
| I-388 | A | B |
| I-389 | A | A |
| I-390 | C | C |
| I-391 | A | B |
| I-392 | A | B |
| I-393 | A | A |
| I-394 | A | A |
| I-395 | A | A |
| I-396 | A | B |
| I-397 | A | |
| I-398 | D | B |
| I-399 | A | A |
| I-400 | A | A |
| I-401 | C | C |
| I-402 | A | A |
| I-403 | A | B |
| I-404 | A | A |
| I-405 | A | A |
| I-406 | A | A |
| I-407 | A | |
| I-408 | C | A |
| I-409 | A | A |
| I-410 | D | A |
| I-411 | A | B |
| I-412 | A | C |
| I-413 | D | C |
| I-414 | A | |
| I-415 | A | A |
| I-416 | B | B |
| I-417 | A | A |

TABLE 1-continued

| Compound | CDA $IC_{50}$ | $GI_{50}$ |
|---|---|---|
| I-418 | A | C |
| I-419 | B | B |
| I-420 | A | |
| I-421 | A | B |
| I-422 | C | C |
| I-423 | A | C |
| I-424 | D | |
| I-425 | A | B |
| I-426 | A | B |
| I-427 | A | B |
| I-428 | A | A |
| I-429 | A | |
| I-430 | A | |
| I-431 | C | C |
| I-432 | A | A |
| I-433 | A | A |
| I-434 | A | A |
| I-435 | A | B |
| I-436 | A | A |
| I-437 | C | B |
| I-438 | C | B |
| I-439 | A | |
| I-440 | A | A |
| I-441 | C | A |
| I-442 | A | B |
| I-443 | B | |
| I-444 | D | B |
| I-445 | A | A |
| I-446 | A | A |
| I-447 | A | A |
| I-448 | A | A |
| I-449 | A | A |
| I-450 | D | C |
| I-451 | D | A |

Example 3. TEAD Compound in Combination with EGFR inhibitor

EGFR-mutant NSCLC PC-9 cells were plated in a 96 well tissue culture plate (Corning #3596). On the next day, PC-9 cells were pre-treated with Osimertinib (100 nM) for 24 h, then co-treated with Osimertinib (100 nM) and compound I-41 for 48 hours at various concentrations. Apoptosis was detected by CellEvent Caspase 3/7 Green ReadyProbes Reagent (ThermoFisher), a fluorogenic indicator of activated caspase-3/7. Cell death (apoptsis) and cell growth (phase confluence) over time were captured by IncuCyte live cell imaging system (Essen Bioscience) and quantified by IncuCyte S3 software (Essen Bioscience). Apoptotic Index was calculated by dividing apoptosis signal with phase confluence. Fold change was calculated by dividing apoptotic index of treatment by apoptotic index of DMSO sample, as shown in Table 2.

TABLE 2

| Sample | Fold Change over DMSO at 48 hrs |
|---|---|
| Osimertinib (100 nM) | 2.6 |
| I-41 (10 μM) | 1.1 |
| Osimertinib (100 nM) + I-41 (0.37 μM) | 4.3 |
| Osimertinib (100 nM) + I-41 (1.1 μM) | 4.9 |
| Osimertinib (100 nM) + I-41 (10 μM) | 5.5 |

Exemplary Enumerated Embodiments

1. A compound of formula I:

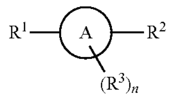

I or a pharmaceutically acceptable salt thereof, wherein:

Ring A is a 9- to 13-membered bicyclic or tricyclic heteroaryl ring having 1-4 heteroatoms independently selected from nitrogen, oxygen, and sulfur;

$R^1$ is halogen, OR, $N(R)_2$, CN, C(O)R, C(O)OR, $C(O)N(R)_2$, $SO_2N(R)_2$, $C(O)N(R)SO_2R$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^2$ is OR, $N(R)_2$, or an optionally substituted group selected from $C_{1-6}$ aliphatic, a 3- to 6-membered saturated or partially unsaturated carbocyclic ring, a saturated or partially unsaturated 3- to 7-membered monocyclic heterocyclic ring having 1-2 heteroatoms independently selected from nitrogen, oxygen, and sulfur, a saturated or partially unsaturated 6- to 10-membered bicyclic heterocyclic ring having 1-2 heteroatoms independently selected from nitrogen, oxygen, and sulfur, a 8- to 11-membered spirocyclic heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur;

$R^3$ is halogen, OR, $N(R)_2$, CN, C(O)R, C(O)OR, $C(O)N(R)_2$, $SO_2N(R)_2$, OC(O)R, N(R)C(O)R, $N(R)SO_2R$, or an optionally substituted group selected from $C_{1-6}$ aliphatic, a 3- to 7-membered saturated or partially unsaturated heterocyclic ring having 1-2 heteroatoms independently selected from nitrogen, oxygen, and sulfur, phenyl, and a 5- to 6-membered heteroaryl ring having 1-4 heteroatoms independently selected from nitrogen, oxygen, and sulfur;

each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur; and n is 0, 1, or 2.

2. The compound according to embodiment 1, wherein Ring A is a 9-membered bicyclic heteroaryl ring having 1-4 heteroatoms independently selected from nitrogen, oxygen, and sulfur.

3. The compound according to embodiment 1, wherein Ring A is a 10-membered bicyclic heteroaryl ring having 1-4 heteroatoms independently selected from nitrogen, oxygen, and sulfur.
4. The compound according to embodiment 1, wherein Ring A is a 13-membered tricyclic heteroaryl ring having 1-4 heteroatoms independently selected from nitrogen, oxygen, and sulfur.
5. The compound according to embodiment 1, wherein Ring A is selected from
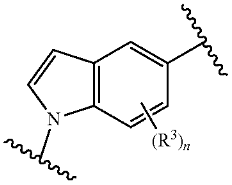
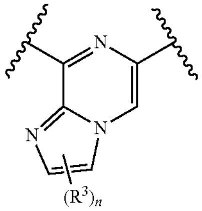
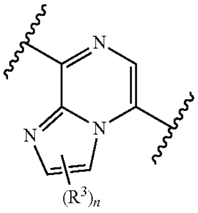
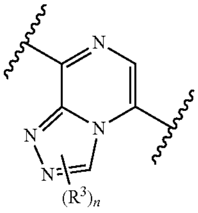
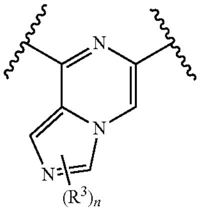
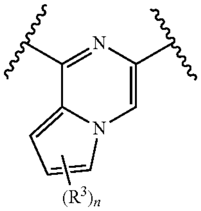
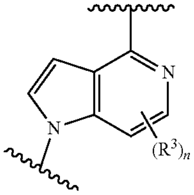
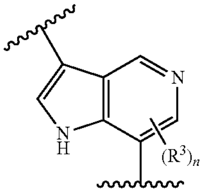
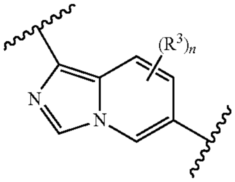
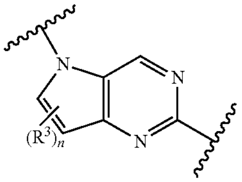
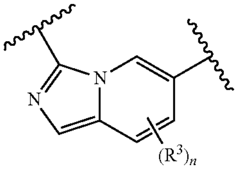
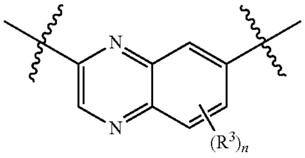
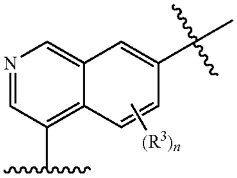
-continued
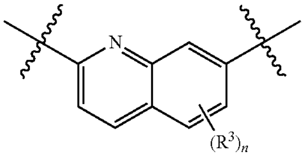
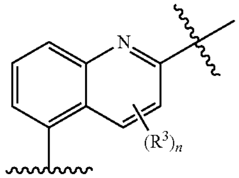
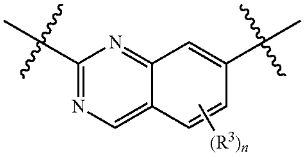
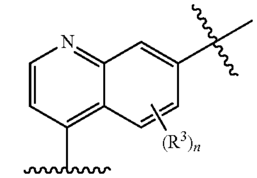
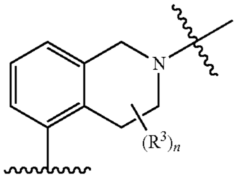
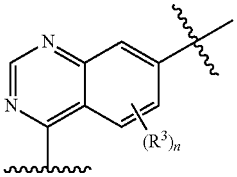
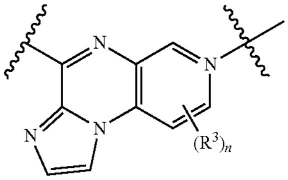
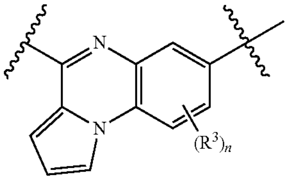
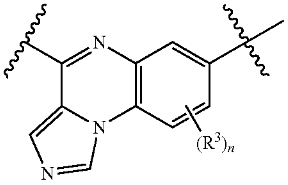
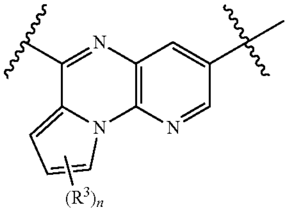
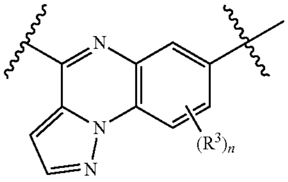

-continued

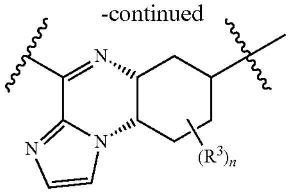

.

6. The compound according to any one of embodiments 1-5, wherein $R^1$ is selected from OR, CN, C(O)R, C(O)OR, $C(O)N(R)_2$, N(R)C(O)R, $C(O)N(R)SO_2R$, $N(R)SO_2R$, or an optionally substituted group selected from $C_{1-6}$ aliphatic and a 5- to 6-membered heteroaryl ring having 1-4 heteroatoms independently selected from nitrogen, oxygen, and sulfur.

7. The compound according to embodiment 6, wherein $R^1$ is C(O)OR.

8. The compound according to embodiment 6, wherein $R^1$ is N(R)C(O)R.

9. The compound according to embodiment 6, wherein $R^1$ is selected from —CN, —OH, —$OCH_3$,

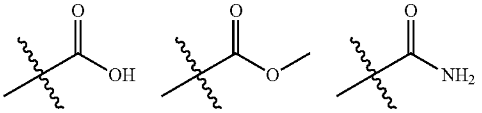

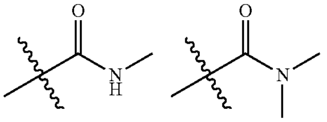

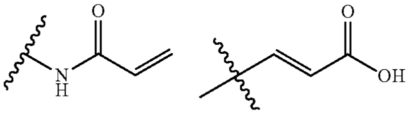

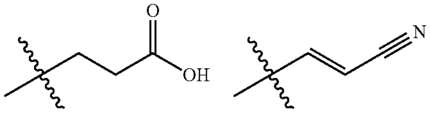

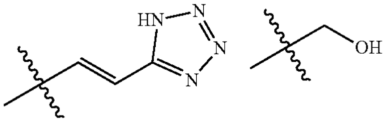

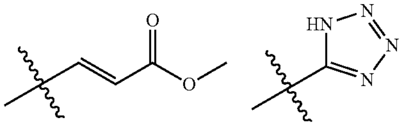

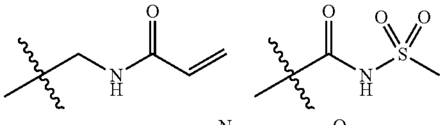

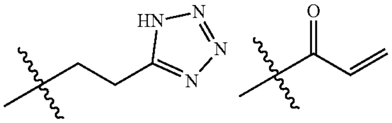

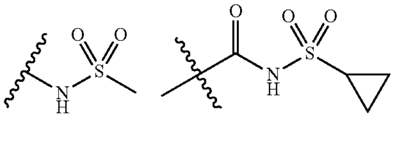

-continued

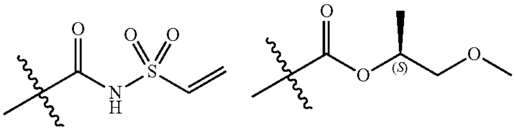

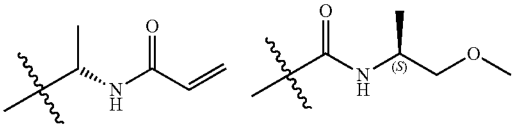

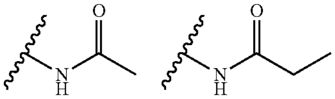

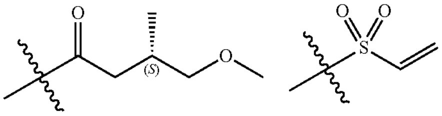

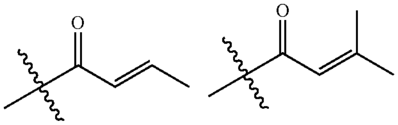

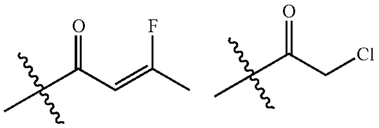

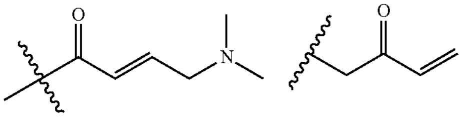

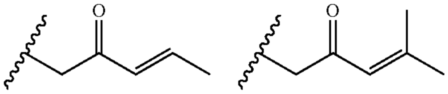

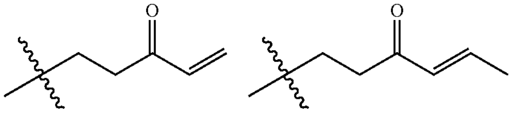

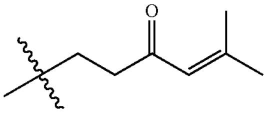

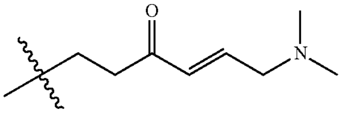

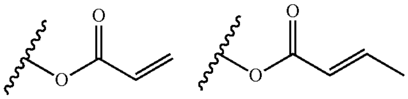

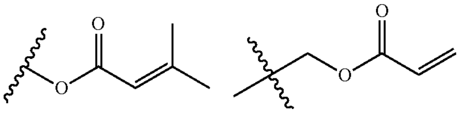

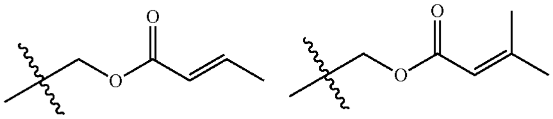

-continued

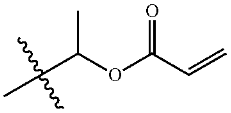 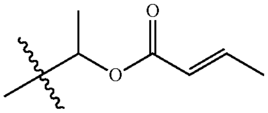

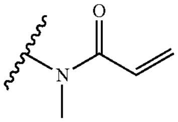 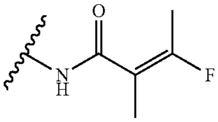

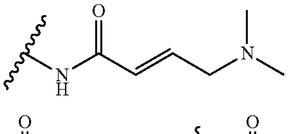

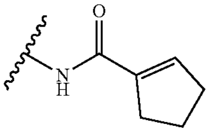 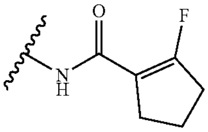

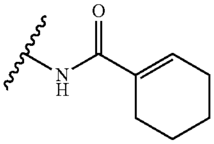 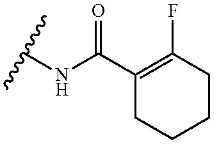

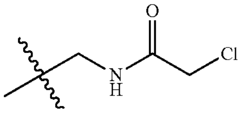 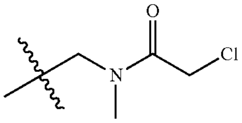

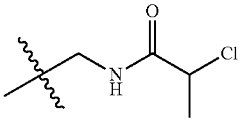 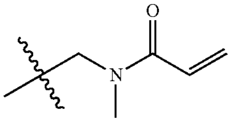

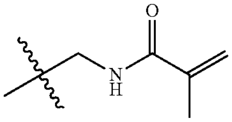 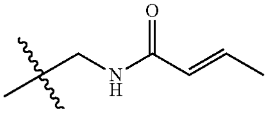

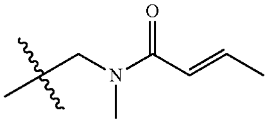 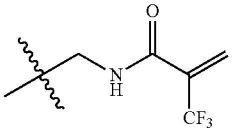

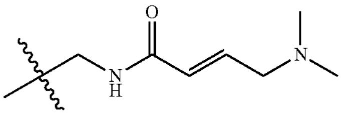

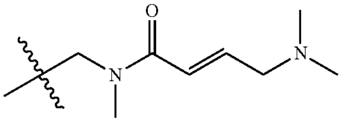

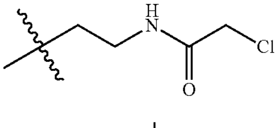 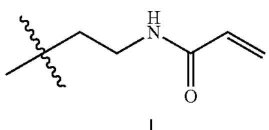

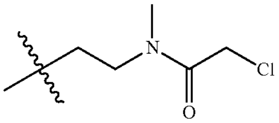 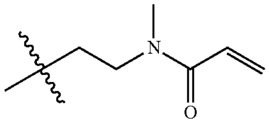

-continued

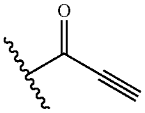 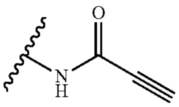 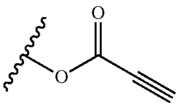

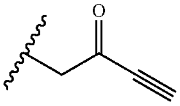 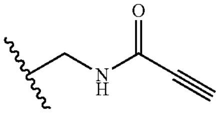

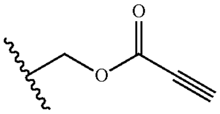 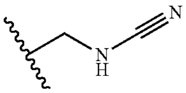

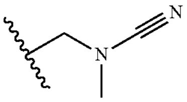 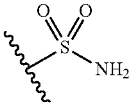 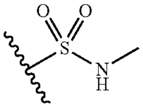

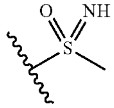 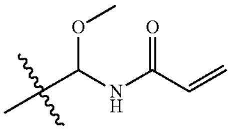

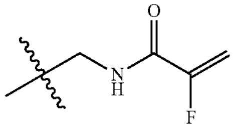 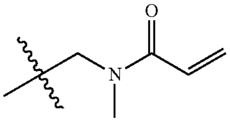

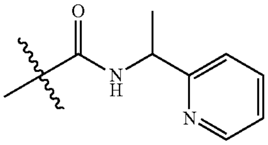 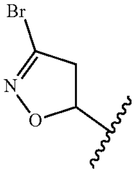.

10. The compound according to any one of embodiments 1-8, wherein $R^2$ is optionally substituted phenyl.
11. The compound according to any one of embodiments 1-8, wherein $R^2$ is an optionally substituted 8- to 10-membered spirocyclic heterocyclic ring having 1-3 heteroatoms independently selected from nitrogen, oxygen, and sulfur.
12. The compound according to any one of embodiments 1-8, wherein $R^2$ is an optionally substituted, a saturated or partially unsaturated 6- to 10-membered bicyclic heterocyclic ring having 1-2 heteroatoms independently selected from nitrogen, oxygen, and sulfur.
13. The compound according to any one of embodiments 1-8, wherein $R^2$ is OR.
14. The compound according to any one of embodiments 1-8, wherein $R^2$ is $N(R)_2$.
15. The compound according to any one of embodiments 1-8, wherein $R^2$ is an optionally substituted 3- to 6-membered saturated or partially unsaturated carbocyclic ring.
16. The compound according to any one of embodiments 1-8, wherein $R^2$ is an optionally substituted 5- to 6-membered heteroaryl ring having 1-3 heteroatoms independently selected from nitrogen, oxygen, and sulfur.
17. The compound according to any one of embodiments 1-8, wherein $R^2$ is an optionally substituted saturated or partially unsaturated 3- to 6-membered heterocyclic ring having 1-3 heteroatoms independently selected from nitrogen, oxygen, and sulfur 18. The compound according to any one of embodiments 1-8, wherein $R^2$ is optionally substituted $C_{1-6}$ aliphatic.
19. The compound according to any one of embodiments 1-8, wherein $R^2$ is selected from cyclopropyl, cyclobutyl, cyclohexyl, trifluoromethyl, phenyl,
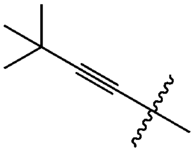
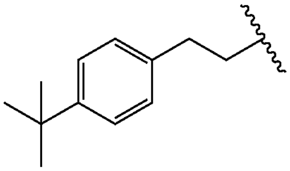
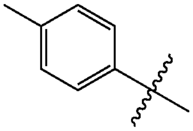
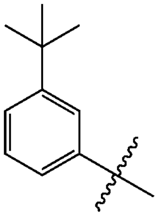
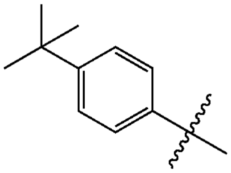
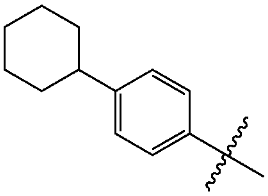
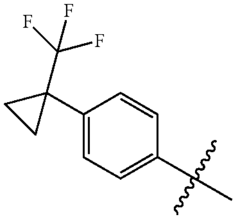
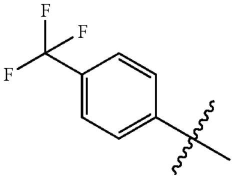
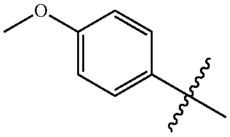
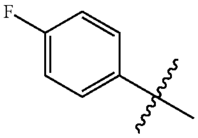
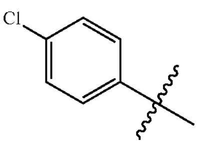
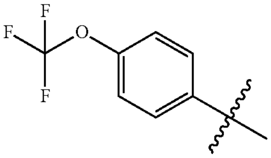
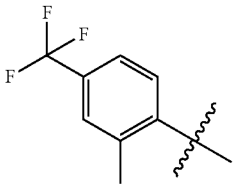
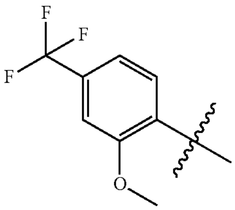
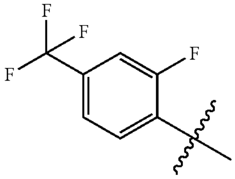
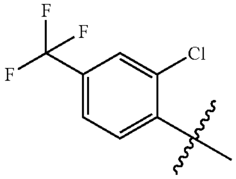
-continued
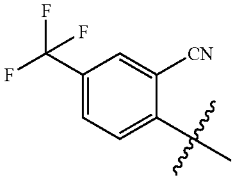
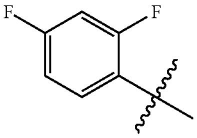
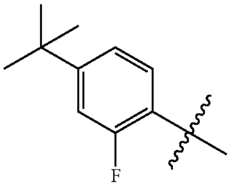
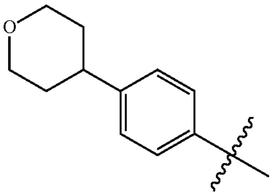
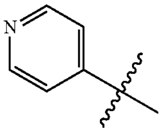
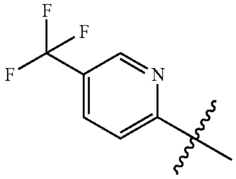
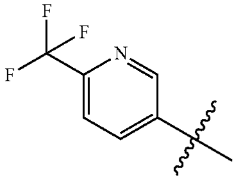
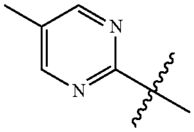
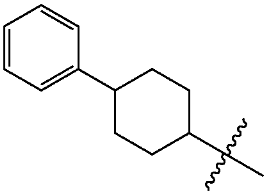
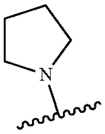
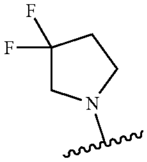
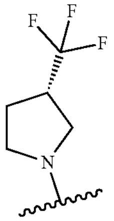
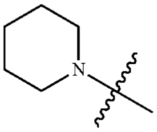
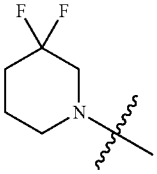
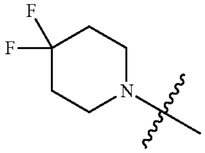
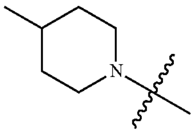
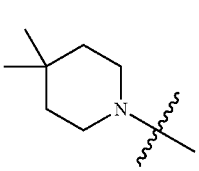
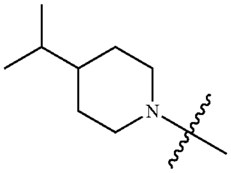
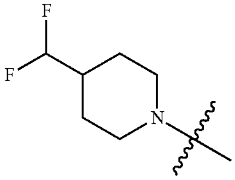
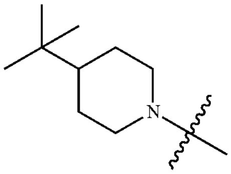

-continued
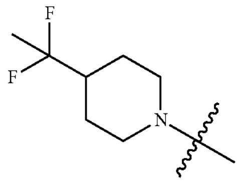
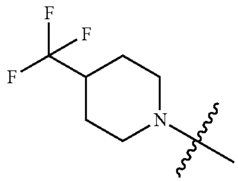
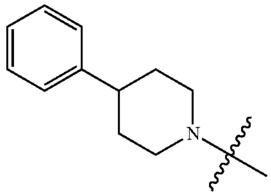
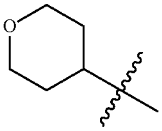
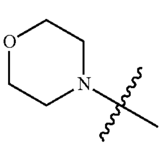
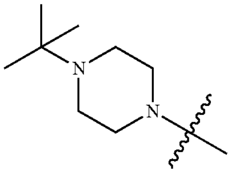
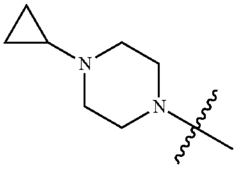
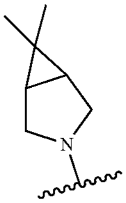
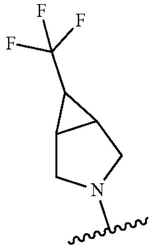
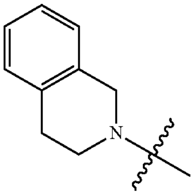
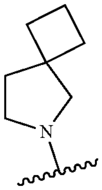
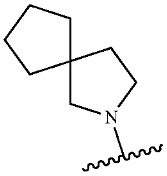
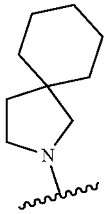
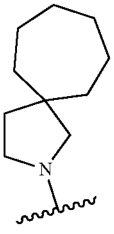
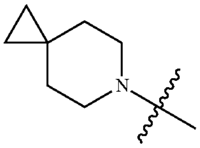
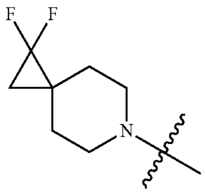
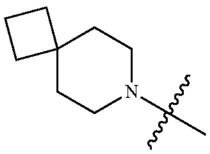
-continued
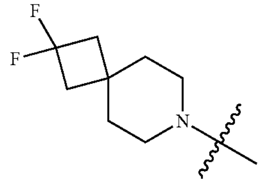
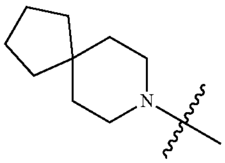
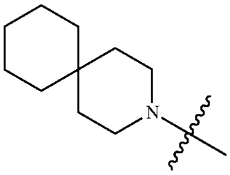
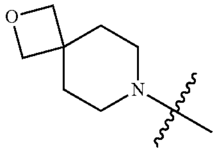
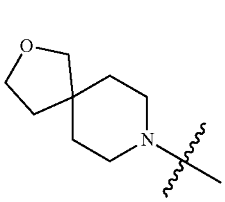
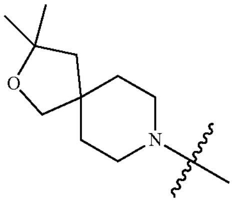
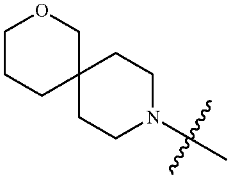
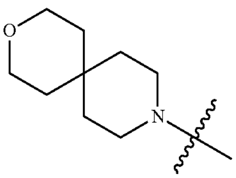
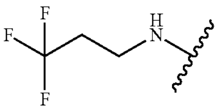
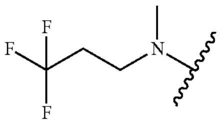
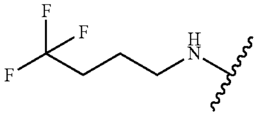
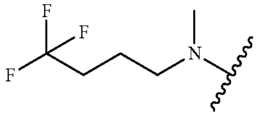
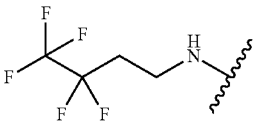
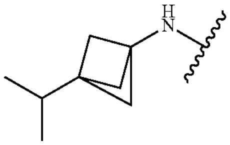
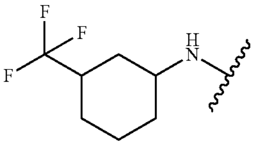
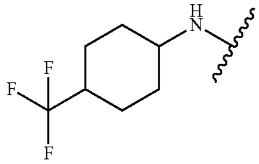
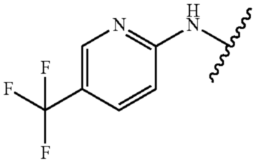
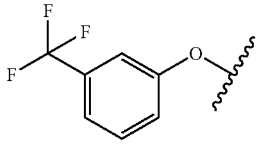
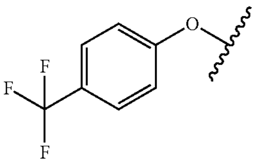
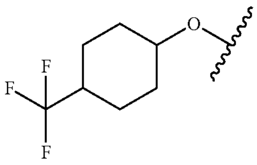

-continued

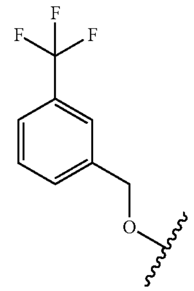

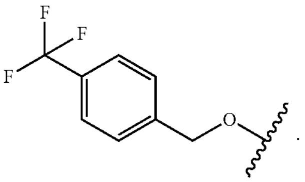

20. The compound according to any one of embodiments 1-19, wherein $R^3$ is selected from halogen, OR, N(R)C(O)R, and optionally substituted $C_{1-6}$ aliphatic.

21. The compound according to any one of embodiments 1-20, wherein R is hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, and phenyl.

22. The compound according to embodiment 21, wherein R is selected from hydrogen and optionally substituted $C_{1-4}$ aliphatic.

23. The compound according to embodiment 21, wherein R is selected from the group consisting of H, $CH_3$, $CH_2CH_3$, cyclopropyl,

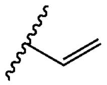
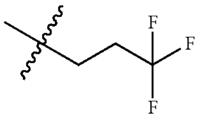
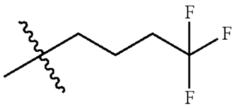
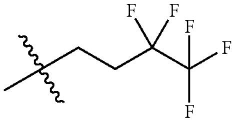
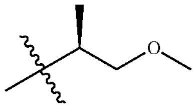
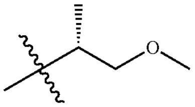
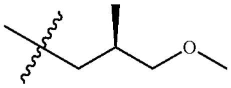
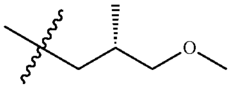
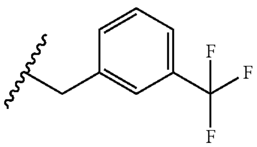
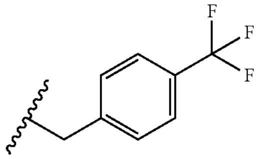
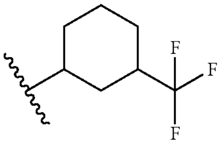
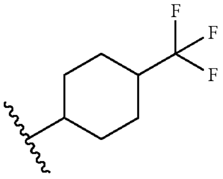
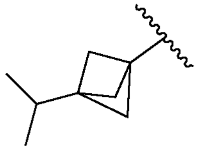

-continued

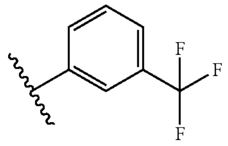
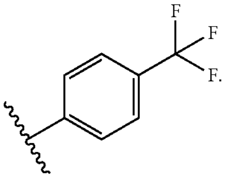

24. The compound according to embodiment 1, wherein the compound is selected from formulae I-a, I-b, I-c, I-d, I-e, I-f, I-g, I-h, I-i, I-j, I-k, I-l, I-m, I-n, I-o, I-p, I-q, I-r, I-s, I-t, I-u, I-v, I-w, I-x, I-y, and I-z:

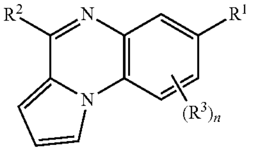

I-a

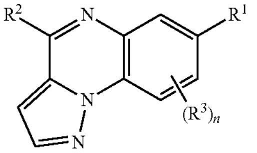

I-b

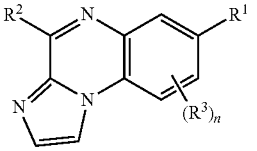

I-c

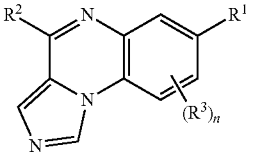

I-d

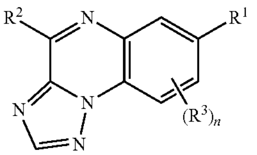

I-e

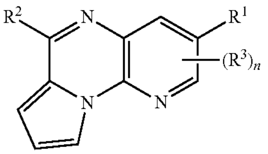

I-f

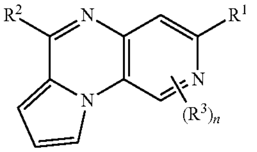

I-g

-continued
I-h
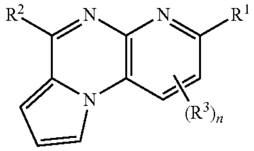
I-i
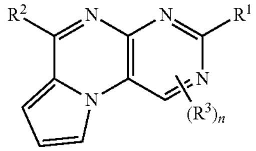
I-j
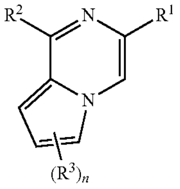
I-k
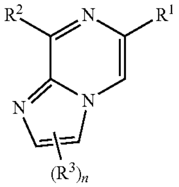
I-l
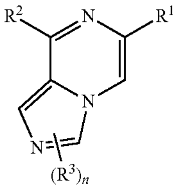
I-m
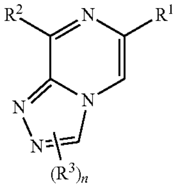
I-n
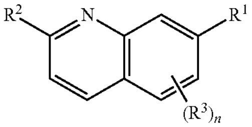
I-o
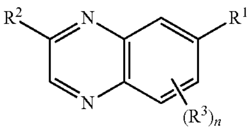
I-p
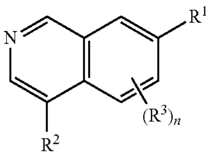
-continued
I-q
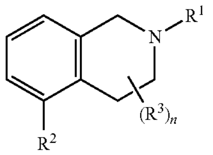
I-r
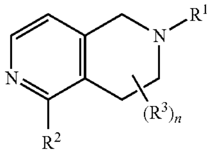
I-s
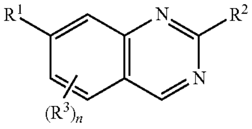
I-t
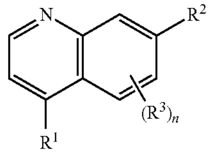
I-u
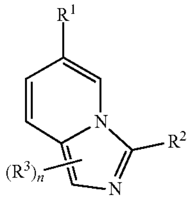
I-v
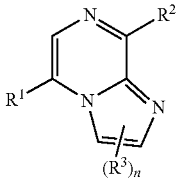
I-w
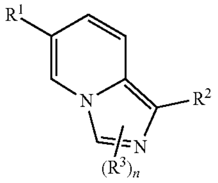
I-x
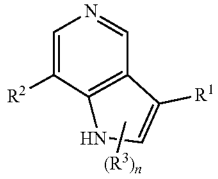
I-y
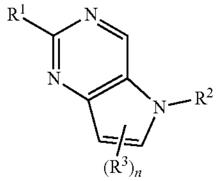

-continued

I-z

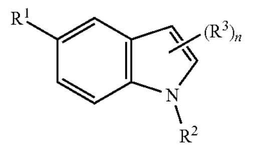

or a pharmaceutically acceptable salt thereof.

25. The compound according to embodiment 1, wherein the compound is selected from formulae I-a-i, I-a-ii, I-c-i, I-c-ii, I-j-i, I-j-ii, I-k-i, I-k-ii, I-k-iii, and I-n-i:

I-a-i

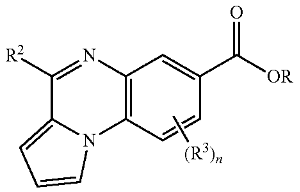

I-a-ii

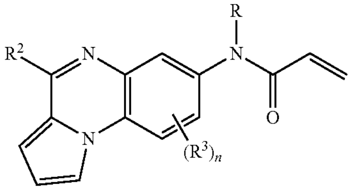

I-c-i

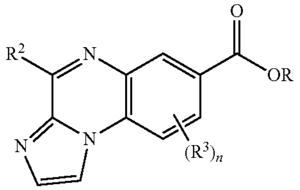

I-c-ii

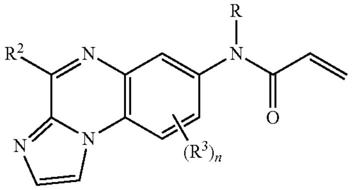

I-j-i

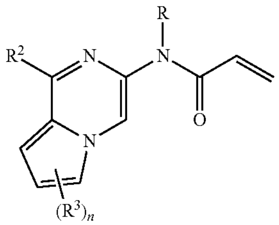

I-j-ii

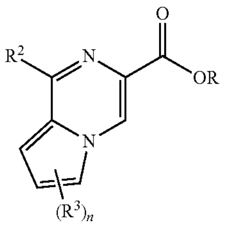

-continued

I-k-i

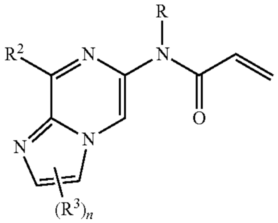

I-k-ii

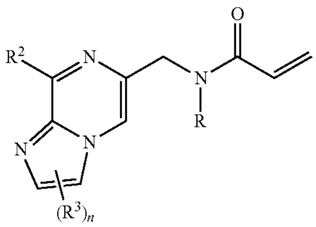

I-k-iii

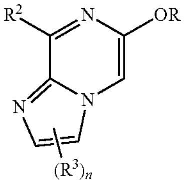

I-n-i

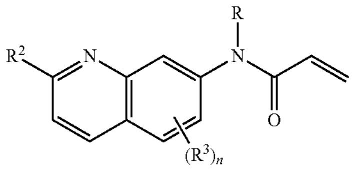

or a pharmaceutically acceptable salt thereof.

26. A pharmaceutical composition comprising a compound according to any one of embodiments 1-25, or a pharmaceutically acceptable salt thereof and a pharmaceutically acceptable carrier, adjuvant, or vehicle.

27. A method of inhibiting activity of a TEAD transcription factor, or a mutant thereof, in a biological sample or in a patient, the method comprising a step of contacting the biological sample or administering to a patient a compound according to any one of embodiments 1-25, or a pharmaceutically acceptable salt thereof.

28. A method of treating a disease or disorder associated with TEAD, the method comprising a step of administering to a patient in need thereof a compound according to any one of embodiments 1-25, or a pharmaceutically acceptable salt thereof.

29. The method according to embodiment 28, wherein the disease or disorder associated with TEAD is a proliferative disease.

30. The method according to embodiment 29, wherein the proliferative disease is a cancer.

31. The method according to embodiment 30, wherein the cancer is selected from a hematological cancer, a lymphoma, a myeloma, a leukemia, a neurological cancer, skin cancer, breast cancer, a prostate cancer, a colorectal cancer, lung cancer, head and neck cancer, a gastrointestinal cancer, a liver cancer, a pancreatic cancer, a genitourinary cancer, a bone cancer, renal cancer, and a vascular cancer.

32. The method according to any one of embodiments 28-31, further comprising co-administration of at least one inhibitor of the RAS/MAPK pathway.

33. The method according to embodiment 32, wherein the RAS/MPAK pathway inhibitor is a KRAS inhibitor, RAF inhibitor, a MEK inhibitor, an ERK inhibitor, an EGFR inhibitor, or a MAPK inhibitor.

The invention claimed is:

1. A compound of Formula I-n-v:

I-n-v

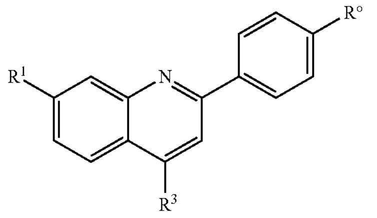

or a pharmaceutically acceptable salt thereof, wherein:

$R^1$ is C(O)OR or N(R)C(O)R;

$R^3$ is OR, $N(R)_2$, SR, CN, C(O)R, C(O)OR, $C(O)N(R)_2$, $SO_2N(R)_2$, OC(O)R, N(R)C(O)R, $N(R)SO_2R$, or an optionally substituted group selected from a 3- to 6-membered saturated or partially unsaturated carbocyclic ring, a 3- to 7-membered saturated or partially unsaturated heterocyclic ring having 1-2 heteroatoms independently selected from nitrogen, oxygen, and sulfur, and a 5- to 6-membered heteroaryl ring having 1-4 heteroatoms independently selected from nitrogen, oxygen, and sulfur;

each R is independently hydrogen or an optionally substituted group selected from $C_{1-6}$ aliphatic, a 3- to 6-membered saturated or partially unsaturated carbocyclic ring, a 4- to 6-membered saturated or partially unsaturated bridged bicyclic or spirocyclic carbocyclic ring, a saturated or partially unsaturated 3- to 6-membered heterocyclic ring having 1-3 heteroatoms independently selected from nitrogen, oxygen, and sulfur, phenyl, and a 5- to 6-membered heteroaryl ring having 1-4 heteroatoms independently selected from nitrogen, oxygen, and sulfur; or:

two R groups on the same nitrogen atom may, together with the atoms to which they are attached, form an optionally substituted saturated or partially unsaturated 3- to 6-membered heterocyclic ring having 0-1 additional heteroatoms selected from nitrogen, oxygen, and sulfur; and $R^\circ$ is $C_{1-6}$ aliphatic or a 5- to 6-membered saturated, partially unsaturated, or aryl ring having 0-4 heteroatoms independently selected from nitrogen, oxygen, or sulfur, wherein $R^\circ$ is optionally substituted with halogen or -(haloR$^\bullet$), wherein $R^\bullet$ is $C_{1-4}$ aliphatic.

2. The compound according to claim 1, wherein $R^1$ is selected from

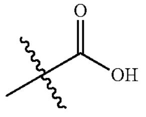
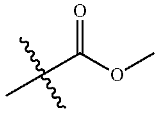
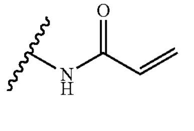

-continued

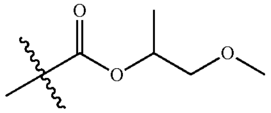
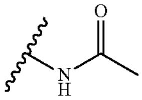
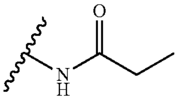
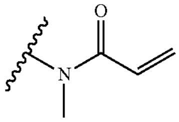
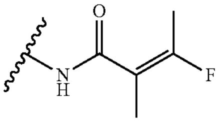
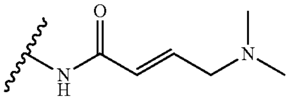
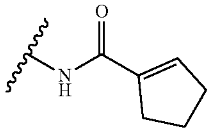
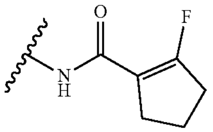
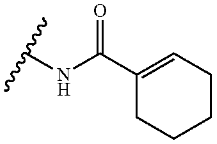
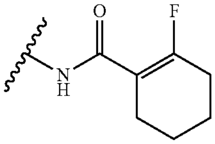
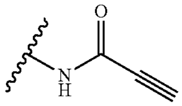
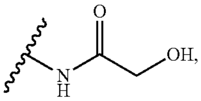
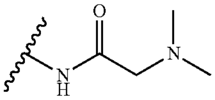
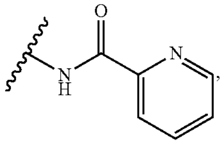
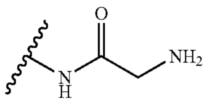
and
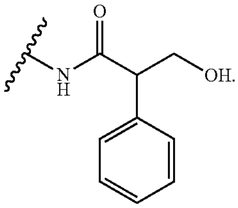

3. The compound according to claim 1, wherein $R^3$ is selected from OR and N(R)C(O)R.

4. The compound according to claim 1, wherein R is selected from the group consisting of H, $CH_3$, $CH_2CH_3$, cyclopropyl,

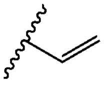
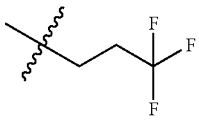

-continued
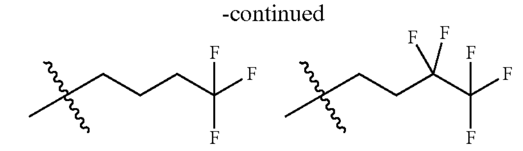
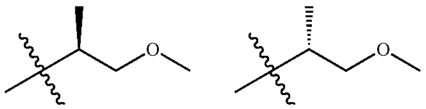
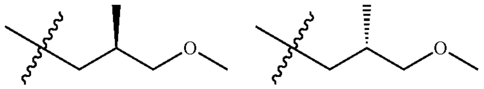
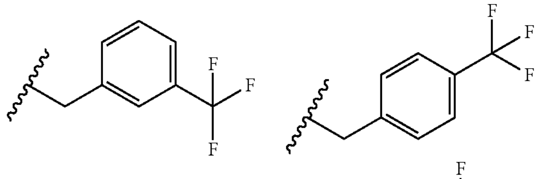
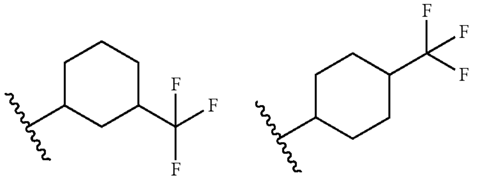
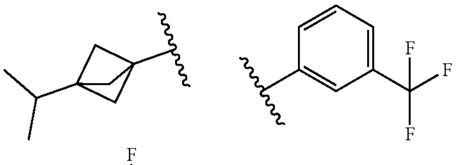
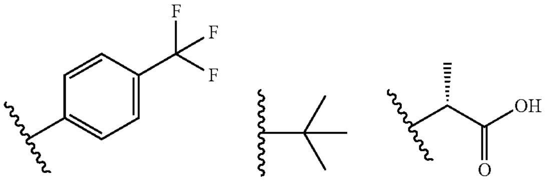
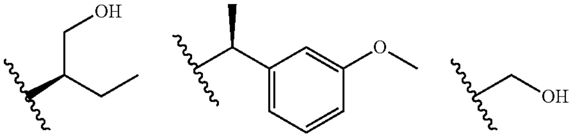
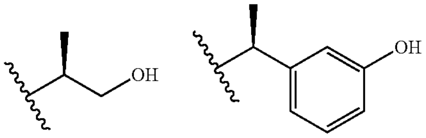
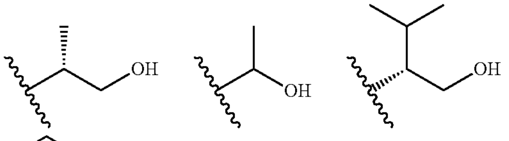
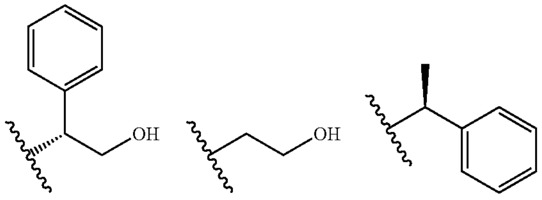
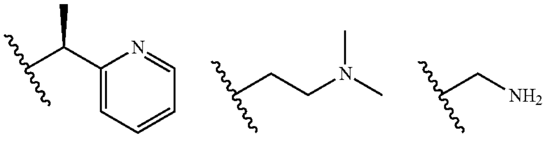
-continued
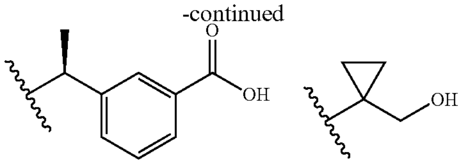
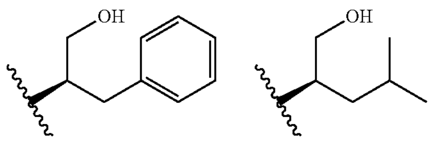
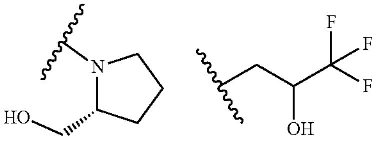
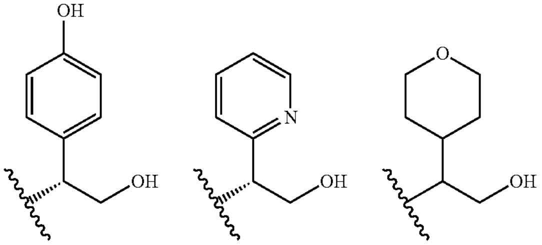
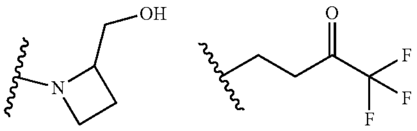
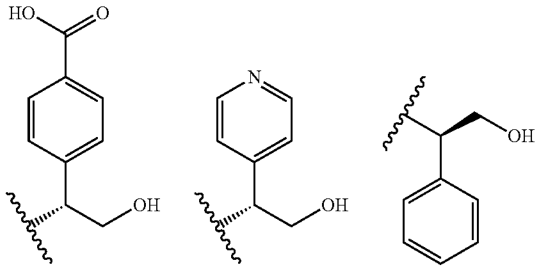
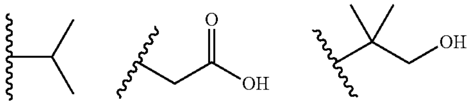
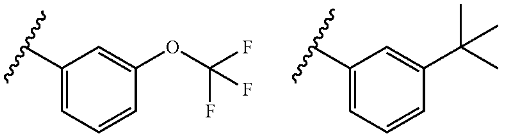
and
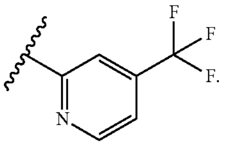
5. The compound according to claim 1, wherein $R^1$ is C(O)OR.
6. The compound according to claim 1, wherein $R^{\circ}$ is —$CF_3$.
7. A pharmaceutical composition comprising a compound according to claim 1, or a pharmaceutically acceptable salt thereof and a pharmaceutically acceptable carrier, adjuvant, or vehicle.

8. A compound selected from
I-85
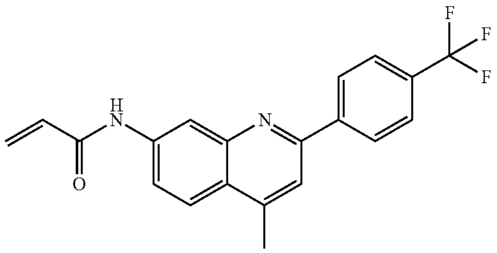
I-86
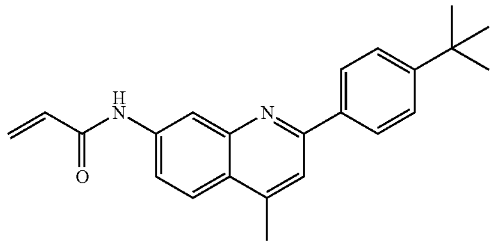
I-87
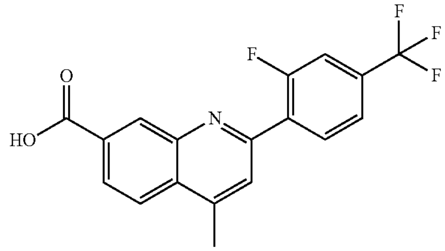
I-88
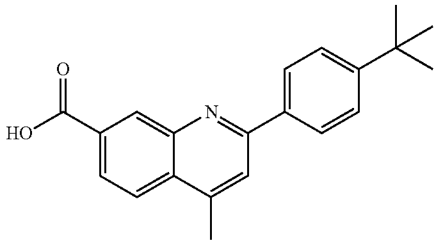
I-89
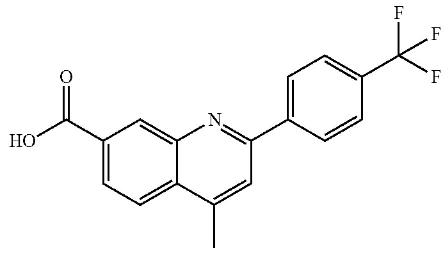
I-90
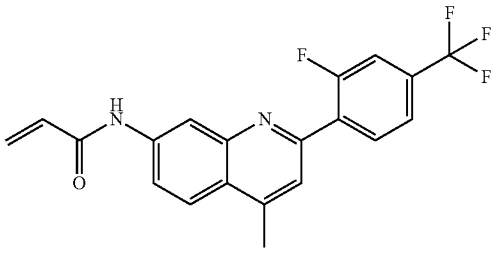
-continued
I-98
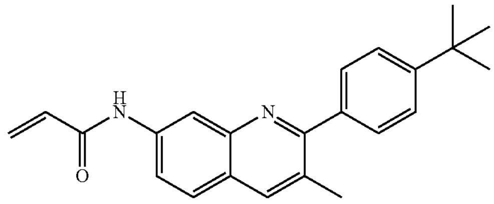
I-103
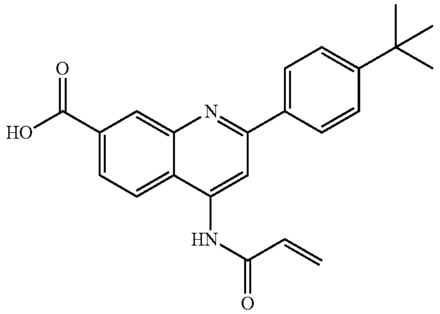
I-106
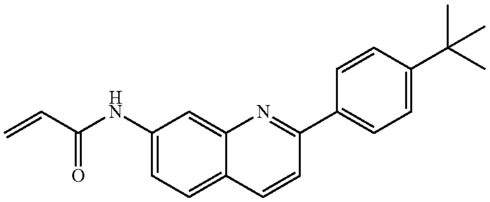
I-181
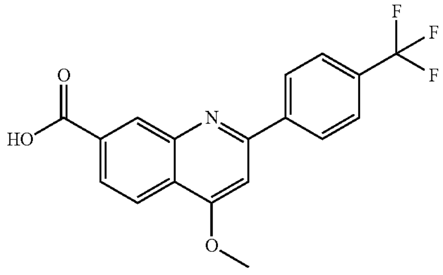
I-252
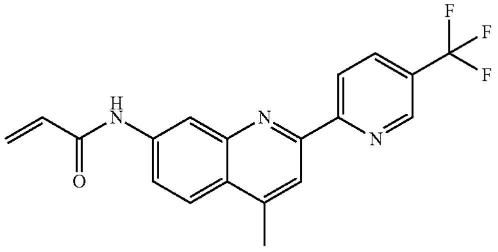
I-254
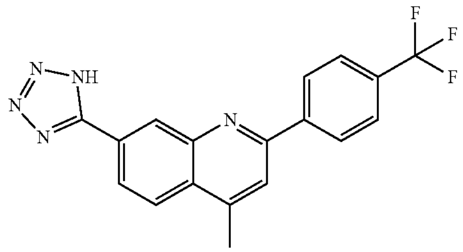

-continued
I-255
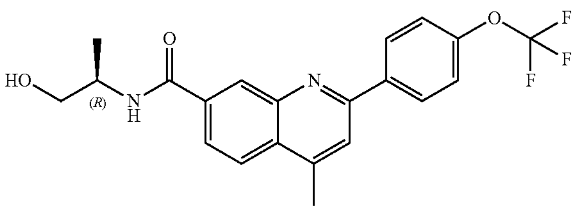
I-256
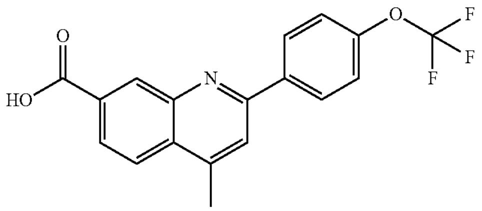
I-258
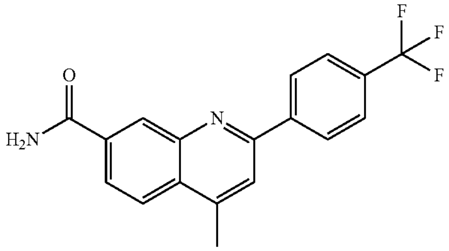
I-259
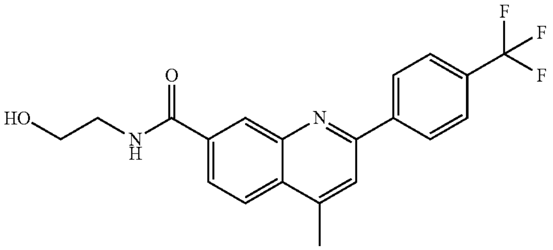
I-260
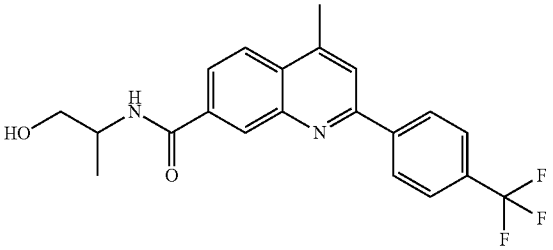
I-261
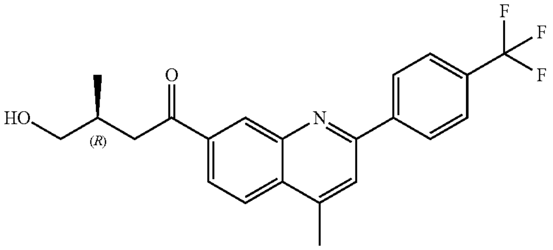
-continued
I-262
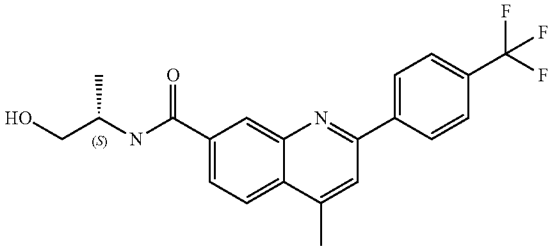
I-263
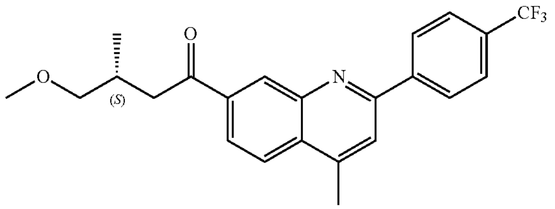
I-264
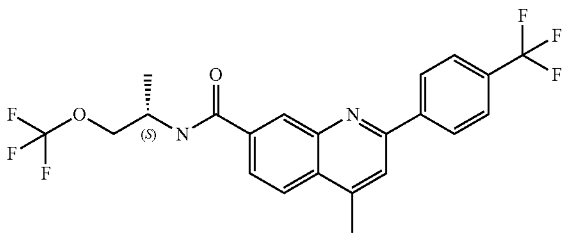
I-265
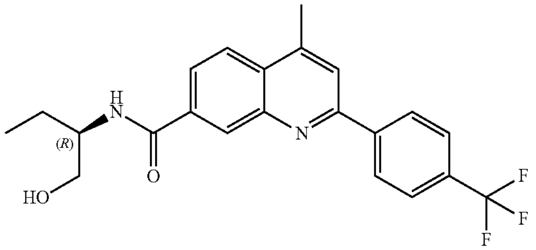
I-266
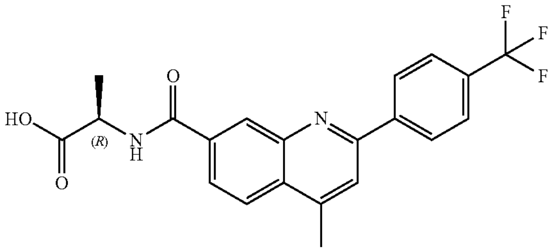
I-267
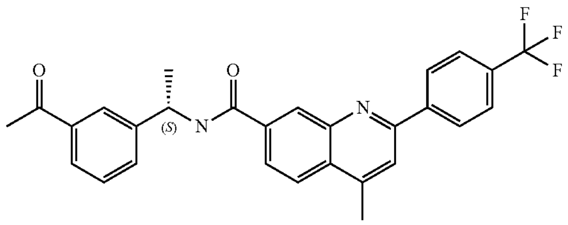

-continued
I-268
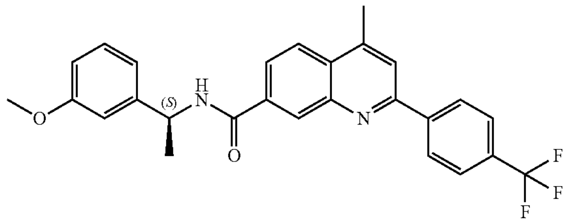
I-269
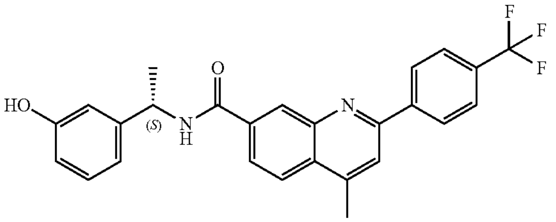
I-270
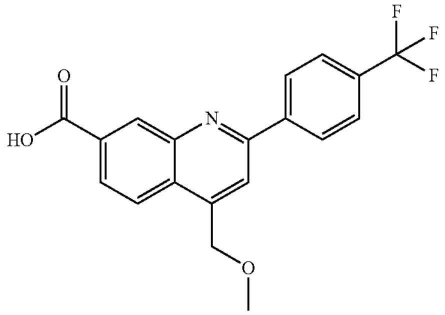
I-271
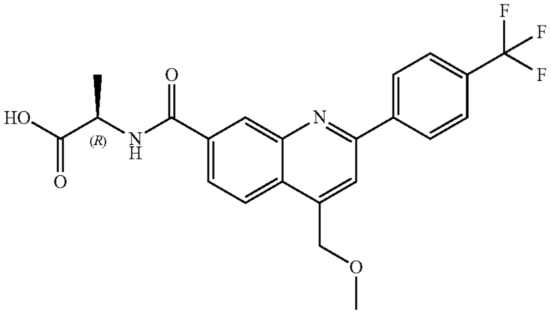
I-324
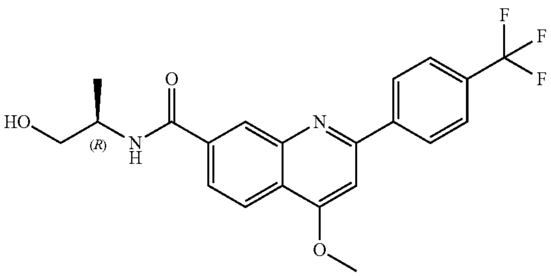
-continued
I-325
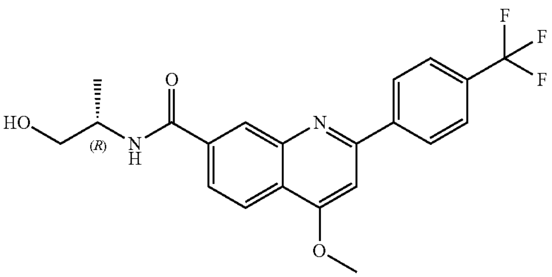
I-326
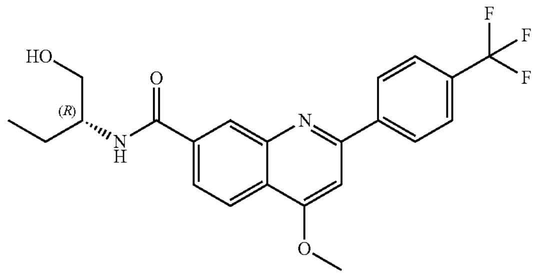
I-327
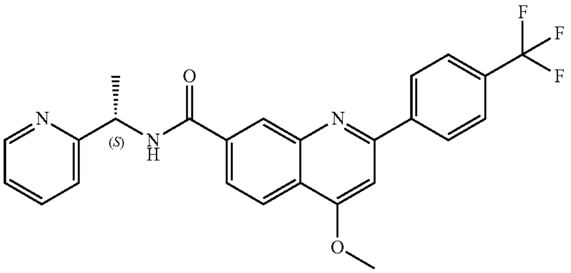
I-329
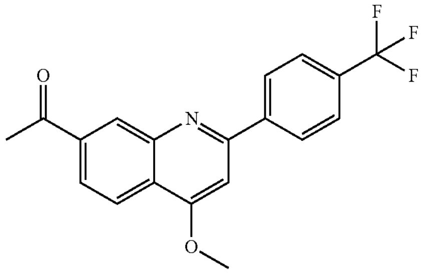
I-330
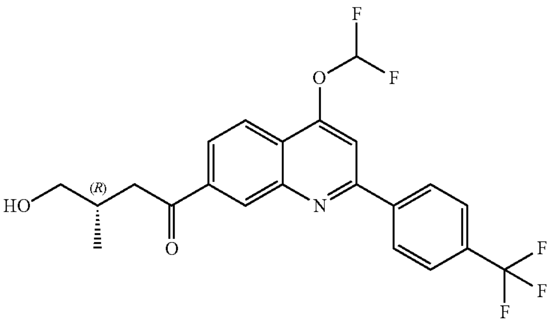

-continued
I-331
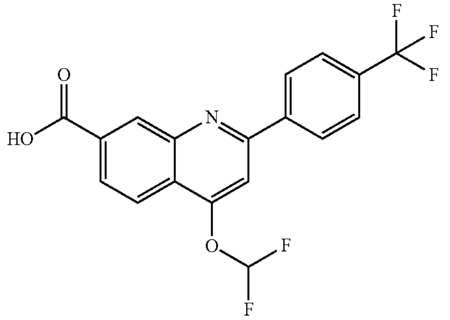
I-332
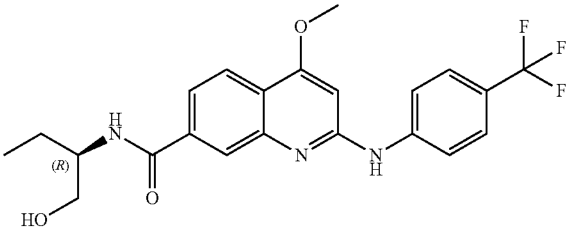
I-333
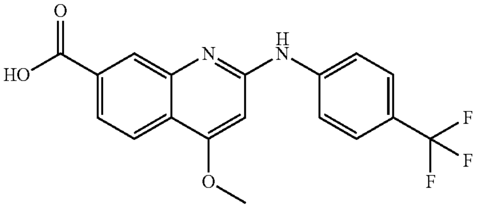
I-334
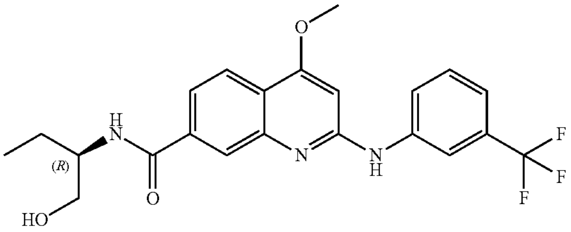
I-335
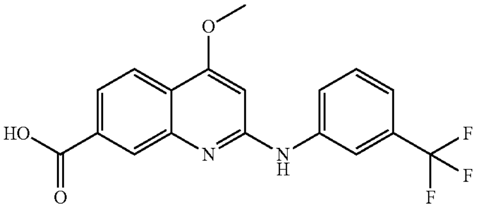
I-336
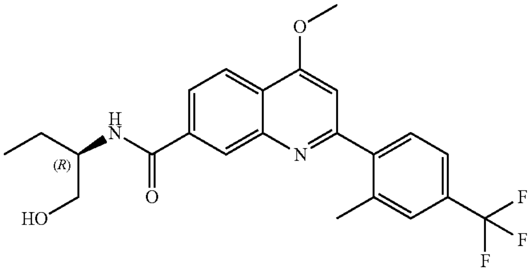
-continued
I-337
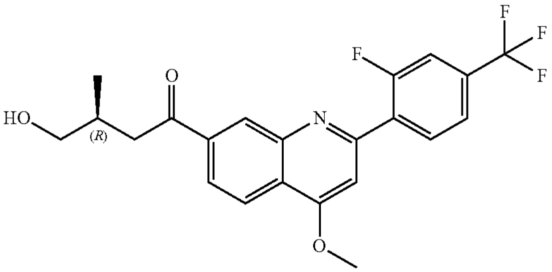
I-338
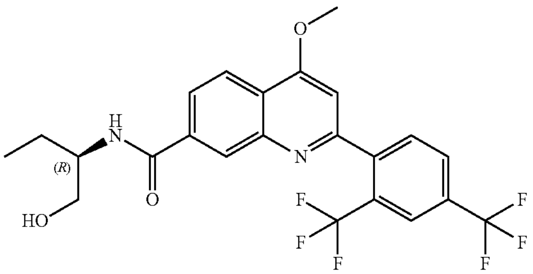
I-339
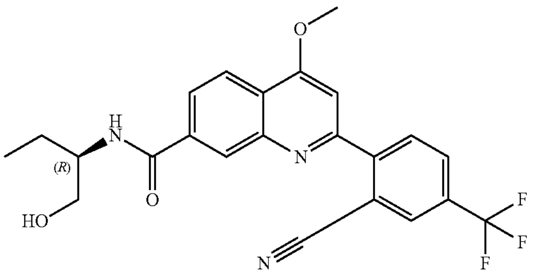
I-340
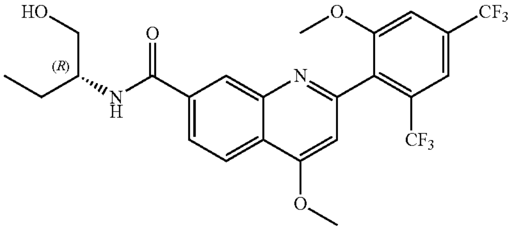
I-341
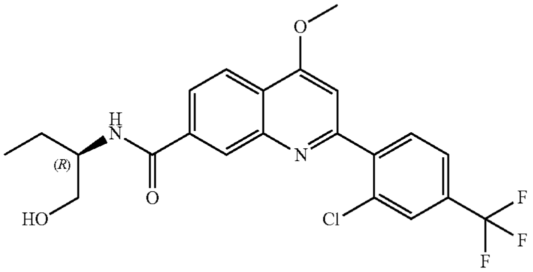

-continued
I-342
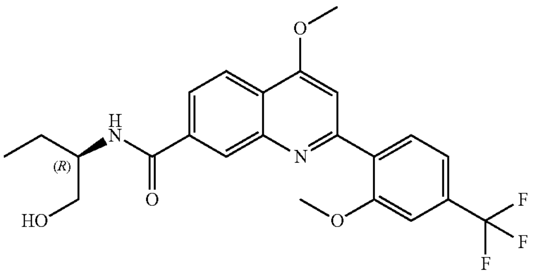
I-343
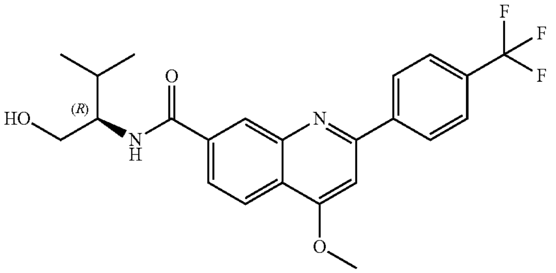
I-344
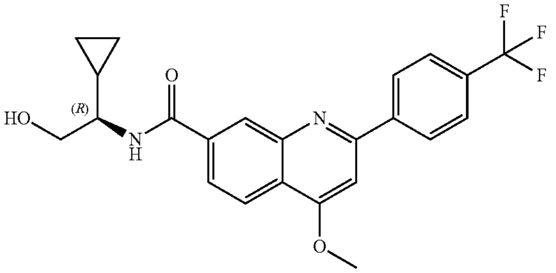
I-345
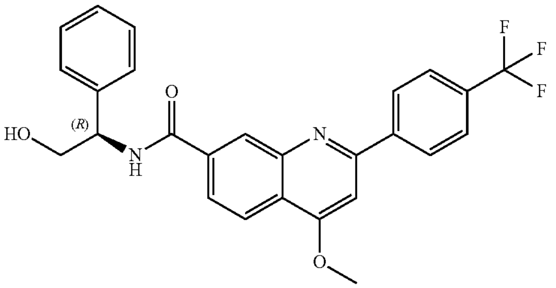
I-346
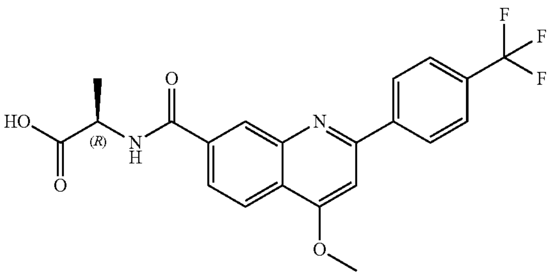
-continued
I-347
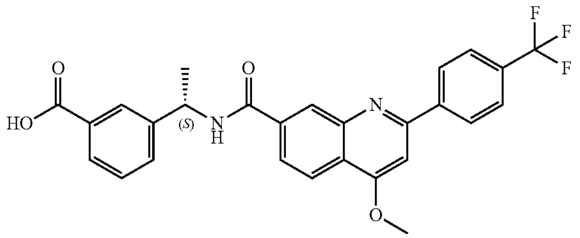
I-348
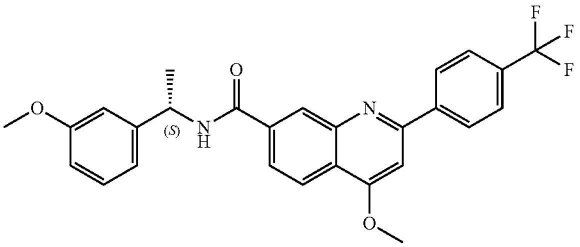
I-349
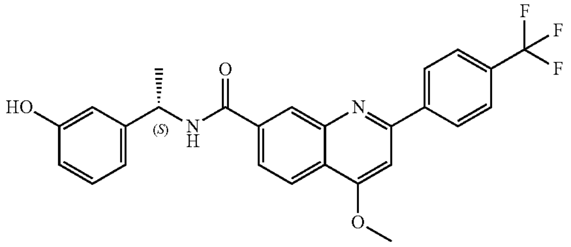
I-350
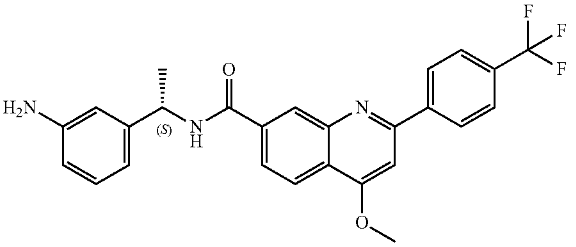
I-351
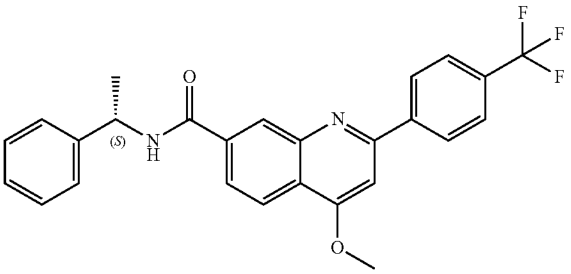

-continued
I-353
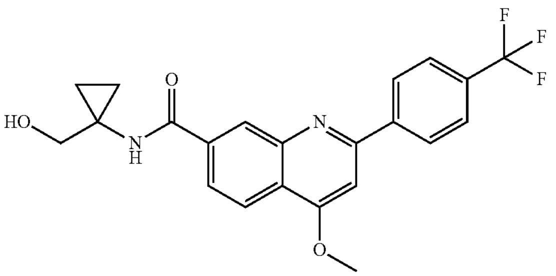
I-352
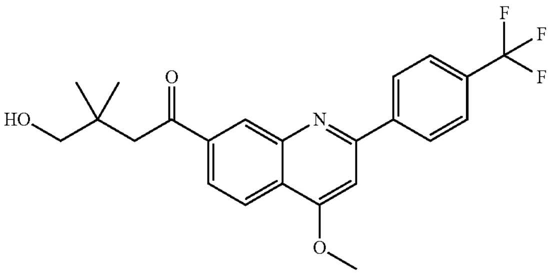
I-355
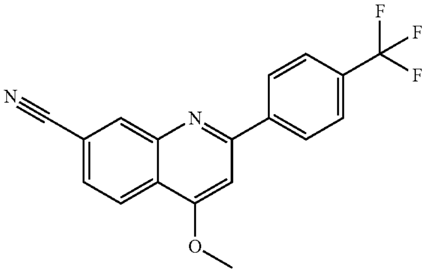
I-354
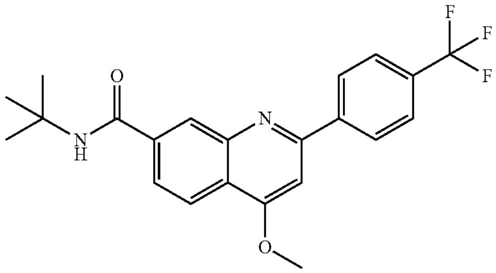
I-357
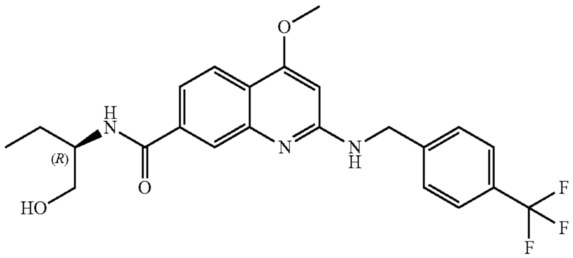
-continued
I-356
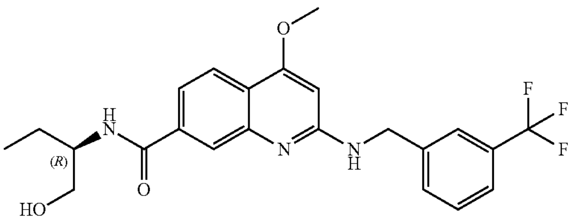
I-359
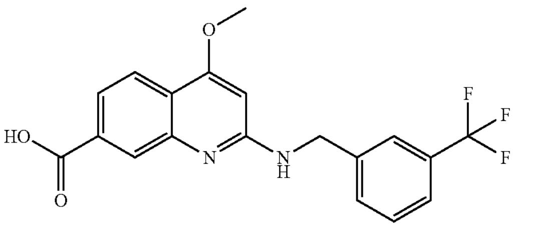
I-358
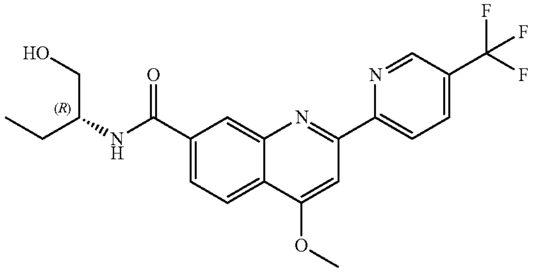
I-361
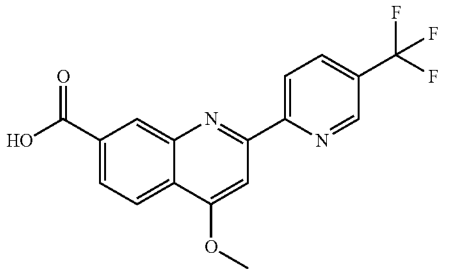
I-360
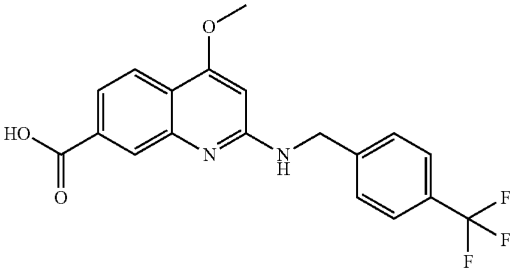

-continued
I-363
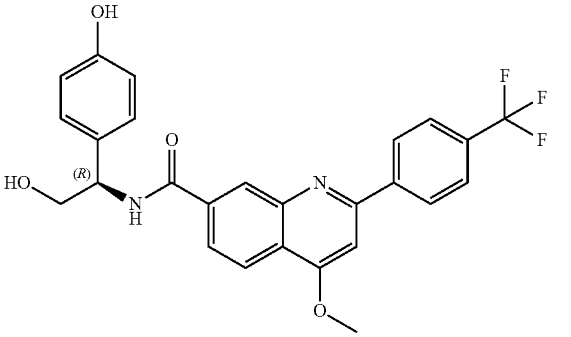
I-362
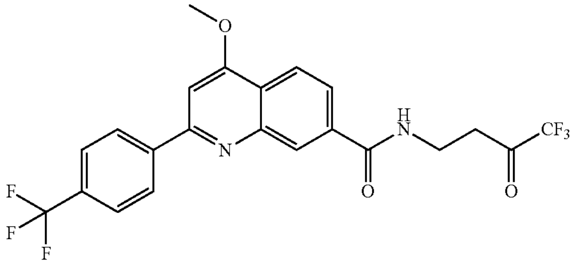
I-365
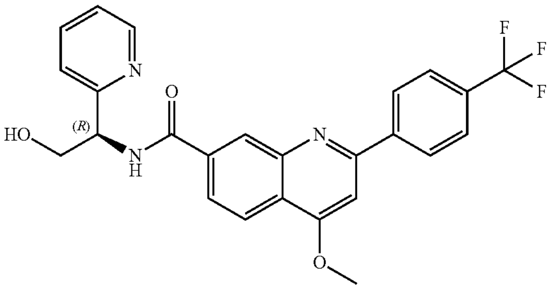
I-364
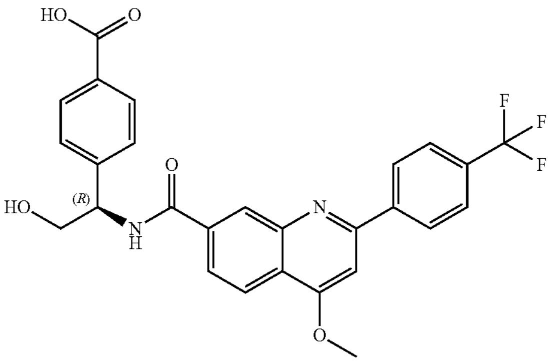
-continued
I-367
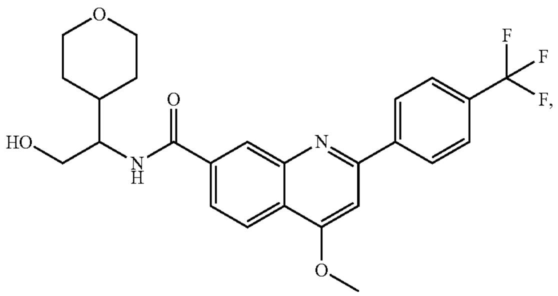
first eluting isomer
I-366
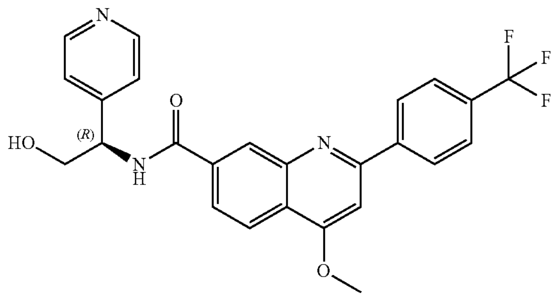
I-368
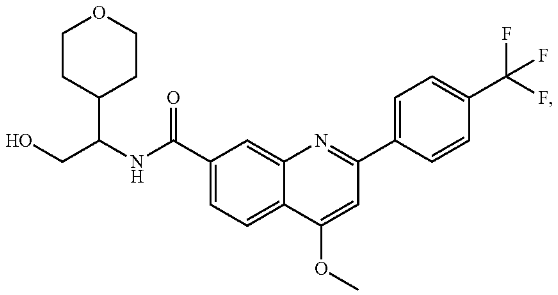
second eluting isomer
I-367a
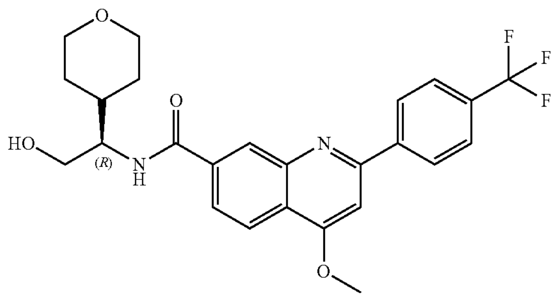
I-369
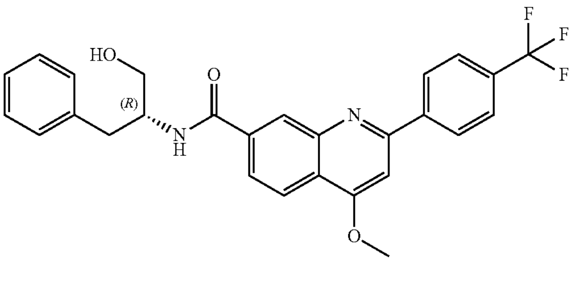

-continued
I-368a
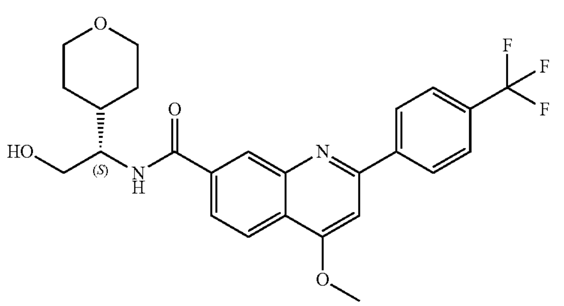
I-371
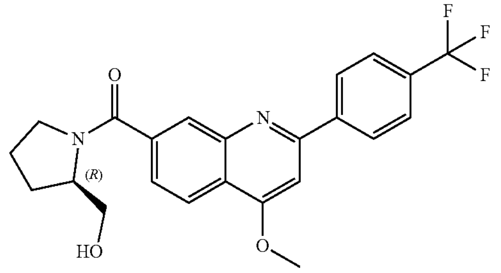
I-370
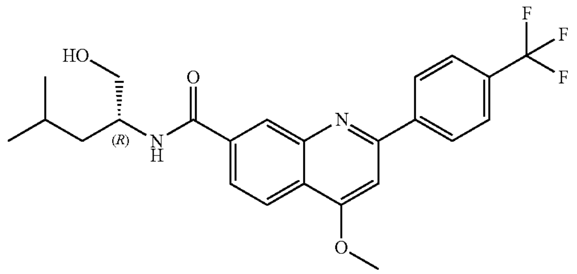
I-372a
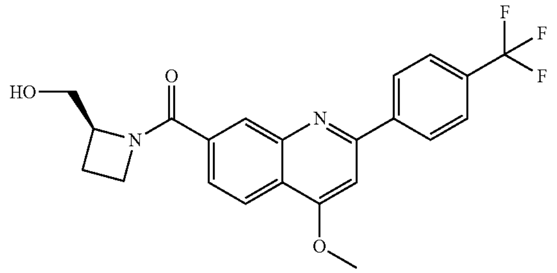
I-372
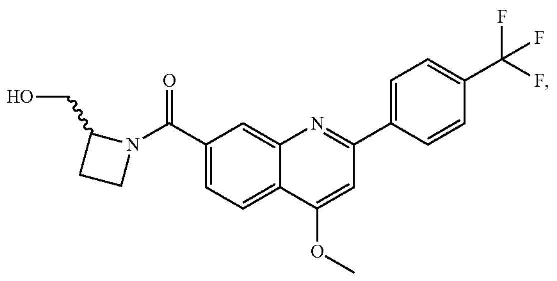
first eluting isomer
-continued
I-373a
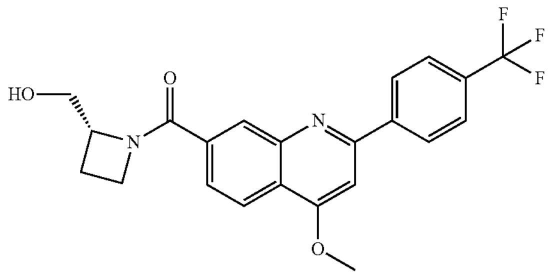
I-373
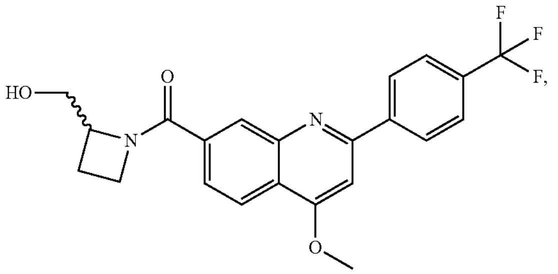
second eluting isomer
I-375
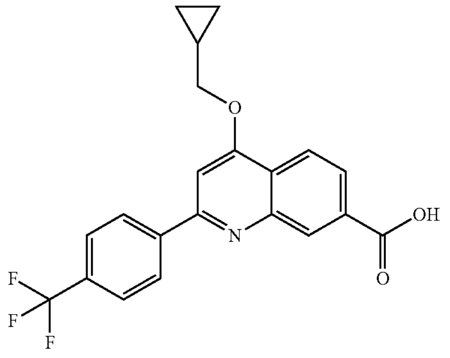
I-374
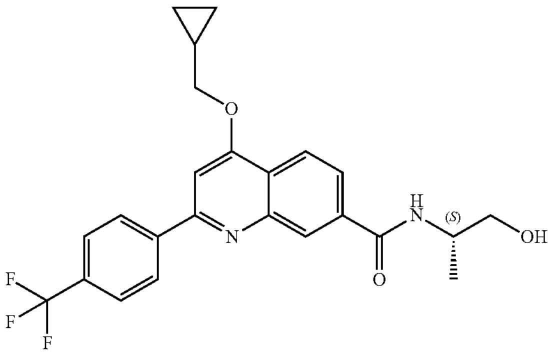
I-377
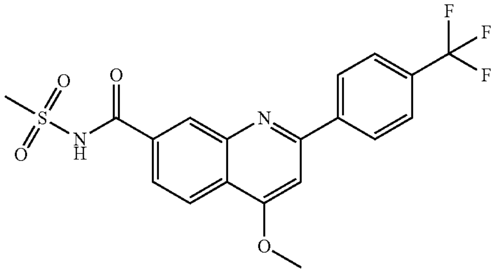

-continued
I-376
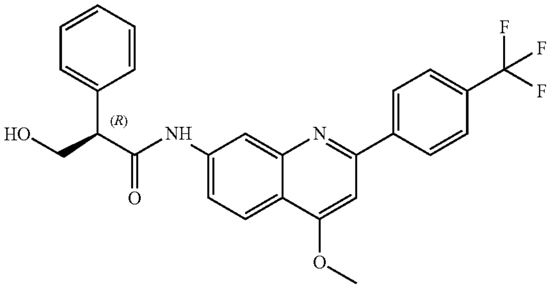
I-379
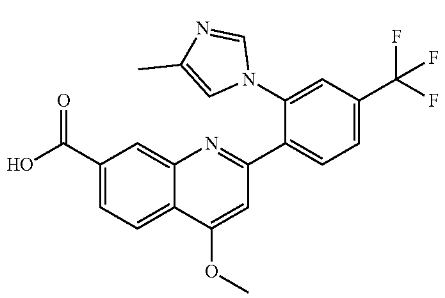
I-378
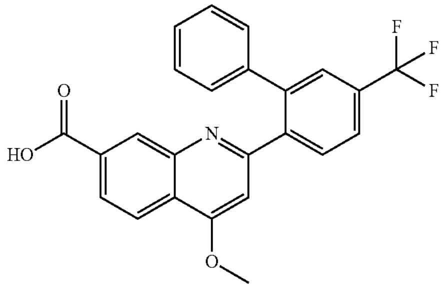
I-381
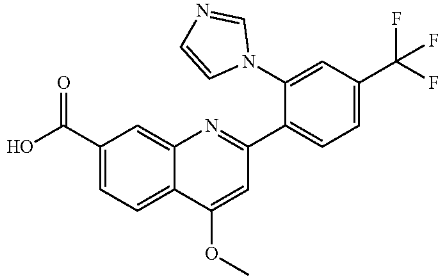
I-380
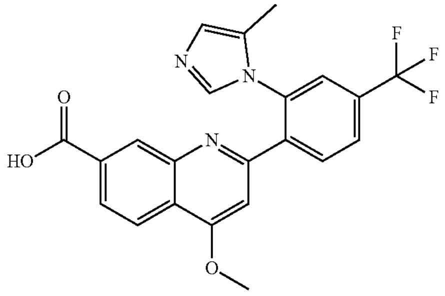
-continued
I-383
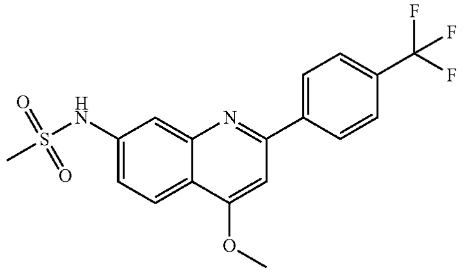
I-382
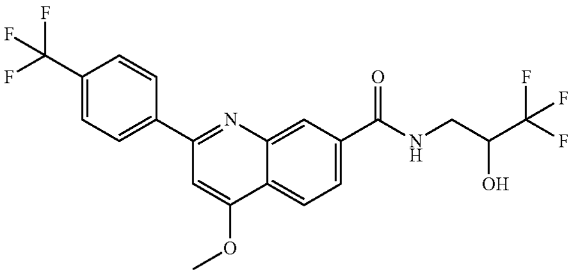
I-387
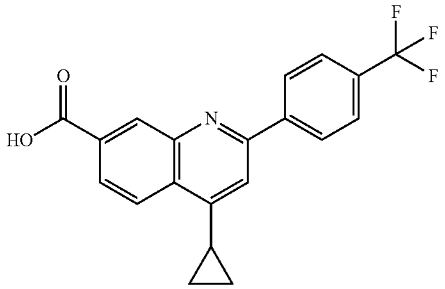
I-384
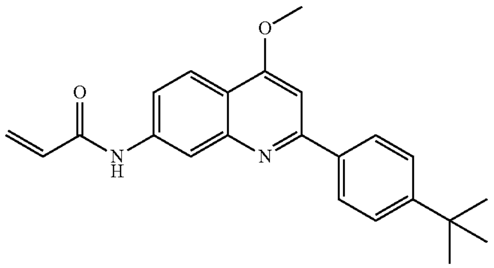
I-389
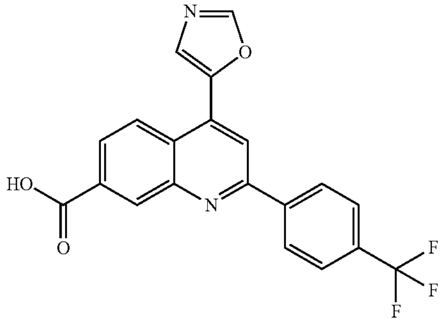

-continued
I-386
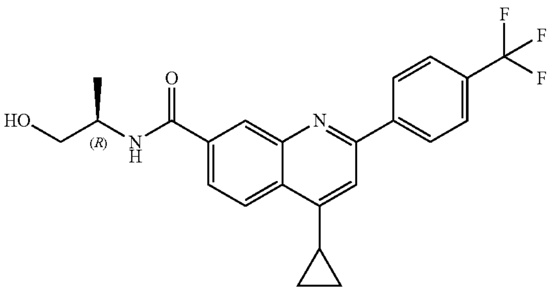
I-391
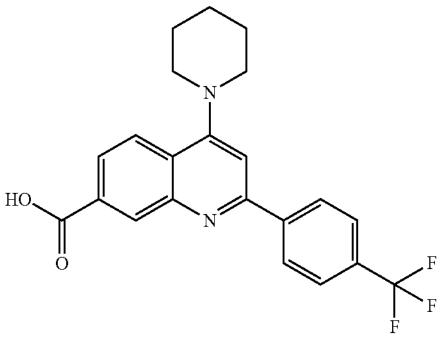
I-388
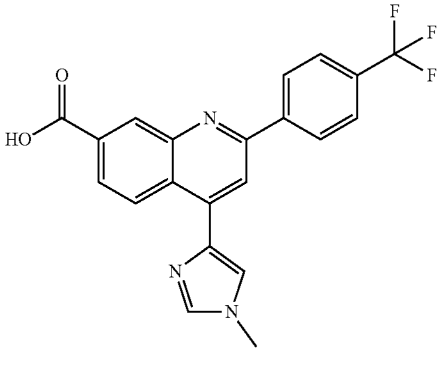
I-393
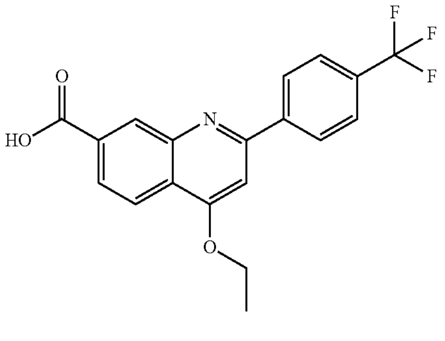
-continued
I-390
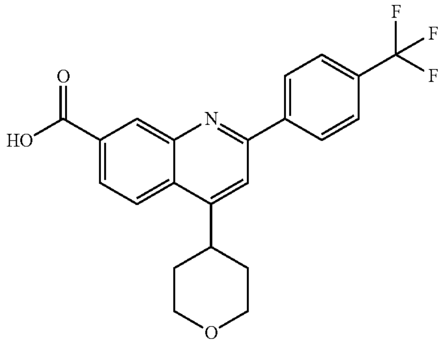
I-395
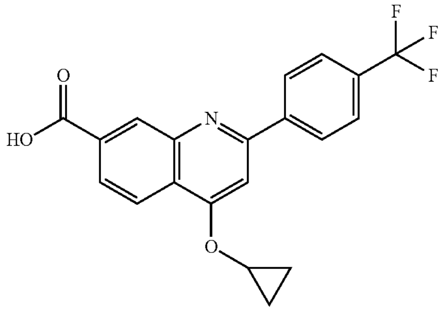
I-392
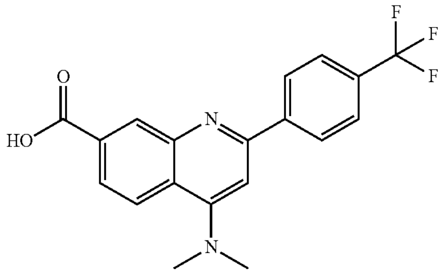
I-399
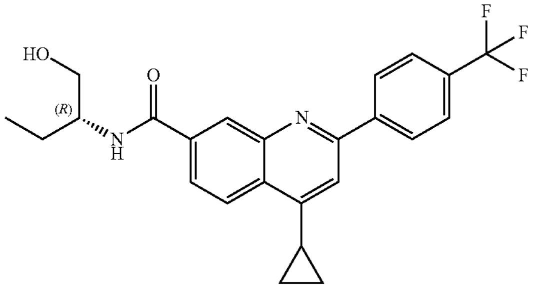
I-394
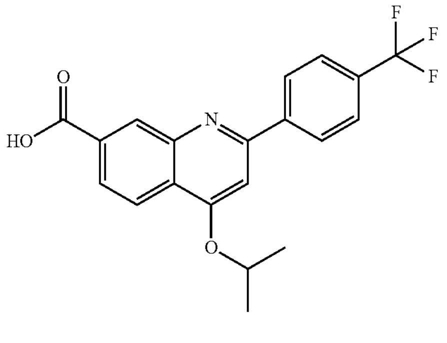

-continued
I-401
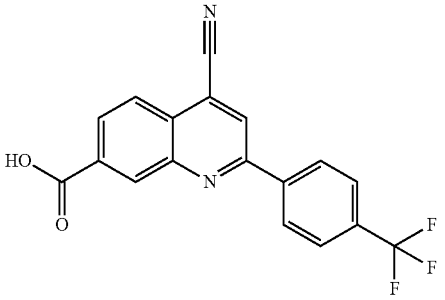
I-396
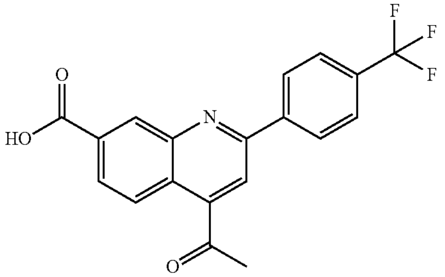
I-403
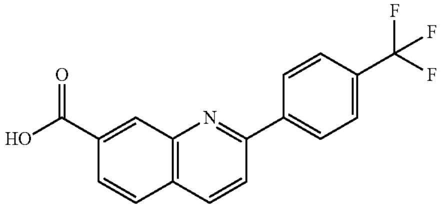
I-398
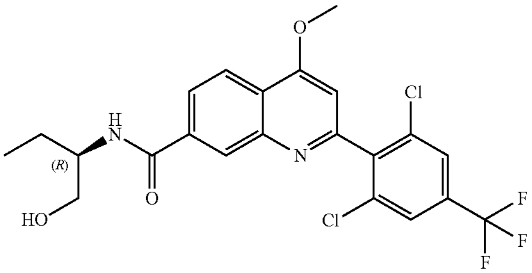
I-413
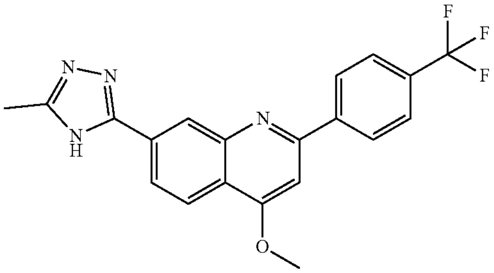
-continued
I-400
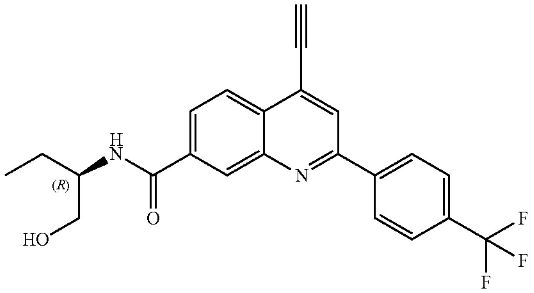
I-415
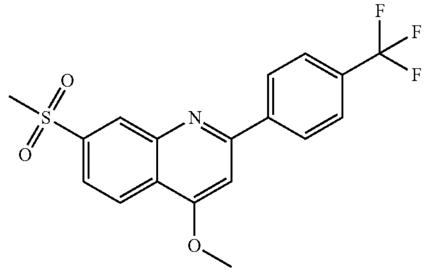
I-402
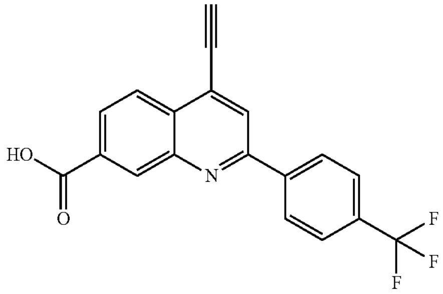
I-417
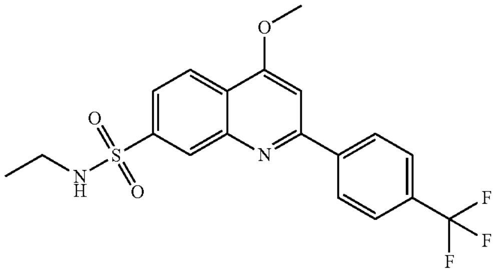
I-414
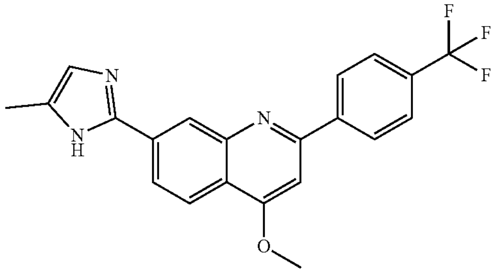

-continued
I-419
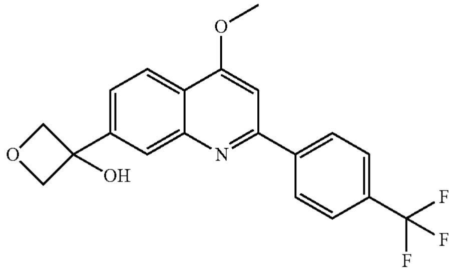
I-416
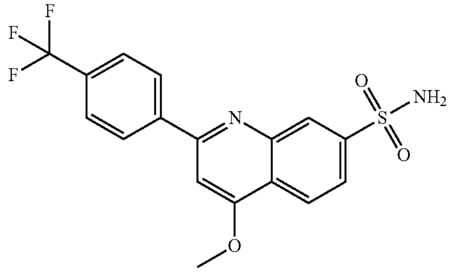
I-425
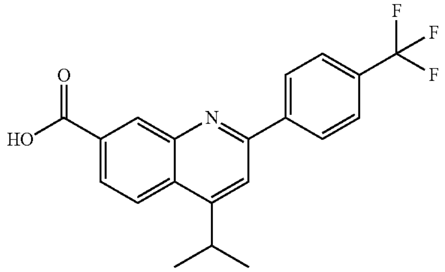
I-418
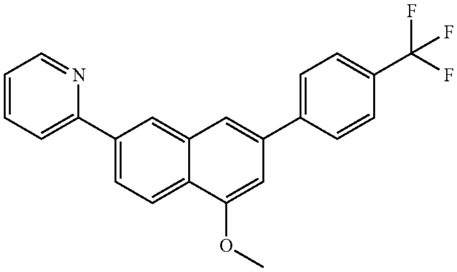
-continued
I-420
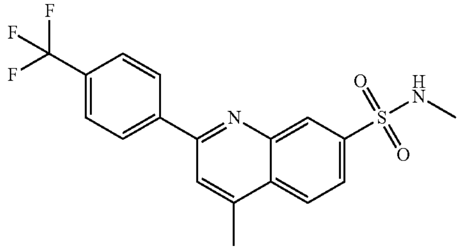
I-426
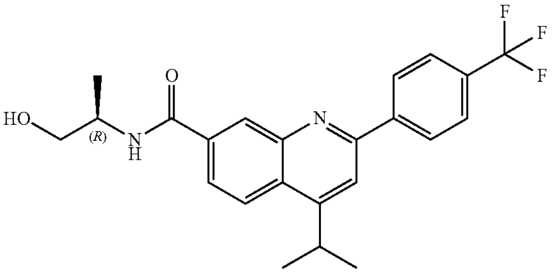
I-427
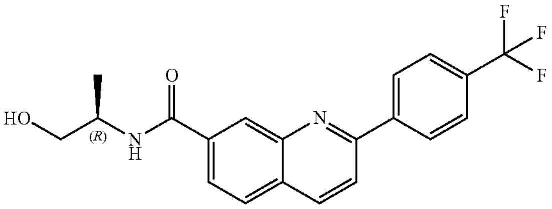
I-429
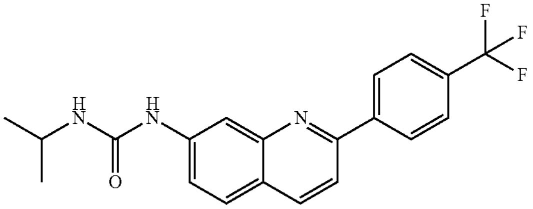
or a pharmaceutically acceptable salt thereof.
* * * * *

SEQUENCE LISTING

```
<160> NUMBER OF SEQ ID NOS: 5

<210> SEQ ID NO 1
<211> LENGTH: 426
<212> TYPE: PRT
<213> ORGANISM: Homo sapiens

<400> SEQUENCE: 1

Met Glu Pro Ser Ser Trp Ser Gly Ser Glu Ser Pro Ala Glu Asn Met
1               5                   10                  15

Glu Arg Met Ser Asp Ser Ala Asp Lys Pro Ile Asp Asn Asp Ala Glu
            20                  25                  30

Gly Val Trp Ser Pro Asp Ile Glu Gln Ser Phe Gln Glu Ala Leu Ala
        35                  40                  45

Ile Tyr Pro Pro Cys Gly Arg Arg Lys Ile Ile Leu Ser Asp Glu Gly
    50                  55                  60

Lys Met Tyr Gly Arg Asn Glu Leu Ile Ala Arg Tyr Ile Lys Leu Arg
65                  70                  75                  80

Thr Gly Lys Thr Arg Thr Arg Lys Gln Val Ser Ser His Ile Gln Val
                85                  90                  95

Leu Ala Arg Arg Lys Ser Arg Asp Phe His Ser Lys Leu Lys Asp Gln
            100                 105                 110

Thr Ala Lys Asp Lys Ala Leu Gln His Met Ala Ala Met Ser Ser Ala
        115                 120                 125

Gln Ile Val Ser Ala Thr Ala Ile His Asn Lys Leu Gly Leu Pro Gly
    130                 135                 140

Ile Pro Arg Pro Thr Phe Pro Gly Ala Pro Gly Phe Trp Pro Gly Met
145                 150                 155                 160

Ile Gln Thr Gly Gln Pro Gly Ser Ser Gln Asp Val Lys Pro Phe Val
                165                 170                 175

Gln Gln Ala Tyr Pro Ile Gln Pro Ala Val Thr Ala Pro Ile Pro Gly
            180                 185                 190

Phe Glu Pro Ala Ser Ala Pro Ala Pro Ser Val Pro Ala Trp Gln Gly
        195                 200                 205

Arg Ser Ile Gly Thr Thr Lys Leu Arg Leu Val Glu Phe Ser Ala Phe
    210                 215                 220

Leu Glu Gln Gln Arg Asp Pro Asp Ser Tyr Asn Lys His Leu Phe Val
225                 230                 235                 240

His Ile Gly His Ala Asn His Ser Tyr Ser Asp Pro Leu Leu Glu Ser
                245                 250                 255

Val Asp Ile Arg Gln Ile Tyr Asp Lys Phe Pro Glu Lys Lys Gly Gly
            260                 265                 270

Leu Lys Glu Leu Phe Gly Lys Gly Pro Gln Asn Ala Phe Phe Leu Val
        275                 280                 285

Lys Phe Trp Ala Asp Leu Asn Cys Asn Ile Gln Asp Asp Ala Gly Ala
    290                 295                 300

Phe Tyr Gly Val Thr Ser Gln Tyr Glu Ser Ser Glu Asn Met Thr Val
```

-continued

```
305                 310                 315                 320

Thr Cys Ser Thr Lys Val Cys Ser Phe Gly Lys Gln Val Val Glu Lys
                325                 330                 335

Val Glu Thr Glu Tyr Ala Arg Phe Glu Asn Gly Arg Phe Val Tyr Arg
            340                 345                 350

Ile Asn Arg Ser Pro Met Cys Glu Tyr Met Ile Asn Phe Ile His Lys
        355                 360                 365

Leu Lys His Leu Pro Glu Lys Tyr Met Met Asn Ser Val Leu Glu Asn
    370                 375                 380

Phe Thr Ile Leu Leu Val Val Thr Asn Arg Asp Thr Gln Glu Thr Leu
385                 390                 395                 400

Leu Cys Met Ala Cys Val Phe Glu Val Ser Asn Ser Glu His Gly Ala
                405                 410                 415

Gln His His Ile Tyr Arg Leu Val Lys Asp
            420                 425


<210> SEQ ID NO 2
<211> LENGTH: 447
<212> TYPE: PRT
<213> ORGANISM: Homo sapiens

<400> SEQUENCE: 2

Met Gly Glu Pro Arg Ala Gly Ala Ala Leu Asp Asp Gly Ser Gly Trp
1               5                   10                  15

Thr Gly Ser Glu Glu Gly Ser Glu Glu Gly Thr Gly Gly Ser Glu Gly
            20                  25                  30

Ala Gly Gly Asp Gly Gly Pro Asp Ala Glu Gly Val Trp Ser Pro Asp
        35                  40                  45

Ile Glu Gln Ser Phe Gln Glu Ala Leu Ala Ile Tyr Pro Pro Cys Gly
    50                  55                  60

Arg Arg Lys Ile Ile Leu Ser Asp Glu Gly Lys Met Tyr Gly Arg Asn
65                  70                  75                  80

Glu Leu Ile Ala Arg Tyr Ile Lys Leu Arg Thr Gly Lys Thr Arg Thr
                85                  90                  95

Arg Lys Gln Val Ser Ser His Ile Gln Val Leu Ala Arg Arg Lys Ser
            100                 105                 110

Arg Glu Ile Gln Ser Lys Leu Lys Asp Gln Val Ser Lys Asp Lys Ala
        115                 120                 125

Phe Gln Thr Met Ala Thr Met Ser Ser Ala Gln Leu Ile Ser Ala Pro
    130                 135                 140

Ser Leu Gln Ala Lys Leu Gly Pro Thr Gly Pro Gln Ala Ser Glu Leu
145                 150                 155                 160

Phe Gln Phe Trp Ser Gly Gly Ser Gly Pro Pro Trp Asn Val Pro Asp
                165                 170                 175

Val Lys Pro Phe Ser Gln Thr Pro Phe Thr Leu Ser Leu Thr Pro Pro
            180                 185                 190

Ser Thr Asp Leu Pro Gly Tyr Glu Pro Pro Gln Ala Leu Ser Pro Leu
        195                 200                 205

Pro Pro Pro Thr Pro Ser Pro Pro Ala Trp Gln Ala Arg Gly Leu Gly
    210                 215                 220

Thr Ala Arg Leu Gln Leu Val Glu Phe Ser Ala Phe Val Glu Pro Pro
225                 230                 235                 240

Asp Ala Val Asp Ser Tyr Gln Arg His Leu Phe Val His Ile Ser Gln
                245                 250                 255
```

His Cys Pro Ser Pro Gly Ala Pro Pro Leu Glu Ser Val Asp Val Arg
260 265 270

Gln Ile Tyr Asp Lys Phe Pro Glu Lys Lys Gly Gly Leu Arg Glu Leu
275 280 285

Tyr Asp Arg Gly Pro Pro His Ala Phe Phe Leu Val Lys Phe Trp Ala
290 295 300

Asp Leu Asn Trp Gly Pro Ser Gly Glu Glu Ala Gly Ala Gly Gly Ser
305 310 315 320

Ile Ser Ser Gly Gly Phe Tyr Gly Val Ser Ser Gln Tyr Glu Ser Leu
325 330 335

Glu His Met Thr Leu Thr Cys Ser Ser Lys Val Cys Ser Phe Gly Lys
340 345 350

Gln Val Val Glu Lys Val Glu Thr Glu Arg Ala Gln Leu Glu Asp Gly
355 360 365

Arg Phe Val Tyr Arg Leu Leu Arg Ser Pro Met Cys Glu Tyr Leu Val
370 375 380

Asn Phe Leu His Lys Leu Arg Gln Leu Pro Glu Arg Tyr Met Met Asn
385 390 395 400

Ser Val Leu Glu Asn Phe Thr Ile Leu Gln Val Val Thr Asn Arg Asp
405 410 415

Thr Gln Glu Leu Leu Leu Cys Thr Ala Tyr Val Phe Glu Val Ser Thr
420 425 430

Ser Glu Arg Gly Ala Gln His His Ile Tyr Arg Leu Val Arg Asp
435 440 445

<210> SEQ ID NO 3
<211> LENGTH: 435
<212> TYPE: PRT
<213> ORGANISM: Homo sapiens

<400> SEQUENCE: 3

Met Ala Ser Asn Ser Trp Asn Ala Ser Ser Ser Pro Gly Glu Ala Arg
1 5 10 15

Glu Asp Gly Pro Glu Gly Leu Asp Lys Gly Leu Asp Asn Asp Ala Glu
20 25 30

Gly Val Trp Ser Pro Asp Ile Glu Gln Ser Phe Gln Glu Ala Leu Ala
35 40 45

Ile Tyr Pro Pro Cys Gly Arg Arg Lys Ile Ile Leu Ser Asp Glu Gly
50 55 60

Lys Met Tyr Gly Arg Asn Glu Leu Ile Ala Arg Tyr Ile Lys Leu Arg
65 70 75 80

Thr Gly Lys Thr Arg Thr Arg Lys Gln Val Ser Ser His Ile Gln Val
85 90 95

Leu Ala Arg Lys Lys Val Arg Glu Tyr Gln Val Gly Ile Lys Ala Met
100 105 110

Asn Leu Asp Gln Val Ser Lys Asp Lys Ala Leu Gln Ser Met Ala Ser
115 120 125

Met Ser Ser Ala Gln Ile Val Ser Ala Ser Val Leu Gln Asn Lys Phe
130 135 140

Ser Pro Pro Ser Pro Leu Pro Gln Ala Val Phe Ser Thr Ser Ser Arg
145 150 155 160

Phe Trp Ser Ser Pro Pro Leu Leu Gly Gln Gln Pro Gly Pro Ser Gln
165 170 175

Asp Ile Lys Pro Phe Ala Gln Pro Ala Tyr Pro Ile Gln Pro Pro Leu
180 185 190

```
Pro Pro Thr Leu Ser Ser Tyr Glu Pro Leu Ala Pro Leu Pro Ser Ala
        195                 200                 205

Ala Ala Ser Val Pro Val Trp Gln Asp Arg Thr Ile Ala Ser Ser Arg
    210                 215                 220

Leu Arg Leu Leu Glu Tyr Ser Ala Phe Met Glu Val Gln Arg Asp Pro
225                 230                 235                 240

Asp Thr Tyr Ser Lys His Leu Phe Val His Ile Gly Gln Thr Asn Pro
                245                 250                 255

Ala Phe Ser Asp Pro Pro Leu Glu Ala Val Asp Val Arg Gln Ile Tyr
            260                 265                 270

Asp Lys Phe Pro Glu Lys Lys Gly Gly Leu Lys Glu Leu Tyr Glu Lys
        275                 280                 285

Gly Pro Pro Asn Ala Phe Phe Leu Val Lys Phe Trp Ala Asp Leu Asn
    290                 295                 300

Ser Thr Ile Gln Glu Gly Pro Gly Ala Phe Tyr Gly Val Ser Ser Gln
305                 310                 315                 320

Tyr Ser Ser Ala Asp Ser Met Thr Ile Ser Val Ser Thr Lys Val Cys
                325                 330                 335

Ser Phe Gly Lys Gln Val Val Glu Lys Val Glu Thr Glu Tyr Ala Arg
            340                 345                 350

Leu Glu Asn Gly Arg Phe Val Tyr Arg Ile His Arg Ser Pro Met Cys
        355                 360                 365

Glu Tyr Met Ile Asn Phe Ile His Lys Leu Lys His Leu Pro Glu Lys
    370                 375                 380

Tyr Met Met Asn Ser Val Leu Glu Asn Phe Thr Ile Leu Gln Val Val
385                 390                 395                 400

Thr Ser Arg Asp Ser Gln Glu Thr Leu Leu Val Ile Ala Phe Val Phe
                405                 410                 415

Glu Val Ser Thr Ser Glu His Gly Ala Gln His His Val Tyr Lys Leu
            420                 425                 430

Val Lys Asp
        435


<210> SEQ ID NO 4
<211> LENGTH: 434
<212> TYPE: PRT
<213> ORGANISM: Homo sapiens

<400> SEQUENCE: 4

Met Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Ala Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
            100                 105                 110

Ile Gln Ala Lys Leu Lys Asp Gln Ala Ala Lys Asp Lys Ala Leu Gln
```

-continued

```
        115                 120                 125

Ser Met Ala Ala Met Ser Ser Ala Gln Ile Ile Ser Ala Thr Ala Phe
    130                 135                 140

His Ser Ser Met Ala Leu Ala Arg Gly Pro Gly Arg Pro Ala Val Ser
145                 150                 155                 160

Gly Phe Trp Gln Gly Ala Leu Pro Gly Gln Ala Gly Thr Ser His Asp
                165                 170                 175

Val Lys Pro Phe Ser Gln Gln Thr Tyr Ala Val Gln Pro Pro Leu Pro
            180                 185                 190

Leu Pro Gly Phe Glu Ser Pro Ala Gly Pro Ala Pro Ser Pro Ser Ala
        195                 200                 205

Pro Pro Ala Pro Pro Trp Gln Gly Arg Ser Val Ala Ser Ser Lys Leu
    210                 215                 220

Trp Met Leu Glu Phe Ser Ala Phe Leu Glu Gln Gln Gln Asp Pro Asp
225                 230                 235                 240

Thr Tyr Asn Lys His Leu Phe Val His Ile Gly Gln Ser Ser Pro Ser
                245                 250                 255

Tyr Ser Asp Pro Tyr Leu Glu Ala Val Asp Ile Arg Gln Ile Tyr Asp
            260                 265                 270

Lys Phe Pro Glu Lys Lys Gly Gly Leu Lys Asp Leu Phe Glu Arg Gly
        275                 280                 285

Pro Ser Asn Ala Phe Phe Leu Val Lys Phe Trp Ala Asp Leu Asn Thr
    290                 295                 300

Asn Ile Glu Asp Glu Gly Ser Ser Phe Tyr Gly Val Ser Ser Gln Tyr
305                 310                 315                 320

Glu Ser Pro Glu Asn Met Ile Ile Thr Cys Ser Thr Lys Val Cys Ser
                325                 330                 335

Phe Gly Lys Gln Val Val Glu Lys Val Glu Thr Glu Tyr Ala Arg Tyr
            340                 345                 350

Glu Asn Gly His Tyr Ser Tyr Arg Ile His Arg Ser Pro Leu Cys Glu
        355                 360                 365

Tyr Met Ile Asn Phe Ile His Lys Leu Lys His Leu Pro Glu Lys Tyr
    370                 375                 380

Met Met Asn Ser Val Leu Glu Asn Phe Thr Ile Leu Gln Val Val Thr
385                 390                 395                 400

Asn Arg Asp Thr Gln Glu Thr Leu Leu Cys Ile Ala Tyr Val Phe Glu
                405                 410                 415

Val Ser Ala Ser Glu His Gly Ala Gln His His Ile Tyr Arg Leu Val
            420                 425                 430

Lys Glu
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES -continued

```
<222> LOCATION: (4)..(5)
<223> OTHER INFORMATION: Any amino acid

<400> SEQUENCE: 5

His Xaa Arg Xaa Xaa Ser
1               5
```